(12) United States Patent
Maekawa et al.

(10) Patent No.: US 8,921,379 B2
(45) Date of Patent: *Dec. 30, 2014

(54) FUSED RING COMPOUND AND USE THEREOF

(75) Inventors: Tsuyoshi Maekawa, Osaka (JP); Hideyuki Igawa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 627 days.

This patent is subject to a terminal disclaimer.

(21) Appl. No.: 13/205,967

(22) Filed: Aug. 9, 2011

(65) Prior Publication Data

US 2011/0294832 A1    Dec. 1, 2011

Related U.S. Application Data

(63) Continuation of application No. 12/696,147, filed on Jan. 29, 2010, now Pat. No. 8,283,353.

(30) Foreign Application Priority Data

Jan. 30, 2009   (JP) ................................. 2009-020720

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 487/04* | (2006.01) | |

(52) U.S. Cl.
CPC .................................... *C07D 487/04* (2013.01)
USPC ....................................... 514/259.3; 544/281

(58) Field of Classification Search
None
See application file for complete search history.

(56) References Cited

U.S. PATENT DOCUMENTS

| | | | |
|---|---|---|---|
| 5,243,054 A | 9/1993 | Naka et al. | |
| 5,387,747 A | 2/1995 | Bru-Magniez et al. | |
| 5,389,632 A | 2/1995 | Bru-Magniez et al. | |
| 5,472,967 A | 12/1995 | Hoornaert et al. | |
| 5,565,464 A | 10/1996 | Salimbeni et al. | |
| 6,927,228 B2 | 8/2005 | Bernardon et al. | |
| 6,984,633 B2 | 1/2006 | Egan et al. | |
| 7,507,740 B2 | 3/2009 | Ishikawa et al. | |
| 8,592,431 B2 * | 11/2013 | Maekawa et al. | 514/259.31 |
| 2004/0127443 A1 | 7/2004 | Pershadsingh | |
| 2005/0288272 A1 | 12/2005 | Ziegler et al. | |
| 2007/0244132 A1 | 10/2007 | Ishikawa et al. | |
| 2008/0064871 A1 | 3/2008 | Hirata et al. | |
| 2009/0012052 A1 | 1/2009 | Coopersmith et al. | |
| 2009/0018335 A1 | 1/2009 | Ishikawa et al. | |
| 2009/0029973 A1 | 1/2009 | Ishikawa et al. | |
| 2009/0203717 A1 | 8/2009 | Ishikawa et al. | |
| 2014/0046056 A1 * | 2/2014 | Maekawa et al. | 544/118 |

FOREIGN PATENT DOCUMENTS

| | | |
|---|---|---|
| CN | 1064269 A | 9/1992 |
| JP | 2006-515566 A | 6/2006 |
| WO | WO 94/17067 A1 | 8/1994 |
| WO | WO 95/26724 A1 | 10/1995 |
| WO | WO 96/40255 A2 | 12/1996 |
| WO | WO 96/40256 A1 | 12/1996 |
| WO | WO 96/40257 A1 | 12/1996 |
| WO | WO 96/40258 A2 | 12/1996 |
| WO | WO 02/12210 A1 | 2/2002 |
| WO | WO 02/090333 A1 | 11/2002 |
| WO | WO 2004/064721 A2 | 8/2004 |
| WO | WO 2005/020984 A2 | 3/2005 |
| WO | WO 2005/118588 A1 | 12/2005 |
| WO | WO 2006/000564 A1 | 1/2006 |
| WO | WO 2007/013078 A2 | 2/2007 |
| WO | WO 2007/051007 A2 | 5/2007 |
| WO | WO 2007/053406 A1 | 5/2007 |
| WO | WO 2007/139002 A1 | 12/2007 |
| WO | WO 2008/060899 A2 | 5/2008 |
| WO | WO 2008/062905 A2 | 5/2008 |
| WO | WO 2008/143262 A1 | 11/2008 |
| WO | WO 2009/039069 A1 | 3/2009 |
| WO | WO 2009/118292 A1 | 10/2009 |
| WO | WO 2009/137465 A2 | 11/2009 |

OTHER PUBLICATIONS

Banker et al., Eds., Modern Pharmaceutics, 1996, 596.
Wolf, Manfred E., Ed., Burger's Medicinal Chemistry and Drug Discovery, 5$^{th}$ Ed., Part 1, 1995, 975-977.

(Continued)

*Primary Examiner* — Jeffrey H Murray
(74) *Attorney, Agent, or Firm* — Foley & Lardner LLP

(57) ABSTRACT

Provided is a novel compound represented by the following formula (I)

Wherein each symbol is as defined in the specification, or a salt thereof, which has an angiotensin II receptor antagonistic activity and a peroxisome proliferator-activated receptor γ agonistic activity, and is useful as an agent for the prophylaxis or treatment of circulatory diseases such as hypertension and the like and/or metabolic diseases such as diabetes and the like, and the like.

4 Claims, No Drawings

(56) References Cited

OTHER PUBLICATIONS

U.S. Appl. No. 13/146,989, filed Jul. 29, 2011, Maekawa et al.
U.S. Appl. No. 12/696,147, filed Jan. 29, 2010, Maekawa et al.
Hoyer et al., "Molecular, pharmacological and functional diversity of 5-HT receptors," Pharmacology, Biochemistry and Behavior, 2002, 71:533-554.
WHO Drug Information, 2006, 20(2):121.
Wang Liuping et al., "Studies on the factors affecting the diabetic model induced by alloxan in mice," Journal of Guangxi Medical University, Feb. 28, 2004, 21(1):33-35, with English abstract on first page.

* cited by examiner

SEQUENCE LISTING

<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
gtgggtaccg aaatgaccat ggttgacaca gag        33

<210> SEQ ID NO 2

```
<211> LENGTH: 33
<212> TYPE: DNA
<213> ORGANISM: Artificial
<220> FEATURE:
<223> OTHER INFORMATION: primer

<400> SEQUENCE: 2
ggggtcgacc aggactctct gctagtacaa gtc                            33

<210> SEQ ID NO 3
<211> LENGTH: 33
<212> TYPE: DNA
<213> ORGANISM: Artificial
<220> FEATURE:
<223> OTHER INFORMATION: primer

<400> SEQUENCE: 3
ttagaattcg acatggacac caaacatttc ctg                            33

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
cccctcgagc taagtcattt ggtgcggcgc ctc                            33

<210> SEQ ID NO 5
<211> LENGTH: 36
<212> TYPE: DNA
<213> ORGANISM: Artificial
<220> FEATURE:
<223> OTHER INFORMATION: primer

<400> SEQUENCE: 5
tcgacagggg accaggacaa aggtcacgtt cgggag                         36

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
tcgactcccg aacgtgacct ttgtcctggt cccctg                         36

<210> SEQ ID NO 7
<211> LENGTH: 28
<212> TYPE: DNA
<213> ORGANISM: Artificial
<220> FEATURE:
<223> OTHER INFORMATION: primer

<400> SEQUENCE: 7
cccagatctc cccagcgtct tgtcattg                                  28
```

```
<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
tcaccatggt caagctttta agcgggtc                                        28
```

FUSED RING COMPOUND AND USE THEREOF

CROSS-REFERENCE TO RELATED APPLICATIONS

This application is a Divisional of U.S. application Ser. No. 12/696,147, filed Jan. 29, 2010, which claims priority from Japanese application JP 2009-020720, filed Jan. 30, 2009.

TECHNICAL FIELD OF THE INVENTION

The present invention relates to a novel fused ring compound having superior properties as a medicament, a production method thereof and use thereof. More particularly, the present invention relates to a fused heterocyclic compound having a particular structure, a superior pharmacological activity such as angiotensin II receptor antagonistic activity, peroxisome proliferator-activated receptor γ agonistic activity and the like, and superior properties such as crystallinity, stability and the like, which is useful as an agent for the prophylaxis or treatment of circulatory diseases such as hypertension, cardiac diseases (cardiac hypertrophy, cardiac failure, myocardial infarction etc.), arteriosclerosis, renal diseases (diabetic nephropathy, chronic glomerulonephritis etc.), ophthalmic diseases, liver diseases, cerebral apoplexy and the like and/or metabolic diseases such as hyperlipidemia, obesity, diabetes and the like, a salt thereof, a prodrug thereof, a production method thereof, and use thereof and the like.

BACKGROUND OF THE INVENTION

Heretofore, compounds having an angiotensin II receptor antagonistic activity and a peroxisome proliferator-activated receptor γ agonistic activity have been reported, for example, in WO2008/062905, WO2008/143262 and the like.

WO 2008/062905 describes a compound of the following formula

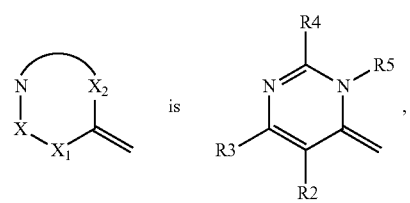

(I)

wherein R1 is (1) an oxo group; (2) a thioxo group; (3) a group represented by the formula: =N—R; R is
(i) an optionally substituted $C_1$-$C_6$ alkyl group or the like; a group represented by the formula:


is

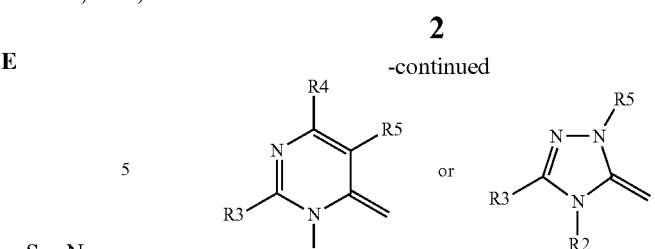

wherein R2 is a group represented by the formula:

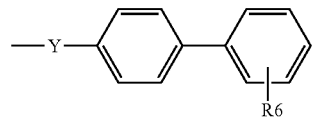

wherein R6 is a group represented by the formula:

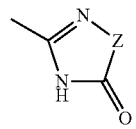

wherein Z is O or S(O)$_n$ (n is an integer of 0 to 2), and
Y is an optionally substituted $C_1$-$C_4$ alkylene group or the like;
R3 and R4 are each independently
(1) a hydrogen,
(2) an optionally substituted $C_1$-$C_6$ alkyl group or the like, and
R5 is
(1) a hydrogen,
(2) an optionally substituted $C_1$-$C_6$ alkyl group,
(3) an optionally substituted $C_2$-$C_6$ alkenyl group,
(4) an optionally substituted cyclic group,
(5) a group represented by the formula: —CO—R8
wherein R8 is an optionally substituted $C_1$-$C_6$ alkyl group or an optionally substituted cyclic group, or
(6) a group represented by the formula: —O—R8'
wherein R8' is an optionally substituted $C_1$-$C_6$ alkyl group or an optionally substituted cyclic group, or a salt thereof.

WO2008/143262 describes a compound represented by the formula (I):

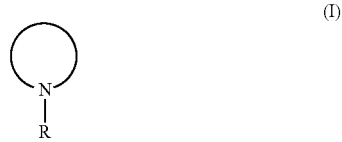

(I)

wherein a group represented by the formula:

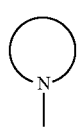

is a group represented by the formula (a):

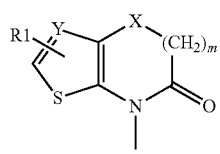

wherein,
R1 is a hydrogen atom, a $(C_1-C_6)$alkyl group optionally having substituent(s) or the like;
X is a group represented by the formula: CO—X1, S(O)n-X1 or (R2)C═C(R3) wherein X1 is a group represented by the formula: N(R4) or (R5)C(R6) wherein R4 and R5 are each a hydrogen atom, a $(C_1-C_6)$alkyl group optionally having substituent(s), or a cyclic group optionally having substituent(s), and R6 is a $(C_1-C_6)$alkyl group optionally having substituent(s), R2 is a hydrogen atom, a $(C_1-C_6)$alkyl group optionally having substituent(s) or the like, R3 is a hydrogen atom, a $(C_1-C_6)$alkyl group optionally having substituent(s), or a cyclic group optionally having substituent(s), and n is 1 or 2;
Y is a nitrogen atom or a group represented by the formula: C(R7) wherein R7 is a hydrogen atom, or a $(C_1-C_6)$alkyl group optionally having substituent(s); and
m is 0 or 1, provided
when m is 1, R3 or R4 is optionally bonded to a carbon atom, which is adjacent to the nitrogen atom or a carbon atom bonded thereto, to form a ring,
R is a group represented by the formula:

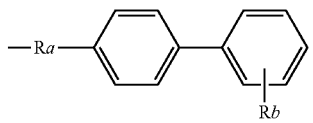

wherein,
Ra is a $(C_1-C_6)$alkylene group optionally having substituent(s) or the like; Rb is a group represented by the formula:

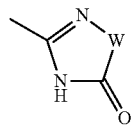

wherein W is an oxygen atom or a sulfur atom, which optionally has substituent(s), wherein the biphenyl group optionally further having substituent(s), or a salt thereof and the like.

In addition, US2004/127443 describes a method for treating or preventing an inflammatory or metabolic disorder in a mammal by administering, to the mammal in need thereof, a therapeutically effective amount of a compound sufficient to (a) at least partially activate peroxisome proliferator activated receptors (PPARs) and (b) at least partially inhibit, antagonize or block an activity of angiotensin II type 1 receptors.

WO1995/26724 describes a method of improving insulin resistance using an angiotensin II receptor antagonist and a method of improving insulin sensitivity accompanying a treatment of hypertension.

WO2007/053406, WO2007/051007, WO2007/013078, WO2006/000564, WO2005/288272, WO2005/020984, WO2004/053903, WO1996/40258, WO1996/40257, WO1996/40256, WO1996/40255, WO2009/137465, WO2009/118292, WO2009/039069, US2009/0012052 and WO2008/060899 describe the compound of the following formula and that the compound has angiotensin II antagonistic activity and hypotensive activity and is useful as therapeutic agents for circulatory disease such as hypertension, cardiac diseases, cerebral apoplexy and the like.

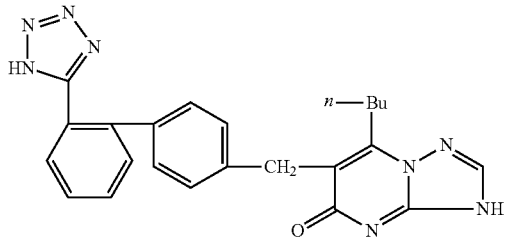

WO1994/17067 describes compounds represented by the following formulas, and that the compounds have angiotensin II antagonistic activity and hypotensive activity and are useful as therapeutic agents for circulatory disease such as hypertension, cardiac diseases, cerebral apoplexy and the like.

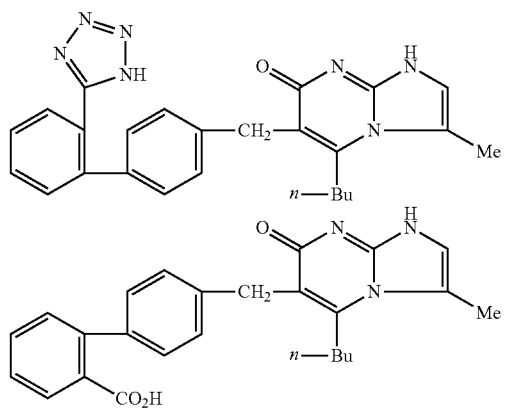

U.S. Pat. No. 5,389,632 describes a compound represented by the following formula

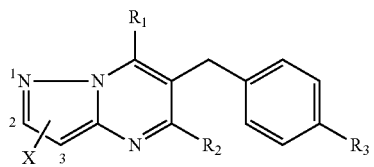

wherein one of $R^1$ and $R^2$ is $C_{1-6}$ alkyl, —$(CH_2)_p$OR (p is an integer of 1 to 6, and R is $C_{1-6}$ alkyl or benzyl) and the other of $R^1$ and $R^2$ is a hydrogen atom, a halogen atom, $C_{1-6}$ alkyl, $OR^4$, $SR^4$, $NR^5R^6$ or $NH(CH_2)_n$—$NR^5R^6$ (wherein $R^4$ is a hydrogen atom, $C_{1-6}$ alkyl, $C_{3-7}$ cycloalkyl, $(CH_2)_m$—COOR' or $(CH_2)_m$—O—R' (wherein m is an integer of 1 to 4, and R' is a hydrogen atom or $C_{1-6}$ alkyl), $R^5$ and $R^6$ are the same or different and each is a hydrogen atom, $C_{1-6}$ alkyl or $C_{3-7}$ cycloalkyl, or $R^5$ and $R^6$ form, together with the nitrogen atom bonded to the both, a hetero ring selected from morpholine, pyrrolidine and piperidine, and n is an integer of 1 to 4), X at the 2-position or the 3-position of pyrazolo[1,5-a]pyrimidine is a hydrogen atom, $C_{1-6}$ alkyl, hydroxyl or COOR' (R' is as defined above), and $R^3$ is the formula

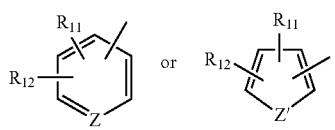

wherein Z is CH or a nitrogen atom, Z' is a sulfur atom or an oxygen atom, $R^{11}$ is a hydrogen atom or a halogen atom, and $R^{12}$ is tetrazolyl, CN, COOH or $CONH_2$, or a salt thereof, and describes that the compound has angiotensin II antagonistic activity and hypotensive activity, and is useful as therapeutic agent for circulatory diseases such as hypertension, cardiac diseases, cerebral apoplexy and the like.

U.S. Pat. No. 5,387,747 describes a compound represented by the following formula

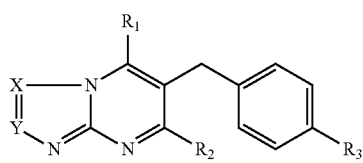

wherein one of $R^1$ and $R^2$ is $C_{1-6}$ alkyl, $-(CH_2)_pOR$ or $-(CH_2)_pOH$ (p is an integer of 1 to 6, and R is $C_{1-6}$ alkyl or benzyl) and the other of $R^1$ and $R^2$ is a hydrogen atom, a halogen atom, $C_{1-6}$ alkyl, $N_3$, $OR^4$, $SR^4$, $NR^5R^6$ or $NH(CH_2)_n-NR^5R^6$ (wherein $R^4$ is a hydrogen atom, $C_{1-6}$ alkyl, $C_{3-7}$ cycloalkyl, $(CH_2)_n-COOR'$ or $(CH_2)_m-O-R'$ (wherein m is an integer of 1 to 4, and R' is a hydrogen atom or $C_{1-6}$ alkyl), $R^5$ and $R^6$ are the same or different and each is a hydrogen atom, $C_{1-6}$ alkyl or $C_{3-7}$ cycloalkyl, or $R^5$ and $R^6$ form, together with the nitrogen atom bonded thereto, a hetero ring selected from morpholine, pyrrolidine and piperidine, and n is an integer of 1 to 4), X and Y are the same or different and when one of them is a nitrogen atom, the other is $C-R^7$ (wherein $R^7$ is a hydrogen atom, $C_{1-6}$ alkyl, $C_{3-7}$ cycloalkyl, $(CH_2)_{n'}OH$ (wherein n' is an integer of 0 to 4), $SR'$ (R' is as defined above), $NR^5R^6$ ($R^5$ and $R^6$ are the same or different and each is a hydrogen atom, $C_{1-6}$ alkyl or $C_{3-7}$ cycloalkyl)), and $R^3$ is the formula

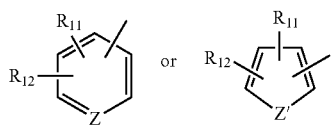

wherein Z is CH or a nitrogen atom, Z' is a sulfur atom or an oxygen atom, $R^{11}$ is a hydrogen atom or a halogen atom, and $R^{12}$ is tetrazolyl, CN, COOH or $CONH_2$, or a salt thereof, and describes that the compound has angiotensin II antagonistic activity and hypotensive activity, and is useful as therapeutic agent for circulatory diseases such as hypertension, cardiac diseases, cerebral apoplexy and the like.

U.S. Pat. No. 5,231,094 describes a compound represented by the formula

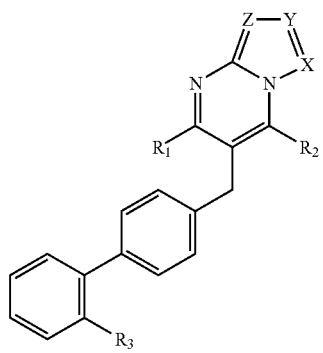

wherein one of $R^1$ and $R^2$ is $C_{1-6}$ alkyl and the other is a hydrogen atom, a halogen atom, $OR^4$, $SR^4$, $NR^5R^6$ or $NR^4(CH_2)_n-NR^5R^6$ (wherein $R^4$ is a hydrogen atom, $C_{1-6}$ alkyl or $C_{3-7}$ cycloalkyl, $R^5$ and $R^6$ are the same or different and each is a hydrogen atom, $C_{1-6}$ alkyl or $C_{3-7}$ cycloalkyl, or $R^5$ and $R^6$ form, together with the nitrogen atom bonded to the both, a hetero ring selected from morpholine, pyrrolidine, piperazine, piperidine and immidazolidine, and n is an integer of 1 to 4, two of X, Y and Z are nitrogen atoms, and the other is $C-R^7$ (wherein $R^2$ is a hydrogen atom or $C_{1-6}$ alkyl), and $R^3$ is tetrazolyl, or a salt thereof, and describes that the compound has angiotensin II antagonistic activity and hypotensive activity, and is useful as a therapeutic agent for circulatory diseases such as hypertension, cardiac diseases, cerebral apoplexy and the like.

Problems to be Solved by the Invention

An object of the present invention is to provide a novel compound superior as a medicament for the prophylaxis or treatment and the like of circulatory diseases such as hypertension and the like and/or metabolic diseases such as diabetes and the like, and the like.

Means of Solving the Problems

The present inventors have conducted intensive studies in an attempt to provide a new compound showing both superior pharmacological activity and superior physicochemical properties so as to afford a medicament useful as an agent for the prophylaxis or treatment of circulatory diseases such as hypertension and the like and/or metabolic diseases such as diabetes and the like and the like, and found that novel fused ring compound represented by the following formula (I) has angiotensin II receptor antagonistic activity and peroxisome proliferator-activated receptor (PPAR) γ agonistic activity (including partial agonistic activity), and is useful as an agent for the prophylaxis or treatment of circulatory diseases such as hypertension, cardiac diseases (cardiac hypertrophy, cardiac failure, myocardial infarction etc.), arteriosclerosis, renal diseases (diabetic nephropathy, chronic glomerulonephritis etc.), ophthalmic diseases, liver diseases, cerebral apoplexy and the like and/or metabolic diseases such as hyperlipidemia, obesity, diabetes and the like, which resulted in the completion of the present invention.

Accordingly, the present invention relates to

[1] a compound represented by the formula (I):

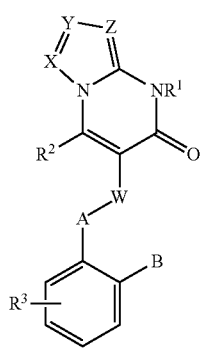

(I)

wherein R[1] is a hydrogen atom, an optionally substituted $C_{1-6}$ alkyl, an optionally substituted 3- to 10-membered nonaromatic cyclic group or an optionally substituted 5- or 6-membered aromatic cyclic group, R[2] is a hydrogen atom, an optionally substituted $C_{1-6}$ alkyl, an optionally substituted $C_{1-6}$ alkoxy, an optionally substituted $C_{1-6}$ alkylthio, an optionally substituted $C_{1-6}$ alkylsulfinyl or an optionally substituted $C_{1-6}$ alkylsulfonyl, R[3] is a hydrogen atom, a halogen atom, an optionally substituted $C_{1-6}$ alkyl or an optionally substituted $C_{1-6}$ alkoxy, X, Y and Z are each independently a nitrogen atom or CR[4] wherein R[4] is a hydrogen atom, a halogen atom, an optionally substituted $C_{1-6}$ alkyl, an optionally substituted $C_{1-6}$ alkoxy or an optionally substituted $C_{3-6}$ cycloalkyl, W is an optionally substituted $C_{1-4}$ alkylene, —O—W'—, —W'—O—, —N(Ra)-W'— or —W'—N(Ra)— wherein W' is a bond or an optionally substituted $C_{1-4}$ alkylene, Ra is a hydrogen atom, an optionally substituted $C_{1-6}$ alkyl or an optionally substituted $C_{3-6}$ cycloalkyl, A is an optionally substituted 5- or 6-membered divalent aromatic ring, and B is an acyl or an optionally substituted 3- to 10-membered heterocyclic group, provided when B is a carboxy, a carbamoyl or a tetrazolyl, R[1] is not a hydrogen atom, or a salt thereof;

[2] the compound of the aforementioned [1], wherein R[1] is an optionally substituted $C_{1-6}$ alkyl, an optionally substituted 3- to 10-membered nonaromatic cyclic group or an optionally substituted 5- or 6-membered aromatic cyclic group;

[3] the compound of the aforementioned [1] or [2], wherein X is a nitrogen atom, and Y and Z are each CR[4] wherein R[4] is as defined above;

[4] the compound of the aforementioned [1] or [2], wherein X and Z are nitrogen atoms, and Y is CR[4] wherein R[4] is as defined above;

[5] the compound of the aforementioned [1], [2], [3] or [4], wherein R[2] is an optionally substituted $C_{1-6}$ alkyl;

[6] the compound of the aforementioned [1], [2], [3], [4] or [5], wherein R[3] is a hydrogen atom;

[7] the compound of the aforementioned [1], [2], [3], [4], [5] or [6], wherein W is an optionally substituted $C_{1-4}$ alkylene;

[8] the compound of the aforementioned [1], [2], [3], [4], [5], [6] or [7], wherein A is an optionally substituted phenylene, an optionally substituted thiophen-di-yl or an optionally substituted pyridin-di-yl;

[9] the compound of the aforementioned [1], [2], [3], [4], [5], [6], [7] or [8], wherein B is a group represented by

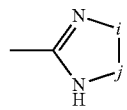

wherein i is —O— or —S—, j is —C(=O)—, —C(=S)— or —S(O)$_m$—, and m is an integer of 0, 1 or 2;

[10] the compound of the aforementioned [1], which is a compound represented by the formula

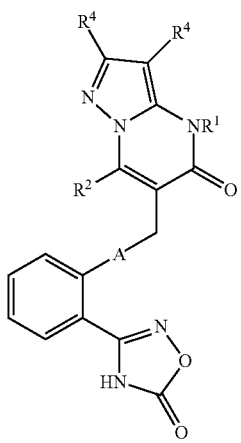

wherein
R[1] is a $C_{3-8}$ cycloalkyl optionally substituted by a $C_{1-6}$ alkoxy optionally substituted by 1) a halogen atom, 2) a cyano, 3) a hydroxy or 4) a $C_{1-6}$ alkoxy optionally substituted by a halogen atom,
R[2] is a $C_{1-6}$ alkyl,
A is a phenylene optionally substituted by a halogen atom, and
R[4] are each independently a hydrogen atom or a methyl;

[11] the compound of the aforementioned [1], which is a compound represented by the formula

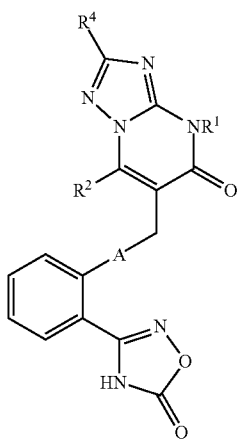

wherein
R[1] is a $C_{3-8}$ cycloalkyl optionally substituted by a $C_{1-6}$ alkoxy optionally substituted by 1) a halogen atom, 2) a cyano, 3) a hydroxy or 4) a $C_{1-6}$ alkoxy optionally substituted by a halogen atom,
R[2] is a $C_{1-6}$ alkyl, A is a phenylene optionally substituted by a halogen atom, and
R[4] is a hydrogen atom or a methyl;

[12] the compound of the aforementioned [1], which is a compound represented by the formula

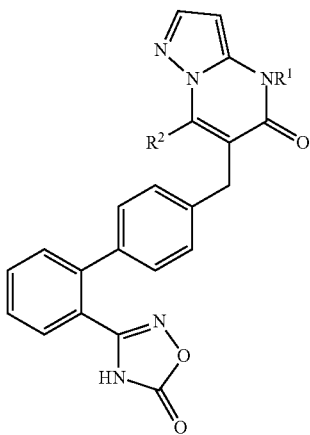

wherein
R[1] is a cyclohexyl optionally substituted by a $C_{1-6}$ alkoxy optionally substituted by a hydroxy, and
R[2] is a $C_{1-6}$ alkyl;

[13] the compound of the aforementioned [1], which is a compound represented by the formula

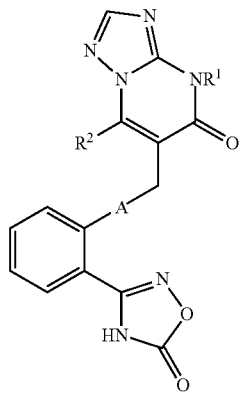

wherein
R[1] is a cyclohexyl optionally substituted by a $C_{1-6}$ alkoxy optionally substituted by a hydroxy,
R[2] is a $C_{1-6}$ alkyl, and
A is a phenylene optionally substituted by a halogen atom;

[14] 4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one or a salt thereof;

[15] 6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one or a salt thereof;

[16] a prodrug of the compound of the aforementioned [1];
[17] a medicament comprising the compound of the aforementioned [1] or a prodrug thereof;
[18] the medicament of the aforementioned [17] having an angiotensin II receptor antagonistic activity and a peroxisome proliferator-activated receptor γ agonistic activity;
[19] the medicament of the aforementioned [17] which is an agent for the prophylaxis or treatment of a circulatory disease;
[20] the medicament of the aforementioned [17] which is an agent for the prophylaxis or treatment of hypertension, a cardiac disease, arteriosclerosis, a renal disease, an ophthalmic disease, a liver disease, cerebral apoplexy, hyperlipidemia, obesity, and/or diabetes;
[21] a method of inhibiting an angiotensin II receptor and activating a peroxisome proliferator-activated receptor γ in a mammal, comprising administering the compound of the aforementioned [1] or a prodrug thereof to the mammal;
[22] a method for the prophylaxis or treatment of a circulatory disease in a mammal, comprising administering the compound of the aforementioned [1] or a prodrug thereof to the mammal;
[23] a method for the prophylaxis or treatment of hypertension, a cardiac disease, arteriosclerosis, a renal disease, an ophthalmic disease, a liver disease, cerebral apoplexy, hyperlipidemia, obesity and/or diabetes in a mammal, comprising administering the compound of the aforementioned [1] or a prodrug thereof to the mammal;
[24] use of the compound of the aforementioned [1] or a prodrug thereof for the production of a medicament having a angiotensin II receptor antagonistic activity and a peroxisome proliferator-activated receptor γ agonistic activity;
[25] use of the compound of the aforementioned [1] or a prodrug thereof for the production of an agent for the prophylaxis or treatment of a circulatory disease;
[26] use of the compound of the aforementioned [1] or a prodrug thereof for the production of an agent for the prophylaxis or treatment of hypertension, a cardiac disease, arteriosclerosis, a renal disease, an ophthalmic disease, a liver disease, cerebral apoplexy, hyperlipidemia, obesity and/or diabetes; and the like.

DETAILED DESCRIPTION OF THE INVENTION

The definition of each symbol of the present specification is described below.

In the present specification, examples of the "halogen atom" include a fluorine atom, a chlorine atom, a bromine atom and an iodine atom.

In the present specification, examples of the "$C_{1-6}$ alkyl" include methyl, ethyl, propyl, isopropyl, butyl, isobutyl, sec-butyl, tert-butyl, pentyl, isopentyl, neopentyl, tert-pentyl, hexyl, —CH$_2$CH$_2$C(CH$_3$)$_3$, —CH$_2$CH(CH$_2$CH$_3$)$_2$ and the like.

In the present specification, examples of the "$C_{2-6}$ alkenyl" include vinyl, allyl, propenyl, isopropenyl, but-3-en-1-yl, pent-4-en-1-yl, hex-5-en-1-yl and the like.

In the present specification, examples of the "$C_{2-6}$ alkynyl" include ethynyl, prop-2-yn-1-yl, but-3-yn-1-yl, pent-4-yn-1-yl, hex-5-yn-1-yl and the like.

In the present specification, examples of the "$C_{3-6}$ cycloalkyl" include cyclopropyl, cyclobutyl, cyclopentyl and cyclohexyl.

In the present specification, examples of the "$C_{6-14}$ aryl" include phenyl, naphthyl (e.g., 1-naphthyl, 2-naphthyl), anthryl, phenanthryl and the like. Preferred is phenyl or naphthyl, and more preferred is phenyl.

In the present specification, examples of the "$C_{7-16}$ aralkyl" include benzyl, 1-phenylethyl, 2-phenylethyl, naphthylmethyl(1-naphthylmethyl, 2-naphthylmethyl), 3-phenylpropyl, 4-phenylbutyl, 5-phenylpentyl and the like.

In the present specification, examples of the "$C_{1-6}$ alkoxy" include methoxy, ethoxy, propoxy, isopropoxy, butoxy, isobutoxy, sec-butoxy, tert-butoxy, pentyloxy, isopentyloxy, neopentyloxy, tert-pentyloxy, —OCH(CH$_2$CH$_3$)$_2$, —OCH(CH$_3$)(CH(CH$_3$)$_2$), —OCH$_2$CH(CH$_3$)(CH$_2$CH$_3$), hexyloxy, —OCH$_2$CH(CH$_2$CH$_3$)$_2$, —OCH(CH$_2$CH$_3$)(CH(CH$_3$)$_2$), —OC(CH$_3$)$_2$(CH(CH$_3$)$_2$) and the like.

In the present specification, examples of the "optionally halogenated C$_{1-6}$ alkyl" include the above-mentioned "C$_{1-6}$ alkyl" optionally substituted by 1 to 5 of the above-mentioned "halogen atom". For example, methyl, ethyl, propyl, isopropyl, butyl, tert-butyl, isobutyl, trifluoromethyl and the like can be mentioned.

In the present specification, examples of the "optionally halogenated C$_{1-6}$ alkoxy" include the above-mentioned "C$_{1-6}$ alkoxy" optionally substituted by 1 to 5 of the above-mentioned "halogen atom". For example, methoxy, ethoxy, propoxy, isopropoxy, butoxy, tert-butoxy, trifluoromethoxy, 2-fluoroethoxy and the like can be mentioned.

In the present specification, examples of the "heterocyclic group" include, unless otherwise specified, a 4- to 14-membered (preferably 5- to 10-membered) (monocyclic, bicyclic or tricyclic) heterocyclic group having, as ring-constituting atom besides carbon atom, 1 to 3 kinds of 1 to 4 hetero atoms selected from the group consisting of a nitrogen atom, a sulfur atom and an oxygen atom, preferably (i) 5- to 14-membered (preferably 5- to 10-membered) aromatic heterocyclic group, (ii) 4- to 10-membered (preferably 5- to 10-membered) non-aromatic heterocyclic group and the like.

Examples of the "aromatic heterocyclic group" include monocyclic aromatic heterocyclic groups such as furyl, thienyl, pyrrolyl, oxazolyl (e.g., 1,3-oxazolyl), isoxazolyl, thiazolyl, isothiazolyl, imidazolyl (e.g., 1H-imidazol-1-yl), pyrazolyl, 1,2,3-oxadiazolyl, 1,2,4-oxadiazolyl, 1,3,4-oxadiazolyl (e.g., 1,3,4-oxadiazol-2-yl), furazanyl, 1,2,3-thiadiazolyl, 1,2,4-thiadiazolyl, 1,3,4-thiadiazolyl, 1,2,3-triazolyl, 1,2,4-triazolyl (e.g., 1,2,4-triazol-3-yl), tetrazolyl, pyridyl, pyridazinyl, pyrimidinyl, pyrazinyl, triazinyl and the like; aromatic fused heterocyclic groups such as benzofuryl, isobenzofuryl, benzo[b]thienyl, indolyl, isoindolyl, 1H-indazolyl, benzimidazolyl, benzoxazolyl, benzo[d]isoxazolyl, benzothiazolyl, benzo[d]isothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenathridinyl, phenathridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl and the like.

Examples of the "nonaromatic heterocyclic group" include monocyclic nonaromatic heterocyclic groups such as azetidinyl, oxetanyl, thietanyl, pyrrolidinyl, tetrahydrofuryl (e.g., tetrahydrofuran-2-yl), thioranyl, imidazolidinyl, pyrazolidinyl, oxazolidinyl, thiazolidinyl, piperidyl, piperidino, tetrahydropyranyl (e.g., tetrahydropyran-4-yl), morpholinyl, morpholino, thiomorpholinyl, thiomorpholino, piperazinyl, dihydrooxazolyl (e.g., 4,5-dihydro-1,3,4-oxadiazol-2-yl), dihydroisoxazolyl (e.g., 4,5-dihydroisoxazolyl) and the like; nonaromatic fused heterocyclic groups such as isochromanyl, dihydrobenzopyranyl, isochromenyl, chromenyl (2H-chromenyl, 4H-chromenyl), 1,2,3,4-tetrahydroisoquinolyl, 1,2,3,4-tetrahydroquinolyl, 2,3-dihydrobenzofuranyl, benzo[1,3]dioxolyl and the like.

In the present specification, examples of the "5- or 6-membered heterocyclic group" include, unless otherwise specified, a 5- or 6-membered heterocyclic group, for example, 5- or 6-membered monocyclic aromatic heterocyclic groups such as furyl, thienyl, pyrrolyl, oxazolyl, isoxazolyl, thiazolyl, isothiazolyl, imidazolyl (e.g., 1H-imidazol-1-yl), pyrazolyl, 1,2,3-oxadiazolyl, 1,2,4-oxadiazolyl, 1,3,4-oxadiazolyl (e.g., 1,3,4-oxadiazol-2-yl), furazanyl, 1,2,3-thiadiazolyl, 1,2,4-thiadiazolyl, 1,3,4-thiadiazolyl, 1,2,3-triazolyl, 1,2,4-triazolyl (e.g., 1,2,4-triazol-3-yl), tetrazolyl, pyridyl, pyridazinyl, pyrimidinyl, pyrazinyl, triazinyl and the like; 5- or 6-membered monocyclic nonaromatic heterocyclic groups such as pyrrolidinyl, tetrahydrofuryl (e.g., tetrahydrofuran-2-yl), thioranyl, imidazolidinyl, pyrazolidinyl, oxazolidinyl, thiazolidinyl, piperidyl, piperidino, tetrahydropyranyl (e.g., tetrahydropyran-4-yl), morpholinyl, morpholino, thiomorpholinyl, thiomorpholino, piperazinyl, dihydroisoxazolyl (e.g., 4,5-dihydroisoxazolyl), dihydrooxadiazolyl (e.g., 4,5-dihydro-1,3,4-oxadiazol-2-yl) and the like and the like, from among the above-mentioned heterocyclic groups exemplified as the "heterocyclic group".

In the present specification, examples of the "C$_{2-6}$ alkenyloxy" include vinyloxy, allyloxy, propenyloxy, isopropenyloxy, but-3-en-1-yloxy, pent-4-en-1-yloxy, hex-5-en-1-yloxy and the like.

In the present specification, examples of the "C$_{2-6}$ alkynyloxy" include ethynyloxy, prop-2-yn-1-yloxy, but-3-yn-1-yloxy, pent-4-yn-1-yloxy, hex-5-yn-1-yloxy, 1-methylbut-3-yn-1-yloxy and the like.

In the present specification, examples of the "C$_{3-6}$ cycloalkyloxy" include cyclopropyloxy, cyclobutyloxy, cyclopentyloxy and cyclohexyloxy.

In the present specification, examples of the "C$_{3-10}$ cycloalkyloxy" include cyclopropyloxy, cyclobutyloxy, cyclopentyloxy, cyclohexyloxy, cycloheptyloxy, cyclooctyloxy and the like.

In the present specification, examples of the "C$_{6-14}$ aryloxy" include phenoxy, 1-naphthyloxy, 2-naphthyloxy and the like.

In the present specification, examples of the "C$_{7-16}$ aralkyloxy" include benzyloxy, phenethyloxy and the like.

In the present specification, examples of the "C$_{1-6}$ alkyl-carbonyloxy" include acetyloxy, isopropylcarbonyloxy and the like.

In the present specification, examples of the "5- or 6-membered heterocyclyl-oxy" include tetrahydrofuryloxy (e.g., tetrahydrofuran-3-yloxy), tetrahydropyranyloxy (e.g., tetrahydropyran-4-yloxy), piperidyloxy (e.g., piperidin-4-yloxy), isoxazolyloxy (e.g., isoxazol-3-yloxy) and the like.

In the present specification, examples of the "5- or 6-membered heterocyclyl-C$_{1-6}$ alkyloxy" include tetrahydrofurylmethoxy (e.g., tetrahydrofuran-3-ylmethoxy), tetrahydropyranylmethoxy (e.g., tetrahydropyran-4-ylmethoxy), piperidylmethoxy (e.g., piperidin-4-ylmethoxy) and the like.

In the present specification, examples of the "C$_{1-6}$ alkylamino" include amino monosubstituted by the above-mentioned "C$_{1-6}$ alkyl". For example, methylamino, ethylamino, propylamino, isopropylamino, butylamino, isobutylamino, sec-butylamino, tert-butylamino, pentylamino, isopentylamino, neopentylamino, tert-pentylamino, hexylamino and the like can be mentioned.

In the present specification, examples of the "di(C$_{1-6}$)alkylamino" include an amino group disubstituted by the above-mentioned "C$_{1-6}$ alkyl". For example, dimethylamino, diethylamino, N-ethyl-N-methylamino and the like can be mentioned.

In the present specification, examples of the "C$_{1-6}$ alkyl-carbonylamino" include acetylamino, propanoylamino, butanoylamino, 2-methylpropanoylamino, pentanoylamino, 3-methylbutanoylamino, 2,2-dimethylpropanoylamino and the like.

In the present specification, examples of the "$C_{1-6}$ alkylthio" include methylthio, ethylthio, propylthio, isopropylthio, butylthio, sec-butylthio, tert-butylthio and the like.

In the present specification, examples of the "$C_{1-6}$ alkylsulfinyl" include methylsulfinyl, ethylsulfinyl, propylsulfinyl, isopropylsulfinyl, butylsulfinyl, sec-butylsulfinyl, tert-butylsulfinyl and the like.

In the present specification, examples of the "$C_{1-6}$ alkylsulfonyl" include methylsulfonyl, ethylsulfonyl, propylsulfonyl, isopropylsulfonyl, butylsulfonyl, sec-butylsulfonyl, tert-butylsulfonyl and the like.

In the present specification, examples of the "optionally esterified carboxy" include carboxy, $C_{1-6}$ alkoxy-carbonyl (e.g., methoxycarbonyl, ethoxycarbonyl, propoxycarbonyl, tert-butoxycarbonyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.) and the like.

In the present specification, examples of the "$C_{1-6}$ alkyl-carbonyl" include acetyl, propanoyl, butanoyl, 2-methylpropanoyl, pentanoyl, 3-methylbutanoyl, 2,2-dimethylpropanoyl and the like.

In the present specification, examples of the "$C_{3-10}$ cycloalkyl-carbonyl" include cyclopropylcarbonyl, cyclopentylcarbonyl, cyclohexylcarbonyl, adamantylcarbonyl and the like.

In the present specification, examples of the "$C_{3-6}$ cycloalkyl-carbonyl" include cyclopropylcarbonyl, cyclopentylcarbonyl, cyclohexylcarbonyl and the like.

In the present specification, examples of the "$C_{6-14}$ arylcarbonyl" include benzoyl, 1-naphthoyl, 2-naphthoyl and the like.

In the present specification, examples of the "$C_{7-16}$ aralkyl-carbonyl" include phenylacetyl, 3-phenylpropanoyl and the like.

In the present specification, examples of the "$C_{1-6}$ alkoxy-carbonyl" include methoxycarbonyl, ethoxycarbonyl, propoxycarbonyl, tert-butoxycarbonyl and the like.

In the present specification, examples of the "$C_{6-14}$ aryloxy-carbonyl" include phenoxycarbonyl, 1-naphthyloxycarbonyl, 2-naphthyloxycarbonyl and the like.

In the present specification, examples of the "$C_{7-16}$ aralkyloxy-carbonyl" include benzyloxycarbonyl, phenethyloxycarbonyl and the like.

In the present specification, examples of the "5- or 6-membered heterocyclyl-carbonyl" include 1-pyrrolidylcarbonyl, piperidinocarbonyl, 1-piperazinylcarbonyl, morpholinocarbonyl, thiomorpholinocarbonyl, tetrahydropyranylcarbonyl (e.g., tetrahydropyran-4-ylcarbonyl) and the like.

In the present specification, examples of the "$C_{1-6}$ alkylcarbamoyl" include carbamoyl monosubstituted by the above-mentioned "$C_{1-6}$ alkyl". For example, methylcarbamoyl, ethylcarbamoyl and the like can be mentioned.

In the present specification, examples of the "di($C_{1-6}$) alkyl-carbamoyl" include carbamoyl disubstituted by the above-mentioned "$C_{1-6}$ alkyl". For example, dimethylcarbamoyl, diethylcarbamoyl, N-ethyl-N-methylcarbamoyl and the like can be mentioned.

In the present specification, examples of the "$C_{6-14}$ arylcarbamoyl" include carbamoyl monosubstituted by the above-mentioned "$C_{6-14}$ aryl". For example, phenylcarbamoyl, 1-naphthylcarbamoyl, 2-naphthylcarbamoyl and the like can be mentioned.

In the present specification, examples of the "di($C_{6-14}$)arylcarbamoyl" include carbamoyl disubstituted by the above-mentioned "$C_{6-14}$ aryl". For example, diphenylcarbamoyl, dinaphthylcarbamoyl and the like can be mentioned.

In the present specification, examples of the "$C_{1-6}$ alkylsulfamoyl" include sulfamoyl monosubstituted by the above-mentioned "$C_{1-6}$ alkyl". For example, methylsulfamoyl, ethylsulfamoyl and the like can be mentioned.

In the present specification, examples of the "di($C_{1-6}$) alkylsulfamoyl" include sulfamoyl disubstituted by the above-mentioned "$C_{1-6}$ alkyl". For example, dimethylsulfamoyl, diethylsulfamoyl, N-ethyl-N-methylsulfamoyl and the like can be mentioned.

In the present specification, examples of the "$C_{6-14}$ arylsulfamoyl" include sulfamoyl monosubstituted by the above-mentioned "$C_{6-14}$ aryl". For example, phenylsulfamoyl, 1-naphthylsulfamoyl, 2-naphthylsulfamoyl and the like can be mentioned.

In the present specification, examples of the "di($C_{6-14}$) arylsulfamoyl" include a sulfamoyl group disubstituted by the above-mentioned "$C_{6-14}$ aryl". For example, diphenylsulfamoyl, dinaphthylsulfamoyl and the like can be mentioned.

In the present specification, examples of the "$C_{1-6}$ alkoxyimino" include methoxyimino, ethoxyimino, propoxyimino, isopropoxyimino, butoxyimino, isobutoxyimino, sec-butoxyimino, tert-butoxyimino, pentyloxyimino, hexyloxyimino and the like.

In the present specification, examples of the "hydroxy-$C_{1-6}$ alkyl" include hydroxymethyl, 2-hydroxyethyl, 1-hydroxyethyl, 3-hydroxypropyl, 1-hydroxy-1-methylethyl and the like.

In the present specification, examples of the "$C_{1-6}$ alkoxy-$C_{1-6}$ alkyl" include methoxymethyl, 2-methoxyethyl, 1-methoxyethyl, ethoxymethyl, 2-ethoxyethyl and the like.

In the present specification, examples of the substituent of the "optionally substituted $C_{1-6}$ alkyl", "optionally substituted $C_{2-6}$ alkenyl", "optionally substituted $C_{2-6}$ alkynyl", "optionally substituted $C_{1-6}$ alkoxy" and "optionally substituted $C_{1-6}$ alkylthio" include 1 to 5, preferably 1 to 3, substituents, selected from the group consisting of (1) a halogen atom,
(2) hydroxy,
(3) amino,
(4) nitro,
(5) cyano,
(6) optionally halogenated $C_{1-6}$ alkoxy,
(7) $C_{3-6}$ cycloalkyloxy,
(8) $C_{6-14}$ aryloxy,
(9) $C_{7-16}$ aralkyloxy,
(10) amino optionally substituted by 1 or 2 substituents selected from
  (a) $C_{1-6}$ alkyl,
  (b) $C_{6-14}$ aryl,
  (c) $C_{7-16}$ aralkyl, and
  (d) $C_{1-6}$ alkyl-carbonyl,
(11) $C_{1-6}$ alkylthio,
(12) $C_{1-6}$ alkylsulfinyl,
(13) $C_{1-6}$ alkylsulfonyl,
(14) optionally esterified carboxy,
(15) $C_{1-6}$ alkyl-carbonyl optionally substituted by 1 to 3 halogen atoms,
(16) $C_{3-10}$ cycloalkyl-carbonyl,
(17) $C_{6-14}$ aryl-carbonyl optionally substituted by 1 to 3 halogen atoms,
(18) $C_{7-16}$ aralkyl-carbonyl,
(19) 5- or 6-membered heterocyclyl-carbonyl (e.g., 1-pyrrolidylcarbonyl, piperidinocarbonyl, 1-piperazinylcarbonyl, morpholinocarbonyl, thiomorpholinocarbonyl, tetrahydropyranylcarbonyl (e.g., tetrahydropyran-4-ylcarbonyl) etc.),
(20) carbamoyl,
(21) thiocarbamoyl,

(22) $C_{1-6}$ alkyl-carbamoyl,
(23) di($C_{1-6}$)alkyl-carbamoyl,
(24) $C_{6-14}$ aryl-carbamoyl,
(25) di($C_{6-14}$)aryl-carbamoyl,
(26) sulfamoyl,
(27) $C_{1-6}$ alkylsulfamoyl,
(28) di($C_{1-6}$)alkylsulfamoyl,
(29) $C_{6-14}$ arylsulfamoyl,
(30) di($C_{6-14}$)arylsulfamoyl,
(31) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) $C_{1-6}$ alkyl optionally substituted by hydroxy, (c) $C_{6-14}$ aryl, (d) $C_{1-6}$ alkoxy and (e) $C_{1-6}$ alkyl-carbonyl,
(32) $C_{1-6}$ alkoxyimino, and the like (hereinafter to be sometimes abbreviated as substituent group A). When the number of the substituents is two or more, the respective substituents may be the same or different.

In the present specification, examples of the "3- to 14-membered cyclic group" of the "optionally substituted 3- to 14-membered cyclic group" include a 3- to 14-membered cyclic hydrocarbon group and a 4- to 14-membered heterocyclic group.

Examples of the "3- to 14-membered cyclic hydrocarbon group" include an alicyclic hydrocarbon group constituted with 3 to 14 carbon atoms, or an aromatic hydrocarbon group constituted with 6 to 14 carbon atoms and the like.

Examples of the "3- to 14-membered alicyclic hydrocarbon group" include $C_{3-6}$ cycloalkyl (e.g., cyclopropyl, cyclobutyl, cyclopentyl, cyclohexyl etc.), $C_{3-6}$ cycloalkenyl (e.g., cyclopentenyl, cyclohexenyl etc.), $C_{5-14}$ cycloalkadienyl (e.g., 2,4-cyclopentadienyl, 1,3-cyclohexadienyl etc.), indanyl, adamantyl and the like.

Examples of the "6- to 14-membered aromatic hydrocarbon group" include $C_{6-14}$ aryl (e.g., phenyl, naphthyl, anthryl, phenanthryl etc.) and the like.

Examples of the "4- to 14-membered heterocyclic group" include those similar to the aforementioned "heterocyclic group".

In the present specification, the "3- to 14-membered cyclic group" of the "optionally substituted 3- to 14-membered cyclic group" optionally has 1 to 5, preferably 1 to 3, substituents at substitutable positions. Examples of such substituent include those similar to the substituents that the "3- to 10-membered nonaromatic cyclic group" of the "optionally substituted 3- to 10-membered nonaromatic cyclic group" mentioned below as $R^1$ and the "5- or 6-membered aromatic cyclic group" of the "optionally substituted 5- or 6-membered aromatic cyclic group" mentioned below as $R^1$ optionally have. When the number of the substituents is two or more, the respective substituents may be the same or different.

In the present specification, the "$C_{6-14}$ aryl-carbonyl" of the "optionally substituted $C_{6-14}$ aryl-carbonyl" optionally has 1 to 5, preferably 1 to 3, substituents at substitutable positions. Examples of such substituent include a halogen atom, hydroxy, optionally halogenated $C_{1-6}$ alkyl, optionally halogenated $C_{1-6}$ alkoxy, amino, $C_{1-6}$ alkylamino, di($C_{1-6}$) alkylamino, $C_{1-6}$ alkylthio, $C_{1-6}$ alkylsulfonyl, carboxy, $C_{1-6}$ alkoxy-carbonyl, $C_{1-6}$ alkyl-carbonyl and the like. When the number of the substituents is two or more, the respective substituents may be the same or different.

In the present specification, examples of the "$C_{1-3}$ alkylidene" include methylene, ethylidene, propylidene, isopropylidene and the like.

Each substituent is explained below.
$R^1$ is a hydrogen atom, optionally substituted $C_{1-6}$ alkyl, an optionally substituted 3- to 10-membered nonaromatic cyclic group or an optionally substituted 5- or 6-membered aromatic cyclic group.

Preferable examples of the "$C_{1-6}$ alkyl" of the "optionally substituted $C_{1-6}$ alkyl" for $R^1$ include methyl, ethyl, propyl, isopropyl, butyl, isobutyl, sec-butyl, neopentyl, —$CH_2CH_2C(CH_3)_3$ and the like.

Preferable examples of the substituent of the "$C_{1-6}$ alkyl" of the "optionally substituted $C_{1-6}$ alkyl" for the above-mentioned $R^1$ include 1 to 5 substituents (preferably 1 to 3) selected from the group consisting of
(1) a halogen atom,
(2) hydroxy,
(3) optionally halogenated $C_{1-6}$ alkoxy,
(4) carboxy optionally substituted by $C_{1-6}$ alkoxy,
(5) $C_{1-6}$ alkyl-carbonyl optionally substituted by 1 to 3 halogen atoms,
(6) $C_{3-10}$ cycloalkyl-carbonyl,
(7) $C_{6-14}$ aryl-carbonyl optionally substituted by 1 to 3 halogen atoms,
(8) carbamoyl,
(9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) $C_{1-6}$ alkyl optionally substituted by hydroxy, (c) $C_{6-14}$ aryl, (d) $C_{1-6}$ alkoxy and (e) $C_{1-6}$ alkyl-carbonyl, and
(10) $C_{1-6}$ alkoxyimino. When the number of the substituents is two or more, the respective substituents may be the same or different.

Examples of the "3- to 10-membered nonaromatic cyclic group" of the "optionally substituted 3- to 10-membered nonaromatic cyclic group" for $R^1$ include a "3- to 10-membered nonaromatic hydrocarbon group" and a "4- to 7-membered nonaromatic heterocyclic group".

Examples of the "3- to 10-membered nonaromatic hydrocarbon group" include cyclopropyl, cyclobutyl, cyclopentyl, cyclohexyl, cyclohexenyl, cycloheptyl, cyclooctyl, adamantyl and the like. Preferred are cyclobutyl, cyclohexyl, cyclohexenyl, adamantyl and the like.

Examples of the "4- to 7-membered nonaromatic heterocyclic group" include azetidinyl, oxetanyl, thietanyl, pyrrolidinyl, tetrahydrofuryl, thioranyl, imidazolidinyl, pyrazolidinyl, oxazolidinyl, thiazolidinyl, piperidyl (e.g., piperidin-4-yl), tetrahydropyranyl, tetrahydrothiopyranyl, tetrahydroindazolyl (e.g., 4,5,6,7-tetrahydroindazol-5-yl), morpholinyl, thiomorpholinyl, piperazinyl, oxepanyl (e.g., oxepan-4-yl) and the like. Preferred are tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), oxepanyl (e.g., oxepan-4-yl) and the like.

Examples of the "5- or 6-membered aromatic cyclic group" of the "optionally substituted 5- or 6-membered aromatic cyclic group" for $R^1$ include phenyl, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like. Preferred are phenyl and thienyl.

The "3- to 10-membered nonaromatic cyclic group" of the "optionally substituted 3- to 10-membered nonaromatic cyclic group" for $R^1$ or the "5- or 6-membered aromatic cyclic group" of the "optionally substituted 5- or 6-membered aromatic cyclic group" for $R^1$ optionally has 1 to 5, preferably 1 to 3, substituents at substitutable positions. Examples of such substituent include
(1) a halogen atom,
(2) oxo,
(3) hydroxy,
(4) amino optionally substituted by 1 or 2 substituents selected from
  (a) $C_{1-6}$ alkyl,
  (b) $C_{6-14}$ aryl,
  (c) $C_{7-16}$ aralkyl,
  (d) $C_{1-6}$ alkyl-carbonyl, and
  (e) a 5- or 6-membered heterocyclic group,
(5) nitro,
(6) cyano,
(7) $C_{1-6}$ alkyl optionally substituted by 1 to 3 substituents selected from
  (a) hydroxy,
  (b) a halogen atom,
  (c) $C_{1-6}$ alkoxy,
  (d) $C_{6-14}$ aryl, and
  (e) a 5- or 6-membered heterocyclic group optionally substituted by 1 to 3 substituents selected from the group consisting of $C_{1-6}$ alkyl, hydroxy and oxo,
(8) $C_{2-6}$ alkenyl optionally substituted by hydroxy,
(9) $C_{2-6}$ alkynyl,
(10) $C_{3-6}$ cycloalkyl,
(11) $C_{6-14}$ aryl optionally substituted by hydroxy,
(12) $C_{7-16}$ aralkyl,
(13) a heterocyclic group optionally substituted by $C_{1-6}$ alkyl,
(14) $C_{1-6}$ alkoxy optionally substituted by 1 to 4 substituents selected from
  (a) a halogen atom,
  (b) hydroxy,
  (c) $C_{3-6}$ cycloalkyl optionally substituted by 1 to 3 substituents selected from the group consisting of $C_{1-6}$ alkyl optionally substituted by hydroxy, hydroxy, oxo, carbamoyl and cyano,
  (d) $C_{2-6}$ alkenyl,
  (e) $C_{1-6}$ alkoxy,
  (f) cyano,
  (g) $C_{1-6}$ alkyl-carbonyl optionally substituted by 1 to 3 halogen atoms,
  (h) $C_{3-10}$ cycloalkyl-carbonyl,
  (i) carbamoyl,
  (j) $C_{1-6}$ alkoxyimino,
  (k) $C_{1-6}$ alkylthio,
  (l) $C_{1-6}$ alkylsulfonyl,
  (m) $C_{1-6}$ alkyl-carbonyloxy,
  (n) $C_{3-6}$ cycloalkyloxy optionally substituted by 1 to 3 substituents selected from the group consisting of $C_{1-6}$ alkyl, hydroxy and oxo, and
  (o) a 5- or 6-membered heterocyclic group optionally substituted by 1 to 3 substituents selected from the group consisting of $C_{1-6}$ alkyl, hydroxy and oxo,
(15) $C_{2-6}$ alkenyloxy optionally substituted by hydroxy,
(16) $C_{2-6}$ alkynyloxy,
(17) $C_{3-10}$ cycloalkyloxy optionally substituted by 1 to 3 substituents selected from the group consisting of
  (a) oxo,
  (b) hydroxy,
  (c) $C_{1-6}$ alkyl optionally substituted by hydroxy, and
  (d) $C_{1-6}$ alkoxy-$C_{1-6}$ alkyl,
(18) $C_{6-14}$ aryloxy optionally substituted by 1 to 3 substituents selected from
  (a) hydroxy,
  (b) $C_{1-6}$ alkyl optionally substituted by hydroxy,
  (c) $C_{1-6}$ alkyl-carbonyl, and
  (d) $C_{1-6}$ alkoxy,
(19) $C_{7-16}$ aralkyloxy,
(20) 5- or 6-membered heterocyclyl-oxy optionally substituted by 1 to 3 substituents selected from
  (a) hydroxy, and
  (b) $C_{1-6}$ alkyl
(preferably, 5- or 6-membered heterocyclyl-oxy optionally substituted by 1 to 3 $C_{1-6}$ alkyl),
(21) 5- or 6-membered heterocyclyl-$C_{1-6}$ alkyloxy,
(22) $C_{1-6}$ alkyl-carbonyloxy optionally substituted by 1 to 3 substituents selected from
  (a) hydroxy, and
  (b) $C_{1-6}$ alkyl-carbonyloxy,
(23) $C_{1-6}$ alkylthio,
(24) $C_{1-6}$ alkylsulfinyl,
(25) $C_{1-6}$ alkylsulfonyl,
(26) carboxy optionally substituted by $C_{1-6}$ alkoxy,
(27) $C_{1-6}$ alkyl-carbonyl,
(28) $C_{3-6}$ cycloalkyl-carbonyl,
(29) $C_{6-14}$ aryl-carbonyl optionally substituted by $C_{1-6}$ alkoxy,
(30) $C_{7-16}$ aralkyl-carbonyl,
(31) 5- or 6-membered heterocyclyl-carbonyl,
(32) carbamoyl,
(33) thiocarbamoyl,
(34) $C_{1-6}$ alkyl-carbamoyl,
(35) di($C_{1-6}$)alkyl-carbamoyl,
(36) $C_{6-14}$ aryl-carbamoyl,
(37) di($C_{6-14}$)aryl-carbamoyl,
(38) sulfamoyl,
(39) $C_{1-6}$ alkylsulfamoyl,
(40) di($C_{1-6}$)alkylsulfamoyl,
(41) $C_{6-14}$ arylsulfamoyl,
(42) di($C_{6-14}$)arylsulfamoyl,
(43) $C_{1-3}$ alkylidene optionally substituted by hydroxy,
(44) imino(=NH) optionally substituted by
  (a) $C_{1-6}$ alkoxy optionally substituted by hydroxy, or
  (b) 5- or 6-membered heterocyclyl-oxy, and the like. When the number of the substituents is two or more, the respective substituents may be the same or different.

When the number of the substituents is two or more, the respective substituents may be bonded to each other to form an "optionally further substituted ring".

Examples of the "ring" of the "optionally further substituted ring" include those similar to the rings of the "3- to 14-membered cyclic group" of the "optionally substituted 3- to 14-membered cyclic group" exemplified as the substituent of the aforementioned "substituent group A", such as tetrahydrofuran, pyrazole, 1,3-dioxolane, 1,3-dioxane, dihydroisoxazole (e.g., 4,5-dihydroisoxazole) and the like.

The "3- to 10-membered nonaromatic cyclic group" of the "optionally substituted 3- to 10-membered nonaromatic cyclic group" for $R^1$ or the "5- or 6-membered aromatic cyclic group" of the "optionally substituted 5- or 6-membered aromatic cyclic group" for $R^1$ and the "optionally further substituted ring" may form a fused cyclic group or a spirocyclic group. Examples of such fused cyclic group include 2,3-dihydro-1-benzofuranyl (e.g., 2,3-dihydro-1-benzofuran-5-yl), 4,5,6,7-tetrahydro-1H-indazolyl (e.g., 4,5,6,7-tetrahydro-1H-indazol-5-yl) and the like. Examples of the spirocyclic group include 1,4-dioxaspiro[4.5]dec-8-yl, 1-oxaspiro[4.5]dec-8-yl, 1,5-dioxaspiro[5.5]undec-9-yl, 1-oxa-2-azaspiro[4.5]dec-2-en-8-yl, tetrahydrospiro[cyclohexane-1,2'-furo[3,4-d][1,3]dioxol]-4-yl and the like.

The "ring" of the "optionally further substituted ring" optionally has 1 to 5, preferably 1 to 3, substituents at substitutable positions. Examples of such substituent include those similar to the substituents that the "3- to 10-membered nonaromatic cyclic group" of the "optionally substituted 3- to 10-membered nonaromatic cyclic group" mentioned above as $R^1$ and the "5- or 6-membered aromatic cyclic group" of the "optionally substituted 5- or 6-membered aromatic cyclic group" mentioned above as $R^1$ optionally have.

The "optionally substituted 3- to 10-membered nonaromatic cyclic group" for $R^1$ is preferably a 3- to 10-membered nonaromatic cyclic group (e.g., cyclopropyl, cyclobutyl, cyclopentyl, cyclohexyl, cycloheptyl, cyclooctyl, cyclohexenyl, azetidinyl, oxetanyl, thietanyl, pyrrolidinyl, tetrahydrofuryl, thioranyl, imidazolidinyl, pyrazolidinyl, oxazolidinyl, thiazolidinyl, piperidyl, tetrahydropyranyl, tetrahydrothiopyranyl, tetrahydroindazolyl, morpholinyl, thiomorpholinyl, piperazinyl, adamantyl, oxepanyl and the like, preferably cyclobutyl, cyclohexyl, cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
(1) oxo,
(2) hydroxy,
(3) amino optionally substituted by 1 or 2 substituents selected from
  (a) $C_{1-6}$ alkyl, and
  (b) a 5- or 6-membered heterocyclic group,
(4) cyano,
(5) $C_{1-6}$ alkyl optionally substituted by 1 to 3 substituents selected from
  (a) hydroxy,
  (b) a halogen atom,
  (c) $C_{1-6}$ alkoxy, and
  (d) a 5- or 6-membered heterocyclic group,
(6) $C_{2-6}$ alkenyl optionally substituted by hydroxyl,
(7) $C_{6-14}$ aryl optionally substituted by hydroxy,
(8) $C_{7-16}$ aralkyl,
(9) a heterocyclic group optionally substituted by $C_{1-6}$ alkyl,
(10) $C_{1-6}$ alkoxy optionally substituted by 1 to 4 substituents selected from
  (a) a halogen atom,
  (b) hydroxy,
  (c) $C_{3-6}$ cycloalkyl optionally substituted by 1 to 3 substituents selected from the group consisting of $C_{1-6}$ alkyl optionally substituted by hydroxy, hydroxy, oxo, carbamoyl and cyano,
  (d) $C_{2-6}$ alkenyl,
  (e) $C_{1-6}$ alkoxy,
  (f) cyano,
  (g) $C_{1-6}$ alkyl-carbonyl optionally substituted by 1 to 3 halogen atoms,
  (h) $C_{3-10}$ cycloalkyl-carbonyl,
  (i) carbamoyl,
  (j) $C_{1-6}$ alkoxyimino,
  (k) $C_{1-6}$ alkylthio,
  (l) $C_{1-6}$ alkylsulfonyl,
  (m) $C_{1-6}$ alkylcarbonyloxy,
  (n) $C_{3-6}$ cycloalkyloxy optionally substituted by hydroxy, and
  (o) a 5- or 6-membered heterocyclic group optionally substituted by 1 to 3 substituents selected from the group consisting of $C_{1-6}$ alkyl, hydroxy and oxo,
(11) $C_{2-6}$ alkenyloxy optionally substituted by hydroxy,
(12) $C_{3-10}$ cycloalkyloxy optionally substituted by 1 to 3 substituents selected from the group consisting of
  (a) oxo,
  (b) hydroxy, and
  (c) $C_{1-6}$ alkyl optionally substituted by hydroxy,
(13) $C_{6-14}$ aryloxy optionally substituted by 1 to 3 substituents selected from
  (a) hydroxy,
  (b) $C_{1-6}$ alkyl optionally substituted by hydroxy,
  (c) $C_{1-6}$ alkyl-carbonyl, and
  (d) $C_{1-6}$ alkoxy,
(14) 5- or 6-membered heterocyclyl-oxy optionally substituted by 1 to 3 substituents selected from
  (a) hydroxy, and
  (b) $C_{1-6}$ alkyl,
(15) $C_{1-6}$ alkyl-carbonyloxy optionally substituted by 1 to 3 substituents selected from
  (a) hydroxy, and
  (b) $C_{1-6}$ alkyl-carbonyloxy,
(16) carboxy optionally substituted by $C_{1-6}$ alkoxy,
(17) $C_{1-6}$ alkyl-carbonyl,
(18) $C_{6-14}$ aryl-carbonyl optionally substituted by $C_{1-6}$ alkoxy,
(19) 5- or 6-membered heterocyclyl-carbonyl,
(20) carbamoyl,
(21) $C_{1-3}$ alkylidene optionally substituted by hydroxy,
(22) imino (=NH) optionally substituted by
  (a) $C_{1-6}$ alkoxy optionally substituted by hydroxy, or
  (b) 5- or 6-membered heterocyclyl-oxy,
and the like (hereinafter sometimes to be abbreviated as substituent group B). When the number of the substituents is two or more, the respective substituents may be the same or different.

The "optionally substituted 5- or 6-membered aromatic cyclic group" for $R^1$ is preferably a 5- or 6-membered aromatic cyclic group (preferably, phenyl, thienyl) optionally substituted by 1 to 3 substituents selected from the group consisting of
(1) a halogen atom,
(2) $C_{1-6}$ alkyl optionally substituted by hydroxy,
(3) $C_{1-6}$ alkoxy optionally substituted by 1 to 3 substituents selected from
  (a) hydroxy, and
  (b) $C_{1-6}$ alkyl-carbonyl,
(4) $C_{1-6}$ alkyl-carbonyl,
and the like. When the number of the substituents is two or more, the respective substituents may be the same or different.

$R^1$ is preferably optionally substituted $C_{1-6}$ alkyl, an optionally substituted 3- to 10-membered nonaromatic ring or an optionally substituted 5- or 6-membered aromatic ring, more preferably an optionally substituted 3- to 10-membered nonaromatic ring.

$R^1$ is more preferably $C_{3-8}$ cycloalkyl optionally substituted by $C_{1-6}$ alkoxy optionally substituted by
1) a halogen atom,
2) cyano,
3) hydroxy, or
4) $C_{1-6}$ alkoxy optionally substituted by a halogen atom. When the number of the substituents is two or more, the respective substituents may be the same or different.

Examples of the "$C_{3-8}$ cycloalkyl" include cyclopropyl, cyclobutyl, cyclopentyl, cyclohexyl and the like.

$R^1$ is particularly preferably cyclohexyl optionally substituted by $C_{1-6}$ alkoxy (e.g., isobutoxy, —OCH(CH$_3$)(CH(CH$_3$)$_2$) etc.) optionally substituted by hydroxy. When the number of the substituents is two or more, the respective substituents may be the same or different.

$R^2$ is a hydrogen atom, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl or optionally substituted $C_{1-6}$ alkylsulfonyl.

Examples of the substituent of the "$C_{1-6}$ alkylsulfinyl" of the "optionally substituted $C_{1-6}$ alkylsulfinyl" and the "$C_{1-6}$ alkylsulfonyl" of the "optionally substituted $C_{1-6}$ alkylsulfonyl" for $R^2$ include 1 to 5, preferably 1 to 3, substituents selected from those exemplified as the substituents of the aforementioned "substituent group A". When the number of the substituents is two or more, the respective substituents may be the same or different.

$R^2$ is preferably optionally substituted $C_{1-6}$ alkyl.

$R^2$ is more preferably $C_{1-6}$ alkyl (e.g., methyl, ethyl, propyl, isopropyl, butyl, isobutyl, sec-butyl, tert-butyl, pentyl, isopentyl, neopentyl, tert-pentyl, hexyl), and particularly preferably propyl, butyl or pentyl.

$R^3$ is a hydrogen atom, a halogen atom, optionally substituted $C_{1-6}$ alkyl or optionally substituted $C_{1-6}$ alkoxy.

$R^3$ is preferably a hydrogen atom or a halogen atom (preferably, fluorine atom), and particularly preferably a hydrogen atom.

W is optionally substituted $C_{1-4}$ alkylene, —O—W'—, —W'—O—, —N(Ra)—W'— or —W'—N(Ra)— wherein W' is a bond or optionally substituted $C_{1-4}$ alkylene, and Ra is a hydrogen atom, optionally substituted $C_{1-6}$ alkyl or optionally substituted $C_{3-6}$ cycloalkyl.

The "$C_{1-4}$ alkylene" of the "optionally substituted $C_{1-4}$ alkylene" for W or W' may be a straight chain or a branched chain and, for example, methylene, ethylene, —(CH$_2$)$_3$—, —(CH$_2$)$_4$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$— and the like.

The "$C_{1-4}$ alkylene" of the "optionally substituted $C_{1-4}$ alkylene" for W or W' may have 1 to 3 substituents at substitutable positions. Examples of such substituent include a halogen atom (e.g., fluorine atom, chlorine atom, bromine atom etc.), oxo, hydroxy, nitro, cyano, optionally halogenated $C_{1-6}$ alkoxy (e.g., methoxy, ethoxy, trifluoromethoxy etc.), amino, $C_{1-6}$ alkylamino (e.g., methylamino etc.), di($C_{1-6}$) alkylamino (e.g., dimethylamino etc.), $C_{1-6}$ alkyl-carbonylamino (e.g., acetylamino etc.) and the like. When the number of the substituents is two or more, the respective substituents may be the same or different.

Preferable examples of the "optionally substituted $C_{1-6}$ alkyl" for Ra include $C_{1-6}$ alkyl and the like.

The "$C_{3-6}$ cycloalkyl" of the "optionally substituted $C_{3-6}$ cycloalkyl" for Ra is optionally substituted by 1 to 5, preferably 1 to 3, substituents selected from the substituent groups exemplified as the substituents of the aforementioned "substituent group B". When the number of the substituents is two or more, the respective substituents may be the same or different.

Preferable examples of the "optionally substituted $C_{3-6}$ cycloalkyl" for Ra include $C_{3-6}$ cycloalkyl and the like.

W is preferably $C_{1-4}$ alkylene, more preferably methylene, ethylene or —CH(CH$_3$)—, and particularly preferably methylene.

A is an optionally substituted 5- or 6-membered divalent aromatic ring.

Examples of the "5- or 6-membered divalent aromatic ring" of the "optionally substituted 5- or 6-membered divalent aromatic ring" for A include phenylene, furan-di-yl, thiophene-di-yl, pyrrole-di-yl, oxazole-di-yl, isoxazole-di-yl, triazole-di-yl, isothiazole-di-yl, imidazole-di-yl, pyrazole-di-yl, 1,2,3-oxadiazole-di-yl, 1,2,4-oxadiazole-di-yl, 1,3,4-oxadiazole-di-yl, furazan-di-yl, 1,2,3-thiadiazole-di-yl, 1,2,4-thiadiazole-di-yl, 1,3,4-thiadiazole-di-yl, 1,2,3-triazole-di-yl, 1,2,4-triazole-di-yl, tetrazole-di-yl, pyridine-di-yl, pyridazine-di-yl, pyrimidine-di-yl, pyrazine-di-yl, triazine-di-yl and the like.

The "5- or 6-membered divalent aromatic ring" of the "optionally substituted 5- or 6-membered divalent aromatic ring" for A optionally has 1 to 4, preferably 1 to 3, substituents at substitutable positions. Examples of such substituent include those similar to the substituents that the "3- to 10-membered nonaromatic cyclic group" of the "optionally substituted 3- to 10-membered nonaromatic cyclic group" mentioned above as $R^1$ and the "5- or 6-membered aromatic cyclic group" of the "optionally substituted 5- or 6-membered aromatic cyclic group" mentioned above as $R^1$ optionally have. When the number of the substituents is two or more, the respective substituents may be the same or different.

When the number of the substituents is two or more, the respective substituents may be bonded to each other to further form a ring. Examples of such ring include those similar to the rings of the "3- to 14-membered cyclic group" of the "optionally substituted 3- to 14-membered cyclic group" exemplified as the substituents of the aforementioned "substituent group A".

The "5- or 6-membered divalent aromatic ring" of the "optionally substituted 5- or 6-membered divalent aromatic ring" for A and said ring may form a fused ring.

Examples of such fused ring include benzothiophene, benzofuran, naphthalene, quinoline, indole and the like.

The "fused ring" optionally has 1 to 5, preferably 1 to 3, substituents at substitutable positions. Examples of such substituent include those similar to the substituents that the "3- to 10-membered nonaromatic cyclic group" of the "optionally substituted 3- to 10-membered nonaromatic cyclic group" mentioned above as $R^1$ and the "5- or 6-membered aromatic cyclic group" of the "optionally substituted 5- or 6-membered aromatic cyclic group" mentioned above as $R^1$ optionally have. When the number of the substituents is two or more, the respective substituents may be the same or different.

A is preferably optionally substituted phenylene, optionally substituted thiophene-di-yl or optionally substituted pyridine-di-yl. Examples of the substituent of the optionally substituted phenylene, optionally substituted thiophene-di-yl or optionally substituted pyridine-di-yl include those similar to the aforementioned substituents exemplified as the substituents of the "3- to 10-membered nonaromatic cyclic group" of the "optionally substituted 3- to 10-membered nonaromatic cyclic group" for $R^1$ and the "5- or 6-membered aromatic cyclic group" of the "optionally substituted 5- or 6-membered aromatic cyclic group" for $R^1$. When the number of the substituents is two or more, the respective substituents may be the same or different.

A is more preferably phenylene, thiophene-di-yl or pyridine-di-yl (preferably, 1,4-phenylene, 2,5-thiophene-di-yl, 3,6-pyridine-di-yl) optionally substituted by 1 to 3 (preferably 1 or 2) substituents selected from (1) a halogen atom (preferably, fluorine atom),
(2) nitro,
(3) $C_{1-6}$ alkyl optionally substituted by 1 to 3 halogen atoms (preferably, methyl, trifluoromethyl), and
(4) $C_{1-6}$ alkoxy (preferably, methoxy). When the number of the substituents is two or more, the respective substituents may be the same or different.

Particularly preferred is phenylene optionally substituted by a halogen atom (preferably, fluorine atom).

B is acyl or an optionally substituted 3- to 10-membered heterocyclic group.

The "acyl" for B is, for example, a group represented by the formula: —COR$^4$, —CO—OR$^4$, —SO$_2$R$^4$, —SOR$^4$, —CO—NR$^{A'}$R$^{B'}$ or —CS—NR$^{A'}$R$^{B'}$ wherein R$^A$ is a hydrogen atom, hydroxy, an optionally substituted hydrocarbon group, an optionally substituted amino or an optionally substituted heterocyclic group; and R$^{A'}$ and R$^{B'}$ are each a hydrogen atom, an optionally substituted hydrocarbon group or an optionally substituted heterocyclic group, or R$^{A'}$ and R$^{B'}$ may form, together with the nitrogen atom bonded thereto, an optionally substituted nitrogen-containing heterocycle and the like.

Examples of the "hydrocarbon group" of the "optionally substituted hydrocarbon group" for R$^A$, R$^{A'}$ or R$^{B'}$ include $C_{1-6}$ alkyl, $C_{2-6}$ alkenyl, $C_{2-6}$ alkynyl, $C_{1-3}$ alkylidene, $C_{3-10}$ cycloalkyl, $C_{3-10}$ cycloalkenyl (e.g., cyclopentenyl, cyclohexenyl etc.), $C_{4-10}$ cycloalkadienyl (e.g., 2,4-cyclopentadienyl, 1,3-cyclohexadienyl etc.), $C_{6-14}$ aryl, $C_{7-16}$ aralkyl, $C_{8-13}$ arylalkenyl (e.g., phenylethyl, phenylpropionyl etc.), $C_{3-10}$ cycloalkyl (e.g., cyclopropyl, cyclobutyl, cyclopentyl, cyclohexyl etc.) —$C_{1-6}$ alkyl (e.g., methyl, ethyl, propyl, butyl etc.) and the like.

The "hydrocarbon group" of the "optionally substituted hydrocarbon group" and the "amino" of the "optionally substituted amino" for R$^A$, R$^{A'}$ or R$^{B'}$ may be each substituted by, 1 to 5, preferably 1 to 3, substituents selected from the aforementioned "substituent group A".

The "heterocyclic group" of the "optionally substituted heterocyclic group" for R$^A$, R$^{A'}$ or R$^{B'}$ optionally has 1 to 5, preferably 1 to 3, substituents at substitutable positions. Examples of such substituent include those similar to the aforementioned substituents exemplified as the substituents of the "3- to 10-membered nonaromatic cyclic group" of the "optionally substituted 3- to 10-membered nonaromatic cyclic group" for R$^1$ and the "5- or 6-membered aromatic cyclic group" of the "optionally substituted 5- or 6-membered aromatic cyclic group" for R$^1$.

Examples of the "nitrogen-containing heterocycle" of the "optionally substituted nitrogen-containing heterocycle" optionally formed by R$^{A'}$ and R$^{B'}$ together with the nitrogen atom bonded thereto include azetidine, pyrrolidine, imidazolidine, pyrazolidine, piperidine, homopiperidine, piperazine, homopiperazine, morpholine, homomorpholine, thiomorpholine, thiohomomorpholine, dihydrobenzoxazine (e.g., 3,4-dihydro-2H-1,4-benzoxazine), 1,2,3,4-tetrahydroquinoline, 7-aza-bicyclo[2.2.1]heptane and the like.

The "nitrogen-containing heterocycle" optionally has 1 to 5, preferably 1 to 3, substituents at substitutable positions. Examples of such substituent include those similar to the aforementioned substituents exemplified as the substituents of the "3- to 10-membered nonaromatic cyclic group" of the "optionally substituted 3- to 10-membered nonaromatic cyclic group" for R$^1$ and the "5- or 6-membered aromatic cyclic group" of the "optionally substituted 5- or 6-membered aromatic cyclic group" for R$^1$. When the number of the substituents is two or more, the respective substituents may be the same or different.

Examples of the "3- to 10-membered heterocyclic group" of the "optionally substituted 3- to 10-membered heterocyclic group" for B include a 3- to 10-membered (preferably, 5- or 6-membered) monocyclic heterocyclic group (preferably, nitrogen-containing heterocyclic group having a protonizable hydrogen atom), which contains one or more from a nitrogen atom, an oxygen atom and a sulfur atom (preferably, nitrogen atom), or a group that can be converted to such group. Examples of the "3- to 10-membered heterocyclic group" include groups represented by the following formulas:

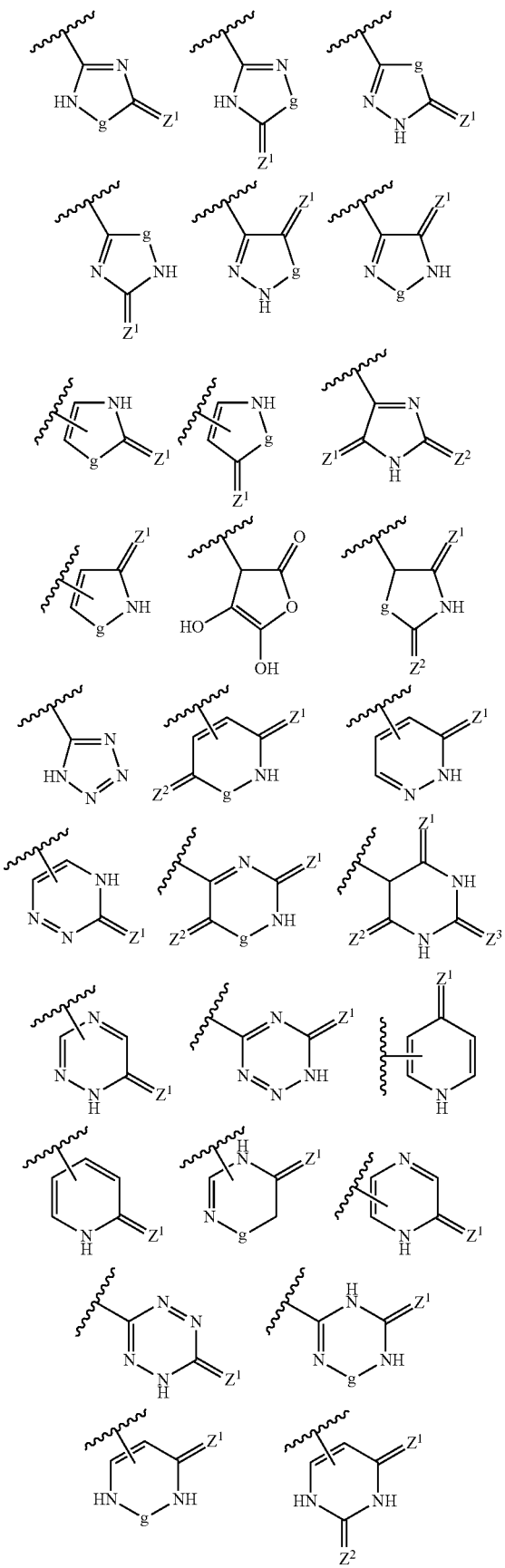

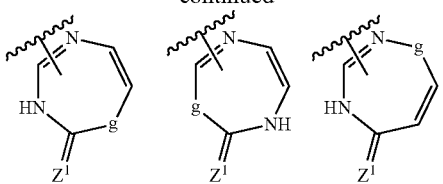

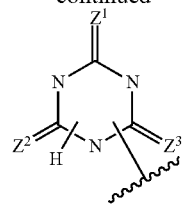

wherein g is —CH$_2$—, —NR$^9$—, —O— or —S(O)$_m$— wherein m is an integer of 0, 1 or 2 and R$^9$ is a hydrogen atom or optionally substituted C$_{1-6}$ alkyl; and Z$^1$, Z$^2$ and Z$^3$ are each independently an oxygen atom or optionally oxidized sulfur atom (preferably an oxygen atom or a sulfur atom, more preferably an oxygen atom), and the like.

The bond of "3- to 10-membered heterocyclic group" of the "optionally substituted 3- to 10-membered heterocyclic group" for B and phenyl may be not only the carbon-carbon bond shown in the above-mentioned formulas but also a bond via one nitrogen atom when the "3- to 10-membered heterocyclic group" contains plural nitrogen atoms.

For example, when the "3- to 10-membered heterocyclic group" is

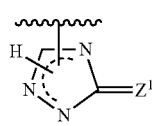

wherein each symbol is as defined above, the bond specifically includes

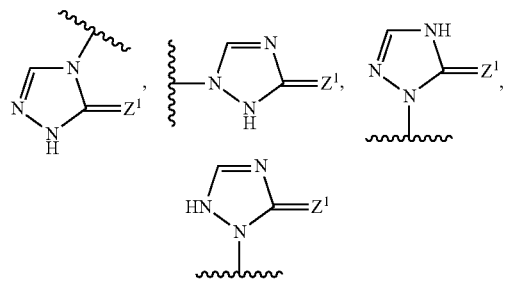

wherein each symbol is as defined above, and the like. Examples of other "3- to 10-membered heterocyclic group" bonded via a nitrogen atom include groups represented by

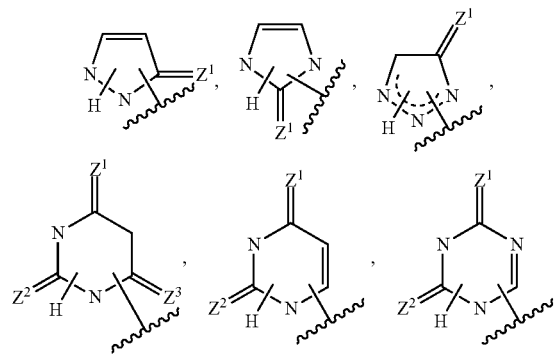

wherein each symbol is as defined above, and the like.

The "3- to 10-membered heterocyclic group" is preferably a group simultaneously having an —NH group or —OH group as a proton donor, and carbonyl, thiocarbonyl, sulfinyl and the like as a proton acceptor such as oxadiazole and thiadiazole. As the "3- to 10-membered heterocyclic group", 5- or 6-membered (more preferably 5-membered) monocyclic heterocyclic group is preferable.

The "3- to 10-membered heterocyclic group" is preferably a group represented by the formula:

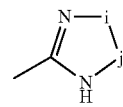

wherein i is —O— or —S—, j is —C(=O)—, —C(=S)— or —S(O)$_m$—, and m is an integer of 0, 1 or 2 (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl).

The "3- to 10-membered heterocyclic group" is more preferably a group represented by the formula:

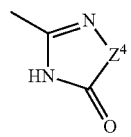

wherein Z$^4$ is an oxygen atom or a sulfur atom.

The "3- to 10-membered heterocyclic group" can have a tautomer. When, for example, Z$^1$=O, g=O in the following formula:

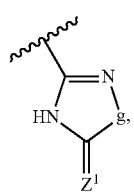

3 tautomers of a', b' and c' below

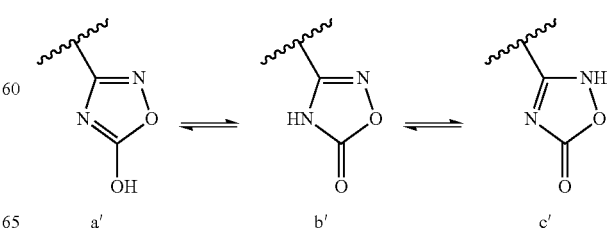

a'   b'   c' are present. In the present specification, when the "3- to 10-membered heterocyclic group" is, for example, represented by the following formula:

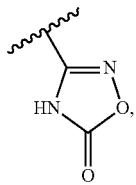

the group contains any tautomer of the above-mentioned a', b' and c'. Similarly, the aforementioned various "3- to 10-membered heterocyclic groups" also contains any of such possible tautomers.

The "3- to 10-membered heterocyclic group" of the "optionally substituted 3- to 10-membered heterocyclic group" for B optionally has 1 to 5, preferably 1 to 3, substituents at substitutable positions. When the number of the substituents is two or more, the respective substituents may be the same or different.

For example, when the "3- to 10-membered heterocyclic group" is represented by the following formula:

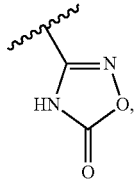 [SMILES: *c1noc(=O)[nH]1]

the group optionally has substituents at the positions shown by the following formulas:

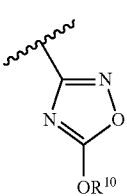
a''

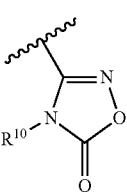
b''

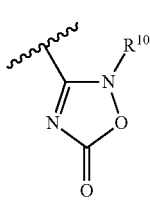
c'' wherein $R^{10}$ is a substituent. Similarly, the aforementioned various "3- to 10-membered heterocyclic groups" optionally have 1 to 5, preferably 1 to 3, substituents at substitutable positions in all tautomers thereof.

Examples of the substituent that the "3- to 10-membered heterocyclic group" optionally has include a group represented by the formula —CH($R^{11}$)—OCOR$^{12}$ wherein $R^{11}$ is a hydrogen atom, $C_{1-6}$ alkyl (e.g., methyl, ethyl, propyl, isopropyl, butyl, isobutyl, sec-butyl, tert-butyl, pentyl, isopentyl, neopentyl etc.), $C_{2-6}$ alkenyl or $C_{3-8}$ cycloalkyl (e.g., cyclopentyl, cyclohexyl, cycloheptyl etc.), and $R^{12}$ is $C_{1-6}$ alkyl (e.g., methyl, ethyl, propyl, isopropyl, butyl, isobutyl, sec-butyl, tert-butyl, pentyl, isopentyl, neopentyl etc.), $C_{2-6}$ alkenyl, $C_{3-8}$ cycloalkyl (e.g., cyclopentyl, cyclohexyl, cycloheptyl etc.), $C_{1-3}$ alkyl substituted by $C_{3-8}$ cycloalkyl (e.g., cyclopentyl, cyclohexyl, cycloheptyl etc.) or optionally substituted $C_{6-14}$ aryl (e.g., phenyl etc.) (e.g., benzyl, p-chlorobenzyl, phenethyl, cyclopentylmethyl, cyclohexylmethyl etc.), $C_{2-3}$ alkenyl (e.g., vinyl, propenyl, allyl, isopropenyl etc.) substituted by $C_{3-8}$ cycloalkyl or optionally substituted $C_{6-14}$ aryl (e.g., phenyl etc.) (e.g., cinnamyl etc.), optionally substituted $C_{6-14}$ aryl (e.g., phenyl, p-tolyl, naphthyl etc.), $C_{1-6}$ alkoxy (e.g., methoxy, ethoxy, propoxy, isopropoxy, butoxy, isobutoxy, sec-butoxy, tert-butoxy, pentyloxy, isopentyloxy, neopentyloxy etc.), $C_{2-8}$ alkenyloxy (e.g., allyloxy, isobutenyloxy etc.), $C_{3-8}$ cycloalkyloxy (e.g., cyclopentyloxy, cyclohexyloxy, cycloheptyloxy etc.), $C_{1-3}$ alkoxy (e.g., methoxy, ethoxy, propoxy, isopropoxy) substituted by $C_{3-8}$ cycloalkyl (e.g., cyclopentyl, cyclohexyl, cycloheptyl etc.) or optionally substituted $C_{6-14}$ aryl (e.g., phenyl etc.) (e.g., benzyloxy, phenethyloxy, cyclopentylmethyloxy, cyclohexylmethyloxy etc.), $C_{2-3}$ alkenyloxy (e.g., vinyloxy, propenyloxy, allyloxy, isopropenyloxy etc.) substituted by $C_{3-8}$ cycloalkyl (e.g., cyclopentyl, cyclohexyl, cycloheptyl etc.) or optionally substituted $C_{6-14}$ aryl (e.g., phenyl etc.) (e.g., cinnamyloxy etc.) or optionally substituted $C_{6-14}$ aryloxy (e.g., phenoxy, p-nitrophenoxy, naphthoxy etc.; optionally substituted alkyl (e.g., $C_{1-6}$ alkyl) (e.g., methyl, trichloromethyl, trifluoromethyl, triphenylmethyl etc.); optionally substituted acyl (e.g., $C_{2-5}$ alkanoyl, optionally substituted benzoyl etc.); a halogen atom (e.g., fluorine atom, chlorine atom, bromine atom etc.); nitro; cyano; $C_{1-6}$ alkoxy; amino; $C_{1-6}$ alkylamino (e.g., methylamino etc.); di($C_{1-6}$ alkyl)amino (e.g., dimethylamino etc.) and the like.

Specific examples of the substituent include ally, methyl, ethyl, propyl, tert-butyl, methoxymethyl, triphenylmethyl, cyanoethyl, acetyl, propionyl, pivaloyloxymethyl, 1-(cyclohexyloxycarbonyloxy)ethyl, 5-methyl-2-oxo-1,3-dioxolen-4-ylmethyl, acetoxymethyl, propionyloxymethyl, butyryloxymethyl, isobutyryloxymethyl, 1-(ethoxycarbonyloxy) ethyl, 1-(acetyloxy)ethyl, 1-(isobutyryloxy)ethyl, cyclohexylcarbonyloxymethyl, benzoyloxymethyl, cinnamyl, cyclopentylcarbonyloxymethyl and the like. As the substituent, those easily removed under biological, namely, physiological conditions (e.g., biological reactions such as oxidation, reduction or hydrolysis and the like by enzymes in the body etc.), or chemically are preferable.

B is preferably an optionally substituted 3- to 10-membered heterocyclic group, and more preferably a 3- to 10-membered heterocyclic group. Particularly preferred are groups represented by the following formulas:

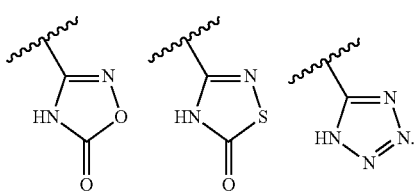 [SMILES: *c1noc(=O)[nH]1 ; *c1nsc(=O)[nH]1 ; *c1nnn[nH]1]

X, Y and Z are each independently $CR^4$ wherein $R^4$ is a hydrogen atom, a halogen atom, optionally substituted $C_{1-6}$ alkyl, optionally substituted $C_{1-6}$ alkoxy or optionally substituted $C_{3-6}$ cycloalkyl, or a nitrogen atom.

The "$C_{3-6}$ cycloalkyl" of the "optionally substituted $C_{3-6}$ cycloalkyl" for $R^4$ is optionally substituted by 1 to 5, preferably 1 to 3, substituents selected from the substituent groups exemplified as the substituents of the aforementioned "sub-

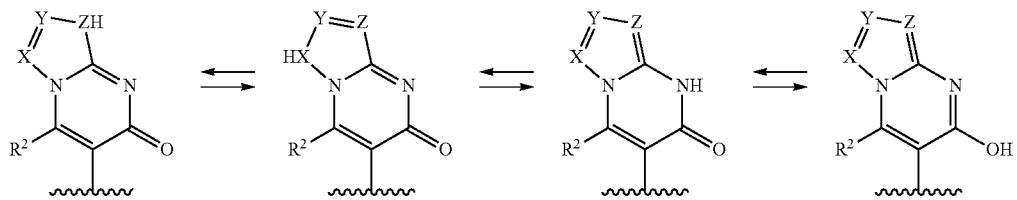

stituent group B". When the number of the substituents is two or more, the respective substituents may be the same or different.

$R^4$ is preferably (a) a hydrogen atom; (b) a halogen atom (preferably, fluorine atom); (c) $C_{1-6}$ alkyl optionally substituted by 1 to 3 substituents selected from the group consisting of hydroxy, a halogen atom (e.g., fluorine atom, bromine atom) and $C_{1-6}$ alkoxy (e.g., methoxy) (e.g., methyl, bromomethyl, trifluoromethyl, hydroxymethyl, methoxymethyl); (d) $C_{3-6}$ cycloalkyl (e.g., cyclopropyl), and the like. When the number of the substituents is two or more, the respective substituents may be the same or different.

Preferably, X is a nitrogen atom, Y and Z are $CR^4$ wherein $R^4$ is (a) a hydrogen atom; (b) a halogen atom (preferably, fluorine atom); (c) $C_{1-6}$ alkyl optionally substituted by 1 to 3 substituents selected from the group consisting of hydroxy, a halogen atom (e.g., fluorine atom, bromine atom) and $C_{1-6}$ alkoxy (e.g., methoxy) (e.g., methyl, bromomethyl, trifluoromethyl, hydroxymethyl, methoxymethyl); (d) $C_{3-6}$ cycloalkyl (e.g., cyclopropyl) and the like. When the number of the substituents is two or more, the respective substituents may be the same or different.

In another preferable embodiment, X and Z are nitrogen atoms, Y is $CR^4$ wherein $R^4$ is (a) a hydrogen atom; (b) a halogen atom (preferably, fluorine atom); (c) $C_{1-6}$ alkyl optionally substituted by 1 to 3 substituents selected from the group consisting of hydroxy, a halogen atom (e.g., fluorine atom, bromine atom) and $C_{1-6}$ alkoxy (e.g., methoxy) (e.g., methyl, bromomethyl, trifluoromethyl, hydroxymethyl, methoxymethyl); (d) $C_{3-6}$ cycloalkyl (e.g., cyclopropyl) and the like. When the number of the substituents is two or more, the respective substituents may be the same or different.

In another preferable embodiment, X and Y are nitrogen atoms, Z is $CR^4$ wherein $R^4$ is (a) a hydrogen atom; (b) a halogen atom (preferably, fluorine atom); (c) $C_{1-6}$ alkyl optionally substituted by 1 to 3 substituents selected from the group consisting of hydroxy, a halogen atom (e.g., fluorine atom, bromine atom) and $C_{1-6}$ alkoxy (e.g., methoxy) (e.g., methyl, bromomethyl, trifluoromethyl, hydroxymethyl, methoxymethyl); (d) $C_{3-6}$ cycloalkyl (e.g., cyclopropyl) and the like. When the number of the substituents is two or more, the respective substituents may be the same or different.

In another preferable embodiment, X is $CR^4$ wherein $R^4$ is (a) a hydrogen atom; (b) a halogen atom (preferably, fluorine atom); (c) $C_{1-6}$ alkyl optionally substituted by 1 to 3 substituents selected from the group consisting of hydroxy, a halogen atom (e.g., fluorine atom, bromine atom) and $C_{1-6}$ alkoxy (e.g., methoxy) (e.g., methyl, bromomethyl, trifluoromethyl, hydroxymethyl, methoxymethyl); (d) $C_{3-6}$ cycloalkyl (e.g., cyclopropyl) and the like. When the number of the substituents is two or more, the respective substituents may be the same or different, and Y and Z are nitrogen atoms.

The parts shown by the following formulas in a compound represented by the formula (I) may contain tautomers shown below.

All these tautomers are all encompassed in the scope of a compound represented by the formula (I).

Preferable embodiments of a compound represented by the formula (I) are the following compounds.

[Compound A1]

a compound represented by the formula:

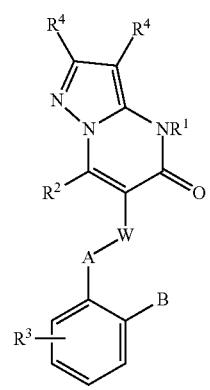

wherein $R^1$ is a hydrogen atom, optionally substituted $C_{1-6}$ alkyl, an optionally substituted 3- to 10-membered nonaromatic ring or an optionally substituted 5- or 6-membered aromatic ring, $R^2$ is optionally substituted $C_{1-6}$ alkyl, $R^3$ is a hydrogen atom or a halogen atom, W is $C_{1-4}$ alkylene, A is optionally substituted phenylene, optionally substituted thiophene-di-yl or optionally substituted pyridine-di-yl, B is a group represented by the formula:

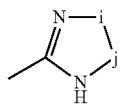

wherein i is —O— or —S—, j is —C(=O)—, —C(=S)— or —S(O)$_m$—, and m is an integer of 0, 1 or 2 (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl), or tetrazolyl and two $R^4$ are each independently a hydrogen atom, a halogen atom, optionally substituted $C_{1-6}$ alkyl, optionally substituted $C_{1-6}$ alkoxy or optionally substituted $C_{3-6}$ cycloalkyl, or a salt thereof.

[Compound A2]

A compound represented by the formula:

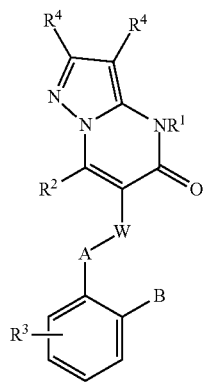

wherein $R^1$ is

[1] a hydrogen atom,

[2] $C_{1-6}$ alkyl optionally substituted by 1 to 5 substituents selected from the group consisting of
 (1) a halogen atom,
 (2) hydroxy,
 (3) optionally halogenated $C_{1-6}$ alkoxy,
 (4) carboxy optionally substituted by $C_{1-6}$ alkoxy,
 (5) $C_{1-6}$ alkyl-carbonyl optionally substituted by 1 to 3 halogen atoms,
 (6) $C_{3-10}$ cycloalkyl-carbonyl,
 (7) $C_{6-14}$ aryl-carbonyl optionally substituted by 1 to 3 halogen atoms,
 (8) carbamoyl,
 (9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) $C_{1-6}$ alkyl optionally substituted by hydroxy, (c) $C_{6-14}$ aryl, (d) $C_{1-6}$ alkoxy and (e) $C_{1-6}$ alkyl-carbonyl, and
 (10) $C_{1-6}$ alkoxyimino,

[3] a 3- to 10-membered nonaromatic cyclic group (preferably, cyclobutyl, cyclohexyl (the cyclohexyl may form, together with the ring formed by two substituents, a spirocyclic group (e.g., 1,4-dioxaspiro[4.5]dec-8-yl)), cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
 (1) oxo,
 (2) hydroxy,
 (3) amino optionally substituted by 1 or 2 substituents selected from
  (a) $C_{1-6}$ alkyl, and
  (b) a 5- or 6-membered heterocyclic group,
 (4) cyano,
 (5) $C_{1-6}$ alkyl optionally substituted by 1 to 3 substituents selected from
  (a) hydroxy,
  (b) a halogen atom,
  (c) $C_{1-6}$ alkoxy, and
  (d) a 5- or 6-membered heterocyclic group,
 (6) $C_{6-14}$ aryl optionally substituted by hydroxy,
 (7) $C_{7-16}$ aralkyl,
 (8) a heterocyclic group optionally substituted by $C_{1-6}$ alkyl,
 (9) $C_{1-6}$ alkoxy optionally substituted by 1 to 4 substituents selected from
  (a) a halogen atom,
  (b) hydroxy,
  (c) $C_{3-6}$ cycloalkyl optionally substituted by 1 to 3 substituents selected from the group consisting of $C_{1-6}$ alkyl optionally substituted by hydroxy, hydroxy, carbamoyl and cyano,
  (d) $C_{1-6}$ alkoxy,
  (e) cyano,
  (f) $C_{1-6}$ alkyl-carbonyl optionally substituted by 1 to 3 halogen atoms,
  (g) $C_{3-10}$ cycloalkyl-carbonyl,
  (h) carbamoyl,
  (i) $C_{1-6}$ alkoxyimino,
  (j) $C_{1-6}$ alkylthio,
  (k) $C_{1-6}$ alkylsulfonyl,
  (l) $C_{1-6}$ alkylcarbonyloxy,
  (m) $C_{3-6}$ cycloalkyloxy optionally substituted by hydroxy, and
  (n) a 5- or 6-membered heterocyclic group optionally substituted by 1 to 3 substituents selected from the group consisting of $C_{1-6}$ alkyl and oxo,
 (10) $C_{2-6}$ alkenyloxy optionally substituted by hydroxy,
 (11) $C_{3-10}$ cycloalkyloxy optionally substituted by 1 to 3 substituents selected from the group consisting of
  (a) oxo,
  (b) hydroxy, and
  (c) $C_{1-6}$ alkyl optionally substituted by hydroxy,
 (12) $C_{6-14}$ aryloxy optionally substituted by 1 to 3 substituents selected from
  (a) hydroxy,
  (b) $C_{1-6}$ alkyl optionally substituted by hydroxy,
  (c) $C_{1-6}$ alkyl-carbonyl, and
  (d) $C_{1-6}$ alkoxy,
 (13) 5- or 6-membered heterocyclyl-oxy optionally substituted by 1 to 3 substituents selected from
  (a) hydroxy, and
  (b) $C_{1-6}$ alkyl,
 (14) $C_{1-6}$ alkyl-carbonyloxy optionally substituted by 1 to 3 substituents selected from
  (a) hydroxy, and
  (b) $C_{1-6}$ alkyl-carbonyloxy,
 (15) carboxy optionally substituted by $C_{1-6}$ alkoxy,
 (16) $C_{1-6}$ alkyl-carbonyl,
 (17) $C_{6-14}$ aryl-carbonyl optionally substituted by $C_{1-6}$ alkoxy,
 (18) 5- or 6-membered heterocyclyl-carbonyl,
 (19) carbamoyl,

(20) $C_{1-3}$ alkylidene optionally substituted by hydroxy, and
(21) imino (=NH) optionally substituted by
  (a) $C_{1-6}$ alkoxy optionally substituted by hydroxy, or
  (b) 5- or 6-membered heterocyclyl-oxy, or
[4] a 5- or 6-membered aromatic cyclic group (preferably, phenyl, thienyl) optionally substituted by 1 to 3 substituents selected from the group consisting of
  (1) a halogen atom,
  (2) $C_{1-6}$ alkyl optionally substituted by hydroxy,
  (3) $C_{1-6}$ alkoxy optionally substituted by 1 to 3 substituents selected from
    (a) hydroxy, and
    (b) $C_{1-6}$ alkyl-carbonyl, and
  (4) $C_{1-6}$ alkyl-carbonyl,
$R^2$ is $C_{1-6}$ alkyl,
$R^3$ is a hydrogen atom or a halogen atom,
W is $C_{1-4}$ alkylene,
A is phenylene, thiophene-di-yl or pyridine-di-yl optionally substituted by 1 to 3 (preferably 1 or 2) substituents selected from the group consisting of
(1) a halogen atom,
(2) nitro,
(3) $C_{1-6}$ alkyl optionally substituted by 1 to 3 halogen atoms, and
(4) $C_{1-6}$ alkoxy,
B is a group represented by the formula:

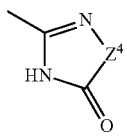

wherein $Z^4$ is an oxygen atom or a sulfur atom, or tetrazolyl, and
two $R^4$ are each independently (a) a hydrogen atom, (b) a halogen atom, (c) $C_{1-6}$ alkyl optionally substituted by 1 to 3 substituents selected from the group consisting of hydroxy, a halogen atom and $C_{1-6}$ alkoxy or (d) $C_{3-6}$ cycloalkyl, or a salt thereof.
[Compound A3]
A group represented by the formula:

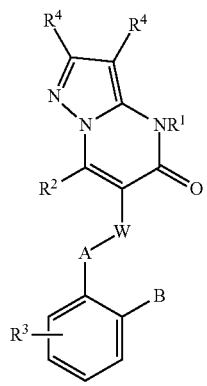

wherein
$R^1$ is
[1] a 3- to 10-membered nonaromatic cyclic group (preferably, cyclohexyl (the cyclohexyl may form, together with the ring formed by two substituents, a spirocyclic group (e.g., 1,4-dioxaspiro[4.5]dec-8-yl)), tetrahydropyranyl) optionally substituted by 1 to 3 substituents selected from the group consisting of
  (1) oxo,
  (2) hydroxy,
  (3) $C_{1-6}$ alkoxy optionally substituted by 1 to 4 substituents selected from
    (a) a halogen atom,
    (b) hydroxy,
    (c) $C_{3-6}$ cycloalkyl optionally substituted by hydroxy,
    (d) $C_{1-6}$ alkyl-carbonyl optionally substituted by 1 to 3 halogen atoms, and
    (e) $C_{3-10}$ cycloalkyl-carbonyl,
  (4) $C_{3-10}$ cycloalkyloxy optionally substituted by 1 to 3 substituents selected from the group consisting of
    (a) hydroxy, and
    (b) $C_{1-6}$ alkyl, and
  (5) $C_{1-6}$ alkyl-carbonyloxy optionally substituted by 1 to 3 substituents selected from
    (a) hydroxy, and
    (b) $C_{1-6}$ alkyl-carbonyloxy, or
[2] 5- or 6-membered aromatic ring (preferably, phenyl) optionally substituted by $C_{1-6}$ alkoxy,
$R^2$ is $C_{1-6}$ alkyl,
$R^3$ is a hydrogen atom,
W is methylene or —CH(CH$_3$)—,
A is phenylene or pyridine-di-yl optionally substituted by 1 to 3 (preferably 1 or 2) substituents selected from
(1) a halogen atom,
(2) nitro,
(3) $C_{1-6}$ alkyl, and
(4) $C_{1-6}$ alkoxy,
B is a group represented by the formula:

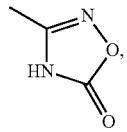

or tetrazolyl, and
two $R^4$ are each independently a hydrogen atom, a halogen atom, or $C_{1-6}$ alkyl, or a salt thereof.
[Compound A4]
A compound represented by the formula:

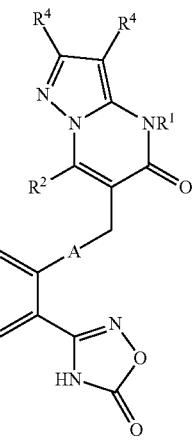

wherein
R² is C₃₋₈ cycloalkyl optionally substituted by C₁₋₆ alkoxy optionally substituted by
1) a halogen atom,
2) cyano,
3) hydroxy, or
4) C₁₋₆ alkoxy optionally substituted by a halogen atom,
R² is C₁₋₆ alkyl,
A is phenylene optionally substituted by a halogen atom, and
R⁴ are each independently a hydrogen atom or methyl, or a salt thereof.

[Compound A5]
A compound represented by the formula:

wherein
R¹ is cyclohexyl optionally substituted by C₁₋₆ alkoxy optionally substituted by hydroxy, and
R² is C₁₋₆ alkyl, or a salt thereof.

[Compound B1]
A compound represented by the formula:

wherein
R¹ is a hydrogen atom, optionally substituted C₁₋₆ alkyl, an optionally substituted 3- to 10-membered nonaromatic ring or an optionally substituted 5- or 6-membered aromatic ring,
R² is optionally substituted C₁₋₆ alkyl,
R³ is a hydrogen atom or a halogen atom,
W is C₁₋₄ alkylene,
A is optionally substituted phenylene, optionally substituted thiophene-di-yl or optionally substituted pyridine-di-yl, B is a group represented by the formula:

wherein i is —O— or —S—, j is —C(=O)—, —C(=S)— or —S(O)ₘ—, and m is an integer of 0, 1 or 2 (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl), or tetrazolyl, and
R⁴ is a hydrogen atom, a halogen atom, optionally substituted C₁₋₆ alkyl, optionally substituted C₁₋₆ alkoxy or optionally substituted C₃₋₆ cycloalkyl, or a salt thereof.

[Compound B2]
A compound represented by the formula:

wherein
R¹ is
[1] a hydrogen atom,
[2] C₁₋₆ alkyl optionally substituted by 1 to 4 substituents selected from the group consisting of
 (1) a halogen atom,
 (2) hydroxy,
 (3) optionally halogenated C₁₋₆ alkoxy,
 (4) carboxy optionally substituted by C₁₋₆ alkoxy,
 (5) C₁₋₆ alkyl-carbonyl optionally substituted by 1 to 3 halogen atoms,
 (6) C₃₋₁₀ cycloalkyl-carbonyl,
 (7) C₆₋₁₄ aryl-carbonyl optionally substituted by 1 to 3 halogen atoms,
 (8) carbamoyl,
 (9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) C₁₋₆ alkyl optionally substituted by hydroxy, (c) C₆₋₁₄ aryl, (d) C₁₋₆ alkoxy and (e) C₁₋₆ alkyl-carbonyl, and
 (10) C₁₋₆ alkoxyimino,
[3] a 3- to 10-membered nonaromatic cyclic group (preferably, cyclobutyl, cyclohexyl, cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
 (1) oxo,
 (2) hydroxy, (3) amino optionally substituted by 1 or 2 substituents selected from
  (a) $C_{1-6}$ alkyl, and
  (b) a 5- or 6-membered heterocyclic group,
(4) cyano,
(5) $C_{1-6}$ alkyl optionally substituted by 1 to 3 substituents selected from
  (a) hydroxy,
  (b) a halogen atom,
  (c) $C_{1-6}$ alkoxy, and
  (d) a 5- or 6-membered heterocyclic group,
(6) $C_{6-14}$ aryl optionally substituted by hydroxy,
(7) $C_{7-16}$ aralkyl,
(8) a heterocyclic group optionally substituted by $C_{1-6}$ alkyl,
(9) $C_{1-6}$ alkoxy optionally substituted by 1 to 4 substituents selected from
  (a) a halogen atom,
  (b) hydroxy,
  (c) $C_{3-6}$ cycloalkyl optionally substituted by 1 to 3 substituents selected from the group consisting of $C_{1-6}$ alkyl optionally substituted by hydroxy, hydroxy, carbamoyl and cyano,
  (d) $C_{1-6}$ alkoxy,
  (e) cyano,
  (f) $C_{1-6}$ alkyl-carbonyl optionally substituted by 1 to 3 halogen atoms,
  (g) $C_{3-10}$ cycloalkyl-carbonyl,
  (h) carbamoyl,
  (i) $C_{1-6}$ alkoxyimino,
  (j) $C_{1-6}$ alkylthio,
  (k) $C_{1-6}$ alkylsulfonyl,
  (l) $C_{1-6}$ alkylcarbonyloxy,
  (m) $C_{3-6}$ cycloalkyloxy optionally substituted by hydroxy, and
  (n) a 5- or 6-membered heterocyclic group optionally substituted by 1 to 3 substituents selected from the group consisting of $C_{1-6}$ alkyl and oxo,
(10) $C_{2-6}$ alkenyloxy optionally substituted by hydroxy,
(11) $C_{3-10}$ cycloalkyloxy optionally substituted by 1 to 3 substituents selected from the group consisting of
  (a) oxo,
  (b) hydroxy, and
  (c) $C_{1-6}$ alkyl optionally substituted by hydroxy,
(12) $C_{6-14}$ aryloxy optionally substituted by 1 to 3 substituents selected from
  (a) hydroxy,
  (b) $C_{1-6}$ alkyl optionally substituted by hydroxy,
  (c) $C_{1-6}$ alkyl-carbonyl, and
  (d) $C_{1-6}$ alkoxy,
(13) 5- or 6-membered heterocyclyl-oxy optionally substituted by 1 to 3 substituents selected from
  (a) hydroxy, and
  (b) $C_{1-6}$ alkyl,
(14) $C_{1-6}$ alkyl-carbonyloxy optionally substituted by 1 to 3 substituents selected from
  (a) hydroxy, and
  (b) $C_{1-6}$ alkyl-carbonyloxy,
(15) carboxy optionally substituted by $C_{1-6}$ alkoxy,
(16) $C_{1-6}$ alkyl-carbonyl,
(17) $C_{6-14}$ aryl-carbonyl optionally substituted by $C_{1-6}$ alkoxy,
(18) 5- or 6-membered heterocyclyl-carbonyl,
(19) carbamoyl,
(20) $C_{1-3}$ alkylidene optionally substituted by hydroxy, and
(21) imino (=NH) optionally substituted by
  (a) $C_{1-6}$ alkoxy optionally substituted by hydroxy, or
  (b) 5- or 6-membered heterocyclyl-oxy, or

[4] 5- or 6-membered aromatic ring (preferably, phenyl, thienyl) optionally substituted by 1 to 3 substituents selected from the group consisting of
  (1) a halogen atom,
  (2) $C_{1-6}$ alkyl optionally substituted by hydroxy,
  (3) $C_{1-6}$ alkoxy optionally substituted by 1 to 3 substituents selected from
    (a) hydroxy, and
    (b) $C_{1-6}$ alkyl-carbonyl, and
  (4) $C_{1-6}$ alkyl-carbonyl,
$R^2$ is $C_{1-6}$ alkyl,
$R^3$ is a hydrogen atom or a halogen atom,
W is $C_{1-4}$ alkylene,
A is phenylene, thiophene-di-yl or pyridine-di-yl optionally substituted by 1 to 3 (preferably 1 or 2) substituents selected from the group consisting of
  (1) a halogen atom,
  (2) nitro,
  (3) $C_{1-6}$ alkyl optionally substituted by 1 to 3 halogen atoms, and
  (4) $C_{1-6}$ alkoxy,
B is a group represented by the formula:

wherein $Z^4$ is an oxygen atom or a sulfur atom, or tetrazolyl, and
$R^4$ is (a) a hydrogen atom, (b) a halogen atom, (c) $C_{1-6}$ alkyl optionally substituted by 1 to 3 substituents selected from the group consisting of hydroxy, a halogen atom and $C_{1-6}$ alkoxy or (d) $C_{3-6}$ cycloalkyl, or a salt thereof.

[Compound B3]
A compound represented by the formula:

wherein
$R^1$ is
[1] a hydrogen atom,
[2] $C_{1-6}$ alkyl optionally substituted by 1 to 4 substituents selected from the group consisting of
  (1) a halogen atom,
  (2) hydroxy,
  (3) optionally halogenated $C_{1-6}$ alkoxy,
  (4) carboxy optionally substituted by $C_{1-6}$ alkoxy, (5) $C_{1-6}$ alkyl-carbonyl optionally substituted by 1 to 3 halogen atoms,
(6) $C_{3-10}$ cycloalkyl-carbonyl,
(7) $C_{6-14}$ aryl-carbonyl optionally substituted by 1 to 3 halogen atoms,
(8) carbamoyl,
(9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of a halogen atom, $C_{1-6}$ alkyl optionally substituted by hydroxy, $C_{6-14}$ aryl, $C_{1-6}$ alkoxy and $C_{1-6}$ alkyl-carbonyl, and
(10) $C_{1-6}$ alkoxyimino,
[3] a 3- to 10-membered nonaromatic cyclic group (e.g., cyclobutyl, cyclohexyl (the cyclohexyl may form, together with the ring formed by two substituents, an optionally substituted fused cyclic group or a spirocyclic group (e.g., 4,5,6,7-tetrahydro-1H-indazol-5-yl, 1-oxaspiro[4.5]dec-8-yl, 1,4-dioxaspiro[4.5]dec-8-yl, 1,5-dioxaspiro[5.5]undec-9-yl, 1-oxa-2-azaspiro[4.5]dec-2-en-8-yl, tetrahydrospiro[cyclohexane-1,2'-furo[3,4-d][1,3]dioxol]-4-yl, which is optionally substituted by 1 to 5 substituents selected from the group consisting of oxo, hydroxy, $C_{1-6}$ alkyl optionally substituted by hydroxyl and $C_{1-3}$ alkylidene)), cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
(1) oxo,
(2) hydroxy,
(3) amino optionally substituted by 1 or 2 substituents selected from
 (a) $C_{1-6}$ alkyl, and
 (b) a 5- or 6-membered heterocyclic group (preferably, tetrahydropyranyl),
(4) cyano,
(5) $C_{1-6}$ alkyl optionally substituted by 1 to 3 substituents selected from
 (a) hydroxy,
 (b) a halogen atom,
 (c) $C_{1-6}$ alkoxy, and
 (d) a 5- or 6-membered heterocyclic group (preferably, morpholino),
(6) $C_{6-14}$ aryl optionally substituted by hydroxy,
(7) $C_{7-16}$ aralkyl,
(8) a heterocyclic group (preferably, morpholino, 1,2,4-oxadiazolyl, 1,3,4-oxadiazolyl, oxazolyl, 4,5-dihydroisoxazolyl, tetrahydropyranyl) optionally substituted by $C_{1-6}$ alkyl,
(9) $C_{1-6}$ alkoxy optionally substituted by 1 to 4 substituents selected from
 (a) hydroxy,
 (b) $C_{3-6}$ cycloalkyl optionally substituted by 1 to 3 substituents selected from the group consisting of $C_{1-6}$ alkyl optionally substituted by hydroxy, hydroxy, carbamoyl and cyano,
 (c) $C_{1-6}$ alkoxy,
 (d) cyano,
 (e) $C_{1-6}$ alkyl-carbonyl optionally substituted by 1 to 3 halogen atoms,
 (f) carbamoyl,
 (g) $C_{1-6}$ alkoxyimino,
 (h) $C_{1-6}$ alkylthio,
 (i) $C_{1-6}$ alkylsulfonyl,
 (j) $C_{1-6}$ alkylcarbonyloxy, and
 (k) a 5- or 6-membered heterocyclic group (preferably, morpholino, imidazolyl, 1,3,4-oxadiazolyl, 4,5-dihydro-1,3,4-oxadiazolyl, 1,2,4-triazolyl, tetrahydrofuryl) optionally substituted by 1 to 3 substituents selected from the group consisting of $C_{1-6}$ alkyl and oxo,
(10) $C_{2-6}$ alkenyloxy optionally substituted by hydroxy,
(11) $C_{3-10}$ cycloalkyloxy optionally substituted by 1 to 3 substituents selected from the group consisting of
 (a) oxo,
 (b) hydroxy, and
 (c) $C_{1-6}$ alkyl optionally substituted by hydroxy,
(12) $C_{6-14}$ aryloxy optionally substituted by 1 to 3 substituents selected from
 (a) hydroxy,
 (b) $C_{1-6}$ alkyl optionally substituted by hydroxy,
 (c) $C_{1-6}$ alkyl-carbonyl, and
 (d) $C_{1-6}$ alkoxy,
(13) 5- or 6-membered heterocyclyl-oxy (preferably, tetrahydrofuryloxy, isoxazolyloxy) optionally substituted by 1 to 3 substituents selected from
 (a) hydroxy, and
 (b) $C_{1-6}$ alkyl,
(14) carboxy optionally substituted by $C_{1-6}$ alkoxy,
(15) $C_{6-14}$ aryl-carbonyl optionally substituted by $C_{1-6}$ alkoxy,
(16) 5- or 6-membered heterocyclyl-carbonyl (preferably, tetrahydropyranylcarbonyl),
(17) carbamoyl,
(18) $C_{1-3}$ alkylidene optionally substituted by hydroxy, and
(19) imino (=NH) optionally substituted by
 (a) $C_{1-6}$ alkoxy optionally substituted by hydroxy, or
 (b) 5- or 6-membered heterocyclyl-oxy (preferably, tetrahydropyranyloxy), or
[4] a 5- or 6-membered aromatic ring (preferably, phenyl (the phenyl may form, together with the ring formed by two substituents, an optionally substituted fused cyclic group or a spirocyclic group (e.g., 2,3-dihydro-1-benzofuran-5-yl optionally substituted by $C_{1-6}$ alkyl)), thienyl) optionally substituted by 1 to 3 substituents selected from the group consisting of
(1) a halogen atom,
(2) $C_{1-6}$ alkyl optionally substituted by hydroxy, and
(3) $C_{1-6}$ alkoxy optionally substituted by 1 to 3 substituents selected from
 (a) hydroxy, and
 (b) $C_{1-6}$ alkyl-carbonyl,
$R^2$ is $C_{1-6}$ alkyl,
W is methylene or —CH(CH$_3$)—,
A is phenylene, thiophene-di-y or pyridine-di-yl optionally substituted by 1 to 3 (preferably 1 or 2) substituents selected from the group consisting of
(1) a halogen atom, and
(2) $C_{1-6}$ alkyl optionally substituted by 1 to 3 halogen atoms,
B is a group represented by the formula:

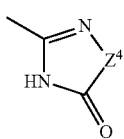

wherein $Z^4$ is an oxygen atom or a sulfur atom, or tetrazolyl, and $R^4$ is (a) a hydrogen atom, (b) a halogen atom, (c) $C_{1-6}$ alkyl optionally substituted by 1 to 3 substituents selected from the group consisting of hydroxy, a halogen atom and $C_{1-6}$ alkoxy or (d) $C_{3-6}$ cycloalkyl, or a salt thereof.

[Compound B4]

A compound represented by the formula:

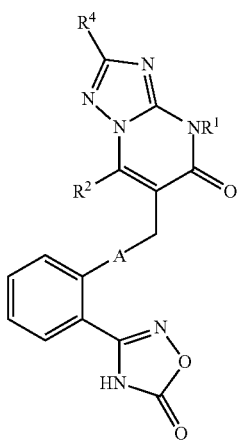

wherein
$R^1$ is $C_{3-8}$ cycloalkyl optionally substituted by $C_{1-6}$ alkoxy optionally substituted by
1) a halogen atom,
2) cyano,
3) hydroxy, or
4) $C_{1-6}$ alkoxy optionally substituted by a halogen atom,
$R^2$ is $C_{1-6}$ alkyl,
A is phenylene optionally substituted by a halogen atom, and
$R^4$ is a hydrogen atom or methyl, or a salt thereof.

[Compound B5]

A compound represented by the formula:

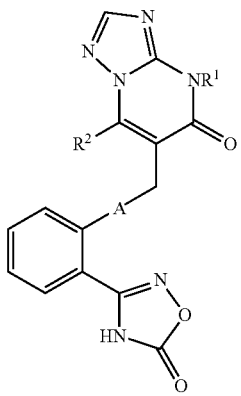

wherein
$R^1$ is cyclohexyl optionally substituted by $C_{1-6}$ alkoxy optionally substituted by hydroxy,
$R^2$ is $C_{1-6}$ alkyl, and
A is phenylene optionally substituted by a halogen atom, or a salt thereof.

[Compound C1]

A compound represented by the formula:

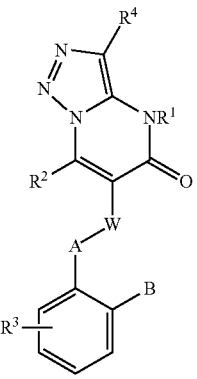

wherein
$R^1$ is a hydrogen atom, optionally substituted $C_{1-6}$ alkyl, an optionally substituted 3- to 10-membered nonaromatic ring or an optionally substituted 5- or 6-membered aromatic ring, more preferably, an optionally substituted 3- to 10-membered nonaromatic ring,
$R^2$ is optionally substituted $C_{1-6}$ alkyl,
$R^3$ is a hydrogen atom or a halogen atom,
W is $C_{1-4}$ alkylene,
A is optionally substituted phenylene, optionally substituted thiophene-di-yl or optionally substituted pyridine-di-yl,
B is a group represented by the formula:

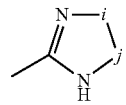

wherein i is —O— or —S—, j is —C(=O)—, —C(=S)— or —S(O)$_m$—, and m is an integer of 0, 1 or 2 (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl), or tetrazolyl, and
$R^4$ is a hydrogen atom, a halogen atom, optionally substituted $C_{1-6}$ alkyl, optionally substituted $C_{1-6}$ alkoxy or optionally substituted $C_{3-6}$ cycloalkyl, or a salt thereof.

[Compound C2]

A compound represented by the formula:

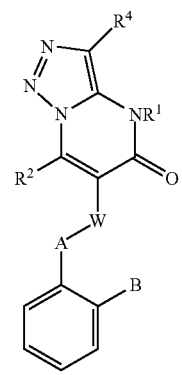

wherein
R¹ is
[1] a hydrogen atom,
[2] $C_{1-6}$ alkyl optionally substituted by 1 to 4 substituents selected from the group consisting of
  (1) a halogen atom,
  (2) hydroxy,
  (3) optionally halogenated $C_{1-6}$ alkoxy,
  (4) carboxy optionally substituted by $C_{1-6}$ alkoxy,
  (5) $C_{1-6}$ alkyl-carbonyl optionally substituted by 1 to 3 halogen atoms,
  (6) $C_{3-10}$ cycloalkyl-carbonyl,
  (7) $C_{6-14}$ aryl-carbonyl optionally substituted by 1 to 3 halogen atoms,
  (8) carbamoyl,
  (9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) $C_{1-6}$ alkyl optionally substituted by hydroxy, (c) $C_{6-14}$ aryl, (d) $C_{1-6}$ alkoxy and (e) $C_{1-6}$ alkyl-carbonyl, and
  (10) $C_{1-6}$ alkoxyimino,
[3] a 3- to 10-membered nonaromatic cyclic group (e.g., cyclobutyl, cyclohexyl, cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
  (1) oxo,
  (2) hydroxy,
  (3) amino optionally substituted by 1 or 2 substituents selected from
    (a) $C_{1-6}$ alkyl, and
    (b) a 5- or 6-membered heterocyclic group,
  (4) cyano,
  (5) $C_{1-6}$ alkyl optionally substituted by 1 to 3 substituents selected from
    (a) hydroxy,
    (b) a halogen atom,
    (c) $C_{1-6}$ alkoxy, and
    (d) a 5- or 6-membered heterocyclic group,
  (6) $C_{6-14}$ aryl optionally substituted by hydroxy,
  (7) $C_{7-16}$ aralkyl,
  (8) a heterocyclic group optionally substituted by $C_{1-6}$ alkyl,
  (9) $C_{1-6}$ alkoxy optionally substituted by 1 to 4 substituents selected from
    (a) a halogen atom,
    (b) hydroxy,
    (c) $C_{3-6}$ cycloalkyl optionally substituted by 1 to 3 substituents selected from the group consisting of $C_{1-6}$ alkyl optionally substituted by hydroxy, hydroxy, carbamoyl and cyano,
    (d) $C_{1-6}$ alkoxy,
    (e) cyano,
    (f) $C_{1-6}$ alkyl-carbonyl optionally substituted by 1 to 3 halogen atoms,
    (g) $C_{3-10}$ cycloalkyl-carbonyl,
    (h) carbamoyl,
    (i) $C_{1-6}$ alkoxyimino,
    (j) $C_{1-6}$ alkylthio,
    (k) $C_{1-6}$ alkylsulfonyl,
    (l) $C_{1-6}$ alkylcarbonyloxy,
    (m) $C_{3-6}$ cycloalkyloxy optionally substituted by hydroxy, and
    (n) a 5- or 6-membered heterocyclic group optionally substituted by 1 to 3 substituents selected from the group consisting of $C_{1-6}$ alkyl and oxo,
  (10) $C_{2-6}$ alkenyloxy optionally substituted by hydroxy,
  (11) $C_{3-10}$ cycloalkyloxy optionally substituted by 1 to 3 substituents selected from the group consisting of
    (a) oxo,
    (b) hydroxy, and
    (c) $C_{1-6}$ alkyl optionally substituted by hydroxy,
  (12) $C_{6-14}$ aryloxy optionally substituted by 1 to 3 substituents selected from
    (a) hydroxy,
    (b) $C_{1-6}$ alkyl optionally substituted by hydroxy,
    (c) $C_{1-6}$ alkyl-carbonyl, and
    (d) $C_{1-6}$ alkoxy,
  (13) 5- or 6-membered heterocyclyl-oxy optionally substituted by 1 to 3 substituents selected from
    (a) hydroxy, and
    (b) $C_{1-6}$ alkyl,
  (14) $C_{1-6}$ alkyl-carbonyloxy optionally substituted by 1 to 3 substituents selected from
    (a) hydroxy, and
    (b) $C_{1-6}$ alkyl-carbonyloxy,
  (15) carboxy optionally substituted by $C_{1-6}$ alkoxy,
  (16) $C_{1-6}$ alkyl-carbonyl,
  (17) $C_{6-14}$ aryl-carbonyl optionally substituted by $C_{1-6}$ alkoxy,
  (18) 5- or 6-membered heterocyclyl-carbonyl,
  (19) carbamoyl,
  (20) $C_{1-3}$ alkylidene optionally substituted by hydroxy, and
  (21) imino (=NH) optionally substituted by
    (a) $C_{1-6}$ alkoxy optionally substituted by hydroxy, or
    (b) 5- or 6-membered heterocyclyl-oxy, or
[4] a 5- or 6-membered aromatic ring (preferably, phenyl, thienyl) optionally substituted by 1 to 3 substituents selected from the group consisting of
  (1) a halogen atom,
  (2) $C_{1-6}$ alkyl optionally substituted by hydroxy,
  (3) $C_{1-6}$ alkoxy optionally substituted by 1 to 3 substituents selected from
    (a) hydroxy, and
    (b) $C_{1-6}$ alkyl-carbonyl, and
  (4) $C_{1-6}$ alkyl-carbonyl,
R² is $C_{1-6}$ alkyl,
W is $C_{1-4}$ alkylene,
A is phenylene, thiophene-di-y or pyridine-di-yl optionally substituted by 1 to 3 (preferably 1 or 2) substituents selected from
  (1) a halogen atom,
  (2) nitro,
  (3) $C_{1-6}$ alkyl optionally substituted by 1 to 3 halogen atoms, and
  (4) $C_{1-6}$ alkoxy,
B is a group represented by the formula:

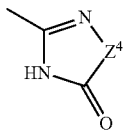

wherein $Z^4$ is an oxygen atom or a sulfur atom, or tetrazolyl, and
R⁴ is (a) a hydrogen atom, (b) a halogen atom, (c) $C_{1-6}$ alkyl optionally substituted by 1 to 3 substituents selected from the group consisting of hydroxy, a halogen atom and $C_{1-6}$ alkoxy or (d) $C_{3-6}$ cycloalkyl, or a salt thereof.

[Compound C3]
A compound represented by the formula:

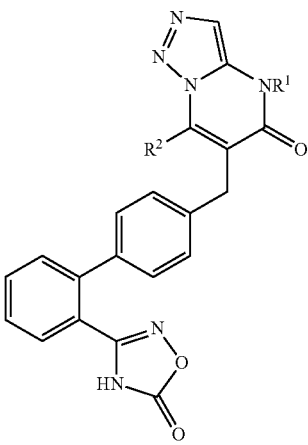

wherein
$R^1$ is a 3- to 10-membered nonaromatic cyclic group (e.g., cyclohexyl, tetrahydropyranyl) optionally substituted by $C_{1-6}$ alkoxy (the $C_{1-6}$ alkoxy is optionally substituted by hydroxy), and
$R^2$ is $C_{1-6}$ alkyl, or a salt thereof.

[Compound D1]
A compound represented by the formula:

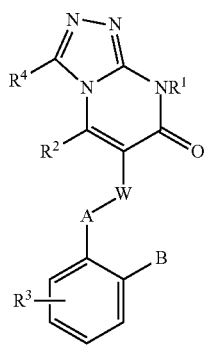

wherein
$R^1$ is a hydrogen atom, optionally substituted $C_{1-6}$ alkyl, an optionally substituted 3- to 10-membered nonaromatic ring or an optionally substituted 5- or 6-membered aromatic ring,
$R^2$ is optionally substituted $C_{1-6}$ alkyl,
$R^3$ is a hydrogen atom or a halogen atom,
W is $C_{1-4}$ alkylene,
A is optionally substituted phenylene, optionally substituted thiophene-di-yl or optionally substituted pyridine-di-yl,
B is a group represented by the formula:

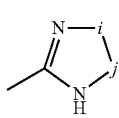

wherein i is —O— or —S—, j is —C(=O)—, —C(=S)— or —S(O)$_m$—, and m is an integer of 0, 1 or 2 (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl), or tetrazolyl, and $R^4$ is a hydrogen atom, a halogen atom, optionally substituted $C_{1-6}$ alkyl, optionally substituted $C_{1-6}$ alkoxy or optionally substituted $C_{3-6}$ cycloalkyl, or a salt thereof.

[Compound D2]
A compound represented by the formula:

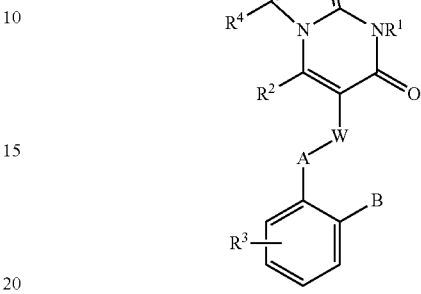

wherein
$R^1$ is
[1] a hydrogen atom,
[2] $C_{1-6}$ alkyl optionally substituted by 1 to 4 substituents selected from the group consisting of
  (1) a halogen atom,
  (2) hydroxy,
  (3) optionally halogenated $C_{1-6}$ alkoxy,
  (4) carboxy optionally substituted by $C_{1-6}$ alkoxy,
  (5) $C_{1-6}$ alkyl-carbonyl optionally substituted by 1 to 3 halogen atoms,
  (6) $C_{3-10}$ cycloalkyl-carbonyl,
  (7) $C_{6-14}$ aryl-carbonyl optionally substituted by 1 to 3 halogen atoms,
  (8) carbamoyl,
  (9) a 3- to 14-membered cyclic group (preferably, cyclopropyl, cyclohexyl, phenyl, pyridyl, oxetanyl, benzimidazolyl (e.g., benzimidazol-2-yl)) optionally substituted by 1 to 3 substituents selected from the group consisting of (a) a halogen atom, (b) $C_{1-6}$ alkyl optionally substituted by hydroxy, (c) $C_{6-14}$ aryl, (d) $C_{1-6}$ alkoxy and (e) $C_{1-6}$ alkyl-carbonyl, and
  (10) $C_{1-6}$ alkoxyimino,
[3] a 3- to 10-membered nonaromatic cyclic group (preferably cyclobutyl, cyclohexyl (the cyclohexyl may form, together with the ring formed by two substituents, a spirocyclic group (e.g., 1,4-dioxaspiro[4.5]dec-8-yl)), cyclohexenyl, tetrahydrofuryl, piperidyl (e.g., piperidin-4-yl), tetrahydropyranyl, tetrahydrothiopyranyl, tetrahydroindazolyl (e.g., 4,5,6,7-tetrahydroindazol-5-yl), adamantyl, oxepanyl (e.g., oxepan-4-yl)) optionally substituted by 1 to 3 substituents selected from the group consisting of
  (1) oxo,
  (2) hydroxy,
  (3) amino optionally substituted by 1 or 2 substituents selected from
    (a) $C_{1-6}$ alkyl, and
    (b) a 5- or 6-membered heterocyclic group,
  (4) cyano,
  (5) $C_{1-6}$ alkyl optionally substituted by 1 to 3 substituents selected from
    (a) hydroxy,
    (b) a halogen atom,
    (c) $C_{1-6}$ alkoxy, and
    (d) a 5- or 6-membered heterocyclic group, (6) $C_{6-14}$ aryl optionally substituted by hydroxy,
(7) $C_{7-16}$ aralkyl,
(8) a heterocyclic group optionally substituted by $C_{1-6}$ alkyl,
(9) $C_{1-6}$ alkoxy optionally substituted by 1 to 4 substituents selected from
  (a) a halogen atom,
  (b) hydroxy,
  (c) $C_{3-6}$ cycloalkyl optionally substituted by 1 to 3 substituents selected from the group consisting of $C_{1-6}$ alkyl optionally substituted by hydroxy, hydroxy, carbamoyl and cyano,
  (d) $C_{1-6}$ alkoxy,
  (e) cyano,
  (f) $C_{1-6}$ alkyl-carbonyl optionally substituted by 1 to 3 halogen atoms,
  (g) $C_{3-10}$ cycloalkyl-carbonyl,
  (h) carbamoyl,
  (i) $C_{1-6}$ alkoxyimino,
  (j) $C_{1-6}$ alkylthio,
  (k) $C_{1-6}$ alkylsulfonyl,
  (l) $C_{1-6}$ alkylcarbonyloxy,
  (m) $C_{3-6}$ cycloalkyloxy optionally substituted by hydroxy, and
  (n) a 5- or 6-membered heterocyclic group optionally substituted by 1 to 3 substituents selected from the group consisting of $C_{1-6}$ alkyl and oxo,
(10) $C_{2-6}$ alkenyloxy optionally substituted by hydroxy,
(11) $C_{3-10}$ cycloalkyloxy optionally substituted by 1 to 3 substituents selected from the group consisting of
  (a) oxo,
  (b) hydroxy, and
  (c) $C_{1-6}$ alkyl optionally substituted by hydroxy,
(12) $C_{6-14}$ aryloxy optionally substituted by 1 to 3 substituents selected from
  (a) hydroxy,
  (b) $C_{1-6}$ alkyl optionally substituted by hydroxy,
  (c) $C_{1-6}$ alkyl-carbonyl, and
  (d) $C_{1-6}$ alkoxy,
(13) 5- or 6-membered heterocyclyl-oxy optionally substituted by 1 to 3 substituents selected from
  (a) hydroxy, and
  (b) $C_{1-6}$ alkyl,
(14) $C_{1-6}$ alkyl-carbonyloxy optionally substituted by 1 to 3 substituents selected from
  (a) hydroxy, and
  (b) $C_{1-6}$ alkyl-carbonyloxy,
(15) carboxy optionally substituted by $C_{1-6}$ alkoxy,
(16) $C_{1-6}$ alkyl-carbonyl,
(17) $C_{6-14}$ aryl-carbonyl optionally substituted by $C_{1-6}$ alkoxy,
(18) 5- or 6-membered heterocyclyl-carbonyl,
(19) carbamoyl,
(20) $C_{1-3}$ alkylidene optionally substituted by hydroxy, and
(21) imino (=NH) optionally substituted by
  (a) $C_{1-6}$ alkoxy optionally substituted by hydroxy, or
  (b) 5- or 6-membered heterocyclyl-oxy, or
[4] a 5- or 6-membered aromatic ring (preferably, phenyl, thienyl) optionally substituted by 1 to 3 substituents selected from the group consisting of
(1) a halogen atom,
(2) $C_{1-6}$ alkyl optionally substituted by hydroxy,
(3) $C_{1-6}$ alkoxy optionally substituted by 1 to 3 substituents selected from
  (a) hydroxy, and
  (b) $C_{1-6}$ alkyl-carbonyl, and
(4) $C_{1-6}$ alkyl-carbonyl, $R^2$ is $C_{1-6}$ alkyl,
$R^3$ is a hydrogen atom or a halogen atom,
W is $C_{1-4}$ alkylene,
A is phenylene, thiophene-di-y or pyridine-di-yl optionally substituted by 1 to 3 (preferably 1 or 2) substituents selected from
(1) a halogen atom,
(2) nitro,
(3) $C_{1-6}$ alkyl optionally substituted by 1 to 3 halogen atoms, and
(4) $C_{1-6}$ alkoxy,
B is a group represented by the formula:

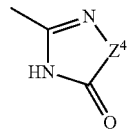

wherein $Z^4$ is an oxygen atom or a sulfur atom, or tetrazolyl, and
$R^4$ is (a) a hydrogen atom, (b) a halogen atom, (c) $C_{1-6}$ alkyl optionally substituted by 1 to 3 substituents selected from the group consisting of hydroxy, a halogen atom and $C_{1-6}$ alkoxy or (d) $C_{3-6}$ cycloalkyl, or a salt thereof.
[Compound D3]
A compound represented by the formula:

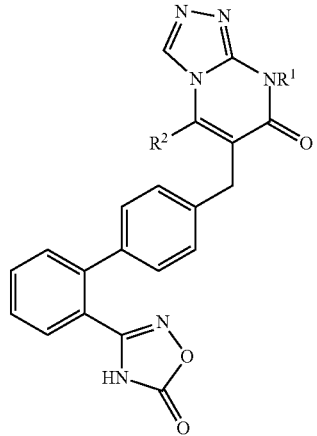

wherein
$R^1$ is a 5- or 6-membered aromatic ring (preferably, phenyl) optionally substituted by $C_{1-6}$ alkoxy, and
$R^2$ is $C_{1-6}$ alkyl, or a salt thereof.
[Compound E]
4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one or a salt thereof, 6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one or a salt thereof, or (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one and (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one monopotassium salt (1/1) hydrate.

Examples of the salt of a compound represented by the formula (I) include a pharmacologically acceptable salt and the like. Examples thereof include acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like; salt with a metal salt such as sodium, potassium, magnesium, calcium and the like; salt with an organic base such as trimethylamine, triethylamine, pyridine, picoline, N-methylpyrrolidine, N-methylpiperidine, N-methylmorpholine and the like, and the like.

A prodrug of a compound represented by the formula (I) or a salt thereof (hereinafter sometimes to be referred to as compound (I)) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; and a compound which is converted to the compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxol-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se.

A prodrug of the compound (I) may also be one which is converted into the compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

When the compound (I) has isomers such as optical isomer, stereoisomer, positional isomer, rotational isomer and the like, any isomers and mixture of isomers are encompassed in the compound (I). For example, when the compound (I) has an optical isomer, an optical isomer separated from a racemate is also encompassed in the compound (I). These isomers can be obtained as independent products by a synthesis means or a separation means (e.g., concentration, solvent extraction, column chromatography, recrystallization and the like) known per se.

The compound (I) may be a crystal or an amorphous form. When the compound (I) is a crystal, both a single crystal and crystal mixtures are encompassed in the compound (I). Crystals can be produced by crystallization according to crystallization methods known per se.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion and the like) at room temperature. The cocrystal and cocrystal salt can be produced by applying a cocrystallization method known per se.

The compound (I) may be a solvate (e.g., hydrate etc.) or a non-solvate, both of which are encompassed in the compound (I).

The compound (I) may be labeled with an isotope (e.g., $^3$H, $^{14}$C, $^{35}$S, $^{125}$I and the like) and the like.

Deuterium-converted compound wherein $^1$H has been converted to $^2$H(D) are also encompassed in the compound (I).

Since compound (I) or a prodrug thereof (hereinafter sometimes to be abbreviated as the compound of the present invention) has a strong angiotensin II antagonistic activity (particularly AT1 receptor antagonistic activity), it is useful as an agent for the prophylaxis or treatment of a disease in a mammal (e.g., human, monkey, cat, swine, horse, bovine, mouse, rat, guinea pig, dog, rabbit etc.), which is developed (or a disease whose onset is promoted) by coarctation or growth of the blood vessel or an organ disorder expressed via an angiotensin II receptor, by the presence of angiotensin II or by a factor induced by the presence of angiotensin II.

Examples of such disease include hypertension, blood pressure circadian rhythm abnormality (e.g., early-morning hypertension, nocturnal hypertension etc.), heart diseases (e.g., cardiac hypertrophy, acute heart failure, chronic heart failure including cardiac failure, impaired vasodilation, cardiac myopathy, angina pectoris, myocarditis, atrial fibrillation, arrhythmia, tachycardia, myocardial infarction etc.), cerebrovascular disorders (e.g., asymptomatic cerebrovascular disorder, transient cerebral ischemia, cerebral apoplexy, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, renal failure, thrombotic vasculopathy, complication of dialysis, organ dysfunction including nephropathy by radiation damage etc.), arteriosclerosis including atherosclerosis (e.g., aneurysm, coronary sclerosis, cerebral arteriosclerosis, peripheral arterial sclerosis etc.), vascular hypertrophy, vascular hypertrophy or obliteration and organ disorders after intervention (e.g., percutaneous transluminal coronary angioplasty, stenting, coronary angioscopy, intravascular ultrasound, intracoronary thrombolysis etc.), vascular re-obliteration and restenosis after bypass, polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Buerger's disease etc.), metabolic and/or nutritional disorders (e.g., obesity, hyperlipemia, hypercholesterolemia, hyperuricacidemia, hyperkalemia, hypernatremia etc.), nerve degeneration diseases (e.g., Alzheimer's disease, Parkinson's disease, amyotrophic lateral sclerosis, AIDS encephalopathy etc.), central nervous system disorders (e.g., disorders such as cerebral hemorrhage, cerebral infarction etc., and their sequela and complication, head injury, spinal injury, cerebral edema, sensory malfunction, sensory functional disorder, autonomic nervous system disorder, autonomic nervous system malfunction, multiple sclerosis etc.), dementia (cerebrovascular, senile etc.), defects of memory, disorder of consciousness, amnesia, anxiety symptom, catatonic symptom, discomfort mental state, psychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation and injury; remission of swelling; pharyngitis; cystitis; pneumonia; atopic dermatitis; inflammatory intestinal diseases such as Crohn's disease, ulcerative colitis etc.; meningitis; inflammatory ocular disease; pulmonary sarcoidosis such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematosus, scleroderma, polyarteritis etc.), hepatic diseases (e.g., nonalcoholic fatty hepatic disease or steatohepatitis, hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, osteoarthritis of the knee and joint tissue dysfunction and the like caused by diseases similar to these etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), sleep apnea syndrome, respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like.

Since the compound of the present invention can maintain a constant hypotensive activity irrespective of day and night, the dose and frequency can be reduced as compared to the administration of a compound other than the compound of the present invention, as well as elevation of blood pressure particularly problematic in patients with hypertension before and after awaking can be suppressed more effectively.

In addition, since the compound of the present invention suppresses the activity of angiotensin II in a sustained manner for a long time, it improves or suppresses progression of a disorder or abnormality in the biological function and physiological activity, which causes various diseases associated with adult diseases, aging and the like, and can primarily and secondarily prevent or suppress progression of a disease or pathology caused thereby. Examples of the disorder or abnormality in the biological function and physiological activity include a disorder or abnormality in the brain circulation or kidney circulation autoregulation, a circulatory disorders (e.g., peripheral, brain, microcirculatory etc.), cerebral blood barrier disorder, sodium chloride sensitivity, coagulation or fibrinolytic system abnormality, abnormality in the property of blood or blood cell components (e.g., enhancement in platelet aggregation, abnormality in red blood cell deformability, enhancement in leukocyte adhesiveness, increased blood viscosity etc.), production and promoted activity of growth factor or cytokine (e.g., PDGF, VEGF, FGF, interleukin, TNF-α, MCP-1 etc.), production and promoted infiltration of inflammatory system cell, promoted production of free radical, promotion of fatty deposition, endothelial dysfunction, endothelial, cell and organ disorder, edema, altered morphology of cell in smooth muscle and the like (altered morphology into proliferative form etc.), production and promoted function of blood vessel vasoactive substance or thrombus-induced substance (e.g., catecholamine, endothelin, thromboxane $A_2$ etc.), abnormal coarctation of blood vessel and the like, abnormal metabolism (e.g., serum lipid abnormality, blood glucose abnormality etc.), abnormal growth of cells and the like, angiogenesis (including abnormal vasculogenesis in abnormal capillary net formation of atherosclerosis focal adventitia) and the like. Particularly, the compound of the present invention can be used as a primary or a secondary agent for the prophylaxis or treatment of organ disorder associated with various diseases (e.g., cardiovascular disorder, cerebrovascular disorder and organ disorders associated therewith, organ disorder associated with circulatory diseases, organ disorder associated with diabetes, organ disorder after intervention etc.). Especially, since the compound of the present invention has a proteinuria suppressive activity, it can be used as a kidney protector. Hence, the compound of the present invention can be advantageously used even when patients with insulin resistance, impaired glucose tolerance, diabetes, hyperinsulinemia or obesity have concomitantly developed the above-mentioned disease or pathology, and can prevent the onset of hypertension or diabetes in such patients.

The compound of the present invention can be used as insulin sensitizer, agent for enhancing insulin sensitivity, retinoid related receptor function regulator, peroxisome proliferator-activated receptor ligand, retinoid X receptor ligand and the like. As used herein, the function regulator means both agonist and antagonist.

The compound of the present invention has hypoglycemic activity, hypolipidemic activity, insulin resistance improving activity, insulin sensitizing activity and peroxisome proliferator-activated receptor (hereinafter sometimes to be abbreviated as PPAR) γ (GenBank Accession No. L40904) agonist activity. As used herein, PPARγ may form a heterodimer receptor with retinoid X receptor (hereinafter sometimes to be abbreviated as RXR) α (GenBank Accession No. X52773), RXRβ (GenBank Accession No. M84820) or RXRγ (GenBank Accession No. U38480). The compound of the present invention has a selective agonist activity on PPARγ.

The compound of the present invention normalizes the intracellular insulin signal transduction mechanism, which mainly causes insulin resistance, thereby reducing insulin resistance and enhancing insulin activity, and has a glucose tolerance improvement activity. Therefore, the compound of the present invention can be used for mammals (e.g., human, monkey, cat, pig, horse, bovine, mouse, rat, guinea pig, dog, rabbit etc.) as an improving agent or an agent for the prophylaxis and/or treatment of the diseases in which insulin resistance is involved.

The compound of the present invention can be used as, for example, an agent for the prophylaxis or treatment of diabetes (e.g., type 1 diabetes, type 2 diabetes, gestational diabetes, obese diabetes); an agent for the prophylaxis or treatment of hyperlipemia or hyperlipidemia (e.g., hypertriglyceridemia, hypercholesterolemia, hypoHDL-emia, postprandial hyperlipemia); an agent for improving insulin resistance; an insulin sensitizer; an agent for the prophylaxis or treatment of impaired glucose tolerance (IGT); or an agent for preventing progression of hypertension, impaired glucose tolerance or obesity to diabetes. In addition, the compound of the present invention can be used as, for example, an agent for the prophylaxis or treatment of hyperinsulinemia or hypertension associated with insulin resistance, hypertension associated with impaired glucose tolerance, hypertension associated with diabetes (e.g., type II diabetes etc.), hypertension associated with hyperinsulinemia, hypertension associated with obesity, insulin resistance occurring in association with hypertension, impaired glucose tolerance occurring in association with hypertension, diabetes occurring in association with hypertension, hyperinsulinemia occurring in association with hypertension, or obesity occurring in association with hypertension. Moreover, the compound of the present invention can also be used for the treatment of patients with high normal blood pressure who has developed diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular disorder, peripheral blood circulation disorder], obesity and obesity complication, sleep apnea syndrome, osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, nonalcoholic steatohepatitis, hypertension, polycystic ovary syndrome, renal diseases (e.g., diabetic nephropathy, glomerulonephritis, glomerulosclerosis, nephrosis syndrome, hypertensive nephrosclerosis, end-stage renal disorder), muscular dystrophy, myocardial infarction, angina pectoris, cardiac failure, cerebrovascular disorders (e.g., cerebral infarction, cerebral apoplexy), insulin resistance syndrome, syndrome X, metabolic syndrome (pathology having 3 or more selected from hyper-triglycerid (TG)emia, low HDL cholesteremia (HDL-C), hypertension, abdomen obesity and impaired glucose tolerance), hyperinsulinemia, perception disorder in hyperinsulinemia, tumor (e.g., leukemia, breast cancer, prostate cancer, skin cancer), irritable bowel syndrome, acute or chronic diarrhea, inflammatory diseases (e.g., arteriosclerosis (e.g., atherosclerosis etc.), rheumatoid arthritis, spondylitis deformans, osteoarthritis, lumbago, gout, hyperuricemia, post-surgical or post-traumatic inflammation, swelling, neuralgia, pharyngolaryngitis, cystitis, hepatitis (including nonalcoholic steatohepatitis), pneumonia, pancreatitis, inflammatory colitis, ulcerative colitis), visceral obesity syndrome and the like.

The compound of the present invention can be used for the improvement of symptoms such as abdominal pain, nausea, vomiting, epigastric discomfort and the like associated with peptic ulcer, acute or chronic gastritis, biliary dyskinesia, cholecystitis or the like.

The compound of the present invention can also be used as an agent for the prophylaxis or treatment of inflammatory diseases involving TNF-α. Here, the inflammatory diseases involving TNF-α is an inflammatory disease developed by the presence of TNF-α and treated via a TNF-α suppressive effect. Examples of the inflammatory disease include diabetic complications (e.g., retinopathy, nephropathy, neuropathy, macroangiopathy), myocarditis, cardiomyopathy, cardiac failure, ischemic cardiac diseases, rheumatoid arthritis, spondylitis deformans, osteoarthritis, lumbago, gout, post-surgical or posttraumatic inflammation, swelling, neuralgia, pharyngolaryngitis, cystitis, hepatitis, pneumonia, gastric mucosa injury (including gastric mucosa injury caused by aspirin) and the like.

The compound of the present invention has an apoptosis suppressive activity and is also used as an agent for the prophylaxis or treatment of diseases involving promoted apoptosis. Here, examples of the disease involving promoted apoptosis include virus diseases (e.g., AIDS, fulminant hepatitis), neurodegenerative diseases (e.g., Alzheimer's disease, Parkinson's disease, amyotrophic lateral sclerosis, pigmentosa, cerebellar degeneration), myelodysplasia (e.g., aplastic anemia), ischemic diseases (e.g., myocardial infarction, cerebral apoplexy), hepatic diseases (e.g., nonalcoholic steatohepatitis, alcoholic hepatitis, Hepatitis B, Hepatitis C), articular diseases (e.g., osteoarthritis), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting oxidized LDL production, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, and the like.

The compound of the present invention is also used for the secondary prevention of various diseases mentioned above (e.g., cardiovascular event such as myocardial infarction etc.) and suppression of progression thereof.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can also be used as an agent for improving or the prophylaxis or treatment of diabetes, borderline type, impaired glucose tolerance, IFG (Impaired Fasting Glucose) and IFG (Impaired Fasting Glycemia), as determined according to the above-mentioned diagnostic criteria, or further, as an agent for treating hypertension of hypertensive patients having not less than the above-mentioned diagnostic criteria (e.g., fasting blood sugar level of 126 mg/dl). Moreover, the compound of the present invention can prevent progression of borderline type, impaired glucose tolerance, IFG (Impaired Fasting Glucose) or IFG (Impaired Fasting Glycemia) into diabetes.

The compound of the present invention is effective as an agent for the suppression or improvement of cardiac hypofunction, progression of cardiac remodeling and aggravation of conditions in, or an agent for the suppression of decreased survival rate of, cardiac patients (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) with diabetes. In addition, it is effective for the prevention of the onset of cardiac diseases (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) and cerebrovascular disorders (e.g., asymptomatic cerebrovascular disorder, transient cerebral ischemic attack, cerebral apoplexy, cerebrovascular dementia, hypertensive encephalopathia, cerebral infarction and the like) in diabetic patients.

Since the compound of the present invention has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia etc. The body weight gain may be caused by excessive feeding or diet without nutrient balance, or may be derived from combination agent, for example, agents for enhancing insulin sensitivity having PPAR-γ-agonistic activity such as troglitazone, rosiglitazone, englitazone, ciglitazone, pioglitazone etc. and the like. In addition, body weight gain may be preliminary to obesity, or may be body weight gain of obesity patients. Here, obesity is defined that BMI (body mass index; body weight (kg)/[height (m)]$^2$) is at least twenty-five for Japanese (criterion by Japan Society for the Study of Obesity), or at least thirty for westerner (criterion by WHO).

The compound of the present invention is useful as an agent for the prophylaxis or treatment of metabolic syndrome. Since patients with metabolic syndrome have an extreme high incidence of cardiovascular diseases as compared to patients with single lifestyle-related diseases, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in the United States, patients with at least three of abdominal obesity, hypertriglyceridemia, hypo-HDL cholesterolemia, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can be used for treating patients of hypertension with metabolic syndrome.

Since the compound of the present invention has an anti-inflammatory activity, it can be used as an anti-inflammatory agent for preventing or treating inflammatory diseases. Examples of the inflammatory diseases include inflammatory diseases due to various diseases such as arthritis (e.g. rheumatoid arthritis, osteoarthritis, rheumatoid myelitis, gouty arthritis, synovitis), asthma, allergic diseases, arteriosclerosis including atherosclerosis (aneurysm, coronary sclerosis, cerebral arterial sclerosis, peripheral arterial sclerosis etc.), digestive tract diseases such as inflammatory intestine disease (e.g. Crohn's disease, ulcerative colitis), diabetic complications (diabetic neuropathy, diabetic vascular disorder), atopic dermatitis, chronic obstructive pulmonary disease, systemic lupus erythematosus, visceral inflammatory diseases (nephritic, hepatitis, nonalcoholic steatohepatitis etc.), autoimmune hemolytic anemia, psoriasis, nervous degenerative diseases (e.g. Alzheimer's disease, Parkinson's diseases, amyotrophic lateral sclerosis, AIDS encephalopathy), central nervous disorders (e.g. cerebrovascular disorders such as cerebral hemorrhage, cerebral infarct etc., head trauma, spinal damage, cerebral edema, multiple sclerosis etc.), meningitis, angina pectoris, cardiac infarct, congestive cardiac failure, vascular hypertrophy or occlusion and organ disorder after intervention (percutaneous transluminal coronary angioplasty, stenting, coronary angioscopy, intravascular ultrasound, intracoronary thrombolysis etc.), vascular reocclusion or restenosis after bypass operation, endothelial functional disorder, other circulatory diseases (intermittent claudication, obstructive peripheral circulatory disorder, arteriosclerosis obliterans, thromboangiitis obliterans, ischemic cerebral circulatory disorder, Raynaud's disease, Buerger's disease etc.), inflammatory ocular disease, inflammatory pulmonary diseases (e.g. chronic pneumonia, silicosis, pulmonary sarcoidosis, pulmonary tuberculosis), endometritis, toxemia (e.g. sepsis, septic shock, endotoxin shock, gram negative sepsis, toxin shock syndrome), cachexia (e.g. cachexia due to infection, carcinomatous cachexia, cachexia due to acquired immunodeficiency syndrome), cancer, Addison's disease, Creutzfeldt-Jakob disease, virus infection (e.g. infection of virus such as cytomegalovirus, influenza virus, herpes virus etc.), disseminated intravascular coagulation and the like.

In addition, since the compound of the present invention has an analgesic activity, it can be also used as an analgesic agent for preventing or treating pain. Examples of the pain disease include acute pain due to inflammation, pains associated with chronic inflammation, pain associated with acute inflammation, pain after operation (incisional pain, deep pain, organ pain, chronic pain after operation etc.), muscular pains (muscular pain associated with chronic pain disease, shoulder stiffness etc.), arthralgia, toothache, gnathicarthralgia, headaches (migraine, stress headache, catatonic headache, headache associated with fever, headache associated hypertension), organ pains (cardiac pain, angina pain, abdominal pain, renal pain, ureterane pain, bladder pain), pains in obstetrics area (mittelschmerz, dysmenorrheal, labor pain), neuralgia (disc hernia, nerve root pain, neuralgia after herpes zoster, trigeminal neuralgia), carcinomatous pain, reflex sympathetic atrophy, complex local pain syndrome, and the like. The compound of the present invention is effective for alleviating directly and rapidly various pains such as nervous pain, carcinomatous pain, inflammatory pain etc., and exhibits the particularly excellent analgesic effect to patients and pathologies (e.g., hypertension, diabetes etc., and complications thereof etc.) in which a pain sense threshold is lowered.

The compound of the present invention is particularly useful as an analgesic agent for pain associated with chronic inflammation or pain associated with hypertension, or as an agent for preventing or treating inflammatory disease or pain due to (1) arteriosclerosis including atherosclerosis, (2) vascular hypertrophy, occlusion or organ disorder after intervention, (3) reocclusion, restenosis or endothelial functional disorder after bypass operation, (4) intermittent claudication, (5) obstructive peripheral circulatory disorder, or (6) arteriosclerosis obliterans.

The content of the compound of the present invention in a medicament is generally about 0.01-about 99.9 wt %, preferably about 0.1-about 50 wt %, relative to the entire preparation.

The dose of the compound of the present invention is determined in consideration of age, body weight, general health condition, sex, diet, administration time, administration method, clearance rate, combination of agents, the level of disease for which the patient is under treatment then, and other factors.

While the dose varies depending on the target disease, symptom, subject of administration, administration method and the like, for oral administration as a therapeutic agent for adult essential hypertension, for example, it is generally about 0.01-100 mg/kg body weight, preferably 0.05-30 mg/kg body weight, more preferably 0.5-10 mg/kg body weight, as one dose, which is preferably administered once to 3 times a day.

In addition, since the compound of the present invention shows low toxicity and superior safety, it can be administered for a long period.

As the medicament of the present invention, the compound of the present invention can be administered orally or parenterally as it is or after admixing with a pharmacologically acceptable carrier.

As the medicament of the present invention comprising compound (I), the compound of the present invention can be safely administered alone or is mixed with a pharmacologically acceptable carrier according to a method known per se as a production method of a pharmaceutical preparation (e.g., the method described in the Japanese Pharmacopoeia etc.) and administered as, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucous membrane patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop etc., orally or parenterally (e.g., intravenous, intramuscular, subcutaneous, intraorgan, intranasal, intradermal, instillation, intracerebral, rectal, vaginal, intraperitoneal and intratumor administrations, administration to the vicinity of tumor etc. and direct administration to the lesion).

When the compound of the present invention is to be produced in the above-mentioned dosage form, it can be produced by adding as necessary an appropriate amount of excipient, binder, disintegrant, lubricant, sweetening agent, surfactant, suspending agent, emulsifier and the like, which are generally used in the pharmaceutical field, during production of the dosage form.

For example, when the compound of the present invention is to be produced as a tablet, it can be produced by adding excipient, binder, disintegrant, lubricant and the like, when it is to be produced as pill or granule, it can be produced by adding excipient, binder, disintegrant and the like. When the compound of the present invention is to be produced as powder or capsule, it can be produced by adding excipient and the like, when it is to be produced as syrup, it can be produced by adding sweetening agent and the like, and when it is to be produced as emulsion or suspension, it can be produced by adding suspending agent, surfactant, emulsifier and the like.

Examples of the excipient include lactose, sucrose, glucose, starch, saccharose, crystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

When the compound of the present invention is administered parenterally, it is generally administered in the form of a liquid formulation (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, i.e., by dissolving, suspending or emulsifying the compound (I) in a sterilized aqueous solution or oily liquid. As an aqueous solution for injection, physiological saline, isotonic solutions comprising glucose or other auxiliary agents (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like may be mixed therewith. A prepared injection is generally filled in an ampoule.

The compound of the present invention can be used in combination with medicaments such as a therapeutic agent for diabetes, a therapeutic agent for diabetic complications, an anti-hyperlipidemia agent, an anti-arteriosclerotic agent, an anti-hypertensive agent, an antiobestic agent, a diuretic, an antigout agent, an antithrombotic agent, an anti-inflammatory agent, a chemotherapeutic agent, an immunotherapeutic agent, a therapeutic agent for osteoporosis, an anti-dementia agent, an erectile dysfunction amelioration agent, a therapeutic agent for urinary incontinence/urinary frequency, a therapeutic agent for dysurea and the like (hereinafter to be abbreviated as a concomitant agent). These concomitant agents may be low-molecular-weight compounds, high-molecular-weight proteins, polypeptides, antibodies, vaccines and the like.

Examples of the therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone (MCC-555), Rivoglitazone (CS-011), FK-614, a compound described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Vildagliptin (LAF237), P32/98, Sitagliptin (MK-431), alogliptin, P93/01, PT-100, Saxagliptin (BMS-477118), BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35)hGLP-1(7,37)$NH_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095, dapagliflozin, remogliflozin), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds etc. described in WO01/25228, WO03/42204, WO98/44921, WO98/45285, WO99/22735), glucokinase activators (e.g., Ro-28-1675), ACC2 (acetyl-CoA carboxylase 2) inhibitor and the like.

Examples of the therapeutic agents for diabetic complications include aldose reductase inhibitors (e.g., tolrestat, epalrestat, zenarestat, zopolrestat, minalrestat, fidarestat, CT-112, ranirestat (AS-3201)), neurotrophic factors and enhancers thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors and the like.

Examples of the anti-hyperlipidemia agents include statin compounds which are cholesterol synthesis inhibitors (e.g., cerivastatin, pravastatin, simvastatin, lovastatin, rosuvastatin, atorvastatin, fluvastatin, pitavastatin or salts thereof (e.g., sodium salt etc.) etc.), squalene synthetase inhibitors or fibrate compounds having a triglyceride lowering effect (e.g., bezafibrate, clofibrate, simfibrate, clinofibrate etc.), cholesterol absorption inhibitors (e.g., zechia), anion exchange resins (e.g., colestyramine), probucol, nicotinic acid drugs (e.g., nicomol, niceritrol), phytosterols (e.g., soysterol, γ-oryzanol), fish oil preparations (EPA, DHA, Omacor etc.) PPARγ agonists, PPARγ agonists, PPARδ agonists, LXR agonists, FXR antagonists, FXR agonists, DGAT inhibitors, MGAT inhibitors, MTP inhibitors (e.g., lomitapide), nucleic acid medicaments containing ApoB antisense (e.g., mipomersen) or PCSK9 siRNA antisense oligonucleotide, and the like.

Examples of the anti-arteriosclerotic agent include Lp-PLA2 inhibitors (e.g., darapladib, rilapladib etc.), FLAP inhibitors (e.g., AM-103, AM-803, DG-031 etc.), sPLA2 inhibitors (e.g., varespladib), 5-lipoxygenase inhibitors (e.g., VIA-2291 etc.), acyl coenzyme A cholesterol acyltransferase (ACAT) inhibitors (e.g., melinamide, Avasimibe, Eflucimibe etc.), lipid-rich plaque regressing agents (e.g., compounds described in WO02/06264, WO03/059900 etc.), HDL preparations (e.g., CSL-111 etc.), CTEP inhibitors (e.g., torcetrapib, anacetrapib, dalcetrapib etc.), MMP inhibitors, chymase inhibitors, SPT inhibitors, ApoA-1 and related molecules thereof (e.g., ApoA-1 Milano, D-4F, L-4F etc.) and the like.

Examples of the anti-hypertensive agents include angiotensin converting enzyme inhibitors (e.g., captopril, enalapril, delapril etc.), angiotensin II antagonists (e.g., candesartan cilexetil, candesartan, azilsartan, azilsartan medoxomil, losartan, losartan potassium, eprosartan, valsartan, termisartan, irbesartan, tasosartan, olmesartan, olmesartan medoxomil etc.), calcium antagonists (e.g., manidipine, nifedipine, amlodipine, efonidipine, nicardipine etc.), β-blockers (e.g., propranolol, nadolol, timolol, nipradilol, bunitrolol, indenolol, Penbutolol, carteolol, carvedilol, pindolol, acebutolol, atenolol, bisoprolol, metoprolol, labetalol, amosulalol, arotinolol etc.), clonidine and the like.

Examples of the antiobestic agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearic acid CoA desaturation enzyme inhibitors, microsomal triglyceride transfer protein inhibitors (e.g., R-256918), Na-glucose cotransport carrier inhibitor (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), feeding deterrents (e.g., P-57) and the like.

Examples of the diuretics include xanthine derivatives (e.g., theobromine sodium salicylate, theobromine calcium salicylate etc.), thiazide preparations (e.g., ethiazide, cyclopenthiazide, trichloromethiazide, hydrochlorothiazide, hydroflumethiazide, benzylhydrochlorothiazide, penfluthiazide, poly5 thiazide, methyclothiazide etc.), antialdosterone preparations (e.g., spironolactone, eplerenone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetanide, furosemide and the like.

Examples of anti-hyperuricemic or antigout agents include allopurinol, probenecid, colchicine, benzbromarone, febuxostat, citrate and the like.

Examples of the antithrombotic agent include anticoagulants [e.g., heparin sodium, heparin calcium, warfarin calcium (warfarin), anti-thrombin drugs (e.g., aragatroban, dabigatran), activated blood coagulation factor Xa inhibitors (e.g., rivaroxaban, apixaban, edoxaban, YM-150, compounds described in WO02/06234, WO2004/048363, WO2005/030740, WO2005/058823, WO2005/113504 and WO2004/048363 etc.) etc.], thrombolytic agents [e.g., tPA, urokinase, tisokinase, alteplase, nateplase, monteplase, pamiteplase], antiplatelet agents [e.g., aspirin, sulfinpyrazone (anturan), dipyridamole (persantin), ticlopidine (panaldine), cilostazol (pletal), GPIIb/IIIa antagonists (e.g., reopro etc.), clopidogrel, prasugrel, ticagrelor, E5555, SHC530348, ethyl icosapentate, beraprost sodium, sarpogrelate hydrochloride etc.] and the like.

Examples of the anti-inflammatory agents include nonsteroidal anti-inflammatory agents such as acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesylate, camostat mesylate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and salts thereof etc., and the like.

Examples of the chemotherapeutic agents include alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agents (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to IL-1, IL-2, IL-12 and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium and the like.

Examples of the anti-dementia agents include tacrine, donepezil, rivastigmine, galanthamine and the like.

Examples of the erectile dysfunction amelioration agents include apomorphine, sildenafil citrate and the like.

Examples of the therapeutic agents for urinary incontinence/urinary frequency include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving activity established in animal models and clinical situations, such as cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like, can be used in combination with the compound of the present invention.

Furthermore, examples of the concomitant agent include nerve regeneration promoting drugs (e.g., Y-128, VX853, prosaptide), antidepressants (e.g., desipramine, amitriptyline, imipramine), antiepileptics (e.g., lamotrigine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), α2 receptor agonists (e.g., clonidine), local analgesics (e.g., capsaicin), antianxiety drugs (e.g., benzodiazepines), dopamine agonists (e.g., apomorphine), midazolam, ketoconazole and the like.

The combination agent preferably includes calcium antagonist, aldosterone receptor antagonist, diuretic, insulin preparation, insulin sensitizer, dipeptidyl peptidase IV inhibitor, α-glucosidase inhibitor, biguanide agent, insulin secretagogue (preferably sulfonylurea agent) and the like. Particularly, calcium antagonists such as amlodipine and the like, aldosterone receptor antagonists such as eplerenone and the like, diuretic such as hydrochlorothiazide, chlortalidone and the like, insulin sensitizers such as pioglitazone hydrochloride and the like, and therapeutic agents for diabetes such as alogliptin, metformin and the like are preferable.

The timing of administration of the aforementioned combination agent is not limited, and the compound of the present invention and a combination agent may be simultaneously administered to the subject of administration, or may be administered with time difference. The dose of the combination agent may be according to the clinical dose, and can be determined appropriately according to the subject of administration, administration route, disease, combination and the like.

The above-mentioned combination agent may be a combination of two or more kinds thereof combined at appropriate ratios. In this case, the timing of administration of the compound of the present invention and a combination agent is not limited, and the compound of the present invention and a combination agent only need to be combined at the time of administration.

Examples of such administration mode include the following:
(1) administration of a single preparation obtained by simultaneously processing the compound of the present invention and the concomitant agent, (2) simultaneous administration of two kinds of preparations of the compound of the present invention and the concomitant agent, which have been separately produced, by the same administration route, (3) administration of two kinds of preparations of the compound of the present invention and the concomitant agent, which have been separately produced, by the same administration route in a staggered manner, (4) simultaneous administration of two kinds of preparations of the compound of the present invention and the concomitant agent, which have been separately produced, by different administration routes, (5) administration of two kinds of preparations of the compound of the present invention and the concomitant agent, which have been separately produced, by different administration routes in a staggered manner (e.g., administration in the order of the compound of the present invention and the concomitant agent, or in the reverse order) and the like. The dose of the concomitant agent can be appropriately determined based on the dose clinically employed. The mixing ratio of the compound of the present invention and the concomitant agent can be appropriately selected according to the administration subject, administration route, target disease, condition, combination, and other factors. In cases where the administration subject is human, for example, the concomitant agent may be used in an amount of 0.01 to 100 parts by weight per part by weight of the compound of the present invention.

When the compound of the present invention is used in combination with a concomitant agent, the amount of each drug can be reduced within a safe range in consideration of the opposite effect of these drugs. Particularly, the dose of the insulin sensitizer, insulin secretagogue and biguanide can be reduced from conventional level. As a result, the side effects possibly caused by these agents can be prevented safely. In addition, the dose of the therapeutic agent for diabetic complications, anti-hyperlipidemia agent or anti-hypertensive agent can be reduced and, as a result, the side effects possibly caused by these drugs can be effectively prevented.

Since the compound of the present invention potentiates hypoglycemic activity of other insulin sensitizers, a combined use of the compound of the present invention and other insulin sensitizers (preferably pioglitazone hydrochloride) markedly enhances a prophylactic and/or therapeutic effect against diseases in which insulin resistance is involved, such as type II diabetes and the like.

Production Method

The production method of compound (I) is explained below.

Compound (I) can be produced, for example, by the method shown in the following or a method analogous thereto and the like. In the following synthesis method, respective starting material compounds may form a salt as long as it does not inhibit the reaction. As such salt, those exemplified as a salt of the aforementioned compound represented by formula (I) are used. The starting material compounds may be commercially available when a specific production method is not described, or can be produced according to a method known per se or a method analogous thereto.

While the yield of compound (I) obtained by each of the following methods may vary depending on the reaction conditions used, compound (I) can be obtained easily at a high purity from the resultant products by a conventional separation and purification means (e.g., recrystallization, column chromatography and the like).

Reaction (a)

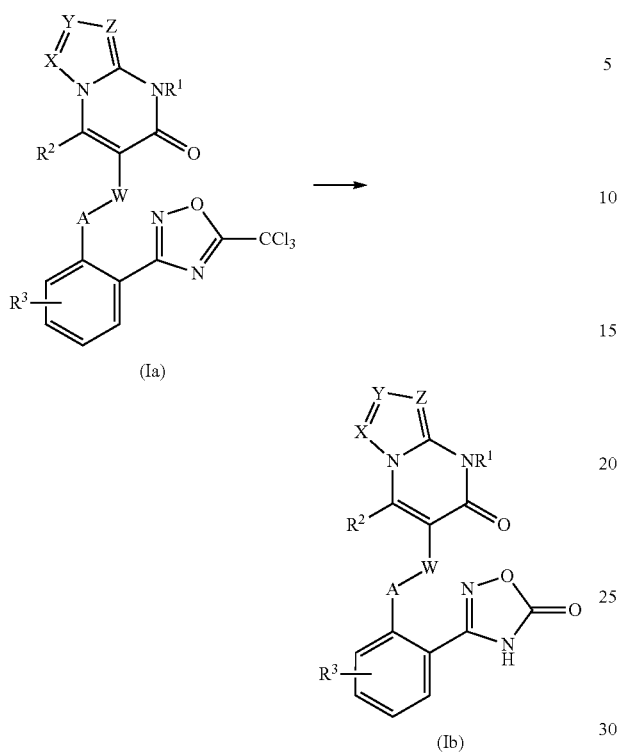

wherein X, Y, Z, R¹, R², R³, W and A are as defined above.

In reaction (a), compound (Ib) [compound (I) wherein B is

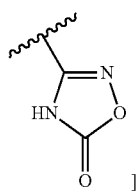

is obtained from compound (Ia) [compound (I) wherein B is

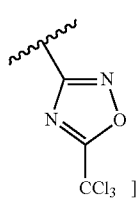

obtained by the below-mentioned reaction (g) or (h) in the presence of an aqueous alkaline solution. This reaction is generally performed using about 1-3 mol of an aqueous alkali solution per 1 mol of compound (Ia) in a solvent inert to the reaction.

Examples of the inert solvent for reaction include ethers such as 1,4-dioxane, tetrahydrofuran and the like; alcohols such as methanol, ethanol and the like; water and the like. These solvents may be used as a mixture of two or more kinds thereof at an appropriate ratio.

Examples of the alkali include sodium hydroxide, potassium hydroxide, lithium hydroxide, sodium carbonate, potassium carbonate and the like.

The reaction temperature is generally about −50° C. to about 150° C., preferably about 0° C. to about 60° C.

The reaction time is generally about 0.5 to about 20 hr.

Reaction (b)

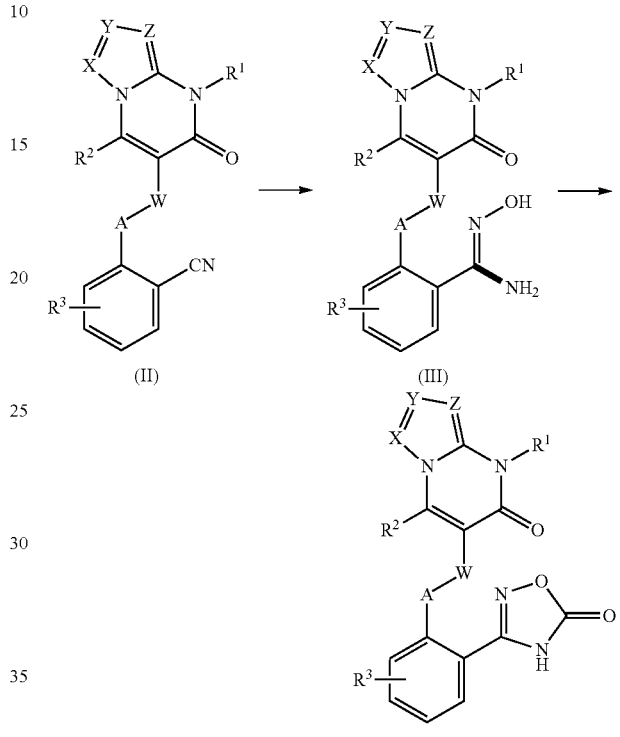

wherein X, Y, Z, R¹, R², R³, W and A are as defined above.

In reaction (b), compound (II) obtained in the below-mentioned reaction (d), (f), (i) or (j) is converted to compound (III), and subjected to ring-closure to give compound (Ib).

The reaction for obtaining compound (III) from compound (II) is performed using about 1-20 mol of hydroxylamine per 1 mol of compound (II) in an organic solvent inert to the reaction.

Examples of the organic solvent inert to the reaction include amides such as N,N-dimethylformamide, N,N-dimethylacetamide and the like; alcohols such as methanol, ethanol and the like; ethers such as 1,4-dioxane, tetrahydrofuran and the like; sulfoxides such as dimethyl sulfoxide and the like, and the like. These solvents may be used in a mixture of two or more kinds thereof at an appropriate ratio.

Examples of hydroxylamine include inorganic acid salts such as hydroxylamine hydrochloride, hydroxylamine hydrosulphate and the like, organic acid salts such as hydroxylamine oxalate etc., and the like. When the inorganic acid salt or organic acid salt of hydroxylamine is used, the reaction is preferably performed in the co-presence of an equivalent or small excess of a suitable base such as potassium carbonate, sodium hydrogen carbonate, sodium hydroxide, triethylamine, sodium methoxide, sodium hydride and the like. When an inorganic acid salt or organic acid salt of hydroxylamine is used, the reaction may be performed using about 5-20% of water in the organic solvent.

The reaction temperature is generally about −50° C. to about 150° C., preferably about 25° C. to about 100° C.

The reaction time is generally about 3 to about 48 hr.

The reaction to obtain compound (1b) from compound (III) is performed using about 1-2 mol of a carbonylation reagent per 1 mol of compound (III) in the presence of an equivalent amount or small excess of a base in a solvent that does not adversely influence the reaction.

Examples of the carbonylation reagent include N,N'-carbonyldiimidazole, triphosgene, methyl chlorocarbonate, ethyl chlorocarbonate and the like.

Examples of the base include organic amines such as triethylamine, pyridine, diisopropylethylamine, 1,8-diazabicyclo[5.4.0]undec-7-ene and the like; inorganic salts such as potassium carbonate, sodium carbonate etc., and the like.

Examples of the solvent that does not adversely influence the reaction include halogenated carbons such as dichloromethane, chloroform, carbon tetrachloride and the like; amides such as N,N-dimethylformamide, N,N-dimethylacetamide and the like; ethers such as diethyl ether, 1,4-dioxane, tetrahydrofuran etc., and the like. These solvents may be used in a mixture of two or more kinds thereof at an appropriate ratio.

The reaction temperature is generally about −50° C. to about 100° C., preferably about 0° C. to about 50° C.

The reaction time is generally about 0.1 to about 5 hr.

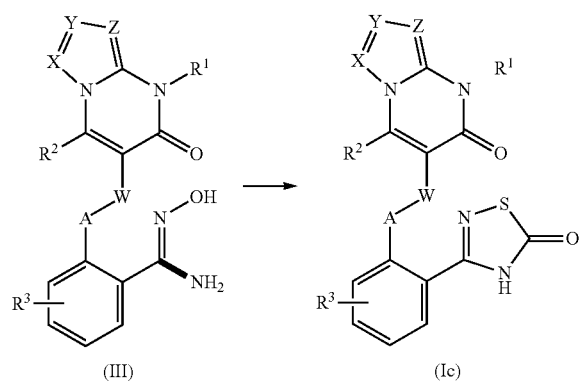

wherein X, Y, Z, $R^1$, $R^2$, $R^3$, W and A are as defined above.

In reaction (c), compound (III) obtained in the aforementioned reaction (b) is subjected to ring-closure to give compound (Ic) [compound (I) wherein B is

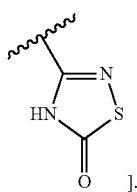

].

This reaction is performed using about 1-2 mol of 1,1-thiocarbonyldiimidazole per 1 mol of compound (III) in the presence of Lewis acid in an organic solvent that does not adversely influence the reaction.

The Lewis acid is not particularly limited as long as the reaction proceeds and, for example, boron trifluoride-diethyl ether complex, tin(II) chloride, zinc chloride, copper(I) chloride and the like can be mentioned. The amount of the Lewis acids is preferably about 1 to 3 mol per 1 mol of compound (III).

Examples of the organic solvent that does not adversely influence the reaction include halogenated carbons such as dichloromethane, chloroform, carbon tetrachloride and the like; amides such as N,N-dimethylformamide, N,N-dimethylacetamide and the like; dimethyl sulfoxide and the like; ethers such as diethyl ether, 1,4-dioxane, tetrahydrofuran and the like and the like. These solvents may be used in a mixture of two or more kinds thereof at an appropriate ratio.

The reaction temperature is generally about −50° C. to about 100° C., preferably about 0° C. to about 50° C.

The reaction time is generally about 0.1 to about 5 hr.

Reaction (d)

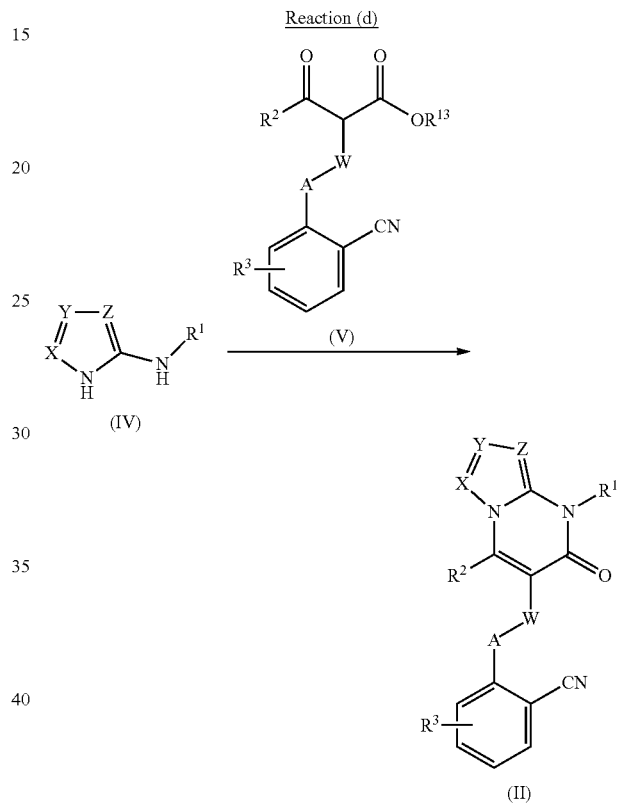

wherein X, Y, Z, $R^1$, $R^2$, $R^3$, W and A are as defined above, and $R^{13}$ is an alkyl group (e.g., methyl, ethyl, tert-butyl).

In reaction (d), compound (II), which is the starting material compound of the aforementioned reaction (b), is obtained by a condensation reaction of compound (IV) obtained by the below-mentioned reaction (e) and compound (V). This reaction is generally performed using about 1-10 mol of compound (V) per 1 mol of compound (IV) without a solvent or in an organic solvent that does not adversely influence the reaction. This reaction may be performed in the presence of a base.

Examples of the organic solvent that does not adversely influence the reaction include amides such as N,N-dimethylformamide, N,N-dimethylacetamide and the like; alcohols such as methanol, ethanol and the like; ethers such as 1,4-dioxane, tetrahydrofuran and the like; aromatic hydrocarbons such as benzene, toluene, trichlorobenzene and the like; and anilines such as aniline, N,N-diethylaniline and the like. These solvents may be used in a mixture of two or more kinds thereof at an appropriate ratio.

The base is not particularly limited as long as the reaction proceeds, and examples thereof include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium tert-butoxide and the like.

The reaction temperature is generally about −50° C. to about 300° C., preferably about 25° C. to about 200° C.

The reaction time is generally about 1 to about 48 hr.

The above-mentioned reaction may be performed using a microwave synthesis apparatus. In this case, the reaction temperature is generally about −50° C. to about 300° C., preferably about 100° C. to about 250° C. The reaction time is generally about 15 min to about 12 hr.

Compound (V), which is the starting material compound of this reaction, can be produced according to a method known per se, for example, the method described in Journal of Medicinal Chemistry vol. 37, page 2371 (1994) or the method described in WO2008/062905, or a method analogous thereto.

Reaction (e)

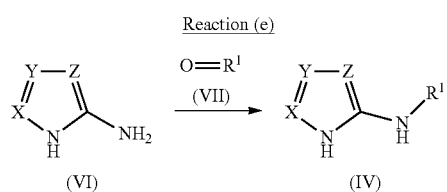

wherein X, Y, Z and $R^1$ are as defined above.

In reaction (e), compound (IV), which is the starting material compound of the aforementioned reaction (d), is obtained by a reductive amination reaction of compound (VI) and compound (VII). This reaction is performed according to a method known per se, for example, the method described in Journal of Organic Chemistry vol. 61, page 3849 (1996) and the like, or a method analogous thereto, and is generally performed using about 1-10 mol of compound (VII) and about 1-10 mol of a suitable reducing agent per 1 mol of compound (VI) in a solvent inert to the reaction.

Examples of the inert solvent for the reaction include halogenated hydrocarbons such as chloroform, dichloromethane and the like; ethers such as 1,4-dioxane, tetrahydrofuran and the like; alcohols such as methanol, ethanol and the like; water, acetic acid and the like. These solvents may be used in a mixture of two or more kinds thereof at an appropriate ratio.

Examples of the reducing agent include formic acid, sodium borohydride, sodium triacetoxyborohydride, sodium cyanoborohydride and the like.

The reaction temperature is generally about −50° C. to about 150° C., preferably about 0° C. to about 60° C.

The reaction time is generally about 0.5 to about 20 hr.

Compound (VI), which is the starting material compound of this reaction, can be produced according to a method known per se, for example, the method described in Bioorganic and Medicinal Chemistry Letters vol. 17, page 6220 (2007) or a method analogous thereto.

Reaction (f)

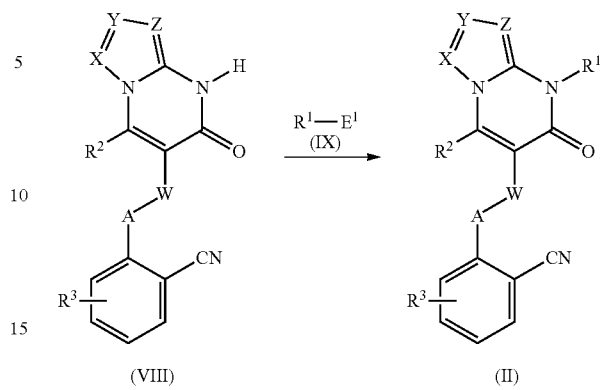

wherein X, Y, Z, $R^1$, $R^2$, $R^3$, W and A are as defined above, and $E^1$ is a leaving group (e.g., halogen atoms such as chlorine, bromine, iodine etc., substituted sulfonic acid esters such as methanesulfonic acid ester, p-toluenesulfonic acid ester, trifluoromethanesulfonic acid ester etc., boronic acid or boronic acid ester, hydroxy etc.).

In Reaction (f), compound (VIII) is reacted with compound (IX) to produce compound (II), which is the starting material compound of the aforementioned reaction (b). This reaction is generally performed using 1-4 mol of compound (IX) per 1 mol of compound (VIII).

Compound (VIII), which is the starting material compound of this reaction, can be produced according to a method analogous to the production method shown in the aforementioned reaction (d).

When $E^1$ is a halogen atom or substituted sulfonic acid ester, the reaction is performed according to a conventional method in the presence of a base in a solvent that does not adversely influence the reaction.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide and potassium tert-butoxide, and the like.

The amount of these bases to be used is preferably about 1-about 5 mol per 1 mol of compound (VIII).

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc., and the like. These solvents may be used in a mixture of two or more kinds thereof at an appropriate ratio.

The reaction temperature is generally about −50° C. to about 150° C., preferably about −10° C. to about 100° C.

The reaction time is generally about 0.5 to about 20 hr.

When $E^1$ is hydroxy, this reaction is performed according to a method known per se, for example, the method described in Synthesis, p. 1 (1981) and the like or a method analogous thereto. That is, this reaction is generally performed in the presence of an organic phosphorus compound and an azo reagent in a solvent that does not adversely influence the reaction.

Examples of the organic phosphorus compound include triphenylphosphine, tri(n-butyl)phosphine and the like.

Examples of the azo reagent include diethyl azodicarboxylate, diisopropyl azodicarboxylate, azodicarbonyl dipiperazine and the like.

The amount of the organic phosphorous compound or azo reagent to be used is preferably about 1-about 5 mol per 1 mol of compound (VIII).

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc., and the like. These solvents may be used in a mixture of two or more kinds thereof at an appropriate ratio.

The reaction temperature is generally about −50° C. to about 150° C., preferably about −10° C. to about 100° C.

The reaction time is generally about 0.5 to about 20 hr.

Particularly, when $E^1$ is a halogen atom or substituted sulfonic acid ester, and $R^1$ is a 5- or 6-membered aromatic cyclic group, this reaction can be promoted according to a method known per se, for example, the method described in Journal of the American Chemical Society vol. 124, page 7421 (2002) and the like, or a method analogous thereto, in the presence of a metal catalyst. Examples of the metal catalyst include palladium complex (e.g., palladium acetate, palladium chloride, tetrakis(triphenylphosphine)palladium, dichlorobis(triphenylphosphine)palladium, [1,1'-bis(diphenylphosphino)ferrocene]dichloropalladium etc.), copper compounds (e.g., copper powder, copper(I) chloride, copper(I) iodide, copper (I) acetate etc.), nickel compounds (e.g., tetrakis(triphenylphosphine)nickel etc.), rhodium compounds (e.g., tris (triphenylphosphine)rhodium chloride etc.), platinum compounds and the like.

The amount of these metal catalysts to be used is about 0.000001 mol-5 mol, preferably 0.0001 mol-1 mol, per 1 mol of compound (VIII).

The above-mentioned reaction may be performed in the presence of a base and/or a ligand. Examples of the base include metal alkoxides such as potassium phenoxide, sodium tert-butoxide and the like; inorganic salts such as potassium carbonate, sodium carbonate, cesium carbonate, potassium phosphate and the like, and the like. Examples of the ligand include organic phosphorus compounds such as triphenylphosphine, tri-tert-butylphosphine, tri-cyclohexylphosphine, BINAP (2,2'-bis(diphenylphosphino)-1,1'-binaphthyl) and the like; organic amine compounds such as N,N'-dimethyl-cyclohexane-1,2-diamine, 2,2-bipyridyl and the like, and the like.

When a metal catalyst unstable to oxygen is used, this reaction is preferably performed under an inert gas (e.g., argon, nitrogen etc.) atmosphere.

The reaction temperature is generally about −50° C. to about 150° C., preferably about −10° C. to about 100° C.

The reaction time is generally about 0.5 to about 20 hr.

When $E^1$ is a boronic acid or a boronic acid ester, this reaction is performed according to a method known per se, for example, the method described in Tetrahedron Letters, vol. 39, p. 2933 (1998) and the like or a method analogous thereto, in the presence of a base and a metal catalyst, in a solvent that does not adversely influence the reaction.

Examples of the base include inorganic salts such as potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5,4,0]undec-7-ene etc., and the like. These bases may be used in a mixture of two or more kinds thereof at an appropriate ratio.

Examples of the metal catalyst include copper or salts thereof (e.g., copper(II) acetate, copper(II) chloride and the like), palladium complexes (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (tris(triphenylphosphine) rhodium chloride and the like), platinum compounds and the like. Of these, copper and salts thereof are preferable.

Examples of the solvent that does not adversely influence the reaction include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc., and the like. These solvents may be used in a mixture of two or more kinds thereof at an appropriate ratio.

When copper or a salt thereof is used as a metal catalyst, this reaction is preferably performed under an air atmosphere or an oxygen atmosphere. When a metal catalyst unstable to oxygen is used, this reaction is preferably performed under an inert gas (e.g., argon, nitrogen and the like) atmosphere. In addition, this reaction may be performed using molecular sieves.

The amount of the metal catalyst to be used is about 0.000001 mol-5 mol, preferably 0.0001 mol-1 mol, per 1 mol of compound (VIII).

The reaction temperature is generally about 0° C. to about 200° C., preferably 10° C. to about 100° C.

The reaction time is generally about 1 to about 96 hr.

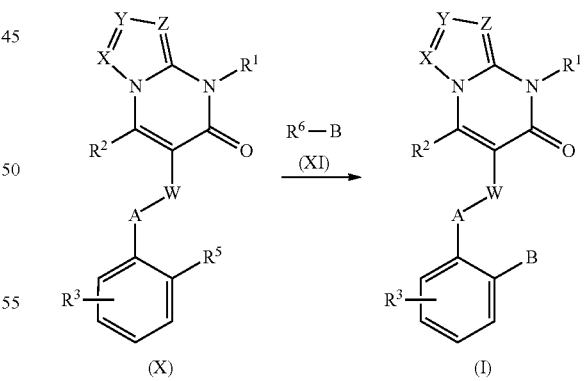

Reaction (g)

wherein X, Y, Z, $R^1$, $R^2$, $R^3$, B, W and A are as defined above, and $R^5$ and $R^6$ are each a leaving group (e.g., halogen atoms such as chlorine, bromine, iodine etc.; substituted sulfonic acid esters such as methanesulfonic acid ester, p-toluenesulfonic acid ester, trifluoromethane sulfonic acid ester etc.; hydroxy group etc.) or a metal (e.g., potassium, sodium, lithium, magnesium, copper, mercury, zinc, thallium, boron, tin etc.).

In reaction (g), compound (X) is reacted with compound (XI) to give compound (I).

This reaction is performed using about 1-3 mol of compound (XI) per 1 mol of compound (X) in an organic solvent that does not adversely influence the reaction.

Examples of the organic solvent that does not adversely influence the reaction include alcohols such as methanol, ethanol, ethylene glycol and the like; ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like and the like. These solvents may be used in a mixture of two or more kinds thereof at an appropriate ratio. Furthermore, water may be added at an appropriate ratio.

Compound (X), which is the starting material compound of this reaction, can be produced according to a method analogous to the production method shown in the aforementioned reaction (d) or reaction (f).

When $R^5$ is a leaving group (e.g., halogen atoms such as chlorine, bromine, iodine and the like; substituted sulfonic acid esters such as trifluoromethane sulfonic acid ester and the like etc.), and $R^6$ is a metal (e.g., potassium, sodium, lithium, magnesium, copper, mercury, zinc, thallium, boron, tin etc.), this reaction can be promoted by performing the reaction in the presence of metal catalyst according to a method known per se, for example, the method described in Journal of the American Chemical Society vol. 124, page 7421 (2002) and the like, or a method analogous thereto. Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium etc.), copper compounds (e.g., copper powder, copper(I) chloride, copper(I) iodide, copper(I) acetate etc.), nickel compounds (e.g., tetrakis(triphenylphosphine)nickel etc.), rhodium compounds (e.g., tris(triphenylphosphine)rhodium chloride etc.), platinum compounds and the like.

The amount of the metal catalyst to be used is about 0.000001 mol-5 mol, preferably 0.0001 mol-1 mol, per 1 mol of compound (X).

The above-mentioned reaction may be performed in the presence of a base and/or a ligand. Examples of the base include metal alkoxides such as potassium phenoxide, sodium tert-butoxide and the like; inorganic salts such as potassium carbonate, sodium carbonate, cesium carbonate, potassium phosphate and the like and the like. Examples of the ligand include organic phosphorus compounds such as triphenylphosphine, tri-tert-butylphosphine, tri-cyclohexylphosphine, BINAP (2,2'-bis(diphenylphosphino)-1,1'-binaphthyl) and the like; organic amine compounds such as N,N'-dimethyl-cyclohexane-1,2-diamine, 2,2-bipyridyl and the like, and the like.

When a metal catalyst unstable to oxygen is used, this reaction is preferably performed under an inert gas (e.g., argon, nitrogen etc.) atmosphere.

The reaction temperature is generally about −50° C. to about 150° C., preferably about −10° C. to about 120° C.

The reaction time is generally about 0.5-about 20 hr.

When $R^5$ is a metal (e.g., potassium, sodium, lithium, magnesium, copper, mercury, zinc, thallium, boron, tin etc.), and $R^6$ is a leaving group (e.g., halogen atoms such as chlorine, bromine, iodine etc.; substituted sulfonic acid esters such as trifluoromethanesulfonic acid ester etc., and the like), this reaction can be promoted by performing the reaction in the presence of a metal catalyst according to a method known per se, for example, the method described in Journal of the American Chemical Society vol. 124, page 7421 (2002) and the like, or a method analogous thereto. Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium etc.), copper compounds (e.g., copper powder, copper(I) chloride, copper(I) iodide, copper(I) acetate etc.), nickel compounds (e.g., tetrakis(triphenylphosphine)nickel etc.), rhodium compounds (e.g., tris(triphenylphosphine)rhodium chloride etc.), platinum compounds and the like.

The amount of the metal catalyst to be used is about 0.000001 mol-5 mol, preferably 0.0001 mol-1 mol, per 1 mol of compound (X).

The above-mentioned reaction may be performed in the presence of a base and/or a ligand. Examples of the base include metal alkoxides such as potassium phenoxide, sodium tert-butoxide and the like; inorganic salts such as potassium carbonate, sodium carbonate, cesium carbonate, potassium phosphate etc., and the like. Examples of the ligand include organic phosphorus compounds such as triphenylphosphine, tri-tert-butylphosphine, tri-cyclohexylphosphine, BINAP (2,2'-bis(diphenylphosphino)-1,1'-binaphthyl) and the like; organic amine compounds such as N,N'-dimethyl-cyclohexane-1,2-diamine, 2,2-bipyridyl etc., and the like.

When a metal catalyst unstable to oxygen is used, this reaction is preferably performed under an inert gas (e.g., argon, nitrogen etc.) atmosphere.

The reaction temperature is generally about −50° C. to about 150° C., preferably about −10° C. to about 120° C.

The reaction time is generally about 0.5 to about 20 hr.

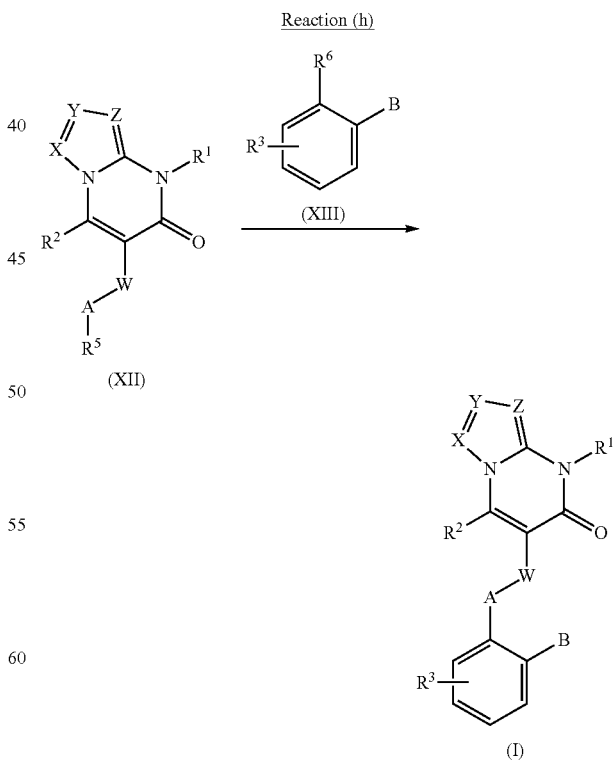

wherein $X, Y, Z, R^1, R^2, R^3, R^5, R^6, W, A$ and $B$ are as defined above.

In reaction (h), compound (XII) is reacted with compound (XIII) to give compound (I).

When $R^5$ is a leaving group (e.g., halogen atoms such as chlorine, bromine, iodine etc.; substituted sulfonic acid esters such as trifluoromethanesulfonic acid ester etc., and the like), and $R^6$ is a metal (e.g., potassium, sodium, lithium, magnesium, copper, mercury, zinc, thallium, boron, tin etc.), this reaction can be performed in the same manner as in reaction (g).

When $R^5$ is a metal (e.g., potassium, sodium, lithium, magnesium, copper, mercury, zinc, thallium, boron, tin etc.), and $R^6$ is a leaving group (e.g., halogen atoms such as chlorine, bromine, iodine etc.; substituted sulfonic acid esters such as trifluoromethanesulfonic acid ester etc., and the like), this reaction can be performed in the same manner as in reaction (g).

Compound (XII), which is the starting material compound of this reaction, can be produced according to a method analogous to the production method shown in the aforementioned reaction (d) or reaction (f).

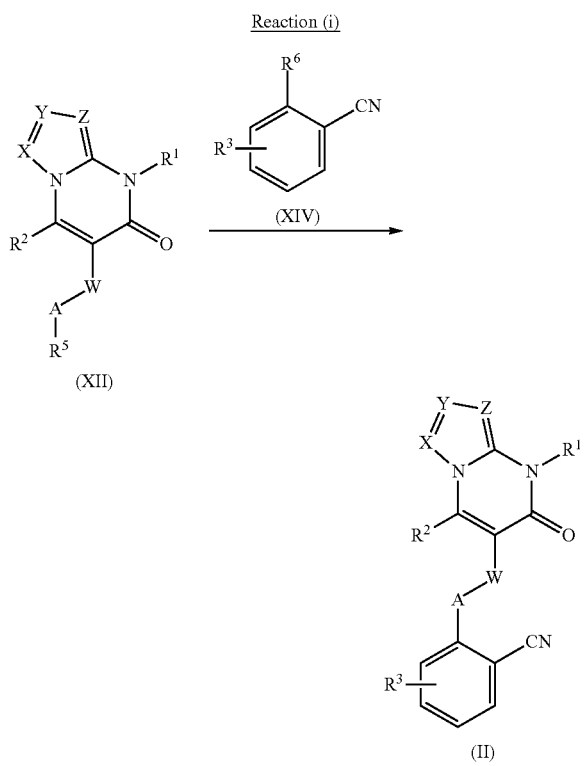

Reaction (i)

(XII)

(XIV)

(II)

wherein X, Y, Z, $R^1$, $R^2$, $R^3$, $R^5$, $R^6$, W and A are as defined above.

In reaction (i), compound (XII) is reacted with compound (XIV) to give compound (II).

When $R^5$ is a leaving group (e.g., halogen atoms such as chlorine, bromine, iodine etc.; substituted sulfonic acid esters such as trifluoromethanesulfonic acid ester etc., and the like), and $R^6$ is a metal (e.g., potassium, sodium, lithium, magnesium, copper, mercury, zinc, thallium, boron, tin etc.), this reaction can be performed in the same manner as in reaction (g).

When $R^5$ is a metal (e.g., potassium, sodium, lithium, magnesium, copper, mercury, zinc, thallium, boron, tin etc.), and $R^6$ is a leaving group (e.g., halogen atoms such as chlorine, bromine, iodine etc.; substituted sulfonic acid esters such as trifluoromethanesulfonic acid ester etc., and the like), this reaction can be performed in the same manner as in reaction (g).

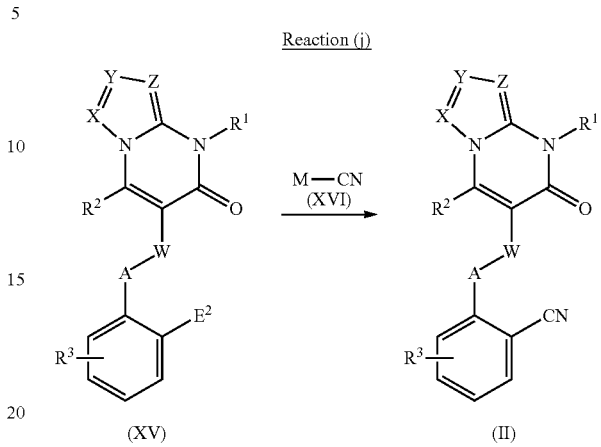

Reaction (j)

(XV)  (II)

wherein X, Y, Z, $R^1$, $R^2$, $R^3$, W and A are as defined above, $E^2$ is a leaving group (e.g., halogen atoms such as chlorine, bromine, iodine etc., and the like; substituted sulfonic acid esters such as trifluoromethanesulfonic acid ester etc., and the like), and M is a metal (e.g., copper, zinc, tin etc.)

In reaction (j), compound (XV) is reacted with compound (XVI) to give compound (II). The amount of compound (XVI) to be used is preferably about 1-about 5 mol, per 1 mol of compound (XV).

This reaction is performed in a solvent that does not adversely influence the reaction. Preferable examples of the solvent that does not adversely influence the reaction include solvents such as alcohols (e.g., methanol, ethanol, ethylene glycol etc.), ethers (e.g., diethyl ether, tetrahydrofuran, 1,4-dioxane, 1,2-dimethoxyethane etc.), amides (e.g., N,N-dimethylformamide, N,N-dimethylacetamide, N-methylpyrrolidone etc.), aromatic hydrocarbons (e.g., toluene, xylene etc.) and the like. These solvents may be used in a mixture of two or more kinds thereof at an appropriate ratio. Furthermore, water may be added at an appropriate ratio.

This reaction can be promoted by performing according to a method known per se, for example, the method described in Tetrahedron Letters vol. 40, page 8193 (1999) and the like, or a method analogous thereto, in the presence of a metal catalyst. Examples of the metal catalyst include palladium compounds (e.g., palladium acetate, palladium chloride, tetrakis (triphenylphosphine)palladium, dichlorobis (triphenylphosphine)palladium, [1,1'-bis (diphenylphosphino)ferrocene]dichloropalladium etc.), copper compounds (e.g., copper powder, copper(I) chloride, copper(I) iodide, copper(I) acetate etc.), nickel compounds (e.g., tetrakis(triphenylphosphine)nickel etc.), rhodium compounds (e.g., tris(triphenylphosphine)rhodium chloride etc.), platinum compounds and the like.

The amount of the metal catalyst to be used is about 0.000001 mol-5 mol, preferably 0.0001 mol-1 mol, per 1 mol of compound (XV).

This reaction may be performed in the presence of a ligand. Examples of the ligand include organic phosphorus compounds such as triphenylphosphine, tri-tert-butylphosphine, tri-cyclohexylphosphine, BINAP (2,2'-bis(diphenylphosphino)-1,1'-binaphthyl) and the like; organic amine compounds such as N,N'-dimethyl-cyclohexane-1,2-diamine, 2,2-bipyridyl etc., and the like.

When a metal catalyst unstable to oxygen is used, this reaction is preferably performed under an inert gas (e.g., argon, nitrogen etc.) atmosphere.

The reaction temperature is generally about −50° C. to about 300° C., preferably about −10° C. to about 150° C.

The reaction time is generally about 0.5-about 20 hr.

Compound (XV), which is the starting material compound of this reaction, can be produced according to a method analogous to the production method shown in the aforementioned reaction (d) or reaction (f).

Reaction (k)

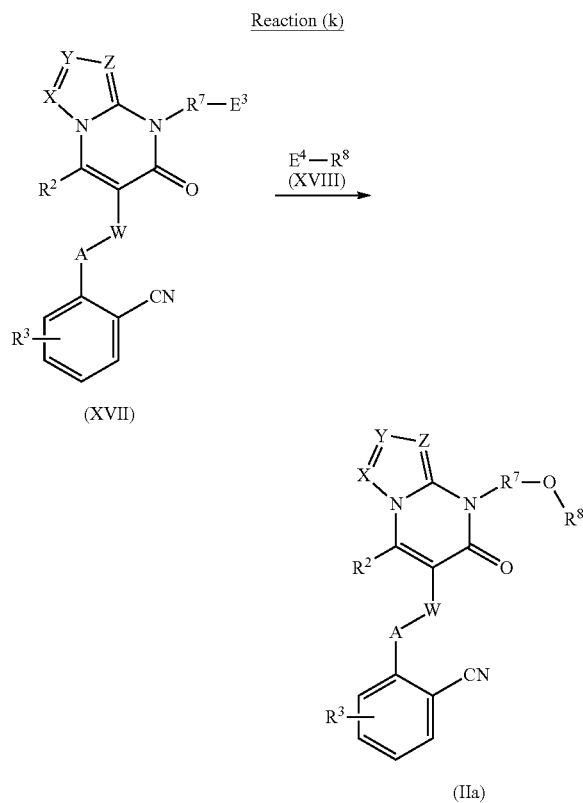

(XVII)

(IIa)

wherein X, Y, Z, W, A, $R^2$ and $R^3$ are as defined above, $R^7$ is optionally substituted $C_{1-6}$ alkylene (e.g., methylene, ethylene, propylene etc.), an optionally substituted 3- to 10-membered nonaromatic cyclic group or an optionally substituted 5- or 6-membered aromatic cyclic group, $R^8$ is optionally substituted $C_{1-6}$ alkyl, optionally substituted $C_{3-10}$ cycloalkyl, optionally substituted $C_{6-14}$ aryl or optionally substituted $C_{7-16}$ aralkyl, $E^3$ is a leaving group (e.g., halogen atoms such as chlorine, bromine, iodine etc.; substituted sulfonic acid esters such as methanesulfonic acid ester, p-toluenesulfonic acid ester, trifluoromethanesulfonic acid ester etc.), or hydroxy, and $E^4$ is a leaving group (e.g., halogen atoms such as chlorine, bromine, iodine etc.; substituted sulfonic acid esters such as methanesulfonic acid ester, p-toluenesulfonic acid ester etc.; diazonio group), or hydroxy.

In reaction (k), compound (XVII) is reacted with compound (XVIII) to give compound (IIa).

This reaction is performed using about 1-10 mol of compound (XVIII) per 1 mol of compound (XVII) in an organic solvent that does not adversely influence the reaction.

Compound (XVII), which is the starting material compound of this reaction, can be produced according to a method analogous to the production method shown in the aforementioned reaction (d), (f), (i) or (j).

When $E^3$ is a leaving group (e.g., halogen atoms such as chlorine, bromine, iodine etc.; substituted sulfonic acid esters such as trifluoromethanesulfonic acid ester etc., and the like), and $E^4$ is hydroxy, this reaction can be promoted according to a method known per se, for example, the method described in Journal of the American Chemical Society vol. 127, page 8146 (2005) and the like, or a method analogous thereto, in the presence of a metal catalyst. Examples of the metal catalyst include palladium compounds (e.g., palladium acetate, palladium chloride, tetrakis(triphenylphosphine)palladium, dichlorobis(triphenylphosphine)palladium, [1,1′-bis(diphenylphosphino)ferrocene]dichloropalladium etc.), copper compounds (e.g., copper powder, copper(I) chloride, copper (I) iodide, copper(I) acetate etc.), nickel compounds (e.g., tetrakis(triphenylphosphine)nickel etc.), rhodium compounds (e.g., tris(triphenylphosphine)rhodium chloride etc.), platinum compounds and the like.

The amount of the metal catalyst to be used is about 0.000001 mol-5 mol, preferably 0.0001 mol-1 mol, per 1 mol of compound (XVII).

This reaction may be performed in the presence of a base and/or a ligand. Examples of the base include metal alkoxides such as potassium phenoxide, sodium tert-butoxide and the like; inorganic salts such as potassium carbonate, sodium carbonate, cesium carbonate, potassium phosphate etc., and the like. Examples of the ligand include organic phosphorus compounds such as triphenylphosphine, tri-tert-butylphosphine, tri-cyclohexylphosphine, BINAP (2,2′-bis(diphenylphosphino)-1,1′-binaphthyl) and the like; organic amine compounds such as N,N′-dimethyl-cyclohexane-1,2-diamine, 2,2-bipyridyl etc., and the like.

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide etc., and the like. These solvents may be used in a mixture of two or more kinds thereof at an appropriate ratio. Furthermore, water may be mixed at an appropriate ratio.

When a metal catalyst unstable to oxygen is used, this reaction is preferably performed under an inert gas (e.g., argon, nitrogen etc.) atmosphere.

The reaction temperature is generally about −50° C. to about 150° C., preferably about −10° C. to about 120° C.

The reaction time is generally about 0.5-about 20 hr.

When $E^3$ and $E^4$ are hydroxy, this reaction is performed according to a method known per se, for example, the method described in Organic Reactions vol. 42, page 335 (1992) and the like, or a method analogous thereto. In other words, this reaction is generally performed in the presence of an organic phosphorus compound and an azo reagent in a solvent that does not adversely influence the reaction.

Examples of the organic phosphorus compound include triphenylphosphine, tri(n-butyl)phosphine and the like.

Examples of the azo reagent include diethyl azodicarboxylate, diisopropyl azodicarboxylate, azodicarbonyl dipiperazine and the like.

The amount of the organic phosphorus compound and azo reagent to be used is preferably about 1-about 5 mol per 1 mol of compound (XVII).

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like;

amides such as N,N-dimethylformamide and the like; sulfoxides such as dimethyl sulfoxide etc., and the like. These solvents may be used in a mixture of two or more kinds thereof at an appropriate ratio.

The reaction temperature is generally about −50° C. to about 150° C., preferably about −10° C. to about 100° C.

The reaction time is generally about 0.5-about 20 hr.

When $E^3$ is hydroxy, and $E^4$ is a leaving group (e.g., halogen atoms such as chlorine, bromine, iodine etc.; substituted sulfonic acid esters such as trifluoromethanesulfonic acid ester etc., and the like), this reaction is performed according to a conventional method in the presence of a base in a solvent that does not adversely influence the reaction.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc., and the like.

The amount of the base to be used is preferably about 1-about 5 mol per 1 mol of compound (XVII).

Examples of the solvent that does not adversely influence the reaction include aqueous basic solutions such as 50% aqueous sodium hydroxide solution, 50% aqueous potassium hydroxide solution and the like; aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc., and the like. These solvents may be used in a mixture of two or more kinds thereof at an appropriate ratio.

When a mixed solvent containing a basic aqueous solution is used in this reaction, the reaction is preferably performed using a phase transfer catalyst such as tetrabutylammonium hydrogensulfate and the like.

The reaction temperature is generally about −50° C. to about 150° C., preferably about −10° C. to about 100° C.

The reaction time is generally about 0.5-about 20 hr.

Particularly, when $E^3$ is hydroxy and $E^4$ is diazonio, this reaction is performed according to a method known per se, for example, the method described in Tetrahedron Letters vol. 38, page 2733 (1982) and the like, or a method analogous thereto, in the presence of a metal catalyst in a solvent that does not adversely influence the reaction.

Examples of the metal catalyst include rhodium compounds (rhodium (II) acetate, rhodium(II) trifluoroacetate etc.), copper and salts thereof (e.g., copper(II) acetate, copper (II) chloride etc.), palladium complexes (e.g., palladium acetate, palladium chloride, tetrakis(triphenylphosphine)palladium, dichlorobis(triphenylphosphine)palladium, [1,1'-bis (diphenylphosphino)ferrocene]dichloropalladium etc.), nickel compounds (e.g., tetrakis(triphenylphosphine)nickel etc.), platinum compounds and the like. Of these, rhodium compounds are preferable.

The amount of the metal catalyst to be used is about 0.000001 mol-5 mol, preferably 0.0001 mol-1 mol, per 1 mol of compound (VIII).

Examples of the solvent that does not adversely influence the reaction include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc., and the like. These solvents may be used in a mixture of two or more kinds thereof at an appropriate ratio.

When a metal catalyst unstable to oxygen is used, this reaction is preferably performed under an inert gas (e.g., argon, nitrogen etc.) atmosphere.

The reaction temperature is generally about −50° C. to about 150° C., preferably about −10° C. to about 100° C.

The reaction time is generally about 0.5-about 20 hr.

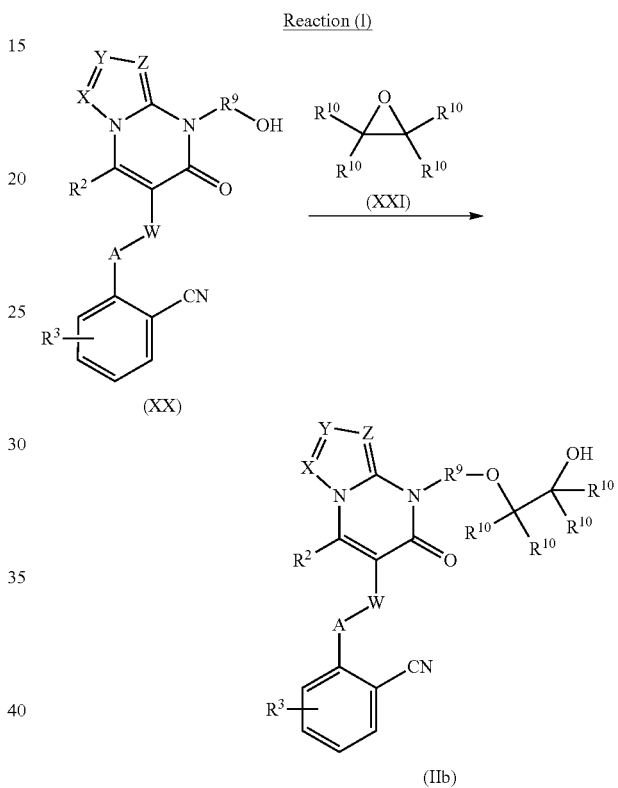

Reaction (1)

wherein X, Y, Z, W, A, $R^2$ and $R^3$ are as defined above, $R^9$ is optionally substituted $C_{1-6}$ alkylene (e.g., methylene, ethylene, propylene etc.), an optionally substituted 3- to 10-membered nonaromatic cyclic group or an optionally substituted 5- or 6-membered aromatic cyclic group, $R^{10}$ is a hydrogen atom, optionally substituted $C_{1-6}$ alkyl, or optionally substituted $C_{3-10}$ cycloalkyl, each of which optionally has an independent substituent or forms a ring between substituents.

In reaction (1), compound (XX) is reacted with compound (XXI) to give compound (IIb). This reaction is generally performed using about 1-10 mol of compound (XXI) per 1 mol of compound (XX) in an organic solvent that does not adversely influence the reaction. This reaction may be performed in the presence of a base.

Compound (XX), which is the starting material compound of this reaction, can be produced according to a method analogous to the production method shown in the aforementioned reaction (d), (f), (i) or (j).

Examples of the organic solvent that does not adversely influence the reaction include amides such as N,N-dimethylformamide, N,N-dimethylacetamide and the like; ethers such as 1,4-dioxane, tetrahydrofuran and the like; aromatic hydrocarbons such as benzene, toluene, trichlorobenzene and the like; and anilines such as aniline, N,N-diethylaniline and the like. These solvents may be used in a mixture of two or more kinds thereof at an appropriate ratio.

The base is not particularly limited as long as the reaction proceeds and, for example, alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as potassium tert-butoxide and the like can be mentioned.

The reaction temperature is generally about −50° C. to about 300° C., preferably about 25° C. to about 200° C.

The reaction time is generally about 1-about 48 hr.

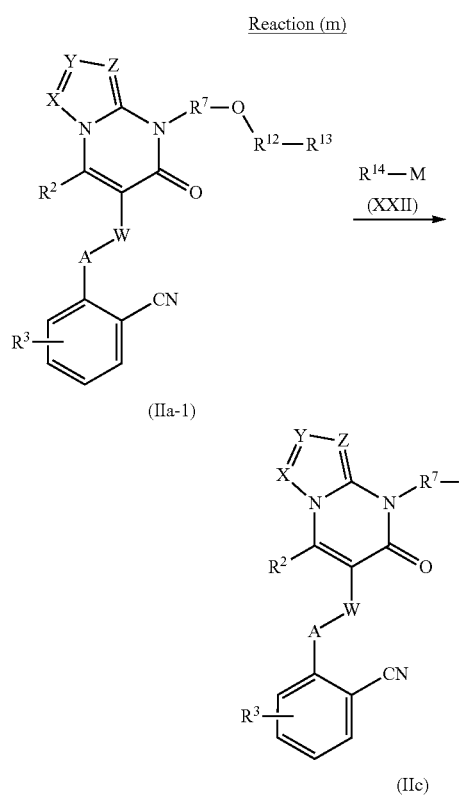

(IIa-1)

(IIc)

wherein X, Y, Z, W, A, $R^2$, $R^3$ and $R^7$ are as defined above, $R^{12}$ is optionally substituted $C_{1-6}$ alkylene (e.g., methylene, ethylene, propylene etc.), optionally substituted $C_{3-10}$ cycloalkylene (e.g., cyclopropylene, cyclopentylene, cyclohexylene), optionally substituted $C_{6-14}$ arylene or optionally substituted $C_{7-16}$ aralkylene, $R^{13}$ is $C_{1-6}$ alkoxy-carbonyl (e.g., methoxycarbonyl, ethoxycarbonyl, propoxycarbonyl, tert-butoxycarbonyl etc.), $R^{14}$ is optionally substituted $C_{1-6}$ alkyl, optionally substituted $C_{3-10}$ cycloalkyl, and M is a metal (e.g., magnesium, lithium, copper, zinc, tin etc.).

In reaction (m), compound (IIa-1) is reacted with alkylmetal (XXII) to give compound (IIc). This reaction is generally performed by using about 2-10 mol of alkylmetal (XXII) per 1 mol of compound (IIa-1) in an organic solvent that does not adversely influence the reaction.

Examples of the organic solvent that does not adversely influence the reaction include ethers such as 1,4-dioxane, tetrahydrofuran and the like; and aromatic hydrocarbons such as benzene, toluene, trichlorobenzene and the like. These solvents may be used in a mixture of two or more kinds thereof at an appropriate ratio.

The reaction temperature is generally about −50° C. to about 150° C., preferably about −10° C. to about 100° C.

The reaction time is generally about 0.5-about 20 hr.

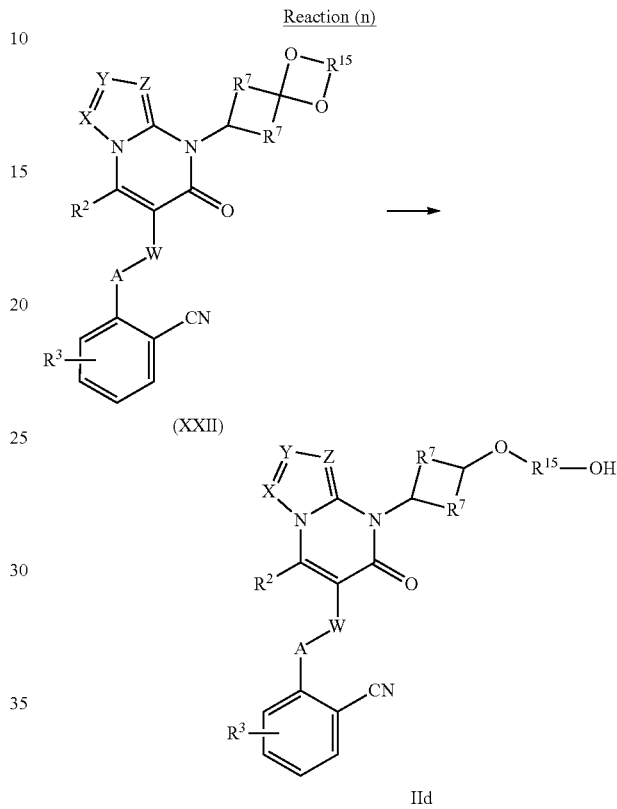

IId wherein X, Y, Z, W, A, $R^2$, $R^3$ and $R^7$ are as defined above, and $R^{15}$ is optionally substituted $C_{2-5}$ alkylene (e.g., ethylene, propylene etc.).

In reaction (n), the ketal moiety of compound (XXII) is subjected to ring opening to give compound (IId).

This reaction is performed according to a method known per se, for example, the method described in Journal of Organic Chemistry vol. 58, page 6756 (1993) and the like, or a method analogous thereto. In other words, this reaction is performed in the presence of a hydride reducing agent in a solvent that does not adversely influence the reaction.

Examples of the hydride reducing agent include aluminum hydride, diisobutylaluminum hydride, sodium cyanoborohydride, borane-dimethyl sulfide complex, triethylsilane and the like.

The amount of the hydride reducing agent to be used is preferably about 1-about 10 mol per 1 mol of compound (XXII).

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like, and the like. These solvents may be used in a mixture of two or more kinds thereof at an appropriate ratio.

The above-mentioned reaction may be performed in the presence of a Lewis acid. Examples of the Lewis acid include aluminum chloride, boron trifluoride-diethylether complex, titanium tetrachloride and the like.

The reaction temperature is generally about −78° C. to about 150° C., preferably about −78° C. to about 100° C.

The reaction time is generally about 0.5-about 20 hr.

In each reaction of the aforementioned (a)-(n), when the starting material compound has hydroxy, amino (including —NH— and —NH$_2$—), carboxy or carbonyl, a protecting group such as those generally used in the peptide chemistry may be introduced into these groups. By removing the protecting group after the reaction as necessary, the object compound can be obtained.

Examples of the hydroxy-protecting group include $C_{1-6}$ alkyl (e.g., methyl, ethyl, propyl, isopropyl, butyl, tert-butyl), phenyl, trityl, $C_{7-10}$ aralkyl (e.g., benzyl), formyl, $C_{1-6}$ alkyl-carbonyl (e.g., acetyl, propionyl), benzoyl, $C_{7-10}$ aralkyl-carbonyl (e.g., benzylcarbonyl), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups may be substituted by 1 to 3 substituents selected from a halogen atom (e.g., fluorine, chlorine, bromine, iodine), $C_{1-6}$ alkyl (e.g., methyl, ethyl, propyl), $C_{1-6}$ alkoxy (e.g., methoxy, ethoxy, propoxy), nitro and the like.

Examples of the amino-protecting group include formyl, $C_{1-6}$ alkyl-carbonyl (e.g., acetyl, propionyl), $C_{1-6}$ alkoxy-carbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups may be substituted by 1 to 3 substituents selected from a halogen atom (e.g., fluorine, chlorine, bromine, iodine), $C_{1-6}$ alkoxy (e.g., methoxy, ethoxy, propoxy), nitro and the like.

Examples of the carboxy-protecting group include $C_{1-6}$ alkyl (e.g., methyl, ethyl, propyl, isopropyl, butyl, tert-butyl), $C_{7-11}$ aralkyl (e.g., benzyl), phenyl, trityl, silyl (e.g., trimethylsilyl, triethylsilyl, dimethylphenylsilyl, tert-butyldimethylsilyl, tert-butyldiethylsilyl, tert-butyldiphenylsilyl), $C_{2-6}$ alkenyl (e.g., 1-allyl) and the like. These groups may be substituted by 1 to 3 substituents selected from a halogen atom (e.g., fluorine, chlorine, bromine, iodine), $C_{1-6}$ alkoxy (e.g., methoxy, ethoxy, propoxy), nitro and the like.

Examples of the carbonyl-protecting group include cyclic acetal (e.g., 1,3-dioxane), non-cyclic acetal (e.g., di-$C_{1-6}$ alkylacetal) and the like.

In addition, these protecting groups may be removed according to a method known per se, for example, the method described in Protective Groups in Organic Synthesis, John Wiley and Sons (1980) and the like. For example, a method using an acid, a base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like can be used.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, (+)-cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (e.g., MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxyl group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

The present invention is explained in more detail in the following by referring to Experimental Examples, Reference Examples, Examples and Preparation Examples, which are not to be construed as limitative.

In the following Reference Examples and Examples, % means weight % unless otherwise indicated. In addition, the room temperature means 1-30° C.

In the following Reference Examples and Examples, the Dess-Martin reagent refers to commercially available 1,1,1-tris(acetyloxy)-1,1-dihydro-1,2-benziodoxol-3-(1H)-one.

In the NMR spectrum, the chemical shift is expressed in δ value (ppm) and the coupling constant is expressed in Hz.

In the case of a mixed solvent, the numerical value indicated in the parenthesis is a volume mixing ratio of each solvent. In addition, % of a solution means the number of grams in 100 mL of the solution. The unit of sample concen tration (c) in specific optical rotation ($[\alpha]_D$) is g/dL. The abbreviations used in the present specification mean the following.
s: singlet
d: doublet
t: triplet
q: quartet
dd: double doublet
dt: double triplet
m: multiplet
br: broad
J: coupling constant
$CDCl_3$: deuterated chloroform
DMSO-$d_6$: dimethyl sulfoxide-$d_6$
$^1$H NMR: proton nuclear magnetic resonance
MeOH: methanol
n-Hex: n-hexane
IPA: isopropanol

REFERENCE EXAMPLE 1

4'-[(2-methyl-5-oxo-7-propyl-4,5-dihydro[1,2,4]triazolo[1,5-a]pyrimidin-6-yl)methyl]biphenyl-2-carbonitrile A solution of 5-methyl-4H-1,2,4-triazol-3-amine (1.7 g) and ethyl 2-[(2'-cyanobiphenyl-4-yl)methyl]-3-oxohexanoate (7.1 g) in 1,2,4-trichlorobenzene (70 mL) was stirred at 190° C. for 6 hr. After evaporation of the solvent under reduced pressure, ethyl acetate was added to the obtained residue. The precipitated solid was collected by filtration to give the title compound as a colorless solid (3.6 g, 44%).
$^1$H NMR (300 MHz, DMSO-$d_6$) δ0.93 (t, J=7.4, 3H), 1.47-1.65 (m, 2H), 2.31 (s, 3H), 2.87-2.97 (m, 2H), 3.94 (s, 2H), 7.34-7.41 (m, 2H), 7.45-7.62 (m, 4H), 7.77 (t, J=7.8, 1H), 7.93 (d, J=7.6, 1H), 12.95 (br s, 1H)

REFERENCE EXAMPLE 2

4'-[(2,4-dimethyl-5-oxo-7-propyl-4,5-dihydro[1,2,4]triazolo[1,5-a]pyrimidin-6-yl)methyl]biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (1 g), methyl iodide (0.19 mL), potassium carbonate (0.41 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.67 g, 67%).
$^1$H NMR (300 MHz, $CDCl_3$) δ1.04 (t, J=6.8, 3H), 1.63-1.80 (m, 2H), 2.46 (s, 3H), 2.95-3.06 (m, 2H), 3.69 (s, 3H), 4.02 (s, 2H), 7.33-7.52 (m, 6H), 7.56-7.66 (m, 1H), 7.74 (d, J=7.6, 1H)

REFERENCE EXAMPLE 3

4'-{[2-methyl-4-(2-methyl-2,3-dihydro-1-benzofuran-5-yl)-5-oxo-7-propyl-4,5-dihydro[1,2,4]triazolo[1,5-a]pyrimidin-6-yl]methyl}biphenyl-2-carbonitrile To a suspension (5 mL) of 4'-[(2-methyl-5-oxo-7-propyl-4,5-dihydro[1,2,4]triazolo[1,5-a]pyrimidin-6-yl)methyl]biphenyl-2-carbonitrile (0.15 g), (2-methyl-2,3-dihydro-1-benzofuran-5-yl)boronic acid (0.13 g), triethylamine (0.15 mL), pyridine (0.3 mL) and molecular sieves 4A (0.3 g) in dichloromethane was added copper(II) acetate (0.14 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.17 g, 87%).
$^1$H NMR (300 MHz, $CDCl_3$) δ1.10 (t, J=7.2, 3H), 1.49 (d, J=6.4, 3H), 1.67-1.86 (m, 2H), 2.39 (s, 3H), 2.87 (dd, J=15.7, 7.8, 1H), 2.99-3.19 (m, 2H), 3.36 (dd, J=15.7, 8.9, 1H), 4.03 (s, 2H), 4.86-5.10 (m, 1H), 6.86 (d, J=8.3, 1H), 7.02-7.21 (m, 2H), 7.33-7.55 (m, 6H), 7.56-7.68 (m, 1H), 7.74 (d, J=7.6, 1H)

REFERENCE EXAMPLE 4

4'-[(5-oxo-7-propyl-4,5-dihydro[1,2,4]triazolo[1,5-a]pyrimidin-6-yl)methyl]biphenyl-2-carbonitrile A solution of 4H-1,2,4-triazol-3-amine (2.4 g) and ethyl 2-[(2'-cyanobiphenyl-4-yl)methyl]-3-oxohexanoate (10 g) in 1,2,4-trichlorobenzene (50 mL) was stirred at 180° C. for 6 hr. After evaporation of the solvent under reduced pressure, the residue was purified by silica gel column chromatography to give the title compound as a colorless solid (4 g, 38%).
$^1$H NMR (300 MHz, DMSO-$d_6$) δ0.94 (t, J=7.2, 3H), 1.51-1.68 (m, 2H), 2.90-3.03 (m, 2H), 3.97 (s, 2H), 7.37-7.44 (m, 2H), 7.45-7.63 (m, 4H), 7.72-7.83 (m, 1H), 7.93 (d, J=7.6, 1H), 8.12 (s, 1H), 13.13 (s, 1H)

REFERENCE EXAMPLE 5

4'-{[4-(4-fluorobenzyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), 1-(bromomethyl)-4-fluorobenzene (0.2 mL), potassium carbonate (0.38 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.58 g, 89%).
$^1$H NMR (300 MHz, $CDCl_3$) δ1.05 (t, J=7.4, 3H), 1.62-1.83 (m, 2H), 2.96-3.08 (m, 2H), 4.03 (s, 2H), 5.38 (s, 2H), 6.94-7.06 (m, 2H), 7.32-7.52 (m, 6H), 7.53-7.67 (m, 3H), 7.75 (d, J=7.6, 1H), 7.94 (s, 1H)

REFERENCE EXAMPLE 6

4'-{[2-methyl-4-(4-fluorobenzyl)-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (0.7 g), 1-(bromomethyl)-4-fluorobenzene (0.27 mL), potassium carbonate (0.51 g) and N,N-dimethylformamide (15 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.56 g, 62%).

$^1$H NMR (300 MHz, CDCl$_3$) δ1.03 (t, J=7.4, 3H), 1.63-1.77 (m, 2H), 2.46 (s, 3H), 2.92-3.02 (m, 2H), 4.00 (s, 2H), 5.34 (s, 2H), 7.00 (t, J=8.7, 2H), 7.30-7.50 (m, 6H), 7.55-7.66 (m, 3H), 7.74 (d, J=7.6, 1H)

REFERENCE EXAMPLE 7

4'-[(2-cyclopropyl-5-oxo-7-propyl-4,5-dihydro[1,2,4]triazolo[1,5-a]pyrimidin-6-yl)methyl]biphenyl-2-carbonitrile A solution of 5-cyclopropyl-4H-1,2,4-triazol-3-amine (1 g) and ethyl 2-[(2'-cyanobiphenyl-4-yl)methyl]-3-oxohexanoate (2.8 g) in 1,2,4-trichlorobenzene (20 mL) was stirred at 180° C. for 6 hr. After evaporation of the solvent under reduced pressure, the residue was purified by silica gel column chromatography to give the title compound as a colorless solid (0.7 g, 21%).

$^1$H NMR (300 MHz, DMSO-d$_6$) δ0.81-1.02 (m, 7H) 1.50-1.72 (m, 2H) 1.98-2.07 (m, 1H) 2.81-3.01 (m, 2H) 3.93 (s, 2H) 7.35-7.42 (m, 2H) 7.44-7.53 (m, 2H) 7.52-7.64 (m, 2H) 7.72-7.82 (m, 1H) 7.93 (dd, J=7.7, 0.9 Hz, 1H) 12.93 (s, 1H)

REFERENCE EXAMPLE 8

4'-{[2-cyclopropyl-4-(4-fluorobenzyl)-5-oxo-7-propyl-4,5-dihydro[1,2,4]triazolo[1,5-a]pyrimidin-6-yl]methyl}biphenyl-2-carbonitrile A mixture of 4'-[(2-cyclopropyl-5-oxo-7-propyl-4,5-dihydro[1,2,4]triazolo[1,5-a]pyrimidin-6-yl)methyl]biphenyl-2-carbonitrile (0.5 g), 1-(bromomethyl)-4-fluorobenzene (0.17 mL), potassium carbonate (0.34 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.44 g, 70%).

$^1$H NMR (300 MHz, CDCl$_3$) δ0.90-1.14 (m, 7H), 1.61-1.77 (m, 2H), 1.99-2.14 (m, 1H), 2.90-3.03 (m, 2H), 3.99 (s, 2H), 5.30 (s, 2H), 6.93-7.06 (m, 2H), 7.28-7.37 (m, 2H), 7.37-7.55 (m, 4H), 7.54-7.67 (m, 3H), 7.74 (d, J=8.0, 1H)

REFERENCE EXAMPLE 9

4'-({4-[(6-ethylpyridin-3-yl)methyl]-2-methyl-5-oxo-7-propyl-4,5-dihydro[1,2,4]triazolo[1,5-a]pyrimidin-6-yl}methyl)biphenyl-2-carbonitrile To a solution of 4'-[(2-methyl-5-oxo-7-propyl-4,5-dihydro[1,2,4]triazolo[1,5-a]pyrimidin-6-yl)methyl]biphenyl-2-carbonitrile (1.5 g), (6-ethylpyridin-3-yl)methanol (0.46 g) and tributylphosphine (1.1 mL) in THF (50 mL) was added 1,1'-(azodicarbonyl)dipiperidine (0.88 g) at 0° C., and the mixture was stirred at room temperature overnight. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.43 g, 49%).

$^1$H NMR (300 MHz, CDCl$_3$) δ0.93 (t, J=7.2, 3H), 1.23-1.31 (m, 3H), 1.50-1.62 (m, 2H), 2.45 (s, 3H), 2.79 (q, J=7.6, 2H), 2.92-3.01 (m, 2H), 4.00 (s, 2H), 5.36 (s, 2H), 7.12 (d, J=8.0, 1H), 7.31-7.51 (m, 6H), 7.57-7.67 (m, 1H), 7.74 (d, J=7.6, 1H), 7.85 (dd, J=8.0, 2.3, 1H), 8.79 (d, J=1.9, 1H)

REFERENCE EXAMPLE 10

4'-[(4-methyl-5-oxo-7-propyl-4,5-dihydro[1,2,4]triazolo[1,5-a]pyrimidin-6-yl)methyl]biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), methyl iodide (0.1 mL), potassium carbonate (0.38 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.52 g, 100%).

$^1$H NMR (300 MHz, CDCl$_3$) δ1.06 (t, J=7.4, 3H), 1.65-1.83 (m, 2H), 3.01-3.13 (m, 2H), 3.72 (s, 3H), 4.04 (s, 2H), 7.35-7.53 (m, 6H), 7.56-7.68 (m, 1H), 7.74 (d, J=7.6, 1H), 7.94 (s, 1H)

REFERENCE EXAMPLE 11

4'-{[4-(2,2-dimethylpropyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), 1-iodo-2,2-dimethylpropane (0.36 mL), cesium carbonate (0.89 g) and N,N-dimethylacetamide (10 mL) was stirred at 90° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.4 g, 67%).

$^1$H NMR (300 MHz, CDCl$_3$) δ0.98-1.13 (m, 12H), 1.66-1.84 (m, 2H), 2.96-3.10 (m, 2H), 4.04 (s, 2H), 4.18 (s, 2H), 7.34-7.54 (m, 6H), 7.59-7.70 (m, 1H), 7.74 (d, J=7.6, 1H), 7.90 (s, 1H)

REFERENCE EXAMPLE 12

4'-{[4-(3,3-dimethyl-2-oxobutyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (1 g), 1-bromo-3,3-dimethylbutan-2-one (0.4 mL), potassium carbonate (0.75 g) and N,N-dimethylformamide (15 mL) was stirred at room temperature for 3 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.4 g, 32%).

¹H NMR (300 MHz, CDCl₃) δ1.00-1.10 (m, 3H), 1.31 (s, 9H), 1.65-1.80 (m, 2H), 2.98-3.09 (m, 2H), 4.04 (s, 2H), 5.21 (s, 2H), 7.30-7.55 (m, 6H), 7.58-7.66 (m, 1H), 7.74 (d, J=6.8, 1H), 7.87 (s, 1H)

REFERENCE EXAMPLE 13

4'-({4-[2-(4-fluorophenyl)-2-oxoethyl]-5-oxo-7-propyl-4,5-dihydro[1,2,4]triazolo[1,5-a]pyrimidin-6-yl}methyl)biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (1 g), 2-bromo-1-(4-fluorophenyl)ethanone (0.65 mL), potassium carbonate (0.75 g) and N,N-dimethylformamide (15 mL) was stirred at room temperature for 3 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.78 g, 57%).
¹H NMR (300 MHz, CDCl₃) δ1.08 (t, J=7.4, 3H), 1.68-1.85 (m, 2H), 3.01-3.14 (m, 2H), 4.06 (s, 2H), 5.66 (s, 2H), 7.19 (t, J=8.5, 2H), 7.33-7.53 (m, 6H), 7.57-7.66 (m, 1H), 7.75 (d, J=6.8, 1H), 7.88 (s, 1H), 8.01-8.13 (m, 2H)

REFERENCE EXAMPLE 14

4'-({4-[2-(4-fluorophenyl)-2-hydroxyethyl]-5-oxo-7-propyl-4,5-dihydro[1,2,4]triazolo[1,5-a]pyrimidin-6-yl}methyl)biphenyl-2-carbonitrile To a solution (15 mL) of 4'-({4-[2-(4-fluorophenyl)-2-oxoethyl]-5-oxo-7-propyl-4,5-dihydro[1,2,4]triazolo[1,5-a]pyrimidin-6-yl}methyl)biphenyl-2-carbonitrile (0.78 g) in methanol was added sodium borohydride (0.12 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.78 g, 100%).
¹H NMR (300 MHz, CDCl₃) δ1.06 (t, J=7.2, 3H), 1.65-1.80 (m, 2H), 3.01-3.08 (m, 2H), 4.03 (s, 2H), 4.07-4.11 (m, 1H), 4.47-4.65 (m, 2H), 5.18-5.28 (m, 1H), 7.04 (t, J=8.5, 2H), 7.32 (d, J=8.3, 2H), 7.39-7.52 (m, 6H), 7.60-7.67 (m, 1H), 7.75 (d, J=8.0, 1H), 7.94 (s, 1H)

REFERENCE EXAMPLE 15

4'-({4-[2-{[tert-butyl(dimethyl)silyl]oxy}-2-(4-fluorophenyl)ethyl]-5-oxo-7-propyl-4,5-dihydro[1,2,4]triazolo[1,5-a]pyrimidin-6-yl}methyl)biphenyl-2-carbonitrile To a mixture of 4'-({4-[2-(4-fluorophenyl)-2-hydroxyethyl]-5-oxo-7-propyl-4,5-dihydro[1,2,4]triazolo[1,5-a]pyrimidin-6-yl}methyl)biphenyl-2-carbonitrile (0.78 g), 2,6-lutidine (0.27 mL) and tetrahydrofuran (20 mL) was added tert-butyl(dimethyl)silyl trifluoromethanesulfonate (0.53 mL), and the mixture was stirred at room temperature for 5 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.56 g, 58%).
¹H NMR (300 MHz, CDCl₃) δ−0.37−−0.33 (m, 3H), −0.32−−0.27 (m, 3H), 0.60-0.72 (m, 9H), 1.07 (t, J=7.3, 3H), 1.65-1.80 (m, 2H), 2.99-3.16 (m, 2H), 3.98-4.09 (m, 2H), 4.19 (dd, J=13.1, 3.7, 1H), 4.53 (dd, J=13.0, 9.6, 1H), 5.30 (dd, J=9.6, 3.8, 1H), 6.94-7.10 (m, 2H), 7.33-7.53 (m, 8H), 7.58-7.66 (m, 1H), 7.75 (dd, J=7.7, 0.9, 1H), 7.94 (s, 1H)

REFERENCE EXAMPLE 16 tert-butyl {6-[(2'-cyanobiphenyl-4-yl)methyl]-5-oxo-7-propyl[1,2,4]triazolo[1,5-a]pyrimidin-4(5H)-yl}acetate A mixture of 4'-[(5-oxo-7-propyl-4,5-dihydro[1,2,4]triazolo[1,5-a]pyrimidin-6-yl)methyl]biphenyl-2-carbonitrile (9 g), tert-butyl bromoacetate (3.8 mL), potassium carbonate (6 g) and N,N-dimethylformamide (100 mL) was stirred at room temperature for 3 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (2.6 g, 25%).
¹H NMR (300 MHz, CDCl₃) δ1.06 (t, J=7.3, 3H), 1.44-1.52 (m, 9H), 1.65-1.82 (m, 2H), 2.96-3.11 (m, 2H), 4.05 (s, 2H), 4.88 (s, 2H), 7.32-7.52 (m, 6H), 7.57-7.67 (m, 1H), 7.74 (dd, J=7.7, 0.9, 1H), 7.91 (s, 1H)

REFERENCE EXAMPLE 17

4'-{[4-(2-{[tert-butyl(dimethyl)silyl]oxy}ethyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.8 g), (2-bromoethoxy)(tert-butyl)dimethylsilane (0.7 mL), potassium carbonate (0.6 g), sodium iodide (0.033 g) and N,N-dimethylformamide (15 mL) was stirred at 50° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.82 g, 71%).
¹H NMR (300 MHz, CHLOROFORM-d) δ−0.08 (s, 6H) 0.76 (s, 9H) 1.05 (t, J=7.4 Hz, 3H) 1.62-1.79 (m, 2H) 2.99-3.12 (m, 2H) 3.96-4.06 (m, 4H) 4.43 (t, J=5.9 Hz, 2H) 7.33-7.53 (m, 6H) 7.57-7.68 (m, 1H) 7.74 (dd, J=7.7, 0.8 Hz, 1H) 7.92 (s, 1H)

REFERENCE EXAMPLE 18

{6-[(2'-cyanobiphenyl-4-yl)methyl]-5-oxo-7-propyl[1,2,4]triazolo[1,5-a]pyrimidin-4(5H)-yl}acetic acid A mixture of tert-butyl {6-[(2'-cyanobiphenyl-4-yl)methyl]-5-oxo-7-propyl[1,2,4]triazolo[1,5-a]pyrimidin-4(5H)-yl}acetate (1.78 g) and trifluoroacetic acid (15 mL) was stirred at room temperature for 1 hr. The reaction mixture was diluted with toluene (15 mL) and the solvent was evaporated under reduced pressure, and the residue was purified by silica gel column chromatography to give the title compound as a colorless solid (1.44 g, 92%).

$^1$H NMR (300 MHz, DMSO-d$_6$) δ0.96 (t, J=7.4, 3H), 1.54-1.71 (m, 2H), 2.98-3.07 (m, 2H), 4.03 (s, 2H), 4.80 (s, 2H), 7.38-7.44 (m, 2H), 7.47-7.62 (m, 4H), 7.73-7.82 (m, 1H), 7.93 (d, J=7.6, 1H), 8.21 (s, 1H), 13.33 (br. s., 1H)

REFERENCE EXAMPLE 19

2-{6-[(2'-cyanobiphenyl-4-yl)methyl]-5-oxo-7-propyl[1,2,4]triazolo[1,5-a]pyrimidin-4(5H)-yl}acetamide A mixture of {6-[(2'-cyanobiphenyl-4-yl)methyl]-5-oxo-7-propyl[1,2,4]triazolo[1,5-a]pyrimidin-4(5H)-yl}acetic acid (0.5 g), 1-hydroxybenzotriazole ammonium salt (0.24 g), 1-ethyl-3-(3-dimethylaminopropyl)carbodiimide hydrochloride (0.27 g) and N,N-dimethylformamide (10 mL) was stirred at room temperature for 15 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless solid (0.48 g, 100%).

$^1$H NMR (300 MHz, DMSO-d$_6$) δ0.96 (t, J=7.3, 3H), 1.54-1.70 (m, 2H), 2.95-3.06 (m, 2H), 4.02 (s, 2H), 4.67 (s, 2H), 7.28 (s, 1H), 7.38-7.43 (m, 2H), 7.46-7.61 (m, 4H), 7.68-7.81 (m, 2H), 7.93 (dd, J=7.7, 0.8, 1H), 8.17 (s, 1H)

REFERENCE EXAMPLE 20

4'-{[4-(1-methylethyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.8 g), 2-iodopropane (0.43 mL), potassium carbonate (0.6 g) and N,N-dimethylacetamide (10 mL) was stirred at 100° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.48 g, 53%).

$^1$H NMR (300 MHz, CDCl$_3$) δ1.06 (t, J=7.4, 3H), 1.30 (s, 3H), 1.33 (s, 3H), 1.70-1.87 (m, 2H), 3.11-3.25 (m, 2H), 4.08 (s, 2H), 5.47-5.60 (m, 1H), 7.24-7.32 (m, 2H), 7.37-7.53 (m, 4H), 7.57-7.68 (m, 1H), 7.75 (d, J=7.6, 1H), 8.18-8.27 (m, 1H)

REFERENCE EXAMPLE 21

4'-{[4-(2-hydroxy-2-methylpropyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.8 g), isobutylene oxide (1.9 mL), potassium carbonate (0.6 g) and N,N-dimethylacetamide (5 mL) was stirred in a sealed tube at 100° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.76 g, 79%).

$^1$H NMR (300 MHz, CDCl$_3$) δ1.07 (t, J=7.4, 3H), 1.30 (s, 6H), 1.67-1.80 (m, 2H), 3.00-3.11 (m, 2H), 4.05 (s, 2H), 4.22 (s, 1H), 4.41 (s, 2H), 7.32-7.52 (m, 6H), 7.63 (t, J=7.6, 1H), 7.75 (d, J=6.4, 1H), 7.92 (s, 1H)

REFERENCE EXAMPLE 22

4'-({4-[(1-methyl-1H-benzimidazol-2-yl)methyl]-5-oxo-7-propyl-4,5-dihydro[1,2,4]triazolo[1,5-a]pyrimidin-6-yl}methyl)biphenyl-2-carbonitrile To a mixture of {6-[(2'-cyanobiphenyl-4-yl)methyl]-5-oxo-7-propyl[1,2,4]triazolo[1,5-a]pyrimidin-4(5H)-yl}acetic acid (0.9 g), oxalyl chloride (0.22 mL) and tetrahydrofuran (50 mL) was added N,N-dimethylformamide (several drops), and the mixture was stirred at room temperature for 2 hr. The reaction mixture was concentrated under reduced pressure, the obtained residue was dissolved in N,N-dimethylacetamide (5 mL) and added to a solution of N-methylbenzene-1,2-diamine (1.2 mL) in N,N-dimethylacetamide (5 mL). The reaction mixture was stirred at room temperature for 2 hr, diluted with ethyl acetate, washed with water and then with saturated brine, and dried over anhydrous magnesium sulfate. The solvent was evaporated under reduced pressure. Then, a mixture of the obtained residue in acetic acid (20 mL) was stirred at 100° C. for 4 hr. The reaction mixture was concentrated and the obtained residue was purified by silica gel column chromatography to give the title compound as a colorless solid (0.84 g, 78%).

$^1$H NMR (300 MHz, CDCl$_3$) δ1.06 (t, J=7.3, 3H), 1.65-1.80 (m, 2H), 2.99-3.10 (m, 2H), 3.96 (s, 3H), 4.04 (s, 2H), 5.68 (s, 2H), 7.16-7.49 (m, 9H), 7.58-7.77 (m, 3H), 7.95 (s, 1H)

REFERENCE EXAMPLE 23

4'-[(4-ethyl-5-oxo-7-propyl-4,5-dihydro[1,2,4]triazolo[1,5-a]pyrimidin-6-yl)methyl]biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), ethyl iodide (0.38 mL), potassium carbonate (0.13 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.55 g, 100%).

$^1$H NMR (300 MHz, CHLOROFORM-d) δ1.06 (t, J=7.4 Hz, 3H), 1.41 (t, J=7.1 Hz, 3H), 1.65-1.79 (m, 2H), 2.98-3.09 (m, 2H), 4.04 (s, 2H), 4.33 (q, J=7.0 Hz, 2H), 7.34-7.53 (m, 6H), 7.57-7.66 (m, 1H), 7.75 (dd, J=7.7, 0.9 Hz, 1H), 7.94 (s, 1H)

REFERENCE EXAMPLE 24

4'-{[4-(cyclopropylmethyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), (bromomethyl)cyclopropane (0.16 mL), potassium carbonate (0.38 g) and N,N-dimethylacetamide (10 mL) was stirred at 70° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.54 g, 93%).

$^1$H NMR (300 MHz, CHLOROFORM-d) δ0.49-0.60 (m, 4H), 1.07 (t, J=7.3 Hz, 3H), 1.37-1.50 (m, 1H), 1.65-1.80 (m, 2H), 2.98-3.13 (m, 2H), 4.05 (s, 2H), 4.13-4.19 (m, 2H), 7.35-7.53 (m, 6H), 7.57-7.67 (m, 1H), 7.75 (dd, J=7.7, 0.9 Hz, 1H), 7.92 (s, 1H)

REFERENCE EXAMPLE 25

4'-{[2-methyl-4-(1-methylethyl)-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (0.8 g), 2-iodopropane (0.4 mL), potassium carbonate (0.55 g) and N,N-dimethylacetamide (10 mL) was stirred at 100° C. for 5 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.24 g, 28%).

$^1$H NMR (300 MHz, CHLOROFORM-d) δ1.04 (t, J=7.3 Hz, 3H) 1.56-1.78 (m, 8H) 2.44 (s, 3H) 2.90-3.01 (m, 2H) 4.00 (s, 2H) 5.30-5.46 (m, 1H) 7.32-7.52 (m, 6H) 7.57-7.67 (m, 1H) 7.74 (dd, J=7.7, 1.3 Hz, 1H)

REFERENCE EXAMPLE 26

4'-{[4-(2-hydroxybutyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), 2-ethyloxirane (1.17 mL), potassium carbonate (0.38 g) and N,N-dimethylacetamide (10 mL) was stirred in a sealed tube at 100° C. for 8 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.45 g, 75%).

$^1$H NMR (300 MHz, CHLOROFORM-d) δ1.00-1.12 (m, 6H), 1.52-1.81 (m, 4H), 2.99-3.10 (m, 2H), 3.18 (d, J=6.2 Hz, 1H), 3.92-4.06 (m, 3H), 4.28-4.47 (m, 2H), 7.33-7.52 (m, 6H), 7.57-7.69 (m, 1H), 7.75 (dd, J=7.7, 0.9 Hz, 1H), 7.92 (s, 1H)

REFERENCE EXAMPLE 27

4'-[(2-cyclopropyl-4-methyl-5-oxo-7-propyl-4,5-dihydro[1,2,4]triazolo[1,5-a]pyrimidin-6-yl)methyl]biphenyl-2-carbonitrile A mixture of 4'-[(2-cyclopropyl-5-oxo-7-propyl-4,5-dihydro[1,2,4]triazolo[1,5-a]pyrimidin-6- yl)methyl]biphenyl-2-carbonitrile (0.18 g), methyl iodide (0.033 mL), potassium carbonate (0.12 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.2 g, 100%).

$^1$H NMR (300 MHz, CHLOROFORM-d) δ0.98-1.08 (m, 7H), 1.64-1.79 (m, 2H), 2.00-2.11 (m, 1H), 2.95-3.04 (m, 2H), 3.65 (s, 3H), 4.01 (s, 2H), 7.32-7.52 (m, 6H), 7.57-7.66 (m, 1H), 7.71-7.77 (m, 1H)

REFERENCE EXAMPLE 28

4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), [4-(1-methylethoxy)phenyl]boronic acid (0.49 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.17 g, 82%).

$^1$H NMR (300 MHz, CHLOROFORM-d) δ1.11 (t, J=7.3 Hz, 3H), 1.35 (s, 3H), 1.37 (s, 3H), 1.71-1.89 (m, 2H), 3.06-3.16 (m, 2H), 4.07 (s, 2H), 4.51-4.63 (m, 1H), 6.98-7.06 (m, 2H), 7.28-7.35 (m, 2H), 7.38-7.53 (m, 6H), 7.58-7.67 (m, 1H), 7.71-7.76 (m, 1H), 7.86 (s, 1H)

REFERENCE EXAMPLE 29 methyl 4-({6-[(2'-cyanobiphenyl-4-yl)methyl]-5-oxo-7-propyl[1,2,4]triazolo[1,5-a]pyrimidin-4(5H)-yl}methyl)benzoate A mixture of 4'-[(5-oxo-7-propyl-4,5-dihydro[1,2,4]triazolo[1,5-a]pyrimidin-6-yl)methyl]biphenyl-2-carbonitrile (5 g), methyl 4-(bromomethyl)benzoate (3.7 mL), potassium carbonate (2.3 g) and N,N-dimethylformamide (50 mL) was stirred at room temperature for 5 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (2.8 g, 40%).

$^1$H NMR (300 MHz, CHLOROFORM-d) δ1.05 (t, J=7.3 Hz, 3H), 1.64-1.81 (m, 2H), 2.97-3.09 (m, 2H), 3.86-3.93 (m, 3H), 4.04 (s, 2H), 5.46 (s, 2H), 7.33-7.53 (m, 6H), 7.57-7.70 (m, 3H), 7.75 (dd, J=7.7, 0.9 Hz, 1H), 7.94 (s, 1H), 7.96-8.03 (m, 2H)

REFERENCE EXAMPLE 30

4'-({4-[4-hydroxymethylbenzyl]-5-oxo-7-propyl-4,5-dihydro[1,2,4]triazolo[1,5-a]pyrimidin-6-yl}methyl)biphenyl-2-carbonitrile A mixture of methyl 4-({6-[(2'-cyanobiphenyl-4-yl)methyl]-5-oxo-7 -propyl[1,2,4]triazolo[1,5-a]pyrimidin-4(5H)- yl}methyl)benzoate (2.8 g), 1N aqueous sodium hydroxide solution (30 mL), tetrahydrofuran (30 mL) and methanol (30 mL) was stirred at 50° C. for 3 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was dissolved in tetrahydrofuran (50 mL), N-methylmorpholine (0.67 mL) and ethyl chlorocarbonate (0.58 mL) was added at 0° C., and the mixture was stirred at the same temperature for 2 hr. The reaction mixture was cooled to −15° C., sodium borohydride (0.57 g) and methanol (10 mL) were added, and the mixture was allowed to gradually warm to room temperature. The reaction mixture was extracted with saturated aqueous ammonium chloride solution and ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless solid (1.86 g, 70%).

$^1$H NMR (300 MHz, CHLOROFORM-d) δ1.05 (t, J=7.4 Hz, 3H), 1.63-1.79 (m, 2H), 2.96-3.08 (m, 2H), 4.03 (s, 2H), 4.65 (s, 2H), 5.42 (s, 2H), 7.28-7.52 (m, 8H), 7.55-7.67 (m, 3H), 7.74 (d, J=8.0 Hz, 1H), 7.94 (s, 1H)

REFERENCE EXAMPLE 31

4'-{[4-(4-formylbenzyl)-5-oxo-7-propyl-4,5-dihydro [1,2,4]triazolo[1,5-a]pyrimidin-6-yl] methyl}biphenyl-2-carbonitrile A mixture of 4'-({4-[4-hydroxymethylbenzyl]-5-oxo-7-propyl-4,5-dihydro[1,2,4]triazolo[1,5-a]pyrimidin-6-yl}methyl)biphenyl-2-carbonitrile (1.3 g), manganese dioxide (7.0 g) and methylene chloride (15 mL) was stirred at room temperature for 16 hr. The insoluble material was filtered off through celite, and the filtrate was concentrated to give the title compound as a colorless solid (1.3 g, 96%).

$^1$H NMR (300 MHz, CHLOROFORM-d) δ1.06 (t, J=7.3 Hz, 3H), 1.65-1.83 (m, 2H), 3.00-3.10 (m, 2H), 4.04 (s, 2H), 5.48 (s, 2H), 7.33-7.53 (m, 6H), 7.58-7.67 (m, 1H), 7.67-7.78 (m, 3H), 7.81-7.88 (m, 2H), 7.94 (s, 1H), 9.98 (s, 1H)

REFERENCE EXAMPLE 32

4'-({4-[4-(1-hydroxyethyl)benzyl]-5-oxo-7-propyl-4, 5-dihydro[1,2,4]triazolo[1,5-a]pyrimidin-6-yl}methyl)biphenyl-2-carbonitrile 4'-{[4-(4-Formylbenzyl)-5-oxo-7-propyl-4,5-dihydro[1, 2,4]triazolo[1,5-a]pyrimidin-6-yl]methyl}biphenyl-2-carbonitrile (1.3 g) was dissolved in tetrahydrofuran (30 mL), and methylmagnesium bromide (1.0 M tetrahydrofuran solution, 2.8 mL) was added at −78° C. The reaction mixture was warmed to 0° C., and stirred for 6 hr. Saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (1.2 g, 90%).

$^1$H NMR (300 MHz, CHLOROFORM-d) δ1.05 (t, J=7.3 Hz, 3H), 1.46 (d, J=6.4 Hz, 3H), 1.63-1.76 (m, 2H), 1.83 (d, J=3.6 Hz, 1H), 2.98-3.06 (m, 2H), 4.03 (s, 2H), 4.81-4.92 (m, 1H), 5.41 (s, 2H), 7.31-7.51 (m, 8H), 7.54-7.66 (m, 3H), 7.75 (dd, J=7.7, 0.9 Hz, 1H), 7.94 (s, 1H)

REFERENCE EXAMPLE 33

4'-({4-[4-(1-{[tert-butyl(dimethyl)silyl]oxy}ethyl) benzyl]-5-oxo-7-propyl-4,5-dihydro[1,2,4]triazolo[1, 5-a]pyrimidin-6-yl}methyl)biphenyl-2-carbonitrile To a mixture of 4'-({4-[4-(1-hydroxyethyl)benzyl]-5-oxo-7-propyl-4,5-dihydro[1,2,4]triazolo[1,5-a]pyrimidin-6-yl}methyl)biphenyl-2-carbonitrile (1.2 g), 2,6-lutidine (0.41 mL) and tetrahydrofuran (30 mL) was added tert-butyldimethylsilyl trifluoromethanesulfonate (0.79 mL) at 0° C., and the mixture was stirred at the same temperature for 3 hr. The reaction mixture was diluted with ethyl acetate, washed with water and saturated brine, and dried over anhydrous magnesium sulfate. The solvent was evaporated under reduced pressure. The obtained residue was purified by silica gel column chromatography to give the title compound as a colorless solid (1.4 g, 100%).

$^1$H NMR (300 MHz, CHLOROFORM-d) δ0.05 (s, 3H), 0.03 (s, 3H), 0.88 (s, 9H), 1.05 (t, J=7.4 Hz, 3H), 1.36 (d, J=6.1 Hz, 3H), 1.63-1.77 (m, 2H), 2.96-3.07 (m, 2H), 4.04 (s, 2H), 4.84 (q, J=6.4 Hz, 1H), 5.40 (s, 2H), 7.24-7.31 (m, 2H), 7.33-7.55 (m, 8H), 7.58-7.67 (m, 1H), 7.74 (d, J=8.0 Hz, 1H), 7.94 (s, 1H)

REFERENCE EXAMPLE 34

4'-[(5-oxo-4,7-dipropyl-4,5-dihydro[1,2,4]triazolo[1, 5-a]pyrimidin-6-yl)methyl]biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (0.5 g), 1-iodopropane (0.16 mL), potassium carbonate (0.38 g) and N,N-dimethylformamide (10 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.5 g, 90%).

$^1$H NMR (300 MHz, CHLOROFORM-d) δ0.96-1.12 (m, 6H) 1.65-1.78 (m, 2H) 1.78-1.94 (m, 2H) 2.99-3.09 (m, 2H) 4.04 (s, 2H) 4.17-4.27 (m, 2H) 7.35-7.52 (m, 6H) 7.57-7.67 (m, 1H) 7.75 (dd, J=7.8, 0.8 Hz, 1H) 7.93 (s, 1H)

REFERENCE EXAMPLE 35

4'-[(5-oxo-4-phenyl-7-propyl-4,5-dihydro[1,2,4] triazolo[1,5-a]pyrimidin-6-yl)methyl]biphenyl-2-carbonitrile To a suspension (20 mL) of 4'-[(5-oxo-7-propyl-4,5-dihydro[1,2,4]triazolo[1,5-a]pyrimidin-6-yl)methyl]biphenyl-2-carbonitrile (0.6 g), phenylboronic acid (0.4 g), triethylamine (0.5 mL), pyridine (1 mL) and molecular sieves 4A (1 g) in dichloromethane was added copper(II) acetate (0.59 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.58 g, 80%).

¹H NMR (300 MHz, CHLOROFORM-d) δ1.12 (t, J=7.3 Hz, 3H), 1.72-1.90 (m, 2H), 3.07-3.19 (m, 2H), 4.07 (s, 2H), 7.35-7.67 (m, 12H), 7.75 (dd, J=7.7, 0.9 Hz, 1H), 7.87 (s, 1H)

REFERENCE EXAMPLE 36

4'-({2-methyl-4-[4-(1-methylethoxy)phenyl]-5-oxo-7-propyl-4,5-dihydro[1,2,4]triazolo[1,5-a]pyrimidin-6-yl}methyl)biphenyl-2-carbonitrile To a suspension (40 mL) of 4'-[(2-methyl-5-oxo-7-propyl-4,5-dihydro[1,2,4]triazolo[1,5-a]pyrimidin-6-yl)methyl]biphenyl-2-carbonitrile (1 g), [4-(1-methylethoxy)phenyl]boronic acid (0.9 g), triethylamine (1 mL), pyridine (2 mL) and molecular sieves 4A (2 g) in dichloromethane was added copper(II) acetate (0.91 g), and the mixture was stirred for 48 hr. The reaction mixture was diluted with ethyl acetate, insoluble material was filtered off through celite, and the filtrate was concentrated. The residue was purified by silica gel column chromatography to give the title compound as a colorless solid (0.55 g, 43%).
¹H NMR (300 MHz, CHLOROFORM-d) δ1.10 (t, J=7.3 Hz, 3H), 1.34 (s, 3H), 1.36 (s, 3H), 1.72-1.85 (m, 2H), 2.39 (s, 3H), 2.98-3.16 (m, 2H), 4.03 (s, 2H), 4.48-4.65 (m, 1H), 6.94-7.07 (m, 2H), 7.22-7.35 (m, 2H), 7.36-7.52 (m, 6H), 7.61 (dd, J=7.6, 1.4 Hz, 1H), 7.74 (dd, J=7.7, 0.9 Hz, 1H)

REFERENCE EXAMPLE 37

4'-{[4-(2,2-dimethyl-2,3-dihydro-1-benzofuran-5-yl)-5-oxo-7-propyl-4,5-dihydro[1,2,4]triazolo[1,5-a]pyrimidin-6-yl]methyl}biphenyl-2-carbonitrile To a suspension (20 mL) of 4'-[(5-oxo-7-propyl-4,5-dihydro[1,2,4]triazolo[1,5-a]pyrimidin-6-yl)methyl]biphenyl-2-carbonitrile (0.6 g), (2,2-dimethyl-2,3-dihydro-1-benzofuran-5-yl)boronic acid (0.62 g), triethylamine (0.5 mL), pyridine (1 mL) and molecular sieves 4A (1 g) in dichloromethane was added copper(II) acetate (0.59 g), and the mixture was stirred for 48 hr. The reaction mixture was diluted with ethyl acetate, insoluble material was filtered off through celite, and the filtrate was concentrated. The residue was purified by silica gel column chromatography to give the title compound as a colorless solid (0.86 g, 100%).
¹H NMR (300 MHz, CHLOROFORM-d) δ1.11 (t, J=7.3 Hz, 3H), 1.50 (s, 6H), 1.72-1.89 (m, 2H), 3.08 (s, 2H), 3.09-3.18 (m, 2H), 4.06 (s, 2H), 6.85 (d, J=8.5 Hz, 1H), 7.09-7.18 (m, 2H), 7.37-7.52 (m, 6H), 7.57-7.66 (m, 1H), 7.75 (dd, J=7.7, 0.9 Hz, 1H), 7.87 (s, 1H)

REFERENCE EXAMPLE 38

3'-fluoro-4'-[(5-oxo-7-propyl-4,5-dihydro[1,2,4]triazolo[1,5-a]pyrimidin-6-yl)methyl]biphenyl-2-carbonitrile A solution of 5-methyl-4H-1,2,4-triazol-3-amine (8.9 g) and ethyl 2-[(2'-cyano-3-fluorobiphenyl-4-yl)methyl]-3-oxohexanoate (25 g) in 1,2,4-trichlorobenzene (120 mL) was stirred at 180° C. for 16 hr. After evaporation of the solvent under reduced pressure, ethyl acetate was added to the obtained residue. The precipitated solid was collected by filtration to give the title compound as a colorless solid (11.8 g, 43%).
¹H NMR (300 MHz, DMSO-d₆) δ0.94 (t, J=7.3 Hz, 3H) 1.53-1.70 (m, 2H) 2.90-3.01 (m, 2H) 3.94 (s, 2H) 7.27-7.50 (m, 3H) 7.55-7.68 (m, 2H) 7.74-7.85 (m, 1H) 7.92-7.99 (m, 1H) 8.12 (s, 1H) 13.13 (s, 1H)

REFERENCE EXAMPLE 39

4'-{[4-(2,4-dimethoxybenzyl)-5-oxo-7-propyl-4,5-dihydro[1,2,4]triazolo[1,5-a]pyrimidin-6-yl]methyl}-3'-fluorobiphenyl-2-carbonitrile A mixture of 3'-fluoro-4'-[(5-oxo-7-propyl-4,5-dihydro[1,2,4]triazolo[1,5-a]pyrimidin-6-yl)methyl]biphenyl-2-carbonitrile (1 g), 1,1'-(azodicarbonyl)dipiperidine (1.3 g), tributylphosphine (1.6 mL), (2,4-dimethoxyphenyl)methanol (0.58 g) and tetrahydrofuran (50 mL) was stirred at room temperature for 4 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless solid (0.36 g, 26%).
¹H NMR (300 MHz, CHLOROFORM-d) δ1.06 (t, J=7.4 Hz, 3H), 1.64-1.80 (m, 2H), 3.02-3.10 (m, 2H), 3.76 (s, 6H), 4.06 (s, 2H), 5.41 (s, 2H), 6.35-6.49 (m, 3H), 7.00 (d, J=8.3 Hz, 1H), 7.21-7.29 (m, 1H), 7.36-7.49 (m, 3H), 7.64 (t, J=7.8 Hz, 1H), 7.75 (d, J=7.6 Hz, 1H), 7.91 (s, 1H)

REFERENCE EXAMPLE 40

4'-{[4-(4-methoxyphenyl)-5-oxo-7-propyl-4,5-dihydro[1,2,4]triazolo[1,5-a]pyrimidin-6-yl]methyl}biphenyl-2-carbonitrile To a suspension (20 mL) of 4'-[(5-oxo-7-propyl-4,5-dihydro[1,2,4]triazolo[1,5-a]pyrimidin-6-yl)methyl]biphenyl-2-carbonitrile (0.5 g), (4-methoxyphenyl)boronic acid (0.41 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.64 g, 99%).
¹H NMR (300 MHz, CHLOROFORM-d) δ1.11 (t, J=7.3 Hz, 3H), 1.73-1.88 (m, 2H), 3.06-3.20 (m, 2H), 3.81-3.87 (m, 3H), 4.07 (s, 2H), 7.02-7.09 (m, 2H), 7.32-7.51 (m, 8H), 7.58-7.66 (m, 1H), 7.75 (dd, J=7.7, 0.9 Hz, 1H), 7.86 (s, 1H)

REFERENCE EXAMPLE 41

3'-fluoro-4'-[(5-oxo-4-phenyl-7-propyl-4,5-dihydro[1,2,4]triazolo[1,5-a]pyrimidin-6-yl)methyl]biphenyl-2-carbonitrile To a suspension (20 mL) of 3'-fluoro-4'-[(5-oxo-7-propyl-4,5-dihydro[1,2,4]triazolo[1,5-a]pyrimidin-6-yl)methyl]biphenyl-2-carbonitrile (0.5 g), phenylboronic acid (0.31 g), triethylamine (0.5 mL), pyridine (1 mL) and molecular sieves 4A (1 g) in dichloromethane was added copper(II) acetate (0.47 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.61 g, 100%).

¹H NMR (300 MHz, CHLOROFORM-d) δ1.12 (t, J=7.4 Hz, 3H), 1.73-1.88 (m, 2H), 3.11-3.21 (m, 2H), 4.09 (s, 2H), 7.21-7.31 (m, 2H), 7.39-7.68 (m, 9H), 7.72-7.78 (m, 1H), 7.87 (s, 1H)

REFERENCE EXAMPLE 42

4'-{[4-(methoxymethyl)-5-oxo-7-propyl-4,5-dihydro[1,2,4]triazolo[1,5-a]pyrimidin-6-yl]methyl}-3'-fluorobiphenyl-2-carbonitrile A mixture of 3'-fluoro-4'-[(5-oxo-7-propyl-4,5-dihydro[1,2,4]triazolo[1,5-a]pyrimidin-6-yl)methyl]biphenyl-2-carbonitrile (0.5 g), chloro(methoxy)methane (0.12 mL), potassium carbonate (0.36 g) and N,N-dimethylformamide (10 mL) was stirred at room temperature for 1 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.38 g, 69%).
¹H NMR (300 MHz, CHLOROFORM-d) δ1.07 (t, J=7.3 Hz, 3H), 1.64-1.80 (m, 2H), 3.03-3.12 (m, 2H), 3.52 (s, 3H), 4.05 (s, 2H), 5.67 (s, 2H), 7.22-7.29 (m, 2H), 7.36-7.50 (m, 3H), 7.59-7.69 (m, 1H), 7.72-7.79 (m, 1H), 7.94 (s, 1H)

REFERENCE EXAMPLE 43

3'-fluoro-4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile To a suspension (20 mL) of 3'-fluoro-4'-[(5-oxo-7-propyl-4,5-dihydro[1,2,4]triazolo[1,5-a]pyrimidin-6-yl)methyl]biphenyl-2-carbonitrile (0.5 g), [4-(1-methylethoxy)phenyl]boronic acid (0.46 g), triethylamine (0.5 mL), pyridine (1 mL) and molecular sieves 4A (1 g) in dichloromethane was added copper(II) acetate (0.47 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.59 g, 100%).
¹H NMR (300 MHz, CHLOROFORM-d) δ1.11 (t, J=7.3 Hz, 3H) 1.36 (d, J=6.2 Hz, 6H) 1.71-1.86 (m, 2H) 3.10-3.20 (m, 2H) 4.07 (s, 2H) 4.50-4.65 (m, 1H) 6.97-7.07 (m, 2H) 7.21-7.36 (m, 4H) 7.40-7.55 (m, 3H) 7.60-7.68 (m, 1H) 7.76 (dd, J=8.0, 1.0 Hz, 1H) 7.87 (s, 1H)

REFERENCE EXAMPLE 44 methyl 2-[(2'-cyano-2-fluorobiphenyl-4-yl)methyl]-3-oxoheptanoate

A solution of methyl 3-oxoheptanoate (7 g) in tetrahydrofuran (30 mL) was added to a mixture of sodium hydride (1.2 g) and tetrahydrofuran (80 mL) at room temperature, and the mixture was stirred at room temperature for 30 min. And then, 4'-(bromomethyl)-2'-fluorobiphenyl-2-carbonitrile (5.3 g) was added to the reaction mixture, and the reaction mixture was stirred at room temperature for 3 days. The reaction mixture was concentrated, the residue was extracted with 5% aqueous potassium hydrogensulfate solution and then with ethyl acetate, and the ethyl acetate layer was washed with saturated brine and concentrated. The residue was purified by silica gel column chromatography to give the title compound as a colorless oil (7.3 g, 90%).
¹H NMR (300 MHz, DMSO-d₆) δ0.75-0.86 (m, 3H), 1.10-1.47 (m, 4H), 2.41-2.66 (m, 2H), 3.03-3.22 (m, 2H), 3.62 (s, 3H), 4.22 (t, J=7.6 Hz, 1H), 7.14-8.01 (m, 7H)

REFERENCE EXAMPLE 45

4'-({4-[4-(1-methylethoxy)phenyl]-5-oxo-7-butyl-4,5-dihydro[1,2,4]triazolo[1,5-a]pyrimidin-6-yl}methyl)biphenyl-2-carbonitrile To a suspension (15 mL) of 4'-[(7-butyl-5-oxo-4,5-dihydro[1,2,4]triazolo[1,5-a]pyrimidin-6-yl)methyl]biphenyl-2-carbonitrile (0.5 g), [4-(1-methylethoxy)phenyl]boronic acid (0.47 g), triethylamine (0.5 mL), pyridine (1 mL) and molecular sieves 4A (1 g) in dichloromethane was added copper(II) acetate (0.47 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.69 g, 100%).
¹H NMR (300 MHz, CHLOROFORM-d) δ0.99 (t, J=7.3 Hz, 3H), 1.35 (d, J=6.2 Hz, 6H), 1.45-1.57 (m, 2H), 1.65-1.82 (m, 2H), 3.07-3.19 (m, 2H), 4.06 (s, 2H), 4.49-4.65 (m, 1H), 6.98-7.05 (m, 2H), 7.29-7.36 (m, 2H), 7.38-7.53 (m, 6H), 7.58-7.67 (m, 1H), 7.75 (dd, J=7.7, 0.9 Hz, 1H), 7.87 (s, 1H)

REFERENCE EXAMPLE 46 methyl 2-[(2'-cyano-3,5-difluorobiphenyl-4-yl)methyl]-3-oxoheptanoate

A solution of methyl 3-oxoheptanoate (6 g) in tetrahydrofuran (50 mL) was added to a mixture of sodium hydride (1 g) and tetrahydrofuran (50 mL) at room temperature, and the mixture was stirred at room temperature for 30 min. And then, 4'-(bromomethyl)-3',5'-difluorobiphenyl-2-carbonitrile (5.9 g) was added to the reaction mixture, and the reaction mixture was stirred at room temperature for 3 days. The reaction mixture was concentrated, the residue was extracted with 5% aqueous potassium hydrogensulfate solution and then with ethyl acetate, and the ethyl acetate layer was washed with saturated brine and concentrated. The residue was purified by silica gel column chromatography to give the title compound as a colorless oil (7.2 g, 98%).
¹H NMR (300 MHz, CHLOROFORM-d) δ0.88 (t, J=7.4 Hz, 3H), 1.20-1.36 (m, 2H), 1.49-1.62 (m, 2H), 2.38-2.53 (m, 1H), 2.54-2.67 (m, 1H), 3.27 (d, J=6.8 Hz, 2H), 3.69-3.74 (m, 3H), 3.91 (t, J=7.6 Hz, 1H), 7.02-7.12 (m, 2H), 7.43-7.53 (m, 2H), 7.66 (t, J=7.6 Hz, 1H), 7.77 (d, J=7.6 Hz, 1H)

REFERENCE EXAMPLE 47

4'-[(7-butyl-5-oxo-4,5-dihydro[1,2,4]triazolo[1,5-a]pyrimidin-6-yl)methyl]-3',5'-difluorobiphenyl-2-carbonitrile A solution of 4H-1,2,4-triazol-3-amine (2.4 g) and methyl 2-[(2'-cyano-3,5-difluorobiphenyl-4-yl)methyl]-3-oxoheptanoate (10 g) in 1,2,4-trichlorobenzene (50 mL) was stirred at 180° C. for 6 hr. After evaporation of the solvent under reduced pressure, ethyl acetate was added to the obtained residue. The precipitated solid was collected by filtration to give the title compound as a colorless solid (4.5 g, 57%).

¹H NMR (300 MHz, DMSO-d₆) δ0.79-0.89 (m, 3H), 1.29-1.51 (m, 4H), 2.94-3.04 (m, 2H), 3.98 (s, 2H), 7.29-7.40 (m, 2H), 7.57-7.70 (m, 2H), 7.75-7.84 (m, 1H), 7.97 (dd, J=7.7, 0.9 Hz, 1H), 8.11 (s, 1H), 13.09 (s, 1H)

REFERENCE EXAMPLE 48

4'-{[7-butyl-4-(methoxymethyl)-5-oxo-4,5-dihydro[1,2,4]triazolo[1,5-a]pyrimidin-6-yl]methyl}-3',5'-difluorobiphenyl-2-carbonitrile A mixture of 4'-[(7-butyl-5-oxo-4,5-dihydro[1,2,4]triazolo[1,5-a]pyrimidin-6-yl)methyl]-3',5'-difluorobiphenyl-2-carbonitrile (0.88 g), chloro(methoxy)methane (0.19 mL), potassium carbonate (0.58 g) and N,N-dimethylformamide (15 mL) was stirred at room temperature for 1 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.77 g, 79%).
¹H NMR (300 MHz, CHLOROFORM-d) δ0.94 (t, J=7.2 Hz, 3H), 1.37-1.52 (m, 2H), 1.53-1.70 (m, 2H), 2.04 (s, 3H), 3.03-3.13 (m, 2H), 4.06 (s, 2H), 5.65 (s, 2H), 7.01-7.14 (m, 2H), 7.41-7.52 (m, 2H), 7.60-7.71 (m, 1H), 7.77 (d, J=8.0 Hz, 1H), 7.93 (s, 1H)

REFERENCE EXAMPLE 49

4'-({7-butyl-4-[3-fluoro-4-methoxyphenyl]-5-oxo-4,5-dihydro[1,2,4]triazolo[1,5-a]pyrimidin-6-yl}methyl)biphenyl-2-carbonitrile To a suspension (15 mL) of 4'-[(7-butyl-5-oxo-4,5-dihydro[1,2,4]triazolo[1,5-a]pyrimidin-6-yl)methyl]biphenyl-2-carbonitrile (0.5 g), (3-fluoro-4-methoxyphenyl)boronic acid (0.44 g), triethylamine (0.5 mL), pyridine (1 mL) and molecular sieves 4A (1 g) in dichloromethane was added copper(II) acetate (0.47 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.78 g, 100%).
¹H NMR (300 MHz, CHLOROFORM-d) δ0.99 (t, J=7.2 Hz, 3H), 1.45-1.56 (m, 2H), 1.66-1.79 (m, 2H), 3.08-3.18 (m, 2H), 3.94 (s, 3H), 4.06 (s, 2H), 7.02-7.24 (m, 3H), 7.37-7.52 (m, 6H), 7.63 (t, J=7.8 Hz, 1H), 7.74 (d, J=7.6 Hz, 1H), 7.87 (s, 1H)

REFERENCE EXAMPLE 50

4'-({7-butyl-4-[3-fluoro-4-(1-methylethoxy)phenyl]-5-oxo-4,5-dihydro[1,2,4]triazolo[1,5-a]pyrimidin-6-yl}methyl)biphenyl-2-carbonitrile To a suspension (15 mL) of 4'-[(7-butyl-5-oxo-4,5-dihydro[1,2,4]triazolo[1,5-a]pyrimidin-6-yl)methyl]biphenyl-2-carbonitrile (0.5 g), [3-fluoro-4-(1-methylethoxy)phenyl]boronic acid (0.51 g), triethylamine (0.5 mL), pyridine (1 mL) and molecular sieves 4A (1 g) in dichloromethane was added copper(II) acetate (0.47 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.68 g, 98%).
¹H NMR (300 MHz, CHLOROFORM-d) δ0.99 (t, J=7.2 Hz, 3H), 1.40 (d, J=6.1 Hz, 6H), 1.45-1.59 (m, 2H), 1.65-1.80 (m, 2H), 3.08-3.18 (m, 2H), 4.05 (s, 2H), 4.52-4.67 (m, 1H), 7.04-7.23 (m, 3H), 7.38-7.52 (m, 6H), 7.57-7.66 (m, 1H), 7.74 (d, J=7.6 Hz, 1H), 7.87 (s, 1H)

REFERENCE EXAMPLE 51

4'-({4-[4-(1-methylethyl)phenyl]]-5-oxo-7-propyl-4,5-dihydro[1,2,4]triazolo[1,5-a]pyrimidin-6-yl}methyl)biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), [4-(1-methylethyl)phenyl]boronic acid (0.49 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.63 g, 95%).
¹H NMR (300 MHz, CHLOROFORM-d) δ1.12 (t, J=7.3 Hz, 3H), 1.28 (d, J=6.8 Hz, 6H), 1.73-1.86 (m, 2H), 2.92-3.04 (m, 1H), 3.09-3.18 (m, 2H), 4.07 (s, 2H), 7.31-7.50 (m, 10H), 7.59-7.67 (m, 1H), 7.75 (dd, J=7.7, 0.9 Hz, 1H), 7.87 (s, 1H)

REFERENCE EXAMPLE 52

4'-({4-[4-(1-hydroxy-1-methylethyl)phenyl]-5-oxo-7-propyl-4,5-dihydro[1,2,4]triazolo[1,5-a]pyrimidin-6-yl}methyl)biphenyl-2-carbonitrile To a suspension (26 mL) of 4'-[(5-oxo-7-propyl-4,5-dihydro[1,2,4]triazolo[1,5-a]pyrimidin-6-yl)methyl]biphenyl-2-carbonitrile (0.86 g), (4-acetylphenyl)boronic acid (0.83 g), triethylamine (0.86 mL), pyridine (1.7 mL) and molecular sieves 4A (1.7 g) in dichloromethane was added copper(II) acetate (0.84 g), and the mixture was stirred for 16 hr. The reaction mixture was diluted with ethyl acetate, insoluble material was filtered off through celite, and the filtrate was concentrated. Methyllithium (2.2M diethyl ether solution, 0.94 mL) was added to the obtained residue at −78° C. The reaction mixture was stirred at the same temperature for 1 hr, and extracted with saturated aqueous ammonium chloride solution and diethyl ether. The diethyl ether layer was washed with saturated brine, and dried over anhydrous magnesium sulfate. The solvent was evaporated under reduced pressure, and the residue was purified by silica gel column chromatography to give the title compound as a colorless solid (0.47 g, 41%).
¹H NMR (300 MHz, CHLOROFORM-d) δ1.12 (t, J=7.4 Hz, 3H) 1.61 (s, 6H) 1.74-1.83 (m, 2H) 3.10-3.18 (m, 2H) 4.07 (s, 2H) 7.38-7.77 (m, 12H) 7.87 (s, 1H)

REFERENCE EXAMPLE 53

4'-{[4-(3-methoxyphenyl)-5-oxo-7-propyl-4,5-dihydro[1,2,4]triazolo[1,5-a]pyrimidin-6-yl]methyl}biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2- carbonitrile (0.5 g), (3-methoxyphenyl)boronic acid (0.41 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.65 g, 100%).

$^1$H NMR (300 MHz, CHLOROFORM-d) δ1.11 (t, J=7.4 Hz, 3H), 1.70-1.89 (m, 2H), 3.07-3.19 (m, 2H), 3.82 (s, 3H), 4.07 (s, 2H), 6.95 (s, 1H), 6.97-7.07 (m, 2H), 7.35-7.52 (m, 7H), 7.62 (t, J=7.8 Hz, 1H), 7.74 (d, J=7.6 Hz, 1H), 7.86 (s, 1H)

REFERENCE EXAMPLE 54

4'-{[4-(3,4-dimethoxyphenyl)-5-oxo-7-propyl-4,5-dihydro[1,2,4]triazolo[1,5-a]pyrimidin-6-yl]methyl}biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), (3,4-dimethoxyphenyl)boronic acid (0.49 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.58 g, 85%).

$^1$H NMR (300 MHz, CHLOROFORM-d) δ1.11 (t, J=7.2 Hz, 3H), 1.67-1.90 (m, 2H), 3.06-3.18 (m, 2H), 3.88 (s, 3H), 3.92 (s, 3H), 4.07 (s, 2H), 6.90 (d, J=1.9 Hz, 1H), 6.96-7.05 (m, 2H), 7.36-7.51 (m, 6H), 7.63 (t, J=7.0 Hz, 1H), 7.75 (d, J=8.0 Hz, 1H), 7.86 (s, 1H)

REFERENCE EXAMPLE 55

4'-({4-[4-(1-{[tert-butyl(dimethyl)silyl]oxy}ethyl)phenyl]-5-oxo-7-propyl-4,5-dihydro[1,2,4]triazolo[1,5-a]pyrimidin-6-yl}methyl)biphenyl-2-carbonitrile To a suspension (19 mL) of 4'-[(5-oxo-7-propyl-4,5-dihydro[1,2,4]triazolo[1,5-a]pyrimidin-6-yl)methyl]biphenyl-2-carbonitrile (0.65 g), (4-acetylphenyl)boronic acid (0.63 g), triethylamine (0.65 mL), pyridine (1.3 mL) and molecular sieves 4A (1.3 g) in dichloromethane was added copper(II) acetate (0.64 g), and the mixture was stirred for 16 hr. The reaction mixture was diluted with ethyl acetate, insoluble material was filtered off through celite, and the filtrate was concentrated. The obtained residue was dissolved in methanol (15 mL), sodium borohydride (0.059 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. The obtained residue was dissolved in tetrahydrofuran (15 mL), 2,6-lutidine (0.14 mL) and tert-butyl(dimethyl)silyl trifluoromethanesulfonate (0.26 mL) were added and the mixture was stirred at room temperature for 3 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.49 g, 45%).

$^1$H NMR (300 MHz, CHLOROFORM-d) δ0.03 (s, 3H), 0.09 (s, 3H), 0.93 (s, 9H), 1.13 (t, J=7.4 Hz, 3H), 1.44 (d, J=6.2 Hz, 3H), 1.76-1.87 (m, 2H), 3.10-3.18 (m, 2H), 4.08 (s, 2H), 4.95 (q, J=6.4 Hz, 1H), 7.35-7.55 (m, 10H), 7.59-7.67 (m, 1H), 7.76 (dd, J=7.7, 0.9 Hz, 1H), 7.89 (s, 1H)

REFERENCE EXAMPLE 56

4'-{[4-(4-fluorophenyl)-5-oxo-7-propyl-4,5-dihydro[1,2,4]triazolo[1,5-a]pyrimidin-6-yl]methyl}biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), (4-fluorophenyl)boronic acid (0.38 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.57 g, 91%).

$^1$H NMR (300 MHz, CHLOROFORM-d) δ1.12 (t, J=7.3 Hz, 3H), 1.73-1.88 (m, 2H), 3.04-3.18 (m, 2H), 4.03 (s, 2H), 7.16-7.29 (m, 2H), 7.36-7.53 (m, 8H), 7.57-7.67 (m, 1H), 7.75 (dd, J=7.7, 0.9 Hz, 1H), 7.87 (s, 1H)

REFERENCE EXAMPLE 57

4'-{[4-(3-fluoro-4-methoxyphenyl)-5-oxo-7-propyl-4,5-dihydro[1,2,4]triazolo[1,5-a]pyrimidin-6-yl]methyl}biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), (3-fluoro-4-methoxyphenyl)boronic acid (0.45 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated. The residue was purified by silica gel column chromatography to give the title compound as a colorless solid (0.6 g, 90%).

$^1$H NMR (300 MHz, CHLOROFORM-d) δ1.11 (t, J=7.4 Hz, 3H) 1.71-1.84 (m, 2H) 3.04-3.19 (m, 2H) 3.94 (s, 3H) 4.07 (s, 2H) 7.03-7.28 (m, 3H) 7.37-7.53 (m, 6H) 7.56-7.67 (m, 1H) 7.75 (dd, J=7.7, 0.8 Hz, 1H) 7.87 (s, 1H)

REFERENCE EXAMPLE 58

4'-{[5-oxo-7-propyl-4-(thiophen-3-yl)-4,5-dihydro[1,2,4]triazolo[1,5-a]pyrimidin-6-yl]methyl}biphenyl-2-carbonitrile To a suspension (15 mL) of 4'-[(5-oxo-7-propyl-4,5-dihydro[1,2,4]triazolo[1,5-a]pyrimidin-6-yl)methyl]biphenyl-2-carbonitrile (0.5 g), thiophen-3-ylboronic acid (0.35 g), triethylamine (0.5 mL), pyridine (1 mL) and molecular sieves 4A (1 g) in dichloromethane was added copper(II) acetate (0.49 g), and the mixture was stirred for 16 hr. The reaction mixture was diluted with ethyl acetate, insoluble material was filtered off through celite, and the filtrate was concentrated.

The residue was purified by silica gel column chromatography to give the title compound as a colorless solid (0.52 g, 85%).

¹H NMR (300 MHz, CHLOROFORM-d) δ1.11 (t, J=7.3 Hz, 3H) 1.70-1.87 (m, 2H) 3.06-3.16 (m, 2H) 4.07 (s, 2H) 7.22-7.32 (m, 1H) 7.37-7.52 (m, 7H) 7.57-7.67 (m, 2H) 7.75 (dd, J=7.7, 0.9 Hz, 1H) 7.90 (s, 1H)

REFERENCE EXAMPLE 59

4'-{[2-methyl-4-(1-methylpropyl)-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (1.5 g), 2-iodobutane (1.4 mL), potassium carbonate (1 g) and N,N-dimethylacetamide (15 mL) was stirred at 100° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.36 g, 22%).

¹H NMR (300 MHz, CHLOROFORM-d) δ0.86 (t, J=7.4 Hz, 3H), 1.04 (t, J=7.3 Hz, 3H), 1.59 (t, J=3.4 Hz, 3H), 1.63-1.79 (m, 2H), 1.88-2.02 (m, 1H), 2.15-2.32 (m, 1H), 2.44 (s, 3H), 2.90-3.02 (m, 2H), 4.00 (s, 2H), 5.02-5.19 (m, 1H), 7.30-7.37 (m, 2H), 7.39-7.51 (m, 4H), 7.58-7.66 (m, 1H), 7.74 (dd, J=7.7, 0.9 Hz, 1H)

REFERENCE EXAMPLE 60

4'-({2-methyl-4-[(1-methylcyclopropyl)methyl]-5-oxo-7-propyl-4,5-dihydro[1,2,4]triazolo[1,5-a]pyrimidin-6-yl}methyl)biphenyl-2-carbonitrile To a solution of 4'-[(2-methyl-5-oxo-7-propyl-4,5-dihydro[1,2,4]triazolo[1,5-a]pyrimidin-6-yl)methyl]biphenyl-2-carbonitrile (1.5 g), (1-methylcyclopropyl)methanol (0.44 g) and tributylphosphine (1.9 mL) in THF (100 mL) was added 1,1'-(azodicarbonyl)dipiperidine (1.9 g) under ice-cooling, and the mixture was stirred at room temperature overnight. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.36 g, 21%).

¹H NMR (300 MHz, CHLOROFORM-d) δ0.30-0.36 (m, 2H), 0.76-0.84 (m, 2H), 0.99-1.10 (m, 6H), 1.64-1.80 (m, 2H), 2.41-2.46 (m, 3H), 2.93-3.04 (m, 2H), 4.03 (s, 2H), 4.20 (s, 2H), 7.32-7.51 (m, 6H), 7.56-7.65 (m, 1H), 7.74 (dd, J=7.8, 0.8 Hz, 1H)

REFERENCE EXAMPLE 61

4'-{[4-(3-{[tert-butyl(dimethyl)silyl]oxy}-2,2-dimethylpropyl)-2-methyl-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (5 g), (3-bromo-2,2-dimethylpropoxy)(tert-butyl)dimethylsilane (4.7 mL), cesium carbonate (8.1 g) and N,N-dimethylacetamide (50 mL) was stirred at 100° C. for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (2 g, 28%).

¹H NMR (300 MHz, CHLOROFORM-d) δ−0.02 (s, 6H), 0.86 (s, 9H), 0.98 (s, 6H), 1.05 (t, J=7.4 Hz, 3H), 1.65-1.78 (m, 2H), 2.42 (s, 3H), 2.91-3.02 (m, 2H), 3.47 (s, 2H), 4.02 (s, 2H), 4.21 (s, 2H), 7.32-7.51 (m, 6H), 7.57-7.65 (m, 1H), 7.75 (d, J=7.6 Hz, 1H)

REFERENCE EXAMPLE 62

4'-({2-methyl-5-oxo-4-[(1-phenylcyclopropyl)methyl]-7-propyl-4,5-dihydro[1,2,4]triazolo[1,5-a]pyrimidin-6-yl}methyl)biphenyl-2-carbonitrile To a solution of 4'-[(2-methyl-5-oxo-7-propyl-4,5-dihydro[1,2,4]triazolo[1,5-a]pyrimidin-6-yl)methyl]biphenyl-2-carbonitrile (1.5 g), (1-phenylcyclopropyl)methanol (0.87 g) and tributylphosphine (2 mL) in THF (100 mL) was added 1,1'-(azodicarbonyl)dipiperidine (2 g) at 0° C., and the mixture was stirred at room temperature overnight. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.43 g, 21%).

¹H NMR (300 MHz, CHLOROFORM-d) δ0.94 (d, J=1.5 Hz, 4H), 1.02 (t, J=7.3 Hz, 3H), 1.66-1.77 (m, 2H), 2.53 (s, 3H), 3.06-3.15 (m, 2H), 4.02 (s, 2H), 4.54 (s, 2H), 7.11-7.32 (m, 7H), 7.37-7.49 (m, 4H), 7.59-7.68 (m, 1H), 7.72-7.80 (m, 1H)

REFERENCE EXAMPLE 63

4'-{[4-(3-hydroxy-2,2-dimethylpropyl)-2-methyl-5-oxo-7-propyl-4,5-dihydro[1,2,4]triazolo[1,5-a]pyrimidin-6-yl]methyl}biphenyl-2-carbonitrile A mixture of 4'-{[4-(3-{[tert-butyl(dimethyl)silyl]oxy}-2,2-dimethylpropyl)-2-methyl-5-oxo-7-propyl-4,5-dihydro[1,2,4]triazolo[1,5-a]pyrimidin-6-yl]methyl}biphenyl-2-carbonitrile (1.5 g), tetrabutylammonium fluoride (1 M tetrahydrofuran solution, 4 mL) and tetrahydrofuran (30 mL) was stirred at room temperature for 3 hr. The reaction mixture was extracted with ethyl acetate and water, and the organic layer was washed with water and then with saturated brine, and dried over anhydrous magnesium sulfate. The solvent was evaporated under reduced pressure. The obtained residue was purified by silica gel column chromatography to give the title compound as a colorless solid (0.98 g, 79%).

¹H NMR (300 MHz, CHLOROFORM-d) δ0.98 (s, 6H) 1.06 (t, J=7.4 Hz, 3H) 1.65-1.79 (m, 2H) 2.42 (s, 3H) 2.95-3.03 (m, 2H) 3.10 (d, J=7.6 Hz, 2H) 4.02 (s, 2H) 4.05-4.26 (m, 2H) 5.31 (t, J=7.8 Hz, 1H) 7.31-7.51 (m, 6H) 7.58-7.66 (m, 1H) 7.74 (d, J=7.6 Hz, 1H)

REFERENCE EXAMPLE 64

4'-{[4-(cyclohex-2-en-1-yl)-2-methyl-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin- 6-yl)methyl]biphenyl-2-carbonitrile (5 g), sodium hydride (0.62 g) and N,N-dimethylformamide (50 mL) was stirred at room temperature for 10 min, 3-bromocyclohexene (1.8 mL) was added, and the mixture was stirred at the same temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (1 g, 17%).

$^1$H NMR (300 MHz, CHLOROFORM-d) δ1.04 (t, J=7.3 Hz, 3H) 1.53-2.57 (m, 11H) 2.91-3.01 (m, 2H) 3.93-4.07 (m, 2H) 5.57-5.95 (m, 3H) 7.32-7.51 (m, 6H) 7.58-7.66 (m, 1H) 7.74 (dd, J=7.7, 0.9 Hz, 1H)

REFERENCE EXAMPLE 65

4'-{[4-(3,3-dimethyl-2-oxobutyl)-2-methyl-5-oxo-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (3 g), 1-bromo-3,3-dimethylbutan-2-one (1.1 mL), potassium carbonate (2.1 g) and N,N-dimethylformamide (30 mL) was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.53 g, 15%).

$^1$H NMR (300 MHz, CHLOROFORM-d) δ1.04 (t, J=7.4 Hz, 3H), 1.31 (s, 9H), 1.65-1.80 (m, 2H), 2.39 (s, 3H), 2.92-3.02 (m, 2H), 4.01 (s, 2H), 5.17 (s, 2H), 7.31-7.36 (m, 2H), 7.38-7.50 (m, 4H), 7.59-7.65 (m, 1H), 7.74 (dd, J=7.7, 0.9 Hz, 1H)

REFERENCE EXAMPLE 66

4'-{[4-(2-hydroxy-3,3-dimethylbutyl)-2-methyl-5-oxo-7-propyl-4,5-dihydro[1,2,4]triazolo[1,5-a]pyrimidin-6-yl]methyl}biphenyl-2-carbonitrile To a solution (10 mL) of 4'-{[4-(3,3-dimethyl-2-oxobutyl)-2-methyl-5-oxo-7-propyl-4,5-dihydro[1,2,4]triazolo[1,5-a]pyrimidin-6-yl]methyl}biphenyl-2-carbonitrile (1.4 g) in methanol was added sodium borohydride (0.017 g), and the mixture was stirred at room temperature for 2 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (1.2 g, 84%).

$^1$H NMR (300 MHz, CHLOROFORM-d) δ1.01-1.09 (m, 12H), 1.65-1.77 (m, 2H), 2.42 (s, 3H), 2.93-3.04 (m, 2H), 3.58-3.68 (m, 2H), 3.94-4.18 (m, 3H), 4.65 (d, J=14.7 Hz, 1H), 7.30-7.51 (m, 6H), 7.58-7.67 (m, 1H), 7.74 (dd, J=7.7, 0.9 Hz, 1H)

REFERENCE EXAMPLE 67

4'-{[4-(2-methoxy-3,3-dimethylbutyl)-2-methyl-5-oxo-7-propyl-4,5-dihydro[1,2,4]triazolo[1,5-a]pyrimidin-6-yl]methyl}biphenyl-2-carbonitrile A mixture of 4'-{[4-(2-hydroxy-3,3-dimethylbutyl)-2-methyl-5-oxo-7-propyl-4,5- dihydro[1,2,4]triazolo[1,5-a]pyrimidin-6-yl]methyl}biphenyl-2-carbonitrile (0.3 g), sodium hydride (0.03 g) and N,N-dimethylformamide (5 mL) was stirred at 0° C. for 10 min, methyl iodide (0.046 mL) was added, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.22 g, 72%).

$^1$H NMR (300 MHz, CHLOROFORM-d) δ0.98-1.10 (m, 12H), 1.66-1.79 (m, 2H), 2.42-2.48 (m, 3H), 2.95-3.08 (m, 2H), 3.12 (s, 3H), 3.52 (dd, J=9.9, 3.1 Hz, 1H), 4.04 (s, 2H), 4.21 (dd, J=13.1, 3.1 Hz, 1H), 4.48 (dd, J=13.0, 10.0 Hz, 1H), 7.33-7.49 (m, 6H), 7.58-7.65 (m, 1H), 7.74 (dd, J=7.7, 0.9 Hz, 1H)

REFERENCE EXAMPLE 68

4'-{[4-(2-{[tert-butyl(dimethyl)silyl]oxy}-3,3-dimethylbutyl)-2-methyl-5-oxo-7-propyl-4,5-dihydro[1,2,4]triazolo[1,5-a]pyrimidin-6-yl]methyl}biphenyl-2-carbonitrile To a mixture of 4'-{[4-(2-hydroxy-3,3-dimethylbutyl)-2-methyl-5-oxo-7-propyl-4,5-dihydro[1,2,4]triazolo[1,5-a]pyrimidin-6-yl]methyl}biphenyl-2-carbonitrile (0.9 g), 2,6-lutidine (0.32 mL) and tetrahydrofuran (20 mL) was added tert-butyl(dimethyl)silyl trifluoromethanesulfonate (0.64 mL), and the mixture was stirred at room temperature for 5 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.9 g, 81%).

$^1$H NMR (300 MHz, CHLOROFORM-d) δ−0.78 (s, 3H), −0.06 (s, 3H), 0.78 (s, 9H), 0.98-1.08 (m, 12H), 1.62-1.78 (m, 2H), 2.43 (s, 3H), 2.90-3.10 (m, 2H), 3.95-4.08 (m, 3H), 4.20-4.28 (m, 1H), 4.33-4.46 (m, 1H), 7.33-7.52 (m, 6H), 7.57-7.68 (m, 1H), 7.75 (dd, J=7.8, 0.8 Hz, 1H)

REFERENCE EXAMPLE 69

4'-({2-methyl-4-[(3-methyloxetan-3-yl)methyl]-5-oxo-7-propyl-4,5-dihydro[1,2,4]triazolo[1,5-a]pyrimidin-6-yl}methyl)biphenyl-2-carbonitrile To a solution of 4'-[(2-methyl-5-oxo-7-propyl-4,5-dihydro[1,2,4]triazolo[1,5-a]pyrimidin-6-yl)methyl]biphenyl-2-carbonitrile (1.5 g), (3-methyloxetan-3-yl)methanol (0.6 g) and tributylphosphine (1.9 mL) in THF (80 mL) was added 1,1'-(azodicarbonyl)dipiperidine (1.9 g) under ice-cooling, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.03 g, 16%).

$^1$H NMR (300 MHz, CHLOROFORM-d) δ1.06 (t, J=7.4 Hz, 3H), 1.40 (s, 3H), 1.66-1.79 (m, 2H), 2.42 (s, 3H), 2.95-3.04 (m, 2H), 4.01 (s, 2H), 4.29 (d, J=6.1 Hz, 2H), 4.35 (s,

2H), 4.81 (d, J=6.4 Hz, 2H), 7.31-7.51 (m, 6H), 7.62 (t, J=7.6 Hz, 1H), 7.74 (d, J=8.0 Hz, 1H)

REFERENCE EXAMPLE 70

5-methyl-N-(tetrahydro-2H-pyran-4-yl)-4H-1,2,4-triazol-3-amine

To a solution (40 mL) of 5-methyl-4H-1,2,4-triazol-3-amine (3 g) and tetrahydro-4H-pyran-4-one (3.7 g) in acetic acid was added sodium cyanoborohydride (9.7 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (0.79 g, 14%).

$^1$H NMR (300 MHz, DMSO-$d_6$) δ1.31-1.48 (m, 2H), 1.76-1.88 (m, 2H), 1.96-2.21 (m, 2H), 3.26-3.37 (m, 3H), 3.37-3.53 (m, 1H), 3.79-3.88 (m, 2H), 5.38-6.41 (m, 1H), 11.54-12.39 (m, 1H)

REFERENCE EXAMPLE 71

4'-{[2-methyl-5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.87 g) and 5-methyl-N-(tetrahydro-2H-pyran-4-yl)-4H-1,2,4-triazol-3-amine (0.3 g) was stirred at 250° C. for 15 min under microwave irradiation. The obtained reaction mixture was purified by silica gel column chromatography to give the title compound as a colorless solid (0.37 g, 48%).

$^1$H NMR (300 MHz, CHLOROFORM-d) δ1.05 (t, J=7.3 Hz, 3H), 1.62-1.80 (m, 4H), 2.45 (s, 3H), 2.92-3.10 (m, 4H), 3.54 (t, J=12.1 Hz, 2H), 4.00 (s, 2H), 4.07-4.17 (m, 2H), 5.18-5.31 (m, 1H), 7.32-7.52 (m, 6H), 7.58-7.67 (m, 1H), 7.75 (dd, J=7.7, 0.9 Hz, 1H)

REFERENCE EXAMPLE 72

N-(2-methoxy-1-methylethyl)-5-methyl-4H-1,2,4-triazol-3-amine

To a solution (40 mL) of 5-methyl-4H-1,2,4-triazol-3-amine (2.5 g) and 1-methoxypropan-2-one (2.7 g) in acetic acid was added sodium cyanoborohydride (8.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (1.4 g, 32%).

$^1$H NMR (300 MHz, DMSO-$d_6$) δ1.08 (d, J=6.4 Hz, 3H), 1.97-2.22 (m, 2H), 3.11-3.39 (m, 6H), 3.65 (br. s., 1H), 5.14-6.14 (m, 1H), 11.49-12.35 (m, 1H)

REFERENCE EXAMPLE 73

4'-{[4-(2-methoxy-1-methylethyl)-2-methyl-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (1.84 g) and N-(2-methoxy-1-methylethyl)-5-methyl-4H-1,2,4-triazol-3-amine (0.4 g) was stirred at 250° C. for 15 min under microwave irradiation. The obtained reaction mixture was purified by silica gel column chromatography to give the title compound as a colorless solid (0.63 g, 52%).

$^1$H NMR (300 MHz, CHLOROFORM-d) δ1.04 (t, J=7.3 Hz, 3H), 1.55 (d, J=7.2 Hz, 3H), 1.65-1.79 (m, 2H), 2.43 (s, 3H), 2.91-3.01 (m, 2H), 3.31 (s, 3H), 3.60 (dd, J=10.1, 5.4 Hz, 1H), 4.00 (s, 2H), 4.33 (t, J=9.9 Hz, 1H), 5.44 (br. s., 1H), 7.31-7.51 (m, 6H), 7.56-7.66 (m, 1H), 7.74 (dd, J=7.7, 0.9 Hz, 1H)

REFERENCE EXAMPLE 74

N-cyclobutyl-5-methyl-4H-1,2,4-triazol-3-amine

To a solution (30 mL) of 5-methyl-4H-1,2,4-triazol-3-amine (2.5 g) and cyclobutanone (2.1 g) in acetic acid was added sodium cyanoborohydride (8.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (2.4 g, 61%).

$^1$H NMR (300 MHz, DMSO-$d_6$) δ1.46-1.68 (m, 2H), 1.75-2.31 (m, 7H), 3.83-4.00 (m, 1H), 5.67-6.69 (m, 1H), 11.57-12.40 (m, 1H)

REFERENCE EXAMPLE 75

4'-[(4-cyclobutyl-2-methyl-5-oxo-7-propyl-4,5-dihydro[1,2,4]triazolo[1,5-a]pyrimidin-6-yl)methyl]biphenyl-2-carbonitrile A mixture of ethyl 2-[(2'-cyanobiphenyl-4-yl)methyl]-3-oxohexanoate (1.8 g) and N-cyclobutyl-5-methyl-4H-1,2,4-triazol-3-amine (0.4 g) was stirred at 250° C. for 15 min under microwave irradiation. The obtained reaction mixture was purified by silica gel column chromatography to give the title compound as a colorless solid (0.63 g, 52%).

$^1$H NMR (300 MHz, CHLOROFORM-d) δ1.04 (t, J=7.3 Hz, 3H), 1.63-2.05 (m, 4H), 2.22-2.34 (m, 2H), 2.45 (s, 3H), 2.92-3.02 (m, 2H), 3.14-3.31 (m, 2H), 3.99 (s, 2H), 5.42-5.59 (m, 1H), 7.32-7.52 (m, 6H), 7.58-7.66 (m, 1H), 7.68-7.77 (m, 1H)

REFERENCE EXAMPLE 76

4'-{[2-methyl-5-oxo-4-(2-oxopropyl)-7-propyl-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (3 g), sodium hydride (0.47 g) and N,N-dimethylformamide (15 mL) was stirred at room temperature for 10 min, 1-chloropropan-2-one (0.75 mL) was added, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.49 g, 14%).

$^1$H NMR (300 MHz, CHLOROFORM-d) δ1.05 (t, J=7.4 Hz, 3H), 1.63-1.80 (m, 2H), 2.31 (s, 3H), 2.40 (s, 3H), 2.94-3.04 (m, 2H), 4.01 (s, 2H), 5.02 (s, 2H), 7.31-7.50 (m, 6H), 7.57-7.66 (m, 1H), 7.74 (d, J=7.6 Hz, 1H)

REFERENCE EXAMPLE 77

4'-{[4-(2-{[tert-butyl(dimethyl)silyl]oxy}propyl)-2-methyl-5-oxo-7-propyl-4,5-dihydro[1,2,4]triazolo[1,5-a]pyrimidin-6-yl]methyl}biphenyl-2-carbonitrile A mixture of 4'-{[2-methyl-5-oxo-4-(2-oxopropyl)-7-propyl-4,5-dihydro[1,2,4]triazolo[1,5-a]pyrimidin-6-yl]methyl}biphenyl-2-carbonitrile (0.49 g), sodium borohydride (0.063 g) and methanol (20 mL) was stirred at room temperature for 2 hr. The reaction mixture was concentrated, and the residue was extracted with ethyl acetate and saturated aqueous ammonium chloride solution. The obtained ethyl acetate layer was washed with saturated brine, and dried over anhydrous magnesium sulfate. The solvent was evaporated under reduced pressure. The obtained residue was dissolved in tetrahydrofuran (15 mL), and 2,6-lutidine (0.19 mL) and tert-butyl(dimethyl)silyl trifluoromethanesulfonate (0.38 mL) were added at 0° C. The reaction mixture was stirred at 0° C. for 3 hr, diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.52 g, 85%).

$^1$H NMR (300 MHz, CHLOROFORM-d) δ−0.78 (s, 3H) −0.06 (s, 3H) 0.78 (s, 9H) 0.99-1.11 (m, 3H) 1.61 (s, 3H) 1.63-1.81 (m, 2H) 2.43 (s, 3H) 2.90-3.09 (m, 2H) 3.94-4.08 (m, 3H) 4.20-4.30 (m, 1H) 4.32-4.46 (m, 1H) 7.35-7.51 (m, 6H) 7.59-7.67 (m, 1H) 7.75 (dd, J=7.7, 0.9 Hz, 1H)

REFERENCE EXAMPLE 78

4'-{[4-(2-cyclohexyl-2-hydroxyethyl)-2-methyl-5-oxo-7-propyl-4,5-dihydro[1,2,4]triazolo[1,5-a]pyrimidin-6-yl]methyl}biphenyl-2-carbonitrile To a mixture of cyclohexanecarbaldehyde (2.9 g), diiodomethane (2.5 mL) and tetrahydrofuran (80 mL) was added methyllithium (2.1M diethyl ether solution, 25 mL) at 0° C., and the mixture was stirred at room temperature for 4 hr. The reaction mixture was extracted with diethyl ether and saturated aqueous ammonium chloride solution. The diethyl ether layer was washed with saturated brine, and dried over anhydrous magnesium sulfate. The solvent was evaporated under reduced pressure. The obtained residue was dissolved in N,N-dimethylformamide (30 mL), 4'-[(2-methyl-5-oxo-7-propyl-4,5-dihydro[1,2,4]triazolo[1,5-a]pyrimidin-6-yl)methyl]biphenyl-2-carbonitrile (4 g) and potassium carbonate (2.9 g) were added, and the mixture was stirred at 80° C. for 16 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as a colorless solid (0.64 g, 12%).

$^1$H NMR (300 MHz, CHLOROFORM-d) δ1.05 (t, J=7.4 Hz, 3H), 1.16-1.31 (m, 4H), 1.62-1.93 (m, 6H), 2.42 (s, 3H), 2.95-3.03 (m, 2H), 3.47 (d, J=5.7 Hz, 1H), 3.95-4.08 (m, 2H), 4.24 (dd, J=13.9, 9.0 Hz, 1H), 4.52 (dd, J=13.8, 2.3 Hz, 1H), 7.32-7.50 (m, 6H), 7.59-7.66 (m, 1H), 7.74 (dd, J=7.7, 0.9 Hz, 1H)

REFERENCE EXAMPLE 79

4'-{[4-(2-{[tert-butyl(dimethyl)silyl]oxy}-2-cyclohexylethyl)-2-methyl-5-oxo-7-propyl-4,5-dihydro[1,2,4]triazolo[1,5-a]pyrimidin-6-yl]methyl}biphenyl-2-carbonitrile To a solution (15 mL) of 4'-{[4-(2-cyclohexyl-2-hydroxyethyl)-2-methyl-5-oxo-7-propyl-4,5-dihydro[1,2,4]triazolo[1,5-a]pyrimidin-6-yl]methyl}biphenyl-2-carbonitrile (0.64 g) in tetrahydrofuran were added 2,6-lutidine (0.22 mL) and tert-butyl(dimethyl)silyl trifluoromethanesulfonate (0.43 mL) at 0° C. The reaction mixture was stirred at 0° C. for 3 hr, diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.52 g, 75%).

$^1$H NMR (300 MHz, CHLOROFORM-d) δ−0.48 (s, 3H), −0.06 (s, 3H), 0.74 (s, 9H), 1.05 (t, J=7.3 Hz, 3H), 1.12-1.24 (m, 4H), 1.62-1.92 (m, 8H), 2.42 (s, 3H), 2.92-3.09 (m, 2H), 4.01 (s, 2H), 4.08-4.22 (m, 3H), 4.31-4.41 (m, 1H), 7.33-7.51 (m, 6H), 7.58-7.67 (m, 1H), 7.71-7.78 (m, 1H)

REFERENCE EXAMPLE 80

4'-formyl-3'-(trifluoromethyl)biphenyl-2-carbonitrile

A mixture of 4-bromo-2-(trifluoromethyl)benzaldehyde (9 g), 2-cyano-phenylboric acid (9.5 g), [1,1'-bis(diphenylphosphino)ferrocene]dichloropalladium (2.9 g), tetrabutylammonium bromide (1.15 g), 2M aqueous sodium carbonate solution (30 mL) and toluene (100 mL) was stirred at 100° C. overnight under an argon atmosphere. The reaction mixture was diluted with ethyl acetate, washed with saturated brine, and dried over anhydrous magnesium sulfate. The solvent was evaporated under reduced pressure, and the residue was purified by silica gel column chromatography to give the title compound as a colorless solid (3.2 g, 32%).

$^1$H NMR (300 MHz, CHLOROFORM-d) δ7.54-7.63 (m, 2H), 7.69-7.80 (m, 1H), 7.81-7.89 (m, 1H), 7.89-7.97 (m, 2H), 8.27 (d, J=7.9 Hz, 1H), 10.46 (s, 1H)

REFERENCE EXAMPLE 81

4'-(hydroxymethyl)-3'-(trifluoromethyl)biphenyl-2-carbonitrile

To a solution (50 mL) of 4'-formyl-3'-(trifluoromethyl)biphenyl-2-carbonitrile (3.2 g) in methanol was added sodium borohydride (0.66 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (3.1 g, 95%).

¹H NMR (300 MHz, CHLOROFORM-d) δ4.97 (s, 2H), 7.46-7.56 (m, 2H), 7.65-7.73 (m, 1H), 7.77-7.84 (m, 3H), 7.87-7.93 (m, 1H)

REFERENCE EXAMPLE 82 ethyl 2-{[2'-cyano-3-(trifluoromethyl)biphenyl-4-yl]methyl}-3-oxohexanoate

A mixture of 4'-(hydroxymethyl)-3'-(trifluoromethyl)biphenyl-2-carbonitrile (3.1 g), carbon tetrabromide (4.2 g), triphenylphosphine (3.4 g) and acetonitrile (200 mL) was stirred at room temperature for 16 hr. The reaction mixture was diluted with ethyl acetate, and filtered through a silica gel column. The filtrate was concentrated and the obtained residue was dissolved in tetrahydrofuran (30 mL), and the mixture was added to a mixture of ethyl 3-oxohexanoate (3.7 g), sodium hydride (0.6 g) and tetrahydrofuran (70 mL) stirred at 0° C. for 30 min in advance. The reaction mixture was stirred at room temperature for 16 hr, 1 N hydrochloric acid (50 mL) was added, and the solvent was evaporated under reduced pressure, and the residue was extracted with ethyl acetate, and the obtained ethyl acetate layer was washed with saturated brine, and dried over anhydrous magnesium sulfate. The solvent was evaporated under reduced pressure, and the residue was purified by silica gel column chromatography to give the title compound as a pale-yellow oil (1.1 g, 24%).

¹H NMR (300 MHz, CHLOROFORM-d) δ0.89 (t, J=7.3 Hz, 3H), 1.23 (t, J=7.2 Hz, 3H), 1.53-1.65 (m, 2H), 2.35-2.47 (m, 1H), 2.52-2.65 (m, 1H), 3.34-3.50 (m, 2H), 3.87 (dd, J=7.7, 6.6 Hz, 1H), 4.12-4.23 (m, 2H), 7.43-7.54 (m, 3H), 7.63-7.72 (m, 2H), 7.75-7.82 (m, 2H)

REFERENCE EXAMPLE 83

5-methyl-N-(1-methylpropyl)-4H-1,2,4-triazol-3-amine

To a solution (50 mL) of 5-methyl-4H-1,2,4-triazol-3-amine (5 g) and butan-2-one (5.5 g) in acetic acid was added sodium cyanoborohydride (16 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (4.8 g, 61%).

¹H NMR (300 MHz, DMSO-d₆) δ0.84 (t, J=7.4 Hz, 3H), 1.06 (d, J=6.4 Hz, 3H), 1.29-1.58 (m, 2H), 2.07 (s, 3H), 3.28-3.45 (m, 1H), 5.81 (br. s., 1H), 11.70 (br. s., 1H)

REFERENCE EXAMPLE 84

5-(methoxymethyl)-4H-1,2,4-triazol-3-amine

A mixture of methoxyacetic acid (15 g), aminoguanidine sulfate (21 g) and 1,2,4-trichlorobenzene (20 mL) was stirred at 200° C. for 24 hr. The reaction mixture was poured into saturated aqueous sodium hydrogen carbonate, and the mixture was extracted with n-butanol. The obtained n-butanol layer was concentrated, and the residue was purified by silica gel column chromatography to give the title compound as a colorless solid (15 g, 75%).

¹H NMR (300 MHz, DMSO-d₆) δ3.24 (s, 3H), 4.16 (s, 2H), 5.81 (br. s., 2H), 11.95 (br. s., 1H)

REFERENCE EXAMPLE 85

5-(methoxymethyl)-N-(1-methylpropyl)-4H-1,2,4-triazol-3-amine

To a solution (5 mL) of 5-(methoxymethyl)-4H-1,2,4-triazol-3-amine (0.3 g) and butan-2-one (0.25 mL) in acetic acid was added sodium cyanoborohydride (0.6 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (0.2 g, 45%).

¹H NMR (300 MHz, DMSO-d₆) δ0.85 (t, J=7.4 Hz, 3H), 1.08 (d, J=6.6 Hz, 3H), 1.34-1.57 (m, 2H), 3.25 (s, 3H), 3.34-3.46 (m, 1H), 4.14 (s, 2H), 5.21-6.29 (m, 1H), 11.74-12.79 (m, 1H)

REFERENCE EXAMPLE 86

4'-{[2-(methoxymethyl)-4-(1-methylpropyl)-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.75 g) and 5-(methoxymethyl)-N-(1-methylpropyl)-4H-1,2,4-triazol-3-amine (0.2 g) was stirred at 250° C. for 15 min under microwave irradiation. The obtained reaction mixture was purified by silica gel column chromatography to give the title compound as a colorless solid (0.2 g, 41%).

¹H NMR (300 MHz, CHLOROFORM-d) δ0.86 (t, J=7.44 Hz, 3H) 1.03 (t, J=7.35 Hz, 3H) 1.55-1.63 (m, 3H) 1.65-1.78 (m, 2H) 1.89-2.03 (m, 1H) 2.18-2.33 (m, 1H) 2.95-3.05 (m, 2H) 3.50 (s, 3H) 4.02 (s, 2H) 4.56 (s, 2H) 5.09-5.20 (m, 1H) 7.31-7.51 (m, 6H) 7.58-7.66 (m, 1H) 7.74 (d, J=7.54 Hz, 1H)

REFERENCE EXAMPLE 87

4'-{[2-methyl-5-oxo-7-propyl-4-(3,3,3-trifluoro-2-hydroxypropyl)-4,5-dihydro[1,2,4]triazolo[1,5-a]pyrimidin-6-yl]methyl}biphenyl-2-carbonitrile A mixture of 4'-[(2-methyl-5-oxo-7-propyl-4,5-dihydro[1,2,4]triazolo[1,5-a]pyrimidin-6-yl)methyl]biphenyl-2-carbonitrile (0.91 g), 3-bromo-1,1,1-trifluoropropan-2-ol (1.2 mL), cesium carbonate (3.8 g) and N,N-dimethylacetamide (20 mL) was stirred at 100° C. for 4 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.76 g, 65%).

¹H NMR (300 MHz, CHLOROFORM-d) δ1.06 (t, J=7.3 Hz, 3H), 1.66-1.81 (m, 2H), 2.44 (s, 3H), 2.97-3.07 (m, 2H), 4.01 (s, 2H), 4.36-4.46 (m, 1H), 4.49-4.59 (m, 1H), 4.62-4.73

(m, 1H), 4.82 (d, J=6.8 Hz, 1H), 7.31-7.52 (m, 6H), 7.56-7.68 (m, 1H), 7.74 (dd, J=7.7, 0.9 Hz, 1H)

REFERENCE EXAMPLE 88

3'-fluoro-4'-{[2-methyl-5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile A mixture of ethyl 2-[(2'-cyano-3-fluorobiphenyl-4-yl)methyl]-3-oxohexanoate (1 g) and 5-methyl-N-(tetrahydro-2H-pyran-4-yl)-4H-1,2,4-triazol-3-amine (0.25 g) was stirred at 250° C. for 15 min under microwave irradiation. The obtained reaction mixture was purified by silica gel column chromatography to give the title compound as a colorless solid (0.43 g, 65%).
$^1$H NMR (300 MHz, CHLOROFORM-d) δ1.05 (t, J=7.3 Hz, 3H) 1.58-1.77 (m, 4H) 2.44 (s, 3H) 2.93-3.10 (m, 4H) 3.56 (t, J=11.9 Hz, 2H) 4.00 (s, 2H) 4.06-4.19 (m, 2H) 5.17-5.31 (m, 1H) 7.20-7.28 (m, 2H) 7.32-7.51 (m, 3H) 7.60-7.69 (m, 1H) 7.72-7.81 (m, 1H)

REFERENCE EXAMPLE 89

N-(tetrahydro-2H-pyran-4-yl)-4H-1,2,4-triazol-3-amine

To a solution (70 mL) of 1H-1,2,4-triazol-3-amine (3.7 g) and tetrahydro-4H-pyran-4-one (5.2 g) in acetic acid was added sodium cyanoborohydride (14 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (0.92 g, 10%).
$^1$H NMR (300 MHz, DMSO-d$_6$) δ1.32-1.51 (m, 2H) 1.76-1.91 (m, 2H) 3.27-3.55 (m, 4H) 3.78-3.91 (m, 2H) 5.57-6.60 (m, 1H) 7.28-8.11 (m, 1H) 11.97-12.91 (m, 1H)

REFERENCE EXAMPLE 90

4'-{[5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (1 g) and N-(tetrahydro-2H-pyran-4-yl)-4H-1,2,4-triazol-3-amine (0.25 g) was stirred at 250° C. for 15 min under microwave irradiation. The obtained reaction mixture was purified by silica gel column chromatography to give the title compound as a colorless solid (0.3 g, 44%).
$^1$H NMR (300 MHz, CHLOROFORM-d) δ1.07 (t, J=7.3 Hz, 3H), 1.61-1.78 (m, 4H), 2.92-3.08 (m, 4H), 3.48-3.60 (m, 2H), 4.02 (s, 2H), 4.08-4.16 (m, 2H), 5.24-5.36 (m, 1H), 7.35-7.51 (m, 6H), 7.59-7.67 (m, 1H), 7.75 (dd, J=7.7, 0.9 Hz, 1H), 7.93 (s, 1H)

REFERENCE EXAMPLE 91

N-(2-methoxycyclohexyl)-5-methyl-4H-1,2,4-triazol-3-amine

To a solution (50 mL) of 5-methyl-4H-1,2,4-triazol-3-amine (2.5 g) and 2-methoxycyclohexanone (3.9 g) in acetic acid was added sodium cyanoborohydride (8.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (2.8 g, 51%).
$^1$H NMR (300 MHz, CHLOROFORM-d) δ1.30-2.03 (m, 9H) 2.30 (s, 3H) 3.34 (s, 3H) 3.44-3.51 (m, 1H) 3.56-3.67 (m, 1H) 4.74 (d, J=8.0 Hz, 1H)

REFERENCE EXAMPLE 92

4'-{[4-(2-methoxycyclohexyl)-2-methyl-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.83 g) and N-(2-methoxycyclohexyl)-5-methyl-4H-1,2,4-triazol-3-amine (0.25 g) was stirred at 250° C. for 15 min under microwave irradiation. The obtained reaction mixture was purified by silica gel column chromatography to give the title compound as a colorless solid (0.27 g, 46%).
$^1$H NMR (300 MHz, CHLOROFORM-d) δ1.04 (t, J=7.4 Hz, 3H) 1.32-2.14 (m, 9H) 2.41-2.47 (m, 3H) 2.95-3.04 (m, 2H) 3.17 (s, 3H) 3.38-3.52 (m, 1H) 3.73 (br. s., 1H) 3.91-4.09 (m, 2H) 4.85-4.94 (m, 1H) 7.33-7.50 (m, 6H) 7.55-7.66 (m, 1H) 7.74 (dd, J=7.7, 0.9 Hz, 1H)

REFERENCE EXAMPLE 93

4'-{[4-(2-{[tert-butyl(dimethyl)silyl]oxy}-1-methylpropyl)-2-methyl-5-oxo-7-propyl-4,5-dihydro[1,2,4]triazolo[1,5-a]pyrimidin-6-yl]methyl}biphenyl-2-carbonitrile To a solution (50 mL) of 5-methyl-4H-1,2,4-triazol-3-amine (1.8 g) and 3-{[tert-butyl(dimethyl)silyl]oxy}butan-2-one (4.4 g) in acetic acid was added sodium cyanoborohydride (5.8 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The extract was dried over anhydrous sodium sulfate, and the solvent was evaporated under reduced pressure. A mixture of the obtained residue and ethyl 2-{[2'-cyano-3-(trifluoromethyl)biphenyl-4-yl]methyl}-3-oxohexanoate (2.3 g) was stirred at 250° C. for 15 min under microwave irradiation. The obtained reaction mixture was purified by silica gel column chromatography to give the title compound as a colorless solid (0.27 g, 14%).
$^1$H NMR (300 MHz, CHLOROFORM-d) δ0.10 (s, 3H), 0.12 (s, 3H), 0.85-1.08 (m, 15H), 1.54-1.76 (m, 5H), 2.36-2.47 (m, 4H), 2.91-3.00 (m, 2H), 4.01 (s, 2H), 4.64-4.77 (m, 1H), 7.30-7.54 (m, 6H), 7.59-7.67 (m, 1H), 7.72-7.78 (m, 1H)

REFERENCE EXAMPLE 94

3'-fluoro-4'-{[4-(2-methoxy-1-methylethyl)-2-methyl-5-oxo-7-propyl-4,5-dihydro[1,2,4]triazolo[1,5-a]pyrimidin-6-yl]methyl}biphenyl-2-carbonitrile A mixture of ethyl 2-[(2'-cyano-3-fluorobiphenyl-4-yl)methyl]-3-oxohexanoate (1 g) and N-(2-methoxy-1-methylethyl)-5-methyl-4H-1,2,4-triazol-3-amine (0.25 g) was stirred at 250° C. for 20 min under microwave irradiation. The obtained reaction mixture was purified by silica gel column chromatography to give the title compound as a colorless solid (0.28 g, 40%).

$^1$H NMR (300 MHz, CHLOROFORM-d) δ1.04 (t, J=7.3 Hz, 3H) 1.52-1.60 (m, 5H) 1.62-1.75 (m, 2H) 2.43 (s, 3H) 2.91-3.01 (m, 2H) 3.31 (s, 3H) 3.59 (dd, J=10.1, 5.2 Hz, 1H) 4.01 (s, 1H) 4.34 (t, J=9.8 Hz, 1H) 5.36-5.51 (m, 1H) 7.20-7.34 (m, 4H) 7.40-7.49 (m, 2H) 7.60-7.67 (m, 1H) 7.72-7.77 (m, 1H)

REFERENCE EXAMPLE 95

5-methyl-N-(tetrahydro-2H-thiopyran-4-yl)-4H-1,2,4-triazol-3-amine

To a solution (50 mL) of 5-methyl-4H-1,2,4-triazol-3-amine (2.5 g) and tetrahydro-4H-thiopyran-4-one (3.6 g) in acetic acid was added sodium cyanoborohydride (8.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (2.4 g, 48%).

$^1$H NMR (300 MHz, DMSO-d$_6$) δ1.44-1.59 (m, 2H), 1.98-2.21 (m, 5H), 2.54-2.67 (m, 4H), 3.21-3.34 (m, 1H), 5.44-6.42 (m, 1H), 11.53-12.35 (m, 1H)

REFERENCE EXAMPLE 96

3'-fluoro-4'-{[2-methyl-5-oxo-7-propyl-4-(tetrahydro-2H-thiopyran-4-yl)-4,5-dihydro[1,2,4]triazolo[1,5-a]pyrimidin-6-yl]methyl}biphenyl-2-carbonitrile A mixture of ethyl 2-[(2'-cyano-3-fluorobiphenyl-4-yl)methyl]-3-oxohexanoate (1.5 g) and 5-methyl-N-(tetrahydro-2H-thiopyran-4-yl)-4H-1,2,4-triazol-3-amine (0.4 g) was stirred at 250° C. for 20 min under microwave irradiation. The obtained reaction mixture was purified by silica gel column chromatography to give the title compound as a colorless solid (0.54 g, 27%).

$^1$H NMR (300 MHz, CHLOROFORM-d) δ1.05 (t, J=7.4 Hz, 3H), 1.63-1.77 (m, 2H), 1.98-2.07 (m, 2H), 2.44 (s, 3H), 2.66-2.80 (m, 2H), 2.84-3.13 (m, 6H), 3.99 (s, 2H), 4.88-5.06 (m, 1H), 7.20-7.30 (m, 2H), 7.35 (t, J=7.8 Hz, 1H), 7.41-7.51 (m, 2H), 7.60-7.67 (m, 1H), 7.75 (d, J=7.9 Hz, 1H)

REFERENCE EXAMPLE 97

3'-fluoro-4'-{[5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile A mixture of ethyl 2-[(2'-cyano-3-fluorobiphenyl-4-yl)methyl]-3-oxohexanoate (1.1 g) and N-(tetrahydro-2H-pyran-4-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.57 g, 81%).

$^1$H NMR (300 MHz, CHLOROFORM-d) δ1.07 (t, J=7.4 Hz, 3H), 1.62-1.79 (m, 4H), 2.90-3.10 (m, 4H), 3.55 (td, J=12.0, 1.8 Hz, 2H), 4.03 (s, 2H), 4.08-4.17 (m, 2H), 5.30 (tt, J=12.2, 4.1 Hz, 1H), 7.23-7.28 (m, 2H), 7.36-7.51 (m, 3H), 7.63 (dd, J=7.5, 1.1 Hz, 1H), 7.75 (d, J=0.9 Hz, 1H), 7.93 (s, 1H)

REFERENCE EXAMPLE 98 tert-butyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]propanoate To a mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (233 g), tert-butyl 2-bromopropanoate (301 g), toluene (1.7 L) and 50% sodium hydroxide (1.7 L) was added tetrabutylammonium hydrogen sulfate (16.3 g), and the mixture was stirred with the internal temperature maintained below 30° C. for 16 hr. Water (1 L) was slowly added under ice-cooling, and phases were separated. The aqueous layer was extracted with tetrahydrofuran (1.0 L). The combined extracts were successively washed with 3M hydrochloric acid (1 L) and brine (1 L), dried over anhydrous magnesium sulfate, and concentrated. The residue was purified by silica gel column chromatography to give the title compound as an amorphous pale-yellow solid (283 g, 96%).

$^1$H NMR (300 MHz, DMSO-d$_6$) δ0.95 (t, J=7.3 Hz, 3H), 1.20-1.47 (m, 14H), 1.56-1.75 (m, 4H), 1.99-2.17 (m, 2H), 2.46-2.64 (m, 2H), 2.92-3.02 (m, 2H), 3.27-3.39 (m, 1H), 3.95-4.08 (m, 3H), 4.81-4.95 (m, 1H), 7.11-7.67 (m, 5H), 7.75-7.84 (m, 1H), 7.96 (d, J=7.7 Hz, 1H), 8.20 (s, 1H)

REFERENCE EXAMPLE 99

4'-({4-[(2R,4r,6S)-2,6-dimethyltetrahydro-2H-pyran-4-yl]-2-methyl-5-oxo-7-propyl-4,5-dihydro[1,2,4]triazolo[1,5-a]pyrimidin-6-yl}methyl)-3'-fluorobiphenyl-2-carbonitrile A mixture of ethyl 2-[(2'-cyano-3-fluorobiphenyl-4-yl)methyl]-3-oxohexanoate (2.1 g) and N-[(2R,6S)-2,6-dimethyltetrahydro-2H-pyran-4-yl]-3-methyl-1H-1,2,4-triazol-5-amine (0.6 g) was stirred at 250° C. for 30 min under microwave irradiation. The obtained reaction mixture was purified by silica gel column chromatography to give the title compound as a colorless solid (0.33 g, 23%).

$^1$H NMR (300 MHz, CHLOROFORM-d) δ1.05 (t, J=7.3 Hz, 3H), 1.26 (s, 3H), 1.28 (s, 3H), 1.63-1.76 (m, 4H), 2.44 (s, 3H), 2.58 (q, J=12.4 Hz, 2H), 2.95-3.03 (m, 2H), 3.56-3.70 (m, 2H), 4.00 (s, 2H), 5.16-5.36 (m, 1H), 7.20-7.30 (m, 2H), 7.35 (t, J=7.8 Hz, 1H), 7.41-7.52 (m, 2H), 7.60-7.67 (m, 1H), 7.71-7.79 (m, 1H)

REFERENCE EXAMPLE 100

4'-({4-[(2R,4s,6S)-2,6-dimethyltetrahydro-2H-pyran-4-yl]-2-methyl-5-oxo-7-propyl-4,5-dihydro[1,2,4]triazolo[1,5-a]pyrimidin-6-yl}methyl)-3'-fluorobiphenyl-2-carbonitrile A mixture of ethyl 2-[(2'-cyano-3-fluorobiphenyl-4-yl)methyl]-3-oxohexanoate (2.1 g) and N-[(2R,6S)-2,6-dimethyltetrahydro-2H-pyran-4-yl]-3-methyl-1H-1,2,4-triazol-5-amine (0.6 g) was stirred at 250° C. for 30 min under microwave irradiation. The obtained reaction mixture was purified by silica gel column chromatography to give the title compound as a colorless solid (0.052 g, 4%).

¹H NMR (300 MHz, CHLOROFORM-d) δ1.04 (t, J=7.4 Hz, 3H), 1.23 (s, 3H), 1.25 (s, 3H), 1.63-1.76 (m, 4H), 2.43 (s, 3H), 2.47-2.58 (m, 2H), 2.93-3.01 (m, 2H), 4.01 (s, 2H), 4.19-4.32 (m, 2H), 5.33-5.47 (m, 1H), 7.21-7.27 (m, 2H), 7.34 (t, J=7.7 Hz, 1H), 7.40-7.50 (m, 2H), 7.59-7.68 (m, 1H), 7.73-7.79 (m, 1H)

REFERENCE EXAMPLE 101

N-(tetrahydro-2H-pyran-3-yl)-4H-1,2,4-triazol-3-amine

A mixture of tetrahydro-2H-pyran-3-ol (2.7 g), pyridinium dichromate (15 g), molecular sieves 4A (15 g) and tetrahydrofuran (200 mL) was stirred at room temperature for 3 hr. The reaction solution was diluted with diethyl ether (200 mL), the insoluble material was filtered off through silica gel, and the filtrate was concentrated. The obtained residue was dissolved in acetic acid (20 mL), 1H-1,2,4-triazol-3-amine (1.1 g) and sodium cyanoborohydride (4.2 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure to give the title compound as a colorless solid (0.19 g, 9%).

¹H NMR (300 MHz, DMSO-d₆) δ1.33-1.57 (m, 2H), 1.61-1.74 (m, 1H), 1.88-2.02 (m, 1H), 2.95-3.14 (m, 1H), 3.32 (s, 1H), 3.35-3.49 (m, 1H), 3.64-3.75 (m, 1H), 3.77-3.91 (m, 1H), 5.37-6.61 (m, 1H), 7.21-8.18 (m, 1H), 11.88-12.86 (m, 1H)

REFERENCE EXAMPLE 102

3'-fluoro-4'-{[5-oxo-7-propyl-4-(tetrahydro-2H-pyran-3-yl)-4,5-dihydro[1,2,4]triazolo[1,5-a]pyrimidin-6-yl]methyl}biphenyl-2-carbonitrile A mixture of ethyl 2-[(2'-cyano-3-fluorobiphenyl-4-yl)methyl]-3-oxohexanoate (0.42 g) and N-(tetrahydro-2H-pyran-3-yl)-4H-1,2,4-triazol-3-amine (0.1 g) was stirred at 250° C. for 20 min under microwave irradiation. The obtained reaction mixture was purified by silica gel column chromatography to give the title compound as a colorless solid (0.17 g, 60%).

¹H NMR (300 MHz, CHLOROFORM-d) δ1.06 (t, J=7.3 Hz, 3H), 1.64-1.97 (m, 5H), 2.75-2.93 (m, 1H), 2.99-3.08 (m, 2H), 3.47-3.56 (m, 1H), 3.85-4.04 (m, 4H), 4.45 (t, J=10.6 Hz, 1H), 5.17-5.30 (m, 1H), 7.23-7.29 (m, 2H), 7.34-7.50 (m, 3H), 7.60-7.69 (m, 1H), 7.72-7.78 (m, 1H), 7.91 (s, 1H)

REFERENCE EXAMPLE 103

N-(1,4-dioxaspiro[4.5]dec-8-yl)-5-methyl-4H-1,2,4-triazol-3-amine

Sodium triacetoxyborohydride (32.4 g) was gradually added to a solution (150 mL) of 5-methyl-4H-1,2,4-triazol-3-amine (10.0 g) and 1,4-cyclohexanedione monoethyleneketal (19.1 g) in acetic acid. The mixture was stirred at room temperature for 16 hr, water was added to the reaction mixture, and the mixture was concentrated under reduced pressure. The obtained residue was poured into saturated aqueous sodium hydrogen carbonate, and the mixture was extracted 3 times with a mixed solvent of ethyl acetate and isopropyl alcohol (3:1). The obtained extract was dried over anhydrous sodium sulfate, and the solvent was evaporated under reduced pressure, and the residue was solidified with diisopropyl ether, and the solid was collected by filtration, and dried to give the title compound (15.6 g).

¹H NMR (300 MHz, DMSO-d₆) δ1.37-1.57 (m, 4H), 1.59-1.73 (m, 2H), 1.74-1.90 (m, 2H), 2.06 (s, 3H), 3.84 (s, 4H), 6.03 (br. s., 1H), 11.88 (br. s., 1H)

REFERENCE EXAMPLE 104

4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-3'-fluorobiphenyl-2-carbonitrile A mixture of ethyl 2-[(2'-cyano-3-fluorobiphenyl-4-yl)methyl]-3-oxohexanoate (1.5 g) and N-(1,4-dioxaspiro[4.5]dec-8-yl)-5-methyl-4H-1,2,4-triazol-3-amine (0.5 g) was stirred at 250° C. for 20 min under microwave irradiation. The obtained reaction mixture was purified by silica gel column chromatography to give the title compound as a colorless solid (0.32 g, 28%).

¹H NMR (300 MHz, CHLOROFORM-d) δ1.06 (t, J=7.4 Hz, 3H), 1.64-1.97 (m, 5H), 2.74-2.94 (m, 1H), 2.96-3.07 (m, 2H), 3.51 (td, J=11.5, 2.8 Hz, 1H), 3.84-4.03 (m, 6H), 3.84-4.03 (m, 4H), 4.45 (t, J=10.6 Hz, 1H), 5.15-5.31 (m, 1H), 7.34-7.53 (m, 6H), 7.58-7.68 (m, 1H), 7.75 (d, J=8.0 Hz, 1H), 7.91 (s, 1H)

REFERENCE EXAMPLE 105

4'-{[5-oxo-7-propyl-4-(tetrahydro-2H-pyran-3-yl)-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.37 g) and N-(tetrahydro-2H-pyran-3-yl)-4H-1,2,4-triazol-3-amine (0.088 g) was stirred at 250° C. for 20 min under microwave irradiation. The obtained reaction mixture was purified by silica gel column chromatography to give the title compound as a colorless solid (0.15 g, 63%).

¹H NMR (300 MHz, CHLOROFORM-d) δ1.06 (t, J=7.4 Hz, 3H), 1.64-1.97 (m, J=15.4, 7.6, 7.4, 7.4 Hz, 5H), 2.74-2.94 (m, 1H), 2.96-3.07 (m, 2H), 3.51 (td, J=11.5, 2.8 Hz, 1H), 3.84-4.03 (m, 6H), 3.84-4.03 (m, 4H), 4.45 (t, J=10.6 Hz, 1H), 5.15-5.31 (m, 1H), 7.34-7.53 (m, 6H), 7.58-7.68 (m, 1H), 7.75 (d, J=8.0 Hz, 1H), 7.91 (s, 1H)

REFERENCE EXAMPLE 106

4'-{[5-oxo-7-butyl-4-(tetrahydro-2H-pyran-4-yl)-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (1.3 g) and N-(tetrahydro-2H-pyran-4-yl)-4H-1,2,4-triazol-3-amine (0.3 g) was stirred at 250° C. for 15 min under microwave irradiation. The obtained reaction mixture was purified by silica gel column chromatography to give the title compound as a colorless solid (0.52 g, 62%).

¹H NMR (300 MHz, CHLOROFORM-d) δ0.96 (t, J=7.2 Hz, 3H), 1.41-1.54 (m, 2H), 1.59-1.73 (m, 4H), 2.91-3.10 (m, 4H), 3.54 (t, J=11.0 Hz, 2H), 4.02 (s, 2H), 4.07-4.17 (m, 2H), 5.21-5.40 (m, 1H), 7.34-7.51 (m, 6H), 7.58-7.68 (m, 1H), 7.75 (d, J=6.8 Hz, 1H), 7.93 (s, 1H)

REFERENCE EXAMPLE 107

3'-fluoro-4'-({4-[trans-4-(2-hydroxy-1,2-dimethyl-propoxy)cyclohexyl]-5-oxo-7-propyl-4,5-dihydro[1,2,4]triazolo[1,5-a]pyrimidin-6-yl}methyl)biphenyl-2-carbonitrile (retention time: short)

tert-Butyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]propanoate (548 g) was dissolved in tetrahydrofuran (2.7 L), and methylmagnesium bromide (1.0 M tetrahydrofuran solution, 3.5 L) was added with the internal temperature maintained below 10° C. The reaction mixture was stirred at the same temperature for 1 hr, and partitioned among saturated aqueous ammonium chloride solution (600 mL), water (600 mL) and ethyl acetate (500 mL). The aqueous layer was extracted with ethyl acetate (1 L). The combined extracts were washed with saturated brine (1 L), dried over anhydrous magnesium sulfate, and concentrated under reduced pressure. The resulting residue was purified by silica gel column chromatography to give the title compound as a racemate (428 g, 84%).

The racemate (500 g) obtained by the above-mentioned method was resolved using a chiral column to give the title compound as a colorless solid (199 g, 99% ee, 40%).

$^1$H NMR (300 MHz, DMSO-$d_6$) δ0.90-1.11 (m, 12H), 1.16-1.39 (m, 2H), 1.54-1.75 (m, 4H), 1.94-2.14 (m, 2H), 2.47-2.68 (m, 2H), 2.91-3.02 (m, 2H), 3.24 (q, J=6.0 Hz, 1H), 3.30-3.44 (m, 1H), 3.97 (s, 2H), 4.06 (s, 1H), 4.80-4.97 (m, 1H), 7.26-7.39 (m, 2H), 7.41-7.50 (m, 1H), 7.54-7.67 (m, 2H), 7.75-7.83 (m, 1H), 7.95 (d, J=7.6 Hz, 1H), 8.20 (s, 1H)

analysis of enantiomeric excess
column: CHIRALPAK IA 4.6 mm ID×250 mL
mobile phase: n-Hex/IPA=90/10 (v/v)
flow rate: 1.0 mL/min
temperature: 40° C.
detection: UV 254 nm
concentration: 1 mg/mL (n-Hex/IPA=90/10)
injection volume: 0.01 mL
retention time: 19.5 min

REFERENCE EXAMPLE 108

4'-({4-[(2R,4r,6S)-2,6-dimethyltetrahydro-2H-pyran-4-yl]-5-oxo-7-propyl-4,5-dihydro[1,2,4]triazolo[1,5-a]pyrimidin-6-yl}methyl)biphenyl-2-carbonitrile A mixture of ethyl 2-[(2'-cyanobiphenyl-4-yl)methyl]-3-oxohexanoate (2.5 g) and N-[(2R,6S)-2,6-dimethyltetrahydro-2H-pyran-4-yl]-1H-1,2,4-triazol-5-amine (0.7 g) was stirred at 250° C. for 20 min under microwave irradiation. The obtained reaction mixture was purified by silica gel column chromatography to give the title compound as a colorless solid (0.53 g, 31%).

$^1$H NMR (300 MHz, CHLOROFORM-d) δ1.06 (t, J=7.3 Hz, 3H), 1.27 (t, J=7.2 Hz, 6H), 1.65-1.78 (m, 4H), 2.46-2.64 (m, 2H), 2.97-3.10 (m, 2H), 3.56-3.72 (m, 2H), 4.02 (s, 2H), 5.24-5.39 (m, 1H), 7.32-7.53 (m, 6H), 7.59-7.67 (m, 1H), 7.75 (dd, J=7.6, 0.8 Hz, 1H), 7.93 (s, 1H)

REFERENCE EXAMPLE 109

4'-({4-[(2R,4s,6S)-2,6-dimethyltetrahydro-2H-pyran-4-yl]-5-oxo-7-propyl-4,5-dihydro[1,2,4]triazolo[1,5-a]pyrimidin-6-yl}methyl)biphenyl-2-carbonitrile A mixture of ethyl 2-[(2'-cyanobiphenyl-4-yl)methyl]-3-oxohexanoate (2.5 g) and N-[(2R,6S)-2,6-dimethyltetrahydro-2H-pyran-4-yl]-1H-1,2,4-triazol-5-amine (0.7 g) was stirred at 250° C. for 20 min under microwave irradiation. The obtained reaction mixture was purified by silica gel column chromatography to give the title compound as a colorless solid (0.098 g, 6%).

$^1$H NMR (300 MHz, CHLOROFORM-d) δ1.06 (t, J=7.4 Hz, 3H), 1.24 (d, J=6.0 Hz, 6H), 1.64-1.80 (m, 4H), 2.47-2.64 (m, 2H), 2.97-3.07 (m, 2H), 4.03 (s, 2H), 4.20-4.34 (m, 2H), 5.40-5.53 (m, 1H), 7.33-7.53 (m, 6H), 7.58-7.68 (m, 1H), 7.75 (dd, J=7.7, 0.9 Hz, 1H), 7.92 (s, 1H)

REFERENCE EXAMPLE 110

4'-{[5-oxo-7-propyl-4-(tetrahydrofuran-3-yl)-4,5-dihydro[1,2,4]triazolo[1,5-a]pyrimidin-6-yl]methyl}biphenyl-2-carbonitrile A mixture of tetrahydrofuran-3-ol (5 g), pyridinium dichromate (32 g), molecular sieves 4A (32 g) and tetrahydrofuran (400 mL) was stirred at room temperature for 3 hr. The reaction solution was diluted with diethyl ether (400 mL), the insoluble material was filtered off through silica gel, and the filtrate was concentrated. The obtained residue was dissolved in acetic acid (30 mL), 1H-1,2,4-triazol-3-amine (2.4 g) and sodium cyanoborohydride (9 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. A mixture of the obtained residue and ethyl 2-[(2'-cyanobiphenyl-4-yl)methyl]-3-oxohexanoate (1.8 g) was stirred at 250° C. for 20 min under microwave irradiation. The obtained reaction mixture was purified by silica gel column chromatography to give the title compound as a colorless solid (0.18 g, 1%).

$^1$H NMR (300 MHz, CHLOROFORM-d) δ1.07 (t, J=7.2 Hz, 3H) 1.65-1.80 (m, 2H) 2.22-2.41 (m, 1H) 2.51-2.68 (m, 1H) 2.98-3.09 (m, 2H) 3.89-4.13 (m, 5H) 4.29-4.45 (m, 1H) 5.77-5.91 (m, 1H) 7.34-7.51 (m, 6H) 7.59-7.67 (m, 1H) 7.71-7.79 (m, 1H) 7.95 (s, 1H)

REFERENCE EXAMPLE 111

N-(2-methyltetrahydro-2H-pyran-4-yl)-4H-1,2,4-triazol-3-amine

A mixture of 2-methyltetrahydro-2H-pyran-4-ol (3.5 g), pyridinium dichromate (34 g), molecular sieves 4A (20 g) and tetrahydrofuran (300 mL) was stirred at room temperature for 3 hr. The reaction solution was diluted with diethyl ether (300 mL), the insoluble material was filtered off through silica gel, and the filtrate was concentrated. The obtained residue was dissolved in acetic acid (30 mL), 1H-1,2,4-triazol-3-amine (1.7 g) and sodium cyanoborohydride (8.5 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure, and the residue was purified by silica gel column chromatography to give the title compound as a colorless solid (2 g, 54%).

$^1$H NMR (300 MHz, DMSO-d$_6$) δ0.99-1.15 (m, 3H), 1.21-1.94 (m, 3H), 3.28-3.90 (m, 4H), 6.39-6.80 (m, 1H), 7.21-8.09 (m, 1H), 11.83-12.88 (m, 1H)

REFERENCE EXAMPLE 112

4'-{[4-(2-methyltetrahydro-2H-pyran-4-yl)-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (1.2 g) and N-(2-methyltetrahydro-2H-pyran-4-yl)-4H-1,2,4-triazol-3-amine (0.3 g) was stirred at 250° C. for 20 min under microwave irradiation. The obtained reaction mixture was purified by silica gel column chromatography to give the title compound as a colorless solid (0.43 g, 56%).

$^1$H NMR (300 MHz, CHLOROFORM-d) δ1.06 (t, J=7.3 Hz, 3H) 1.21-1.83 (m, 9H) 2.52-3.19 (m, 4H) 3.53-4.45 (m, 4H) 5.23-5.65 (m, 1H) 7.34-7.53 (m, 6H) 7.59-7.67 (m, 1H) 7.75 (d, J=7.7 Hz, 1H) 7.93 (s, 1H)

REFERENCE EXAMPLE 113

4'-{[7-butyl-4-(2-methyltetrahydro-2H-pyran-4-yl)-5-oxo-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (1.2 g) and N-(2-methyltetrahydro-2H-pyran-4-yl)-4H-1,2,4-triazol-3-amine (0.3 g) was stirred at 250° C. for 20 min under microwave irradiation. The obtained reaction mixture was purified by silica gel column chromatography to give the title compound as a mixture of 4 kinds of isomers (0.49 g, 62%).

$^1$H NMR (300 MHz, CHLOROFORM-d) δ0.95 (t, J=7.3 Hz, 3H), 1.23-1.29, 1.38-1.42 (m, combined 3H), 1.42-1.78 (m, 6H), 2.55-2.71, 2.78-3.19 (m, combined 4H), 3.54-3.70 (m, 4H), 3.84-3.91 (m, combined 2H), 4.02 (s, 2H), 4.08-4.17, 4.33-4.45 (m, combined 1H), 5.23-5.40, 5.51-5.66 (m, combined 1H), 7.34-7.53 (m, 6H), 7.59-7.67 (m, 1H), 7.75 (dd, J=7.7, 0.9 Hz, 1H), 7.94 (s, 1H)

The obtained isomer mixture was subjected to the following conditions to give 4 kinds of single isomers [tR1 (148 mg), tR2 (57 mg), tR3 (141 mg), tR4 (58 mg), retention time arranged in the ascending order].

column: CHIRALPAK AD (IL001) 50 mm ID×500 mL
mobile phase: n-Hex/IPA=900/100 (v/v)
flow rate: 75 ml/min
temperature: 30° C.
detection: UV 220 nm
concentration: 0.5 mg/ml (n-Hex/IPA=900/100)
injection volume: 50 ml
load: 25 mg
cycle time: 95 min

REFERENCE EXAMPLE 114

4'-{[7-butyl-2-methyl-5-oxo-4-(tetrahydro-2H-pyran-4-yl)-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (1.2 g) and 5-methyl-N-(tetrahydro-2H-pyran-4-yl)-4H-1,2,4-triazol-3-amine (0.3 g) was stirred at 250° C. for 20 min under microwave irradiation. The obtained reaction mixture was purified by silica gel column chromatography to give the title compound as a colorless solid (0.52 g, 66%).

$^1$H NMR (300 MHz, CHLOROFORM-d) δ0.95 (t, J=7.4 Hz, 3H) 1.38-1.52 (m, 2H) 1.58-1.70 (m, 4H) 2.44 (s, 3H) 2.93-3.10 (m, 4H) 3.53 (t, J=12.2 Hz, 2H) 3.99 (s, 2H) 4.05-4.15 (m, 2H) 5.17-5.33 (m, 1H) 7.32-7.52 (m, 6H) 7.57-7.66 (m, 1H) 7.75 (dd, J=7.7, 0.9 Hz, 1H)

REFERENCE EXAMPLE 115

N-(2,2-dimethyltetrahydro-2H-pyran-4-yl)-4H-1,2,4-triazol-3-amine

A mixture of 2,2-dimethyltetrahydro-2H-pyran-4-ol (5 g), pyridinium dichromate (22 g), molecular sieves 4A (22 g) and tetrahydrofuran (200 mL) was stirred at room temperature for 3 hr. The reaction solution was diluted with diethyl ether (200 mL), the insoluble material was filtered off through silica gel, and the filtrate was concentrated. The obtained residue was dissolved in acetic acid (30 mL), 1H-1,2,4-triazol-3-amine (2.2 g) and sodium cyanoborohydride (11 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure, and the residue was purified by silica gel column chromatography to give the title compound as a colorless solid (1.8 g, 60%).

$^1$H NMR (300 MHz, DMSO-d$_6$) δ1.09-1.33 (m, 8H), 1.71-1.88 (m, 2H), 3.51-3.70 (m, 3H), 5.42-6.47 (m, 1H), 7.22-8.07 (m, 1H), 11.97-12.81 (m, 1H)

REFERENCE EXAMPLE 116

4'-{[4-(2,2-dimethyltetrahydro-2H-pyran-4-yl)-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.89 g) and N-(2,2-dimethyltetrahydro-2H-pyran-4-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.41 g, 67%).

$^1$H NMR (300 MHz, CHLOROFORM-d) δ1.06 (t, J=7.3 Hz, 3H), 1.32 (s, 3H), 1.37 (s, 3H), 1.54-1.79 (m, 5H), 2.78 (t, J=12.6 Hz, 1H), 2.84-3.11 (m, 3H), 3.75-3.96 (m, 2H), 4.03 (s, 2H), 5.43-5.62 (m, 1H), 7.33-7.52 (m, 6H), 7.58-7.66 (m, 1H), 7.75 (d, J=7.7 Hz, 1H), 7.94 (s, 1H)

REFERENCE EXAMPLE 117

4'-{[7-butyl-4-(2,2-dimethyltetrahydro-2H-pyran-4-yl)-5-oxo-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (0.89 g) and N-(2,2-dimethyltetrahydro-2H-pyran-4-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.45 g, 71%).

$^1$H NMR (300 MHz, CHLOROFORM-d) δ0.95 (t, J=7.2 Hz, 3H) 1.32 (s, 3H) 1.36 (s, 3H) 1.40-1.54 (m, 2H) 1.56-1.70 (m, 4H) 2.78 (t, J=12.6 Hz, 1H) 2.86-3.09 (m, 3H) 3.74-3.96 (m, 2H) 4.02 (s, 2H) 5.45-5.59 (m, 1H) 7.33-7.51 (m, 6H) 7.57-7.66 (m, 1H) 7.75 (d, J=7.7 Hz, 1H) 7.94 (s, 1H)

REFERENCE EXAMPLE 118

4'-{[7-butyl-2-methyl-5-oxo-4-(tetrahydro-2H-pyran-4-yl)-4,5-dihydro[1,2,4]triazolo[1,5-a]pyrimidin-6-yl]methyl}-3'-fluorobiphenyl-2-carbonitrile A mixture of methyl 2-[(2'-cyano-3-fluorobiphenyl-4-yl)methyl]-3-oxoheptanoate (1 g) and 5-methyl-N-(tetrahydro-2H-pyran-4-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.49 g, 72%).

$^1$H NMR (300 MHz, CHLOROFORM-d) δ0.94 (t, J=7.3 Hz, 3H), 1.38-1.53 (m, 2H), 1.57-1.70 (m, 4H), 2.44 (s, 3H), 2.93-3.11 (m, 4H), 3.55 (t, J=11.2 Hz, 2H), 4.00 (s, 2H), 4.06-4.17 (m, 2H), 5.17-5.31 (m, 1H), 7.20-7.27 (m, 2H), 7.32-7.49 (m, 3H), 7.61-7.70 (m, 1H), 7.76 (d, J=7.7 Hz, 1H)

REFERENCE EXAMPLE 119

N-(2,2-dimethyltetrahydro-2H-pyran-4-yl)-5-methyl-4H-1,2,4-triazol-3-amine

A mixture of 2,2-dimethyltetrahydro-2H-pyran-4-ol (5 g), pyridinium dichromate (22 g), molecular sieves 4A (22 g) and tetrahydrofuran (200 mL) was stirred at room temperature for 3 hr. The reaction solution was diluted with diethyl ether (200 mL), the insoluble material was filtered off through silica gel, and the filtrate was concentrated. The obtained residue was dissolved in acetic acid (30 mL), 5-methyl-4H-1,2,4-triazol-3-amine (2.5 g) and sodium cyanoborohydride (11 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure, and the residue was purified by silica gel column chromatography to give the title compound as a colorless solid (1.6 g, 49%).

$^1$H NMR (300 MHz, DMSO-$d_6$) δ1.03-1.30 (m, 8H), 1.70-1.85 (m, 2H), 2.07 (br.s., 3H), 3.48-3.66 (m, 3H), 5.17-6.39 (m, 1H), 11.47-12.45 (m, 1H)

REFERENCE EXAMPLE 120

4'-{[4-(2,2-dimethyltetrahydro-2H-pyran-4-yl)-2-methyl-5-oxo-7-propyl-4,5-dihydro[1,2,4]triazolo[1,5-a]pyrimidin-6-yl]methyl}-3'-fluorobiphenyl-2-carbonitrile A mixture of ethyl 2-[(2'-cyano-3-fluorobiphenyl-4-yl)methyl]-3-oxohexanoate (0.87 g) and N-(2,2-dimethyltetrahydro-2H-pyran-4-yl)-5-methyl-4H-1,2,4-triazol-3-amine (0.25 g) was stirred at 250° C. for 20 min under microwave irradiation. The obtained reaction mixture was purified by silica gel column chromatography to give the title compound as a colorless solid (0.34 g, 56%).

$^1$H NMR (300 MHz, CHLOROFORM-d) δ1.05 (t, J=7.3 Hz, 3H), 1.32 (s, 3H), 1.36 (s, 3H), 1.52-1.76 (m, 4H), 2.44 (s, 3H), 2.80 (t, J=12.6 Hz, 1H), 2.90-3.06 (m, 3H), 3.73-3.95 (m, 2H), 4.01 (s, 2H), 5.40-5.56 (m, 1H), 7.21-7.30 (m, 2H), 7.34 (t, J=7.7 Hz, 1H), 7.41-7.51 (m, 2H), 7.59-7.68 (m, 1H), 7.75 (d, J=7.7 Hz, 1H)

REFERENCE EXAMPLE 121

4'-{[7-butyl-4-(2,2-dimethyltetrahydro-2H-pyran-4-yl)-2-methyl-5-oxo-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (0.83 g) and N-(2,2-dimethyltetrahydro-2H-pyran-4-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.39 g, 64%).

$^1$H NMR (300 MHz, CHLOROFORM-d) δ0.94 (t, J=7.3 Hz, 3H), 1.31 (s, 3H), 1.35 (s, 3H), 1.38-1.50 (m, 2H), 1.51-1.69 (m, 4H), 2.44 (s, 3H), 2.80 (t, J=12.6 Hz, 1H), 2.88-3.05 (m, 3H), 3.76-3.93 (m, 2H), 3.99 (s, 2H), 5.42-5.55 (m, 1H), 7.32-7.52 (m, 6H), 7.59-7.66 (m, 1H), 7.75 (dd, J=7.7, 0.9 Hz, 1H)

REFERENCE EXAMPLE 122

4'-({7-butyl-4-[(2R,4r,6S)-2,6-dimethyltetrahydro-2H-pyran-4-yl]-5-oxo-4,5-dihydro[1,2,4]triazolo[1,5-a]pyrimidin-6-yl}methyl)biphenyl-2-carbonitrile A mixture of methyl 2-[(2'-cyanobiphenyl-4-yl)methyl]-3-oxoheptanoate (0.89 g) and N-[(2R,6S)-2,6-dimethyltetrahydro-2H-pyran-4-yl]-1H-1,2,4-triazol-5-amine (0.25 g) was stirred at 250° C. for 20 min under microwave irradiation. The obtained reaction mixture was purified by silica gel column chromatography to give the title compound as a colorless solid (0.27 g, 64%).

$^1$H NMR (300 MHz, CHLOROFORM-d) δ0.95 (t, J=7.2 Hz, 3H), 1.28 (d, J=6.2 Hz, 6H), 1.38-1.54 (m, 2H), 1.57-1.75 (m, 4H), 2.56 (q, J=12.2 Hz, 2H), 3.01-3.09 (m, 2H), 3.58-3.71 (m, 2H), 4.02 (s, 2H), 5.26-5.41 (m, 1H), 7.34-7.52 (m, 6H), 7.58-7.66 (m, 1H), 7.75 (d, J=7.7 Hz, 1H), 7.93 (s, 1H)

REFERENCE EXAMPLE 123

4'-({7-butyl-4-[(2R,4s,6S)-2,6-dimethyltetrahydro-2H-pyran-4-yl]-5-oxo-4,5-dihydro[1,2,4]triazolo[1,5-a]pyrimidin-6-yl}methyl)biphenyl-2-carbonitrile A mixture of methyl 2-[(2'-cyanobiphenyl-4-yl)methyl]-3-oxoheptanoate (0.89 g) and N-[(2R,6S)-2,6-dimethyltetrahydro-2H-pyran-4-yl]-1H-1,2,4-triazol-5-amine (0.25 g) was stirred at 250° C. for 20 min under microwave irradiation. The obtained reaction mixture was purified by silica gel column chromatography to give the title compound as a colorless solid (0.094 g, 15%).

$^1$H NMR (300 MHz, CHLOROFORM-d) δ0.95 (t, J=7.3 Hz, 3H), 1.22-1.27 (m, 6H), 1.39-1.53 (m, 2H), 1.59-1.75 (m, 2H), 2.49-2.63 (m, 2H), 2.99-3.10 (m, 2H), 4.02 (s, 2H), 4.20-4.32 (m, 2H), 5.39-5.52 (m, 1H), 7.33-7.52 (m, 6H), 7.58-7.67 (m, 1H), 7.75 (dd, J=7.7, 0.9 Hz, 1H), 7.92 (s, 1H)

REFERENCE EXAMPLE 124

N-(1,4-dioxaspiro[4.5]dec-8-yl)-4H-1,2,4-triazol-3-amine

To a solution of 1H-1,2,4-triazol-3-amine (66.6 g) and 1,4-dioxaspiro[4.5]decan-8-one (175 g) in acetic acid (1.25 L) was gradually added sodium triacetoxyborohydride (252 g) under ice-cooling. After stirring at room temperature for 16 hr, water (1 L) was added to the reaction mixture, and the mixture was concentrated under reduced pressure. The obtained residue was poured into saturated aqueous sodium hydrogen carbonate (1 L). The mixture was neutralized with sodium bicarbonate, and extracted 3 times with a mixed solvent of ethyl acetate and isopropyl alcohol (3:1, 2 L). The combined extracts were dried over anhydrous sodium sulfate, and concentrated under reduced pressure. The residue was solidified with diisopropyl ether (500 mL), and the resulting solid was collected by filtration, washed twice with diisopropyl ether (250 mL), and dried to give the title compound (166 g, 94%).

$^1$H NMR (300 MHz, CHLOROFORM-d) δ1.51-1.88 (m, 6H), 2.01-2.13 (m, 2H), 3.56 (br.s., 1H), 3.96 (s, 4H), 4.53 (br. s., 1H), 7.72 (s, 1H)

REFERENCE EXAMPLE 125

4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (1.9 g) and N-(1,4-dioxaspiro[4.5]dec-8-yl)-4H-1,2,4-triazol-3-amine (0.6 g) was stirred at 250° C. for 20 min under microwave irradiation. The obtained reaction mixture was purified by silica gel column chromatography to give the title compound as a colorless solid (0.78 g, 56%).

$^1$H NMR (300 MHz, CHLOROFORM-d) δ1.06 (t, J=7.3 Hz, 3H), 1.64-1.97 (m, 8H), 2.84-3.07 (m, 4H), 3.91-4.06 (m, 6H), 5.06-5.22 (m, 1H), 7.33-7.53 (m, 6H), 7.57-7.67 (m, 1H), 7.74 (d, J=7.7 Hz, 1H), 7.96 (s, 1H)

REFERENCE EXAMPLE 126

4'-{[7-butyl-4-(1,4-dioxaspiro[4.5]dec-8-yl)-5-oxo-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (1.9 g) and N-(1,4-dioxaspiro[4.5]dec-8-yl)-4H-1,2,4-triazol-3-amine (0.6 g) was stirred at 250° C. for 20 min under microwave irradiation. The obtained reaction mixture was purified by silica gel column chromatography to give the title compound as a colorless solid (0.75 g, 53%).

$^1$H NMR (300 MHz, CHLOROFORM-d) δ0.95 (t, J=7.3 Hz, 3H) 1.39-1.53 (m, 2H) 1.57-1.94 (m, 8H) 2.90-3.07 (m, 4H) 3.91-4.06 (m, 6H) 5.05-5.23 (m, 1H) 7.34-7.52 (m, 6H) 7.57-7.68 (m, 1H) 7.75 (dd, J=7.7, 0.9 Hz, 1H) 7.97 (s, 1H)

REFERENCE EXAMPLE 127

5-methyl-N-(6-methyltetrahydro-2H-pyran-3-yl)-4H-1,2,4-triazol-3-amine

A mixture of 6-methyltetrahydro-2H-pyran-3-ol (2.5 g), pyridinium dichromate (16 g), molecular sieves 4A (16 g) and tetrahydrofuran (100 mL) was stirred at room temperature for 3 hr. The reaction solution was diluted with diethyl ether (100 mL), the insoluble material was filtered off through silica gel, and the filtrate was concentrated. The obtained residue was dissolved in acetic acid (50 mL), 5-methyl-4H-1,2,4-triazol-3-amine (1.4 g) and sodium cyanoborohydride (6 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure, and the residue was purified by silica gel column chromatography to give the title compound as a colorless solid (0.04 g, 48%).

$^1$H NMR (300 MHz, DMSO-d$_6$) δ1.03-1.11 (m, 3H), 1.16-2.30 (m, 7H), 2.89-3.97 (m, 3H), 5.37-6.32 (m, 1H), 11.26-11.75 (m, 1H)

REFERENCE EXAMPLE 128

4'-{[2-methyl-4-(6-methyltetrahydro-2H-pyran-3-yl)-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (0.89 g) and 5-methyl-N-(6-methyltetrahydro-2H-pyran-3-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.18 g, 30%).

$^1$H NMR (300 MHz, CHLOROFORM-d) δ1.04 (t, J=7.3 Hz, 3H), 1.21 (d, J=6.2 Hz, 3H), 1.41-1.54 (m, 1H), 1.63-1.77 (m, 2H), 1.79-1.91 (m, 2H), 2.43 (s, 3H), 2.79-2.99 (m, 3H), 3.58-3.69 (m, 1H), 3.82-3.90 (m, 1H), 3.98 (s, 2H), 4.55 (t, J=10.6 Hz, 1H), 5.08-5.21 (m, 1H), 7.34 (d, J=8.3 Hz, 2H), 7.38-7.51 (m, 4H), 7.58-7.66 (m, 1H), 7.74 (dd, J=7.7, 0.9 Hz, 1H)

REFERENCE EXAMPLE 129

4'-{[5-oxo-7-pentyl-4-(tetrahydro-2H-pyran-4-yl)-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxooctanoate (1.1 g) and 5-methyl-N-(6-methyltetrahydro-2H-pyran-3-yl)-4H-1,2,4-triazol-3-amine (0.25 g) was stirred at 250° C. for 20 min under microwave irradiation. The obtained reaction mixture was purified by silica gel column chromatography to give the title compound as a colorless solid (0.48 g, 67%).

$^1$H NMR (300 MHz, CHLOROFORM-d) δ1.04 (t, J=7.3 Hz, 3H), 1.21 (d, J=6.2 Hz, 3H), 1.41-1.54 (m, 1H), 1.63-1.77 (m, 2H), 1.79-1.91 (m, 2H), 2.43 (s, 3H), 2.79-2.99 (m, 3H), 3.58-3.69 (m, 1H), 3.82-3.90 (m, 1H), 3.98 (s, 2H), 4.55 (t, J=10.6 Hz, 1H), 5.08-5.21 (m, 1H), 7.34 (d, J=8.3 Hz, 2H), 7.38-7.51 (m, 4H), 7.58-7.66 (m, 1H), 7.74 (dd, J=7.7, 0.9 Hz, 1H)

REFERENCE EXAMPLE 130

4'-{[7-butyl-4-(4-hydroxycyclohexyl)-5-oxo-4,5-dihydro[1,2,4]triazolo[1,5-a]pyrimidin-6-yl]methyl}biphenyl-2-carbonitrile A mixture of 4'-{[7-butyl-4-(1,4-dioxaspiro[4.5]dec-8-yl)-5-oxo-4,5-dihydro[1,2,4]triazolo[1,5-a]pyrimidin-6-yl]methyl}biphenyl-2-carbonitrile (0.34 g), 6N hydrochloric acid (2 mL) and tetrahydrofuran (10 mL) was stirred at 40° C. for 3 hr. The reaction mixture was diluted with ethyl acetate, washed with saturated brine, and dried over anhydrous magnesium sulfate. The solvent was evaporated under reduced pressure. The residue obtained by silica gel column chromatography was dissolved in methanol (10 mL), sodium borohydride (0.047 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.31 g, 100%).

$^{1}$H NMR (300 MHz, CHLOROFORM-d) δ0.95 (t, J=7.3 Hz, 3H), 1.39-1.83 (m, 8H), 1.93-2.17 (m, 2H), 2.65-2.82 (m, 2H), 2.90-3.08 (m, 2H), 3.75-3.89 (m, 1H), 3.98-4.04 (m, 2H), 4.98-5.13 (m, 1H), 7.34-7.52 (m, 6H), 7.59-7.66 (m, 1H), 7.75 (dd, J=7.7, 0.9 Hz, 1H), 7.90-7.96 (m, 1H)

REFERENCE EXAMPLE 131

4'-{[7-butyl-4-(4-methoxycyclohexyl)-5-oxo-4,5-dihydro[1,2,4]triazolo[1,5-a]pyrimidin-6-yl]methyl}biphenyl-2-carbonitrile To a mixture of 4'-{[7-butyl-4-(4-hydroxycyclohexyl)-5-oxo-4,5-dihydro[1,2,4]triazolo[1,5-a]pyrimidin-6-yl]methyl}biphenyl-2-carbonitrile (0.37 g), methyl iodide (0.053 mL) and N,N-dimethylformamide (10 mL) was added sodium hydride (0.034 g), and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.16 g, 42%).

$^{1}$H NMR (300 MHz, CHLOROFORM-d) δ0.95 (t, J=7.4 Hz, 3H), 1.37-1.52 (m, 4H), 1.59-1.71 (m, 2H), 1.75-1.86 (m, 2H), 2.14-2.27 (m, 2H), 2.62-2.79 (m, 2H), 2.99-3.08 (m, 2H), 3.27-3.39 (m, 4H), 4.01 (s, 2H), 5.00-5.14 (m, 1H), 7.34-7.51 (m, 6H), 7.59-7.65 (m, 1H), 7.75 (dd, J=7.8, 1.0 Hz, 1H), 7.91-7.95 (m, 1H)

REFERENCE EXAMPLE 132

4'-{[2-methyl-4-(5-methyltetrahydrofuran-3-yl)-5-oxo-7-propyl[1,2,4]triazolo[1,5-a]pyrimidin-6-yl]methyl}biphenyl-2-carbonitrile A mixture of 2,5-anhydro-1,3-dideoxypentitol (2 g), pyridinium dichromate (11 g), molecular sieves 4A (11 g) and tetrahydrofuran (100 mL) was stirred at room temperature for 3 hr. The reaction solution was diluted with diethyl ether (100 mL), the insoluble material was filtered off through silica gel, and the filtrate was concentrated. The obtained residue was dissolved in acetic acid (20 mL), 5-methyl-4H-1,2,4-triazol-3-amine (1.2 g) and sodium cyanoborohydride (5.4 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. A mixture of the obtained residue and ethyl 2-[(2'-cyanobiphenyl-4-yl)methyl]-3-oxohexanoate (3.5 g) was stirred at 250° C. for 20 min under microwave irradiation. The obtained reaction mixture was purified by silica gel column chromatography to give the title compound as a colorless solid (0.1 g, 2%).

$^{1}$H NMR (300 MHz, CHLOROFORM-d) δ1.04 (t, J=7.3 Hz, 3H) 1.33 (d, J=6.0 Hz, 3H) 1.63-1.90 (m, 3H) 2.43 (s, 3H) 2.56-2.66 (m, 1H) 2.92-3.02 (m, 2H) 4.00 (s, 2H) 4.06-4.22 (m, 2H) 4.64-4.77 (m, 1H) 5.67-5.81 (m, 1H) 7.31-7.53 (m, 6H) 7.59-7.65 (m, 1H) 7.75 (dd, J=7.7, 0.9 Hz, 1H)

REFERENCE EXAMPLE 133

N-(1-oxaspiro[4.5]dec-8-yl)-4H-1,2,4-triazol-3-amine

To a solution (70 mL) of 1H-1,2,4-triazol-3-amine (0.29 g) and 1-oxaspiro[4.5]decan-8-one (0.64 g) in acetic acid was added sodium cyanoborohydride (1.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. The obtained reaction mixture was purified by silica gel column chromatography to give the title compound as a colorless solid (0.25 g, 34%).

$^{1}$H NMR (300 MHz, DMSO-d$_{6}$) δ1.23-1.94 (m, 12H), 3.17-3.38 (m, 1H), 3.62-3.74 (m, 2H), 5.44-6.42 (m, 1H), 7.24-8.05 (m, 1H), 11.86-12.74 (m, 1H)

REFERENCE EXAMPLE 134

4'-{[4-(4-methoxycyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (2 g), 6N hydrochloric acid (20 mL) and tetrahydrofuran (30 mL) was stirred at 70° C. for 16 hr. The reaction mixture was diluted with ethyl acetate, washed with saturated brine, and dried over anhydrous magnesium sulfate. The solvent was evaporated under reduced pressure. The obtained residue was dissolved in methanol (30 mL), sodium borohydride (0.18 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. The residue obtained by silica gel column chromatography was dissolved in N,N-dimethylformamide (10 mL), methyl iodide (0.13 mL) and sodium hydride (0.05 g) were added, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.21 g, 28%).

$^1$H NMR (300 MHz, CHLOROFORM-d) δ1.05 (t, J=7.2 Hz, 3H), 1.31-1.86 (m, 6H), 2.09-2.25 (m, 2H), 2.60-2.81 (m, 2H), 2.97-3.06 (m, 2H), 3.25-3.50 (m, 4H), 4.01 (s, 2H), 4.99-5.16 (m, 1H), 7.31-7.53 (m, 6H), 7.57-7.66 (m, 1H), 7.74 (d, J=8.0 Hz, 1H), 7.92 (s, 1H)

REFERENCE EXAMPLE 135

N-[4-(prop-2-en-1-yloxy)cyclohexyl]-4H-1,2,4-triazol-3-amine

To a solution (100 mL) of 1H-1,2,4-triazol-3-amine (2.4 g) and 4-(prop-2-en-1-yloxy)cyclohexanone (5.3 g) in acetic acid was added sodium cyanoborohydride (9.1 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. The obtained reaction mixture was purified by silica gel column chromatography to give the title compound as a colorless solid (3.2 g, 50%).

$^1$H NMR (300 MHz, DMSO-d$_6$) δ1.20-1.98 (m, 8H) 3.16-3.40 (m, 1H) 3.42-3.52 (m, 1H) 3.86-3.98 (m, 2H) 5.04-5.16 (m, 1H) 5.18-5.37 (m, 1H) 5.72-6.04 (m, 1H) 6.39 (br. s., 1H) 6.99-7.70 (m, 1H) 11.70-12.22 (m, 1H)

REFERENCE EXAMPLE 136

4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile A mixture of ethyl 2-[(2'-cyanobiphenyl-4-yl)methyl]-3-oxohexanoate (4 g) and N-[4-(prop-2-en-1-yloxy)cyclohexyl]-4H-1,2,4-triazol-3-amine (1.3 g) was stirred at 250° C. for 20 min under microwave irradiation. The obtained reaction mixture was purified by silica gel column chromatography to give the title compound as a colorless solid (0.7 g, 24%).

$^1$H NMR (300 MHz, CHLOROFORM-d) δ1.01-1.13 (m, 3H) 1.39-1.87 (m, 6H) 2.06-2.27 (m, 2H) 2.60-3.12 (m, 4H) 3.37-3.57 (m, 0.5H) 3.63-3.71 (m, 0.5H) 3.97-4.07 (m, 4H) 4.96-5.13 (m, 1H) 5.14-5.22 (m, 1H) 5.22-5.47 (m, 1H) 5.83-6.10 (m, 1H) 7.33-7.54 (m, 6H) 7.58-7.67 (m, 1H) 7.74 (d, J=7.95 Hz, 1H) 7.91 (s, 0.5H) 7.92 (s, 0.5H)

REFERENCE EXAMPLE 137

4'-({4-[4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (0.5 g), osmium oxide (7% immobilized catalyst, 0.5 g), sodium periodate (1.1 g), acetone (5 mL), acetonitrile (5 mL) and water (5 mL) was stirred at room temperature for 3 hr. The reaction mixture was diluted with ethyl acetate and water, and the insoluble material was filtered off through celite. The obtained organic layer was washed with saturated brine, and dried over anhydrous magnesium sulfate. The solvent was evaporated under reduced pressure, and the residue was dissolved in methanol (5 mL) and tetrahydrofuran (5 mL), sodium borohydride (0.045 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.4 g, 79%).

$^1$H NMR (300 MHz, CHLOROFORM-d) δ1.01-1.10 (m, 3H), 1.38-1.56 (m, 3H), 1.67-1.84 (m, 3H), 2.07-2.25 (m, 2H), 2.62-2.78 (m, 1H), 2.89-3.06 (m, 3H), 3.41-3.75 (m, 4H), 3.78-3.85 (m, 1H), 4.02 (d, J=3.0 Hz, 2H), 7.33-7.52 (m, 6H), 7.59-7.66 (m, 1H), 7.75 (dd, J=7.7, 1.1 Hz, 1H), 7.92 (d, J=6.2 Hz, 1H)

REFERENCE EXAMPLE 138

4'-({4-[4-(2-methoxyethoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (0.2 g), sodium hydride (0.019 g) and N,N-dimethylformamide (10 mL) was stirred at 0° C. for 10 min, methyl iodide (0.029 mL) was added, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure and the residue was purified by silica gel column chromatography to give the title compound as a colorless solid (0.078 g, 38%).

$^1$H NMR (300 MHz, CHLOROFORM-d) δ1.01-1.10 (m, 3H), 1.44-1.57 (m, 3H), 1.66-1.83 (m, 3H), 2.09-2.25 (m, 2H), 2.64-2.78 (m, 1H), 2.89-3.10 (m, 3H), 3.37-3.47 (m, 3H), 3.51-3.67 (m, 5H), 4.02 (d, J=2.6 Hz, 2H), 4.96-5.12 (m, 1H), 7.34-7.51 (m, 6H), 7.58-7.66 (m, 1H), 7.71-7.78 (m, 1H), 7.91 (d, J=1.9 Hz, 1H)

REFERENCE EXAMPLE 139

2'-fluoro-4'-(hydroxymethyl)biphenyl-2-carbonitrile

A mixture of (2-fluoro-4-formylphenyl)boronic acid (35.3 g), 2-cyano-phenylboronic acid (40.0 g), [1,1'-bis(diphenylphosphino)ferrocene]dichloropalladium (1.7 g), tetrabutylammonium bromide (0.68 g), 2M aqueous sodium carbonate solution (200 mL) and toluene (600 mL) was stirred at 100° C. for 72 hr under an argon atmosphere. The reaction mixture was diluted with ethyl acetate, washed with saturated brine, and dried over anhydrous magnesium sulfate. The solvent was evaporated under reduced pressure. The obtained residue was dissolved in tetrahydrofuran (150 mL) and methanol (150 mL), sodium borohydride (8.7 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (14.1 g, 30%).

$^1$H NMR (300 MHz, DMSO-d$_6$) δ4.60 (d, J=5.8 Hz, 2H), 5.43 (t, J=5.8 Hz, 1H), 7.32 (d, J=3.8 Hz, 2H), 7.46 (t, J=7.9 Hz, 1H), 7.57-7.76 (m, 2H), 7.82 (t, J=7.0 Hz, 1H), 7.98 (dd, J=7.7, 0.9 Hz, 1H)

REFERENCE EXAMPLE 140

4'-{[5-oxo-4-(4-oxocyclohexyl)-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (20 g), 6N hydrochloric acid (150 mL) and tetrahydrofuran (200 mL) was stirred at 70° C. for 16 hr. The reaction mixture was diluted with ethyl acetate, washed with saturated brine, and dried over anhydrous magnesium sulfate. The solvent was evaporated under reduced pressure and the residue was purified by silica gel column chromatography to give the title compound as a colorless solid (14 g, 77%).

$^1$H NMR (300 MHz, CHLOROFORM-d) δ1.07 (t, J=7.3 Hz, 3H), 1.67-1.80 (m, 2H), 2.01-2.13 (m, 2H), 2.51-2.59 (m, 4H), 2.99-3.18 (m, 2H), 4.03 (s, 2H), 5.48-5.62 (m, 1H), 7.34-7.53 (m, 6H), 7.58-7.68 (m, 1H), 7.75 (dd, J=7.7, 0.9 Hz, 1H), 7.91 (s, 1H)

REFERENCE EXAMPLE 141

4'-{[4-(4-morpholin-4-ylcyclohexyl)-5-oxo-7-propyl-4,5-dihydro[1,2,4]triazolo[1,5-a]pyrimidin-6-yl]methyl}biphenyl-2-carbonitrile To a solution (5 mL) of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.5 g) and morpholine (0.14 mL) in acetic acid was added sodium cyanoborohydride (0.34 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with ethyl acetate. The obtained extract was washed with saturated brine, and dried over anhydrous magnesium sulfate. The solvent was evaporated under reduced pressure and the residue was purified by silica gel column chromatography to give the title compound as a colorless solid (0.2 g, 35%).

$^1$H NMR (300 MHz, CHLOROFORM-d) δ1.05 (t, J=7.5 Hz, 3H), 1.41-1.77 (m, 6H), 2.08-2.26 (m, 3H), 2.50 (br. s., 4H), 2.86-3.05 (m, 4H), 3.75-3.82 (m, 4H), 4.03 (s, 2H), 4.98-5.18 (m, 1H), 7.32-7.52 (m, 6H), 7.58-7.67 (m, 1H), 7.71-7.76 (m, 1H), 7.92 (s, 1H)

REFERENCE EXAMPLE 142

4'-({5-oxo-4-[4-(2-oxopropoxy)cyclohexyl]-7-propyl-4,5-dihydro[1,2,4]triazolo[1,5-a]pyrimidin-6-yl}methyl)biphenyl-2-carbonitrile A mixture of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (1.8 g), osmium oxide (7% immobilized catalyst, 0.92 g), sodium periodate (3.9 g), acetone (20 mL), acetonitrile (20 mL) and water (20 mL) was stirred at room temperature for 3 hr. The reaction mixture was diluted with ethyl acetate and water, and the insoluble material was filtered off through celite. The obtained organic layer was washed with saturated brine, and dried over anhydrous magnesium sulfate. The solvent was evaporated under reduced pressure. The residue obtained by silica gel chromatography was dissolved in tetrahydrofuran (20 mL), and methylmagnesium bromide (1.0 M tetrahydrofuran solution, 1.9 mL) was added at −78° C. The reaction mixture was warmed to 0° C., and stirred for 16 hr. Saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The residue obtained by silica gel chromatography was dissolved in acetonitrile (15 mL), 1,1,1-triacetoxy-1,1-dihydro-1,2-benziodoxol-3(1H)-one (0.3 g) was added, and the mixture was stirred at room temperature for 3 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as a colorless solid (0.17 g, 68%).

$^1$H NMR (300 MHz, CHLOROFORM-d) δ1.07 (t, J=7.6 Hz, 3H) 1.49-1.80 (m, 6H) 2.08-2.18 (m, 2H) 2.33 (s, 3H) 2.91-3.11 (m, 4H) 3.65 (br. s., 1H) 4.03 (s, 4H) 4.99-5.15 (m, 1H) 7.34-7.53 (m, 6H) 7.58-7.66 (m, 1H) 7.75 (d, J=8.0 Hz, 1H) 7.91 (s, 1H)

REFERENCE EXAMPLE 143

4'-({4-[4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile 4'-({5-Oxo-4-[4-(2-oxopropoxy)cyclohexyl]-7-propyl-4,5-dihydro[1,2,4]triazolo[1,5-a]pyrimidin-6-yl}methyl)biphenyl-2-carbonitrile (0.17 g) was dissolved in tetrahydrofuran (15 mL), and methylmagnesium bromide (1.0 M tetrahydrofuran solution, 0.27 mL) was added at room temperature. The reaction mixture was stirred for 3 hr, saturated aqueous ammonium chloride solution was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.14 g, 78%).

$^1$H NMR (300 MHz, CHLOROFORM-d) δ1.05 (t, J=7.3 Hz, 3H), 1.30 (s, 6H), 1.45-1.78 (m, 6H), 2.08-2.16 (m, 2H), 2.90-3.08 (m, 4H), 3.28 (s, 2H), 3.67 (br. s., 2H), 4.02 (s, 2H), 5.10-5.28 (m, 1H), 7.34-7.52 (m, 6H), 7.58-7.66 (m, 1H), 7.70-7.79 (m, 1H), 7.92 (s, 1H)

REFERENCE EXAMPLE 144

4'-(bromomethyl)-2'-fluorobiphenyl-2-carbonitrile

To a solution (150 mL) of 2'-fluoro-4'-(hydroxymethyl)biphenyl-2-carbonitrile (14.1 g) in toluene was added phosphorus tribromide (18.7 g) at room temperature, and the mixture was stirred for 16 hr. Saturated aqueous sodium hydrogen carbonate was added to the reaction mixture, and the solvent was evaporated under reduced pressure, and the residue was extracted with ethyl acetate, and the obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (15.3 g, 100%).

$^1$H NMR (300 MHz, DMSO-$d_6$) δ4.79 (s, 2H), 7.43-7.56 (m, 3H), 7.61-7.69 (m, 2H), 7.83 (t, J=8.5 Hz, 1H), 7.99 (d, J=7.6 Hz, 1H)

REFERENCE EXAMPLE 145

4'-({4-[cis-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (1.1 g), osmium oxide (7% immobilized catalyst, 0.48 g), sodium periodate (2.4 g), acetone (15 mL), acetonitrile (15 mL) and water (15 mL) was stirred at room temperature for 3 hr. The reaction mixture was diluted with ethyl acetate and water, and the insoluble material was filtered off through celite. The obtained organic layer was washed with saturated brine, and dried over anhydrous magnesium sulfate. The solvent was evaporated under reduced pressure and the residue was dissolved in methanol (20 mL), sodium borohydride (0.13 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.29 g, 26%).

$^1$H NMR (300 MHz, CHLOROFORM-d) δ1.06 (t, J=7.2 Hz, 3H) 1.46-1.63 (m, 4H) 1.67-1.77 (m, 2H) 2.08-2.18 (m, 2H) 2.89-3.06 (m, 4H) 3.54-3.62 (m, 2H) 3.69-3.88 (m, 4H) 4.02 (s, 2H) 5.13-5.29 (m, 1H) 7.32-7.52 (m, 6H) 7.59-7.66 (m, 1H) 7.75 (dd, J=7.6, 1.0 Hz, 1H) 7.93 (s, 1H)

REFERENCE EXAMPLE 146

4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (1.1 g), osmium oxide (7% immobilized catalyst, 0.48 g), sodium periodate (2.4 g), acetone (15 mL), acetonitrile (15 mL) and water (15 mL) was stirred at room temperature for 3 hr. The reaction mixture was diluted with ethyl acetate and water, and insoluble material was filtered off through celite. The obtained organic layer was washed with saturated brine, and dried over anhydrous magnesium sulfate. The solvent was evaporated under reduced pressure. The residue was dissolved in methanol (20 mL), sodium borohydride (0.13 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.23 g, 20%).

$^1$H NMR (300 MHz, CHLOROFORM-d) δ1.06 (t, J=7.3 Hz, 3H), 1.36-1.52 (m, 2H), 1.67-1.86 (m, 4H), 1.98-2.04 (m, 1H), 2.13-2.24 (m, 2H), 2.71 (dd, J=12.6, 3.4 Hz, 2H), 2.98-3.07 (m, 2H), 3.38-3.52 (m, 1H), 3.57-3.63 (m, 2H), 3.68-3.76 (m, 2H), 4.01 (s, 2H), 5.01-5.15 (m, 1H), 7.33-7.52 (m, 6H), 7.59-7.66 (m, 1H), 7.75 (dd, J=7.8, 1.0 Hz, 1H), 7.91 (s, 1H)

REFERENCE EXAMPLE 147

4'-{[4-(4-hydroxy-4-prop-2-en-1-ylcyclohexyl)-5-oxo-7-propyl-4,5-dihydro[1,2,4]triazolo[1,5-a]pyrimidin-6-yl]methyl}biphenyl-2-carbonitrile 4'-{[5-Oxo-4-(4-oxocyclohexyl)-7-propyl-4,5-dihydro[1,2,4]triazolo[1,5-a]pyrimidin-6-yl]methyl}biphenyl-2-carbonitrile (0.8 g) was dissolved in tetrahydrofuran (10 mL), and allylmagnesium bromide (1.0 M diethyl ether solution, 2.1 mL) was added at −78° C. The reaction mixture was warmed to room temperature, and the mixture was stirred for 16 hr. Saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.26 g, 30%).

$^1$H NMR (300 MHz, CHLOROFORM-d) δ1.07 (t, J=7.2 Hz, 3H) 1.62-1.78 (m, 6H) 1.82-1.93 (m, 2H) 2.51-2.65 (m, 2H) 2.73-2.91 (m, 1H) 2.97-3.15 (m, 2H) 3.39-3.50 (m, 1H) 4.02 (s, 2H) 5.04-5.18 (m, 1H) 5.20-5.30 (m, 2H) 5.84-6.02 (m, 1H) 7.32-7.52 (m, 6H) 7.58-7.67 (m, 1H) 7.75 (dd, J=7.7, 1.1 Hz, 1H) 7.92 (s, 1H)

REFERENCE EXAMPLE 148

4'-({4-[4-hydroxy-4-(2-hydroxyethyl)cyclohexyl]-5-oxo-7-propyl-4,5-dihydro[1,2,4]triazolo[1,5-a]pyrimidin-6-yl}methyl)biphenyl-2-carbonitrile A mixture of 4'-{[4-(4-hydroxy-4-prop-2-en-1-ylcyclohexyl)-5-oxo-7-propyl-4,5-dihydro[1,2,4]triazolo[1,5-a]pyrimidin-6-yl]methyl}biphenyl-2-carbonitrile (0.26 g), osmium oxide (7% immobilized catalyst, 0.19 g), sodium periodate (0.55 g), acetone (5 mL), acetonitrile (5 mL) and water (5 mL) was stirred at room temperature for 3 hr. The reaction mixture was diluted with ethyl acetate and water, and the insoluble material was filtered off through celite. The obtained organic layer was washed with saturated brine, and dried over anhydrous magnesium sulfate. The solvent was evaporated under reduced pressure. The residue was dissolved in methanol (10 mL), sodium borohydride (0.039 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.093 g, 36%).

¹H NMR (300 MHz, CHLOROFORM-d) δ1.06 (t, J=7.3 Hz, 3H), 1.59-1.77 (m, 6H), 1.98-2.16 (m, 4H), 2.62-2.82 (m, 2H), 2.96-3.08 (m, 2H), 3.93-4.05 (m, 4H), 5.02-5.17 (m, 1H), 7.32-7.52 (m, 6H), 7.57-7.67 (m, 1H), 7.75 (d, J=7.7 Hz, 1H), 7.91 (s, 1H)

REFERENCE EXAMPLE 149

4'-{[4-(1,4-dioxaspiro[4.5]dec-8-yl)-5-oxo-7-propyl-4,5-dihydro[1,2,4]triazolo[1,5-a]pyrimidin-6-yl]methyl}-3'-fluorobiphenyl-2-carbonitrile A mixture of ethyl 2-[(2'-cyano-3-fluorobiphenyl-4-yl)methyl]-3-oxohexanoate (408 g) and N-(1,4-dioxaspiro[4.5]dec-8-yl)-4H-1,2,4-triazol-3-amine (125 g) were dissolved in N,N-diethylaniline (1.5 L) at 160° C. (internal temperature). A solution of 1,8-diazabicyclo[5.4.0]undec-7-ene (38 mL) in N,N-diethylaniline (400 mL) was added dropwise over 30 min, and the mixture was stirred at 180° C. (internal temperature) for 22 hr. The reaction mixture was cooled to room temperature, and ethyl acetate (1 L) and 3M hydrochloric acid (1 L) were added. The mixture was transferred into a separatory funnel with ethyl acetate (2 L) and 3M hydrochlorid acid (1 L). The organic layer was successively washed with 3M hydrochloric acid (2 L) twice and brine (2 L), dried over anhydrous magnesium sulfate, and concentrated under reduced pressure. The obtained residue was purified by silica gel chromatography to give the title compound as a brown solid (246 g, 84%).

¹H NMR (300 MHz, CHLOROFORM-d) δ1.07 (t, J=7.3 Hz, 3H), 1.66-1.93 (m, 8H), 2.90-3.08 (m, 4H), 3.91-4.06 (m, 6H), 5.03-5.20 (m, 1H), 7.21-7.29 (m, 2H), 7.34-7.51 (m, 3H), 7.60-7.68 (m, 1H), 7.71-7.80 (m, 1H), 7.96 (s, 1H)

REFERENCE EXAMPLE 150

3'-fluoro-4'-{[4-(cis-4-hydroxycyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}-3'-fluorobiphenyl-2-carbonitrile (1 g), 6N hydrochloric acid (10 mL) and tetrahydrofuran (15 mL) was stirred at 80° C. for 16 hr. The reaction mixture was diluted with ethyl acetate, washed with saturated brine, and dried over anhydrous magnesium sulfate. The solvent was evaporated under reduced pressure. The obtained residue was dissolved in methanol (10 mL), sodium borohydride (0.11 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.085 g, 9%).

¹H NMR (300 MHz, CHLOROFORM-d) δ1.07 (t, J=7.3 Hz, 3H), 1.54-1.78 (m, 6H), 1.92-2.03 (m, 2H), 2.90-3.09 (m, 4H), 4.03 (s, 2H), 4.07-4.14 (m, 1H), 5.01-5.20 (m, 1H), 7.22-7.29 (m, 2H), 7.33-7.51 (m, 3H), 7.58-7.69 (m, 1H), 7.71-7.80 (m, 1H), 7.95 (s, 1H)

REFERENCE EXAMPLE 151

3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}-3'-fluorobiphenyl-2-carbonitrile (347 g), 3M hydrochloric acid (1.4 L) and tetrahydrofuran (2.1 L) was stirred under reflux for 16 hr. The reaction mixture was cooled to room temperature, and extracted with ethyl acetate (2 L). The resulting aqueous layer was extracted with ethyl acetate (1 L). The combined extracts were successively washed with saturated aqueous sodium hydrogen carbonate (1 L) and brine (1 L), dried over anhydrous magnesium sulfate, and concentrated under reduced pressure. The residue obtained was dissolved in methanol (650 mL) and tetrahydrofuran (960 mL), and the resulting solution was added to a suspension of sodium borohydride (37.3 g) in tetrahydrofuran (1.6 L) with the internal temperature maintained below 10° C. After stirring at the same temperature for 0.5 hr, saturated aqueous ammonium chloride solution (640 mL) was added to the reaction mixture, and the solvent was evaporated under reduced pressure. The resulting residue was extracted with ethyl acetate (2 L). The organic layer was washed with saturated brine (1 L), dried over anhydrous magnesium sulfate, and concentrated under reduced pressure. The resulting residue was purified by silica gel chromatography to give the title compound as a diastereomeric mixture. The diastereomeric mixture obtained was dissolved in ethyl acetate (940 mL) at 50° C. Hexane (1.6 L) was added to the solution, and the resulting mixture was stirred at the same temperature for 2 hr. Additional hexane (940 mL) was added to the mixture, which was cooled to room temperature and stirred for further 0.5 hr. The precipitate was collected by filtration to give the title compound as a white solid (233 g, 73%).

¹H NMR (300 MHz, CHLOROFORM-d) δ1.07 (t, J=7.3 Hz, 3H), 1.41-1.54 (m, 2H), 1.65-1.84 (m, 4H), 2.08-2.17 (m, 2H), 2.64-2.83 (m, 2H), 2.99-3.09 (m, 2H), 3.75-3.87 (m, 1H), 4.02 (s, 2H), 4.99-5.12 (m, 1H), 7.20-7.30 (m, 2H), 7.33-7.51 (m, 3H), 7.59-7.68 (m, 1H), 7.72-7.79 (m, 1H), 7.92 (s, 1H)

REFERENCE EXAMPLE 152 ethyl 4-(4H-1,2,4-triazol-3-ylamino)cyclohexanecarboxylate

To a solution (200 mL) of 1H-1,2,4-triazol-3-amine (11 g) and ethyl 4-oxocyclohexanecarboxylate (28 g) in acetic acid was added sodium cyanoborohydride (35 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. The obtained residue was purified by silica gel column chromatography to give the title compound as a colorless solid (13 g, 40%).

¹H NMR (300 MHz, DMSO-d₆) δ1.12-1.69 (m, 8H), 1.81-2.28 (m, 4H), 3.13-3.49 (m, 1H), 4.05 (q, J=7.1 Hz, 2H), 5.54, 6.39 (br. s., combined 1H), 7.33, 8.01 (br. s, combined 1H), 11.99, 12.72 (br. s., combined 1H)

REFERENCE EXAMPLE 153 ethyl trans-4-{6-[(2'-cyanobiphenyl-4-yl)methyl]-5-oxo-7-propyl[1,2,4]triazolo[1,5-a]pyrimidin-4(5H)-yl}cyclohexanoate A mixture of ethyl 2-[(2'-cyanobiphenyl-4-yl)methyl]-3-oxohexanoate (0.5 g), ethyl 4-(4H-1,2,4-triazol-3-ylamino)

cyclohexanecarboxylate (0.68 g) and N,N-diethylaniline (2.5 mL) was stirred at 180° C. for 16 hr. The obtained reaction mixture was diluted with ethyl acetate, washed 3 times with 1 N hydrochloric acid and saturated brine, and dried over anhydrous magnesium sulfate. The solvent was evaporated under reduced pressure and the residue was purified by silica gel column chromatography to give the title compound as a colorless solid (0.23 g, 31%).
$^1$H NMR (300 MHz, CHLOROFORM-d) δ1.06 (t, J=7.2 Hz, 3H), 1.26 (t, J=7.2 Hz, 3H), 1.59-1.90 (m, 6H), 2.09-2.22 (m, 2H), 2.36-2.50 (m, 1H), 2.62-2.80 (m, 2H), 2.97-3.05 (m, 2H), 4.02 (s, 2H), 4.06-4.19 (m, 2H), 4.98-5.11 (m, 1H), 7.48 (d, J=8.0 Hz, 6H), 7.58-7.67 (m, 1H), 7.74 (d, J=8.0 Hz, 1H), 7.91 (s, 1H)

REFERENCE EXAMPLE 154 trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid A mixture of ethyl trans-4-{6-[(2'-cyanobiphenyl-4-yl)methyl]-5-oxo-7-propyl[1,2,4]triazolo[1,5-a]pyrimidin-4(5H)-yl}cyclohexanoate (13 g), 2 N aqueous sodium hydroxide solution (50 mL), methanol (50 mL) and tetrahydrofuran (50 mL) was stirred at 50° C. for 3 hr. Water (20 mL) and 1 N hydrochloric acid were added to the reaction mixture, and the mixture was adjusted to pH 4, and extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (11 g, 93%).
$^1$H NMR (300 MHz, CHLOROFORM-d) δ1.06 (t, J=7.3 Hz, 3H) 1.57-1.78 (m, 4H) 1.80-1.91 (m, 2H) 2.15-2.27 (m, 2H) 2.51 (t, J=12.2 Hz, 1H) 2.61-2.82 (m, 2H) 2.98-3.07 (m, 2H) 4.02 (s, 2H) 4.99-5.14 (m, 1H) 7.33-7.52 (m, 6H) 7.57-7.66 (m, 1H) 7.75 (d, J=7.5 Hz, 1H) 7.89-7.97 (m, 1H)

REFERENCE EXAMPLE 155

4'-({4-[trans-4-(3-methyl-1,2,4-oxadiazol-5-yl)cyclohexyl]-5-oxo-7-propyl-4,5-dihydro[1,2,4]triazolo[1,5-a]pyrimidin-6-yl}methyl)biphenyl-2-carbonitrile A mixture of trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid (0.5 g) and thionyl chloride (5 mL) was stirred at 80° C. for 16 hr. Toluene (5 mL) was added to the reaction mixture, and the solvent was evaporated under reduced pressure. Toluene (5 mL) was further added to the obtained residue, and the solvent was evaporated under reduced pressure, and the residue was dissolved in pyridine (5 mL), N'-hydroxyethane imidamide (0.22 g) was added, and the mixture was stirred at 80° C. for 12 hr. The reaction mixture was diluted with ethyl acetate, washed with 1 N hydrochloric acid and then with saturated brine, and dried over anhydrous magnesium sulfate. The solvent was evaporated under reduced pressure and the residue was purified by silica gel column chromatography to give the title compound as a colorless solid (0.16 g, 29%).
$^1$H NMR (300 MHz, CHLOROFORM-d) δ1.06 (t, J=7.3 Hz, 3H), 1.65-1.89 (m, 6H) 1.99 (s, 3H) 2.15-2.27 (m, 2H) 2.52-2.80 (m, 3H) 2.97-3.09 (m, 2H) 4.02 (s, 2H) 5.01-5.16 (m, 1H) 7.33-7.51 (m, 6H) 7.58-7.68 (m, 1H) 7.71-7.77 (m, 1H) 7.91 (s, 1H)

REFERENCE EXAMPLE 156

4'-{[4-(3,3-dimethyl-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.5 g), 2,2-dimethylpropane-1,3-diol (0.22 g), p-toluenesulfonic acid monohydrate (0.002 g) and toluene (20 mL) was subjected to an azeotropic dehydration reaction by stirring at 110° C. for 3 hr in a reaction vessel equipped with a Dean-stark trap. The reaction mixture was concentrated, and the obtained residue was purified by silica gel column chromatography to give the title compound as a colorless solid (0.66 g, 100%).
$^1$H NMR (300 MHz, CHLOROFORM-d) δ0.98 (s, 6H) 1.06 (t, J=7.3 Hz, 3H) 1.46-1.78 (m, 6H) 2.38-2.49 (m, 2H) 2.80-2.96 (m, 2H) 2.97-3.06 (m, 2H) 3.54 (s, 2H) 3.58 (s, 2H) 4.02 (s, 2H) 5.04-5.17 (m, 1H) 7.33-7.51 (m, 6H) 7.59-7.66 (m, 1H) 7.74 (d, J=7.7 Hz, 1H) 7.92 (s, 1H)

REFERENCE EXAMPLE 157

2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]ethyl methanesulfonate A mixture of 4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (1.2 g), triethylamine (0.38 mL), methanesulfonyl chloride (0.21 mL), N,N-dimethylpyridin-4-amine (0.028 g) and acetonitrile (20 mL) was stirred at room temperature for 3 hr. The reaction mixture was washed with water and then with saturated brine, and dried over anhydrous magnesium sulfate. The solvent was evaporated under reduced pressure. The obtained residue was purified by silica gel column chromatography to give the title compound as a colorless solid (1.2 g, 89%).
$^1$H NMR (300 MHz, CHLOROFORM-d) δ1.06 (t, J=7.3 Hz, 3H) 1.37-1.52 (m, 2H) 1.65-1.86 (m, 4H) 2.11-2.24 (m, 2H) 2.61-2.82 (m, 2H) 2.97-3.09 (m, 5H) 3.37-3.54 (m, 1H) 3.76 (dd, J=5.4, 3.7 Hz, 2H) 4.01 (s, 2H) 4.37 (dd, J=5.5, 3.8 Hz, 2H) 5.06 (t, J=12.4 Hz, 1H) 7.32-7.52 (m, 6H) 7.58-7.68 (m, 1H) 7.75 (d, J=7.7 Hz, 1H) 7.91 (s, 1H)

REFERENCE EXAMPLE 158

4'-({4-[trans-4-(2-morpholin-4-ylethoxy)cyclohexyl]-5-oxo-7-propyl-4,5-dihydro[1,2,4]triazolo[1,5-a]pyrimidin-6-yl}methyl)biphenyl-2-carbonitrile A mixture of 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]ethyl methanesulfonate (0.3 g), morpholine (0.88 g), sodium iodide (0.015 g) and tetrahydrofuran (10 mL) was stirred at 70° C. for 5 hr. The reaction mixture was concentrated, and the obtained residue was purified by silica gel column chromatography to give the title compound as a colorless solid (0.3 g, 100%).
$^1$H NMR (300 MHz, CHLOROFORM-d) δ1.06 (t, J=7.4 Hz, 3H), 1.37-1.53 (m, 2H), 1.65-1.85 (m, 4H), 2.12-2.22 (m, 2H), 2.48-2.54 (m, 4H), 2.55-2.77 (m, 4H), 2.97-3.07 (m, 2H), 3.34-3.47 (m, 1H), 3.60-3.76 (m, 6H), 4.01 (s, 2H), 4.99-5.14 (m, 1H), 7.32-7.53 (m, 6H), 7.59-7.67 (m, 1H), 7.74 (d, J=7.6 Hz, 1H), 7.91 (s, 1H)

REFERENCE EXAMPLE 159

4'-[(4-{trans-4-[2-(1H-imidazol-1-yl)ethoxy]cyclohexyl}-5-oxo-7-propyl-4,5-dihydro[1,2,4]triazolo[1,5-a]pyrimidin-6-yl)methyl]biphenyl-2-carbonitrile To a mixture of 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]ethyl methanesulfonate (0.3 g), imidazole (0.042 g) and N,N-dimethylformamide (5 mL) was added sodium hydride (0.024 g), and the mixture was stirred at 60° C. for 2 hr. The reaction mixture was diluted with ethyl acetate, washed with water and then with saturated brine, and dried over anhydrous magnesium sulfate. The solvent was evaporated under reduced pressure. The obtained residue was purified by silica gel column chromatography to give the title compound as a colorless solid (0.24 g, 83%).

$^1$H NMR (300 MHz, CHLOROFORM-d) δ1.06 (t, J=7.3 Hz, 3H), 1.33-1.49 (m, 2H), 1.64-1.84 (m, 4H), 2.06-2.16 (m, 2H), 2.59-2.76 (m, 2H), 2.97-3.06 (m, 2H), 3.30-3.42 (m, 1H), 3.73 (t, J=5.2 Hz, 2H), 4.01 (s, 2H), 4.05-4.11 (m, 2H), 4.97-5.12 (m, 1H), 7.02 (d, J=19.4 Hz, 2H), 7.32-7.56 (m, 7H), 7.58-7.66 (m, 1H), 7.75 (dd, J=7.7, 0.9 Hz, 1H), 7.90 (s, 1H)

REFERENCE EXAMPLE 160 trans-N'-acetyl-4-{6-[(2'-cyanobiphenyl-4-yl)methyl]-5-oxo-7-propyl[1,2,4]triazolo[1,5-a]pyrimidin-4(5H)-yl}cyclohexanecarbohydrazide A mixture of trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid (0.5 g), acetohydrazide (0.09 g), 1-hydroxybenzotriazole (0.19 g), 1-ethyl-3-(3-dimethylaminopropyl)carbodiimide hydrochloride (0.23 g) and N,N-dimethylformamide (10 mL) was stirred at room temperature for 16 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.4 g, 72%).

$^1$H NMR (300 MHz, DMSO-d$_6$) δ0.95 (t, J=7.3 Hz, 3H), 1.41-1.95 (m, 11H), 2.20-2.34 (m, 1H), 2.52-2.67 (m, 2H), 2.91-3.02 (m, 2H), 4.00 (s, 2H), 4.83-4.99 (m, 1H), 7.36-7.44 (m, 2H), 7.45-7.62 (m, 4H), 7.73-7.82 (m, 1H), 7.93 (d, J=8.1 Hz, 1H), 8.20 (s, 1H), 9.65-9.74 (m, 2H)

REFERENCE EXAMPLE 161

4'-({4-[trans-4-(5-methyl-1,3,4-oxadiazol-2-yl)cyclohexyl]-5-oxo-7-propyl-4,5-dihydro[1,2,4]triazolo[1,5-a]pyrimidin-6-yl}methyl)biphenyl-2-carbonitrile A mixture of trans-N'-acetyl-4-{6-[(2'-cyanobiphenyl-4-yl)methyl]-5-oxo-7-propyl[1,2,4]triazolo[1,5-a]pyrimidin-4(5H)-yl}cyclohexanecarbohydrazide (0.4 g), p-toluenesulfonyl chloride (0.42 g) and pyridine (10 mL) was stirred at 110° C. for 5 hr. The reaction mixture was diluted with ethyl acetate, washed with 1 N hydrochloric acid and then with saturated brine, and dried over anhydrous magnesium sulfate. The solvent was evaporated under reduced pressure and the residue was purified by silica gel column chromatography to give the title compound as a colorless solid (0.33 g, 85%).

$^1$H NMR (300 MHz, CHLOROFORM-d) δ1.07 (t, J=7.3 Hz, 3H), 1.67-1.97 (m, 6H), 2.32 (d, J=15.3 Hz, 2H), 2.51 (s, 3H), 2.73-2.92 (m, 2H), 2.96-3.08 (m, 3H), 4.02 (s, 2H), 5.05-5.24 (m, 1H), 7.33-7.52 (m, 6H), 7.58-7.66 (m, 1H), 7.75 (d, J=7.7 Hz, 1H), 7.92 (s, 1H)

REFERENCE EXAMPLE 162

4'-({4-[trans-4-(hydroxymethyl)cyclohexyl]-5-oxo-7-propyl-4,5-dihydro[1,2,4]triazolo[1,5-a]pyrimidin-6-yl}methyl)biphenyl-2-carbonitrile To a mixture of trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid (7 g), N-methylmorpholine (1.9 mL) and tetrahydrofuran (100 mL) was added ethyl chlorocarbonate (1.6 mL) at 0° C., and the mixture was stirred at the same temperature for 2 hr. The reaction mixture was cooled to −15° C., sodium borohydride (1.6 g) and methanol (25 mL) were added, and the mixture was allowed to gradually warm to room temperature. Saturated aqueous ammonium chloride solution was added to the reaction mixture, and the mixture was extracted with ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless solid (5.3 g, 78%).

$^1$H NMR (300 MHz, CHLOROFORM-d) δ1.06 (t, J=7.3 Hz, 3H), 1.11-1.26 (m, 2H), 1.34 (br. s., 1H), 1.64-1.87 (m, 5H), 1.92-2.02 (m, 2H), 2.60-2.75 (m, 2H), 2.98-3.07 (m, 2H), 3.51 (d, J=6.4 Hz, 2H), 4.02 (s, 2H), 4.96-5.09 (m, 1H), 7.33-7.51 (m, 6H), 7.59-7.67 (m, 1H), 7.75 (d, J=7.7 Hz, 1H), 7.92 (s, 1H)

REFERENCE EXAMPLE 163

4'-{[4-(trans-4-formylcyclohexyl)-5-oxo-7-propyl-4,5-dihydro[1,2,4]triazolo[1,5-a]pyrimidin-6-yl]methyl}biphenyl-2-carbonitrile To a mixture of 4'-({4-[trans-4-(hydroxymethyl)cyclohexyl]-5-oxo-7-propyl-4,5-dihydro[1,2,4]triazolo[1,5-a]pyrimidin-6-yl}methyl)biphenyl-2-carbonitrile (5.3 g), triethylamine (7.7 mL) and dimethyl sulfoxide (25 mL) was added a solution (40 mL) of sulfur trioxide-pyridine complex (5.3 g) in dimethyl sulfoxide at room temperature, and the mixture was stirred for 2 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (5 g, 95%).

$^1$H NMR (300 MHz, CHLOROFORM-d) δ1.06 (t, J=7.4 Hz, 3H), 1.40-1.54 (m, 2H), 1.66-1.81 (m, 2H), 1.84-1.94 (m, 2H), 2.13-2.26 (m, 2H), 2.33-2.47 (m, 1H), 2.61-2.83 (m, 2H), 2.98-3.08 (m, 2H), 4.02 (s, 2H), 4.95-5.11 (m, 1H), 7.33-7.51 (m, 6H), 7.58-7.67 (m, 1H), 7.75 (d, J=7.2 Hz, 1H), 7.91 (s, 1H), 9.67 (s, 1H)

REFERENCE EXAMPLE 164

4'-[(4-{trans-4-[hydroxy(4-methoxyphenyl)methyl]cyclohexyl}-5-oxo-7-propyl-4,5-dihydro[1,2,4]triazolo[1,5-a]pyrimidin-6-yl)methyl]biphenyl-2-carbonitrile 4'-{[4-(trans-4-Formylcyclohexyl)-5-oxo-7-propyl-4,5-dihydro[1,2,4]triazolo[1,5-a]pyrimidin-6-yl]methyl}biphenyl-2-carbonitrile (2.6 g) was dissolved in tetrahydrofuran (50 mL), and bromo(4-methoxyphenyl) magnesium (0.5M tetrahydrofuran solution, 16 mL) was added at −78° C. The reaction mixture was stirred at −78° C. for 2 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (2.2 g, 70%).

$^1$H NMR (300 MHz, CHLOROFORM-d) δ1.05 (t, J=7.4 Hz, 3H), 1.47-1.89 (m, 8H), 2.18-2.30 (m, 1H), 2.47-2.78 (m, 3H), 2.96-3.05 (m, 2H), 3.81 (s, 3H), 4.00 (s, 2H), 4.34 (d, J=7.3 Hz, 1H), 4.92-5.08 (m, 1H), 6.84-6.92 (m, 2H), 7.21-7.27 (m, 2H), 7.31-7.51 (m, 6H), 7.58-7.67 (m, 1H), 7.70-7.76 (m, 1H), 7.88-7.92 (m, 1H)

REFERENCE EXAMPLE 165

4'-[(4-{trans-4-[(4-methoxyphenyl)carbonyl]cyclohexyl}-5-oxo-7-propyl-4,5-dihydro[1,2,4]triazolo[1,5-a]pyrimidin-6-yl)methyl]biphenyl-2-carbonitrile To a mixture of 4'-[(4-{trans-4-[hydroxy(4-methoxyphenyl)methyl]cyclohexyl}-5-oxo-7-propyl-4,5-dihydro[1,2,4]triazolo[1,5-a]pyrimidin-6-yl)methyl]biphenyl-2-carbonitrile (2.2 g), triethylamine (2.6 mL) and dimethyl sulfoxide (10 mL) was added a solution (10 mL) of sulfur trioxide-pyridine complex (1.8 g) in dimethyl sulfoxide at room temperature, and the mixture was stirred for 2 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (1.7 g, 77%).

$^1$H NMR (300 MHz, CHLOROFORM-d) δ1.07 (t, J=7.3 Hz, 3H), 1.67-1.95 (m, 6H), 2.01-2.12 (m, 2H), 2.72-2.91 (m, 2H), 2.97-3.10 (m, 2H), 3.33-3.47 (m, 1H), 3.88 (s, 3H), 4.03 (s, 2H), 5.05-5.20 (m, 1H), 6.95 (d, J=8.9 Hz, 2H), 7.35-7.53 (m, 6H), 7.58-7.68 (m, 1H), 7.74 (d, J=7.7 Hz, 1H), 7.92-8.02 (m, 3H)

REFERENCE EXAMPLE 166 trans-4-{6-[(2'-cyanobiphenyl-4-yl)methyl]-5-oxo-7-propyl[1,2,4]triazolo[1,5-a]pyrimidin-4(5H)-yl}cyclohexanecarboxamide A mixture of trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid (0.5 g), 1-hydroxybenzotriazole ammonium salt (0.21 g), 1-ethyl-3-(3-dimethylaminopropyl)carbodiimide hydrochloride (0.23 g) and N,N-dimethylformamide (10 mL) was stirred at room temperature for 16 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.36 g, 67%).

$^1$H NMR (300 MHz, DMSO-d$_6$) δ0.95 (t, J=7.3 Hz, 3H) 1.37-1.64 (m, 4H) 1.67-1.77 (m, 2H) 1.82-1.94 (m, 2H) 2.10-2.24 (m, 1H) 2.51-2.63 (m, 2H) 2.92-3.01 (m, 2H) 4.00 (s, 2H) 4.82-4.98 (m, 1H) 6.74 (br. s., 1H) 7.25 (br. s., 1H) 7.37-7.43 (m, 2H) 7.46-7.52 (m, 2H) 7.53-7.63 (m, 2H) 7.72-7.81 (m, 1H) 7.93 (d, J=7.7 Hz, 1H) 8.19 (s, 1H)

REFERENCE EXAMPLE 167

4'-{[4-(2,2-dimethyl-1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.5 g), 2-methylpropane-1,2-diol (0.15 g), p-toluenesulfonic acid monohydrate (0.02 g) and toluene (15 mL) was subjected to an azeotropic dehydration reaction by stirring at 110° C. for 16 hr in a reaction vessel equipped with a Dean-stark trap. The reaction mixture was concentrated under reduced pressure, and the obtained residue was purified by silica gel column chromatography to give the title compound as a colorless solid (0.66 g, 100%).

$^1$H NMR (300 MHz, CHLOROFORM-d) δ1.06 (t, J=7.4 Hz, 3H), 1.33 (d, J=7.7 Hz, 6H), 1.66-1.83 (m, 6H), 1.86-1.98 (m, 2H), 2.87-3.08 (m, 4H), 3.71-3.82 (m, 2H), 4.02 (s, 2H), 4.98-5.22 (m, 1H), 7.34-7.51 (m, 6H), 7.58-7.66 (m, 1H), 7.74 (d, J=7.7 Hz, 1H), 7.95 (s, 1H)

REFERENCE EXAMPLE 168

4'-{[4-(trans-4-{2-[(2R,6S)-2,6-dimethylmorpholin-4-yl]ethoxy}cyclohexyl)-5-oxo-7-propyl-4,5-dihydro[1,2,4]triazolo[1,5-a]pyrimidin-6-yl]methyl}biphenyl-2-carbonitrile A mixture of 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]ethyl methanesulfonate (0.3 g), cis-2,6-dimethylmorpholine (1.2 g), sodium iodide (0.015 g) and tetrahydrofuran (10 mL) was stirred at 70° C. for 5 hr. The reaction mixture was concentrated, and the obtained residue was purified by silica gel column chromatography to give the title compound as a colorless solid (0.3 g, 96%).

$^1$H NMR (300 MHz, CHLOROFORM-d) δ1.06 (t, J=7.3 Hz, 3H), 1.14 (d, J=6.2 Hz, 6H), 1.35-1.52 (m, 2H), 1.67-1.85 (m, 6H), 2.11-2.22 (m, 2H), 2.56 (t, J=6.0 Hz, 2H), 2.61-2.81 (m, 4H), 2.98-3.06 (m, 2H), 3.35-3.47 (m, 1H), 3.59-3.75 (m, 4H), 4.01 (s, 2H), 5.00-5.13 (m, 1H), 7.33-7.51 (m, 6H), 7.58-7.66 (m, 1H), 7.74 (d, J=7.7 Hz, 1H), 7.91 (s, 1H)

REFERENCE EXAMPLE 169

4'-{[5-oxo-7-propyl-4-(2,2,3,3-tetramethyl-1,4-dioxaspiro[4.5]dec-8-yl)-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.5 g), 2,3-dimethylbutane-2,3-diol (0.57 g), p-toluenesulfonic acid monohydrate (0.061 g) and toluene (30 mL) was subjected to an azeotropic dehydration reaction by stirring at 110° C. for 16 hr in a reaction vessel equipped with a Dean-stark trap. The reaction mixture was concentrated under reduced pressure, and the obtained residue was purified by silica gel column chromatography to give the title compound as a colorless solid (0.85 g, 47%).

$^1$H NMR (300 MHz, CHLOROFORM-d) δ1.06 (t, J=7.3 Hz, 3H), 1.24 (s, 6H), 1.27 (s, 6H), 1.65-1.83 (m, 6H), 1.91-

2.00 (m, 2H), 2.86-3.06 (m, 4H), 4.02 (s, 2H), 4.97-5.10 (m, 1H), 7.33-7.52 (m, 6H), 7.58-7.66 (m, 1H), 7.74 (d, J=7.7 Hz, 1H), 7.95 (s, 1H)

REFERENCE EXAMPLE 170

4'-({4-[cis-4-(2-hydroxyethoxy)-4-methylcyclohexyl]-5-oxo-7-propyl-4,5-dihydro[1,2,4]triazolo[1,5-a]pyrimidin-6-yl}methyl)biphenyl-2-carbonitrile To a solution (15 mL) of 4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (1 g) in methylene chloride was added trimethylaluminum (1.4M hexane solution, 11 mL) at 0° C., and the mixture was stirred at 40° C. for 40 hr. Methanol (1 mL) was gradually added to the reaction mixture, the mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.36 g, 35%).

$^1$H NMR (300 MHz, CHLOROFORM-d) δ1.06 (t, J=7.2 Hz, 3H), 1.20 (s, 3H), 1.37-1.56 (m, 4H), 1.67-1.78 (m, 2H), 1.94-2.03 (m, 2H), 2.91-3.06 (m, 4H), 3.46-3.51 (m, 2H), 3.78-3.85 (m, 2H), 4.02 (s, 2H), 4.43 (br. s., 1H), 5.13-5.26 (m, 1H), 7.34-7.51 (m, 6H), 7.59-7.66 (m, 1H), 7.75 (d, J=8.0 Hz, 1H), 7.94 (s, 1H)

REFERENCE EXAMPLE 171

4'-({4-[trans-4-(2-hydroxyethoxy)-4-methylcyclohexyl]-5-oxo-7-propyl-4,5-dihydro[1,2,4]triazolo[1,5-a]pyrimidin-6-yl}methyl)biphenyl-2-carbonitrile To a solution (15 mL) of 4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (1 g) in methylene chloride was added trimethylaluminum (1.4M hexane solution, 11 mL) at 0° C., and the mixture was stirred at 40° C. for 40 hr. Methanol (1 mL) was gradually added to the reaction mixture, the mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.44 g, 43%).

$^1$H NMR (300 MHz, CHLOROFORM-d) δ1.06 (t, J=7.4 Hz, 3H), 1.44 (s, 3H), 1.64-1.77 (m, 6H), 1.83-1.93 (m, 2H), 2.06-2.13 (m, 1H), 2.71-2.89 (m, 2H), 2.95-3.06 (m, 2H), 3.50-3.58 (m, 2H), 3.66-3.73 (m, 2H), 4.02 (s, 2H), 4.99-5.16 (m, 1H), 7.33-7.51 (m, 6H), 7.58-7.67 (m, 1H), 7.74 (d, J=8.0 Hz, 1H), 7.92 (s, 1H)

REFERENCE EXAMPLE 172 ethyl 5-(trans-4-{6-[(2'-cyanobiphenyl-4-yl)methyl]-5-oxo-7-propyl[1,2,4]triazolo[1,5-a]pyrimidin-4(5H)-yl}cyclohexyl)-1,3-oxazole-4-carboxylate To a mixture of trans-4-{6-[(2'-cyanobiphenyl-4-yl)methyl]-5-oxo-7-propyl[1,2,4]triazolo[1,5-a]pyrimidin-4(5H)-yl}cyclohexanecarboxylic acid (1.2 g), oxalyl chloride (0.25 mL) and tetrahydrofuran (15 mL) was added N,N-dimethylformamide (1 drop), and the mixture was stirred at room temperature for 3 hr. The reaction mixture was concentrated, the obtained residue was dissolved in tetrahydrofuran (5 mL), and the solution was added to potassium tert-butoxide (0.54 g), ethyl isocyanoacetate (0.54 g) and tetrahydrofuran (5 mL) stirred at 0° C. for 30 min in advance at 0° C. The reaction mixture was stirred at 0° C. for 1 hr, and the mixture was extracted with 1 N hydrochloric acid and ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (1.3 g, 91%).

$^1$H NMR (300 MHz, CHLOROFORM-d) δ1.07 (t, J=7.4 Hz, 3H), 1.42 (t, J=7.2 Hz, 3H), 1.70-1.93 (m, 6H), 2.05-2.15 (m, 2H), 2.78-2.95 (m, 2H), 3.00-3.08 (m, 2H), 3.61-3.73 (m, 1H), 4.03 (s, 2H), 4.41 (q, J=7.2 Hz, 2H), 5.09-5.21 (m, 1H), 7.34-7.52 (m, 6H), 7.58-7.67 (m, 1H), 7.72-7.78 (m, 2H), 7.92 (s, 1H)

REFERENCE EXAMPLE 173

5-(trans-4-{6-[(2'-cyanobiphenyl-4-yl)methyl]-5-oxo-7-propyl[1,2,4]triazolo[1,5-a]pyrimidin-4(5H)-yl}cyclohexyl)-1,3-oxazole-4-carboxylic acid A mixture of ethyl 5-(trans-4-{6-[(2'-cyanobiphenyl-4-yl)methyl]-5-oxo-7-propyl[1,2,4]triazolo[1,5-a]pyrimidin-4(5H)-yl}cyclohexyl)-1,3-oxazole-4-carboxylate (1.3 g), 1N aqueous sodium hydroxide solution (10 mL), tetrahydrofuran (10 mL) and methanol (10 mL) was stirred at 50° C. for 16 hr. 1N Aqueous hydrochloric acid solution was added to the reaction mixture, and the mixture was extracted with ethyl acetate. The obtained ethyl acetate layer was washed with saturated brine, and dried over anhydrous magnesium sulfate. The solvent was evaporated under reduced pressure to give the title compound as a colorless solid (0.94 g, 76%).

$^1$H NMR (300 MHz, DMSO-d$_6$) δ0.96 (t, J=7.3 Hz, 3H), 1.53-1.88 (m, 6H), 1.94-2.05 (m, 2H), 2.60-2.78 (m, 2H), 2.92-3.05 (m, 2H), 3.51 (t, J=12.3 Hz, 1H), 4.02 (s, 2H), 4.97-5.12 (m, 1H), 7.40-7.45 (m, 2H), 7.46-7.62 (m, 4H), 7.73-7.82 (m, 1H), 7.93 (d, J=7.7 Hz, 1H), 8.22 (s, 1H), 8.34 (s, 1H), 13.05 (br. s., 1H)

REFERENCE EXAMPLE 174

4'-({4-[trans-4-(1,3-oxazol-5-yl)cyclohexyl]-5-oxo-7-propyl-4,5-dihydro[1,2,4]triazolo[1,5-a]pyrimidin-6-yl}methyl)biphenyl-2-carbonitrile A mixture of 5-(trans-4-{6-[(2'-cyanobiphenyl-4-yl)methyl]-5-oxo-7-propyl[1,2,4]triazolo[1,5-a]pyrimidin-4(5H)-yl}cyclohexyl)-1,3-oxazole-4-carboxylic acid (0.94 g), copper(II) oxide (0.005 g) and quinoline (5 mL) was stirred at 180° C. for 16 hr. 1 N Hydrochloric acid and ethyl acetate were added to the reaction mixture, and the insoluble material was filtered off through celite. The obtained organic layer was washed with saturated brine, and dried over anhydrous magnesium sulfate. The solvent was evaporated under reduced pressure to give the title compound as a colorless solid (0.65 g, 75%).

$^1$H NMR (300 MHz, CHLOROFORM-d) δ1.07 (t, J=7.3 Hz, 3H), 1.53-1.93 (m, 6H), 2.18-2.28 (m, 2H), 2.72-2.90 (m, 3H), 2.97-3.09 (m, 2H), 4.03 (s, 2H), 5.05-5.20 (m, 1H), 6.77 (s, 1H), 7.33-7.52 (m, 6H), 7.59-7.68 (m, 1H), 7.72-7.79 (m, 2H), 7.92 (s, 1H)

REFERENCE EXAMPLE 175

4'-{[4-(1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.5 g), propane-1,3-diol (0.12 g), p-toluenesulfonic acid monohydrate (0.01 g) and toluene (15 mL) was subjected to an azeotropic dehydration reaction by stirring at 110° C. for 16 hr in a reaction vessel equipped with a Dean-stark trap. The reaction mixture was concentrated, and the obtained residue was purified by silica gel column chromatography to give the title compound as a colorless solid (0.56 g, 100%).
$^1$H NMR (300 MHz, CHLOROFORM-d) δ1.07 (t, J=7.4 Hz, 3H), 1.44-1.79 (m, 8H), 2.40-2.50 (m, 2H), 2.79-2.95 (m, 2H), 2.97-3.06 (m, 2H), 3.91-4.03 (m, 6H), 5.02-5.17 (m, 1H), 7.33-7.52 (m, 6H), 7.58-7.66 (m, 1H), 7.75 (dd, J=7.6, 0.8 Hz, 1H), 7.92 (s, 1H)

REFERENCE EXAMPLE 176

4'-({4-[trans-4-(3-hydroxypropoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-{[4-(1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile (0.56 g), sodium cyanoborohydride (0.2 g), boron trifluoride-diethyl ether complex (0.4 mL) and tetrahydrofuran (15 mL) was stirred at 50° C. for 6 hr. The reaction mixture was diluted with ethyl acetate, washed with water and then with saturated brine, and dried over anhydrous magnesium sulfate. The solvent was evaporated under reduced pressure and the residue was purified by silica gel column chromatography to give the title compound as a colorless solid (0.28 g, 33%).
$^1$H NMR (300 MHz, CHLOROFORM-d) δ1.06 (t, J=7.4 Hz, 3H), 1.35-1.51 (m, 2H), 1.66-1.88 (m, 6H), 2.14-2.24 (m, 2H), 2.41-2.48 (m, 1H), 2.63-2.78 (m, 2H), 2.98-3.07 (m, 2H), 3.36-3.51 (m, 1H), 3.70 (t, J=5.7 Hz, 2H), 3.74-3.83 (m, 2H), 4.01 (s, 2H), 5.00-5.13 (m, 1H), 7.32-7.52 (m, 6H), 7.59-7.67 (m, 1H), 7.75 (dd, J=7.7, 1.1 Hz, 1H), 7.91 (s, 1H)

REFERENCE EXAMPLE 177 ethyl trans-4-{6-[(2'-cyanobiphenyl-4-yl)methyl]-5-oxo-7-propyl[1,2,4]triazolo[1,5-a]pyrimidin-4(5H)-yl}-1-methylcyclohexanecarboxylate To a solution (20 mL) of ethyl trans-4-{6-[(2'-cyanobiphenyl-4-yl)methyl]-5-oxo-7-propyl[1,2,4]triazolo[1,5-a]pyrimidin-4(5H)-yl}cyclohexanoate (1.9 g) in tetrahydrofuran was added potassium hexamethyldisilazide (1.1 M tetrahydrofuran solution, 3.9 mL) at −78° C., and the mixture was stirred at the same temperature for 1 hr. Methyl iodide (0.33 mL) was added to the reaction mixture, and the mixture was warmed to room temperature and stirred for 16 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was dissolved in tetrahydrofuran (20 mL), potassium hexamethyldisilazide (1.1 M tetrahydrofuran solution, 3.9 mL) was added at −78° C., and the mixture was stirred at the same temperature for 1 hr. Methyl iodide (0.33 mL) was added to the reaction mixture, and the mixture was warmed to room temperature and stirred for 16 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.58 g, 30%).
$^1$H NMR (300 MHz, CHLOROFORM-d) δ1.05 (t, J=7.4 Hz, 3H) 1.20 (s, 3H) 1.34 (t, J=7.1 Hz, 3H) 1.57-1.76 (m, 6H) 2.30-2.41 (m, 2H) 2.66-2.84 (m, 2H) 2.96-3.04 (m, 2H) 4.01 (s, 2H) 4.28 (q, J=7.0 Hz, 2H) 4.97-5.11 (m, 1H) 7.33-7.51 (m, 6H) 7.59-7.66 (m, 1H) 7.75 (dd, J=7.7, 0.9 Hz, 1H) 7.85 (s, 1H)

REFERENCE EXAMPLE 178

4'-({4-[trans-4-(hydroxymethyl)-4-methylcyclohexyl]-5-oxo-7-propyl-4,5-dihydro[1,2,4]triazolo[1,5-a]pyrimidin-6-yl}methyl)biphenyl-2-carbonitrile To a solution (15 mL) of ethyl trans-4-{6-[(2'-cyanobiphenyl-4-yl)methyl]-5-oxo-7-propyl[1,2,4]triazolo[1,5-a]pyrimidin-4(5H)-yl}-1-methylcyclohexanecarboxylate (0.56 g) in tetrahydrofuran was added diisobutylaluminium hydride (1.0 M hexane solution, 10 mL) at −78° C., and the mixture was stirred at the same temperature for 6 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.22 g, 43%).
$^1$H NMR (300 MHz, CHLOROFORM-d) δ0.98 (s, 3H), 1.06 (t, J=7.3 Hz, 3H), 1.29-1.42 (m, 2H), 1.50-1.83 (m, 6H), 2.66-2.85 (m, 2H), 2.97-3.06 (m, 2H), 3.78 (s, 2H), 3.99-4.05 (m, 2H), 4.96-5.11 (m, 1H), 7.34-7.52 (m, 6H), 7.58-7.67 (m, 1H), 7.71-7.78 (m, 1H), 7.91 (s, 1H)

REFERENCE EXAMPLE 179

4'-({4-[(3R,6R)-1-oxaspiro[2.5]oct-6-yl]-5-oxo-7-propyl-4,5-dihydro[1,2,4]triazolo[1,5-a]pyrimidin-6-yl}methyl)biphenyl-2-carbonitrile To a mixture of trimethylsulfoxonium iodide (0.57 g) and dimethyl sulfoxide (10 mL) was added sodium hydride, and the mixture was stirred at room temperature for 30 min. A solution of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1 g) in dimethyl sulfoxide (5 mL) was added to the reaction mixture, and the mixture was further stirred at room temperature for 3 hr. The reaction mixture was extracted with water and ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.72 g, 70%).
$^1$H NMR (300 MHz, CHLOROFORM-d) δ1.07 (t, J=7.4 Hz, 3H) 1.37-1.46 (m, 2H) 1.67-1.84 (m, 4H) 2.07-2.19 (m, 2H) 2.71 (s, 2H) 2.97-3.14 (m, 4H) 4.03 (s, 2H) 5.11-5.26 (m, 1H) 7.33-7.51 (m, 6H) 7.58-7.68 (m, 1H) 7.74 (d, J=7.9 Hz, 1H) 7.93 (s, 1H)

REFERENCE EXAMPLE 180

4'-({4-[cis-4-hydroxy-4-(morpholin-4-ylmethyl)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[(3R,6R)-1-oxaspiro[2.5]oct-6-yl]-5-oxo-7-propyl-4,5-dihydro[1,2,4]triazolo[1,5-a]pyrimidin-6-yl}methyl)biphenyl-2-carbonitrile (0.72 g), morpholine (3.9 g) and tetrahydrofuran (10 mL) was stirred at 70° C. for 48 hr. The reaction mixture was concentrated and the obtained residue was purified by silica gel column chromatography to give the title compound as a colorless solid (0.56 g, 65%).
$^1$H NMR (300 MHz, CHLOROFORM-d) δ1.06 (t, J=7.3 Hz, 3H), 1.39-1.83 (m, 8H), 2.35 (s, 2H), 2.59-2.68 (m, 4H), 2.98-3.28 (m, 4H), 3.67-3.75 (m, 4H), 4.02 (s, 2H), 4.98-5.15 (m, 1H), 7.33-7.51 (m, 6H), 7.58-7.67 (m, 1H), 7.70-7.78 (m, 1H), 7.95 (s, 1H)

REFERENCE EXAMPLE 181 ethyl(4-{6-[(2'-cyanobiphenyl-4-yl)methyl]-5-oxo-7-propyl[1,2,4]triazolo[1,5-a]pyrimidin-4(5H)-yl}cyclohexylidene)acetate To a solution (10 mL) of ethyl(diethoxyphosphoryl)acetate (1.2 g) in tetrahydrofuran was added sodium hydride (0.21 g), and the mixture was stirred at room temperature for 1 hr. A solution (10 mL) of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (2 g) in tetrahydrofuran was added to the reaction mixture, and the mixture was stirred at room temperature for 3 hr. The reaction mixture was extracted with 1 N hydrochloric acid and ethyl acetate, and the obtained ethyl acetate layer was washed with saturated brine, and dried over anhydrous magnesium sulfate. The solvent was evaporated under reduced pressure and the residue was purified by silica gel column chromatography to give the title compound as a colorless solid (1.9 g, 86%). $^1$H NMR (300 MHz, CHLOROFORM-d) δ1.06 (t, J=7.4 Hz, 3H), 1.28 (t, J=7.2 Hz, 3H), 1.66-1.80 (m, 2H), 1.87-1.98 (m, 2H), 1.99-2.12 (m, 2H), 2.33-2.51 (m, 2H), 2.65-2.89 (m, 2H), 2.98-3.08 (m, 2H), 4.02 (s, 2H), 4.07-4.19 (m, 2H), 5.23-5.38 (m, 1H), 5.71 (s, 1H), 7.35-7.52 (m, 6H), 7.58-7.67 (m, 1H), 7.75 (d, J=7.6 Hz, 1H), 7.90 (s, 1H)

REFERENCE EXAMPLE 182

4'-({4-[4-(2-hydroxyethylidene)cyclohexyl]-5-oxo-7-propyl-4,5-dihydro[1,2,4]triazolo[1,5-a]pyrimidin-6-yl}methyl)biphenyl-2-carbonitrile A mixture of calcium chloride (1.6 g), sodium borohydride (1.1 g), tetrahydrofuran (40 mL) and ethanol (40 mL) was stirred at 0° C. for 1 hr. A solution (20 mL) of ethyl(4-{6-[(2'-cyanobiphenyl-4-yl)methyl]-5-oxo-7-propyl[1,2,4]triazolo[1,5-a]pyrimidin-4(5H)-yl}cyclohexylidene)acetate (1.9 g) in tetrahydrofuran was added to the reaction mixture, and the mixture was stirred at room temperature for 16 hr. The reaction mixture was extracted with 1 N hydrochloric acid and ethyl acetate, and the obtained ethyl acetate layer was washed with saturated brine, and dried over anhydrous magnesium sulfate. The solvent was evaporated under reduced pressure and the residue was purified by silica gel column chromatography to give the title compound as a colorless solid (0.9 g, 49%).
$^1$H NMR (300 MHz, CHLOROFORM-d) δ1.06 (t, J=7.4 Hz, 3H), 1.64-1.79 (m, 2H), 1.82-2.00 (m, 3H), 2.22-2.44 (m, 2H), 2.59-2.86 (m, 3H), 2.99-3.07 (m, 2H), 3.73 (br. s., 1H), 4.02 (s, 2H), 4.14-4.22 (m, 2H), 5.18-5.30 (m, 1H), 5.45-5.53 (m, 1H), 7.34-7.51 (m, 6H), 7.58-7.67 (m, 1H), 7.75 (d, J=7.7 Hz, 1H), 7.91 (s, 1H)

REFERENCE EXAMPLE 183

4'-({4-[4-hydroxy-4-(trifluoromethyl)cyclohexyl]-5-oxo-7-propyl-4,5-dihydro[1,2,4]triazolo[1,5-a]pyrimidin-6-yl}methyl)biphenyl-2-carbonitrile To a solution (10 mL) of 1H-1,2,4-triazol-3-amine (0.39 g) and 4-hydroxy-4-(trifluoromethyl)cyclohexanone (1 g) in acetic acid was added sodium cyanoborohydride (1.5 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. A mixture of the residue obtained by purification by silica gel column chromatography and ethyl 2-[(2'-cyanobiphenyl-4-yl)methyl]-3-oxohexanoate (2.5 g) was stirred at 250° C. for 30 min under microwave irradiation. The obtained reaction mixture was purified by silica gel column chromatography to give the title compound as a colorless solid (0.28 g, 11%).
$^1$H NMR (300 MHz, CHLOROFORM-d) δ1.07 (t, J=7.2 Hz, 3H), 1.68-2.07 (m, 8H), 3.04 (dd, 4H), 4.02 (s, 2H), 5.03-5.20 (m, 1H), 7.34-7.52 (m, 6H), 7.59-7.68 (m, 1H), 7.75 (d, J=7.7 Hz, 1H), 7.94 (s, 1H)

REFERENCE EXAMPLE 184

4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile A mixture of ethyl 2-[(2'-cyanobiphenyl-4-yl)methyl]-3-oxohexanoate (44 g), N-(1,4-dioxaspiro[4.5]dec-8-yl)-5-methyl-4H-1,2,4-triazol-3-amine (15 g) and N,N-diethylaniline (100 mL) was stirred at 200° C. for 48 hr. The obtained reaction mixture was diluted with ethyl acetate, washed 3 times with 1 N hydrochloric acid and saturated brine, and dried over anhydrous magnesium sulfate. The solvent was evaporated under reduced pressure and the residue was purified by silica gel column chromatography to give the title compound as a colorless solid (12 g, 36%).
$^1$H NMR (300 MHz, CHLOROFORM-d) δ1.04 (t, J=7.3 Hz, 3H), 1.66-1.94 (m, 8H), 2.45 (s, 3H), 2.88-3.02 (m, 4H), 3.93-4.06 (m, 6H), 4.98-5.11 (m, 1H), 7.32-7.51 (m, 6H), 7.58-7.65 (m, 1H), 7.74 (dd, J=7.7, 0.9 Hz, 1H)

REFERENCE EXAMPLE 185

4'-({4-[trans-4-(2-hydroxyethoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile To a solution (30 mL) of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile (3 g) in methylene chloride was added trimethylaluminum (1.4M hexane solution, 33 mL) at 0° C., and the mixture was stirred at 40° C. for 72 hr. Methanol (3 mL) was gradually added to the reaction mixture, the mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure and the residue was purified by silica gel column chromatography to give the title compound as a colorless solid (0.75 g, 24%).

$^1$H NMR (300 MHz, CHLOROFORM-d) δ1.04 (t, J=7.2 Hz, 3H), 1.45 (s, 3H), 1.63-1.76 (m, 6H), 1.81-1.92 (m, 2H), 2.11 (t, J=6.2 Hz, 1H), 2.44 (s, 3H), 2.71-2.89 (m, 2H), 2.92-3.01 (m, 2H), 3.51-3.57 (m, 2H), 3.65-3.73 (m, 2H), 3.99 (s, 2H), 4.93-5.08 (m, 1H), 7.31-7.51 (m, 6H), 7.57-7.66 (m, 1H), 7.74 (d, J=8.0 Hz, 1H)

REFERENCE EXAMPLE 186

4'-({4-[trans-4-(2-hydroxypropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxyethoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.75 g), triethylamine (0.97 mL) and dimethyl sulfoxide (5 mL) was added a solution (5 mL) of sulfur trioxide-pyridine complex (0.66 g) in dimethyl sulfoxide at room temperature, and the mixture was stirred for 2 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The residue obtained by purification by silica gel column chromatography was dissolved in tetrahydrofuran (15 mL), methylmagnesium bromide (1.0 M tetrahydrofuran solution, 4.2 mL) was added at room temperature, and the mixture was stirred for 4 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.25 g, 33%).

$^1$H NMR (300 MHz, CHLOROFORM-d) δ1.04 (t, J=7.3 Hz, 3H), 1.15 (d, J=6.2 Hz, 3H), 1.42 (s, 3H), 1.61-1.76 (m, 6H), 1.79-1.91 (m, 2H), 2.43 (s, 3H), 2.51 (br. s., 1H), 2.72-2.89 (m, 2H), 2.92-3.01 (m, 2H), 3.20 (t, J=8.5 Hz, 1H), 3.42 (dd, J=8.9, 3.2 Hz, 1H), 3.83-3.94 (m, 1H), 3.99 (s, 2H), 4.92-5.06 (m, 1H), 7.31-7.51 (m, 6H), 7.57-7.67 (m, 1H), 7.74 (d, J=7.7 Hz, 1H)

REFERENCE EXAMPLE 187

4'-({4-[trans-4-(2-hydroxy-2-methylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxypropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.25 g), triethylamine (0.63 mL) and dimethyl sulfoxide (5 mL) was added a solution (5 mL) of sulfur trioxide-pyridine complex (0.36 g) in dimethyl sulfoxide at room temperature, and the mixture was stirred for 2 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The residue obtained by purification by silica gel column chromatography was dissolved in tetrahydrofuran (15 mL), methylmagnesium bromide (1.0 M tetrahydrofuran solution, 1.4 mL) was added at room temperature, and the mixture was stirred for 4 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.11 g, 43%).

$^1$H NMR (300 MHz, CHLOROFORM-d) δ1.04 (t, J=7.3 Hz, 3H), 1.20 (s, 6H), 1.41 (s, 3H), 1.58-1.90 (m, 8H), 2.43 (s, 3H), 2.50 (s, 1H), 2.72-2.89 (m, 2H), 2.92-3.01 (m, 2H), 3.24 (s, 2H), 4.00 (s, 2H), 4.93-5.06 (m, 1H), 7.32-7.52 (m, 6H), 7.58-7.66 (m, 1H), 7.74 (dd, J=7.7, 0.9 Hz, 1H)

REFERENCE EXAMPLE 188

4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile (27 g), 6N hydrochloric acid (80 mL) and tetrahydrofuran (160 mL) was stirred at 70° C. for 16 hr. The reaction mixture was diluted with ethyl acetate, washed with saturated brine, and dried over anhydrous magnesium sulfate. The solvent was evaporated under reduced pressure, and the residue was purified by silica gel column chromatography to give the title compound as a colorless solid (20 g, 80%).

$^1$H NMR (300 MHz, CHLOROFORM-d) δ1.06 (t, J=7.5 Hz, 3H), 1.66-1.79 (m, 2H), 2.04-2.08 (m, 2H), 2.42 (s, 3H), 2.53-2.57 (m, 4H), 2.97-3.18 (m, 4H), 4.00 (s, 2H), 5.47-5.54 (m, 1H), 7.34-7.49 (m, 6H), 7.59-7.64 (m, 1H), 7.74 (d, J=7.8 Hz, 1H)

REFERENCE EXAMPLE 189

4'-{[4-(4-hydroxycyclohexyl)-2-methyl-5-oxo-7-propyl-4,5-dihydro[1,2,4]triazolo[1,5-a]pyrimidin-6-yl]methyl}biphenyl-2-carbonitrile To a mixture of 4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile (2 g), methanol (15 mL) and tetrahydrofuran (15 mL) was added sodium borohydride (0.24 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (1.8 g, 90%).

$^1$H NMR (300 MHz, CHLOROFORM-d) δ1.05 (t, J=7.3 Hz, 3H), 1.42-1.81 (m, 6H), 1.92-2.15 (m, 2H), 2.44 (s, 3H), 2.65-2.84 (m, 2H), 2.91-3.03 (m, 2H), 3.74-3.88 (m, 1H), 3.99 (s, 2H), 4.90-5.10 (m, 1H), 7.32-7.52 (m, 6H), 7.58-7.67 (m, 1H), 7.71-7.77 (m, 1H)

REFERENCE EXAMPLE 190 ethyl[(4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]acetate To a mixture of 4'-{[4-(4-hydroxycyclohexyl)-2-methyl-5-oxo-7-propyl-4,5-dihydro[1,2,4]triazolo[1,5-a]pyrimidin-6-yl]methyl}biphenyl-2-carbonitrile (1.2 g), rhodium(I) acetate (0.055 g) and toluene (40 mL) was added dropwise ethyl diazoacetate (1.2 mL) at 80° C., and the mixture was stirred at the same temperature for 1 hr. The reaction mixture was concentrated under reduced pressure, and the obtained residue was subjected to silica gel column chromatography to give the title compound as a colorless solid (1.1 g, 76%).
$^1$H NMR (300 MHz, CHLOROFORM-d) δ1.03 (t, J=7.4 Hz, 3H), 1.29 (t, J=7.2 Hz, 3H), 1.43-1.61 (m, 2H), 1.64-1.83 (m, 4H), 2.11-2.27 (m, 2H), 2.43 (s, 3H), 2.63-2.82 (m, 2H), 2.89-3.02 (m, 2H), 3.43-3.74 (m, 1H), 3.99 (s, 2H), 4.13 (s, 2H), 4.18-4.28 (m, 2H), 4.90-5.06 (m, 1H), 7.32-7.51 (m, 6H), 7.58-7.66 (m, 1H), 7.74 (dd, J=7.7, 0.9 Hz, 1H)

REFERENCE EXAMPLE 191

4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile Ethyl[(4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]acetate (0.5 g) was dissolved in tetrahydrofuran (10 mL), and methylmagnesium bromide (1.0 M tetrahydrofuran solution, 4.2 mL) was added at 0° C. After stirring at the same temperature for 1 hr, 1 N hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.32 g, 56%).
$^1$H NMR (300 MHz, CHLOROFORM-d) δ1.04 (t, J=7.4 Hz, 3H), 1.20 (s, 6H), 1.37-1.52 (m, 2H), 1.64-1.84 (m, 4H), 2.12-2.22 (m, 2H), 2.43 (s, 3H), 2.62-2.81 (m, 2H), 2.92-3.02 (m, 2H), 3.31 (s, 2H), 3.38-3.51 (m, 1H), 3.98 (s, 2H), 4.93-5.07 (m, 1H), 7.30-7.52 (m, 6H), 7.62 (t, J=7.8 Hz, 1H), 7.74 (d, J=7.2 Hz, 1H)

REFERENCE EXAMPLE 192

4'-({4-[trans-4-(2-ethyl-2-hydroxybutoxy)cyclohexyl]-2-methyl-5-oxo-7-propyl-4,5-dihydro[1,2,4]triazolo[1,5-a]pyrimidin-6-yl}methyl)biphenyl-2-carbonitrile Ethyl[(4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]acetate (0.6 g) was dissolved in tetrahydrofuran (15 mL), and ethylmagnesium bromide (3.0 M diethyl ether solution, 1.7 mL) was added at 0° C. After stirring at the same temperature for 1 hr, 1 N hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.4 g, 55%).
$^1$H NMR (300 MHz, CHLOROFORM-d) δ0.87 (t, J=7.4 Hz, 6H) 1.04 (t, J=7.4 Hz, 3H) 1.35-1.56 (m, 6H) 1.63-1.82 (m, 4H) 2.10-2.21 (m, 2H) 2.43 (s, 3H) 2.63-2.79 (m, 2H) 2.92-3.00 (m, 2H) 3.34 (s, 2H) 3.38-3.47 (m, 1H) 3.97 (s, 2H) 4.93-5.06 (m, 1H) 7.31-7.52 (m, 6H) 7.62 (t, J=7.8 Hz, 1H) 7.74 (d, J=8.0 Hz, 1H)

REFERENCE EXAMPLE 193

4'-{[4-(4-methylidenecyclohexyl)-5-oxo-7-propyl-4,5-dihydro[1,2,4]triazolo[1,5-a]pyrimidin-6-yl]methyl}biphenyl-2-carbonitrile To a solution (15 mL) of methyltriphenylphosphonium bromide (1.2 g) in tetrahydrofuran was added n-butyllithium (1.6M hexane solution, 2 mL) at 0° C., and the mixture was stirred at the same temperature for 30 min. The reaction mixture was warmed to room temperature, and further stirred for 30 min. A solution (5 mL) of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1 g) in tetrahydrofuran was added, and the mixture was stirred at 70° C. for 3 hr. The insoluble material was filtered off, and the obtained filtrate was extracted with ethyl acetate and 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless solid (0.8 g, 80%).
$^1$H NMR (300 MHz, CHLOROFORM-d) δ1.06 (t, J=7.3 Hz, 3H), 1.66-1.78 (m, 2H), 1.80-1.89 (m, 2H), 2.15-2.31 (m, 2H), 2.40-2.50 (m, 2H), 2.62-2.79 (m, 2H), 2.98-3.07 (m, 2H), 4.02 (s, 2H), 4.73 (s, 2H), 5.14-5.28 (m, 1H), 7.34-7.52 (m, 6H), 7.58-7.66 (m, 1H), 7.75 (dd, J=7.7, 0.9 Hz, 1H), 7.91 (s, 1H)

REFERENCE EXAMPLE 194

4'-({4-[(5S,8S)-3-methyl-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile To a solution (15 mL) of 4'-{[4-(4-methylidenecyclohexyl)-5-oxo-7-propyl-4,5-dihydro[1,2,4]triazolo[1,5-a]pyrimidin-6-yl]methyl}biphenyl-2-carbonitrile (0.8 g) and triethylamine (0.72 mL) in methylene chloride was added N-hydroxyethanimidoyl chloride (0.49 g) at 0° C. The reaction mixture was stirred at room temperature for 16 hr, washed with 1 N hydrochloric acid and then with saturated brine, and dried over anhydrous magnesium sulfate. The solvent was evaporated under reduced pressure. The obtained residue was purified by silica gel column chromatography to give the title compound as a colorless solid (0.2 g, 22%).
$^1$H NMR (300 MHz, CHLOROFORM-d) δ1.06 (t, J=7.3 Hz, 3H), 1.60-1.80 (m, 6H), 1.98 (s, 3H), 2.05-2.13 (m, 2H), 2.68 (s, 2H), 2.97-3.20 (m, 4H), 4.02 (s, 2H), 5.03-5.18 (m, 1H), 7.34-7.51 (m, 6H), 7.58-7.66 (m, 1H), 7.75 (dd, J=7.7, 0.9 Hz, 1H), 7.94 (s, 1H)

REFERENCE EXAMPLE 195

4'-({4-[(5R,8R)-3-methyl-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile To a solution (15 mL) of 4'-{[4-(4-methylidenecyclohexyl)-5-oxo-7-propyl-4,5-dihydro[1,2,4]triazolo[1,5-a]pyrimidin-6-yl]methyl}biphenyl-2-carbonitrile (0.8 g) and triethylamine (0.72 mL) in methylene chloride was added N-hydroxyethanimidoyl chloride (0.49 g) at 0° C. The reaction mixture was stirred at room temperature for 16 hr, washed with 1 N hydrochloric acid and then with saturated brine, and dried over anhydrous magnesium sulfate. The solvent was evaporated under reduced pressure. The obtained residue was purified by silica gel column chromatography to give the title compound as a colorless solid (0.23 g, 26%).

$^1$H NMR (300 MHz, CHLOROFORM-d) δ1.06 (t, J=7.4 Hz, 3H), 1.64-1.94 (m, 8H), 2.01 (s, 3H), 2.65-2.82 (m, 2H), 2.93 (s, 2H), 2.98-3.06 (m, 2H), 4.01 (s, 2H), 5.06-5.16 (m, 1H), 7.34-7.51 (m, 6H), 7.59-7.67 (m, 1H), 7.75 (dd, J=7.7, 0.9 Hz, 1H), 7.91 (s, 1H)

REFERENCE EXAMPLE 196

4'-{[7-butyl-5-oxo-4-(4-oxocyclohexyl)-4,5-dihydro[1,2,4]triazolo[1,5-a]pyrimidin-6-yl]methyl}biphenyl-2-carbonitrile A mixture of 4'-{[7-butyl-4-(1,4-dioxaspiro[4.5]dec-8-yl)-5-oxo-4,5-dihydro[1,2,4]triazolo[1,5-a]pyrimidin-6-yl]methyl}biphenyl-2-carbonitrile (3.1 g), p-toluenesulfonic acid monohydrate (0.1 g), methanol (50 mL) and tetrahydrofuran (50 mL) was stirred at 60° C. for 16 hr. The reaction mixture was diluted with ethyl acetate, washed with saturated brine, and dried over anhydrous magnesium sulfate. The solvent was evaporated under reduced pressure. The obtained residue was dissolved in acetone (20 mL), 1 N hydrochloric acid (20 mL) was added, and the mixture was stirred at room temperature for 2 hr. The reaction mixture was diluted with ethyl acetate, washed with saturated brine, and dried over anhydrous magnesium sulfate. The solvent was evaporated under reduced pressure and the residue was purified by silica gel column chromatography to give the title compound as a colorless solid (2 g, 67%).

$^1$H NMR (300 MHz, CHLOROFORM-d) δ0.96 (t, J=7.2 Hz, 3H), 1.40-1.70 (m, 4H), 2.03-2.12 (m, 2H), 2.51-2.60 (m, 4H), 3.01-3.17 (m, 4H), 4.03 (s, 2H), 5.48-5.62 (m, 1H), 7.35-7.53 (m, 6H), 7.59-7.67 (m, 1H), 7.75 (dd, J=7.7, 0.9 Hz, 1H), 7.92 (s, 1H)

REFERENCE EXAMPLE 197

4'-{[7-butyl-4-(2,3-dimethyl-1,4-dioxaspiro[4.5]dec-8-yl)-5-oxo-4,5-dihydro[1,2,4]triazolo[1,5-a]pyrimidin-6-yl]methyl}biphenyl-2-carbonitrile A mixture of 4'-{[7-butyl-5-oxo-4-(4-oxocyclohexyl)-4,5-dihydro[1,2,4]triazolo[1,5-a]pyrimidin-6-yl]methyl}biphenyl-2-carbonitrile (1 g), 2,3-dimethylpropane-1,3-diol (0.56 g), p-toluenesulfonic acid monohydrate (0.036 g) and toluene (30 mL) was subjected to an azeotropic dehydration reaction by stirring at 110° C. for 3 hr in a reaction vessel equipped with a Dean-stark trap. The reaction mixture was concentrated under reduced pressure, and the obtained residue was purified by silica gel column chromatography to give the title compound as a colorless solid (1.2 g, 100%).

$^1$H NMR (300 MHz, CHLOROFORM-d) δ0.95 (t, J=7.3 Hz, 3H) 1.14-1.33 (m, 6H) 1.40-1.54 (m, 2H) 1.58-2.01 (m, 8H) 2.84-3.08 (m, 4H) 3.62-3.72 (m, 0H) 4.01 (s, 2H) 4.19-4.35 (m, 0H) 5.09 (t, J=12.6 Hz, 1H) 7.35-7.51 (m, 6H) 7.59-7.66 (m, 1H) 7.75 (dd, J=7.7, 0.9 Hz, 1H) 7.94-7.96 (m, 1H)

REFERENCE EXAMPLE 198

4'-({7-butyl-4-[trans-4-(2-hydroxy-1-methylpropoxy)cyclohexyl]-5-oxo-4,5-dihydro[1,2,4]triazolo[1,5-a]pyrimidin-6-yl}methyl)biphenyl-2-carbonitrile A mixture of 4'-{[7-butyl-4-(2,3-dimethyl-1,4-dioxaspiro[4.5]dec-8-yl)-5-oxo-4,5-dihydro[1,2,4]triazolo[1,5-a]pyrimidin-6-yl]methyl}biphenyl-2-carbonitrile (1.2 g), sodium cyanoborohydride (0.71 g), boron trifluoride-diethyl ether complex (1.4 mL) and tetrahydrofuran (20 mL) was stirred at 50° C. for 24 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.66 g, 53%).

$^1$H NMR (300 MHz, CHLOROFORM-d) δ0.93 (t, J=7.2 Hz, 3H) 1.09-1.22 (m, 6H) 1.39-2.37 (m, 9H) 2.63-2.88 (m, 3H) 2.98-3.08 (m, 2H) 3.34-3.68 (m, 3H) 4.02 (s, 2H) 5.00-5.16 (m, 1H) 7.29-7.51 (m, 6H) 7.60-7.69 (m, 1H) 7.71-7.78 (m, 1H) 7.95 (s, 1H)

REFERENCE EXAMPLE 199

4'-({7-butyl-4-[trans-4-(2-hydroxy-1,2-dimethylpropoxy)cyclohexyl]-5-oxo-4,5-dihydro[1,2,4]triazolo[1,5-a]pyrimidin-6-yl}methyl)biphenyl-2-carbonitrile A mixture of 4'-({7-butyl-4-[trans-4-(2-hydroxy-1-methylpropoxy)cyclohexyl]-5-oxo-4,5-dihydro[1,2,4]triazolo[1,5-a]pyrimidin-6-yl}methyl)biphenyl-2-carbonitrile (0.66 g), 1,1,1-triacetoxy-1,1-dihydro-1,2-benziodoxol-3(1H)-one (0.76 g) and acetonitrile (20 mL) was stirred at room temperature for 3 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was dissolved in tetrahydrofuran (15 mL), and methylmagnesium bromide (1.0 M tetrahydrofuran solution, 2.4 mL) was added at 0° C. The reaction mixture was warmed to 0° C., and stirred for 6 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.32 g, 47%).

$^1$H NMR (300 MHz, CHLOROFORM-d) δ0.95 (t, J=7.2 Hz, 3H), 1.09-1.14 (m, 6H), 1.17 (s, 3H), 1.35-1.55 (m, 4H), 1.60-1.85 (m, 4H), 2.03-2.24 (m, 2H), 2.59-2.81 (m, 2H), 3.00-3.08 (m, 2H), 3.34 (q, J=6.1 Hz, 1H), 3.43-3.57 (m, 1H), 4.01 (s, 2H), 4.99-5.15 (m, 1H), 7.33-7.51 (m, 6H), 7.63 (t, J=7.8 Hz, 1H), 7.75 (d, J=7.2 Hz, 1H), 7.92 (s, 1H)

REFERENCE EXAMPLE 200

N-(4-{[tert-butyl(dimethyl)silyl]oxy}cyclohexyl)-4H-1,2,4-triazol-3-amine

To a solution (30 mL) of 1H-1,2,4-triazol-3-amine (3 g) and 4-{[tert-butyl(dimethyl)silyl]oxy}cyclohexanone (10 g) in acetic acid was added sodium cyanoborohydride (9.3 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. The obtained residue was purified by silica gel column chromatography to give the title compound as a colorless solid (2.2 g, 20%).
$^1$H NMR (300 MHz, CHLOROFORM-d) δ0.00 (s, 6H) 0.85 (s, 9H) 1.44-1.81 (m, 9H) 3.44 (br. s., 1H) 3.80-3.90 (m, 1H) 4.79 (br. s., 1H) 7.57-7.65 (m, 1H)

REFERENCE EXAMPLE 201

4'-[(7-butyl-5-oxo-4,5-dihydro[1,2,4]triazolo[1,5-a]pyrimidin-6-yl)methyl]biphenyl-2-carbonitrile A solution of 1H-1,2,4-triazol-3-amine (1.5 g) and methyl 2-[(2'-cyanobiphenyl-4-yl)methyl]-3-oxoheptanoate (7.1 g) in 1,2,4-trichlorobenzene (70 mL) was stirred at 190° C. for 6 hr. After evaporation of the solvent under reduced pressure, ethyl acetate was added to the obtained residue. The precipitated solid was collected by filtration to give the title compound as a colorless solid (3.6 g, 44%).
$^1$H NMR (300 MHz, DMSO-d$_6$) δ0.84 (t, J=7.2 Hz, 3H) 1.27-1.57 (m, 4H) 2.91-3.03 (m, 2H) 3.96 (s, 2H) 7.37-7.44 (m, 2H) 7.46-7.62 (m, 4H) 7.73-7.82 (m, 1H) 7.93 (dd, J=7.7, 0.9 Hz, 1H) 8.12 (s, 1H) 13.13 (br. s., 1H)

REFERENCE EXAMPLE 202

3'-fluoro-4'-({4-[trans-4-(2-hydroxy-1,2-dimethyl-propoxy)cyclohexyl]-5-oxo-7-propyl-4,5-dihydro[1,2,4]triazolo[1,5-a]pyrimidin-6-yl}methyl)biphenyl-2-carbonitrile (retention time: long)

The racemate (500 g) of the title compound obtained in Reference Example 107 was resolved using a chiral column to give the title compound as a colorless solid (185 g, 99% ee, 37%).
$^1$H NMR (300 MHz, DMSO-d$_6$) δ0.90-1.11 (m, 12H), 1.16-1.39 (m, 2H), 1.54-1.75 (m, 4H), 1.94-2.14 (m, 2H), 2.47-2.68 (m, 2H), 2.91-3.02 (m, 2H), 3.24 (q, J=6.0 Hz, 1H), 3.30-3.44 (m, 1H), 3.97 (s, 2H), 4.06 (s, 1H), 4.80-4.97 (m, 1H), 7.26-7.39 (m, 2H), 7.41-7.50 (m, 1H), 7.54-7.67 (m, 2H), 7.75-7.83 (m, 1H), 7.95 (d, J=7.6 Hz, 1H), 8.20 (s, 1H)
analysis of enantiomeric excess
column: CHIRALPAK IA 4.6 mm ID×250 mL
mobile phase: n-Hex/IPA=90/10 (v/v)
flow rate: 1.0 mL/min
temperature: 40° C.
detection: UV 254 nm
concentration: 1 mg/mL (n-Hex/IPA=90/10)
injection volume: 0.01 mL
retention time: 26.4 min

REFERENCE EXAMPLE 203

4'-({5-oxo-7-propyl-4-[(3a'R,6a'S)-tetrahydrospiro[cyclohexane-1,2'-furo[3,4-d][1,3]dioxol]-4-yl]-4,5-dihydro[1,2,4]triazolo[1,5-a]pyrimidin-6-yl}methyl)biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.75 g), tetrahydrofuran-3,4-diol (0.48 g), p-toluenesulfonic acid monohydrate (0.028 g) and toluene (25 mL) was subjected to an azeotropic dehydration reaction by stirring at 110° C. for 16 hr in a reaction vessel equipped with a Dean-stark trap. The reaction mixture was concentrated under reduced pressure, and the obtained residue was purified by silica gel column chromatography to give the title compound as a colorless solid (0.77 g, 90%).
$^1$H NMR (300 MHz, CHLOROFORM-d) δ1.06 (t, J=7.3 Hz, 3H), 1.57-2.11 (m, 8H), 2.83-3.07 (m, 4H), 3.39-3.47 (m, 2H), 4.00-4.18 (m, 4H), 4.75-4.86 (m, 2H), 5.02-5.15 (m, 1H), 7.34-7.52 (m, 6H), 7.58-7.67 (m, 1H), 7.75 (dd, J=7.7, 0.9 Hz, 1H), 7.96 (s, 1H)

REFERENCE EXAMPLE 204

4'-{[4-(trans-4-{[(3R,4S)-4-hydroxytetrahydrofuran-3-yl]oxy}cyclohexyl)-5-oxo-7-propyl-4,5-dihydro[1,2,4]triazolo[1,5-a]pyrimidin-6-yl]methyl}biphenyl-2-carbonitrile A mixture of 4'-({5-oxo-7-propyl-4-[(3a'R,6a'S)-tetrahydrospiro[cyclohexane-1,2'-furo[3,4-d][1,3]dioxol]-4-yl]-4,5-dihydro[1,2,4]triazolo[1,5-a]pyrimidin-6-yl}methyl)biphenyl-2-carbonitrile (0.77 g), sodium cyanoborohydride (0.45 g), boron trifluoride-diethyl ether complex (0.88 mL) and tetrahydrofuran (20 mL) was stirred at 70° C. for 16 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.14 g, 18%).
$^1$H NMR (300 MHz, CHLOROFORM-d) δ1.06 (t, J=7.19 Hz, 3H) 1.42-1.88 (m, 6H) 2.07-2.26 (m, 2H) 2.63-2.87 (m, 3H) 2.98-3.08 (m, 2H) 3.39-4.27 (m, 9H) 4.99-5.15 (m, 1H) 7.32-7.52 (m, 6H) 7.59-7.67 (m, 1H) 7.75 (d, J=7.57 Hz, 1H) 7.91 (s, 1H)

REFERENCE EXAMPLE 205

4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile To a mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (5 g), methanol (20 mL) and tetrahydrofuran (20 mL) was added sodium borohydride (0.61 g) at 0° C., and the mixture was stirred at the same temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (3 g, 58%).

$^1$H NMR (300 MHz, CHLOROFORM-d) δ1.06 (t, J=7.35 Hz, 3H) 1.42-1.85 (m, 8H) 2.06-2.18 (m, 2H) 2.65-2.82 (m, 2H) 2.98-3.07 (m, 2H) 3.74-3.90 (m, 1H) 4.99-5.14 (m, 1H) 7.33-7.53 (m, 6H) 7.59-7.67 (m, 1H) 7.75 (dd, J=7.72, 0.94 Hz, 1H) 7.90-7.93 (m, 1H)

REFERENCE EXAMPLE 206 ethyl[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetate To a mixture of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (1 g), rhodium(I) acetate (0.023 g) and methylene chloride (10 mL) was added dropwise ethyl diazoacetate (0.64 mL) at room temperature, and the mixture was stirred for 1 hr. The reaction mixture was concentrated, and the obtained residue was subjected to silica gel column chromatography to give the title compound as a colorless solid (0.68 g, 59%).

$^1$H NMR (300 MHz, CHLOROFORM-d) δ1.06 (t, J=7.35 Hz, 3H) 1.30 (t, J=7.20 Hz, 3H) 1.43-1.87 (m, 6H) 2.16-2.28 (m, 2H) 2.62-2.79 (m, 2H) 2.97-3.08 (m, 2H) 3.44-3.58 (m, 1H) 4.01 (s, 2H) 4.13 (s, 2H) 4.23 (q, J=7.20 Hz, 2H) 5.01-5.14 (m, 1H) 7.33-7.52 (m, 6H) 7.59-7.66 (m, 1H) 7.75 (dd, J=7.82, 1.04 Hz, 1H) 7.91 (s, 1H)

REFERENCE EXAMPLE 207

4'-({4-[(5R,8R)-3-(1-hydroxy-1-methylethyl)-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile To a solution (40 mL) of 4'-{[4-(4-methylidenecyclohexyl)-5-oxo-7-propyl-4,5-dihydro[1,2,4]triazolo[1,5-a]pyrimidin-6-yl]methyl}biphenyl-2-carbonitrile (0.89 g) and triethylamine (5.4 mL) in methylene chloride was added ethyl chloro(hydroxyimino)ethanoate (5.8 g) at 0° C. The reaction mixture was stirred at room temperature for 16 hr, washed with 1 N hydrochloric acid and then with saturated brine, and dried over anhydrous magnesium sulfate. The solvent was evaporated under reduced pressure. The residue obtained by purification by silica gel column chromatography was dissolved in tetrahydrofuran (10 mL), and the mixture was added to a mixture of methylmagnesium bromide (1.0 M tetrahydrofuran solution, 11 mL), cerium chloride anhydrous (0.92 g) and tetrahydrofuran (15 mL) stirred at 0° C. for 1 hr in advance. The reaction mixture was stirred at 70° C. for 16 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.12 g, 19%).

$^1$H NMR (300 MHz, CHLOROFORM-d) δ1.06 (t, J=7.35 Hz, 3H) 1.51 (s, 6H) 1.65-1.99 (m, 8H) 2.66-2.84 (m, 2H) 2.97-3.08 (m, 4H) 4.02 (s, 2H) 5.04-5.18 (m, 1H) 7.33-7.52 (m, 6H) 7.59-7.67 (m, 1H) 7.75 (dd, J=7.72, 0.94 Hz, 1H) 7.93 (s, 1H)

REFERENCE EXAMPLE 208

4'-({4-[(5S,8S)-3-(1-hydroxy-1-methylethyl)-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile To a solution (40 mL) of 4'-{[4-(4-methylidenecyclohexyl)-5-oxo-7-propyl-4,5-dihydro[1,2,4]triazolo[1,5-a]pyrimidin-6-yl]methyl}biphenyl-2-carbonitrile (0.89 g) and triethylamine (5.4 mL) in methylene chloride was added ethyl chloro(hydroxyimino)ethanoate (5.8 g) at 0° C. The reaction mixture was stirred at room temperature for 16 hr, washed with 1 N hydrochloric acid and then with saturated brine, and dried over anhydrous magnesium sulfate. The solvent was evaporated under reduced pressure. The residue obtained by purification by silica gel column chromatography was dissolved in tetrahydrofuran (10 mL), and the mixture was added to a mixture of methylmagnesium bromide (1.0 M tetrahydrofuran solution, 9.3 mL), cerium chloride anhydrous (0.77 g) and tetrahydrofuran (15 mL) stirred at 0° C. for 1 hr in advance. The reaction mixture was stirred at 70° C. for 16 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.1 g, 19%).

$^1$H NMR (300 MHz, CHLOROFORM-d) δ1.06 (t, J=7.35 Hz, 3H) 1.48 (s, 6H) 1.61-1.79 (m, 6H) 2.06-2.18 (m, 2H) 2.82 (s, 2H) 2.99-3.21 (m, 4H) 4.02 (s, 2H) 5.12 (t, J=12.62 Hz, 1H) 7.34-7.52 (m, 6H) 7.59-7.67 (m, 1H) 7.75 (dd, J=7.72, 0.94 Hz, 1H) 7.95 (s, 1H)

REFERENCE EXAMPLE 209

4'-[(4-{trans-4-[(3-methyl-4,5-dihydroisoxazol-5-yl)methoxy]cyclohexyl}-5-oxo-7-propyl-4,5-dihydro[1,2,4]triazolo[1,5-a]pyrimidin-6-yl)methyl]biphenyl-2-carbonitrile To a solution (40 mL) of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (2.7 g) and triethylamine (7.5 mL) in methylene chloride was added N-hydroxyethanimidoyl chloride (5 g) at 0° C. The reaction mixture was stirred at room temperature for 16 hr, washed with 1 N hydrochloric acid and then with saturated brine, and dried over anhydrous magnesium sulfate. The solvent was evaporated under reduced pressure. The obtained residue was purified by silica gel column chromatography to give the title compound as a colorless solid (0.86 g, 28%).

$^1$H NMR (300 MHz, CHLOROFORM-d) δ1.06 (t, J=7.38 Hz, 3H) 1.35-1.52 (m, 2H) 1.66-1.84 (m, 4H) 1.99 (s, 3H) 2.12-2.21 (m, 2H) 2.60-2.85 (m, 3H) 2.93-3.07 (m, 3H) 3.41-3.53 (m, 2H) 3.57-3.67 (m, 1H) 4.01 (s, 2H) 4.63-4.76 (m, 1H) 4.98-5.12 (m, 1H) 7.34-7.52 (m, 6H) 7.59-7.66 (m, 1H) 7.74 (d, J=7.95 Hz, 1H) 7.91 (s, 1H)

REFERENCE EXAMPLE 210

[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetic acid A mixture of ethyl[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetate (1.1 g), 1N aqueous sodium hydroxide solution (10 mL), methanol (10 mL) and tetrahydrofuran (10 mL) was stirred at room temperature for 2 hr. The reaction mixture was adjusted to pH 4 with water (20 mL) and 1 N hydrochloric acid, and extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.9 g, 90%).

$^1$H NMR (300 MHz, DMSO-d$_6$) δ0.95 (t, J=7.3 Hz, 3H) 1.23-1.40 (m, 2H) 1.54-1.76 (m, 4H) 2.06-2.18 (m, 2H) 2.53-2.66 (m, 2H) 2.91-3.02 (m, 2H) 3.29-3.48 (m, 1H) 4.00 (s, 2H) 4.06 (s, 2H) 4.85-4.98 (m, 1H) 7.38-7.64 (m, 6H) 7.74-7.82 (m, 1H) 7.93 (d, J=7.7 Hz, 1H) 8.18 (s, 1H) 12.37 (br. s., 1H)

REFERENCE EXAMPLE 211

2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide A mixture of [(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetic acid (0.9 g), N-methoxymethanamine hydrochloride (0.25 g), 1-hydroxybenzotriazole (0.39 g), 1-ethyl-3-(3-dimethylaminopropyl)carbodiimide hydrochloride (0.49 g), triethylamine (0.36 mL) and N,N-dimethylformamide (10 mL) was stirred at room temperature for 16 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless solid (0.75 g, 77%).

$^1$H NMR (300 MHz, CHLOROFORM-d) δ1.06 (t, J=7.4 Hz, 3H) 1.44-1.85 (m, 6H) 2.20-2.31 (m, 2H) 2.62-2.81 (m, 2H) 2.99-3.07 (m, 2H) 3.20 (s, 3H) 3.47-3.62 (m, 1H) 3.70 (s, 3H) 4.01 (s, 2H) 4.32 (s, 2H) 5.00-5.15 (m, 1H) 7.33-7.50 (m, 6H) 7.59-7.66 (m, 1H) 7.74 (d, J=8.7 Hz, 1H) 7.90 (s, 1H)

REFERENCE EXAMPLE 212

4'-({5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile 2-[(trans-4-{6-[(2'-Cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide (0.75 g) was dissolved in tetrahydrofuran (10 mL), and methylmagnesium bromide (1.0 M tetrahydrofuran solution, 4 mL) was added at room temperature. The reaction mixture was warmed to 70° C. and stirred for 3 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.48 g, 69%).

$^1$H NMR (300 MHz, CHLOROFORM-d) δ1.06 (t, J=7.4 Hz, 3H) 1.43-1.85 (m, 6H) 2.15-2.27 (m, 5H) 2.59-2.78 (m, 2H) 2.98-3.08 (m, 2H) 3.40-3.54 (m, 1H) 4.01 (s, 2H) 4.09 (s, 2H) 5.00-5.14 (m, 1H) 7.34-7.52 (m, 6H) 7.58-7.66 (m, 1H) 7.75 (d, J=7.6 Hz, 1H) 7.91 (s, 1H)

REFERENCE EXAMPLE 213

4'-({4-[trans-4-(2-{[tert-butyl(dimethyl)silyl]oxy}propoxy)cyclohexyl]-5-oxo-7-propyl-4,5-dihydro[1,2,4]triazolo[1,5-a]pyrimidin-6-yl}methyl)biphenyl-2-carbonitrile To a mixture of 4'-({5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.48 g), methanol (5 mL) and tetrahydrofuran (5 mL) was added sodium borohydride (0.042 g), and the mixture was stirred at room temperature for 2 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. The obtained residue was dissolved in tetrahydrofuran (5 mL), 2,6-lutidine (0.16 mL) and tert-butyl(dimethyl)silyl trifluoromethanesulfonate (0.32 mL) were added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The obtained residue was purified by silica gel column chromatography to give the title compound as a colorless solid (0.45 g, 77%).

$^1$H NMR (300 MHz, CHLOROFORM-d) δ0.08 (s, 6H) 0.90 (s, 9H) 1.07 (t, J=7.4 Hz, 3H) 1.14 (d, J=6.1 Hz, 3H) 1.32-1.52 (m, 2H) 1.67-1.84 (m, 4H) 2.14-2.25 (m, 2H) 2.60-2.78 (m, 2H) 3.04 (dd, J=10.4, 5.5 Hz, 2H) 3.22-3.51 (m, 1H) 3.36-3.48 (m, 2H) 3.85-3.95 (m, 1H) 4.02 (s, 2H) 4.99-5.15 (m, 1H) 7.34-7.52 (m, 6H) 7.60-7.67 (m, 1H) 7.75 (d, J=8.0 Hz, 1H) 7.92 (s, 1H)

REFERENCE EXAMPLE 214

4'-({5-oxo-7-propyl-4-[(3a'R,6a'S)-tetrahydro-3a'H-spiro[cyclohexane-1,2'-cyclopenta[d][1,3]dioxol]-4-yl]-4,5-dihydro[1,2,4]triazolo[1,5-a]pyrimidin-6-yl}methyl)biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.75 g), cyclopentane-1,2-diol (0.42 g), p-toluenesulfonic acid monohydrate (0.018 g) and toluene (30 mL) was subjected to an azeotropic dehydration reaction by stirring at 110° C. for 16 hr in a reaction vessel equipped with a Dean-stark trap. The reaction mixture was concentrated, and the obtained residue was purified by silica gel column chromatography to give the title compound as a colorless solid (1.2 g, 100%).

$^1$H NMR (300 MHz, CHLOROFORM-d) δ1.06 (t, J=7.3 Hz, 3H), 1.33-1.59 (m, 4H), 1.65-2.10 (m, 10H), 2.80-3.06 (m, 4H), 4.02 (s, 2H), 4.60-4.70 (m, 2H), 5.00-5.14 (m, 1H), 7.34-7.52 (m, 6H), 7.59-7.67 (m, 1H), 7.75 (dd, J=7.7, 0.9 Hz, 1H), 7.95 (s, 1H)

REFERENCE EXAMPLE 215

4'-{[4-(trans-4-{[(1R,2S)-2-hydroxycyclopentyl]oxy}cyclohexyl)-5-oxo-7-propyl-4,5-dihydro[1,2,4]triazolo[1,5-a]pyrimidin-6-yl]methyl}biphenyl-2-carbonitrile A mixture of 4'-({5-oxo-7-propyl-4-[(3a'R,6a'S)-tetrahydro-3a'H-spiro[cyclohexane-1,2'-cyclopenta[d][1,3]dioxol]-4-yl]-4,5-dihydro[1,2,4]triazolo[1,5-a]pyrimidin-6-yl}methyl)biphenyl-2-carbonitrile (1.2 g), sodium cyanoborohydride (0.65 g), boron trifluoride-diethyl ether complex (1.3 mL) and tetrahydrofuran (30 mL) was stirred at 70° C. for 16 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.82 g, 72%).

$^1$H NMR (300 MHz, CHLOROFORM-d) δ1.06 (t, J=7.3 Hz, 3H), 1.39-1.89 (m, 12H), 2.11-2.25 (m, 2H), 2.62-2.81 (m, 2H), 2.99-3.07 (m, 2H), 3.38-3.45 (m, 1H), 3.48-3.59 (m, 1H), 3.81-3.89 (m, 1H), 3.98-4.06 (m, 2H), 4.99-5.15 (m, 1H), 7.34-7.51 (m, 6H), 7.59-7.67 (m, 1H), 7.72-7.77 (m, 1H), 7.92 (s, 1H)

REFERENCE EXAMPLE 216

2-[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]-N-methoxy-N-methylacetamide A mixture of ethyl[(4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]acetate (3.6 g), 1N aqueous sodium hydroxide solution (50 mL), methanol (50 mL) and tetrahydrofuran (50 mL) was stirred at room temperature for 3 hr. The reaction mixture was adjusted to pH 4 with water (20 mL) and 1 N hydrochloric acid and extracted with ethyl acetate. The obtained residue was dissolved in N,N-dimethylformamide (30 mL), N-methoxymethanamine hydrochloride (0.92 g), 1-hydroxybenzotriazole (1.5 g), 1-ethyl-3-(3-dimethylaminopropyl)carbodiimide hydrochloride (1.8 g) and triethylamine (1.3 mL) were added, and the mixture was stirred at room temperature for 16 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless solid (1.1 g, 33%).

$^1$H NMR (300 MHz, CHLOROFORM-d) δ1.05 (t, J=7.25 Hz, 3H) 1.43-1.84 (m, 6H) 2.20-2.31 (m, 2H) 2.43 (s, 3H) 2.64-2.81 (m, 2H) 2.92-3.01 (m, 2H) 3.20 (s, 3H) 3.52-3.63 (m, 1H) 3.70 (s, 3H) 3.98 (s, 2H) 4.33 (s, 2H) 4.94-5.11 (m, 1H) 7.31-7.52 (m, 6H) 7.58-7.68 (m, 1H) 7.74 (dd, J=7.72, 0.94 Hz, 1H)

REFERENCE EXAMPLE 217

4'-({2-methyl-5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile 2-[(trans-4-{6-[(2'-Cyanobiphenyl-4-yl)methyl]-2-methyl-5-oxo-7-propyl[1,2,4]triazolo[1,5-a]pyrimidin-4(5H)-yl}cyclohexyl)oxy]-N-methoxy-N-methylacetamide (1 g) was dissolved in tetrahydrofuran (15 mL), and methylmagnesium bromide (1.0 M tetrahydrofuran solution, 1.7 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.56 g, 60%).

$^1$H NMR (300 MHz, CHLOROFORM-d) δ1.05 (t, J=7.3 Hz, 3H) 1.41-1.58 (m, 2H) 1.66-1.84 (m, 4H) 2.13-2.24 (m, 5H) 2.43 (s, 3H) 2.62-2.79 (m, 2H) 2.94-3.02 (m, 2H) 3.40-3.53 (m, 1H) 3.98 (s, 2H) 4.10 (s, 2H) 4.94-5.09 (m, 1H) 7.32-7.51 (m, 6H) 7.59-7.66 (m, 1H) 7.75 (dd, J=7.7, 0.9 Hz, 1H)

REFERENCE EXAMPLE 218

4'-[(4-{trans-4-[(2-{[tert-butyl(dimethyl)silyl]oxy}prop-2-en-1-yl)oxy]cyclohexyl}-2-methyl-5-oxo-7-propyl-4,5-dihydro[1,2,4]triazolo[1,5-a]pyrimidin-6-yl)methyl]biphenyl-2-carbonitrile To a solution (10 mL) of 4'-({2-methyl-5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.56 g) and diisopropylethylamine (0.36 mL) in methylene chloride was added tert-butyl(dimethyl)silyl trifluoromethanesulfonate (0.36 mL), and the mixture was stirred at room temperature for 3 hr. The reaction mixture was diluted with ethyl acetate, washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a colorless solid (0.5 g, 72%).

$^1$H NMR (300 MHz, CHLOROFORM-d) δ0.18 (s, 6H) 0.94 (s, 9H) 1.05 (t, J=7.3 Hz, 3H) 1.39-1.56 (m, 2H) 1.65-1.82 (m, 4H) 2.13-2.23 (m, 2H) 2.44 (s, 3H) 2.63-2.80 (m, 2H) 2.93-3.03 (m, 2H) 3.42-3.56 (m, 1H) 3.86 (s, 2H) 3.99 (s, 2H) 4.24 (s, 1H) 4.39 (s, 1H) 4.92-5.09 (m, 1H) 7.33-7.51 (m, 6H) 7.59-7.67 (m, 1H) 7.75 (dd, J=7.7, 0.9 Hz, 1H)

REFERENCE EXAMPLE 219

4'-[(4-{trans-4-[(1-{[tert-butyl(dimethyl)silyl]oxy}cyclopropyl)methoxy]cyclohexyl}-2-methyl-5-oxo-7-propyl-4,5-dihydro[1,2,4]triazolo[1,5-a]pyrimidin-6-yl)methyl]biphenyl-2-carbonitrile To a solution (10 mL) of diethylzinc (1.0 M hexane solution, 5.3 mL) in methylene chloride was added a solution (5 mL) of chloro(iodo)methane (0.38 mL) in methylene chloride at 0° C., and the mixture was stirred at the same temperature for 10 min. A solution (5 mL) of 4'-[(4-{trans-4-[(2-{[tert-butyl(dimethyl)silyl]oxy}prop-2-en-1-yl)oxy]cyclohexyl}-2-methyl-5-oxo-7-propyl-4,5-dihydro[1,2,4]triazolo[1,5-a]pyrimidin-6-yl)methyl]biphenyl-2-carbonitrile (0.5 g) in methylene chloride was added to the reaction mixture, and the mixture was further stirred at room temperature for 3 hr. Saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.26 g, 52%).

$^1$H NMR (300 MHz, CHLOROFORM-d) δ0.13 (s, 6H) 0.55-0.62 (m, 2H) 0.70-0.77 (m, 2H) 0.85 (s, 9H) 1.05 (t, J=7.3 Hz, 3H) 1.37-1.55 (m, 2H) 1.66-1.83 (m, 4H) 2.13-2.23 (m, 2H) 2.44 (s, 3H) 2.62-2.80 (m, 2H) 2.93-3.02 (m, 2H)

3.37-3.49 (m, 3H) 3.99 (s, 2H) 5.00 (t, J=12.6 Hz, 1H) 7.33-7.51 (m, 6H) 7.59-7.67 (m, 1H) 7.72-7.78 (m, 1H)

REFERENCE EXAMPLE 220

4'-({4-[trans-4-(2-{[tert-butyl(dimethyl)silyl]oxy}propoxy)cyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({2-methyl-5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.33 g), methanol (5 mL) and tetrahydrofuran (5 mL) was added sodium borohydride (0.034 g), and the mixture was stirred at room temperature for 2 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. The obtained residue was dissolved in tetrahydrofuran (5 mL), 2,6-lutidine (0.11 mL) and tert-butyl(dimethyl)silyl trifluoromethanesulfonate (0.21 mL) were added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The obtained residue was purified by silica gel column chromatography to give the title compound as a colorless solid (0.27 g, 67%).

$^1$H NMR (300 MHz, CHLOROFORM-d) δ0.08 (s, 6H) 0.90 (s, 9H) 1.05 (t, J=7.3 Hz, 3H) 1.15 (d, J=6.2 Hz, 3H) 1.35-1.51 (m, 2H) 1.64-1.82 (m, 4H) 2.13-2.23 (m, 2H) 2.44 (s, 3H) 2.62-2.80 (m, 2H) 2.92-3.02 (m, 2H) 3.24-3.31 (m, 1H) 3.37-3.49 (m, 2H) 3.87-3.96 (m, 1H) 3.99 (s, 2H) 5.00 (t, J=12.2 Hz, 1H) 7.33-7.52 (m, 6H) 7.59-7.66 (m, 1H) 7.75 (dd, J=7.7, 0.9 Hz, 1H)

REFERENCE EXAMPLE 221

4'-({2-methyl-5-oxo-4-[trans-4-(2-oxobutoxy)cyclohexyl]-7-propyl-4,5-dihydro[1,2,4]triazolo[1,5-a]pyrimidin-6-yl}methyl)biphenyl-2-carbonitrile 2-[(trans-4-{6-[(2'-Cyanobiphenyl-4-yl)methyl]-2-methyl-5-oxo-7-propyl[1,2,4]triazolo[1,5-a]pyrimidin-4(5H)-yl}cyclohexyl)oxy]-N-methoxy-N-methylacetamide (0.3 g) was dissolved in tetrahydrofuran (10 mL), and ethylmagnesium bromide (3.0 M diethyl ether solution, 0.52 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.34 g, 100%).

$^1$H NMR (300 MHz, CHLOROFORM-d) δ1.01-1.11 (m, 6H) 1.41-1.85 (m, 6H) 2.14-2.24 (m, 2H) 2.43 (s, 3H) 2.52 (q, J=7.2 Hz, 2H) 2.63-2.81 (m, 2H) 2.93-3.02 (m, 2H) 3.39-3.53 (m, 1H) 3.98 (s, 2H) 4.11 (s, 2H) 4.95-5.08 (m, 1H) 7.33-7.50 (m, 6H) 7.59-7.66 (m, 1H) 7.74 (dd, J=7.7, 0.9 Hz, 1H)

REFERENCE EXAMPLE 222

4'-({4-[trans-4-(2-{[tert-butyl(dimethyl)silyl]oxy}butoxy)cyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({2-methyl-5-oxo-4-[trans-4-(2-oxobutoxy)cyclohexyl]-7-propyl-4,5-dihydro[1,2,4]triazolo[1,5-a]pyrimidin-6-yl}methyl)biphenyl-2-carbonitrile (0.34 g), methanol (5 mL) and tetrahydrofuran (5 mL) was added sodium borohydride (0.035 g), and the mixture was stirred at room temperature for 2 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. The obtained residue was dissolved in tetrahydrofuran (5 mL), 2,6-lutidine (0.10 mL) and tert-butyl(dimethyl)silyl trifluoromethanesulfonate (0.21 mL) were added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The obtained residue was purified by silica gel column chromatography to give the title compound as a colorless solid (0.29 g, 71%).

$^1$H NMR (300 MHz, CHLOROFORM-d) δ0.08 (s, 6H) 0.90 (s, 12H) 1.05 (t, J=7.3 Hz, 3H) 1.32-1.81 (m, 8H) 2.12-2.23 (m, 2H) 2.44 (s, 3H) 2.63-2.80 (m, 2H) 2.94-3.02 (m, 2H) 3.30-3.48 (m, 3H) 3.66-3.75 (m, 1H) 3.99 (s, 2H) 4.93-5.07 (m, 1H) 7.33-7.53 (m, 6H) 7.59-7.67 (m, 1H) 7.72-7.78 (m, 1H)

REFERENCE EXAMPLE 223

4'-({4-[trans-4-(2-ethyl-2-hydroxybutoxy)cyclohexyl]-5-oxo-7-propyl-4,5-dihydro[1,2,4]triazolo[1,5-a]pyrimidin-6-yl}methyl)biphenyl-2-carbonitrile Ethyl[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetate (0.5 g) was dissolved in tetrahydrofuran (10 mL), and ethylmagnesium bromide (3.0 M diethyl ether solution, 0.75 mL) was added at 0° C. After stirring at the same temperature for 16 hr, 1 N hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.25 g, 49%).

$^1$H NMR (300 MHz, CHLOROFORM-d) δ0.87 (t, J=7.5 Hz, 6H) 1.06 (t, J=7.3 Hz, 3H) 1.34-1.56 (m, 6H) 1.65-1.84 (m, 4H) 2.11-2.22 (m, 2H) 2.60-2.78 (m, 2H) 2.97-3.08 (m, 2H) 3.34 (s, 2H) 3.42 (t, J=11.0 Hz, 1H) 4.01 (s, 2H) 5.00-5.13 (m, 1H) 7.34-7.52 (m, 6H) 7.58-7.66 (m, 1H) 7.75 (dd, J=7.8, 0.8 Hz, 1H) 7.91 (s, 1H)

REFERENCE EXAMPLE 224

4'-{[4-(6,13-dioxadispiro[3.2.5.2]tetradec-10-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]thiazolo[1,5-a]pyrimidin-6-yl]methyl}biphenyl-2-carbonitrile (3 g), cyclobutane-1,1-diyldimethanol (1.1 g), p-toluenesulfonic acid monohydrate (0.036 g) and toluene (60 mL) was subjected to an azeotropic dehydration reaction by stirring at 110° C. for 16 hr in a reaction vessel equipped with a Dean-stark trap. The reaction mixture was concentrated under reduced pressure, and the obtained residue was purified by silica gel column chromatography to give the title compound as a colorless solid (3.7 g, 100%).

$^1$H NMR (300 MHz, CHLOROFORM-d) δ 0.95 (t, J=7.3 Hz, 3H) 1.29-1.43 (m, 2H) 1.46-1.65 (m, 4H) 1.67-1.91 (m, 6H) 2.22-2.34 (m, 2H) 2.60-2.80 (m, 2H) 2.91-3.02 (m, 2H) 3.70 (d, J=8.1 Hz, 4H) 3.98 (s, 2H) 4.94 (t, J=12.2 Hz, 1H) 7.37-7.43 (m, 2H) 7.45-7.63 (m, 4H) 7.73-7.82 (m, 1H) 7.92 (d, J=1.1 Hz, 1H) 8.20 (s, 1H)

REFERENCE EXAMPLE 225

4'-{[4-(trans-4-{[1-(hydroxymethyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(6,13-dioxadispiro[3.2.5.2]tetradec-10-yl)-5-oxo-7-propyl-4,5-dihydro[1,2,4]triazolo[1,5-a]pyrimidin-6-yl]methyl}biphenyl-2-carbonitrile (3.7 g), sodium cyanoborohydride (1.3 g), boron trifluoride-diethyl ether complex (2.5 mL) and tetrahydrofuran (50 mL) was stirred at 70° C. for 16 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (1.8 g, 47%).

$^1$H NMR (300 MHz, CHLOROFORM-d) δ 0.95 (t, J=7.3 Hz, 3H), 1.19-1.36 (m, 2H), 1.48-1.86 (m, 10H), 2.05-2.16 (m, 2H), 2.52-2.69 (m, 2H), 2.92-3.02 (m, 2H), 3.22-3.37 (m, 3H), 3.39 (s, 2H), 4.00 (s, 2H), 4.45 (t, J=5.0 Hz, 1H), 4.82-5.00 (m, 1H), 7.36-7.43 (m, 2H), 7.46-7.63 (m, 4H), 7.72-7.83 (m, 1H), 7.93 (dd, J=7.7, 0.9 Hz, 1H), 8.19 (s, 1H)

REFERENCE EXAMPLE 226

4'-[(4-{trans-4-[(1-formylcyclobutyl)methoxy]cyclohexyl}-5-oxo-7-propyl-4,5-dihydro[1,2,4]triazolo[1,5-a]pyrimidin-6-yl)methyl]biphenyl-2-carbonitrile To a mixture of 4'-{[4-(trans-4-{[1-(hydroxymethyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile (0.7 g), triethylamine (0.86 mL) and dimethyl sulfoxide (10 mL) was added a solution (5 mL) of sulfur trioxide-pyridine complex (0.59 g) in dimethyl sulfoxide at room temperature, and the mixture was stirred for 3 hr. The reaction mixture was poured into 1 N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.7 g, 100%).

$^1$H NMR (300 MHz, CHLOROFORM-d) δ 0.95 (t, J=7.3 Hz, 3H), 1.20-1.37 (m, 2H), 1.53-1.96 (m, 8H), 2.03-2.23 (m, 4H), 2.52-2.68 (m, 2H), 2.92-3.01 (m, 2H), 3.25-3.44 (m, 3H), 3.99 (s, 2H), 4.90 (t, J=12.2 Hz, 1H), 7.38-7.43 (m, 2H), 7.46-7.62 (m, 4H), 7.73-7.82 (m, 1H), 7.93 (dd, J=7.7, 0.9 Hz, 1H), 8.19 (s, 1H), 9.57 (s, 1H)

REFERENCE EXAMPLE 227

1-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]methyl}cyclobutanecarboxylic acid A mixture of 4'-[(4-{trans-4-[(1-formylcyclobutyl)methoxy]cyclohexyl}-5-oxo-7-propyl-4,5-dihydro[1,2,4]triazolo[1,5-a]pyrimidin-6-yl)methyl]biphenyl-2-carbonitrile (0.7 g), sodium chlorite (0.21 g), sodium dihydrogen phosphate (0.15 g), 2-methyl-2-butene (0.53 mL), n-butanol (10 mL), tetrahydrofuran (5 mL) and water (5 mL) was stirred at room temperature for 16 hr. The reaction mixture was extracted with 1 N hydrochloric acid and ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.47 g, 65%).

$^1$H NMR (300 MHz, CHLOROFORM-d) δ 0.95 (t, J=7.3 Hz, 3H), 1.19-1.36 (m, 2H), 1.53-1.94 (m, 8H), 2.03-2.29 (m, 4H), 2.52-2.66 (m, 2H), 2.92-3.01 (m, 2H), 3.25-3.39 (m, 1H), 3.68 (s, 2H), 3.99 (s, 2H), 4.83-4.97 (m, 1H), 7.37-7.44 (m, 2H), 7.45-7.61 (m, 4H), 7.72-7.82 (m, 1H), 7.92 (d, J=0.9 Hz, 1H), 8.19 (s, 1H), 12.13 (br.s., 1H)

REFERENCE EXAMPLE 228

1-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]methyl}cyclobutanecarboxamide A mixture of 1-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]methyl}cyclobutanecarboxylic acid (0.4 g), 1-hydroxybenzotriazole ammonium salt (0.24 g), 1-ethyl-3-(3-dimethylaminopropyl)carbodiimide hydrochloride (0.26 g) and N,N-dimethylformamide (10 mL) was stirred at room temperature for 15 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless solid (0.37 g, 93%).

$^1$H NMR (300 MHz, DMSO-d$_6$) δ 0.95 (t, J=7.2 Hz, 3H), 1.21-1.39 (m, 2H), 1.51-1.92 (m, 8H), 2.04-2.28 (m, 4H), 2.52-2.66 (m, 2H), 2.91-3.01 (m, 2H), 3.26-3.40 (m, 1H), 3.64 (s, 2H), 3.99 (s, 2H), 4.91 (t, J=12.3 Hz, 1H), 6.80 (s, 1H), 6.93 (s, 1H), 7.37-7.43 (m, 2H), 7.45-7.62 (m, 4H), 7.77 (t, J=7.8 Hz, 1H), 7.93 (t, J=7.6 Hz, 1H), 8.19 (s, 1H)

REFERENCE EXAMPLE 229

4'-{[4-(trans-4-{[1-({[tert-butyl(dimethyl)silyl]oxy}methyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile To a mixture of 4'-{[4-(trans-4-{[1-(hydroxymethyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile (0.3 g), 2,6-lutidine (0.14 mL) and tetrahydrofuran (10 mL) was added tert-butyl(dimethyl)silyl trifluoromethanesulfonate (0.18 mL), and the mixture was stirred at room temperature for 5 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.31 g, 86%).

$^1$H NMR (300 MHz, DMSO-d$_6$) δ 0.05 (s, 6H), 0.88 (s, 9H), 0.94 (t, J=7.4 Hz, 3H), 1.21-1.36 (m, 2H), 1.51-1.86 (m, 10H), 2.04-2.15 (m, 2H), 2.52-2.66 (m, 2H), 2.91-3.02 (m,

2H), 3.21-3.30 (m, 1H), 3.40 (s, 2H), 3.51 (s, 2H), 3.99 (s, 2H), 4.91 (t, J=12.1 Hz, 1H), 7.37-7.43 (m, 2H), 7.46-7.62 (m, 4H), 7.73-7.83 (m, 1H), 7.93 (d, J=6.8 Hz, 1H), 8.18 (s, 1H)

REFERENCE EXAMPLE 230

4'-{[4-(1,4-dioxaspiro[4.5]dec-8-yl)-5-oxo-7-propyl-4,5-dihydro[1,2,4]triazolo[1,5-a]pyrimidin-6-yl]methyl}-2'-fluorobiphenyl-2-carbonitrile A mixture of ethyl 2-[(2'-cyano-2-fluorobiphenyl-4-yl)methyl]-3-oxohexanoate (3.3 g) and N-(1,4-dioxaspiro[4.5]dec-8-yl)-4H-1,2,4-triazol-3-amine (1 g) was stirred at 250° C. for 1 hr under microwave irradiation. The reaction mixture was purified by silica gel column chromatography to give the title compound as a colorless solid (1.2 g, 50%).

$^1$H NMR (300 MHz, DMSO-$d_6$) δ0.96 (t, J=7.3 Hz, 3H), 1.52-1.84 (m, 8H), 2.71-2.88 (m, 2H), 2.92-3.01 (m, 2H), 3.83-3.97 (m, 4H), 4.02 (s, 2H), 4.98 (t, J=12.5 Hz, 1H), 7.24-7.45 (m, 3H), 7.55-7.66 (m, 2H), 7.81 (t, J=7.1 Hz, 1H), 7.96 (dd, J=7.7, 0.9 Hz, 1H), 8.20 (s, 1H)

REFERENCE EXAMPLE 231

2'-fluoro-4'-{[4-(4-hydroxycyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}-2'-fluorobiphenyl-2-carbonitrile (1.2 g), 3N hydrochloric acid (50 mL) and tetrahydrofuran (50 mL) was stirred at 80° C. for 16 hr. The reaction mixture was diluted with ethyl acetate, washed with saturated brine, and dried over anhydrous magnesium sulfate. The solvent was evaporated under reduced pressure. The obtained residue was dissolved in tetrahydrofuran (10 mL) and methanol (10 mL), sodium borohydride (0.17 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.95 g, 88%).

$^1$H NMR (300 MHz, CHLOROFORM-d) δ0.95 (t, J=7.3 Hz, 3H) 1.21-1.71 (m, 6H) 1.88-1.99 (m, 2H) 2.52-2.65 (m, 2H) 2.92-3.01 (m, 2H) 3.41-3.54 (m, 1H) 4.02 (s, 2H) 4.64 (d, J=4.5 Hz, 1H) 4.87 (t, J=12.2 Hz, 1H) 7.21-7.45 (m, 3H) 7.55-7.66 (m, 2H) 7.76-7.85 (m, 1H) 7.96 (d, J=7.7, 0.9 Hz, 1H) 8.19 (s, 1H)

REFERENCE EXAMPLE 232

2'-fluoro-4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile To a mixture of 2'-fluoro-4'-{[4-(4-hydroxycyclohexyl)-5-oxo-7-propyl-4,5-dihydro[1,2,4]triazolo[1,5-a]pyrimidin-6-yl]methyl}biphenyl-2-carbonitrile (0.95 g), rhodium(I) acetate (0.007 g) and toluene (20 mL) was added dropwise ethyl diazoacetate (0.96 mL) at 80° C., and the mixture was stirred at the same temperature for 1 hr. The reaction mixture was concentrated, and the obtained residue was purified by silica gel column chromatography. The obtained residue was dissolved in tetrahydrofuran (15 mL), and methylmagnesium bromide (1.0 M tetrahydrofuran solution, 5.8 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.25 g, 23%).

$^1$H NMR (300 MHz, DMSO-$d_6$) δ0.95 (t, J=7.3 Hz, 3H), 1.07 (s, 6H), 1.22-1.38 (m, 2H), 1.53-1.77 (m, 4H), 2.06-2.15 (m, 2H), 2.52-2.68 (m, 2H), 2.92-3.01 (m, 2H), 3.20 (s, 2H), 3.25-3.37 (m, 1H), 4.02 (s, 2H), 4.22 (s, 1H), 4.82-4.99 (m, 1H), 7.22-7.45 (m, 3H), 7.54-7.66 (m, 2H), 7.80 (t, J=7.7 Hz, 1H), 7.96 (dd, J=7.7, 0.9 Hz, 1H), 8.19 (s, 1H)

REFERENCE EXAMPLE 233

4'-({7-butyl-4-[trans-4-(2-hydroxy-2-methylpropoxy)cyclohexyl]-5-oxo-4,5-dihydro[1,2,4]triazolo[1,5-a]pyrimidin-6-yl}methyl)biphenyl-2-carbonitrile To a mixture of 4'-{[7-butyl-4-(4-hydroxycyclohexyl)-5-oxo-4,5-dihydro[1,2,4]triazolo[1,5-a]pyrimidin-6-yl]methyl}biphenyl-2-carbonitrile (0.61 g), rhodium(I) acetate (0.006 g) and toluene (30 mL) was added dropwise ethyl diazoacetate (0.62 mL) at 80° C., and the mixture was stirred at the same temperature for 1 hr. The reaction mixture was concentrated under reduced pressure, and the obtained residue was purified by silica gel column chromatography. The obtained residue was dissolved in tetrahydrofuran (15 mL), and methylmagnesium bromide (1.0 M tetrahydrofuran solution, 1.9 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.22 g, 31%).

$^1$H NMR (300 MHz, DMSO-$d_6$) δ0.82 (t, J=7.2 Hz, 3H), 1.07 (s, 6H), 1.21-1.56 (m, 6H), 1.65-1.76 (m, 2H), 2.06-2.16 (m, 2H), 2.53-2.65 (m, 2H), 2.91-3.03 (m, 2H), 3.20 (s, 2H), 3.99 (s, 2H), 4.23 (s, 1H), 4.92 (t, J=12.4 Hz, 1H), 7.37-7.43 (m, 2H), 7.46-7.62 (m, 4H), 7.74-7.81 (m, 1H), 7.91 (d, J=0.9 Hz, 1H), 8.18 (s, 1H)

REFERENCE EXAMPLE 234

3'-fluoro-4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile To a mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (0.71 g), rhodium(I) acetate (0.006 g) and toluene (30 mL) was added dropwise ethyl diazoacetate (0.71 mL) at 80° C., and the mixture was stirred at the same temperature for 1 hr. The reaction mixture was concentrated under reduced pressure, and the obtained residue was purified by silica gel column chromatography. The obtained residue was dissolved in tetrahydrofuran (15 mL), and methylmagnesium bromide (1.0 M tetrahydrofuran solution, 2.2 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.18 g, 22%).

$^1$H NMR (300 MHz, DMSO-$d_6$) δ0.95 (t, J=7.3 Hz, 3H) 1.07 (s, 6H) 1.21-1.37 (m, 2H) 1.56-1.75 (m, 4H) 2.04-2.16 (m, 2H) 2.51-2.65 (m, 2H) 2.92-3.01 (m, 2H) 3.19 (s, 2H) 3.24-3.35 (m, 1H) 3.97 (s, 2H) 4.22 (s, 1H) 4.81-4.97 (m, 1H) 7.25-7.49 (m, 3H) 7.55-7.68 (m, 2H) 7.75-7.83 (m, 1H) 7.95 (dd, J=7.7, 0.9 Hz, 1H) 8.20 (s, 1H)

REFERENCE EXAMPLE 235

4'-[(4-{trans-4-[2-(methylsulfanyl)ethoxy]cyclohexyl}-5-oxo-7-propyl-4,5-dihydro[1,2,4]triazolo[1,5-a]pyrimidin-6-yl)methyl]biphenyl-2-carbonitrile A mixture of 4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (0.2 g), p-toluenesulfonyl chloride (0.089 g), triethylamine (0.066 mL), 4-dimethylaminopyridine (0.005 g) and acetonitrile (10 mL) was stirred for 4 hr. The reaction mixture was washed with water and then with saturated brine, and dried over anhydrous magnesium sulfate. The solvent was evaporated under reduced pressure. The obtained residue was dissolved in acetonitrile (15 mL), sodium thiomethylate (15% aqueous solution, 1.8 g) was added, and the mixture was stirred at 50° C. for 16 hr. The reaction mixture was diluted with ethyl acetate, washed with water and then with saturated brine, and dried over anhydrous magnesium sulfate. The solvent was evaporated under reduced pressure. The obtained residue was purified by silica gel column chromatography to give the title compound as a colorless solid (0.2 g, 94%).

$^1$H NMR (300 MHz, DMSO-$d_6$) δ0.95 (t, J=7.3 Hz, 3H), 1.21-1.37 (m, 2H), 1.52-1.76 (m, 4H), 2.05-2.15 (m, 5H), 2.55-2.68 (m, 4H), 2.91-3.02 (m, 2H), 3.32-3.41 (m, 1H), 3.61 (t, J=6.8 Hz, 2H), 3.99 (s, 2H), 4.82-4.99 (m, 1H), 7.38-7.44 (m, 2H), 7.46-7.62 (m, 4H), 7.73-7.82 (m, 1H), 7.92 (d, J=0.8 Hz, 1H), 8.18 (s, 1H)

REFERENCE EXAMPLE 236

2-[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]-1,1-dimethylethyl acetate A mixture of 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.2 g), acetic anhydride (5 mL) and pyridine (5 mL) was stirred at 120° C. for 6 hr. The reaction mixture was diluted with ethyl acetate, washed with 1 N hydrochloric acid and then with saturated brine, and dried over anhydrous magnesium sulfate. The solvent was evaporated under reduced pressure. The obtained residue was purified by silica gel column chromatography to give the title compound as a colorless solid (0.1 g, 47%).

$^1$H NMR (300 MHz, DMSO-$d_6$) δ0.94 (t, J=7.3 Hz, 3H), 1.22-1.39 (m, 8H), 1.51-1.74 (m, 4H), 1.93 (s, 3H), 2.03-2.14 (m, 2H), 2.36 (s, 3H), 2.52-2.63 (m, 2H), 2.86-2.96 (m, 2H), 3.23-3.31 (m, 1H), 3.57 (s, 2H), 3.97 (s, 2H), 4.81-4.95 (m, 1H), 7.35-7.43 (m, 2H), 7.45-7.62 (m, 4H), 7.73-7.81 (m, 1H), 7.90-7.96 (m, 1H)

REFERENCE EXAMPLE 237

4'-{[7-butyl-4-(1,4-dioxaspiro[4.5]dec-8-yl)-2-methyl-5-oxo-4,5-dihydro[1,2,4]triazolo[1,5-a]pyrimidin-6-yl]methyl}biphenyl-2-carbonitrile A mixture of methyl 2-[(2'-cyanobiphenyl-4-yl)methyl]-3-oxoheptanoate (15 g), N-(1,4-dioxaspiro[4.5]dec-8-yl)-5-methyl-4H-1,2,4-triazol-3-amine (5 g), 1,8-diazabicyclo[5.4.0]undec-7-ene (1.4 mL) and N,N-diethylaniline (80 mL) was stirred at 180° C. for 16 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a colorless solid (6.4 g, 57%).

$^1$H NMR (300 MHz, DMSO-$d_6$) δ0.83 (t, J=7.2 Hz, 3H), 1.28-1.84 (m, 10H), 2.37 (s, 3H), 2.68-2.87 (m, 2H), 2.88-2.97 (m, 2H), 3.82-4.00 (m, 6H), 4.93 (t, J=12.3 Hz, 1H), 7.36-7.42 (m, 2H), 7.44-7.61 (m, 4H), 7.73-7.83 (m, 1H), 7.93 (d, J=8.0 Hz, 1H)

REFERENCE EXAMPLE 238

4'-{[7-butyl-4-(trans-4-hydroxycyclohexyl)-2-methyl-5-oxo-4,5-dihydro[1,2,4]triazolo[1,5-a]pyrimidin-6-yl]methyl}biphenyl-2-carbonitrile A mixture of 4'-{[7-butyl-4-(1,4-dioxaspiro[4.5]dec-8-yl)-2-methyl-5-oxo-4,5-dihydro[1,2,4]triazolo[1,5-a]pyrimidin-6-yl]methyl}biphenyl-2-carbonitrile (6.4 g), 3N hydrochloric acid (40 mL) and tetrahydrofuran (40 mL) was stirred at 80° C. for 16 hr. The reaction mixture was diluted with ethyl acetate, washed with saturated brine, and dried over anhydrous magnesium sulfate. The solvent was evaporated under reduced pressure. The obtained residue was dissolved in tetrahydrofuran (30 mL) and methanol (30 mL), sodium borohydride (0.67 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (4.9 g, 83%).

$^1$H NMR (300 MHz, DMSO-$d_6$) δ0.83 (t, J=7.2 Hz, 3H), 1.19-1.69 (m, 8H), 1.88-2.00 (m, 2H), 2.36 (s, 3H), 2.51-2.64 (m, 2H), 2.87-2.97 (m, 2H), 3.39-3.55 (m, 1H), 3.96 (s, 2H), 4.65 (d, J=4.2 Hz, 1H), 4.83 (t, J=11.9 Hz, 1H), 7.34-7.42 (m, 2H), 7.45-7.62 (m, 4H), 7.78 (t, J=7.8 Hz, 1H), 7.93 (d, J=7.2 Hz, 1H)

REFERENCE EXAMPLE 239

4'-({7-butyl-4-[trans-4-(2-hydroxy-1,2-dimethylpropoxy)cyclohexyl]-2-methyl-5-oxo-4,5-dihydro[1,2,4]triazolo[1,5-a]pyrimidin-6-yl}methyl)biphenyl-2-carbonitrile To a mixture of 4'-{[7-butyl-4-(trans-4-hydroxycyclohexyl)-2-methyl-5-oxo-4,5-dihydro[1,2,4]triazolo[1,5-a]pyrimidin-6-yl]methyl}biphenyl-2-carbonitrile (0.45 g), rhodium(I) acetate (0.004 g) and toluene (10 mL) was added dropwise 3-ethoxy-2-methyl-3-oxopropane-1-diazonium (0.72 L) at 80° C., and the mixture was stirred at the same temperature for 1 hr. The reaction mixture was concentrated under reduced pressure, and the obtained residue was purified by silica gel column chromatography. The obtained residue was dissolved in tetrahydrofuran (10 mL), and methylmagnesium bromide (1.0 M tetrahydrofuran solution, 2.5 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.33 g, 63%).

$^1$H NMR (300 MHz, DMSO-$d_6$) δ0.91-1.09 (m, 12H), 1.21-1.73 (m, 8H), 2.01-2.15 (m, 2H), 2.36 (s, 3H), 2.52-2.66 (m, 2H), 2.85-2.97 (m, 2H), 3.25 (q, J=6.1 Hz, 1H), 3.33-3.42 (m, 1H), 3.97 (s, 1H), 4.07 (s, 1H), 4.79-4.93 (m, 1H), 7.38 (d, J=8.3 Hz, 2H), 7.45-7.61 (m, 4H), 7.73-7.82 (m, 1H), 7.93 (d, J=7.6 Hz, 1H)

REFERENCE EXAMPLE 240

3'-fluoro-4'-{[4-(trans-4-hydroxycyclohexyl)-2-methyl-5-oxo-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}-3'-fluorobiphenyl-2-carbonitrile (14 g), 3N hydrochloric acid (50 mL) and tetrahydrofuran (50 mL) was stirred at 80° C. for 16 hr. The reaction mixture was diluted with ethyl acetate, washed with saturated brine, and dried over anhydrous magnesium sulfate. The solvent was evaporated under reduced pressure. The obtained residue was dissolved in tetrahydrofuran (40 mL) and methanol (40 mL), sodium borohydride (1.5 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (12 g, 93%).

$^1$H NMR (300 MHz, DMSO-$d_6$) δ0.94 (t, J=7.2 Hz, 3H), 1.12-1.98 (m, 8H), 2.37 (s, 3H), 2.50-2.62 (m, 2H), 2.85-2.98 (m, 2H), 3.38-3.55 (m, 1H), 3.94 (s, 2H), 4.64 (d, J=4.5 Hz, 1H), 4.81 (t, J=12.1 Hz, 1H), 7.24-7.38 (m, 2H), 7.45 (d, J=11.0 Hz, 1H), 7.54-7.67 (m, 2H), 7.79 (t, J=7.8 Hz, 1H), 7.95 (d, J=7.6 Hz, 1H)

REFERENCE EXAMPLE 241

3'-fluoro-4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile To a mixture of 3'-fluoro-4'-{[4-(trans-4-hydroxycyclohexyl)-2-methyl-5-oxo-7-propyl-4,5-dihydro[1,2,4]triazolo[1,5-a]pyrimidin-6-yl]methyl}biphenyl-2-carbonitrile (0.46 g), rhodium(I) acetate (0.004 g) and toluene (10 mL) was added dropwise 3-ethoxy-2-methyl-3-oxopropane-1-diazonium (0.69 mL) at 80° C., and the mixture was stirred at the same temperature for 1 hr. The reaction mixture was concentrated, and the obtained residue was purified by silica gel column chromatography. The obtained residue was dissolved in tetrahydrofuran (10 mL), and methylmagnesium bromide (1.0 M tetrahydrofuran solution, 2.5 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.27 g, 50%).

$^1$H NMR (300 MHz, DMSO-$d_6$) δ0.90-1.10 (m, 12H), 1.21-1.38 (m, 2H), 1.53-1.72 (m, 4H), 2.00-2.15 (m, 2H), 2.37 (s, 3H), 2.52-2.65 (m, 2H), 2.86-2.96 (m, 2H), 3.24 (q, J=6.4 Hz, 1H), 3.34-3.42 (m, 1H), 3.94 (s, 2H), 4.06 (s, 1H), 7.25-7.66 (m, 5H), 7.76-7.82 (m, 1H), 7.95 (d, J=7.6 Hz, 1H)

REFERENCE EXAMPLE 242

2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]propanoic acid To a mixture of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (4 g), rhodium(I) acetate (0.028 g) and toluene (70 mL) was added dropwise a solution (10 mL) of 3-ethoxy-2-methyl-3-oxopropane-1-diazonium (5.5 mL) in toluene at 80° C., and the mixture was stirred at the same temperature for 1 hr. The reaction mixture was concentrated, and the obtained residue was purified by silica gel column chromatography. The obtained residue was dissolved in tetrahydrofuran (20 mL) and methanol (20 mL), and 1N aqueous sodium hydroxide solution (20 mL) was added. The reaction mixture was stirred for 1 hr, 1N aqueous hydrochloric acid solution was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (4.1 g, 89%).

$^1$H NMR (300 MHz, DMSO-$d_6$) δ0.95 (t, J=7.4 Hz, 3H), 1.26 (d, J=6.8 Hz, 3H), 1.37-1.75 (m, 6H), 2.20-2.18 (m, 2H), 2.51-2.65 (m, 2H), 2.91-3.02 (m, 2H), 3.33-3.44 (m, 1H), 3.99 (s, 2H), 4.05-4.14 (m, 1H), 4.91 (t, J=12.1 Hz, 1H), 7.38-7.44 (m, 2H), 7.46-7.62 (m, 4H), 7.73-7.81 (m, 1H), 7.93 (d, J=7.6 Hz, 1H), 8.18 (s, 1H), 12.47 (br.s., 1H)

REFERENCE EXAMPLE 243

2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]propanamide A mixture of 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]propanoic acid (1.1 g), 1-hydroxybenzotriazole ammonium salt (0.42 g), 1-ethyl-3-(3-dimethylaminopropyl)carbodiimide hydrochloride (0.47 g) and N,N-dimethylformamide (10 mL) was stirred at room temperature for 15 hr. The reaction mixture was diluted with ethyl acetate, washed with dilute hydrochloric acid and then with saturated brine, and dried over anhydrous magnesium sulfate. The solvent was evaporated under reduced pressure, and the residue was purified by silica gel column chromatography to give the title compound as a colorless solid (0.8 g, 73%).

$^1$H NMR (300 MHz, DMSO-d$_6$) δ0.95 (t, J=7.3 Hz, 3H), 1.21 (d, J=6.6 Hz, 3H), 1.26-1.77 (m, 6H), 2.04-2.17 (m, 2H), 2.52-2.67 (m, 2H), 2.93-3.02 (m, 2H), 3.30-3.40 (m, 1H), 3.90 (q, J=6.8 Hz, 1H), 4.00 (s, 2H), 4.85-4.98 (m, 1H), 7.14 (s, 2H), 7.38-7.44 (m, 2H), 7.45-7.62 (m, 4H), 7.74-7.82 (m, 1H), 7.89-7.98 (m, 1H), 8.18 (s, 1H)

REFERENCE EXAMPLE 244

3'-fluoro-4'-{[5-oxo-4-(4-oxocyclohexyl)-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-5-oxo-7-propyl-4,5-dihydro[1,2,4]triazolo[1,5-a]pyrimidin-6-yl]methyl}-3'-fluorobiphenyl-2-carbonitrile (3.1 g), p-toluenesulfonic acid monohydrate (0.1 g), methanol (50 mL) and tetrahydrofuran (50 mL) was stirred at 60° C. for 16 hr. The reaction mixture was diluted with ethyl acetate, washed with saturated brine, and dried over anhydrous magnesium sulfate. The solvent was evaporated under reduced pressure. The obtained residue was dissolved in acetone (20 mL), 1 N hydrochloric acid (20 mL) was added, and the mixture was stirred at room temperature for 2 hr. The reaction mixture was diluted with ethyl acetate, washed with saturated brine, and dried over anhydrous magnesium sulfate. The solvent was evaporated under reduced pressure and the residue was purified by silica gel column chromatography to give the title compound as a colorless solid (2.1 g, 76%).

$^1$H NMR (300 MHz, CHLOROFORM-d) δ1.08 (t, J=7.3 Hz, 3H) 1.65-1.81 (m, 2H) 2.03-2.13 (m, 2H) 2.51-2.61 (m, 4H) 3.01-3.17 (m, 4H) 4.04 (s, 2H) 5.49-5.62 (m, 1H) 7.22-7.29 (m, 2H) 7.36-7.52 (m, 3H) 7.61-7.68 (m, 1H) 7.74-7.80 (m, 1H) 7.91 (s, 1H)

REFERENCE EXAMPLE 245

3'-fluoro-4'-({5-oxo-7-propyl-4-[(3a'R,6a'S)-tetrahydrospiro[cyclohexane-1,2'-furo[3,4-d][1,3]dioxol]-4-yl]-4,5-dihydro[1,2,4]triazolo[1,5-a]pyrimidin-6-yl}methyl)biphenyl-2-carbonitrile A mixture of 3'-fluoro-4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1 g), tetrahydrofuran-3,4-diol (0.26 g), p-toluenesulfonic acid monohydrate (0.005 g) and toluene (50 mL) was subjected to an azeotropic dehydration reaction by stirring at 110° C. for 3 hr in a reaction vessel equipped with a Dean-stark trap. The reaction mixture was concentrated, and the obtained residue was purified by silica gel column chromatography to give the title compound as a colorless solid (1.3 g, 100%).

$^1$H NMR (300 MHz, DMSO-d$_6$) δ0.95 (t, J=7.35 Hz, 3H) 1.41-1.99 (m, 8H) 2.65-2.87 (m, 2H) 2.92-3.01 (m, 2H) 3.32-3.39 (m, 2H) 3.78-4.00 (m, 4H) 4.74-4.84 (m, 2H) 4.87-5.01 (m, 1H) 7.26-7.48 (m, 3H) 7.55-7.66 (m, 2H) 7.75-7.83 (m, 1H) 7.95 (dd, J=7.72, 0.94 Hz, 1H) 8.22 (s, 1H)

REFERENCE EXAMPLE 246

3'-fluoro-4'-{[4-(trans-4-{[(3R,4S)-4-hydroxytetrahydrofuran-3-yl]oxy}cyclohexyl)-5-oxo-7-propyl-4,5-dihydro[1,2,4]triazolo[1,5-a]pyrimidin-6-yl]methyl}biphenyl-2-carbonitrile A mixture of 3'-fluoro-4'-({5-oxo-7-propyl-4-[(3a'R,6a'S)-tetrahydrospiro[cyclohexane-1,2'-furo[3,4-d][1,3]dioxol]-4-yl]-4,5-dihydro[1,2,4]triazolo[1,5-a]pyrimidin-6-yl}methyl)biphenyl-2-carbonitrile (1.3 g), sodium cyanoborohydride (2.9 g), boron trifluoride-diethyl ether complex (5.9 mL) and tetrahydrofuran (50 mL) was stirred at 70° C. for 2 days. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless solid (0.39 g, 30%).

$^1$H NMR (300 MHz, DMSO-d$_6$) δ0.95 (t, J=7.4 Hz, 3H) 1.25-1.75 (m, 6H) 2.07-2.22 (m, 2H) 2.53-2.67 (m, 2H) 2.91-3.02 (m, 2H) 3.28-4.15 (m, 9H) 4.54 (d, J=5.1 Hz, 1H) 4.81-4.96 (m, 1H) 7.26-7.50 (m, 3H) 7.55-7.67 (m, 2H) 7.75-7.84 (m, 1H) 7.92-8.00 (m, 1H) 8.20 (s, 1H)

REFERENCE EXAMPLE 247

3'-fluoro-4'-{[5-oxo-4-(trans-4-{[(3R)-4-oxotetrahydrofuran-3-yl]oxy}cyclohexyl)-7-propyl-4,5-dihydro[1,2,4]triazolo[1,5-a]pyrimidin-6-yl]methyl}biphenyl-2-carbonitrile 3'-Fluoro-4'-{[4-(trans-4-{[(3R,4S)-4-hydroxytetrahydrofuran-3-yl]oxy}cyclohexyl)-5-oxo-7-propyl-4,5-dihydro[1,2,4]triazolo[1,5-a]pyrimidin-6-yl]methyl}biphenyl-2-carbonitrile (0.39 g) was dissolved in acetonitrile (10 mL), 1,1,1-triacetoxy-1,1-dihydro-1,2-benziodoxol-3(1H)-one (0.45 g) was added, and the mixture was stirred at room temperature for 4 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as a colorless solid (0.18 g, 45%).

$^1$H NMR (300 MHz, DMSO-d$_6$) δ1.07 (t, J=7.4 Hz, 3H) 1.41-1.90 (m, 6H) 2.10-2.34 (m, 2H) 2.65-2.84 (m, 2H) 3.00-3.09 (m, 2H) 3.68-4.21 (m, 7H) 4.38-4.47 (m, 1H) 4.99-5.15 (m, 1H) 7.22-7.30 (m, 2H) 7.34-7.52 (m, 3H) 7.61-7.69 (m, 1H) 7.76 (d, J=7.6 Hz, 1H) 7.92 (s, 1H)

REFERENCE EXAMPLE 248

3'-fluoro-4'-[(4-{trans-4-[(4-hydroxy-4-methyltetrahydrofuran-3-yl)oxy]cyclohexyl}-5-oxo-7-propyl-4,5-dihydro[1,2,4]triazolo[1,5-a]pyrimidin-6-yl)methyl]biphenyl-2-carbonitrile 3'-Fluoro-4'-{[5-oxo-4-(trans-4-{[(3R)-4-oxotetrahydrofuran-3-yl]oxy}cyclohexyl)-7-propyl-4,5-dihydro[1,2,4]triazolo[1,5-a]pyrimidin-6-yl]methyl}biphenyl-2-carbonitrile (0.18 g) was dissolved in tetrahydrofuran (10 mL), and methylmagnesium bromide (1.0 M tetrahydrofuran solution, 0.95 mL) was added at room temperature. The reaction mixture was stirred for 3 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.077 g, 42%).

$^1$H NMR (300 MHz, CHLOROFORM-d) δ1.07 (t, J=7.3 Hz, 3H) 1.34 (s, 3H) 1.42-1.87 (m, 6H) 2.06-2.27 (m, 2H)

2.62-2.80 (m, 2H) 3.00-3.09 (m, 3H) 3.49-3.78 (m, 4H) 3.99-4.08 (m, 3H) 5.00-5.15 (m, 1H) 7.22-7.29 (m, 2H) 7.33-7.50 (m, 3H) 7.64 (t, J=7.6 Hz, 1H) 7.66 (d, J=7.7 Hz, 1H) 7.91 (s, 1H)

REFERENCE EXAMPLE 249

4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-4-fluorobiphenyl-2-carbonitrile A mixture of ethyl 2-[(2'-cyano-4'-fluorobiphenyl-4-yl)methyl]-3-oxohexanoate (2.9 g), N-(1,4-dioxaspiro[4.5]dec-8-yl)-5-methyl-4H-1,2,4-triazol-3-amine (0.93 g), 1,8-diazabicyclo[5.4.0]undec-7-ene (0.29 mL) and N,N-diethylaniline (30 mL) was stirred at 180° C. for 16 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a colorless solid (1.1 g, 48%).
$^1$H NMR (300 MHz, DMSO-$d_6$) δ0.94 (t, J=7.3 Hz, 3H) 1.51-1.84 (m, 8H) 2.36 (s, 3H) 2.67-2.97 (m, 4H) 3.81-3.99 (m, 6H) 4.92 (t, J=12.4 Hz, 1H) 7.36-7.50 (m, 4H) 7.57-7.72 (m, 2H) 7.94 (dd, J=8.7, 1.9 Hz, 1H)

REFERENCE EXAMPLE 250

4'-{[4-(2,3-dimethyl-1,4-dioxaspiro[4.5]dec-8-yl)-2-methyl-5-oxo-7-propyl-4,5-dihydro[1,2,4]triazolo[1,5-a]pyrimidin-6-yl]methyl}-4-fluorobiphenyl-2-carbonitrile A mixture of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-4-fluorobiphenyl-2-carbonitrile (1.1 g), 3N hydrochloric acid (30 mL) and tetrahydrofuran (30 mL) was stirred at 70° C. for 16 hr. The reaction mixture was diluted with ethyl acetate, washed with saturated brine, and dried over anhydrous magnesium sulfate. The solvent was evaporated under reduced pressure. The obtained residue was dissolved in toluene (30 mL), 2,3-dimethylpropane-1,3-diol (0.2 g) and p-toluenesulfonic acid monohydrate (0.004 g) were added, and the mixture was subjected to an azeotropic dehydration reaction by stirring at 110° C. for 3 hr in a reaction vessel equipped with a Dean-stark trap. The reaction mixture was concentrated under reduced pressure, and the obtained residue was purified by silica gel column chromatography to give the title compound as a colorless solid (1.3 g, 100%).
$^1$H NMR (300 MHz, DMSO-$d_6$) δ0.94 (t, J=7.4 Hz, 3H) 1.01-1.25 (m, 6H) 1.37-1.97 (m, 8H) 2.36 (s, 3H) 2.66-2.84 (m, 2H) 2.87-2.97 (m, 2H) 3.54-4.30 (m, 4H) 4.87 (t, J=12.5 Hz, 1H) 7.34-7.51 (m, 4H) 7.59-7.72 (m, 2H) 7.94 (dd, J=8.5, 2.1 Hz, 1H)

REFERENCE EXAMPLE 251

4'-{[4-(1,4-dioxaspiro[4.5]dec-8-yl)-5-oxo-7-propyl-4,5-dihydropyrazolo[1,5-a]pyrimidin-6-yl]methyl}biphenyl-2-carbonitrile To a solution of N-(1,4-dioxaspiro[4.5]dec-8-yl)-1H-pyrazol-5-amine (11.8 g) and 1,8-diazabicyclo[5.4.0]undec-7-ene (1.6 mL) in N,N-diethylaniline (60 mL) was added dropwise a solution of ethyl 2-[(2'-cyanobiphenyl-4-yl)methyl]-3-oxohexanoate (24 g) in N,N-diethylaniline (40 mL) at 180° C. The mixture was stirred for 3 hr and allowed to cool to room temperature, and ethyl acetate and water were added. The mixture was extracted with ethyl acetate, and the organic layer was successively washed with water and saturated brine, dried over anhydrous magnesium sulfate, and concentrated. The residue was purified by silica gel column chromatography to give the title compound as a pale-yellow amorphous solid (19.5 g, 73%).
$^1$H NMR (300 MHz, CHLOROFORM-d) δ1.06 (t, J=7.5 Hz, 3H), 1.65-1.92 (m, 8H), 2.48-2.68 (m, 2H), 3.02-3.12 (m, 2H), 3.94-4.06 (m, 6H), 5.23 (br. s., 1H), 6.18 (d, J=2.1 Hz, 1H), 7.34-7.48 (m, 6H), 7.56-7.64 (m, 1H), 7.68-7.75 (m, 2H)

REFERENCE EXAMPLE 252

4-fluoro-4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-{[4-(2,3-dimethyl-1,4-dioxaspiro[4.5]dec-8-yl)-2-methyl-5-oxo-7-propyl-4,5-dihydro[1,2,4]triazolo[1,5-a]pyrimidin-6-yl]methyl}-4-fluorobiphenyl-2-carbonitrile (1.3 g), sodium cyanoborohydride (0.71 g), boron trifluoride-diethyl ether complex (1.4 mL) and tetrahydrofuran (30 mL) was stirred at 40° C. for 40 hr. The reaction mixture was diluted with ethyl acetate, washed with water and then with saturated brine, and dried over anhydrous magnesium sulfate. The solvent was evaporated under reduced pressure. The residue obtained by purification by silica gel column chromatography was dissolved in acetonitrile (20 mL), 1,1,1-triacetoxy-1,1-dihydro-1,2-benziodoxol-3(1H)-one (0.96 g) was added, and the mixture was stirred at room temperature for 4 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (10 mL), and methylmagnesium bromide (1.0 M tetrahydrofuran solution, 0.65 mL) was added at room temperature. The reaction mixture was stirred for 3 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.24 g, 18%).
$^1$H NMR (300 MHz, DMSO-$d_6$) δ0.93 (t, J=7.2 Hz, 3H) 1.14-1.21 (m, 9H) 1.25-1.74 (m, 6H) 2.04-2.13 (m, 2H) 2.35 (s, 3H) 2.52-2.64 (m, 2H) 2.86-2.96 (m, 2H) 3.22-3.40 (m, 1H) 3.93-4.09 (m, 3H) 4.88 (t, J=11.9 Hz, 1H) 7.35-7.49 (m, 4H) 7.59-7.71 (m, 2H) 7.94 (dd, J=8.7, 2.3 Hz, 1H)

REFERENCE EXAMPLE 253

2-[(trans-4-{6-[(2'-cyano-3-fluorobiphenyl-4-yl)methyl]-2-methyl-5-oxo-7-propyl[1,2,4]triazolo[1,5-a]pyrimidin-4(5H)-yl}cyclohexyl)oxy]propanamide To a mixture of 3'-fluoro-4'-{[4-(trans-4-hydroxycyclohexyl)-2-methyl-5-oxo-7-propyl-4,5-dihydro[1,2,4]triazolo

[1,5-a]pyrimidin-6-yl]methyl}biphenyl-2-carbonitrile (1 g), rhodium(I) acetate (0.009 g) and toluene (20 mL) was added dropwise 3-ethoxy-2-methyl-3-oxopropane-1-diazonium (1.5 mL) at 80° C., and the mixture was stirred at the same temperature for 1 hr. The reaction mixture was concentrated, and the residue obtained by purification by silica gel column chromatography was dissolved in tetrahydrofuran (10 mL) and methanol (10 mL). 1N Aqueous sodium hydroxide solution (10 mL) was added, and the mixture was stirred at room temperature for 3 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was dissolved in N,N-dimethylformamide (10 mL), 1-hydroxybenzotriazole ammonium salt (0.21 g) and 1-ethyl-3-(3-dimethylaminopropyl)carbodiimide hydrochloride (0.3 g) were added, and the mixture was stirred at room temperature for 16 hr. The reaction mixture was diluted with ethyl acetate, washed with dilute hydrochloric acid and then with saturated brine, and dried over anhydrous magnesium sulfate. The solvent was evaporated under reduced pressure, and the residue was purified by silica gel column chromatography to give the title compound as a colorless solid (0.37 g, 65%).

$^1$H NMR (300 MHz, DMSO-d$_6$) δ0.93 (t, J=7.3 Hz, 3H) 1.18-1.47 (m, 5H) 1.53-1.74 (m, 4H) 2.04-2.17 (m, 2H) 2.37 (s, 3H) 2.49-2.64 (m, 2H) 2.88-2.96 (m, 2H) 3.27-3.41 (m, 1H) 3.85-3.98 (m, 3H) 4.87 (t, J=12.2 Hz, 1H) 7.14 (br. s., 2H) 7.25-7.48 (m, 3H) 7.56-7.65 (m, 2H) 7.75-7.83 (m, 1H) 7.95 (d, J=7.3 Hz, 1H)

REFERENCE EXAMPLE 254

4'-{[4-(6,13-dioxadispiro[3.2.5.2]tetradec-10-yl)-5-oxo-7-propyl-4,5-dihydro[1,2,4]triazolo[1,5-a]pyrimidin-6-yl]methyl}-3'-fluorobiphenyl-2-carbonitrile A mixture of 3'-fluoro-4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (3.5 g), cyclobutane-1,1-diyldimethanol (1 g), p-toluenesulfonic acid monohydrate (0.014 g) and toluene (60 mL) was subjected to an azeotropic dehydration reaction by stirring at 110° C. for 16 hr in a reaction vessel equipped with a Dean-stark trap. The reaction mixture was concentrated, and the obtained residue was purified by silica gel column chromatography to give the title compound as a colorless solid (3.6 g, 86%).

$^1$H NMR (300 MHz, DMSO-d$_6$) δ0.95 (t, J=7.3 Hz, 3H), 1.28-1.90 (m, 12H), 2.28 (d, J=13.2 Hz, 2H), 2.59-2.77 (m, 2H), 2.91-3.01 (m, 2H), 3.70 (d, J=8.1 Hz, 4H), 3.97 (s, 2H), 4.83-5.01 (m, 1H), 7.25-7.48 (m, 3H), 7.55-7.66 (m, 2H), 7.75-7.84 (m, 1H), 7.95 (dd, J=7.7, 0.9 Hz, 1H), 8.21 (s, 1H)

REFERENCE EXAMPLE 255

3'-fluoro-4'-{[4-(trans-4-{[1-(1-hydroxyethyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile A mixture of 4'-{[4-(6,13-dioxadispiro[3.2.5.2]tetradec-10-yl)-5-oxo-7-propyl-4,5-dihydro[1,2,4]triazolo[1,5-a]pyrimidin-6-yl]methyl}-3'-fluorobiphenyl-2-carbonitrile (3.6 g), sodium cyanoborohydride (5.3 g), boron trifluoride-diethyl ether complex (3.1 mL) and tetrahydrofuran (150 mL) was stirred at 50° C. for 24 hr. The reaction mixture was diluted with ethyl acetate, washed with water and then with saturated brine, and dried over anhydrous magnesium sulfate. The solvent was evaporated under reduced pressure. The residue obtained by purification by silica gel column chromatography was dissolved in acetonitrile (30 mL), 1,1,1-triacetoxy-1,1-dihydro-1,2-benziodoxol-3(1H)-one (3.4 g) was added, and the mixture was stirred at room temperature for 4 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (20 mL), and methylmagnesium bromide (1.0 M tetrahydrofuran solution, 4.5 mL) was added at room temperature. The reaction mixture was stirred for 2 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.72 g, 19%).

$^1$H NMR (300 MHz, DMSO-d$_6$) δ0.91-1.00 (m, 5H) 1.21-1.37 (m, 2H) 1.49-2.17 (m, 12H) 2.51-2.66 (m, 2H) 2.91-3.02 (m, 2H) 3.22-3.32 (m, 1H) 3.36-3.52 (m, 2H) 3.57-3.67 (m, 1H) 3.98 (s, 2H) 4.28 (d, J=5.30 Hz, 1H) 4.90 (t, J=12.12 Hz, 1H) 7.26-7.39 (m, 2H) 7.42-7.49 (m, 1H) 7.55-7.66 (m, 2H) 7.75-7.83 (m, 1H) 7.95 (d, J=7.57 Hz, 1H) 8.20 (s, 1H)

REFERENCE EXAMPLE 256

4'-[(4-{trans-4-[(1-acetylcyclobutyl)methoxy]cyclohexyl}-5-oxo-7-propyl-4,5-dihydro[1,2,4]triazolo[1,5-a]pyrimidin-6-yl)methyl]-3'-fluorobiphenyl-2-carbonitrile 3'-Fluoro-4'-{[4-(trans-4-{[1-(1-hydroxyethyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile (0.72 g) was dissolved in acetonitrile (20 mL), 1,1,1-triacetoxy-1,1-dihydro-1,2-benziodoxol-3(1H)-one (0.77 g) was added, and the mixture was stirred at room temperature for 4 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as a colorless solid (0.65 g, 89%).

$^1$H NMR (300 MHz, DMSO-d$_6$) δ0.95 (t, J=7.38 Hz, 3H) 1.18-1.34 (m, 2H) 1.54-1.95 (m, 8H) 2.03-2.13 (m, 5H) 2.17-2.29 (m, 2H) 2.52-2.64 (m, 2H) 2.91-3.01 (m, 2H) 3.25-3.39 (m, 1H) 3.77 (s, 2H) 3.97 (s, 2H) 4.81-4.96 (m, 1H) 7.25-7.39 (m, 2H) 7.42-7.50 (m, 1H) 7.55-7.67 (m, 2H) 7.75-7.83 (m, 1H) 7.95 (d, J=7.57 Hz, 1H) 8.20 (s, 1H)

REFERENCE EXAMPLE 257

3'-fluoro-4'-[(4-{trans-4-[(1-hydroxycyclobutyl)methoxy]cyclohexyl}-5-oxo-7-propyl-4,5-dihydro[1,2,4]triazolo[1,5-a]pyrimidin-6-yl)methyl]biphenyl-2-carbonitrile To a mixture of 4'-[(4-{trans-4-[(1-acetylcyclobutyl)methoxy]cyclohexyl}-5-oxo-7-propyl-4,5-dihydro[1,2,4]triazolo

[1,5-a]pyrimidin-6-yl)methyl]-3'-fluorobiphenyl-2-carbonitrile (0.3 g), 30% hydrogen peroxide water (2.1 g) and chloroform (10 mL) was gradually added trifluoroacetic acid anhydride (2.1 mL) at room temperature, and the reaction mixture was warmed to 60° C. and stirred for 24 hr. Saturated aqueous sodium hydrogen carbonate and sodium thiosulfate were added to the reaction mixture, and the mixture was extracted with ethyl acetate. The organic layer was washed with saturated brine, and dried over anhydrous magnesium sulfate. The solvent was evaporated under reduced pressure. The obtained residue was dissolved in tetrahydrofuran (5 mL) and methanol (5 mL), 1N aqueous sodium hydroxide solution (5 mL) was added, and the mixture was stirred at room temperature for 30 min. 1N Aqueous hydrochloric acid solution was added to the reaction mixture, and the mixture was extracted with ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless solid (0.19 g, 65%).

$^1$H NMR (300 MHz, DMSO-d$_6$) δ0.95 (t, J=7.2 Hz, 3H) 1.21-1.76 (m, 8H) 1.80-2.19 (m, 6H) 2.51-2.66 (m, 2H) 2.92-3.01 (m, 2H) 3.32-3.43 (m, 3H) 3.97 (s, 2H) 4.81-4.97 (m, 2H) 7.26-7.49 (m, 3H) 7.55-7.66 (m, 2H) 7.75-7.84 (m, 1H) 7.95 (d, J=6.8 Hz, 1H) 8.20 (s, 1H)

REFERENCE EXAMPLE 258 propyl 3-methylidenecyclobutanecarboxylate

A mixture of 3-methylidenecyclobutanecarboxylic acid (18 g), sodium hydride (6.9 g) and N,N-dimethylformamide (300 mL) was stirred at room temperature for 10 min, propyl iodide (17 mL) was added, and the mixture was stirred at room temperature for 16 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure, and the residue was purified by distillation (45-50° C., 2 mmHg) to give the title compound as a colorless oil (16 g, 66%).

$^1$H NMR (300 MHz, DMSO-d$_6$) δ0.88 (t, J=7.4 Hz, 3H) 1.52-1.65 (m, 2H) 2.78-2.94 (m, 4H) 3.08-3.23 (m, 1H) 4.00 (t, J=6.7 Hz, 2H) 4.76-4.83 (m, 2H)

REFERENCE EXAMPLE 259 propyl 3-oxocyclobutanecarboxylate

An ozone gas was blown into a solution (200 mL) of propyl 3-methylidenecyclobutanecarboxylate (15 g) in methanol at −78° C. for 2 hr. Dimethyl sulfide (21 g) was added to the reaction mixture at the same temperature, and the mixture was warmed to room temperature over 1 hr. The obtained mixture was concentrated and purified by silica gel column chromatography to give the title compound as a colorless oil (13 g, 88%).

$^1$H NMR (300 MHz, DMSO-d$_6$) δ0.89 (t, J=7.4 Hz, 3H) 1.54-1.69 (m, 2H) 3.17-3.40 (m, 5H) 4.04 (t, J=6.2 Hz, 2H)

REFERENCE EXAMPLE 260 propyl 3-(4H-1,2,4-triazol-3-ylamino)cyclobutanecarboxylate

To a solution (100 mL) of 1H-1,2,4-triazol-3-amine (6.7 g) and propyl 3-oxocyclobutanecarboxylate (14 g) in acetic acid was added sodium cyanoborohydride (14 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate. The solvent was evaporated under reduced pressure, and the residue was purified by silica gel column chromatography to give the title compound as a colorless solid (8.8 g, 49%).

$^1$H NMR (300 MHz, DMSO-d$_6$) δ0.83-0.93 (m, 3H) 1.50-1.66 (m, 2H) 2.00-2.58 (m, 4H) 2.70-3.08 (m, 1H) 3.82-4.19 (m, 3H) 6.67-7.57 (m, 1H) 11.79-13.06 (m, 1H)

REFERENCE EXAMPLE 261 propyl 3-{6-[(2'-cyanobiphenyl-4-yl)methyl]-5-oxo-7-propyl[1,2,4]triazolo[1,5-a]pyrimidin-4(5H)-yl}cyclobutanecarboxylate A mixture of ethyl 2-[(2'-cyanobiphenyl-4-yl)methyl]-3-oxohexanoate (12 g), propyl 3-(4H-1,2,4-triazol-3-ylamino)cyclobutanecarboxylate (4 g), 1,8-diazabicyclo[5.4.0]undec-7-ene (1.2 mL) and N,N-diethylaniline (50 mL) was stirred at 180° C. for 16 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a mixture of geometric isomers (5 g, 55%).

A trans form: $^1$H NMR (300 MHz, CHLOROFORM-d) δ0.97 (t, J=7.38 Hz, 3H) 1.06 (t, J=7.38 Hz, 3H) 1.63-1.80 (m, 4H) 2.61-2.73 (m, 2H) 2.99-3.08 (m, 2H) 3.32-3.52 (m, 3H) 4.02 (s, 2H) 4.11 (t, J=6.63 Hz, 2H) 5.82-5.95 (m, 1H) 7.35-7.52 (m, 6H) 7.59-7.66 (m, 1H) 7.74 (d, J=7.95 Hz, 1H) 7.95 (s, 1H)

A cis form: $^1$H NMR (300 MHz, CHLOROFORM-d) δ0.97 (t, J=7.38 Hz, 3H) 1.05 (t, J=7.38 Hz, 3H) 1.61-1.79 (m, 4H) 2.61-2.76 (m, 2H) 2.87-3.09 (m, 3H) 3.37-3.53 (m, 2H) 4.02 (s, 2H) 4.06-4.16 (m, 2H) 5.31-5.48 (m, 1H) 7.36-7.52 (m, 6H) 7.58-7.66 (m, 1H) 7.73 (d, J=7.57 Hz, 1H) 7.93 (s, 1H)

REFERENCE EXAMPLE 262

4'-{[4-(trans-3-acetylcyclobutyl)-5-oxo-7-propyl-4,5-dihydro[1,2,4]triazolo[1,5-a]pyrimidin-6-yl]methyl}biphenyl-2-carbonitrile A mixture of propyl 3-{6-[(2'-cyanobiphenyl-4-yl)methyl]-5-oxo-7-propyl[1,2,4]triazolo[1,5-a]pyrimidin-4(5H)-yl}cyclobutanecarboxylate (5 g), 1N aqueous sodium hydroxide solution (10 mL), methanol (10 mL) and tetrahydrofuran (10 mL) was stirred at room temperature for 2 hr. The reaction mixture was adjusted to pH 4 with water and 1 N hydrochloric acid, and extracted with ethyl acetate. The organic layer was washed with saturated brine, dried over anhydrous magnesium sulfate, and concentrated under reduced pressure. The obtained extract was dissolved in N,N-dimethylformamide (50 mL), N-methoxymethanamine hydrochloride (1.4 g), 1-hydroxybenzotriazole (2.3 g), 1-ethyl-3-(3-dimethylaminopropyl)carbodiimide hydrochloride (2.8 g) and triethylamine (2.1 mL) were added, and the mixture was stirred at room temperature for 16 hr. The reaction mixture was diluted with ethyl acetate, washed with 1 N hydrochloric acid and then with saturated brine, and dried over anhydrous magnesium sulfate. The solvent was evaporated under reduced pressure. The residue obtained by purification by silica gel column chromatography was dissolved in tetrahydrofuran (20 mL), and methylmagnesium bromide (1.0 M tetrahydrofuran solution, 8.1 mL) was added at room temperature. The reaction mixture was stirred for 3 hr, saturated aqueous ammonium chloride solution was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (1.3 g, 28%).

$^1$H NMR (300 MHz, DMSO-$d_6$) δ0.95 (t, J=7.3 Hz, 3H) 1.51-1.72 (m, 2H) 2.16 (s, 3H) 2.41-2.49 (m, 2H) 2.91-3.00 (m, 2H) 3.15-3.31 (m, 2H) 3.39-3.51 (m, 1H) 3.99 (s, 2H) 5.34-5.54 (m, 1H) 7.37-7.62 (m, 6H) 7.74-7.81 (m, 1H) 7.93 (dd, J=7.7, 0.9 Hz, 1H) 8.23 (s, 1H)

REFERENCE EXAMPLE 263

4'-{[4-(cis-3-acetylcyclobutyl)-5-oxo-7-propyl-4,5-dihydro[1,2,4]triazolo[1,5-a]pyrimidin-6-yl]methyl}biphenyl-2-carbonitrile A mixture of propyl 3-{6-[(2'-cyanobiphenyl-4-yl)methyl]-5-oxo-7-propyl[1,2,4]triazolo[1,5-a]pyrimidin-4(5H)-yl}cyclobutanecarboxylate (5 g), 1N aqueous sodium hydroxide solution (10 mL), methanol (10 mL) and tetrahydrofuran (10 mL) was stirred at room temperature for 2 hr. The reaction mixture was adjusted to pH 4 with water and 1 N hydrochloric acid and extracted with ethyl acetate. The organic layer was washed with saturated brine, dried over anhydrous magnesium sulfate, and concentrated under reduced pressure. The obtained extract was dissolved in N,N-dimethylformamide (50 mL), N-methoxymethanamine hydrochloride (1.4 g), 1-hydroxybenzotriazole (2.3 g), 1-ethyl-3-(3-dimethylaminopropyl)carbodiimide hydrochloride (2.8 g) and triethylamine (2.1 mL) were added, and the mixture was stirred at room temperature for 16 hr. The reaction mixture was diluted with ethyl acetate, washed with 1 N hydrochloric acid and then with saturated brine, and dried over anhydrous magnesium sulfate. The solvent was evaporated under reduced pressure. The residue obtained by purification by silica gel column chromatography was dissolved in tetrahydrofuran (20 mL), and methylmagnesium bromide (1.0 M tetrahydrofuran solution, 6.1 mL) was added at room temperature. The reaction mixture was stirred for 3 hr, saturated aqueous ammonium chloride solution was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (2.2 g, 49%).

$^1$H NMR (300 MHz, DMSO-$d_6$) δ0.94 (t, J=7.3 Hz, 3H) 1.49-1.69 (m, 2H) 2.11 (s, 3H) 2.40-2.49 (m, 2H) 2.89-3.23 (m, 5H) 3.98 (s, 2H) 5.28-5.43 (m, 1H) 7.37-7.63 (m, 6H) 7.72-7.82 (m, 1H) 7.93 (dd, J=7.7, 0.9 Hz, 1H) 8.19 (s, 1H)

REFERENCE EXAMPLE 264

4'-{[4-(trans-3-hydroxycyclobutyl)-5-oxo-7-propyl-4,5-dihydro[1,2,4]triazolo[1,5-a]pyrimidin-6-yl]methyl}biphenyl-2-carbonitrile To a mixture of 4'-{[4-(trans-3-acetylcyclobutyl)-5-oxo-7-propyl-4,5-dihydro[1,2,4]triazolo[1,5-a]pyrimidin-6-yl]methyl}biphenyl-2-carbonitrile (1.3 g), 30% hydrogen peroxide water (3.5 g) and chloroform (20 mL) was gradually added trifluoroacetic acid anhydride (7.7 mL) at room temperature, and the reaction mixture was warmed to 60° C. and stirred for 24 hr. Saturated aqueous sodium hydrogen carbonate and sodium thiosulfate were added to the reaction mixture, and the mixture was extracted with ethyl acetate. The organic layer was washed with saturated brine, and dried over anhydrous magnesium sulfate. The solvent was evaporated under reduced pressure. The obtained residue was dissolved in tetrahydrofuran (10 mL) and methanol (10 mL), 1N aqueous sodium hydroxide solution (5 mL) was added, and the mixture was stirred at room temperature for 30 min. 1N Aqueous hydrochloric acid solution was added to the reaction mixture, and the mixture was extracted with ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless solid (0.28 g, 23%).

$^1$H NMR (300 MHz, DMSO-$d_6$) δ0.94 (t, J=7.2 Hz, 3H) 1.51-1.67 (m, 2H) 2.11-2.24 (m, 2H) 2.92-3.01 (m, 2H) 3.15-3.28 (m, 2H) 3.99 (s, 2H) 4.42-4.54 (m, 1H) 5.12 (d, J=4.9 Hz, 1H) 5.78 (t, J=8.7 Hz, 1H) 7.37-7.63 (m, 6H) 7.73-7.81 (m, 1H) 7.93 (d, J=7.6 Hz, 1H) 8.21 (s, 1H)

REFERENCE EXAMPLE 265

4'-{[4-(cis-3-hydroxycyclobutyl)-5-oxo-7-propyl-4,5-dihydro[1,2,4]triazolo[1,5-a]pyrimidin-6-yl]methyl}biphenyl-2-carbonitrile To a mixture of 4'-{[4-(cis-3-acetylcyclobutyl)-5-oxo-7-propyl-4,5-dihydro[1,2,4]triazolo[1,5-a]pyrimidin-6-yl]methyl}biphenyl-2-carbonitrile (2.2 g), 30% hydrogen peroxide water (5.9 g) and chloroform (30 mL) was gradually added trifluoroacetic acid anhydride (13 mL) at room temperature, and the reaction mixture was warmed to 60° C. and stirred for 24 hr. Saturated aqueous sodium hydrogen carbonate and sodium thiosulfate were added to the reaction mixture, and the mixture was extracted with ethyl acetate. The organic layer was washed with saturated brine, and dried over anhydrous magnesium sulfate. The solvent was evaporated under reduced pressure. The obtained residue was dissolved in tetrahydrofuran (10 mL) and methanol (10 mL), 1N aqueous sodium hydroxide solution (5 mL) was added, and the mixture was stirred at room temperature for 30 min. 1N Aqueous hydrochloric acid solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.58 g, 27%).

$^1$H NMR (300 MHz, DMSO-$d_6$) δ0.94 (t, J=7.3 Hz, 3H) 1.51-1.68 (m, 2H) 2.11-2.23 (m, 2H) 2.91-3.02 (m, 2H) 3.17-3.29 (m, 2H) 3.99 (s, 2H) 4.49 (t, J=6.6 Hz, 1H) 5.12 (br.s., 1H) 5.70-5.86 (m, 1H) 7.37-7.62 (m, 6H), 7.74-7.81 (m, 1H), 7.92 (d, J=1.1 Hz, 1H) 8.21 (s, 1H)

REFERENCE EXAMPLE 266 ethyl[(cis-3-{6-[(2'-cyanobiphenyl-4-yl)methyl]-5-oxo-7-propyl[1,2,4]triazolo[1,5-a]pyrimidin-4(5H)-yl}cyclobutyl)oxy]acetate To a mixture of 4'-{[4-(cis-3-hydroxycyclobutyl)-5-oxo-7-propyl-4,5-dihydro[1,2,4]triazolo[1,5-a]pyrimidin-6-yl]methyl}biphenyl-2-carbonitrile (0.3 g), rhodium(I) acetate (0.003 g) and toluene (20 mL) was added dropwise ethyl diazoacetate (0.66 mL) at 80° C., and the mixture was stirred at the same temperature for 1 hr. The reaction mixture was concentrated under reduced pressure, and the obtained residue was subjected to silica gel column chromatography to give the title compound as a colorless solid (0.2 g, 57%).

$^1$H NMR (300 MHz, DMSO-$d_6$) δ0.89-0.99 (m, 3H) 1.14-1.25 (m, 3H) 1.52-1.68 (m, 2H) 2.56-2.66 (m, 2H) 2.91-3.19 (m, 4H) 3.85-4.19 (m, 7H) 4.88-5.05 (m, 1H) 7.38-7.62 (m, 4H) 7.73-7.82 (m, 1H) 7.93 (d, J=7.6 Hz, 1H) 8.22 (s, 1H)

REFERENCE EXAMPLE 267

4'-({4-[cis-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile Ethyl[(cis-3-{6-[(2'-cyanobiphenyl-4-yl)methyl]-5-oxo-7-propyl[1,2,4]triazolo[1,5-a]pyrimidin-4(5H)-yl}cyclobutyl)oxy]acetate (0.2 g) was dissolved in tetrahydrofuran (10 mL), and methylmagnesium bromide (1.0 M tetrahydrofuran solution, 1.2 mL) was added at room temperature. The reaction mixture was stirred for 6 hr, saturated aqueous ammonium chloride solution was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.15 g, 78%).

$^1$H NMR (300 MHz, DMSO-$d_6$) δ0.95 (t, J=7.3 Hz, 3H) 1.09 (s, 6H) 1.53-1.68 (m, 2H) 2.54-2.66 (m, 2H) 2.91-3.08 (m, 4H) 3.11 (s, 2H) 3.76-3.88 (m, 1H) 3.99 (s, 2H) 4.31 (s, 1H) 4.85-4.99 (m, 1H) 7.38-7.63 (m, 6H), 7.73-7.82 (m, 1H) 7.93 (dd, J=7.8, 0.8 Hz, 1H) 8.21 (s, 1H)

REFERENCE EXAMPLE 268 ethyl[(trans-3-{6-[(2'-cyanobiphenyl-4-yl)methyl]-5-oxo-7-propyl[1,2,4]triazolo[1,5-a]pyrimidin-4(5H)-yl}cyclobutyl)oxy]acetate To a mixture of 4'-{[4-(trans-3-hydroxycyclobutyl)-5-oxo-7-propyl-4,5-dihydro[1,2,4]triazolo[1,5-a]pyrimidin-6-yl]methyl}biphenyl-2-carbonitrile (0.28 g), rhodium(I) acetate (0.0028 g) and toluene (10 mL) was added dropwise ethyl diazoacetate (0.62 mL) at 80° C., and the mixture was stirred at the same temperature for 1 hr. The reaction mixture was concentrated, and the obtained residue was subjected to silica gel column chromatography to give the title compound as a colorless solid (0.056 g, 17%).

$^1$H NMR (300 MHz, CHLOROFORM-d) δ1.05 (t, J=7.3 Hz, 3H) 1.26-1.33 (m, 3H) 1.65-1.78 (m, 2H) 2.49-2.61 (m, 2H) 2.97-3.06 (m, 2H) 3.21-3.36 (m, 2H) 4.02 (s, 2H) 4.05 (s, 2H) 4.19-4.28 (m, 2H) 4.52-4.64 (m, 1H) 5.82-5.99 (m, 1H) 7.33-7.51 (m, 6H) 7.58-7.67 (m, 1H) 7.75 (dd, J=7.7, 1.3 Hz, 1H) 7.93 (s, 1H)

REFERENCE EXAMPLE 269

4'-({4-[trans-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile Ethyl[(trans-3-{6-[(2'-cyanobiphenyl-4-yl)methyl]-5-oxo-7-propyl[1,2,4]triazolo[1,5-a]pyrimidin-4(5H)-yl}cyclobutyl)oxy]acetate (0.08 g) was dissolved in tetrahydrofuran (5 mL), and methylmagnesium bromide (1.0 M tetrahydrofuran solution, 0.46 mL) was added at room temperature. The reaction mixture was stirred for 6 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.056 g, 72%).

$^1$H NMR (300 MHz, CHLOROFORM-d) δ1.06 (t, J=7.2 Hz, 3H) 1.24 (s, 6H) 1.66-1.79 (m, 2H) 2.33 (br. s., 1H) 2.40-2.51 (m, 2H) 2.99-3.07 (m, 2H) 3.22 (s, 2H) 3.25-3.38 (m, 2H) 4.02 (s, 2H) 4.43 (t, J=6.8 Hz, 1H) 5.81-5.95 (m, 1H) 7.34-7.51 (m, 6H), 7.58-7.67 (m, 1H) 7.74 (d, J=8.0 Hz, 1H) 7.94 (s, 1H)

REFERENCE EXAMPLE 270

4'-({4-[trans-3-(2-ethyl-2-hydroxybutoxy)cyclobutyl]-5-oxo-7-propyl-4,5-dihydro[1,2,4]triazolo[1,5-a]pyrimidin-6-yl}methyl)biphenyl-2-carbonitrile Ethyl[(trans-3-{6-[(2'-cyanobiphenyl-4-yl)methyl]-5-oxo-7-propyl[1,2,4]triazolo[1,5-a]pyrimidin-4(5H)-yl}cyclobutyl)oxy]acetate (0.077 g) was dissolved in tetrahydrofuran (10 mL), and ethylmagnesium bromide (3.0 M diethyl ether solution, 0.15 mL) was added at room temperature. The reaction mixture was stirred for 6 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.06 g, 76%).

$^1$H NMR (300 MHz, CHLOROFORM-d) δ0.89 (t, J=7.5 Hz, 6H) 1.06 (t, J=7.4 Hz, 3H) 1.46-1.61 (m, 4H) 1.63-1.79 (m, 2H) 2.40-2.51 (m, 2H) 2.98-3.08 (m, 2H) 3.22-3.37 (m, 4H) 4.02 (s, 2H) 4.36-4.45 (m, 1H) 5.78-5.94 (m, 1H) 7.34-7.51 (m, 6H), 7.59-7.67 (m, 1H) 7.75 (dd, J=7.8, 1.0 Hz, 1H) 7.94 (s, 1H)

REFERENCE EXAMPLE 271

4'-{[4-(trans-4-hydroxycyclohexyl)-5-oxo-7-propyl-4,5-dihydropyrazolo[1,5-a]pyrimidin-6-yl]methyl}biphenyl-2-carbonitrile To a solution of 4'-{[4-(1,4-dioxaspiro[4.5]dec-8-yl)-5-oxo-7-propyl-4,5-dihydropyrazolo[1,5-a]pyrimidin-6-yl]methyl}biphenyl-2-carbonitrile (27.7 g) in tetrahydrofuran (200 mL) was added 3M hydrochloric acid (200 mL), and the mixture was stirred at 60° C. for 15 hr. The mixture was allowed to cool to room temperature, diluted with ethyl acetate, and neutralized with 8M aqueous sodium hydroxide solution. The mixture was extracted with ethyl acetate, and the organic layer was successively washed with water and brine, dried over anhydrous magnesium sulfate, and concentrated. The residue was crystallized using ethyl acetate, and the resulting solid was collected by filtration, and dissolved in tetrahydrofuran (100 mL). This solution was added dropwise to a solution of lithium borohydride (2M tetrahydrofuran solution, 37 mL) in tetrahydrofuran (150 mL) at −5° C. over 30 min. After stirring for 1.5 hr, ethyl acetate and saturated aqueous ammonium chloride solution were added. The mixture was extracted with ethyl acetate, and the organic layer was successively washed with water and brine, dried over anhydrous magnesium sulfate, and concentrated. The residue was purified by silica gel column chromatography to give the title compound as a pale-yellow amorphous solid (21.1 g, 83%).

$^1$H NMR (300 MHz, CHLOROFORM-d) δ1.06 (t, J=7.3 Hz, 3H), 1.41-1.62 (m, 3H), 1.63-1.89 (m, 4H), 2.08-2.19 (m, 2H), 2.36-2.58 (m, 2H), 3.00-3.12 (m, 2H), 3.67-3.84 (m, 1H), 4.01 (s, 2H), 4.76 (br. s., 1H), 5.99 (d, J=2.1 Hz, 1H), 7.33-7.78 (m, 9H)

REFERENCE EXAMPLE 272

2-(5-{[4-(trans-4-hydroxycyclohexyl)-5-oxo-7-propyl-4,5-dihydro[1,2,4]triazolo[1,5-a]pyrimidin-6-yl]methyl}thiophen-2-yl)benzonitrile A mixture of 2-(5-{[4-(1,4-dioxaspiro[4.5]dec-8-yl)-5-oxo-7-propyl-4,5-dihydro[1,2,4]triazolo[1,5-a]pyrimidin-6-yl]methyl}thiophen-2-yl)benzonitrile (0.69 g), 3N hydrochloric acid (20 mL) and tetrahydrofuran (20 mL) was stirred at 70° C. for 16 hr. The reaction mixture was diluted with ethyl acetate, washed with saturated brine, and dried over anhydrous magnesium sulfate. The solvent was evaporated under reduced pressure. The obtained residue was dissolved in tetrahydrofuran (5 mL) and methanol (5 mL), sodium borohydride (0.076 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.41 g, 63%).

$^1$H NMR (300 MHz, CHLOROFORM-d) δ1.11 (t, J=7.4 Hz, 3H) 1.44-1.57 (m, 2H) 1.73-1.86 (m, 4H) 2.07-2.18 (m, 2H) 2.65-2.82 (m, 2H) 3.01-3.11 (m, 2H) 3.75-3.90 (m, 1H) 4.13 (s, 2H) 4.99-5.14 (m, 1H) 6.95 (d, J=3.8 Hz, 1H) 7.30-7.39 (m, 1H) 7.47 (d, J=3.6 Hz, 1H) 7.55 (d, J=4.0 Hz, 2H) 7.70 (d, J=7.7 Hz, 1H) 7.91 (s, 1H)

REFERENCE EXAMPLE 273 ethyl({trans-4-[6-{[5-(2-cyanophenyl)thiophen-2-yl]methyl}-5-oxo-7-propyl[1,2,4]triazolo[1,5-a]pyrimidin-4(5H)-yl]cyclohexyl}oxy)acetate To a mixture of 2-(5-{[4-(trans-4-hydroxycyclohexyl)-5-oxo-7-propyl-4,5-dihydro[1,2,4]triazolo[1,5-a]pyrimidin-6-yl]methyl}thiophen-2-yl)benzonitrile (0.4 g), rhodium(I) acetate (0.0019 g) and toluene (10 mL) was added dropwise ethyl diazoacetate (0.46 mL) at 80° C., and the mixture was stirred at the same temperature for 1 hr. The reaction mixture was concentrated, and the obtained residue was subjected to silica gel column chromatography to give the title compound as a colorless solid (0.25 g, 53%).

$^1$H NMR (300 MHz, CHLOROFORM-d) δ1.11 (t, J=7.3 Hz, 3H) 1.27-1.34 (m, 3H) 1.44-1.58 (m, 2H) 1.74-1.86 (m, 4H) 2.17-2.29 (m, 2H) 2.60-2.78 (m, 2H) 3.01-3.10 (m, 2H) 3.45-3.57 (m, 1H) 4.13 (s, 4H) 4.19-4.29 (m, 2H) 4.99-5.13 (m, 1H) 6.95 (d, J=3.8 Hz, 1H) 7.30-7.38 (m, 1H) 7.47 (d, J=3.8 Hz, 1H) 7.53-7.57 (m, 2H) 7.70 (d, J=7.7 Hz, 1H) 7.90 (s, 1H)

REFERENCE EXAMPLE 274

2-[5-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)thiophen-2-yl]benzonitrile Ethyl({trans-4-[6-{[5-(2-cyanophenyl)thiophen-2-yl]methyl}-5-oxo-7-propyl[1,2,4]triazolo[1,5-a]pyrimidin-4(5H)-yl]cyclohexyl}oxy)acetate (0.25 g) was dissolved in tetrahydrofuran (10 mL), and methylmagnesium bromide (1.0 M tetrahydrofuran solution, 0.44 mL) was added at room temperature. The reaction mixture was stirred at 70° C. for 6 hr, saturated aqueous ammonium chloride solution was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless solid (0.12 g, 49%).

$^1$H NMR (300 MHz, CHLOROFORM-d) δ1.11 (t, J=7.4 Hz, 3H) 1.21 (s, 6H) 1.39-1.54 (m, 2H) 1.74-1.87 (m, 4H) 2.13-2.24 (m, 2H) 2.60-2.79 (m, 2H) 3.02-3.10 (m, 2H) 3.31 (s, 2H) 3.39-3.51 (m, 1H) 4.12 (q, J=7.2 Hz, 2H) 5.01-5.16 (m, 1H) 6.95 (d, J=3.8 Hz, 1H) 7.30-7.39 (m, 1H) 7.47 (d, J=3.8 Hz, 1H) 7.55 (d, J=3.8 Hz, 2H) 7.70 (d, J=8.0 Hz, 1H) 7.91 (s, 1H)

REFERENCE EXAMPLE 275

4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)-2'-methylbiphenyl-2-carbonitrile Ethyl[(trans-4-{6-[(2'-cyano-2-methylbiphenyl-4-yl)methyl]-2-methyl-5-oxo-7-propyl[1,2,4]triazolo[1,5-a]pyrimidin-4(5H)-yl}cyclohexyl)oxy]acetate (0.71 g) was dissolved in tetrahydrofuran (10 mL), and methylmagnesium bromide (1.4 M tetrahydrofuran solution, 2.7 mL) was added at 0° C. The reaction mixture was stirred for 30 min, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless oil (0.41 g, 59%).

$^1$H NMR (300 MHz, CDCl$_3$) δ1.04 (t, J=7.2, 3H), 1.20 (s, 6H), 1.36-2.30 (m, 12H), 2.43 (s, 3H), 2.64-3.06 (m, 4H), 3.31 (s, 2H), 3.38-3.52 (m, 1H), 3.94 (s, 2H), 4.94-5.08 (m, 1H), 7.06-7.17 (m, 3H), 7.30-7.46 (m, 2H), 7.56-7.64 (m, 1H), 7.68-7.74 (m, 1H)

REFERENCE EXAMPLE 276

2-(5-{[4-(4-{[tert-butyl(dimethyl)silyl]oxy}cyclohexyl)-5-oxo-7-propyl-4,5-dihydro[1,2,4]triazolo[1,5-a]pyrimidin-6-yl]methyl}pyridin-2-yl)benzonitrile A mixture of ethyl 2-{[6-(2-cyanophenyl)pyridin-3-yl]methyl}-3-oxohexanoate (1.8 g), N-(4-{[tert-butyl(dimethyl)silyl]oxy}cyclohexyl)-4H-1,2,4-triazol-3-amine (1.4 g) and N,N-diethylaniline (30 mL) was stirred at 180° C. for 8 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a colorless solid (0.42 g, 21%).

$^1$H NMR (300 MHz, DMSO-d$_6$) δ0.05 (s, 6H) 0.79-1.00 (m, 12H) 1.35-2.68 (m, 10H) 2.91-3.06 (m, 2H) 3.57-3.77 (m, 0H) 4.02 (s, 2H) 4.77-4.97 (m, 1H) 7.56-7.67 (m, 1H) 7.71-7.99 (m, 4H) 8.10-8.23 (m, 1H) 8.64-8.71 (m, 1H)

REFERENCE EXAMPLE 277 ethyl({trans-4-[6-{[6-(2-cyanophenyl)pyridin-3-yl]methyl}-5-oxo-7-propyl[1,2,4]triazolo[1,5-a]pyrimidin-4(5H)-yl]cyclohexyl}oxy)acetate A mixture of 2-(5-{[4-(4-{[tert-butyl(dimethyl)silyl]oxy}cyclohexyl)-5-oxo-7-propyl-4,5-dihydro[1,2,4]triazolo[1,5-a]pyrimidin-6-yl]methyl}pyridin-2-yl)benzonitrile (0.42 g), tetrabutylammonium fluoride (1 M tetrahydrofuran solution, 1.1 mL) and tetrahydrofuran (20 mL) was stirred at 70° C. for 16 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure. The obtained residue was dissolved in acetonitrile (20 mL), 1,1,1-triacetoxy-1,1-dihydro-1,2-benziodoxol-3(1H)-one (0.31 g) was added, and the mixture was stirred at room temperature for 3 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was dissolved in tetrahydrofuran (3 mL) and methanol (3 mL), sodium borohydride (0.016 g) was added, and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure. To a solution (10 mL) of the obtained residue in toluene was added dropwise ethyl diazoacetate (0.14 mL) in the presence of rhodium(I) acetate (0.0012 g) at 80° C., and the mixture was stirred at the same temperature for 1 hr. The reaction mixture was concentrated, and the obtained residue was subjected to silica gel column chromatography to give the title compound as a colorless solid (0.06 g, 15%).

$^1$H NMR (300 MHz, DMSO-d$_6$) δ1.09 (t, J=7.3 Hz, 3H) 1.30 (t, J=7.1 Hz, 3H) 1.46-1.86 (m, 6H) 2.18-2.27 (m, 2H) 2.60-2.76 (m, 2H) 3.01-3.09 (m, 2H) 3.43-3.58 (m, 1H) 4.00 (s, 2H) 4.13 (s, 2H) 4.23 (q, J=7.2 Hz, 2H) 4.97-5.13 (m, 1H) 7.49 (t, J=7.5 Hz, 1H) 7.64-7.84 (m, 5H) 7.92 (s, 1H) 8.68 (s, 1H)

REFERENCE EXAMPLE 278

4'-{[4-butyl-2-(methylsulfanyl)-6-oxo-1,6-dihydropyrimidin-5-yl]methyl}biphenyl-2-carbonitrile A mixture of 4'-[(4-butyl-6-oxo-2-sulfanyl-1,6-dihydropyrimidin-5-yl)methyl]biphenyl-2-carbonitrile (3.6 g), methyl iodide (0.83 mL), potassium hydroxide (0.68 g) and methanol (30 mL) was stirred at room temperature for 3 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (3.5 g, 95%).

$^1$H NMR (300 MHz, DMSO-d$_6$) δ0.79-0.87 (m, 3H) 1.19-1.34 (m, 2H) 1.41-1.56 (m, 2H) 2.46-2.57 (m, 5H) 3.84 (s, 2H) 7.32 (q, J=8.3 Hz, 2H) 7.44-7.51 (m, 2H) 7.52-7.61 (m, 2H) 7.72-7.81 (m, 1H) 7.89-8.00 (m, 1H) 12.7 (br. s., 1H)

REFERENCE EXAMPLE 279

4'-[(4-butyl-2-hydrazino-6-oxo-1,6-dihydropyrimidin-5-yl)methyl]biphenyl-2-carbonitrile A mixture of 4'-{[4-butyl-2-(methylsulfanyl)-6-oxo-1,6-dihydropyrimidin-5-yl]methyl}biphenyl-2-carbonitrile (3.5 g), hydrazine hydrate (10 mL) and n-butanol (100 mL) was stirred at 120° C. for 6 hr. The reaction mixture was cooled to room temperature, and the precipitated solid was collected by filtration. The obtained solid was washed with methanol to give the title compound as a colorless solid (2.6 g, 77%).

$^1$H NMR (300 MHz, DMSO-d$_6$) δ0.81 (t, J=7.2 Hz, 3H) 1.16-1.33 (m, 2H) 1.33-1.51 (m, 2H) 2.36 (t, J=7.4 Hz, 2H) 3.76 (s, 2H) 7.31 (q, J=8.3 Hz, 2H) 7.41-7.50 (m, 2H) 7.51-7.64 (m, 2H) 7.72-7.83 (m, 1H) 7.92 (d, J=8.0 Hz, 1H) 8.25 (br. s., 1H)

REFERENCE EXAMPLE 280

4'-[(5-butyl-7-oxo-7,8-dihydro[1,2,4]triazolo[4,3-a]pyrimidin-6-yl)methyl]biphenyl-2-carbonitrile A mixture of 4'-[(4-butyl-2-hydrazino-6-oxo-1,6-dihydropyrimidin-5-yl)methyl]biphenyl-2-carbonitrile (2.6 g) and triethyl orthoformate (30 mL) was stirred at 100° C. for 16 hr. The reaction mixture was concentrated, and ethyl acetate and water were added to the obtained residue. The ethyl acetate layer was washed with saturated brine, and dried over anhydrous magnesium sulfate. The solvent was evaporated under reduced pressure. The obtained residue was purified by silica gel column chromatography to give the title compound as a colorless solid (0.46 g, 17%).

$^1$H NMR (300 MHz, DMSO-d$_6$) δ0.82 (t, J=7.3 Hz, 3H) 1.23-1.39 (m, 2H) 1.41-1.58 (m, 2H) 2.58-2.67 (m, 2H) 3.96 (s, 2H) 7.33-7.41 (m, 2H) 7.43-7.51 (m, 2H) 7.52-7.62 (m, 2H) 7.71-7.81 (m, 1H) 7.92 (dd, J=7.8, 0.85 Hz, 1H) 9.01 (s., 1H), 13.5 (br. s., 1H)

REFERENCE EXAMPLE 281

4'-{[5-butyl-8-[4-(1-methylethoxyphenyl)-7-oxo-7,8-dihydro[1,2,4]triazolo[4,3-a]pyrimidin-6-yl]methyl}biphenyl-2-carbonitrile To a suspension (15 mL) of 4'-[(5-butyl-7-oxo-7,8-dihydro[1,2,4]triazolo[4,3-a]pyrimidin-6-yl)methyl]biphenyl-2-carbonitrile (0.43 g), [4-(1-methylethoxy)phenyl]boronic acid (0.4 g), triethylamine (0.5 mL), pyridine (1 mL) and molecular sieves 4A (1 g) in dichloromethane was added copper(II) acetate (0.41 g), and the mixture was stirred for 16 hr. The reaction mixture was diluted with ethyl acetate, the insoluble material was filtered off through celite, and the filtrate was concentrated. The residue was purified by silica gel column chromatography to give the title compound as a colorless solid (0.33 g, 56%).

¹H NMR (300 MHz, CHLOROFORM-d) δ1.00 (t, J=7.2 Hz, 3H) 1.32-1.41 (m, 6H) 1.46-1.58 (m, 2H) 1.58-1.72 (m, 2H) 2.91-3.01 (m, 2H) 4.04 (s, 2H) 4.51-4.63 (m, 1H) 7.02 (d, J=8.7 Hz, 2H) 7.30-7.44 (m, 5H) 7.44-7.52 (m, 3H) 7.59-7.68 (m, 1H) 7.75 (d, J=7.6 Hz, 1H) 8.36 (s, 1H)

REFERENCE EXAMPLE 282

3-methyl-N-(tetrahydro-2H-pyran-4-yl)-1H-pyrazol-5-amine hydrochloride

To a solution (20 mL) of 1-benzyl-3-methyl-1H-pyrazol-5-amine (1 g) and tetrahydro-4H-pyran-4-one (0.8 g) in acetic acid was added sodium cyanoborohydride (1.7 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. The obtained residue was dissolved in methanol (30 mL) and acetic acid (30 mL), activated carbon-supported 20 mass % palladium hydroxide (1 g) was added, and the mixture was stirred at room temperature for 4 days under hydrogen stream. The insoluble material was filtered through celite, and the filtrate was concentrated. The obtained residue was dissolved in ethyl acetate (20 mL), and 4N hydrochloric acid-ethyl acetate (1.8 mL) was added at room temperature. The precipitated solid was collected by filtration to give the title compound as a colorless solid (0.71 g, 61%).
¹H NMR (300 MHz, DMSO-d₆) δ1.34-1.51 (m, 2H) 1.76-1.89 (m, 2H) 2.21 (s, 3H) 3.28-3.41 (m, 2H) 3.41-3.55 (m, 1H) 3.78-3.93 (m, 2H) 5.62 (s, 1H) 7.39 (br. s., 1H) 13.87 (br. s., 1H)

REFERENCE EXAMPLE 283

4'-{[2-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile A mixture of ethyl 2-[(2'-cyanobiphenyl-4-yl)methyl]-3-oxohexanoate (0.96 g), 3-methyl-N-(tetrahydro-2H-pyran-4-yl)-1H-pyrazol-5-amine hydrochloride (0.3 g) and N,N-diethylaniline (10 mL) was stirred at 180° C. for 2 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a colorless solid (0.27 g, 42%).
¹H NMR (300 MHz, CHLOROFORM-d) δ1.05 (t, J=7.3 Hz, 3H) 1.59-1.79 (m, 4H) 2.35 (s, 3H) 2.51-2.69 (m, 2H) 2.96-3.08 (m, 2H) 3.48-3.60 (m, 2H) 4.00 (s, 2H) 4.07-4.18 (m, 2H) 5.26-5.41 (m, 1H) 5.95 (s, 1H) 7.33-7.52 (m, 6H) 7.56-7.66 (m, 1H) 7.74 (dd, J=7.8, 1.0 Hz, 1H)

REFERENCE EXAMPLE 284 tert-butyl[(trans-4-{6-[(2'-cyanobiphenyl-4-yl)methyl]-5-oxo-7-propylpyrazolo[1,5-a]pyrimidin-4(5H)-yl}cyclohexyl)oxy]acetate To a suspension of 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (21.1 g) and tetrabutylammonium hydrogen sulfate (1.5 g) in toluene (160 mL) –50% sodium hydroxide (160 mL) was added dropwise tert-butyl bromoacetate (20 mL) at 50° C., and the mixture was stirred at 50° C. for 1.5 hr. The mixture was allowed to cool to room temperature, diluted with ethyl acetate and then neutralized with 6M hydrochloric acid. The mixture was extracted with ethyl acetate, and the organic layer was washed with water and brine, dried over anhydrous magnesium sulfate, and concentrated. The residue was purified by silica gel column chromatography to give the title compound as an amorphous pale-yellow solid (24.4 g, 93%).
¹H NMR (300 MHz, DMSO-d₆) δ0.94 (t, J=7.2 Hz, 3H), 1.28-1.73 (m, 15H), 2.04-2.46 (m, 4H), 2.92-3.02 (m, 2H), 3.37-3.52 (m, 1H), 3.97 (s, 2H), 4.00 (s, 2H), 4.62 (br. s., 1H), 6.42 (d, J=1.1 Hz, 1H), 7.34-7.97 (m, 9H)

REFERENCE EXAMPLE 285

4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile To a solution of tert-butyl [(trans-4-{6-[(2'-cyanobiphenyl-4-yl)methyl]-5-oxo-7-propylpyrazolo[1,5-a]pyrimidin-4(5H)-yl}cyclohexyl)oxy]acetate (38.0 g) in tetrahydrofuran (200 mL) was added dropwise methylmagnesium bromide (1 M tetrahydrofuran solution, 200 mL) at 0° C., and the mixture was stirred for 2 hr. The mixture was diluted with ethyl acetate, and then saturated aqueous ammonium chloride solution was added. The mixture was extracted with ethyl acetate, washed with brine, dried over anhydrous magnesium sulfate, and concentrated. The residue was purified by silica gel column chromatography to give the title compound as a pale-yellow amorphous solid (32.1 g, 91%).
¹H NMR (300 MHz, CHLOROFORM-d) δ1.05 (t, J=7.4 Hz, 3H), 1.21 (s, 6H), 1.36-1.90 (m, 7H), 2.13-2.54 (m, 4H), 3.01-3.10 (m, 2H), 3.31 (s, 2H), 3.32-3.44 (m, 1H), 4.01 (s, 2H), 4.74 (br. s., 1H), 5.98 (d, J=2.3 Hz, 1H), 7.33-7.78 (m, 9H)

REFERENCE EXAMPLE 286

4'-{[3-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile A mixture of ethyl 2-[(2'-cyanobiphenyl-4-yl)methyl]-3-oxohexanoate (1.5 g), 4-methyl-N-(tetrahydro-2H-pyran-4-yl)-1H-pyrazol-5-amine (0.4 g), 1,8-diazabicyclo[5.4.0]undec-7-ene (0.3 mL) and N,N-diethylaniline (10 mL) was stirred at 180° C. for 16 hr. The obtained reaction mixture was diluted with ethyl acetate, washed 3 times with 1 N hydrochloric acid and saturated brine, and dried over anhydrous magnesium sulfate. The solvent was evaporated under reduced pressure, and the residue was purified by silica gel column chromatography to give the title compound as a colorless solid (0.63 g, 61%).
¹H NMR (300 MHz, CHLOROFORM-d) δ1.03 (t, J=7.3 Hz, 3H) 1.62-1.76 (m, 4H) 2.35 (s, 3H) 2.96-3.16 (m, 4H) 3.38-3.52 (m, 2H) 3.98 (s, 2H) 4.07-4.18 (m, 2H) 4.44-4.58 (m, 1H) 7.32-7.53 (m, 7H) 7.57-7.65 (m, 1H) 7.74 (dd, J=7.7, 0.9 Hz, 1H)

REFERENCE EXAMPLE 287 ethyl 2-[(2'-cyano-2-fluorobiphenyl-4-yl)methyl]-3-oxohexanoate

To a suspension (200 mL) of 60% sodium hydride (1.8 g) in tetrahydrofuran was added dropwise a solution (50 mL) of ethyl 3-oxohexanoate (10.9 g) in tetrahydrofuran at 0° C. The mixture was stirred at the same temperature for 30 min, 4'-(bromomethyl)-2'-fluorobiphenyl-2-carbonitrile (10.0 g) was added, and the mixture was stirred at room temperature for 16 hr. The reaction mixture was poured into 1 N hydrochloric acid, and the mixture was extracted with ethyl acetate. The obtained ethyl acetate layer was washed with saturated brine, dried over anhydrous magnesium sulfate, and concentrated. The residue was purified by silica gel column chromatography to give the title compound as a pale-yellow oil (12.9 g, 100%).

$^1$H NMR (300 MHz, DMSO-d$_6$) δ0.80 (t, J=7.4 Hz, 3H) 1.11 (t, J=7.1 Hz, 3H) 1.39-1.54 (m, 2H) 2.41-2.64 (m, 2H) 3.04-3.21 (m, 2H) 4.08 (q, J=7.7 Hz, 2H) 7.18-7.32 (m, 2H) 7.41 (t, J=7.9 Hz, 1H) 7.54-7.67 (m, 2H) 7.81 (t, J=7.1 Hz, 1H) 7.97 (dd, J=7.8, 0.8 Hz, 1H)

REFERENCE EXAMPLE 288

4'-{[4-(cis-4-hydroxycyclohexyl)-5-oxo-7-propyl-4, 5-dihydro[1,2,4]triazolo[1,5-a]pyrimidin-6-yl] methyl}biphenyl-2-carbonitrile Sodium tetrahydroborate (0.55 g) was dissolved in methanol (30 mL), a mixture of 4'-{[5-oxo-4-(4-oxocyclohexyl)-7-propyl-4,5-dihydro[1,2,4]triazolo[1,5-a]pyrimidin-6-yl] methyl}biphenyl-2-carbonitrile (5.9 g) and methanol (30 mL) was added dropwise at 0° C., and tetrahydrofuran (10 mL) was added. The mixture was stirred at room temperature for 1.5 hr, sodium tetrahydroborate (0.23 g) was added, and the mixture was stirred at room temperature for 30 min. Saturated aqueous ammonium chloride solution was added to the reaction mixture. The solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.29 g, 13%).

$^1$H NMR (300 MHz, CHLOROFORM-d) δ1.07 (t, J=7.35 Hz, 3H) 1.54-1.80 (m, 6H) 1.90-2.02 (m, 2H) 2.88-3.11 (m, 4H) 4.03 (s, 2H) 4.06-4.20 (m, 1H) 5.01-5.21 (m, 1H) 7.33-7.53 (m, 6H) 7.57-7.68 (m, 1H) 7.75 (dd, J=7.72, 0.94 Hz, 1H) 7.94 (s, 1H)

REFERENCE EXAMPLE 289

4'-({4-[trans-4-(4-{[tert-butyl(dimethyl)silyl] oxy}phenoxy)cyclohexyl]-5-oxo-7-propyl-4,5-dihydro[1,2,4]triazolo[1,5-a]pyrimidin-6-yl}methyl)biphenyl-2-carbonitrile 4'-{[4-(cis-4-Hydroxycyclohexyl)-5-oxo-7-propyl-4,5-dihydro[1,2,4]triazolo[1,5-a]pyrimidin-6-yl] methyl}biphenyl-2-carbonitrile (0.46 g), 4-{[tert-butyl(dimethyl)silyl]oxy}phenol (0.49 g) and triphenylphosphine (0.29 g) were dissolved in tetrahydrofuran (2 mL), a solution of diisopropyl azodicarboxylate (0.58 mL, 1.9 M toluene solution) in tetrahydrofuran (1 mL) was added dropwise at 0° C., and the mixture was stirred at room temperature for 45 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as an oily compound (0.22 g, 33%).

$^1$H NMR (300 MHz, CHLOROFORM-d) δ0.16 (s, 6H) 0.98 (s, 9H) 1.07 (t, J=7.38 Hz, 3H) 1.61-1.90 (m, 6H) 2.18-2.33 (m, 2H) 2.68-2.93 (m, 2H) 2.97-3.09 (m, 2H) 3.99-4.06 (m, 2H) 4.17-4.31 (m, 1H) 5.03-5.23 (m, 1H) 6.65-6.87 (m, 4H) 7.32-7.51 (m, 6H) 7.58-7.66 (m, 1H) 7.74 (d, J=7.95 Hz, 1H) 7.90-7.94 (m, 1H)

REFERENCE EXAMPLE 290

4'-({4-[cis-4-(4-{[tert-butyl(dimethyl)silyl] oxy}phenoxy)cyclohexyl]-5-oxo-7-propyl-4,5-dihydro[1,2,4]triazolo[1,5-a]pyrimidin-6-yl}methyl)biphenyl-2-carbonitrile 4'-{[4-(trans-4-Hydroxycyclohexyl)-5-oxo-7-propyl-4,5-dihydro[1,2,4]triazolo[1,5-a]pyrimidin-6-yl] methyl}biphenyl-2-carbonitrile (0.46 g), 4-{[tert-butyl(dimethyl)silyl]oxy}phenol (0.49 g) and triphenylphosphine (0.29 g) were dissolved in tetrahydrofuran (2 mL), a solution of diisopropyl azodicarboxylate (0.58 mL, 1.9 M toluene solution) in tetrahydrofuran (1 mL) was added dropwise at 0° C., and the mixture was stirred at room temperature for 45 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as an oily compound (0.31 g, 47%).

$^1$H NMR (300 MHz, CHLOROFORM-d) δ0.16 (s, 6H) 0.98 (s, 9H) 1.06 (t, J=7.38 Hz, 3H) 1.59-1.86 (m, 6H) 2.12-2.33 (m, 2H) 2.88-3.24 (m, 4H) 4.03 (s, 2H) 4.41-4.50 (m, 1H) 4.98-5.22 (m, 1H) 6.67-6.81 (m, 2H) 6.86-6.98 (m, 2H) 7.34-7.54 (m, 6H) 7.57-7.67 (m, 1H) 7.74 (d, J=7.57 Hz, 1H) 7.96 (s, 1H)

REFERENCE EXAMPLE 291

4'-{[4-(cis-4-hydroxy-4-methylcyclohexyl)-5-oxo-7-propyl-4,5-dihydro[1,2,4]triazolo[1,5-a]pyrimidin-6-yl]methyl}biphenyl-2-carbonitrile To a mixture of 4'-{[5-oxo-4-(4-oxocyclohexyl)-7-propyl-4,5-dihydro[1,2,4]triazolo[1,5-a]pyrimidin-6-yl] methyl}biphenyl-2-carbonitrile (1.8 g) and diethyl ether (15 mL) was added dropwise methylmagnesium bromide (2.0 mL, 3.0 M diethyl ether solution) at 0° C., and the mixture was stirred at room temperature for 4 hr. Tetrahydrofuran (15 mL) was added, methylmagnesium bromide (4.0 mL, 1.0 M tetrahydrofuran solution) was added dropwise, and the mixture was stirred at 40° C. for 24 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.41 g, 21%).

$^1$H NMR (300 MHz, CHLOROFORM-d) δ1.06 (t, J=7.35 Hz, 3H) 1.29 (s, 3H) 1.58-1.97 (m, 8H) 2.82-3.10 (m, 4H) 4.02 (s, 2H) 4.98-5.16 (m, 1H) 7.32-7.53 (m, 6H) 7.58-7.68 (m, 1H) 7.71-7.78 (m, 1H) 7.94 (s, 1H)

REFERENCE EXAMPLE 292

4'-{[4-(trans-4-hydroxy-4-methylcyclohexyl)-5-oxo-7-propyl-4,5-dihydro[1,2,4]triazolo[1,5-a]pyrimidin-6-yl]methyl}biphenyl-2-carbonitrile To a mixture of 4'-{[5-oxo-4-(4-oxocyclohexyl)-7-propyl-4,5-dihydro[1,2,4]triazolo[1,5-a]pyrimidin-6-yl] methyl}biphenyl-2-carbonitrile (1.8 g) and diethyl ether (15 mL) was added dropwise methylmagnesium bromide (2.0 mL, 3.0 M diethyl ether solution) at 0° C., and the mixture was stirred at room temperature for 4 hr. Tetrahydrofuran (15 mL) was added, methylmagnesium bromide (4.0 mL, 1.0 M tetrahydrofuran solution) was added dropwise, and the mixture was stirred at 40° C. for 24 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.35 g, 18%).

$^1$H NMR (300 MHz, CHLOROFORM-d) δ1.06 (t, J=7.35 Hz, 3H) 1.39 (s, 1H) 1.48 (s, 3H) 1.58-1.98 (m, 8H) 2.67-2.94 (m, 2H) 2.96-3.09 (m, 2H) 4.02 (s, 2H) 4.98-5.18 (m, 1H) 7.31-7.52 (m, 6H) 7.58-7.69 (m, 1H) 7.71-7.79 (m, 1H) 7.92 (s, 1H)

REFERENCE EXAMPLE 293

4'-({4-[cis-4-(4-acetylphenoxy)cyclohexyl]-5-oxo-7-propyl-4,5-dihydro[1,2,4]triazolo[1,5-a]pyrimidin-6-yl}methyl)biphenyl-2-carbonitrile 4'-{[4-(trans-4-Hydroxycyclohexyl)-5-oxo-7-propyl-4,5-dihydro[1,2,4]triazolo[1,5-a]pyrimidin-6-yl]methyl}biphenyl-2-carbonitrile (4.6 g), 4-bromophenol (3.4 g) and triphenylphosphine (5.2 g) were dissolved in tetrahydrofuran (5 mL), a solution of diisopropyl azodicarboxylate (10 mL, 1.9 M toluene solution) in tetrahydrofuran (5 mL) was added dropwise, and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was mixed with dibutyl(1-ethoxyethenyl)pentylstannane (4.0 mL), dichlorobis(triphenylphosphine)palladium (0.35 g) and tetrahydrofuran (30 mL), and the mixture was heated under reflux for 64 hr. Aqueous potassium fluoride solution was added, and the obtained mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.8 g, 32%).

$^1$H NMR (300 MHz, CHLOROFORM-d) δ1.06 (t, J=7.19 Hz, 3H) 1.60-1.85 (m, 6H) 2.17-2.32 (m, 2H) 2.56 (s, 3H) 2.95-3.20 (m, 4H) 4.03 (s, 2H) 4.66-4.77 (m, 1H) 5.05-5.23 (m, 1H) 7.07 (d, J=9.09 Hz, 2H) 7.33-7.53 (m, 6H) 7.58-7.67 (m, 1H) 7.74 (d, J=7.57 Hz, 1H) 7.91-7.99 (m, 3H)

REFERENCE EXAMPLE 294

4'-({4-[trans-4-(4-bromophenoxy)cyclohexyl]-5-oxo-7-propyl-4,5-dihydro[1,2,4]triazolo[1,5-a]pyrimidin-6-yl}methyl)biphenyl-2-carbonitrile 4'-{[4-(cis-4-Hydroxycyclohexyl)-5-oxo-7-propyl-4,5-dihydro[1,2,4]triazolo[1,5-a]pyrimidin-6-yl]methyl}biphenyl-2-carbonitrile (1.2 g), 4-bromophenol (0.93 g) and triphenylphosphine (1.4 g) were dissolved in tetrahydrofuran (1.5 mL), a solution of diisopropyl azodicarboxylate (2.8 mL, 1.9 M toluene solution) in tetrahydrofuran (2.0 mL) was added dropwise, and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.67 g, 40%).

$^1$H NMR (300 MHz, CHLOROFORM-d) δ1.07 (t, J=7.38 Hz, 3H) 1.59-1.94 (m, 6H) 2.18-2.39 (m, 2H) 2.70-2.90 (m, 2H) 2.96-3.10 (m, 2H) 4.02 (s, 2H) 4.23-4.39 (m, 1H) 5.02-5.21 (m, 1H) 6.81 (d, J=9.09 Hz, 2H) 7.32-7.53 (m, 8H) 7.58-7.68 (m, 1H) 7.75 (d, J=7.95 Hz, 1H) 7.93 (s, 1H)

REFERENCE EXAMPLE 295

4'-({4-[trans-4-(4-acetylphenoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[trans-4-(4-bromophenoxy)cyclohexyl]-5-oxo-7-propyl-4,5-dihydro[1,2,4]triazolo[1,5-a]pyrimidin-6-yl}methyl)biphenyl-2-carbonitrile (0.67 g), dibutyl(1-ethoxyethenyl)pentylstannane (0.45 mL), dichlorobis(triphenylphosphine)palladium (0.038 g) and tetrahydrofuran (3 mL) was heated under reflux for 64 hr. Aqueous potassium fluoride solution was added, and the obtained mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.39 g, 62%).

$^1$H NMR (300 MHz, CHLOROFORM-d) δ1.07 (t, J=7.35 Hz, 3H) 1.63-1.96 (m, 6H) 2.23-2.38 (m, 2H) 2.55 (s, 3H) 2.74-2.93 (m, 2H) 2.98-3.11 (m, 2H) 4.02 (s, 2H) 4.37-4.58 (m, 1H) 5.03-5.22 (m, 1H) 6.95 (d, J=8.67 Hz, 2H) 7.32-7.54 (m, 6H) 7.57-7.66 (m, 1H) 7.75 (d, J=7.72 Hz, 1H) 7.86-7.99 (m, 3H)

REFERENCE EXAMPLE 296

4'-[(4-{cis-4-[4-(1-hydroxy-1-methylethyl)phenoxy]cyclohexyl}-5-oxo-7-propyl-4,5-dihydro[1,2,4]triazolo[1,5-a]pyrimidin-6-yl)methyl]biphenyl-2-carbonitrile 4'-({4-[cis-4-(4-Acetylphenoxy)cyclohexyl]-5-oxo-7-propyl-4,5-dihydro[1,2,4]triazolo[1,5-a]pyrimidin-6-yl}methyl)biphenyl-2-carbonitrile (0.50 g) was dissolved in tetrahydrofuran (2 mL), methylmagnesium bromide (1.8 mL, 1.0 M tetrahydrofuran solution) was added dropwise, and the mixture was stirred at room temperature for 17 hr. Methylmagnesium bromide (1.0 mL, 1.0 M tetrahydrofuran solution) was further added dropwise, and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.21 g, 41%).

$^1$H NMR (300 MHz, CHLOROFORM-d) δ1.06 (t, J=7.35 Hz, 3H) 1.58 (s, 6H) 1.63-1.81 (m, 6H) 2.16-2.31 (m, 2H) 2.95-3.22 (m, 4H) 4.03 (s, 2H) 4.53-4.66 (m, 1H) 5.03-5.24 (m, 1H) 6.95-7.04 (m, 2H) 7.33-7.53 (m, 8H) 7.57-7.68 (m, 1H) 7.74 (d, J=7.54 Hz, 1H) 7.96 (s, 1H)

REFERENCE EXAMPLE 297

4'-[(4-{trans-4-[4-(1-hydroxy-1-methylethyl)phenoxy]cyclohexyl}-5-oxo-7-propyl-4,5-dihydro[1,2,4]triazolo[1,5-a]pyrimidin-6-yl)methyl]biphenyl-2-carbonitrile 4'-({4-[trans-4-(4-Acetylphenoxy)cyclohexyl]-5-oxo-7-propyl-4,5-dihydro[1,2,4]triazolo[1,5-a]pyrimidin-6-yl}methyl)biphenyl-2-carbonitrile (0.27 g) was dissolved in tetrahydrofuran (1 mL), methylmagnesium bromide (1.4 mL, 1.0 M tetrahydrofuran solution) was added dropwise, and the mixture was stirred at room temperature for 16 hr. Methylmagnesium bromide (0.11 mL, 1.0 M tetrahydrofuran solution) was further added dropwise, and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 60%).

$^1$H NMR (300 MHz, CHLOROFORM-d) δ1.07 (t, J=7.38 Hz, 3H) 1.57 (s, 6H) 1.59-1.94 (m, 6H) 2.23-2.37 (m, 2H) 2.69-2.89 (m, 2H) 2.96-3.09 (m, 2H) 4.02 (s, 2H) 4.28-4.48 (m, 1H) 5.01-5.22 (m, 1H) 6.90 (d, J=8.71 Hz, 2H) 7.32-7.54 (m, 8H) 7.57-7.68 (m, 1H) 7.75 (d, J=7.57 Hz, 1H) 7.93 (s, 1H)

REFERENCE EXAMPLE 298

4'-({5-oxo-7-propyl-4-[trans-4-(tetrahydro-2H-pyran-4-ylamino)cyclohexyl]-4,5-dihydro[1,2,4]triazolo[1,5-a]pyrimidin-6-yl}methyl)biphenyl-2-carbonitrile 4'-{[5-Oxo-4-(4-oxocyclohexyl)-7-propyl-4,5-dihydro[1,2,4]triazolo[1,5-a]pyrimidin-6-yl]methyl}biphenyl-2-carbonitrile (2.0 g) and tetrahydro-2H-pyran-4-amine (0.43 g) were dissolved in acetic acid (20 mL) and tetrahydrofuran (8 mL), sodium triacetoxyborohydride (1.3 g) was gradually added at room temperature, and the mixture was stirred at room temperature for 24 hr. Water was added, and the solvent was evaporated under reduced pressure. The residue was gradually added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.77 g, 32%).

$^1$H NMR (300 MHz, CHLOROFORM-d) δ1.06 (t, J=7.35 Hz, 3H) 1.43-2.00 (m, 12H) 2.70-2.85 (m, 3H) 2.96-3.05 (m, 2H) 3.06-3.12 (m, 1H) 3.37-3.49 (m, 2H) 3.93-4.06 (m, 4H) 4.99-5.15 (m, 1H) 7.33-7.52 (m, 6H) 7.59-7.66 (m, 1H) 7.75 (d, J=7.91 Hz, 1H) 7.91 (s, 1H)

REFERENCE EXAMPLE 299

4'-[(4-{trans-4-[methyl(tetrahydro-2H-pyran-4-yl)amino]cyclohexyl}-5-oxo-7-propyl-4,5-dihydro[1,2,4]triazolo[1,5-a]pyrimidin-6-yl)methyl]biphenyl-2-carbonitrile To a mixture of 4'-({5-oxo-7-propyl-4-[trans-4-(tetrahydro-2H-pyran-4-ylamino)cyclohexyl]-4,5-dihydro[1,2,4]triazolo[1,5-a]pyrimidin-6-yl}methyl)biphenyl-2-carbonitrile (0.33 g), sodium sulfate (1.5 g), aqueous formaldehyde solution (0.50 mL) and tetrahydrofuran (4 mL) was gradually added sodium triacetoxyborohydride (0.63 g) at room temperature, and the mixture was stirred at room temperature for 114 hr. 0.5M Aqueous sodium hydroxide solution was added, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.13 g, 39%).

$^1$H NMR (300 MHz, CHLOROFORM-d) δ1.05 (t, J=7.19 Hz, 3H) 1.40-1.85 (m, 10H) 2.10-2.19 (m, 2H) 2.24 (s, 3H) 2.62-2.70 (m, 1H) 2.81-3.07 (m, 5H) 3.39 (t, J=11.36 Hz, 2H) 3.98-4.08 (m, 4H) 4.99-5.17 (m, 1H) 7.32-7.52 (m, 6H) 7.57-7.68 (m, 1H) 7.74 (d, J=7.95 Hz, 1H) 7.91 (s, 1H)

REFERENCE EXAMPLE 300

4'-{[4-(3-methylidene-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.50 g), 2-methylidenepropane-1,3-diol (0.18 g), 4-methylbenzenesulfonic acid (0.020 g) and toluene (20 mL) was heated with a Dean-Stark apparatus under reflux for 21 hr. The reaction mixture was concentrated under reduced pressure, and the residue was purified by silica gel column chromatography to give the title compound as a colorless solid (0.36 g, 64%).

$^1$H NMR (300 MHz, CHLOROFORM-d) δ1.06 (t, J=7.35 Hz, 3H) 1.56-1.79 (m, 6H) 2.33-2.44 (m, 2H) 2.82-3.09 (m, 4H) 4.02 (s, 2H) 4.36 (s, 2H) 4.40 (s, 2H) 4.87 (br. s., 2H) 5.03-5.18 (m, 1H) 7.33-7.52 (m, 6H) 7.59-7.67 (m, 1H) 7.74 (d, J=7.54 Hz, 1H) 7.93 (s, 1H)

REFERENCE EXAMPLE 301

4'-{[4-(3-hydroxy-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile To a mixture of 4'-{[4-(3-methylidene-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile (2.0 g), sodium periodate (4.1 g), acetone (40 mL), acetonitrile (40 mL) and water (40 mL) was added osmium tetraoxide (1.48 g, 7% immobilized catalyst) at 0° C., and the mixture was stirred at room temperature for 8 hr. Sodium periodate (1.6 g) and osmium tetraoxide (0.60 g, 7% immobilized catalyst) were added, and the mixture was further stirred at room temperature for 16 hr. Ethyl acetate and water were added to the reaction mixture, the precipitate was filtered off, and the filtrate was extracted with ethyl acetate. The organic layer was washed with saturated brine, and dried over anhydrous magnesium sulfate. The solvent was evaporated under reduced pressure, and the residue was dissolved in tetrahydrofuran (10 mL) and methanol (20 mL), sodium tetrahydroborate (0.29 g) was added, and the mixture was stirred at room temperature for 2 hr. Saturated aqueous sodium hydrogen carbonate solution was added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.5 g, 73%).

$^1$H NMR (300 MHz, CHLOROFORM-d) δ1.06 (t, J=7.19 Hz, 3H) 1.38-1.83 (m, 6H) 2.09-2.21 (m, 1H) 2.64-3.09 (m, 6H) 3.52-3.63 (m, 1H) 3.73-3.83 (m, 1H) 3.85-3.95 (m, 1H) 4.02 (s, 2H) 4.05-4.18 (m, 2H) 5.01-5.21 (m, 1H) 7.33-7.52 (m, 6H) 7.58-7.67 (m, 1H) 7.74 (d, J=7.95 Hz, 1H) 7.93 (s, 1H)

REFERENCE EXAMPLE 302

4'-{[4-(3-{[tert-butyl(dimethyl)silyl]oxy}-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile 4'-{[4-(3-Hydroxy-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile (1.5 g) and 2,6-lutidine (0.50 mL) were dissolved in tetrahydrofuran (5 mL), and tert-butyl(dimethyl)silyl trifluoromethanesulfonate (0.98 mL) was added at 0° C. The mixture was stirred at room temperature for 1.5 hr. Ethyl acetate and water were added to the reaction mixture, the mixture was added to 1 M hydrochloric acid, and the mixture was extracted with ethyl acetate. The organic layer was washed with saturated brine, and dried over anhydrous magnesium sulfate. The solvent was evaporated under reduced pressure to give the title compound as a colorless solid (1.9 g, 100%).

$^1$H NMR (300 MHz, CHLOROFORM-d) δ0.01 (s, 6H) 0.88 (s, 9H) 1.06 (t, J=7.19 Hz, 3H) 1.34-2.03 (m, 8H) 2.68-3.09 (m, 4H) 3.52-3.71 (m, 2H) 3.76-3.99 (m, 3H) 4.01 (s, 2H) 5.02-5.18 (m, 1H) 7.33-7.52 (m, 6H) 7.58-7.68 (m, 1H) 7.70-7.77 (m, 1H) 7.92 (s, 1H)

REFERENCE EXAMPLE 303

4'-({4-[cis-4-(2-hydroxyethoxy)cyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile (1.0 g), sodium cyanoborohydride (0.32 g), boron trifluoride etherate (0.64 mL) and tetrahydrofuran (20 mL) was heated under reflux for 15 hr. Saturated aqueous sodium hydrogen carbonate solution was added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.44 g, 42%).

$^1$H NMR (300 MHz, CHLOROFORM-d) δ1.08 (t, J=7.35 Hz, 3H) 1.49-1.86 (m, 6H) 2.05-2.15 (m, 2H) 2.48 (s, 3H) 2.51-2.66 (m, 2H) 2.99-3.09 (m, 2H) 3.56-3.63 (m, 2H) 3.65-3.74 (m, 1H) 3.76-3.85 (m, 2H) 4.00 (s, 2H) 4.90-5.09 (m, 1H) 7.27-7.34 (m, 2H) 7.41-7.55 (m, 4H) 7.62-7.71 (m, 1H) 7.72-7.79 (m, 1H)

REFERENCE EXAMPLE 304

4'-({4-[trans-4-(2-hydroxyethoxy)cyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile (1.0 g), sodium cyanoborohydride (0.32 g), boron trifluoride etherate (0.64 mL) and tetrahydrofuran (20 mL) was heated under reflux for 15 hr. Saturated aqueous sodium hydrogen carbonate solution was added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.60 g, 58%).

$^1$H NMR (300 MHz, CHLOROFORM-d) δ1.05 (t, J=7.35 Hz, 3H) 1.36-1.87 (m, 6H) 2.01-2.10 (m, 1H) 2.13-2.24 (m, 2H) 2.43 (s, 3H) 2.64-2.83 (m, 2H) 2.93-3.03 (m, 2H) 3.39-3.54 (m, 1H) 3.57-3.65 (m, 2H) 3.68-3.77 (m, 2H) 3.98 (s, 2H) 4.91-5.09 (m, 1H) 7.30-7.52 (m, 6H) 7.58-7.67 (m, 1H) 7.74 (dd, J=7.72, 0.94 Hz, 1H)

REFERENCE EXAMPLE 305

4'-({4-[(3S,6S)-1-oxaspiro[2.5]oct-6-yl]-5-oxo-7-propyl-4,5-dihydro[1,2,4]triazolo[1,5-a]pyrimidin-6-yl}methyl)biphenyl-2-carbonitrile To a mixture of trimethylsulfoxonium iodide (1.1 g) and dimethyl sulfoxide (20 mL) was added sodium hydride (0.20 g) at room temperature, and the mixture was stirred at room temperature for 1 hr. 4'-{[5-Oxo-4-(4-oxocyclohexyl)-7-propyl-4,5-dihydro[1,2,4]triazolo[1,5-a]pyrimidin-6-yl]methyl}biphenyl-2-carbonitrile (2.0 g) was added, and the mixture was stirred at room temperature for 17 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.6 g, 78%).

$^1$H NMR (300 MHz, CHLOROFORM-d) δ1.07 (t, J=7.35 Hz, 3H) 1.36-1.48 (m, 2H) 1.66-1.86 (m, 4H) 2.06-2.21 (m, 2H) 2.72 (s, 2H) 2.92-3.19 (m, 4H) 4.03 (s, 2H) 5.10-5.27 (m, 1H) 7.35-7.52 (m, 6H) 7.58-7.67 (m, 1H) 7.75 (dd, J=7.72, 0.94 Hz, 1H) 7.94 (s, 1H)

REFERENCE EXAMPLE 306

4'-({4-[cis-4-hydroxy-4-(methoxymethyl)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[(3S,6S)-1-oxaspiro[2.5]oct-6-yl]-5-oxo-7-propyl-4,5-dihydro[1,2,4]triazolo[1,5-a]pyrimidin-6-yl}methyl)biphenyl-2-carbonitrile (0.40 g), sodium methoxide (0.22 g), methanol (5 mL) and tetrahydrofuran (3 mL) was stirred at room temperature for 22 hr and then at 50° C. for 24 hr. After evaporation of the solvent under reduced pressure, water was added, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.35 g, 84%).

$^1$H NMR (300 MHz, CHLOROFORM-d) δ1.06 (t, J=7.44 Hz, 3H) 1.43-1.79 (m, 6H) 1.83-1.95 (m, 2H) 2.35 (s, 1H) 2.93-3.11 (m, 4H) 3.26 (s, 2H) 3.41 (s, 3H) 4.02 (s, 2H) 4.98-5.18 (m, 1H) 7.32-7.53 (m, 6H) 7.58-7.67 (m, 1H) 7.71-7.78 (m, 1H) 7.96 (s, 1H)

REFERENCE EXAMPLE 307

4'-({4-[4-(2-hydroxy-2-methylpropoxy)phenyl]-5-oxo-7-propyl-4,5-dihydro[1,2,4]triazolo[1,5-a]pyrimidin-6-yl}methyl)biphenyl-2-carbonitrile To a mixture of sodium hydride (0.020 g) and N,N-dimethylformamide (2 mL) was added 4'-{[4-(4-hydroxyphenyl)-5-oxo-7-propyl-4,5-dihydro[1,2,4]triazolo[1,5-a]pyrimidin-6-yl]methyl}biphenyl-2-carbonitrile (0.20 g) at 0° C. The mixture was stirred at 0° C. for 30 min, 2,2-dimethyloxirane (0.11 mL) was added, and the mixture was stirred at 90° C. for 24 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.14 g, 61%).

$^1$H NMR (300 MHz, CHLOROFORM-d) δ1.11 (t, J=7.35 Hz, 3H) 1.35 (s, 6H) 1.73-1.88 (m, 2H) 3.06-3.18 (m, 2H) 3.83 (s, 2H) 4.07 (s, 2H) 7.04-7.12 (m, 2H) 7.31-7.53 (m, 8H) 7.58-7.67 (m, 1H) 7.75 (dd, J=7.72, 0.94 Hz, 1H) 7.86 (s, 1H)

REFERENCE EXAMPLE 308

4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: short)

A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1.0 g), butane-2,3-diol (0.38 g), 4-methylbenzenesulfonic acid (0.042 g) and toluene (20 mL) was heated with a Dean-Stark apparatus under reflux for 9 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was dissolved in tetrahydrofuran (20 mL), sodium cyanoborohydride (0.67 g) and boron trifluoride etherate (1.3 mL) were added, and the mixture was heated under reflux for 7 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. 60% of the residue was dissolved in acetonitrile (3 mL), Dess-Martin periodinane (1.0 g) was added, and the mixture was stirred at room temperature for 2 hr. Saturated aqueous sodium hydrogen carbonate solution and aqueous sodium thiosulfate solution were added to the reaction mixture, and the mixture was stirred for 1 hr. The solvent was evaporated under reduced pressure, and the residue was extracted with ethyl acetate. The organic layer was washed with saturated brine, and dried over anhydrous magnesium sulfate. The solvent was evaporated under reduced pressure, and the residue was dissolved in tetrahydrofuran (3 mL), methylmagnesium bromide (1.9 mL, 1.0 M tetrahydrofuran solution) was added dropwise at 0° C., and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a racemate (0.19 g, 27%).

The obtained racemate (0.16 g) was resolved using a chiral column to give the title compound as a colorless solid (0.088 g, 99.9% ee, 54%).

$^1$H NMR (300 MHz, CHLOROFORM-d) δ1.06 (t, J=7.35 Hz, 3H) 1.09-1.14 (m, 6H) 1.17 (s, 3H) 1.32-1.55 (m, 2H) 1.66-1.87 (m, 4H) 2.08-2.25 (m, 2H) 2.43 (s, 1H) 2.55-2.83 (m, 2H) 2.97-3.09 (m, 2H) 3.34 (q, J=6.40 Hz, 1H) 3.42-3.58 (m, 1H) 4.01 (s, 2H) 4.95-5.17 (m, 1H) 7.32-7.52 (m, 6H) 7.58-7.68 (m, 1H) 7.75 (dd, J=7.72, 0.94 Hz, 1H) 7.92 (s, 1H)
enantiomeric excess measurement condition
CHIRALPACK AD-H 4.6 mm ID×150 mmL LF001
Hexane/2-Propanol=500/500
0.5 ml/min
retention time 20.28 min

REFERENCE EXAMPLE 309

4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: long)

The racemate (0.16 g) of the title compound obtained in Reference Example 308 was resolved using a chiral column to give the title compound as a colorless solid (0.071 g, 99.9% ee, 44%).

$^1$H NMR (300 MHz, CHLOROFORM-d) δ1.06 (t, J=7.35 Hz, 3H) 1.09-1.14 (m, 6H) 1.17 (s, 3H) 1.32-1.55 (m, 2H) 1.66-1.87 (m, 4H) 2.08-2.25 (m, 2H) 2.43 (s, 1H) 2.55-2.83 (m, 2H) 2.97-3.09 (m, 2H) 3.34 (q, J=6.40 Hz, 1H) 3.42-3.58 (m, 1H) 4.01 (s, 2H) 4.95-5.17 (m, 1H) 7.32-7.52 (m, 6H) 7.58-7.68 (m, 1H) 7.75 (dd, J=7.72, 0.94 Hz, 1H) 7.92 (s, 1H)
enantiomeric excess measurement condition
CHIRALPACK AD-H 4.6 mm ID×150 mL LF001
Hexane/2-Propanol=500/500
0.5 ml/min
retention time 25.43 min

REFERENCE EXAMPLE 310

4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile (5.0 g), butane-2,3-diol (1.8 g), 4-methylbenzenesulfonic acid (0.19 g) and toluene (20 mL) was heated with a Dean-Stark apparatus under reflux for 8 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. 40% of the residue was dissolved in tetrahydrofuran (30 mL), sodium cyanoborohydride (1.3 g) and boron trifluoride etherate (2.6 mL) were added, and the mixture was heated under reflux for 13 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in acetonitrile (10 mL), Dess-Martin periodinane (1.7 g) was added, and the mixture was stirred at room temperature for 14 hr. Saturated aqueous sodium hydrogen carbonate solution and aqueous sodium thiosulfate solution were added to the reaction mixture, and the mixture was stirred for 3 hr. The solvent was evaporated under reduced pressure, and the mixture was extracted with ethyl acetate. The organic layer was washed with saturated brine, and dried over anhydrous magnesium sulfate. The solvent was evaporated under reduced pressure, and the residue was dissolved in tetrahydrofuran (10 mL). Methylmagnesium bromide (6.2 mL, 1.0 M tetrahydrofuran solution) was added dropwise at 0° C., and the mixture was stirred at room temperature for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.24 g, 10%).

$^1$H NMR (300 MHz, CHLOROFORM-d) δ1.04 (t, J=7.35 Hz, 3H) 1.09-1.15 (m, 6H) 1.17 (s, 3H) 1.32-1.56 (m, 2H) 1.64-1.84 (m, 4H) 2.06-2.23 (m, 2H) 2.44 (s, 3H) 2.59-2.84 (m, 2H) 2.91-3.03 (m, 2H) 3.34 (q, J=6.22 Hz, 1H) 3.39-3.59 (m, 1H) 3.98 (s, 2H) 4.91-5.09 (m, 1H) 7.30-7.52 (m, 6H) 7.58-7.67 (m, 1H) 7.74 (dd, J=7.72, 0.94 Hz, 1H)

REFERENCE EXAMPLE 311

4'-({4-[trans-4-(2-hydroxy-1-methylethoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile (1.7 g), propane-1,2-diol (0.55 g), 4-methylbenzenesulfonic acid (0.070 g) and toluene (20 mL) was heated with a Dean-Stark apparatus under reflux for 5 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was dissolved in methylene chloride (20 mL). Trimethylaluminum (20 mL, 1.4M hexane solution) was added under an argon atmosphere, and the mixture was stirred at 40° C. for 64 hr. The reaction mixture was cooled to 0° C., and diluted with ethyl acetate. Methanol was gradually added, and the reaction was discontinued. The mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.63 g, 31%).

$^1$H NMR (300 MHz, CHLOROFORM-d) δ1.04 (t, J=7.35 Hz, 3H) 1.13 (d, J=6.22 Hz, 3H) 1.45 (s, 3H) 1.60-1.93 (m, 8H) 1.99 (dd, J=8.29, 4.71 Hz, 1H) 2.43 (s, 3H) 2.70-2.90 (m, 2H) 2.91-3.03 (m, 2H) 3.30-3.44 (m, 1H) 3.44-3.55 (m, 1H) 3.80-3.94 (m, 1H) 3.99 (s, 2H) 4.84-5.12 (m, 1H) 7.31-7.54 (m, 6H) 7.57-7.67 (m, 1H) 7.70-7.78 (m, 1H)

REFERENCE EXAMPLE 312

4'-({4-[trans-4-(2-hydroxy-1-methylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxy-1-methylethoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.63 g), triethylamine (0.80 mL) and dimethyl sulfoxide (3 mL) was added dropwise a solution of sulfur trioxide-pyridine complex (0.54 g) in dimethyl sulfoxide (3 mL), and the mixture was stirred at room temperature for 12 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was dissolved in tetrahydrofuran (10 mL). Methylmagnesium bromide (2.3 mL, 1.0 M tetrahydrofuran solution) was added dropwise at 0° C., and the mixture was stirred at room temperature for 2 hr. Methylmagnesium bromide (1.1 mL, 1.0 M tetrahydrofuran solution) was added, and the mixture was stirred at room temperature for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.34 g, 52%).

$^1$H NMR (300 MHz, CHLOROFORM-d) δ1.04 (t, J=7.35 Hz, 3H) 1.07-1.11 (m, 4.2H) 1.12-1.18 (m, 1.8H) 1.43 (s, 2.1H) 1.46 (s, 0.9H) 1.62-1.90 (m, 8H) 2.25 (d, J=3.77 Hz, 1H) 2.43 (s, 3H) 2.71-2.89 (m, 2H) 2.90-3.02 (m, 2H) 3.41-3.53 (m, 0.6H) 3.62-3.82 (m, 1.4H) 3.99 (s, 2H) 4.89-5.08 (m, 1H) 7.31-7.53 (m, 6H) 7.58-7.67 (m, 1H) 7.75 (dd, J=7.63, 0.85 Hz, 1H)

REFERENCE EXAMPLE 313

4'-({4-[trans-4-(2-hydroxy-1,2-dimethylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxy-1-methylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.34 g), triethylamine (0.42 mL) and dimethyl sulfoxide (2 mL) was added dropwise a solution of sulfur trioxide-pyridine complex (0.28 g) in dimethyl sulfoxide (2 mL), and the mixture was stirred at room temperature for 14 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (3 mL), methylmagnesium bromide (1.0 mL, 1.0 M tetrahydrofuran solution) was added dropwise at 0° C., and the mixture was stirred at room temperature for 2 hr. Methylmagnesium bromide (0.50 mL, 1.0 M tetrahydrofuran solution) was added, and the mixture was stirred at room temperature for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (3 mL), methylmagnesium bromide (3.0 mL, 1.0 M tetrahydrofuran solution) was added dropwise, and the mixture was stirred at room temperature for 14 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 50%).

$^1$H NMR (300 MHz, CHLOROFORM-d) δ1.04 (t, J=7.35 Hz, 3H) 1.09-1.15 (m, 6H) 1.17 (s, 3H) 1.45 (s, 3H) 1.63-1.92 (m, 8H) 2.43 (s, 3H) 2.45 (br. s., 1H) 2.71-2.90 (m, 2H) 2.91-3.02 (m, 2H) 3.56 (q, J=6.22 Hz, 1H) 3.99 (s, 2H) 4.84-5.07 (m, 1H) 7.31-7.53 (m, 6H) 7.57-7.67 (m, 1H) 7.74 (dd, J=7.72, 0.94 Hz, 1H)

REFERENCE EXAMPLE 314

4'-({4-[trans-4-(2-hydroxy-1-methylethoxy)-4-methylcyclohexyl]-5-oxo-7-propyl-4,5-dihydro[1,2,4]triazolo[1,5-a]pyrimidin-6-yl}methyl)biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.50 g), propane-1,2-diol (0.24 g), 4-methylbenzenesulfonic acid (0.021 g) and toluene (20 mL) was heated with a Dean-Stark apparatus under reflux for 6 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was dissolved in methylene chloride (2 mL), trimethylaluminum (6.1 mL, 1.4M hexane solution) was added under an argon atmosphere, and the mixture was stirred at 40° C. for 14 hr. The reaction mixture was cooled to 0° C., methanol was gradually added, and the reaction was discontinued. The mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.13 g, 22%).

$^1$H NMR (300 MHz, CHLOROFORM-d) δ1.06 (t, J=7.38 Hz, 3H) 1.13 (d, J=6.44 Hz, 3H) 1.46 (s, 3H) 1.61-1.93 (m, 8H) 1.98 (dd, J=7.95, 4.54 Hz, 1H) 2.71-2.90 (m, 2H) 2.95-3.07 (m, 2H) 3.33-3.43 (m, 1H) 3.45-3.55 (m, 1H) 3.81-3.94 (m, 1H) 4.02 (s, 2H) 4.96-5.15 (m, 1H) 7.33-7.52 (m, 6H) 7.59-7.66 (m, 1H) 7.72-7.78 (m, 1H) 7.92 (s, 1H)

REFERENCE EXAMPLE 315

4'-({4-[trans-4-(2-hydroxy-1-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxy-1-methylethoxy)-4-methylcyclohexyl]-5-oxo-7-propyl-4,5-dihydro[1,2,4]triazolo[1,5-a]pyrimidin-6-yl}methyl)biphenyl-2-carbonitrile (1.8 g), triethylamine (2.4 mL) and dimethyl sulfoxide (10 mL) was added dropwise a solution of sulfur trioxide-pyridine complex (1.6 g) in dimethyl sulfoxide (10 mL), and the mixture was stirred at room temperature for 1.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was dissolved in tetrahydrofuran (20 mL). Methylmagnesium bromide (6.9 mL, 1.0 M tetrahydrofuran solution) was added dropwise at 0° C., and the mixture was stirred at 0° C. for 2 hr and then at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.4 g, 75%).

$^1$H NMR (300 MHz, CHLOROFORM-d) δ1.00-1.21 (m, 9H) 1.43 (s, 2.25H) 1.47 (s, 0.75H) 1.62-1.95 (m, 8H) 2.25 (d, J=3.41 Hz, 0.75H) 2.62 (s, 0.25H) 2.67-2.89 (m, 2H) 2.94-3.09 (m, 2H) 3.40-3.56 (m, 0.5H) 3.62-3.86 (m, 1.5H) 4.02 (s, 2H) 4.95-5.15 (m, 1H) 7.33-7.55 (m, 6H) 7.58-7.69 (m, 1H) 7.75 (d, J=6.82 Hz, 1H) 7.92 (s, 1H)

REFERENCE EXAMPLE 316

4'-({4-[trans-4-(2-hydroxy-1,2-dimethylpropoxy)-4-methylcyclohexyl]-5-oxo-7-propyl-4,5-dihydro[1,2,4]triazolo[1,5-a]pyrimidin-6-yl}methyl)biphenyl-2-carbonitrile To a mixture of 4'-({4-[trans-4-(2-hydroxy-1-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile (1.4 g), triethylamine (1.8 mL) and dimethyl sulfoxide (8 mL) was added dropwise a solution of sulfur trioxide-pyridine complex (1.2 g) in dimethyl sulfoxide (7 mL), and the mixture was stirred at room temperature for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (15 mL), methylmagnesium bromide (10 mL, 1.0 M tetrahydrofuran solution) was added dropwise at 0° C., and the mixture was stirred at room temperature for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.0 g, 67%).

$^1$H NMR (300 MHz, CHLOROFORM-d) δ1.06 (t, J=7.35 Hz, 3H) 1.10-1.15 (m, 6H) 1.17 (s, 3H) 1.46 (s, 3H) 1.61-1.94 (m, 8H) 2.44 (s, 1H) 2.69-2.92 (m, 2H) 2.95-3.08 (m, 2H) 3.56 (q, J=6.15 Hz, 1H) 4.02 (s, 2H) 4.93-5.16 (m, 1H) 7.32-7.55 (m, 6H) 7.57-7.69 (m, 1H) 7.75 (dd, J=7.82, 0.85 Hz, 1H) 7.92 (s, 1H)

REFERENCE EXAMPLE 317

4'-({4-[4-hydroxy-4-(tetrahydro-2H-pyran-4-yl)cyclohexyl]-5-oxo-7-propyl-4,5-dihydro[1,2,4]triazolo[1,5-a]pyrimidin-6-yl}methyl)biphenyl-2-carbonitrile To a mixture of magnesium (0.10 g) and tetrahydrofuran (1 mL) were added 4-chlorotetrahydro-2H-pyran (0.050 g) and 1,2-dibromoethane (10 drops) under an argon atmosphere. The mixture was heated to initiate the reaction, a solution of 4-chlorotetrahydro-2H-pyran (0.46 g) in tetrahydrofuran (5 mL) was added dropwise at 50° C., and the mixture was stirred at 50° C. for 4 hr. The reaction mixture was cooled to 0° C., a solution of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (0.50 g) in tetrahydrofuran (5 mL) was added dropwise, and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and HPLC to give the title compound as a colorless solid (0.12 g, 20%).

$^1$H NMR (300 MHz, CHLOROFORM-d) δ1.07 (t, J=7.38 Hz, 3H) 1.48-1.87 (m, 13H) 2.79-2.99 (m, 2H) 2.99-3.11 (m, 2H) 3.41-3.54 (m, 2H) 4.03 (s, 2H) 4.08-4.23 (m, 2H) 4.93-5.10 (m, 1H) 7.32-7.53 (m, 6H) 7.59-7.68 (m, 1H) 7.73-7.79 (m, 1H) 8.02 (s, 1H)

REFERENCE EXAMPLE 318 tert-butyl 2-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetyl}hydrazinecarboxylate A mixture of [(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetic acid (0.77 g), tert-butyl hydrazinecarboxylate (0.23 g), 1-ethyl-3-(3-dimethylaminopropyl)carbodiimide hydrochloride (0.34 g), 1-hydroxybenzotriazole (0.24 g) and N,N-dimethylformaldehyde (8 mL) was stirred at room temperature for 12 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.69 g, 72%).

$^1$H NMR (300 MHz, CHLOROFORM-d) δ1.06 (t, J=7.35 Hz, 3H) 1.39-1.89 (m, 6H) 1.48 (s, 9H) 2.10-2.26 (m, 2H) 2.61-2.81 (m, 2H) 2.95-3.08 (m, 2H) 3.43-3.61 (m, 1H) 4.01 (s, 2H) 4.13 (s, 2H) 4.97-5.18 (m, 1H) 7.32-7.52 (m, 6H) 7.58-7.68 (m, 1H) 7.75 (dd, J=7.72, 0.94 Hz, 1H) 7.91 (s, 1H) 8.08-8.16 (m, 1H)

REFERENCE EXAMPLE 319

4'-({4-[trans-4-(1,3,4-oxadiazol-2-ylmethoxy)cyclohexyl]-5-oxo-7-propyl-4,5-dihydro[1,2,4]triazolo[1,5-a]pyrimidin-6-yl}methyl)biphenyl-2-carbonitrile A mixture of [(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetic acid (0.45 g), tert-butyl hydrazinecarboxylate (0.13 g), 1-ethyl-3-(3-dimethylaminopropyl)carbodiimide hydrochloride (0.19 g), 1-hydroxybenzotriazole (0.13 g) and N,N-dimethylformaldehyde (5 mL) was stirred at room temperature for 13 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, the residue was dissolved in trifluoroacetic acid (5 mL), and the mixture was stirred at room temperature for 1 hr. 1 M Aqueous sodium hydroxide solution was added to the reaction mixture, and the mixture was extracted with ethyl acetate. The organic layer was washed with saturated brine, and dried over anhydrous magnesium sulfate. The solvent was evaporated under reduced pressure, and the residue was mixed with ethyl orthoformate (0.37 g), methanesulfonic acid (0.016 g) and tetrahydrofuran (7 mL), and the mixture was heated under reflux for 2 hr. The solvent was evaporated under reduced pressure, and the residue was purified by silica gel column chromatography to give the title compound as a colorless solid (0.17 g, 37%).

$^1$H NMR (300 MHz, CHLOROFORM-d) δ1.06 (t, J=7.35 Hz, 3H) 1.40-1.89 (m, 6H) 2.13-2.28 (m, 2H) 2.61-2.85 (m, 2H) 2.94-3.10 (m, 2H) 3.53-3.70 (m, 1H) 4.01 (s, 2H) 4.81 (s, 2H) 4.97-5.18 (m, 1H) 7.32-7.53 (m, 6H) 7.59-7.67 (m, 1H) 7.75 (dd, J=7.82, 0.85 Hz, 1H) 7.92 (s, 1H) 8.44 (s, 1H)

REFERENCE EXAMPLE 320

4'-{[5-oxo-7-propyl-4-(4,5,6,7-tetrahydro-1H-indazol-5-yl)-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1.0 g), 1,1-dimethoxy-N,N-dimethylmethanamine (2.5 mL) and N,N-dimethylformaldehyde (2.5 mL) was stirred at 85° C. for 11 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was dissolved in ethanol (10 mL). Hydrazine monohydrate (1 mL) was added, and the mixture was heated under reflux for 1.5 hr. Ethyl acetate and water were added to the reaction mixture. After evaporation of the solvent under reduced pressure, the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.74 g, 71%).

$^1$H NMR (300 MHz, CHLOROFORM-d) δ1.08 (t, J=7.35 Hz, 3H) 1.66-1.85 (m, 2H) 1.97-2.09 (m, 1H) 2.73-3.26 (m, 6H) 3.60-3.74 (m, 1H) 4.04 (s, 2H) 5.37-5.56 (m, 1H) 7.32 (s, 1H) 7.35-7.54 (m, 6H) 7.58-7.70 (m, 1H) 7.75 (dd, J=7.82, 0.85 Hz, 1H) 7.91 (s, 1H)

REFERENCE EXAMPLE 321

4'-({4-[1-(2-hydroxy-2-methylpropyl)-4,5,6,7-tetrahydro-1H-indazol-5-yl]-5-oxo-7-propyl-4,5-dihydro[1,2,4]triazolo[1,5-a]pyrimidin-6-yl}methyl)biphenyl-2-carbonitrile A mixture of 4'-{[5-oxo-7-propyl-4-(4,5,6,7-tetrahydro-1H-indazol-5-yl)-4,5-dihydro[1,2,4]triazolo[1,5-a]pyrimidin-6-yl]methyl}biphenyl-2-carbonitrile (0.36 g), sodium hydride (0.044 g) and N,N-dimethylacetamide (3 mL) was stirred at 0° C. for 5 min and then at room temperature for 20 min. 2,2-Dimethyloxirane (0.65 mL) was added, and the mixture was stirred at 120° C. for 1.5 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography to give the title compound as a colorless solid (0.035 g, 8%).

$^1$H NMR (300 MHz, CHLOROFORM-d) δ1.08 (t, J=7.35 Hz, 3H) 1.12 (s, 3H) 1.16 (s, 3H) 1.64-1.86 (m, 2H) 2.00-2.12 (m, 1H) 2.70-2.93 (m, 3H) 2.98-3.11 (m, 2H) 3.11-3.27 (m, 1H) 3.57-3.74 (m, 1H) 3.83-3.97 (m, 2H) 4.04 (s, 2H) 4.52 (s, 1H) 5.31-5.52 (m, 1H) 7.31 (s, 1H) 7.35-7.55 (m, 6H) 7.58-7.68 (m, 1H) 7.75 (dd, J=7.72, 0.94 Hz, 1H) 7.91 (s, 1H)

REFERENCE EXAMPLE 322

4'-({4-[2-(2-hydroxy-2-methylpropyl)-4,5,6,7-tetrahydro-2H-indazol-5-yl]-5-oxo-7-propyl-4,5-dihydro[1,2,4]triazolo[1,5-a]pyrimidin-6-yl}methyl)biphenyl-2-carbonitrile A mixture of 4'-{[5-oxo-7-propyl-4-(4,5,6,7-tetrahydro-1H-indazol-5-yl)-4,5-dihydro[1,2,4]triazolo[1,5-a]pyrimidin-6-yl]methyl}biphenyl-2-carbonitrile (0.36 g), sodium hydride (0.044 g) and N,N-dimethylacetamide (3 mL) was stirred at 0° C. for 5 min and then at room temperature for 20 min. 2,2-Dimethyloxirane (0.65 mL) was added, and the mixture was stirred at 120° C. for 1.5 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography to give the title compound as a colorless solid (0.047 g, 11%).

$^1$H NMR (300 MHz, CHLOROFORM-d) δ1.08 (t, J=7.35 Hz, 3H) 1.15 (s, 6H) 1.65-1.83 (m, 2H) 1.97-2.08 (m, 1H) 2.74-3.23 (m, 6H) 3.60-3.74 (m, 1H) 3.97 (s, 2H) 4.04 (s, 2H) 4.11 (s, 1H) 5.35-5.54 (m, 1H) 7.12 (s, 1H) 7.36-7.53 (m, 6H) 7.59-7.67 (m, 1H) 7.75 (dd, J=7.72, 0.94 Hz, 1H) 7.92 (s, 1H)

REFERENCE EXAMPLE 323

N'-acetyl-2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetohydrazide A mixture of [(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetic acid (0.50 g), acetohydrazide (0.085 g), 1-ethyl-3-(3-dimethylaminopropyl)carbodiimide hydrochloride (0.21 g), 1-hydroxybenzotriazole (0.15 g) and N,N-dimethylformaldehyde (5 mL) was stirred at room temperature for 22 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.42 g, 76%).

$^1$H NMR (300 MHz, CHLOROFORM-d) δ1.06 (t, J=7.38 Hz, 3H) 1.42-1.89 (m, 6H) 2.08 (s, 3H) 2.15-2.29 (m, 2H) 2.58-2.81 (m, 2H) 2.96-3.09 (m, 2H) 3.45-3.62 (m, 1H) 4.01 (s, 2H) 4.14 (s, 2H) 4.93-5.21 (m, 1H) 7.32-7.53 (m, 6H) 7.58-7.69 (m, 1H) 7.75 (d, J=7.57 Hz, 1H) 7.91 (s, 1H) 8.01-8.10 (m, 1H) 8.79 (d, J=5.30 Hz, 1H)

REFERENCE EXAMPLE 324

4'-[(4-{trans-4-[(5-methyl-1,3,4-oxadiazol-2-yl)methoxy]cyclohexyl}-5-oxo-7-propyl-4,5-dihydro[1,2,4]triazolo[1,5-a]pyrimidin-6-yl)methyl]biphenyl-2-carbonitrile A mixture of N'-acetyl-2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetohydrazide (0.42 g), 4-methylbenzenesulfonyl chloride (0.16 g) and pyridine (5 mL) was stirred at 110° C. for 16 hr. 4-Methylbenzenesulfonyl chloride (0.083 g) was added, and the mixture was stirred at 110° C. for 8 hr. Ethyl acetate and 1 M hydrochloric acid were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.24 g, 60%).

$^1$H NMR (300 MHz, CHLOROFORM-d) δ1.06 (t, J=7.35 Hz, 3H) 1.41-1.58 (m, 2H) 1.65-1.89 (m, 4H) 2.10-2.29 (m, 2H) 2.56 (s, 3H) 2.61-2.82 (m, 2H) 2.95-3.11 (m, 2H) 3.49-3.67 (m, 1H) 4.01 (s, 2H) 4.72 (s, 2H) 4.96-5.17 (m, 1H) 7.32-7.53 (m, 6H) 7.57-7.68 (m, 1H) 7.75 (dd, J=7.72, 0.75 Hz, 1H) 7.90 (s, 1H)

REFERENCE EXAMPLE 325

4'-({5-oxo-4-[trans-4-(2-oxoethoxy)cyclohexyl]-7-propyl-4,5-dihydro[1,2,4]triazolo[1,5-a]pyrimidin-6-yl}methyl)biphenyl-2-carbonitrile To a mixture of 4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (1.3 g), triethylamine (1.8 mL) and dimethyl sulfoxide (8 mL) was added dropwise a solution of sulfur trioxide-pyridine complex (1.2 g) in dimethyl sulfoxide (7 mL), and the mixture was stirred at room temperature for 1.5 hr. A solution of triethylamine (1.8 mL) and sulfur trioxide-pyridine complex (1.2 g) in dimethyl sulfoxide (5 mL) was added, and the mixture was stirred at room temperature for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.31 g, 23%).

$^1$H NMR (300 MHz, CHLOROFORM-d) δ1.06 (t, J=7.38 Hz, 3H) 1.42-1.62 (m, 2H) 1.63-1.90 (m, 4H) 2.14-2.29 (m, 2H) 2.60-2.83 (m, 2H) 2.95-3.09 (m, 2H) 3.44-3.59 (m, 1H) 4.01 (s, 2H) 4.13 (s, 2H) 4.96-5.20 (m, 1H) 7.32-7.53 (m, 6H) 7.58-7.68 (m, 1H) 7.75 (d, J=7.57 Hz, 1H) 7.91 (s, 1H) 9.75 (s, 1H)

REFERENCE EXAMPLE 326

4'-({5-oxo-7-propyl-4-[trans-4-(3,3,3-trifluoro-2-hydroxypropoxy)cyclohexyl]-4,5-dihydro[1,2,4]triazolo[1,5-a]pyrimidin-6-yl}methyl)biphenyl-2-carbonitrile 4'-({5-Oxo-4-[trans-4-(2-oxoethoxy)cyclohexyl]-7-propyl-4,5-dihydro[1,2,4]triazolo[1,5-a]pyrimidin-6-yl}methyl)biphenyl-2-carbonitrile (0.31 g) and trimethyl(trifluoromethyl)silane (0.12 g) were dissolved in tetrahydrofuran (5 mL), tetrabutylammonium fluoride (0.74 mL, 1.0 M tetrahydrofuran solution) was added dropwise, and the mixture was stirred at room temperature for 16 hr. 1 M Hydrochloric acid was added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.054 g, 15%).

$^1$H NMR (300 MHz, CHLOROFORM-d) δ1.06 (t, J=7.38 Hz, 3H) 1.38-1.61 (m, 2H) 1.67-1.88 (m, 4H) 2.12-2.26 (m, 2H) 2.61-2.81 (m, 2H) 2.85-2.94 (m, 1H) 2.98-3.08 (m, 2H) 3.43-3.58 (m, 1H) 3.63-3.72 (m, 1H) 3.73-3.81 (m, 1H) 4.01 (s, 2H) 4.99-5.15 (m, 1H) 7.33-7.53 (m, 6H) 7.59-7.68 (m, 1H) 7.75 (d, J=7.95 Hz, 1H) 7.91 (s, 1H)

REFERENCE EXAMPLE 327

4'-({5-oxo-4-[trans-4-(2-oxobutoxy)cyclohexyl]-7-propyl-4,5-dihydro[1,2,4]triazolo[1,5-a]pyrimidin-6-yl}methyl)biphenyl-2-carbonitrile 2-[(trans-4-{6-[(2'-Cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide (1.0 g) was dissolved in tetrahydrofuran (10 mL), ethylmagnesium bromide (1.7 mL, 3.0 M diethyl ether solution) was added dropwise, and the mixture was stirred at room temperature for 15 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.64 g, 67%).

$^1$H NMR (300 MHz, CHLOROFORM-d) δ1.01-1.11 (m, 6H) 1.43-1.56 (m, 2H) 1.68-1.88 (m, 4H) 2.13-2.27 (m, 2H) 2.51 (q, J=7.45 Hz, 2H) 2.61-2.80 (m, 2H) 2.98-3.10 (m, 2H) 3.37-3.52 (m, 1H) 4.01 (s, 2H) 4.10 (s, 2H) 4.97-5.17 (m, 1H) 7.33-7.54 (m, 6H) 7.58-7.68 (m, 1H) 7.75 (d, J=7.57 Hz, 1H) 7.91 (s, 1H)

REFERENCE EXAMPLE 328

4'-({4-[trans-4-(2-hydroxybutoxy)cyclohexyl]-5-oxo-7-propyl-4,5-dihydro[1,2,4]triazolo[1,5-a]pyrimidin-6-yl}methyl)biphenyl-2-carbonitrile 4'-({5-Oxo-4-[trans-4-(2-oxobutoxy)cyclohexyl]-7-propyl-4,5-dihydro[1,2,4]triazolo[1,5-a]pyrimidin-6-yl}methyl)biphenyl-2-carbonitrile (0.64 g) was dissolved in tetrahydrofuran (3 mL) and methanol (6 mL), and sodium tetrahydroborate (0.060 g) was added at 0° C. The reaction mixture was stirred at 0° C. for 2 hr. Saturated aqueous ammonium chloride solution was added to the reaction mixture, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.48 g, 74%).

$^1$H NMR (300 MHz, CHLOROFORM-d) δ0.97 (t, J=7.44 Hz, 3H) 1.06 (t, J=7.35 Hz, 3H) 1.35-1.54 (m, 4H) 1.64-1.87 (m, 4H) 2.10-2.26 (m, 2H) 2.35 (d, J=3.20 Hz, 1H) 2.58-2.81 (m, 2H) 2.96-3.09 (m, 2H) 3.30 (dd, J=9.23, 8.10 Hz, 1H) 3.38-3.50 (m, 1H) 3.55 (dd, J=9.42, 3.01 Hz, 1H) 3.61-3.75 (m, 1H) 4.01 (s, 2H) 4.98-5.17 (m, 1H) 7.32-7.53 (m, 6H) 7.58-7.67 (m, 1H) 7.75 (dd, J=7.72, 0.94 Hz, 1H) 7.91 (s, 1H)

REFERENCE EXAMPLE 329

4'-[(4-{trans-4-[(1-{[tert-butyl(dimethyl)silyl]oxy}cyclopropyl)methoxy]cyclohexyl}-5-oxo-7-propyl-4,5-dihydro[1,2,4]triazolo[1,5-a]pyrimidin-6-yl)methyl]biphenyl-2-carbonitrile 4'-({5-Oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.55 g) was dissolved in methylene chloride (4 mL) under an argon atmosphere, N,N-diisopropylethylamine (0.44 mL) was added dropwise at −78° C., and the mixture was stirred at −78° C. for 40 min. tert-Butyl(dimethyl)silyl trifluoromethanesulfonate (0.58 mL) was added, and the mixture was stirred at −78° C. for 1.5 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in methylene chloride (10 mL), and the mixture was added dropwise to a mixture of diethylzinc (6.5 mL, 1.0 M hexane solution), chloroiodomethane (1.1 g) and methylene chloride (10 mL) stirred at 0° C. for 10 min under an argon atmosphere in advance. The mixture was slowly warmed to room temperature, and the mixture was stirred at room temperature for 2 hr. The reaction mixture was added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.24 g, 40%).

$^1$H NMR (300 MHz, CHLOROFORM-d) δ0.12 (s, 6H) 0.52-0.62 (m, 2H) 0.68-0.76 (m, 2H) 0.85 (s, 9H) 1.06 (t, J=7.35 Hz, 3H) 1.39-1.55 (m, 2H) 1.64-1.85 (m, 4H) 2.08-2.25 (m, 2H) 2.58-2.79 (m, 2H) 2.97-3.08 (m, 2H) 3.34-3.44 (m, 1H) 3.46 (s, 2H) 4.01 (s, 2H) 4.96-5.16 (m, 1H) 7.33-7.56 (m, 6H) 7.57-7.68 (m, 1H) 7.75 (dd, J=7.72, 0.94 Hz, 1H) 7.92 (s, 1H)

REFERENCE EXAMPLE 330

4'-[(5-oxo-4-{trans-4-[(2-oxobut-3-en-1-yl)oxy]cyclohexyl}-7-propyl-4,5-dihydro[1,2,4]triazolo[1,5-a]pyrimidin-6-yl)methyl]biphenyl-2-carbonitrile 2-[(trans-4-{6-[(2'-Cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide (0.50 g) was dissolved in tetrahydrofuran (5 mL), vinylmagnesium bromide (2.6 mL, 1.0 M tetrahydrofuran solution) was added dropwise, and the mixture was stirred at room temperature for 24 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.21 g, 46%).

$^1$H NMR (300 MHz, CHLOROFORM-d) δ1.06 (t, J=7.38 Hz, 3H) 1.41-1.55 (m, 2H) 1.65-1.87 (m, 4H) 2.15-2.30 (m, 2H) 2.60-2.79 (m, 2H) 2.97-3.09 (m, 2H) 3.42-3.55 (m, 1H) 4.01 (s, 2H) 4.31 (s, 2H) 5.00-5.16 (m, 1H) 5.84 (dd, J=10.60, 1.51 Hz, 1H) 6.32-6.41 (m, 1H) 6.54-6.67 (m, 1H) 7.31-7.56 (m, 6H) 7.58-7.68 (m, 1H) 7.75 (d, J=7.95 Hz, 1H) 7.91 (s, 1H)

REFERENCE EXAMPLE 331

4'-[(4-{trans-4-[(2-hydroxybut-3-en-1-yl)oxy]cyclohexyl}-5-oxo-7-propyl-4,5-dihydro[1,2,4]triazolo[1,5-a]pyrimidin-6-yl)methyl]biphenyl-2-carbonitrile Under an argon atmosphere, a mixture of 4'-[(5-oxo-4-{trans-4-[(2-oxobut-3-en-1-yl)oxy]cyclohexyl}-7-propyl-4,5-dihydro[1,2,4]triazolo[1,5-a]pyrimidin-6-yl)methyl]biphenyl-2-carbonitrile (0.21 g), cerium chloride anhydrous (0.15 g), tetrahydrofuran (4 mL) and methanol (2 mL) was stirred at 0° C. for 10 min, and the mixture was cooled to −78° C. Sodium tetrahydroborate (0.026 g) was added, and the mixture was stirred at −78° C. for 1 hr. The reaction mixture was added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.035 g, 16%).

$^1$H NMR (300 MHz, CHLOROFORM-d) δ1.06 (t, J=7.35 Hz, 3H) 1.36-1.56 (m, 2H) 1.65-1.87 (m, 4H) 2.12-2.29 (m, 2H) 2.48 (d, J=3.20 Hz, 1H) 2.61-2.80 (m, 2H) 2.98-3.09 (m, 2H) 3.35 (dd, J=9.51, 8.19 Hz, 1H) 3.41-3.54 (m, 1H) 3.58 (dd, J=9.51, 3.30 Hz, 1H) 4.01 (s, 2H) 4.23-4.38 (m, 1H) 4.99-5.14 (m, 1H) 5.17-5.42 (m, 2H) 5.84 (ddd, J=17.19, 10.50, 5.65 Hz, 1H) 7.33-7.55 (m, 6H) 7.59-7.68 (m, 1H) 7.75 (dd, J=7.72, 0.94 Hz, 1H) 7.92 (s, 1H)

REFERENCE EXAMPLE 332

4'-({4-[trans-4-(2-cyclopropyl-2-oxoethoxy)cyclohexyl]-5-oxo-7-propyl-4,5-dihydro[1,2,4]triazolo[1,5-a]pyrimidin-6-yl}methyl)biphenyl-2-carbonitrile 2-[(trans-4-{6-[(2'-Cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide (0.32 g) was dissolved in tetrahydrofuran (4 mL), cyclopropylmagnesium bromide (3.3 mL, 0.5M tetrahydrofuran solution) was added dropwise, and the mixture was stirred at room temperature for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.23 g, 75%).

$^1$H NMR (300 MHz, CHLOROFORM-d) δ0.87-1.01 (m, 2H) 1.02-1.15 (m, 5H) 1.45-1.63 (m, 2H) 1.64-1.89 (m, 4H) 2.10-2.32 (m, 3H) 2.61-2.82 (m, 2H) 2.96-3.11 (m, 2H) 3.37-3.60 (m, 1H) 4.01 (s, 2H) 4.23 (s, 2H) 5.00-5.14 (m, 1H) 7.31-7.54 (m, 6H) 7.58-7.68 (m, 1H) 7.74 (d, J=7.95 Hz, 1H) 7.91 (s, 1H)

REFERENCE EXAMPLE 333

4'-({4-[trans-4-(2-cyclopropyl-2-hydroxyethoxy)cyclohexyl]-5-oxo-7-propyl-4,5-dihydro[1,2,4]triazolo[1,5-a]pyrimidin-6-yl}methyl)biphenyl-2-carbonitrile 4'-({4-[trans-4-(2-cyclopropyl-2-oxoethoxy)cyclohexyl]-5-oxo-7-propyl-4,5-dihydro[1,2,4]triazolo[1,5-a]pyrimidin-6-yl}methyl)biphenyl-2-carbonitrile (0.23 g) was dissolved in tetrahydrofuran (2 mL) and methanol (4 mL), sodium tetrahydroborate (0.027 g) was added at 0° C., and the mixture was stirred at 0° C. for 1 hr. Saturated aqueous ammonium chloride solution was added to the reaction mixture, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 72%).

$^1$H NMR (300 MHz, CHLOROFORM-d) δ0.16-0.29 (m, 1H) 0.31-0.67 (m, 3H) 0.77-0.93 (m, 1H) 1.06 (t, J=7.38 Hz, 3H) 1.37-1.55 (m, 2H) 1.65-1.91 (m, 4H) 2.11-2.28 (m, 2H) 2.40 (s, 1H) 2.57-2.84 (m, 2H) 2.96-3.13 (m, 3H) 3.37-3.56 (m, 2H) 3.66 (dd, J=9.47, 2.65 Hz, 1H) 4.01 (s, 2H) 4.95-5.23 (m, 1H) 7.32-7.53 (m, 6H) 7.58-7.68 (m, 1H) 7.74 (d, J=7.57 Hz, 1H) 7.91 (s, 1H)

REFERENCE EXAMPLE 334

4'-({5-oxo-7-propyl-4-[trans-4-(3,3,3-trifluoro-2-hydroxy-2-methylpropoxy)cyclohexyl]-4,5-dihydro[1,2,4]triazolo[1,5-a]pyrimidin-6-yl}methyl)biphenyl-2-carbonitrile 4'-({5-Oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.30 g) and trimethyl(trifluoromethyl)silane (0.20 g) were dissolved in tetrahydrofuran (3 mL), tetrabutylammonium fluoride (0.22 mL, 1.0 M tetrahydrofuran solution) was added dropwise at 0° C., and the mixture was stirred at 0° C. for 1 hr. Trimethyl(trifluoromethyl)silane (0.20 g) and tetrabutylammonium fluoride (0.22 mL, 1.0 M tetrahydrofuran solution) were added, and the mixture was stirred at 0° C. for 1 hr and then at room temperature for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.092 g, 27%).

$^1$H NMR (300 MHz, CHLOROFORM-d) δ1.06 (t, J=7.38 Hz, 3H) 1.34 (s, 3H) 1.40-1.56 (m, 2H) 1.64-1.87 (m, 4H) 2.11-2.26 (m, 2H) 2.60-2.80 (m, 2H) 2.97-3.08 (m, 2H) 3.36-3.57 (m, 2H) 3.72 (d, J=9.84 Hz, 1H) 4.01 (s, 2H) 4.95-5.15 (m, 1H) 7.32-7.52 (m, 6H) 7.59-7.68 (m, 1H) 7.74 (d, J=7.95 Hz, 1H) 7.91 (s, 1H)

REFERENCE EXAMPLE 335

4'-({4-[trans-4-(oxiran-2-ylmethoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (1.1 g), m-chloroperbenzoic acid (1.8 g) and acetonitrile (10 mL) was stirred at 50° C. for 15 hr. Saturated aqueous sodium hydrogen carbonate solution and aqueous sodium thiosulfate solution were added to the reaction mixture, and the mixture was stirred for 30 min. The solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.25 g, 20%).

$^1$H NMR (300 MHz, CHLOROFORM-d) δ1.06 (t, J=7.38 Hz, 3H) 1.37-1.56 (m, 2H) 1.68-1.88 (m, 4H) 2.09-2.31 (m, 2H) 2.62 (dd, J=5.30, 2.65 Hz, 1H) 2.65-2.79 (m, 2H) 2.79-2.85 (m, 1H) 2.98-3.08 (m, 2H) 3.11-3.20 (m, 1H) 3.40-3.58 (m, 2H) 3.74 (dd, J=11.36, 3.41 Hz, 1H) 4.01 (s, 2H) 4.95-5.15 (m, 1H) 7.32-7.53 (m, 6H) 7.58-7.67 (m, 1H) 7.73 (dd, J=7.57, 1.51 Hz, 1H) 7.91 (s, 1H)

REFERENCE EXAMPLE 336

4'-({4-[trans-4-(3-fluoro-2-hydroxypropoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[trans-4-(oxiran-2-ylmethoxy)cyclohexyl]-5-oxo-7-propyl-4,5-dihydro[1,2,4]triazolo[1,5-a]pyrimidin-6-yl}methyl)biphenyl-2-carbonitrile (0.25 g), potassium hydrogen fluoride (0.075 g), tetra-n-butylammonium dihydrogentrifluoride (0.015 g) and chlorobenzene (1 mL) was stirred at 120° C. for 5 hr. Potassium hydrogen fluoride (0.075 g) and tetra-n-butylammonium dihydrogentrifluoride (0.014 g) were added, and the mixture was stirred at 120° C. for 16 hr. Toluene was added, and the precipitate was filtered off. The filtrate was concentrated under reduced pressure, and the residue was purified by silica gel column chromatography to give the title compound as a colorless solid (0.15 g, 60%).

$^1$H NMR (300 MHz, CHLOROFORM-d) δ1.06 (t, J=7.38 Hz, 3H) 1.36-1.54 (m, 2H) 1.65-1.89 (m, 4H) 2.12-2.27 (m, 2H) 2.40 (d, J=5.30 Hz, 1H) 2.60-2.82 (m, 2H) 2.96-3.10 (m, 2H) 3.39-3.51 (m, 1H) 3.52-3.67 (m, 2H) 3.92-4.08 (m, 3H) 4.32-4.46 (m, 1H) 4.47-4.61 (m, 1H) 4.95-5.17 (m, 1H) 7.32-7.53 (m, 6H) 7.58-7.69 (m, 1H) 7.74 (d, J=7.57 Hz, 1H) 7.91 (s, 1H)

REFERENCE EXAMPLE 337

4'-({4-[trans-4-(3-fluoro-2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-({4-[trans-4-(3-fluoro-2-hydroxypropoxy)cyclohexyl]-5-oxo-7-propyl-4,5-dihydro[1,2,4]triazolo[1,5-a]pyrimidin-6-yl}methyl)biphenyl-2-carbonitrile (0.15 g), Dess-Martin periodinane (0.24 g) and acetonitrile (2 mL) was stirred at room temperature for 2 hr. Saturated aqueous sodium hydrogen carbonate solution and aqueous sodium thiosulfate solution were added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, and the residue was dissolved in tetrahydrofuran (2 mL). Methylmagnesium bromide (0.58 mL, 1.0 M tetrahydrofuran solution) was added dropwise at 0° C., and the mixture was stirred at room temperature for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.10 g, 62%).

$^1$H NMR (300 MHz, CHLOROFORM-d) δ1.06 (t, J=7.19 Hz, 3H) 1.21 (d, J=2.27 Hz, 3H) 1.35-1.53 (m, 2H) 1.64-1.88 (m, 4H) 2.13-2.25 (m, 2H) 2.61-2.82 (m, 2H) 2.98-3.09 (m, 2H) 3.31-3.57 (m, 3H) 4.01 (s, 2H) 4.12 (dd, J=32.56, 8.71 Hz, 1H) 4.34 (dd, J=32.56, 8.71 Hz, 1H) 4.94-5.16 (m, 1H) 7.32-7.52 (m, 6H) 7.59-7.68 (m, 1H) 7.75 (d, J=7.95 Hz, 1H) 7.91 (s, 1H)

REFERENCE EXAMPLE 338

4'-[(4-{trans-4-[(1-hydroxycyclobutyl)methoxy]cyclohexyl}-5-oxo-7-propyl-4,5-dihydro[1,2,4]triazolo[1,5-a]pyrimidin-6-yl)methyl]biphenyl-2-carbonitrile 4'-[(4-{trans-4-[(Methylsulfanyl)methoxy]cyclohexyl}-5-oxo-7-propyl-4,5-dihydro[1,2,4]triazolo[1,5-a]pyrimidin-6-yl)methyl]biphenyl-2-carbonitrile (1.4 g) was dissolved in dichloromethane (10 mL), and sulfuryl chloride (0.23 mL) was added at 0° C. The mixture was stirred at room temperature for 24 hr, and the solvent was evaporated under reduced pressure. The residue was mixed with cyclobutanone (0.050 g) and tetrahydrofuran (3 mL), and samarium iodide (14 mL, 0.1 M tetrahydrofuran solution) was added dropwise at room temperature under an argon atmosphere. The mixture was stirred at room temperature for 16 hr and added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.021 g, 8.1%).

$^1$H NMR (300 MHz, CHLOROFORM-d) δ1.06 (t, J=7.38 Hz, 3H) 1.37-1.87 (m, 8H) 1.99-2.28 (m, 6H) 2.60-2.82 (m, 3H) 2.94-3.10 (m, 2H) 3.40-3.49 (m, 1H) 3.51 (s, 2H) 4.02 (s, 2H) 4.96-5.21 (m, 1H) 7.33-7.54 (m, 6H) 7.57-7.69 (m, 1H) 7.75 (d, J=7.95 Hz, 1H) 7.91 (s, 1H)

REFERENCE EXAMPLE 339

4'-{[4-(trans-4-{[2-(fluoromethyl)oxiran-2-yl]methoxy}cyclohexyl)-5-oxo-7-propyl-4,5-dihydro[1,2,4]triazolo[1,5-a]pyrimidin-6-yl]methyl}biphenyl-2-carbonitrile A mixture of 4'-({4-[trans-4-(3-fluoro-2-hydroxypropoxy)cyclohexyl]-5-oxo-7-propyl-4,5-dihydro[1,2,4]triazolo[1,5-a]pyrimidin-6-yl}methyl)biphenyl-2-carbonitrile (0.33 g), Dess-Martin periodinane (0.51 g) and acetonitrile (4 mL) was stirred at room temperature for 14 hr. Saturated aqueous sodium hydrogen carbonate solution and aqueous sodium thiosulfate solution were added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, the residue was added to a mixture of trimethylsulfoxonium iodide (0.16 g), sodium hydride (0.030 g) and dimethyl sulfoxide (5 mL) stirred at room temperature for 1 hr in advance, and the mixture was stirred at room temperature for 2 hr. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 52%).

$^1$H NMR (300 MHz, DMSO-$d_6$) δ0.95 (t, J=7.35 Hz, 3H) 1.21-1.43 (m, 2H) 1.50-1.79 (m, 4H) 2.05-2.18 (m, 2H) 2.52-2.69 (m, 2H) 2.76-2.86 (m, 2H) 2.90-3.04 (m, 2H) 3.33-3.46 (m, 1H) 3.55-3.73 (m, 2H) 3.99 (s, 2H) 4.29-4.77 (m, 2H) 4.85-5.02 (m, 1H) 7.35-7.44 (m, 2H) 7.46-7.52 (m, 2H) 7.53-7.64 (m, 2H) 7.72-7.81 (m, 1H) 7.93 (dd, J=7.72, 0.94 Hz, 1H) 8.18 (s, 1H)

REFERENCE EXAMPLE 340

4'-[(4-{trans-4-[3-fluoro-2-(fluoromethyl)-2-hydroxypropoxy]cyclohexyl}-5-oxo-7-propyl-4,5-dihydro[1,2,4]triazolo[1,5-a]pyrimidin-6-yl)methyl]biphenyl-2-carbonitrile A mixture of 4'-{[4-(trans-4-{[2-(fluoromethyl)oxiran-2-yl]methoxy}cyclohexyl)-5-oxo-7-propyl-4,5-dihydro[1,2,4]triazolo[1,5-a]pyrimidin-6-yl]methyl}biphenyl-2-carbonitrile (0.17 g), potassium hydrogen fluoride (0.15 g), tetra-n-butylammonium dihydrogentrifluoride (0.097 g) and chlorobenzene (0.5 mL) was stirred at 120° C. for 14 hr. The precipitate was filtered off, and the filtrate was concentrated under reduced pressure. The residue was purified by silica gel column chromatography to give the title compound as a colorless solid (0.16 g, 87%).

$^1$H NMR (300 MHz, DMSO-$d_6$) δ0.95 (t, J=7.35 Hz, 3H) 1.19-1.41 (m, 2H) 1.49-1.80 (m, 4H) 2.04-2.19 (m, 2H) 2.52-2.68 (m, 2H) 2.87-3.04 (m, 2H) 3.26-3.40 (m, 1H) 3.45 (s, 2H) 3.99 (s, 2H) 4.36 (d, J=47.47 Hz, 4H) 4.81-5.02 (m, 1H) 5.35 (s, 1H) 7.37-7.44 (m, 2H) 7.46-7.52 (m, 2H) 7.53-7.64 (m, 2H) 7.72-7.82 (m, 1H) 7.92 (dd, J=7.72, 0.94 Hz, 1H) 8.19 (s, 1H)

REFERENCE EXAMPLE 341

4'-[(4-{trans-4-[4-(1,3-dioxan-2-yl)-2-hydroxybutoxy]cyclohexyl}-5-oxo-7-propyl-4,5-dihydro[1,2,4]triazolo[1,5-a]pyrimidin-6-yl)methyl]biphenyl-2-carbonitrile 2-[(trans-4-{6-[(2'-Cyanobiphenyl-4-yl)methyl]-5-oxo-7-propyl[1,2,4]triazolo[1,5-a]pyrimidin-4(5H)-yl}cyclohexyl)oxy]-N-methoxy-N-methylacetamide (1.5 g) was dissolved in tetrahydrofuran (15 mL), 2-(1,3-dioxan-2-yl)ethylmagnesium bromide (15 mL, 0.5M tetrahydrofuran solution) was added dropwise, and the mixture was stirred at room temperature for 18 hr. The reaction mixture was added to 1 M hydrochloric acid, and the mixture was extracted with ethyl acetate. The organic layer was washed with saturated aqueous sodium hydrogen carbonate solution and then with saturated brine, and dried over anhydrous magnesium sulfate. The solvent was evaporated under reduced pressure, the residue was dissolved in tetrahydrofuran (5 mL) and methanol (10 mL), and sodium tetrahydroborate (0.16 g) was added at 0° C. The reaction mixture was stirred at 0° C. for 2 hr and then at room temperature for 18 hr. Saturated aqueous ammonium chloride solution was added to the reaction mixture, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.71 g, 44%).

$^1$H NMR (300 MHz, CHLOROFORM-d) δ1.06 (t, J=7.38 Hz, 3H) 1.30-1.91 (m, 12H) 2.13-2.26 (m, 2H) 2.56-2.80 (m, 3H) 2.94-3.11 (m, 2H) 3.33 (dd, J=9.09, 7.57 Hz, 1H) 3.38-3.47 (m, 1H) 3.50 (dd, J=9.28, 3.60 Hz, 1H) 3.67-3.85 (m, 3H) 4.01 (s, 2H) 4.07-4.20 (m, 2H) 4.58 (t, J=4.92 Hz, 1H) 4.96-5.18 (m, 1H) 7.32-7.54 (m, 6H) 7.58-7.68 (m, 1H) 7.74 (d, J=7.57 Hz, 1H) 7.91 (s, 1H)

REFERENCE EXAMPLE 342

4'-[(4-{trans-4-[(2,5-dihydroxypentyl)oxy]cyclohexyl}-5-oxo-7-propyl-4,5-dihydro[1,2,4]triazolo[1,5-a]pyrimidin-6-yl)methyl]biphenyl-2-carbonitrile A mixture of 4'-[(4-{trans-4-[4-(1,3-dioxan-2-yl)-2-hydroxybutoxy]cyclohexyl}-5-oxo-7-propyl-4,5-dihydro[1,2,4]triazolo[1,5-a]pyrimidin-6-yl)methyl]biphenyl-2-carbonitrile (0.71 g), tert-butylchlorodiphenylsilane (0.47 g), imidazole (0.11 g), N,N-dimethylaminopyridine (0.015 g) and tetrahydrofuran (8 mL) was stirred at room temperature for 7 days. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the residue was mixed with 3M hydrochloric acid (10 mL), acetone (20 mL) and tetrahydrofuran (10 mL), and the mixture was stirred at room temperature for 24 hr. The reaction mixture was neutralized, the solvent was evaporated under reduced pressure, and the residue was extracted with ethyl acetate. The organic layer was washed with saturated brine, and dried over anhydrous magnesium sulfate. The solvent was evaporated under reduced pressure. The residue obtained by purification by silica gel column chromatography was mixed with 3M hydrochloric acid (10 mL) and tetrahydrofuran (20 mL), and the mixture was stirred at 70° C. for 2 days and then at room temperature for 3 days. The reaction mixture was neutralized, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was dissolved in tetrahydrofuran (2 mL) and methanol (4 mL). Sodium tetrahydroborate (0.034 g) was added at 0° C., and the reaction mixture was stirred at 0° C. for 2 hr. Saturated aqueous ammonium chloride solution was added to the reaction mixture, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was dissolved in tetrahydrofuran (5 mL). Tetrabutylammonium fluoride (1.0 mL, 1.0 M tetrahydrofuran solution) was added, and the mixture was stirred at 70° C. for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 26%).
$^1$H NMR (300 MHz, DMSO-$d_6$) δ0.95 (t, J=7.25 Hz, 3H) 1.20-1.81 (m, 10H) 2.02-2.19 (m, 2H) 2.52-2.69 (m, 2H) 2.90-3.04 (m, 2H) 3.23-3.43 (m, 5H) 3.45-3.58 (m, 1H) 3.99 (s, 2H) 4.36 (t, J=5.18 Hz, 1H) 4.48 (d, J=5.09 Hz, 1H) 4.78-5.06 (m, 1H) 7.35-7.45 (m, 2H) 7.46-7.51 (m, 2H) 7.52-7.62 (m, 2H) 7.72-7.83 (m, 1H) 7.92 (dd, J=7.91, 0.94 Hz, 1H) 8.18 (s, 1H)

REFERENCE EXAMPLE 343

4'-({5-oxo-7-propyl-4-[trans-4-(tetrahydrofuran-2-ylmethoxy)cyclohexyl]-4,5-dihydro[1,2,4]triazolo[1,5-a]pyrimidin-6-yl}methyl)biphenyl-2-carbonitrile 4'-[(4-{trans-4-[(2,5-Dihydroxypentyl)oxy]cyclohexyl}-5-oxo-7-propyl-4,5-dihydro[1,2,4]triazolo[1,5-a]pyrimidin-6-yl)methyl]biphenyl-2-carbonitrile (0.17 g) was dissolved in tetrahydrofuran (3 mL), triphenylphosphine (0.24 g) and then diethyl azodicarboxylate (0.40 g, 40% toluene solution) were added, and the mixture was stirred at room temperature for 18 hr. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.12 g, 74%).
$^1$H NMR (300 MHz, DMSO-$d_6$) δ0.95 (t, J=7.25 Hz, 3H) 1.13-1.96 (m, 10H) 2.02-2.18 (m, 2H) 2.52-2.68 (m, 2H) 2.91-3.03 (m, 2H) 3.27-3.36 (m, 1H) 3.37-3.44 (m, 2H) 3.56-3.67 (m, 1H) 3.68-3.78 (m, 1H) 3.83-3.94 (m, 1H) 3.99 (s, 2H) 4.81-5.01 (m, 1H) 7.37-7.44 (m, 2H) 7.45-7.51 (m, 2H) 7.52-7.68 (m, 2H) 7.74-7.82 (m, 1H) 7.93 (dd, J=7.82, 0.85 Hz, 1H) 8.18 (s, 1H)

REFERENCE EXAMPLE 344

4'-[(4-{trans-4-[(1-hydroxycyclopentyl)methoxy]cyclohexyl}-5-oxo-7-propyl-4,5-dihydro[1,2,4]triazolo[1,5-a]pyrimidin-6-yl)methyl]biphenyl-2-carbonitrile 4'-[(4-{trans-4-[(Methylsulfanyl)methoxy]cyclohexyl}-5-oxo-7-propyl-4,5-dihydro[1,2,4]triazolo[1,5-a]pyrimidin-6-yl)methyl]biphenyl-2-carbonitrile (1.0 g) was dissolved in toluene (10 mL), and sulfuryl chloride (0.16 mL) was added at 0° C. The mixture was stirred at room temperature for 2 hr, the precipitate was filtered off, and the filtrate was concentrated under reduced pressure. The residue was mixed with cyclopentanone (0.16 g) and tetrahydrofuran (10 mL), and samarium iodide (57 mL, 0.1 M tetrahydrofuran solution) was added dropwise at room temperature under an argon atmosphere. The mixture was stirred at room temperature for 65 hr and added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.026 g, 2.4%).
$^1$H NMR (300 MHz, CHLOROFORM-d) δ1.06 (t, J=7.35 Hz, 3H) 1.30-2.03 (m, 12H) 2.13-2.23 (m, 2H) 2.25-2.44 (m, 2H) 2.60-2.82 (m, 2H) 2.97-3.08 (m, 2H) 3.36-3.53 (m, 3H) 4.01 (s, 2H) 4.99-5.17 (m, 1H) 7.32-7.52 (m, 6H) 7.58-7.67 (m, 1H) 7.75 (dd, J=7.72, 1.32 Hz, 1H) 7.91 (s, 1H)

REFERENCE EXAMPLE 345

4'-[(4-{trans-4-[(methylsulfanyl)methoxy]cyclohexyl}-5-oxo-7-propyl-4,5-dihydro[1,2,4]triazolo[1,5-a]pyrimidin-6-yl)methyl]biphenyl-2-carbonitrile A mixture of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (2.0 g), dimethyl sulfoxide (30 mL) and acetic anhydride (10 mL) was stirred at room temperature for 14 hr. The reaction mixture was added to water, and the mixture was extracted with ethyl acetate. The organic layer was washed with saturated aqueous sodium hydrogen carbonate solution and then with saturated brine, and dried over anhydrous magnesium sulfate. The solvent was evaporated under reduced pressure, and the residue was purified by silica gel column chromatography to give the title compound as a colorless solid (1.3 g, 59%).
$^1$H NMR (300 MHz, CHLOROFORM-d) δ1.06 (t, J=7.38 Hz, 3H) 1.38-1.89 (m, 6H) 2.11-2.21 (m, 5H) 2.62-2.84 (m, 2H) 2.98-3.10 (m, 2H) 3.66-3.89 (m, 1H) 4.01 (s, 2H) 4.68 (s, 2H) 4.98-5.17 (m, 1H) 7.32-7.53 (m, 6H) 7.57-7.69 (m, 1H) 7.74 (d, J=7.57 Hz, 1H) 7.91 (s, 1H)

REFERENCE EXAMPLE 346

4'-({4-[trans-4-(2-hydroxy-2-methylbutoxy)cyclohexyl]-5-oxo-7-propyl-4,5-dihydro[1,2,4]triazolo[1,5-a]pyrimidin-6-yl}methyl)biphenyl-2-carbonitrile 4'-({5-Oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (0.094 g) was dissolved in tetrahydrofuran (1 mL), ethylmagnesium bromide (0.12 mL, 3.0 M tetrahydrofuran solution) was added dropwise, and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.060 g, 61%).
$^1$H NMR (300 MHz, CHLOROFORM-d) δ0.90 (t, J=7.54 Hz, 3H) 1.06 (t, J=7.35 Hz, 3H) 1.13 (s, 3H) 1.36-1.59 (m, 4H) 1.65-1.86 (m, 4H) 2.08-2.28 (m, 2H) 2.57-2.82 (m, 2H) 2.95-3.10 (m, 2H) 3.29 (d, J=8.85 Hz, 1H) 3.35 (d, J=8.85 Hz, 1H) 3.38-3.51 (m, 1H) 4.01 (s, 2H) 4.96-5.16 (m, 1H) 7.32-7.54 (m, 6H) 7.57-7.68 (m, 1H) 7.75 (dd, J=7.72, 0.94 Hz, 1H) 7.91 (s, 1H)

REFERENCE EXAMPLE 347 ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]butanoate A mixture of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (0.87 g), rhodium(II) acetate (dimer) (0.0084 g) and toluene (10 mL) was heated to 80° C.

under an argon atmosphere, a solution of 2-diazobutyric acid ethyl ester (1.0 g) in toluene (10 mL) was added dropwise, and the mixture was stirred at 80° C. for 30 min. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.78 g, 71%).

$^1$H NMR (300 MHz, DMSO-$d_6$) δ0.88 (t, J=7.35 Hz, 3H) 0.95 (t, J=7.35 Hz, 3H) 1.18-1.78 (m, 11H) 1.99-2.22 (m, 2H) 2.52-2.67 (m, 2H) 2.89-3.04 (m, 2H) 3.25-3.41 (m, 1H) 3.93-4.22 (m, 5H) 4.81-5.01 (m, 1H) 7.36-7.44 (m, 2H) 7.45-7.52 (m, 2H) 7.52-7.63 (m, 2H) 7.73-7.82 (m, 1H) 7.92 (dd, J=7.72, 1.13 Hz, 1H) 8.18 (s, 1H)

REFERENCE EXAMPLE 348

4'-({4-[trans-4-(1-ethyl-2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile Ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]butanoate (0.20 g) was dissolved in tetrahydrofuran (2 mL), methylmagnesium bromide (1.0 mL, 1.0 M tetrahydrofuran solution) was added dropwise at 0° C., and the mixture was stirred at room temperature for 1 hr. Methylmagnesium bromide (1.0 mL, 1.0 M tetrahydrofuran solution) was added, and the mixture was stirred at room temperature for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.12 g, 65%).

$^1$H NMR (300 MHz, DMSO-$d_6$) δ0.89-0.99 (m, 6H) 1.02 (s, 3H) 1.08 (s, 3H) 1.13-1.41 (m, 4H) 1.45-1.81 (m, 4H) 2.02-2.22 (m, 2H) 2.52-2.67 (m, 2H) 2.88-3.09 (m, 3H) 3.44-3.62 (m, 1H) 3.99 (s, 2H) 4.11 (s, 1H) 4.76-5.00 (m, 1H) 7.35-7.44 (m, 2H) 7.46-7.51 (m, 2H) 7.53-7.63 (m, 2H) 7.72-7.82 (m, 1H) 7.92 (dd, J=7.72, 0.94 Hz, 1H) 8.18 (s, 1H)

REFERENCE EXAMPLE 349 ethyl 2-[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]butanoate A mixture of 4'-{[4-(trans-4-hydroxycyclohexyl)-2-methyl-5-oxo-7-propyl-4,5-dihydro[1,2,4]triazolo[1,5-a]pyrimidin-6-yl]methyl}biphenyl-2-carbonitrile (0.77 g), rhodium(II) acetate (dimer) (0.0070 g) and toluene (10 mL) was heated to 80° C. under an argon atmosphere, a solution of 2-diazobutyric acid ethyl ester (0.91 g) in toluene (10 mL) was added dropwise, and the mixture was stirred at 80° C. for 30 min. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.69 g, 73%).

$^1$H NMR (300 MHz, DMSO-$d_6$) δ0.88 (t, J=7.44 Hz, 3H) 0.95 (t, J=7.35 Hz, 3H) 1.18-1.76 (m, 11H) 2.00-2.21 (m, 2H) 2.35 (s, 3H) 2.52-2.64 (m, 2H) 2.84-2.98 (m, 2H) 3.33-3.41 (m, 1H) 3.91-4.22 (m, 5H) 4.75-4.99 (m, 1H) 7.32-7.43 (m, 2H) 7.45-7.51 (m, 2H) 7.53-7.62 (m, 2H) 7.72-7.82 (m, 1H) 7.92 (dd, J=7.91, 0.94 Hz, 1H)

REFERENCE EXAMPLE 350

4'-({4-[trans-4-(1-ethyl-2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile Ethyl 2-[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]butanoate (0.20 g) was dissolved in tetrahydrofuran (2 mL), methylmagnesium bromide (1.0 mL, 1.0 M tetrahydrofuran solution) was added dropwise at 0° C., and the mixture was stirred at room temperature for 1 hr. Methylmagnesium bromide (1.0 mL, 1.0 M tetrahydrofuran solution) was added, and the mixture was stirred at room temperature for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.11 g, 60%).

$^1$H NMR (300 MHz, DMSO-$d_6$) δ0.87-0.98 (m, 6H) 1.02 (s, 3H) 1.08 (s, 3H) 1.12-1.37 (m, 4H) 1.46-1.75 (m, 4H) 2.02-2.19 (m, 2H) 2.36 (s, 3H) 2.52-2.64 (m, 2H) 2.86-2.98 (m, 2H) 3.04 (dd, J=9.14, 2.92 Hz, 1H) 3.42-3.61 (m, 1H) 3.97 (s, 2H) 4.12 (s, 1H) 4.74-4.98 (m, 1H) 7.35-7.43 (m, 2H) 7.45-7.52 (m, 2H) 7.52-7.63 (m, 2H) 7.72-7.83 (m, 1H) 7.92 (dd, J=7.72, 1.13 Hz, 1H)

REFERENCE EXAMPLE 351

4'-({4-[trans-4-(2-{[tert-butyl(dimethyl)silyl]oxy}-3-oxopropoxy)cyclohexyl]-5-oxo-7-propyl-4,5-dihydro[1,2,4]triazolo[1,5-a]pyrimidin-6-yl}methyl)biphenyl-2-carbonitrile A mixture of 4'-[(4-{trans-4-[(2-hydroxybut-3-en-1-yl)oxy]cyclohexyl}-5-oxo-7-propyl-4,5-dihydro[1,2,4]triazolo[1,5-a]pyrimidin-6-yl)methyl]biphenyl-2-carbonitrile (0.43 g), 2,6-lutidine (0.18 mL), tert-butyl(dimethyl)silyl trifluoromethanesulfonate (0.36 mL) and tetrahydrofuran (5 mL) was stirred at room temperature for 24 hr. The reaction mixture was added to 1 M hydrochloric acid, and the mixture was extracted with ethyl acetate. The organic layer was washed with saturated sodium hydrogen carbonate and then with saturated brine, and dried over anhydrous magnesium sulfate. The solvent was evaporated under reduced pressure. The residue obtained by purification by silica gel column chromatography was mixed with sodium periodate (0.85 g), acetone (10 mL), acetonitrile (10 mL), water (10 mL) and osmium tetraoxide (0.14 g, 7% immobilized catalyst), and the mixture was stirred at room temperature for 40 hr. The precipitate was filtered off, and the filtrate was extracted with ethyl acetate. The organic layer was washed with saturated brine, and dried over anhydrous magnesium sulfate. The solvent was evaporated under reduced pressure to give the title compound as a colorless solid (0.43 g, 83%).

$^1$H NMR (300 MHz, DMSO-$d_6$) δ0.00 (s, 6H) 0.90 (s, 9H) 0.95 (t, J=7.35 Hz, 3H) 1.19-1.37 (m, 2H) 1.47-1.79 (m, 4H) 2.01-2.22 (m, 2H) 2.52-2.68 (m, 2H) 2.86-3.08 (m, 2H) 3.34-3.49 (m, 1H) 3.64-3.76 (m, 2H) 3.99 (s, 2H) 4.33 (t, J=4.62

Hz, 1H) 4.76-5.03 (m, 1H) 7.36-7.44 (m, 2H) 7.45-7.51 (m, 2H) 7.53-7.63 (m, 2H) 7.71-7.84 (m, 1H) 7.93 (dd, J=7.72, 0.94 Hz, 1H) 8.18 (s, 1H) 9.58 (s, 1H)

REFERENCE EXAMPLE 352

4'-({4-[trans-4-(2-{[tert-butyl(dimethyl)silyl]oxy}-3,3-difluoropropoxy)cyclohexyl]-5-oxo-7-propyl-4,5-dihydro[1,2,4]triazolo[1,5-a]pyrimidin-6-yl}methyl)biphenyl-2-carbonitrile 4'-({4-[trans-4-(2-{[tert-Butyl(dimethyl)silyl]oxy}-3-oxopropoxy)cyclohexyl]-5-oxo-7-propyl-4,5-dihydro[1,2,4]triazolo[1,5-a]pyrimidin-6-yl}methyl)biphenyl-2-carbonitrile (batch 1: 0.37 g, batch 2: 0.050 g) was dissolved in toluene (batch 1: 4 mL, batch 2: 1 mL), N,N-diethylaminosulfur trifluoride (batch 1: 0.28 g, batch 2: 0.037 g) was added at room temperature, and the mixture was stirred at room temperature (batch 1: 1.5 hr, batch 2: 3 hr). The reaction mixtures of batch 1 and batch 2 were combined, saturated aqueous sodium hydrogen carbonate solution was gradually added, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.30 g, 67%).
$^1$H NMR (300 MHz, DMSO-d$_6$) δ0.09 (d, J=6.44 Hz, 6H) 0.88 (s, 9H) 0.95 (t, J=7.19 Hz, 3H) 1.20-1.42 (m, 2H) 1.48-1.84 (m, 4H) 2.01-2.21 (m, 2H) 2.53-2.70 (m, 2H) 2.90-3.05 (m, 2H) 3.34-3.43 (m, 1H) 3.44-3.64 (m, 2H) 3.89-4.01 (m, 3H) 4.75-5.04 (m, 1H) 5.93 (dt, J=55.09, 3.41 Hz, 1H) 7.34-7.45 (m, 2H) 7.45-7.52 (m, 2H) 7.53-7.64 (m, 2H) 7.72-7.84 (m, 1H) 7.93 (d, J=7.57 Hz, 1H) 8.19 (s, 1H)

REFERENCE EXAMPLE 353 ethyl[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]acetate A mixture of 4'-{[4-(trans-4-hydroxycyclohexyl)-2-methyl-5-oxo-7-propyl-4,5-dihydro[1,2,4]triazolo[1,5-a]pyrimidin-6-yl]methyl}biphenyl-2-carbonitrile (1.5 g), rhodium (II) acetate (dimer) (0.0070 g) and toluene (15 mL) was heated to 80° C. under an argon atmosphere, a solution of ethyl 2-diazoacetate (1.6 g) in toluene (15 mL) was added dropwise, and the mixture was stirred at 80° C. for 10 min. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.0 g, 56%).
$^1$H NMR (300 MHz, DMSO-d$_6$) δ0.94 (t, J=7.19 Hz, 3H) 1.21 (t, J=7.19 Hz, 3H) 1.24-1.40 (m, 2H) 1.47-1.81 (m, 4H) 2.09-2.20 (m, 2H) 2.35 (s, 3H) 2.51-2.66 (m, 2H) 2.85-2.98 (m, 2H) 3.34-3.48 (m, 1H) 3.97 (s, 2H) 4.06-4.18 (m, 4H) 4.77-4.99 (m, 1H) 7.36-7.43 (m, 2H) 7.45-7.51 (m, 2H) 7.52-7.62 (m, 2H) 7.70-7.83 (m, 1H) 7.93 (d, J=7.57 Hz, 1H)

REFERENCE EXAMPLE 354

4'-[(2-methyl-4-{trans-4-[(2-methyloxiran-2-yl)methoxy]cyclohexyl}-5-oxo-7-propyl-4,5-dihydro[1,2,4]triazolo[1,5-a]pyrimidin-6-yl)methyl]biphenyl-2-carbonitrile 2-[(trans-4-{6-[(2'-Cyanobiphenyl-4-yl)methyl]-2-methyl-5-oxo-7-propyl[1,2,4]triazolo[1,5-a]pyrimidin-4(5H)-yl}cyclohexyl)oxy]-N-methoxy-N-methylacetamide (0.45 g) was dissolved in tetrahydrofuran (5 mL), methylmagnesium bromide (2.3 mL, 1.0 M tetrahydrofuran solution) was added dropwise, and the mixture was stirred at room temperature for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the residue was added to a mixture of trimethylsulfoxonium iodide (0.20 g), sodium hydride (0.038 g) and dimethyl sulfoxide (5 mL) stirred at room temperature for 1 hr in advance, and the mixture was stirred at room temperature for 16 hr. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.19 g, 46%).
$^1$H NMR (300 MHz, DMSO-d$_6$) δ0.94 (t, J=7.25 Hz, 3H) 1.20-1.38 (m, 5H) 1.48-1.77 (m, 4H) 2.03-2.18 (m, 2H) 2.36 (s, 3H) 2.52-2.68 (m, 4H) 2.86-2.98 (m, 2H) 3.33-3.42 (m, 2H) 3.56 (d, J=11.30 Hz, 1H) 3.97 (s, 2H) 4.68-4.99 (m, 1H) 7.33-7.44 (m, 2H) 7.45-7.52 (m, 2H) 7.52-7.63 (m, 2H) 7.71-7.83 (m, 1H) 7.92 (dd, J=7.72, 0.94 Hz, 1H)

REFERENCE EXAMPLE 355

4'-({4-[trans-4-(3-fluoro-2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile A mixture of 4'-[(2-methyl-4-{trans-4-[(2-methyloxiran-2-yl)methoxy]cyclohexyl}-5-oxo-7-propyl-4,5-dihydro[1,2,4]triazolo[1,5-a]pyrimidin-6-yl)methyl]biphenyl-2-carbonitrile (0.19 g), tetra-n-butylammonium dihydrogentrifluoride (0.65 g) and chlorobenzene (0.5 mL) was stirred at 120° C. for 20 hr. The reaction mixture was purified by silica gel column chromatography to give the title compound as a colorless solid (0.094 g, 46%).
$^1$H NMR (300 MHz, DMSO-d$_6$) δ0.94 (t, J=7.25 Hz, 3H) 1.06 (d, J=2.07 Hz, 3H) 1.19-1.41 (m, 2H) 1.50-1.78 (m, 4H) 2.03-2.17 (m, 2H) 2.36 (s, 3H) 2.52-2.67 (m, 2H) 2.82-2.98 (m, 2H) 3.21-3.43 (m, 3H) 3.97 (s, 2H) 4.19 (d, J=47.85 Hz, 2H) 4.78 (s, 1H) 4.80-4.96 (m, 1H) 7.34-7.42 (m, 2H) 7.45-7.52 (m, 2H) 7.52-7.64 (m, 2H) 7.73-7.83 (m, 1H) 7.92 (dd, J=7.72, 0.94 Hz, 1H)

REFERENCE EXAMPLE 356 ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]butanoate A mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (0.50 g), rhodium(II) acetate (dimer) (0.0050 g) and toluene (5 mL) was heated to 80° C. under an argon atmosphere, a solution of 2-diazobutyric acid ethyl ester (0.87 g) in toluene (5 mL) was added dropwise, and the mixture was stirred at 80° C. for 10 min. The reaction mixture was concentrated under reduced pressure, and the residue was purified by silica gel column chromatography to give the title compound as a colorless solid (0.35 g, 56%).

¹H NMR (300 MHz, DMSO-d₆) δ0.88 (t, J=7.38 Hz, 3H) 0.95 (t, J=7.38 Hz, 3H) 1.13-1.79 (m, 11H) 1.87-2.22 (m, 2H) 2.52-3.03 (m, 4H) 3.25-3.38 (m, 1H) 3.81-4.25 (m, 5H) 4.75-4.98 (m, 1H) 7.21-7.39 (m, 2H) 7.46 (dd, J=11.17, 1.70 Hz, 1H) 7.54-7.67 (m, 2H) 7.75-7.84 (m, 1H) 7.91-7.99 (m, 1H) 8.19 (s, 1H)

REFERENCE EXAMPLE 357

4'-({4-[trans-4-(1-ethyl-2-hydroxy-2-methylpropoxy)cyclohexyl]-5-oxo-7-propyl-4,5-dihydro[1,2,4]triazolo[1,5-a]pyrimidin-6-yl}methyl)-3'-fluorobiphenyl-2-carbonitrile Ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]butanoate (0.35 g) was dissolved in tetrahydrofuran (4 mL), methylmagnesium bromide (1.7 mL, 1.0 M tetrahydrofuran solution) was added dropwise at 0° C., and the mixture was stirred at room temperature for 3 hr. Methylmagnesium bromide (3.5 mL, 1.0 M tetrahydrofuran solution) was added, and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.20 g, 60%).

¹H NMR (300 MHz, DMSO-d₆) δ0.89-0.99 (m, 6H) 1.01 (s, 3H) 1.08 (s, 3H) 1.13-1.81 (m, 8H) 2.01-2.21 (m, 2H) 2.52-2.66 (m, 2H) 2.87-3.09 (m, 3H) 3.44-3.62 (m, 1H) 3.97 (s, 2H) 4.11 (s, 1H) 4.77-5.00 (m, 1H) 7.25-7.40 (m, 2H) 7.46 (dd, J=10.98, 1.51 Hz, 1H) 7.55-7.70 (m, 2H) 7.75-7.86 (m, 1H) 7.90-8.02 (m, 1H) 8.20 (s, 1H)

REFERENCE EXAMPLE 358

4'-[(2-methyl-4-{trans-4-[(methylsulfanyl)methoxy]cyclohexyl}-5-oxo-7-propyl-4,5-dihydro[1,2,4]triazolo[1,5-a]pyrimidin-6-yl)methyl]biphenyl-2-carbonitrile A mixture of 4'-{[4-(trans-4-hydroxycyclohexyl)-2-methyl-5-oxo-7-propyl-4,5-dihydro[1,2,4]triazolo[1,5-a]pyrimidin-6-yl]methyl}biphenyl-2-carbonitrile (1.5 g), dimethyl sulfoxide (45 mL) and acetic anhydride (15 mL) was stirred at room temperature for 17 hr. The reaction mixture was added to water, and the mixture was extracted with ethyl acetate. The organic layer was washed with saturated aqueous sodium hydrogen carbonate solution and then with saturated brine, and dried over anhydrous magnesium sulfate. The solvent was evaporated under reduced pressure, and the residue was purified by silica gel column chromatography to give the title compound as a colorless solid (0.83 g, 49%).

¹H NMR (300 MHz, DMSO-d₆) δ0.94 (t, J=7.35 Hz, 3H) 1.22-1.45 (m, 2H) 1.50-1.81 (m, 4H) 2.02-2.15 (m, 5H) 2.37 (s, 3H) 2.52-2.72 (m, 2H) 2.82-3.04 (m, 2H) 3.53-3.73 (m, 1H) 3.97 (s, 2H) 4.69 (s, 2H) 4.80-5.06 (m, 1H) 7.34-7.44 (m, 2H) 7.45-7.52 (m, 2H) 7.53-7.66 (m, 2H) 7.72-7.85 (m, 1H) 7.92 (dd, J=7.91, 1.13 Hz, 1H)

REFERENCE EXAMPLE 359

4'-[(4-{trans-4-[(1-hydroxycyclobutyl)methoxy]cyclohexyl}-2-methyl-5-oxo-7-propyl-4,5-dihydro[1,2,4]triazolo[1,5-a]pyrimidin-6-yl)methyl]biphenyl-2-carbonitrile 4'-[(2-Methyl-4-{trans-4-[(methylsulfanyl)methoxy]cyclohexyl}-5-oxo-7-propyl-4,5-dihydro[1,2,4]triazolo[1,5-a]pyrimidin-6-yl)methyl]biphenyl-2-carbonitrile (1.3 g) was dissolved in toluene (10 mL), and sulfuryl chloride (0.20 mL) was added at 0° C. The mixture was stirred at room temperature for 1 hr, the precipitate was filtrated off, and the filtrate was concentrated under reduced pressure. The residue was mixed with cyclobutanone (1.7 g) and tetrahydrofuran (5 mL), and samarium iodide (48 mL, 0.1 M tetrahydrofuran solution) was added dropwise at room temperature under an argon atmosphere. The mixture was stirred at room temperature for 18 hr. The reaction mixture was added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.098 g, 7.1%).

¹H NMR (300 MHz, DMSO-d₆) δ0.94 (t, J=7.19 Hz, 3H) 1.19-2.22 (m, 14H) 2.36 (s, 3H) 2.54-2.69 (m, 2H) 2.84-3.03 (m, 2H) 3.33-3.43 (m, 3H) 3.97 (s, 2H) 4.73-4.98 (m, 2H) 7.34-7.44 (m, 2H) 7.45-7.52 (m, 2H) 7.53-7.65 (m, 2H) 7.71-7.82 (m, 1H) 7.93 (d, J=7.19 Hz, 1H)

REFERENCE EXAMPLE 360

3'-fluoro-4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile Ethyl[(trans-4-{6-[(2'-cyano-3-fluorobiphenyl-4-yl)methyl]-2-methyl-5-oxo-7-propyl[1,2,4]triazolo[1,5-a]pyrimidin-4(5H)-yl}cyclohexyl)oxy]acetate (0.60 g) was dissolved in tetrahydrofuran (6 mL), methylmagnesium bromide (3.0 mL, 1.0 M tetrahydrofuran solution) was added dropwise at 0° C., and the mixture was stirred at 0° C. for 1 hr and then at room temperature for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.39 g, 66%).

¹H NMR (300 MHz, DMSO-d₆) δ0.94 (t, J=7.19 Hz, 3H) 1.06 (s, 6H) 1.21-1.38 (m, 2H) 1.46-1.77 (m, 4H) 2.03-2.17 (m, 2H) 2.37 (s, 3H) 2.51-2.65 (m, 2H) 2.82-2.98 (m, 2H) 3.19 (s, 2H) 3.24-3.38 (m, 1H) 3.94 (s, 2H) 4.22 (s, 1H) 4.66-5.01 (m, 1H) 7.23-7.38 (m, 2H) 7.45 (d, J=9.47 Hz, 1H) 7.54-7.69 (m, 2H) 7.73-7.85 (m, 1H) 7.95 (d, J=7.95 Hz, 1H)

REFERENCE EXAMPLE 361 ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]pent-4-enoate A mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (2.0 g), rhodium(II) acetate (dimer) (0.018 g) and toluene (20 mL) was heated to 80° C. under an argon atmosphere, a solution of ethyl 2-diazopent-4-enoate (3.8 g) in toluene (20 mL) was added dropwise, and the mixture was stirred at 80° C. for 10 min. A solution of ethyl 2-diazopent-4-enoate (3.8 g) in toluene (10 mL) was further added, and the mixture was stirred at 80° C. for 10 min. The reaction mixture was concentrated under reduced pressure, and the residue was purified by silica gel column chromatography to give the title compound as a colorless solid (0.81 g, 32%).

$^1$H NMR (300 MHz, DMSO-$d_6$) δ0.95 (t, J=7.35 Hz, 3H) 1.13-1.77 (m, 9H) 1.87-2.19 (m, 2H) 2.26-2.48 (m, 2H) 2.53-3.06 (m, 4H) 3.33-3.43 (m, 1H) 3.97 (s, 2H) 4.07-4.22 (m, 3H) 4.78-4.97 (m, 2H) 4.99-5.24 (m, 2H) 5.66-5.88 (m, 1H) 7.25-7.40 (m, 2H) 7.41-7.51 (m, 1H) 7.54-7.68 (m, 2H) 7.74-7.87 (m, 1H) 7.95 (dd, J=7.82, 1.04 Hz, 1H) 8.19 (s, 1H)

REFERENCE EXAMPLE 362 ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]-4-hydroxybutanoate A mixture of ethyl 2-[(trans-4-{6-[(2'-cyano-3-fluorophenyl-4-yl)methyl]-5-oxo-7-propyl[1,2,4]triazolo[1,5-a]pyrimidin-4(5H)-yl}cyclohexyl)oxy]pent-4-enoate (0.81 g), sodium periodate (1.4 g), acetone (20 mL), acetonitrile (20 mL), water (20 mL) and osmium tetraoxide (0.24 g, 7% immobilized catalyst) was stirred at room temperature for 14 hr. The precipitate was filtered off, and the filtrate was extracted with ethyl acetate. The organic layer was washed with saturated brine, and dried over anhydrous magnesium sulfate. The solvent was evaporated under reduced pressure, and the residue was dissolved in tetrahydrofuran (5 mL) and methanol (10 mL). Sodium tetrahydroborate (0.084 g) was added at 0° C., and the mixture was stirred at 0° C. for 3 hr. Saturated aqueous sodium hydrogen carbonate solution was added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.29 g, 36%).

$^1$H NMR (300 MHz, DMSO-$d_6$) δ0.95 (t, J=7.35 Hz, 3H) 1.21 (t, J=7.06 Hz, 3H) 1.25-1.89 (m, 8H) 1.95-2.20 (m, 2H) 2.52-2.65 (m, 2H) 2.90-3.05 (m, 2H) 3.26-3.41 (m, 1H) 3.42-3.56 (m, 2H) 3.97 (s, 2H) 4.06-4.23 (m, 3H) 4.52 (t, J=5.09 Hz, 1H) 4.77-4.99 (m, 1H) 7.25-7.40 (m, 2H) 7.46 (dd, J=11.11, 1.70 Hz, 1H) 7.55-7.69 (m, 2H) 7.73-7.86 (m, 1H) 7.95 (dd, J=7.72, 0.94 Hz, 1H) 8.19 (s, 1H)

REFERENCE EXAMPLE 363 ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]-4-{[(4-methylphenyl)sulfonyl]oxy}butanoate A mixture of ethyl 2-[(trans-4-{6-[(2'-cyano-3-fluorophenyl-4-yl)methyl]-5-oxo-7-propyl[1,2,4]triazolo[1,5-a]pyrimidin-4(5H)-yl}cyclohexyl)oxy]-4-hydroxybutanoate (0.47 g), 4-methylbenzenesulfonyl chloride (0.59 g) and pyridine (5 mL) was stirred at room temperature for 3 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.42 g, 70%).

$^1$H NMR (300 MHz, DMSO-$d_6$) δ0.95 (t, J=7.38 Hz, 3H) 1.14-2.05 (m, 13H) 2.39 (s, 3H) 2.42-2.59 (m, 2H) 2.89-3.03 (m, 2H) 3.19-3.31 (m, 1H) 3.98 (s, 2H) 4.03-4.18 (m, 5H) 4.70-4.91 (m, 1H) 7.25-7.41 (m, 2H) 7.42-7.55 (m, 3H) 7.55-7.67 (m, 2H) 7.74-7.85 (m, 3H) 7.95 (d, J=7.95 Hz, 1H) 8.21 (s, 1H)

REFERENCE EXAMPLE 364 ethyl 1-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]cyclopropanecarboxylate A mixture of ethyl 2-[(trans-4-{6-[(2'-cyano-3-fluorophenyl-4-yl)methyl]-5-oxo-7-propyl[1,2,4]triazolo[1,5-a]pyrimidin-4(5H)-yl}cyclohexyl)oxy]-4-{[(4-methylphenyl)sulfonyl]oxy}butanoate (0.42 g), potassium tert-butoxide (0.24 g) and tetrahydrofuran (5 mL) was stirred at 0° C. for 10 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.051 g, 15%).

$^1$H NMR (300 MHz, CHLOROFORM-d) δ1.07 (t, J=7.25 Hz, 3H) 1.14-1.88 (m, 13H) 2.17-2.32 (m, 2H) 2.59-2.82 (m, 2H) 2.98-3.11 (m, 2H) 3.56-3.78 (m, 1H) 4.02 (s, 2H) 4.19 (q, J=7.16 Hz, 2H) 4.87-5.16 (m, 1H) 7.21-7.52 (m, 5H) 7.59-7.69 (m, 1H) 7.76 (d, J=7.72 Hz, 1H) 7.91 (s, 1H)

REFERENCE EXAMPLE 365

3'-fluoro-4'-{[4-(trans-4-{[1-(1-hydroxy-1-methylethyl)cyclopropyl]oxy}cyclohexyl)-5-oxo-7-propyl-4,5-dihydro[1,2,4]triazolo[1,5-a]pyrimidin-6-yl]methyl}biphenyl-2-carbonitrile Ethyl 1-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]cyclopropanecarboxylate (0.051 g) was dissolved in tetrahydrofuran (1 mL), methylmagnesium bromide (0.25 mL, 1.0 M tetrahydrofuran solution) was added dropwise at 0° C., and the mixture was stirred at 0° C. for 30 min and then at room temperature for 30 min. Methylmagnesium bromide (1.0 mL, 1.0 M tetrahydrofuran solution) was added, and the mixture was stirred at room temperature for 10 min. Methylmagnesium bromide (1.0 mL, 1.0 M tetrahydrofuran solution) was added, and the mixture was stirred at room temperature for 10 min. Methylmagnesium bromide (1.0 mL, 1.0 M tetrahydrofuran solution) was added, and the mixture was stirred at room temperature for 10 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.032 g, 65%).

$^1$H NMR (300 MHz, CHLOROFORM-d) δ0.64-0.91 (m, 4H) 1.06 (t, J=7.35 Hz, 3H) 1.23 (s, 6H) 1.39-1.55 (m, 2H) 1.64-1.86 (m, 4H) 2.06-2.14 (m, 2H) 2.58-2.82 (m, 2H) 2.96-3.12 (m, 2H) 3.49-3.70 (m, 1H) 4.01 (s, 2H) 4.90-5.14 (m, 1H) 7.19-7.30 (m, 2H) 7.30-7.55 (m, 3H) 7.59-7.69 (m, 1H) 7.72-7.82 (m, 1H) 7.92 (s, 1H)

REFERENCE EXAMPLE 366 ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]pent-4-enoate A mixture of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (1.8 g), rhodium(II) acetate (dimer) (0.018 g) and toluene (20 mL) was heated to 80° C. under an argon atmosphere, a solution of ethyl 2-diazopent-4-enoate (3.7 g) in toluene (20 mL) was added dropwise, and the mixture was stirred at 80° C. for 10 min. A solution of ethyl 2-diazopent-4-enoate (3.7 g) in toluene (10 mL) was further added, and the mixture was stirred at 80° C. for 10 min. The reaction mixture was concentrated under reduced pressure, and the residue was purified by silica gel column chromatography to give the title compound as a colorless solid (0.98 g, 41%).

$^1$H NMR (300 MHz, DMSO-$d_6$) δ0.95 (t, J=7.38 Hz, 3H) 1.21 (t, J=7.00 Hz, 3H) 1.27-1.76 (m, 6H) 1.90-2.18 (m, 2H) 2.26-2.48 (m, 2H) 2.52-3.04 (m, 4H) 3.32-3.43 (m, 1H) 3.99 (s, 2H) 4.05-4.22 (m, 3H) 4.83-4.98 (m, 1H) 5.02-5.25 (m, 2H) 5.66-5.87 (m, 1H) 7.35-7.44 (m, 2H) 7.45-7.52 (m, 2H) 7.53-7.63 (m, 2H) 7.71-7.83 (m, 1H) 7.89-7.98 (m, 1H) 8.18 (s, 1H)

REFERENCE EXAMPLE 367 ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]-4-hydroxybutanoate A mixture of ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]pent-4-enoate (0.98 g), sodium periodate (1.7 g), acetone (20 mL), acetonitrile (20 mL), water (20 mL) and osmium tetraoxide (0.30 g, 7% immobilized catalyst) was stirred at room temperature for 14 hr. The precipitate was filtered off, and the filtrate was extracted with ethyl acetate. The organic layer was washed with saturated brine, and dried over anhydrous magnesium sulfate. The solvent was evaporated under reduced pressure, and the residue was dissolved in tetrahydrofuran (5 mL) and methanol (10 mL), sodium tetrahydroborate (0.10 g) was added at 0° C., and the mixture was stirred at 0° C. for 2 hr. Saturated aqueous sodium hydrogen carbonate solution was added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.37 g, 37%).

$^1$H NMR (300 MHz, DMSO-$d_6$) δ0.95 (t, J=7.38 Hz, 3H) 1.21 (t, J=7.19 Hz, 3H) 1.25-1.88 (m, 8H) 1.99-2.21 (m, 2H) 2.52-2.66 (m, 2H) 2.90-3.04 (m, 2H) 3.29-3.41 (m, 1H) 3.43-3.54 (m, 2H) 3.99 (s, 2H) 4.06-4.21 (m, 3H) 4.53 (t, J=5.30 Hz, 1H) 4.79-5.03 (m, 1H) 7.36-7.44 (m, 2H) 7.45-7.52 (m, 2H) 7.52-7.64 (m, 2H) 7.73-7.83 (m, 1H) 7.88-8.00 (m, 1H) 8.18 (s, 1H)

REFERENCE EXAMPLE 368 ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]-4-{[(4-methylphenyl)sulfonyl]oxy}butanoate A mixture of ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]-4-hydroxybutanoate (0.54 g), 4-methylbenzenesulfonyl chloride (0.70 g) and pyridine (6 mL) was stirred at room temperature for 75 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.45 g, 65%).

$^1$H NMR (300 MHz, DMSO-$d_6$) δ0.95 (t, J=7.19 Hz, 3H) 1.15-1.35 (m, 5H) 1.47-1.73 (m, 4H) 1.74-1.89 (m, 2H) 1.90-2.07 (m, 2H) 2.40 (s, 3H) 2.43-2.61 (m, 2H) 2.90-3.06 (m, 2H) 3.20-3.31 (m, 1H) 3.95-4.19 (m, 7H) 4.64-4.99 (m, 1H) 7.32-7.65 (m, 8H) 7.71-7.88 (m, 3H) 7.93 (d, J=7.95 Hz, 1H) 8.19 (s, 1H)

REFERENCE EXAMPLE 369 ethyl 1-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]cyclopropanecarboxylate A mixture of ethyl 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]-4-{[(4-methylphenyl)sulfonyl]oxy}butanoate (0.45 g), potassium tert-butoxide (0.26 g) and tetrahydrofuran (20 mL) was stirred at −10° C. for 10 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.19 g, 55%).

$^1$H NMR (300 MHz, DMSO-$d_6$) δ0.94 (t, J=7.38 Hz, 3H) 1.06-1.80 (m, 13H) 2.02-2.22 (m, 2H) 2.51-2.68 (m, 2H) 2.87-3.04 (m, 2H) 3.48-3.71 (m, 1H) 3.99 (s, 2H) 4.11 (q, J=7.07 Hz, 2H) 4.68-5.03 (m, 1H) 7.36-7.45 (m, 2H) 7.45-7.51 (m, 2H) 7.52-7.64 (m, 2H) 7.71-7.82 (m, 1H) 7.93 (d, J=7.95 Hz, 1H) 8.18 (s, 1H)

REFERENCE EXAMPLE 370

4'-{[4-(trans-4-{[1-(1-hydroxy-1-methylethyl)cyclopropyl]oxy}cyclohexyl)-5-oxo-7-propyl-4,5-dihydro[1,2,4]triazolo[1,5-a]pyrimidin-6-yl]methyl}biphenyl-2-carbonitrile Ethyl 1-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]cyclopropanecarboxylate (0.19 g) was dissolved in tetrahydrofuran (2 mL), methylmagnesium bromide (3.3 mL, 1.0 M tetrahydrofuran solution) was added dropwise at 0° C., and the mixture was stirred at room temperature for 30 min. Methylmagnesium bromide (3.3 mL, 1.0 M tetrahydrofuran solution) was added, and the mixture was stirred at room temperature for 10 min. Methylmagnesium bromide (3.3 mL, 1.0 M tetrahydrofuran solution) was added, and the mixture was stirred at room temperature for 10 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.049 g, 26%).

¹H NMR (300 MHz, DMSO-d₆) δ0.55-0.67 (m, 2H) 0.68-0.77 (m, 2H) 0.94 (t, J=7.35 Hz, 3H) 1.14 (s, 6H) 1.21-1.39 (m, 2H) 1.45-1.73 (m, 4H) 1.96-2.07 (m, 2H) 2.53-2.67 (m, 2H) 2.90-3.04 (m, 2H) 3.44-3.62 (m, 1H) 3.99 (s, 2H) 4.20 (s, 1H) 4.74-4.97 (m, 1H) 7.32-7.64 (m, 6H) 7.72-7.81 (m, 1H) 7.90-7.97 (m, 1H) 8.18 (s, 1H)

REFERENCE EXAMPLE 371 ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]propanoate A mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (3.0 g), rhodium(II) acetate (dimer) (0.027 g) and toluene (30 mL) was heated to 80° C. under an argon atmosphere, a solution of ethyl 2-diazopropionate (3.2 g) in toluene (30 mL) was added dropwise, and the mixture was stirred at 80° C. for 10 min. A solution of ethyl 2-diazopropionate (1.6 g) in toluene (10 mL) was added, and the mixture was stirred at 80° C. for 10 min. The reaction mixture was concentrated under reduced pressure, and the residue was purified by silica gel column chromatography to give the title compound as a colorless solid (3.2 g, 88%).
¹H NMR (300 MHz, DMSO-d₆) δ0.95 (t, J=7.38 Hz, 3H) 1.13-1.76 (m, 12H) 1.88-2.18 (m, 2H) 2.52-2.64 (m, 2H) 2.91-3.04 (m, 2H) 3.33-3.43 (m, 1H) 3.97 (s, 2H) 4.06-4.23 (m, 3H) 4.79-4.96 (m, 1H) 7.25-7.40 (m, 2H) 7.42-7.49 (m, 1H) 7.56-7.67 (m, 2H) 7.74-7.86 (m, 1H) 7.92-8.00 (m, 1H) 8.19 (s, 1H)

REFERENCE EXAMPLE 372

3'-fluoro-4'-({4-[trans-4-(2-hydroxy-1-methylethoxy)cyclohexyl]-5-oxo-7-propyl-4,5-dihydro[1,2,4]triazolo[1,5-a]pyrimidin-6-yl}methyl)biphenyl-2-carbonitrile A mixture of ethyl 2-[(trans-4-{6-[(2'-cyano-3-fluorobiphenyl-4-yl)methyl]-5-oxo-7-propyl[1,2,4]triazolo[1,5-a]pyrimidin-4(5H)-yl}cyclohexyl)oxy]propanoate (1.5 g), lithium tetrahydroborate (0.18 g) and tetrahydrofuran (15 mL) was stirred at 0° C. for 1 hr and then at room temperature for 6 hr. Lithium tetrahydroborate (0.18 g) was further added, and the mixture was stirred at room temperature for 15 hr. The reaction mixture was added to saturated aqueous ammonium chloride solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.81 g, 58%).
¹H NMR (300 MHz, DMSO-d₆) δ0.95 (t, J=7.35 Hz, 3H) 1.03 (d, J=6.22 Hz, 3H) 1.22-1.41 (m, 2H) 1.52-1.76 (m, 4H) 1.99-2.14 (m, 2H) 2.52-2.68 (m, 2H) 2.86-3.05 (m, 2H) 3.17-3.60 (m, 4H) 3.97 (s, 2H) 4.75-4.98 (m, 1H) 7.24-7.68 (m, 5H) 7.70-7.88 (m, 1H) 7.95 (dd, J=7.72, 0.94 Hz, 1H) 8.20 (s, 1H)

REFERENCE EXAMPLE 373

3'-fluoro-4'-({4-[trans-4-(1-oxiran-2-ylethoxy)cyclohexyl]-5-oxo-7-propyl-4,5-dihydro[1,2,4]triazolo[1,5-a]pyrimidin-6-yl}methyl)biphenyl-2-carbonitrile A mixture of 3'-fluoro-4'-({4-[trans-4-(2-hydroxy-1-methylethoxy)cyclohexyl]-5-oxo-7-propyl-4,5-dihydro[1,2,4]triazolo[1,5-a]pyrimidin-6-yl}methyl)biphenyl-2-carbonitrile (0.81 g), Dess-Martin periodinane (1.2 g) and acetonitrile (10 mL) was stirred at room temperature for 2 hr. Saturated aqueous sodium hydrogen carbonate solution and aqueous sodium thiosulfate solution were added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure, the residue was added to a mixture of trimethylsulfoxonium iodide (0.39 g), sodium hydride (0.072 g) and dimethyl sulfoxide (10 mL) stirred at room temperature for 1 hr in advance, and the mixture was stirred at room temperature for 15 hr. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.15 g, 18%).
¹H NMR (300 MHz, DMSO-d₆) δ0.73-1.01 (m, 3H) 1.06-1.80 (m, 9H) 1.92-2.14 (m, 2H) 2.20-3.11 (m, 6H) 3.18-3.69 (m, 3H) 3.97 (s, 2H) 4.23-5.16 (m, 1H) 7.20-7.51 (m, 3H) 7.53-7.70 (m, 2H) 7.74-7.83 (m, 1H) 7.86 (s, 0.33H) 7.95 (dd, J=7.72, 0.94 Hz, 1H) 8.20 (s, 0.67H)

REFERENCE EXAMPLE 374

3'-fluoro-4'-({4-[trans-4-(3-fluoro-2-hydroxy-1-methylpropoxy)cyclohexyl]-5-oxo-7-propyl-4,5-dihydro[1,2,4]triazolo[1,5-a]pyrimidin-6-yl}methyl)biphenyl-2-carbonitrile A mixture of 3'-fluoro-4'-({4-[trans-4-(1-oxiran-2-ylethoxy)cyclohexyl]-5-oxo-7-propyl-4,5-dihydro[1,2,4]triazolo[1,5-a]pyrimidin-6-yl}methyl)biphenyl-2-carbonitrile (0.15 g), tetra-n-butylammonium dihydrogentrifluoride (0.49 g) and chlorobenzene (0.5 mL) was stirred at 120° C. for 24 hr and then at room temperature for 40 hr. The reaction mixture was concentrated under reduced pressure, and the residue was purified by silica gel column chromatography to give the title compound as a colorless solid (0.081 g, 51%).
¹H NMR (300 MHz, CHLOROFORM-d) δ0.92-1.12 (m, 3H) 1.16-1.54 (m, 6H) 1.60-1.89 (m, 3H) 1.99-2.30 (m, 2H) 2.42-3.12 (m, 4H) 3.39-3.78 (m, 3H) 4.02 (s, 2H) 4.29-4.67 (m, 2H) 4.98-5.18 (m, 1H) 7.22-7.55 (m, 6H) 7.60-7.72 (m, 1H) 7.73-7.83 (m, 1H) 7.92 (s, 1H)

REFERENCE EXAMPLE 375

3'-fluoro-4'-{[4-(trans-4-{1-[2-(fluoromethyl)oxiran-2-yl]ethoxy}cyclohexyl)-5-oxo-7-propyl-4,5-dihydro[1,2,4]triazolo[1,5-a]pyrimidin-6-yl]methyl}biphenyl-2-carbonitrile A mixture of 3'-fluoro-4'-({4-[trans-4-(3-fluoro-2-hydroxy-1-methylpropoxy)cyclohexyl]-5-oxo-7-propyl-4,5-dihydro[1,2,4]triazolo[1,5-a]pyrimidin-6-yl}methyl)biphenyl-2-carbonitrile (0.15 g), Dess-Martin periodinane (0.22 g) and acetonitrile (2 mL) was stirred at room temperature for 12 hr. Saturated aqueous sodium hydrogen carbonate solution and aqueous sodium thiosulfate solution were added to the reaction mixture, and the mixture was extracted with ethyl acetate. The organic layer was washed with saturated brine, and dried over anhydrous magnesium sulfate. The solvent was evaporated under reduced pressure, the residue was added to a mixture of trimethylsulfoxonium iodide (0.057 g), sodium hydride (0.010 g) and dimethyl sulfoxide (4 mL) stirred at room temperature for 1 hr in advance, and the mixture was stirred at room temperature for 1 hr. The reaction mixture was added to water, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.079 g, 52%).

$^1$H NMR (300 MHz, DMSO-$d_6$) δ0.95 (t, J=7.35 Hz, 3H) 1.04-1.84 (m, 9H) 2.00-2.15 (m, 2H) 2.52-3.04 (m, 6H) 3.34-3.76 (m, 2H) 3.97 (s, 2H) 4.43-4.74 (m, 2H) 4.77-5.00 (m, 1H) 7.12-7.53 (m, 3H) 7.54-7.69 (m, 2H) 7.72-7.88 (m, 1H) 7.95 (dd, J=7.72, 0.94 Hz, 1H) 8.20 (s, 1H)

REFERENCE EXAMPLE 376 ethyl 3-{6-[(2'-cyano-3-fluorobiphenyl-4-yl)methyl]-5-oxo-7-propyl[1,2,4]triazolo[1,5-a]pyrimidin-4(5H)-yl}cyclobutanecarboxylate A mixture of ethyl 3-(4H-1,2,4-triazol-3-ylamino)cyclobutanecarboxylate (4.0 g), ethyl 2-[(2'-cyano-3-fluorobiphenyl-4-yl)methyl]-3-oxohexanoate (12 g) and N,N-diethylaniline (15 mL) was stirred at 180° C. for 48 hr and then at room temperature for 38 hr. The reaction mixture was added to 1 M hydrochloric acid, and the mixture was extracted with ethyl acetate. The organic layer was washed with 1 M hydrochloric acid and then with saturated brine, and dried over anhydrous magnesium sulfate. The solvent was evaporated under reduced pressure, and the residue was purified by silica gel column chromatography to give the title compound as a colorless solid (4.0 g, 41%).

$^1$H NMR (300 MHz, DMSO-$d_6$) δ0.94 (t, J=7.38 Hz, 3H) 1.11-1.27 (m, 3H) 1.44-1.77 (m, 2H) 2.36-3.48 (m, 7H) 3.87-4.24 (m, 4H) 5.06-5.85 (m, 1H) 7.17-7.53 (m, 3H) 7.54-7.73 (m, 2H) 7.74-7.85 (m, 1H) 7.90-8.01 (m, 1H) 8.13-8.30 (m, 1H)

REFERENCE EXAMPLE 377

4'-{[4-(3-acetylcyclobutyl)-5-oxo-7-propyl-4,5-dihydro[1,2,4]triazolo[1,5-a]pyrimidin-6-yl]methyl}-3'-fluorobiphenyl-2-carbonitrile A mixture of ethyl 3-{6-[(2'-cyano-3-fluorobiphenyl-4-yl)methyl]-5-oxo-7-propyl[1,2,4]triazolo[1,5-a]pyrimidin-4(5H)-yl}cyclobutanecarboxylate (4.0 g), tetrahydrofuran (40 mL), ethanol (40 mL) and 1 M aqueous sodium hydroxide solution (40 mL) was stirred at room temperature for 2 hr. The reaction mixture was neutralized with 1 M hydrochloric acid. After evaporation of the solvent under reduced pressure, the residue was extracted with ethyl acetate. The organic layer was washed with saturated brine, and dried over anhydrous magnesium sulfate. The solvent was evaporated under reduced pressure, the residue was mixed with N,O-dimethylhydroxyamine hydrochloride (1.1 g), 1-ethyl-3-(3-dimethylaminopropyl)carbodiimide hydrochloride (2.2 g), 1-hydroxybenzotriazole (1.6 g), triethylamine (3.3 mL) and N,N-dimethylformaldehyde (40 mL), and the mixture was stirred at room temperature for 14 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (40 mL), methylmagnesium bromide (23 mL, 1.0 M tetrahydrofuran solution) was added dropwise at 0° C., and the mixture was stirred at 0° C. for 2 hr. Methylmagnesium bromide (11 mL, 1.0 M tetrahydrofuran solution) was added, and the mixture was stirred at room temperature for 30 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (2.8 g, 73%).

$^1$H NMR (300 MHz, DMSO-$d_6$) δ0.94 (t, J=7.38 Hz, 3H) 1.46-1.77 (m, 2H) 2.07-2.20 (m, 3H) 2.37-2.48 (m, 2H) 2.85-3.57 (m, 5H) 3.96 (s, 2H) 5.16-5.64 (m, 1H) 7.20-7.53 (m, 3H) 7.54-7.70 (m, 2H) 7.74-7.85 (m, 1H) 7.95 (d, J=7.95 Hz, 1H) 8.13-8.31 (m, 1H)

REFERENCE EXAMPLE 378

3'-fluoro-4'-{[4-(cis-3-hydroxycyclobutyl)-5-oxo-7-propyl-4,5-dihydro[1,2,4]triazolo[1,5-a]pyrimidin-6-yl]methyl}biphenyl-2-carbonitrile To a mixture of 4'-{[4-(3-acetylcyclobutyl)-5-oxo-7-propyl-4,5-dihydro[1,2,4]triazolo[1,5-a]pyrimidin-6-yl]methyl}-3'-fluorobiphenyl-2-carbonitrile (2.8 g), 30% hydrogen peroxide (48 mL) and chloroform (50 mL) was gradually added dropwise trifluoroacetic acid anhydride (32 mL), and the mixture was heated under reflux for 15 hr. Saturated aqueous sodium hydrogen carbonate solution and aqueous sodium thiosulfate solution were gradually added to the reaction mixture, and the mixture was extracted with ethyl acetate. The organic layer was washed with saturated brine, and dried over anhydrous magnesium sulfate. The solvent was evaporated under reduced pressure, the residue was mixed with tetrahydrofuran (30 mL), methanol (30 mL) and 1 M aqueous sodium hydroxide solution (30 mL), and the mixture was stirred at room temperature for 1 hr. The reaction mixture was neutralized with 1 M hydrochloric acid. After evaporation of the solvent under reduced pressure, the residue was extracted with ethyl acetate. The organic layer was washed with saturated brine, and dried over anhydrous magnesium sulfate. The solvent was evaporated under reduced pressure. The residue obtained by purification by silica gel column chromatography was mixed with Dess-Martin periodinane (2.8 g) and acetonitrile (15 mL), and the mixture was stirred at room temperature for 2 hr. Saturated sodium hydrogen carbonate solution and aqueous sodium thiosulfate solution were added to the reaction mixture. After evaporation of the solvent under reduced pressure, the residue was extracted with ethyl acetate. The organic layer was washed with saturated brine, and dried over anhydrous magnesium sulfate. The solvent was evaporated under reduced pressure. 33% of the residue was dissolved in tetrahydrofuran (3 mL) and methanol (5 mL), sodium tetrahydroborate (0.094 g) was added at 0° C., and the mixture was stirred at room temperature for 14 hr. Saturated aqueous ammonium chloride solution was added to the reaction mixture, the solvent was evaporated under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.67 g, 75%).

¹H NMR (300 MHz, DMSO-d₆) δ0.95 (t, J=7.19 Hz, 3H) 1.48-1.73 (m, 2H) 2.52-2.63 (m, 2H) 2.82-3.06 (m, 4H) 3.82-3.98 (m, 3H) 4.69-4.92 (m, 1H) 5.21 (d, J=5.68 Hz, 1H) 7.19-7.51 (m, 3H) 7.53-7.68 (m, 2H) 7.73-7.84 (m, 1H) 7.95 (d, J=7.57 Hz, 1H) 8.22 (s, 1H)

REFERENCE EXAMPLE 379 ethyl[(cis-3-{6-[(2'-cyano-3-fluorobiphenyl-4-yl) methyl]-5-oxo-7-propyl[1,2,4]triazolo[1,5-a]pyrimidin-4(5H)-yl}cyclobutyl)oxy]acetate A mixture of 3'-fluoro-4'-{[4-(cis-3-hydroxycyclobutyl)-5-oxo-7-propyl-4,5-dihydro[1,2,4]triazolo[1,5-a]pyrimidin-6-yl]methyl}biphenyl-2-carbonitrile (0.67 g), rhodium(II) acetate (dimer) (0.0066 g) and toluene (10 mL) was heated to 80° C. under an argon atmosphere, a solution of ethyl diazoacetate (1.5 g) in toluene (10 mL) was added dropwise, and the mixture was stirred at 80° C. for 10 min. The reaction mixture was concentrated under reduced pressure, and the residue was purified by silica gel column chromatography to give the title compound as a colorless solid (0.29 g, 37%).

¹H NMR (300 MHz, DMSO-d₆) δ0.95 (t, J=7.38 Hz, 3H) 1.20 (t, J=7.38 Hz, 3H) 1.52-1.75 (m, 2H) 2.52-2.67 (m, 2H) 2.86-3.26 (m, 4H) 3.82-3.99 (m, 3H) 4.07-4.20 (m, 4H) 4.79-5.08 (m, 1H) 7.18-7.51 (m, 3H) 7.54-7.71 (m, 2H) 7.73-7.86 (m, 1H) 7.95 (d, J=7.57 Hz, 1H) 8.23 (s, 1H)

REFERENCE EXAMPLE 380

3'-fluoro-4'-({4-[cis-3-(2-hydroxy-2-methylpropoxy) cyclobutyl]-5-oxo-7-propyl-4,5-dihydro[1,2,4]triazolo[1,5-a]pyrimidin-6-yl}methyl)biphenyl-2-carbonitrile Ethyl[(cis-3-{6-[(2'-cyano-3-fluorobiphenyl-4-yl)methyl]-5-oxo-7-propyl[1,2,4]triazolo[1,5-a]pyrimidin-4(5H)-yl}cyclobutyl)oxy]acetate (0.29 g) was dissolved in tetrahydrofuran (3 mL), methylmagnesium bromide (1.6 mL, 1.0 M tetrahydrofuran solution) was added dropwise at 0° C., and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.17 g, 60%).

¹H NMR (300 MHz, DMSO-d₆) δ0.95 (t, J=7.38 Hz, 3H) 1.08 (s, 6H) 1.49-1.73 (m, 2H) 2.53-2.71 (m, 2H) 2.87-3.07 (m, 4H) 3.11 (s, 2H) 3.73-3.87 (m, 1H) 3.96 (s, 2H) 4.29 (s, 1H) 4.70-5.03 (m, 1H) 7.22-7.51 (m, 3H) 7.54-7.68 (m, 2H) 7.73-7.84 (m, 1H) 7.95 (d, J=7.57 Hz, 1H) 8.22 (s, 1H)

REFERENCE EXAMPLE 381 ethyl trans-3-{6-[(2'-cyano-3-fluorobiphenyl-4-yl) methyl]-5-oxo-7-propyl[1,2,4]triazolo[1,5-a]pyrimidin-4(5H)-yl}cyclobutanecarboxylate A mixture of ethyl 3-(4H-1,2,4-triazol-3-ylamino)cyclobutanecarboxylate (2.5 g), ethyl 2-[(2'-cyano-3-fluorobiphenyl-4-yl)methyl]-3-oxohexanoate (7.9 g) and N,N-diethylaniline (10 mL) was stirred at 180° C. for 18 hr. The reaction mixture was added to 1 M hydrochloric acid, and the mixture was extracted with ethyl acetate. The organic layer was washed with 1 M hydrochloric acid and then with saturated brine, and dried over anhydrous magnesium sulfate. The solvent was evaporated under reduced pressure, and the residue was purified by silica gel column chromatography to give the title compound as a colorless solid (0.86 g, 14%).

¹H NMR (300 MHz, DMSO-d₆) δ0.95 (t, J=7.19 Hz, 3H) 1.18-1.27 (m, 3H) 1.28-1.73 (m, 2H) 2.17-3.46 (m, 7H) 3.97 (s, 2H) 4.14 (q, J=7.07 Hz, 2H) 5.50-5.77 (m, 1H) 7.22-7.51 (m, 3H) 7.53-7.71 (m, 2H) 7.73-7.85 (m, 1H) 7.95 (d, J=7.57 Hz, 1H) 8.24 (s, 1H)

REFERENCE EXAMPLE 382

4'-{[4-(trans-3-acetylcyclobutyl)-5-oxo-7-propyl-4, 5-dihydro[1,2,4]triazolo[1,5-a]pyrimidin-6-yl]methyl}-3'-fluorobiphenyl-2-carbonitrile A mixture of ethyl trans-3-{6-[(2'-cyano-3-fluorobiphenyl-4-yl)methyl]-5-oxo-7-propyl[1,2,4]triazolo[1,5-a]pyrimidin-4(5H)-yl}cyclobutanecarboxylate (0.86 g), tetrahydrofuran (10 mL), ethanol (10 mL) and 1 M aqueous sodium hydroxide solution (10 mL) was stirred at room temperature for 2 hr. The reaction mixture was neutralized with 1 M hydrochloric acid. After evaporation of the solvent under reduced pressure, the residue was extracted with ethyl acetate. The organic layer was washed with saturated brine, and dried over anhydrous magnesium sulfate. The solvent was evaporated under reduced pressure, the residue was mixed with N,O-dimethylhydroxyamine hydrochloride (0.24 g), 1-ethyl-3-(3-dimethylaminopropyl)carbodiimide hydrochloride (0.48 g), 1-hydroxybenzotriazole (0.33 g), triethylamine (0.69 mL) and N,N-dimethylformaldehyde (10 mL), and the mixture was stirred at room temperature for 14 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by silica gel column chromatography was dissolved in tetrahydrofuran (10 mL), methylmagnesium bromide (6.6 mL, 1.0 M tetrahydrofuran solution) was added dropwise at 0° C., and the mixture was stirred at 0° C. for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.49 g, 60%).

¹H NMR (300 MHz, DMSO-d₆) δ0.95 (t, J=7.38 Hz, 3H) 1.40-1.82 (m, 2H) 2.15 (s, 3H) 2.38-2.48 (m, 2H) 2.83-3.05 (m, 2H) 3.12-3.28 (m, 2H) 3.34-3.56 (m, 1H) 3.96 (s, 2H) 5.10-5.60 (m, 1H) 7.15-7.51 (m, 3H) 7.51-7.67 (m, 2H) 7.71-7.86 (m, 1H) 7.95 (d, J=7.57 Hz, 1H) 8.24 (s, 1H)

REFERENCE EXAMPLE 383

3'-fluoro-4'-{[4-(trans-3-hydroxycyclobutyl)-5-oxo-7-propyl-4,5-dihydro[1,2,4]triazolo[1,5-a]pyrimidin-6-yl]methyl}biphenyl-2-carbonitrile To a mixture of 4'-{[4-(trans-3-acetylcyclobutyl)-5-oxo-7-propyl-4,5-dihydro[1,2,4]triazolo[1,5-a]pyrimidin-6-yl]methyl}-3'-fluorobiphenyl-2-carbonitrile (0.49 g), 30% hydrogen peroxide (8.3 mL) and chloroform (10 mL) was gradually added dropwise trifluoroacetic acid anhydride (5.6 mL), and the mixture was heated under reflux for 14 hr. Saturated aqueous sodium hydrogen carbonate solution and aqueous sodium thiosulfate solution were gradually added to the reaction mixture, and the mixture was extracted with ethyl acetate. The organic layer was washed with saturated brine, and dried over anhydrous magnesium sulfate. The solvent was evaporated under reduced pressure, and the residue was mixed with tetrahydrofuran (5 mL), methanol (5 mL) and 1 M aqueous sodium hydroxide solution (5 mL). The mixture was stirred at room temperature for 4 hr, and the reaction mixture was neutralized with 1 M hydrochloric acid. After evaporation of the solvent under reduced pressure, and the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.29 g, 62%).

$^1$H NMR (300 MHz, DMSO-$d_6$) δ0.94 (t, J=7.19 Hz, 3H) 1.48-1.71 (m, 2H) 2.07-2.24 (m, 2H) 2.80-3.05 (m, 2H) 3.09-3.29 (m, 2H) 3.97 (s, 2H) 4.33-4.61 (m, 1H) 5.11 (d, J=4.92 Hz, 1H) 5.51-5.88 (m, 1H) 7.21-7.50 (m, 3H) 7.54-7.71 (m, 2H) 7.73-7.88 (m, 1H) 7.95 (d, J=7.95 Hz, 1H) 8.22 (s, 1H)

REFERENCE EXAMPLE 384 ethyl[(trans-3-{6-[(2'-cyano-3-fluorobiphenyl-4-yl) methyl]-5-oxo-7-propyl[1,2,4]triazolo[1,5-a]pyrimidin-4(5H)-yl}cyclobutyl)oxy]acetate A mixture of 3'-fluoro-4'-{[4-(trans-3-hydroxycyclobutyl)-5-oxo-7-propyl-4,5-dihydro[1,2,4]triazolo[1,5-a]pyrimidin-6-yl]methyl}biphenyl-2-carbonitrile (0.29 g), rhodium(II) acetate (dimer) (0.0028 g) and toluene (3 mL) was heated to 80° C. under an argon atmosphere, a solution of ethyl diazoacetate (0.16 g) in toluene (3 mL) was added dropwise, and the mixture was stirred at 80° C. for 10 min. The reaction mixture was concentrated under reduced pressure, and the residue was purified by silica gel column chromatography to give the title compound as a colorless solid (0.95 g, 27%).

$^1$H NMR (300 MHz, CHLOROFORM-d) δ1.06 (t, J=7.35 Hz, 3H) 1.26-1.36 (m, 3H) 1.61-1.82 (m, 2H) 2.39-2.68 (m, 2H) 2.95-3.12 (m, 2H) 3.18-3.43 (m, 2H) 4.02 (s, 2H) 4.05 (s, 2H) 4.24 (q, J=7.10 Hz, 2H) 4.49-4.67 (m, 1H) 5.77-6.02 (m, 1H) 7.21-7.31 (m, 2H) 7.33-7.57 (m, 3H) 7.58-7.71 (m, 1H) 7.72-7.80 (m, 1H) 7.93 (s, 1H)

REFERENCE EXAMPLE 385

3'-fluoro-4'-({4-[trans-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile Ethyl[(trans-3-{6-[(2'-cyano-3-fluorobiphenyl-4-yl)methyl]-5-oxo-7-propyl[1,2,4]triazolo[1,5-a]pyrimidin-4(5H)-yl}cyclobutyl)oxy]acetate (0.13 g) was dissolved in tetrahydrofuran (2 mL), methylmagnesium bromide (0.62 mL, 1.0 M tetrahydrofuran solution) was added dropwise at 0° C., and the mixture was stirred at 0° C. for 1 hr. Methylmagnesium bromide (0.62 mL, 1.0 M tetrahydrofuran solution) was added, and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.059 g, 45%).

$^1$H NMR (300 MHz, CHLOROFORM-d) δ1.06 (t, J=7.38 Hz, 3H) 1.24 (s, 6H) 1.58-1.83 (m, 2H) 2.30 (s, 1H) 2.37-2.57 (m, 2H) 2.94-3.11 (m, 2H) 3.22 (s, 2H) 3.24-3.44 (m, 2H) 4.02 (s, 2H) 4.31-4.57 (m, 1H) 5.69-6.03 (m, 1H) 7.15-7.30 (m, 2H) 7.30-7.52 (m, 3H) 7.58-7.71 (m, 1H) 7.75 (d, J=7.95 Hz, 1H) 7.94 (s, 1H)

REFERENCE EXAMPLE 386 ethyl[(trans-4-{6-[(2'-cyano-3-fluorobiphenyl-4-yl) methyl]-2-methyl-5-oxo-7-propyl[1,2,4]triazolo[1,5-a]pyrimidin-4(5H)-yl}-1-methylcyclohexyl)oxy] acetate 3'-Fluoro-4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile (12 g) was dissolved in tetrahydrofuran (120 mL), methylmagnesium bromide (49 mL, 1.0 M tetrahydrofuran solution) was added dropwise at 70° C., and the mixture was stirred at 70° C. for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue obtained by silica gel column chromatography was mixed with rhodium(II) acetate (dimer) (0.0080 g) and toluene (10 mL). A solution of ethyl diazoacetate (0.48 g) in toluene (10 mL) was added dropwise at 80° C. under an argon atmosphere, and the mixture was stirred at 80° C. for 10 min. The reaction mixture was concentrated under reduced pressure, and the residue was purified by silica gel column chromatography to give the title compound as a colorless solid (0.26 g, 1.7%).

$^1$H NMR (300 MHz, DMSO-$d_6$) δ0.94 (t, J=7.25 Hz, 3H) 1.17-1.22 (m, 3H) 1.32 (s, 3H) 1.46-1.89 (m, 8H) 2.37 (s, 3H) 2.54-2.76 (m, 2H) 2.80-3.04 (m, 2H) 3.95 (s, 2H) 4.05-4.17 (m, 4H) 4.72-4.99 (m, 1H) 7.04-7.39 (m, 2H) 7.45 (dd, J=11.11, 1.32 Hz, 1H) 7.52-7.70 (m, 2H) 7.73-7.85 (m, 1H) 7.95 (dd, J=7.63, 1.04 Hz, 1H)

REFERENCE EXAMPLE 387

3'-fluoro-4'-({4-[trans-4-(2-hydroxy-2-methylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile Ethyl[(trans-4-{6-[(2'-cyano-3-fluorobiphenyl-4-yl)methyl]-2-methyl-5-oxo-7-propyl[1,2,4]triazolo[1,5-a]pyrimidin-4(5H)-yl}-1-methylcyclohexyl)oxy]acetate (0.26 g) was dissolved in tetrahydrofuran (3 mL), methylmagnesium bromide (1.1 mL, 1.0 M tetrahydrofuran solution) was added dropwise at 0° C., and the mixture was stirred at room temperature for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.19 g, 75%).

$^1$H NMR (300 MHz, DMSO-$d_6$) δ0.94 (t, J=7.19 Hz, 3H) 1.06 (s, 6H) 1.30 (s, 3H) 1.36-1.87 (m, 8H) 2.37 (s, 3H) 2.53-2.75 (m, 2H) 2.82-3.00 (m, 2H) 3.12 (s, 2H) 3.95 (s, 2H) 4.13 (s, 1H) 4.67-5.02 (m, 1H) 7.19-7.39 (m, 2H) 7.40-7.51 (m, 1H) 7.52-7.67 (m, 2H) 7.70-7.88 (m, 1H) 7.95 (d, J=6.44 Hz, 1H)

REFERENCE EXAMPLE 388

1-[1-({[tert-butyl(dimethyl)silyl]oxy}methyl)cyclobutyl]ethanol

Methylmagnesium bromide (21 mL, 1.0 M tetrahydrofuran solution) was cooled to 0° C., a solution of 1-({[tert-butyl (dimethyl)silyl]oxy}methyl)cyclobutanecarbaldehyde (4.0 g) in tetrahydrofuran (40 mL) was added dropwise, and the mixture was stirred at 0° C. for 1 hr. Methylmagnesium bromide (10 mL, 1.0 M tetrahydrofuran solution) was added, and the mixture was stirred at 0° C. for 30 min. The reaction mixture was added to saturated aqueous ammonium chloride solution, and the mixture was extracted with ethyl acetate. The organic layer was dried over anhydrous magnesium sulfate, and the solvent was evaporated under reduced pressure. The residue was purified by silica gel column chromatography to give the title compound as an oily compound (2.5 g, 58%).

$^1$H NMR (300 MHz, DMSO-$d_6$) δ0.04 (s, 6H) 0.88 (s, 9H) 0.97 (d, J=6.44 Hz, 3H) 1.52-2.09 (m, 6H) 3.46-3.69 (m, 3H) 4.30 (d, J=4.92 Hz, 1H)

REFERENCE EXAMPLE 389

1-[1-(hydroxymethyl)cyclobutyl]ethanol

1-[1-({[tert-Butyl(dimethyl)silyl]oxy}methyl)cyclobutyl] ethanol (3.2 g) was dissolved in tetrahydrofuran (30 mL), tetrabutylammonium fluoride (32 mL, 1.0 M tetrahydrofuran solution) was added dropwise, and the mixture was stirred at room temperature for 5 hr. The reaction mixture was added to 1 M hydrochloric acid, and the mixture was extracted with ethyl acetate/2-propanol (3/1). The organic layer was dried over magnesium sulfate, and the solvent was evaporated under reduced pressure. The residue was purified by silica gel column chromatography to give the title compound as an oily compound (1.3 g, 79%).

$^1$H NMR (300 MHz, DMSO-$d_6$) δ0.97 (d, J=6.06 Hz, 3H) 1.49-1.95 (m, 6H) 3.24-3.78 (m, 3H) 4.20-4.60 (m, 2H)

REFERENCE EXAMPLE 390

3'-fluoro-4'-{[4-(5-methyl-6,13-dioxadispiro[3.2.5.2] tetradec-10-yl)-5-oxo-7-propyl-4,5-dihydro[1,2,4] triazolo[1,5-a]pyrimidin-6-yl]methyl}biphenyl-2-carbonitrile A mixture of 3'-fluoro-4'-{[5-oxo-4-(4-oxocyclohexyl)-7-propyl-4,5-dihydro[1,2,4]triazolo[1,5-a]pyrimidin-6-yl] methyl}biphenyl-2-carbonitrile (23 g), 1-[1-(hydroxymethyl)cyclobutyl]ethanol (7.6 g), 4-methylbenzenesulfonic acid (0.093 g) and toluene (200 mL) was heated with a Dean-Stark apparatus under reflux for 2 hr. The reaction mixture was concentrated under reduced pressure, and the residue was purified by silica gel column chromatography to give the title compound as a colorless solid (26 g, 90%).

$^1$H NMR (300 MHz, DMSO-$d_6$) δ0.95 (t, J=7.19 Hz, 3H) 1.07-3.11 (m, 21H) 3.59-3.89 (m, 3H) 3.97 (s, 2H) 4.72-5.04 (m, 1H) 7.23-7.40 (m, 2H) 7.45 (d, J=10.98 Hz, 1H) 7.54-7.69 (m, 2H) 7.72-7.84 (m, 1H) 7.95 (d, J=7.57 Hz, 1H) 8.17-8.23 (m, 1H)

REFERENCE EXAMPLE 391

3'-fluoro-4'-[(4-{4-[1-(1-formylcyclobutyl)ethoxy] cyclohexyl}-5-oxo-7-propyl-4,5-dihydro[1,2,4]triazolo[1,5-a]pyrimidin-6-yl)methyl]biphenyl-2-carbonitrile A mixture of 3'-fluoro-4'-{[4-(5-methyl-6,13-dioxadispiro [3.2.5.2]tetradec-10-yl)-5- oxo-7-propyl-4,5-dihydro[1,2,4] triazolo[1,5-a]pyrimidin-6-yl]methyl}biphenyl-2-carbonitrile (0.64 g), sodium cyanoborohydride (0.33 g), boron trifluoride etherate (0.67 mL) and tetrahydrofuran (6 mL) was stirred at 70° C. for 20 hr. Saturated aqueous sodium hydrogen carbonate solution was added to the reaction mixture, and the mixture was extracted with ethyl acetate. The organic layer was washed with saturated brine, and dried over anhydrous magnesium sulfate. The solvent was evaporated under reduced pressure. The residue obtained by purification by silica gel column chromatography was mixed with Dess-Martin periodinane (0.49 g) and acetonitrile (5 mL), and the mixture was stirred at room temperature for 4 hr. Saturated aqueous sodium hydrogen carbonate solution and aqueous sodium thiosulfate solution were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.21 g, 32%).

$^1$H NMR (300 MHz, DMSO-$d_6$) δ0.95 (t, J=6.82 Hz, 3H) 1.01-1.11 (m, 3H) 1.21-2.37 (m, 14H) 2.53-3.09 (m, 4H) 3.33-3.75 (m, 1H) 3.77-3.94 (m, 1H) 3.97 (s, 2H) 4.73-5.07 (m, 1H) 7.20-7.38 (m, 2H) 7.45 (dd, J=10.98, 1.51 Hz, 1H) 7.51-7.70 (m, 2H) 7.72-7.87 (m, 1H) 7.95 (d, J=7.57 Hz, 1H) 8.09-8.27 (m, 1H) 9.54-9.85 (m, 1H)

REFERENCE EXAMPLE 392

3'-fluoro-4'-{[4-(4-{1-[1-(1-hydroxyethyl)cyclobutyl]ethoxy}cyclohexyl)-5-oxo-7-propyl-4,5-dihydro [1,2,4]triazolo[1,5-a]pyrimidin-6-yl] methyl}biphenyl-2-carbonitrile 3'-Fluoro-4'-[(4-{4-[1-(1-formylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (14 g) was dissolved in tetrahydrofuran (150 mL), methylmagnesium bromide (35 mL, 1.0 M tetrahydrofuran solution) was added dropwise at 0° C., and the mixture was stirred at room temperature for 30 min. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (13 g, 90%).

$^1$H NMR (300 MHz, DMSO-$d_6$) δ0.88-1.17 (m, 9H) 1.21-2.22 (m, 14H) 2.53-3.11 (m, 4H) 3.33-3.81 (m, 3H) 3.98 (s, 2H) 4.18-4.39 (m, 1H) 4.73-5.05 (m, 1H) 7.23-7.51 (m, 3H) 7.53-7.69 (m, 2H) 7.72-7.86 (m, 1H) 7.95 (d, J=7.95 Hz, 1H) 8.10-8.27 (m, 1H)

REFERENCE EXAMPLE 393

4'-[(4-{4-[1-(1-acetylcyclobutyl)ethoxy]cyclohexyl}-5-oxo-7-propyl-4,5-dihydro[1,2,4]triazolo[1,5-a] pyrimidin-6-yl)methyl]-3'-fluorobiphenyl-2-carbonitrile A mixture of 3'-fluoro-4'-{[4-(4-{1-[1-(1-hydroxyethyl) cyclobutyl]ethoxy}cyclohexyl)-5-oxo-7-propyl-4,5-dihydro [1,2,4]triazolo[1,5-a]pyrimidin-6-yl]methyl}biphenyl-2-carbonitrile (13 g), Dess-Martin periodinane (10 g) and acetonitrile (130 mL) was stirred at room temperature for 30 min. Saturated aqueous sodium hydrogen carbonate solution and 1 M aqueous sodium thiosulfate solution were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (11 g, 88%).

$^1$H NMR (300 MHz, DMSO-$d_6$) δ0.85-1.00 (m, 6H) 1.22-2.39 (m, 17H) 2.54-3.07 (m, 4H) 3.34-3.73 (m, 1H) 3.74-3.92 (m, 1H) 3.98 (s, 2H) 4.78-5.08 (m, 1H) 7.23-7.50 (m, 3H) 7.55-7.70 (m, 2H) 7.74-7.85 (m, 1H) 7.95 (d, J=7.95 Hz, 1H) 8.08-8.28 (m, 1H)

REFERENCE EXAMPLE 394

3'-fluoro-4'-[(4-{trans-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile To a mixture of 4'-[(4-{4-[1-(1-acetylcyclobutyl)ethoxy]cyclohexyl}-5-oxo-7-propyl-4,5-dihydro[1,2,4]triazolo[1,5-a]pyrimidin-6-yl)methyl]-3'-fluorobiphenyl-2-carbonitrile (11 g), 30% hydrogen peroxide (157 mL) and chloroform (150 mL) was gradually added dropwise trifluoroacetic acid anhydride (105 mL), and the mixture was stirred at 60° C. for 24 hr and then at room temperature for 40 hr. Saturated aqueous sodium hydrogen carbonate solution and aqueous sodium thiosulfate solution were gradually added to the reaction mixture, and the mixture was extracted with ethyl acetate. The organic layer was washed with saturated brine, and dried over anhydrous magnesium sulfate. The solvent was evaporated under reduced pressure. The residue was mixed with tetrahydrofuran (100 mL), methanol (100 mL) and 1 M aqueous sodium hydroxide solution (100 mL), and the mixture was stirred at room temperature for 1 hr. The reaction mixture was neutralized with 1 M hydrochloric acid. After evaporation of the solvent under reduced pressure, the residue was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.3 g, 12%).

$^1$H NMR (300 MHz, DMSO-$d_6$) δ0.95 (t, J=7.35 Hz, 3H) 1.01 (d, J=6.03 Hz, 3H) 1.20-1.94 (m, 10H) 1.96-2.22 (m, 4H) 2.53-2.72 (m, 2H) 2.80-3.10 (m, 2H) 3.26-3.49 (m, 2H) 3.97 (s, 2H) 4.65 (br. s., 1H) 4.78-4.99 (m, 1H) 7.23-7.50 (m, 3H) 7.53-7.69 (m, 2H) 7.74-7.86 (m, 1H) 7.95 (d, J=7.91 Hz, 1H) 8.20 (s, 1H)

REFERENCE EXAMPLE 395

4'-{[4-(1-benzylpiperidin-4-yl)-5-oxo-7-propyl-4,5-dihydro[1,2,4]triazolo[1,5-a]pyrimidin-6-yl]methyl}biphenyl-2-carbonitrile A solution of 1-benzyl-N-(1H-1,2,4-triazol-5-yl)-piperidine-4-amine (7.53 g) and ethyl 2-[(2'-cyanobiphenyl-4-yl)methyl]-3-oxohexanoate (14.41 g) in 1,2,4-trichlorobenzene (20 mL) was stirred at 195° C. for 2 days. The reaction mixture was cooled to room temperature and purified by silica gel chromatography [eluent: hexane/ethyl acetate=65/35→50/50 (volume ratio)] to give the title compound (4.82 g, 30%) as a brown amorphous compound.

$^1$H NMR (300 MHz, CDCl$_3$) δ1.06 (t, J=7.4 Hz, 3H), 1.65-1.79 (m, 4H), 2.13-2.20 (m, 2H), 2.89-3.05 (m, 6H), 3.55 (s, 2H), 4.01 (s, 2H), 5.01-5.13 (m, 1H), 7.21-7.48 (m, 11H), 7.58-7.64 (m, 1H), 7.72-7.75 (m, 1H), 7.92 (s, 1H).

REFERENCE EXAMPLE 396

4'-[(5-oxo-4-piperidin-4-yl-7-propyl-4,5-dihydro[1,2,4]triazolo[1,5-a]pyrimidin-6-yl)methyl]biphenyl-2-carbonitrile A mixture of 4'-{[4-(1-benzylpiperidin-4-yl)-5-oxo-7-propyl-4,5-dihydro[1,2,4]triazolo[1,5-a]pyrimidin-6-yl]methyl}biphenyl-2-carbonitrile (4.82 g), 10% palladium-carbon (containing water by 50%, 2.39 g), tetrahydrofuran (30 mL) and ethanol (60 mL) was stirred at room temperature for 2 days under a hydrogen atmosphere. The reaction mixture was filtered, and the solvent was evaporated. The residue was purified by basic silica gel chromatography [eluent: methanol/ethyl acetate=0/10→05/95 (volume ratio)] to give the title compound as a colorless amorphous compound (2.97 g, 74%).

$^1$H NMR (300 MHz, CDCl$_3$) δ1.06 (t, J=7.2 Hz, 3H), 1.67-1.79 (m, 4H), 2.01 (br s, 1H), 2.70-2.81 (m, 4H), 3.01-3.06 (m, 2H), 3.23-3.26 (m, 2H), 4.02 (s, 2H), 5.12-5.23 (m, 1H), 7.36 (d, J=8.1 Hz, 2H), 7.38-7.44 (m, 1H), 7.46-7.50 (m, 3H), 7.59-7.64 (m, 1H), 7.72-7.75 (m, 1H), 7.91 (s, 1H).

REFERENCE EXAMPLE 397

4'-{[4-(1-ethylpiperidin-4-yl)-5-oxo-7-propyl-4,5-dihydro[1,2,4]triazolo[1,5-a]pyrimidin-6-yl]methyl}biphenyl-2-carbonitrile A mixture of 4'-{[4-(1-benzylpiperidin-4-yl)-5-oxo-7-propyl-4,5-dihydro[1,2,4]triazolo[1,5-a]pyrimidin-6-yl]methyl}biphenyl-2-carbonitrile (4.82 g), 10% palladium-carbon (2.39 g), tetrahydrofuran (30 mL) and ethanol (60 mL) was stirred at room temperature for 2 days under a hydrogen atmosphere. The reaction mixture was filtered, and the solvent was evaporated. The residue was purified by basic silica gel chromatography [eluent: methanol/ethyl acetate=0/10→05/95 (volume ratio)] to give the title compound as a colorless amorphous compound (146 mg, 3%).

$^1$H NMR (300 MHz, CDCl$_3$) δ1.06 (t, J=7.2 Hz, 3H), 1.13 (t, J=7.2 Hz, 3H), 1.69-1.79 (m, 4H), 2.11-2.18 (m, 2H), 2.50 (q, J=7.2 Hz, 2H), 2.92-3.15 (m, 6H), 4.01 (s, 2H), 5.05-5.15 (m, 1H), 7.36 (d, J=8.4 Hz, 2H), 7.38-7.44 (m, 1H), 7.46-7.8 (m, 3H), 7.59-7.64 (m, 1H), 7.72-7.75 (m, 1H), 7.90 (s, 1H).

REFERENCE EXAMPLE 398

4'-({5-oxo-7-propyl-4-[1-(tetrahydro-2H-pyran-4-yl)piperidin-4-yl]-4,5-dihydro[1,2,4]triazolo[1,5-a]pyrimidin-6-yl}methyl)biphenyl-2-carbonitrile To a solution of 4'-[(5-oxo-4-piperidin-4-yl-7-propyl-4,5-dihydro[1,2,4]triazolo[1,5-a]pyrimidin-6-yl)methyl]biphenyl-2-carbonitrile (453 mg) and tetrahydropyran-4H-pyran-4-one (120 mg) in tetrahydrofuran (20 mL) was added sodium triacetoxyborohydride (318 mg), and the mixture was stirred at room temperature for 15 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: methanol/ethyl acetate=0/

100→10/90 (volume ratio)] to give the title compound as a colorless amorphous compound (317 mg, 59%).

¹H NMR (300 MHz, CDCl₃) δ1.06 (t, J=7.5 Hz, 3H), 1.55-1.79 (m, 8H), 2.30-2.37 (m, 2H), 2.50-2.58 (m, 1H), 2.84-3.11 (m, 6H), 3.34-3.41 (m, 2H), 4.01 (s, 2H), 4.01-4.05 (m, 2H), 5.00-5.11 (m, 1H), 7.36 (d, J=8.7 Hz, 2H), 7.39-7.48 (m, 4H), 7.58-7.64 (m, 1H), 7.72-7.75 (m, 1H), 7.91 (s, 1H).

REFERENCE EXAMPLE 399

4'-({4-[4-(1-hydroxy-1-methylethyl)cyclohexyl]-5-oxo-7-propyl-4,5-dihydro[1,2,4]triazolo[1,5-a]pyrimidin-6-yl}methyl)biphenyl-2-carbonitrile To a solution of ethyl 4-{6-[(2'-cyanobiphenyl-4-yl)methyl]-5-oxo-7-propyl[1,2,4]triazolo[1,5-a]pyrimidin-4(5H)-yl}cyclohexanecarboxylate (524 mg) in tetrahydrofuran (5 mL) was added 1 M methylmagnesium bromide-tetrahydrofuran solution (5 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→50/50 (volume ratio)] to give the title compound as a colorless amorphous compound (388 mg, 76%).

¹H NMR (300 MHz, CDCl₃) δ1.06 (t, J=7.5 Hz, 3H), 1.20 (s, 6H), 1.23-1.35 (m, 1H), 1.43-1.55 (m, 1H), 1.69-1.86 (m, 6H), 1.99-2.04 (m, 2H), 2.60-2.72 (m, 2H), 3.00-3.05 (m, 2H), 4.01 (s, 2H), 4.97-5.07 (m, 1H), 7.29-7.51 (m, 4H), 7.59-7.64 (m, 1H), 7.74-7.76 (m, 1H), 7.91 (s, 1H).

REFERENCE EXAMPLE 400

4'-({5-oxo-7-propyl-4-[1-(tetrahydro-2H-pyran-4-ylcarbonyl)piperidin-4-yl]-4,5-dihydro[1,2,4]triazolo[1,5-a]pyrimidin-6-yl}methyl)biphenyl-2-carbonitrile To a solution of 4'-[(5-oxo-4-piperidin-4-yl-7-propyl-4,5-dihydro[1,2,4]triazolo[1,5-a]pyrimidin-6-yl)methyl]biphenyl-2-carbonitrile (453 mg), tetrahydropyran-2H-pyran-4-carboxylic acid (150 mg) and 1-hydroxy-1H-benzotriazole (84 mg) in acetonitrile (20 mL) was added 1-ethyl-3-(3-dimethylaminopropyl)carbodiimide hydrochloride (249 mg), and the mixture was stirred at room temperature for 15 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=35/65→0/100 (volume ratio)] to give the title compound as a colorless amorphous compound (518 mg, 92%).

¹H NMR (300 MHz, CDCl₃) δ1.07 (t, J=7.5 Hz, 3H), 1.63-2.04 (m, 8H), 2.61-2.95 (m, 4H), 3.01-3.06 (m, 2H), 3.14-3.23 (m, 1H), 3.42-3.50 (m, 2H), 4.01 (s, 2H), 4.01-4.13 (m, 3H), 4.86 (br d, J=12.0 Hz, 1H), 5.21-5.31 (m, 1H), 7.36 (d, J=8.7 Hz, 2H), 7.39-7.45 (m, 1H), 7.46-7.49 (m, 3H), 7.60-7.65 (m, 1H), 7.73-7.76 (m, 1H), 7.89 (s, 1H).

REFERENCE EXAMPLE 401

4'-({4-[1-(2-hydroxyethyl)piperidin-4-yl]-5-oxo-7-propyl-4,5-dihydro[1,2,4]triazolo[1,5-a]pyrimidin-6-yl}methyl)biphenyl-2-carbonitrile A mixture of 4'-[(5-oxo-4-piperidin-4-yl-7-propyl-4,5-dihydro[1,2,4]triazolo[1,5-a]pyrimidin-6-yl)methyl]biphenyl-2-carbonitrile (300 mg), 2-bromoethanol (170 mg), sodium carbonate (280 mg) and ethanol (20 mL) was stirred at 80° C. for 15 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=35/65→0/100 (volume ratio)] to give the title compound as a colorless amorphous compound (205 mg, 63%).

¹H NMR (300 MHz, CDCl₃) δ1.06 (t, J=7.2 Hz, 3H), 1.60-1.79 (m, 5H), 2.17-2.31 (m, 2H), 2.58 (t, J=5.4 Hz, 2H), 2.87-3.08 (m, 6H), 3.61 (t, J=5.4 Hz, 2H), 4.01 (s, 2H), 5.04-5.14 (m, 1H), 7.36 (d, J=8.4 Hz, 2H), 7.38-7.44 (m, 1H), 7.46-7.49 (m, 3H), 7.59-7.65 (m, 1H), 7.74 (d, J=8.1 Hz, 1H), 7.92 (s, 1H).

REFERENCE EXAMPLE 402

4'-({5-oxo-4-[trans-4-(2-oxoethoxy)cyclohexyl]-7-propyl-4,5-dihydro[1,2,4]triazolo[1,5-a]pyrimidin-6-yl}methyl)biphenyl-2-carbonitrile (different production method of the same compound as Reference Example 325)

To a solution of 4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (1.19 g) in acetonitrile (20 mL) was added 1,1,1-triacetoxy-1,1-dihydro-1,2-benziodoxol-3(1H)-one (1.27 g) under ice-cooling, and the mixture was stirred at room temperature for 3 days. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=65/35→40/60 (volume ratio)] to give the title compound as a colorless amorphous compound (739 mg, 63%).

¹H NMR (300 MHz, CDCl₃) δ1.06 (t, J=7.2 Hz, 3H), 1.46-1.59 (m, 2H), 1.66-1.84 (m, 4H), 2.21 (br d, J=11.7 Hz, 2H), 2.64-2.78 (m, 2H), 3.00-3.05 (m, 2H), 3.46-3.55 (m, 1H), 4.01 (s, 2H), 4.13 (s, 2H), 5.03-5.13 (m, 1H), 7.35 (d, J=8.4 Hz, 2H), 7.39-7.44 (m, 1H), 7.46-7.49 (m, 3H), 7.59-7.65 (m, 1H), 7.72-7.75 (m, 1H), 7.90 (s, 1H), 9.73 (s, 1H).

REFERENCE EXAMPLE 403

4'-({4-[trans-4-(2-hydroxypropoxy)cyclohexyl]-5-oxo-7-propyl-4,5-dihydro[1,2,4]triazolo[1,5-a]pyrimidin-6-yl}methyl)biphenyl-2-carbonitrile To a solution of 4'-({5-oxo-4-[trans-4-(2-oxoethoxy)cyclohexyl]-7-propyl-4,5-dihydro[1,2,4]triazolo[1,5-a]pyrimidin-6-yl}methyl)biphenyl-2-carbonitrile (841 mg) in tetrahydrofuran (15 mL) was added 1 M methylmagnesium bromide-tetrahydrofuran solution (2.2 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=70/30→40/60 (volume ratio)] to give the title compound as a colorless amorphous compound (387 mg, 76%).

$^1$H NMR (300 MHz, CDCl$_3$) δ1.06 (t, J=7.5 Hz, 3H), 1.15 (d, J=6.3 Hz, 3H), 1.40-1.52 (m, 2H), 1.66-1.83 (m, 4H), 2.17-2.21 (m, 2H), 2.56 (br s, 1H), 2.64-2.78 (m, 2H), 3.00-3.06 (m, 2H), 3.26 (dd, J=9.3, 8.1 Hz, 1H), 3.40-3.52 (m, 2H), 3.91-3.96 (m, 1H), 4.02 (s, 2H), 5.03-5.11 (m, 1H), 7.36 (d, J=8.7 Hz, 2H), 7.39-7.49 (m, 4H), 7.59-7.65 (m, 1H), 7.72-7.75 (m, 1H), 7.91 (s, 1H).

REFERENCE EXAMPLE 404 methyl(4-{6-[(2'-cyanobiphenyl-4-yl)methyl]-5-oxo-7-propyl[1,2,4]triazolo[1,5-a]pyrimidin-4(5H)-yl}piperidin-1-yl)acetate A mixture of 4'-[(5-oxo-4-piperidin-4-yl-7-propyl-4,5-dihydro[1,2,4]triazolo[1,5-a]pyrimidin-6-yl)methyl]biphenyl-2-carbonitrile (453 mg), ethyl bromoacetate (184 mg), potassium carbonate (276 mg) and N,N-dimethylformamide (5 mL) was stirred at 60° C. for 16 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=60/40→35/65 (volume ratio)] to give the title compound as a colorless amorphous compound (418 mg, 80%).

$^1$H NMR (300 MHz, CDCl$_3$) δ1.06 (t, J=7.5 Hz, 3H), 1.66-1.79 (m, 4H), 2.44-2.52 (m, 2H), 2.96-3.08 (m, 6H), 3.32 (s, 2H), 3.72 (s, 3H), 4.02 (s, 2H), 5.05-5.13 (m, 1H), 7.37 (d, J=8.4 Hz, 2H), 7.39-7.44 (m, 1H), 7.46-7.49 (m, 3H), 7.59-7.65 (m, 1H), 7.72-7.75 (m, 1H), 7.90 (s, 1H).

REFERENCE EXAMPLE 405

4'-({4-[1-(2-hydroxy-2-methylpropyl)piperidin-4-yl]-5-oxo-7-propyl-4,5-dihydro[1,2,4]triazolo[1,5-a]pyrimidin-6-yl}methyl)biphenyl-2-carbonitrile To a solution of methyl(4-{6-[(2'-cyanobiphenyl-4-yl)methyl]-5-oxo-7-propyl[1,2,4]triazolo[1,5-a]pyrimidin-4(5H)-yl}piperidin-1-yl)acetate (418 mg) in tetrahydrofuran (6 mL) was added 1 M methylmagnesium bromide-tetrahydrofuran solution (3 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=40/60→0/100 (volume ratio)] to give the title compound as a colorless amorphous compound (325 mg, 77%).

$^1$H NMR (300 MHz, CDCl$_3$) δ1.07 (t, J=7.2 Hz, 3H), 1.18 (s, 6H), 1.64-1.77 (m, 5H), 2.37 (s, 2H), 2.55 (br t, J=12.0 Hz, 2H), 2.89-3.06 (m, 6H), 4.01 (s, 2H), 4.99-5.09 (m, 1H), 7.36 (d, J=8.4 Hz, 2H), 7.38-7.44 (m, 1H), 7.46-7.49 (m, 3H), 7.59-7.64 (m, 1H), 7.72-7.75 (m, 1H), 7.93 (s, 1H).

REFERENCE EXAMPLE 406

4'-({5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (different production method of the same compound as Reference Example 212)

To a solution of 4'-({4-[trans-4-(2-hydroxypropoxy)cyclohexyl]-5-oxo-7-propyl-4,5-dihydro[1,2,4]triazolo[1,5-a]pyrimidin-6-yl}methyl)biphenyl-2-carbonitrile (280 mg) in acetonitrile (5 mL) was added 1,1,1-triacetoxy-1,1-dihydro-1,2-benziodoxol-3(1H)-one (293 mg) under ice-cooling, and the mixture was stirred at room temperature for 16 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=65/35→40/60 (volume ratio)] to give the title compound as a colorless amorphous compound (254 mg, 92%).

$^1$H NMR (300 MHz, CDCl$_3$) δ1.06 (t, J=7.5 Hz, 3H), 1.44-1.58 (m, 2H), 1.65-1.85 (m, 4H), 2.18 (s, 3H), 2.18-2.23 (m, 2H), 2.63-2.77 (m, 2H), 3.00-3.05 (m, 2H), 3.40-3.50 (m, 1H), 4.01 (s, 2H), 4.09 (s, 2H), 5.02-5.12 (m, 1H), 7.35 (d, J=8.4 Hz, 2H), 7.39-7.44 (m, 1H), 7.46-7.49 (m, 3H), 7.59-7.65 (m, 1H), 7.72-7.75 (m, 1H), 7.90 (s, 1H).

REFERENCE EXAMPLE 407

4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile To a solution of 4'-({5-oxo-4-[trans-4-(2-oxopropoxy)cyclohexyl]-7-propyl-4,5-dihydro[1,2,4]triazolo[1,5-a]pyrimidin-6-yl}methyl)biphenyl-2-carbonitrile (251 mg) in tetrahydrofuran (3 mL) was added 1 M methylmagnesium bromide-tetrahydrofuran solution (1 mL), and the mixture was stirred at room temperature for 16 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=70/30→40/60 (volume ratio)] to give the title compound as a colorless amorphous compound (237 mg, 91%).

$^1$H NMR (300 MHz, CDCl$_3$) δ1.06 (t, J=7.5 Hz, 3H), 1.20 (s, 6H), 1.39-1.50 (m, 2H), 1.66-1.82 (m, 4H), 2.17-2.20 (m, 2H), 2.37 (br s, 1H), 2.63-2.77 (m, 2H), 3.00-3.05 (m, 2H), 3.30 (s, 2H), 3.39-3.49 (m, 1H), 4.01 (s, 2H), 5.01-5.12 (m, 1H), 7.35 (d, J=8.7 Hz, 2H), 7.39-7.44 (m, 1H), 7.45-7.49 (m, 3H), 7.59-7.64 (m, 1H), 7.72-7.75 (m, 1H), 7.90 (s, 1H).

REFERENCE EXAMPLE 408

4'-[(4-{1-[4-(benzyloxy)phenyl]piperidin-4-yl}-5-oxo-7-propyl-4,5-dihydro[1,2,4]triazolo[1,5-a]pyrimidin-6-yl)methyl]biphenyl-2-carbonitrile A mixture of 4'-[(5-oxo-4-piperidin-4-yl-7-propyl-4,5-dihydro[1,2,4]triazolo[1,5-a]pyrimidin-6-yl)methyl]biphenyl- 2-carbonitrile (452 mg), 4-benzyloxyphenylboric acid (456 mg), copper(II) acetate (276 mg), molecular sieves 4A (1.50 g), triethylamine (506 mg), pyridine (396 mg) and tetrahydrofuran (10 mL) was stirred at room temperature for 2 days. Ethyl acetate was added to the reaction mixture, and the mixture was filtered through Celite-basic silica gel. The solvent was evaporated under reduced pressure, and the residue was purified by silica gel chromatography [eluent: hexane/ethyl acetate=75/25→60/40 (volume ratio)] to give the title compound as a colorless amorphous compound (364 mg, 57%).

$^1$H NMR (300 MHz, CDCl$_3$) δ1.07 (t, J=7.5 Hz, 3H), 1.68-1.83 (m, 4H), 2.77-2.85 (m, 2H), 3.02-3.16 (m, 4H), 4.03 (s, 2H), 5.01 (s, 2H), 5.13-5.24 (m, 1H), 6.87-6.95 (m, 4H), 7.26-7.50 (m, 11H), 7.59-7.64 (m, 1H), 7.71-7.74 (m, 1H), 7.92 (s, 1H).

REFERENCE EXAMPLE 409

4'-({4-[1-(4-hydroxyphenyl)piperidin-4-yl]-5-oxo-7-propyl-4,5-dihydro[1,2,4]triazolo[1,5-a]pyrimidin-6-yl}methyl)biphenyl-2-carbonitrile A mixture of 4'-[(4-{1-[4-(benzyloxy)phenyl]piperidin-4-yl}-5-oxo-7-propyl-4,5-dihydro[1,2,4]triazolo[1,5-a]pyrimidin-6-yl)methyl]biphenyl-2-carbonitrile (364 mg), 10% palladium-carbon (containing water by 50%, 91 mg), tetrahydrofuran (10 mL) and methanol (10 mL) was stirred at room temperature for 16 hr under a hydrogen atmosphere. The reaction mixture was filtered, and the solvent was evaporated. The residue was purified by preparative HPLC [eluent: 0.1% trifluoroacetic acid-containing acetonitrile/0.1% trifluoroacetic acid-containing water=5/95→100/0 (volume ratio)] to give the title compound as a colorless amorphous compound (183 mg, 59%).

$^1$H NMR (300 MHz, CDCl$_3$) δ1.07 (t, J=7.5 Hz, 3H), 1.68-1.83 (m, 4H), 2.72-2.80 (m, 2H), 3.02-3.15 (m, 4H), 3.59 (br d, J=11.7 Hz, 2H), 4.02 (s, 2H), 4.70-5.10 (br, 1H), 5.11-5.21 (m, 1H), 6.76 (d, J=9.0 Hz, 2H), 6.87 (d, J=9.0 Hz, 2H), 7.38 (d, J=8.7 Hz, 2H), 7.41-7.44 (m, 1H), 7.46-7.50 (m, 3H), 7.59-7.65 (m, 1H), 7.72-7.75 (m, 1H), 7.93 (s, 1H).

REFERENCE EXAMPLE 410

1-(1,4-dioxaspiro[4.5]dec-8-yloxy)-2-methylpropan-2-ol

To a solution of 1,4-dioxaspiro[4.5]decan-8-ol (4.90 g) in N,N-dimethylformamide (20 mL) was added 60% sodium hydride in oil (1.24 g) under ice-cooling, and the mixture was stirred at room temperature for 1 hr. Isobutylene oxide (2.52 g) was added to this mixture, and the mixture was stirred at 90° C. for 15 hr. The reaction mixture was cooled to room temperature and diluted with water, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=90/10→70/30 (volume ratio)] to give the title compound as a colorless oil (5.59 g, 78%).

$^1$H NMR (300 MHz, CDCl$_3$) δ1.20 (s, 6H), 1.52-1.61 (m, 2H), 1.68-1.83 (m, 6H), 2.39 (m, 1H), 3.24 (s, 2H), 3.45 (br s, 1H), 3.94 (br s, 4H).

REFERENCE EXAMPLE 411

4-(2-hydroxy-2-methylpropoxy)cyclohexanone

A mixture of 1-(1,4-dioxaspiro[4.5]dec-8-yloxy)-2-methylpropan-2-ol (5.53 g), 3N hydrochloric acid (30 mL) and acetone (30 mL) was stirred at room temperature for 16 hr. The reaction mixture was diluted with water, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→60/40 (volume ratio)] to give the title compound as a colorless oil (3.25 g, 73%).

$^1$H NMR (300 MHz, CDCl$_3$) δ1.24 (s, 6H), 1.90-2.00 (m, 2H), 2.08-2.18 (m, 2H), 2.23-2.32 (m, 2H), 2.36 (br s, 1H), 2.52-2.63 (m, 2H), 3.34 (s, 2H), 3.74-3.79 (m, 1H).

REFERENCE EXAMPLE 412

4'-({4-[cis-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile 1) To a solution of 3-amino-1H-1,2,4-triazole (1.46 g) and 4-(2-hydroxy-2-methylpropoxy)cyclohexanone (3.25 g) in acetic acid (30 mL) was added sodium triacetoxyborohydride (5.53 g), and the mixture was stirred at room temperature for 15 hr. The solvent was evaporated under reduced pressure, and the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: methanol/ethyl acetate=0/100→6/94 (volume ratio)] to give colorless amorphous 2-methyl-1-{[4-(1H-1,2,4-triazol-3-ylamino)cyclohexyl]oxy}propan-2-ol (2.84 g, 64%) as a diastereomixture.

2) A solution of 2-methyl-1-{[4-(1H-1,2,4-triazol-3-ylamino)cyclohexyl]oxy}propan-2-ol (2.80 g) and ethyl 2-[(2'-cyanobiphenyl-4-yl)methyl]-3-oxohexanoate (7.69 g) in 1,2,4-trichlorobenzene (15 mL) was stirred at 195° C. for 2 days. The reaction mixture was cooled to room temperature, and purified by silica gel chromatography [eluent: hexane/ethyl acetate=70/30→50/50 (volume ratio)] to give the title compound as a brown amorphous compound (620 mg, 10%).

$^1$H NMR (300 MHz, CDCl$_3$) δ1.05 (t, J=7.5 Hz, 3H), 1.30 (s, 6H), 1.48-1.56 (m, 4H), 1.67-1.75 (m, 2H), 2.09-2.14 (m, 2H), 2.95-3.04 (m, 4H), 3.28 (s, 2H), 3.66-3.69 (m, 2H), 4.01 (s, 2H), 5.12-5.23 (m, 1H), 7.36 (d, J=8.1 Hz, 2H), 7.38-7.49 (m, 4H), 7.58-7.64 (m, 1H), 7.72-7.75 (m, 1H), 7.91 (s, 1H).

REFERENCE EXAMPLE 413

2-methyl-1-[(8-methyl-1,4-dioxaspiro[4.5]dec-8-yl)oxy]propan-2-ol

To a solution of 8-methyl-1,4-dioxaspiro[4.5]decan-8-ol (4.01 g) in N,N-dimethylformamide (20 mL) was added 60% sodium hydride in oil (960 mg) under ice-cooling, and the mixture was stirred at room temperature for 1 hr. To this mixture was added isobutylene oxide (2.52 g), and the mixture was stirred at 90° C. for 15 hr. The reaction mixture was cooled to room temperature, and diluted with water, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→65/35 (volume ratio)] to give the title compound as a colorless oil (1.81 g, 32%).

$^1$H NMR (300 MHz, CDCl$_3$) δ1.15 (s, 3H), 1.21 (s, 6H), 1.50-1.64 (m, 4H), 1.76-1.82 (m, 4H), 2.43 (s, 1H), 3.12 (s, 2H), 3.45 (br s, 1H), 3.92-3.95 (m, 4H).

REFERENCE EXAMPLE 414

4-(2-hydroxy-2-methylpropoxy)-4-methylcyclohexanone

A mixture of 2-methyl-1-[(8-methyl-1,4-dioxaspiro[4.5]dec-8-yl)oxy]propan-2-ol (1.81 g), 3N hydrochloric acid (20 mL) and acetone (20 mL) was stirred at room temperature for 18 hr. The reaction mixture was diluted with water, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→65/35 (volume ratio)] to give the title compound as a colorless oil (1.05 g, 71%).
$^1$H NMR (300 MHz, CDCl$_3$) δ1.26 (s, 9H), 1.70-1.81 (m, 2H), 2.11-2.25 (m, 4H), 2.32 (br s, 1H), 2.54-2.65 (m, 2H), 3.25 (s, 2H).

REFERENCE EXAMPLE 415

4'-({4-[cis-4-(2-hydroxy-2-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile 1) To a solution of 3-amino-1H-1,2,4-triazole (441 mg) and 4-(2-hydroxy-2-methylpropoxy)-4-methylcyclohexanone (1.05 g) in acetic acid (10 mL) was added sodium triacetoxyborohydride (1.67 g), and the mixture was stirred at room temperature for 15 hr. The solvent was evaporated under reduced pressure, the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: methanol/ethyl acetate=0/100→10/90 (volume ratio)] to give colorless amorphous 2-methyl-1-{[1-methyl-4-(1H-1,2,4-triazol-3-ylamino)cyclohexyl]oxy}propan-2-ol (810 mg, 54%) as a diastereomixture.

2) A solution of 2-methyl-1-{[1-methyl-4-(1H-1,2,4-triazol-3-ylamino)cyclohexyl]oxy}propan-2-ol (810 mg) and ethyl 2-[(2'-cyanobiphenyl-4-yl)methyl]-3-oxohexanoate (1.99 g) in 1,2,4-trichlorobenzene (10 mL) was stirred at 195° C. for 3 days. The reaction mixture was cooled to room temperature, and purified by silica gel chromatography [eluent: hexane/ethyl acetate=70/30→50/50 (volume ratio)] to give the title compound as a brown amorphous compound (223 mg, 14%).
$^1$H NMR (300 MHz, CDCl$_3$) δ1.04 (t, J=7.2 Hz, 3H), 1.18 (s, 3H), 1.20 (s, 6H), 1.36-1.50 (m, 4H), 1.64-1.77 (m, 2H), 1.97-2.01 (m, 2H), 2.93-3.08 (m, 4H), 3.20 (s, 2H), 4.02 (s, 2H), 4.29 (br s, 1H), 5.11-5.22 (m, 1H), 7.36 (d, J=8.1 Hz, 2H), 7.38-7.44 (m, 1H), 7.46-7.49 (m, 3H), 7.59-7.64 (m, 1H), 7.72-7.75 (m, 1H), 7.94 (s, 1H).

REFERENCE EXAMPLE 416

4'-({4-[trans-4-(2-hydroxy-2-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile 1) To a solution of 3-amino-1H-1,2,4-triazole (441 mg) and 4-(2-hydroxy-2-methylpropoxy)-4-methylcyclohexanone (1.05 g) in acetic acid (10 mL) was added sodium triacetoxyborohydride (1.67 g), and the mixture was stirred at room temperature for 15 hr. The reaction mixture was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: methanol/ethyl acetate=0/100→10/90 (volume ratio)] to give colorless amorphous 2-methyl-1-{[1-methyl-4-(1H-1,2,4-triazol-3-ylamino)cyclohexyl]oxy}propan-2-ol (810 mg, 54%) as a diastereomixture.

2) A solution of 2-methyl-1-{[1-methyl-4-(1H-1,2,4-triazol-3-ylamino)cyclohexyl]oxy}propan-2-ol (810 mg) and ethyl 2-[(2'-cyanobiphenyl-4-yl)methyl]-3-oxohexanoate (1.99 g) in 1,2,4-trichlorobenzene (10 mL) was stirred at 195° C. for 3 days. The reaction mixture was cooled to room temperature, and purified by silica gel chromatography [eluent: hexane/ethyl acetate=70/30→50/50 (volume ratio)] to give the title compound as a brown amorphous compound (104 mg, 7%).
$^1$H NMR (300 MHz, CDCl$_3$) δ1.06 (t, J=7.2 Hz, 3H), 1.20 (s, 6H), 1.42 (s, 3H), 1.61-1.78 (m, 6H), 1.84-1.89 (m, 2H), 2.49 (br s, 1H), 2.72-2.86 (m, 2H), 2.99-3.04 (m, 2H), 3.24 (s, 2H), 4.02 (s, 2H), 5.01-5.12 (m, 1H), 7.36 (d, J=8.1 Hz, 2H), 7.39-7.44 (m, 1H), 7.47-7.49 (m, 3H), 7.59-7.65 (m, 1H), 7.72-7.75 (m, 1H), 7.91 (s, 1H).

REFERENCE EXAMPLE 417

1-benzyl-N-(tetrahydro-2H-pyran-4-yl)-1H-1,2,3-triazol-5-amine

To a solution of 1-benzyl-1H-1,2,3-triazol-5-amine (835 mg) and tetrahydropyran-4H-pyran-4-one (481 mg) in acetic acid (10 mL) was added sodium triacetoxyborohydride (1.53 g), and the mixture was stirred at room temperature for 15 hr. The solvent was evaporated under reduced pressure, the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: hexane/ethyl acetate=35/65→0/100 (volume ratio)], and crystallized from diisopropyl ether to give the title compound as pale-beige crystals (573 mg, 46%).
$^1$H NMR (300 MHz, CDCl$_3$) δ1.22-1.34 (m, 2H), 1.83-1.88 (m, 2H), 3.02 (br d, J=6.6 Hz, 1H), 3.11-3.23 (m, 1H), 3.35-3.43 (m, 2H), 3.79-3.86 (m, 2H), 5.38 (s, 2H), 7.00 (s, 1H), 7.18-7.21 (m, 2H), 7.31-7.40 (m, 3H).

REFERENCE EXAMPLE 418

N-(tetrahydro-2H-pyran-4-yl)-1H-1,2,3-triazol-5-amine

A mixture of 1-benzyl-N-(tetrahydro-2H-pyran-4-yl)-1H-1,2,3-triazol-5-amine (450 mg), 10% palladium-carbon (containing water by 50%, 450 mg), ammonium formate (631 mg), acetic acid (1.2 mL) and methanol (12 mL) was stirred at 60° C. for 16 hr under a nitrogen atmosphere. The reaction mixture was filtered, and the solvent was evaporated. The residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure to give the title compound as a white powder (209 mg, 73%).
¹H NMR (300 MHz, CDCl₃) δ1.45-1.55 (m, 2H), 2.03-2.08 (m, 2H), 3.46-3.55 (m, 3H), 3.63-3.65 (m, 1H), 3.97-4.04 (m, 2H), 7.06 (s, 1H), 10.75-11.00 (br, 1H).

REFERENCE EXAMPLE 419

4'-{[5-oxo-7-propyl-4-(tetrahydro-2H-pyran-4-yl)-4,5-dihydro[1,2,3]triazolo[1,5-a]pyrimidin-6-yl]methyl}biphenyl-2-carbonitrile A solution of N-(tetrahydro-2H-pyran-4-yl)-1H-1,2,3-triazol-5-amine (260 mg), ethyl 2-[(2'-cyanobiphenyl-4-yl)methyl]-3-oxohexanoate (1.08 g) and 1,8-diazabicyclo[5.4.0]undec-7-ene (236 mg) in N,N-diethylaniline (20 mL) was stirred at 180° C. for 16 hr. The reaction mixture was diluted with ethyl acetate-tetrahydrofuran (1:1), and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=50/50→10/90 (volume ratio)] to give the title compound as a brown amorphous compound (207 mg, 29%).
¹H NMR (300 MHz, CDCl₃) δ1.09 (t, J=7.5 Hz, 3H), 1.69-1.74 (m, 2H), 1.78-1.86 (m, 2H), 2.39-2.53 (m, 2H), 3.20-3.25 (m, 2H), 3.51-3.60 (m, 2H), 4.05 (s, 2H), 4.10-4.17 (m, 2H), 5.24-5.35 (m, 1H), 7.38 (d, J=8.4 Hz, 2H), 7.39-7.45 (m, 1H), 7.46-7.50 (m, 3H), 7.49 (d, J=8.4 Hz, 2H), 7.60-7.65 (m, 1H), 7.63 (s, 1H), 7.73-7.76 (m, 1H).

REFERENCE EXAMPLE 420

4'-({4-[(1R,3S,5S,7S)-5-hydroxytricyclo[3.3.1.1³,⁷]dec-2-yl]-5-oxo-7-propyl-4,5-dihydro[1,2,4]triazolo[1,5-a]pyrimidin-6-yl}methyl)biphenyl-2-carbonitrile (less polar isomer)

1) To a solution of 3-amino-1H-1,2,4-triazole (841 mg) and 5-hydroxy-2-adamantanone (1.66 g) in acetic acid (10 mL) was added sodium triacetoxyborohydride (3.18 g), and the mixture was stirred at room temperature for 15 hr. The solvent was evaporated under reduced pressure, and the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was crystallized from ethyl acetate to give colorless solid (1S,3R,5S,7S)-4-(1H-1,2,4-triazol-3-ylamino)tricyclo[3.3.1.1³,⁷]decan-1-ol (1.50 g, 64%) as a diastereomixture.
2) (1S,3R,5S,7S)-4-(1H-1,2,4-Triazol-3-ylamino)tricyclo[3.3.1.1³,⁷]decan-1-ol (1.01 g), and a solution of ethyl 2-[(2'-cyanobiphenyl-4-yl)methyl]-3-oxohexanoate (3.01 g) and 1,8-diazabicyclo[5.4.0]undec-7-ene (655 mg) in N,N-diethylaniline (5 mL) were stirred at 180° C. for 16 hr. The reaction mixture was diluted with 10% methanol-containing ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=50/50→10/90 (volume ratio)] to give the title compound as a brown amorphous compound (90 mg, 4%).

¹H NMR (300 MHz, CDCl₃) δ1.06 (t, J=7.5 Hz, 3H), 1.66-1.82 (m, 7H), 1.91-1.95 (m, 2H), 2.23 (br s, 1H), 2.32 (br d, J=12.0 Hz, 2H), 3.00-3.05 (m, 4H), 4.00 (s, 2H), 4.73-4.90 (m, 3H), 5.11-5.22 (m, 1H), 7.34 (d, J=8.4 Hz, 2H), 7.38-7.44 (m, 1H), 7.45-7.49 (m, 3H), 7.59-7.64 (m, 1H), 7.72-7.74 (m, 1H), 7.91 (s, 1H).

REFERENCE EXAMPLE 421

4'-({4-[(1R,3S,5S,7S)-5-hydroxytricyclo[3.3.1.1³,⁷]dec-2-yl]-5-oxo-7-propyl-4,5-dihydro[1,2,4]triazolo[1,5-a]pyrimidin-6-yl}methyl)biphenyl-2-carbonitrile (highly-polar isomer)

1) To a solution of 3-amino-1H-1,2,4-triazole (841 mg) and 5-hydroxy-2-adamantanone (1.66 g) in acetic acid (10 mL) was added sodium triacetoxyborohydride (3.18 g), and the mixture was stirred at room temperature for 15 hr. The solvent was evaporated under reduced pressure. The residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was crystallized from ethyl acetate to give colorless solid (1S,3R,5S,7S)-4-(1H-1,2,4-triazol-3-ylamino)tricyclo[3.3.1.1³,⁷]decan-1-ol (1.50 g, 64%) as a diastereomixture.
2) (1S,3R,5S,7S)-4-(1H-1,2,4-Triazol-3-ylamino)tricyclo[3.3.1.1³,⁷]decan-1-ol (1.01 g), and a solution of ethyl 2-[(2'-cyanobiphenyl-4-yl)methyl]-3-oxohexanoate (3.01 g) and 1,8-diazabicyclo[5.4.0]undec-7-ene (655 mg) in N,N-diethylaniline (5 mL) were stirred at 180° C. for 16 hr. The reaction mixture was diluted with 10% methanol-containing ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=50/50→10/90 (volume ratio)] to give the title compound as a brown amorphous compound (99 mg, 4%).
¹H NMR (300 MHz, CDCl₃) δ1.05 (t, J=7.5 Hz, 3H), 1.53-1.89 (m, 9H), 2.01-2.04 (m, 2H), 2.19-2.27 (m, 3H), 2.98-3.04 (m, 4H), 4.01 (s, 2H), 4.82 (br s, 1H), 7.34 (d, J=8.4 Hz, 2H), 7.38-7.44 (m, 1H), 7.45-7.48 (m, 3H), 7.59-7.64 (m, 1H), 7.72-7.75 (m, 1H), 7.89 (s, 1H).

REFERENCE EXAMPLE 422

4'-({4-[cis-4-(but-3-en-1-yl)-4-hydroxycyclohexyl]-5-oxo-7-propyl-4,5-dihydro[1,2,4]triazolo[1,5-a]pyrimidin-6-yl}methyl)biphenyl-2-carbonitrile To a solution of ice-cooled cerium(III) chloride in tetrahydrofuran (10 mL) was added dropwise 0.5M 3-butenylmagnesium bromide-tetrahydrofuran solution (9.6 mL) under an argon atmosphere, and the mixture was stirred at 0° C. for 30 min. A solution of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1.86 g) in tetrahydrofuran (10 mL) was added dropwise to this reaction mixture, and the mixture was stirred at 0° C. for 30 min and then at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=80/20→50/50 (volume ratio)] to give the title compound as a colorless amorphous compound (506 mg, 24%).

$^1$H NMR (300 MHz, CDCl$_3$) δ1.06 (t, J=7.2 Hz, 3H), 1.49-1.85 (m, 11H), 2.16-2.26 (m, 2H), 2.89-3.06 (m, 4H), 4.02 (s, 2H), 4.94-5.13 (m, 3H), 5.80-5.93 (m, 1H), 7.37 (d, J=8.1 Hz, 2H), 7.38-7.44 (m, 1H), 7.46-7.49 (m, 3H), 7.59-7.65 (m, 1H), 7.72-7.75 (m, 1H), 7.93 (s, 1H).

REFERENCE EXAMPLE 423

4'-({4-[trans-4-(but-3-en-1-yl)-4-hydroxycyclohexyl]-5-oxo-7-propyl-4,5-dihydro[1,2,4]triazolo[1,5-a]pyrimidin-6-yl}methyl)biphenyl-2-carbonitrile To a solution of ice-cooled cerium(III) chloride in tetrahydrofuran (10 mL) was added dropwise 0.5M 3-butenylmagnesium bromide-tetrahydrofuran solution (9.6 mL) under an argon atmosphere, and the mixture was stirred at 0° C. for 30 min. A solution of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1.86 g) in tetrahydrofuran (10 mL) was added dropwise to this reaction mixture, and the mixture was stirred at 0° C. for 30 min and then at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=80/20→50/50 (volume ratio)] to give the title compound as a colorless amorphous compound (210 mg, 10%).

$^1$H NMR (300 MHz, CDCl$_3$) δ1.06 (t, J=7.5 Hz, 3H), 1.41 (br s, 1H), 1.58-1.78 (m, 6H), 1.90-1.96 (m, 4H), 2.18-2.26 (m, 2H), 2.69-2.84 (m, 2H), 2.99-3.04 (m, 2H), 4.01 (s, 2H), 5.00-5.15 (m, 3H), 5.89-6.02 (m, 1H), 7.36 (d, J=8.1 Hz, 2H), 7.39-7.44 (m, 1H), 7.46-7.49 (m, 3H), 7.59-7.65 (m, 1H), 7.72-7.75 (m, 1H), 7.91 (s, 1H).

REFERENCE EXAMPLE 424

4'-({4-[(5S,8S)-2-(hydroxymethyl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile To a solution of 4'-({4-[cis-4-(but-3-en-1-yl)-4-hydroxycyclohexyl]-5-oxo-7-propyl-4,5-dihydro[1,2,4]triazolo[1,5-a]pyrimidin-6-yl}methyl)biphenyl-2-carbonitrile (506 mg) in acetonitrile (10 mL) was added m-chloroperbenzoic acid (365 mg), and the mixture was stirred at room temperature for 2 days. The reaction mixture was diluted with ethyl acetate, and the mixture was washed with 5% aqueous sodium thiosulfate solution and then with saturated brine, and dried over anhydrous magnesium sulfate. The solvent was evaporated under reduced pressure, and the residue was purified by silica gel chromatography [eluent: hexane/ethyl acetate=50/50→20/80 (volume ratio)] to give the title compound as a colorless amorphous compound (456 mg, 87%).

$^1$H NMR (300 MHz, CDCl$_3$) δ1.06 (t, J=7.5 Hz, 3H), 1.49-2.01 (m, 11H), 2.20-2.60 (br, 2H), 2.90-3.05 (m, 4H), 3.50 (dd, J=11.4, 6.0 Hz, 1H), 3.74 (dd, J=11.4, 3.3 Hz, 1H), 4.02 (s, 2H), 4.10-4.20 (m, 1H), 5.01-5.12 (m, 1H), 7.37 (d, J=8.7 Hz, 2H), 7.38-7.44 (m, 1H), 7.46-7.49 (m, 3H), 7.59-7.65 (m, 1H), 7.72-7.75 (m, 1H), 7.93 (s, 1H).

REFERENCE EXAMPLE 425

4'-({4-[(5R,8R)-2-(hydroxymethyl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile To a solution of 4'-({4-[trans-4-(but-3-en-1-yl)-4-hydroxycyclohexyl]-5-oxo-7-propyl-4,5-dihydro[1,2,4]triazolo[1,5-a]pyrimidin-6-yl}methyl)biphenyl-2-carbonitrile (210 mg) in acetonitrile (10 mL) was added m-chloroperbenzoic acid (150 mg), and the mixture was stirred at room temperature for 18 hr. The reaction mixture was diluted with ethyl acetate, and the mixture was washed with 5% aqueous sodium thiosulfate solution and then with saturated brine, and dried over anhydrous magnesium sulfate. The solvent was evaporated under reduced pressure, and the residue was purified by silica gel chromatography [eluent: hexane/ethyl acetate=60/40→20/80 (volume ratio)] to give the title compound as a colorless amorphous compound (138 mg, 64%).

$^1$H NMR (300 MHz, CDCl$_3$) δ1.06 (t, J=7.5 Hz, 3H), 1.66-1.91 (m, 9H), 1.95-2.11 (m, 4H), 2.67-2.82 (m, 2H), 2.99-3.05 (m, 2H), 3.49 (dd, J=11.4, 5.4 Hz, 1H), 3.70 (dd, J=11.4, 3.3 Hz, 1H), 4.01 (s, 2H), 4.08-4.17 (m, 1H), 5.03-5.14 (m, 1H), 7.36 (d, J=8.1 Hz, 2H), 7.39-7.44 (m, 1H), 7.46-7.49 (m, 3H), 7.59-7.65 (m, 1H), 7.72-7.75 (m, 1H), 7.91 (s, 1H).

REFERENCE EXAMPLE 426

4'-({4-[(5S,8S)-2-(2-hydroxypropan-2-yl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile To a solution of 4'-({4-[(5S,8S)-2-(hydroxymethyl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (456 mg) in acetonitrile (10 mL) was added 1,1,1-triacetoxy-1,1-dihydro-1,2-benziodoxol-3(1H)-one (467 mg) under ice-cooling, and the mixture was stirred at room temperature for 5 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. 1 M Methylmagnesium bromide-tetrahydrofuran solution (1.3 mL) was added to a solution of the obtained residue in tetrahydrofuran (5 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure. 1,1,1-Triacetoxy-1,1-dihydro-1,2-benziodoxol-3(1H)-one (331 mg) was added to a solution of the obtained residue in acetonitrile (10 mL) under ice-cooling, and the mixture was stirred at room temperature for 5 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. 1 M Methylmagnesium bromide-tetrahydrofuran solution (0.9 mL) was added to a solution of the residue in tetrahydrofuran (5 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→50/50 (volume ratio)] to give the title compound as a brown amorphous compound (158 mg, 33%).

$^1$H NMR (300 MHz, CDCl$_3$) δ1.06 (t, J=7.5 Hz, 3H), 1.16 (s, 6H), 1.51-1.89 (m, 12H), 2.10-2.60 (br, 1H), 2.95-3.08 (m, 4H), 3.81-3.86 (m, 1H), 4.02 (s, 2H), 5.01-5.12 (m, 1H), 7.37 (d, J=8.1 Hz, 2H), 7.38-7.44 (m, 1H), 7.47-7.50 (m, 3H), 7.59-7.65 (m, 1H), 7.72-7.75 (m, 1H), 7.90 (s, 1H).

REFERENCE EXAMPLE 427

1-benzyl-N-(4-{[tert-butyl(dimethyl)silyl]oxy}cyclohexyl)-1H-1,2,3-triazol-5-amine To a solution of 1-benzyl-1H-1,2,3-triazol-5-amine (10.61 g) and 4-{[tert-butyl(dimethyl)silyl]oxy}cyclohexanone (15.07 g) in acetic acid (80 mL) was added sodium triacetoxyborohydride (19.37 g), and the mixture was stirred at room temperature for 18 hr. The solvent was evaporated under reduced pressure, the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: hexane/ethyl acetate=80/20→60/40 (volume ratio)] to give the title compound as a pale-yellow oil (11.12 g, 47%).

$^1$H NMR (300 MHz, CDCl$_3$) δ0.02 (s, 6H), 0.87 (s, 9H), 1.30-1.95 (m, 8H), 2.90-3.10 (m, 2H), 3.50-3.80 (m, 1H), 5.37 (s, 2H), 6.96 (s, 1H), 7.16-7.22 (m, 2H), 7.31-7.39 (m, 3H).

REFERENCE EXAMPLE 428

N-(4-{[tert-butyl(dimethyl)silyl]oxy}cyclohexyl)-1H-1,2,3-triazol-5-amine

A mixture of 1-benzyl-N-(4-{[tert-butyl(dimethyl)silyl]oxy}cyclohexyl)-1H-1,2,3-triazol-5-amine (11.10 g), 10% palladium-carbon (containing water by 50%, 6.66 g), ammonium formate (9.05 g), acetic acid (22 mL) and methanol (220 mL) was stirred at 60° C. for 16 hr under a nitrogen atmosphere. The reaction mixture was filtered, and the solvent was evaporated. The residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by basic silica gel chromatography [eluent: hexane/ethyl acetate=70/30→30/70 (volume ratio)] to give the title compound as a colorless oil (5.56 g, 65%).

$^1$H NMR (300 MHz, CDCl$_3$) δ0.06 (s, 6H), 0.91 (s, 9H), 1.20-2.13 (m, 8H), 3.15-4.20 (m, 3H), 7.03 (s, 1H), 10.00-11.50 (br, 1H).

REFERENCE EXAMPLE 429

4'-{[4-(4-{[tert-butyl(dimethyl)silyl]oxy}cyclohexyl)-5-oxo-7-propyl-4,5-dihydro[1,2,3]triazolo[1,5-a]pyrimidin-6-yl]methyl}biphenyl-2-carbonitrile N-(4-{[tert-Butyl(dimethyl)silyl]oxy}cyclohexyl)-1H-1,2,3-triazol-5-amine (5.55 g) and a solution of ethyl 2-[(2'-cyanobiphenyl-4-yl)methyl]-3-oxohexanoate (13.07 g) and 1,8-diazabicyclo[5.4.0]undec-7-ene (2.85 g) in N,N-diethylaniline (30 mL) were stirred at 185° C. for 15 hr. The reaction mixture was diluted with ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=90/10→80/20 (volume ratio)] to give the title compound as a brown amorphous compound (1.58 g, 15%).

$^1$H NMR (300 MHz, CDCl$_3$) δ0.12 (s, 6H), 0.98 (s, 9H), 1.09 (t, J=7.5 Hz, 3H), 1.51-2.05 (m, 8H), 2.20-2.60 (m, 2H), 3.17-3.24 (m, 2H), 3.60-4.07 (m, 3H), 4.60-5.25 (m, 1H), 7.36-7.50 (m, 6H), 7.59-7.65 (m, 1H), 7.66 (s, 1H), 7.72-7.75 (m, 1H).

REFERENCE EXAMPLE 430

4'-{[4-(trans-4-hydroxycyclohexyl)-5-oxo-7-propyl-4,5-dihydro[1,2,3]triazolo[1,5-a]pyrimidin-6-yl]methyl}biphenyl-2-carbonitrile To a solution of 4'-{[4-(4-{[tert-butyl(dimethyl)silyl]oxy}cyclohexyl)-5-oxo-7-propyl-4,5-dihydro[1,2,3]triazolo[1,5-a]pyrimidin-6-yl]methyl}biphenyl-2-carbonitrile (1.58 g) in tetrahydrofuran (10 mL) was added 1 M tetra-n-butylammonium fluoride-tetrahydrofuran solution (10 mL), and the mixture was stirred at room temperature for 15 hr. Saturated aqueous ammonium chloride solution was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (293 mg, 23%).

$^1$H NMR (300 MHz, CDCl$_3$) δ1.09 (t, J=7.5 Hz, 3H), 1.48-1.62 (m, 3H), 1.75-1.87 (m, 4H), 2.13-2.17 (m, 2H), 2.22-2.36 (m, 2H), 3.18-3.23 (m, 2H), 3.71-3.81 (m, 1H), 4.03 (s, 2H), 4.75-4.95 (br, 1H), 7.37 (d, J=8.7 Hz, 2H), 7.39-7.45 (m, 1H), 7.46-7.49 (m, 1H), 7.48 (d, J=8.7 Hz, 2H), 7.49 (s, 1H), 7.59-7.65 (m, 1H), 7.73-7.76 (m, 1H).

REFERENCE EXAMPLE 431 ethyl[(trans-4-{6-[(2'-cyanobiphenyl-4-yl)methyl]-5-oxo-7-propyl[1,2,3]triazolo[1,5-a]pyrimidin-4(5H)-yl}cyclohexyl)oxy]acetate To a mixture of 4'-{[4-(trans-4-hydroxycyclohexyl)-5-oxo-7-propyl-4,5-dihydro[1,2,3]triazolo[1,5-a]pyrimidin-6-yl]methyl}biphenyl-2-carbonitrile (470 mg), rhodium(II) acetate (dimer) (22 mg) and methylene chloride (10 mL) was added dropwise ethyl diazoacetate (137 mg) under an argon atmosphere, and the mixture was stirred at room temperature for 3 days. The reaction mixture was washed with water and then with saturated brine, and dried over anhydrous magnesium sulfate. The solvent was evaporated under reduced pressure, and the residue was purified by silica gel chromatography [eluent: hexane/ethyl acetate=70/30→20/80 (volume ratio)] to give the title compound as a colorless amorphous compound (203 mg, 37%).

$^1$H NMR (300 MHz, CDCl$_3$) δ1.09 (t, J=7.2 Hz, 3H), 1.30 (t, J=7.2 Hz, 3H), 1.52-1.63 (m, 2H), 1.74-1.88 (m, 4H), 2.20-2.32 (m, 4H), 3.18-3.23 (m, 2H), 3.41-3.51 (m, 1H), 4.03 (s, 2H), 4.14 (s, 2H), 4.23 (q, J=7.2 Hz, 2H), 4.75-4.95

(br, 1H), 7.36 (d, J=8.7 Hz, 2H), 7.39-7.45 (m, 1H), 7.46-7.49 (m, 1H), 7.48 (d, J=8.7 Hz, 2H), 7.48 (s, 1H), 7.60-7.65 (m, 1H), 7.73-7.76 (m, 1H).

REFERENCE EXAMPLE 432

4'-({4-[trans-4-(2-hydroxy-2-methylpropoxy)cyclohexyl]-5-oxo-7-propyl-4,5-dihydro[1,2,3]triazolo[1,5-a]pyrimidin-6-yl}methyl)biphenyl-2-carbonitrile To a solution of ethyl[(trans-4-{6-[(2'-cyanobiphenyl-4-yl)methyl]-5-oxo-7-propyl[1,2,3]triazolo[1,5-a]pyrimidin-4(5H)-yl}cyclohexyl)oxy]acetate (203 mg) in tetrahydrofuran (5 mL) was added 1 M methylmagnesium bromide-tetrahydrofuran solution (1.8 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→30/70 (volume ratio)] to give the title compound as a colorless amorphous compound (153 mg, 77%).
$^1$H NMR (300 MHz, CDCl$_3$) δ1.08 (t, J=7.2 Hz, 3H), 1.21 (s, 6H), 1.42-1.55 (m, 2H), 1.74-1.88 (m, 4H), 2.17-2.27 (m, 4H), 2.32 (br s, 1H), 3.18-3.23 (m, 2H), 3.32 (s, 2H), 3.34-3.42 (m, 1H), 4.03 (s, 2H), 4.75-4.95 (br, 1H), 7.37 (d, J=8.4 Hz, 2H), 7.39-7.45 (m, 1H), 7.46-7.49 (m, 1H), 7.49 (d, J=8.4 Hz, 2H), 7.49 (s, 1H), 7.60-7.65 (m, 1H), 7.73-7.76 (m, 1H).

REFERENCE EXAMPLE 433

4'-(4-[cis-4-hydroxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile A mixture of tetraallyltin(IV) (142 mg), gadorinium chloride hexahydrate (19 mg), 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (466 mg), tetrahydrofuran (3 mL) and acetonitrile (5 mL) was stirred at room temperature for 15 hr under an argon atmosphere. The reaction mixture was diluted with water, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=70/30→40/60 (volume ratio)] to give the title compound as a colorless amorphous compound (383 mg, 75%).
$^1$H NMR (300 MHz, CDCl$_3$) δ1.06 (t, J=7.5 Hz, 3H), 1.51-1.99 (m, 9H), 2.26 (d, J=7.5 Hz, 2H), 2.90-3.05 (m, 4H), 4.02 (s, 2H), 5.01-5.18 (m, 3H), 5.84-5.98 (m, 1H), 7.37 (d, J=8.1 Hz, 2H), 7.38-7.44 (m, 1H), 7.46-7.49 (m, 3H), 7.59-7.65 (m, 1H), 7.72-7.75 (m, 1H), 7.93 (s, 1H).

REFERENCE EXAMPLE 434

4'-({4-[trans-4-hydroxy-(4-prop-2-en-1-yl)cyclohexyl]-5-oxo-7-propyl-4,5-dihydro[1,2,4]triazolo[1,5-a]pyrimidin-6-yl}methyl)biphenyl-2-carbonitrile A mixture of tetraallyltin(IV) (142 mg), gadorinium chloride hexahydrate (19 mg), 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (466 mg), tetrahydrofuran (3 mL) and acetonitrile (5 mL) was stirred at room temperature for 15 hr under an argon atmosphere. The reaction mixture was diluted with water, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=70/30→40/60 (volume ratio)] to give the title compound as a colorless amorphous compound (113 mg, 22%).
$^1$H NMR (300 MHz, CDCl$_3$) δ1.06 (t, J=7.5 Hz, 3H), 1.60-1.79 (m, 6H), 1.86-1.91 (m, 2H), 2.62 (d, J=7.5 Hz, 2H), 2.74-2.89 (m, 2H), 2.99-3.05 (m, 2H), 4.02 (s, 2H), 5.06-5.17 (m, 1H), 5.21-5.28 (m, 2H), 5.87-6.01 (m, 1H), 7.36 (d, J=8.4 Hz, 2H), 7.39-7.44 (m, 1H), 7.46-7.50 (m, 3H), 7.59-7.65 (m, 1H), 7.72-7.75 (m, 1H), 7.91 (s, 1H).

REFERENCE EXAMPLE 435

4'-({4-[cis-4-hydroxy-4-(oxiran-2-ylmethyl)cyclohexyl]-5-oxo-7-propyl-4,5-dihydro[1,2,4]triazolo[1,5-a]pyrimidin-6-yl}methyl)biphenyl-2-carbonitrile To a mixture of 4'-({4-[cis-4-hydroxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile (548 mg), sodium hydrogen carbonate (136 mg) and methylene chloride (5 mL) was added m-chloroperbenzoic acid (370 mg) at 0° C., and the mixture was stirred at room temperature for 15 hr. The reaction mixture was diluted with ethyl acetate, and the mixture was washed with 5% aqueous sodium thiosulfate solution and then with saturated brine, and dried over anhydrous magnesium sulfate. The solvent was evaporated under reduced pressure, and the residue was purified by silica gel chromatography [eluent: hexane/ethyl acetate=60/40→35/65 (volume ratio)] to give the title compound as a colorless amorphous compound (490 mg, 94%).
$^1$H NMR (300 MHz, CDCl$_3$) δ1.06 (t, J=7.2 Hz, 3H), 1.55-1.79 (m, 7H), 1.82-2.03 (m, 4H), 2.49 (dd, J=4.8, 2.7 Hz, 1H), 2.80 (dd, J=4.8, 4.2 Hz, 1H), 2.92-3.05 (m, 4H), 3.16-3.22 (m, 1H), 4.02 (s, 2H), 5.05-5.16 (m, 1H), 7.36 (d, J=8.4 Hz, 2H), 7.38-7.44 (m, 1H), 7.45-7.49 (m, 3H), 7.59-7.64 (m, 1H), 7.72-7.75 (m, 1H), 7.93 (s, 1H).

REFERENCE EXAMPLE 436

4'-({4-[trans-4-hydroxy-4-(oxiran-2-ylmethyl)cyclohexyl]-5-oxo-7-propyl-4,5-dihydro[1,2,4]triazolo[1,5-a]pyrimidin-6-yl}methyl)biphenyl-2-carbonitrile To a mixture of 4'-({4-[trans-4-hydroxy-(4-prop-2-en-1-yl)cyclohexyl]-5-oxo-7-propyl-4,5-dihydro[1,2,4]triazolo[1,5-a]pyrimidin-6-yl}methyl)biphenyl-2-carbonitrile (162 mg), sodium hydrogen carbonate (42 mg) and methylene chloride (3 mL) was added m-chloroperbenzoic acid (118 mg) at 0° C., and the mixture was stirred at room temperature for 15 hr. The reaction mixture was diluted with ethyl acetate, and the mixture was washed with 5% aqueous sodium thiosulfate solution and then with saturated brine, and dried over anhydrous magnesium sulfate. The solvent was evaporated under reduced pressure, and the residue was purified by silica gel chromatography [eluent: hexane/ethyl acetate=60/40→35/65 (volume ratio)] to give the title compound as a colorless amorphous compound (136 mg, 81%).
$^1$H NMR (300 MHz, CDCl$_3$) δ1.06 (t, J=7.5 Hz, 3H), 1.65-1.76 (m, 8H), 1.95-1.99 (m, 1H), 2.08-2.12 (m, 1H), 2.44 (dd, J=14.7, 3.9 Hz, 1H), 2.60 (dd, J=5.1, 2.7 Hz, 1H), 2.71-2.87 (m, 2H), 2.85 (dd, J=5.1, 3.9 Hz, 1H), 2.99-3.04 (m, 2H), 3.21-3.27 (m, 1H), 4.01 (s, 2H), 5.07-5.18 (m, 1H), 7.36 (d, J=8.7 Hz, 2H), 7.39-7.44 (m, 1H), 7.46-7.49 (m, 3H), 7.59-7.65 (m, 1H), 7.72-7.75 (m, 1H), 7.90 (s, 1H).

REFERENCE EXAMPLE 437

4'-({4-[(5S,8S)-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile Under an argon atmosphere, a mixture of a solution of 4'-({4-[cis-4-hydroxy-4-(oxiran-2-ylmethyl)cyclohexyl]-5-oxo-7-propyl-4,5-dihydro[1,2,4]triazolo[1,5-a]pyrimidin-6-yl}methyl)biphenyl-2-carbonitrile (245 mg) in tetrahydrofuran (5 mL) and magnesium bromide (18.4 mg) was stirred at 60° C. for 20 hr. The reaction mixture was diluted with water, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=50/50→20/80 (volume ratio)] to give the title compound as a colorless amorphous compound (238 mg, 97%).
$^1$H NMR (300 MHz, CDCl$_3$) δ1.06 (t, J=7.2 Hz, 3H), 1.50-1.86 (m, 8H), 1.96-2.18 (m, 3H), 2.99-3.05 (m, 4H), 3.88 (d, J=9.9 Hz, 1H), 3.97 (dd, J=9.9, 4.2 Hz, 1H), 4.02 (s, 2H), 4.46 (br s, 1H), 5.02-5.11 (m, 1H), 7.35-7.48 (m, 6H), 7.59-7.64 (m, 1H), 7.72-7.74 (m, 1H), 7.94 (s, 1H).

REFERENCE EXAMPLE 438

4'-({4-[(5R,8R)-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile Under an argon atmosphere, a mixture of a solution of 4'-({4-[trans-4-hydroxy-4-(oxiran-2-ylmethyl)cyclohexyl]-5-oxo-7-propyl-4,5-dihydro[1,2,4]triazolo[1,5-a]pyrimidin-6-yl}methyl)biphenyl-2-carbonitrile (136 mg) in tetrahydrofuran (3 mL) and magnesium bromide (9.6 mg) was stirred at 60° C. for 20 hr. The reaction mixture was diluted with water and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=70/30→0/100 (volume ratio)] to give the title compound as a colorless amorphous compound (59 mg, 43%).
$^1$H NMR (300 MHz, CDCl$_3$) δ1.06 (t, J=7.5 Hz, 3H), 1.66-1.89 (m, 8H), 2.04-2.22 (m, 3H), 2.64-2.83 (m, 2H), 2.99-3.04 (m, 2H), 3.83 (dd, J=9.9, 2.4 Hz, 1H), 3.96 (dd, J=9.9, 4.5 Hz, 1H), 4.01 (s, 2H), 4.54 (br s, 1H), 5.04-5.12 (m, 1H), 7.35 (d, J=8.4 Hz, 2H), 7.38-7.44 (m, 1H), 7.45-7.49 (m, 3H), 7.59-7.64 (m, 1H), 7.72-7.75 (m, 1H), 7.90 (s, 1H).

REFERENCE EXAMPLE 439

4'-({5-oxo-4-[(5R,8R)-3-oxo-1-oxaspiro[4.5]dec-8-yl]-7-propyl-4,5-dihydro[1,2,4]triazolo[1,5-a]pyrimidin-6-yl}methyl)biphenyl-2-carbonitrile To a solution of 4'-({4-[(5R,8R)-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (356 mg) in acetonitrile (10 mL) was added 1,1,1-triacetoxy-1,1-dihydro-1,2-benziodoxol-3(1H)-one (433 mg) under ice-cooling, and the mixture was stirred at room temperature for 16 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→30/70 (volume ratio)] to give the title compound as a colorless amorphous compound (345 mg, 97%).
$^1$H NMR (300 MHz, CDCl$_3$) δ1.06 (t, J=7.2 Hz, 3H), 1.66-2.04 (m, 8H), 2.67 (s, 2H), 2.67-2.80 (m, 2H), 3.00-3.06 (m, 2H), 4.01 (s, 2H), 4.06 (s, 2H), 5.10-5.20 (m, 1H), 7.36 (d, J=8.1 Hz, 2H), 7.39-7.44 (m, 1H), 7.47-7.50 (m, 3H), 7.59-7.65 (m, 1H), 7.72-7.75 (m, 1H), 7.90 (s, 1H).

REFERENCE EXAMPLE 440

4'-({4-[(5R,8R)-3-hydroxy-3-methyl-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile To a solution of 4'-({5-oxo-4-[(5R,8R)-3-oxo-1-oxaspiro[4.5]dec-8-yl]-7-propyl-4,5-dihydro[1,2,4]triazolo[1,5-a]pyrimidin-6-yl}methyl)biphenyl-2-carbonitrile (181 mg) in tetrahydrofuran (3 mL) was added 2M methylmagnesium iodide-diethyl ether solution (0.4 mL), and the mixture was stirred at room temperature for 18 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→30/70 (volume ratio)] to give the title compound as a colorless amorphous compound (109 mg, 58%).
$^1$H NMR (300 MHz, CDCl$_3$) δ1.06 (t, J=7.5 Hz, 3H), 1.43 (s, 3H), 1.64-2.08 (m, 10H), 2.26 (d, J=13.8 Hz, 1H), 2.62-2.82 (m, 2H), 2.99-3.04 (m, 2H), 3.68 (d, J=9.3 Hz, 1H), 3.79 (d, J=9.3 Hz, 1H), 4.01 (s, 2H), 5.02-5.13 (m, 1H), 7.36 (d, J=8.4 Hz, 2H), 7.39-7.44 (m, 1H), 7.45-7.49 (m, 3H), 7.59-7.65 (m, 1H), 7.72-7.75 (m, 1H), 7.91 (s, 1H).

REFERENCE EXAMPLE 441

4'-({4-[(5R,8R)-3-ethyl-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile To a solution of 4'-({5-oxo-4-[(5R,8R)-3-oxo-1-oxaspiro[4.5]dec-8-yl]-7-propyl-4,5-dihydro[1,2,4]triazolo[1,5-a]pyrimidin-6-yl}methyl)biphenyl-2-carbonitrile (150 mg) in tetrahydrofuran (2 mL) was added 3M ethylmagnesium bromide-diethyl ether solution (0.3 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→30/70 (volume ratio)] to give the title compound as a colorless amorphous compound (106 mg, 66%).
$^1$H NMR (300 MHz, CDCl$_3$) δ1.03 (t, J=7.5 Hz, 3H), 1.06 (t, J=7.5 Hz, 3H), 1.66-1.93 (m, 11H), 2.07-2.11 (m, 1H), 2.22 (d, J=13.5 Hz, 1H), 2.62-2.81 (m, 2H), 2.99-3.04 (m, 2H), 3.71 (d, J=9.6 Hz, 1H), 3.78 (d, J=9.6 Hz, 1H), 4.01 (s, 2H), 5.03-5.11 (m, 1H), 7.36 (d, J=8.1 Hz, 2H), 7.38-7.44 (m, 1H), 7.46-7.49 (m, 3H), 7.59-7.65 (m, 1H), 7.72-7.75 (m, 1H), 7.91 (s, 1H).

REFERENCE EXAMPLE 442

N-(1,4-dioxaspiro[4.5]dec-8-yl)-5-(trifluoromethyl)-1H-1,2,4-triazol-3-amine

To a solution of 5-(trifluoromethyl)-1H-1,2,4-triazol-3-amine (12.19 g) and 1,4-dioxaspiro[4.5]decan-8-one (12.49 g) in acetic acid (180 mL) was added sodium triacetoxyborohydride (25.43 g), and the mixture was stirred at room temperature for 3 days. The solvent was evaporated under reduced pressure, the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: methanol/ethyl acetate=0/100→10/90 (volume ratio)] and crystallized from diisopropyl ether to give the title compound as a colorless solid (9.88 g, 42%).
$^1$H NMR (300 MHz, DMSO-$d_6$) δ1.42-1.83 (m, 8H), 3.39 (br s, 1H), 3.82-3.87 (m, 4H), 7.07 (d, J=8.1 Hz, 1H), 12.75 (br s, 1H).

REFERENCE EXAMPLE 443

4'-{[4-(1,4-dioxaspiro[4.5]dec-8-yl)-5-oxo-7-propyl-2-(trifluoromethyl)-4,5-dihydro[1,2,4]triazolo[1,5-a]pyrimidin-6-yl]methyl}biphenyl-2-carbonitrile A solution of N-(1,4-dioxaspiro[4.5]dec-8-yl)-5-(trifluoromethyl)-1H-1,2,4-triazol-3-amine (9.87 g), ethyl 2-[(2'-cyanobiphenyl-4-yl)methyl]-3-oxohexanoate (23.59 g) and 1,8-diazabicyclo[5.4.0]undec-7-ene (5.05 mL) in N,N-diethylaniline (50 mL) was stirred at 180° C. for 16 hr. The reaction mixture was diluted with ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=80/20→60/40 (volume ratio)], and crystallized from diisopropyl ether to give the title compound as a colorless solid (7.91 g, 41%).
$^1$H NMR (300 MHz, CDCl$_3$) δ1.06 (t, J=7.2 Hz, 3H), 1.65-1.93 (m, 8H), 2.87-3.08 (m, 4H), 3.93-4.03 (m, 6H), 5.00-5.08 (m, 1H), 7.35 (d, J=8.1 Hz, 2H), 7.39-7.44 (m, 1H), 7.45-7.48 (m, 3H), 7.59-7.65 (m, 1H), 7.72-7.75 (m, 1H).

REFERENCE EXAMPLE 444

4'-{[4-(4-hydroxycyclohexyl)-5-oxo-7-propyl-2-(trifluoromethyl)-4,5-dihydro[1,2,4]triazolo[1,5-a]pyrimidin-6-yl]methyl}biphenyl-2-carbonitrile To a solution of 4'-{[4-(1,4-dioxaspiro[4.5]dec-8-yl)-5-oxo-7-propyl-2-(trifluoromethyl)-4,5-dihydro[1,2,4]triazolo[1,5-a]pyrimidin-6-yl]methyl}biphenyl-2-carbonitrile (7.69 g) in tetrahydrofuran (25 mL) was added 6N hydrochloric acid (25 mL), and the mixture was stirred at 90° C. for 20 hr. The reaction mixture was cooled to room temperature, neutralized with 2 N aqueous sodium hydroxide solution, and extracted with ethyl acetate. The extract was washed with saturated brine, and dried over anhydrous magnesium sulfate. The solvent was evaporated under reduced pressure. To a solution of the obtained residue in ethanol (20 mL)-tetrahydrofuran (10 mL) was added sodium borohydride (631 mg) under ice-cooling, and the mixture was stirred at room temperature for 8 hr. The reaction mixture was concentrated under reduced pressure, and the residue was partitioned between ethyl acetate and water. The organic layer was washed with saturated brine, and dried over anhydrous magnesium sulfate. The solvent was evaporated under reduced pressure, and the residue was purified by silica gel chromatography [eluent: hexane/ethyl acetate=80/30→50/50 (volume ratio)] to give the title compound as a colorless amorphous compound (4.27 g, 60%).
$^1$H NMR (300 MHz, CDCl$_3$) δ1.06 (t, J=7.2 Hz, 3H), 1.44-1.79 (m, 7H), 2.11-2.15 (m, 2H), 2.64-2.78 (m, 2H), 3.00-3.06 (m, 2H), 3.77-3.88 (m, 1H), 4.02 (s, 2H), 4.97-5.08 (m, 1H), 7.34 (d, J=8.4 Hz, 2H), 7.39-7.45 (m, 1H), 7.46-7.49 (m, 3H), 7.60-7.65 (m, 1H), 7.73-7.76 (m, 1H).

REFERENCE EXAMPLE 445 ethyl[(4-{6-[(2'-cyanobiphenyl-4-yl)methyl]-5-oxo-7-propyl-2-(trifluoromethyl) [1,2,4]triazolo[1,5-a]pyrimidin-4(5H)-yl}cyclohexyl)oxy]acetate To a mixture of 4'-{[4-(4-hydroxycyclohexyl)-5-oxo-7-propyl-2-(trifluoromethyl)-4,5-dihydro[1,2,4]triazolo[1,5-a]pyrimidin-6-yl]methyl}biphenyl-2-carbonitrile (2.14 g), rhodium(II) acetate (dimer) (88 mg) and toluene (20 mL) was added dropwise ethyl diazoacetate (571 mg) under an argon atmosphere at 80° C., and the mixture was stirred at 80° C. for 1 hr. The reaction mixture was concentrated under reduced pressure, and the residue was purified by silica gel chromatography [eluent: hexane/ethyl acetate=80/20→65/35 (volume ratio)] to give the title compound as a colorless amorphous compound (695 mg, 28%).
$^1$H NMR (300 MHz, CDCl$_3$) δ1.06 (t, J=7.2 Hz, 3H), 1.30 (t, J=7.2 Hz, 3H), 1.46-1.83 (m, 6H), 2.21-2.25 (m, 2H), 2.60-2.74 (m, 2H), 2.99-3.06 (m, 2H), 3.46-3.56 (m, 1H), 4.02 (s, 2H), 4.14 (s, 2H), 4.22 (q, J=7.2 Hz, 2H), 4.99-5.10 (m, 1H), 7.34 (d, J=8.4 Hz, 2H), 7.39-7.45 (m, 1H), 7.46-7.49 (m, 3H), 7.59-7.65 (m, 1H), 7.72-7.76 (m, 1H).

REFERENCE EXAMPLE 446

4'-({4-[trans-4-(2-hydroxy-2-methylpropoxy)cyclohexyl]-5-oxo-7-propyl-2-(trifluoromethyl)-4,5-dihydro[1,2,4]triazolo[1,5-a]pyrimidin-6-yl}methyl)biphenyl-2-carbonitrile To a solution of ethyl[(4-{6-[(2'-cyanobiphenyl-4-yl)methyl]-5-oxo-7-propyl-2-(trifluoromethyl)[1,2,4]triazolo[1,5-a]pyrimidin-4(5H)-yl}cyclohexyl)oxy]acetate (684 mg) in tetrahydrofuran (4 mL) was added 1 M methylmagnesium bromide-tetrahydrofuran solution (4 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→40/60 (volume ratio)] to give the title compound as a colorless amorphous compound (472 mg, 70%).
$^1$H NMR (300 MHz, CDCl$_3$) δ1.06 (t, J=7.2 Hz, 3H), 1.21 (s, 6H), 1.65-1.81 (m, 4H), 2.17-2.21 (m, 2H), 2.34 (br s, 1H), 2.60-2.74 (m, 2H), 3.00-3.06 (m, 2H), 3.32 (s, 2H), 3.40-3.50 (m, 1H), 4.02 (s, 2H), 4.99-5.10 (m, 1H), 7.34 (d, J=8.7 Hz, 2H), 7.39-7.45 (m, 1H), 7.46-7.49 (m, 3H), 7.60-7.65 (m, 1H), 7.73-7.76 (m, 1H).

REFERENCE EXAMPLE 447

4'-({4-[cis-4-methoxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile To a solution of 4'-({4-[cis-4-hydroxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile (1.32 g) in tetrahydrofuran (10 mL) was added 60% sodium hydride in oil (120 mg) at 0° C., and the mixture was stirred at room temperature for 30 min. Iodomethane (0.19 mL) was added and the mixture was further stirred for 15 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=80/20→60/40 (volume ratio)] to give the title compound as a colorless amorphous compound (1.29 g, 97%).

$^1$H NMR (300 MHz, CDCl$_3$) δ1.05 (t, J=7.2 Hz, 3H), 1.36-1.75 (m, 6H), 1.98-2.02 (m, 2H), 2.24 (d, J=7.2 Hz, 2H), 2.85-3.04 (m, 4H), 3.28 (s, 3H), 4.02 (s, 2H), 4.90-5.10 (m, 3H), 5.75-5.89 (m, 1H), 7.36 (d, J=8.4 Hz, 2H), 7.38-7.49 (m, 4H), 7.59-7.64 (m, 1H), 7.72-7.75 (m, 1H), 7.91 (s, 1H).

REFERENCE EXAMPLE 448

4'-({4-[cis-4-(2-hydroxypropyl)-4-methoxycyclohexyl]-5-oxo-7-propyl-4,5-dihydro[1,2,4]triazolo[1,5-a]pyrimidin-6-yl}methyl)biphenyl-2-carbonitrile To a solution of dimethyl sulfide-borane (0.34 mL) in tetrahydrofuran (5 mL) was added dropwise a solution of 4'-({4-[cis-4-methoxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile (1.66 g) in tetrahydrofuran (10 mL) at 0° C., and the mixture was stirred at room temperature for 2 hr. The reaction mixture was cooled to 0° C., 8N aqueous sodium hydroxide solution (2.5 mL) and then 30% aqueous hydrogen peroxide solution (3.5 mL) were added, and the mixture was further refluxed with heating for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (0.20 g, 12%).

$^1$H NMR (300 MHz, CDCl$_3$) δ1.06 (t, J=7.2 Hz, 3H), 1.18 (d, J=6.0 Hz, 3H), 1.23-2.23 (m, 10H), 2.78-3.08 (m, 4H), 3.33 (s, 3H), 3.75 (br s, 1H), 4.03 (s, 2H), 4.10-4.25 (m, 1H), 5.01-5.12 (m, 1H), 7.36-7.50 (m, 6H), 7.59-7.65 (m, 1H), 7.72-7.75 (m, 1H), 7.93 (s, 1H).

REFERENCE EXAMPLE 449

4'-({4-[cis-4-(2-hydroxy-2-methylpropyl)-4-methoxycyclohexyl]-5-oxo-7-propyl-4,5-dihydro[1,2,4]triazolo[1,5-a]pyrimidin-6-yl}methyl)biphenyl-2-carbonitrile To a solution of 4'-({4-[cis-4-(2-hydroxypropyl)-4-methoxycyclohexyl]-5-oxo-7-propyl-4,5-dihydro[1,2,4]triazolo[1,5-a]pyrimidin-6-yl}methyl)biphenyl-2-carbonitrile (200 mg) in acetonitrile (5 mL) was added 1,1,1-triacetoxy-1,1-dihydro-1,2-benziodoxol-3(1H)-one (238 mg) under ice-cooling, and the mixture was stirred at room temperature for 15 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. To a solution of the residue in tetrahydrofuran (5 mL) was added 1 M methylmagnesium bromide-tetrahydrofuran solution (0.56 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=60/40→40/60 (volume ratio)] to give the title compound as a colorless amorphous compound (79 mg, 39%).

$^1$H NMR (300 MHz, CDCl$_3$) δ1.06 (t, J=7.2 Hz, 3H), 1.32 (s, 6H), 1.44-1.78 (m, 8H), 2.25-2.29 (m, 2H), 2.56 (br s, 1H), 2.86-3.05 (m, 4H), 3.34 (s, 3H), 3.78 (br s, 1H), 4.02 (s, 2H), 5.00-5.10 (m, 1H), 7.37 (d, J=8.4 Hz, 2H), 7.38-7.44 (m, 1H), 7.46-7.49 (m, 3H), 7.59-7.65 (m, 1H), 7.72-7.75 (m, 1H), 7.93 (s, 1H).

REFERENCE EXAMPLE 450

4'-({4-[cis-4-(3-hydroxypropyl)-4-methoxycyclohexyl]-5-oxo-7-propyl-4,5-dihydro[1,2,4]triazolo[1,5-a]pyrimidin-6-yl}methyl)biphenyl-2-carbonitrile To a solution of dimethyl sulfide-borane (0.34 mL) in tetrahydrofuran (5 mL) was added dropwise a solution of 4'-({4-[cis-4-methoxy-4-(prop-2-en-1-yl)cyclohexyl]-5-oxo-7-propyl-4,5-dihydro[1,2,4]triazolo[1,5-a]pyrimidin-6-yl}methyl)biphenyl-2-carbonitrile (1.66 g) in tetrahydrofuran (10 mL) at 0° C., and the mixture was stirred at room temperature for 2 hr. The reaction mixture was cooled to 0° C., 8N aqueous sodium hydroxide solution (2.5 mL) and then 30% aqueous hydrogen peroxide solution (3.5 mL) were added, and the mixture was further refluxed with heating for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (1.39 g, 81%).

$^1$H NMR (300 MHz, CDCl$_3$) δ1.06 (t, J=7.5 Hz, 3H), 1.33-1.43 (m, 2H), 1.53-1.82 (m, 9H), 2.03-2.08 (m, 2H), 2.85-3.04 (m, 4H), 3.24 (s, 3H), 3.63-3.69 (m, 2H), 4.02 (s, 2H), 4.96-4.57 (m, 1H), 7.35-7.49 (m, 6H), 7.59-7.64 (m, 1H), 7.72-7.75 (m, 1H), 7.92 (s, 1H).

REFERENCE EXAMPLE 451

3-(cis-4-{6-[(2'-cyanobiphenyl-4-yl)methyl]-5-oxo-7-propyl[1,2,4]triazolo[1,5-a]pyrimidin-4(5H)-yl}-1-methoxycyclohexyl)propanoic acid To a solution of 4'-({4-[cis-4-(3-hydroxypropyl)-4-methoxycyclohexyl]-5-oxo-7-propyl-4,5-dihydro[1,2,4]triazolo[1,5-a]pyrimidin-6-yl}methyl)biphenyl-2-carbonitrile (1.39 g) in acetonitrile (20 mL) was added 1,1,1-triacetoxy-1,1-dihydro-1,2-benziodoxol-3(1H)-one (1.64 g) under ice-cooling, and the mixture was stirred at room temperature for 15 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure. To a solution of the residue in tetrahydrofuran (10 mL) was added 1 M methylmagnesium bromide-tetrahydrofuran solution (3.87 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=60/40→10/90 (volume ratio)] to give the title compound as a colorless amorphous compound (743 mg, 52%).

$^1$H NMR (300 MHz, CDCl$_3$) δ1.06 (t, J=7.2 Hz, 3H), 1.32-1.43 (m, 2H), 1.54-1.58 (m, 2H), 1.68-1.85 (m, 2H), 2.00-2.04 (m, 2H), 2.39-2.45 (m, 2H), 2.84-3.04 (m, 2H), 3.23 (s, 3H), 4.02 (s, 2H), 4.97-5.07 (m, 1H), 7.36 (d, J=8.7 Hz, 2H), 7.38-7.44 (m, 1H), 7.45-7.49 (m, 3H), 7.59-7.64 (m, 1H), 7.72-7.75 (m, 1H), 7.92 (s, 1H), 8.40-9.80 (br, 1H).

REFERENCE EXAMPLE 452 methyl 3-(cis-4-{6-[(2'-cyanobiphenyl-4-yl)methyl]-5-oxo-7-propyl[1,2,4]triazolo[1,5-a]pyrimidin-4(5H)-yl}-1-methoxycyclohexyl)propanoate To a mixture of 3-(cis-4-{6-[(2'-cyanobiphenyl-4-yl)methyl]-5-oxo-7-propyl[1,2,4]triazolo[1,5-a]pyrimidin-4(5H)-yl}-1-methoxycyclohexyl)propanoic acid (743 mg), potassium carbonate (276 mg) and acetone (5 mL) was added iodomethane (0.13 mL), and the mixture was stirred at room temperature for 12 hr. 1 N Hydrochloric acid was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→50/50 (volume ratio)] to give the title compound as a colorless amorphous compound (607 mg, 80%).

$^1$H NMR (300 MHz, CDCl$_3$) δ1.06 (t, J=7.2 Hz, 3H), 1.31-1.42 (m, 2H), 1.53-1.83 (m, 6H), 1.98-2.02 (m, 2H), 2.34-2.39 (m, 2H), 2.84-3.04 (m, 4H), 3.22 (s, 3H), 3.68 (s, 3H), 4.02 (s, 2H), 4.96-5.07 (m, 1H), 7.36 (d, J=8.1 Hz, 2H), 7.38-7.44 (m, 1H), 7.45-7.49 (m, 3H), 7.59-7.64 (m, 1H), 7.72-7.75 (m, 1H), 7.91 (s, 1H).

REFERENCE EXAMPLE 453

4'-({4-[cis-4-(3-hydroxy-3-methylbutyl)-4-methoxycyclohexyl]-5-oxo-7-propyl-4,5-dihydro[1,2,4]triazolo[1,5-a]pyrimidin-6-yl}methyl)biphenyl-2-carbonitrile To a solution of methyl 3-(cis-4-{6-[(2'-cyanobiphenyl-4-yl)methyl]-5-oxo-7-propyl[1,2,4]triazolo[1,5-a]pyrimidin-4(5H)-yl}-1-methoxycyclohexyl)propanoate (601 mg) in tetrahydrofuran (4 mL) was added 1 M methylmagnesium bromide-tetrahydrofuran solution (6 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=65/35→40/60 (volume ratio)] to give the title compound as a colorless amorphous compound (390 mg, 65%).

$^1$H NMR (300 MHz, CDCl$_3$) δ1.06 (t, J=7.5 Hz, 3H), 1.24 (s, 6H), 1.32-1.78 (m, 11H), 2.01-2.04 (m, 2H), 2.86-3.04 (m, 4H), 3.23 (s, 3H), 4.02 (s, 2H), 4.96-5.07 (m, 1H), 7.36 (d, J=8.4 Hz, 2H), 7.38-7.44 (m, 1H), 7.45-7.49 (m, 3H), 7.59-7.64 (m, 1H), 7.72-7.75 (m, 1H), 7.92 (s, 1H).

REFERENCE EXAMPLE 454 ethyl 3-[(5-methyl-4H-1,2,4-triazol-3-yl)amino]cyclobutanecarboxylate

To a solution of 5-methyl-4H-1,2,4-triazol-3-amine (16.35 g) and ethyl 3-oxocyclobutanecarboxylate (12.41 g) in acetic acid (150 mL) was added sodium triacetoxyborohydride (36.56 g), and the mixture was stirred at room temperature for 5 days. The solvent was evaporated under reduced pressure, the residue was diluted with saturated aqueous sodium hydrogen carbonate solution, and the mixture was extracted with ethyl acetate-isopropyl alcohol (3:1). The extract was washed with saturated brine, and dried over anhydrous magnesium sulfate. The solvent was evaporated under reduced pressure, and the residue was purified by silica gel chromatography [eluent: methanol/ethyl acetate=0/100→10/90 (volume ratio)], and crystallized from diethyl ether to give the title compound as a colorless solid (15.93 g, 62%).

$^1$H NMR (300 MHz, DMSO-d$_6$) δ1.17 (t, J=7.2 Hz, 3H), 1.98-2.46 (m, 7H), 2.67-2.79 (m, 1H), 3.82-3.94 (m, 1H), 4.04 (q, J=7.2 Hz, 2H), 6.44 (br s, 1H), 11.60-12.60 (br, 1H).

REFERENCE EXAMPLE 455 ethyl trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutanecarboxylate A solution of ethyl 3-[(5-methyl-4H-1,2,4-triazol-3-yl)amino]cyclobutanecarboxylate (7.85 g), ethyl 2-[(2'-cyano-3-fluorobiphenyl-4-yl)methyl]-3-oxohexanoate (23.15 g) and 1,8-diazabicyclo[5.4.0]undec-7-ene (2.62 mL) in N,N-diethylaniline (70 mL) was stirred at 180° C. for 20 hr. The reaction mixture was diluted with ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=85/15→65/35 (volume ratio)] to give the title compound as a pale-yellow amorphous compound (1.89 g, 10%).

$^1$H NMR (300 MHz, CDCl$_3$) δ1.05 (t, J=7.2 Hz, 3H), 1.29 (t, J=7.2 Hz, 3H), 1.63-1.76 (m, 2H), 2.44 (s, 3H), 2.62-2.68 (m, 2H), 2.96-3.01 (m, 2H), 3.33-3.48 (m, 3H), 3.99 (s, 2H), 4.19 (q, J=7.2 Hz, 2H), 5.76-5.92 (m, 1H), 7.22-7.26 (m, 2H), 7.33-7.38 (m, 1H), 7.42-7.48 (m, 2H), 7.60-7.66 (m, 1H), 7.74 (d, J=7.5 Hz, 1H).

REFERENCE EXAMPLE 456

4'-{[4-(trans-3-acetylcyclobutyl)-2-methyl-5-oxo-7-propyl-4,5-dihydro[1,2,4]triazolo[1,5-a]pyrimidin-6-yl]methyl}-3'-fluorobiphenyl-2-carbonitrile 1) To a solution of ethyl trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutanecarboxylate (1.89 g) in tetrahydrofuran (2.5 mL)-methanol (2.5 mL) was added 2 N aqueous sodium hydroxide solution (2.5 mL), and the mixture was stirred at room temperature for 3 hr. The reaction mixture was acidified with 1 N hydrochloric acid, and extracted with ethyl acetate. The extract was washed with saturated brine, and dried over anhydrous magnesium sulfate. The solvent was evaporated under reduced pressure. To a solution of the obtained residue, N,O-dimethylhydroxylamine hydrochloride (488 mg), triethylamine (506 mg) and 1-hydroxy-1H-benzotriazole (766 mg) in acetonitrile (20 mL) was added 1-ethyl-3-(3-dimethylaminopropyl)carbodiimide hydrochloride (959 mg), and the mixture was stirred at room temperature for 15 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→40/60 (volume ratio)] to give colorless amorphous trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}-N-methoxy-N-methylcyclobutanecarboxamide (1.90 g, 97%).

2) To a solution of trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}-N-methoxy-N-methylcyclobutanecarboxamide (1.90 g) in tetrahydrofuran (5 mL) was added 1 M methylmagnesium bromide-tetrahydrofuran solution (5.3 mL), and the mixture was stirred at room temperature for 3 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→50/50 (volume ratio)] to give the title compound as a colorless amorphous compound (1.38 g, 79%).

$^1$H NMR (300 MHz, CDCl$_3$) δ1.04 (t, J=7.2 Hz, 3H), 1.63-1.76 (m, 2H), 2.18 (s, 3H), 2.44 (s, 3H), 2.59-2.67 (m, 2H), 2.95-3.01 (m, 2H), 3.28-3.39 (m, 2H), 3.50-3.59 (m, 1H), 3.99 (s, 2H), 5.55-5.67 (m, 1H), 7.22-7.47 (m, 5H), 7.60-7.66 (m, 1H), 7.73-7.75 (m, 1H).

REFERENCE EXAMPLE 457

3'-fluoro-4'-{[4-(trans-3-hydroxycyclobutyl)-2-methyl-5-oxo-7-propyl-4,5-dihydro[1,2,4]triazolo[1,5-a]pyrimidin-6-yl]methyl}biphenyl-2-carbonitrile To a mixture of 4'-{[4-(trans-3-acetylcyclobutyl)-2-methyl-5-oxo-7-propyl-4,5-dihydro[1,2,4]triazolo[1,5-a]pyrimidin-6-yl]methyl}-3'-fluorobiphenyl-2-carbonitrile (1.38 g), 30% aqueous hydrogen peroxide solution (13.85 mL) and chloroform (20 mL) was added trifluoroacetic acid anhydride (7.66 mL), and the mixture was stirred at 60° C. for 15 hr. The reaction mixture was cooled to room temperature, saturated aqueous sodium hydrogen carbonate solution and sodium thiosulfate were added, and the mixture was extracted with ethyl acetate. The extract was washed with saturated brine, and dried over anhydrous magnesium sulfate. The solvent was evaporated under reduced pressure. To a solution of the obtained residue in tetrahydrofuran (3 mL)-methanol (3 mL) was added 2 N aqueous sodium hydroxide solution (2 mL), and the mixture was stirred at room temperature for 1 hr. The reaction mixture was acidified with 1 N hydrochloric acid, and extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=60/40→35/65 (volume ratio)] to give the title compound as a colorless amorphous compound (0.90 g, 69%).

$^1$H NMR (300 MHz, CDCl$_3$) δ1.04 (t, J=7.2 Hz, 3H), 1.63-1.75 (m, 2H), 1.78 (br s, 1H), 2.35-2.43 (m, 2H), 2.44 (s, 3H), 2.95-3.00 (m, 2H), 3.35-3.45 (m, 2H), 4.00 (s, 2H), 4.85 (br s, 1H), 5.84-5.95 (m, 1H), 7.22-7.26 (m, 2H), 7.34 (d, J=7.8 Hz, 1H), 7.41-7.48 (m, 2H), 7.60-7.66 (m, 1H), 7.73-7.76 (m, 1H).

REFERENCE EXAMPLE 458 ethyl[(trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]acetate To a mixture of 3'-fluoro-4'-{[4-(trans-3-hydroxycyclobutyl)-2-methyl-5-oxo-7-propyl-4,5-dihydro[1,2,4]triazolo[1,5-a]pyrimidin-6-yl]methyl}biphenyl-2-carbonitrile (899 mg), rhodium(II) acetate (dimer) (42 mg) and toluene (20 mL) was added dropwise ethyl diazoacetate (464 μL) under an argon atmosphere at 70° C., and the mixture was stirred at 70° C. for 1 hr. The reaction mixture was concentrated under reduced pressure, and the residue was purified by silica gel chromatography [eluent: hexane/ethyl acetate=70/30→55/45 (volume ratio)] to give the title compound as a colorless amorphous compound (557 mg, 53%).

$^1$H NMR (300 MHz, CDCl$_3$) δ1.04 (t, J=7.2 Hz, 3H), 1.30 (t, J=7.2 Hz, 3H), 1.63-1.75 (m, 2H), 2.43 (s, 3H), 2.49-2.58 (m, 2H), 2.95-3.00 (m, 2H), 3.25-3.35 (m, 2H), 3.99 (s, 2H), 4.04 (s, 2H), 4.23 (q, J=7.2 Hz, 2H), 4.54-4.61 (m, 1H), 5.77-5.89 (m, 1H), 7.22-7.26 (m, 2H), 7.31-7.36 (m, 1H), 7.41-7.48 (m, 2H), 7.60-7.66 (m, 1H), 7.73-7.76 (m, 1H).

REFERENCE EXAMPLE 459

3'-fluoro-4'-({4-[trans-3-(2-hydroxy-2-methylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile To a solution of ethyl[(trans-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]acetate (557 mg) in tetrahydrofuran (5 mL) was added 1 M methylmagnesium bromide-tetrahydrofuran solution (5 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=65/35→40/60 (volume ratio)] to give the title compound as a colorless amorphous compound (437 mg, 80%).

$^1$H NMR (300 MHz, CDCl$_3$) δ1.04 (t, J=7.2 Hz, 3H), 1.24 (s, 6H), 1.63-1.76 (m, 2H), 2.32 (s, 1H), 2.37-2.48 (m, 2H), 2.44 (s, 3H), 2.95-3.01 (m, 2H), 3.20 (s, 2H), 3.26-3.36 (m, 2H), 4.00 (s, 2H), 4.40-4.45 (m, 1H), 5.75-5.86 (m, 1H), 7.22-7.26 (m, 2H), 7.35 (t, J=10.8 Hz, 1H), 7.41-7.48 (m, 2H), 7.60-7.66 (m, 1H), 7.73-7.76 (m, 1H).

REFERENCE EXAMPLE 460 ethyl cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutanecarboxylate A solution of ethyl 3-[(5-methyl-4H-1,2,4-triazol-3-yl)amino]cyclobutanecarboxylate (7.85 g), ethyl 2-[(2'-cyano-3-fluorobiphenyl-4-yl)methyl]-3-oxohexanoate (23.15 g) and 1,8-diazabicyclo[5.4.0]undec-7-ene (2.62 mL) in N,N-diethylaniline (70 mL) was stirred at 180° C. for 20 hr. The reaction mixture was diluted with ethyl acetate, and the mixture was washed with 1 N hydrochloric acid and then with saturated brine, and dried over anhydrous magnesium sulfate. The solvent was evaporated under reduced pressure, and the residue was purified by silica gel chromatography [eluent: hexane/ethyl acetate=85/15→65/35 (volume ratio)] to give the title compound as a pale-yellow amorphous compound (3.91 g, 21%).

$^1$H NMR (300 MHz, CDCl$_3$) δ1.04 (t, J=7.2 Hz, 3H), 1.29 (t, J=7.2 Hz, 3H), 1.63-1.75 (m, 2H), 2.43 (s, 3H), 2.63-2.72 (m, 2H), 2.82-3.00 (m, 3H), 3.36-3.46 (m, 2H), 3.99 (s, 2H), 4.19 (q, J=7.2 Hz, 2H), 5.24-5.36 (m, 1H), 7.22-7.26 (m, 2H), 7.35 (d, J=7.8 Hz, 1H), 7.41-7.48 (m, 2H), 7.60-7.66 (m, 1H), 7.73-7.76 (m, 1H).

REFERENCE EXAMPLE 461 cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}-N-methoxy-N-methylcyclobutanecarboxamide To a solution of ethyl cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutanecarboxylate (3.91 g) in tetrahydrofuran (5.5 mL)-methanol (5.5 mL) was added 2 N aqueous sodium hydroxide solution (5.5 mL), and the mixture was stirred at room temperature for 3 hr. The reaction mixture was acidified with 1 N hydrochloric acid, and extracted with ethyl acetate. The extract was washed with saturated brine, and dried over anhydrous magnesium sulfate. The solvent was evaporated under reduced pressure. To a solution of the obtained residue, N,O-dimethylhydroxylamine hydrochloride (1.07 g), triethylamine (1.11 g) and 1-hydroxy-1H-benzotriazole (1.68 g) in acetonitrile (40 mL) was added 1-ethyl-3-(3-dimethylaminopropyl)carbodiimide hydrochloride (2.11 g), and the mixture was stirred at room temperature for 15 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→40/60 (volume ratio)] to give the title compound as a colorless amorphous compound (3.65 g, 91%).

$^1$H NMR (300 MHz, CDCl$_3$) δ1.06 (t, J=7.2 Hz, 3H), 1.63-1.73 (m, 3H), 2.43 (s, 3H), 2.65-2.73 (m, 2H), 2.94-2.99 (m, 2H), 3.20 (s, 3H), 3.20-3.38 (m, 2H), 3.68 (s, 3H), 3.99 (s, 2H), 5.12-5.24 (m, 1H), 7.21-7.48 (m, 5H), 7.60-7.66 (m, 1H), 7.73-7.76 (m, 1H).

REFERENCE EXAMPLE 462

4'-{[4-(cis-3-acetylcyclobutyl)-2-methyl-5-oxo-7-propyl-4,5-dihydro[1,2,4]triazolo[1,5-a]pyrimidin-6-yl]methyl}-3'-fluorobiphenyl-2-carbonitrile To a solution of cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}-N-methoxy-N-methylcyclobutanecarboxamide (3.65 g) in tetrahydrofuran (10 mL) was added 1 M methylmagnesium bromide-tetrahydrofuran solution (10 mL), and the mixture was stirred at room temperature for 3 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=70/30→50/50 (volume ratio)] to give the title compound as a colorless amorphous compound (2.83 g, 85%).

$^1$H NMR (300 MHz, CDCl$_3$) δ1.04 (t, J=7.2 Hz, 3H), 1.62-1.73 (m, 2H), 2.24 (s, 3H), 2.42 (s, 3H), 2.57-2.67 (m, 2H), 2.89-3.01 (m, 3H), 3.33-3.44 (m, 2H), 3.98 (s, 2H), 5.36-5.47 (m, 1H), 7.22-7.48 (m, 5H), 7.60-7.66 (m, 1H), 7.73-7.76 (m, 1H).

REFERENCE EXAMPLE 463

3'-fluoro-4'-{[4-(cis-3-hydroxycyclobutyl)-2-methyl-5-oxo-7-propyl-4,5-dihydro[1,2,4]triazolo[1,5-a]pyrimidin-6-yl]methyl}biphenyl-2-carbonitrile To a mixture of 4'-{[4-(cis-3-acetylcyclobutyl)-2-methyl-5-oxo-7-propyl-4,5-dihydro[1,2,4]triazolo[1,5-a]pyrimidin-6-yl]methyl}-3'-fluorobiphenyl-2-carbonitrile (2.83 g), 30% aqueous hydrogen peroxide solution (28.5 mL) and chloroform (30 mL) was added trifluoroacetic acid anhydride (15.75 mL), and the mixture was stirred at 60° C. for 15 hr. The reaction mixture was cooled to room temperature, saturated aqueous sodium hydrogen carbonate solution and sodium thiosulfate were added, and the mixture was extracted with ethyl acetate. The extract was washed with saturated brine, and dried over anhydrous magnesium sulfate. The solvent was evaporated under reduced pressure. To a solution of the obtained residue in tetrahydrofuran (5 mL)-methanol (5 mL) was added 2 N aqueous sodium hydroxide solution (4 mL), and the mixture was stirred at room temperature for 1 hr. The reaction mixture was acidified with 1 N hydrochloric acid, and extracted with ethyl acetate. The extract was washed with saturated brine, and dried over anhydrous magnesium sulfate. The solvent was evaporated under reduced pressure, and the residue was purified by basic silica gel chromatography [eluent: hexane/ethyl acetate=60/40→35/65 (volume ratio)] to give the title compound as a colorless amorphous compound (1.70 g, 63%).

$^1$H NMR (300 MHz, CDCl$_3$) δ1.06 (t, J=7.5 Hz, 3H), 1.65-1.78 (m, 2H), 2.48 (s, 3H), 2.86-3.06 (m, 6H), 4.00 (s, 2H), 4.11-4.21 (m, 1H), 5.11 (d, J=11.4 Hz, 1H), 5.46-5.57 (m, 1H), 7.22-7.26 (m, 2H), 7.36 (d, J=7.5 Hz, 1H), 7.41-7.47 (m, 2H), 7.60-7.66 (m, 1H), 7.73-7.75 (m, 1H).

REFERENCE EXAMPLE 464 ethyl[(cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]acetate To a mixture of 3'-fluoro-4'-{[4-(cis-3-hydroxycyclobutyl)-2-methyl-5-oxo-7-propyl-4,5-dihydro[1,2,4]triazolo[1,5-a]pyrimidin-6-yl]methyl}biphenyl-2-carbonitrile (1.70 g), rhodium(II) acetate (dimer) (80 mg) and toluene (40 mL) was added dropwise ethyl diazoacetate (0.88 mL) under an argon atmosphere at 70° C., and the mixture was stirred at 70° C. for 1 hr. The reaction mixture was concentrated under reduced pressure, and the residue was purified by silica gel chromatography [eluent: hexane/ethyl acetate=70/30→55/45 (volume ratio)] to give the title compound as a colorless amorphous compound (895 mg, 45%).

$^1$H NMR (300 MHz, CDCl$_3$) δ1.04 (t, J=7.2 Hz, 3H), 1.29 (t, J=7.2 Hz, 3H), 1.65-1.76 (m, 2H), 2.44 (s, 3H), 2.68-2.78 (m, 2H), 2.95-3.01 (m, 2H), 3.26-3.37 (m, 2H), 3.99 (s, 2H), 4.14 (s, 2H), 4.23 (q, J=7.2 Hz, 2H), 4.93-5.05 (m, 1H), 7.22-7.26 (m, 2H), 7.33-7.38 (m, 1H), 7.41-7.48 (m, 2H), 7.60-7.66 (m, 1H), 7.73-7.76 (m, 1H).

REFERENCE EXAMPLE 465

3'-fluoro-4'-({4-[cis-3-(2-hydroxy-2-methylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile To a solution of ethyl[(cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]acetate (895 mg) in tetrahydrofuran (8 mL) was added 1 M methylmagnesium bromide-tetrahydrofuran solution (8 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=65/35→40/60 (volume ratio)] to give the title compound as a colorless amorphous compound (606 mg, 70%).

$^1$H NMR (300 MHz, CDCl$_3$) δ1.04 (t, J=7.5 Hz, 3H), 1.24 (s, 6H), 1.63-1.76 (m, 2H), 2.44 (s, 3H), 2.67-2.76 (m, 2H), 2.81 (br s, 1H), 2.95-3.01 (m, 2H), 3.19-3.29 (m, 2H), 3.25 (s, 2H), 3.87-3.96 (m, 1H), 3.99 (s, 2H), 5.08-5.20 (m, 1H), 7.22-7.25 (m, 2H), 7.35 (t, J=10.8 Hz, 1H), 7.41-7.47 (m, 2H), 7.60-7.65 (m, 1H), 7.73-7.76 (m, 1H).

REFERENCE EXAMPLE 466 ethyl 2-[(cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]propanoate To a mixture of 3'-fluoro-4'-{[4-(cis-3-hydroxycyclobutyl)-2-methyl-5-oxo-7-propyl-4,5-dihydro[1,2,4]triazolo[1,5-a]pyrimidin-6-yl]methyl}biphenyl-2-carbonitrile (659 mg), rhodium(II) acetate (dimer) (31 mg) and methylene chloride (5 mL) was added dropwise ethyl 2-diazopropanoate (359 mg) under an argon atmosphere at 70° C., and the mixture was stirred at room temperature for 2 hr. The reaction mixture was concentrated under reduced pressure, and the residue was purified by basic silica gel chromatography [eluent: hexane/ethyl acetate=90/10→70/30 (volume ratio)] to give the title compound as a colorless amorphous compound (553 mg, 69%).

$^1$H NMR (300 MHz, CDCl$_3$) δ1.04 (t, J=7.2 Hz, 3H), 1.29 (t, J=7.2 Hz, 3H), 1.44 (d, J=6.9 Hz, 3H), 1.63-1.75 (m, 2H), 2.43 (s, 3H), 2.69-2.77 (m, 2H), 2.95-3.00 (m, 2H), 3.16-3.33 (m, 2H), 3.87-3.96 (m, 1H), 3.98 (s, 2H), 4.08 (d, J=6.9 Hz, 1H), 4.20 (q, J=7.2 Hz, 2H), 4.85-4.97 (m, 1H), 7.21-7.26 (m, 2H), 7.32-7.37 (m, 1H), 7.41-7.47 (m, 2H), 7.60-7.65 (m, 1H), 7.72-7.75 (m, 1H).

REFERENCE EXAMPLE 467

3'-fluoro-4'-({4-[cis-3-(2-hydroxy-1,2-dimethylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile To a solution of ethyl 2-[(cis-3-{6-[(2'-cyano-3-fluorobiphenyl-4-yl)methyl]-2-methyl-5-oxo-7-propyl[1,2,4]triazolo[1,5-a]pyrimidin-4(5H)-yl}cyclobutyl)oxy]propanoate (553 mg) in tetrahydrofuran (5 mL) was added 1 M methylmagnesium bromide-tetrahydrofuran solution (5 mL), and the mixture was stirred at room temperature for 15 hr. The reaction mixture was diluted with saturated aqueous ammonium chloride solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→60/40 (volume ratio)] to give the title compound as a colorless amorphous compound (430 mg, 79%).

$^1$H NMR (300 MHz, CDCl$_3$) δ1.04 (t, J=7.5 Hz, 3H), 1.11 (d, J=6.3 Hz, 3H), 1.18 (s, 3H), 1.20 (s, 3H), 1.63-1.75 (m, 2H), 2.46 (s, 3H), 2.62-2.80 (m, 2H), 2.96-3.01 (m, 2H), 3.20-3.34 (m, 2H), 3.40-3.70 (br, 1H), 3.99 (s, 2H), 3.99-4.08 (m, 1H), 5.24-5.36 (m, 1H), 7.22-7.26 (m, 2H), 7.35 (d, J=7.8 Hz, 1H), 7.41-7.47 (m, 2H), 7.60-7.66 (m, 1H), 7.73-7.76 (m, 1H).

REFERENCE EXAMPLE 468

4'-{[4-(5-methyl-6,13-dioxadispiro[3.2.5.2]tetradec-10-yl)-5-oxo-7-propyl-4,5-dihydro[1,2,4]triazolo[1,5-a]pyrimidin-6-yl]methyl}biphenyl-2-carbonitrile A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (12.67 g), 1-[1-(hydroxymethyl)cyclobutyl]ethanol (4.26 g), p-toluenesulfonic acid hydrate (0.57 g) and toluene (300 mL) was refluxed with heating for 5 hr while dehydrating with a Dean-Stark trap. The reaction mixture was cooled to room temperature, and diluted with ethyl acetate, and the mixture was washed with saturated aqueous sodium hydrogen carbonate solution and saturated brine, and dried over anhydrous magnesium sulfate. The solvent was evaporated under reduced pressure, and the residue was purified by silica gel chromatography [eluent: hexane/ethyl acetate=80/20→40/60 (volume ratio)] to give the title compound as a colorless amorphous compound (13.64 g, 87%).

$^1$H NMR (300 MHz, CDCl$_3$) δ1.06 (t, J=7.5 Hz, 3H), 1.26-1.45 (m, 5H), 1.57-1.90 (m, 10H), 2.18-2.30 (m, 1H), 2.74-3.04 (m, 5H), 3.68-3.92 (m, 3H), 4.01 (s, 2H), 5.03-5.13 (m, 1H), 7.36 (d, J=7.5 Hz, 2H), 7.38-7.44 (m, 1H), 7.45-7.48 (m, 3H), 7.59-7.64 (m, 1H), 7.72-7.75 (m, 1H), 7.89 (s, 0.4H), 7.92 (s, 0.6H).

REFERENCE EXAMPLE 469

4'-[(4-{4-[1-(1-formylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile A mixture of 4'-{[4-(5-methyl-6,13-dioxadispiro[3.2.5.2]tetradec-10-yl)-5-oxo-7-propyl-4,5-dihydro[1,2,4]triazolo[1,5-a]pyrimidin-6-yl]methyl}biphenyl-2-carbonitrile (15.33 g), sodium cyanotrihydroborate (7.01 g), anhydrous magnesium sulfate (12.76 g) and tetrahydrofuran (330 mL) was stirred at room temperature for 10 min. Then, boron trifluoride-diethyl ether complex (13.4 mL) was added dropwise, and the mixture was stirred under an argon atmosphere at 50° C. for 8 hr. The reaction mixture was cooled to room temperature, saturated aqueous sodium hydrogen carbonate solution was added, and the mixture was extracted with ethyl acetate. The extract was washed with saturated brine, and dried over anhydrous magnesium sulfate. The solvent was evaporated under reduced pressure. To a solution of the obtained residue in acetonitrile (300 mL) was added 1,1,1-triacetoxy-1,1-dihydro-1,2-benziodoxol-3(1H)-one (1.64 g) under ice-cooling, and the mixture was stirred at room temperature for 15 hr. The reaction mixture was diluted with saturated aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→50/50 (volume ratio)] to give the title compound as a colorless amorphous compound (7.21 g, 47%).

$^1$H NMR (300 MHz, CDCl$_3$) δ1.06 (t, J=7.2 Hz, 3H), 1.10 (d, J=6.3 Hz, 3H), 1.39-2.34 (m, 14H), 2.60-2.80 (m, 1H), 2.95-3.11 (m, 3H), 3.44-3.71 (m, 1H), 3.81 (q, J=6.3 Hz, 1H), 4.02 (s, 2H), 5.03-5.10 (m, 1H), 7.35-7.49 (m, 6H), 7.59-7.65 (m, 1H), 7.72-7.75 (m, 1H), 7.88 (s, 0.6H), 7.91 (s, 0.4H), 9.73 (s, 0.4H), 9.91 (s, 0.6H).

REFERENCE EXAMPLE 470

4'-[(4-{4-[1-(1-acetylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile To a solution of 4'-[(4-{4-[1-(1-formylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (10.35 g) in tetrahydrofuran (50 mL) was added 1 M methylmagnesium bromide-tetrahydrofuran solution (27 mL), and the mixture was stirred at room temperature for 15 hr. 1 N Hydrochloric acid was added to the reaction mixture, and the mixture was extracted with ethyl acetate. The extract was washed with saturated brine, and dried over anhydrous magnesium sulfate. The solvent was evaporated under reduced pressure. To a solution of the residue in acetonitrile (200 mL) was added 1,1,1-triacetoxy-1,1-dihydro-1,2-benziodoxol-3(1H)-one (8.48 g), and the mixture was stirred at room temperature for 2 hr. Saturated aqueous sodium hydrogen carbonate solution was added to the reaction mixture, and the mixture was extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→60/40 (volume ratio)] to give the title compound as a colorless amorphous compound (8.32 g, 79%).

$^1$H NMR (300 MHz, CDCl$_3$) δ1.00-1.08 (m, 6H), 1.25-2.39 (m, 17H), 2.64-2.80 (m, 1H), 2.99-3.12 (m, 3H), 3.45-3.69 (m, 1H), 3.73-3.81 (m, 1H), 4.01 (s, 2H), 5.03-5.13 (m, 1H), 7.36 (d, J=7.8 Hz, 2H), 7.38-7.44 (s, 1H), 7.46-7.49 (m, 3H), 7.59-7.64 (m, 1H), 7.73 (d, J=7.8 Hz, 1H), 7.83 (s, 0.6H), 7.91 (s, 0.4H).

REFERENCE EXAMPLE 471

4'-[(4-{trans-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile To a mixture of 4'-[(4-{4-[1-(1-acetylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (9.20 g), 30% aqueous hydrogen peroxide solution (77.5 mL) and chloroform (80 mL) was added trifluoroacetic acid anhydride (42.8 mL), and the mixture was stirred at 60° C. for 15 hr. The reaction mixture was cooled to room temperature, saturated aqueous sodium hydrogen carbonate solution and 1 M sodium thiosulfate were added, and the mixture was extracted with ethyl acetate. The extract was washed with saturated brine, and dried over anhydrous magnesium sulfate. The solvent was evaporated under reduced pressure. To a solution of the obtained residue in tetrahydrofuran (15 mL)-methanol (15 mL) was added 2 N aqueous sodium hydroxide solution (15 mL), and the mixture was stirred at room temperature for 2 hr. The reaction mixture was acidified with 1 N hydrochloric acid, and extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→40/60 (volume ratio)] to give the title compound as a colorless amorphous compound (1.45 g, 17%).

$^1$H NMR (300 MHz, CDCl$_3$) δ1.06 (t, J=7.2 Hz, 3H), 1.16 (d, J=6.0 Hz, 3H), 1.38-1.60 (m, 3H), 1.66-1.84 (m, 4H), 2.00-2.18 (m, 6H), 2.64-2.78 (m, 2H), 3.00-3.06 (m, 4H), 3.48-3.60 (m, 2H), 4.01 (s, 2H), 5.02-5.10 (m, 1H), 7.36 (d, J=8.1 Hz, 2H), 7.39-7.44 (m, 1H), 7.47-7.49 (m, 3H), 7.59-7.65 (m, 1H), 7.72-7.75 (m, 1H), 7.92 (s, 1H).

REFERENCE EXAMPLE 472

4'-[(4-{cis-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile To a mixture of 4'-[(4-{4-[1-(1-acetylcyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (9.20 g), 30% aqueous hydrogen peroxide solution (77.5 mL) and chloroform (80 mL) was added trifluoroacetic acid anhydride (42.8 mL), and the mixture was stirred at 60° C. for 15 hr. The reaction mixture was cooled to room temperature, saturated aqueous sodium hydrogen carbonate solution and 1 M sodium thiosulfate were added, and the mixture was extracted with ethyl acetate. The extract was washed with saturated brine, and dried over anhydrous magnesium sulfate. The solvent was evaporated under reduced pressure. To a solution of the obtained residue in tetrahydrofuran (15 mL)-methanol (15 mL) was added 2 N aqueous sodium hydroxide solution (15 mL), and the mixture was stirred at room temperature for 2 hr. The reaction mixture was acidified with 1 N hydrochloric acid, and extracted with ethyl acetate. The extract was washed with saturated brine, and dried over anhydrous magnesium sulfate. The solvent was evaporated under reduced pressure, and the residue was purified by silica gel chromatography [eluent: hexane/ethyl acetate=80/20→40/60 (volume ratio)] to give the title compound as a colorless amorphous compound (0.50 g, 6%).

$^1$H NMR (300 MHz, CDCl$_3$) δ1.05 (t, J=7.2 Hz, 3H), 1.20 (d, J=6.0 Hz, 3H), 1.42-2.05 (m, 14H), 2.85-3.11 (m, 4H), 3.56 (q, J=6.0 Hz, 1H), 3.74-3.80 (m, 2H), 4.02 (s, 2H), 5.10-5.19 (m, 1H), 7.37 (d, J=8.4 Hz, 2H), 7.39-7.44 (m, 1H), 7.46-7.49 (m, 3H), 7.59-7.64 (m, 1H), 7.72-7.75 (m, 1H), 7.93 (s, 1H).

REFERENCE EXAMPLE 473

4'-({4-[4-(2-hydroxy-1,1,2-trimethylpropoxy)phenyl]-5-oxo-7-propyl-4,5-dihydro[1,2,4]triazolo[1,5-a]pyrimidin-6-yl}methyl)biphenyl-2-carbonitrile To a solution of methyl 2-(4-{6-[(2'-cyanobiphenyl-4-yl)methyl]-5-oxo-7-propyl[1,2,4]triazolo[1,5-a]pyrimidin-4(5H)-yl}phenoxy)-2-methylpropanoate (1.0 g) in tetrahydrofuran (9 mL) was added dropwise methylmagnesium bromide (1 M tetrahydrofuran solution, 1.8 mL) at 0° C., and the mixture was stirred for 3 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.98 g, 98%).
$^1$H NMR (300 MHz, CHLOROFORM-d) δ1.11 (t, J=7.4 Hz, 3H), 1.33 (s, 6H), 1.34 (s, 6H), 1.72-1.88 (m, 2H), 2.67 (s, 1H), 3.13 (dd, J=10.2, 5.7 Hz, 2H), 4.07 (s, 2H), 7.10-7.91 (m, 13H)

REFERENCE EXAMPLE 474

4'-({4-[4-(2-hydroxy-1,1-dimethylethoxy)phenyl]-5-oxo-7-propyl-4,5-dihydro[1,2,4]triazolo[1,5-a]pyrimidin-6-yl}methyl)biphenyl-2-carbonitrile To a solution of methyl 2-(4-{6-[(2'-cyanobiphenyl-4-yl)methyl]-5-oxo-7-propyl[1,2,4]triazolo[1,5-a]pyrimidin-4(5H)-yl}phenoxy)-2-methylpropanoate (2.0 g) in tetrahydrofuran (16 mL) was added lithium borohydride (0.49 g) and the mixture was stirred for 18 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.97 g, 51%).
$^1$H NMR (300 MHz, CHLOROFORM-d) δ1.11 (t, J=7.4 Hz, 3H), 1.35 (s, 6H), 1.70-1.88 (m, J=15.4, 7.6, 7.4, 7.4 Hz, 2H), 2.19 (t, J=6.6 Hz, 1H), 3.13 (dd, J=10.4, 5.5 Hz, 2H), 3.62 (d, J=6.4 Hz, 2H), 4.07 (s, 2H), 7.10-7.92 (m, 13H)

REFERENCE EXAMPLE 475

4'-({4-[4-(1,1-dimethyl-2-oxoethoxy)phenyl]-5-oxo-7-propyl-4,5-dihydro[1,2,4]triazolo[1,5-a]pyrimidin-6-yl}methyl)biphenyl-2-carbonitrile To a solution of 4'-({4-[4-(2-hydroxy-1,1-dimethylethoxy)phenyl]-5-oxo-7-propyl-4,5-dihydro[1,2,4]triazolo[1,5-a]pyrimidin-6-yl}methyl)biphenyl-2-carbonitrile (0.97 g) in methylene chloride (10 mL) was added 1,1,1-tris(acetyloxy)-1,1-dihydro-1,2-benziodoxol-3-(1H)-one (2.3 g), and the mixture was stirred for 3 hr. Ethyl acetate, water and sodium thiosulfate were added to the reaction mixture, and the mixture was stirred for 30 min, and extracted with ethyl acetate. The organic layer was washed with saturated brine and dried over anhydrous magnesium sulfate, and the solvent was evaporated. The residue was purified by silica gel column chromatography to give the title compound as a colorless solid (0.97 g, 99%).
$^1$H NMR (300 MHz, CHLOROFORM-d) δ1.11 (t, J=7.3 Hz, 3H), 1.50 (s, 6H), 1.69-1.89 (m, J=15.3, 7.6, 7.4, 7.4 Hz, 2H), 3.04-3.21 (m, 2H), 4.06 (s, 2H), 6.93-7.93 (m, 13H), 9.84 (s, 1H)

REFERENCE EXAMPLE 476

4'-({4-[4-(2-hydroxy-1,1-dimethylpropoxy)phenyl]-5-oxo-7-propyl-4,5-dihydro[1,2,4]triazolo[1,5-a]pyrimidin-6-yl}methyl)biphenyl-2-carbonitrile To a solution of 4'-({4-[4-(1,1-dimethyl-2-oxoethoxy)phenyl]-5-oxo-7-propyl-4,5-dihydro[1,2,4]triazolo[1,5-a]pyrimidin-6-yl}methyl)biphenyl-2-carbonitrile (0.97 g) in tetrahydrofuran (10 mL) was added dropwise methylmagnesium bromide (1 M tetrahydrofuran solution, 0.91 mL) at 0° C., and the mixture was stirred for 3 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.72 g, 72%).
$^1$H NMR (300 MHz, CHLOROFORM-d) δ1.11 (t, J=7.4 Hz, 3H), 1.23 (d, J=6.4 Hz, 3H), 1.29 (s, 6H), 1.71-1.89 (m, 2H), 2.61 (d, J=3.4 Hz, 1H), 3.08-3.18 (m, 2H), 3.84-3.94 (m, 1H), 4.07 (s, 2H), 7.08-7.91 (m, 13H)

REFERENCE EXAMPLE 477

4'-(1-hydroxyethyl)biphenyl-2-carbonitrile

To a solution of 4'-formylbiphenyl-2-carbonitrile (10.00 g) in tetrahydrofuran (100 mL) was slowly added dropwise a 1 M solution (50 mL) of methylmagnesium bromide in tetrahydrofuran at 0° C., and the mixture was stirred at room temperature for 2 hr. The reaction mixture was poured into 1 M hydrochloric acid (60 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (10.03 g, 93%).
$^1$H NMR (300 MHz, CDCl$_3$) δ1.55 (d, J=6.6, 3H), 1.88 (d, J=3.6, 1H), 4.92-5.03 (m, 1H), 7.39-7.58 (m, 6H), 7.60-7.67 (m, 1H), 7.73-7.78 (m, 1H)

REFERENCE EXAMPLE 478

4'-(1-bromoethyl)biphenyl-2-carbonitrile

To a solution (15 mL) of 4'-(1-hydroxyethyl)biphenyl-2-carbonitrile (3.52 g) in toluene was added phosphine tribromide (5.00 g) at room temperature, and the mixture was stirred at room temperature overnight. The reaction mixture was concentrated, and the residue was dissolved in ethyl acetate. The obtained ethyl acetate solution was washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a pale-yellow oil (3.93 g, 87%).
$^1$H NMR (300 MHz, CDCl$_3$) δ2.09 (d, J=6.9, 3H), 5.26 (q, J=6.9, 1H), 7.40-7.68 (m, 7H), 7.72-7.78 (m, 1H)

REFERENCE EXAMPLE 479

N-[(2R,6S)-2,6-dimethyltetrahydro-2H-pyran-4-yl]-3-methyl-1H-1,2,4-triazol-5-amine To a solution of 3-methyl-1H-1,2,4-triazol-5-amine (1.6 g) in acetic acid (30 mL) was added (2R,6S)-2,6-dimethyltetrahydro-4H-pyran-4-one (2.5 g) at room temperature, and the mixture was stirred for 30 min. Sodium triacetoxyborohydride (5.2 g) was added, and the mixture was stirred at room temperature for 20 hr. Acetic acid was evaporated and ethyl acetate and water were added to the residue. The mixture was neutralized with sodium hydrogen carbonate, and the mixture was extracted with ethyl acetate. The organic layer was washed with water and saturated brine, dried over anhydrous magnesium sulfate, and concentrated. The residue was dissolved in a small amount of ethyl acetate, and the mixture was crystallized from diisopropyl ether. The resulting solid was collected by filtration, washed with diisopropyl ether, and dried by heating under reduced pressure to give the title compound as a pale-yellow solid (0.75 g, 22%).

$^1$H NMR (300 MHz, CHLOROFORM-d) δ1.16-1.24 (m, 6H), 1.44-2.13 (m, 4H), 2.34 (s, 3H), 3.49-4.93 (m, 4H), 9.30-10.92 (m, 1H)

REFERENCE EXAMPLE 480

N-[(2R,6S)-2,6-dimethyltetrahydro-2H-pyran-4-yl]-1H-1,2,4-triazol-5-amine

To a solution of 1H-1,2,4-triazol-5-amine (1.6 g) in acetic acid (30 mL) was added (2R,6S)-2,6-dimethyltetrahydro-4H-pyran-4-one (2.5 g) at room temperature, and the mixture was stirred for 30 min. After stirring, sodium triacetoxyborohydride (5.2 g) was added, and the mixture was stirred at room temperature for 20 hr. Acetic acid was evaporated and ethyl acetate and water were added to the residue. The mixture was neutralized with sodium hydrogen carbonate, and extracted with ethyl acetate. The organic layer was washed with water and saturated brine, dried over anhydrous magnesium sulfate, and concentrated. The residue was dissolved in a small amount of ethyl acetate, and the mixture was crystallized from diisopropyl ether. The resulting solid was collected by filtration, washed with diisopropyl ether, and dried by heating under reduced pressure to give the title compound as a pale-yellow solid (1.6 g, 49%).

$^1$H NMR (300 MHz, DMSO-$d_6$) δ0.91-1.13 (m, 7H), 1.22-1.36 (m, 1H), 1.63-1.93 (m, 2H), 3.37-3.84 (m, 3H), 5.87-8.13 (m, 2H), 11.62-12.91 (m, 1H)

REFERENCE EXAMPLE 481

1-benzyl-4-methyl-N-(tetrahydro-2H-pyran-4-yl)-1H-pyrazol-5-amine

To a solution (50 mL) of 1-benzyl-4-methyl-1H-pyrazol-5-amine (5 g) and tetrahydro-4H-pyran-4-one (3.2 g) in acetic acid was added sodium cyanoborohydride (6.8 g), and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with ethyl acetate. The obtained extract was dried over anhydrous sodium sulfate, the solvent was evaporated under reduced pressure, and the residue was purified by silica gel column chromatography to give the title compound as a colorless solid (1.9 g, 38%).

$^1$H NMR (300 MHz, DMSO-$d_6$) δ1.24-1.41 (m, 2H) 1.55-1.67 (m, 2H) 1.92 (s, 3H) 2.78-2.93 (m, 1H) 3.01-3.14 (m, 2H) 3.76 (dd, J=8.2, 2.7 Hz, 2H) 4.42 (d, J=8.7 Hz, 1H) 5.16 (s, 2H) 7.06-7.14 (m, 3H) 7.19-7.33 (m, 3H)

REFERENCE EXAMPLE 482

4-methyl-N-(tetrahydro-2H-pyran-4-yl)-1H-pyrazol-5-amine

A mixture of 1-benzyl-4-methyl-N-(tetrahydro-2H-pyran-4-yl)-1H-pyrazol-5-amine (1.9 g), activated carbon-supported 20 mass % palladium hydroxide (0.6 g) and formic acid (20 mL) was stirred at room temperature for 16 hr. The insoluble material was filtered off through celite, and the filtrate was concentrated under reduced pressure. The residue was purified by silica gel column chromatography to give the title compound as a colorless solid (0.73 g, 40%).

$^1$H NMR (300 MHz, DMSO-$d_6$) δ1.29-1.47 (m, 2H) 1.82 (s, 3H) 1.85-1.94 (m, 2H) 3.25-3.50 (m, 3H) 3.79-3.90 (m, 2H) 4.37-4.50 (m, 1H) 7.13 (s, 1H) 11.17 (br. s., 1H)

REFERENCE EXAMPLE 483

4'-({4-[trans-4-(2-hydroxy-1,2-dimethylpropoxy)cyclohexyl]-5-oxo-7-propyl-4,5-dihydropyrazolo[1,5-a]pyrimidin-6-yl}methyl)biphenyl-2-carbonitrile To a solution of 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (0.70 g) and rhodium acetate (dimer, 0.066 g) in methylene chloride (5 mL) was added dropwise a solution of ethyl 2-diazopropanoate (1.0 g) in methylene chloride (2 mL), and the mixture was stirred for 18 hr. Ethyl acetate and water were added to the reaction mixture, and the mixture was extracted with ethyl acetate. The organic layer was washed with water and then with saturated brine, dried over anhydrous magnesium sulfate, and concentrated. The residue was crudely purified by silica gel column chromatography. This was dissolved in tetrahydrofuran (5 mL), methylmagnesium bromide (1 M tetrahydrofuran solution, 3 mL) was added dropwise at 0° C., and the mixture was stirred for 1 hr. The mixture was diluted with ethyl acetate and then saturated aqueous ammonium chloride solution was added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.45 g, 84%).

$^1$H NMR (300 MHz, CHLOROFORM-d) δ1.01-1.20 (m, 12H), 1.32-1.57 (m, 2H), 1.64-1.91 (m, 4H), 2.05-2.26 (m, 2H), 2.32-2.57 (m, 3H), 3.02-3.10 (m, 2H), 3.29-3.52 (m, 2H), 4.01 (s, 2H), 4.71 (br. s., 1H), 5.98 (d, J=2.3 Hz, 1H), 7.34-7.77 (m, 9H)

REFERENCE EXAMPLE 484 ethyl[(trans-4-{6-[(2'-cyanobiphenyl-4-yl)methyl]-5-oxo-7-propylpyrazolo[1,5-a]pyrimidin-4(5H)-yl}cyclohexyl)oxy]acetate To a solution of 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (2.63 g) and rhodium acetate (dimer, 0.12 g) in methylene chloride (20 mL) was added dropwise a solution of ethyl diazoacetate (2.6 g) in methylene chloride (10 mL), and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (2.17 g, 70%).

$^1$H NMR (300 MHz, CHLOROFORM-d) δ1.05 (t, J=7.4 Hz, 3H), 1.30 (t, J=7.2 Hz, 3H), 1.41-1.93 (m, 6H), 2.16-2.56 (m, 4H), 3.01-3.10 (m, 2H), 3.39-3.53 (m, 1H), 4.00 (s, 2H), 4.13 (s, 2H), 4.23 (q, J=6.9 Hz, 2H), 4.73 (br. s., 1H), 5.97 (d, J=2.3 Hz, 1H), 7.31-7.79 (m, 9H)

REFERENCE EXAMPLE 485

4'-({4-[trans-4-(2-hydroxyethoxy)cyclohexyl]-5-oxo-7-propyl-4,5-dihydropyrazolo[1,5-a]pyrimidin-6-yl}methyl)biphenyl-2-carbonitrile To a solution of ethyl[(trans-4-{6-[(2'-cyanobiphenyl-4-yl)methyl]-5-oxo-7-propylpyrazolo[1,5-a]pyrimidin-4(5H)-yl}cyclohexyl)oxy]acetate (1.16 g) in tetrahydrofuran (8 mL)-ethanol (2 mL) was added lithium borohydride (0.46 g), and the mixture was stirred for 18 hr. To the reaction mixture were added ethyl acetate and saturated aqueous ammonium chloride solution, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.64 g, 60%).

$^1$H NMR (300 MHz, CHLOROFORM-d) δ1.06 (t, J=7.3 Hz, 3H), 1.37-1.54 (m, 2H), 1.64-1.91 (m, 4H), 2.00 (t, J=6.1 Hz, 1H), 2.15-2.55 (m, 4H), 3.00-3.10 (m, 2H), 3.33-3.46 (m, 1H), 3.58-3.64 (m, 2H), 3.70-3.77 (m, 2H), 4.01 (s, 2H), 4.53-4.98 (m, 1H), 5.98 (d, J=2.3 Hz, 1H), 7.34-7.77 (m, 9H)

REFERENCE EXAMPLE 486

2-[(trans-4-{6-[(2'-cyanobiphenyl-4-yl)methyl]-5-oxo-7-propylpyrazolo[1,5-a]pyrimidin-4(5H)-yl}cyclohexyl)oxy]-N-methoxy-N-methylacetamide To a solution of ethyl[(trans-4-{6-[(2'-cyanobiphenyl-4-yl)methyl]-5-oxo-7-propylpyrazolo[1,5-a]pyrimidin-4(5H)-yl}cyclohexyl)oxy]acetate (1.17 g) in tetrahydrofuran (10 mL) was added 1 M aqueous sodium hydroxide solution (10 mL), and the mixture was stirred at 50° C. for 15 hr. The mixture was allowed to cool, and neutralized with 1 M hydrochloric acid, and the mixture was extracted with ethyl acetate. The organic layer was washed with water and then with saturated brine, dried over anhydrous magnesium sulfate, and concentrated. The residue was dissolved in acetonitrile (20 mL), methoxymethylamine hydrochloride (0.62 g), 4-dimethylaminopyridine (0.078 g), diisopropylethylamine (1.9 mL), 1-hydroxybenzotriazole (0.37 g) and 1-(3-dimethylaminopropyl)-3-ethylcarbodiimide hydrochloride (0.81 g) were added, and the mixture was stirred for 3 days. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.65 g, 54%).

$^1$H NMR (300 MHz, CHLOROFORM-d) δ1.06 (t, J=7.4 Hz, 3H), 1.44-1.90 (m, 6H), 2.22-2.54 (m, 4H), 3.01-3.10 (m, 2H), 3.20 (s, 3H), 3.42-3.58 (m, 1H), 3.70 (s, 3H), 4.01 (s, 2H), 4.33 (s, 2H), 4.59-5.09 (m, 1H), 5.98 (d, J=2.3 Hz, 1H), 7.32-7.79 (m, 9H)

REFERENCE EXAMPLE 487

4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile To a solution of 2-[(trans-4-{6-[(2'-cyanobiphenyl-4-yl)methyl]-5-oxo-7-propylpyrazolo[1,5-a]pyrimidin-4(5H)-yl}cyclohexyl)oxy]-N-methoxy-N-methylacetamide (0.65 g) in tetrahydrofuran (6 mL) was added dropwise methylmagnesium bromide (1 M tetrahydrofuran solution, 2.3 mL) at 0° C., and the mixture was stirred for 1 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was dissolved in ethanol (6 mL), and sodium borohydride (0.044 g) was added at 0° C. After stirring at 0° C. for 1 hr, ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.57 g, 95%).

$^1$H NMR (300 MHz, CHLOROFORM-d) δ1.06 (t, J=7.4 Hz, 3H), 1.15 (d, J=6.4 Hz, 3H), 1.34-1.54 (m, 2H), 1.64-1.91 (m, 4H), 2.13-2.28 (m, 2H), 2.33-2.55 (m, 3H), 3.06 (dd, J=10.4, 5.5 Hz, 2H), 3.20-3.29 (m, 1H), 3.32-3.45 (m, 1H), 3.51 (dd, J=9.1, 3.0 Hz, 1H), 3.87-4.04 (m, 3H), 4.76 (br. s., 1H), 5.98 (d, J=1.9 Hz, 1H), 7.33-7.77 (m, 9H)

REFERENCE EXAMPLE 488

4'-({4-[trans-4-(2-cyclopropyl-2-hydroxyethoxy)cyclohexyl]-5-oxo-7-propyl-4,5-dihydropyrazolo[1,5-a]pyrimidin-6-yl}methyl)biphenyl-2-carbonitrile To a solution of 2-[(trans-4-{6-[(2'-cyanobiphenyl-4-yl)methyl]-5-oxo-7-propylpyrazolo[1,5-a]pyrimidin-4(5H)-yl}cyclohexyl)oxy]-N-methoxy-N-methylacetamide (0.57 g) in tetrahydrofuran (6 mL) was added dropwise cyclopropylmagnesium bromide (0.5M tetrahydrofuran solution, 4 mL) at 0° C., and the mixture was stirred for 1.5 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was dissolved in ethanol (10 mL), sodium borohydride (0.04 g) was added, and the mixture was stirred for 18 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.45 g, 81%).

$^1$H NMR (300 MHz, CHLOROFORM-d) δ0.17-0.62 (m, 4H), 0.79-0.94 (m, 1H), 1.06 (t, J=7.3 Hz, 3H), 1.37-1.54 (m, 2H), 1.64-1.90 (m, 4H), 2.13-2.57 (m, 5H), 2.99-3.12 (m,

3H), 3.33-3.50 (m, 2H), 3.67 (dd, J=9.4, 3.0 Hz, 1H), 4.01 (s, 2H), 4.75 (br. s., 1H), 5.98 (d, J=2.3 Hz, 1H), 7.33-7.78 (m, 9H)

REFERENCE EXAMPLE 489

4'-({4-[trans-4-(2-hydroxy-3-methylbutoxy)cyclohexyl]-5-oxo-7-propyl-4,5-dihydropyrazolo[1,5-a]pyrimidin-6-yl}methyl)biphenyl-2-carbonitrile To a solution of 2-[(trans-4-{6-[(2'-cyanobiphenyl-4-yl)methyl]-5-oxo-7-propylpyrazolo[1,5-a]pyrimidin-4(5H)-yl}cyclohexyl)oxy]-N-methoxy-N-methylacetamide (0.57 g) in tetrahydrofuran (5 mL) was added dropwise isopropylmagnesium bromide (1 M tetrahydrofuran solution, 2 mL) at 0° C., and the mixture was stirred for 1.5 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was dissolved in ethanol (10 mL), sodium borohydride (0.04 g) was added, and the mixture was stirred for 18 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.31 g, 56%).
$^1$H NMR (300 MHz, CHLOROFORM-d) δ0.92 (d, J=6.8 Hz, 3H), 0.98 (d, J=6.8 Hz, 3H), 1.06 (t, J=7.3 Hz, 3H), 1.37-1.53 (m, 2H), 1.65-1.91 (m, 5H), 2.14-2.55 (m, 5H), 3.01-3.11 (m, 2H), 3.31-3.63 (m, 4H), 4.01 (s, 2H), 4.77 (br. s., 1H), 5.98 (d, J=2.3 Hz, 1H), 7.34-7.77 (m, 9H)

REFERENCE EXAMPLE 490

4'-({5-oxo-4-[trans-4-(2-oxopropoxy)cyclohexyl]-7-propyl-4,5-dihydropyrazolo[1,5-a]pyrimidin-6-yl}methyl)biphenyl-2-carbonitrile To a solution of 2-[(trans-4-{6-[(2'-cyanobiphenyl-4-yl)methyl]-5-oxo-7-propylpyrazolo[1,5-a]pyrimidin-4(5H)-yl}cyclohexyl)oxy]-N-methoxy-N-methylacetamide (1.3 g) in tetrahydrofuran (10 mL) was added dropwise methylmagnesium bromide (1 M tetrahydrofuran solution, 1.3 mL) at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (1.12 g, 94%).
$^1$H NMR (300 MHz, CHLOROFORM-d) δ1.06 (t, J=7.4 Hz, 3H), 1.41-1.56 (m, 2H), 1.64-1.91 (m, 4H), 2.12-2.29 (m, 5H), 2.32-2.54 (m, 2H), 2.99-3.11 (m, 2H), 3.31-3.50 (m, 1H), 4.01 (s, 2H), 4.10 (s, 2H), 4.74 (br. s., 1H), 5.97 (d, J=2.3 Hz, 1H), 7.33-7.78 (m, 9H)

REFERENCE EXAMPLE 491

4'-({4-[trans-4-({2-methyl-2-[(triethylsilyl)oxy]cyclopropyl}oxy)cyclohexyl]-5-oxo-7-propyl-4,5-dihydropyrazolo[1,5-a]pyrimidin-6-yl}methyl)biphenyl-2-carbonitrile To a solution of 4'-({5-oxo-4-[trans-4-(2-oxopropoxy)cyclohexyl]-7-propyl-4,5-dihydropyrazolo[1,5-a]pyrimidin-6-yl}methyl)biphenyl-2-carbonitrile (1.12 g) and triethylsilyl chloride (0.72 mL) in tetrahydrofuran (15 mL) was added dropwise lithium hexamethyldisilazide (1.1 M tetrahydrofuran solution, 2.9 mL) at −78° C., and the mixture was stirred for 2 hr. To the reaction mixture were added ethyl acetate and then saturated aqueous sodium hydrogen carbonate solution, and the mixture was extracted with ethyl acetate. The organic layer was washed with saturated brine, dried over anhydrous magnesium sulfate, and concentrated. The residue was dissolved in methylene chloride (5 mL), and the solution was added dropwise to a solution of diethylzinc (1 M hexane solution, 15 mL) and chloroiodomethane (1.09 mL) in methylene chloride (20 mL) at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.44 g, 31%).
$^1$H NMR (300 MHz, CHLOROFORM-d) δ0.59-0.77 (m, 8H), 0.93-1.01 (m, 9H), 1.06 (t, J=7.4 Hz, 3H), 1.28 (s, 3H), 1.39-1.56 (m, 2H), 1.66-1.88 (m, 4H), 2.17-2.53 (m, 4H), 2.92-3.11 (m, 3H), 3.49-3.62 (m, 1H), 4.01 (s, 2H), 4.79 (br. s., 1H), 6.01 (d, J=1.9 Hz, 1H), 7.35-7.76 (m, 9H)

REFERENCE EXAMPLE 492

4'-[(4-{trans-4-[(1-{[tert-butyl(dimethyl)silyl]oxy}cyclopropyl)methoxy]cyclohexyl}-5-oxo-7-propyl-4,5-dihydropyrazolo[1,5-a]pyrimidin-6-yl)methyl]biphenyl-2-carbonitrile To a solution of 4'-({5-oxo-4-[trans-4-(2-oxopropoxy)cyclohexyl]-7-propyl-4,5-dihydropyrazolo[1,5-a]pyrimidin-6-yl}methyl)biphenyl-2-carbonitrile (0.93 g) and diisopropylethylamine (0.77 mL) in methylene chloride (10 mL) was added dropwise tert-butyldimethylsilyl trifluoromethanesulfonate (1.02 mL) at −78° C., and the mixture was stirred for 3 hr while warming to 0° C. To the reaction mixture were added ethyl acetate and saturated aqueous sodium hydrogen carbonate solution, and the mixture was extracted with ethyl acetate. The organic layer was washed with saturated brine, dried over anhydrous magnesium sulfate, and concentrated. The residue was crudely purified by silica gel column chromatography, and dissolved in methylene chloride (5 mL), and the mixture was added dropwise to a solution of diethylzinc (1 M hexane solution, 7.5 mL) and chloroiodomethane (0.55 mL) in methylene chloride (10 mL) at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.67 g, 68%).
$^1$H NMR (300 MHz, CHLOROFORM-d) δ0.13 (s, 6H), 0.54-0.78 (m, 4H), 0.85 (s, 9H), 1.05 (t, J=7.3 Hz, 3H), 1.36-1.90 (m, 6H), 2.14-2.53 (m, 4H), 3.01-3.12 (m, 2H), 3.29-3.64 (m, 3H), 4.01 (s, 2H), 4.75 (br. s., 1H), 5.98 (d, J=2.1 Hz, 1H), 7.33-7.79 (m, 9H)

REFERENCE EXAMPLE 493

4'-({5-oxo-7-propyl-4-[trans-4-(3,3,3-trifluoro-2-hydroxypropoxy)cyclohexyl]-4,5-dihydropyrazolo[1,5-a]pyrimidin-6-yl}methyl)biphenyl-2-carbonitrile To a solution of ethyl[(trans-4-{6-[(2'-cyanobiphenyl-4-yl)methyl]-5-oxo-7-propylpyrazolo[1,5-a]pyrimidin-4(5H)- yl}cyclohexyl)oxy]acetate (0.75 g) and tetrabutylammonium acetate (0.042 g) in toluene (7 mL) was added dropwise trifluoromethanetrimethylsilyl (0.61 mL) at 0° C., and the mixture was stirred for 3 hr. To the reaction mixture were added ethyl acetate and saturated aqueous ammonium chloride solution, and the mixture was extracted with ethyl acetate. The organic layer was washed with saturated brine, dried over anhydrous magnesium sulfate, and concentrated. The residue was dissolved in tetrahydrofuran (7 mL), 1 M hydrochloric acid (7 mL) was added, and the mixture was stirred at 60° C. for 1 hr. To the reaction mixture were added ethyl acetate and then 1 M aqueous sodium hydroxide solution, and the mixture was extracted with ethyl acetate. The organic layer was washed with saturated brine, dried over anhydrous magnesium sulfate, and concentrated. The residue was dissolved in ethanol (7 mL), sodium borohydride (0.05 g) was added at 0° C., and the mixture was stirred for 1 hr. To the reaction mixture were added ethyl acetate and saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.67 g, 84%).

$^1$H NMR (300 MHz, DMSO-$d_6$) δ0.94 (t, J=7.4 Hz, 3H), 1.26-1.75 (m, 6H), 2.03-2.16 (m, 2H), 2.29-2.48 (m, 2H), 2.91-3.04 (m, 2H), 3.42-3.69 (m, 3H), 3.97 (s, 2H), 4.02-4.17 (m, 1H), 4.68 (br. s., 1H), 6.33 (d, J=6.4 Hz, 1H), 6.43 (d, J=2.3 Hz, 1H), 7.34-7.96 (m, 9H)

REFERENCE EXAMPLE 494 trans-4-{6-[(2'-cyanobiphenyl-4-yl)methyl]-5-oxo-7-propylpyrazolo[1,5-a]pyrimidin-4(5H)-yl}cyclohexyl 2-(acetyloxy)-2-methylpropanoate To a solution of 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (0.47 g) in pyridine (3 mL) was added 2-chloro-1,1-dimethyl-2-oxoethyl acetate (0.44 mL) and the mixture was stirred for 2 hr. Ethyl acetate and water were added to the reaction mixture, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.47 g, 79%).

$^1$H NMR (300 MHz, DMSO-$d_6$) δ0.94 (t, J=7.4 Hz, 3H), 1.47 (s, 6H), 1.49-1.77 (m, 6H), 1.93-2.04 (m, 5H), 2.34-2.49 (m, 2H), 2.91-3.03 (m, 2H), 3.98 (s, 2H), 4.55-4.90 (m, 2H), 6.54 (d, J=2.3 Hz, 1H), 7.34-7.98 (m, 9H)

REFERENCE EXAMPLE 495

4'-({4-[trans-4-(2-cyclopropyl-2-hydroxypropoxy)cyclohexyl]-5-oxo-7-propyl-4,5-dihydropyrazolo[1,5-a]pyrimidin-6-yl}methyl)biphenyl-2-carbonitrile To a solution of 4'-({5-oxo-4-[trans-4-(2-oxopropoxy)cyclohexyl]-7-propyl-4,5-dihydropyrazolo[1,5-a]pyrimidin-6-yl}methyl)biphenyl-2-carbonitrile (0.30 g) in tetrahydrofuran (3 mL) was added dropwise cyclopropylmagnesium bromide (0.5M tetrahydrofuran solution, 2.3 mL) at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.22 g, 68%).

$^1$H NMR (300 MHz, CHLOROFORM-d) δ0.29-0.51 (m, 4H), 0.83-0.95 (m, 1H), 1.05 (t, J=7.4 Hz, 3H), 1.10 (s, 3H), 1.35-1.54 (m, 2H), 1.65-1.90 (m, 3H), 2.10 (s, 1H), 2.15-2.55 (m, 4H), 3.01-3.10 (m, 2H), 3.32-3.45 (m, 3H), 4.01 (s, 2H), 4.52-4.98 (m, 1H), 5.98 (d, J=2.3 Hz, 1H), 7.34-7.78 (m, 9H)

REFERENCE EXAMPLE 496

4'-{[7-butyl-4-(1,4-dioxaspiro[4.5]dec-8-yl)-5-oxo-4,5-dihydropyrazolo[1,5-a]pyrimidin-6-yl]methyl}biphenyl-2-carbonitrile A solution of N-(1,4-dioxaspiro[4.5]dec-8-yl)-1H-pyrazol-5-amine (2.2 g), 1,8-diazabicyclo[5.4.0]undec-7-ene (0.30 mL) and methyl 2-[(2'-cyanobiphenyl-4-yl)methyl]-3-oxoheptanoate (7.0 g) in diethylaniline (10 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (3.6 g, 69%).

$^1$H NMR (300 MHz, CHLOROFORM-d) δ0.94 (t, J=7.2 Hz, 3H), 1.40-1.55 (m, 2H), 1.59-1.93 (m, 8H), 2.48-2.69 (m, 2H), 3.03-3.14 (m, 2H), 3.93-4.06 (m, 6H), 5.13-5.37 (m, 1H), 6.19 (d, J=2.3 Hz, 1H), 7.35-7.78 (m, 9H)

REFERENCE EXAMPLE 497

4'-{[7-butyl-4-(trans-4-hydroxycyclohexyl)-5-oxo-4,5-dihydropyrazolo[1,5-a]pyrimidin-6-yl]methyl}biphenyl-2-carbonitrile To a solution of 4'-{[7-butyl-4-(1,4-dioxaspiro[4.5]dec-8-yl)-5-oxo-4,5-dihydropyrazolo[1,5-a]pyrimidin-6-yl]methyl}biphenyl-2-carbonitrile (3.6 g) in tetrahydrofuran (40 mL) was added 3M hydrochloric acid (40 mL), and the mixture was stirred at 70° C. for 2 hr. The mixture was allowed to cool, and diluted with ethyl acetate, and the mixture was neutralized with 8M aqueous sodium hydroxide solution. The mixture was extracted with ethyl acetate, and the organic layer was washed with water and saturated brine, dried over anhydrous magnesium sulfate, and concentrated. The residue was dissolved in ethanol (20 mL)-tetrahydrofuran (20 mL). Thereto was added sodium borohydride (0.26 g) at 0° C. After stirring for 1 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (2.9 g, 87%).

$^1$H NMR (300 MHz, CHLOROFORM-d) δ0.94 (t, J=7.2 Hz, 3H), 1.41-1.55 (m, 5H), 1.59-1.73 (m, 2H), 1.76-1.90 (m, 2H), 2.07-2.20 (m, 2H), 2.34-2.58 (m, 2H), 3.01-3.13 (m, 2H), 3.67-3.85 (m, 1H), 4.01 (s, 2H), 4.49-5.04 (m, 1H), 5.98 (d, J=2.3 Hz, 1H), 7.31-7.80 (m, 9H)

REFERENCE EXAMPLE 498 ethyl[(trans-4-{7-butyl-6-[(2'-cyanobiphenyl-4-yl)methyl]-5-oxopyrazolo[1,5-a]pyrimidin-4(5H)-yl}cyclohexyl)oxy]acetate To a solution of 4'-{[7-butyl-4-(trans-4-hydroxycyclohexyl)-5-oxo-4,5-dihydropyrazolo[1,5-a]pyrimidin-6-yl]methyl}biphenyl-2-carbonitrile (2.9 g) and rhodium acetate (dimer, 0.070 g) in methylene chloride (15 mL) was added dropwise a solution of ethyl diazoacetate (3.1 mL) in methylene chloride (3 mL), and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (2.1 g, 61%).

$^1$H NMR (300 MHz, CHLOROFORM-d) δ0.94 (t, J=7.3 Hz, 3H), 1.17-1.72 (m, 9H), 1.78-1.92 (m, 2H), 2.15-2.57 (m, 4H), 3.01-3.12 (m, 2H), 3.36-3.54 (m, 1H), 4.00 (s, 2H), 4.13 (s, 2H), 4.23 (q, J=7.2 Hz, 2H), 4.52-4.98 (m, 1H), 5.97 (d, J=2.3 Hz, 1H), 7.31-7.78 (m, 9H)

REFERENCE EXAMPLE 499

4'-({7-butyl-4-[trans-4-(2-hydroxy-2-methylpropoxy)cyclohexyl]-5-oxo-4,5-dihydropyrazolo[1,5-a]pyrimidin-6-yl}methyl)biphenyl-2-carbonitrile To a solution of ethyl[(trans-4-{7-butyl-6-[(2'-cyanobiphenyl-4-yl)methyl]-5-oxopyrazolo[1,5-a]pyrimidin-4(5H)-yl}cyclohexyl)oxy]acetate (0.40 g) in tetrahydrofuran (4 mL) was added dropwise methylmagnesium bromide (1 M tetrahydrofuran solution, 0.71 mL) at 0° C., and the mixture was stirred for 30 min. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.31 g, 83%).

$^1$H NMR (300 MHz, CHLOROFORM-d) δ0.94 (t, J=7.2 Hz, 3H), 1.21 (s, 6H), 1.36-1.54 (m, 4H), 1.58-1.72 (m, 2H), 1.77-1.91 (m, 2H), 2.13-2.27 (m, 2H), 2.34-2.55 (m, 2H), 3.01-3.12 (m, 2H), 3.26-3.45 (m, 3H), 4.01 (s, 2H), 4.50-5.00 (m, 1H), 5.97 (s, 1H), 7.32-7.78 (m, 9H)

REFERENCE EXAMPLE 500

4'-{[4-(1,4-dioxaspiro[4.5]dec-8-yl)-5-oxo-7-propyl-4,5-dihydropyrazolo[1,5-a]pyrimidin-6-yl]methyl}-3'-fluorobiphenyl-2-carbonitrile A solution of N-(1,4-dioxaspiro[4.5]dec-8-yl)-1H-pyrazol-5-amine (2.2 g), 1,8-diazabicyclo[5.4.0]undec-7-ene (0.30 mL) and ethyl 2-[(2'-cyano-3-fluorobiphenyl-4-yl)methyl]-3-oxohexanoate (7.4 g) in diethylaniline (10 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (4.0 g, 75%).

$^1$H NMR (300 MHz, CHLOROFORM-d) δ1.06 (t, J=7.4 Hz, 3H), 1.64-1.92 (m, 8H), 2.49-2.70 (m, 2H), 3.00-3.15 (m, 2H), 3.90-4.07 (m, 6H), 5.08-5.38 (m, 1H), 6.19 (d, J=2.3 Hz, 1H), 7.19-7.79 (m, 8H)

REFERENCE EXAMPLE 501

3'-fluoro-4'-{[4-(trans-4-hydroxycyclohexyl)-5-oxo-7-propyl-4,5-dihydropyrazolo[1,5-a]pyrimidin-6-yl]methyl}biphenyl-2-carbonitrile To a solution of 4'-{[4-(1,4-dioxaspiro[4.5]dec-8-yl)-5-oxo-7-propyl-4,5-dihydropyrazolo[1,5-a]pyrimidin-6-yl]methyl}-3'-fluorobiphenyl-2-carbonitrile (4.0 g) in tetrahydrofuran (40 mL) was added 3M hydrochloric acid (40 mL), and the mixture was stirred at 70° C. for 2 hr. The mixture was allowed to cool, and diluted with ethyl acetate, and the mixture was neutralized with 8M aqueous sodium hydroxide solution. The mixture was extracted with ethyl acetate, and the organic layer was washed with water and saturated brine, dried over anhydrous magnesium sulfate, and concentrated. The residue was dissolved in ethanol (20 mL)-tetrahydrofuran (20 mL), and sodium borohydride (0.28 g) was added at 0° C. After stirring for 1 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (3.3 g, 91%).

$^1$H NMR (300 MHz, CHLOROFORM-d) δ1.06 (t, J=7.2 Hz, 3H), 1.42-1.90 (m, 7H), 2.08-2.22 (m, 2H), 2.36-2.62 (m, 2H), 3.00-3.14 (m, 2H), 3.68-3.85 (m, 1H), 4.02 (s, 2H), 4.55-5.04 (m, 1H), 5.99 (d, J=1.9 Hz, 1H), 7.20-7.83 (m, 9H)

REFERENCE EXAMPLE 502 ethyl[(trans-4-{6-[(2'-cyano-3-fluorobiphenyl-4-yl)methyl]-5-oxo-7-propylpyrazolo[1,5-a]pyrimidin-4(5H)-yl}cyclohexyl)oxy]acetate To a solution of 3'-fluoro-4'-{[4-(trans-4-hydroxycyclohexyl)-5-oxo-7-propyl-4,5-dihydropyrazolo[1,5-a]pyrimidin-6-yl]methyl}biphenyl-2-carbonitrile (3.3 g) and rhodium acetate (dimer, 0.075 g) in methylene chloride (15 mL) was added dropwise a solution of ethyl diazoacetate (3.1 mL) in methylene chloride (5 mL), and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (2.1 g, 53%).

$^1$H NMR (300 MHz, CHLOROFORM-d) δ1.06 (t, J=7.3 Hz, 3H), 1.21-1.92 (m, 9H), 2.17-2.54 (m, 4H), 3.01-3.10 (m, 2H), 3.38-3.54 (m, 1H), 4.01 (s, 2H), 4.13 (s, 2H), 4.23 (q, J=7.2 Hz, 2H), 4.53-4.96 (m, 1H), 5.97 (d, J=2.1 Hz, 1H), 7.20-7.78 (m, 9H)

REFERENCE EXAMPLE 503

3'-fluoro-4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile To a solution of ethyl[(trans-4-{6-[(2'-cyano-3-fluorobiphenyl-4-yl)methyl]-5-oxo-7-propylpyrazolo[1,5-a]pyrimidin-4(5H)-yl}cyclohexyl)oxy]acetate (0.40 g) in tetrahydrofuran (4 mL) was added dropwise methylmagnesium bromide (1 M tetrahydrofuran solution, 0.71 mL) at 0° C., and the mixture was stirred for 30 min. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.26 g, 88%).

¹H NMR (300 MHz, CHLOROFORM-d) δ1.06 (t, J=7.3 Hz, 3H), 1.21 (s, 6H), 1.36-1.54 (m, 2H), 1.62-1.92 (m, 4H), 2.15-2.26 (m, 2H), 2.34-2.54 (m, 2H), 3.00-3.10 (m, 2H), 3.27-3.46 (m, 3H), 4.02 (s, 2H), 4.52-4.98 (m, 1H), 5.98 (d, J=2.1 Hz, 1H), 7.19-7.81 (m, 8H)

REFERENCE EXAMPLE 504

2-[(trans-4-{7-butyl-6-[(2'-cyanobiphenyl-4-yl)methyl]-5-oxopyrazolo[1,5-a]pyrimidin-4(5H)-yl}cyclohexyl)oxy]-N-methoxy-N-methylacetamide To a solution of ethyl[(trans-4-{7-butyl-6-[(2'-cyanobiphenyl-4-yl)methyl]-5-oxopyrazolo[1,5-a]pyrimidin-4(5H)-yl}cyclohexyl)oxy]acetate (1.68 g) in tetrahydrofuran (15 mL) was added 1 M aqueous sodium hydroxide solution (15 mL), and the mixture was stirred at 60° C. for 2 hr. The mixture was allowed to cool, and neutralized with 1 M hydrochloric acid, and the mixture was extracted with ethyl acetate. The organic layer was washed with water and then with saturated brine, dried over anhydrous magnesium sulfate, and concentrated. The residue was dissolved in acetonitrile (30 mL), methoxymethylamine hydrochloride (0.87 g), 4-dimethylaminopyridine (0.11 g), diisopropylethylamine (2.6 mL), 1-hydroxybenzotriazole (0.52 g) and 1-(3-dimethylaminopropyl)-3-ethylcarbodiimide hydrochloride (1.1 g) were added, and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (1.23 g, 71%).

¹H NMR (300 MHz, CHLOROFORM-d) δ0.94 (t, J=7.4 Hz, 3H), 1.37-1.92 (m, 10H), 2.21-2.53 (m, 4H), 3.02-3.11 (m, 2H), 3.20 (s, 3H), 3.42-3.58 (m, 1H), 3.70 (s, 3H), 4.00 (s, 2H), 4.33 (s, 2H), 4.80 (br. s., 1H), 5.98 (d, J=2.3 Hz, 1H), 7.33-7.78 (m, 9H)

REFERENCE EXAMPLE 505

4'-({7-butyl-4-[trans-4-(2-hydroxypropoxy)cyclohexyl]-5-oxo-4,5-dihydropyrazolo[1,5-a]pyrimidin-6-yl}methyl)biphenyl-2-carbonitrile To a solution of 2-[(trans-4-{7-butyl-6-[(2'-cyanobiphenyl-4-yl)methyl]-5-oxopyrazolo[1,5-a]pyrimidin-4(5H)-yl}cyclohexyl)oxy]-N-methoxy-N-methylacetamide (0.30 g) in tetrahydrofuran (3 mL) was added dropwise methylmagnesium bromide (1 M tetrahydrofuran solution, 0.74 mL) at 0° C., and the mixture was stirred for 1 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was dissolved in ethanol (6 mL), and sodium borohydride (0.020 g) was added at 0° C. After stirring at 0° C. for 30 min, ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.27 g, 98%).

¹H NMR (300 MHz, CHLOROFORM-d) δ0.94 (t, J=7.4 Hz, 3H), 1.15 (d, J=6.4 Hz, 3H), 1.36-1.54 (m, 4H), 1.61-1.93 (m, 4H), 2.14-2.56 (m, 5H), 3.00-3.57 (m, 5H), 3.87-4.05 (m, 3H), 4.75 (br. s., 1H), 5.98 (d, J=1.9 Hz, 1H), 7.32-7.78 (m, 9H)

REFERENCE EXAMPLE 506

2-[(trans-4-{6-[(2'-cyano-3-fluorobiphenyl-4-yl)methyl]-5-oxo-7-propylpyrazolo[1,5-a]pyrimidin-4(5H)-yl}cyclohexyl)oxy]-N-methoxy-N-methylacetamide To a solution of ethyl[(trans-4-{6-[(2'-cyano-3-fluorobiphenyl-4-yl)methyl]-5-oxo-7-propylpyrazolo[1,5-a]pyrimidin-4(5H)-yl}cyclohexyl)oxy]acetate (1.68 g) in tetrahydrofuran (15 mL) was added 1 M aqueous sodium hydroxide solution (15 mL), and the mixture was stirred at 60° C. for 2 hr. The mixture was allowed to cool, and neutralized with 1 M hydrochloric acid, and the mixture was extracted with ethyl acetate. The organic layer was washed with water and then with saturated brine, dried over anhydrous magnesium sulfate, and concentrated. The residue was dissolved in acetonitrile (30 mL), methoxymethylamine hydrochloride (0.87 g), 4-dimethylaminopyridine (0.11 g), diisopropylethylamine (2.6 mL), 1-hydroxybenzotriazole (0.52 g) and 1-(3-dimethylaminopropyl)-3-ethylcarbodiimide hydrochloride (1.1 g) were added, and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (1.49 g, 83%).

¹H NMR (300 MHz, CHLOROFORM-d) δ1.06 (t, J=7.4 Hz, 3H), 1.41-1.92 (m, 8H), 2.19-2.57 (m, 4H), 3.01-3.11 (m, 2H), 3.20 (s, 3H), 3.41-3.58 (m, 1H), 3.70 (s, 3H), 4.02 (s, 2H), 4.33 (s, 2H), 4.79 (br. s., 1H), 5.98 (d, J=2.3 Hz, 1H), 7.16-7.81 (m, 8H)

REFERENCE EXAMPLE 507

3'-fluoro-4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile To a solution of 2-[(trans-4-{6-[(2'-cyano-3-fluorobiphenyl-4-yl)methyl]-5-oxo-7-propylpyrazolo[1,5-a]pyrimidin-4(5H)-yl}cyclohexyl)oxy]-N-methoxy-N-methylacetamide (0.30 g) in tetrahydrofuran (3 mL) was added dropwise methylmagnesium bromide (1 M tetrahydrofuran solution, 0.73 mL) at 0° C., and the mixture was stirred for 1 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was dissolved in ethanol (6 mL), and sodium borohydride (0.020 g) was added at 0° C. After stirring at 0° C. for 30 min, ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.28 g, 99%).

¹H NMR (300 MHz, DMSO-d₆) δ0.92 (t, J=7.4 Hz, 3H), 1.03 (d, J=6.1 Hz, 3H), 1.25-1.74 (m, 6H), 2.02-2.46 (m, 4H), 2.90-3.00 (m, 2H), 3.17-3.45 (m, 3H), 3.62-3.76 (m, 1H), 3.92 (s, 2H), 4.46-4.85 (m, 2H), 6.43 (d, J=2.3 Hz, 1H), 6.95-7.89 (m, 8H), 12.44 (s, 1H)

REFERENCE EXAMPLE 508

4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (optically active form, retention time: short)

A racemate of 4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (1.0 g) was optically resolved by chiral HPLC to give an optically active form (retention time: short) as a pale-yellow amorphous solid (0.42 g, 79%).
$^1$H NMR (300 MHz, CHLOROFORM-d) δ1.06 (t, J=7.4 Hz, 3H), 1.15 (d, J=6.4 Hz, 3H), 1.34-1.54 (m, 2H), 1.64-1.91 (m, 4H), 2.13-2.28 (m, 2H), 2.33-2.55 (m, 3H), 3.06 (dd, J=10.4, 5.5 Hz, 2H), 3.20-3.29 (m, 1H), 3.32-3.45 (m, 1H), 3.51 (dd, J=9.1, 3.0 Hz, 1H), 3.87-4.04 (m, 3H), 4.76 (br. s., 1H), 5.98 (d, J=1.9 Hz, 1H), 7.33-7.77 (m, 9H)
HPLC (CHIRALPAK AD-H, 25% MeOH, 2.35 mL/min), 20.9 min, 98.8% ee

REFERENCE EXAMPLE 509

4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (optically active form, retention time: long)

A racemate of 4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (1.0 g) was optically resolved by chiral HPLC to give an optically active form (retention time: long) as a pale-yellow amorphous solid (0.43 g, 82%).
$^1$H NMR (300 MHz, CHLOROFORM-d) δ1.06 (t, J=7.4 Hz, 3H), 1.15 (d, J=6.4 Hz, 3H), 1.34-1.54 (m, 2H), 1.64-1.91 (m, 4H), 2.13-2.28 (m, 2H), 2.33-2.55 (m, 3H), 3.06 (dd, J=10.4, 5.5 Hz, 2H), 3.20-3.29 (m, 1H), 3.32-3.45 (m, 1H), 3.51 (dd, J=9.1, 3.0 Hz, 1H), 3.87-4.04 (m, 3H), 4.76 (br. s., 1H), 5.98 (d, J=1.9 Hz, 1H), 7.33-7.77 (m, 9H)
HPLC (CHIRALPAK AD-H, 25% MeOH, 2.35 mL/min), 23.4 min, 99.3% ee

REFERENCE EXAMPLE 510

4'-{[4-(trans-4-{[tert-butyl(dimethyl)silyl]oxy}cyclohexyl)-5-oxo-7-propyl-4,5-dihydropyrazolo[1,5-a]pyrimidin-6-yl]methyl}biphenyl-2-carbonitrile To a solution of 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (1.68 g) and imidazole (0.74 g) in N,N-dimethylformamide (20 mL) was added tert-butyl(chloro)dimethylsilane (1.1 g), and the mixture was stirred for 2 hr. To the reaction mixture were added ethyl acetate and saturated aqueous sodium hydrogen carbonate solution, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (1.89 g, 90%).
$^1$H NMR (300 MHz, CHLOROFORM-d) δ0.07 (s, 6H), 0.89 (s, 9H), 1.05 (t, J=7.4 Hz, 3H), 1.37-1.54 (m, 2H), 1.63-1.84 (m, 4H), 1.94-2.04 (m, 2H), 2.36-2.57 (m, 2H), 3.00-3.10 (m, 2H), 3.62-3.76 (m, 1H), 4.01 (s, 2H), 4.63 (br. s., 1H), 5.98 (d, J=1.9 Hz, 1H), 7.31-7.84 (m, 9H)

REFERENCE EXAMPLE 511

4'-{[4-(trans-4-{[tert-butyl(dimethyl)silyl]oxy}cyclohexyl)-3-fluoro-5-oxo-7-propyl-4,5-dihydropyrazolo[1,5-a]pyrimidin-6-yl]methyl}biphenyl-2-carbonitrile To a solution of 4'-{[4-(trans-4-{[tert-butyl(dimethyl)silyl]oxy}cyclohexyl)-5-oxo-7-propyl-4,5-dihydropyrazolo[1,5-a]pyrimidin-6-yl]methyl}biphenyl-2-carbonitrile (1.76 g) in acetonitrile (15 mL) was added 1-chloromethyl-4-fluoro-1,4-diazoniabicyclo[2.2.2]octane bis(tetrafluoroborate) (1.1 g), and the mixture was stirred at 80° C. for 3 hr. To the reaction mixture were added ethyl acetate and saturated aqueous sodium hydrogen carbonate solution, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.24 g, 13%).
$^1$H NMR (300 MHz, DMSO-d$_6$) δ0.06 (s, 6H), 0.86 (s, 9H), 0.93 (t, J=7.3 Hz, 3H), 1.28-1.97 (m, 8H), 2.09-2.38 (m, 2H), 2.86-3.05 (m, 2H), 3.56-3.71 (m, 1H), 3.96 (s, 2H), 4.71 (br. s., 1H), 7.34-8.09 (m, 9H)

REFERENCE EXAMPLE 512 ethyl[(trans-4-{6-[(2'-cyanobiphenyl-4-yl)methyl]-3-fluoro-5-oxo-7-propylpyrazolo[1,5-a]pyrimidin-4(5H)-yl}cyclohexyl)oxy]acetate To a solution of 4'-{[4-(trans-4-{[tert-butyl(dimethyl)silyl]oxy}cyclohexyl)-3-fluoro-5-oxo-7-propyl-4,5-dihydropyrazolo[1,5-a]pyrimidin-6-yl]methyl}biphenyl-2-carbonitrile (0.24 g) in tetrahydrofuran (2 mL) was added tetrabutylammonium fluoride (1 mL), and the mixture was stirred at 70° C. for 2 hr. Ethyl acetate and saturated aqueous ammonium chloride solution were added to the reaction mixture, and the mixture was extracted with ethyl acetate. The organic layer was washed with water and then with saturated brine, dried over anhydrous magnesium sulfate, and concentrated. The residue was dissolved in toluene (2 mL), rhodium acetate (dimer, 0.016 g) was added, ethyl diazoacetate (0.19 mL) was added dropwise at 100° C., and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.087 g, 42%).
$^1$H NMR (300 MHz, DMSO-d$_6$) δ0.93 (t, J=7.3 Hz, 3H), 1.20 (t, J=7.2 Hz, 3H), 1.26-2.23 (m, 10H), 2.90-3.00 (m, 2H), 3.33-3.45 (m, 1H), 3.96 (s, 2H), 4.06-4.17 (m, 4H), 4.75 (br. s., 1H), 7.34-8.11 (m, 9H)

REFERENCE EXAMPLE 513

1-benzyl-N-(4-{[tert-butyl(dimethyl)silyl]oxy}cyclohexyl)-1H-pyrazol-5-amine

To a solution of 1-benzyl-1H-pyrazol-5-amine (6.3 g) in acetic acid (70 mL) was added 4-{[tert-butyl(dimethyl)silyl]

oxy}cyclohexanone (10 g) and the mixture was stirred for 30 min. After stirring, sodium triacetoxyborohydride (12.0 g) was added, and the mixture was stirred for 18 hr. Acetic acid was evaporated and ethyl acetate and water were added to the residue. The mixture was neutralized with sodium hydrogen carbonate, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.27 g, 9%).

$^1$H NMR (300 MHz, DMSO-$d_6$) δ0.01-0.06 (m, 6H), 0.83-0.91 (m, 9H), 1.14-1.96 (m, 8H), 2.87-3.11 (m, 1H), 3.52-3.91 (m, 1H), 5.05-5.41 (m, 4H), 7.02-7.33 (m, 6H)

REFERENCE EXAMPLE 514

N-(4-{[tert-butyl(dimethyl)silyl]oxy}cyclohexyl)-1H-pyrazol-5-amine

To a suspension of 1-benzyl-N-(4-{[tert-butyl(dimethyl)silyl]oxy}cyclohexyl)-1H-pyrazol-5-amine (1.3 g) and palladium hydroxide (10 wt %, 1.27 g) in ethanol (6 mL)-acetic acid (0.6 mL) was added ammonium formate (0.62 g) by small portions at 80° C. After stirring at 80° C. for 2 hr, the mixture was allowed to cool, ethyl acetate was added, and the insoluble material was filtered off. Saturated aqueous sodium hydrogen carbonate was added to the filtrate, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.68 g, 69%).

$^1$H NMR (300 MHz, DMSO-$d_6$) δ0.00-0.07 (m, 6H), 0.81-0.91 (m, 9H), 1.03-2.01 (m, 8H), 3.00-3.24 (m, 1H), 3.53-3.92 (m, 1H), 4.68-5.14 (m, 1H), 5.38 (s, 1H), 7.26 (br. s., 1H), 11.34 (br. s., 1H)

REFERENCE EXAMPLE 515

2-(5-{[7-butyl-4-(trans-4-hydroxycyclohexyl)-5-oxo-4,5-dihydropyrazolo[1,5-a]pyrimidin-6-yl]methyl}pyridin-2-yl)benzonitrile A solution of N-(4-{[tert-butyl(dimethyl)silyl]oxy}cyclohexyl)-1H-pyrazol-5-amine (0.67 g), 1,8-diazabicyclo[5.4.0]undec-7-ene (0.067 mL) and methyl 2-{[6-(2-cyanophenyl)pyridin-3-yl]methyl}-3-oxoheptanoate (0.8 g) in diethylaniline (5 mL) was stirred at 180° C. for 5 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was crudely purified by silica gel column chromatography. This was dissolved in tetrahydrofuran (4 mL). Tetrabutylammonium fluoride (2.5 mL) was added, and the mixture was stirred at 70° C. for 2 hr. The mixture was allowed to cool, ethyl acetate and saturated aqueous ammonium chloride solution were added, and the mixture was extracted with ethyl acetate. The organic layer was washed with water and saturated brine, dried over anhydrous magnesium sulfate, and concentrated. This was dissolved in acetonitrile (6 mL), 1,1,1-tris(acetyloxy)-1,1-dihydro-1,2-benziodoxol-3-(1H)-one (1.0 g) was added, and the mixture was stirred for 3 hr. Ethyl acetate, water and sodium thiosulfate were added to the reaction mixture, and the mixture was stirred for 30 min. After stirring, the mixture was extracted with ethyl acetate. The organic layer was washed with saturated brine, and dried over anhydrous magnesium sulfate, and the solvent was evaporated. The residue was dissolved in ethanol (3 mL)-tetrahydrofuran (3 mL), and sodium borohydride (0.045 g) was added at 0° C. After stirring at 0° C. for 2 hr, ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.48 g, 44%).

$^1$H NMR (300 MHz, DMSO-$d_6$) δ0.78-0.89 (m, 3H), 1.26-1.70 (m, 8H), 1.85-1.97 (m, 2H), 2.25-2.46 (m, 2H), 2.98-3.10 (m, 2H), 3.46-3.65 (m, 1H), 3.99 (s, 2H), 4.51-4.81 (m, 2H), 6.42 (d, J=2.3 Hz, 1H), 7.56-7.99 (m, 7H), 8.65 (d, J=0.9 Hz, 1H)

REFERENCE EXAMPLE 516 ethyl({trans-4-[7-butyl-6-{[6-(2-cyanophenyl)pyridin-3-yl]methyl}-5-oxopyrazolo[1,5-a]pyrimidin-4(5H)-yl]cyclohexyl}oxy)acetate To a solution of 2-(5-{[7-butyl-4-(trans-4-hydroxycyclohexyl)-5-oxo-4,5-dihydropyrazolo[1,5-a]pyrimidin-6-yl]methyl}pyridin-2-yl)benzonitrile (0.48 g) and rhodium acetate (dimer, 0.044 g) in toluene (5 mL) was added dropwise ethyl diazoacetate (0.52 mL), and the mixture was stirred for 5 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.26 g, 47%).

$^1$H NMR (300 MHz, DMSO-$d_6$) δ0.80-0.87 (m, 3H), 1.21 (t, J=7.2 Hz, 3H), 1.30-1.73 (m, 8H), 2.03-2.17 (m, 2H), 2.29-2.47 (m, 2H), 2.99-3.08 (m, 2H), 3.41-3.54 (m, 1H), 3.98 (s, 2H), 4.08-4.17 (m, 4H), 4.68 (br. s., 1H), 6.43 (d, J=2.3 Hz, 1H), 7.58-7.98 (m, 7H), 8.65 (s, 1H)

REFERENCE EXAMPLE 517

2-[5-({7-butyl-4-[trans-4-(2-hydroxy-2-methylpropoxy)cyclohexyl]-5-oxo-4,5-dihydropyrazolo[1,5-a]pyrimidin-6-yl}methyl)pyridin-2-yl]benzonitrile To a solution of ethyl({trans-4-[7-butyl-6-{[6-(2-cyanophenyl)pyridin-3-yl]methyl}-5-oxopyrazolo[1,5-a]pyrimidin-4(5H)-yl]cyclohexyl}oxy)acetate (0.26 g) in tetrahydrofuran (3 mL) was added dropwise methylmagnesium bromide (1 M tetrahydrofuran solution, 1.4 mL) at 0° C., and the mixture was stirred for 3 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.16 g, 63%).

$^1$H NMR (300 MHz, DMSO-$d_6$) δ0.84 (t, J=7.2 Hz, 3H), 1.07 (s, 6H), 1.30-1.74 (m, 8H), 2.04-2.46 (m, 4H), 3.00-3.08 (m, 2H), 3.19 (s, 2H), 3.35-3.45 (m, 1H), 3.99 (s, 2H), 4.24 (s, 1H), 4.66 (br. s., 1H), 6.43 (d, J=1.9 Hz, 1H), 7.57-7.98 (m, 7H), 8.65 (s, 1H)

REFERENCE EXAMPLE 518

4'-{[4-(1,4-dioxaspiro[4.5]dec-8-yl)-5-oxo-7-propyl-4,5-dihydropyrazolo[1,5-a]pyrimidin-6-yl]methyl}-2'-fluorobiphenyl-2-carbonitrile A solution of N-(1,4-dioxaspiro[4.5]dec-8-yl)-1H-pyrazol-5-amine (2.2 g), 1,8-diazabicyclo[5.4.0]undec-7-ene (0.30 mL) and ethyl 2-[(2'-cyano-2-fluorobiphenyl-4-yl)methyl]-3-oxohexanoate (6.4 g) in diethylaniline (10 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (4.3 g, 82%).

$^1$H NMR (300 MHz, DMSO-$d_6$) δ0.87-1.01 (m, 3H), 1.46-1.84 (m, 8H), 2.53-2.63 (m, 2H), 2.94-3.04 (m, 2H), 3.84-4.02 (m, 6H), 4.82 (br. s., 1H), 6.24 (s, 1H), 7.18-8.01 (m, 8H)

REFERENCE EXAMPLE 519

2'-fluoro-4'-{[4-(trans-4-hydroxycyclohexyl)-5-oxo-7-propyl-4,5-dihydropyrazolo[1,5-a]pyrimidin-6-yl]methyl}biphenyl-2-carbonitrile To a solution of 4'-{[4-(1,4-dioxaspiro[4.5]dec-8-yl)-5-oxo-7-propyl-4,5-dihydropyrazolo[1,5-a]pyrimidin-6-yl]methyl}-2'-fluorobiphenyl-2-carbonitrile (4.3 g) in tetrahydrofuran (40 mL) was added 3M hydrochloric acid (40 mL), and the mixture was stirred at 70° C. for 2 hr. The mixture was allowed to cool, and diluted with ethyl acetate, and the mixture was neutralized with 8M aqueous sodium hydroxide solution. The mixture was extracted with ethyl acetate, and the organic layer was washed with water and saturated brine, dried over anhydrous magnesium sulfate, and concentrated. The residue was dissolved in ethanol (15 mL)-tetrahydrofuran (15 mL). Thereto was added sodium borohydride (0.25 g) at 0° C. After stirring for 2 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (3.0 g, 91%).

$^1$H NMR (300 MHz, DMSO-$d_6$) δ0.95 (t, J=7.3 Hz, 3H), 1.25-1.98 (m, 8H), 2.29-2.46 (m, 2H), 2.89-3.07 (m, 2H), 3.48-3.65 (m, 1H), 3.99 (s, 2H), 4.50-4.84 (m, 2H), 6.42 (d, J=2.3 Hz, 1H), 7.18-8.01 (m, 8H)

REFERENCE EXAMPLE 520 ethyl[(trans-4-{6-[(2'-cyano-2-fluorobiphenyl-4-yl)methyl]-5-oxo-7-propylpyrazolo[1,5-a]pyrimidin-4(5H)-yl}cyclohexyl)oxy]acetate To a solution of 2'-fluoro-4'-{[4-(trans-4-hydroxycyclohexyl)-5-oxo-7-propyl-4,5-dihydropyrazolo[1,5-a]pyrimidin-6-yl]methyl}biphenyl-2-carbonitrile (0.48 g) and rhodium acetate (dimer, 0.044 g) in toluene (5 mL) was added dropwise ethyl diazoacetate (0.52 mL) at 100° C., and the mixture was stirred for 5 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.33 g, 58%).

$^1$H NMR (300 MHz, DMSO-$d_6$) δ0.95 (t, J=7.3 Hz, 3H), 1.21 (t, J=7.2 Hz, 3H), 1.30-1.73 (m, 6H), 2.03-2.46 (m, 4H), 2.94-3.02 (m, 2H), 3.40-3.56 (m, 1H), 3.99 (s, 2H), 4.07-4.17 (m, 4H), 4.66 (br. s., 1H), 6.43 (d, J=2.3 Hz, 1H), 7.17-7.99 (m, 9H)

REFERENCE EXAMPLE 521

2'-fluoro-4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile To a solution of ethyl[(trans-4-{6-[(2'-cyano-2-fluorobiphenyl-4-yl)methyl]-5-oxo-7-propylpyrazolo[1,5-a]pyrimidin-4(5H)-yl}cyclohexyl)oxy]acetate (0.33 g) in tetrahydrofuran (3 mL) was added dropwise methylmagnesium bromide (1 M tetrahydrofuran solution, 1.74 mL) at 0° C., and the mixture was stirred for 3 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.23 g, 72%).

$^1$H NMR (300 MHz, DMSO-$d_6$) δ0.94 (t, J=7.4 Hz, 3H), 1.07 (s, 6H), 1.26-1.75 (m, 6H), 2.03-2.45 (m, 4H), 2.94-3.02 (m, 2H), 3.19 (s, 2H), 3.35-3.46 (m, 1H), 3.99 (s, 2H), 4.25 (s, 1H), 4.68 (br. s., 1H), 6.43 (d, J=1.9 Hz, 1H), 7.17-7.99 (m, 8H)

REFERENCE EXAMPLE 522

4'-{[4-(1,4-dioxaspiro[4.5]dec-8-yl)-5-oxo-7-propyl-4,5-dihydropyrazolo[1,5-a]pyrimidin-6-yl]methyl}-2'-methylbiphenyl-2-carbonitrile A solution of N-(1,4-dioxaspiro[4.5]dec-8-yl)-1H-pyrazol-5-amine (0.59 g), 1,8-diazabicyclo[5.4.0]undec-7-ene (0.080 mL) and ethyl 2-[(2'-cyano-2-methylbiphenyl-4-yl)methyl]-3-oxohexanoate (1.5 g) in diethylaniline (3 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.0 g, 74%).

$^1$H NMR (300 MHz, DMSO-$d_6$) δ0.94 (t, J=7.3 Hz, 3H), 1.46-1.83 (m, 8H), 2.08 (s, 3H), 2.54-2.65 (m, 2H), 2.92-3.05 (m, 2H), 3.84-3.97 (m, 6H), 4.81 (br. s., 1H), 6.23 (s, 1H), 7.05-7.98 (m, 8H)

REFERENCE EXAMPLE 523

4'-{[4-(trans-4-hydroxycyclohexyl)-5-oxo-7-propyl-4,5-dihydropyrazolo[1,5-a]pyrimidin-6-yl]methyl}-2'-methylbiphenyl-2-carbonitrile To a solution of 4'-{[4-(1,4-dioxaspiro[4.5]dec-8-yl)-5-oxo-7-propyl-4,5-dihydropyrazolo[1,5-a]pyrimidin-6-yl]methyl}-2'-methylbiphenyl-2-carbonitrile (1.0 g) in tetrahydrofuran (10 mL) was added 3M hydrochloric acid (10 mL), and the mixture was stirred at 60° C. for 12 hr. The mixture was allowed to cool, and diluted with ethyl acetate, and the mixture was neutralized with 1 M aqueous sodium hydroxide solution. The mixture was extracted with ethyl acetate, and the organic layer was washed with water and saturated brine, dried over anhydrous magnesium sulfate, and concentrated. The residue was dissolved in ethanol (5 mL)-tetrahydrofuran (5 mL). Sodium borohydride (0.074 g) was added thereto at 0° C. After stirring for 2 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (0.88 g, 94%).

$^1$H NMR (300 MHz, DMSO-$d_6$) δ0.94 (t, J=7.3 Hz, 3H), 1.26-1.69 (m, 6H), 1.86-1.98 (m, 2H), 2.08 (s, 3H), 2.28-2.46 (m, 2H), 2.92-3.02 (m, 2H), 3.51-3.58 (m, 1H), 3.93 (s, 2H), 4.55-4.81 (m, 2H), 6.41 (d, J=2.3 Hz, 1H), 7.03-8.02 (m, 8H)

REFERENCE EXAMPLE 524

4'-{1-[4-(1,4-dioxaspiro[4.5]dec-8-yl)-5-oxo-7-propyl-4,5-dihydropyrazolo[1,5-a]pyrimidin-6-yl]ethyl}biphenyl-2-carbonitrile A solution of N-(1,4-dioxaspiro[4.5]dec-8-yl)-1H-pyrazol-5-amine (0.59 g), 1,8-diazabicyclo[5.4.0]undec-7-ene (0.080 mL) and ethyl 2-[1-(2'-cyanobiphenyl-4-yl)ethyl]-3-oxohexanoate (0.5 g) in diethylaniline (3 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.0 g, 74%).

$^1$H NMR (300 MHz, DMSO-$d_6$) δ0.92 (t, J=7.4 Hz, 3H), 1.30-1.82 (m, 12H), 2.38-2.48 (m, 2H), 2.88-3.11 (m, 2H), 3.83-3.98 (m, 4H), 4.47-4.99 (m, 2H), 6.19 (d, J=1.5 Hz, 1H), 7.40-7.98 (m, 9H)

REFERENCE EXAMPLE 525

4'-{1-[4-(trans-4-hydroxycyclohexyl)-5-oxo-7-propyl-4,5-dihydropyrazolo[1,5-a]pyrimidin-6-yl]ethyl}biphenyl-2-carbonitrile To a solution of 4'-{1-[4-(1,4-dioxaspiro[4.5]dec-8-yl)-5-oxo-7-propyl-4,5-dihydropyrazolo[1,5-a]pyrimidin-6-yl]ethyl}biphenyl-2-carbonitrile (0.37 g) in tetrahydrofuran (4 mL) was added 3M hydrochloric acid (4 mL), and the mixture was stirred at 60° C. for 3 hr. The mixture was allowed to cool, and diluted with ethyl acetate, and the mixture was neutralized with 1 M aqueous sodium hydroxide solution. The mixture was extracted with ethyl acetate, and the organic layer was washed with water and saturated brine, dried over anhydrous magnesium sulfate, and concentrated. The residue was dissolved in ethanol (3 mL)-tetrahydrofuran (3 mL). Thereto was added sodium borohydride (0.026 g) at 0° C. After stirring for 2 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (0.33 g, 99%).

$^1$H NMR (300 MHz, DMSO-$d_6$) δ0.91 (t, J=7.3 Hz, 3H), 1.23-1.96 (m, 11H), 2.18-2.44 (m, 2H), 2.85-3.11 (m, 2H), 3.46-3.63 (m, 1H), 4.46-4.77 (m, 3H), 6.37 (d, J=2.1 Hz, 1H), 7.38-8.01 (m, 9H)

REFERENCE EXAMPLE 526

4'-{[4-(1,4-dioxaspiro[4.5]dec-8-yl)-5-oxo-7-propyl-4,5-dihydropyrazolo[1,5-a]pyrimidin-6-yl]methyl}-2'-nitrobiphenyl-2-carbonitrile A solution of N-(1,4-dioxaspiro[4.5]dec-8-yl)-1H-pyrazol-5-amine (0.45 g), 1,8-diazabicyclo[5.4.0]undec-7-ene (0.060 mL) and ethyl 2-[(2'-cyano-2-nitrobiphenyl-4-yl)methyl]-3-oxohexanoate (1.6 g) in diethylaniline (2 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.96 g, 87%).

$^1$H NMR (300 MHz, DMSO-$d_6$) δ0.96 (t, J=7.4 Hz, 3H), 1.48-1.85 (m, 8H), 2.53-2.66 (m, 2H), 2.97-3.08 (m, 2H), 3.84-3.98 (m, 4H), 4.10 (s, 2H), 4.79 (br. s., 1H), 6.25 (s, 1H), 7.41-8.14 (m, 8H)

REFERENCE EXAMPLE 527

4'-{[7-butyl-4-(1,4-dioxaspiro[4.5]dec-8-yl)-5-oxo-4,5-dihydropyrazolo[1,5-a]pyrimidin-6-yl]methyl}-2'-fluorobiphenyl-2-carbonitrile A solution of N-(1,4-dioxaspiro[4.5]dec-8-yl)-1H-pyrazol-5-amine (2.2 g), 1,8-diazabicyclo[5.4.0]undec-7-ene (0.30 mL) and methyl 2-[(2'-cyano-2-fluorobiphenyl-4-yl)methyl]-3-oxoheptanoate (6.4 g) in diethylaniline (10 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (4.7 g, 87%).

$^1$H NMR (300 MHz, DMSO-$d_6$) δ0.73-0.93 (m, 3H), 1.28-1.85 (m, 10H), 2.52-2.66 (m, 2H), 2.93-3.06 (m, 2H), 3.84-4.01 (m, 6H), 4.81 (br. s., 1H), 6.24 (s, 1H), 7.19-8.00 (m, 8H)

REFERENCE EXAMPLE 528

4'-{[7-butyl-4-(trans-4-hydroxycyclohexyl)-5-oxo-4,5-dihydropyrazolo[1,5-a]pyrimidin-6-yl]methyl}-2'-fluorobiphenyl-2-carbonitrile To a solution of 4'-{[7-butyl-4-(1,4-dioxaspiro[4.5]dec-8-yl)-5-oxo-4,5-dihydropyrazolo[1,5-a]pyrimidin-6-yl]methyl}-2'-fluorobiphenyl-2-carbonitrile (4.7 g) in tetrahydrofuran (40 mL) was added 3M hydrochloric acid (40 mL), and the mixture was stirred at 70° C. for 2 hr. The mixture was allowed to cool, and diluted with ethyl acetate, and the mixture was neutralized with 8M aqueous sodium hydroxide solution. The mixture was extracted with ethyl acetate, and the organic layer was washed with water and saturated brine, dried over anhydrous magnesium sulfate, and concentrated. The residue was dissolved in ethanol (20 mL)-tetrahydrofuran (20 mL). Thereto was added sodium borohydride (0.26 g) at 0° C. After stirring for 1 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (3.3 g, 98%).

$^1$H NMR (300 MHz, DMSO-$d_6$) δ0.79-0.88 (m, 3H), 1.27-1.98 (m, 10H), 2.27-2.46 (m, 2H), 2.94-3.05 (m, 2H), 3.49-3.65 (m, 1H), 3.99 (s, 2H), 4.55-4.80 (m, 2H), 6.42 (d, J=2.3 Hz, 1H), 7.18-8.01 (m, 8H)

REFERENCE EXAMPLE 529 ethyl[(trans-4-{7-butyl-6-[(2'-cyano-2-fluorobiphenyl-4-yl)methyl]-5-oxopyrazolo[1,5-a]pyrimidin-4(5H)-yl}cyclohexyl)oxy]acetate To a solution of 4'-{[7-butyl-4-(trans-4-hydroxycyclohexyl)-5-oxo-4,5-dihydropyrazolo[1,5-a]pyrimidin-6-yl]methyl}-2'-fluorobiphenyl-2-carbonitrile (1.0 g) and rhodium acetate (dimer, 0.044 g) in toluene (10 mL) was added dropwise ethyl diazoacetate (0.83 mL) at 100° C., and the mixture was stirred for 5 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.47 g, 42%).

$^1$H NMR (300 MHz, DMSO-$d_6$) δ0.84 (t, J=7.2 Hz, 3H), 1.17-1.24 (m, 3H), 1.28-2.47 (m, 12H), 2.94-3.05 (m, 2H), 3.39-3.58 (m, 1H), 3.94-4.16 (m, 4H), 4.67 (br. s., 1H), 6.43 (d, J=2.1 Hz, 1H), 7.16-8.00 (m, 7H)

REFERENCE EXAMPLE 530

4'-({7-butyl-4-[trans-4-(2-hydroxy-2-methylpropoxy)cyclohexyl]-5-oxo-4,5-dihydropyrazolo[1,5-a]pyrimidin-6-yl}methyl)-2'-fluorobiphenyl-2-carbonitrile To a solution of ethyl[(trans-4-{7-butyl-6-[(2'-cyano-2-fluorobiphenyl-4-yl)methyl]-5-oxopyrazolo[1,5-a]pyrimidin-4(5H)-yl}cyclohexyl)oxy]acetate (0.47 g) in tetrahydrofuran (4 mL) was added dropwise methylmagnesium bromide (1 M tetrahydrofuran solution, 1.8 mL) at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.32 g, 66%).

$^1$H NMR (300 MHz, DMSO-$d_6$) δ0.84 (t, J=7.2 Hz, 3H), 1.07 (s, 6H), 1.27-1.80 (m, 8H), 2.02-2.46 (m, 4H), 2.94-3.04 (m, 2H), 3.35-3.46 (m, 1H), 3.99 (s, 2H), 4.25 (s, 1H), 4.68 (br. s., 1H), 6.43 (d, J=2.1 Hz, 1H), 7.15-7.99 (m, 8H)

REFERENCE EXAMPLE 531

1-benzyl-N-[4-(1-methylethoxy)phenyl]-1H-pyrazol-5-amine

A suspension of 1-benzyl-1H-pyrazol-5-amine (1.7 g), 4-isopropylphenylboric acid (2.0 g), copper acetate (1.8 g), pyridine (4.0 mL) and molecular sieves 4A (4 g) in tetrahydrofuran (50 mL) was stirred for 15 hr. The reaction mixture was diluted with ethyl acetate, the insoluble material was filtered off through celite, and the filtrate was concentrated. The residue was purified by silica gel column chromatography to give the title compound as a pale-yellow amorphous solid (0.80 g, 26%).

$^1$H NMR (300 MHz, DMSO-$d_6$) δ1.21 (d, J=6.1 Hz, 6H), 4.42 (spt, J=6.1 Hz, 1H), 5.23 (s, 2H), 5.90 (d, J=1.9 Hz, 1H), 6.73-6.86 (m, 4H), 7.05-7.41 (m, 6H), 7.75 (s, 1H)

REFERENCE EXAMPLE 532

N-[4-(1-methylethoxy)phenyl]-1H-pyrazol-5-amine

To a suspension of 1-benzyl-N-[4-(1-methylethoxy)phenyl]-1H-pyrazol-5-amine (0.80 g) and palladium hydroxide (10 wt %, 0.80 g) in ethanol (4.5 mL)-acetic acid (0.5 mL) was added ammonium formate (0.49 g) at 80° C. After stirring at 80° C. for 2 hr, the mixture was allowed to cool, ethyl acetate was added, and the insoluble material was filtered off. Saturated aqueous sodium hydrogen carbonate solution was added to the filtrate, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.37 g, 66%).

$^1$H NMR (300 MHz, DMSO-$d_6$) δ1.21 (d, J=6.0 Hz, 6H), 4.41 (spt, J=6.0 Hz, 1H), 5.74 (d, J=2.1 Hz, 1H), 6.70-6.81 (m, 2H), 7.24 (d, J=8.5 Hz, 2H), 7.50 (s, 1H), 8.06 (s, 1H), 11.83 (br. s., 1H)

REFERENCE EXAMPLE 533

4'-({4-[4-(1-methylethoxy)phenyl]-5-oxo-7-propyl-4,5-dihydropyrazolo[1,5-a]pyrimidin-6-yl}methyl)biphenyl-2-carbonitrile N-[4-(1-Methylethoxy)phenyl]-1H-pyrazol-5-amine (0.37 g) and a solution of 1,8-diazabicyclo[5.4.0]undec-7-ene (0.051 mL) and ethyl 2-[(2'-cyanobiphenyl-4-yl)methyl]-3-oxohexanoate (1.2 g) in diethylaniline (5 mL) were stirred at 180° C. for 1 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.76 g, 89%).

$^1$H NMR (300 MHz, DMSO-$d_6$) δ0.98 (t, J=7.3 Hz, 3H), 1.31 (d, J=6.0 Hz, 6H), 1.55-1.72 (m, 2H), 2.99-3.10 (m, 2H), 4.02 (s, 2H), 4.69 (spt, J=6.1 Hz, 1H), 5.45 (d, J=2.1 Hz, 1H), 7.01-7.98 (m, 13H)

REFERENCE EXAMPLE 534 methyl 2'-cyano-3-methoxybiphenyl-4-carboxylate

A suspension of methyl 4-bromo-2-methoxybenzoate (4.9 g), (2-cyanophenyl)boronic acid (5.9 g), Pd(dppf)$_2$Cl$_2$ (0.49 g) and 2M aqueous cesium carbonate solution (20 mL) in tetrahydrofuran (60 mL) was stirred under an argon atmosphere at 70° C. for 3 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.9 g, 35%).

$^1$H NMR (300 MHz, DMSO-d$_6$) δ3.82 (s, 3H), 3.90 (s, 3H), 7.18-8.04 (m, 7H)

REFERENCE EXAMPLE 535 ethyl 2-[(2'-cyano-3-methoxybiphenyl-4-yl)methyl]-3-oxohexanoate

To a solution of methyl 2'-cyano-3-methoxybiphenyl-4-carboxylate (1.86 g) in tetrahydrofuran (40 mL) was added lithium borohydride (0.67 g) at 0° C., and the mixture was stirred at room temperature for 12 hr. To the reaction mixture were added ethyl acetate and saturated aqueous ammonium chloride solution, and the mixture was extracted with ethyl acetate. The organic layer was washed with water and saturated brine, dried over anhydrous magnesium sulfate, and concentrated. The residue was dissolved in toluene (30 mL), phosphorus tribromide (0.33 mL) was added, and the mixture was stirred for 3 hr. Ethyl acetate and water were added to the reaction mixture, and the mixture was extracted with ethyl acetate. The organic layer was washed with water and saturated brine, dried over anhydrous magnesium sulfate, and concentrated. This was dissolved in tetrahydrofuran (10 mL), the mixture was added dropwise to a solution of ethyl 3-oxohexanoate (1.7 g) and 60% sodium hydride (0.28 g) in tetrahydrofuran (15 mL) at 0° C., and the mixture was stirred at room temperature for 15 hr. To the reaction mixture were added ethyl acetate and saturated aqueous ammonium chloride solution, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.8 g, 89%).

$^1$H NMR (300 MHz, DMSO-d$_6$) δ0.79 (t, J=7.4 Hz, 3H), 1.11 (t, J=7.2 Hz, 3H), 1.39-1.52 (m, 2H), 2.37-2.47 (m, 2H), 2.97-3.15 (m, 2H), 3.87 (s, 3H), 3.97-4.10 (m, 3H), 6.96-8.04 (m, 7H)

REFERENCE EXAMPLE 536

4'-{[4-(1,4-dioxaspiro[4.5]dec-8-yl)-5-oxo-7-propyl-4,5-dihydropyrazolo[1,5-a]pyrimidin-6-yl]methyl}-3'-methoxybiphenyl-2-carbonitrile A solution of N-(1,4-dioxaspiro[4.5]dec-8-yl)-1H-pyrazol-5-amine (0.53 g), 1,8-diazabicyclo[5.4.0]undec-7-ene (0.071 mL) and ethyl 2-[(2'-cyano-3-methoxybiphenyl-4-yl)methyl]-3-oxohexanoate (1.81 g) in diethylaniline (3 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (1.1 g, 83%).

$^1$H NMR (300 MHz, DMSO-d$_6$) δ0.92 (t, J=7.2 Hz, 3H), 1.46-1.86 (m, 8H), 2.55-2.68 (m, 2H), 2.87-2.97 (m, 2H), 3.84-3.98 (m, 9H), 4.80 (br. s., 1H), 6.24 (s, 1H), 6.96-8.00 (m, 8H)

REFERENCE EXAMPLE 537

4'-{[4-(trans-4-hydroxycyclohexyl)-5-oxo-7-propyl-4,5-dihydropyrazolo[1,5-a]pyrimidin-6-yl]methyl}-3'-methoxybiphenyl-2-carbonitrile To a solution of 4'-{[4-(1,4-dioxaspiro[4.5]dec-8-yl)-5-oxo-7-propyl-4,5-dihydropyrazolo[1,5-a]pyrimidin-6-yl]methyl}-3'-methoxybiphenyl-2-carbonitrile (1.1 g) in tetrahydrofuran (10 mL) was added 3M hydrochloric acid (10 mL), and the mixture was stirred at 60° C. for 5 hr. The mixture was allowed to cool, and diluted with ethyl acetate, and the mixture was neutralized with 8M aqueous sodium hydroxide solution. The mixture was extracted with ethyl acetate, and the organic layer was washed with water and saturated brine, dried over anhydrous magnesium sulfate, and concentrated. The residue was dissolved in ethanol (10 mL)-tetrahydrofuran (10 mL). Thereto was added sodium borohydride (0.075 g) at 0° C. After stirring for 2 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was purified by silica gel column chromatography to give the title compound as a pale-yellow amorphous solid (0.93 g, 95%).

$^1$H NMR (300 MHz, DMSO-d$_6$) δ0.92 (t, J=7.3 Hz, 3H), 1.27-1.68 (m, 6H), 1.87-1.97 (m, 2H), 2.25-2.47 (m, 2H), 2.85-2.97 (m, 2H), 3.48-3.63 (m, 1H), 3.87 (s, 2H), 3.92 (s, 3H), 4.49-4.84 (m, 2H), 6.41 (d, J=2.1 Hz, 1H), 6.89-8.07 (m, 8H)

REFERENCE EXAMPLE 538 ethyl[(trans-4-{6-[(2'-cyano-3-methoxybiphenyl-4-yl)methyl]-5-oxo-7-propylpyrazolo[1,5-a]pyrimidin-4(5H)-yl}cyclohexyl)oxy]acetate To a solution of 4'-{[4-(trans-4-hydroxycyclohexyl)-5-oxo-7-propyl-4,5-dihydropyrazolo[1,5-a]pyrimidin-6-yl]methyl}-3'-methoxybiphenyl-2-carbonitrile (0.93 g) and rhodium acetate (dimer, 0.020 g) in methylene chloride (10 mL) was added dropwise ethyl diazoacetate (0.86 mL), and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.52 g, 47%).

$^1$H NMR (300 MHz, DMSO-d$_6$) δ0.92 (t, J=7.3 Hz, 3H), 1.17-1.25 (m, 3H), 1.29-1.73 (m, 6H), 2.04-2.16 (m, 2H), 2.30-2.46 (m, 2H), 2.86-2.95 (m, 2H), 3.40-3.54 (m, 1H), 3.86 (s, 2H), 3.92 (s, 3H), 4.07-4.18 (m, 4H), 4.64 (br. s., 1H), 6.42 (d, J=2.3 Hz, 1H), 6.93-8.07 (m, 8H)

REFERENCE EXAMPLE 539

4'-({4-[trans-4-(2-hydroxy-2-methylpropoxy)cyclohexyl]-5-oxo-7-propyl-4,5-dihydropyrazolo[1,5-a]pyrimidin-6-yl}methyl)-3'-methoxybiphenyl-2-carbonitrile To a solution of ethyl[(trans-4-{6-[(2'-cyano-3-methoxybiphenyl-4-yl)methyl]-5-oxo-7-propylpyrazolo[1,5-a]pyrimidin-4(5H)-yl}cyclohexyl)oxy]acetate (0.51 g) in tetrahydrofuran (5 mL) was added dropwise methylmagnesium bromide (1 M tetrahydrofuran solution, 3.5 mL) at 0° C., and the mixture was stirred for 3 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated.

The residue was purified by silica gel column chromatography to give the title compound as a pale-yellow amorphous solid (0.44 g, 87%).

$^1$H NMR (300 MHz, DMSO-d$_6$) δ0.92 (t, J=7.3 Hz, 3H), 1.07 (s, 6H), 1.22-1.77 (m, 6H), 2.02-2.16 (m, 2H), 2.30-2.46 (m, 2H), 2.83-2.97 (m, 2H), 3.19 (s, 2H), 3.34-3.45 (m, 1H), 3.87 (s, 2H), 3.92 (s, 3H), 4.24 (s, 1H), 4.66 (br. s., 1H), 6.42 (d, J=2.1 Hz, 1H), 6.99-7.97 (m, 8H)

REFERENCE EXAMPLE 540 ethyl 2'-cyano-2-methoxybiphenyl-4-carboxylate

A suspension of ethyl 3-methoxy-4-{[(trifluoromethyl)sulfonyl]oxy}benzoate (7.0 g), (2-cyanophenyl)boronic acid (5.9 g), Pd(dppf)$_2$Cl$_2$ (0.50 g) and 2M aqueous cesium carbonate solution (20 mL) in tetrahydrofuran (60 mL) was stirred under an argon atmosphere at 70° C. for 3 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.28 g, 5%).

$^1$H NMR (300 MHz, DMSO-d$_6$) δ1.35 (t, J=7.0 Hz, 3H), 3.84 (s, 3H), 4.37 (q, J=7.2 Hz, 2H), 7.40-7.97 (m, 7H)

REFERENCE EXAMPLE 541 ethyl 2-[(2'-cyano-2-methoxybiphenyl-4-yl)methyl]-3-oxohexanoate

To a solution of ethyl 2'-cyano-2-methoxybiphenyl-4-carboxylate (0.28 g) in tetrahydrofuran (10 mL) was added lithium borohydride (0.22 g), and the mixture was stirred at room temperature for 15 hr. To the reaction mixture were added ethyl acetate and saturated aqueous ammonium chloride solution, and the mixture was extracted with ethyl acetate. The organic layer was washed with water and saturated brine, dried over anhydrous magnesium sulfate, and concentrated. The residue was dissolved in toluene (5 mL), phosphorus tribromide (0.050 mL) was added, and the mixture was stirred for 1 hr. Ethyl acetate and water were added to the reaction mixture, and the mixture was extracted with ethyl acetate. The organic layer was washed with water and saturated brine, dried over anhydrous magnesium sulfate, and concentrated. This was dissolved in tetrahydrofuran (2 mL), the mixture was added dropwise to a solution of ethyl 3-oxohexanoate (0.25 g) and 60% sodium hydride (0.047 g) in tetrahydrofuran (2 mL) at 0° C., and the mixture was stirred at room temperature for 15 hr. To the reaction mixture were added ethyl acetate and saturated aqueous ammonium chloride solution, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.26 g, 85%).

$^1$H NMR (300 MHz, DMSO-d$_6$) δ0.79 (t, J=7.4 Hz, 3H), 1.12 (t, J=7.2 Hz, 3H), 1.38-1.53 (m, 2H), 2.38-2.62 (m, 2H), 3.01-3.19 (m, 2H), 3.75 (s, 3H), 3.98-4.19 (m, 3H), 6.85-7.88 (m, 7H)

REFERENCE EXAMPLE 542

4'-{[4-(1,4-dioxaspiro[4.5]dec-8-yl)-5-oxo-7-propyl-4,5-dihydropyrazolo[1,5-a]pyrimidin-6-yl]methyl}-2'-methoxybiphenyl-2-carbonitrile A solution of N-(1,4-dioxaspiro[4.5]dec-8-yl)-1H-pyrazol-5-amine (0.30 g), 1,8-diazabicyclo[5.4.0]undec-7-ene (0.017 mL) and ethyl 2-[(2'-cyano-2-methoxybiphenyl-4-yl)methyl]-3-oxohexanoate (0.26 g) in diethylaniline (2 mL) was stirred at 180° C. for 2 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.25 g, 70%).

$^1$H NMR (300 MHz, DMSO-d$_6$) δ0.91-0.99 (m, 3H), 1.48-1.83 (m, 8H), 2.53-2.67 (m, 2H), 2.95-3.05 (m, 2H), 3.73 (s, 3H), 3.85-4.00 (m, 6H), 4.80 (br. s., 1H), 6.24 (d, J=1.5 Hz, 1H), 6.84-7.90 (m, 8H)

REFERENCE EXAMPLE 543 ethyl[(trans-4-{6-[(2'-cyano-2-methoxybiphenyl-4-yl)methyl]-5-oxo-7-propylpyrazolo[1,5-a]pyrimidin-4(5H)-yl}cyclohexyl)oxy]acetate To a solution of 4'-{[4-(1,4-dioxaspiro[4.5]dec-8-yl)-5-oxo-7-propyl-4,5-dihydropyrazolo[1,5-a]pyrimidin-6-yl]methyl}-2'-methoxybiphenyl-2-carbonitrile (0.25 g) in tetrahydrofuran (3 mL) was added 3M hydrochloric acid (3 mL), and the mixture was stirred at 60° C. for 12 hr. The mixture was allowed to cool, and diluted with ethyl acetate, and the mixture was neutralized with 1 M aqueous sodium hydroxide solution. The mixture was extracted with ethyl acetate, and the organic layer was washed with water and saturated brine, dried over anhydrous magnesium sulfate, and concentrated. The residue was dissolved in ethanol (3 mL)-tetrahydrofuran (3 mL). Thereto was added sodium borohydride (0.019 g) at 0° C. After stirring for 1 hr, ethyl acetate and saturated aqueous ammonium chloride solution were added. The mixture was extracted with ethyl acetate, and the organic layer was washed with water and saturated brine, dried over anhydrous magnesium sulfate, and concentrated. The residue was dissolved in methylene chloride (2 mL), rhodium acetate (dimer, 0.020 g) and then ethyl diazoacetate (0.86 mL) were added dropwise, and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.13 g, 53%).

$^1$H NMR (300 MHz, DMSO-d$_6$) δ0.95 (t, J=7.2 Hz, 3H), 1.18-1.25 (m, 3H), 1.29-1.80 (m, 6H), 2.03-2.45 (m, 4H), 2.93-3.04 (m, 2H), 3.40-3.55 (m, 1H), 3.73 (s, 3H), 3.97 (s, 2H), 4.08-4.19 (m, 5H), 4.63 (br. s., 1H), 6.42 (d, J=2.3 Hz, 1H), 6.81-7.91 (m, 8H)

REFERENCE EXAMPLE 544

4'-({4-[trans-4-(2-hydroxy-2-methylpropoxy)cyclohexyl]-5-oxo-7-propyl-4,5-dihydropyrazolo[1,5-a]pyrimidin-6-yl}methyl)-2'-methoxybiphenyl-2-carbonitrile To a solution of ethyl[(trans-4-{6-[(2'-cyano-2-methoxybiphenyl-4-yl)methyl]-5-oxo-7-propylpyrazolo[1,5-a]pyrimidin-4(5H)-yl}cyclohexyl)oxy]acetate (0.13 g) in tetrahydrofuran (1.5 mL) was added dropwise methylmagnesium bromide (1 M tetrahydrofuran solution, 0.88 mL) at 0° C., and the mixture was stirred for 3 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.085 g, 68%).

$^1$H NMR (300 MHz, DMSO-d$_6$) δ0.95 (t, J=7.2 Hz, 3H), 1.07 (s, 6H), 1.27-1.77 (m, 6H), 2.03-2.15 (m, 2H), 2.31-2.47 (m, 2H), 2.94-3.04 (m, 2H), 3.20 (s, 2H), 3.34-3.46 (m, 1H), 3.73 (s, 3H), 3.97 (s, 2H), 4.22 (br. s., 1H), 4.65 (br. s., 1H), 6.42 (d, J=2.3 Hz, 1H), 6.80-7.93 (m, 8H)

REFERENCE EXAMPLE 545

1-benzyl-N-(4-{[tert-butyl(dimethyl)silyl]oxy}phenyl)-1H-pyrazol-5-amine

A suspension of 1-benzyl-1H-pyrazol-5-amine (5.0 g), (4-{[tert-butyl(dimethyl)silyl]oxy}phenyl)boronic acid (15 g), copper acetate (11 g), pyridine (12 mL) and molecular sieves 4A (10 g) in tetrahydrofuran (150 mL) was stirred for 12 hr. The reaction mixture was diluted with ethyl acetate, the insoluble material was filtered off through celite, and the filtrate was concentrated. The residue was purified by silica gel column chromatography to give the title compound as a pale-yellow amorphous solid (4.9 g, 45%).

$^1$H NMR (300 MHz, DMSO-d$_6$) δ0.14 (s, 6H), 0.93 (s, 9H), 5.23 (s, 2H), 5.91 (d, J=1.5 Hz, 1H), 6.62-6.84 (m, 4H), 7.04-7.41 (m, 6H), 7.76 (s, 1H)

REFERENCE EXAMPLE 546

N-(4-{[tert-butyl(dimethyl)silyl]oxy}phenyl)-1H-pyrazol-5-amine

To a suspension of 1-benzyl-N-(4-{[tert-butyl(dimethyl)silyl]oxy}phenyl)-1H-pyrazol-5-amine (4.9 g) and palladium hydroxide (10 wt %, 5.0 g) in ethanol (22.5 mL)-acetic acid (2.5 mL) was added ammonium formate (2.4 g) at 80° C. After stirring at 80° C. for 3 hr, the mixture was allowed to cool, ethyl acetate was added, and the insoluble material was filtered off. Saturated aqueous sodium hydrogen carbonate solution was added to the filtrate, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (2.8 g, 74%).

$^1$H NMR (300 MHz, DMSO-d$_6$) δ0.14 (s, 6H), 0.94 (s, 9H), 5.74 (s, 1H), 6.67 (d, J=9.1 Hz, 2H), 7.21 (d, J=8.3 Hz, 2H), 7.50 (s, 1H), 8.07 (s, 1H), 11.83 (s, 1H)

REFERENCE EXAMPLE 547

4'-{[4-(4-hydroxyphenyl)-5-oxo-7-propyl-4,5-dihydropyrazolo[1,5-a]pyrimidin-6-yl]methyl}biphenyl-2-carbonitrile A solution of N-(4-{[tert-butyl(dimethyl)silyl]oxy}phenyl)-1H-pyrazol-5-amine (2.8 g), 1,8-diazabicyclo[5.4.0]undec-7-ene (0.30 mL) and ethyl 2-[(2'-cyanobiphenyl-4-yl)methyl]-3-oxohexanoate (7.0 g) in diethylaniline (15 mL) was stirred at 180° C. for 8 hr. The mixture was allowed to cool, tetrahydrofuran (5 mL) and tetrabutylammonium fluoride (1.0 M tetrahydrofuran solution, 5 mL) were added, and the mixture was stirred for 1 hr. To the reaction mixture were added ethyl acetate and saturated aqueous ammonium chloride solution, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (3.5 g, 79%).

$^1$H NMR (300 MHz, DMSO-d$_6$) δ0.98 (t, J=7.4 Hz, 3H), 1.54-1.71 (m, 2H), 2.99-3.09 (m, 2H), 4.02 (s, 2H), 5.43 (d, J=1.9 Hz, 1H), 6.86-7.96 (m, 13H), 9.82 (s, 1H)

REFERENCE EXAMPLE 548 ethyl(4-{6-[(2'-cyanobiphenyl-4-yl)methyl]-5-oxo-7-propylpyrazolo[1,5-a]pyrimidin-4(5H)-yl}phenoxy)acetate To a solution of 4'-{[4-(4-hydroxyphenyl)-5-oxo-7-propyl-4,5-dihydropyrazolo[1,5-a]pyrimidin-6-yl]methyl}biphenyl-2-carbonitrile (0.92 g) in N,N-dimethylformamide (10 mL) were added ethyl bromoacetate (0.66 mL) and cesium carbonate (1.3 g) and the mixture was stirred at 70° C. for 15 hr. The mixture was allowed to cool, ethyl acetate and water were added, and the mixture was extracted with ethyl acetate. The organic layer was washed with water and saturated brine, dried over anhydrous magnesium sulfate, and concentrated. The residue was purified by silica gel column chromatography to give the title compound as a pale-yellow amorphous solid (0.82 g, 75%).

$^1$H NMR (300 MHz, DMSO-d$_6$) δ0.98 (t, J=7.4 Hz, 3H), 1.23 (t, J=7.2 Hz, 3H), 1.56-1.70 (m, 2H), 2.99-3.10 (m, 2H), 4.02 (s, 2H), 4.19 (q, J=7.1 Hz, 2H), 4.87 (s, 2H), 5.42 (d, J=2.3 Hz, 1H), 7.05-7.97 (m, 13H)

REFERENCE EXAMPLE 549

4'-({4-[4-(2-hydroxy-2-methylpropoxy)phenyl]-5-oxo-7-propyl-4,5-dihydropyrazolo[1,5-a]pyrimidin-6-yl}methyl)biphenyl-2-carbonitrile To a solution of ethyl(4-{6-[(2'-cyanobiphenyl-4-yl)methyl]-5-oxo-7-propylpyrazolo[1,5-a]pyrimidin-4(5H)-yl}phenoxy)acetate (0.30 g) in tetrahydrofuran (3 mL) was added dropwise methylmagnesium bromide (1 M tetrahydrofuran solution, 2.2 mL) at 0° C., and the mixture was stirred for 3 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.25 g, 85%).

$^1$H NMR (300 MHz, DMSO-d$_6$) δ0.98 (t, J=7.2 Hz, 3H), 1.23 (s, 6H), 1.53-1.72 (m, 2H), 3.00-3.09 (m, 2H), 3.78 (s, 2H), 4.02 (s, 2H), 5.44 (d, J=1.9 Hz, 1H), 7.05-7.97 (m, 13H)

REFERENCE EXAMPLE 550

4'-{[4-(4-{[(1R,2S)-2-hydroxy-1-methylpropyl]oxy}phenyl)-5-oxo-7-propyl-4,5-dihydropyrazolo[1,5-a]pyrimidin-6-yl]methyl}biphenyl-2-carbonitrile To a solution of 4'-{[4-(4-hydroxyphenyl)-5-oxo-7-propyl-4,5-dihydropyrazolo[1,5-a]pyrimidin-6-yl]methyl}biphenyl-2-carbonitrile (0.92 g) in N,N-dimethylformamide (10 mL) were added trans-2,3-epoxybutane (1.8 mL) and then cesium carbonate (2.0 g), and the mixture was stirred at 100° C. for 15 hr. The mixture was allowed to cool, to the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. The residue was purified by silica gel column chromatography to give the title compound as a pale-yellow amorphous solid (0.57 g, 54%).

$^1$H NMR (300 MHz, DMSO-d$_6$) δ0.98 (t, J=7.2 Hz, 3H), 1.11 (d, J=6.4 Hz, 3H), 1.21 (d, J=6.4 Hz, 3H), 1.56-1.72 (m, 2H), 3.00-3.09 (m, 2H), 3.73-3.86 (m, 1H), 4.02 (s, 2H), 4.28-4.42 (m, 1H), 4.82 (d, J=4.9 Hz, 1H), 5.46 (d, J=2.3 Hz, 1H), 7.05-7.97 (m, 13H)

REFERENCE EXAMPLE 551

2-(4-{6-[(2'-cyanobiphenyl-4-yl)methyl]-5-oxo-7-propylpyrazolo[1,5-a]pyrimidin-4(5H)-yl}phenoxy)-N-methoxy-N-methylacetamide To a solution of ethyl(4-{6-[(2'-cyanobiphenyl-4-yl)methyl]-5-oxo-7-propylpyrazolo[1,5-a]pyrimidin-4(5H)-yl}phenoxy)acetate (0.51 g) in tetrahydrofuran (5 mL) was added 1 M aqueous sodium hydroxide solution (5 mL) and the mixture was stirred at 60° C. for 1 hr. The mixture was allowed to cool, and neutralized with 1 M hydrochloric acid, and the mixture was extracted with ethyl acetate. The organic layer was washed with water and then with saturated brine, dried over anhydrous magnesium sulfate, and concentrated. The residue was dissolved in acetonitrile (30 mL), methoxymethylamine hydrochloride (0.27 g), 4-dimethylaminopyridine (0.034 g), diisopropylethylamine (0.81 mL), 1-hydroxybenzotriazole (0.16 g) and 1-(3-dimethylaminopropyl)-3-ethylcarbodiimide hydrochloride (0.36 g) were added and the mixture was stirred for 15 hr. Ethyl acetate and water were added to the reaction mixture, and the mixture was extracted with ethyl acetate. The organic layer was washed with water and then with saturated brine, dried over anhydrous magnesium sulfate, and concentrated. The residue was purified by silica gel column chromatography to give the title compound as a pale-yellow amorphous solid (0.44 g, 84%).

$^1$H NMR (300 MHz, DMSO-d$_6$) δ0.98 (t, J=7.2 Hz, 3H), 1.55-1.70 (m, 2H), 3.00-3.09 (m, 2H), 3.15 (s, 3H), 3.77 (s, 3H), 4.02 (s, 2H), 4.99 (s, 2H), 5.43 (d, J=1.1 Hz, 1H), 6.97-8.07 (m, 13H)

REFERENCE EXAMPLE 552

4'-({4-[4-(2-hydroxypropoxy)phenyl]-5-oxo-7-propyl-4,5-dihydropyrazolo[1,5-a]pyrimidin-6-yl}methyl)biphenyl-2-carbonitrile To a solution of 2-(4-{6-[(2'-cyanobiphenyl-4-yl)methyl]-5-oxo-7-propylpyrazolo[1,5-a]pyrimidin-4(5H)-yl}phenoxy)-N-methoxy-N-methylacetamide (0.44 g) in tetrahydrofuran (4 mL) was added dropwise methylmagnesium bromide (1 M tetrahydrofuran solution, 1.6 mL) at 0° C., and the mixture was stirred for 1 hr. Ethyl acetate and then saturated aqueous ammonium chloride solution were added. The mixture was extracted with ethyl acetate, and the organic layer was washed with saturated brine, dried over anhydrous magnesium sulfate, and concentrated. The residue was dissolved in ethanol (4 mL), and sodium borohydride (0.030 g) was added at 0° C. After stirring at 0° C. for 30 min, ethyl acetate and then saturated aqueous ammonium chloride solution were added. The mixture was extracted with ethyl acetate, and the organic layer was washed with saturated brine, dried over anhydrous magnesium sulfate, and concentrated. The residue was purified by silica gel column chromatography to give the title compound as a pale-yellow amorphous solid (0.30 g, 73%).

$^1$H NMR (300 MHz, DMSO-d$_6$) δ0.98 (t, J=7.4 Hz, 3H), 1.17 (d, J=6.1 Hz, 3H), 1.56-1.71 (m, 2H), 2.99-3.10 (m, 2H), 3.82-4.04 (m, 5H), 4.90 (d, J=1.9 Hz, 1H), 5.44 (d, J=1.9 Hz, 1H), 7.04-7.97 (m, 13H)

REFERENCE EXAMPLE 553

2-[5-(hydroxymethyl)thiophen-2-yl]benzonitrile

A mixture of 5-bromothiophene-2-carboxyaldehyde (5.00 g), 2-cyanophenylboric acid (3.95 g), [1,1'-bis(diphenylphosphino)ferrocene]dichloropalladium(II), dichloromethane adduct (0.22 g), tetrabutylammonium bromide (0.26 g), 2M aqueous sodium carbonate solution (20 mL) and toluene (200 mL) was refluxed under an argon atmosphere overnight. The reaction mixture was concentrated, and the residue was dissolved in ethyl acetate. The obtained ethyl acetate solution was washed with saturated brine, and dried over anhydrous magnesium sulfate. The solvent was evaporated under reduced pressure. To a mixture of the obtained residue, methanol (20 mL) and hydrofuran (20 mL) was gradually added sodium borohydride (0.50 g) at 0° C., and the mixture was stirred at room temperature for 10 min. The reaction mixture was poured into a saturated aqueous potassium hydrogensulfate solution, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow solid (2.60 g, 46%).

$^1$H NMR (300 MHz, CDCl$_3$) δ1.89 (t, J=6.0, 1H), 4.88 (d, J=6.0, 2H), 7.04-7.07 (m, 1H), 7.33-7.43 (m, 1H), 7.48-7.52 (m, 1H), 7.56-7.62 (m, 2H), 7.70-7.75 (m, 1H)

REFERENCE EXAMPLE 554

2-[5-(bromomethyl)thiophen-2-yl]benzonitrile

To a solution (50 mL) of 2-[5-(hydroxymethyl)thiophen-2-yl]benzonitrile (2.60 g) in toluene was added phosphine tribromide (2.60 g) at room temperature, and the mixture was stirred at room temperature overnight. The reaction mixture was concentrated, and the residue was dissolved in ethyl acetate. The obtained ethyl acetate solution was washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a colorless solid (3.20 g, 95%).

$^1$H NMR (300 MHz, CDCl$_3$) δ4.75 (s, 2H), 7.14-7.17 (m, 1H), 7.36-7.43 (m, 1H), 7.45-7.49 (m, 1H), 7.57-7.62 (m, 2H), 7.71-7.76 (m, 1H)

REFERENCE EXAMPLE 555 ethyl 2-{[5-(2-cyanophenyl)thiophen-2-yl]methyl}-3-oxohexanoate

To a mixture of 60% sodium hydride in oil (0.71 g) and tetrahydrofuran (20 mL) was added dropwise a mixture of ethyl 3-oxohexanoate (3.65 g) in tetrahydrofuran (10 mL) at 0° C., and the mixture was stirred at room temperature for 30 min. Then, 2-[5-(bromomethyl)thiophen-2-yl]benzonitrile (3.20 g) was added, and the mixture was stirred at room temperature overnight. The reaction mixture was poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (3.30 g, 81%).

$^1$H NMR (300 MHz, CDCl$_3$) δ0.89 (t, J=6.6, 3H), 1.26 (t, J=7.2, 3H), 1.54-1.70 (m, 2H), 2.38-2.70 (m, 2H), 3.31-3.48 (m, 2H), 3.85 (t, J=7.5, 1H), 4.14-4.28 (m, 2H), 6.85 (d, J=3.6, 1H), 7.32-7.39 (m, 1H), 7.43 (d, J=3.6, 1H), 7.52-7.60 (m, 2H), 7.68-7.74 (m, 1H)

REFERENCE EXAMPLE 556

2-(5-{[4-(1,4-dioxaspiro[4.5]dec-8-yl)-5-oxo-7-propyl-4,5-dihydro[1,2,4]triazolo[1,5-a]pyrimidin-6-yl]methyl}thiophen-2-yl)benzonitrile A mixture of N-(1,4-dioxaspiro[4.5]dec-8-yl)-4H-1,2,4-triazol-3-amine (1.10 g), ethyl 2-{[5-(2-cyanophenyl)thiophen-2-yl]methyl}-3-oxohexanoate (3.30 g), 1,8-diazabicyclo[5.4.0]undec-7-ene (0.15 mL) and N,N-diethylaniline (20 mL) was stirred at 180° C. overnight. The mixture was allowed to cool and poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (0.85 g, 34%).

$^1$H NMR (300 MHz, CDCl$_3$) δ1.11 (t, J=7.2, 3H), 1.70-2.00 (m, 8H), 2.88-3.14 (m, 4H), 3.94-4.10 (m, 4H), 4.13 (s, 2H), 5.06-5.22 (m, 1H), 6.95 (d, J=3.6, 1H), 7.28-7.38 (m, 1H), 7.46 (d, J=3.6, 1H), 7.52-7.57 (m, 2H), 7.67-7.72 (m, 1H), 7.95 (s, 1H)

REFERENCE EXAMPLE 557 ethyl 2-{[6-(2-cyanophenyl)pyridin-3-yl]methyl}-3-oxohexanoate

To a mixture of 60% sodium hydride in oil (1.64 g) and tetrahydrofuran (30 mL) was added dropwise a mixture of ethyl 3-oxohexanoate (8.10 g) in tetrahydrofuran (20 mL) at 0° C., and the mixture was stirred at room temperature for 30 min. Then, 2-[5-(chloromethyl)pyridin-2-yl]benzonitrile (2.25 g) and tetrabutylammonium iodide (1.25 g) were added, and the mixture was stirred at room temperature overnight. The reaction mixture was poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a yellow oil (2.20 g, 62%).

$^1$H NMR (300 MHz, CDCl$_3$) δ0.87 (t, J=7.2, 3H), 1.23 (t, J=7.2, 3H), 1.52-1.70 (m, 2H), 2.36-2.68 (m, 2H), 3.15-3.30 (m, 2H), 3.81 (t, J=7.5, 1H), 4.10-4.24 (m, 2H), 7.44-7.52 (m, 1H), 7.62-7.72 (m, 3H), 7.76-7.86 (m, 2H), 8.57-8.64 (m, 1H)

REFERENCE EXAMPLE 558

1-benzyl-N-(tetrahydro-2H-pyran-4-yl)-1H-pyrazol-5-amine

To a solution of 1-benzyl-1H-pyrazol-5-amine (2.09 g) in acetic acid (20 mL) was added tetrahydro-4H-pyran-4-one (1.25 g), and the mixture was stirred at room temperature for 30 min. After stirring, sodium triacetoxyborohydride (3.90 g) was added at room temperature, and the mixture was stirred overnight. Acetic acid was evaporated under reduced pressure and ethyl acetate and water were added to the residue. The mixture was neutralized with sodium hydrogen carbonate, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (3.00 g, 97%).

$^1$H NMR (300 MHz, CDCl$_3$) δ1.34-1.40 (m, 2H), 1.84-1.94 (m, 2H), 3.34-3.46 (m, 2H), 3.78-3.92 (m, 3H), 5.19 (s, 2H), 5.52 (d, J=2.1, 1H), 7.09-7.16 (m, 2H), 7.25-7.36 (m, 4H)

REFERENCE EXAMPLE 559

N-(tetrahydro-2H-pyran-4-yl)-1H-pyrazol-5-amine

A mixture of 1-benzyl-N-(tetrahydro-2H-pyran-4-yl)-1H-pyrazol-5-amine (3.00 g), palladium-carbon (10 wt %, 2.33 g) and ethanol (100 mL) was stirred under a hydrogen atmosphere at 50° C. and 5 atm for 9 hr. The insoluble material was filtered off, and the solvent was evaporated under reduced pressure. The residue was purified by silica gel column chromatography to give the title compound as a colorless solid (1.70 g, 87%).

$^1$H NMR (300 MHz, CDCl$_3$) δ1.42-1.56 (m, 2H), 2.01-2.10 (m, 2H), 3.42-3.64 (m, 4H), 3.74-4.03 (m, 2H), 6.64 (d, J=2.4, 1H), 7.34 (d, J=2.4, 1H), 9.10 (br. s, 1H)

REFERENCE EXAMPLE 560

4'-{[5-oxo-7-propyl-4-(tetrahydro-2H-pyran-4-yl)-4,5-dihydropyrazolo[1,5-a]pyrimidin-6-yl]methyl}biphenyl-2-carbonitrile A mixture of N-(tetrahydro-2H-pyran-4-yl)-1H-pyrazol-5-amine (1.00 g), ethyl 2-[(2'-cyanobiphenyl-4-yl)methyl]-3-oxohexanoate (4.20 g), 1,8-diazabicyclo[5.4.0]undec-7-ene (0.9 mL) and N,N-diethylaniline (10 mL) was stirred at 180° C. overnight, allowed to cool, and poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless solid (2.39 g, 88%).

$^1$H NMR (300 MHz, CDCl$_3$) δ1.06 (t, J=6.9, 3H), 1.63-1.82 (m, 4H), 2.52-2.68 (m, 2H), 3.04-3.12 (m, 2H), 3.48-3.62 (m, 2H), 4.02 (s, 2H), 4.08-4.16 (m, 2H), 5.33 (br. s, 1H), 6.13 (d, J=2.1, 1H), 7.35-7.52 (m, 6H), 7.57-7.65 (m, 1H), 7.71-7.76 (m, 2H)

REFERENCE EXAMPLE 561 methyl 2-{[6-(2-cyanophenyl)pyridin-3-yl]methyl}-3-oxoheptanoate

To a mixture of 60% sodium hydride in oil (3.27 g) and tetrahydrofuran (50 mL) was added dropwise a mixture of methyl 3-oxoheptanoate (16.18 g) in tetrahydrofuran (50 mL) at 0° C., and the mixture was stirred at room temperature for 30 min. Then, 2-[5-(chloromethyl)pyridin-2-yl]benzonitrile (4.45 g) and tetrabutylammonium iodide (2.27 g) were added, and the mixture was stirred at room temperature overnight. The reaction mixture was poured into 1 M hydrochloric acid (70 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a yellow oil (0.88 g, 12%).

$^1$H NMR (300 MHz, CDCl$_3$) δ0.87 (t, J=7.2, 3H), 1.18-1.32 (m, 2H), 1.48-1.62 (m, 2H), 2.34-2.68 (m, 2H), 3.15-3.30 (m, 2H), 3.72 (s, 3H), 3.84 (t, J=7.5, 1H), 7.44-7.53 (m, 1H), 7.62-7.72 (m, 3H), 7.76-7.86 (m, 2H), 8.57-8.63 (m, 1H)

REFERENCE EXAMPLE 562

4'-(hydroxymethyl)-2'-methylbiphenyl-2-carbonitrile

A mixture of 4-bromo-3-methylbenzylalcohol (15.16 g), 2-cyanophenylboric acid (14.80 g), [1,1'-bis(diphenylphosphino)ferrocene]dichloropalladium(II), dichloromethane adduct (3.08 g), tetrabutylammonium bromide (1.22 g), 2M aqueous sodium carbonate solution (75 mL) and toluene (300 mL) was refluxed under an argon atmosphere for 30 hr. The reaction mixture was concentrated, and the residue was dissolved in ethyl acetate. The obtained ethyl acetate solution was washed with saturated brine, and dried over anhydrous magnesium sulfate. The solvent was evaporated under reduced pressure, and the residue was purified by silica gel column chromatography to give the title compound as a pale-yellow oil (4.12 g, 24%).

$^1$H NMR (300 MHz, CDCl$_3$) δ2.20 (s, 3H), 4.73 (d, J=5.1, 2H), 7.15-7.50 (m, 5H), 7.57-7.67 (m, 1H), 7.70-7.78 (m, 1H)

REFERENCE EXAMPLE 563 ethyl 2-[(2'-cyano-2-methylbiphenyl-4-yl)methyl]-3-oxohexanoate

To a solution (15 mL) of 4'-(hydroxymethyl)-2'-methylbiphenyl-2-carbonitrile (4.12 g) in toluene was added phosphine tribromide (6.00 g) at room temperature, and the mixture was stirred at room temperature overnight. The reaction mixture was concentrated, and the residue was dissolved in ethyl acetate. The obtained ethyl acetate solution was washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a pale-yellow oil (5.08 g, 96%). To a mixture of 60% sodium hydride in oil (1.10 g) and tetrahydrofuran (20 mL) was added dropwise a mixture of ethyl 3-oxohexanoate (5.62 g) in tetrahydrofuran (20 mL) at 0° C., and the mixture was stirred at room temperature for 30 min. Then, 4'-(bromomethyl)-2'-methylbiphenyl-2-carbonitrile (5.08 g) was added, and the mixture was stirred at room temperature overnight. The reaction mixture was poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (4.53 g, 70%).

$^1$H NMR (300 MHz, CDCl$_3$) δ0.86 (t, J=7.5, 3H), 1.23 (t, J=7.2, 3H), 1.50-1.66 (m, 2H), 2.15 (s, 3H), 2.30-2.64 (m, 2H), 3.10-3.26 (m, 2H), 3.82 (t, J=7.5, 1H), 4.16 (q, J=7.2, 2H), 7.04-7.16 (m, 3H), 7.28-7.36 (m, 1H), 7.38-7.48 (m, 1H), 7.57-7.65 (m, 1H), 7.68-7.76 (m, 1H)

REFERENCE EXAMPLE 564

4'-formyl-2'-nitrobiphenyl-2-carbonitrile

A mixture of 4-bromo-3-nitrobenzaldehyde (10.0 g), 2-cyanophenylboric acid (8.25 g), [1,1'-bis(diphenylphosphino)ferrocene]dichloropalladium(II), dichloromethane adduct (3.45 g), tetrabutylammonium bromide (1.36 g), 2M aqueous sodium carbonate solution (40 mL) and toluene (400 mL) was refluxed under an argon atmosphere for 3 days. The reaction mixture was concentrated, and the residue was dissolved in ethyl acetate. The obtained ethyl acetate solution was washed with saturated brine, and dried over anhydrous magnesium sulfate. The solvent was evaporated under reduced pressure, and the residue was purified by silica gel column chromatography to give the title compound as a pale-yellow solid (5.15 g, 40%).

$^1$H NMR (300 MHz, CDCl$_3$) δ7.34-7.42 (m, 1H), 7.54-7.85 (m, 4H), 8.21-8.26 (m, 1H), 8.64 (d, J=1.5, 1H), 10.16 (s, 1H)

REFERENCE EXAMPLE 565

4'-(hydroxymethyl)-2'-nitrobiphenyl-2-carbonitrile

To a mixture of 4'-formyl-2'-nitrobiphenyl-2-carbonitrile (5.15 g), methanol (30 mL) and hydrofuran (30 mL) was gradually added sodium borohydride (0.40 g) at 0° C., and the mixture was stirred at room temperature for 30 min. The reaction mixture was poured into 1 M hydrochloric acid (20 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (3.62 g, 70%).

$^1$H NMR (300 MHz, CDCl$_3$) δ4.87 (s, 2H), 7.32-7.83 (m, 6H), 8.12-8.20 (m, 1H)

REFERENCE EXAMPLE 566 ethyl 2-[(2'-cyano-2-nitrobiphenyl-4-yl)methyl]-3-oxohexanoate

To a solution (15 mL) of 4'-(hydroxymethyl)-2'-nitrobiphenyl-2-carbonitrile (3.62 g) in toluene was added phosphine tribromide (4.63 g) at room temperature, and the mixture was stirred at room temperature overnight. The reaction mixture was concentrated, and the residue was dissolved in ethyl acetate. The obtained ethyl acetate solution was washed with saturated aqueous sodium hydrogen carbonate and then with saturated brine, and dried over anhydrous magnesium sulfate. The solvent was evaporated under reduced pressure, and the residue was purified by silica gel column chromatography to give 4'-(bromomethyl)-2'-nitrobiphenyl-2-carbonitrile as a pale-yellow oil.

To a mixture of 60% sodium hydride in oil (0.85 g) and tetrahydrofuran (20 mL) was added dropwise a mixture of ethyl 3-oxohexanoate (4.50 g) in tetrahydrofuran (10 mL) at 0° C., and the mixture was stirred at room temperature for 30 min. Then, the aforementioned 4'-(bromomethyl)-2'-nitrobiphenyl-2-carbonitrile was added, and the mixture was stirred at room temperature overnight. The reaction mixture was poured into 1 M hydrochloric acid (30 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a yellow oil (4.60 g, 82%).

$^1$H NMR (300 MHz, CDCl$_3$) δ0.89 (t, J=7.5, 3H), 1.25 (t, J=7.2, 3H), 1.52-1.70 (m, 2H), 2.36-2.68 (m, 2H), 3.22-3.40 (m, 2H), 3.85 (t, J=6.9, 1H), 4.19 (q, J=7.2, 2H), 7.28-7.38 (m, 2H), 7.46-7.68 (m, 3H), 7.72-7.80 (m, 1H), 7.94-8.02 (m, 1H)

REFERENCE EXAMPLE 567

4'-{[4-(4-hydroxyphenyl)-5-oxo-7-propyl-4,5-dihydro[1,2,4]triazolo[1,5-a]pyrimidin-6-yl]methyl}biphenyl-2-carbonitrile A mixture of 4'-[(5-oxo-7-propyl-4,5-dihydro[1,2,4]triazolo[1,5-a]pyrimidin-6-yl)methyl]biphenyl-2-carbonitrile (6.00 g), 4-isopropoxyphenylboric acid (5.85 g), copper(II) acetate (5.90 g), pyridine (18 mL), triethylamine (9 mL), molecular sieves 4A (18.0 g) and tetrahydrofuran (100 mL) was stirred at room temperature for 1 day. Ethyl acetate (100 mL) was added to the reaction mixture, the mixture was stirred at room temperature for 1 hr, and the insoluble material was filtered off. The filtrate was concentrated, and the residue was purified by silica gel column chromatography to give 4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile as a colorless solid (6.53 g, 80%). A mixture of 4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile (6.53 g) and 25% hydrobromic acid-acetic acid solution (10 mL) was stirred under refluxing for 2 hr. The reaction mixture was concentrated, and the residue was dissolved in ethyl acetate. The obtained ethyl acetate solution was washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a colorless solid (4.38 g, 73%).

$^1$H NMR (300 MHz, CDCl$_3$) δ1.12 (t, J=7.2, 3H), 1.73-1.88 (m, 2H), 3.08-3.18 (m, 2H), 4.07 (s, 2H), 6.69-6.77 (m, 2H), 7.08-7.16 (m, 2H), 7.37-7.52 (m, 5H), 7.57-7.66 (m, 2H), 7.71-7.76 (m, 1H), 7.93 (s, 1H)

REFERENCE EXAMPLE 568 methyl 2-(4-{6-[(2'-cyanobiphenyl-4-yl)methyl]-5-oxo-7-propyl[1,2,4]triazolo[1,5-a]pyrimidin-4(5H)-yl}phenoxy)-2-methylpropanoate A mixture of 4'-{[4-(4-hydroxyphenyl)-5-oxo-7-propyl-4,5-dihydro[1,2,4]triazolo[1,5-a]pyrimidin-6-yl]methyl}biphenyl-2-carbonitrile (3.70 g), methyl 2-bromo-2-methylpropanoate (7.30 g), cesium carbonate (13.07 g) and N,N-dimethylformamide (20 mL) was stirred at 80° C. overnight. The reaction mixture was poured into 1 M hydrochloric acid (40 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (4.50 g, quantitative).

$^1$H NMR (300 MHz, CDCl$_3$) δ1.11 (t, J=7.5, 3H), 1.64 (s, 6H), 1.73-1.88 (m, 2H), 3.08-3.18 (m, 2H), 3.76 (s, 3H), 4.05 (s, 2H), 6.89-6.97 (m, 2H), 7.25-7.33 (m, 2H), 7.38-7.50 (m, 6H), 7.58-7.65 (m, 1H), 7.70-7.76 (m, 1H), 7.86 (s, 1H)

REFERENCE EXAMPLE 569

4'-{[7-butyl-4-(1,4-dioxaspiro[4.5]dec-8-yl)-5-oxo-4,5-dihydro[1,2,4]triazolo[1,5-a]pyrimidin-6-yl]methyl}-3'-fluorobiphenyl-2-carbonitrile A mixture of methyl 2-[(2'-cyano-3-fluorobiphenyl-4-yl)methyl]-3-oxoheptanoate (6.55 g), N-(1,4-dioxaspiro[4.5]dec-8-yl)-4H-1,2,4-triazol-3-amine (2.00 g), 1,8-diazabicyclo[5.4.0]undec-7-ene (0.5 mL) and N,N-diethylaniline (20 mL) was stirred at 180° C. overnight, allowed to cool, and poured into 1 M hydrochloric acid (100 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (2.88 g, 60%).

$^1$H NMR (300 MHz, CDCl$_3$) δ0.95 (t, J=7.2, 3H), 1.40-2.00 (m, 10H), 2.88-3.14 (m, 4H), 3.94-4.10 (m, 6H), 5.06-5.22 (m, 1H), 7.20-7.52 (m, 5H), 7.59-7.66 (m, 1H), 7.72-7.78 (m, 1H), 7.95 (s, 1H)

REFERENCE EXAMPLE 570

4'-{[7-butyl-5-oxo-4-(4-oxocyclohexyl)-4,5-dihydro[1,2,4]triazolo[1,5-a]pyrimidin-6-yl]methyl}-3'-fluorobiphenyl-2-carbonitrile A mixture of 4'-{[7-butyl-4-(1,4-dioxaspiro[4.5]dec-8-yl)-5-oxo-4,5-dihydro[1,2,4]triazolo[1,5-a]pyrimidin-6-yl]methyl}-3'-fluorobiphenyl-2-carbonitrile (2.88 g), 3N hydrochloric acid (20 mL) and tetrahydrofuran (20 mL) was stirred under refluxing for 16 hr. The reaction mixture was neutralized with 1 M aqueous sodium hydroxide solution (60 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (2.61 g, 99%).

$^1$H NMR (300 MHz, CDCl$_3$) δ0.96 (t, J=7.2, 3H), 1.40-1.74 (m, 4H), 2.00-2.16 (m, 2H), 2.50-2.62 (m, 4H), 3.00-3.20 (m, 4H), 4.03 (s, 2H), 5.46-5.62 (m, 1H), 7.22-7.50 (m, 5H), 7.59-7.68 (m, 1H), 7.72-7.78 (m, 1H), 7.90 (s, 1H)

REFERENCE EXAMPLE 571

4'-{[7-butyl-4-(trans-4-hydroxycyclohexyl)-5-oxo-4,5-dihydro[1,2,4]triazolo[1,5-a]pyrimidin-6-yl]methyl}-3'-fluorobiphenyl-2-carbonitrile To a mixture of 4'-{[7-butyl-5-oxo-4-(4-oxocyclohexyl)-4,5-dihydro[1,2,4]triazolo[1,5-a]pyrimidin-6-yl]methyl}-3'-fluorobiphenyl-2-carbonitrile (2.61 g), tetrahydrofuran (10 mL) and methanol (10 mL) was added sodium borohydride (0.15 g) at 0° C., and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless oil (2.14 g, 82%).

$^1$H NMR (300 MHz, CDCl$_3$) δ0.95 (t, J=7.2, 3H), 1.40-1.84 (m, 8H), 2.06-2.20 (m, 2H), 2.64-2.84 (m, 2H), 3.00-3.14 (m, 2H), 3.74-3.88 (m, 1H), 4.01 (s, 2H), 4.96-5.14 (m, 1H), 7.20-7.48 (m, 5H), 7.59-7.68 (m, 1H), 7.72-7.78 (m, 1H), 7.90 (s, 1H)

REFERENCE EXAMPLE 572 ethyl[(trans-4-{7-butyl-6-[(2'-cyano-3-fluorobiphenyl-4-yl)methyl]-5-oxo[1,2,4]triazolo[1,5-a]pyrimidin-4(5H)-yl}cyclohexyl)oxy]acetate To a mixture of 4'-{[7-butyl-4-(trans-4-hydroxycyclohexyl)-5-oxo-4,5-dihydro[1,2,4]triazolo[1,5-a]pyrimidin-6-yl]methyl}-3'-fluorobiphenyl-2-carbonitrile (2.14 g), rhodium(I) acetate (0.57 g) and toluene (30 mL) was added dropwise a solution of ethyl diazoacetate (2.30 g) in toluene (10 mL) at 70° C., and the mixture was stirred at the same temperature for 30 min. The reaction mixture was poured into water, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (1.24 g, 49%).

$^1$H NMR (300 MHz, CDCl$_3$) δ0.95 (t, J=7.5, 3H), 1.30 (t, J=7.2, 3H), 1.40-1.90 (m, 8H), 2.14-2.38 (m, 2H), 2.60-2.78 (m, 2H), 3.00-3.10 (m, 2H), 3.44-3.60 (m, 1H), 4.01 (s, 2H), 4.13 (s, 2H), 4.22 (q, J=7.2, 2H), 4.96-5.14 (m, 1H), 7.21-7.50 (m, 5H), 7.59-7.66 (m, 1H), 7.72-7.78 (m, 1H), 7.90 (s, 1H)

REFERENCE EXAMPLE 573

4'-({7-butyl-4-[trans-4-(2-hydroxy-2-methylpropoxy)cyclohexyl]-5-oxo-4,5-dihydro[1,2,4]triazolo[1,5-a]pyrimidin-6-yl}methyl)-3'-fluorobiphenyl-2-carbonitrile Ethyl[(trans-4-{7-butyl-6-[(2'-cyano-3-fluorobiphenyl-4-yl)methyl]-5-oxo[1,2,4]triazolo[1,5-a]pyrimidin-4(5H)-yl}cyclohexyl)oxy]acetate (1.24 g) was dissolved in tetrahydrofuran (15 mL), and methylmagnesium bromide (1.0 M tetrahydrofuran solution, 6.5 mL) was added at room temperature. The reaction mixture was stirred for 1 hr, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless oil (0.76 g, 63%).

$^1$H NMR (300 MHz, CDCl$_3$) δ0.95 (t, J=7.2, 3H), 1.20 (s, 6H), 1.36-1.86 (m, 8H), 2.14-2.24 (m, 2H), 2.60-2.80 (m, 2H), 3.02-3.10 (m, 2H), 3.30 (s, 2H), 3.38-3.51 (m, 1H), 4.01 (s, 2H), 5.00-5.14 (m, 1H), 7.21-7.28 (m, 2H), 7.32-7.49 (m, 3H), 7.59-7.67 (m, 1H), 7.72-7.78 (m, 1H), 7.90 (s, 1H)

REFERENCE EXAMPLE 574

1-benzyl-N-(1,4-dioxaspiro[4.5]dec-8-yl)-1H-pyrazol-5-amine

To a solution of 1-benzyl-1H-pyrazol-5-amine (43.3 g) in acetic acid (500 mL) was added 1,4-dioxaspiro[4.5]decan-8-one (47 g) at room temperature, and the mixture was stirred for 30 min. Sodium triacetoxyborohydride (64 g) was added by small portions at room temperature, and the mixture was stirred for 18 hr. Acetic acid was evaporated, and ethyl acetate and water were added to the residue. The mixture was neutralized with sodium hydrogen carbonate, and the mixture was extracted with ethyl acetate. The organic layer was washed with water and brine, dried over anhydrous magnesium sulfate, and concentrated. The residue was dissolved in a small amount of ethyl acetate, and the mixture was crystallized using diisopropyl ether. The resulting solid was collected by filtration, washed with diisopropyl ether, and dried under reduced pressure to give the title compound as a pale-yellow solid (61 g, 78%).

$^1$H NMR (300 MHz, DMSO-d$_6$) δ1.38-1.87 (m, 8H), 3.00-3.16 (m, 1H), 3.84 (s, 4H), 5.14 (s, 2H), 5.26 (d, J=7.2 Hz, 1H), 5.40 (d, J=1.9 Hz, 1H), 7.02-7.33 (m, 6H)

REFERENCE EXAMPLE 575

N-(1,4-dioxaspiro[4.5]dec-8-yl)-1H-pyrazol-5-amine

To a suspension of 1-benzyl-N-(1,4-dioxaspiro[4.5]dec-8-yl)-1H-pyrazol-5-amine (38 g) and palladium hydroxide (10 wt %, 11.4 g) in ethanol (200 mL)-acetic acid (40 mL) was added ammonium formate (32 g) by small portions at 80° C. After stirring at 80° C. for 4 hr, the mixture was allowed to cool to room temperature, ethyl acetate was added, and the insoluble material was filtered off. Saturated aqueous sodium hydrogen carbonate was added to the filtrate, and the mixture was extracted with ethyl acetate. The organic layer was washed with water and brine, dried over anhydrous magnesium sulfate, and concentrated. The residue was crystallized using ethyl acetate, and the resulting solid was collected by filtration, washed with diisopropyl ether, and dried under reduced pressure to give the title compound as a pale-yellow solid (22 g, 81%).

$^1$H NMR (300 MHz, DMSO-d$_6$) δ1.34-1.92 (m, 8H), 3.11-3.29 (m, 1H), 3.84 (s, 4H), 4.68-5.08 (m, 1H), 5.40 (br. s., 1H), 7.30 (br. s., 1H), 11.39 (br. s., 1H)

REFERENCE EXAMPLE 576 ethyl 2-[1-(2'-cyanobiphenyl-4-yl)ethyl]-3-oxohexanoate

To a mixture of 60% sodium hydride in oil (0.82 g) and tetrahydrofuran (20 mL) was added dropwise a mixture of ethyl 3-oxohexanoate (4.35 g) in tetrahydrofuran (20 mL) at 0° C., and the mixture was stirred at room temperature for 30 min. Then, 4'-(1-bromoethyl)biphenyl-2-carbonitrile (3.93 g) was added, and the mixture was stirred at 50° C. overnight. The reaction mixture was poured into 1 M hydrochloric acid (30 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (4.70 g, 94%).

$^1$H NMR (300 MHz, CDCl$_3$) δ0.64-1.75 (m, 11H), 2.04-2.70 (m, 2H), 3.58-4.30 (m, 4H), 7.28-7.52 (m, 6H), 7.58-7.66 (m, 1H), 7.70-7.78 (m, 1H)

REFERENCE EXAMPLE 577

4'-{1-[4-(1,4-dioxaspiro[4.5]dec-8-yl)-5-oxo-7-propyl-4,5-dihydro[1,2,4]triazolo[1,5-a]pyrimidin-6-yl]ethyl}biphenyl-2-carbonitrile A mixture of ethyl 2-[1-(2'-cyanobiphenyl-4-yl)ethyl]-3-oxohexanoate (4.80 g), N-(1,4-dioxaspiro[4.5]dec-8-yl)-4H-

1,2,4-triazol-3-amine (1.50 g), 1,8-diazabicyclo[5.4.0]undec-7-ene (0.2 mL) and N,N-diethylaniline (20 mL) was stirred at 180° C. overnight, allowed to cool and poured into 1 M hydrochloric acid (100 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (1.50 g, 43%).

$^1$H NMR (300 MHz, CDCl$_3$) δ1.01 (t, J=7.5, 3H), 1.40-1.94 (m, 11H), 2.84-3.10 (m, 4H), 3.92-4.06 (m, 4H), 4.52-4.66 (m, 1H), 5.02-5.16 (m, 1H), 7.37-7.54 (m, 6H), 7.59-7.66 (m, 1H), 7.71-7.77 (m, 1H), 7.93 (s, 1H)

REFERENCE EXAMPLE 578

4'-{1-[5-oxo-4-(4-oxocyclohexyl)-7-propyl-4,5-dihydro[1,2,4]triazolo[1,5-a]pyrimidin-6-yl]ethyl}biphenyl-2-carbonitrile A mixture of 4'-{1-[4-(1,4-dioxaspiro[4.5]dec-8-yl)-5-oxo-7-propyl-4,5-dihydro[1,2,4]triazolo[1,5-a]pyrimidin-6-yl]ethyl}biphenyl-2-carbonitrile (1.50 g), 3N hydrochloric acid (30 mL) and tetrahydrofuran (20 mL) was stirred under refluxing for 15 hr. The reaction mixture was neutralized with 1 M aqueous sodium hydroxide solution (90 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (1.38 g, quantitative).

$^1$H NMR (300 MHz, CDCl$_3$) δ1.03 (t, J=7.2, 3H), 1.62-2.12 (m, 7H), 2.42-2.62 (m, 4H), 2.90-3.20 (m, 4H), 4.52-4.64 (m, 1H), 5.42-5.60 (m, 1H), 7.38-7.57 (m, 6H), 7.59-7.66 (m, 1H), 7.72-7.78 (m, 1H), 7.88 (s, 1H)

REFERENCE EXAMPLE 579

4'-{1-[4-(trans-4-hydroxycyclohexyl)-5-oxo-7-propyl-4,5-dihydro[1,2,4]triazolo[1,5-a]pyrimidin-6-yl]ethyl}biphenyl-2-carbonitrile To a mixture of 4'-{1-[5-oxo-4-(4-oxocyclohexyl)-7-propyl-4,5-dihydro[1,2,4]triazolo[1,5-a]pyrimidin-6-yl]ethyl}biphenyl-2-carbonitrile (1.38 g), tetrahydrofuran (15 mL) and methanol (10 mL) was added sodium borohydride (0.50 g) at 0° C., and the mixture was stirred at room temperature for 30 min. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless oil (1.24 g, 89%).

$^1$H NMR (300 MHz, CDCl$_3$) δ1.01 (t, J=7.2, 3H), 1.40-2.16 (m, 12H), 2.62-3.10 (m, 4H), 3.72-3.88 (m, 1H), 4.52-4.66 (m, 1H), 4.94-5.10 (m, 1H), 7.38-7.54 (m, 6H), 7.59-7.66 (m, 1H), 7.72-7.76 (m, 1H), 7.89 (s, 1H)

REFERENCE EXAMPLE 580 ethyl[(trans-4-{6-[1-(2'-cyanobiphenyl-4-yl)ethyl]-5-oxo-7-propyl[1,2,4]triazolo[1,5-a]pyrimidin-4(5H)-yl}cyclohexyl)oxy]acetate To a mixture of 4'-{1-[4-(trans-4-hydroxycyclohexyl)-5-oxo-7-propyl-4,5-dihydro[1,2,4]triazolo[1,5-a]pyrimidin-6-yl]ethyl}biphenyl-2-carbonitrile (1.24 g), rhodium(I) acetate (0.34 g) and toluene (20 mL) was added dropwise a solution of ethyl diazoacetate (1.38 g) in toluene (10 mL) at 70° C., and the mixture was stirred at the same temperature for 30 min. The reaction mixture was poured into water, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (0.70 g, 48%).

$^1$H NMR (300 MHz, CDCl$_3$) δ1.01 (t, J=7.5, 3H), 1.28 (t, J=7.2, 3H), 1.40-2.16 (m, 11H), 2.56-2.78 (m, 2H), 2.88-3.06 (m, 2H), 3.40-3.56 (m, 1H), 4.08-4.28 (m, 4H), 4.50-4.64 (m, 1H), 4.96-5.06 (m, 1H), 7.18-7.30 (m, 1H), 7.38-7.54 (m, 5H), 7.58-7.66 (m, 1H), 7.71-7.76 (m, 1H), 7.88 (s, 1H)

REFERENCE EXAMPLE 581

4'-(1-{4-[trans-4-(2-hydroxy-2-methylpropoxy)cyclohexyl]-5-oxo-7-propyl-4,5-dihydro[1,2,4]triazolo[1,5-a]pyrimidin-6-yl}ethyl)biphenyl-2-carbonitrile Ethyl[(trans-4-{6-[1-(2'-cyanobiphenyl-4-yl)ethyl]-5-oxo-7-propyl[1,2,4]triazolo[1,5-a]pyrimidin-4(5H)-yl}cyclohexyl)oxy]acetate (0.70 g) was dissolved in tetrahydrofuran (10 mL), and methylmagnesium bromide (1.0 M tetrahydrofuran solution, 3.6 mL) was added at 0° C. The reaction mixture was stirred for 30 min, 1 N hydrochloric acid was added, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless oil (0.39 g, 57%).

$^1$H NMR (300 MHz, CDCl$_3$) δ1.01 (t, J=7.5, 3H), 1.20 (s, 6H), 1.24-1.86 (m, 10H), 2.10-2.24 (m, 2H), 2.58-2.76 (m, 2H), 2.88-3.10 (m, 2H), 3.29 (s, 2H), 3.36-3.51 (m, 1H), 4.52-4.66 (m, 1H), 4.94-5.10 (m, 1H), 7.38-7.54 (m, 6H), 7.59-7.66 (m, 1H), 7.71-7.77 (m, 1H), 7.88 (s, 1H)

REFERENCE EXAMPLE 582

4'-(hydroxymethyl)-2'-methylbiphenyl-2-carbonitrile

A mixture of 4-bromo-3-methylbenzylalcohol (15.16 g), 2-cyanophenylboric acid (14.80 g), [1,1'-bis(diphenylphosphino)ferrocene]dichloropalladium(II), dichloromethane adduct (3.08 g), tetrabutylammonium bromide (1.22 g), 2M aqueous sodium carbonate solution (75 mL) and toluene (300 mL) was refluxed under an argon atmosphere for 30 hr. The reaction mixture was concentrated, and the residue was dissolved in ethyl acetate. The obtained ethyl acetate solution was washed with saturated brine, and dried over anhydrous magnesium sulfate. The solvent was evaporated under reduced pressure, and the residue was purified by silica gel column chromatography to give the title compound as a pale-yellow oil (4.12 g, 24%).

$^1$H NMR (300 MHz, CDCl$_3$) δ2.20 (s, 3H), 4.73 (d, J=5.1, 2H), 7.15-7.50 (m, 5H), 7.57-7.67 (m, 1H), 7.70-7.78 (m, 1H)

REFERENCE EXAMPLE 583

4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-2'-methylbiphenyl-2-carbonitrile A mixture of ethyl 2-[(2'-cyano-2-methylbiphenyl-4-yl)methyl]-3-oxohexanoate (3.00 g), N-(1,4-dioxaspiro[4.5]

dec-8-yl)-3-methyl-1H-1,2,4-triazol-5-amine (1.00 g), 1,8-diazabicyclo[5.4.0]undec-7-ene (0.3 mL) and N,N-diethylaniline (10 mL) was stirred at 180° C. overnight, allowed to cool and poured into 1 M hydrochloric acid (50 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a brown oil (1.20 g, 53%).

$^1$H NMR (300 MHz, CDCl$_3$) δ1.04 (t, J=7.2, 3H), 1.56-1.95 (m, 8H), 2.14 (s, 3H), 2.44 (s, 3H), 2.88-3.08 (m, 4H), 3.90-4.06 (m, 6H), 4.98-5.12 (m, 1H), 7.06-7.19 (m, 3H), 7.30-7.46 (m, 2H), 7.56-7.64 (m, 1H), 7.68-7.75 (m, 1H)

REFERENCE EXAMPLE 584

2'-methyl-4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile A mixture of 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-2'-methylbiphenyl-2-carbonitrile (1.20 g), 3N hydrochloric acid (15 mL) and tetrahydrofuran (15 mL) was stirred under refluxing for 15 hr. The reaction mixture was neutralized with 1 M aqueous sodium hydroxide solution (45 mL), and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a pale-yellow oil (1.10 g, quantitative).

$^1$H NMR (300 MHz, CDCl$_3$) δ1.06 (t, J=7.2, 3H), 1.50-2.20 (m, 7H), 2.42 (s, 3H), 2.50-2.62 (m, 4H), 2.92-3.22 (m, 4H), 3.96 (s, 2H), 5.44-5.60 (m, 1H), 7.08-7.19 (m, 3H), 7.30-7.48 (m, 2H), 7.56-7.65 (m, 1H), 7.68-7.76 (m, 1H)

REFERENCE EXAMPLE 585

4'-{[4-(trans-4-hydroxycyclohexyl)-2-methyl-5-oxo-7-propyl-4,5-dihydro[1,2,4]triazolo[1,5-a]pyrimidin-6-yl]methyl}-2'-methylbiphenyl-2-carbonitrile To a mixture of 2'-methyl-4'-{[2-methyl-5-oxo-4-(4-oxocyclohexyl)-7-propyl-4,5-dihydro[1,2,4]triazolo[1,5-a]pyrimidin-6-yl]methyl}biphenyl-2-carbonitrile (1.10 g), tetrahydrofuran (10 mL) and methanol (10 mL) was added sodium borohydride (0.05 g) at 0° C., and the mixture was stirred at room temperature for 30 min. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless oil (1.01 g, 91%).

$^1$H NMR (300 MHz, CDCl$_3$) δ1.05 (t, J=7.5, 3H), 1.42-2.20 (m, 12H), 2.44 (s, 3H), 2.67-3.04 (m, 4H), 3.74-3.90 (m, 1H), 3.94 (s, 2H), 4.92-5.08 (m, 1H), 7.08-7.18 (m, 3H), 7.30-7.46 (m, 2H), 7.56-7.64 (m, 1H), 7.68-7.74 (m, 1H)

REFERENCE EXAMPLE 586 ethyl[(trans-4-{6-[(2'-cyano-2-methylbiphenyl-4-yl)methyl]-2-methyl-5-oxo-7-propyl[1,2,4]triazolo[1,5-a]pyrimidin-4(5H)-yl}cyclohexyl)oxy]acetate To a mixture of 4'-{[4-(trans-4-hydroxycyclohexyl)-2-methyl-5-oxo-7-propyl-4,5- dihydro[1,2,4]triazolo[1,5-a]pyrimidin-6-yl]methyl}-2'-methylbiphenyl-2-carbonitrile (1.01 g), rhodium(I) acetate (0.30 g) and toluene (20 mL) was added dropwise a solution of ethyl diazoacetate (1.20 g) in toluene (10 mL) at 70° C., and the mixture was stirred at the same temperature for 30 min. The reaction mixture was poured into water, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as a colorless oil (0.71 g, 60%).

$^1$H NMR (300 MHz, CDCl$_3$) δ1.04 (t, J=7.2, 3H), 1.30 (t, J=7.2, 3H), 1.42-2.30 (m, 11H), 2.43 (s, 3H), 2.64-3.06 (m, 4H), 3.46-3.60 (m, 1H), 3.94 (s, 2H), 4.08-4.30 (m, 4H), 4.92-5.08 (m, 1H), 7.08-7.20 (m, 3H), 7.31-7.46 (m, 2H), 7.56-7.64 (m, 1H), 7.68-7.74 (m, 1H)

REFERENCE EXAMPLE 587

N-(1,4-dioxaspiro[4.5]dec-8-yl)-1H-pyrazol-5-amine

A solution of 1H-pyrazol-3-amine (10.0 g) and 1,4-dioxaspiro[4.5]decan-8-one (20.7 g) in methanol (30 mL) was stirred at room temperature for 30 min. After stirring, a solution of sodium tetrahydroborate (3.6 g) in 1 M sodium hydroxide (30 mL) was added dropwise at 0° C. After warming to room temperature, the mixture was stirred for 4 hr, 1 M hydrochloric acid (100 mL) was added dropwise at 0° C., and the mixture was stirred for 1 hr. The resulting solid was collected by filtration, washed with water, and dried by heating under reduced pressure to give the title compound as a pale-yellow solid (17.2 g, 64%).

$^1$H NMR (300 MHz, DMSO-d$_6$) δ1.34-1.92 (m, 8H), 3.11-3.29 (m, 1H), 3.84 (s, 4H), 4.68-5.08 (m, 1H), 5.40 (br. s., 1H), 7.30 (br. s., 1H), 11.39 (br. s., 1H)

REFERENCE EXAMPLE 588 ethyl 2-[(2'-cyano-3-fluorobiphenyl-4-yl)methyl]-3-oxohexanoate

To a mixture of 3'-fluoro-4'-methylbiphenyl-2-carbonitrile (110 g), N-bromosuccinimide (97.3 g) and benzotrifluoride (1.0 L) was added azobisisobutyronitrile (1.71 g), and the mixture was heated to an internal temperature of 78° C. and stirred for 16 hr. The reaction mixture was cooled to around 40° C., and the insoluble material was removed to give a solution of 4'-(bromomethyl)-3'-fluorobiphenyl-2-carbonitrile in benzotrifluoride.

To a suspension of sodium hydride (60% in oil, 25 g) in tetrahydrofuran (750 mL) was added dropwise a solution of ethyl 3-oxohexanoate (164 g) in tetrahydrofuran (250 mL) at 0° C. The reaction mixture was stirred at room temperature for 1 hr, and a solution of 4'-(bromomethyl)-3'-fluorobiphenyl-2-carbonitrile in benzotrifluoride above mentioned was added at 0° C. The reaction mixture was further stirred at room temperature for 16 hr, and added to 1 M hydrochloric acid (1.0 L), and the obtained mixture was concentrated under reduced pressure. The obtained mixture was extracted with ethyl acetate, and the obtained extract was washed with saturated brine and dried over anhydrous magnesium sulfate. The solvent was evaporated under reduced pressure and the obtained residue was purified by silica gel column chromatography to give the title compound as a colorless oil (145 g, 76%).

$^1$H NMR (300 MHz, DMSO-d$_6$) δ 0.80 (t, J=7.3 Hz, 3H), 1.10 (t, J=7.2 Hz, 3H), 1.40-1.54 (m, 2H), 2.44-2.61 (m, 2H), 3.05-3.22 (m, 2H), 3.98-4.13 (m, 3H), 7.32-7.48 (m, 3H), 7.53-7.65 (m, 2H), 7.75-7.83 (m, 1H), 7.96 (d, J=7.5 Hz, 1H)

EXAMPLE 1

2,4-dimethyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

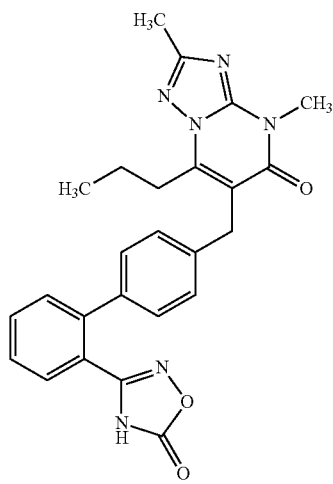 [SMILES: CCCc1c(Cc2ccc(-c3ccccc3-c3noc(=O)[nH]3)cc2)c(=O)n(C)c2nc(C)nn12]

A mixture of hydroxylammonium chloride (1.77 g), sodium hydrogen carbonate (2.84 g) and dimethyl sulfoxide (15 mL) was stirred at 40° C. for 30 min, 4'-[(2,4-dimethyl-5-oxo-7-propyl-4,5-dihydro[1,2,4]triazolo[1,5-a]pyrimidin-6-yl)methyl]biphenyl-2-carbonitrile (0.67 g) was added, and the mixture was stirred at 90° C. for 16 hr. The reaction mixture was diluted with ethyl acetate, and the mixture was washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.33 g) and then 1,8-diazabicyclo[5.4.0]undec-7-ene (0.28 mL) were added, and the mixture was stirred at room temperature for 2 hr. The reaction mixture was diluted with ethyl acetate, and the mixture was washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.41 g, 53%).

$^1$H NMR (300 MHz, DMSO-$d_6$) δ0.94 (t, J=7.3, 3H), 1.60 (d, J=7.7, 2H), 2.36 (s, 3H), 2.85-3.04 (m, 2H), 3.52 (s, 3H), 3.99 (s, 2H), 7.35-7.43 (m, 2H), 7.44-7.63 (m, 4H), 7.76 (dd, J=7.7, 1.3, 1H), 7.84-7.95 (m, 1H)

EXAMPLE 2

4-(2,2-dimethylpropyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

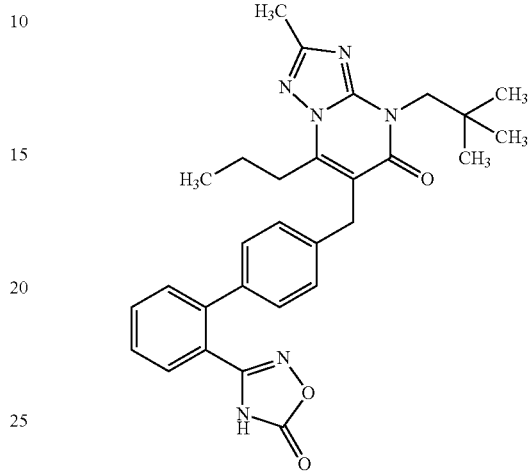

A mixture of 4'-[(2-methyl-5-oxo-7-propyl-4,5-dihydro[1,2,4]triazolo[1,5-a]pyrimidin-6-yl)methyl]biphenyl-2-carbonitrile (0.8 g), 1-iodo-2,2-dimethylpropane (0.79 mL), cesium carbonate (1.3 g) and N,N-dimethylacetamide (10 mL) was stirred at 130° C. for 2 hr. The reaction mixture was diluted with ethyl acetate, and the mixture was washed with 5% aqueous potassium hydrogensulfate solution and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.38 g), sodium hydrogen carbonate (0.88 g) and dimethyl sulfoxide (10 mL), which had been stirred in advance at 40° C. for 30 min. The reaction mixture was stirred at 90° C. for 16 hr, and diluted with ethyl acetate, and the mixture was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, and the mixture was washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.2 g, 20%).

$^1$H NMR (300 MHz, DMSO-$d_6$) δ0.88-0.98 (m, 12H), 1.44-1.66 (m, 2H), 2.33 (s, 3H), 2.83-2.97 (m, 2H), 3.95 (s, 2H), 4.01 (s, 2H), 7.17-7.24 (m, 2H), 7.24-7.32 (m, 2H), 7.52 (dd, J=17.2, 7.8, 2H), 7.60-7.75 (m, 2H), 12.37 (s, 1H)

EXAMPLE 3

2-methyl-4-(2-methyl-2,3-dihydro-1-benzofuran-5-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

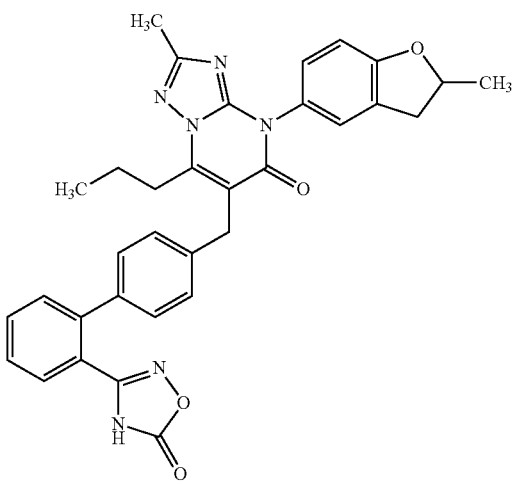 [SMILES: CCCc1c(Cc2ccc(-c3ccccc3-c3noc(=O)[nH]3)cc2)c(=O)n(-c2ccc3c(c2)CC(C)O3)c2nc(C)nn12]

A mixture of hydroxylammonium chloride (0.34 g), sodium hydrogen carbonate (0.54 g) and dimethyl sulfoxide (10 mL) was stirred at 40° C. for 30 min, 4'-{[2-methyl-4-(2-methyl-2,3-dihydro-1-benzofuran-5-yl)-5-oxo-7-propyl-4,5-dihydro[1,2,4]triazolo[1,5-a]pyrimidin-6-yl]methyl}biphenyl-2-carbonitrile (0.17 g) was added, and the mixture was stirred at 90° C. for 16 hr. The reaction mixture was diluted with ethyl acetate, and the mixture was washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.062 g) and then 1,8-diazabicyclo[5.4.0]undec-7-ene (0.052 mL) were added, and the mixture was stirred at room temperature for 2 hr. The reaction mixture was diluted with ethyl acetate, and the mixture was washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.094 g, 50%).

$^1$H NMR (300 MHz, DMSO-$d_6$) δ0.95 (t, J=7.3 Hz, 3H), 1.42 (d, J=6.2 Hz, 3H), 1.50-1.72 (m, 2H), 2.26 (s, 3H), 2.76-2.99 (m, 3H), 3.35-3.45 (m, 1H), 3.96 (s, 2H), 4.90-5.14 (m, 1H), 6.83 (d, J=8.5 Hz, 1H), 7.14 (dd, J=8.4, 2.2 Hz, 1H), 7.20-7.27 (m, 3H), 7.29-7.39 (m, 2H), 7.42-7.58 (m, 2H), 7.60-7.75 (m, 2H), 12.40 (s, 1H)

EXAMPLE 4

4-(4-fluorobenzyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

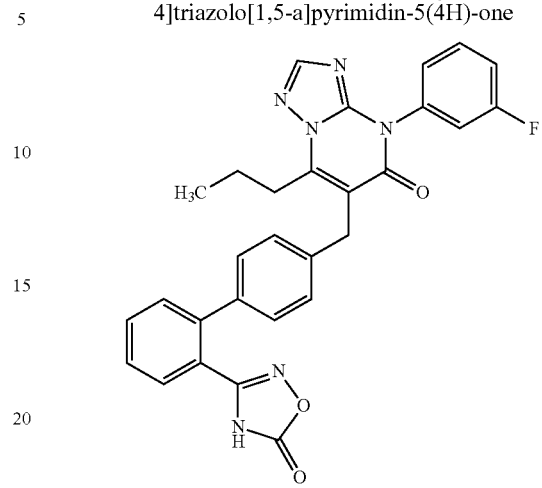

A mixture of hydroxylammonium chloride (1.3 g), sodium hydrogen carbonate (2 g) and dimethyl sulfoxide (15 mL) was stirred at 40° C. for 30 min, 4'-{[4-(4-fluorobenzyl)-5-oxo-7-propyl-4,5-dihydro[1,2,4]triazolo[1,5-a]pyrimidin-6-yl]methyl}biphenyl-2-carbonitrile (0.58 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.24 g, 36%).

$^1$H NMR (300 MHz, DMSO-$d_6$) δ0.92 (t, J=7.4, 3H), 1.43-1.70 (m, 2H), 2.85-3.05 (m, 2H), 3.98 (s, 2H), 5.28 (s, 2H), 7.07-7.26 (m, 4H), 7.27-7.35 (m, 2H), 7.39-7.61 (m, 4H), 7.62-7.73 (m, 2H), 8.21 (s, 1H), 12.40 (s, 1H)

EXAMPLE 5

4-(4-fluorobenzyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

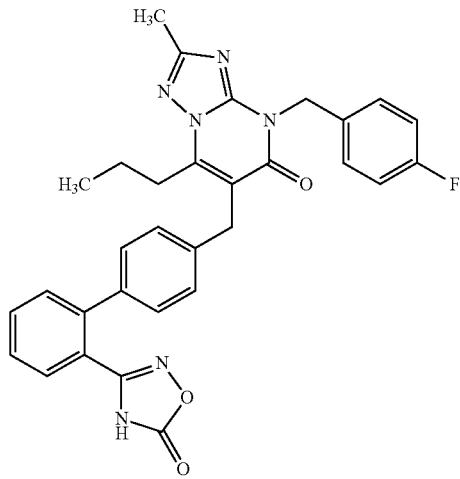 [SMILES: CCCc1c(Cc2ccc(-c3ccccc3-c3noc(=O)[nH]3)cc2)c(=O)n(Cc2ccc(F)cc2)c2nc(C)nn12]

A mixture of hydroxylammonium chloride (1.2 g), sodium hydrogen carbonate (1.9 g) and dimethyl sulfoxide (15 mL) was stirred at 40° C. for 30 min, 4'-{[2-methyl-4-(4-fluorobenzyl)-5-oxo-7-propyl-4,5-dihydro[1,2,4]triazolo[1,5-a]pyrimidin-6-yl]methyl}biphenyl-2-carbonitrile (0.56 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.22 g) and then 1,8-diazabicyclo[5.4.0]undec-7-ene (0.19 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.26 g, 41%).

$^1$H NMR (300 MHz, DMSO-$d_6$) δ0.92 (t, J=7.4, 3H), 1.47-1.64 (m, 2H), 2.35 (s, 3H), 2.84-3.02 (m, 2H), 3.96 (s, 2H), 5.25 (s, 2H), 7.11-7.26 (m, 4H), 7.27-7.36 (m, 2H), 7.39-7.48 (m, 2H), 7.53 (dd, J=15.7, 7.8, 2H), 7.61-7.75 (m, 2H), 12.39 (s, 1H)

EXAMPLE 6

2-cyclopropyl-4-(4-fluorobenzyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

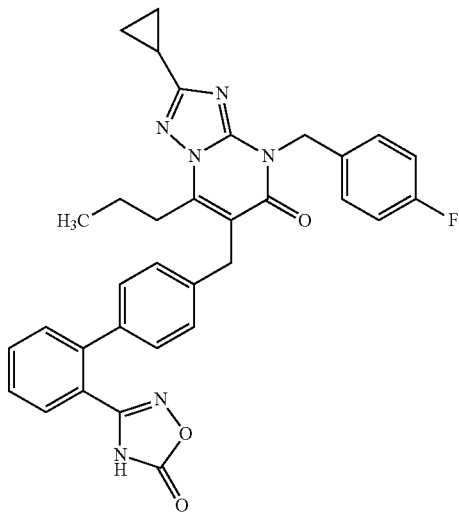 [SMILES: CCCc1c(Cc2ccc(-c3ccccc3-c3noc(=O)[nH]3)cc2)c(=O)n(Cc2ccc(F)cc2)c2nc(C3CC3)nn12]

A mixture of hydroxylammonium chloride (0.89 g), sodium hydrogen carbonate (1.4 g) and dimethyl sulfoxide (15 mL) was stirred at 40° C. for 30 min, 4'-{[2-cyclopropyl-4-(4-fluorobenzyl)-5-oxo-7-propyl-4,5-dihydro[1,2,4]triazolo[1,5-a]pyrimidin-6-yl]methyl}biphenyl-2-carbonitrile (0.44 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.2 g, 58%).

$^1$H NMR (300 MHz, DMSO-$d_6$) δ0.84-0.96 (m, 5H), 0.96-1.08 (m, 2H), 1.43-1.67 (m, 2H), 2.01-2.14 (m, 1H), 2.82-2.95 (m, 2H), 3.94 (s, 2H), 5.20 (s, 2H), 7.11-7.25 (m, 4H), 7.26-7.33 (m, 2H), 7.39-7.47 (m, 2H), 7.47-7.59 (m, 2H), 7.61-7.75 (m, 2H), 12.39 (s, 1H)

EXAMPLE 7

4-[(6-ethylpyridin-3-yl)methyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

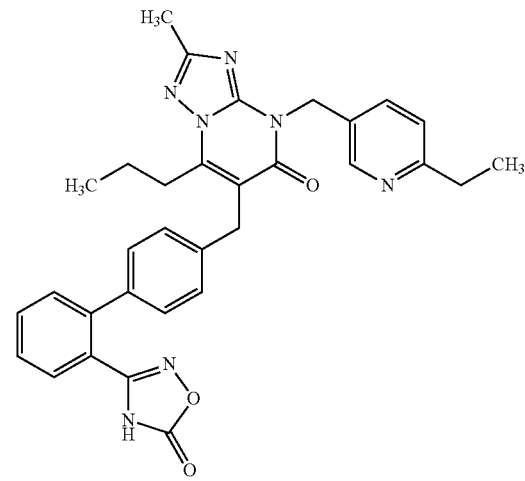 [SMILES: CCCc1c(Cc2ccc(-c3ccccc3-c3noc(=O)[nH]3)cc2)c(=O)n(Cc2ccc(CC)nc2)c2nc(C)nn12]

A mixture of hydroxylammonium chloride (0.9 g), sodium hydrogen carbonate (1.4 g) and dimethyl sulfoxide (10 mL) was stirred at 40° C. for 30 min, 4'-({4-[(6-ethylpyridin-3-yl)methyl]-2-methyl-5-oxo-7-propyl-4,5-dihydro[1,2,4]triazolo[1,5-a]pyrimidin-6-yl}methyl)biphenyl-2-carbonitrile (0.43 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.22 g, 46%).

$^1$H NMR (300 MHz, DMSO-$d_6$) δ0.92 (t, J=7.3, 3H), 1.17 (t, J=7.2, 3H), 1.48-1.62 (m, 2H), 2.36 (s, 3H), 2.70 (q, J=7.5, 2H), 2.84-2.95 (m, 2H), 3.96 (s, 2H), 5.26 (s, 2H), 7.18-7.25 (m, 3H), 7.27-7.34 (m, 2H), 7.47-7.59 (m, 2H), 7.62-7.73 (m, 3H), 8.54 (d, J=2.1, 1H), 12.39 (br. s., 1H)

EXAMPLE 8

4-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

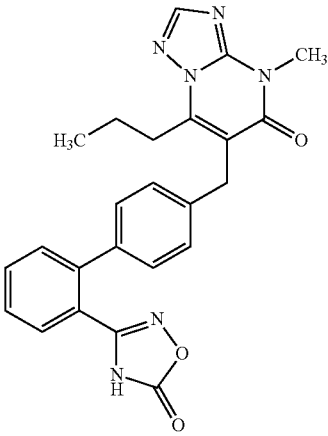 [SMILES: CCCc1c(Cc2ccc(-c3ccccc3-c3noc(=O)[nH]3)cc2)c(=O)n(C)c2ncnn12]

A mixture of hydroxylammonium chloride (1.49 g), sodium hydrogen carbonate (2.4 g) and dimethyl sulfoxide (15 mL) was stirred at 40° C. for 30 min, 4'-[(4-methyl-5-oxo-7-propyl-4,5-dihydro[1,2,4]triazolo[1,5-a]pyrimidin-6-yl)methyl]biphenyl-2-carbonitrile (0.52 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.28 g) and then 1,8-diazabicyclo[5.4.0]undec-7-ene (0.24 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.24 g, 38%).

$^1$H NMR (300 MHz, DMSO-$d_6$) δ 0.88-0.96 (m, 3H), 1.48-1.63 (m, 2H), 2.89-3.00 (m, 2H), 3.55 (s, 3H), 3.97 (s, 2H), 7.18-7.24 (m, 2H), 7.28-7.34 (m, 2H), 7.47-7.58 (m, 2H), 7.62-7.74 (m, 2H), 8.18 (s, 1H), 12.39 (s, 1H)

EXAMPLE 9

4-(2,2-dimethylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

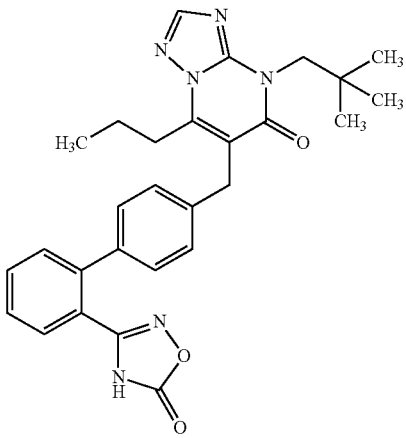 [SMILES: CCCc1c(Cc2ccc(-c3ccccc3-c3noc(=O)[nH]3)cc2)c(=O)n(CC(C)(C)C)c2ncnn12]

A mixture of hydroxylammonium chloride (0.95 g), sodium hydrogen carbonate (1.53 g) and dimethyl sulfoxide (15 mL) was stirred at 40° C. for 30 min, 4'-{[4-(2,2-dimethylpropyl)-5-oxo-7-propyl-4,5-dihydro[1,2,4]triazolo[1,5-a]pyrimidin-6-yl]methyl}biphenyl-2-carbonitrile (0.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.18 g, 40%).

$^1$H NMR (300 MHz, DMSO-$d_6$) δ 0.88-1.01 (m, 12H) 1.46-1.63 (m, 2H) 2.90-3.02 (m, 2H) 3.98 (s, 2H) 4.01-4.08 (m, 2H) 7.16-7.25 (m, 2H) 7.27-7.35 (m, 2H) 7.52 (dd, J=17.4, 7.6 Hz, 2H) 7.59-7.70 (m, 2H) 8.15 (s, 1H) 12.38 (br. s., 1H)

EXAMPLE 10

4-(3,3-dimethyl-2-oxobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

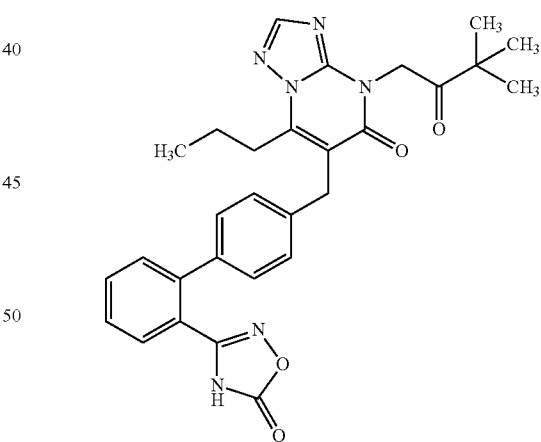

A mixture of hydroxylammonium chloride (0.9 g), sodium hydrogen carbonate (1.4 g) and dimethyl sulfoxide (10 mL) was stirred at 40° C. for 30 min, 4'-{[4-(3,3-dimethyl-2-oxobutyl)-5-oxo-7-propyl-4,5-dihydro[1,2,4]triazolo[1,5-a]pyrimidin-6-yl]methyl}biphenyl-2-carbonitrile (0.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.17 g, 37%).

$^1$H NMR (300 MHz, DMSO-$d_6$) δ0.94 (t, J=7.3 Hz, 3H) 1.23 (s, 9H) 1.48-1.68 (m, 2H) 2.95-3.05 (m, 2H) 3.98 (s, 2H) 5.20 (s, 2H) 7.19-7.27 (m, 2H) 7.27-7.35 (m, 2H) 7.46-7.59 (m, 2H) 7.61-7.73 (m, 2H) 8.17 (s, 1H) 12.38 (br. s., 1H)

EXAMPLE 11

4-[2-(4-fluorophenyl)-2-hydroxyethyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

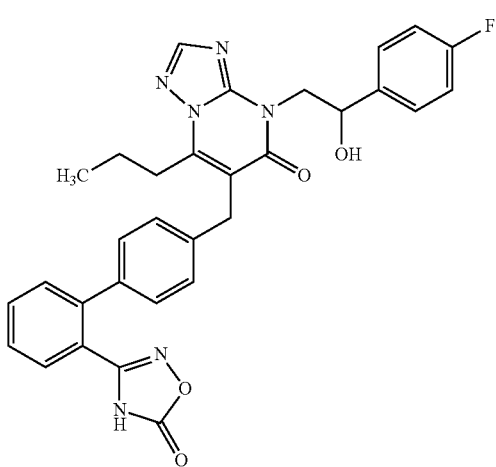 [SMILES: CCCc1c(Cc2ccc(-c3ccccc3-c3noc(=O)[nH]3)cc2)c(=O)n(CC(O)c2ccc(F)cc2)c2ncnn12]

A mixture of hydroxylammonium chloride (0.94 g), sodium hydrogen carbonate (1.51 g) and dimethyl sulfoxide (10 mL) was stirred at 50° C. for 30 min, 4'-({4-[2-{[tert-butyl(dimethyl)silyl]oxy}-2-(4-fluorophenyl)ethyl]-5-oxo-7-propyl-4,5-dihydro[1,2,4]triazolo[1,5-a]pyrimidin-6-yl}methyl)biphenyl-2-carbonitrile (0.56 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 2.7 mL) was added, and the mixture was stirred at room temperature for 3 hr. The reaction mixture was extracted with ethyl acetate and 1 N hydrochloric acid, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.31 g, 61%).

$^1$H NMR (300 MHz, DMSO-$d_6$) δ0.91 (t, J=7.3, 3H), 1.46-1.62 (m, 2H), 2.89-3.00 (m, 2H), 3.96 (s, 2H), 4.15 (dd, J=13.0, 4.9, 1H), 4.37 (dd, J=13.0, 8.7, 1H), 5.11-5.21 (m, 1H), 5.66 (d, J=4.5, 1H), 7.09-7.28 (m, 6H), 7.32-7.41 (m, 2H), 7.46-7.58 (m, 2H), 7.62-7.72 (m, 2H), 8.18 (s, 1H), 12.40 (s, 1H)

EXAMPLE 12

4-[2-(4-fluorophenyl)-2-oxoethyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

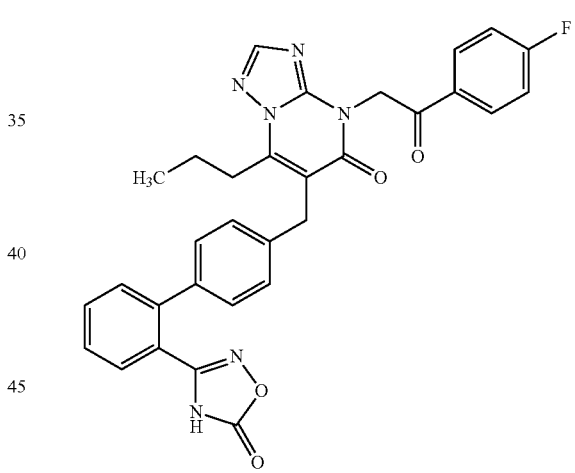

A mixture of 4-[2-(4-fluorophenyl)-2-hydroxyethyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.31 g), Dess-Martin reagent (0.35 g) and acetonitrile (10 mL) was stirred at room temperature for 2 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as a colorless amorphous solid (0.2 g, 65%).

$^1$H NMR (300 MHz, DMSO-$d_6$) δ0.96 (t, J=7.3, 3H), 1.54-1.67 (m, 2H), 2.97-3.08 (m, 2H), 4.00 (s, 2H), 5.71 (s, 2H), 7.20-7.27 (m, 2H), 7.28-7.35 (m, 2H), 7.40-7.59 (m, 4H), 7.62-7.72 (m, 2H), 8.16-8.25 (m, 3H), 12.39 (s, 1H)

EXAMPLE 13 tert-butyl [5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]acetate

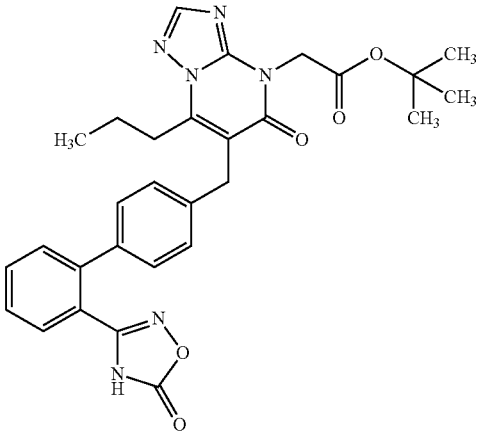 [SMILES: CCCc1c(Cc2ccc(-c3ccccc3-c3noc(=O)[nH]3)cc2)c(=O)n(CC(=O)OC(C)(C)C)c2ncnn12]

A mixture of hydroxylammonium chloride (1.7 g), sodium hydrogen carbonate (2.7 g) and dimethyl sulfoxide (15 mL) was stirred at 40° C. for 30 min, tert-butyl {6-[(2'-cyanobiphenyl-4-yl)methyl]-5-oxo-7-propyl[1,2,4]triazolo[1,5-a]pyrimidin-4(5H)-yl}acetate (0.8 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.32 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.73 g, 82%).

$^1$H NMR (300 MHz, DMSO-$d_6$) δ0.93 (t, J=7.3 Hz, 3H), 1.39 (s, 9H), 1.49-1.61 (m, 2H), 2.94-3.05 (m, 2H), 3.99 (s, 2H), 4.78 (s, 2H), 7.19-7.26 (m, 2H), 7.27-7.33 (m, 2H), 7.47-7.59 (m, 2H), 7.62-7.72 (m, 2H), 8.21 (s, 1H), 12.38 (s, 1H)

EXAMPLE 14

4-(2-hydroxyethyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

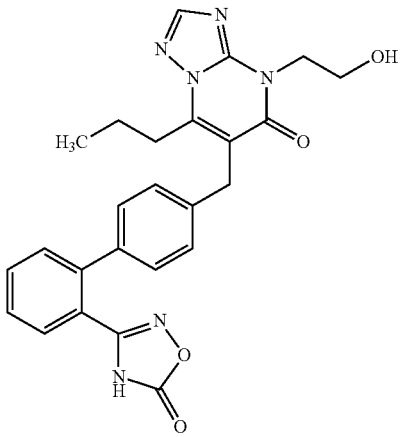 [SMILES: CCCc1c(Cc2ccc(-c3ccccc3-c3noc(=O)[nH]3)cc2)c(=O)n(CCO)c2ncnn12]

A mixture of hydroxylammonium chloride (1.6 g), sodium hydrogen carbonate (2.6 g) and dimethyl sulfoxide (15 mL) was stirred at 50° C. for 30 min, 4'-{[4-(2-{[tert-butyl(dimethyl)silyl]oxy}ethyl)-5-oxo-7-propyl-4,5-dihydro[1,2,4]triazolo[1,5-a]pyrimidin-6-yl]methyl}biphenyl-2-carbonitrile (0.82 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.3 g) and then 1,8-diazabicyclo[5.4.0]undec-7-ene (0.15 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 2.7 mL) was added, and the mixture was stirred at room temperature for 3 hr. The reaction mixture was extracted with ethyl acetate and 1 N hydrochloric acid, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.31 g, 61%).

$^1$H NMR (300 MHz, DMSO-$d_6$) δ0.93 (t, J=7.3, 3H), 1.45-1.65 (m, 2H), 2.88-3.00 (m, 2H), 3.66-3.76 (m, 2H), 3.98 (s, 2H), 4.18-4.26 (m, 2H), 4.86 (t, J=6.0, 1H), 7.19-7.26 (m, 2H), 7.29-7.35 (m, 2H), 7.47-7.58 (m, 2H), 7.61-7.72 (m, 2H), 8.17 (s, 1H), 12.39 (br. s., 1H)

EXAMPLE 15

2-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]acetamide

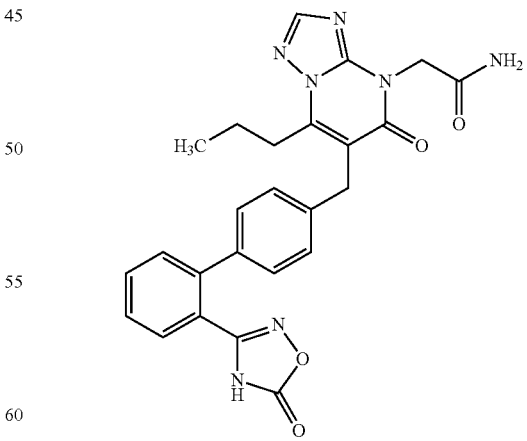

A mixture of hydroxylammonium chloride (1.3 g), sodium hydrogen carbonate (2.1 g) and dimethyl sulfoxide (10 mL) was stirred at 40° C. for 30 min, 2-{6-[(2'-cyanobiphenyl-4-yl)methyl]-5-oxo-7-propyl[1,2,4]triazolo[1,5-a]pyrimidin-4(5H)-yl}acetamide (0.48 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.25 g, 42%).

$^1$H NMR (300 MHz, DMSO-$d_6$) δ0.94 (t, J=7.3, 3H), 1.47-1.65 (m, 2H), 2.91-3.03 (m, 2H), 3.98 (s, 2H), 4.67 (s, 2H), 7.20-7.36 (m, 5H), 7.48-7.59 (m, 2H), 7.61-7.76 (m, 3H), 8.17 (s, 1H), 12.39 (br. s., 1H)

EXAMPLE 16

[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]acetic acid

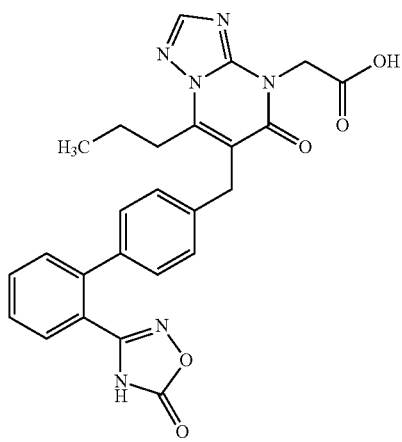 [SMILES: CCCc1c(Cc2ccc(-c3ccccc3-c3noc(=O)[nH]3)cc2)c(=O)n(CC(=O)O)c2ncnn12]

A mixture of tert-butyl [5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]acetate (0.58 g) and trifluoroacetic acid (10 mL) was stirred at room temperature for 2 hr. The reaction mixture was diluted with toluene (10 mL), and the solvent was evaporated under reduced pressure. The residue was purified by silica gel column chromatography to give the title compound as a colorless solid (0.19 g, 36%).

$^1$H NMR (300 MHz, DMSO-$d_6$) δ0.94 (t, J=7.3, 3H), 1.46-1.67 (m, 2H), 2.91-3.06 (m, 2H), 3.99 (s, 2H), 4.81 (s, 2H), 7.20-7.25 (m, 2H), 7.28-7.35 (m, 2H), 7.47-7.58 (m, 2H), 7.62-7.73 (m, 2H), 8.21 (s, 1H), 12.15-13.63 (m, 2H)

EXAMPLE 17

4-(1-methylethyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

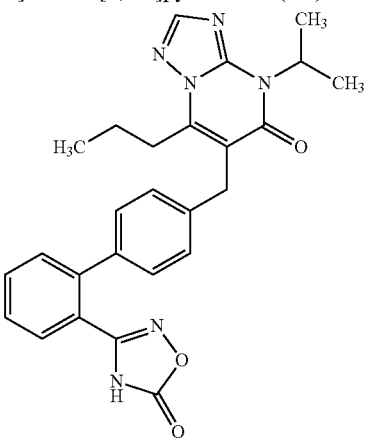

A mixture of hydroxylammonium chloride (1.2 g), sodium hydrogen carbonate (1.9 g) and dimethyl sulfoxide (10 mL) was stirred at 40° C. for 30 min, 4'-{[4-(1-methylethyl)-5-oxo-7-propyl-4,5-dihydro[1,2,4]triazolo[1,5-a]pyrimidin-6-yl]methyl}biphenyl-2-carbonitrile (0.48 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.22 g) and then 1,8-diazabicyclo[5.4.0]undec-7-ene (0.19 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.19 g, 35%).

$^1$H NMR (300 MHz, DMSO-$d_6$) δ0.92 (t, J=7.3, 3H), 1.47-1.61 (m, 8H), 2.88-2.97 (m, 2H), 3.96 (s, 2H), 5.22-5.35 (m, 1H), 7.19-7.27 (m, 2H), 7.28-7.34 (m, 2H), 7.48-7.58 (m, 2H), 7.61-7.72 (m, 2H), 8.19 (s, 1H), 12.38 (s, 1H)

EXAMPLE 18

4-(2-hydroxy-2-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

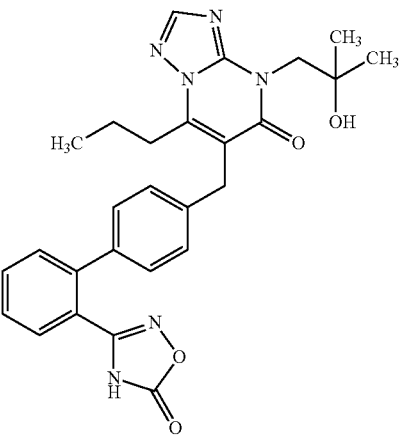 [SMILES: CCCc1c(Cc2ccc(-c3ccccc3-c3noc(=O)[nH]3)cc2)c(=O)n(CC(C)(C)O)c2ncnn12]

A mixture of hydroxylammonium chloride (1.8 g), sodium hydrogen carbonate (2.9 g) and dimethyl sulfoxide (15 mL) was stirred at 40° C. for 30 min, 4'-{[4-(2-hydroxy-2-methylpropyl)-5-oxo-7-propyl-4,5-dihydro[1,2,4]triazolo[1,5-a]pyrimidin-6-yl]methyl}biphenyl-2-carbonitrile (0.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.33 g) and then 1,8-diazabicyclo[5.4.0]undec-7-ene (0.28 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.2 g, 24%).

$^1$H NMR (300 MHz, DMSO-$d_6$) δ0.93 (t, J=7.3, 3H), 1.13 (s, 6H), 1.50-1.66 (m, 2H), 2.90-2.99 (m, 2H), 3.99 (s, 2H), 4.18 (s, 2H), 4.63 (s, 1H), 7.19-7.25 (m, 2H), 7.29-7.35 (m, 2H), 7.47-7.59 (m, 2H), 7.61-7.72 (m, 2H), 8.16 (s, 1H), 12.38 (s, 1H)

EXAMPLE 19

4-[(1-methyl-1H-benzimidazol-2-yl)methyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one hydrochloride

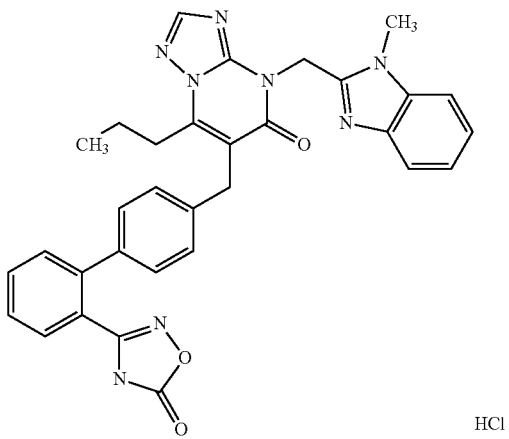 [SMILES: CCCc1c(Cc2ccc(-c3ccccc3-c3noc(=O)[nH]3)cc2)c(=O)n(Cc2nc3ccccc3n2C)c2ncnn12 ; Cl]

HCl

A mixture of hydroxylammonium chloride (1.7 g), sodium hydrogen carbonate (2.8 g) and dimethyl sulfoxide (15 mL) was stirred at 40° C. for 30 min, 4'-({4-[(1-methyl-1H-benzimidazol-2-yl)methyl]-5-oxo-7-propyl-4,5-dihydro[1,2,4]triazolo[1,5-a]pyrimidin-6-yl}methyl)biphenyl-2-carbonitrile (0.84 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.32 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography, and dissolved in ethyl acetate (10 mL), hydrochloric acid (4N ethyl acetate solution, 0.051 mL) was added, and the mixture was stirred at room temperature. The precipitated solid was collected by filtration to give the title compound as a colorless amorphous solid (0.13 g, 39%).

$^1$H NMR (300 MHz, DMSO-$d_6$) δ0.96 (t, J=7.4 Hz, 3H), 1.52-1.69 (m, 2H), 2.94-3.05 (m, 2H), 4.00 (s, 2H), 4.07 (s, 3H), 5.84 (s, 2H), 7.18-7.26 (m, 2H), 7.30-7.37 (m, 2H), 7.43-7.60 (m, 4H), 7.63-7.76 (m, 3H), 7.89 (d, J=8.0 Hz, 1H), 8.25 (s, 1H), 12.47 (s, 1H)

EXAMPLE 20

4-ethyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

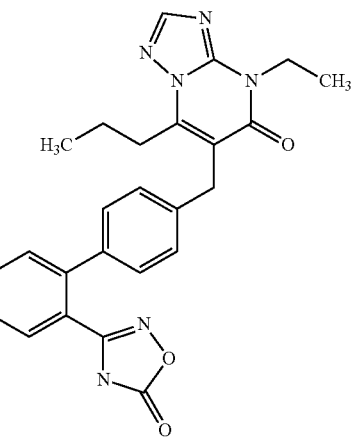

A mixture of hydroxylammonium chloride (1.4 g), sodium hydrogen carbonate (2.3 g) and dimethyl sulfoxide (15 mL) was stirred at 40° C. for 30 min, 4'-[(4-ethyl-5-oxo-7-propyl-4,5-dihydro[1,2,4]triazolo[1,5-a]pyrimidin-6-yl)methyl]biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.21 g, 34%).

$^1$H NMR (300 MHz, DMSO-$d_6$) δ0.93 (t, J=7.2 Hz, 3H), 1.27 (t, J=7.0 Hz, 3H), 1.45-1.64 (m, 2H), 2.88-3.01 (m, 2H), 3.98 (s, 2H), 4.16 (q, J=6.8 Hz, 2H), 7.18-7.27 (m, 2H), 7.28-7.38 (m, 2H), 7.53 (dd, J=16.1, 7.8 Hz, 2H), 7.61-7.77 (m, 2H), 8.20 (s, 1H), 12.39 (br. s., 1H)

EXAMPLE 21

4-(cyclopropylmethyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

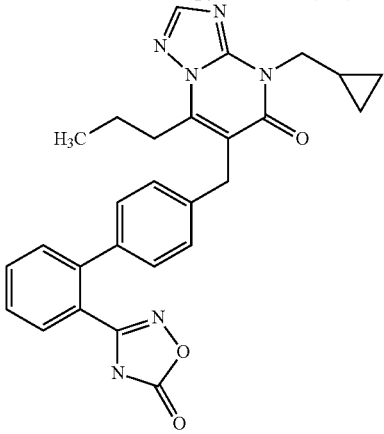 [SMILES: CCCc1c(Cc2ccc(-c3ccccc3-c3noc(=O)[nH]3)cc2)c(=O)n(CC2CC2)c2ncnn12]

A mixture of hydroxylammonium chloride (1.3 g), sodium hydrogen carbonate (2.2 g) and dimethyl sulfoxide (15 mL) was stirred at 40° C. for 30 min, 4'-{[4-(cyclopropylmethyl)-5-oxo-7-propyl-4,5-dihydro[1,2,4]triazolo[1,5-a]pyrimidin-6-yl]methyl}biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.17 g, 27%).

$^1$H NMR (300 MHz, DMSO-$d_6$) δ0.40-0.54 (m, 4H), 0.93 (t, J=7.2 Hz, 3H), 1.25-1.41 (m, 1H), 1.46-1.65 (m, 2H), 2.92-3.02 (m, 2H), 3.95-4.07 (m, 4H), 7.20-7.27 (m, 2H), 7.29-7.37 (m, 2H), 7.53 (dd, J=15.9, 7.6 Hz, 2H), 7.63-7.75 (m, 2H), 8.19 (s, 1H), 12.39 (s, 1H)

EXAMPLE 22

2-methyl-4-(1-methylethyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

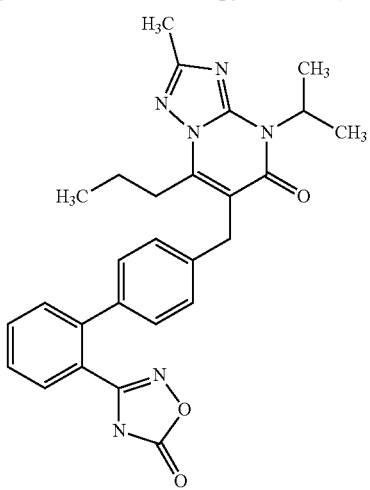 [SMILES: CCCc1c(Cc2ccc(-c3ccccc3-c3noc(=O)[nH]3)cc2)c(=O)n(C(C)C)c2nc(C)nn12]

A mixture of hydroxylammonium chloride (0.68 g), sodium hydrogen carbonate (1.1 g) and dimethyl sulfoxide (10 mL) was stirred at 40° C. for 30 min, 4'-{[2-methyl-4-(1-methylethyl)-5-oxo-7-propyl-4,5-dihydro[1,2,4]triazolo[1,5-a]pyrimidin-6-yl]methyl}biphenyl-2-carbonitrile (0.28 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.18 g, 56%).

$^1$H NMR (300 MHz, DMSO-$d_6$) δ0.92 (t, J=7.4 Hz, 3H) 1.42-1.61 (m, 8H) 2.36 (s, 3H) 2.83-2.96 (m, 2H) 3.94 (s, 2H) 5.16-5.33 (m, 1H) 7.18-7.26 (m, 2H) 7.26-7.33 (m, 2H) 7.45-7.59 (m, 2H) 7.61-7.71 (m, 2H) 12.38 (br. s., 1H)

EXAMPLE 23

4-(2-hydroxybutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

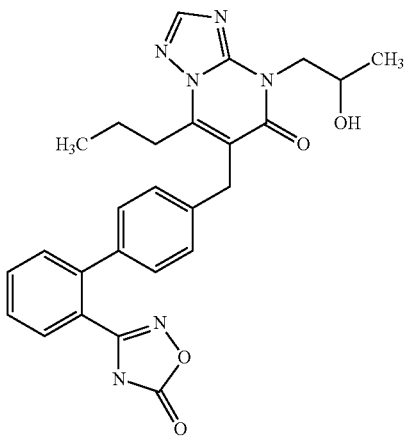 [SMILES: CCCc1c(Cc2ccc(-c3ccccc3-c3noc(=O)[nH]3)cc2)c(=O)n(CC(C)O)c2ncnn12]

A mixture of hydroxylammonium chloride (1.1 g), sodium hydrogen carbonate (1.7 g) and dimethyl sulfoxide (15 mL) was stirred at 40° C. for 30 min, 4'-{[4-(2-hydroxybutyl)-5-oxo-7-propyl-4,5-dihydro[1,2,4]triazolo[1,5-a]pyrimidin-6-yl]methyl}biphenyl-2-carbonitrile (0.28 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.28 g, 54%).

$^1$H NMR (300 MHz, DMSO-$d_6$) δ0.85-0.98 (m, 6H), 1.29-1.64 (m, 4H), 2.88-2.98 (m, 2H), 3.85-4.00 (m, 4H), 4.14-4.26 (m, 1H), 4.78 (d, J=5.3 Hz, 1H), 7.18-7.25 (m, 2H), 7.26-7.36 (m, 2H), 7.53 (dd, J=16.3, 7.6 Hz, 2H), 7.61-7.75 (m, 2H), 8.16 (s, 1H), 12.38 (s, 1H)

EXAMPLE 24

2-cyclopropyl-4-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

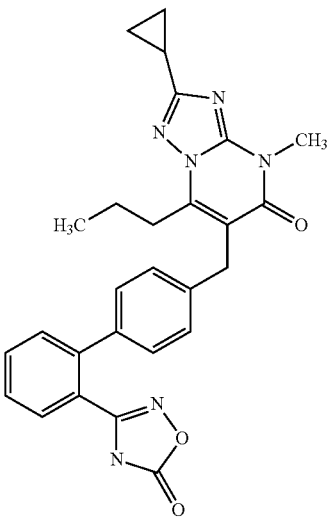 [SMILES: CCCc1c(Cc2ccc(-c3ccccc3-c3noc(=O)[nH]3)cc2)c(=O)n(C)c2nc(C3CC3)nn12]

A mixture of hydroxylammonium chloride (0.65 g), sodium hydrogen carbonate (0.99 g) and dimethyl sulfoxide (10 mL) was stirred at 40° C. for 30 min, 4'-[(2-cyclopropyl-4-methyl-5-oxo-7-propyl-4,5-dihydro[1,2,4]triazolo[1,5-a]pyrimidin-6-yl)methyl]biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.091 g) and then 1,8-diazabicyclo[5.4.0]undec-7-ene (0.077 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.16 g, 71%).

$^1$H NMR (300 MHz, DMSO-$d_6$) δ0.88-1.04 (m, 7H), 1.45-1.65 (m, 2H), 2.01-2.14 (m, 1H), 2.84-2.95 (m, 2H), 3.48 (s, 3H), 3.94 (s, 2H), 7.17-7.25 (m, 2H), 7.25-7.33 (m, 2H), 7.52 (dd, J=16.7, 7.6 Hz, 2H), 7.61-7.72 (m, 2H), 12.38 (br. s., 1H)

EXAMPLE 25

4-[4-(1-methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

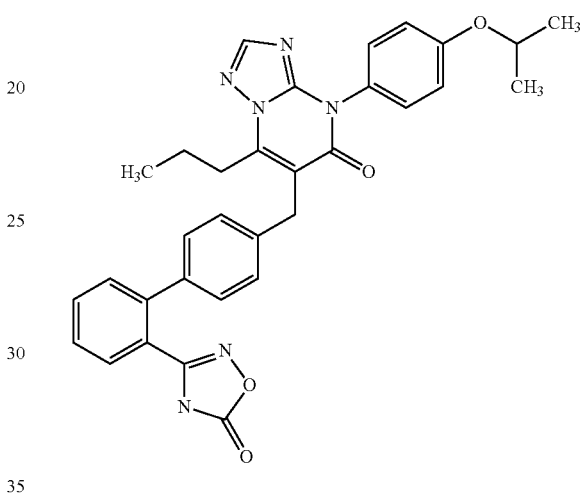

A mixture of hydroxylammonium chloride (1.2 g), sodium hydrogen carbonate (1.9 g) and dimethyl sulfoxide (15 mL) was stirred at 40° C. for 30 min, 4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile (0.57 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.22 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.39 g, 61%).

$^1$H NMR (300 MHz, DMSO-$d_6$) δ0.96 (t, J=7.0 Hz, 3H), 1.31 (dd, J=6.1, 1.5 Hz, 6H), 1.49-1.68 (m, 2H), 2.89-3.05 (m, 2H), 3.99 (s, 2H), 4.57-4.76 (m, 1H), 7.03 (d, J=7.2 Hz, 2H), 7.23 (d, J=6.8 Hz, 2H), 7.36 (d, J=8.7 Hz, 4H), 7.48-7.60 (m, 2H), 7.61-7.73 (m, 2H), 8.06 (d, J=1.9 Hz, 1H), 12.4 (br. s., 1H)

EXAMPLE 26

4-[4-(1-methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

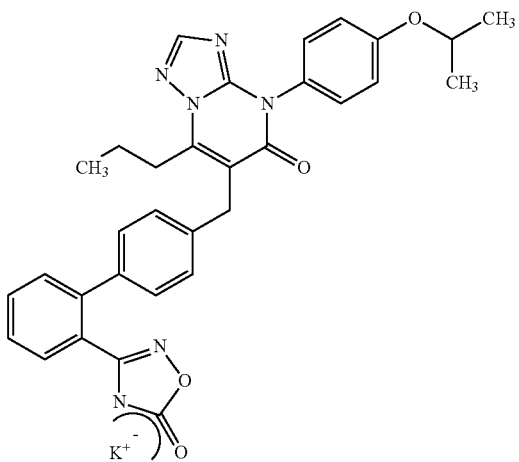 [SMILES: CCCc1c(Cc2ccc(-c3ccccc3-c3noc(=O)[nH]3)cc2)c(=O)n(-c2ccc(OC(C)C)cc2)c2ncnn12 ; [K+]]

4-[4-(1-Methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.39 g) was suspended in water (3 mL), 2N potassium hydroxide solution (0.34 mL) was added, and the solvent was evaporated under reduced pressure. The residue was solidified with diisopropyl ether to give the title compound as a colorless solid (0.42 g, 100%).

$^1$H NMR (300 MHz, DMSO-$d_6$) δ0.96-1.06 (m, 3H), 1.30 (s, 3H), 1.32 (s, 3H), 1.59-1.73 (m, 2H), 2.96-3.06 (m, 2H), 3.95 (s, 2H), 4.60-4.75 (m, 1H), 7.03 (d, J=8.7 Hz, 2H), 7.19-7.50 (m, 10H), 8.04 (s, 1H)

EXAMPLE 27

4-[4-(1-hydroxyethyl)benzyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

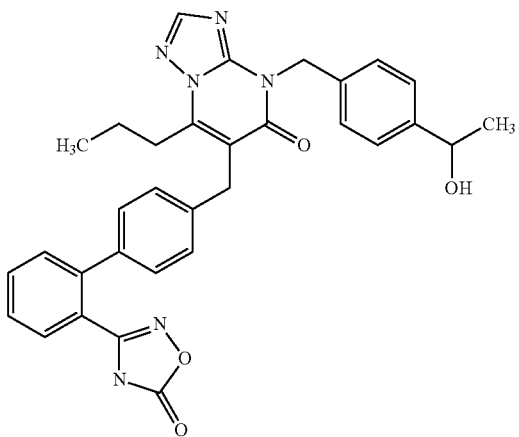 [SMILES: CCCc1c(Cc2ccc(-c3ccccc3-c3noc(=O)[nH]3)cc2)c(=O)n(Cc2ccc(C(C)O)cc2)c2ncnn12]

A mixture of hydroxylammonium chloride (2.4 g), sodium hydrogen carbonate (3.9 g) and dimethyl sulfoxide (15 mL) was stirred at 40° C. for 30 min, 4'-({4-[4-(1-{[tert-butyl(dimethyl)silyl]oxy}ethyl)benzyl]-5-oxo-7-propyl-4,5-dihydro[1,2,4]triazolo[1,5-a]pyrimidin-6-yl}methyl)biphenyl-2-carbonitrile (1.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.45 g) and then 1,8-diazabicyclo[5.4.0]undec-7-ene (0.38 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (30 mL). Tetrabutylammonium bromide (1.0 M tetrahydrofuran solution, 5.8 mL) was added, and the mixture was stirred at 50° C. for 3 hr. The reaction mixture was extracted with 1 N hydrochloric acid and ethyl acetate, and the ethyl acetate layer was washed with saturated brine and concentrated. The residue was purified by silica gel column chromatography to give the title compound as colorless crystals (0.72 g, 56%).

$^1$H NMR (300 MHz, DMSO-$d_6$) δ0.92 (t, J=7.3 Hz, 3H), 1.27 (d, J=6.4 Hz, 3H), 1.49-1.63 (m, 2H), 2.89-3.02 (m, 2H), 3.99 (s, 2H), 4.60-4.74 (m, 1H), 5.09 (d, J=4.1 Hz, 1H), 5.28 (s, 2H), 7.18-7.36 (m, 8H), 7.46-7.59 (m, 2H), 7.62-7.73 (m, 2H), 8.20 (s, 1H), 12.39 (s, 1H)

EXAMPLE 28

4-(4-acetylbenzyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

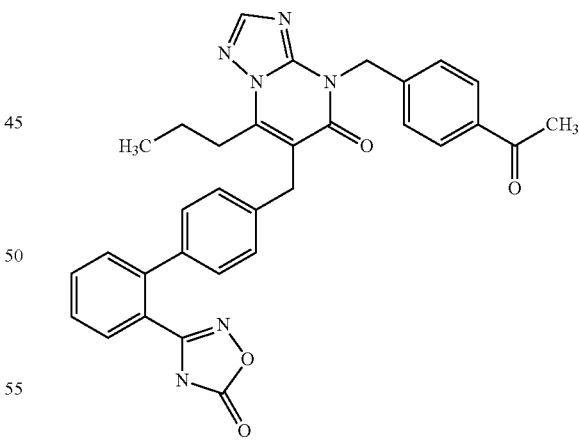

A mixture of 4-[4-(1-hydroxyethyl)benzyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.5 g), manganese dioxide (2.3 g) and methylene chloride (20 mL) was stirred at room temperature for 16 hr. The insoluble material was filtered off through celite, and the filtrate was concentrated. The obtained residue was purified by silica gel column chromatography to give the title compound as colorless crystals (0.43 g, 85%).

$^1$H NMR (300 MHz, DMSO-d$_6$) δ0.93 (t, J=7.3 Hz, 3H), 1.49-1.65 (m, 2H), 2.54 (s, 3H), 2.90-3.03 (m, 2H), 3.99 (s, 2H), 5.37 (s, 2H), 7.18-7.26 (m, 2H), 7.28-7.36 (m, 2H), 7.44-7.59 (m, 4H), 7.62-7.71 (m, 2H), 7.87-7.96 (m, 2H), 8.19 (s, 1H), 12.39 (s, 1H)

EXAMPLE 29

6-{[2'-(5-oxo-4,5-dihydro-1,2,4-oxadiazol-3-yl)biphenyl-4-yl]methyl}-4,7-dipropyl[1,2,4]triazolo[1,5-a]pyrimidin-5(4H)-one

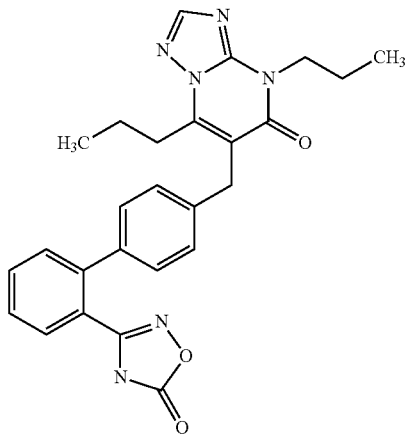 [SMILES: CCCc1c(Cc2ccc(-c3ccccc3-c3noc(=O)[nH]3)cc2)c(=O)n(CCC)c2ncnn12]

A mixture of hydroxylammonium chloride (1.3 g), sodium hydrogen carbonate (2.1 g) and dimethyl sulfoxide (15 mL) was stirred at 40° C. for 30 min, 4'-[(5-oxo-4,7-dipropyl-4,5-dihydro[1,2,4]triazolo[1,5-a]pyrimidin-6-yl)methyl]biphenyl-2-carbonitrile (0.5 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.26 g, 45%).

$^1$H NMR (300 MHz, DMSO-d$_6$) δ0.91 (q, J=7.6 Hz, 6H), 1.45-1.63 (m, 2H), 1.63-1.81 (m, 2H), 2.88-3.02 (m, 2H), 3.97 (s, 2H), 4.05-4.15 (m, 2H), 7.19-7.25 (m, 2H), 7.27-7.36 (m, 2H), 7.53 (dd, J=16.5, 7.8 Hz, 2H), 7.60-7.73 (m, 2H), 8.18 (s, 1H), 12.36 (s, 1H)

EXAMPLE 30

6-{[2'-(5-oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one

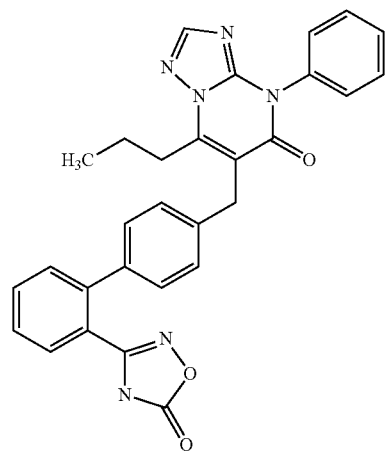 [SMILES: CCCc1c(Cc2ccc(-c3ccccc3-c3noc(=O)[nH]3)cc2)c(=O)n(-c2ccccc2)c2ncnn12]

A mixture of hydroxylammonium chloride (1.4 g), sodium hydrogen carbonate (2.2 g) and dimethyl sulfoxide (15 mL) was stirred at 40° C. for 30 min, 4'-[(5-oxo-4-phenyl-7-propyl-4,5-dihydro[1,2,4]triazolo[1,5-a]pyrimidin-6-yl)methyl]biphenyl-2-carbonitrile (0.58 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.23 g, 44%).

$^1$H NMR (300 MHz, DMSO-d$_6$) δ0.97 (t, J=7.4 Hz, 3H), 1.50-1.70 (m, 2H), 2.91-3.05 (m, 2H), 4.01 (s, 2H), 7.23 (d, J=8.0 Hz, 2H), 7.37 (d, J=8.3 Hz, 2H), 7.42-7.60 (m, 7H), 7.61-7.74 (m, 2H), 8.06 (s, 1H), 12.38 (s, 1H)

EXAMPLE 31

2-methyl-4-[4-(1-methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

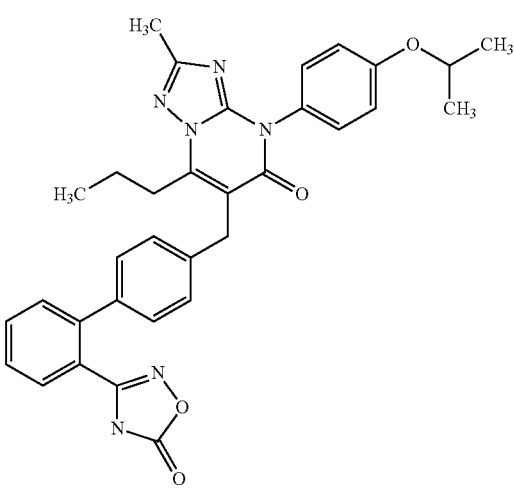 [SMILES: CCCc1c(Cc2ccc(-c3ccccc3-c3noc(=O)[nH]3)cc2)c(=O)n(-c2ccc(OC(C)C)cc2)c2nc(C)nn12]

A mixture of hydroxylammonium chloride (0.81 g), sodium hydrogen carbonate (1.3 g) and dimethyl sulfoxide (10 mL) was stirred at 40° C. for 30 min, 4'-({2-methyl-4-[4-(1-methylethoxy)phenyl]-5-oxo-7-propyl-4,5-dihydro[1,2,4]triazolo[1,5-a]pyrimidin-6-yl}methyl)biphenyl-2-carbonitrile (0.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.15 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.24 g, 53%).

$^1$H NMR (300 MHz, DMSO-$d_6$) δ0.96 (t, J=7.3 Hz, 3H), 1.31 (d, J=6.0 Hz, 6H), 1.50-1.69 (m, 2H), 2.26 (s, 3H), 2.94 (dd, J=9.0, 6.4 Hz, 2H), 3.97 (s, 2H), 4.58-4.74 (m, 1H), 6.96-7.09 (m, 2H), 7.17-7.26 (m, 2H), 7.29-7.40 (m, 4H), 7.46-7.58 (m, 2H), 7.61-7.77 (m, 2H), 12.39 (s, 1H)

EXAMPLE 32

2-methyl-4-[4-(1-methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt 2-Methyl-4-[4-(1-methylethoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.24 g) was suspended in isopropyl alcohol (5 mL), 2N potassium hydroxide solution (0.21 mL) was added, and the solvent was evaporated under reduced pressure. The residue was solidified with diisopropyl ether to give the title compound as a colorless solid (0.23 g, 95%).

$^1$H NMR (300 MHz, DMSO-$d_6$) δ0.99 (t, J=7.4 Hz, 3H), 1.31 (d, J=6.1 Hz, 6H), 1.58-1.72 (m, 2H), 2.25 (s, 3H), 2.89-3.01 (m, 2H), 3.92 (s, 2H), 4.60-4.74 (m, 1H), 7.02 (d, J=8.7 Hz, 2H), 7.22 (s, 4H), 7.25-7.53 (m, 6H)

EXAMPLE 33

4-(2,2-dimethyl-2,3-dihydro-1-benzofuran-5-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

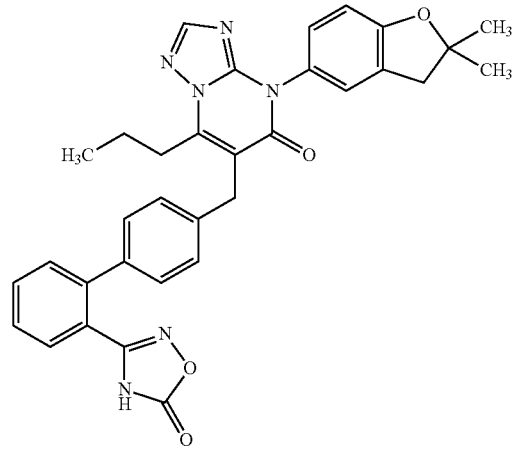 [SMILES: CCCc1c(Cc2ccc(-c3ccccc3-c3noc(=O)[nH]3)cc2)c(=O)n(-c2ccc3c(c2)CC(C)(C)O3)c2ncnn12]

A mixture of hydroxylammonium chloride (1.7 g), sodium hydrogen carbonate (2.8 g) and dimethyl sulfoxide (15 mL) was stirred at 40° C. for 30 min, 4'-{[4-(2,2-dimethyl-2,3-dihydro-1-benzofuran-5-yl)-5-oxo-7-propyl-4,5-dihydro[1,2,4]triazolo[1,5-a]pyrimidin-6-yl]methyl}biphenyl-2-carbonitrile (0.86 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.32 g) and then 1,8-diazabicyclo[5.4.0]undec-7-ene (0.27 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.44 g, 46%).

$^1$H NMR (300 MHz, DMSO-$d_6$) δ0.96 (t, J=7.3 Hz, 3H), 1.46 (s, 6H), 1.53-1.67 (m, 2H), 2.93-3.02 (m, 2H), 3.06 (s, 2H), 3.99 (s, 2H), 6.81 (d, J=8.5 Hz, 1H), 7.15 (dd, J=8.5, 2.3 Hz, 1H), 7.21-7.27 (m, 3H), 7.32-7.39 (m, 2H), 7.46-7.58 (m, 2H), 7.62-7.75 (m, 2H), 8.06 (s, 1H), 12.39 (s, 1H)

EXAMPLE 34

4-(2,2-dimethyl-2,3-dihydro-1-benzofuran-5-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

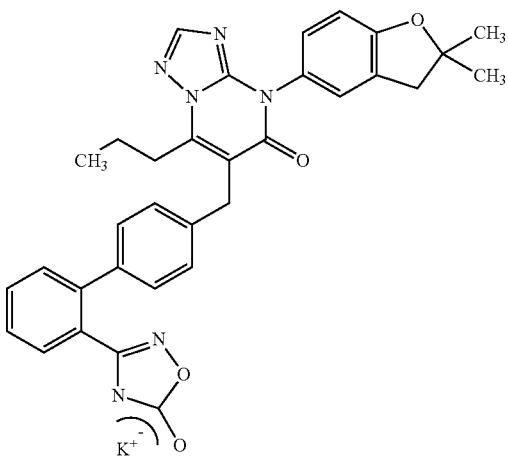 [SMILES: CCCc1c(Cc2ccc(-c3ccccc3C3=NOC(O)N3)cc2)c(=O)n(-c2ccc3c(c2)CC(C)(C)O3)c2ncnn12 ; [K+]]

4-(2,2-Dimethyl-2,3-dihydro-1-benzofuran-5-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.44 g) was suspended in isopropyl alcohol (5 mL), 2N potassium hydroxide solution (0.39 mL) was added, and the solvent was evaporated under reduced pressure. The residue was solidified with diisopropyl ether to give the title compound as a colorless solid (0.45 g, 95%).

$^1$H NMR (300 MHz, DMSO-$d_6$) δ0.95-1.03 (m, 3H) 1.46 (s, 6H) 1.59-1.72 (m, 2H) 2.95-3.11 (m, 4H) 3.94 (s, 2H) 6.80 (d, J=8.3 Hz, 1H) 7.12-7.51 (m, 10H) 8.03 (s, 1H)

EXAMPLE 35

6-{[2'-(5-oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one potassium salt

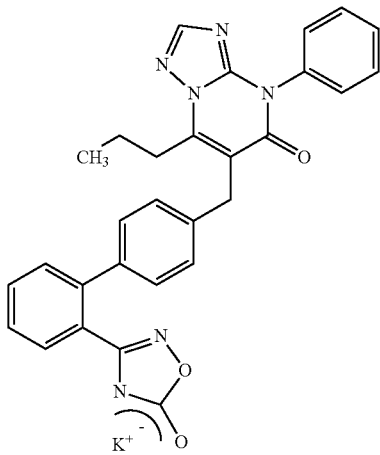 [SMILES: CCCc1c(Cc2ccc(-c3ccccc3C3=NOC(O)N3)cc2)c(=O)n(-c2ccccc2)c2ncnn12 ; [K+]]

6-{[2'-(5-Oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one (0.21 g) was suspended in isopropyl alcohol (5 mL), 2N potassium hydroxide solution (0.2 mL) was added, and the solvent was evaporated under reduced pressure. The residue was solidified with diisopropyl ether to give the title compound as a colorless solid (0.2 g, 89%).

$^1$H NMR (300 MHz, DMSO-$d_6$) δ0.97 (t, J=7.4 Hz, 3H), 1.50-1.70 (m, 2H), 2.91-3.05 (m, 2H), 4.01 (s, 2H), 7.23 (d, J=8.0 Hz, 2H), 7.37 (d, J=8.3 Hz, 2H), 7.42-7.60 (m, 7H), 7.61-7.74 (m, 2H), 8.06 (s, 1H), 12.38 (s, 1H)

EXAMPLE 36

4-ethyl-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

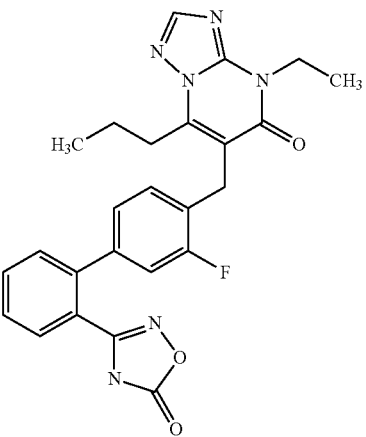 [SMILES: CCCc1c(Cc2ccc(-c3ccccc3-c3noc(=O)[nH]3)cc2F)c(=O)n(CC)c2ncnn12]

A mixture of 3'-fluoro-4'-[(5-oxo-7-propyl-4,5-dihydro[1,2,4]triazolo[1,5-a]pyrimidin-6-yl)methyl]biphenyl-2-carbonitrile (1 g), iodoethane (0.25 mL), potassium carbonate (0.71 g) and N,N-dimethylformamide (10 mL) was stirred at room temperature for 3 hr. The reaction mixture was diluted with ethyl acetate, washed with 5% aqueous potassium hydrogensulfate solution and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.4 g), sodium hydrogen carbonate (0.65 g) and dimethyl sulfoxide (5 mL), which had been stirred in advance at 40° C. for 30 min. The reaction mixture was stirred at 90° C. for 16 hr, and diluted with ethyl acetate, and the mixture was washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.075 g) and then 1,8-diazabicyclo[5.4.0]undec-7-ene (0.063 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.1 g, 8%).

$^1$H NMR (300 MHz, DMSO-$d_6$) δ0.93 (t, J=7.3 Hz, 3H), 1.25 (t, J=7.1 Hz, 3H), 1.51-1.67 (m, 2H), 2.87-3.00 (m, 2H), 3.96 (s, 2H), 4.14 (q, J=6.9 Hz, 2H), 6.99 (dd, J=7.9, 1.7 Hz, 1H), 7.17 (dd, J=11.2, 1.8 Hz, 1H), 7.24 (t, J=8.1 Hz, 1H), 7.50-7.63 (m, 2H), 7.63-7.76 (m, 2H), 8.20 (s, 1H), 12.46 (s, 1H)

EXAMPLE 37

4-(2,4-dimethoxybenzyl)-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

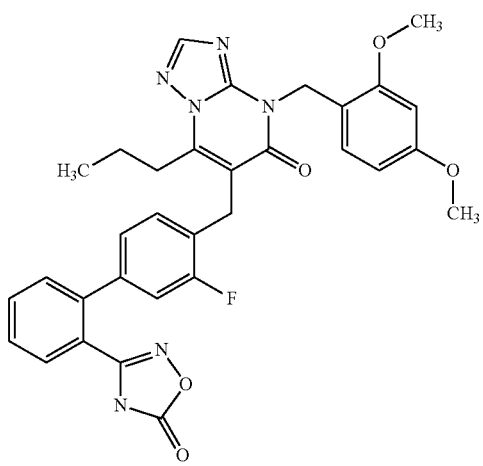 [SMILES: CCCc1c(Cc2ccc(-c3ccccc3-c3noc(=O)[nH]3)cc2F)c(=O)n(Cc2ccc(OC)cc2OC)c2ncnn12]

A mixture of hydroxylammonium chloride (0.7 g), sodium hydrogen carbonate (1.1 g) and dimethyl sulfoxide (15 mL) was stirred at 40° C. for 30 min, 4'-{[4-(2,4-dimethoxybenzyl)-5-oxo-7-propyl-4,5-dihydro[1,2,4]triazolo[1,5-a]pyrimidin-6-yl]methyl}-3'-fluorobiphenyl-2-carbonitrile (0.36 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.18 g, 45%).

$^1$H NMR (300 MHz, DMSO-$d_6$) δ0.94 (t, J=7.3 Hz, 3H), 1.51-1.70 (m, 2H), 2.91-3.04 (m, 2H), 3.71 (s, 3H), 3.77 (s, 3H), 3.98 (s, 2H), 5.19 (s, 2H), 6.39 (dd, J=8.5, 2.4 Hz, 1H), 6.56 (d, J=2.3 Hz, 1H), 6.75 (d, J=8.5 Hz, 1H), 7.00 (dd, J=8.0, 1.8 Hz, 1H), 7.18 (dd, J=11.1, 1.7 Hz, 1H), 7.26 (t, J=8.0 Hz, 1H), 7.47-7.62 (m, 2H), 7.63-7.76 (m, 2H), 8.15 (s, 1H), 12.47 (s, 1H)

EXAMPLE 38

6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

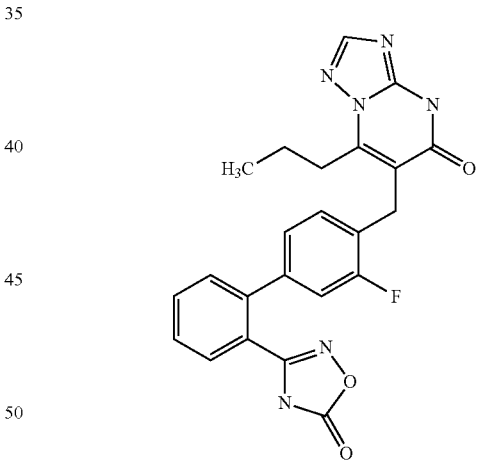

A mixture of 4-(2,4-dimethoxybenzyl)-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.3 g), trifluoroacetic acid (5 mL) and toluene (5 mL) was stirred at room temperature for 16 hr. The reaction mixture was concentrated, and the residue was purified by silica gel column chromatography to give the title compound as a colorless amorphous solid (0.022 g, 10%).

$^1$H NMR (300 MHz, DMSO-$d_6$) δ0.92 (t, J=7.3 Hz, 3H), 1.47-1.67 (m, 2H), 2.83-2.99 (m, 2H), 3.91 (s, 2H), 7.00 (dd, J=7.8, 1.4 Hz, 1H), 7.16 (dd, J=11.1, 1.3 Hz, 1H), 7.24 (t, J=7.9 Hz, 1H), 7.46-7.63 (m, 2H), 7.64-7.75 (m, 2H), 8.11 (s, 1H), 12.46 (br. s., 1H), 13.11 (br. s., 1H)

EXAMPLE 39

4-(4-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

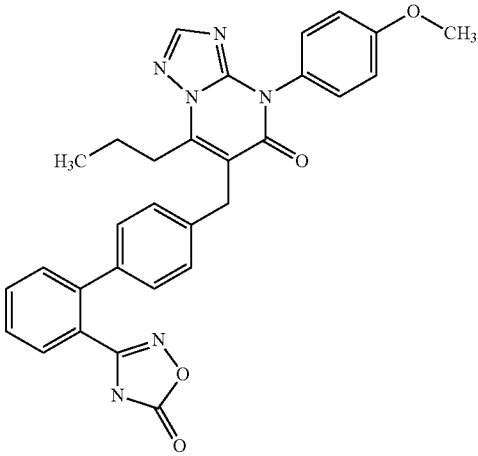 [SMILES: CCCc1c(Cc2ccc(-c3ccccc3-c3noc(=O)[nH]3)cc2)c(=O)n(-c2ccc(OC)cc2)c2ncnn12]

A mixture of hydroxylammonium chloride (1.4 g), sodium hydrogen carbonate (2.3 g) and dimethyl sulfoxide (15 mL) was stirred at 40° C. for 30 min, 4'-{[4-(4-methoxyphenyl)-5-oxo-7-propyl-4,5-dihydro[1,2,4]triazolo[1,5-a]pyrimidin-6-yl]methyl}biphenyl-2-carbonitrile (0.64 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.45 g, 63%).

$^1$H NMR (300 MHz, DMSO-$d_6$) δ 0.96 (t, J=7.4 Hz, 3H), 1.51-1.69 (m, 2H), 2.91-3.06 (m, 2H), 3.82 (s, 3H), 4.00 (s, 2H), 7.01-7.10 (m, 2H), 7.23 (d, J=8.3 Hz, 2H), 7.33-7.42 (m, 4H), 7.47-7.58 (m, 2H), 7.62-7.73 (m, 2H), 8.06 (s, 1H), 12.38 (s, 1H)

EXAMPLE 40

6-{[3-fluoro-2'-(5-oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one

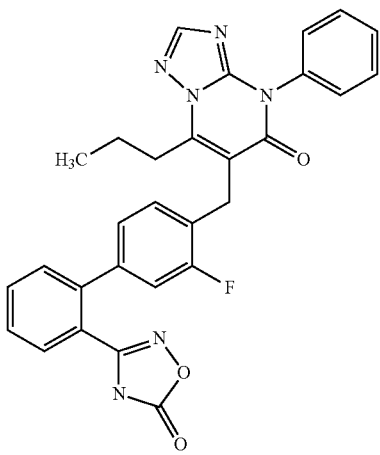 [SMILES: CCCc1c(Cc2ccc(-c3ccccc3-c3noc(=O)[nH]3)cc2F)c(=O)n(-c2ccccc2)c2ncnn12]

A mixture of hydroxylammonium chloride (1.4 g), sodium hydrogen carbonate (2.2 g) and dimethyl sulfoxide (15 mL) was stirred at 40° C. for 30 min, 3'-fluoro-4'-[(5-oxo-4-phenyl-7-propyl-4,5-dihydro[1,2,4]triazolo[1,5-a]pyrimidin-6-yl)methyl]biphenyl-2-carbonitrile (0.61 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.25 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.34 g, 48%).

$^1$H NMR (300 MHz, DMSO-$d_6$) δ 0.98 (t, J=7.4 Hz, 3H), 1.56-1.73 (m, 2H), 2.94-3.05 (m, 2H), 3.99 (s, 2H), 7.01 (dd, J=8.0, 1.9 Hz, 1H), 7.17 (dd, J=11.2, 1.7 Hz, 1H), 7.36 (t, J=8.1 Hz, 1H), 7.42-7.75 (m, 9H), 8.08 (s, 1H), 12.45 (s, 1H)

EXAMPLE 41

6-{[3-fluoro-2'-(5-oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one potassium salt

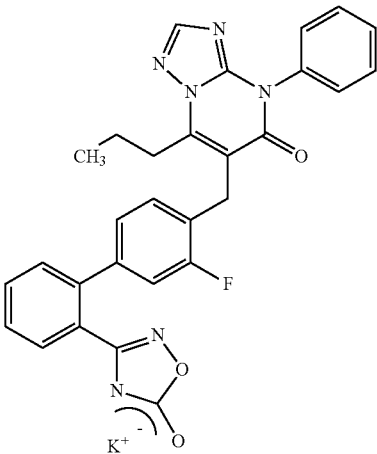 [SMILES: CCCc1c(Cc2ccc(-c3ccccc3C3=NOC(O)N3)cc2F)c(=O)n(-c2ccccc2)c2ncnn12 ; [K+]]

6-{[3-Fluoro-2'-(5-oxo-4,5-dihydro-1,2,4-oxadiazol-3-yl)biphenyl-4-yl]methyl}-4-phenyl-7-propyl[1,2,4]triazolo[1,5-a]pyrimidin-5(4H)-one (0.34 g) was suspended in isopropyl alcohol (5 mL), 2N potassium hydroxide solution (0.32 mL) was added, and the solvent was evaporated under reduced pressure. The residue was solidified with diisopropyl ether to give the title compound as a colorless solid (0.35 g, 97%).

$^1$H NMR (300 MHz, DMSO-$d_6$) δ 0.96-1.03 (m, 3H), 1.58-1.76 (m, 2H), 2.96-3.06 (m, 2H), 3.95 (s, 2H), 6.99-7.14 (m, 2H), 7.19-7.57 (m, 10H), 8.06 (s, 1H)

EXAMPLE 42

6-{[3-fluoro-2'-(5-oxo-4,5-dihydro-1,2,4-thiadiazol-3-yl)biphenyl-4-yl]methyl}-7-propyl[1,2,4]triazolo[1,5-a]pyrimidin-5(4H)-one

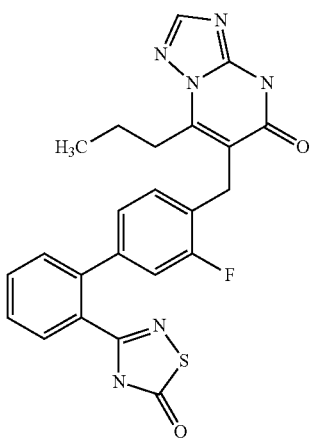 [SMILES: CCCc1c(Cc2ccc(-c3ccccc3-c3nsc(=O)[nH]3)cc2F)c(=O)[nH]c2ncnn12]

A mixture of hydroxylammonium chloride (0.93 g), sodium hydrogen carbonate (1.5 g) and dimethyl sulfoxide (10 mL) was stirred at 40° C. for 30 min, 4'-{[4-(methoxymethyl)-5-oxo-7-propyl-4,5-dihydro[1,2,4]triazolo[1,5-a]pyrimidin-6-yl]methyl}-3'-fluorobiphenyl-2-carbonitrile (0.38 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). Thiocarbonyldiimidazole (0.19 g) was added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL), boron trifluoride-diethyl ether complex (0.56 mL) was added at 0° C., and the mixture was stirred for 1 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. The residue obtained by purification by silica gel column chromatography was dissolved in methylene chloride solution (10 mL), boron tribromide (1.0 M methylene chloride solution, 1.1 mL) was added, and the mixture was stirred at room temperature for 1 day. The reaction mixture was extracted with ethyl acetate and water. The organic layer was washed with saturated brine, and dried over anhydrous magnesium sulfate, and the solvent was evaporated. The residue was purified by silica gel column chromatography to give the title compound as colorless crystals (0.029 g, 7%).

$^1$H NMR (300 MHz, DMSO-$d_6$) δ 0.91 (t, J=7.2 Hz, 3H), 1.46-1.66 (m, 2H), 2.82-2.95 (m, 2H), 3.89 (s, 2H), 6.93 (dd, J=8.0, 1.5 Hz, 1H), 7.02-7.12 (m, 1H), 7.21 (t, J=8.1 Hz, 1H), 7.53 (t, J=7.8 Hz, 2H), 7.58-7.69 (m, 2H), 8.11 (s, 1H), 12.93 (s, 1H), 13.10 (br. s., 1H)

EXAMPLE 43

6-{[3-fluoro-2'-(5-oxo-4,5-dihydro-1,2,4-oxadiazol-3-yl)biphenyl-4-yl]methyl}-4-[4-(1-methylethoxy)phenyl]-7-propyl[1,2,4]triazolo[1,5-a]pyrimidin-5(4H)-one

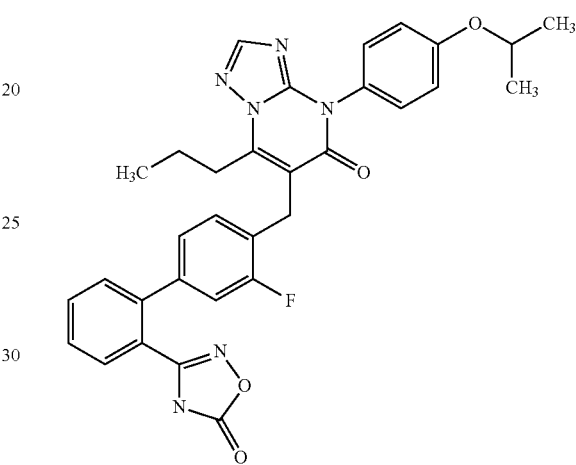

A mixture of hydroxylammonium chloride (1.2 g), sodium hydrogen carbonate (1.9 g) and dimethyl sulfoxide (15 mL) was stirred at 40° C. for 30 min, 3'-fluoro-4'-({4-[4-(1-methylethoxy)phenyl]-5-oxo-7-propyl-4,5-dihydro[1,2,4]triazolo[1,5-a]pyrimidin-6-yl}methyl)biphenyl-2-carbonitrile (0.59 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.22 g) and then 1,8-diazabicyclo[5.4.0]undec-7-ene (0.19 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.42 g, 64%).

$^1$H NMR (300 MHz, DMSO-$d_6$) δ 0.97 (t, J=7.3 Hz, 3H), 1.30 (d, J=6.0 Hz, 6H), 1.55-1.72 (m, 2H), 2.94-3.04 (m, 2H), 3.98 (s, 2H), 4.60-4.76 (m, 1H), 6.96-7.08 (m, 3H), 7.17 (dd, J=11.1, 1.7 Hz, 1H), 7.29-7.39 (m, 3H), 7.49-7.61 (m, 2H), 7.65-7.75 (m, 2H), 8.04-8.10 (m, 1H), 12.46 (br. s., 1H)

EXAMPLE 44

4-(4-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

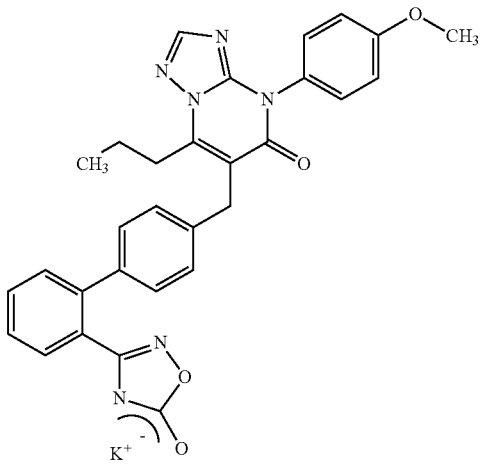 [SMILES: CCCc1c(Cc2ccc(-c3ccccc3C3=NOC(O)N3)cc2)c(=O)n(-c2ccc(OC)cc2)c2ncnn12 ; [K+]]

4-(4-Methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.3 g) was suspended in isopropyl alcohol (5 mL), 2N potassium hydroxide solution (0.28 mL) was added, and the solvent was evaporated under reduced pressure. The residue was solidified with diisopropyl ether to give the title compound as a colorless solid (0.3 g, 94%).

$^1$H NMR (300 MHz, DMSO-$d_6$) δ0.95-1.03 (m, 3H), 1.58-1.73 (m, 2H), 2.95-3.06 (m, 2H), 3.82 (s, 3H), 3.95 (s, 2H), 7.03-7.10 (m, 2H), 7.19-7.50 (m, 10H), 8.04 (s, 1H)

EXAMPLE 45

6-{[3-fluoro-2'-(5-oxo-4,5-dihydro-1,2,4-oxadiazol-3-yl)biphenyl-4-yl]methyl}-4-[4-(1-methylethoxy)phenyl]-7-propyl[1,2,4]triazolo[1,5-a]pyrimidin-5(4H)-one potassium salt

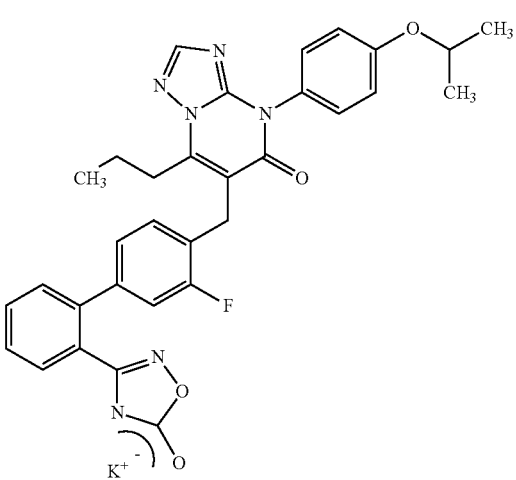 [SMILES: CCCc1c(Cc2ccc(-c3ccccc3C3=NOC(O)N3)cc2F)c(=O)n(-c2ccc(OC(C)C)cc2)c2ncnn12 ; [K+]]

6-{[3-Fluoro-2'-(5-oxo-4,5-dihydro-1,2,4-oxadiazol-3-yl)biphenyl-4-yl]methyl}-4-[4-(1-methylethoxy)phenyl]-7-propyl[1,2,4]triazolo[1,5-a]pyrimidin-5(4H)-one (0.36 g) was suspended in isopropyl alcohol (10 mL), 2N potassium hydroxide solution (0.31 mL) was added, and the solvent was evaporated under reduced pressure. The residue was solidified with diisopropyl ether to give the title compound as a colorless solid (0.35 g, 92%).

$^1$H NMR (300 MHz, DMSO-$d_6$) δ0.95-1.02 (m, 3H), 1.27-1.34 (m, 6H), 1.62-1.74 (m, 2H), 2.95-3.06 (m, 2H), 3.94 (s, 2H), 4.59-4.75 (m, 1H), 6.97-7.13 (m, 4H), 7.23 (t, J=8.1 Hz, 1H), 7.27-7.46 (m, 5H), 7.48-7.53 (m, 1H), 8.06 (s, 1H)

EXAMPLE 46

7-butyl-4-[4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

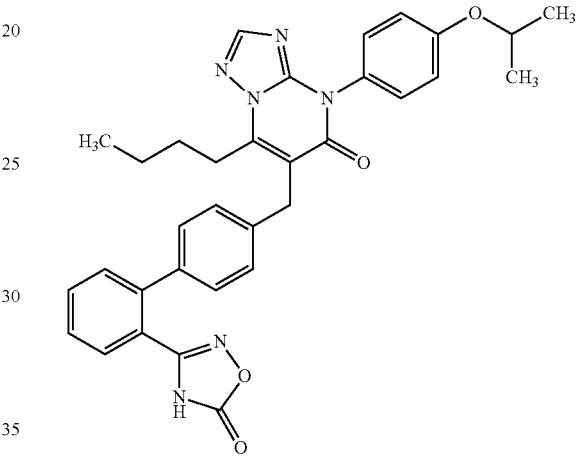

A mixture of hydroxylammonium chloride (1.4 g), sodium hydrogen carbonate (2.2 g) and dimethyl sulfoxide (15 mL) was stirred at 40° C. for 30 min, 4'-({4-[4-(1-methylethoxy)phenyl]-5-oxo-7-butyl-4,5-dihydro[1,2,4]triazolo[1,5-a]pyrimidin-6-yl}methyl)biphenyl-2-carbonitrile (0.69 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.31 g, 40%).

$^1$H NMR (300 MHz, DMSO-$d_6$) δ0.79-0.92 (m, 3H), 1.31 (d, J=6.0 Hz, 6H), 1.35-1.46 (m, 2H), 1.47-1.62 (m, 2H), 2.93-3.04 (m, 2H), 3.99 (s, 2H), 4.61-4.76 (m, 1H), 6.99-7.06 (m, 2H), 7.18-7.28 (m, 2H), 7.32-7.40 (m, 4H), 7.45-7.58 (m, 2H), 7.62-7.72 (m, 2H), 8.06 (s, 1H), 12.40 (s, 1H)

EXAMPLE 47

7-butyl-4-[4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

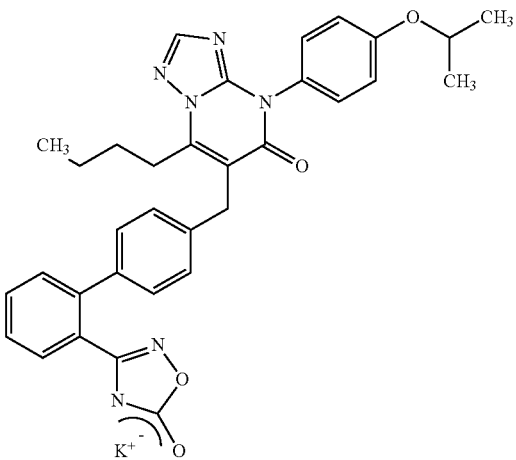 [SMILES: CCCCc1c(Cc2ccc(-c3ccccc3C3=NOC(O)N3)cc2)c(=O)n(-c2ccc(OC(C)C)cc2)c2ncnn12 ; [K+]]

7-Butyl-4-[4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.069 g) was suspended in isopropyl alcohol (15 mL), 2N potassium hydroxide solution (0.066 mL) was added, and the solvent was evaporated under reduced pressure. The residue was solidified with diisopropyl ether to give the title compound as a colorless solid (0.051 g, 63%).

$^1$H NMR (300 MHz, DMSO-$d_6$) δ0.88 (t, J=7.2 Hz, 3H), 1.31 (d, J=6.1 Hz, 6H), 1.37-1.46 (m, 2H), 1.51-1.63 (m, 2H), 2.95-3.08 (m, 2H), 3.94 (s, 2H), 4.63-4.74 (m, 1H), 6.97-7.08 (m, 2H), 7.18-7.51 (m, 10H), 8.03 (s, 1H)

EXAMPLE 48

7-butyl-6-{[3,5-difluoro-2'-(5-oxo-4,5-dihydro-1,2,4-oxadiazol-3-yl)biphenyl-4-yl]methyl}[1,2,4]triazolo[1,5-a]pyrimidin-5(4H)-one

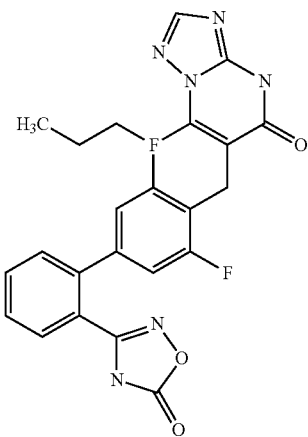

A mixture of hydroxylammonium chloride (0.87 g), sodium hydrogen carbonate (1.4 g) and dimethyl sulfoxide (10 mL) was stirred at 40° C. for 30 min, 4'-{[7-butyl-4-(methoxymethyl)-5-oxo-4,5-dihydro[1,2,4]triazolo[1,5-a]pyrimidin-6-yl]methyl}-3',5'-difluorobiphenyl-2-carbonitrile (0.39 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. The residue obtained by purification by silica gel column chromatography was dissolved in methylene chloride solution (10 mL), boron tribromide (1.0 M methylene chloride solution, 2.2 mL) was added, and the mixture was stirred at room temperature for 1 day. Ethyl acetate and water were added to the reaction mixture, and the mixture was extracted with ethyl acetate. The organic layer was washed with saturated brine, and dried over anhydrous magnesium sulfate, and the solvent was evaporated. The residue was purified by silica gel column chromatography to give the title compound as colorless crystals (0.029 g, 7%).

$^1$H NMR (300 MHz, DMSO-$d_6$) δ0.81-0.90 (m, 3H), 1.30-1.52 (m, 4H), 2.90-3.02 (m, 2H), 3.94 (s, 2H), 7.01 (d, J=8.7 Hz, 2H), 7.48-7.75 (m, 4H), 8.11 (s, 1H), 12.55 (br. s., 1H), 13.08 (br. s., 1H)

EXAMPLE 49

7-butyl-4-(3-fluoro-4-methoxyphenyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

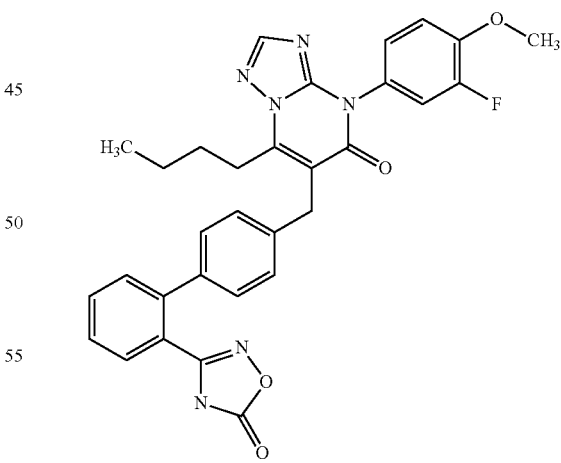

A mixture of hydroxylammonium chloride (1.6 g), sodium hydrogen carbonate (2.6 g) and dimethyl sulfoxide (15 mL) was stirred at 40° C. for 30 min, 4'-({7-butyl-4-[3-fluoro-4-methoxyphenyl]-5-oxo-4,5-dihydro[1,2,4]triazolo[1,5-a]pyrimidin-6-yl}methyl)biphenyl-2-carbonitrile (0.78 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.3 g) and then with 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.46 g, 53%).

$^1$H NMR (300 MHz, DMSO-d$_6$) δ0.82-0.90 (m, 3H) 1.31-1.46 (m, 2H) 1.45-1.58 (m, 2H) 2.94-3.05 (m, 2H) 3.91 (s, 3H) 3.99 (s, 2H) 7.23 (d, J=8.3 Hz, 2H) 7.28-7.39 (m, 4H) 7.45-7.57 (m, 3H) 7.63-7.73 (m, 2H) 8.08 (s, 1H) 12.40 (s, 1H)

EXAMPLE 50

7-butyl-4-(3-fluoro-4-methoxyphenyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

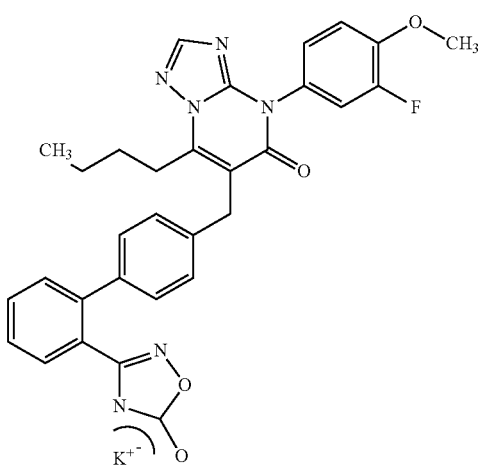 [SMILES: CCCCc1c(Cc2ccc(-c3ccccc3C3=NOC(O)N3)cc2)c(=O)n(-c2ccc(OC)c(F)c2)c2ncnn12 ; [K+]]

7-Butyl-4-(3-fluoro-4-methoxyphenyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.46 g) was suspended in isopropyl alcohol (15 mL), 2N potassium hydroxide solution (0.41 mL) was added, and the solvent was evaporated under reduced pressure. The residue was solidified with diisopropyl ether to give the title compound as a colorless solid (0.45 g, 90%).

$^1$H NMR (300 MHz, DMSO-d$_6$) δ0.84-0.93 (m, 3H) 1.33-1.49 (m, 2H) 1.50-1.64 (m, 2H) 2.95-3.07 (m, 2H) 3.91 (s, 3H) 3.95 (s, 2H) 7.23 (s, 4H) 7.25-7.53 (m, 7H) 8.06 (s, 1H)

EXAMPLE 51

7-butyl-4-[3-fluoro-4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

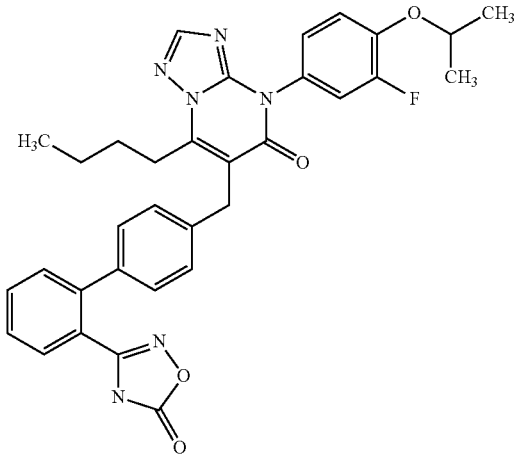 [SMILES: CCCCc1c(Cc2ccc(-c3ccccc3-c3noc(=O)[nH]3)cc2)c(=O)n(-c2ccc(OC(C)C)c(F)c2)c2ncnn12]

A mixture of hydroxylammonium chloride (1.3 g), sodium hydrogen carbonate (2.1 g) and dimethyl sulfoxide (15 mL) was stirred at 40° C. for 30 min, 4'-({7-butyl-4-[3-fluoro-4-(1-methylethoxy)phenyl]-5-oxo-4,5-dihydro[1,2,4]triazolo[1,5-a]pyrimidin-6-yl}methyl)biphenyl-2-carbonitrile (0.68 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.37 g, 49%).

$^1$H NMR (300 MHz, DMSO-d$_6$) δ0.82-0.91 (m, 3H), 1.31-1.44 (m, 8H), 1.46-1.60 (m, 2H), 2.94-3.06 (m, 2H), 3.99 (s, 2H), 4.64-4.79 (m, 1H), 7.21-7.40 (m, 6H), 7.40-7.59 (m, 3H), 7.61-7.74 (m, 2H), 8.08 (s, 1H), 12.39 (s, 1H)

EXAMPLE 52

7-butyl-4-[3-fluoro-4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

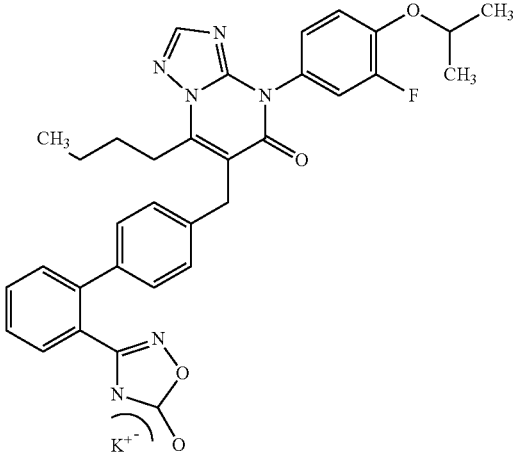 [SMILES: CCCCc1c(Cc2ccc(-c3ccccc3C3=NOC(O)N3)cc2)c(=O)n(-c2ccc(OC(C)C)c(F)c2)c2ncnn12 ; [K+]]

7-Butyl-4-[3-fluoro-4-(1-methylethoxy)phenyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.37 g) was suspended in isopropyl alcohol (15 mL), 2N potassium hydroxide solution (0.31 mL) was added, and the solvent was evaporated under reduced pressure. The residue was solidified with diisopropyl ether to give the title compound as a colorless solid (0.33 g, 84%).

$^1$H NMR (300 MHz, DMSO-$d_6$) δ0.88 (t, J=7.3 Hz, 3H), 1.33 (d, J=6.0 Hz, 6H), 1.36-1.49 (m, 2H), 1.49-1.64 (m, 2H), 2.95-3.06 (m, 2H), 3.94 (s, 2H), 4.65-4.78 (m, 1H), 7.19-7.50 (m, 11H), 8.06 (s, 1H)

EXAMPLE 53

7-butyl-6-{[3,5-difluoro-2'-(5-oxo-4,5-dihydro-1,2,4-thiadiazol-3-yl)biphenyl-4-yl]methyl}[1,2,4]triazolo[1,5-a]pyrimidin-5(4H)-one

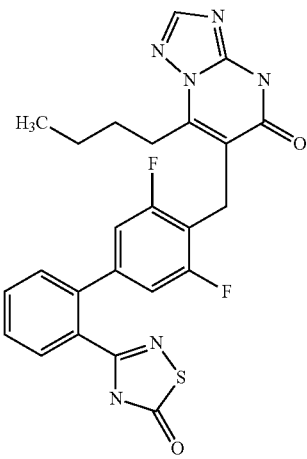 [SMILES: CCCCc1c(Cc2c(F)cc(-c3ccccc3-c3nsc(=O)[nH]3)cc2F)c(=O)[nH]c2ncnn12]

A mixture of hydroxylammonium chloride (0.89 g), sodium hydrogen carbonate (1.4 g) and dimethyl sulfoxide (10 mL) was stirred at 40° C. for 30 min, 4'-{[7-butyl-4-(methoxymethyl)-5-oxo-4,5-dihydro[1,2,4]triazolo[1,5-a]pyrimidin-6-yl]methyl}-3',5'-difluorobiphenyl-2-carbonitrile (0.39 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). Thiocarbonyldiimidazole (0.18 g) was added, and the mixture was stirred at room temperature for 1 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL), boron trifluoride-diethyl ether complex (0.52 mL) was added at 0° C., and the mixture was stirred for 1 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. The residue obtained by purification by silica gel column chromatography was dissolved in methylene chloride solution (10 mL), boron tribromide (1.0 M methylene chloride solution, 0.56 mL) was added, and the mixture was stirred at room temperature for 1 day. Ethyl acetate and water were added to the reaction mixture, and the mixture was extracted with ethyl acetate. The organic layer was washed with saturated brine, and dried over anhydrous magnesium sulfate, and the solvent was evaporated. The residue was purified by silica gel column chromatography to give the title compound as colorless crystals (0.035 g, 9%).

$^1$H NMR (300 MHz, DMSO-$d_6$) δ0.81-0.89 (m, 3H), 1.27-1.51 (m, 4H), 2.89-3.01 (m, 2H), 3.93 (s, 2H), 6.86-6.97 (m, 2H), 7.49-7.60 (m, 2H), 7.60-7.69 (m, 2H), 8.10 (s, 1H), 13.01 (s, 1H), 13.07 (s, 1H)

EXAMPLE 54

4-[4-(1-methylethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

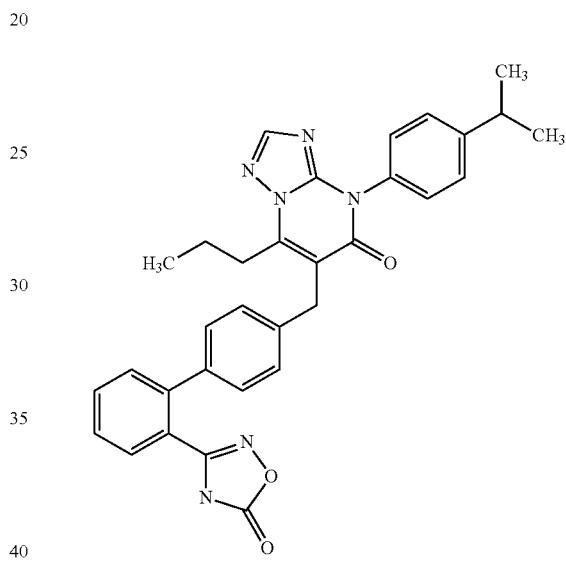

A mixture of hydroxylammonium chloride (1.3 g), sodium hydrogen carbonate (2.2 g) and dimethyl sulfoxide (15 mL) was stirred at 40° C. for 30 min, 4'-({4-[4-(1-methylethyl)phenyl]-5-oxo-7-propyl-4,5-dihydro[1,2,4]triazolo[1,5-a]pyrimidin-6-yl}methyl)biphenyl-2-carbonitrile (0.63 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.25 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.29 g, 42%).

$^1$H NMR (300 MHz, DMSO-$d_6$) δ0.97 (t, J=7.3 Hz, 3H), 1.26 (d, J=6.8 Hz, 6H), 1.52-1.68 (m, 2H), 2.93-3.05 (m, 3H), 4.00 (s, 2H), 7.23 (d, J=8.3 Hz, 2H), 7.32-7.44 (m, 6H), 7.48-7.58 (m, 2H), 7.62-7.73 (m, 2H), 8.06 (s, 1H), 12.39 (s, 1H)

EXAMPLE 55

4-[4-(1-methylethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

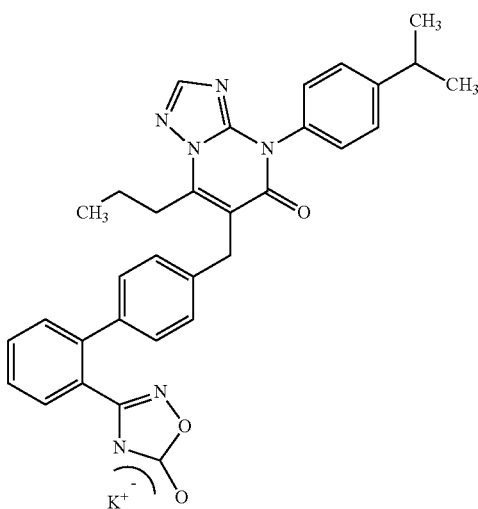 [SMILES: CCCc1c(Cc2ccc(-c3ccccc3C3=NOC(O)N3)cc2)c(=O)n(-c2ccc(C(C)C)cc2)c2ncnn12 ; [K+]]

4-[4-(1-Methylethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.24 g) was suspended in isopropyl alcohol (10 mL), 2N potassium hydroxide solution (0.22 mL) was added, and the solvent was evaporated under reduced pressure. The residue was solidified with diisopropyl ether to give the title compound as a colorless solid (0.26 g, 100%).

$^1$H NMR (300 MHz, DMSO-$d_6$) δ1.00 (t, J=7.5 Hz, 3H), 1.25 (s, 3H), 1.27 (s, 3H), 1.58-1.73 (m, 2H), 2.91-3.08 (m, 3H), 3.95 (s, 2H), 7.17-7.49 (m, 12H), 8.04 (s, 1H)

EXAMPLE 56

4-[4-(1-hydroxy-1-methylethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

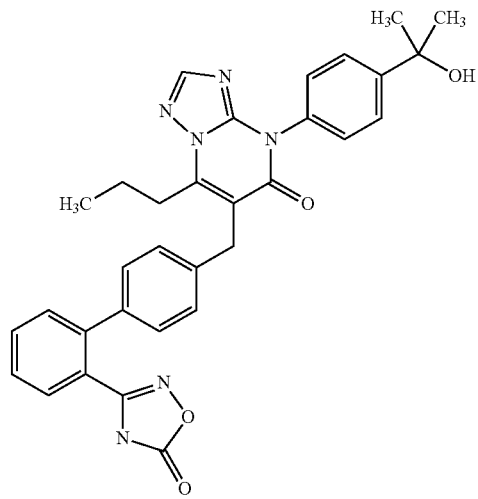 [SMILES: CCCc1c(Cc2ccc(-c3ccccc3-c3noc(=O)[nH]3)cc2)c(=O)n(-c2ccc(C(C)(C)O)cc2)c2ncnn12]

A mixture of hydroxylammonium chloride (0.97 g), sodium hydrogen carbonate (1.7 g) and dimethyl sulfoxide (15 mL) was stirred at 40° C. for 30 min, 4'-({4-[4-(1-hydroxy-1-methylethyl)phenyl]-5-oxo-7-propyl-4,5-dihydro[1,2,4]triazolo[1,5-a]pyrimidin-6-yl}methyl)biphenyl-2-carbonitrile (0.47 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.13 g, 24%).

$^1$H NMR (300 MHz, DMSO-$d_6$) δ0.97 (t, J=7.3 Hz, 3H), 1.48 (s, 6H), 1.55-1.68 (m, 2H), 2.93-3.06 (m, 2H), 4.00 (s, 2H), 7.23 (d, J=8.1 Hz, 2H), 7.33-7.41 (m, 4H), 7.47-7.73 (m, 6H), 8.06 (s, 1H), 12.39 (s, 1H)

EXAMPLE 57

4-(3-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

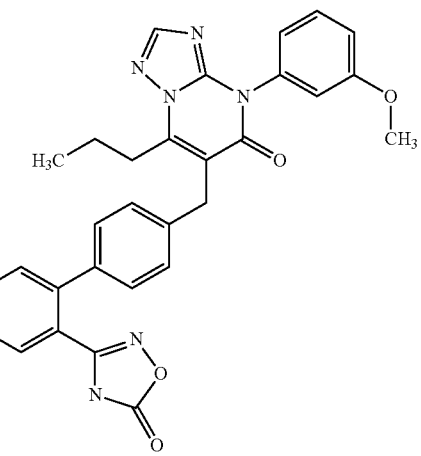

A mixture of hydroxylammonium chloride (1.4 g), sodium hydrogen carbonate (2.3 g) and dimethyl sulfoxide (15 mL) was stirred at 40° C. for 30 min, 4'-{[4-(3-methoxyphenyl)-5-oxo-7-propyl-4,5-dihydro[1,2,4]triazolo[1,5-a]pyrimidin-6-yl]methyl}biphenyl-2-carbonitrile (0.65 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.27 g) and then 1,8-diazabicyclo[5.4.0]undec-7-ene (0.23 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.34 g, 46%).

$^1$H NMR (300 MHz, DMSO-d$_6$) δ0.97 (t, J=7.4 Hz, 3H), 1.52-1.68 (m, 2H), 2.94-3.04 (m, 2H), 3.77 (s, 3H), 4.00 (s, 2H), 7.00-7.13 (m, 3H), 7.23 (d, J=8.3 Hz, 2H), 7.33-7.58 (m, 5H), 7.61-7.74 (m, 2H), 8.07 (s, 1H), 12.40 (br. s., 1H)

EXAMPLE 58

4-(3,4-dimethoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

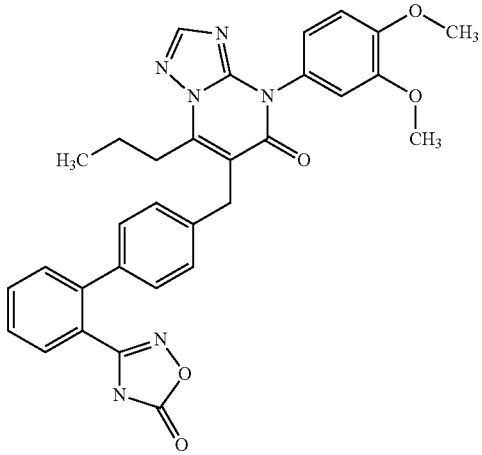 [SMILES: CCCc1c(Cc2ccc(-c3ccccc3-c3noc(=O)[nH]3)cc2)c(=O)n(-c2ccc(OC)c(OC)c2)c2ncnn12]

A mixture of hydroxylammonium chloride (1.2 g), sodium hydrogen carbonate (1.9 g) and dimethyl sulfoxide (15 mL) was stirred at 40° C. for 30 min, 4'-{[4-(3,4-dimethoxyphenyl)-5-oxo-7-propyl-4,5-dihydro[1,2,4]triazolo[1,5-a]pyrimidin-6-yl]methyl}biphenyl-2-carbonitrile (0.58 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.22 g) and then 1,8-diazabicyclo[5.4.0]undec-7-ene (0.19 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.41 g, 63%).

$^1$H NMR (300 MHz, DMSO-d$_6$) δ0.96 (t, J=7.5 Hz, 3H), 1.53-1.70 (m, 2H), 2.92-3.05 (m, 2H), 3.72 (s, 3H), 3.81 (s, 3H), 4.00 (s, 2H), 6.96-7.16 (m, 3H), 7.24 (d, J=8.3 Hz, 2H), 7.37 (d, J=8.3 Hz, 2H), 7.47-7.59 (m, 2H), 7.62-7.74 (m, 2H), 8.07 (s, 1H), 12.40 (br. s., 1H)

EXAMPLE 59

4-[4-(1-hydroxyethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

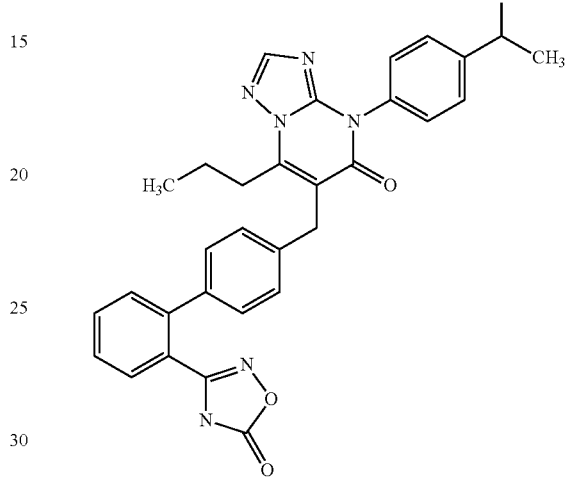

A mixture of hydroxylammonium chloride (0.83 g), sodium hydrogen carbonate (1.4 g) and dimethyl sulfoxide (10 mL) was stirred at 50° C. for 30 min, 4'-({4-[4-(1-{[tert-butyl(dimethyl)silyl]oxy}ethyl)phenyl]-5-oxo-7-propyl-4,5-dihydro[1,2,4]triazolo[1,5-a]pyrimidin-6-yl}methyl)biphenyl-2-carbonitrile (0.49 g) was added, and the mixture was stirred at 90° C. for 20 hr. After allowing to cool to room temperature, the reaction mixture was extracted with ethyl acetate and water, and the organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.16 g) and then 1,8-diazabicyclo[5.4.0]undec-7-ene (0.13 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (15 mL). Tetrabutylammonium fluoride (1 M tetrahydrofuran solution, 2 mL) was added, and the mixture was stirred at 50° C. for 3 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure. The obtained residue was purified by silica gel column chromatography to give the title compound as colorless crystals (0.2 g, 44%).

$^1$H NMR (300 MHz, DMSO-d$_6$) δ0.97 (t, J=7.3 Hz, 3H), 1.37 (d, J=6.4 Hz, 3H), 1.52-1.69 (m, 2H), 2.94-3.04 (m, 2H), 4.00 (s, 2H), 4.73-4.85 (m, 1H), 5.29 (d, J=4.1 Hz, 1H), 7.23

(d, J=8.3 Hz, 2H), 7.34-7.43 (m, 4H), 7.46-7.59 (m, 4H), 7.63-7.72 (m, 2H), 8.06 (s, 1H), 12.39 (s, 1H)

EXAMPLE 60

4-(4-fluorophenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

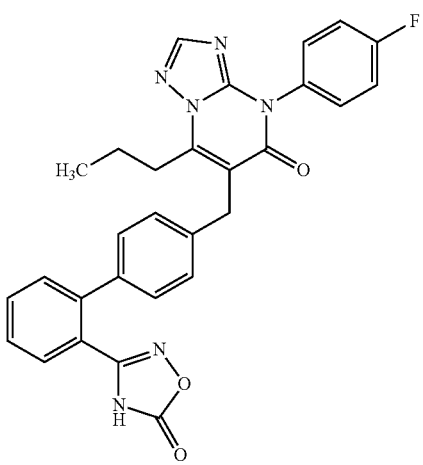 [SMILES: CCCc1c(Cc2ccc(-c3ccccc3-c3noc(=O)[nH]3)cc2)c(=O)n(-c2ccc(F)cc2)c2ncnn12]

A mixture of hydroxylammonium chloride (1.3 g), sodium hydrogen carbonate (2.1 g) and dimethyl sulfoxide (15 mL) was stirred at 40° C. for 30 min, 4'-{[4-(4-fluorophenyl)-5-oxo-7-propyl-4,5-dihydro[1,2,4]triazolo[1,5-a]pyrimidin-6-yl]methyl}biphenyl-2-carbonitrile (0.57 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.36 g, 55%).

$^1$H NMR (300 MHz, DMSO-$d_6$) δ0.97 (t, J=7.5 Hz, 3H), 1.52-1.70 (m, 2H), 2.94-3.06 (m, 2H), 4.00 (s, 2H), 7.23 (d, J=8.3 Hz, 2H), 7.33-7.44 (m, 4H), 7.46-7.60 (m, 4H), 7.62-7.75 (m, 2H), 8.08 (s, 1H), 12.39 (br. s., 1H)

EXAMPLE 61

4-(4-fluorophenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

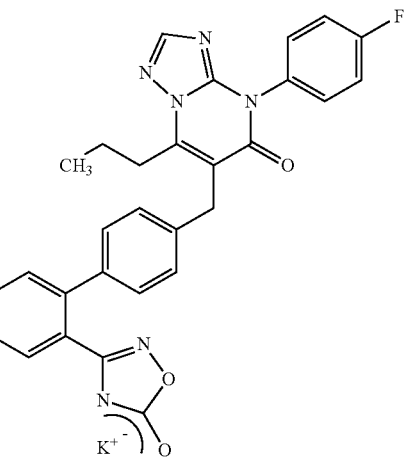

4-(4-Fluorophenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.36 g) was suspended in isopropyl alcohol (15 mL), 2N potassium hydroxide solution (0.34 mL) was added, and the solvent was evaporated under reduced pressure. The residue was solidified with diisopropyl ether to give the title compound as a colorless solid (0.3 g, 79%).

$^1$H NMR (300 MHz, DMSO-$d_6$) δ1.00 (t, J=7.4 Hz, 3H), 1.59-1.73 (m, 2H), 2.97-3.06 (m, 2H), 3.95 (s, 2H), 7.20-7.49 (m, 10H), 7.54-7.61 (m, 2H), 8.05 (s, 1H)

EXAMPLE 62

4-(3-fluoro-4-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

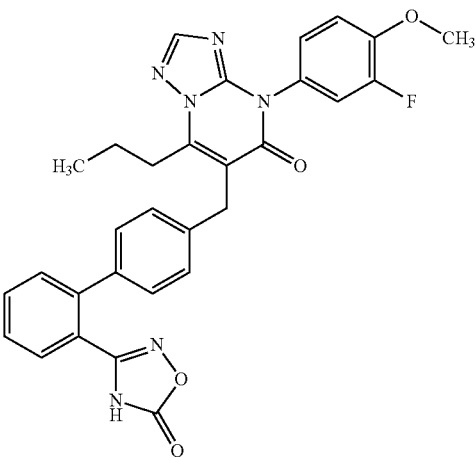 [SMILES: CCCc1c(Cc2ccc(-c3ccccc3-c3noc(=O)[nH]3)cc2)c(=O)n(-c2ccc(OC)c(F)c2)c2ncnn12]

A mixture of hydroxylammonium chloride (1.3 g), sodium hydrogen carbonate (2.1 g) and dimethyl sulfoxide (15 mL) was stirred at 40° C. for 30 min, 4'-{[4-(3-fluoro-4-methoxyphenyl)-5-oxo-7-propyl-4,5-dihydro[1,2,4]triazolo[1,5-a]pyrimidin-6-yl]methyl}biphenyl-2-carbonitrile (0.6 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.4 g, 60%).

$^1$H NMR (300 MHz, DMSO-$d_6$) δ0.96 (t, J=7.3 Hz, 3H), 1.52-1.67 (m, 2H), 2.90-3.04 (m, 2H), 3.91 (s, 3H), 4.01 (s, 2H), 7.23 (d, J=8.1 Hz, 2H), 7.28-7.33 (m, 2H), 7.37 (d, J=8.3 Hz, 2H), 7.43-7.59 (m, 3H), 7.62-7.74 (m, 2H), 8.08 (s, 1H), 12.39 (s, 1H)

EXAMPLE 63

4-(3-fluoro-4-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

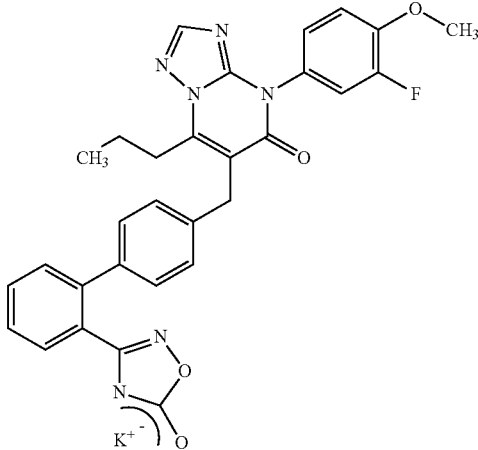 [SMILES: CCCc1c(Cc2ccc(-c3ccccc3C3=NOC(O)N3)cc2)c(=O)n(-c2ccc(OC)c(F)c2)c2ncnn12 ; [K+]]

4-(3-Fluoro-4-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.4 g) was suspended in isopropyl alcohol (15 mL), 2N potassium hydroxide solution (0.37 mL) was added, and the solvent was evaporated under reduced pressure. The residue was solidified with diisopropyl ether to give the title compound as a colorless solid (0.34 g, 80%).

$^1$H NMR (300 MHz, DMSO-$d_6$) δ1.00 (t, J=7.4 Hz, 3H), 1.59-1.72 (m, 2H), 2.94-3.06 (m, 2H), 3.91 (s, 3H), 3.95 (s, 2H), 7.19-7.52 (m, 11H), 8.06 (s, 1H)

EXAMPLE 64

4-(3-methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

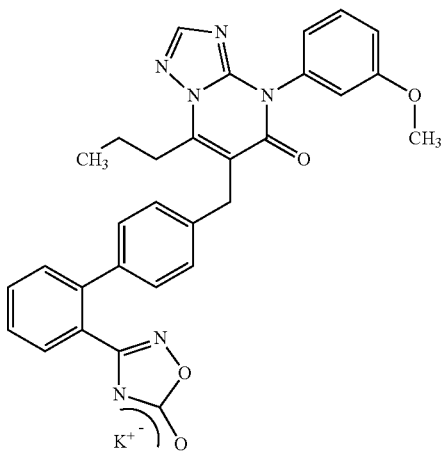 [SMILES: CCCc1c(Cc2ccc(-c3ccccc3C3=NOC(O)N3)cc2)c(=O)n(-c2cccc(OC)c2)c2ncnn12 ; [K+]]

4-(3-Methoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.29 g) was suspended in isopropyl alcohol (15 mL), 2N potassium hydroxide solution (0.27 mL) was added, and the solvent was evaporated under reduced pressure. The residue was solidified with diisopropyl ether to give the title compound as a colorless solid (0.3 g, 100%).

$^1$H NMR (300 MHz, DMSO-$d_6$) δ1.00 (t, J=7.4 Hz, 3H), 1.57-1.73 (m, 2H), 2.97-3.06 (m, 2H), 3.77 (s, 3H), 3.95 (s, 2H), 7.06 (dd, J=8.1, 3.4 Hz, 2H), 7.13 (t, J=2.2 Hz, 1H), 7.20-7.48 (m, 9H), 8.05 (s, 1H)

EXAMPLE 65

4-(3,4-dimethoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

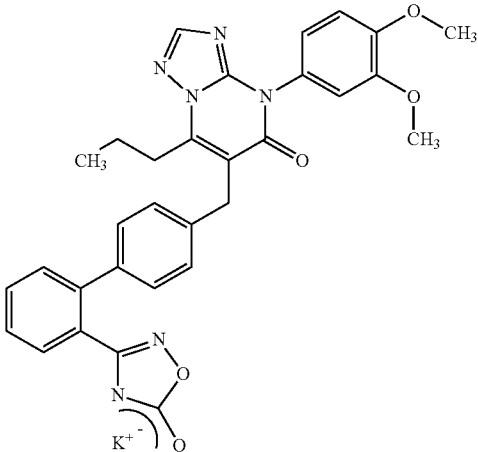 [SMILES: CCCc1c(Cc2ccc(-c3ccccc3C3=NOC(O)N3)cc2)c(=O)n(-c2ccc(OC)c(OC)c2)c2ncnn12 ; [K+]]

4-(3,4-Dimethoxyphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.36 g) was suspended in isopropyl alcohol (15 mL), 2N potassium hydroxide solution (0.32 mL) was added, and the solvent was evaporated under reduced pressure. The residue was solidified with diisopropyl ether to give the title compound as a colorless solid (0.36 g, 94%).

$^1$H NMR (300 MHz, DMSO-$d_6$) δ0.99 (t, J=7.5 Hz, 3H), 1.57-1.73 (m, 2H), 2.95-3.07 (m, 2H), 3.72 (s, 3H), 3.82 (s, 3H), 3.95 (s, 2H), 6.97-7.10 (m, 2H), 7.13 (d, J=2.3 Hz, 1H), 7.21-7.50 (m, 8H), 8.04 (s, 1H)

EXAMPLE 66

6-{[2'-(5-oxo-4,5-dihydro-1,2,4-oxadiazol-3-yl)biphenyl-4-yl]methyl}-7-propyl-4-(thiophen-3-yl)[1,2,4]triazolo[1,5-a]pyrimidin-5(4H)-one

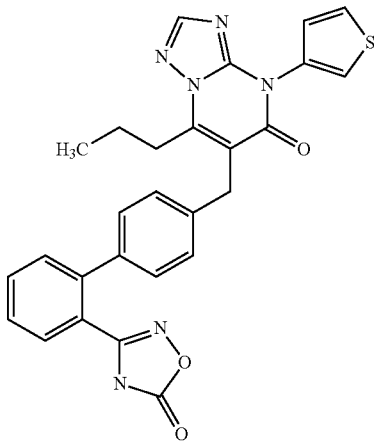 [SMILES: CCCc1c(Cc2ccc(-c3ccccc3-c3noc(=O)[nH]3)cc2)c(=O)n(-c2ccsc2)c2ncnn12]

A mixture of hydroxylammonium chloride (1.2 g), sodium hydrogen carbonate (1.9 g) and dimethyl sulfoxide (15 mL) was stirred at 40° C. for 30 min, 4'-[(5-oxo-7-propyl-4-thiophen-3-yl-4,5-dihydro[1,2,4]triazolo[1,5-a]pyrimidin-6-yl)methyl]biphenyl-2-carbonitrile (0.52 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.22 g) and then 1,8-diazabicyclo[5.4.0]undec-7-ene (0.19 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.2 g, 33%).

$^1$H NMR (300 MHz, DMSO-$d_6$) δ0.96 (t, J=7.6 Hz, 3H), 1.52-1.70 (m, 2H), 2.94-3.05 (m, 2H), 4.00 (s, 2H), 7.20-7.29 (m, 3H), 7.33-7.39 (m, 2H), 7.47-7.58 (m, 2H), 7.63-7.72 (m, 3H), 7.79 (d, J=1.5 Hz, 1H), 8.11 (s, 1H), 12.38 (br. s., 1H)

EXAMPLE 67

4-(4-acetylphenyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

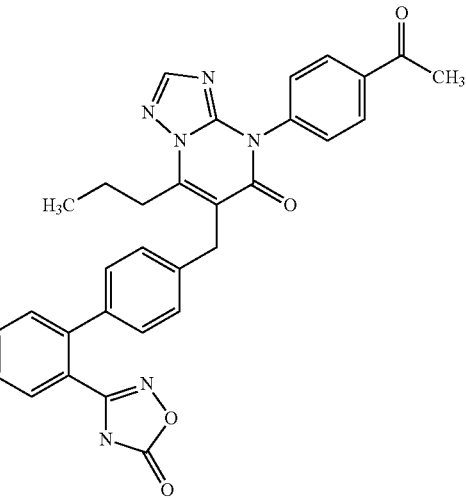

To a solution (10 mL) of 4-[4-(1-hydroxyethyl)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.05 g) in methanol was added sodium borohydride (0.039 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.036 g, 72%).

$^1$H NMR (300 MHz, DMSO-$d_6$) δ0.97 (t, J=7.2 Hz, 3H), 1.51-1.69 (m, 2H), 2.65 (s, 3H), 2.92-3.07 (m, 2H), 4.02 (s, 2H), 7.24 (d, J=8.0 Hz, 2H), 7.38 (d, J=8.0 Hz, 2H), 7.47-7.61 (m, 2H), 7.61-7.73 (m, 4H), 8.03-8.17 (m, 3H), 12.38 (br. s., 1H)

EXAMPLE 68

2-methyl-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

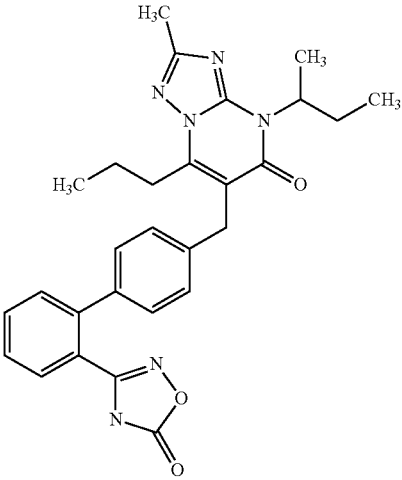 [SMILES: CCCc1c(Cc2ccc(-c3ccccc3-c3noc(=O)[nH]3)cc2)c(=O)n(C(C)CC)c2nc(C)nn12]

A mixture of hydroxylammonium chloride (0.85 g), sodium hydrogen carbonate (1.4 g) and dimethyl sulfoxide (10 mL) was stirred at 40° C. for 30 min, 4'-{[2-methyl-4-(1-methylpropyl)-5-oxo-7-propyl-4,5-dihydro[1,2,4]triazolo[1,5-a]pyrimidin-6-yl]methyl}biphenyl-2-carbonitrile (0.36 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.064 g, 16%).

$^1$H NMR (300 MHz, DMSO-d$_6$) δ0.75 (t, J=7.3 Hz, 3H), 0.91 (t, J=7.5 Hz, 3H), 1.45-1.60 (m, 5H), 1.78-1.93 (m, 1H), 2.07-2.25 (m, 1H), 2.35 (s, 3H), 2.83-2.93 (m, 2H), 3.95 (s, 2H), 4.93-5.11 (m, 1H), 7.20-7.31 (m, 4H), 7.48-7.58 (m, 2H), 7.61-7.74 (m, 2H), 12.37 (br. s., 1H)

EXAMPLE 69

2-methyl-4-[(1-methylcyclopropyl)methyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

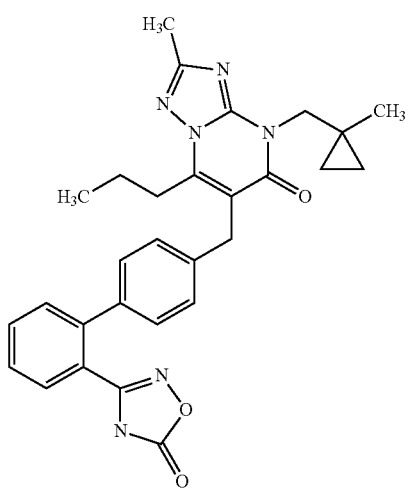 [SMILES: CCCc1c(Cc2ccc(-c3ccccc3-c3noc(=O)[nH]3)cc2)c(=O)n(CC2(C)CC2)c2nc(C)nn12]

A mixture of hydroxylammonium chloride (0.83 g), sodium hydrogen carbonate (1.3 g) and dimethyl sulfoxide (10 mL) was stirred at 40° C. for 30 min, 4'-({2-methyl-4-[(1-methylcyclopropyl)methyl]-5-oxo-7-propyl-4,5-dihydro[1,2,4]triazolo[1,5-a]pyrimidin-6-yl}methyl)biphenyl-2-carbonitrile (0.36 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.16 g, 40%).

$^1$H NMR (300 MHz, DMSO-d$_6$) δ0.25-0.31 (m, 2H), 0.71-0.78 (m, 2H), 0.92 (t, J=7.2 Hz, 3H), 0.99 (s, 3H), 1.49-1.60 (m, 2H), 2.34 (s, 3H), 2.86-2.95 (m, 2H), 3.96 (s, 2H), 4.06 (s, 2H), 7.19-7.25 (m, 2H), 7.26-7.34 (m, 2H), 7.47-7.59 (m, 2H), 7.61-7.72 (m, 2H), 12.37 (br. s., 1H)

EXAMPLE 70

6-{[2'-(5-oxo-4,5-dihydro-1,2,4-oxadiazol-3-yl)biphenyl-4-yl]methyl}-7-propyl-4-(thiophen-3-yl)[1,2,4]triazolo[1,5-a]pyrimidin-5(4H)-one potassium salt

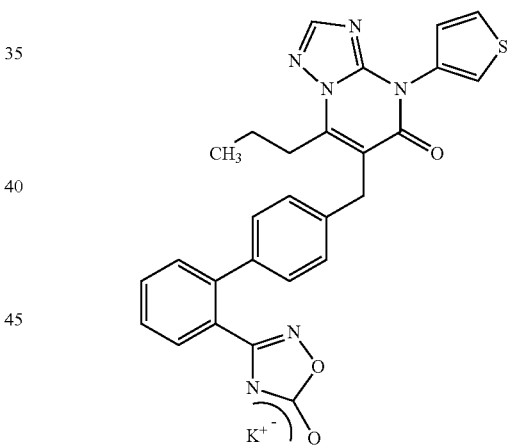

6-{[2'-(5-Oxo-4,5-dihydro-1,2,4-oxadiazol-3-yl)biphenyl-4-yl]methyl}-7-propyl-4-(thiophen-3-yl)[1,2,4]triazolo[1,5-a]pyrimidin-5(4H)-one (0.2 g) was suspended in isopropyl alcohol (10 mL), 2N potassium hydroxide solution (0.19 mL) was added, and the solvent was evaporated under reduced pressure. The residue was solidified with diisopropyl ether to give the title compound as a colorless solid (0.18 g, 86%).

$^1$H NMR (300 MHz, DMSO-d$_6$) δ1.00 (t, J=7.6 Hz, 3H), 1.56-1.75 (m, 2H), 2.95-3.08 (m, 2H), 3.95 (s, 2H), 7.20-7.50 (m, 9H), 7.65 (dd, J=5.3, 3.2 Hz, 1H), 7.81 (dd, J=3.2, 1.3 Hz, 1H), 8.09 (s, 1H)

EXAMPLE 71

4-(3-hydroxy-2,2-dimethylpropyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

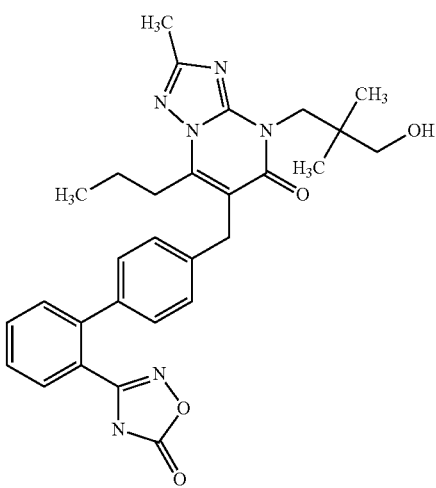 [SMILES: CCCc1c(Cc2ccc(-c3ccccc3-c3noc(=O)[nH]3)cc2)c(=O)n(CC(C)(C)CO)c2nc(C)nn12]

A mixture of hydroxylammonium chloride (0.92 g), sodium hydrogen carbonate (1.51 g) and dimethyl sulfoxide (10 mL) was stirred at 50° C. for 30 min, 4'-{[4-(3-{[tert-butyl(dimethyl)silyl]oxy}-2,2-dimethylpropyl)-2-methyl-5-oxo-7-propyl-4,5-dihydro[1,2,4]triazolo[1,5-a]pyrimidin-6-yl]methyl}biphenyl-2-carbonitrile (0.5 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.17 g) and then 1,8-diazabicyclo[5.4.0]undec-7-ene (0.15 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (15 mL). Tetrabutylammonium fluoride (1 M tetrahydrofuran solution, 2.2 mL) was added, and the mixture was stirred at room temperature for 3 hr. The reaction mixture was extracted with ethyl acetate and water, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.26 g, 56%).

$^1$H NMR (300 MHz, DMSO-$d_6$) δ0.84-0.96 (m, 9H), 1.48-1.64 (m, 2H), 2.34 (s, 3H), 2.85-2.95 (m, 2H), 3.08-3.15 (m, 2H), 3.96 (s, 2H), 4.02 (s, 2H), 4.86 (t, J=6.3 Hz, 1H), 7.19-7.24 (m, 2H), 7.26-7.32 (m, 2H), 7.53 (dd, J=17.7, 7.0 Hz, 2H), 7.62-7.72 (m, 2H), 12.37 (br. s., 1H)

EXAMPLE 72

2-methyl-6-{[2'-(5-oxo-4,5-dihydro-1,2,4-oxadiazol-3-yl)biphenyl-4-yl]methyl}-4-[(1-phenylcyclopropyl)methyl]-7-propyl[1,2,4]triazolo[1,5-a]pyrimidin-5(4H)-one

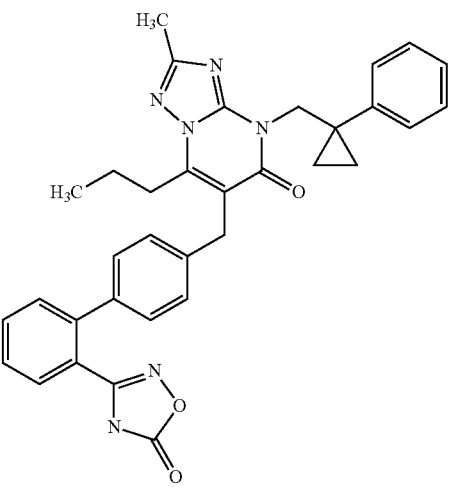 [SMILES: CCCc1c(Cc2ccc(-c3ccccc3-c3noc(=O)[nH]3)cc2)c(=O)n(CC2(c3ccccc3)CC2)c2nc(C)nn12]

A mixture of hydroxylammonium chloride (0.88 g), sodium hydrogen carbonate (1.4 g) and dimethyl sulfoxide (15 mL) was stirred at 40° C. for 30 min, 4'-({2-methyl-5-oxo-4-[(1-phenylcyclopropyl)methyl]-7-propyl-4,5-dihydro[1,2,4]triazolo[1,5-a]pyrimidin-6-yl}methyl)biphenyl-2-carbonitrile (0.43 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.069 g, 14%).

$^1$H NMR (300 MHz, CHLOROFORM-d) δ0.89-0.99 (m, 2H) 1.05 (t, J=7.3 Hz, 3H) 1.67-1.83 (m, 2H) 2.51 (s, 3H)

3.10-3.19 (m, 2H) 3.99 (s, 2H) 4.54 (s, 2H) 7.07-7.39 (m, 10H) 7.47-7.67 (m, 2H) 7.84-7.91 (m, 1H)

EXAMPLE 73

4-(3-methoxy-2,2-dimethylpropyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

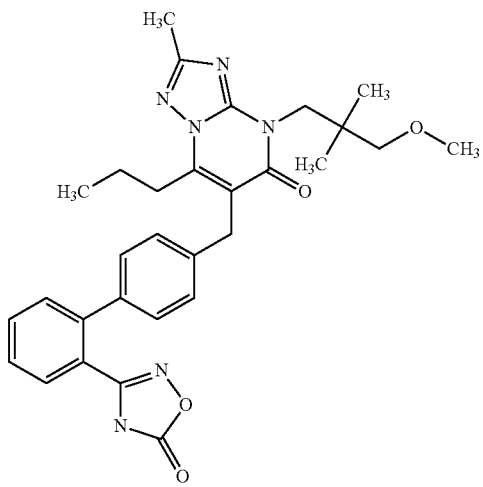 [SMILES: CCCc1c(Cc2ccc(-c3ccccc3-c3noc(=O)[nH]3)cc2)c(=O)n(CC(C)(C)COC)c2nc(C)nn12]

To a solution (10 mL) of 4'-{[4-(3-hydroxy-2,2-dimethylpropyl)-2-methyl-5-oxo-7-propyl-4,5-dihydro[1,2,4]triazolo[1,5-a]pyrimidin-6-yl]methyl}biphenyl-2-carbonitrile (0.24 g) in methylene chloride were added tetrafluoroboric acid (42% aqueous solution, 0.15 mL) and trimethylsilyldiazomethane (2M hexane solution, 0.51 mL), and the mixture was stirred at room temperature for 1 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.33 g), sodium hydrogen carbonate (0.53 g) and dimethyl sulfoxide (5 mL), which had been stirred in advance at 40° C. for 30 min. The reaction mixture was stirred at 90° C. for 16 hr, and diluted with ethyl acetate, and the mixture was washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.061 g) and then 1,8-diazabicyclo[5.4.0]undec-7-ene (0.052 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.082 g, 30%).

$^1$H NMR (300 MHz, DMSO-d$_6$) δ0.86-0.95 (m, 9H), 1.46-1.61 (m, 2H), 2.34 (s, 3H), 2.85-2.95 (m, 2H), 3.13 (s, 5H), 3.95 (s, 2H), 4.08 (s, 2H), 7.18-7.24 (m, 2H), 7.26-7.32 (m, 2H), 7.46-7.57 (m, 2H), 7.61-7.73 (m, 2H), 12.37 (br. s., 1H)

EXAMPLE 74

4-(cyclohex-2-en-1-yl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

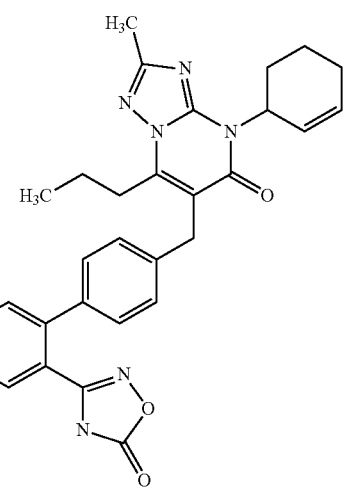

A mixture of hydroxylammonium chloride (0.67 g), sodium hydrogen carbonate (1.1 g) and dimethyl sulfoxide (15 mL) was stirred at 40° C. for 30 min, 4'-{4-(cyclohex-2-en-1-yl)-2-methyl-5-oxo-7-propyl-4,5-dihydro[1,2,4]triazolo[1,5-a]pyrimidin-6-yl]methyl}biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.15 g, 43%).

$^1$H NMR (300 MHz, DMSO-d$_6$) δ0.92 (t, J=7.3 Hz, 3H) 1.45-2.17 (m, 6H) 2.31-2.45 (m, 5H) 2.82-2.94 (m, 2H) 3.93

(s, 2H) 5.49-5.64 (m, 2H) 5.75-5.84 (m, 1H) 7.18-7.26 (m, 2H) 7.28-7.33 (m, 2H) 7.47-7.59 (m, 2H) 7.61-7.72 (m, 2H) 12.38 (br. s., 1H)

EXAMPLE 75

4-(2-methoxy-3,3-dimethylbutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

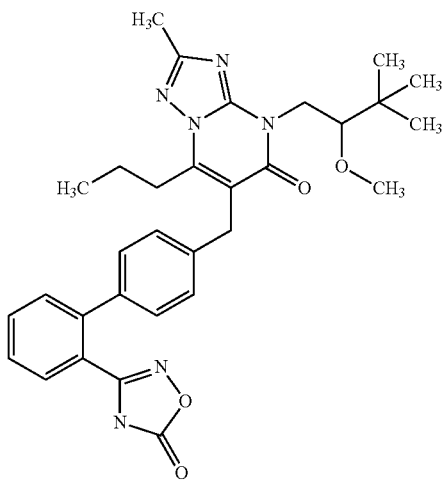 [SMILES: CCCc1c(Cc2ccc(-c3ccccc3-c3noc(=O)[nH]3)cc2)c(=O)n(CC(OC)C(C)(C)C)c2nc(C)nn12]

A mixture of hydroxylammonium chloride (0.47 g), sodium hydrogen carbonate (0.76 g) and dimethyl sulfoxide (10 mL) was stirred at 40° C. for 30 min, 4'-{[4-(2-methoxy-3,3-dimethylbutyl)-2-methyl-5-oxo-7-propyl-4,5-dihydro[1,2,4]triazolo[1,5-a]pyrimidin-6-yl]methyl}biphenyl-2-carbonitrile (0.22 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.087 g) and then 1,8-diazabicyclo[5.4.0]undec-7-ene (0.074 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.058 g, 23%).

$^1$H NMR (300 MHz, DMSO-$d_6$) δ 0.87-0.99 (m, 12H) 1.47-1.64 (m, 2H) 2.37 (s, 3H) 2.88-2.99 (m, 2H) 3.00 (s, 3H) 3.42 (dd, J=9.5, 3.1 Hz, 1H) 3.93-4.00 (m, 2H) 4.08 (dd, J=13.4, 2.8 Hz, 1H) 4.34 (dd, J=13.4, 9.6 Hz, 1H) 7.18-7.24 (m, 2H) 7.26-7.32 (m, 2H) 7.46-7.60 (m, 2H) 7.61-7.75 (m, 2H) 12.37 (br. s., 1H)

EXAMPLE 76

4-(2-hydroxy-3,3-dimethylbutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

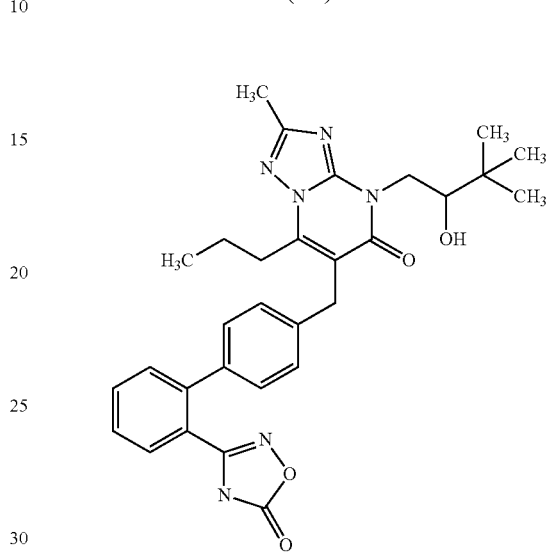

A mixture of hydroxylammonium chloride (1.6 g), sodium hydrogen carbonate (2.5 g) and dimethyl sulfoxide (10 mL) was stirred at 50° C. for 30 min, 4'-{[4-(2-{[tert-butyl(dimethyl)silyl]oxy}-3,3-dimethylbutyl)-2-methyl-5-oxo-7-propyl-4,5-dihydro[1,2,4]triazolo[1,5-a]pyrimidin-6-yl]methyl}biphenyl-2-carbonitrile (0.9 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.29 g) and then 1,8-diazabicyclo[5.4.0]undec-7-ene (0.25 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (15 mL). Tetrabutylammonium fluoride (1 M tetrahydrofuran solution, 7.5 mL) was added and the mixture was stirred at 70° C. for 5 hr. The reaction mixture was extracted with ethyl acetate and water, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.59 g, 72%).

$^1$H NMR (300 MHz, DMSO-$d_6$) δ 0.88-0.97 (m, 12H), 1.48-1.63 (m, 2H), 2.35 (s, 3H), 2.81-2.96 (m, 2H), 3.66-3.76 (m, 1H), 3.95 (s, 2H), 3.97-4.06 (m, 1H), 4.26 (dd, J=12.9, 10.3 Hz, 1H), 4.70 (d, J=5.5 Hz, 1H), 7.18-7.25 (m, 2H), 7.26-7.33 (m, 2H), 7.44-7.59 (m, 2H), 7.61-7.73 (m, 2H), 12.39 (br. s., 1H)

EXAMPLE 77

4-(3,3-dimethyl-2-oxobutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

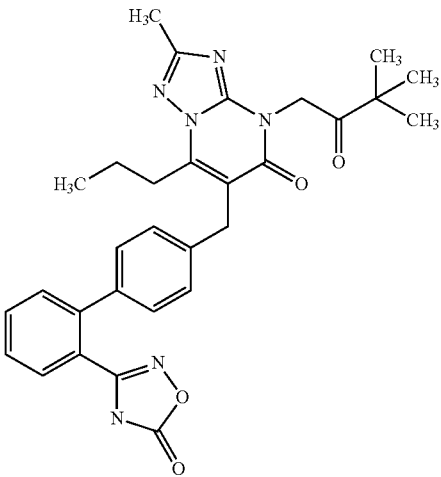 [SMILES: CCCc1c(Cc2ccc(-c3ccccc3-c3noc(=O)[nH]3)cc2)c(=O)n(CC(=O)C(C)(C)C)c2nc(C)nn12]

A mixture of 4-(2-hydroxy-3,3-dimethylbutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.52 g), Dess-Martin reagent (0.81 g) and acetonitrile (15 mL) was stirred at room temperature for 3 hr. Saturated aqueous sodium hydrogen carbonate and sodium thiosulfate-pentahydrate were added to the reaction mixture, and the mixture was stirred at room temperature for 2 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.43 g, 85%).

$^{1}$H NMR (300 MHz, DMSO-d$_{6}$) δ0.93 (t, J=7.3 Hz, 3H), 1.22 (s, 9H), 1.48-1.64 (m, 2H), 2.32 (s, 3H), 2.94 (dd, J=9.0, 6.6 Hz, 2H), 3.95 (s, 2H), 5.16 (s, 2H), 7.25 (q, J=8.4 Hz, 4H), 7.47-7.58 (m, 2H), 7.63-7.72 (m, 2H), 12.37 (s, 1H)

EXAMPLE 78

4-cyclohexyl-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

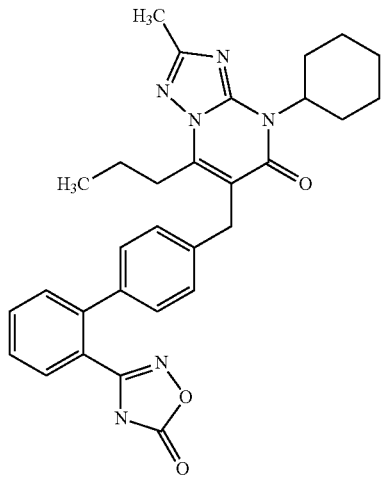 [SMILES: CCCc1c(Cc2ccc(-c3ccccc3-c3noc(=O)[nH]3)cc2)c(=O)n(C2CCCCC2)c2nc(C)nn12]

To a solution (10 mL) of 4'-{4-(cyclohex-2-en-1-yl)-2-methyl-5-oxo-7-propyl-4,5-dihydro[1,2,4]triazolo[1,5-a]pyrimidin-6-ylmethyl}biphenyl-2-carbonitrile (0.59 g) in ethyl acetate was added 10% palladium-carbon (containing water by 50%, 0.1 g), and the mixture was stirred under a hydrogen atmosphere for 4 hr. The reaction mixture was diluted with ethyl acetate, the insoluble material was filtered off through celite, and the solvent was evaporated under reduced pressure. The residue was added to a mixture of hydroxylammonium chloride (1.1 g), sodium hydrogen carbonate (1.8 g) and dimethyl sulfoxide (5 mL), which had been stirred at 40° C. for 30 min in advance, and the mixture was stirred at 90° C. for 18 hr. After allowing to cool to room temperature, ethyl acetate and water were added to the reaction mixture, and the mixture was extracted with ethyl acetate. The organic layer was washed with saturated brine, and dried over anhydrous magnesium sulfate, and the solvent was evaporated. The residue was dissolved in tetrahydrofuran (15 mL). N,N'-Carbonyldiimidazole (0.21 g) and then 1,8-diazabicyclo[5.4.0]undec-7-ene (0.18 mL) were added, and the mixture was stirred at room temperature for 3 hr. The reaction mixture was diluted with ethyl acetate, washed with 1 N hydrochloric acid and then with saturated brine, and dried over anhydrous magnesium sulfate. The solvent was evaporated under reduced pressure, and the residue was purified by silica gel column chromatography to give the title compound as a colorless amorphous solid (0.35 g, 62%).

$^{1}$H NMR (300 MHz, DMSO-d$_{6}$) δ0.92 (t, J=7.3 Hz, 3H), 1.10-1.44 (m, 3H), 1.46-1.58 (m, 2H), 1.58-1.71 (m, 3H), 1.75-1.89 (m, 2H), 2.35 (s, 3H), 2.41-2.56 (m, 2H), 2.83-2.94 (m, 2H), 3.93 (s, 2H), 4.77-4.93 (m, 1H), 7.17-7.24 (m, 2H), 7.25-7.32 (m, 2H), 7.46-7.60 (m, 2H), 7.61-7.74 (m, 2H), 12.37 (s, 1H)

EXAMPLE 79

4-[(2Z)-2-(methoxyimino)-3,3-dimethylbutyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

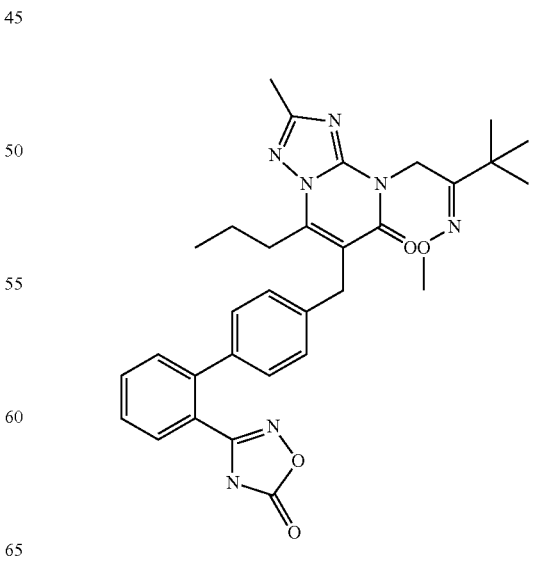

A mixture of 4-(3,3-dimethyl-2-oxobutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.3 g), (aminooxy)methane hydrochloride (0.93 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.16 g, 49%).

$^1$H NMR (300 MHz, DMSO-$d_6$) δ0.87 (t, J=7.3 Hz, 3H), 1.17 (s, 9H), 1.44-1.61 (m, 2H), 2.34 (s, 3H), 2.85-2.98 (m, 2H), 3.36 (s, 3H), 3.94 (s, 2H), 4.91 (s, 2H), 7.16-7.31 (m, 4H), 7.45-7.59 (m, 2H), 7.61-7.73 (m, 2H), 12.37 (s, 1H)

EXAMPLE 80

2-methyl-4-[(3-methyloxetan-3-yl)methyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

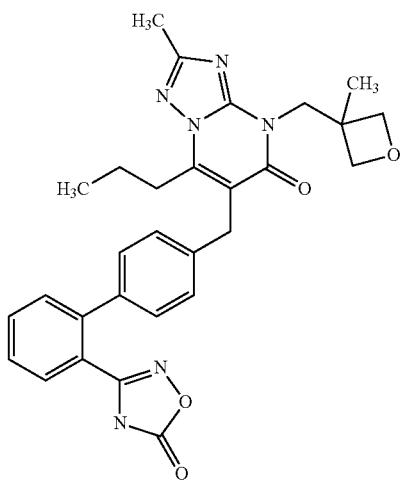 [SMILES: CCCc1c(Cc2ccc(-c3ccccc3-c3noc(=O)[nH]3)cc2)c(=O)n(CC2(C)COC2)c2nc(C)nn12]

A mixture of hydroxylammonium chloride (0.67 g), sodium hydrogen carbonate (1.1 g) and dimethyl sulfoxide (10 mL) was stirred at 40° C. for 30 min, 4'-({2-methyl-4-[(3-methyloxetan-3-yl)methyl]-5-oxo-7-propyl-4,5-dihydro[1,2,4]triazolo[1,5-a]pyrimidin-6-yl}methyl)biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.079 g, 23%).

$^1$H NMR (300 MHz, DMSO-$d_6$) δ0.92 (t, J=7.3 Hz, 3H), 1.25 (s, 3H), 1.45-1.63 (m, 2H), 2.34 (s, 3H), 2.87-2.95 (m, 2H), 3.96 (s, 2H), 4.14 (d, J=6.0 Hz, 2H), 4.28 (s, 2H), 4.66 (d, J=6.0 Hz, 2H), 7.18-7.24 (m, 2H), 7.26-7.32 (m, 2H), 7.46-7.59 (m, 2H), 7.62-7.72 (m, 2H), 12.37 (s, 1H)

EXAMPLE 81

2-methyl-6-{[2'-(5-oxo-4,5-dihydro-1,2,4-oxadiazol-3-yl)biphenyl-4-yl]methyl}-7-propyl-4-(tetrahydro-2H-pyran-4-yl)[1,2,4]triazolo[1,5-a]pyrimidin-5(4H)-one

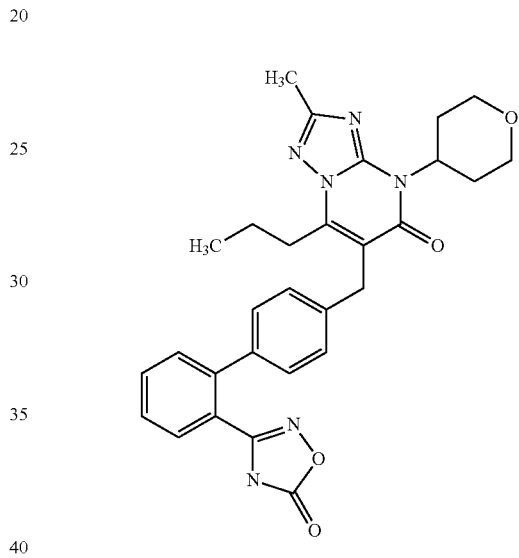

A mixture of hydroxylammonium chloride (0.83 g), sodium hydrogen carbonate (1.3 g) and dimethyl sulfoxide (10 mL) was stirred at 40° C. for 30 min, 4'-{[2-methyl-5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile (0.37 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.23 g, 55%).

$^1$H NMR (300 MHz, DMSO-$d_6$) δ0.92 (t, J=7.3 Hz, 3H), 1.46-1.63 (m, 4H), 2.37 (s, 3H), 2.66-2.93 (m, 4H), 3.43 (t,

J=11.3 Hz, 2H), 3.90-4.02 (m, 4H), 5.05-5.20 (m, 1H), 7.19-7.24 (m, 2H), 7.27-7.33 (m, 2H), 7.45-7.59 (m, 2H), 7.61-7.74 (m, 2H), 12.37 (s, 1H)

EXAMPLE 82

4-(2-methoxy-1-methylethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

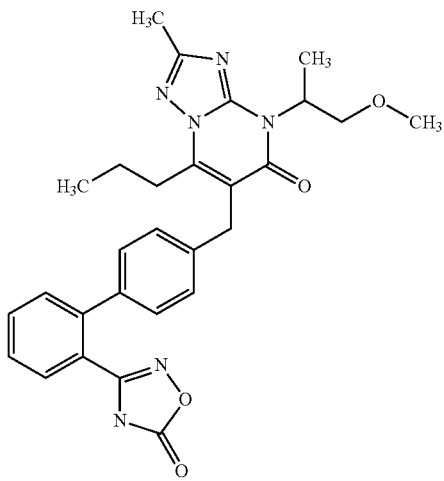 [SMILES: CCCc1c(Cc2ccc(-c3ccccc3-c3noc(=O)[nH]3)cc2)c(=O)n(C(C)COC)c2nc(C)nn12]

A mixture of hydroxylammonium chloride (1.4 g), sodium hydrogen carbonate (2.3 g) and dimethyl sulfoxide (15 mL) was stirred at 40° C. for 30 min, 4'-{[4-(2-methoxy-1-methylethyl)-2-methyl-5-oxo-7-propyl-4,5-dihydro[1,2,4]triazolo[1,5-a]pyrimidin-6-yl]methyl}biphenyl-2-carbonitrile (0.63 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.27 g) and then 1,8-diazabicyclo[5.4.0]undec-7-ene (0.23 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.39 g, 55%).

$^1$H NMR (300 MHz, DMSO-d$_6$) δ 0.92 (t, J=7.3 Hz, 3H), 1.45 (d, J=7.0 Hz, 3H), 1.47-1.60 (m, 2H), 2.35 (s, 3H), 2.82-2.96 (m, 2H), 3.18 (s, 3H), 3.57 (dd, J=10.0, 5.5 Hz, 1H), 3.94 (s, 2H), 4.16 (t, J=9.7 Hz, 1H), 5.29 (br. s., 1H), 7.19-7.31 (m, 4H), 7.44-7.58 (m, 2H), 7.60-7.74 (m, 2H), 12.37 (s, 1H)

EXAMPLE 83

4-cyclobutyl-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

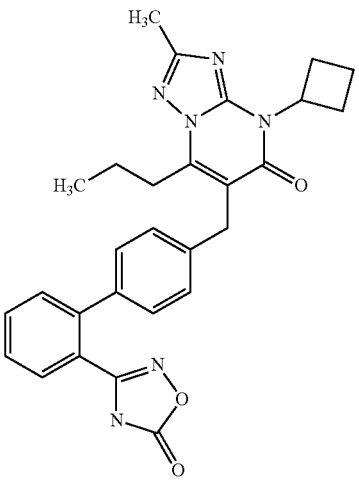 [SMILES: CCCc1c(Cc2ccc(-c3ccccc3-c3noc(=O)[nH]3)cc2)c(=O)n(C2CCC2)c2nc(C)nn12]

A mixture of hydroxylammonium chloride (1.4 g), sodium hydrogen carbonate (2.2 g) and dimethyl sulfoxide (15 mL) was stirred at 40° C. for 30 min, 4'-[(4-cyclobutyl-2-methyl-5-oxo-7-propyl-4,5-dihydro[1,2,4]triazolo[1,5-a]pyrimidin-6-yl)methyl]biphenyl-2-carbonitrile (0.58 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.38 g, 57%).

$^1$H NMR (300 MHz, DMSO-d$_6$) δ 0.92 (t, J=7.3 Hz, 3H), 1.46-1.61 (m, 2H), 1.68-1.97 (m, 2H), 2.08-2.25 (m, 2H), 2.38 (s, 3H), 2.81-2.94 (m, 2H), 3.03-3.19 (m, 2H), 3.92 (s,

2H), 5.32-5.51 (m, 1H), 7.18-7.25 (m, 2H), 7.24-7.34 (m, 2H), 7.44-7.59 (m, 2H), 7.60-7.74 (m, 2H), 12.37 (br. s., 1H)

EXAMPLE 84

4-(2-hydroxypropyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

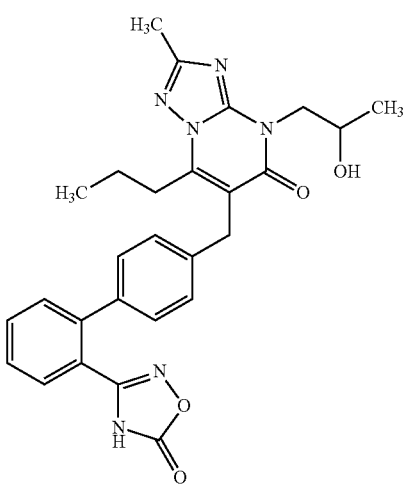 [SMILES: CCCc1c(Cc2ccc(-c3ccccc3-c3noc(=O)[nH]3)cc2)c(=O)n(CC(C)O)c2nc(C)nn12]

A mixture of hydroxylammonium chloride (1.6 g), sodium hydrogen carbonate (2.5 g) and dimethyl sulfoxide (10 mL) was stirred at 50° C. for 30 min, 4'-{[4-(2-{[tert-butyl(dimethyl)silyl]oxy}-3,3-dimethylbutyl)-2-methyl-5-oxo-7-propyl-4,5-dihydro[1,2,4]triazolo[1,5-a]pyrimidin-6-yl]methyl}biphenyl-2-carbonitrile (0.9 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.29 g) and then 1,8-diazabicyclo[5.4.0]undec-7-ene (0.25 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (15 mL). Tetrabutylammonium fluoride (1 M tetrahydrofuran solution, 7.5 mL) was added and the mixture was stirred at 70° C. for 5 hr. The reaction mixture was extracted with ethyl acetate and water, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.59 g, 72%).

$^1$H NMR (300 MHz, DMSO-$d_6$) δ0.92 (t, J=7.5 Hz, 3H), 1.09 (d, J=5.8 Hz, 3H), 1.47-1.62 (m, 2H), 2.34 (s, 3H), 2.84-2.93 (m, 2H), 3.86-3.97 (m, 3H), 4.09-4.20 (m, 2H), 4.83 (d, J=4.7 Hz, 1H), 7.17-7.24 (m, 2H), 7.26-7.33 (m, 2H), 7.47-7.59 (m, 2H), 7.62-7.72 (m, 2H), 12.38 (s, 1H)

EXAMPLE 85

2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one

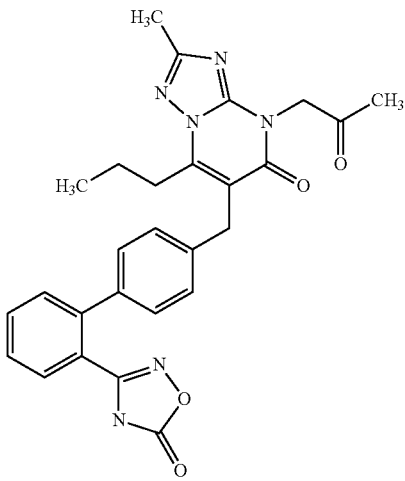 [SMILES: CCCc1c(Cc2ccc(-c3ccccc3-c3noc(=O)[nH]3)cc2)c(=O)n(CC(C)=O)c2nc(C)nn12]

A mixture of 4-(2-hydroxypropyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.42 g), Dess-Martin reagent (0.71 g) and acetonitrile (10 mL) was stirred at room temperature for 3 hr. Saturated aqueous sodium hydrogen carbonate and sodium thiosulfate-pentahydrate were added to the reaction mixture, and the mixture was stirred at room temperature for 2 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.26 g, 62%).

$^1$H NMR (300 MHz, DMSO-$d_6$) δ0.93 (t, J=7.3 Hz, 3H), 1.45-1.63 (m, 2H), 2.27 (s, 3H), 2.32 (s, 3H), 2.88-3.00 (m, 2H), 3.95 (s, 2H), 5.02 (s, 2H), 7.19-7.32 (m, 4H), 7.46-7.59 (m, 2H), 7.61-7.74 (m, 2H), 12.38 (br. s., 1H)

EXAMPLE 86

4-(2-cyclohexyl-2-hydroxyethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

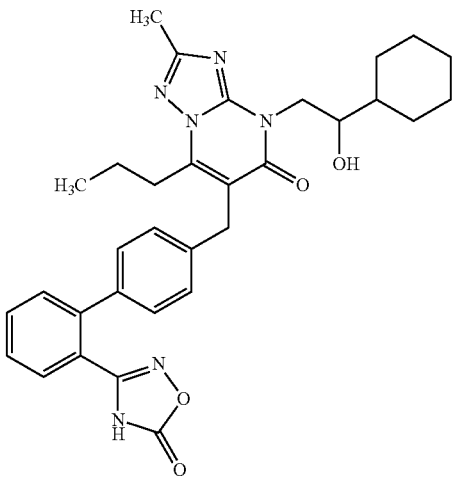 [SMILES: CCCc1c(Cc2ccc(-c3ccccc3-c3noc(=O)[nH]3)cc2)c(=O)n(CC(O)C2CCCCC2)c2nc(C)nn12]

A mixture of hydroxylammonium chloride (1.3 g), sodium hydrogen carbonate (2.1 g) and dimethyl sulfoxide (10 mL) was stirred at 50° C. for 30 min, 4'-{[4-(2-{[tert-butyl(dimethyl)silyl]oxy}-2-cyclohexylethyl)-2-methyl-5-oxo-7-propyl-4,5-dihydro[1,2,4]triazolo[1,5-a]pyrimidin-6-yl]methyl}biphenyl-2-carbonitrile (0.76 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (15 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 3.1 mL) was added and the mixture was stirred at 70° C. for 5 hr. The reaction mixture was extracted with ethyl acetate and water, and the organic layer was washed with water and then with saturated brine, and dried over anhydrous magnesium sulfate. The solvent was evaporated under reduced pressure. The obtained residue was purified by silica gel column chromatography to give the title compound as a colorless amorphous solid (0.6 g, 86%).

$^1$H NMR (300 MHz, DMSO-$d_6$) δ0.92 (t, J=7.3 Hz, 3H), 1.03-1.90 (m, 13H), 2.34 (s, 3H), 2.83-2.95 (m, 2H), 3.74-3.86 (m, 1H), 3.91-4.07 (m, 3H), 4.15-4.25 (m, 1H), 4.66 (d, J=5.5 Hz, 1H), 7.18-7.25 (m, 2H), 7.27-7.33 (m, 2H), 7.46-7.59 (m, 2H), 7.62-7.72 (m, 2H), 12.38 (br. s., 1H)

EXAMPLE 87

4-(2-cyclohexyl-2-oxoethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

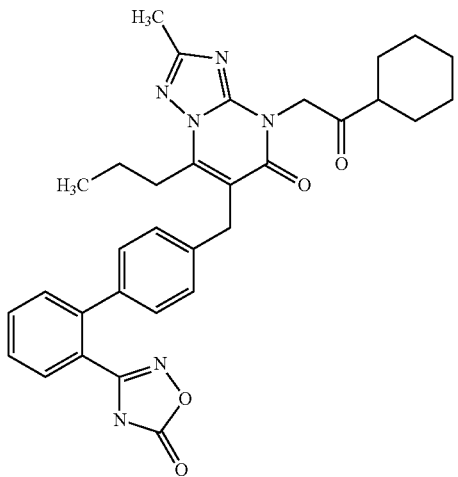 [SMILES: CCCc1c(Cc2ccc(-c3ccccc3-c3noc(=O)[nH]3)cc2)c(=O)n(CC(=O)C2CCCCC2)c2nc(C)nn12]

A mixture of 4-(2-cyclohexyl-2-hydroxyethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.6 g), Dess-Martin reagent (0.89 g) and acetonitrile (10 mL) was stirred at room temperature for 3 hr. Saturated aqueous sodium hydrogen carbonate and sodium thiosulfate-pentahydrate were added to the reaction mixture, and the mixture was stirred at room temperature for 2 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.52 g, 87%).

$^1$H NMR (300 MHz, DMSO-$d_6$) δ0.92 (t, J=7.3 Hz, 3H), 1.09-1.40 (m, 5H), 1.47-1.66 (m, 3H), 1.68-1.78 (m, 2H), 1.84-1.98 (m, 2H), 2.32 (s, 3H), 2.58-2.73 (m, 1H), 2.87-2.98 (m, 2H), 3.94 (s, 2H), 5.06 (s, 2H), 7.17-7.31 (m, 4H), 7.45-7.58 (m, 2H), 7.60-7.72 (m, 2H), 12.37 (br. s., 1H)

EXAMPLE 88

4-[(2E)-2-(ethoxyimino)-3,3-dimethylbutyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

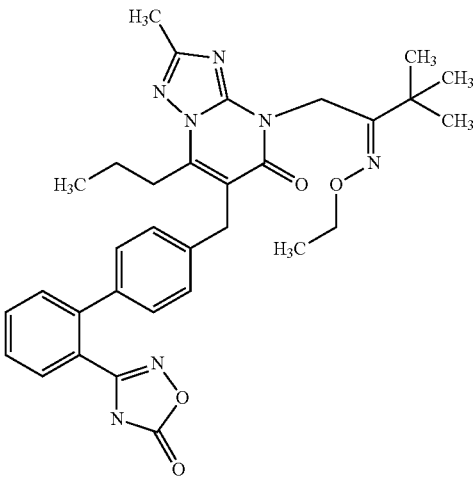 [SMILES: CCCc1c(Cc2ccc(-c3ccccc3-c3noc(=O)[nH]3)cc2)c(=O)n(C/C(=N\OCC)C(C)(C)C)c2nc(C)nn12]

A mixture of 4-(3,3-dimethyl-2-oxobutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.3 g), (aminooxy)ethane hydrochloride (1.1 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.16 g, 49%).

$^1$H NMR (300 MHz, DMSO-$d_6$) δ0.56 (t, J=7.1 Hz, 3H) 0.90 (t, J=7.3 Hz, 3H) 1.19 (s, 9H) 1.43-1.57 (m, 2H) 2.34 (s, 3H) 2.82-2.95 (m, 2H) 3.60 (q, J=7.0 Hz, 2H) 3.94 (s, 2H) 4.89 (s, 2H) 7.18-7.30 (m, 4H) 7.46-7.59 (m, 2H) 7.60-7.73 (m, 2H) 12.37 (s, 1H)

EXAMPLE 89

4-[(2Z)-2-cyclohexyl-2-(methoxyimino)ethyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

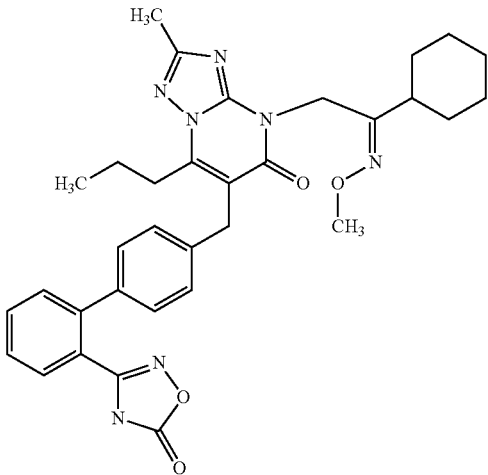 [SMILES: CCCc1c(Cc2ccc(-c3ccccc3-c3noc(=O)[nH]3)cc2)c(=O)n(C/C(=N\OC)C2CCCCC2)c2nc(C)nn12]

A mixture of 4-(2-cyclohexyl-2-oxoethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.25 g), (aminooxy)methane hydrochloride (0.74 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.067 g, 26%).
$^1$H NMR (300 MHz, DMSO-$d_6$) δ0.85-1.27 (m, 8H), 1.47-1.67 (m, 7H), 1.72-1.85 (m, 1H), 2.35 (s, 3H), 2.86-3.01 (m, s, 3H), 3.97 (s, 2H), 4.93 (s, 2H), 7.15-7.29 (m, 4H), 7.43-7.59 (m, 2H), 7.62-7.72 (m, 2H), 12.38 (s, 1H)

EXAMPLE 90

4-[(2E)-2-cyclohexyl-2-(methoxyimino)ethyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

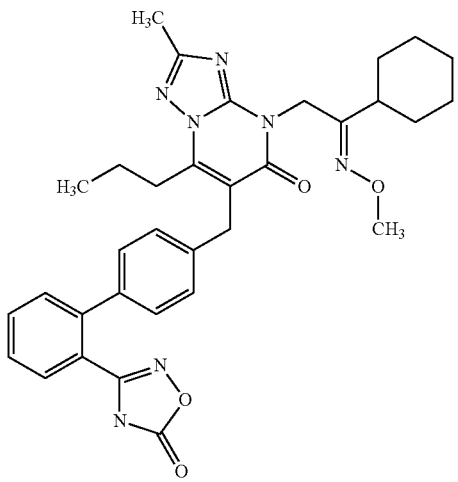 [SMILES: CCCc1c(Cc2ccc(-c3ccccc3-c3noc(=O)[nH]3)cc2)c(=O)n(C/C(=N/OC)C2CCCCC2)c2nc(C)nn12]

2H), 3.74 (

A mixture of 4-(2-cyclohexyl-2-oxoethyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.25 g), (aminooxy)methane hydrochloride (0.74 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.066 g, 26%).
$^1$H NMR (300 MHz, DMSO-$d_6$) δ0.88 (t, J=7.3 Hz, 3H), 1.17-1.59 (m, 7H), 1.61-1.81 (m, 5H), 2.34 (s, 3H), 2.86-3.02 (m, 3H), 3.51 (s, 3H), 3.96 (s, 2H), 4.84 (s, 2H), 7.17-7.29 (m, 4H), 7.44-7.59 (m, 2H), 7.60-7.73 (m, 2H), 12.37 (s, 1H)

EXAMPLE 91

4-[(2Z)-2-(methoxyimino)propyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

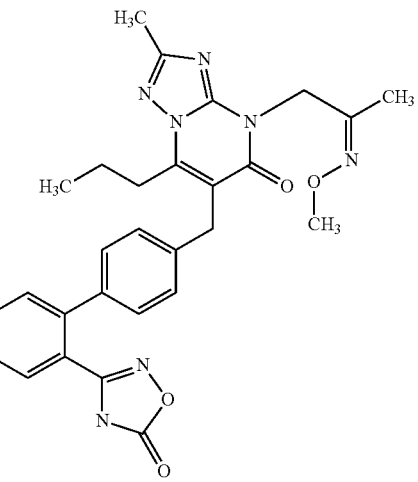

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.2 g), (aminooxy)methane hydrochloride (0.67 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.016 g, 8%).
$^1$H NMR (300 MHz, DMSO-$d_6$) δ0.92 (t, J=7.3 Hz, 3H), 1.48-1.64 (m, 5H), 2.36 (s, 3H), 2.87-2.98 (m, 2H), 3.80 (s, 3H), 3.97 (s, 2H), 4.90 (s, 2H), 7.17-7.25 (m, 2H), 7.26-7.33 (m, 2H), 7.47-7.58 (m, 2H), 7.62-7.71 (m, 2H), 12.38 (br. s., 1H)

EXAMPLE 92

4-[(2E)-2-(ethoxyimino)-3,3-dimethylbutyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

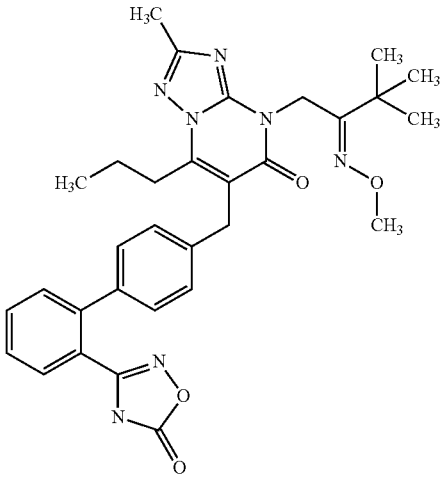 [SMILES: CCCc1c(Cc2ccc(-c3ccccc3-c3noc(=O)[nH]3)cc2)c(=O)n(C/C(=N/OC)C(C)(C)C)c2nc(C)nn12]

A mixture of 4-(3,3-dimethyl-2-oxobutyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.3 g), (aminooxy)ethane hydrochloride (1.1 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.024 g, 7%).

$^1$H NMR (300 MHz, DMSO-d$_6$) δ0.83-0.93 (m, 6H), 1.27 (s, 9H), 1.44-1.61 (m, 2H), 2.33 (s, 3H), 2.87-2.96 (m, 2H), 3.66 (q, J=7.0 Hz, 2H), 3.96 (s, 2H), 4.88 (s, 2H), 7.16-7.29 (m, 4H), 7.45-7.58 (m, 2H), 7.62-7.73 (m, 2H)

EXAMPLE 93

4-[(2E)-2-(methoxyimino)propyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

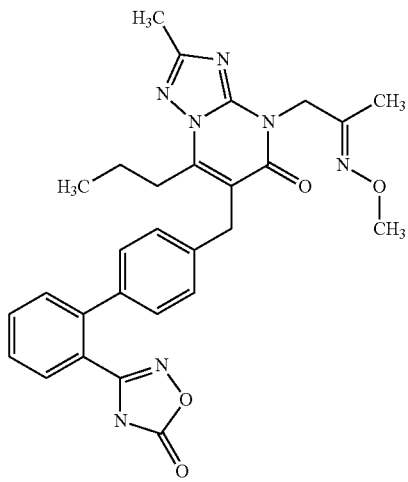 [SMILES: CCCc1c(Cc2ccc(-c3ccccc3-c3noc(=O)[nH]3)cc2)c(=O)n(C/C(C)=N/OC)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.2 g), (aminooxy)methane hydrochloride (0.67 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.071 g, 34%).

$^1$H NMR (300 MHz, DMSO-d$_6$) δ0.89 (t, J=7.2 Hz, 3H), 1.46-1.65 (m, 2H), 1.80 (s, 3H), 2.35 (s, 3H), 2.83-2.97 (m, 2H), 3.62 (s, 3H), 3.96 (s, 2H), 4.80 (s, 2H), 7.17-7.32 (m, 4H), 7.52 (dd, J=16.8, 7.4 Hz, 2H), 7.60-7.74 (m, 2H), 12.37 (br. s., 1H)

EXAMPLE 94

4-[(2Z)-2-(methoxyimino)-3,3-dimethylbutyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

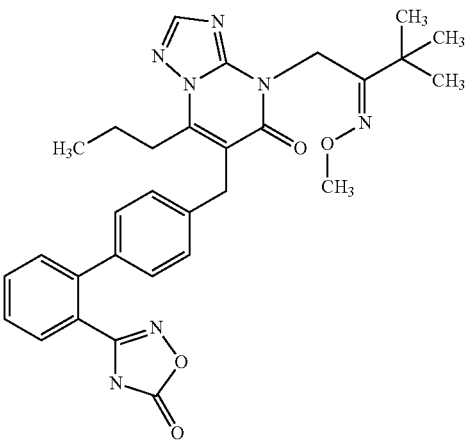 [SMILES: CCCc1c(Cc2ccc(-c3ccccc3-c3noc(=O)[nH]3)cc2)c(=O)n(C/C(=N\OC)C(C)(C)C)c2ncnn12]

A mixture of 4-(3,3-dimethyl-2-oxobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.1 g), (aminooxy)methane hydrochloride (0.32 g) and pyridine (5 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.022 g, 21%).

$^1$H NMR (300 MHz, DMSO-d$_6$) δ0.88 (t, J=7.4 Hz, 3H), 1.15 (s, 9H), 1.45-1.61 (m, 2H), 2.90-3.05 (m, 2H), 3.35 (s, 3H), 3.97 (s, 2H), 4.96 (s, 2H), 7.19-7.32 (m, 4H), 7.52 (dd, J=17.6, 7.8 Hz, 2H), 7.59-7.73 (m, 2H), 8.18 (s, 1H), 12.37 (br. s., 1H)

EXAMPLE 95

2-methyl-4-(1-methylpropyl)-6-{[2'-(5-oxo-4,5-dihydro-1,2,4-oxadiazol-3-yl)-3-(trifluoromethyl)biphenyl-4-yl]methyl}-7-propyl[1,2,4]triazolo[1,5-a]pyrimidin-5(4H)-one

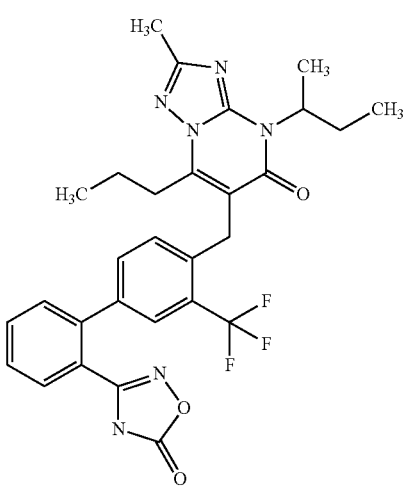 [SMILES: CCCc1c(Cc2ccc(-c3ccccc3-c3noc(=O)[nH]3)cc2C(F)(F)F)c(=O)n(C(C)CC)c2nc(C)nn12]

A mixture of ethyl 2-[(2'-cyanobiphenyl-4-yl)methyl]-3-oxohexanoate (1.84 g) and 5-methyl-N-(1-methylpropyl)-4H-1,2,4-triazol-3-amine (0.4 g) was stirred under microwave irradiation at 250° C. for 15 min. The residue obtained by silica gel column chromatography was dissolved in dimethyl sulfoxide (5 mL), and the mixture was added to a mixture of hydroxylammonium chloride (0.8 g), sodium hydrogen carbonate (1.3 g) and dimethyl sulfoxide (10 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.15 g) and then with 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.26 g, 32%).

$^1$H NMR (300 MHz, DMSO-$d_6$) δ0.76 (t, J=7.4 Hz, 3H), 0.88 (t, J=7.4 Hz, 3H), 1.45-1.66 (m, 5H), 1.77-1.91 (m, 1H), 2.08-2.26 (m, 1H), 2.38 (s, 3H), 2.73-2.85 (m, 2H), 4.07 (s, 2H), 4.89-5.08 (m, 1H), 7.22 (d, J=8.0 Hz, 1H), 7.41 (d, J=8.3 Hz, 1H), 7.53-7.77 (m, 5H), 12.47 (br. s., 1H)

EXAMPLE 96

4-{(2Z)-3,3-dimethyl-2-[(1-methylethoxy)imino]butyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

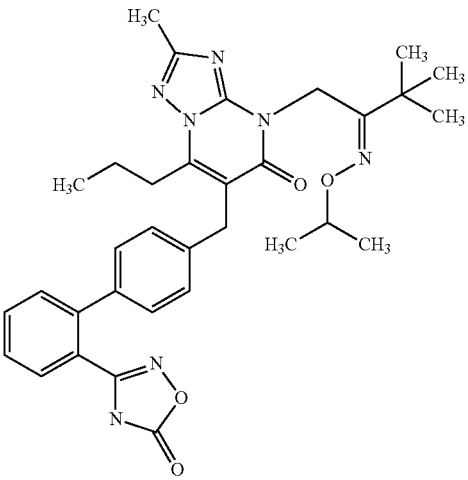 [SMILES: CCCc1c(Cc2ccc(-c3ccccc3-c3noc(=O)[nH]3)cc2)c(=O)n(C/C(=N\OC(C)C)C(C)(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.3 g), 2-(aminooxy)propane hydrochloride (0.93 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.11 g, 33%).

$^1$H NMR (300 MHz, DMSO-$d_6$) δ0.62 (d, J=6.0 Hz, 6H), 0.92 (t, J=7.3 Hz, 3H), 1.21 (s, 9H), 1.44-1.57 (m, 2H), 2.34 (s, 3H), 2.84-2.96 (m, 2H), 3.26-3.36 (m, 1H), 3.93 (s, 2H), 4.86 (s, 2H), 7.15-7.30 (m, 4H), 7.44-7.58 (m, 2H), 7.60-7.72 (m, 2H), 12.38 (br. s., 1H)

EXAMPLE 97

4-{(2E)-3,3-dimethyl-2-[(1-methylethoxy)imino]butyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

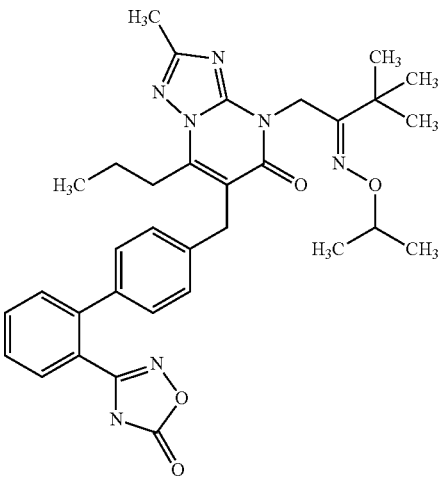 [SMILES: CCCc1c(Cc2ccc(-c3ccccc3-c3noc(=O)[nH]3)cc2)c(=O)n(C/C(=N/OC(C)C)C(C)(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.3 g), 2-(aminooxy)propane hydrochloride (0.93 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.017 g, 5%).

$^1$H NMR (300 MHz, DMSO-$d_6$) δ0.83-0.92 (m, 9H), 1.27 (s, 9H), 1.44-1.58 (m, 2H), 2.32 (s, 3H), 2.85-2.96 (m, 2H), 3.66-3.81 (m, 1H), 3.95 (s, 2H), 4.88 (s, 2H), 7.17-7.28 (m, 4H), 7.45-7.58 (m, 2H), 7.61-7.74 (m, 2H), 12.37 (br. s., 1H)

EXAMPLE 98

4-[(2Z)-2-(tert-butoxyimino)-3,3-dimethylbutyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

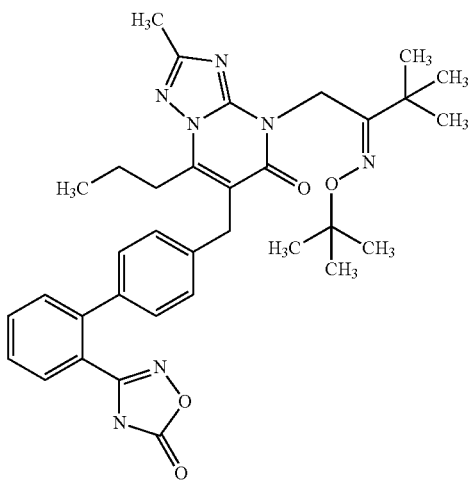 [SMILES: CCCc1c(Cc2ccc(-c3ccccc3-c3noc(=O)[nH]3)cc2)c(=O)n(C/C(=N\OC(C)(C)C)C(C)(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.3 g), 2-(aminooxy)-2-methylpropane hydrochloride (1.1 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless amorphous crystals (0.074 g, 22%).

$^1$H NMR (300 MHz, DMSO-$d_6$) δ0.76 (s, 9H), 0.91 (t, J=7.3 Hz, 3H), 1.22 (s, 9H), 1.44-1.57 (m, 2H), 2.33 (s, 3H), 2.82-2.94 (m, 2H), 3.92 (s, 2H), 4.84 (s, 2H), 7.16-7.30 (m, 4H), 7.44-7.58 (m, 2H), 7.60-7.71 (m, 2H), 12.37 (br. s., 1H)

EXAMPLE 99

4-[(2E)-2-(tert-butoxyimino)-3,3-dimethylbutyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

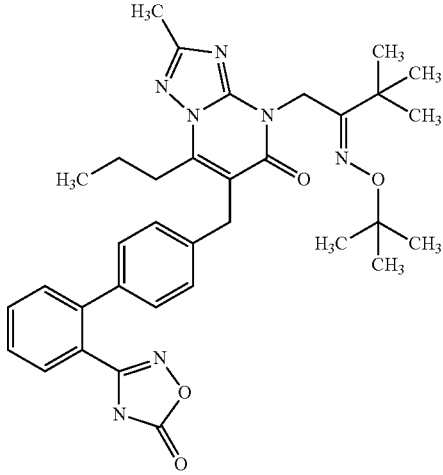 [SMILES: CCCc1c(Cc2ccc(-c3ccccc3-c3noc(=O)[nH]3)cc2)c(=O)n(C/C(=N/OC(C)(C)C)C(C)(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.3 g), 2-(aminooxy)-2-methylpropane hydrochloride (1.1 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless amorphous crystals (0.069 g, 20%).

$^1$H NMR (300 MHz, DMSO-$d_6$) δ0.84 (s, 9H), 0.89 (t, J=7.3 Hz, 3H), 1.26 (s, 9H), 1.44-1.63 (m, 2H), 2.31 (s, 3H), 2.86-2.99 (m, 2H), 3.94 (s, 2H), 4.88 (s, 2H), 7.14-7.32 (m, 4H), 7.44-7.59 (m, 2H), 7.61-7.73 (m, 2H), 12.39 (br. s., 1H)

EXAMPLE 100

2-(methoxymethyl)-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

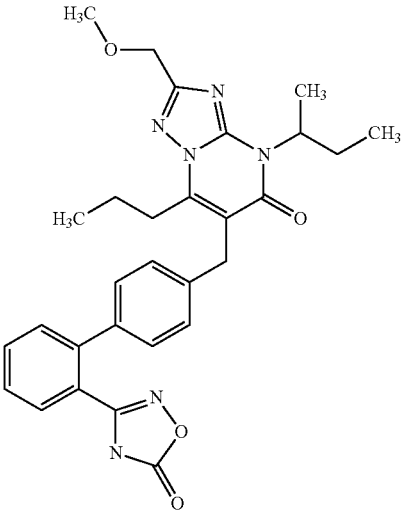 [SMILES: CCCc1c(Cc2ccc(-c3ccccc3-c3noc(=O)[nH]3)cc2)c(=O)n(C(C)CC)c2nc(COC)nn12]

A mixture of hydroxylammonium chloride (0.45 g), sodium hydrogen carbonate (0.73 g) and dimethyl sulfoxide (10 mL) was stirred at 40° C. for 30 min, 4'-{[2-(methoxymethyl)-4-(1-methylpropyl)-5-oxo-7-propyl-4,5-dihydro[1,2,4]triazolo[1,5-a]pyrimidin-6-yl]methyl}biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.072 g) and then 1,8-diazabicyclo[5.4.0]undec-7-ene (0.084 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.11 g, 49%).

$^1$H NMR (300 MHz, DMSO-$d_6$) δ0.76 (t, J=7.3 Hz, 3H) 1.46-1.61 (m, 5H) 1.81-1.95 (m, 1H) 2.07-2.24 (m, 1H) 2.87-2.95 (m, 2H) 3.32 (s, 4H) 3.36 (s, 3H) 3.96 (s, 2H) 4.47 (s, 2H) 4.95-5.11 (m, 1H) 7.19-7.24 (m, 2H) 7.27-7.31 (m, 2H) 7.47-7.58 (m, 2H) 7.61-7.71 (m, 2H) 12.37 (s, 1H)

EXAMPLE 101

2-(hydroxymethyl)-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

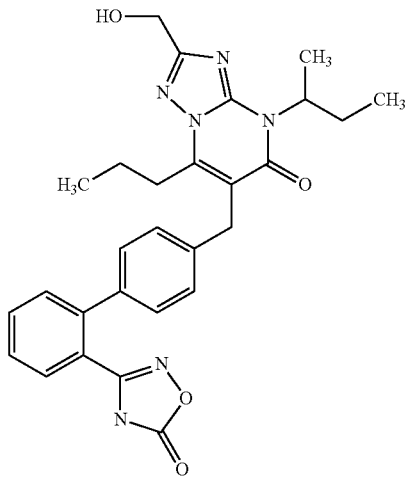 [SMILES: CCCc1c(Cc2ccc(-c3ccccc3-c3noc(=O)[nH]3)cc2)c(=O)n(C(C)CC)c2nc(CO)nn12]

A mixture of 2-(methoxymethyl)-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.07 g), boron tribromide (1.0 M dichloromethane solution, 0.4 mL) and dichloromethane (5 mL) was stirred at room temperature for 2 hr, saturated aqueous sodium hydrogen carbonate (10 mL) was added, and the mixture was further stirred for 1 hr. The reaction mixture was adjusted to pH 5 with 1 N hydrochloric acid, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as colorless crystals (0.02 g, 29%).

$^1$H NMR (300 MHz, DMSO-$d_6$) δ0.76 (t, J=7.4 Hz, 3H) 0.92 (t, J=7.3 Hz, 3H) 1.48-1.61 (m, 5H) 1.80-1.94 (m, 1H) 2.09-2.27 (m, 1H) 2.85-2.97 (m, 2H) 3.96 (s, 2H) 4.50 (d, J=6.0 Hz, 2H) 4.95-5.09 (m, 1H) 5.45 (t, J=6.1 Hz, 1H) 7.18-7.31 (m, 4H) 7.46-7.59 (m, 2H) 7.61-7.74 (m, 2H) 12.37 (s, 1H)

EXAMPLE 102

2-(bromomethyl)-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

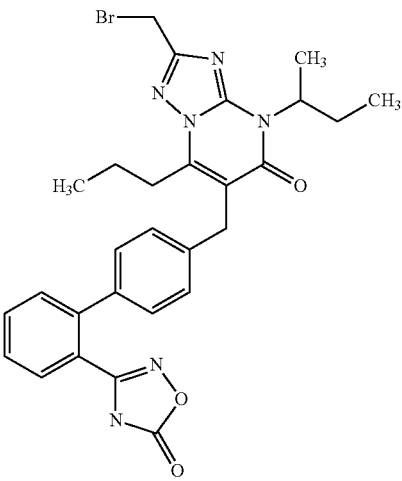 [SMILES: CCCc1c(Cc2ccc(-c3ccccc3-c3noc(=O)[nH]3)cc2)c(=O)n(C(C)CC)c2nc(CBr)nn12]

A mixture of 2-(methoxymethyl)-4-(1-methylpropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.07 g), boron tribromide (1.0 M dichloromethane solution, 0.4 mL) and dichloromethane (5 mL) was stirred at room temperature for 2 hr, saturated aqueous sodium hydrogen carbonate (10 mL) was added, and the mixture was further stirred for 1 hr. The reaction mixture was adjusted to pH 5 with 1 N hydrochloric acid, and the mixture was extracted with ethyl acetate. The ethyl acetate layer was washed with saturated brine, and dried over anhydrous magnesium sulfate. The solvent was evaporated under reduced pressure, and the residue was purified by silica gel column chromatography to give the title compound as colorless crystals (0.013 g, 2%).

$^1$H NMR (300 MHz, DMSO-$d_6$) δ0.76 (t, J=7.3 Hz, 3H), 0.92 (t, J=7.3 Hz, 3H), 1.47-1.61 (m, 5H), 1.79-1.93 (m, 1H), 2.05-2.24 (m, 1H), 2.81-2.96 (m, 2H), 3.96 (s, 2H), 4.69 (s, 2H), 4.92-5.08 (m, 1H), 7.19-7.33 (m, 4H), 7.47-7.59 (m, 2H), 7.61-7.74 (m, 2H), 12.37 (s, 1H)

EXAMPLE 103

2-methyl-4-{(2Z)-2-[(1-methylethoxy)imino]propyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

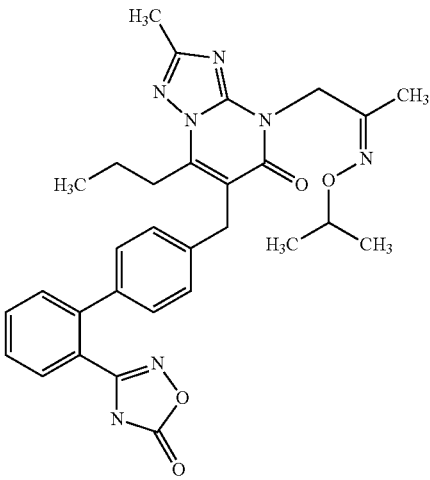 [SMILES: CCCc1c(Cc2ccc(-c3ccccc3-c3noc(=O)[nH]3)cc2)c(=O)n(C/C(C)=N\OC(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.4 g), 2-(aminooxy)propane hydrochloride (1.8 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.059 g, 11%).

$^1$H NMR (300 MHz, DMSO-$d_6$) δ0.92 (t, J=7.3 Hz, 3H), 1.10 (d, J=6.2 Hz, 6H), 1.47-1.60 (m, 2H), 1.63 (s, 3H), 2.35 (s, 3H), 2.89-3.00 (m, 2H), 3.96 (s, 2H), 4.10-4.25 (m, 1H), 4.86 (s, 2H), 7.18-7.33 (m, 4H), 7.44-7.60 (m, 2H), 7.58-7.74 (m, 2H), 12.38 (br. s., 1H)

EXAMPLE 104

2-methyl-4-{(2E)-2-[(1-methylethoxy)imino]propyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

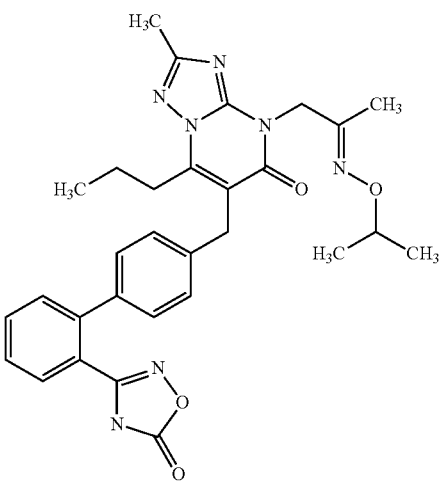 [SMILES: CCCc1c(Cc2ccc(-c3ccccc3-c3noc(=O)[nH]3)cc2)c(=O)n(C/C(C)=N/OC(C)C)c2nc(C)nn12]

A mixture of 2-methyl-6-{[2'-(5-oxo-4,5-dihydro-1,2,4-oxadiazol-3-yl)biphenyl-4-yl]methyl}-4-(2-oxopropyl)-7-propyl[1,2,4]triazolo[1,5-a]pyrimidin-5(4H)-one (0.4 g), 2-(aminooxy)propane hydrochloride (1.8 g) and pyridine (10 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.2 g, 36%).

$^1$H NMR (300 MHz, DMSO-$d_6$) δ0.88 (t, J=7.3 Hz, 3H), 1.00 (d, J=6.2 Hz, 6H), 1.46-1.59 (m, 2H), 1.80 (s, 3H), 2.33 (s, 3H), 2.86-2.97 (m, 2H), 3.90-4.05 (m, 3H), 4.81 (s, 2H), 7.15-7.33 (m, 4H), 7.46-7.59 (m, 2H), 7.61-7.72 (m, 2H), 12.37 (s, 1H)

EXAMPLE 105

2-methyl-6-{[2'-(5-oxo-4,5-dihydro-1,2,4-oxadiazol-3-yl)biphenyl-4-yl]methyl}-7-propyl-4-(3,3,3-trifluoro-2-hydroxypropyl)[1,2,4]triazolo[1,5-a]pyrimidin-5(4H)-one

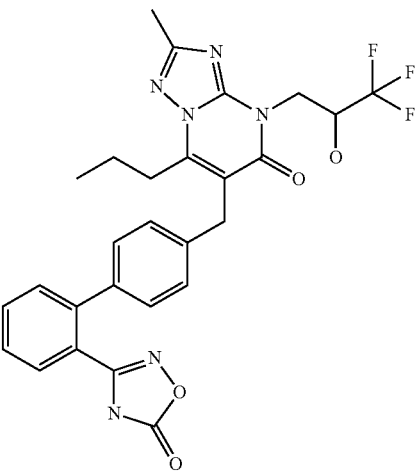 [SMILES: CCCc1c(Cc2ccc(-c3ccccc3-c3noc(=O)[nH]3)cc2)c(=O)n(CC(O)C(F)(F)F)c2nc(C)nn12]

A mixture of hydroxylammonium chloride (1.6 g), sodium hydrogen carbonate (2.6 g) and dimethyl sulfoxide (15 mL) was stirred at 40° C. for 30 min, 4'-{[2-methyl-5-oxo-7-propyl-4-(3,3,3-trifluoro-2-hydroxypropyl)-4,5-dihydro[1,2,4]triazolo[1,5-a]pyrimidin-6-yl]methyl}biphenyl-2-carbonitrile (0.76 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.025 g) and then 1,8-diazabicyclo[5.4.0]undec-7-ene (0.21 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.41 g, 49%).

$^1$H NMR (300 MHz, DMSO-$d_6$) δ0.91 (t, J=7.3 Hz, 3H), 1.44-1.62 (m, 2H), 2.37 (s, 3H), 2.83-3.02 (m, 2H), 3.96 (s, 2H), 4.20 (dd, J=13.4, 4.0 Hz, 1H), 4.38-4.49 (m, 1H), 4.61 (br. s., 1H), 6.59 (d, J=6.2 Hz, 1H), 7.15-7.32 (m, 4H), 7.52 (dd, J=17.0, 7.5 Hz, 2H), 7.60-7.72 (m, 2H), 12.39 (br. s., 1H)

EXAMPLE 106

2-methyl-6-{[2'-(5-oxo-4,5-dihydro-1,2,4-oxadiazol-3-yl)biphenyl-4-yl]methyl}-7-propyl-4-(3,3,3-trifluoro-2-oxopropyl)[1,2,4]triazolo[1,5-a]pyrimidin-5(4H)-one

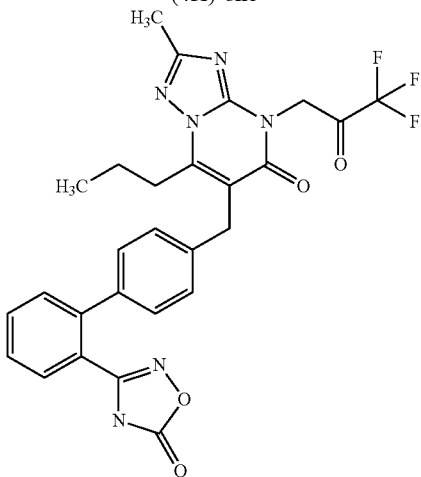

A mixture of 2-methyl-6-{[2'-(5-oxo-4,5-dihydro-1,2,4-oxadiazol-3-yl)biphenyl-4-yl]methyl}-7-propyl-4-(3,3,3-trifluoro-2-hydroxypropyl) [1,2,4]triazolo[1,5-a]pyrimidin-5(4H)-one (0.41 g), Dess-Martin reagent (0.47 g) and acetonitrile (10 mL) was stirred at room temperature for 3 hr. Saturated aqueous sodium hydrogen carbonate and sodium thiosulfate-pentahydrate were added to the reaction mixture, and the mixture was stirred at room temperature for 2 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.18 g, 43%).

$^1$H NMR (300 MHz, DMSO-$d_6$) δ0.92 (t, J=7.3 Hz, 3H), 1.46-1.61 (m, 2H), 2.37 (s, 3H), 2.85-2.97 (m, 2H), 3.98 (s, 2H), 4.50 (s, 2H), 7.19-7.25 (m, 2H), 7.27-7.34 (m, 2H), 7.46-7.58 (m, 2H), 7.62-7.72 (m, 2H), 12.39 (br. s., 1H)

EXAMPLE 107

4-[(2E)-2-(ethoxyimino)-3,3,3-trifluoropropyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

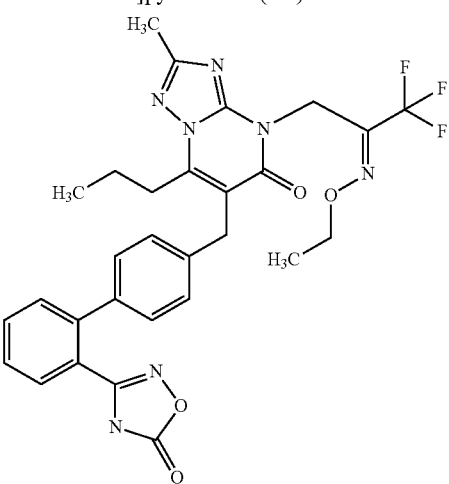

A mixture of 2-methyl-6-{[2'-(5-oxo-4,5-dihydro-1,2,4-oxadiazol-3-yl)biphenyl-4-yl]methyl}-7-propyl-4-(3,3,3-trifluoro-2-oxopropyl) [1,2,4]triazolo[1,5-a]pyrimidin-5(4H)-one (0.14 g), 2-(aminooxy)ethane hydrochloride (0.37 g) and pyridine (5 mL) was stirred at 110° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.041 g, 28%).

$^1$H NMR (300 MHz, DMSO-$d_6$) δ0.89 (t, J=7.2 Hz, 3H), 0.98 (t, J=7.0 Hz, 3H), 1.44-1.59 (m, 2H), 2.36 (s, 3H), 2.85-3.00 (m, 2H), 3.95 (s, 2H), 4.12 (q, J=7.2 Hz, 2H), 5.12 (s, 2H), 7.17-7.28 (m, 4H), 7.46-7.58 (m, 2H), 7.59-7.73 (m, 2H), 12.36 (br. s., 1H)

EXAMPLE 108

6-{[3-fluoro-2'-(5-oxo-4,5-dihydro-1,2,4-oxadiazol-3-yl)biphenyl-4-yl]methyl}-2-methyl-7-propyl-4-(tetrahydro-2H-pyran-4-yl)[1,2,4]triazolo[1,5-a]pyrimidin-5(4H)-one

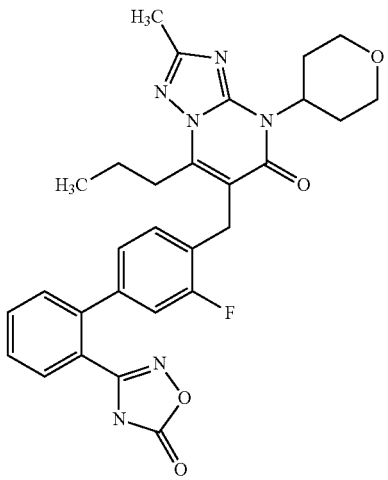 [SMILES: CCCc1c(Cc2ccc(-c3ccccc3-c3noc(=O)[nH]3)cc2F)c(=O)n(C2CCOCC2)c2nc(C)nn12]

A mixture of hydroxylammonium chloride (0.92 g), sodium hydrogen carbonate (1.5 g) and dimethyl sulfoxide (15 mL) was stirred at 40° C. for 30 min, 3'-fluoro-4'-{[2-methyl-5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile (0.43 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.17 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.23 g, 49%).

$^1$H NMR (300 MHz, DMSO-$d_6$) δ0.92 (t, J=7.4 Hz, 3H), 1.51-1.63 (m, 4H), 2.37 (s, 3H), 2.64-2.83 (m, 2H), 2.88 (dd, J=9.1, 6.4 Hz, 2H), 3.42 (t, J=11.4 Hz, 2H), 3.87-4.01 (m,

4H), 4.99-5.20 (m, 1H), 6.98 (dd, J=8.0, 1.5 Hz, 1H), 7.10-7.29 (m, 2H), 7.56 (dd, J=16.7, 7.2 Hz, 2H), 7.63-7.77 (m, 2H), 12.44 (s, 1H)

EXAMPLE 109

6-{[2'-(5-oxo-4,5-dihydro-1,2,4-oxadiazol-3-yl)biphenyl-4-yl]methyl}-7-propyl-4-(tetrahydro-2H-pyran-4-yl)[1,2,4]triazolo[1,5-a]pyrimidin-5(4H)-one

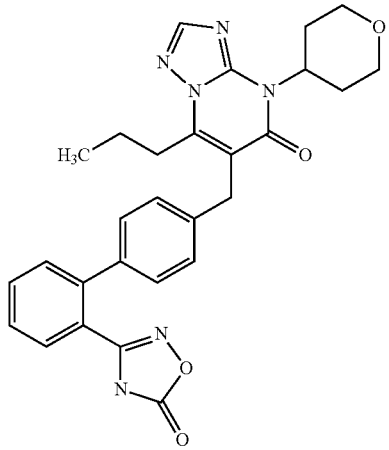 [SMILES: CCCc1c(Cc2ccc(-c3ccccc3-c3noc(=O)[nH]3)cc2)c(=O)n(C2CCOCC2)c2ncnn12]

A mixture of hydroxylammonium chloride (0.69 g), sodium hydrogen carbonate (1.1 g) and dimethyl sulfoxide (10 mL) was stirred at 40° C. for 30 min, 4'-{[5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.19 g, 56%).

$^1$H NMR (300 MHz, DMSO-d$_6$) δ0.93 (t, J=7.4 Hz, 3H), 1.47-1.67 (m, 4H), 2.68-2.86 (m, 2H), 2.88-2.99 (m, 2H), 3.43 (t, J=11.4 Hz, 2H), 3.92-4.02 (m, 4H), 5.10-5.26 (m, 1H), 7.17-7.24 (m, 2H), 7.27-7.38 (m, 2H), 7.53 (dd, J=17.4, 6.8 Hz, 2H), 7.63-7.73 (m, 2H), 8.20 (s, 1H), 12.37 (s, 1H)

EXAMPLE 110

4-(2-methoxycyclohexyl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

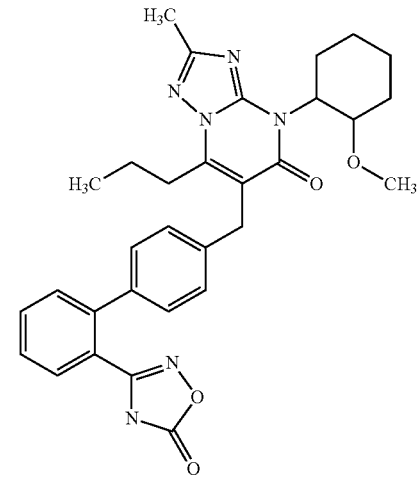 [SMILES: CCCc1c(Cc2ccc(-c3ccccc3-c3noc(=O)[nH]3)cc2)c(=O)n(C2CCCCC2OC)c2nc(C)nn12]

A mixture of hydroxylammonium chloride (0.59 g), sodium hydrogen carbonate (0.92 g) and dimethyl sulfoxide (10 mL) was stirred at 40° C. for 30 min, 4'-{[4-(2-methoxycyclohexyl)-2-methyl-5-oxo-7-propyl-4,5-dihydro[1,2,4]triazolo[1,5-a]pyrimidin-6-yl]methyl}biphenyl-2-carbonitrile (0.27 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.11 g) and then 1,8-diazabicyclo[5.4.0]undec-7-ene (0.09 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.16 g, 53%).

$^1$H NMR (300 MHz, DMSO-d$_6$) δ0.92 (t, J=7.4 Hz, 3H), 1.21-1.62 (m, 6H), 1.78 (dd, J=32.0, 10.4 Hz, 2H), 2.03 (d, J=11.4 Hz, 1H), 2.33 (s, 3H), 2.91 (t, J=7.8 Hz, 2H), 3.03 (s, 3H), 3.22-3.40 (m, 1H), 3.61 (br. s., 1H), 3.83-4.04 (m, 2H), 4.76 (d, J=12.9 Hz, 1H), 7.17-7.33 (m, 4H), 7.52 (dd, J=17.2, 7.4 Hz, 2H), 7.61-7.73 (m, 2H), 12.37 (br. s., 1H)

EXAMPLE 111

2-methyl-4-(1-methyl-2-oxopropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

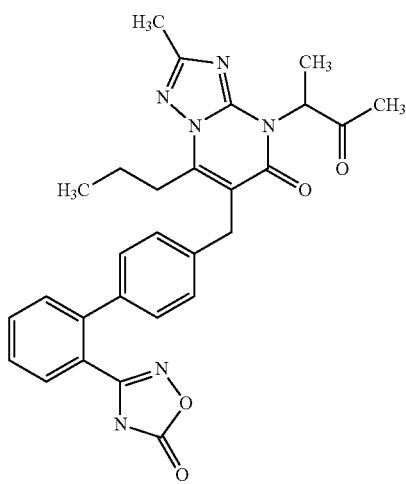 [SMILES: CCCc1c(Cc2ccc(-c3ccccc3-c3noc(=O)[nH]3)cc2)c(=O)n(C(C)C(C)=O)c2nc(C)nn12]

A mixture of hydroxylammonium chloride (2.7 g), sodium hydrogen carbonate (4.4 g) and dimethyl sulfoxide (25 mL) was stirred at 50° C. for 30 min, 4'-{[4-(2-{[tert-butyl(dimethyl)silyl]oxy}-1-methylpropyl)-2-methyl-5-oxo-7-propyl-4,5-dihydro[1,2,4]triazolo[1,5-a]pyrimidin-6-yl]methyl}biphenyl-2-carbonitrile (1.5 g) was added, and the mixture was stirred at 90° C. for 20 hr. After allowing to cool to room temperature, the reaction mixture was extracted with ethyl acetate and water, and the organic layer was washed with water and then with saturated brine, and dried over anhydrous magnesium sulfate. The solvent was evaporated under reduced pressure, and the residue was purified by silica gel column chromatography, and dissolved in tetrahydrofuran (30 mL). N,N'-Carbonyldiimidazole (0.51 g) and then 1,8-diazabicyclo[5.4.0]undec-7-ene (0.43 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (30 mL). Tetrabutylammonium fluoride (1 M tetrahydrofuran solution, 6.6 mL) was added, and the mixture was stirred at room temperature for 3 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure. The residue obtained by silica gel column chromatography was dissolved in acetonitrile (20 mL), Dess-Martin reagent (1.1 g) was added, and the mixture was stirred at room temperature for 2 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure, and the residue was recrystallized from acetone and hexane to give the title compound as colorless crystals (0.5 g, 37%).

$^1$H NMR (300 MHz, DMSO-$d_6$) δ0.94 (t, J=7.4 Hz, 3H), 1.48-1.63 (m, 5H), 2.08 (s, 3H), 2.35 (s, 3H), 2.86-2.99 (m, 2H), 5.36 (q, J=7.2 Hz, 1H), 7.19-7.26 (m, 2H), 7.26-7.34 (m, 2H), 7.46-7.59 (m, 2H), 7.61-7.72 (m, 2H), 12.37 (br. s., 1H)

EXAMPLE 112

6-{[3-fluoro-2'-(5-oxo-4,5-dihydro-1,2,4-oxadiazol-3-yl)biphenyl-4-yl]methyl}-4-(2-methoxy-1-methylethyl)-2-methyl-7-propyl[1,2,4]triazolo[1,5-a]pyrimidin-5(4H)-one

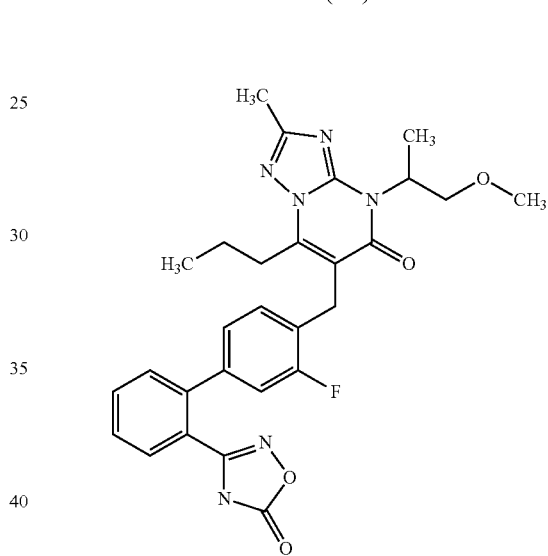

A mixture of hydroxylammonium chloride (0.62 g), sodium hydrogen carbonate (0.99 g) and dimethyl sulfoxide (10 mL) was stirred at 40° C. for 30 min, 3'-fluoro-4'-{[4-(2-methoxy-1-methylethyl)-2-methyl-5-oxo-7-propyl-4,5-dihydro[1,2,4]triazolo[1,5-a]pyrimidin-6-yl]methyl}biphenyl-2-carbonitrile (0.28 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.097 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.15 g, 49%).

$^1$H NMR (300 MHz, DMSO-$d_6$) δ0.92 (t, J=7.4 Hz, 3H) 1.44 (d, J=7.2 Hz, 3H) 1.49-1.63 (m, 2H) 2.36 (s, 3H) 2.83-2.95 (m, 2H) 3.17 (s, 3H) 3.51-3.60 (m, 1H) 3.93 (s, 2H)

5.16-5.40 (m, 1H) 7.00 (dd, J=8.0, 1.9 Hz, 1H) 7.11-7.24 (m, 2H) 7.51-7.64 (m, 2H) 7.62-7.77 (m, 2H) 12.45 (br. s., 1H)

EXAMPLE 113

6-{[3-fluoro-2'-(5-oxo-4,5-dihydro-1,2,4-oxadiazol-3-yl)biphenyl-4-yl]methyl}-2-methyl-7-propyl-4-(tetrahydro-2H-thiopyran-4-yl)[1,2,4]triazolo[1,5-a]pyrimidin-5(4H)-one

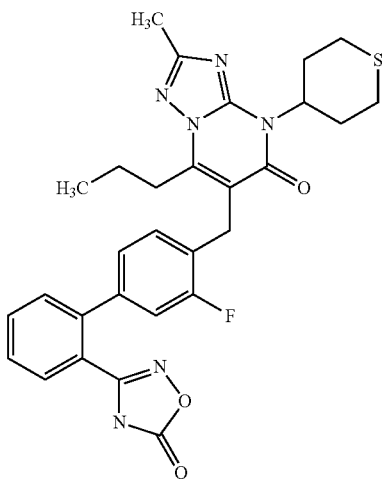 [SMILES: CCCc1c(Cc2ccc(-c3ccccc3-c3noc(=O)[nH]3)cc2F)c(=O)n(C2CCSCC2)c2nc(C)nn12]

A mixture of hydroxylammonium chloride (1.1 g), sodium hydrogen carbonate (1.8 g) and dimethyl sulfoxide (10 mL) was stirred at 40° C. for 30 min, 3'-fluoro-4'-{[2-methyl-5-oxo-7-propyl-4-(tetrahydro-2H-thiopyran-4-yl)-4,5-dihydro [1,2,4]triazolo[1,5-a]pyrimidin-6-yl]methyl}biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.21 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.41 g, 68%).

$^1$H NMR (300 MHz, DMSO-$d_6$) d ppm 0.92 (t, J=7.3 Hz, 3H), 1.46-1.64 (m, 2H), 1.87-1.99 (m, 2H), 2.37 (s, 3H), 2.63-2.96 (m, 8H), 3.92 (s, 2H), 4.85 (br. s., 1H), 6.98 (dd, J=8.0, 1.8 Hz, 1H), 7.16 (dd, J=11.1, 1.7 Hz, 1H), 7.23 (t, J=8.0 Hz, 1H), 7.49-7.63 (m, 2H), 7.64-7.74 (m, 2H), 12.45 (s, 1H)

EXAMPLE 114

4-[(2E)-2-(ethoxyimino)-1-methylpropyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

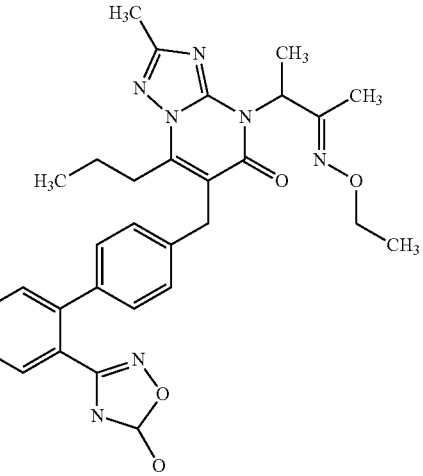

A mixture of 2-methyl-4-(1-methyl-2-oxopropyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), (aminooxy)ethane hydrochloride (0.76 g) and pyridine (5 mL) was stirred at 100° C. for 48 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.14 g, 66%).

$^1$H NMR (300 MHz, DMSO-$d_6$) δ0.91 (t, J=7.3 Hz, 3H), 1.12 (t, J=7.1 Hz, 3H), 1.47-1.58 (m, 2H), 1.61-1.69 (m, 6H), 2.34 (s, 3H), 2.85-2.95 (m, 2H), 3.88-4.04 (m, 4H), 5.61 (q, J=7.0 Hz, 1H), 7.17-7.30 (m, 4H), 7.46-7.58 (m, 2H), 7.61-7.72 (m, 2H), 12.38 (br. s., 1H)

EXAMPLE 115

6-{[3-fluoro-2'-(5-oxo-4,5-dihydro-1,2,4-oxadiazol-3-yl)biphenyl-4-yl]methyl}-2-methyl-4-(1-oxidetetrahydro-2H-thiopyran-4-yl)-7-propyl[1,2,4]triazolo[1,5-a]pyrimidin-5(4H)-one

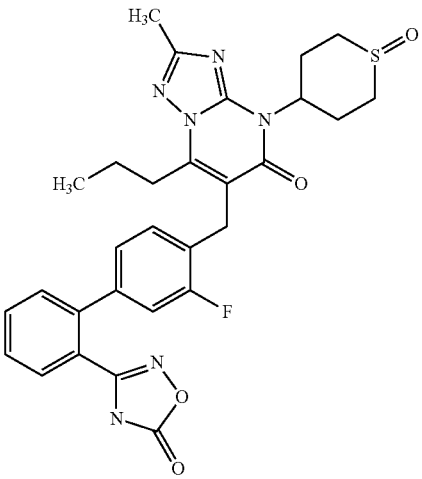 [SMILES: CCCc1c(Cc2ccc(-c3ccccc3-c3noc(=O)[nH]3)cc2F)c(=O)n(C2CCS(=O)CC2)c2nc(C)nn12]

A mixture of 6-{[3-fluoro-2'-(5-oxo-4,5-dihydro-1,2,4-oxadiazol-3-yl)biphenyl-4-yl]methyl}-2-methyl-7-propyl-4-(tetrahydro-2H-thiopyran-4-yl)[1,2,4]triazolo[1,5-a]pyrimidin-5(4H)-one (0.35 g), m-chloroperbenzoic acid (0.22 g), acetonitrile (15 mL) and dimethylformamide (5 mL) was stirred at room temperature for 3 hr. The reaction mixture was diluted with chloroform, washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as colorless crystals (0.18 g, 49%).

$^1$H NMR (300 MHz, DMSO-$d_6$) δ0.92 (t, J=7.4 Hz, 3H), 1.48-1.62 (m, 2H), 1.88-2.00 (m, 2H), 2.37 (s, 3H), 2.76-2.98 (m, 6H), 3.29-3.44 (m, 2H), 3.91 (s, 2H), 4.98-5.19 (m, 1H), 6.94-7.03 (m, 1H), 7.12-7.28 (m, 2H), 7.49-7.61 (m, 2H), 7.64-7.76 (m, 2H), 12.47 (br. s., 1H)

EXAMPLE 116

4-(1,1-dioxidotetrahydro-2H-thiopyran-4-yl)-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one

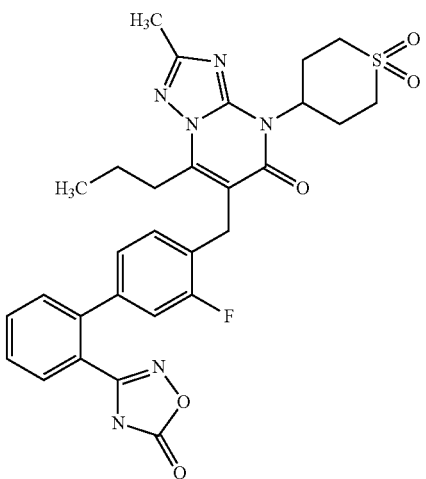 [SMILES: CCCc1c(Cc2ccc(-c3ccccc3-c3noc(=O)[nH]3)cc2F)c(=O)n(C2CCS(=O)(=O)CC2)c2nc(C)nn12]

A mixture of 6-{[3-fluoro-2'-(5-oxo-4,5-dihydro-1,2,4-oxadiazol-3-yl)biphenyl-4-yl]methyl}-2-methyl-7-propyl-4-(tetrahydro-2H-thiopyran-4-yl)[1,2,4]triazolo[1,5-a]pyrimidin-5(4H)-one (0.35 g), m-chloroperbenzoic acid (0.22 g), acetonitrile (15 mL) and dimethylformamide (5 mL) was stirred at room temperature for 3 hr. The reaction mixture was diluted with chloroform, washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as colorless crystals (0.14 g, 35%).

$^1$H NMR (300 MHz, DMSO-$d_6$) δ0.93 (t, J=7.3 Hz, 3H) 1.47-1.63 (m, 2H) 1.95-2.07 (m, 2H) 2.38 (s, 3H) 2.83-2.92 (m, 2H) 3.03-3.26 (m, 4H) 3.40-3.54 (m, 2H) 3.92 (s, 2H) 5.17-5.31 (m, 1H) 6.98 (dd, J=7.9, 1.7 Hz, 1H) 7.16 (dd, J=11.1, 1.7 Hz, 1H) 7.25 (t, J=8.1 Hz, 1H) 7.51-7.62 (m, 2H) 7.63-7.74 (m, 2H) 12.47 (s, 1H)

EXAMPLE 117

6-{[3-fluoro-2'-(5-oxo-4,5-dihydro-1,2,4-oxadiazol-3-yl)biphenyl-4-yl]methyl}-7-propyl-4-(tetrahydro-2H-pyran-4-yl)[1,2,4]triazolo[1,5-a]pyrimidin-5(4H)-one

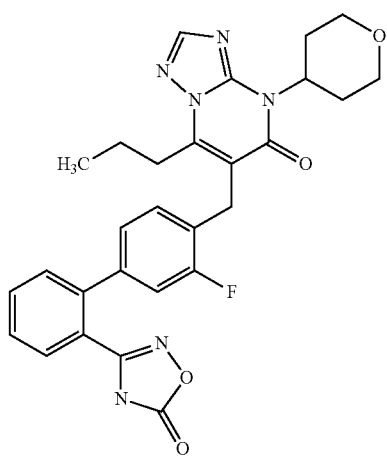 [SMILES: CCCc1c(Cc2ccc(-c3ccccc3-c3noc(=O)[nH]3)cc2F)c(=O)n(C2CCOCC2)c2ncnn12]

A mixture of hydroxylammonium chloride (1.3 g), sodium hydrogen carbonate (2 g) and dimethyl sulfoxide (10 mL) was stirred at 40° C. for 30 min, 3'-fluoro-4'-{[5-oxo-7-propyl-4-(tetrahydro-2H-pyran-4-yl)-4,5-dihydro[1,2,4]triazolo[1,5-a]pyrimidin-6-yl]methyl}biphenyl-2-carbonitrile (0.57 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.24 g) and then 1,8-diazabicyclo[5.4.0]undec-7-ene (0.2 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.46 g, 72%).

$^1$H NMR (300 MHz, DMSO-$d_6$) δ0.94 (t, J=7.3 Hz, 3H), 1.50-1.66 (m, 4H), 2.66-2.85 (m, 2H), 2.94 (dd, J=9.8, 5.8 Hz, 2H), 3.42 (t, J=11.3 Hz, 2H), 3.87-4.01 (m, 4H), 5.06-5.22 (m, 1H), 6.99 (dd, J=7.9, 1.7 Hz, 1H), 7.17 (dd, J=11.1, 1.7

Hz, 1H), 7.26 (t, J=8.0 Hz, 1H), 7.50-7.63 (m, 2H), 7.64-7.76 (m, 2H), 8.22 (s, 1H), 12.47 (br. s., 1H)

EXAMPLE 118

4-[(2R,4r,6S)-2,6-dimethyltetrahydro-2H-pyran-4-yl]-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one

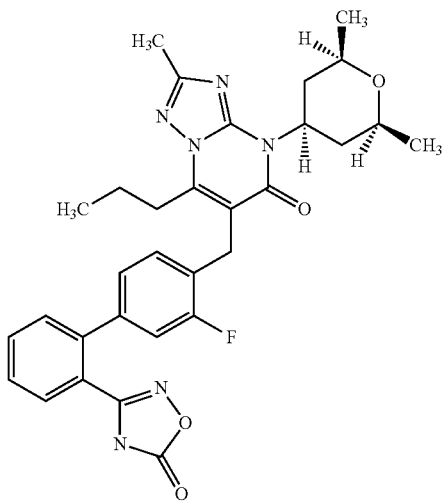 [SMILES: CCCc1c(Cc2ccc(-c3ccccc3-c3noc(=O)[nH]3)cc2F)c(=O)n([C@H]2C[C@@H](C)O[C@@H](C)C2)c2nc(C)nn12]

A mixture of hydroxylammonium chloride (0.67 g), sodium hydrogen carbonate (1.1 g) and dimethyl sulfoxide (10 mL) was stirred at 40° C. for 30 min, 4'-({4-[(2R,4r,6S)-2,6-dimethyltetrahydro-2H-pyran-4-yl]-2-methyl-5-oxo-7-propyl-4,5-dihydro[1,2,4]triazolo[1,5-a]pyrimidin-6-yl}methyl)-3'-fluorobiphenyl-2-carbonitrile (0.33 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.25 g, 68%).

¹H NMR (300 MHz, DMSO-d₆) δ0.92 (t, J=7.4 Hz, 3H), 1.14 (d, J=6.1 Hz, 6H), 1.48-1.69 (m, 4H), 2.25-2.40 (m, 5H), 2.84-2.93 (m, 2H), 3.49-3.62 (m, 2H), 3.92 (s, 2H), 5.03-5.21 (m, 1H), 6.99 (dd, J=8.0, 1.9 Hz, 1H), 7.16 (dd, J=11.0, 1.9 Hz, 1H), 7.23 (t, J=8.1 Hz, 1H), 7.49-7.62 (m, 2H), 7.64-7.75 (m, 2H), 12.45 (s, 1H)

EXAMPLE 119

4-[(2R,4s,6S)-2,6-dimethyltetrahydro-2H-pyran-4-yl]-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one

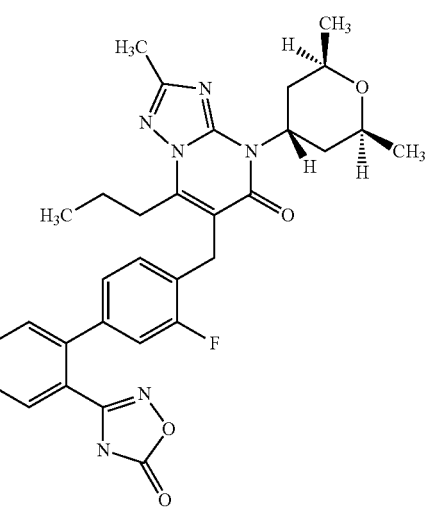

A mixture of hydroxylammonium chloride (0.11 g), sodium hydrogen carbonate (0.17 g) and dimethyl sulfoxide (5 mL) was stirred at 40° C. for 30 min, 4'-({4-[(2R,4s,6S)-2,6-dimethyltetrahydro-2H-pyran-4-yl]-2-methyl-5-oxo-7-propyl-4,5-dihydro[1,2,4]triazolo[1,5-a]pyrimidin-6-yl}methyl)-3'-fluorobiphenyl-2-carbonitrile (0.052 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.02 g) and then 1,8-diazabicyclo[5.4.0]undec-7-ene (0.017 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.035 g, 61%).

¹H NMR (300 MHz, DMSO-d₆) δ0.92 (t, J=7.2 Hz, 3H), 1.09 (d, J=6.4 Hz, 6H), 1.46-1.60 (m, 4H), 2.34-2.47 (m, 5H), 2.82-2.91 (m, 2H), 3.92 (s, 2H), 4.06-4.19 (m, 2H), 5.17-5.29

(m, 1H), 6.98 (dd, J=7.8, 1.7 Hz, 1H), 7.12-7.27 (m, 2H), 7.50-7.62 (m, 2H), 7.64-7.75 (m, 2H), 12.45 (s, 1H)

EXAMPLE 120

6-{[3-fluoro-2'-(5-oxo-4,5-dihydro-1,2,4-oxadiazol-3-yl)biphenyl-4-yl]methyl}-2-methyl-7-propyl-4-(tetrahydrofuran-3-yl)[1,2,4]triazolo[1,5-a]pyrimidin-5(4H)-one

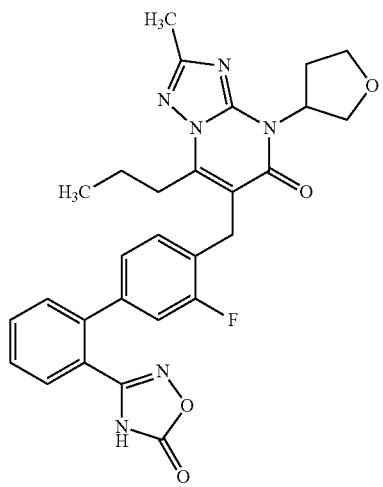 [SMILES: CCCc1c(Cc2ccc(-c3ccccc3-c3noc(=O)[nH]3)cc2F)c(=O)n(C2CCOC2)c2nc(C)nn12]

A mixture of tetrahydrofuran-3-ol (2.5 g), pyridinium dichromate (16 g), molecular sieves 4A (16 g) and tetrahydrofuran (200 mL) was stirred at room temperature for 3 hr. The reaction solution was diluted with diethyl ether (200 mL), the insoluble material was filtered off through silica gel, and the filtrate was concentrated. The obtained residue was dissolved in acetic acid (20 mL), 1H-1,2,4-triazol-3-amine (1.4 g) and sodium cyanoborohydride (4.5 g) were added, and the mixture was stirred at room temperature for 16 hr. Water was added to the reaction mixture, and the solvent was evaporated under reduced pressure. The obtained residue was poured into saturated aqueous sodium hydrogen carbonate, and the mixture was extracted with a mixed solvent of ethyl acetate and isopropyl alcohol (3:1). The obtained extract was dried over anhydrous sodium sulfate, and the solvent was evaporated under reduced pressure. A mixture of the obtained residue and ethyl 2-[(2'-cyano-3-fluorobiphenyl-4-yl)methyl]-3-oxohexanoate (0.79 g) was stirred under microwave irradiation at 250° C. for 20 min. The reaction mixture was purified by silica gel column chromatography and the obtained residue was dissolved in dimethyl sulfoxide (5 mL), and the mixture was added to a mixture of hydroxylammonium chloride (0.36 g), sodium hydrogen carbonate (0.58 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.067 g) and then 1,8-diazabicyclo[5.4.0]undec-7-ene (0.057 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.052 g, 0.3%).

$^1$H NMR (300 MHz, DMSO-$d_6$) δ0.92 (t, J=7.3 Hz, 3H), 1.48-1.66 (m, 2H), 2.07-2.22 (m, 1H), 2.37 (s, 3H), 2.41-2.48 (m, 1H), 2.83-2.92 (m, 2H), 3.81-3.96 (m, 5H), 4.09-4.20 (m, 1H), 5.51-5.66 (m, 1H), 6.99 (dd, J=8.0, 1.6 Hz, 1H), 7.12-7.28 (m, 2H), 7.51-7.62 (m, 2H), 7.64-7.73 (m, 2H), 12.46 (br. s., 1H)

EXAMPLE 121

6-{[3-fluoro-2'-(5-oxo-4,5-dihydro-1,2,4-oxadiazol-3-yl)biphenyl-4-yl]methyl}-7-propyl-4-(tetrahydro-2H-pyran-3-yl)[1,2,4]triazolo[1,5-a]pyrimidin-5(4H)-one

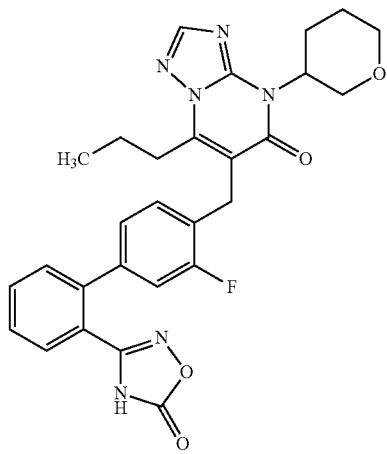 [SMILES: CCCc1c(Cc2ccc(-c3ccccc3-c3noc(=O)[nH]3)cc2F)c(=O)n(C2CCCOC2)c2ncnn12]

A mixture of hydroxylammonium chloride (0.37 g), sodium hydrogen carbonate (0.6 g) and dimethyl sulfoxide (10 mL) was stirred at 40° C. for 30 min, 3'-fluoro-4'-{[5-oxo-7-propyl-4-(tetrahydro-2H-pyran-3-yl)-4,5-dihydro[1,2,4]triazolo[1,5-a]pyrimidin-6-yl]methyl}biphenyl-2-carbonitrile (0.17 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.07 g) and then 1,8-diazabicyclo[5.4.0]undec-7-ene (0.059 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.11 g, 56%).

$^1$H NMR (300 MHz, DMSO-$d_6$) δ0.93 (t, J=7.3 Hz, 3H), 1.48-1.63 (m, 2H), 1.65-1.89 (m, 3H), 2.64-2.82 (m, 1H), 2.87-3.00 (m, 2H), 3.25-3.42 (m, 2H), 3.73-3.89 (m, 2H), 3.94 (s, 2H), 4.90-5.06 (m, 1H), 6.99 (dd, J=7.9, 1.9 Hz, 1H), 7.17 (dd, J=11.1, 1.7 Hz, 1H), 7.25 (t, J=8.0 Hz, 1H), 7.49-7.62 (m, 2H), 7.64-7.74 (m, 2H), 8.20 (s, 1H), 12.46 (br. s., 1H)

EXAMPLE 122

4-(1,4-dioxaspiro[4.5]dec-8-yl)-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one

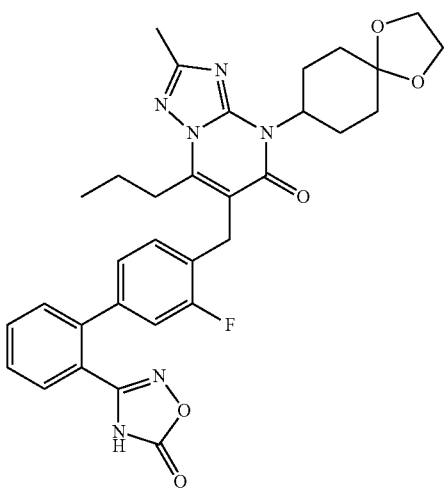 [SMILES: CCCc1c(Cc2ccc(-c3ccccc3-c3noc(=O)[nH]3)cc2F)c(=O)n(C2CCC3(CC2)OCCO3)c2nc(C)nn12]

A mixture of hydroxylammonium chloride (0.62 g), sodium hydrogen carbonate (1 g) and dimethyl sulfoxide (10 mL) was stirred at 40° C. for 30 min, 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}-3'-fluorobiphenyl-2-carbonitrile (0.32 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.098 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.25 g, 75%).

$^1$H NMR (300 MHz, DMSO-d$_6$) δ0.92 (t, J=7.3 Hz, 3H), 1.50-1.82 (m, 8H), 2.37 (s, 3H), 2.67-2.92 (m, 4H), 3.81-3.96 (m, 6H), 4.83-4.96 (m, 1H), 6.99 (dd, J=8.0, 1.8 Hz, 1H), 7.12-7.27 (m, 2H), 7.50-7.63 (m, 2H), 7.64-7.73 (m, 2H), 12.46 (br. s., 1H)

EXAMPLE 123

6-{[3-fluoro-2'-(5-oxo-4,5-dihydro-1,2,4-oxadiazol-3-yl)biphenyl-4-yl]methyl}-2-methyl-4-(4-oxocyclohexyl)-7-propyl[1,2,4]triazolo[1,5-a]pyrimidin-5(4H)-one

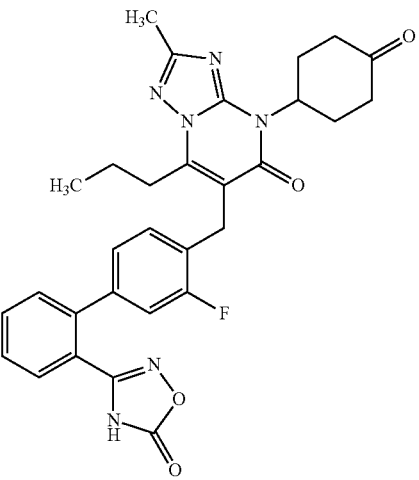 [SMILES: CCCc1c(Cc2ccc(-c3ccccc3-c3noc(=O)[nH]3)cc2F)c(=O)n(C2CCC(=O)CC2)c2nc(C)nn12]

A mixture of 4-(1,4-dioxaspiro[4.5]dec-8-yl)-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one (0.25 g), 6N hydrochloric acid (2 mL) and tetrahydrofuran (10 mL) was stirred at room temperature for 2 hr. The reaction mixture was poured into saturated aqueous sodium hydrogen carbonate, and the mixture was adjusted to pH 4 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was recrystallized from ethyl acetate and hexane to give the title compound as colorless crystals (0.18 g, 74%).

$^1$H NMR (300 MHz, DMSO-d$_6$) δ0.93 (t, J=7.4 Hz, 3H), 1.48-1.62 (m, 2H), 1.93-2.04 (m, 2H), 2.24-2.39 (m, 5H), 2.56-2.72 (m, 2H), 2.76-2.95 (m, 4H), 3.94 (s, 2H), 5.37-5.49 (m, 1H), 6.98 (dd, J=8.0, 1.9 Hz, 1H), 7.16 (dd, J=11.2, 1.7 Hz, 1H), 7.25 (t, J=8.0 Hz, 1H), 7.50-7.62 (m, 2H), 7.63-7.76 (m, 2H), 12.45 (s, 1H)

EXAMPLE 124

6-{[2'-(5-oxo-4,5-dihydro-1,2,4-oxadiazol-3-yl)biphenyl-4-yl]methyl}-7-propyl-4-(tetrahydro-2H-pyran-3-yl)[1,2,4]triazolo[1,5-a]pyrimidin-5(4H)-one

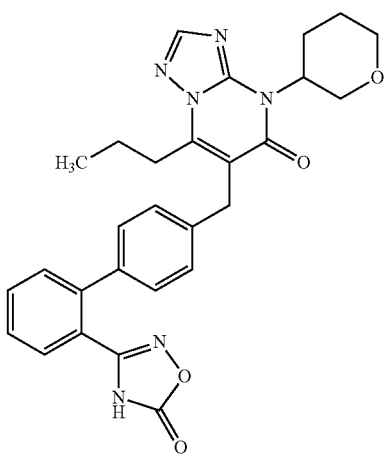 [SMILES: CCCc1c(Cc2ccc(-c3ccccc3-c3noc(=O)[nH]3)cc2)c(=O)n(C2CCCOC2)c2ncnn12]

A mixture of hydroxylammonium chloride (0.66 g), sodium hydrogen carbonate (1.1 g) and dimethyl sulfoxide (10 mL) was stirred at 40° C. for 30 min, 4'-{[5-oxo-7-propyl-4-(tetrahydro-2H-pyran-3-yl)-4,5-dihydro[1,2,4]triazolo[1,5-a]pyrimidin-6-yl]methyl}biphenyl-2-carbonitrile (0.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.1 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.057 g, 18%).

$^1$H NMR (300 MHz, DMSO-d$_6$) δ 0.92 (t, J=7.2 Hz, 3H), 1.45-1.60 (m, 2H), 1.63-1.96 (m, 3H), 2.64-2.84 (m, 1H), 2.87-2.97 (m, 2H), 3.32-3.41 (m, 1H), 3.75-3.90 (m, 2H), 3.96 (s, 2H), 4.22 (t, J=10.6 Hz, 1H), 4.92-5.07 (m, 1H), 7.18-7.25 (m, 2H), 7.28-7.36 (m, 2H), 7.53 (dd, J=16.1, 7.8 Hz, 2H), 7.61-7.73 (m, 2H), 8.19 (s, 1H), 12.38 (s, 1H)

EXAMPLE 125

7-butyl-6-{[2'-(5-oxo-4,5-dihydro-1,2,4-oxadiazol-3-yl)biphenyl-4-yl]methyl}-4-(tetrahydro-2H-pyran-4-yl)[1,2,4]triazolo[1,5-a]pyrimidin-5(4H)-one

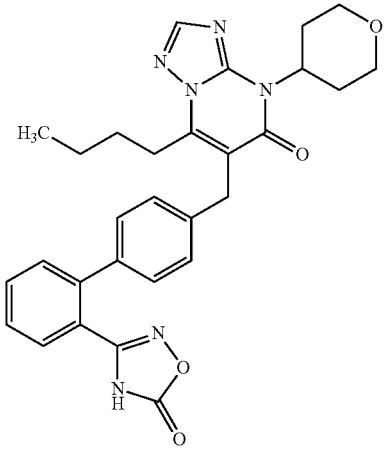 [SMILES: CCCCc1c(Cc2ccc(-c3ccccc3-c3noc(=O)[nH]3)cc2)c(=O)n(C2CCOCC2)c2ncnn12]

A mixture of hydroxylammonium chloride (1.2 g), sodium hydrogen carbonate (1.9 g) and dimethyl sulfoxide (10 mL) was stirred at 40° C. for 30 min, 7-butyl-6-{[2'-(5-oxo-4,5-dihydro-1,2,4-oxadiazol-3-yl)biphenyl-4-yl]methyl}-4-(tetrahydro-2H-pyran-4-yl)[1,2,4]triazolo[1,5-a]pyrimidin-5(4H)-one (0.52 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.22 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.29 g, 50%).

$^1$H NMR (300 MHz, DMSO-d$_6$) δ 0.84 (t, J=7.2 Hz, 3H), 1.29-1.41 (m, 2H), 1.42-1.55 (m, 2H), 1.55-1.67 (m, 2H), 2.65-2.87 (m, 2H), 2.88-3.00 (m, 2H), 3.43 (t, J=11.3 Hz, 2H), 3.93-4.04 (m, 4H), 5.09-5.25 (m, 1H), 7.18-7.25 (m, 2H), 7.28-7.34 (m, 2H), 7.46-7.59 (m, 2H), 7.59-7.73 (m, 2H), 8.20 (s, 1H), 12.39 (s, 1H)

EXAMPLE 126

4-[(2R,4r,6S)-2,6-dimethyltetrahydro-2H-pyran-4-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

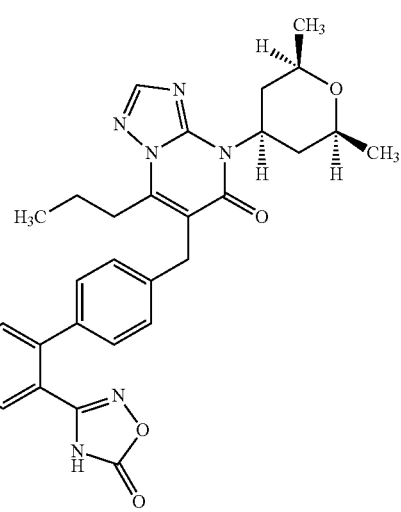

A mixture of hydroxylammonium chloride (1.2 g), sodium hydrogen carbonate (1.9 g) and dimethyl sulfoxide (10 mL) was stirred at 40° C. for 30 min, 4'-({4-[(2R,4r,6S)-2,6-dimethyltetrahydro-2H-pyran-4-yl]-5-oxo-7-propyl-4,5-dihydro[1,2,4]triazolo[1,5-a]pyrimidin-6-yl}methyl)biphenyl-2-carbonitrile (0.54 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.22 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.41 g, 69%).

$^1$H NMR (300 MHz, DMSO-d$_6$) δ 0.92 (t, J=7.3 Hz, 3H), 1.14 (d, J=6.0 Hz, 6H), 1.48-1.60 (m, 2H), 1.60-1.73 (m, 2H), 2.36 (q, J=12.0 Hz, 2H), 2.89-2.98 (m, 2H), 3.51-3.63 (m,

2H), 3.96 (s, 2H), 5.12-5.29 (m, 1H), 7.18-7.25 (m, 2H), 7.27-7.36 (m, 2H), 7.46-7.59 (m, 2H), 7.61-7.75 (m, 2H), 8.19 (s, 1H), 12.38 (s, 1H)

EXAMPLE 127

4-[(2R,4s,6S)-2,6-dimethyltetrahydro-2H-pyran-4-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

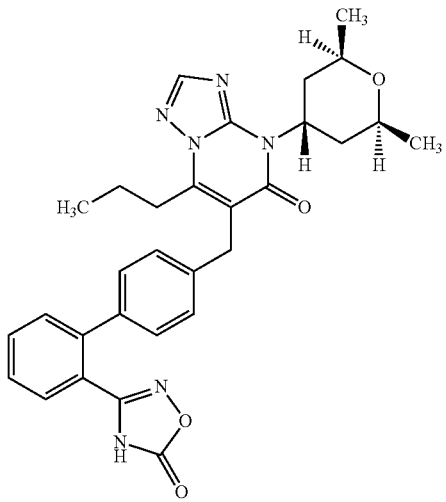 [SMILES: CCCc1c(Cc2ccc(-c3ccccc3-c3noc(=O)[nH]3)cc2)c(=O)n([C@@H]2C[C@@H](C)O[C@@H](C)C2)c2ncnn12]

A mixture of hydroxylammonium chloride (0.21 g), sodium hydrogen carbonate (0.34 g) and dimethyl sulfoxide (5 mL) was stirred at 40° C. for 30 min, 4'-({4-[(2R,4s,6S)-2,6-dimethyltetrahydro-2H-pyran-4-yl]-5-oxo-7-propyl-4,5-dihydro[1,2,4]triazolo[1,5-a]pyrimidin-6-yl}methyl)biphenyl-2-carbonitrile (0.098 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.039 g) and then 1,8-diazabicyclo[5.4.0]undec-7-ene (0.033 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.058 g, 53%).

$^1$H NMR (300 MHz, DMSO-d$_6$) δ0.92 (t, J=7.3 Hz, 3H), 1.10 (d, J=6.2 Hz, 6H), 1.48-1.69 (m, 4H), 2.37-2.48 (m, 2H), 2.86-2.98 (m, 2H), 3.98 (s, 2H), 4.09-4.20 (m, 2H), 5.29 (t, J=7.1 Hz, 1H), 7.19-7.26 (m, 2H), 7.28-7.35 (m, 2H), 7.47-7.58 (m, 2H), 7.61-7.71 (m, 2H), 8.17-8.21 (m, 1H), 12.38 (s, 1H)

EXAMPLE 128

6-{[3-fluoro-2'-(5-oxo-4,5-dihydro-1,2,4-oxadiazol-3-yl)biphenyl-4-yl]methyl}-4-(4-hydroxycyclohexyl)-2-methyl-7-propyl[1,2,4]triazolo[1,5-a]pyrimidin-5(4H)-one

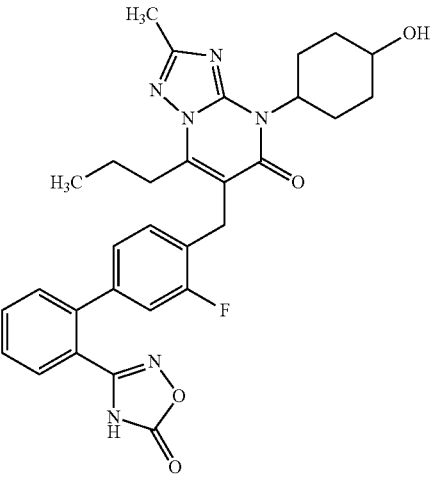 [SMILES: CCCc1c(Cc2ccc(-c3ccccc3-c3noc(=O)[nH]3)cc2F)c(=O)n(C2CCC(O)CC2)c2nc(C)nn12]

To a solution (5 mL) of 6-{[3-fluoro-2'-(5-oxo-4,5-dihydro-1,2,4-oxadiazol-3-yl)biphenyl-4-yl]methyl}-2-methyl-4-(4-oxocyclohexyl)-7-propyl[1,2,4]triazolo[1,5-a]pyrimidin-5(4H)-one (0.1 g) in methanol was added sodium borohydride (0.014 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless solid (0.046 g, 46%).

$^1$H NMR (300 MHz, DMSO-d$_6$) δ0.92 (t, J=7.3 Hz, 3H) 1.20-1.42 (m, 4H) 1.44-1.66 (m, 4H) 1.71-1.82, 1.88-1.97 (m, combined 2H) 2.36 (s, 3H) 2.83-2.92 (m, 2H) 3.40-3.54, 3.82-3.88 (m, combined 1H) 3.91 (s, 2H) 4.33-4.66 (m, 1H) 4.72-4.87 (m, 1H) 6.98 (dd, J=7.9, 1.7 Hz, 1H) 7.10-7.27 (m, 2H) 7.49-7.63 (m, 2H) 7.64-7.75 (m, 2H) 12.45 (s, 1H)

EXAMPLE 129

6-{[2'-(5-oxo-4,5-dihydro-1,2,4-oxadiazol-3-yl)biphenyl-4-yl]methyl}-7-propyl-4-(tetrahydrofuran-3-yl)[1,2,4]triazolo[1,5-a]pyrimidin-5(4H)-one

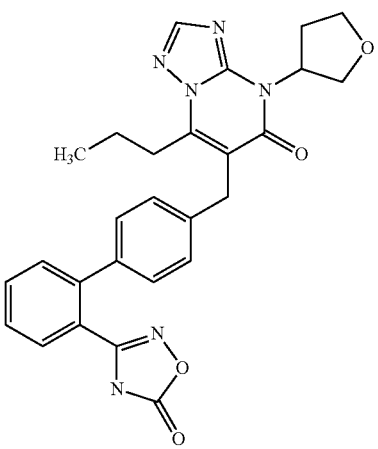 [SMILES: CCCc1c(Cc2ccc(-c3ccccc3-c3noc(=O)[nH]3)cc2)c(=O)n(C2CCOC2)c2ncnn12]

A mixture of hydroxylammonium chloride (0.42 g), sodium hydrogen carbonate (0.67 g) and dimethyl sulfoxide (10 mL) was stirred at 40° C. for 30 min, 4'-{[5-oxo-7-propyl-4-(tetrahydrofuran-3-yl)-4,5-dihydro[1,2,4]triazolo[1,5-a]pyrimidin-6-yl]methyl}biphenyl-2-carbonitrile (0.18 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.078 g) and then 1,8-diazabicyclo[5.4.0]undec-7-ene (0.066 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.025 g, 13%).

$^1$H NMR (300 MHz, DMSO-$d_6$) δ0.92 (t, J=7.3 Hz, 3H), 1.47-1.64 (m, 2H), 2.06-2.24 (m, 1H), 2.42-2.48 (m, 1H), 2.87-2.99 (m, 2H), 3.82-4.00 (m, 5H), 4.17 (q, J=7.7 Hz, 1H), 5.57-5.72 (m, 1H), 7.20-7.25 (m, 2H), 7.30-7.35 (m, 2H), 7.48-7.58 (m, 2H), 7.62-7.73 (m, 2H), 8.20 (s, 1H), 12.38 (s, 1H)

EXAMPLE 130

4-(2-methyltetrahydro-2H-pyran-4-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

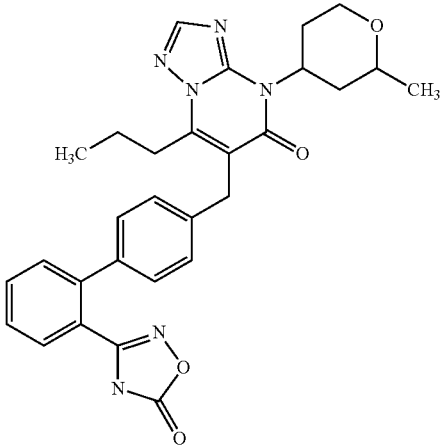 [SMILES: CCCc1c(Cc2ccc(-c3ccccc3-c3noc(=O)[nH]3)cc2)c(=O)n(C2CCOC(C)C2)c2ncnn12]

A mixture of hydroxylammonium chloride (0.95 g), sodium hydrogen carbonate (1.5 g) and dimethyl sulfoxide (15 mL) was stirred at 40° C. for 30 min, 4'-{[4-(2-methyltetrahydro-2H-pyran-4-yl)-5-oxo-7-propyl-4,5-dihydro[1,2,4]triazolo[1,5-a]pyrimidin-6-yl]methyl}biphenyl-2-carbonitrile (0.43 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.23 g, 47%).

$^1$H NMR (300 MHz, DMSO-$d_6$) δ0.93 (t, J=7.3 Hz, 3H), 1.13-1.30 (m, 3H), 1.44-1.75 (m, 4H), 2.34-2.47, 2.59-2.99 (m, combined 4H), 3.41-3.58, 3.66-3.82 (m, combined 2H), 3.91-4.03, 4.22-4.31 (m, combined 3H), 5.08-5.24, 5.36-5.51 (m, combined 1H), 7.17-7.25 (m, 2H), 7.27-7.36 (m, 2H), 7.47-7.58 (m, 2H), 7.61-7.73 (m, 2H), 8.20 (s, 1H), 12.38 (br. s., 1H)

EXAMPLE 131

4-[trans-4-(2-hydroxy-2-methylpropoxy)cyclohexyl]-6-{1-[2'-(5-oxo-4,5-dihydro-1,2,4-oxadiazol-3-yl)biphenyl-4-yl]ethyl}-7-propyl[1,2,4]triazolo[1,5-a]pyrimidin-5(4H)-one

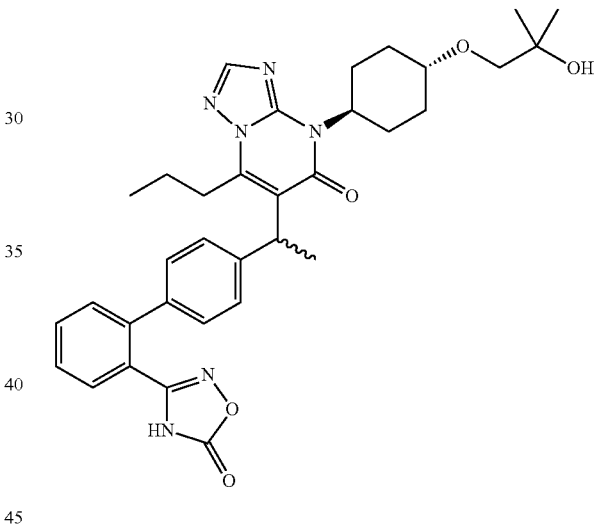

A mixture of hydroxylammonium chloride (0.75 g), sodium hydrogen carbonate (1.20 g) and dimethyl sulfoxide (10 mL) was stirred at 40° C. for 30 min, 4'-(1-{4-[trans-4-(2-hydroxy-2-methylpropoxy)cyclohexyl]-5-oxo-7-propyl-4,5-dihydro[1,2,4]triazolo[1,5-a]pyrimidin-6-yl}ethyl)biphenyl-2-carbonitrile (0.39 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.20 g) and then 1,8-diazabicyclo[5.4.0]undec-7-ene (0.20 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.16 g, 37%).

$^1$H NMR (300 MHz, CDCl$_3$) δ1.12 (t, J=7.5 Hz, 3H), 1.18 (s, 6H), 1.34-1.94 (m, 9H), 2.10-2.24 (m, 2H), 2.35 (s, 1H), 2.54-2.72 (m, 2H), 3.00-3.20 (m, 2H), 3.28 (s, 2H), 3.34-3.48 (m, 1H), 4.36-4.48 (m, 1H), 4.86-5.02 (m, 1H), 7.24-7.30 (m, 2H), 7.36-7.52 (m, 4H), 7.56-7.64 (m, 1H), 7.84-7.88 (m, 1H), 7.90 (s, 1H)

EXAMPLE 132

7-butyl-2-methyl-6-{[2'-(5-oxo-4,5-dihydro-1,2,4-oxadiazol-3-yl)biphenyl-4-yl]methyl}-4-(tetrahydro-2H-pyran-4-yl)[1,2,4]triazolo[1,5-a]pyrimidin-5(4H)-one

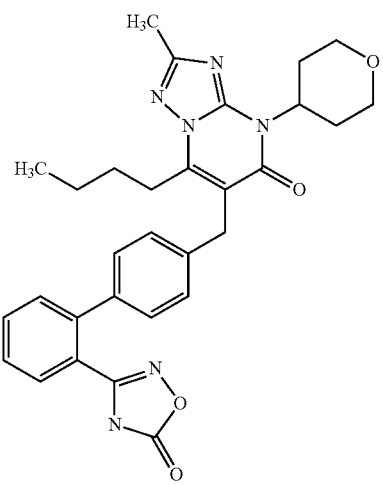 [SMILES: CCCCc1c(Cc2ccc(-c3ccccc3-c3noc(=O)[nH]3)cc2)c(=O)n(C2CCOCC2)c2nc(C)nn12]

A mixture of hydroxylammonium chloride (1.1 g), sodium hydrogen carbonate (1.8 g) and dimethyl sulfoxide (15 mL) was stirred at 40° C. for 30 min, 4'-{[7-butyl-2-methyl-5-oxo-4-(tetrahydro-2H-pyran-4-yl)-4,5-dihydro[1,2,4]triazolo[1,5-a]pyrimidin-6-yl]methyl}biphenyl-2-carbonitrile (0.52 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.21 g) and then 1,8-diazabicyclo[5.4.0]undec-7-ene (0.18 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.31 g, 52%).

$^1$H NMR (300 MHz, DMSO-d$_6$) δ0.21 (t, J=7.1 Hz, 3H), 0.64-1.05 (m, 6H), 1.74 (s, 3H), 2.05-2.37 (m, 4H), 2.80 (t, J=11.6 Hz, 2H), 3.28-3.41 (m, 4H), 4.43-4.59 (m, 1H), 6.55-6.63 (m, 2H), 6.64-6.72 (m, 2H), 6.81-6.97 (m, 2H), 6.98-7.10 (m, 2H), 11.76 (s, 1H)

EXAMPLE 133

4-(2,2-dimethyltetrahydro-2H-pyran-4-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

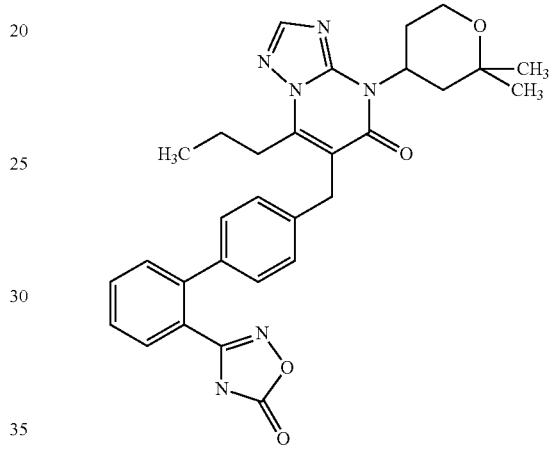

A mixture of hydroxylammonium chloride (0.89 g), sodium hydrogen carbonate (1.4 g) and dimethyl sulfoxide (10 mL) was stirred at 40° C. for 30 min, 4'-{[4-(2,2-dimethyltetrahydro-2H-pyran-4-yl)-5-oxo-7-propyl-4,5-dihydro[1,2,4]triazolo[1,5-a]pyrimidin-6-yl]methyl}biphenyl-2-carbonitrile (0.41 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.25 g, 54%).

$^1$H NMR (300 MHz, DMSO-d$_6$) δ0.93 (t, J=7.4 Hz, 3H), 1.18 (s, 3H), 1.26 (s, 3H), 1.46-1.65 (m, 4H), 2.52-2.62 (m, 1H), 2.65-2.83 (m, 1H), 2.90-2.97 (m, 2H), 3.62-3.81 (m, 2H), 3.97 (s, 2H), 5.28-5.45 (m, 1H), 7.18-7.25 (m, 2H), 7.26-7.37 (m, 2H), 7.53 (dd, J=16.1, 7.8 Hz, 2H), 7.63-7.74 (m, 2H), 8.20 (s, 1H), 12.38 (s, 1H)

EXAMPLE 134

7-butyl-4-(2,2-dimethyltetrahydro-2H-pyran-4-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

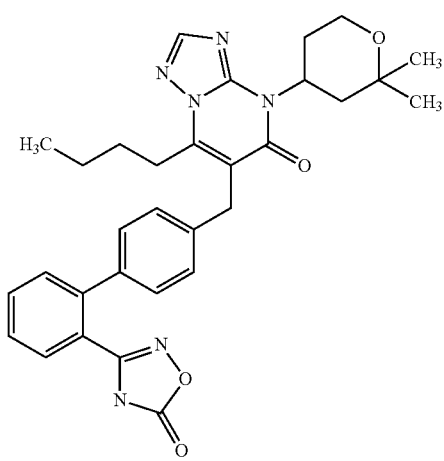 [SMILES: CCCCc1c(Cc2ccc(-c3ccccc3-c3noc(=O)[nH]3)cc2)c(=O)n(C2CCOC(C)(C)C2)c2ncnn12]

A mixture of hydroxylammonium chloride (0.95 g), sodium hydrogen carbonate (1.5 g) and dimethyl sulfoxide (10 mL) was stirred at 40° C. for 30 min, 4'-{[7-butyl-4-(2,2-dimethyltetrahydro-2H-pyran-4-yl)-5-oxo-4,5-dihydro[1,2,4]triazolo[1,5-a]pyrimidin-6-yl]methyl}biphenyl-2-carbonitrile (0.45 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.18 g) and then 1,8-diazabicyclo[5.4.0]undec-7-ene (0.15 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.21 g, 42%).

$^1$H NMR (300 MHz, DMSO-d$_6$) δ0.84 (t, J=7.2 Hz, 3H), 1.19 (s, 3H), 1.26 (s, 3H), 1.28-1.41 (m, 2H), 1.40-1.64 (m, 4H), 2.52-2.61 (m, 1H), 2.62-2.82 (m, 1H), 2.89-3.01 (m, 2H), 3.63-3.81 (m, 2H), 3.96 (s, 2H), 5.31-5.47 (m, 1H), 7.19-7.26 (m, 2H), 7.28-7.35 (m, 2H), 7.46-7.59 (m, 2H), 7.61-7.74 (m, 2H), 8.20 (s, 1H), 12.39 (s, 1H)

EXAMPLE 135

7-butyl-6-{[3-fluoro-2'-(5-oxo-4,5-dihydro-1,2,4-oxadiazol-3-yl)biphenyl-4-yl]methyl}-2-methyl-4-(tetrahydro-2H-pyran-4-yl)[1,2,4]triazolo[1,5-a]pyrimidin-5(4H)-one

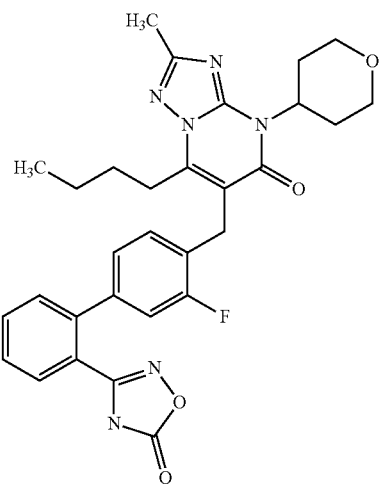 [SMILES: CCCCc1c(Cc2ccc(-c3ccccc3-c3noc(=O)[nH]3)cc2F)c(=O)n(C2CCOCC2)c2nc(C)nn12]

A mixture of hydroxylammonium chloride (1 g), sodium hydrogen carbonate (1.7 g) and dimethyl sulfoxide (10 mL) was stirred at 40° C. for 30 min, 4'-{[7-butyl-2-methyl-5-oxo-4-(tetrahydro-2H-pyran-4-yl)-4,5-dihydro[1,2,4]triazolo[1,5-a]pyrimidin-6-yl]methyl}-3'-fluorobiphenyl-2-carbonitrile (0.49 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.19 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.32 g, 57%).

$^1$H NMR (300 MHz, DMSO-d$_6$) δ0.84 (t, J=7.2 Hz, 3H), 1.26-1.42 (m, 2H), 1.45-1.62 (m, 4H), 2.37 (s, 3H), 2.66-2.84 (m, 2H), 2.84-2.93 (m, 2H), 3.42 (t, J=11.4 Hz, 2H), 3.89-

4.00 (m, 4H), 5.02-5.18 (m, 1H), 6.98 (dd, J=8.0, 1.5 Hz, 1H), 7.13-7.28 (m, 2H), 7.49-7.62 (m, 2H), 7.63-7.75 (m, 2H), 12.46 (s, 1H)

EXAMPLE 136

4-(2,2-dimethyltetrahydro-2H-pyran-4-yl)-6-{[3-fluoro-2'-(5-oxo-4,5-dihydro-1,2,4-oxadiazol-3-yl)biphenyl-4-yl]methyl}-2-methyl-7-propyl[1,2,4]triazolo[1,5-a]pyrimidin-5(4H)-one

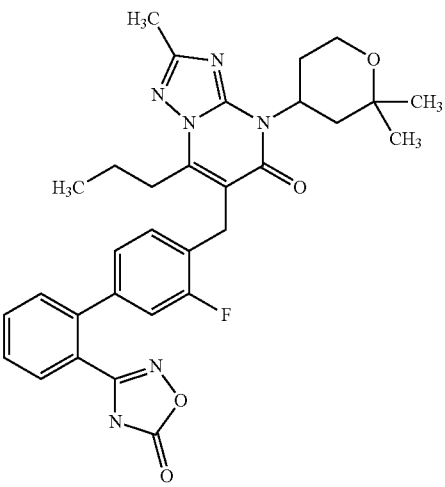 [SMILES: CCCc1c(Cc2ccc(-c3ccccc3-c3noc(=O)[nH]3)cc2F)c(=O)n(C2CCOC(C)(C)C2)c2nc(C)nn12]

A mixture of hydroxylammonium chloride (0.69 g), sodium hydrogen carbonate (1.1 g) and dimethyl sulfoxide (10 mL) was stirred at 40° C. for 30 min, 4'-{[4-(2,2-dimethyltetrahydro-2H-pyran-4-yl)-2-methyl-5-oxo-7-propyl-4,5-dihydro[1,2,4]triazolo[1,5-a]pyrimidin-6-yl]methyl}-3'-fluorobiphenyl-2-carbonitrile (0.34 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.23 g, 62%).

$^1$H NMR (300 MHz, DMSO-d$_6$) δ 0.92 (t, J=7.4 Hz, 3H), 1.18 (s, 3H), 1.24 (s, 3H), 1.48-1.64 (m, 4H), 2.38 (s, 3H), 2.51-2.59 (m, 1H), 2.64-2.81 (m, 1H), 2.83-2.93 (m, 2H), 3.61-3.79 (m, 2H), 3.92 (s, 2H), 5.20-5.41 (m, 1H), 6.99 (dd, J=8.0, 1.5 Hz, 1H), 7.11-7.27 (m, 2H), 7.49-7.62 (m, 2H), 7.64-7.77 (m, 2H), 12.45 (s, 1H)

EXAMPLE 137

7-butyl-4-(2,2-dimethyltetrahydro-2H-pyran-4-yl)-2-methyl-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

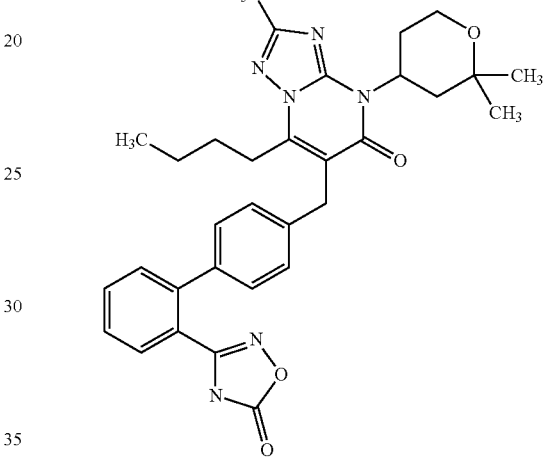

A mixture of hydroxylammonium chloride (0.8 g), sodium hydrogen carbonate (1.3 g) and dimethyl sulfoxide (10 mL) was stirred at 40° C. for 30 min, 4'-{[7-butyl-4-(2,2-dimethyltetrahydro-2H-pyran-4-yl)-2-methyl-5-oxo-4,5-dihydro[1,2,4]triazolo[1,5-a]pyrimidin-6-yl]methyl}biphenyl-2-carbonitrile (0.39 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.15 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.25 g, 58%).

$^1$H NMR (300 MHz, DMSO-d$_6$) δ 0.83 (t, J=7.4 Hz, 3H), 1.18 (s, 3H), 1.25 (s, 3H), 1.28-1.40 (m, 2H), 1.42-1.61 (m, 4H), 2.37 (s, 3H), 2.52-2.59 (m, 1H), 2.65-2.81 (m, 1H), 2.84-2.95 (m, 2H), 3.62-3.80 (m, 2H), 3.93 (s, 2H), 5.24-5.42

(m, 1H), 7.18-7.25 (m, 2H), 7.25-7.33 (m, 2H), 7.45-7.59 (m, 2H), 7.61-7.74 (m, 2H), 12.38 (br. s., 1H)

EXAMPLE 138

7-butyl-4-[(2R,4s,6S)-2,6-dimethyltetrahydro-2H-pyran-4-yl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

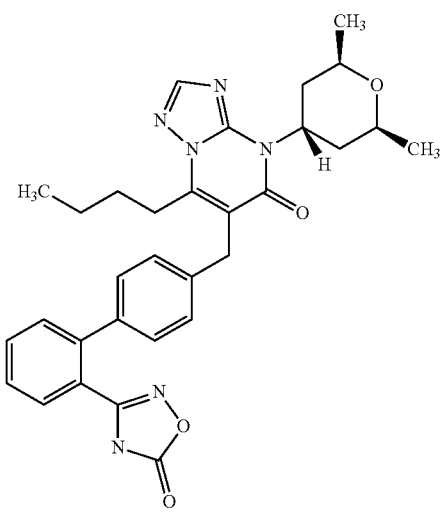 [SMILES: CCCCc1c(Cc2ccc(-c3ccccc3-c3noc(=O)[nH]3)cc2)c(=O)n([C@@H]2C[C@@H](C)O[C@@H](C)C2)c2ncnn12]

A mixture of hydroxylammonium chloride (0.2 g), sodium hydrogen carbonate (3.2 g) and dimethyl sulfoxide (5 mL) was stirred at 40° C. for 30 min, 4'-({7-butyl-4-[(2R,4s,6S)-2,6-dimethyltetrahydro-2H-pyran-4-yl]-5-oxo-4,5-dihydro[1,2,4]triazolo[1,5-a]pyrimidin-6-yl}methyl)biphenyl-2-carbonitrile (0.094 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.037 g) and then 1,8-diazabicyclo[5.4.0]undec-7-ene (0.031 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.029 g, 28%).

¹H NMR (300 MHz, DMSO-d$_6$) δ0.84 (t, J=7.2 Hz, 3H), 1.07-1.17 (m, 6H), 1.28-1.41 (m, 2H), 1.41-1.69 (m, 4H), 2.39-2.48 (m, 2H), 2.88-2.98 (m, 2H), 3.98 (s, 2H), 4.09-4.22 (m, 2H), 5.22-5.35 (m, 1H), 7.20-7.25 (m, 2H), 7.28-7.35 (m, 2H), 7.47-7.60 (m, 2H), 7.62-7.72 (m, 2H), 8.18 (s, 1H), 12.39 (s, 1H)

EXAMPLE 139

7-butyl-4-[(2R,4r,6S)-2,6-dimethyltetrahydro-2H-pyran-4-yl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

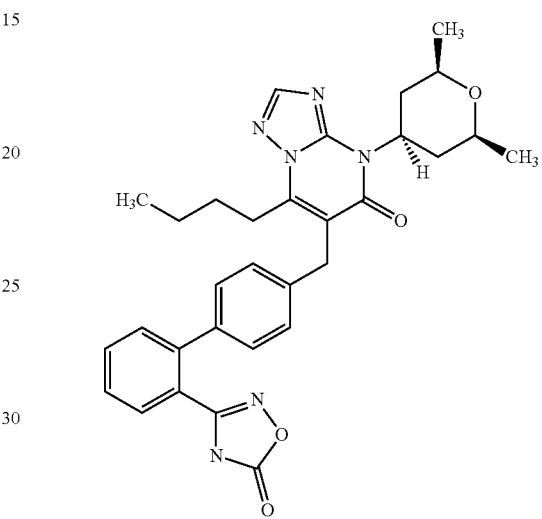

A mixture of hydroxylammonium chloride (0.58 g), sodium hydrogen carbonate (0.93 g) and dimethyl sulfoxide (5 mL) was stirred at 40° C. for 30 min, 4'-({7-butyl-4-[(2R,4r,6S)-2,6-dimethyltetrahydro-2H-pyran-4-yl]-5-oxo-4,5-dihydro[1,2,4]triazolo[1,5-a]pyrimidin-6-yl}methyl)biphenyl-2-carbonitrile (0.27 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.11 g) and then 1,8-diazabicyclo[5.4.0]undec-7-ene (0.092 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.2 g, 66%).

¹H NMR (300 MHz, DMSO-d$_6$) δ0.84 (t, J=7.2 Hz, 3H), 1.15 (d, J=6.1 Hz, 6H), 1.28-1.41 (m, 2H), 1.42-1.54 (m, 2H), 1.60-1.72 (m, 2H), 2.36 (q, J=12.1 Hz, 2H), 2.90-2.99 (m, 2H), 3.48-3.62 (m, 2H), 3.96 (s, 2H), 5.12-5.26 (m, 1H), 7.18-7.25 (m, 2H), 7.28-7.33 (m, 2H), 7.46-7.59 (m, 2H), 7.61-7.74 (m, 2H), 8.19 (s, 1H), 12.39 (s, 1H)

EXAMPLE 140

4-(1,4-dioxaspiro[4.5]dec-8-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

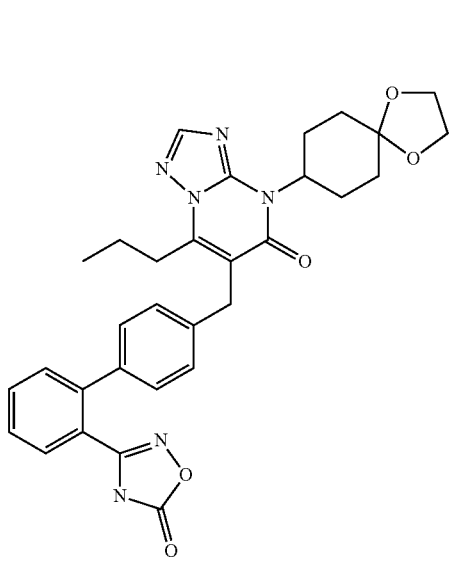 [SMILES: CCCc1c(Cc2ccc(-c3ccccc3-c3noc(=O)[nH]3)cc2)c(=O)n(C2CCC3(CC2)OCCO3)c2ncnn12]

A mixture of hydroxylammonium chloride (0.82 g), sodium hydrogen carbonate (1.3 g) and dimethyl sulfoxide (10 mL) was stirred at 40° C. for 30 min, 4'-{[4-(1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (0.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.15 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.27 g, 64%).

$^1$H NMR (300 MHz, DMSO-$d_6$) δ0.93 (t, J=7.3 Hz, 3H), 1.44-1.82 (m, 8H), 2.68-2.84 (m, 2H), 2.86-2.98 (m, 2H), 3.82-3.99 (m, 6H), 4.88-5.03 (m, 1H), 7.15-7.26 (m, 2H), 7.28-7.34 (m, 2H), 7.45-7.58 (m, 2H), 7.60-7.73 (m, 2H), 8.19 (s, 1H), 12.38 (s, 1H)

EXAMPLE 141

7-butyl-4-(1,4-dioxaspiro[4.5]dec-8-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

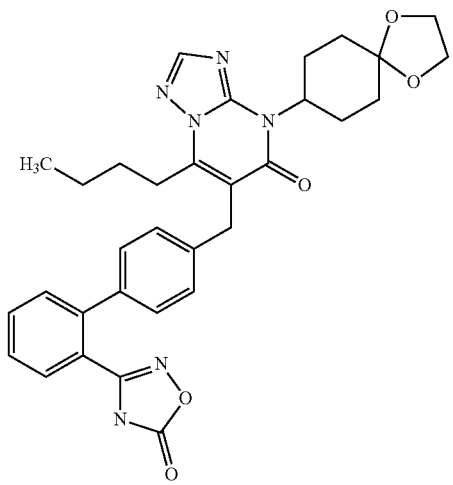 [SMILES: CCCCc1c(Cc2ccc(-c3ccccc3-c3noc(=O)[nH]3)cc2)c(=O)n(C2CCC3(CC2)OCCO3)c2ncnn12]

A mixture of hydroxylammonium chloride (0.79 g), sodium hydrogen carbonate (1.3 g) and dimethyl sulfoxide (10 mL) was stirred at 40° C. for 30 min, 4'-{[7-butyl-4-(1,4-dioxaspiro[4.5]dec-8-yl)-5-oxo-4,5-dihydro[1,2,4]triazolo[1,5-a]pyrimidin-6-yl]methyl}biphenyl-2-carbonitrile (0.4 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.15 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.32 g, 72%).

$^1$H NMR (300 MHz, DMSO-$d_6$) δ0.84 (t, J=7.2 Hz, 3H), 1.29-1.54 (m, 4H), 1.56-1.70 (m, 4H), 1.71-1.83 (m, 2H), 2.70-2.88 (m, 2H), 2.90-2.99 (m, 2H), 3.83-3.98 (m, 6H), 4.90-5.04 (m, 1H), 7.19-7.25 (m, 2H), 7.27-7.35 (m, 2H), 7.46-7.58 (m, 2H), 7.61-7.72 (m, 2H), 8.19 (s, 1H), 12.39 (s, 1H)

EXAMPLE 142

7-butyl-4-(4-oxocyclohexyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

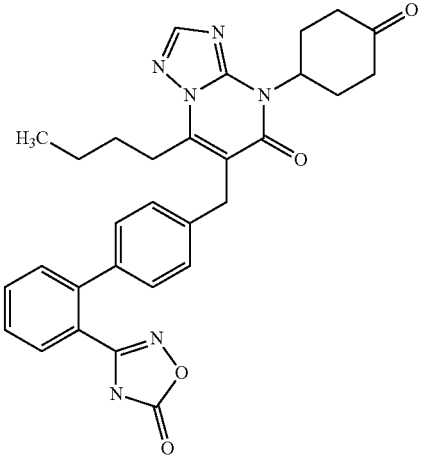 [SMILES: CCCCc1c(Cc2ccc(-c3ccccc3-c3noc(=O)[nH]3)cc2)c(=O)n(C2CCC(=O)CC2)c2ncnn12]

A mixture of 7-butyl-4-(1,4-dioxaspiro[4.5]dec-8-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.27 g), 6N hydrochloric acid (2 mL) and tetrahydrofuran (10 mL) was stirred at 40° C. for 3 hr. The reaction mixture was diluted with ethyl acetate, washed with saturated brine, and dried over anhydrous magnesium sulfate. The solvent was evaporated under reduced pressure, and the residue was purified by silica gel column chromatography to give the title compound as colorless crystals (0.21 g, 83%).

$^1$H NMR (300 MHz, DMSO-d$_6$) δ0.84 (t, J=7.2 Hz, 3H), 1.27-1.40 (m, 2H), 1.43-1.55 (m, 2H), 1.96-2.06 (m, 2H), 2.32 (d, J=14.8 Hz, 2H), 2.58-2.75 (m, 2H), 2.78-2.99 (m, 4H), 3.98 (s, 2H), 5.39-5.56 (m, 1H), 7.19-7.26 (m, 2H), 7.28-7.36 (m, 2H), 7.45-7.59 (m, 2H), 7.62-7.72 (m, 2H), 8.19 (s, 1H), 12.40 (s, 1H)

EXAMPLE 143

4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

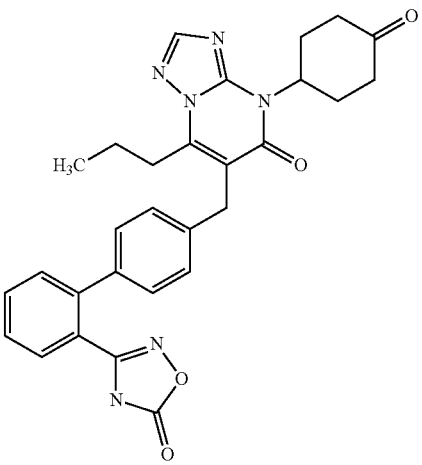 [SMILES: CCCc1c(Cc2ccc(-c3ccccc3-c3noc(=O)[nH]3)cc2)c(=O)n(C2CCC(=O)CC2)c2ncnn12]

A mixture of 4-(1,4-dioxaspiro[4.5]dec-8-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.27 g), 6N hydrochloric acid (2 mL) and tetrahydrofuran (10 mL) was stirred at 40° C. for 3 hr. The reaction mixture was diluted with ethyl acetate, washed with saturated brine, and dried over anhydrous magnesium sulfate. The solvent was evaporated under reduced pressure, and the residue was purified by silica gel column chromatography to give the title compound as colorless crystals (0.2 g, 81%).

$^1$H NMR (300 MHz, DMSO-d$_6$) δ0.93 (t, J=7.4 Hz, 3H), 1.48-1.62 (m, 2H), 1.96-2.06 (m, 2H), 2.26-2.37 (m, 2H), 2.59-2.75 (m, 2H), 2.77-2.99 (m, 4H), 3.98 (s, 2H), 5.40-5.55 (m, 1H), 7.16-7.25 (m, 2H), 7.28-7.36 (m, 2H), 7.53 (dd, J=16.1, 7.8 Hz, 2H), 7.61-7.75 (m, 2H), 8.20 (s, 1H), 12.39 (s, 1H)

EXAMPLE 144

2-methyl-4-(6-methyltetrahydro-2H-pyran-3-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

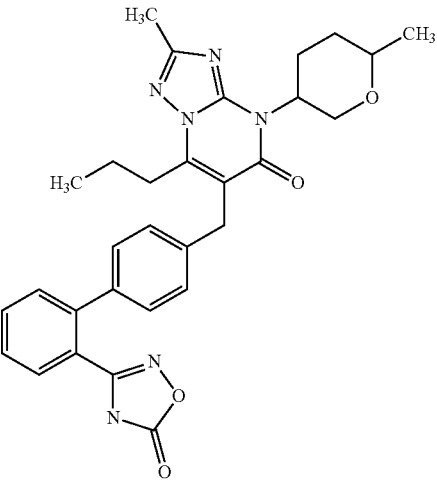 [SMILES: CCCc1c(Cc2ccc(-c3ccccc3-c3noc(=O)[nH]3)cc2)c(=O)n(C2CCC(C)OC2)c2nc(C)nn12]

A mixture of hydroxylammonium chloride (0.39 g), sodium hydrogen carbonate (0.64 g) and dimethyl sulfoxide (5 mL) was stirred at 40° C. for 30 min, 4'-{[2-methyl-4-(6-methyltetrahydro-2H-pyran-3-yl)-5-oxo-7-propyl-4,5-dihydro[1,2,4]triazolo[1,5-a]pyrimidin-6-yl]methyl}biphenyl-2-carbonitrile (0.18 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.073 g) and then 1,8-diazabicyclo[5.4.0]undec-7-ene (0.062 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.097 g, 47%).

¹H NMR (300 MHz, DMSO-d$_6$) δ0.91 (t, J=7.3 Hz, 3H), 1.13 (d, J=6.2 Hz, 3H), 1.30-1.59 (m, 3H), 1.72-1.87 (m, 2H), 2.35 (s, 3H), 2.69-2.92 (m, 3H), 3.42-3.55 (m, 1H), 3.78 (dd, J=8.5, 2.3 Hz, 1H), 3.93 (s, 2H), 4.28 (t, J=10.7 Hz, 1H), 4.86-5.00 (m, 1H), 7.18-7.25 (m, 2H), 7.26-7.32 (m, 2H), 7.47-7.59 (m, 2H), 7.61-7.74 (m, 2H), 12.38 (br. s., 1H)

EXAMPLE 145

6-{[2'-(5-oxo-4,5-dihydro-1,2,4-oxadiazol-3-yl)biphenyl-4-yl]methyl}-7-pentyl-4-(tetrahydro-2H-pyran-4-yl)[1,2,4]triazolo[1,5-a]pyrimidin-5(4H)-one

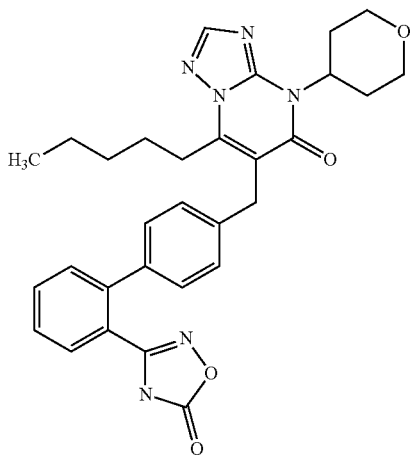 [SMILES: CCCCCc1c(Cc2ccc(-c3ccccc3-c3noc(=O)[nH]3)cc2)c(=O)n(C2CCOCC2)c2ncnn12]

A mixture of hydroxylammonium chloride (1 g), sodium hydrogen carbonate (1.7 g) and dimethyl sulfoxide (10 mL) was stirred at 40° C. for 30 min, 4'-{[5-oxo-7-pentyl-4-(tetrahydro-2H-pyran-4-yl)-4,5-dihydro[1,2,4]triazolo[1,5-a]pyrimidin-6-yl]methyl}biphenyl-2-carbonitrile (0.48 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.19 g) and then 1,8-diazabicyclo[5.4.0]undec-7-ene (0.16 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.37 g, 68%).

¹H NMR (300 MHz, DMSO-d$_6$) δ0.81 (t, J=7.0 Hz, 3H), 1.17-1.37 (m, 4H), 1.45-1.64 (m, 4H), 2.67-2.84 (m, 2H), 2.87-2.98 (m, 2H), 3.43 (t, J=11.2 Hz, 2H), 3.93-4.03 (m, 4H), 5.09-5.25 (m, 1H), 7.18-7.25 (m, 2H), 7.28-7.34 (m, 2H), 7.44-7.59 (m, 2H), 7.62-7.74 (m, 2H), 8.20 (s, 1H), 12.39 (s, 1H)

EXAMPLE 146

4-(4-hydroxycyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

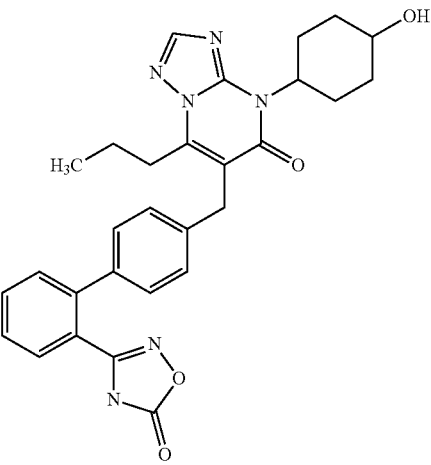 [SMILES: CCCc1c(Cc2ccc(-c3ccccc3-c3noc(=O)[nH]3)cc2)c(=O)n(C2CCC(O)CC2)c2ncnn12]

To a solution (10 mL) of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.14 g) in methanol was added sodium borohydride (0.011 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless amorphous solid (0.09 g, 66%).

¹H NMR (300 MHz, DMSO-d$_6$) δ0.92 (t, J=7.3 Hz, 3H), 1.21-1.99 (m, 8H), 2.51-2.65 (m, 2H), 2.86-3.00 (m, 2H), 3.39-3.99 (m, 3H), 4.33-4.69 (m, 1H), 4.79-4.96 (m, 1H), 7.18-7.25 (m, 2H), 7.27-7.34 (m, 2H), 7.46-7.59 (m, 2H), 7.62-7.73 (m, 2H), 8.18 (s, 1H), 12.38 (s, 1H)

EXAMPLE 147

7-butyl-4-(4-hydroxycyclohexyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

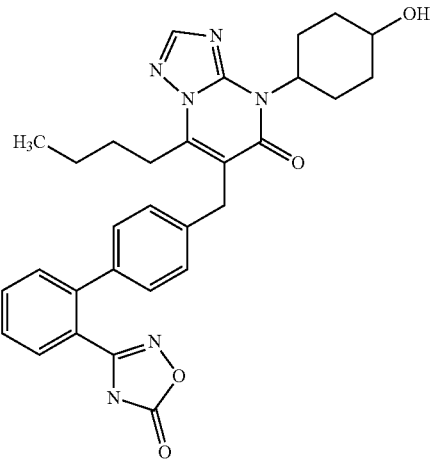 [SMILES: CCCCc1c(Cc2ccc(-c3ccccc3-c3noc(=O)[nH]3)cc2)c(=O)n(C2CCC(O)CC2)c2ncnn12]

To a mixture of 7-butyl-4-(4-oxocyclohexyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.08 g), tetrahydrofuran (3 mL) and methanol (3 mL) was added sodium borohydride (0.007 g), and the mixture was stirred at room temperature for 1 hr. After evaporation of the solvent under reduced pressure, the residue was extracted with water and ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless amorphous solid (0.04 g, 48%).

$^1$H NMR (300 MHz, DMSO-$d_6$) δ0.84 (t, J=7.2 Hz, 3H) 1.21-1.99 (m, 10H) 2.52-2.62 (m, 2H) 2.88-3.00 (m, 2H) 3.39-3.56, 3.84-3.90 (m, combined 0H) 3.95 (s, 2H) 4.34-4.68 (m, 1H) 4.80-4.94 (m, 1H) 7.18-7.34 (m, 4H) 7.44-7.58 (m, 1H) 7.61-7.73 (m, 1H) 8.18 (s, 1H) 12.39 (s, 1H)

EXAMPLE 148

7-butyl-4-(4-methoxycyclohexyl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

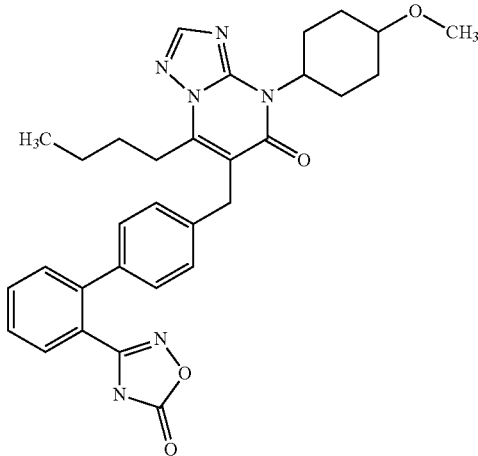 [SMILES: CCCCc1c(Cc2ccc(-c3ccccc3-c3noc(=O)[nH]3)cc2)c(=O)n(C2CCC(OC)CC2)c2ncnn12]

A mixture of hydroxylammonium chloride (0.34 g), sodium hydrogen carbonate (0.54 g) and dimethyl sulfoxide (5 mL) was stirred at 40° C. for 30 min, 4'-{[7-butyl-4-(4-methoxycyclohexyl)-5-oxo-4,5-dihydro[1,2,4]triazolo[1,5-a]pyrimidin-6-yl]methyl}biphenyl-2-carbonitrile (0.16 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.063 g) and then 1,8-diazabicyclo[5.4.0]undec-7-ene (0.053 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.069 g, 39%).

$^1$H NMR (300 MHz, DMSO-$d_6$) δ0.83 (t, J=6.9 Hz, 3H), 1.21-1.54 (m, 8H), 1.65-1.76 (m, 2H), 2.06-2.18 (m, 2H), 2.90-2.99 (m, 2H), 3.13-3.28 (m, 4H), 3.95 (s, 2H), 4.84-4.99 (m, 1H), 7.19-7.25 (m, 2H), 7.27-7.33 (m, 2H), 7.46-7.58 (m, 2H), 7.62-7.72 (m, 2H), 8.16-8.20 (m, 1H), 12.38 (s, 1H)

EXAMPLE 149

2-methyl-4-(5-methyltetrahydrofuran-3-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

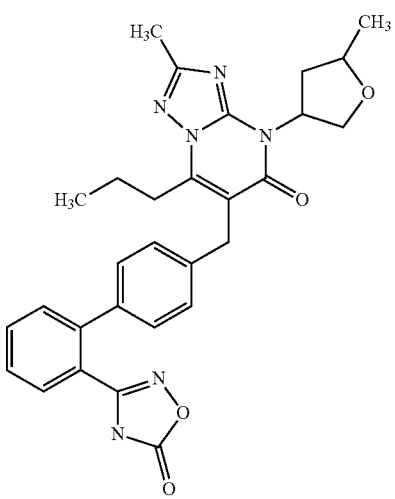 [SMILES: CCCc1c(Cc2ccc(-c3ccccc3-c3noc(=O)[nH]3)cc2)c(=O)n(C2COC(C)C2)c2nc(C)nn12]

A mixture of hydroxylammonium chloride (0.22 g), sodium hydrogen carbonate (0.36 g) and dimethyl sulfoxide (5 mL) was stirred at 40° C. for 30 min, 4'-{[2-methyl-4-(5-methyltetrahydrofuran-3-yl)-5-oxo-7-propyl[1,2,4]triazolo[1,5-a]pyrimidin-6-yl]methyl}biphenyl-2-carbonitrile (0.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.042 g) and then 1,8-diazabicyclo[5.4.0]undec-7-ene (0.035 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.076 g, 67%).

$^1$H NMR (300 MHz, DMSO-$d_6$) δ0.91 (t, J=7.3 Hz, 3H), 1.21 (d, J=6.0 Hz, 3H), 1.45-1.61 (m, 2H), 1.66-1.82 (m, 1H), 2.36 (s, 3H), 2.42-2.56 (m, 1H), 2.81-2.93 (m, 2H), 3.89-4.07

(m, 4H), 4.48-4.61 (m, 1H), 5.55-5.68 (m, 1H), 7.19-7.25 (m, 2H), 7.27-7.33 (m, 2H), 7.47-7.58 (m, 2H), 7.61-7.73 (m, 2H), 12.38 (s, 1H)

EXAMPLE 150

4-[(5S,8S)-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

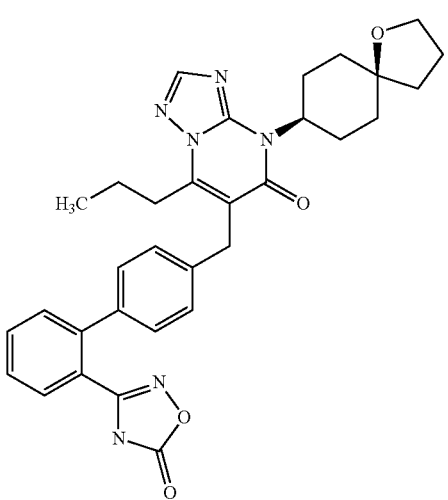 [SMILES: CCCc1c(Cc2ccc(-c3ccccc3-c3noc(=O)[nH]3)cc2)c(=O)n([C@H]2CC[C@]3(CCCO3)CC2)c2ncnn12]

A mixture of ethyl 2-[(2'-cyanobiphenyl-4-yl)methyl]-3-oxohexanoate (0.78 g) and N-(1-oxaspiro[4.5]dec-8-yl)-4H-1,2,4-triazol-3-amine (0.25 g) was stirred under microwave irradiation at 250° C. for 20 min. The reaction mixture was purified by silica gel column chromatography, the obtained residue was dissolved in dimethyl sulfoxide (5 mL), and the mixture was added to a mixture of hydroxylammonium chloride (0.55 g), sodium hydrogen carbonate (0.89 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.1 g) and then 1,8-diazabicyclo[5.4.0]undec-7-ene (0.088 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.055 g, 9%).

$^1$H NMR (300 MHz, DMSO-$d_6$) δ 0.93 (t, J=7.4 Hz, 3H), 1.40-1.77 (m, 10H), 1.80-1.91 (m, 2H), 2.71-3.00 (m, 4H), 3.75 (t, J=6.6 Hz, 2H), 3.96 (s, 2H), 4.82-4.97 (m, 1H), 7.17-7.25 (m, 2H), 7.28-7.34 (m, 2H), 7.47-7.58 (m, 2H), 7.61-7.73 (m, 2H), 8.19 (s, 1H), 12.38 (s, 1H)

EXAMPLE 151

4-[(5R,8R)-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

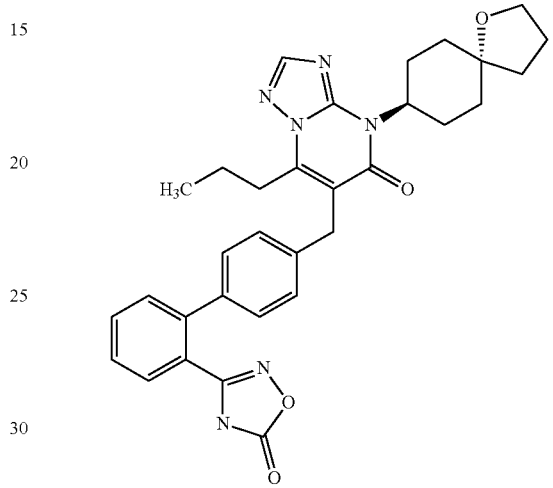

A mixture of ethyl 2-[(2'-cyanobiphenyl-4-yl)methyl]-3-oxohexanoate (0.78 g) and N-(1-oxaspiro[4.5]dec-8-yl)-4H-1,2,4-triazol-3-amine (0.25 g) was stirred under microwave irradiation at 250° C. for 20 min. The reaction mixture was purified by silica gel column chromatography, the obtained residue was dissolved in dimethyl sulfoxide (5 mL), and the mixture was added to a mixture of hydroxylammonium chloride (0.55 g), sodium hydrogen carbonate (0.89 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.1 g) and then 1,8-diazabicyclo[5.4.0]undec-7-ene (0.088 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.058 g, 9%).

$^1$H NMR (300 MHz, DMSO-$d_6$) δ 0.93 (t, J=7.4 Hz, 3H), 1.43-1.74 (m, 8H), 1.79-1.94 (m, 4H), 2.53-2.69 (m, 2H), 2.88-2.97 (m, 2H), 3.72 (t, J=6.2 Hz, 2H), 3.96 (s, 2H), 4.83-5.02 (m, 1H), 7.18-7.25 (m, 2H), 7.27-7.36 (m, 2H), 7.53 (dd, J=16.7, 7.6 Hz, 2H), 7.61-7.75 (m, 2H), 8.20 (s, 1H), 12.38 (s, 1H)

EXAMPLE 152

4-(4-methoxycyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (m, 2H), 7.27-7.34 (m, 2H), 7.46-7.58 (m, 2H), 7.61-7.72 (m, 2H), 8.19 (s, 1H), 12.37 (s, 1H)

EXAMPLE 153

6-{[2'-(5-oxo-4,5-dihydro-1,2,4-oxadiazol-3-yl)biphenyl-4-yl]methyl}-4-[4-(prop-2-en-1-yloxy)cyclohexyl]-7-propyl[1,2,4]triazolo[1,5-a]pyrimidin-5(4H)-one

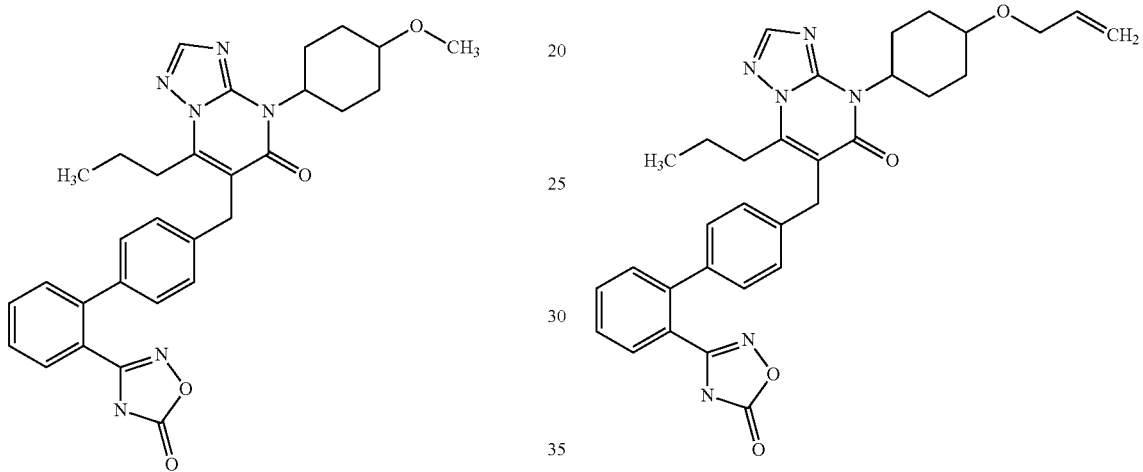

A mixture of hydroxylammonium chloride (0.38 g), sodium hydrogen carbonate (0.61 g) and dimethyl sulfoxide (10 mL) was stirred at 40° C. for 30 min, 4'-{[4-(4-methoxycyclohexyl)-5-oxo-7-propyl-4,5-dihydro[1,2,4]triazolo[1,5-a]pyrimidin-6-yl]methyl}biphenyl-2-carbonitrile (0.21 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.07 g) and then 1,8-diazabicyclo[5.4.0]undec-7-ene (0.059 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.049 g, 25%).

$^1$H NMR (300 MHz, DMSO-$d_6$) δ 0.93 (t, J=7.3 Hz, 3H), 1.12-1.76 (m, 6H), 1.90-2.20 (m, 3H), 2.54-2.97 (m, 4H), 3.19-3.27 (m, 3H), 3.96 (s, 2H), 4.80-4.98 (m, 1H), 7.19-7.23

A mixture of hydroxylammonium chloride (0.41 g), sodium hydrogen carbonate (0.66 g) and dimethyl sulfoxide (10 mL) was stirred at 40° C. for 30 min, 4'-({5-oxo-4-[4-(prop-2-en-1-yloxy)cyclohexyl]-7-propyl-4,5-dihydro[1,2,4]triazolo[1,5-a]pyrimidin-6-yl}methyl)biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.077 g) and then 1,8-diazabicyclo[5.4.0]undec-7-ene (0.065 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.13 g, 56%).

$^1$H NMR (300 MHz, DMSO-$d_6$) δ 0.93 (t, J=7.3 Hz, 3H) 1.22-1.61 (m, 6H) 1.63-1.75 (m, 1H) 1.93-2.16 (m, 2H) 2.52-2.97 (m, 4H) 3.91-4.03 (m, 4H) 4.84-5.00 (m, 1H) 5.08-5.18 (m, 1H) 5.21-5.40 (m, 1H) 5.80-6.01 (m, 1H) 7.19-7.25 (m, 2H) 7.26-7.35 (m, 2H) 7.46-7.59 (m, 2H) 7.61-7.72 (m, 2H) 8.14-8.21 (m, 1H) 12.38 (s, 1H)

EXAMPLE 154

4-[4-(2-methoxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

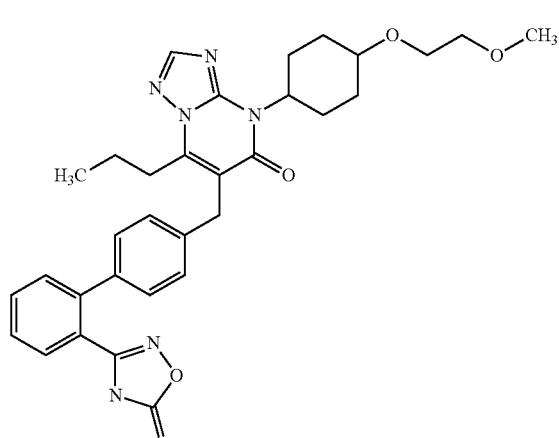

A mixture of hydroxylammonium chloride (0.15 g), sodium hydrogen carbonate (0.25 g) and dimethyl sulfoxide (10 mL) was stirred at 40° C. for 30 min, 4'-({4-[4-(2-methoxyethoxy)cyclohexyl]-5-oxo-7-propyl-4,5-dihydro[1,2,4]triazolo[1,5-a]pyrimidin-6-yl}methyl)biphenyl-2-carbonitrile (0.078 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.029 g) and then 1,8-diazabicyclo[5.4.0]undec-7-ene (0.024 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.04 g, 46%).

$^1$H NMR (300 MHz, DMSO-d$_6$) δ 0.92 (t, J=7.2 Hz, 3H), 1.17-1.74 (m, 6H), 1.92-2.15 (m, 2H), 2.52-2.85 (m, 2H), 2.89-2.98 (m, 2H), 3.24 (s, 3H), 3.38-3.45 (m, 1H), 3.47-3.59 (m, 4H), 3.96 (s, 2H), 4.84-4.98 (m, 1H), 7.18-7.34 (m, 4H), 7.53 (dd, J=16.5, 7.8 Hz, 2H), 7.61-7.72 (m, 2H), 8.18 (s, 1H), 12.37 (br. s., 1H)

EXAMPLE 155

4-[trans-4-(2-hydroxy-2-methylpropoxy)cyclohexyl]-2-methyl-6-{[2-methyl-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

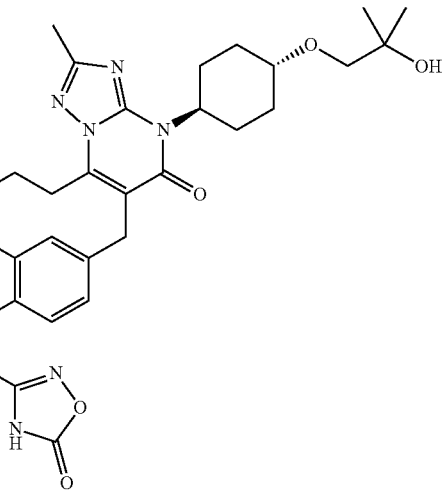

A mixture of hydroxylammonium chloride (0.75 g), sodium hydrogen carbonate (1.21 g) and dimethyl sulfoxide (10 mL) was stirred at 40° C. for 30 min, 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)-2'-methylbiphenyl-2-carbonitrile (0.41 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.20 g) and then 1,8-diazabicyclo[5.4.0]undec-7-ene (0.20 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.26 g, 58%).

$^1$H NMR (300 MHz, CDCl$_3$) δ 1.08 (t, J=7.2 Hz, 3H), 1.20 (s, 6H), 1.36-1.85 (m, 6H), 2.01 (s, 3H), 2.10-2.24 (m, 2H), 2.43 (s, 3H), 2.60-2.80 (m, 2H), 2.96-3.10 (m, 2H), 3.31 (s, 2H), 3.38-3.52 (m, 1H), 3.94 (s, 2H), 4.92-5.06 (m, 1H), 7.06-7.30 (m, 4H), 7.46-7.64 (m, 2H), 7.98-8.06 (m, 1H)

EXAMPLE 156

4-(4-morpholin-4-ylcyclohexyl)-7-propyl-6-{[2'-(1H-tetrazol-5-yl)biphenyl-4-yl]methyl}[1,2,4]triazolo[1,5-a]pyrimidin-5(4H)-one

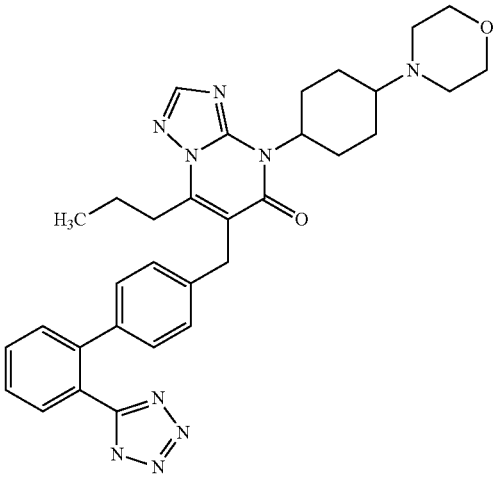 [SMILES: CCCc1c(Cc2ccc(-c3ccccc3-c3nnn[nH]3)cc2)c(=O)n(C2CCC(N3CCOCC3)CC2)c2ncnn12]

A mixture of 4'-{[4-(4-morpholin-4-ylcyclohexyl)-5-oxo-7-propyl-4,5-dihydro[1,2,4]triazolo[1,5-a]pyrimidin-6-yl]methyl}biphenyl-2-carbonitrile (0.08 g), dibutyltin oxide (0.0037 g), azidotrimethylsilane (0.26 g) and toluene (10 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.02 g, 23%).

$^1$H NMR (300 MHz, DMSO-$d_6$) δ0.90 (t, J=7.1 Hz, 3H), 1.36-1.61 (m, 6H), 2.06-2.17 (m, 3H), 2.41-2.60 (m, 4H), 2.68-2.93 (m, 4H), 3.69 (br. s., 4H), 3.91 (s, 2H), 4.86-4.99 (m, 1H), 6.99 (d, J=8.1 Hz, 2H), 7.17 (d, J=8.1 Hz, 2H), 7.53 (dd, J=13.6, 7.3 Hz, 2H), 7.58-7.68 (m, 2H), 8.19 (s, 1H)

EXAMPLE 157

4-(4-morpholin-4-ylcyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

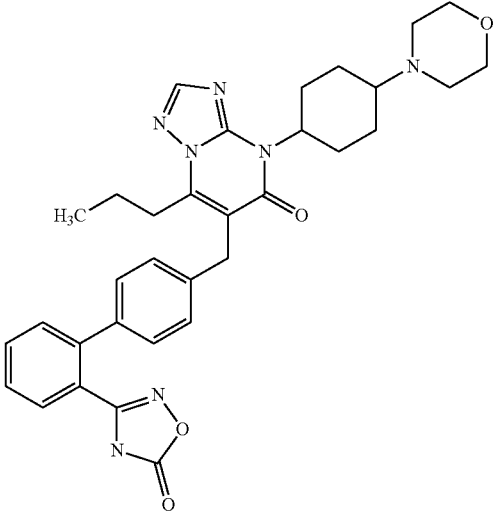 [SMILES: CCCc1c(Cc2ccc(-c3ccccc3-c3noc(=O)[nH]3)cc2)c(=O)n(C2CCC(N3CCOCC3)CC2)c2ncnn12]

A mixture of hydroxylammonium chloride (0.23 g), sodium hydrogen carbonate (0.38 g) and dimethyl sulfoxide (10 mL) was stirred at 40° C. for 30 min, 4'-{[4-(4-morpholin-4-ylcyclohexyl)-5-oxo-7-propyl-4,5-dihydro[1,2,4]triazolo[1,5-a]pyrimidin-6-yl]methyl}biphenyl-2-carbonitrile (0.12 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.043 g) and then 1,8-diazabicyclo[5.4.0]undec-7-ene (0.037 mL) were added, and the mixture was stirred at room temperature for 2 hr. The reaction mixture was poured into water, and the mixture was adjusted to pH 7 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as a colorless amorphous solid (0.025 g, 20%).

$^1$H NMR (300 MHz, DMSO-$d_6$) δ0.92 (t, J=7.3 Hz, 3H), 1.31-1.59 (m, 6H), 2.03-2.20 (m, 3H), 2.42 (br. s., 4H), 2.71-2.96 (m, 4H), 3.61-3.69 (m, 4H), 3.96 (s, 2H), 4.86-5.01 (m, 1H), 7.19-7.26 (m, 2H), 7.27-7.33 (m, 2H), 7.46-7.58 (m, 2H), 7.60-7.72 (m, 2H), 8.18 (s, 1H), 12.32 (br. s., 1H)

EXAMPLE 158

4-[cis-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

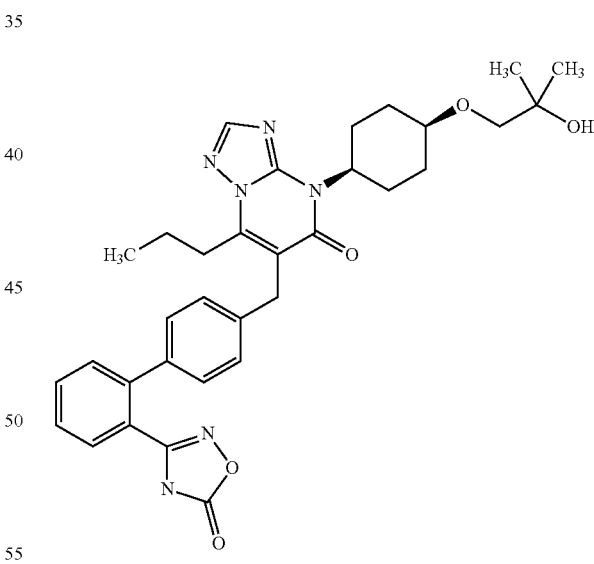

A mixture of hydroxylammonium chloride (0.26 g), sodium hydrogen carbonate (0.42 g) and dimethyl sulfoxide (10 mL) was stirred at 40° C. for 30 min, 4'-({4-[4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (0.14 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.049 g) and then 1,8-diazabicyclo[5.4.0]undec-7-ene (0.041 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.069 g, 46%).

$^1$H NMR (300 MHz, DMSO-$d_6$) δ0.94 (t, J=7.2 Hz, 3H), 1.18 (s, 6H), 1.37-1.60 (m, 6H), 1.93-2.08 (m, 2H), 2.74-2.97 (m, 4H), 3.15 (s, 2H), 3.96 (s, 2H), 4.23 (s, 1H), 4.85-5.04 (m, 1H), 7.17-7.26 (m, 2H), 7.27-7.34 (m, 2H), 7.53 (dd, J=16.1, 7.6 Hz, 2H), 7.62-7.71 (m, 2H), 8.14 (s, 1H), 12.38 (br. s., 1H)

EXAMPLE 159

7-butyl-4-(2-methyltetrahydro-2H-pyran-4-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

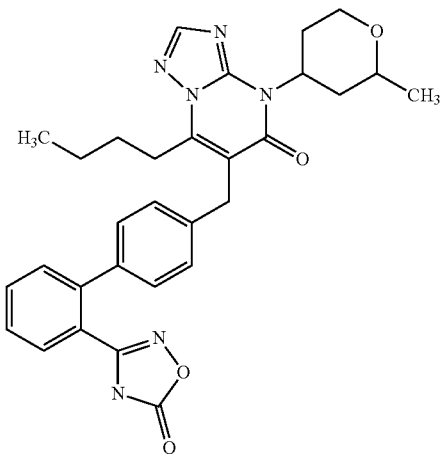 [SMILES: CCCCc1c(Cc2ccc(-c3ccccc3-c3noc(=O)[nH]3)cc2)c(=O)n(C2CCOC(C)C2)c2ncnn12]

A mixture of hydroxylammonium chloride (0.33 g), sodium hydrogen carbonate (0.53 g) and dimethyl sulfoxide (10 mL) was stirred at 40° C. for 30 min, 4'-{[7-butyl-4-(2-methyltetrahydro-2H-pyran-4-yl)-5-oxo-4,5-dihydro[1,2,4]triazolo[1,5-a]pyrimidin-6-yl]methyl}biphenyl-2-carbonitrile (tR1, 0.15 g) obtained in Reference Example 113 was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.061 g) and then 1,8-diazabicyclo[5.4.0]undec-7-ene (0.052 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.061 g, 36%).

$^1$H NMR (300 MHz, DMSO-$d_6$) δ0.84 (t, J=7.3 Hz, 3H) 1.10-1.72 (m, 9H) 2.34-2.47 (m, 1H) 2.63-2.78 (m, 1H) 2.90-3.00 (m, 2H) 3.41-3.56 (m, 2H) 3.92-4.05 (m, 3H) 5.10-5.26 (m, 1H) 7.19-7.34 (m, 4H) 7.47-7.59 (m, 2H) 7.63-7.73 (m, 2H) 8.20 (s, 1H) 12.39 (s, 1H)

EXAMPLE 160

7-butyl-4-(2-methyltetrahydro-2H-pyran-4-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

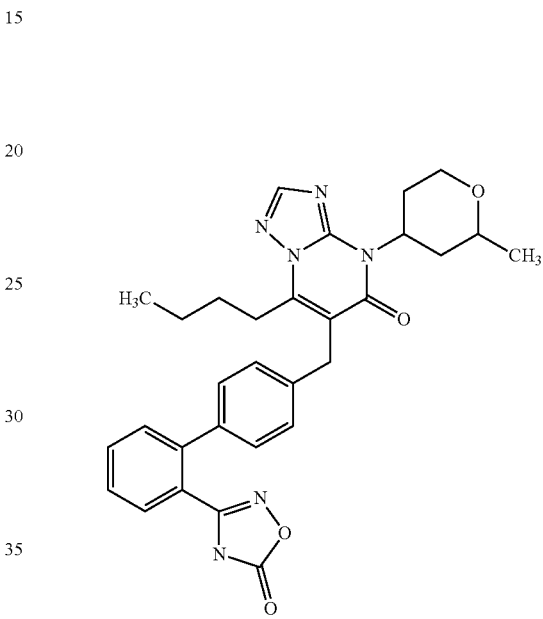

A mixture of hydroxylammonium chloride (0.13 g), sodium hydrogen carbonate (0.21 g) and dimethyl sulfoxide (5 mL) was stirred at 40° C. for 30 min, 4'-{[7-butyl-4-(2-methyltetrahydro-2H-pyran-4-yl)-5-oxo-4,5-dihydro[1,2,4]triazolo[1,5-a]pyrimidin-6-yl]methyl}biphenyl-2-carbonitrile (tR2, 0.057 g) obtained in Reference Example 113 was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.024 g) and then 1,8-diazabicyclo[5.4.0]undec-7-ene (0.02 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.026 g, 39%).

$^1$H NMR (300 MHz, DMSO-$d_6$) δ0.84 (t, J=7.2 Hz, 3H) 1.22-1.67 (m, 9H) 2.69-3.03 (m, 4H) 3.64-3.84 (m, 2H) 3.96

(s, 2H) 4.19-4.34 (m, 1H) 5.34-5.50 (m, 1H) 7.17-7.36 (m, 4H) 7.45-7.60 (m, 2H) 7.61-7.73 (m, 2H) 8.20 (s, 1H) 12.39 (s, 1H)

EXAMPLE 161

7-butyl-4-(2-methyltetrahydro-2H-pyran-4-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

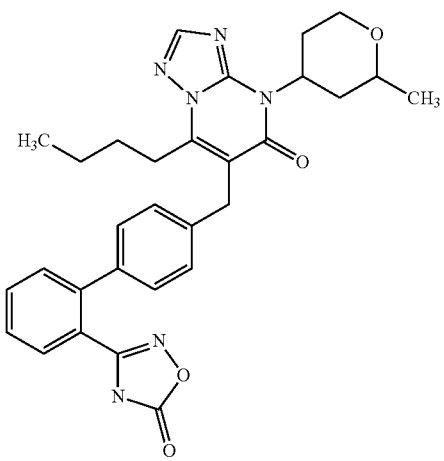 [SMILES: CCCCc1c(Cc2ccc(-c3ccccc3-c3noc(=O)[nH]3)cc2)c(=O)n(C2CCOC(C)C2)c2ncnn12]

A mixture of hydroxylammonium chloride (0.32 g), sodium hydrogen carbonate (0.51 g) and dimethyl sulfoxide (10 mL) was stirred at 40° C. for 30 min, 4'-{[7-butyl-4-(2-methyltetrahydro-2H-pyran-4-yl)-5-oxo-4,5-dihydro[1,2,4]triazolo[1,5-a]pyrimidin-6-yl]methyl}biphenyl-2-carbonitrile (tR3, 0.14 g) obtained in Reference Example 113 was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.059 g) and then 1,8-diazabicyclo[5.4.0]undec-7-ene (0.05 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.043 g, 26%).

$^1$H NMR (300 MHz, DMSO-$d_6$) δ 0.84 (t, J=7.2 Hz, 3H) 1.08-1.74 (m, 9H) 2.35-2.47 (m, 1H) 2.59-2.78 (m, 1H) 2.89-3.01 (m, 2H) 3.42-3.59 (m, 2H) 3.89-4.03 (m, 3H) 5.10-5.25 (m, 1H) 7.18-7.35 (m, 4H) 7.46-7.59 (m, 2H) 7.61-7.73 (m, 2H) 8.20 (s, 1H) 12.39 (s, 1H)

EXAMPLE 162

7-butyl-4-(2-methyltetrahydro-2H-pyran-4-yl)-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

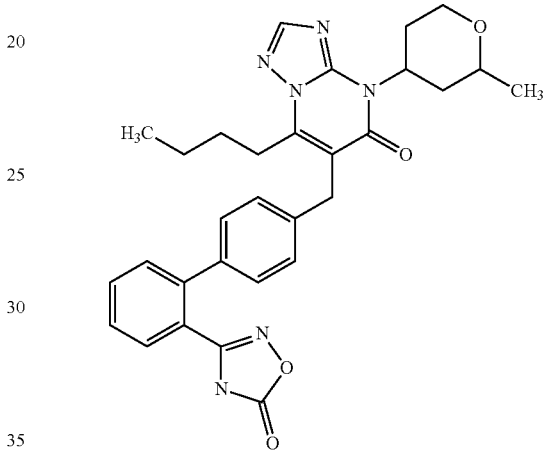

A mixture of hydroxylammonium chloride (0.13 g), sodium hydrogen carbonate (0.21 g) and dimethyl sulfoxide (5 mL) was stirred at 40° C. for 30 min, 4'-{[7-butyl-4-(2-methyltetrahydro-2H-pyran-4-yl)-5-oxo-4,5-dihydro[1,2,4]triazolo[1,5-a]pyrimidin-6-yl]methyl}biphenyl-2-carbonitrile (tR4, 0.14 g) obtained in Reference Example 113 was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.024 g) and then 1,8-diazabicyclo[5.4.0]undec-7-ene (0.02 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.029 g, 43%).

$^1$H NMR (300 MHz, DMSO-$d_6$) δ 0.84 (t, J=7.2 Hz, 3H) 1.23-1.66 (m, 9H) 2.68-3.01 (m, 4H) 3.67-3.83 (m, 2H) 3.96

(s, 2H) 4.20-4.35 (m, 1H) 5.34-5.51 (m, 1H) 7.19-7.34 (m, 4H) 7.47-7.59 (m, 2H) 7.61-7.73 (m, 2H) 8.20 (s, 1H) 12.39 (s, 1H)

EXAMPLE 163

4-[cis-4-(2-hydroxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

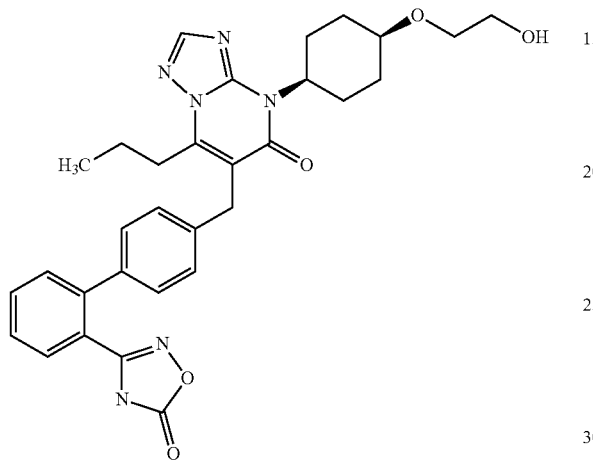

A mixture of 4'-({4-[cis-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (0.29 g), tert-butyl(dimethyl)silyl trifluoromethanesulfonate (0.19 mL), 2,6-lutidine (0.099 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.59 g), sodium hydrogen carbonate (0.95 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.11 g) and then 1,8-diazabicyclo[5.4.0]undec-7-ene (0.093 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (15 mL). Tetrabutylammonium bromide (1.0 M tetrahydrofuran solution, 1.4 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.11 g, 34%).

$^1$H NMR (300 MHz, DMSO-d$_6$) δ0.93 (t, J=7.3 Hz, 3H), 1.36-1.60 (m, 6H), 1.93-2.04 (m, 2H), 2.69-2.99 (m, 4H), 3.37-3.47 (m, 2H), 3.50-3.60 (m, 3H), 3.96 (s, 2H), 4.53 (t, J=5.5 Hz, 1H), 4.83-5.00 (m, 1H), 7.18-7.26 (m, 2H), 7.27-7.35 (m, 2H), 7.47-7.60 (m, 2H), 7.62-7.72 (m, 2H), 8.18 (s, 1H), 12.38 (s, 1H)

EXAMPLE 164

4-[trans-4-(2-hydroxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

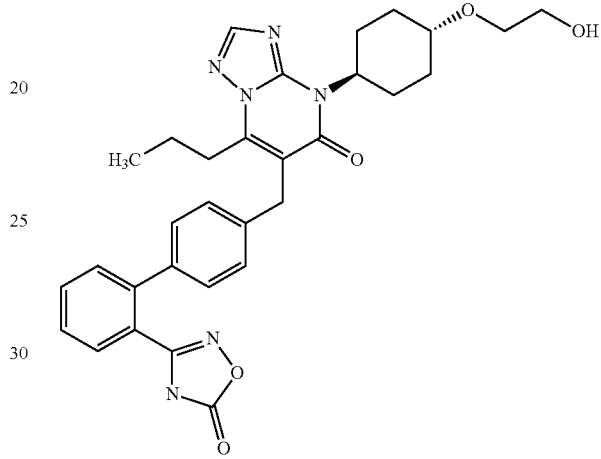

A mixture of 4'-({4-[trans-4-(2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (0.23 g), tert-butyl(dimethyl)silyl trifluoromethanesulfonate (0.16 mL), 2,6-lutidine (0.079 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.47 g), sodium hydrogen carbonate (0.76 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.088 g) and then 1,8-diazabicyclo[5.4.0]undec-7-ene (0.074 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 1.1 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.12 g, 45%).

¹H NMR (300 MHz, DMSO-d₆) δ0.93 (t, J=7.3 Hz, 3H), 1.19-1.37 (m, 3H), 1.46-1.60 (m, 2H), 1.64-1.75 (m, 2H), 2.05-2.17 (m, 2H), 2.54-2.65 (m, 2H), 2.88-2.97 (m, 2H), 3.41-3.51 (m, 4H), 3.96 (s, 2H), 4.51-4.60 (m, 1H), 4.85-4.97 (m, 1H), 7.18-7.25 (m, 2H), 7.27-7.33 (m, 2H), 7.46-7.59 (m, 2H), 7.61-7.72 (m, 2H), 8.18 (s, 1H), 12.38 (s, 1H)

EXAMPLE 165

4-[4-hydroxy-4-(2-hydroxyethyl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

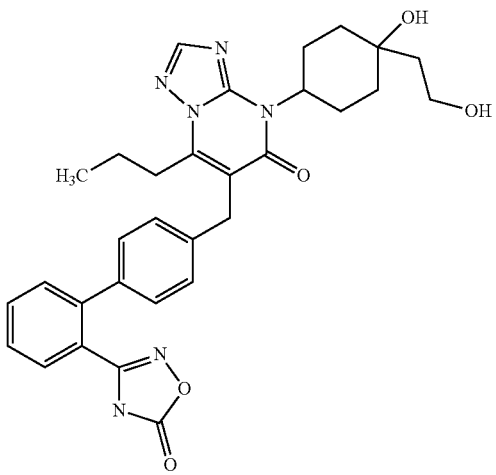 [SMILES: CCCc1c(Cc2ccc(-c3ccccc3-c3noc(=O)[nH]3)cc2)c(=O)n(C2CCC(O)(CCO)CC2)c2ncnn12]

A mixture of 4'-({4-[4-hydroxy-4-(2-hydroxyethyl)cyclohexyl]-5-oxo-7-propyl-4,5-dihydro[1,2,4]triazolo[1,5-a]pyrimidin-6-yl}methyl)biphenyl-2-carbonitrile (0.093 g), tert-butyl(dimethyl)silyl trifluoromethanesulfonate (0.063 mL), 2,6-lutidine (0.032 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.19 g), sodium hydrogen carbonate (0.31 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.035 g) and then 1,8-diazabicyclo[5.4.0]undec-7-ene (0.03 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 0.46 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.024 g, 23%).

¹H NMR (300 MHz, DMSO-d₆) δ0.92 (t, J=7.2 Hz, 3H), 1.38-1.60 (m, 6H), 1.72-1.90 (m, 4H), 2.58-2.76 (m, 2H), 2.88-2.97 (m, 2H), 3.56-3.65 (m, 2H), 3.96 (s, 2H), 4.40-4.46 (m, 2H), 4.81-4.99 (m, 1H), 7.18-7.26 (m, 2H), 7.28-7.32 (m, 2H), 7.47-7.60 (m, 2H), 7.62-7.71 (m, 2H), 8.21 (s, 1H), 12.38 (br. s., 1H)

EXAMPLE 166

6-{[3-fluoro-2'-(5-oxo-4,5-dihydro-1,2,4-oxadiazol-3-yl)biphenyl-4-yl]methyl}-4-(cis-4-hydroxycyclohexyl)-7-propyl[1,2,4]triazolo[1,5-a]pyrimidin-5(4H)-one

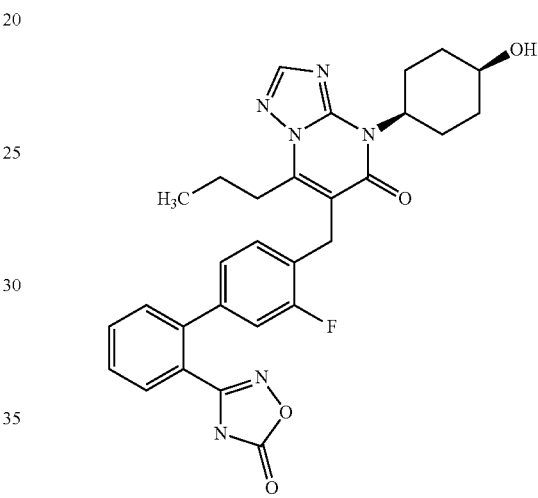

A mixture of 3'-fluoro-4'-{[4-(cis-4-hydroxycyclohexyl)-5-oxo-7-propyl-4,5-dihydro[1,2,4]triazolo[1,5-a]pyrimidin-6-yl]methyl}biphenyl-2-carbonitrile (0.085 g), tert-butyl(dimethyl)silyl trifluoromethanesulfonate (0.06 mL), 2,6-lutidine (0.03 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.18 g), sodium hydrogen carbonate (0.29 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.034 g) and then 1,8-diazabicyclo[5.4.0]undec-7-ene (0.029 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 0.44 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.036 g, 38%).

$^1$H NMR (300 MHz, DMSO-d$_6$) δ0.93 (t, J=7.3 Hz, 3H), 1.31-1.41 (m, 2H), 1.43-1.63 (m, 4H), 1.72-1.82 (m, 2H), 2.83-2.98 (m, 4H), 3.86 (br. s., 1H), 3.94 (s, 2H), 4.37 (d, J=2.1 Hz, 1H), 4.79-4.94 (m, 1H), 6.99 (dd, J=8.0, 1.8 Hz, 1H), 7.16 (dd, J=11.1, 1.7 Hz, 1H), 7.20-7.29 (m, 1H), 7.49-7.61 (m, 2H), 7.64-7.74 (m, 2H), 8.19 (s, 1H), 12.46 (br. s., 1H)

EXAMPLE 167

6-{[3-fluoro-2'-(5-oxo-4,5-dihydro-1,2,4-oxadiazol-3-yl)biphenyl-4-yl]methyl}-4-(trans-4-hydroxycyclohexyl)-7-propyl[1,2,4]triazolo[1,5-a]pyrimidin-5(4H)-one

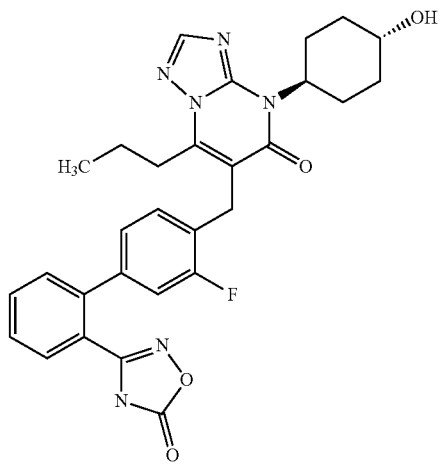 [SMILES: CCCc1c(Cc2ccc(-c3ccccc3-c3noc(=O)[nH]3)cc2F)c(=O)n([C@H]2CC[C@H](O)CC2)c2ncnn12]

A mixture of 3'-fluoro-4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (0.27 g), tert-butyl(dimethyl)silyl trifluoromethanesulfonate (0.19 mL), 2,6-lutidine (0.1 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.59 g), sodium hydrogen carbonate (0.95 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.11 g) and then 1,8-diazabicyclo[5.4.0]undec-7-ene (0.093 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (15 mL). Tetrabutylammonium bromide (1.0 M tetrahydrofuran solution, 1.4 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.12 g, 40%).

$^1$H NMR (300 MHz, DMSO-d$_6$) δ0.93 (t, J=7.3 Hz, 3H), 1.21-1.37 (m, 2H), 1.48-1.69 (m, 4H), 1.87-1.97 (m, 2H), 2.51-2.62 (m, 2H), 2.88-2.97 (m, 2H), 3.38-3.52 (m, 1H), 3.94 (s, 2H), 4.65 (d, J=4.3 Hz, 1H), 4.77-4.91 (m, 1H), 6.99 (dd, J=7.9, 1.7 Hz, 1H), 7.16 (dd, J=11.1, 1.7 Hz, 1H), 7.24 (t, J=8.0 Hz, 1H), 7.50-7.62 (m, 2H), 7.64-7.74 (m, 2H), 8.19 (s, 1H), 12.46 (s, 1H)

EXAMPLE 168 ethyl trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexanecarboxylate

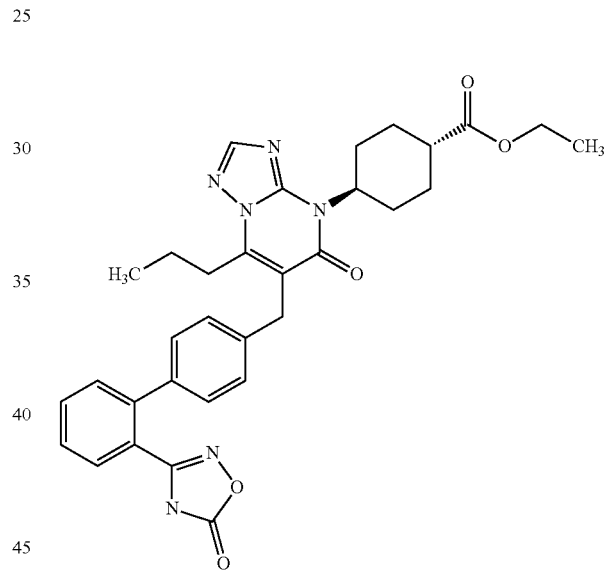

A mixture of hydroxylammonium chloride (0.16 g), sodium hydrogen carbonate (0.26 g) and dimethyl sulfoxide (10 mL) was stirred at 40° C. for 30 min, ethyl trans-4-{6-[(2'-cyanobiphenyl-4-yl)methyl]-5-oxo-7-propyl[1,2,4]triazolo[1,5-a]pyrimidin-4(5H)-yl}cyclohexanoate (0.08 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.03 g) and then 1,8-diazabicyclo[5.4.0]undec-7-ene (0.025 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.033 g, 37%).

¹H NMR (300 MHz, DMSO-d₆) δ 0.92 (t, J=7.3 Hz, 3H) 1.19 (t, J=7.1 Hz, 3H) 1.41-1.60 (m, 5H) 1.68-1.78 (m, 2H) 1.99-2.10 (m, 2H) 2.24-2.38 (m, 2H) 2.88-2.97 (m, 2H) 3.96 (s, 2H) 4.02-4.12 (m, 2H) 4.82-4.97 (m, 1H) 7.18-7.24 (m, 2H) 7.26-7.34 (m, 2H) 7.53 (dd, J=16.6, 7.7 Hz, 2H) 7.61-7.73 (m, 2H) 8.19 (s, 1H) 12.38 (br. s., 1H)

EXAMPLE 169

4-[trans-4-(3-methyl-1,2,4-oxadiazol-5-yl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

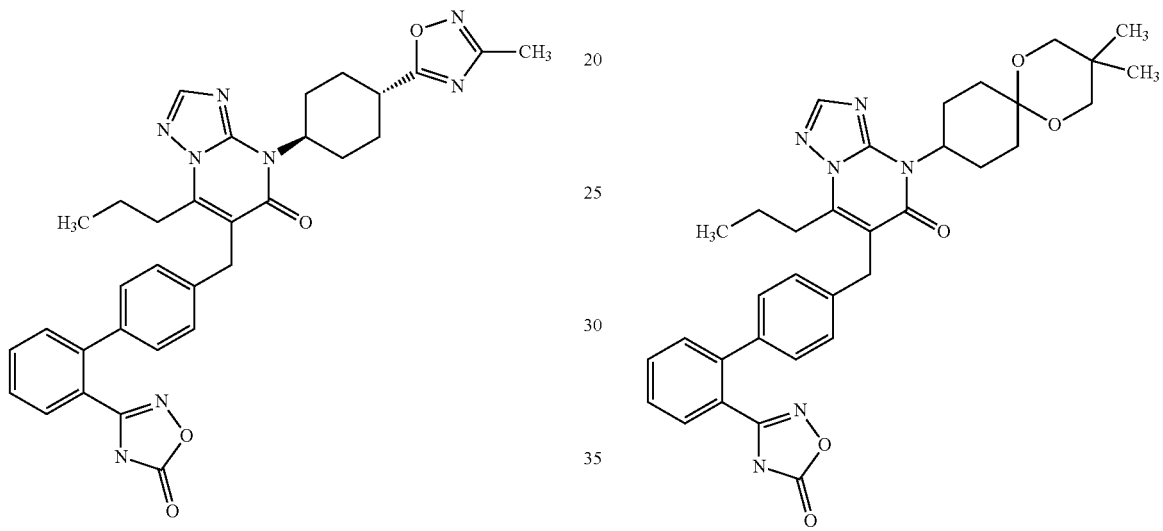

A mixture of hydroxylammonium chloride (0.3 g), sodium hydrogen carbonate (0.49 g) and dimethyl sulfoxide (10 mL) was stirred at 40° C. for 30 min, 4'-({4-[trans-4-(3-methyl-1,2,4-oxadiazol-5-yl)cyclohexyl]-5-oxo-7-propyl-4,5-dihydro[1,2,4]triazolo[1,5-a]pyrimidin-6-yl}methyl)biphenyl-2-carbonitrile (0.16 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.057 g) and then 1,8-diazabicyclo[5.4.0]undec-7-ene (0.048 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.066 g, 38%).

¹H NMR (300 MHz, DMSO-d₆) δ 0.93 (t, J=7.2 Hz, 3H), 1.47-1.76 (m, 4H), 1.78-1.86 (m, 2H), 2.18-2.28 (m, 2H), 2.32 (s, 3H), 2.61-2.78 (m, 2H), 2.89-3.11 (m, 3H), 3.97 (s, 2H), 4.92-5.06 (m, 1H), 7.18-7.25 (m, 2H), 7.29-7.35 (m, 2H), 7.53 (dd, J=16.1, 7.8 Hz, 2H), 7.61-7.73 (m, 2H), 8.20 (s, 1H), 12.38 (s, 1H)

EXAMPLE 170

4-(3,3-dimethyl-1,5-dioxaspiro[5.5]undec-9-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one A mixture of hydroxylammonium chloride (0.66 g), sodium hydrogen carbonate (1.1 g) and dimethyl sulfoxide (10 mL) was stirred at 40° C. for 30 min, 4'-{[4-(3,3-dimethyl-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile (0.35 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.13 g, 34%).

¹H NMR (300 MHz, DMSO-d₆) δ 0.85-0.97 (m, 9H), 1.30-1.45 (m, 2H), 1.47-1.60 (m, 4H), 2.28-2.39 (m, 2H), 2.61-2.78 (m, 2H), 2.87-2.99 (m, 2H), 3.47 (d, J=8.3 Hz, 4H), 3.95

(s, 2H), 4.88-5.01 (m, 1H), 7.18-7.25 (m, 2H), 7.27-7.35 (m, 2H), 7.53 (dd, J=16.7, 7.6 Hz, 2H), 7.60-7.73 (m, 2H), 8.19 (s, 1H), 12.38 (br. s., 1H)

EXAMPLE 171

4-{trans-4-[2-(1H-imidazol-1-yl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

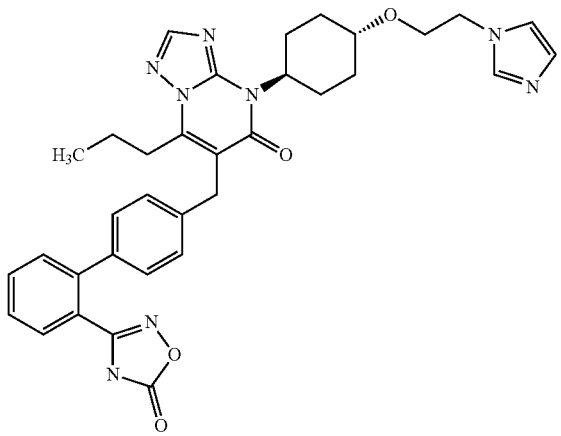 [SMILES: CCCc1c(Cc2ccc(-c3ccccc3-c3noc(=O)[nH]3)cc2)c(=O)n([C@H]2CC[C@H](OCCn3ccnc3)CC2)c2ncnn12]

A mixture of hydroxylammonium chloride (0.44 g), sodium hydrogen carbonate (0.71 g) and dimethyl sulfoxide (10 mL) was stirred at 40° C. for 30 min, 4'-[(4-{trans-4-[2-(1H-imidazol-1-yl)ethoxy]cyclohexyl}-5-oxo-7-propyl-4,5-dihydro[1,2,4]triazolo[1,5-a]pyrimidin-6-yl)methyl]biphenyl-2-carbonitrile (0.24 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.083 g) and then 1,8-diazabicyclo[5.4.0]undec-7-ene (0.07 mL) were added, and the mixture was stirred at room temperature for 2 hr. The reaction mixture was poured into water, and the mixture was adjusted to pH 7 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as colorless crystals (0.086 g, 33%).

$^1$H NMR (300 MHz, DMSO-$d_6$) δ0.92 (t, J=7.3 Hz, 3H), 1.15-1.33 (m, 2H), 1.47-1.58 (m, 2H), 1.63-1.72 (m, 2H), 1.99-2.12 (m, 2H), 2.51-2.64 (m, 2H), 2.87-2.98 (m, 2H), 3.23-3.38 (m, 1H), 3.72 (t, J=5.2 Hz, 2H), 3.95 (s, 2H), 4.11 (t, J=5.1 Hz, 2H), 4.82-4.95 (m, 1H), 6.92 (br. s., 1H), 7.15-7.25 (m, 3H), 7.26-7.33 (m, 2H), 7.45-7.58 (m, 2H), 7.60-7.81 (m, 3H), 8.17 (s, 1H), 12.52 (br. s., 1H)

EXAMPLE 172

4-[trans-4-(2-morpholin-4-ylethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

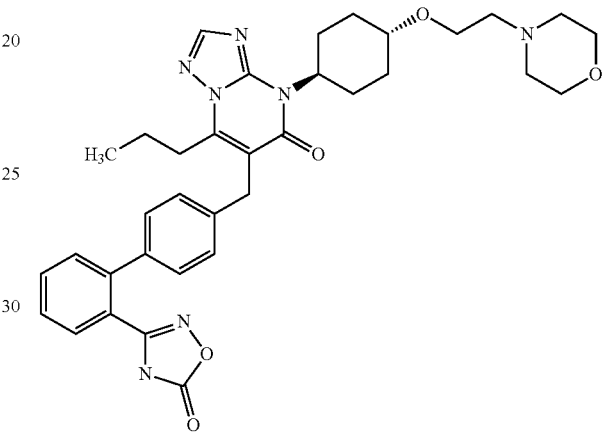

A mixture of hydroxylammonium chloride (0.54 g), sodium hydrogen carbonate (0.87 g) and dimethyl sulfoxide (10 mL) was stirred at 40° C. for 30 min, 4'-({4-[trans-4-(2-morpholin-4-ylethoxy)cyclohexyl]-5-oxo-7-propyl-4,5-dihydro[1,2,4]triazolo[1,5-a]pyrimidin-6-yl}methyl)biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.1 g) and then 1,8-diazabicyclo[5.4.0]undec-7-ene (0.085 mL) were added, and the mixture was stirred at room temperature for 2 hr. The reaction mixture was poured into water, and the mixture was adjusted to pH 7 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as colorless crystals (0.2 g, 59%).

$^1$H NMR (300 MHz, DMSO-$d_6$) δ0.93 (t, J=7.2 Hz, 3H), 1.19-1.36 (m, 2H), 1.47-1.61 (m, 2H), 1.64-1.75 (m, 2H), 2.04-2.16 (m, 2H), 2.43-2.67 (m, 8H), 2.88-2.99 (m, 2H), 3.25-3.38 (m, 1H), 3.53-3.60 (m, 6H), 3.95 (s, 2H), 4.83-4.96

(m, 1H), 7.18-7.24 (m, 2H), 7.27-7.33 (m, 2H), 7.45-7.57 (m, 2H), 7.62-7.71 (m, 2H), 8.18 (s, 1H), 12.09 (br. s., 1H)

EXAMPLE 173

4-[trans-4-(5-methyl-1,3,4-oxadiazol-2-yl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

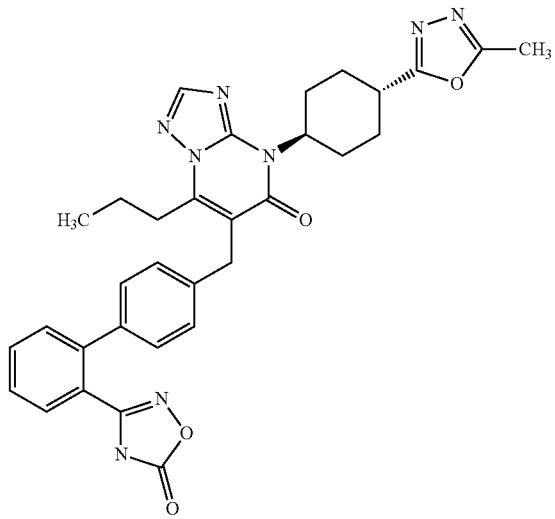 [SMILES: CCCc1c(Cc2ccc(-c3ccccc3-c3noc(=O)[nH]3)cc2)c(=O)n([C@H]2CC[C@H](c3nnc(C)o3)CC2)c2ncnn12]

A mixture of hydroxylammonium chloride (0.35 g), sodium hydrogen carbonate (0.57 g) and dimethyl sulfoxide (10 mL) was stirred at 40° C. for 30 min, 4'-({4-[trans-4-(5-methyl-1,3,4-oxadiazol-2-yl)cyclohexyl]-5-oxo-7-propyl-4,5-dihydro[1,2,4]triazolo[1,5-a]pyrimidin-6-yl}methyl)biphenyl-2-carbonitrile (0.18 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.066 g) and then 1,8-diazabicyclo[5.4.0]undec-7-ene (0.056 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.083 g, 42%).

$^1$H NMR (300 MHz, DMSO-$d_6$) δ0.93 (t, J=7.3 Hz, 3H), 1.49-1.87 (m, 6H), 2.15-2.27 (m, 2H), 2.47 (s, 3H), 2.60-2.79 (m, 2H), 2.87-3.01 (m, 3H), 3.97 (s, 2H), 4.90-5.05 (m, 1H), 7.20-7.26 (m, 2H), 7.29-7.35 (m, 2H), 7.53 (dd, J=16.0, 7.7 Hz, 2H), 7.61-7.73 (m, 2H), 8.20 (s, 1H), 12.38 (s, 1H)

EXAMPLE 174

4-[trans-4-(5-methyl-1,3,4-oxadiazol-2-yl)cyclohexyl]-7-propyl-6-{[2'-(1H-tetrazol-5-yl)biphenyl-4-yl]methyl}[1,2,4]triazolo[1,5-a]pyrimidin-5(4H)-one

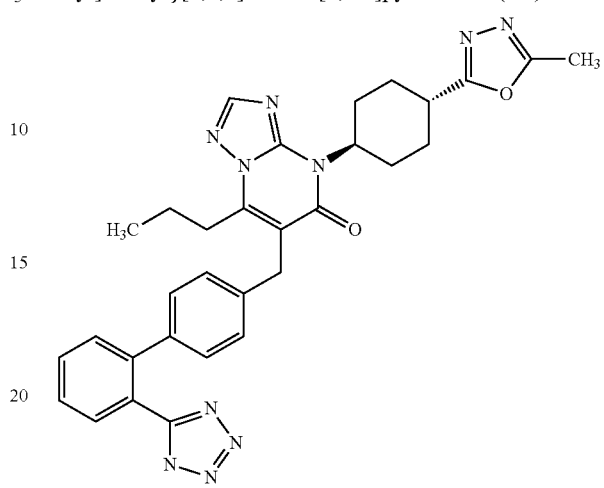

A mixture of 4'-({4-[trans-4-(5-methyl-1,3,4-oxadiazol-2-yl)cyclohexyl]-5-oxo-7-propyl-4,5-dihydro[1,2,4]triazolo[1,5-a]pyrimidin-6-yl}methyl)biphenyl-2-carbonitrile (0.15 g), dibutyltin oxide (0.035 g), azidotrimethylsilane (0.97 g) and toluene (15 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.023 g, 14%).

$^1$H NMR (300 MHz, DMSO-$d_6$) δ0.92 (t, J=7.3 Hz, 3H), 1.46-1.86 (m, 6H), 2.14-2.26 (m, 2H), 2.47 (s, 3H), 2.59-2.76 (m, 2H), 2.85-3.00 (m, 3H), 3.91 (s, 2H), 4.91-5.03 (m, 1H), 6.99 (d, J=8.3 Hz, 2H), 7.19 (d, J=8.3 Hz, 2H), 7.49-7.70 (m, 4H), 8.20 (s, 1H)

EXAMPLE 175

4-{trans-4-[(4-methoxyphenyl)carbonyl]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

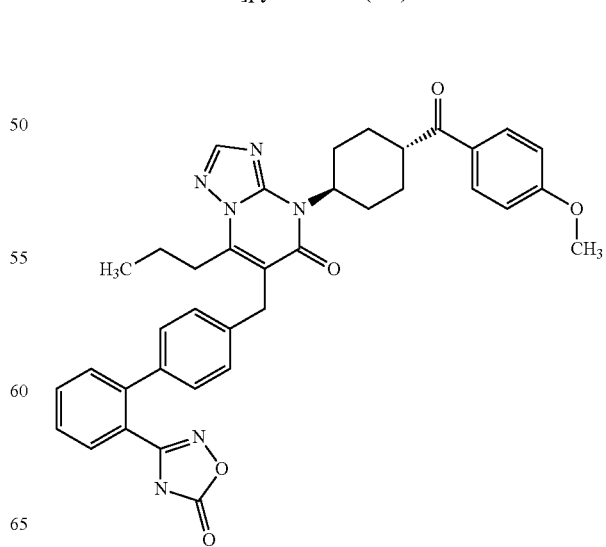

A mixture of hydroxylammonium chloride (0.88 g), sodium hydrogen carbonate (1.4 g) and dimethyl sulfoxide (10 mL) was stirred at 40° C. for 30 min, 4'-[(4-{trans-4-[(4-methoxyphenyl)carbonyl]cyclohexyl}-5-oxo-7-propyl-4,5-dihydro[1,2,4]triazolo[1,5-a]pyrimidin-6-yl)methyl]biphenyl-2-carbonitrile (0.5 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in tetrahydrofuran (10 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. 25% Sulfuric acid (5 mL) and ethanol (15 mL) were added to the obtained residue, and the mixture was stirred at 100° C. for 16 hr. The precipitated solid was collected by filtration to give the title compound as a colorless amorphous solid (0.24 g, 44%).

$^1$H NMR (300 MHz, DMSO-$d_6$) δ0.94 (t, J=7.3 Hz, 3H), 1.48-1.62 (m, 4H), 1.73-1.83 (m, 2H), 1.91-2.01 (m, 2H), 2.66-2.83 (m, 2H), 2.89-2.98 (m, 2H), 3.36-3.49 (m, 1H), 3.86 (s, 3H), 3.97 (s, 2H), 4.87-5.02 (m, 1H), 7.05 (d, J=9.0 Hz, 2H), 7.19-7.26 (m, 2H), 7.28-7.36 (m, 2H), 7.53 (dd, J=15.5, 7.8 Hz, 2H), 7.61-7.73 (m, 2H), 8.01 (d, J=8.9 Hz, 2H), 8.22 (s, 1H), 12.38 (s, 1H)

EXAMPLE 176 trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexanecarboxamide

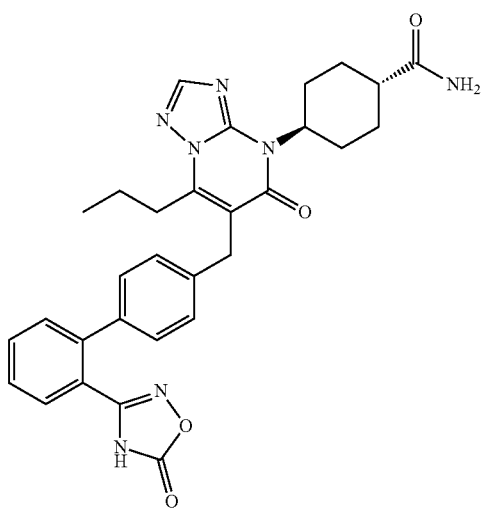 [SMILES: CCCc1c(Cc2ccc(-c3ccccc3-c3noc(=O)[nH]3)cc2)c(=O)n([C@H]2CC[C@H](C(N)=O)CC2)c2ncnn12]

A mixture of hydroxylammonium chloride (0.71 g), sodium hydrogen carbonate (1.1 g) and dimethyl sulfoxide (10 mL) was stirred at 40° C. for 30 min, trans-4-{6-[(2'-cyanobiphenyl-4-yl)methyl]-5-oxo-7-propyl[1,2,4]triazolo[1,5-a]pyrimidin-4(5H)-yl}cyclohexanecarboxamide (0.34 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.31 g, 82%).

$^1$H NMR (300 MHz, CHLOROFORM-d) δ0.93 (t, J=7.4 Hz, 3H), 1.40-1.60 (m, 4H), 1.66-1.77 (m, 2H), 1.85-1.94 (m, 2H), 2.10-2.24 (m, 1H), 2.53-2.65 (m, 2H), 2.87-2.97 (m, 2H), 3.96 (s, 2H), 4.83-4.99 (m, 1H), 6.73 (s, 1H), 7.18-7.26 (m, 3H), 7.28-7.35 (m, 2H), 7.53 (dd, J=16.1, 7.8 Hz, 2H), 7.61-7.72 (m, 2H), 8.18 (s, 1H)

EXAMPLE 177 trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexanecarbonitrile

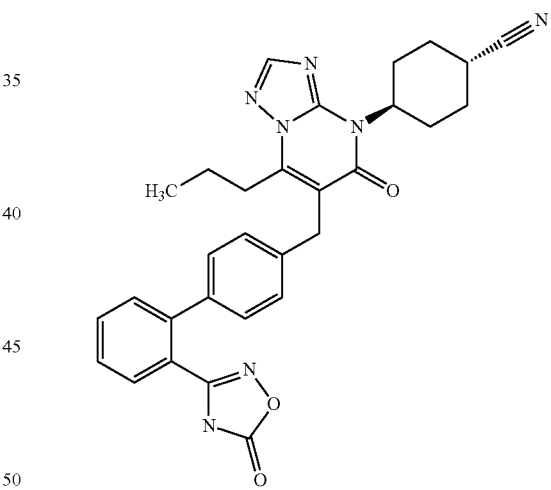

To a solution (10 mL) of trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexanecarboxamide (0.31 g) and pyridine (0.18 mL) in tetrahydrofuran was added trifluoroacetic acid anhydride (0.15 mL) at 0° C., and the mixture was stirred for 30 min. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.18 g, 60%).

$^1$H NMR (300 MHz, DMSO-$d_6$) δ0.93 (t, J=7.3 Hz, 3H), 1.46-1.81 (m, 6H), 2.09-2.22 (m, 2H), 2.52-2.62 (m, 2H), 2.74 (t, J=12.1 Hz, 1H), 2.87-2.98 (m, 2H), 3.96 (s, 2H), 4.93

(t, J=12.0 Hz, 1H), 7.19-7.25 (m, 2H), 7.27-7.34 (m, 2H), 7.45-7.59 (m, 2H), 7.62-7.74 (m, 2H), 8.18 (s, 1H), 12.38 (br. s., 1H)

EXAMPLE 178

4-(trans-4-{2-[(2R,6S)-2,6-dimethylmorpholin-4-yl]ethoxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

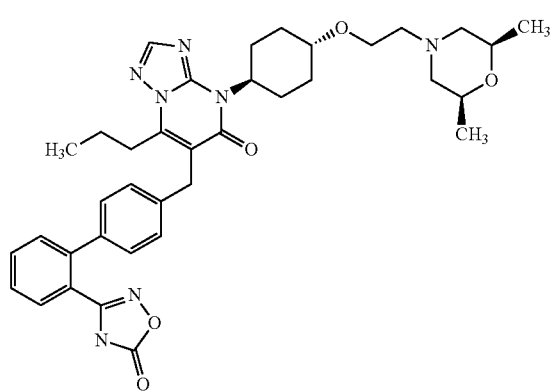 [SMILES: CCCc1c(Cc2ccc(-c3ccccc3-c3noc(=O)[nH]3)cc2)c(=O)n([C@H]2CC[C@H](OCCN3C[C@@H](C)O[C@@H](C)C3)CC2)c2ncnn12]

A mixture of hydroxylammonium chloride (0.51 g), sodium hydrogen carbonate (0.82 g) and dimethyl sulfoxide (10 mL) was stirred at 40° C. for 30 min, 4'-{[4-(trans-4-{2-[(2R,6S)-2,6-dimethylmorpholin-4-yl]ethoxy}cyclohexyl)-5-oxo-7-propyl-4,5-dihydro[1,2,4]triazolo[1,5-a]pyrimidin-6-yl]methyl}biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.095 g) and then 1,8-diazabicyclo[5.4.0]undec-7-ene (0.081 mL) were added, and the mixture was stirred at room temperature for 2 hr. The reaction mixture was poured into water, and the mixture was adjusted to pH 7 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as colorless crystals (0.19 g, 59%).

$^1$H NMR (300 MHz, DMSO-$d_6$) δ0.93 (t, J=7.3 Hz, 3H), 1.03 (d, J=6.2 Hz, 6H), 1.21-1.35 (m, 2H), 1.47-1.61 (m, 2H), 1.65-1.80 (m, 5H), 2.05-2.14 (m, 2H), 2.51-2.66 (m, 2H), 2.79 (d, J=10.4 Hz, 2H), 2.87-2.97 (m, 2H), 3.24-3.39 (m, 1H), 3.49-3.64 (m, 5H), 3.95 (s, 2H), 4.82-4.96 (m, 1H), 7.17-7.26 (m, 2H), 7.26-7.33 (m, 2H), 7.44-7.58 (m, 2H), 7.61-7.70 (m, 2H), 8.18 (s, 1H)

EXAMPLE 179

4-(2,2-dimethyl-1,4-dioxaspiro[4.5]dec-8-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

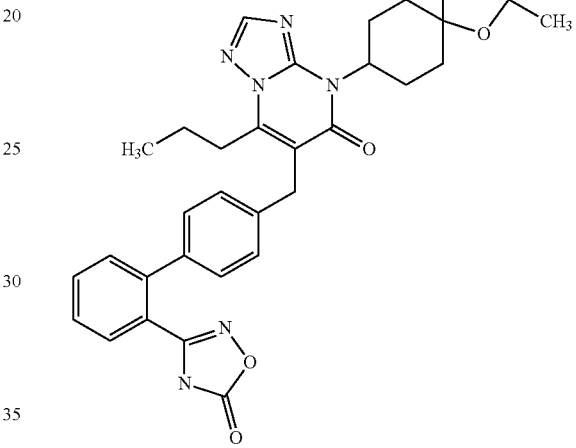

A mixture of hydroxylammonium chloride (0.39 g), sodium hydrogen carbonate (0.63 g) and dimethyl sulfoxide (10 mL) was stirred at 40° C. for 30 min, 4'-{[4-(2,2-dimethyl-1,4-dioxaspiro[4.5]dec-8-yl)-5-oxo-7-propyl-4,5-dihydro[1,2,4]triazolo[1,5-a]pyrimidin-6-yl]methyl}biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.072 g) and then 1,8-diazabicyclo[5.4.0]undec-7-ene (0.061 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.1 g, 47%).

$^1$H NMR (300 MHz, DMSO-$d_6$) δ0.93 (t, J=7.3 Hz, 3H), 1.21-1.30 (m, 6H), 1.46-1.70 (m, 6H), 1.74-1.86 (m, 2H), 2.71-2.86 (m, 2H), 2.88-2.98 (m, 2H), 3.69-3.75 (m, 2H), 3.96 (s, 2H), 4.86-5.02 (m, 1H), 7.19-7.25 (m, 2H), 7.28-7.36 (m, 2H), 7.46-7.58 (m, 2H), 7.62-7.72 (m, 2H), 8.17-8.21 (m, 1H), 12.38 (br. s., 1H)

EXAMPLE 180

6-{[2'-(5-oxo-4,5-dihydro-1,2,4-oxadiazol-3-yl)biphenyl-4-yl]methyl}-7-propyl-4-(2,2,3,3-tetramethyl-1,4-dioxaspiro[4.5]dec-8-yl)[1,2,4]triazolo[1,5-a]pyrimidin-5(4H)-one

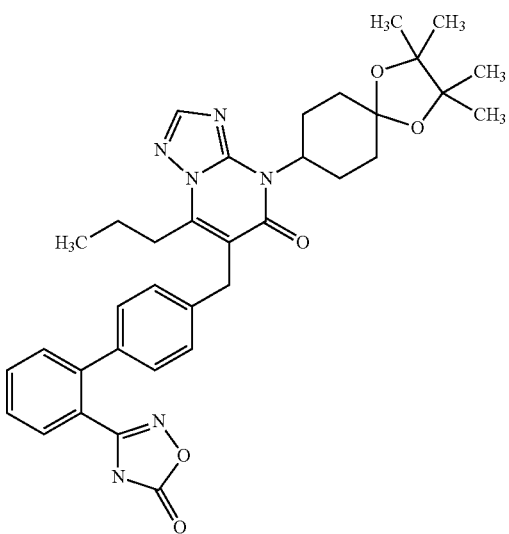 [SMILES: CCCc1c(Cc2ccc(-c3ccccc3-c3noc(=O)[nH]3)cc2)c(=O)n(C2CCC3(CC2)OC(C)(C)C(C)(C)O3)c2ncnn12]

A mixture of hydroxylammonium chloride (0.28 g), sodium hydrogen carbonate (0.45 g) and dimethyl sulfoxide (10 mL) was stirred at 40° C. for 30 min, 4'-{[5-oxo-7-propyl-4-(2,2,3,3-tetramethyl-1,4-dioxaspiro[4.5]dec-8-yl)-4,5-dihydro[1,2,4]triazolo[1,5-a]pyrimidin-6-yl]methyl}biphenyl-2-carbonitrile (0.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.052 g) and then 1,8-diazabicyclo[5.4.0]undec-7-ene (0.044 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.068 g, 41%).

$^1$H NMR (300 MHz, DMSO-$d_6$) δ0.93 (t, J=7.4 Hz, 3H), 1.17 (s, 6H), 1.21 (s, 6H), 1.47-1.72 (m, 6H), 1.78-1.88 (m, 2H), 2.70-2.98 (m, 4H), 3.95 (s, 2H), 4.84-4.97 (m, 1H), 7.19-7.25 (m, 2H), 7.28-7.34 (m, 2H), 7.53 (dd, J=16.5, 7.4 Hz, 2H), 7.61-7.72 (m, 2H), 8.20 (s, 1H), 12.37 (s, 1H)

EXAMPLE 181

7-propyl-4-(2,2,3,3-tetramethyl-1,4-dioxaspiro[4.5]dec-8-yl)-6-{[2'-(1H-tetrazol-5-yl)biphenyl-4-yl]methyl}[1,2,4]triazolo[1,5-a]pyrimidin-5(4H)-one

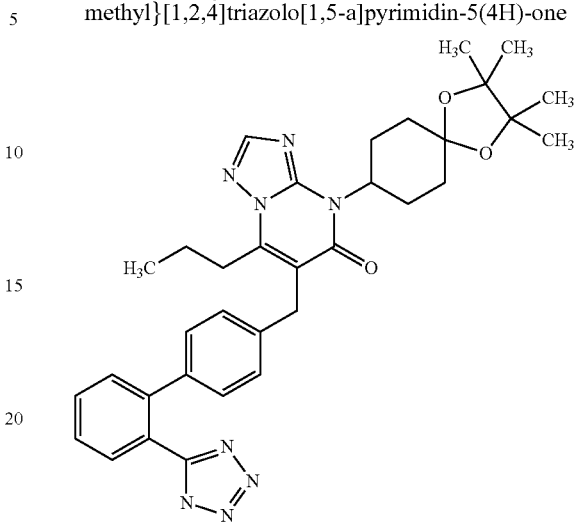

A mixture of 4'-{[5-oxo-7-propyl-4-(2,2,3,3-tetramethyl-1,4-dioxaspiro[4.5]dec-8-yl)-4,5-dihydro[1,2,4]triazolo[1,5-a]pyrimidin-6-yl]methyl}biphenyl-2-carbonitrile (0.2 g), dibutyltin oxide (0.026 g), azidotrimethylsilane (1.2 g) and toluene (15 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.06 g, 28%).

$^1$H NMR (300 MHz, DMSO-$d_6$) δ0.92 (t, J=7.4 Hz, 3H), 1.16 (s, 6H), 1.21 (s, 6H), 1.46-1.70 (m, 6H), 1.78-1.88 (m, 2H), 2.69-2.94 (m, 4H), 3.89 (s, 2H), 4.89 (t, J=12.7 Hz, 1H), 6.99 (d, J=8.3 Hz, 2H), 7.18 (d, J=8.0 Hz, 2H), 7.53 (dd, J=13.3, 7.2 Hz, 2H), 7.59-7.71 (m, 2H), 8.19 (s, 1H), 16.26 (br. s., 1H)

EXAMPLE 182

4-[cis-4-(2-hydroxyethoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

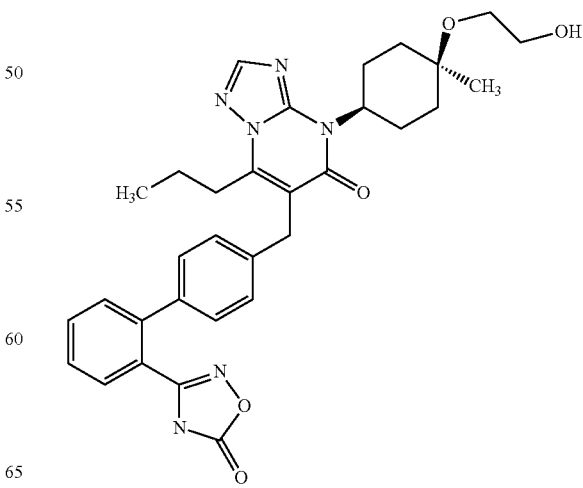

A mixture of 4'-({4-[cis-4-(2-hydroxyethoxy)-4-methylcyclohexyl]-5-oxo-7-propyl-4,5-dihydro[1,2,4]triazolo[1,5-a]pyrimidin-6-yl}methyl)biphenyl-2-carbonitrile (0.36 g), tert-butyl(dimethyl)silyl trifluoromethanesulfonate (0.24 mL), 2,6-lutidine (0.12 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.72 g), sodium hydrogen carbonate (1.2 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 1.7 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.11 g, 27%).

$^1$H NMR (300 MHz, DMSO-$d_6$) δ0.92 (t, J=7.4 Hz, 3H), 1.12 (s, 3H), 1.33-1.64 (m, 6H), 1.82-1.92 (m, 2H), 2.72-2.97 (m, 4H), 3.32-3.37 (m, 2H), 3.53-3.64 (m, 2H), 3.96 (s, 2H), 4.43 (t, J=6.1 Hz, 1H), 4.86-5.00 (m, 1H), 7.18-7.24 (m, 2H), 7.28-7.35 (m, 2H), 7.53 (dd, J=16.1, 7.8 Hz, 2H), 7.62-7.72 (m, 2H), 8.16 (s, 1H), 12.37 (s, 1H)

EXAMPLE 183

4-[trans-4-(2-hydroxyethoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

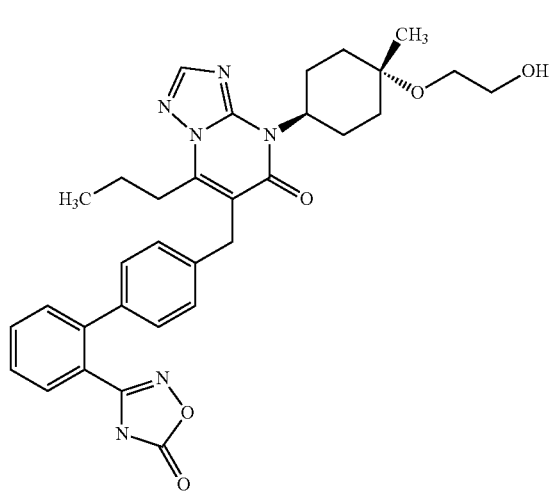 [SMILES: CCCc1c(Cc2ccc(-c3ccccc3-c3noc(=O)[nH]3)cc2)c(=O)n([C@H]2CC[C@](C)(OCCO)CC2)c2ncnn12]

A mixture of 4'-({4-[trans-4-(2-hydroxyethoxy)-4-methylcyclohexyl]-5-oxo-7-propyl-4,5-dihydro[1,2,4]triazolo[1,5-a]pyrimidin-6-yl}methyl)biphenyl-2-carbonitrile (0.44 g), tert-butyl(dimethyl)silyl trifluoromethanesulfonate (0.29 mL), 2,6-lutidine (0.15 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.87 g), sodium hydrogen carbonate (1.4 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 2.1 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.25 g, 51%).

$^1$H NMR (300 MHz, DMSO-$d_6$) δ0.93 (t, J=7.4 Hz, 3H) 1.32 (s, 3H) 1.46-1.66 (m, 6H) 1.74-1.85 (m, 2H) 2.57-2.74 (m, 2H) 2.88-2.98 (m, 2H) 3.36-3.47 (m, 4H) 3.96 (s, 2H) 4.48 (t, J=5.1 Hz, 1H) 4.84-5.01 (m, 1H) 7.19-7.25 (m, 2H) 7.27-7.33 (m, 2H) 7.53 (dd, J=16.8, 7.8 Hz, 2H) 7.62-7.71 (m, 2H) 8.20 (s, 1H) 12.37 (s, 1H)

EXAMPLE 184

4-[trans-4-(1,3-oxazol-5-yl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

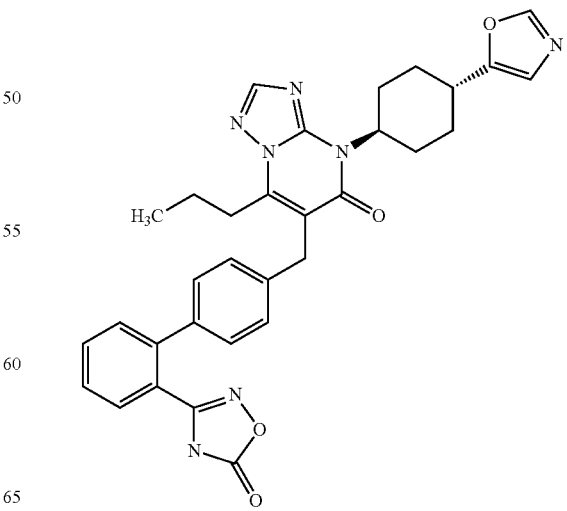

A mixture of hydroxylammonium chloride (0.6 g), sodium hydrogen carbonate (0.97 g) and dimethyl sulfoxide (10 mL) was stirred at 40° C. for 30 min, 4'-({4-[trans-4-(1,3-oxazol-5-yl)cyclohexyl]-5-oxo-7-propyl-4,5-dihydro[1,2,4]triazolo[1,5-a]pyrimidin-6-yl}methyl)biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.11 g) and then 1,8-diazabicyclo[5.4.0]undec-7-ene (0.95 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.098 g, 29%).

$^1$H NMR (300 MHz, DMSO-$d_6$) δ0.93 (t, J=7.3 Hz, 3H), 1.45-1.62 (m, 4H), 1.74-1.86 (m, 2H), 2.09-2.20 (m, 2H), 2.56-2.85 (m, 3H), 2.89-2.98 (m, 2H), 3.97 (s, 2H), 4.91-5.04 (m, 1H), 6.91 (s, 1H), 7.20-7.26 (m, 2H), 7.29-7.35 (m, 2H), 7.46-7.58 (m, 2H), 7.62-7.72 (m, 2H), 8.20 (s, 1H), 8.23 (s, 1H), 12.38 (br. s., 1H)

EXAMPLE 185

4-[trans-4-(1,3-oxazol-5-yl)cyclohexyl]-7-propyl-6-{[2'-(1H-tetrazol-5-yl)biphenyl-4-yl]methyl}[1,2,4]triazolo[1,5-a]pyrimidin-5(4H)-one

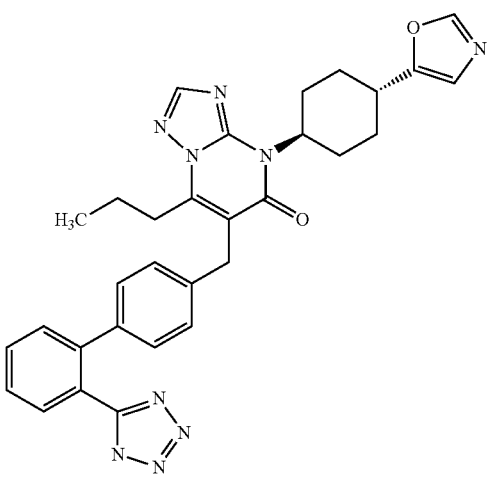 [SMILES: CCCc1c(Cc2ccc(-c3ccccc3-c3nnn[nH]3)cc2)c(=O)n([C@H]2CC[C@H](c3cnco3)CC2)c2ncnn12]

A mixture of 4'-({4-[trans-4-(1,3-oxazol-5-yl)cyclohexyl]-5-oxo-7-propyl-4,5-dihydro[1,2,4]triazolo[1,5-a]pyrimidin-6-yl}methyl)biphenyl-2-carbonitrile (0.35 g), dibutyltin oxide (0.051 g), azidotrimethylsilane (2.3 g) and toluene (15 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.18 g, 46%).

$^1$H NMR (300 MHz, DMSO-$d_6$) δ0.92 (t, J=7.3 Hz, 3H), 1.45-1.62 (m, 4H), 1.73-1.83 (m, 2H), 2.09-2.19 (m, 2H), 2.59-2.84 (m, 3H), 2.87-2.94 (m, 2H), 3.92 (s, 2H), 4.89-5.03 (m, 1H), 6.91 (s, 1H), 6.99 (d, J=8.1 Hz, 2H), 7.19 (d, J=8.1 Hz, 2H), 7.54 (dd, J=13.1, 7.1 Hz, 2H), 7.60-7.70 (m, 2H), 8.20 (s, 1H), 8.23 (s, 1H)

EXAMPLE 186

4-[trans-4-(3-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

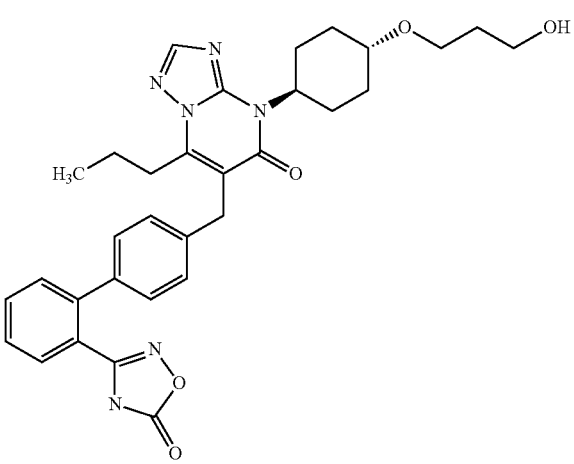 [SMILES: CCCc1c(Cc2ccc(-c3ccccc3-c3noc(=O)[nH]3)cc2)c(=O)n([C@H]2CC[C@H](OCCCO)CC2)c2ncnn12]

A mixture of 4'-({4-[trans-4-(3-hydroxypropoxy)cyclohexyl]-5-oxo-7-propyl-4,5-dihydro[1,2,4]triazolo[1,5-a]pyrimidin-6-yl}methyl)biphenyl-2-carbonitrile (0.19 g), tert-butyl(dimethyl)silyl trifluoromethanesulfonate (0.097 mL), 2,6-lutidine (0.049 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.37 g), sodium hydrogen carbonate (0.59 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.069 g) and then 1,8-diazabicyclo[5.4.0]undec-7-ene (0.058 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 0.88 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.1 g, 49%).

¹H NMR (300 MHz, DMSO-d₆) δ0.92 (t, J=7.3 Hz, 3H), 1.17-1.34 (m, 2H), 1.45-1.75 (m, 6H), 2.03-2.14 (m, 2H), 2.52-2.64 (m, 2H), 2.87-2.99 (m, 2H), 3.22-3.30 (m, 1H), 3.41-3.54 (m, 4H), 3.95 (s, 2H), 4.36 (t, J=5.2 Hz, 1H), 4.90 (t, J=12.2 Hz, 1H), 7.19-7.24 (m, 2H), 7.27-7.34 (m, 2H), 7.53 (dd, J=17.1, 7.7 Hz, 2H), 7.61-7.72 (m, 2H), 8.18 (s, 1H), 12.38 (br. s., 1H)

EXAMPLE 187

6-{[2'-(5-oxo-4,5-dihydro-1,2,4-oxadiazol-3-yl)biphenyl-4-yl]methyl}-4-(2-oxo-1,4-dioxaspiro[4.5]dec-8-yl)-7-propyl[1,2,4]triazolo[1,5-a]pyrimidin-5(4H)-one

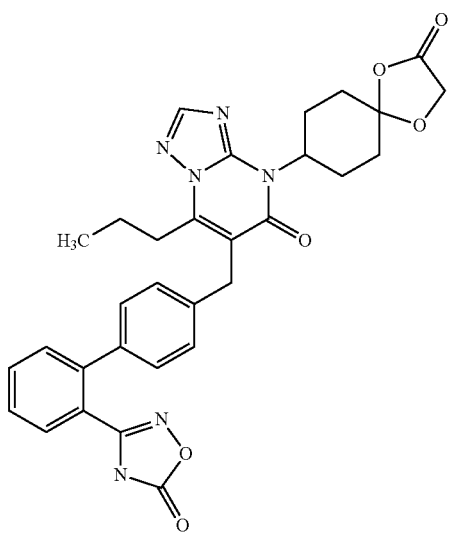 [SMILES: CCCc1c(Cc2ccc(-c3ccccc3-c3noc(=O)[nH]3)cc2)c(=O)n(C2CCC3(CC2)OCC(=O)O3)c2ncnn12]

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), trimethylsilyl [(trimethylsilyl)oxy]acetate (0.16 mL), tert-butyl(dimethyl)silyl trifluoromethanesulfonate (0.18 mL) and methylene chloride (5 mL) was stirred at −78° C. for 1 hr, and then at room temperature for 16 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.066 g, 26%).

¹H NMR (300 MHz, DMSO-d₆) δ0.93 (t, J=7.3 Hz, 3H), 1.46-1.61 (m, 2H), 1.64-1.76 (m, 2H), 1.89-2.12 (m, 4H), 2.76-2.97 (m, 4H), 3.96 (s, 2H), 4.52 (s, 2H), 4.95-5.15 (m, 1H), 7.18-7.25 (m, 2H), 7.27-7.37 (m, 2H), 7.53 (dd, J=17.0, 7.5 Hz, 2H), 7.62-7.72 (m, 2H), 8.19 (s, 1H), 12.38 (br. s., 1H)

EXAMPLE 188

4-[4-(methoxyimino)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

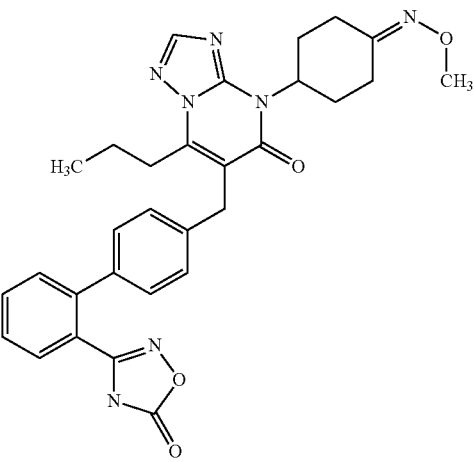 [SMILES: CCCc1c(Cc2ccc(-c3ccccc3-c3noc(=O)[nH]3)cc2)c(=O)n(C2CCC(=NOC)CC2)c2ncnn12]

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), (aminooxy)methane hydrochloride (0.32 g) and pyridine (10 mL) was stirred at 100° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.15 g, 71%).

¹H NMR (300 MHz, DMSO-d₆) δ0.93 (t, J=7.3 Hz, 3H), 1.46-1.62 (m, 2H), 1.75-2.00 (m, 3H), 2.22-2.45 (m, 2H), 2.52-2.71 (m, 2H), 2.88-2.98 (m, 2H), 3.14-3.24 (m, 1H), 3.75 (s, 3H), 3.97 (s, 2H), 5.14-5.27 (m, 1H), 7.18-7.26 (m, 2H), 7.28-7.35 (m, 2H), 7.47-7.59 (m, 2H), 7.62-7.73 (m, 2H), 8.18 (s, 1H), 12.38 (s, 1H)

EXAMPLE 189

4-[trans-4-(hydroxymethyl)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

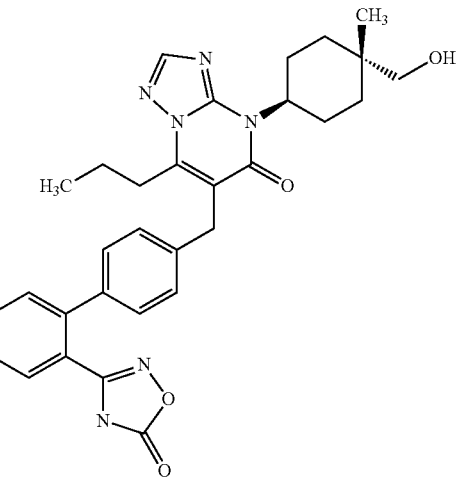

A mixture of 4'-({4-[trans-4-(hydroxymethyl)-4-methyl-cyclohexyl]-5-oxo-7-propyl-4,5-dihydro[1,2,4]triazolo[1,5-a]pyrimidin-6-yl}methyl)biphenyl-2-carbonitrile (0.22 g), tert-butyl(dimethyl)silyl trifluoromethanesulfonate (0.31 mL), 2,6-lutidine (0.15 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.46 g), sodium hydrogen carbonate (0.74 g) and dimethyl sulfoxide (10 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.086 g) and then 1,8-diazabicyclo[5.4.0]undec-7-ene (0.073 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 1.3 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.065 g, 26%).

$^1$H NMR (300 MHz, DMSO-$d_6$) δ0.84-0.97 (m, 6H), 1.13-1.28 (m, 2H), 1.36-1.61 (m, 4H), 1.64-1.74 (m, 2H), 2.56-2.74 (m, 2H), 2.88-2.97 (m, 2H), 3.49 (d, J=4.9 Hz, 2H), 3.96 (s, 2H), 4.46 (t, J=5.3 Hz, 1H), 4.80-4.97 (m, 1H), 7.19-7.26 (m, 2H), 7.27-7.35 (m, 2H), 7.53 (dd, J=17.2, 7.4 Hz, 2H), 7.62-7.73 (m, 2H), 8.20 (s, 1H), 12.37 (s, 1H)

EXAMPLE 190

4-[cis-4-hydroxy-4-(morpholin-4-ylmethyl)cyclo-hexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

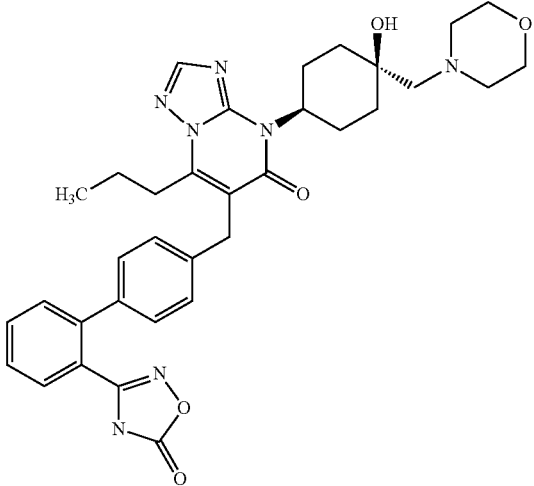 [SMILES: CCCc1c(Cc2ccc(-c3ccccc3-c3noc(=O)[nH]3)cc2)c(=O)n([C@H]2CC[C@](O)(CN3CCOCC3)CC2)c2ncnn12]

A mixture of hydroxylammonium chloride (0.46 g), sodium hydrogen carbonate (0.74 g) and dimethyl sulfoxide (10 mL) was stirred at 40° C. for 30 min, 4'-({4-[cis-4-hydroxy-4-(morpholin-4-ylmethyl)cyclohexyl]-5-oxo-7-propyl-4,5-dihydro[1,2,4]triazolo[1,5-a]pyrimidin-6-yl}methyl)biphenyl-2-carbonitrile (0.25 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.085 g) and then 1,8-diazabicyclo[5.4.0]undec-7-ene (0.073 mL) were added, and the mixture was stirred at room temperature for 2 hr. The reaction mixture was poured into water, and the mixture was adjusted to pH 7 with 1 N hydrochloric acid and extracted with ethyl acetate. The obtained ethyl acetate layer was washed with saturated brine, and dried over anhydrous magnesium sulfate. The solvent was evaporated under reduced pressure, and the residue was purified by silica gel column chromatography to give the title compound as colorless crystals (0.12 g, 44%).

$^1$H NMR (300 MHz, DMSO-$d_6$) δ0.93 (t, J=7.4 Hz, 3H), 1.36-1.74 (m, 8H), 2.25 (s, 2H), 2.50-2.55 (m, 4H), 2.81-2.99 (m, 4H), 3.53-3.64 (m, 4H), 3.96 (s, 2H), 4.77-4.90 (m, 1H), 7.19-7.25 (m, 2H), 7.26-7.34 (m, 2H), 7.52 (dd, J=16.7, 7.6 Hz, 2H), 7.61-7.72 (m, 2H), 8.18 (s, 1H), 12.25 (br. s., 1H)

EXAMPLE 191

4-[4-(2-hydroxyethylidene)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

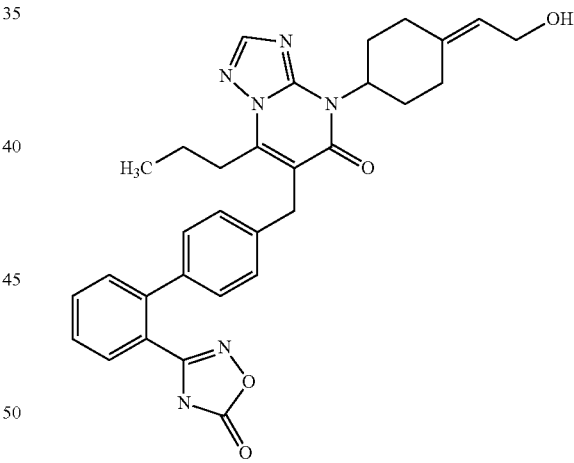

A mixture of 4'-({4-[4-(2-hydroxyethylidene)cyclohexyl]-5-oxo-7-propyl-4,5-dihydro[1,2,4]triazolo[1,5-a]pyrimidin-6-yl}methyl)biphenyl-2-carbonitrile (0.25 g), tert-butyl(dimethyl)silyl trifluoromethanesulfonate (0.17 mL), 2,6-lutidine (0.088 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.53 g), sodium hydrogen carbonate (0.85 g) and dimethyl sulfoxide (10 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.098 g) and then 1,8-diazabicyclo[5.4.0]undec-7-ene (0.083 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 1.3 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as colorless crystals (0.04 g, 14%).

$^1$H NMR (300 MHz, DMSO-$d_6$) δ0.93 (t, J=7.3 Hz, 3H), 1.47-1.60 (m, 2H), 1.70-1.92 (m, 3H), 2.09-2.32 (m, 2H), 2.42-2.75 (m, 3H), 2.87-2.98 (m, 2H), 3.88-4.04 (m, 4H), 4.53 (t, J=5.3 Hz, 1H), 5.01-5.18 (m, 1H), 5.32 (t, J=6.7 Hz, 1H), 7.18-7.25 (m, 2H), 7.28-7.35 (m, 2H), 7.47-7.58 (m, 2H), 7.61-7.72 (m, 2H), 8.13-8.18 (m, 1H), 12.38 (br. s., 1H)

EXAMPLE 192

4-[4-hydroxy-4-(trifluoromethyl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

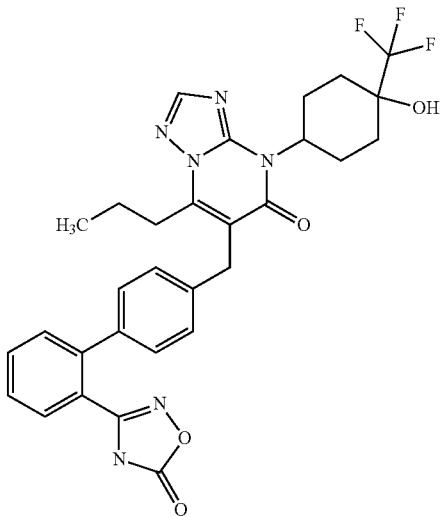 [SMILES: CCCc1c(Cc2ccc(-c3ccccc3-c3noc(=O)[nH]3)cc2)c(=O)n(C2CCC(O)(C(F)(F)F)CC2)c2ncnn12]

A mixture of hydroxylammonium chloride (0.54 g), sodium hydrogen carbonate (0.88 g) and dimethyl sulfoxide (10 mL) was stirred at 40° C. for 30 min, 4'-({4-[4-hydroxy-4-(trifluoromethyl)cyclohexyl]-5-oxo-7-propyl-4,5-dihydro[1,2,4]triazolo[1,5-a]pyrimidin-6-yl}methyl)biphenyl-2-carbonitrile (0.28 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.1 g) and then 1,8-diazabicyclo[5.4.0]undec-7-ene (0.086 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.16 g, 51%).

$^1$H NMR (300 MHz, DMSO-$d_6$) δ0.94 (t, J=7.3 Hz, 3H), 1.50-1.74 (m, 6H), 1.81-1.93 (m, 2H), 2.84-3.02 (m, 4H), 3.99 (s, 2H), 4.87-5.00 (m, 1H), 5.88 (s, 1H), 7.19-7.27 (m, 2H), 7.29-7.35 (m, 2H), 7.47-7.60 (m, 2H), 7.61-7.74 (m, 2H), 8.20 (s, 1H), 12.39 (br. s., 1H)

EXAMPLE 193

4-{4-[(1-methylethoxy)imino]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

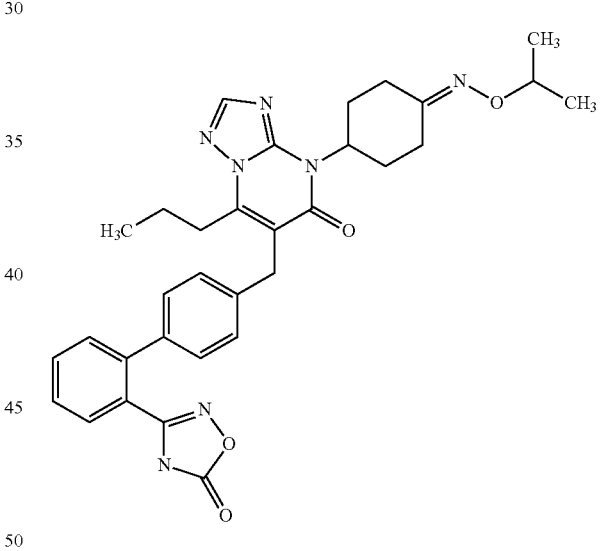

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), 2-(aminooxy)propane hydrochloride (0.43 g) and pyridine (10 mL) was stirred at 100° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.18 g, 79%).

$^1$H NMR (300 MHz, DMSO-$d_6$) δ0.93 (t, J=7.3 Hz, 3H), 1.18 (t, J=6.1 Hz, 6H), 1.46-1.62 (m, 2H), 1.76-1.99 (m, 3H), 2.22-2.46 (m, 2H), 2.52-2.74 (m, 2H), 2.88-2.98 (m, 2H), 3.17-3.26 (m, 1H), 3.97 (s, 2H), 4.15-4.28 (m, 1H), 5.13-5.27

(m, 1H), 7.18-7.26 (m, 2H), 7.28-7.35 (m, 2H), 7.46-7.59 (m, 2H), 7.62-7.72 (m, 2H), 8.18 (s, 1H), 12.38 (br. s., 1H)

EXAMPLE 194

4-[trans-4-(2-hydroxy-2-methylpropoxy)-4-methyl-cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

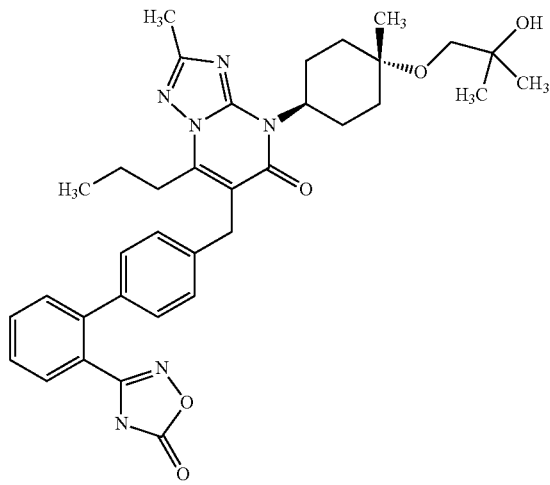 [SMILES: CCCc1c(Cc2ccc(-c3ccccc3-c3noc(=O)[nH]3)cc2)c(=O)n([C@H]2CC[C@](C)(OCC(C)(C)O)CC2)c2nc(C)nn12]

A mixture of hydroxylammonium chloride (0.2 g), sodium hydrogen carbonate (0.33 g) and dimethyl sulfoxide (5 mL) was stirred at 40° C. for 30 min, 4'-({4-[trans-4-(2-hydroxypropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.11 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.038 g) and then 1,8-diazabicyclo[5.4.0]undec-7-ene (0.032 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.047 g, 37%).

$^1$H NMR (300 MHz, DMSO-d$_6$) δ0.92 (t, J=7.3 Hz, 3H), 1.07 (s, 6H), 1.31 (s, 3H), 1.44-1.67 (m, 6H), 1.73-1.83 (m, 2H), 2.36 (s, 3H), 2.57-2.76 (m, 2H), 2.83-2.94 (m, 2H), 3.12 (s, 2H), 3.93 (s, 2H), 4.15 (s, 1H), 4.81-4.95 (m, 1H), 7.19-7.24 (m, 2H), 7.26-7.32 (m, 2H), 7.47-7.57 (m, 2H), 7.61-7.71 (m, 2H), 12.37 (br. s., 1H)

EXAMPLE 195

6-{[2'-(5-oxo-4,5-dihydro-1,2,4-oxadiazol-3-yl)biphenyl-4-yl]methyl}-7-propyl-4-{4-[(tetrahydro-2H-pyran-4-yloxy)imino]cyclohexyl}[1,2,4]triazolo[1,5-a]pyrimidin-5(4H)-one

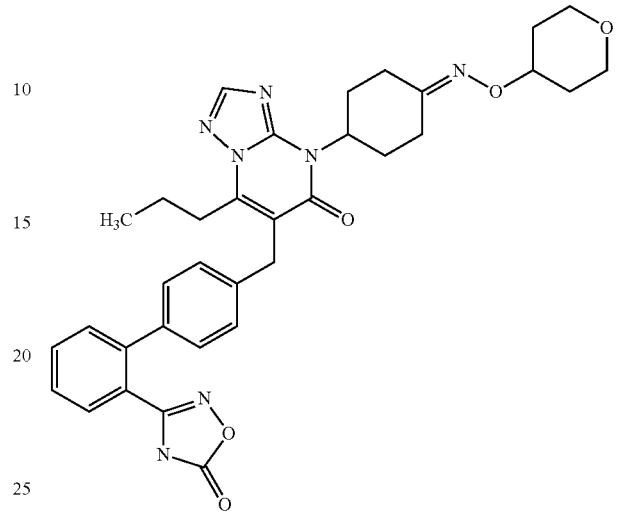

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), 4-(aminooxy)tetrahydro-2H-pyran (0.45 g) and pyridine (5 mL) was stirred at 100° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.18 g, 76%).

$^1$H NMR (300 MHz, DMSO-d$_6$) δ0.93 (t, J=7.3 Hz, 3H), 1.44-1.60 (m, 4H), 1.75-2.04 (m, 5H), 2.23-2.47 (m, 2H), 2.53-2.70 (m, 2H), 2.87-2.99 (m, 2H), 3.21-3.29 (m, 1H), 3.35-3.46 (m, 2H), 3.75-3.84 (m, 2H), 3.97 (s, 2H), 4.09-4.25 (m, 1H), 5.12-5.28 (m, 1H), 7.17-7.26 (m, 2H), 7.28-7.36 (m, 2H), 7.53 (dd, J=17.3, 7.5 Hz, 2H), 7.62-7.72 (m, 2H), 8.18 (s, 1H), 12.38 (br. s., 1H)

EXAMPLE 196

4-{4-[(2-hydroxy-2-methylpropoxy)imino]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

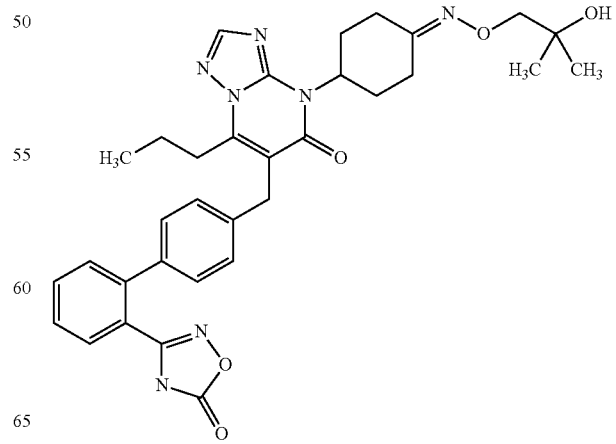

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.2 g), 1-(aminooxy)-2-methylpropan-2-ol (0.4 g) and pyridine (5 mL) was stirred at 100° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.15 g, 63%).

$^1$H NMR (300 MHz, DMSO-$d_6$) δ0.93 (t, J=7.3 Hz, 3H), 1.11 (s, 6H), 1.47-1.62 (m, 2H), 1.79-2.02 (m, 3H), 2.21-2.45 (m, 2H), 2.53-2.71 (m, 2H), 2.89-2.97 (m, 2H), 3.26-3.36 (m, 1H), 3.79 (s, 2H), 3.97 (s, 2H), 4.43 (s, 1H), 5.21 (t, J=11.8 Hz, 1H), 7.19-7.26 (m, 2H), 7.29-7.36 (m, 2H), 7.53 (dd, J=17.1, 7.5 Hz, 2H), 7.62-7.73 (m, 2H), 8.18 (s, 1H), 12.38 (br. s., 1H)

EXAMPLE 197

4-[trans-4-(2-ethyl-2-hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

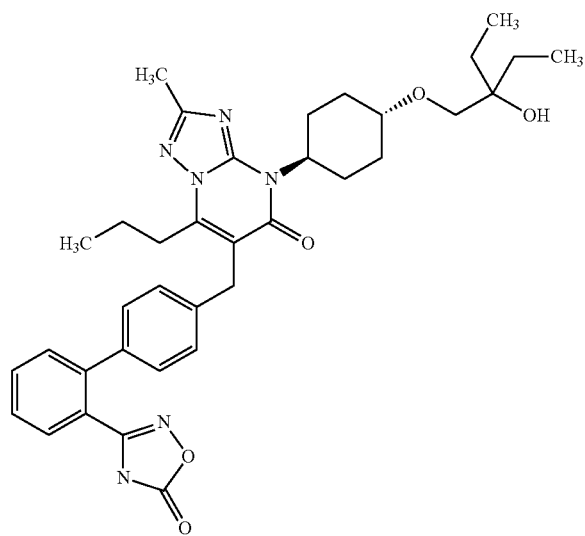 [SMILES: CCCc1c(Cc2ccc(-c3ccccc3-c3noc(=O)[nH]3)cc2)c(=O)n([C@H]2CC[C@H](OCC(O)(CC)CC)CC2)c2nc(C)nn12]

A mixture of hydroxylammonium chloride (0.27 g), sodium hydrogen carbonate (0.43 g) and dimethyl sulfoxide (5 mL) was stirred at 40° C. for 30 min, 4'-({4-[trans-4-(2-ethyl-2-hydroxybutoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.05 g) and then 1,8-diazabicyclo[5.4.0]undec-7-ene (0.043 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.08 g, 48%).

$^1$H NMR (300 MHz, DMSO-$d_6$) δ0.80 (t, J=7.4 Hz, 6H), 0.92 (t, J=7.2 Hz, 3H), 1.15-1.42 (m, 6H), 1.45-1.58 (m, 2H), 1.62-1.72 (m, 2H), 2.05-2.15 (m, 2H), 2.35 (s, 3H), 2.51-2.63 (m, 2H), 2.84-2.92 (m, 2H), 3.22 (s, 2H), 3.25-3.29 (m, 1H), 3.93 (s, 2H), 4.78-4.93 (m, 1H), 7.17-7.31 (m, 4H), 7.52 (dd, J=16.7, 7.6 Hz, 2H), 7.61-7.72 (m, 2H), 12.37 (br. s., 1H)

EXAMPLE 198

4-[trans-4-(2-hydroxy-2-methylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one

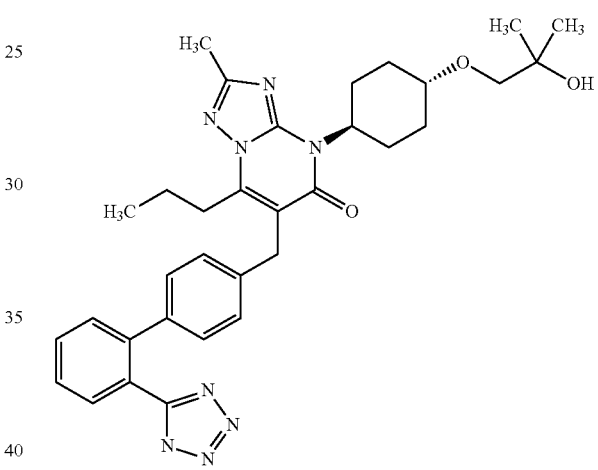

A mixture of 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.32 g), dibutyltin oxide (0.072 g), azidotrimethylsilane (2 g) and toluene (15 mL) was stirred at 110° C. for 48 hr. The reaction mixture was diluted with ethyl acetate, washed with saturated aqueous potassium fluoride solution and then with saturated brine, and dried over anhydrous magnesium sulfate. The solvent was evaporated under reduced pressure. The residue obtained by purification by silica gel column chromatography was dissolved in tetrahydrofuran (5 mL). Tetrabutylammonium fluoride (1 M tetrahydrofuran solution, 0.67 mL) was added and the mixture was stirred at 70° C. for 1 hr. The reaction mixture was extracted with ethyl acetate and 1 N hydrochloric acid, and the ethyl acetate layer was washed with saturated brine, and dried over anhydrous magnesium sulfate. The solvent was evaporated under reduced pressure. The obtained residue was purified by silica gel column chromatography to give the title compound as colorless crystals (0.16 g, 45%).

$^1$H NMR (300 MHz, DMSO-$d_6$) δ0.90 (t, J=7.3 Hz, 3H) 1.05-1.10 (m, 6H) 1.18-1.35 (m, 2H) 1.43-1.58 (m, 2H) 1.62-1.73 (m, 2H) 2.05-2.15 (m, 2H) 2.35 (s, 3H) 2.53-2.64 (m, 2H) 2.79-2.91 (m, 2H) 3.20 (s, 2H) 3.87 (s, 2H) 4.23 (s, 1H)

4.78-4.94 (m, 1H) 6.98 (d, J=8.1 Hz, 2H) 7.16 (d, J=8.1 Hz, 2H) 7.48-7.58 (m, 2H) 7.60-7.70 (m, 2H)

EXAMPLE 199

4-[trans-4-(2-ethyl-2-hydroxybutoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one

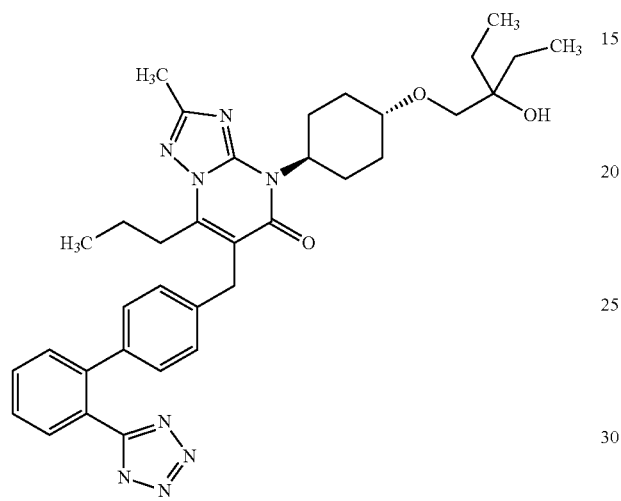

A mixture of 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.25 g), dibutyltin oxide (0.054 g), azidotrimethylsilane (1.5 g) and toluene (15 mL) was stirred at 110° C. for 48 hr. The reaction mixture was diluted with ethyl acetate, washed with saturated aqueous potassium fluoride solution and then with saturated brine, and dried over anhydrous magnesium sulfate. The solvent was evaporated under reduced pressure. The residue obtained by purification by silica gel column chromatography was dissolved in tetrahydrofuran (5 mL). Tetrabutylammonium fluoride (1 M tetrahydrofuran solution, 0.4 mL) was added and the mixture was stirred at 70° C. for 1 hr. Ethyl acetate and 1 N hydrochloric acid were added to the reaction mixture, and the mixture was extracted with ethyl acetate. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.087 g, 32%).

$^1$H NMR (300 MHz, DMSO-$d_6$) δ0.80 (t, J=7.4 Hz, 6H), 0.90 (t, J=7.3 Hz, 3H), 1.21-1.31 (m, 2H), 1.38 (d, J=7.5 Hz, 4H), 1.44-1.56 (m, 2H), 1.62-1.72 (m, 2H), 2.04-2.16 (m, 2H), 2.35 (s, 3H), 2.52-2.63 (m, 2H), 2.81-2.90 (m, 2H), 3.22 (s, 2H), 3.84-3.92 (m, 3H), 4.76-4.93 (m, 1H), 6.98 (d, J=8.1 Hz, 2H), 7.16 (d, J=8.1 Hz, 2H), 7.48-7.58 (m, 2H), 7.59-7.71 (m, 2H)

EXAMPLE 200

4-[trans-4-(2-hydroxy-2-methylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one potassium salt

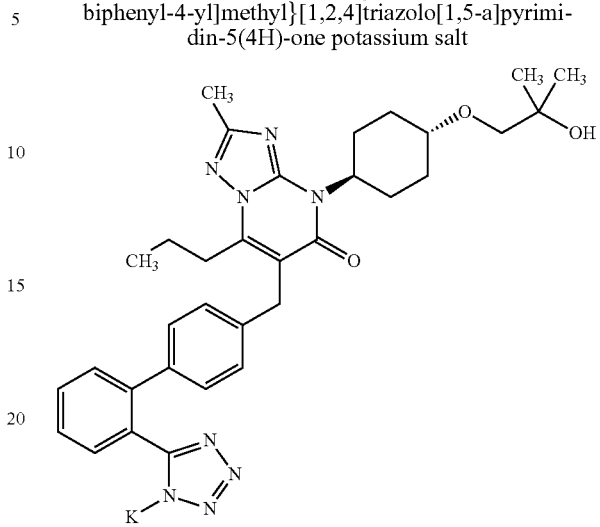

4-[trans-4-(2-Hydroxy-2-methylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one (0.09 g) was suspended in isopropyl alcohol (3 mL), 0.5N potassium hydroxide solution (0.3 mL) was added, and the solvent was evaporated under reduced pressure. The residue was solidified with diisopropyl ether to give the title compound as a colorless solid (0.086 g, 90%).

$^1$H NMR (300 MHz, DMSO-$d_6$) δ0.94 (t, J=7.3 Hz, 3H), 1.07 (s, 6H), 1.20-1.36 (m, 2H), 1.50-1.72 (m, 4H), 2.03-2.14 (m, 2H), 2.34 (s, 3H), 2.53-2.63 (m, 2H), 2.82-2.91 (m, 2H), 3.20 (s, 2H), 3.83 (s, 2H), 4.24 (s, 1H), 4.86 (t, J=12.7 Hz, 1H), 6.97-7.08 (m, 4H), 7.24-7.38 (m, 3H), 7.46-7.54 (m, 1H)

EXAMPLE 201

4-[trans-4-(2-ethyl-2-hydroxybutoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one potassium salt

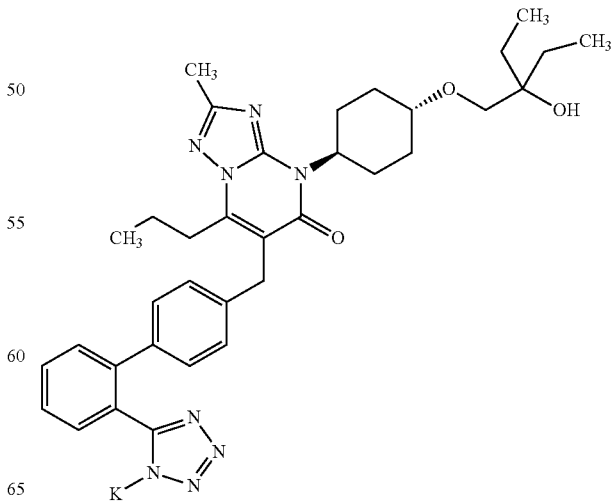

4-[trans-4-(2-Ethyl-2-hydroxybutoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one (0.063 g) was suspended in isopropyl alcohol (3 mL), 0.5N potassium hydroxide solution (0.2 mL) was added, and the solvent was evaporated under reduced pressure. The residue was solidified with diisopropyl ether to give the title compound as a colorless solid (0.045 g, 67%).

$^1$H NMR (300 MHz, DMSO-$d_6$) δ0.80 (t, J=7.4 Hz, 6H) 0.94 (t, J=7.3 Hz, 3H) 1.17-1.42 (m, 6H) 1.50-1.73 (m, 4H) 2.03-2.16 (m, 2H) 2.34 (s, 3H) 2.52-2.64 (m, 2H) 2.83-2.91 (m, 2H) 3.22 (s, 2H) 3.83 (s, 2H) 3.91 (s, 1H) 4.79-4.92 (m, 1H) 6.97-7.07 (m, 4H) 7.24-7.39 (m, 3H) 7.46-7.52 (m, 1H)

EXAMPLE 202

4-[trans-4-(2-ethyl-2-hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

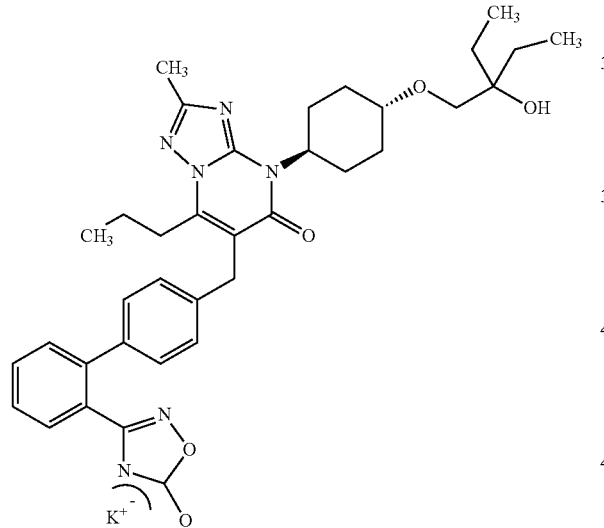

4-[trans-4-(2-Ethyl-2-hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.082 g) was suspended in isopropyl alcohol (3 mL), 0.5N potassium hydroxide solution (0.26 mL) was added, and the solvent was evaporated under reduced pressure. The residue was solidified with diisopropyl ether to give the title compound as a colorless solid (0.046 g, 53%).

$^1$H NMR (300 MHz, DMSO-$d_6$) δ0.80 (t, J=7.4 Hz, 6H) 0.95 (t, J=7.3 Hz, 3H) 1.37 (q, J=7.4 Hz, 6H) 1.52-1.74 (m, 4H) 2.03-2.15 (m, 2H) 2.35 (s, 3H) 2.52-2.65 (m, 2H) 2.83-2.93 (m, 2H) 3.22 (s, 2H) 3.84-3.94 (m, 3H) 4.86 (t, J=11.8 Hz, 1H) 7.12-7.23 (m, 4H) 7.25-7.49 (m, 4H)

EXAMPLE 203

4-[trans-4-(2-hydroxy-2-methylpropoxy)cyclohexyl]-7-propyl-6-{[2'-(1H-tetrazol-5-yl)biphenyl-4-yl]methyl}[1,2,4]triazolo[1,5-a]pyrimidin-5(4H)-one

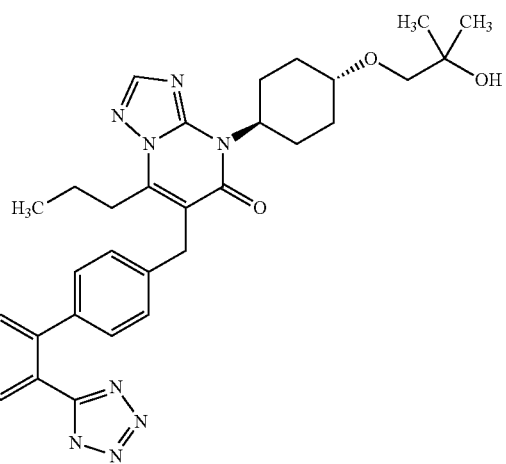

A mixture of 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.2 g), dibutyltin oxide (0.046 g), azidotrimethylsilane (1.3 g) and toluene (15 mL) was stirred at 110° C. for 48 hr. The reaction mixture was diluted with ethyl acetate, washed with saturated aqueous potassium fluoride solution and then with saturated brine, and dried over anhydrous magnesium sulfate. The solvent was evaporated under reduced pressure. The obtained residue was dissolved in tetrahydrofuran (10 mL). Tetrabutylammonium fluoride (1 M tetrahydrofuran solution, 0.93 mL) was added and the mixture was stirred at 70° C. for 1 hr. Ethyl acetate and 1 N hydrochloric acid were added to the reaction mixture, and the mixture was extracted with ethyl acetate. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.033 g, 15%).

$^1$H NMR (300 MHz, DMSO-$d_6$) δ0.91 (t, J=7.4 Hz, 3H), 1.08 (s, 6H), 1.21-1.36 (m, 2H), 1.44-1.59 (m, 2H), 1.63-1.75 (m, 2H), 2.05-2.16 (m, 2H), 2.51-2.67 (m, 2H), 2.84-2.95 (m, 2H), 3.20 (s, 2H), 3.85 (s, 2H), 4.24 (s, 1H), 4.90 (t, J=12.1 Hz, 1H), 6.99 (d, J=8.0 Hz, 2H), 7.18 (d, J=8.0 Hz, 2H), 7.54 (dd, J=13.4, 7.4 Hz, 2H), 7.60-7.71 (m, 2H), 8.18 (s, 1H)

EXAMPLE 204

4-[(5R,8R)-3-methyl-1-oxa-2-azaspiro[4.5]dec-2-en-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

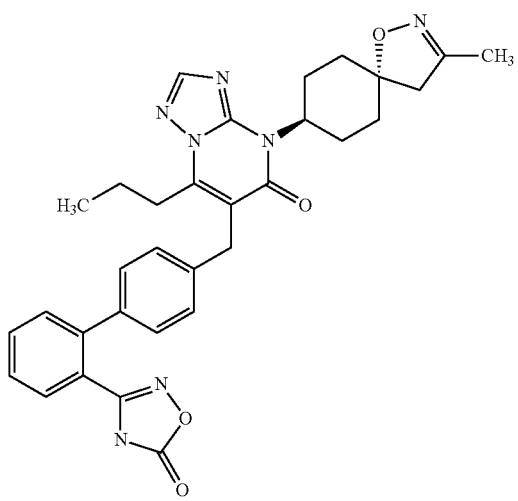 [SMILES: CCCc1c(Cc2ccc(-c3ccccc3-c3noc(=O)[nH]3)cc2)c(=O)n([C@H]2CC[C@]3(CC2)CC(C)=NO3)c2ncnn12]

A mixture of hydroxylammonium chloride (0.46 g), sodium hydrogen carbonate (0.74 g) and dimethyl sulfoxide (10 mL) was stirred at 40° C. for 30 min, 4'-({4-[(5R,8R)-3-methyl-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile (0.23 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.086 g) and then 1,8-diazabicyclo[5.4.0]undec-7-ene (0.073 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.12 g, 47%).

$^1$H NMR (300 MHz, DMSO-d$_6$) δ0.93 (t, J=7.4 Hz, 3H), 1.46-1.84 (m, 8H), 1.92 (s, 3H), 2.54-2.72 (m, 2H), 2.87-2.98 (m, 4H), 3.98 (s, 2H), 4.97 (t, J=12.3 Hz, 1H), 7.18-7.26 (m, 2H), 7.28-7.35 (m, 2H), 7.47-7.58 (m, 2H), 7.62-7.73 (m, 2H), 8.20 (s, 1H), 12.39 (br. s., 1H)

EXAMPLE 205

4-[(5S,8S)-3-methyl-1-oxa-2-azaspiro[4.5]dec-2-en-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

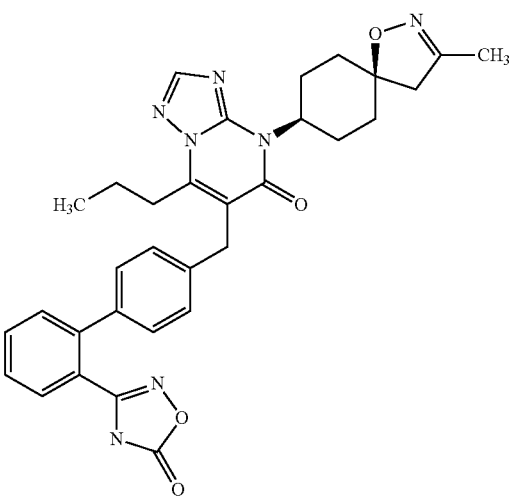 [SMILES: CCCc1c(Cc2ccc(-c3ccccc3-c3noc(=O)[nH]3)cc2)c(=O)n([C@H]2CC[C@@]3(CC2)CC(C)=NO3)c2ncnn12]

A mixture of hydroxylammonium chloride (0.4 g), sodium hydrogen carbonate (0.65 g) and dimethyl sulfoxide (10 mL) was stirred at 40° C. for 30 min, 4'-({4-[(5S,8S)-3-methyl-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.075 g) and then 1,8-diazabicyclo[5.4.0]undec-7-ene (0.063 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.078 g, 35%).

$^1$H NMR (300 MHz, DMSO-d$_6$) δ0.93 (t, J=7.4 Hz, 3H), 1.47-1.73 (m, 6H), 1.82-1.92 (m, 5H), 2.71 (s, 2H), 2.75-2.99 (m, 4H), 3.96 (s, 2H), 4.89-5.04 (m, 1H), 7.18-7.25 (m, 2H), 7.28-7.35 (m, 2H), 7.46-7.58 (m, 2H), 7.62-7.70 (m, 2H), 8.20 (s, 1H), 12.38 (br. s., 1H)

EXAMPLE 206

7-butyl-4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

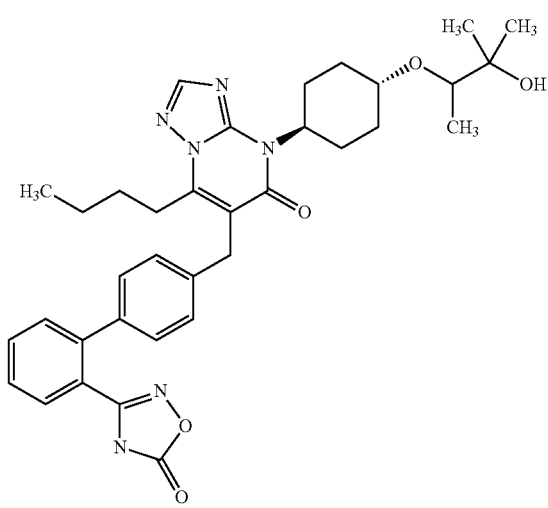 [SMILES: CCCCc1c(Cc2ccc(-c3ccccc3-c3noc(=O)[nH]3)cc2)c(=O)n([C@H]2CC[C@H](OC(C)C(C)(C)O)CC2)c2ncnn12]

A mixture of hydroxylammonium chloride (0.58 g), sodium hydrogen carbonate (0.93 g) and dimethyl sulfoxide (10 mL) was stirred at 40° C. for 30 min, 4'-({7-butyl-4-[trans-4-(2-hydroxy-1,2-dimethylpropoxy)cyclohexyl]-5-oxo-4,5-dihydro[1,2,4]triazolo[1,5-a]pyrimidin-6-yl}methyl)biphenyl-2-carbonitrile (0.32 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.11 g) and then 1,8-diazabicyclo[5.4.0]undec-7-ene (0.092 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.2 g, 56%).

$^1$H NMR (300 MHz, DMSO-$d_6$) δ0.84 (t, J=7.2 Hz, 3H), 1.00 (s, 3H), 1.03 (d, J=6.4 Hz, 3H), 1.08 (s, 3H), 1.21-1.54 (m, 6H), 1.63-1.74 (m, 2H), 1.96-2.15 (m, 2H), 2.58 (t, J=11.9 Hz, 2H), 2.89-2.97 (m, 2H), 3.25 (q, J=6.1 Hz, 1H), 3.34-3.43 (m, 1H), 3.95 (s, 2H), 4.06 (s, 1H), 4.90 (t, J=12.3 Hz, 1H), 7.19-7.25 (m, 2H), 7.27-7.32 (m, 2H), 7.46-7.58 (m, 2H), 7.62-7.73 (m, 2H), 8.18 (s, 1H), 12.39 (s, 1H)

EXAMPLE 207

4-(trans-4-{[(3R,4S)-4-hydroxytetrahydrofuran-3-yl]oxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

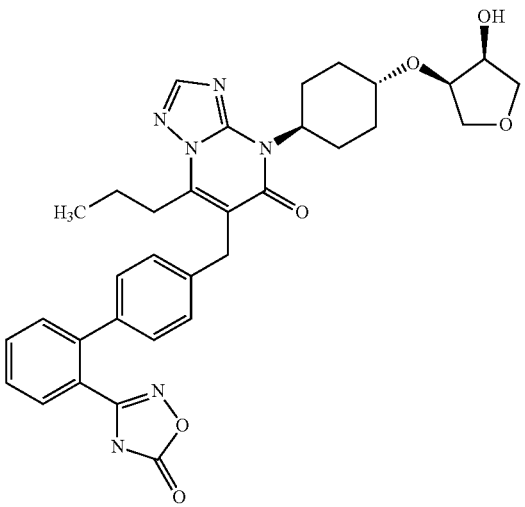 [SMILES: CCCc1c(Cc2ccc(-c3ccccc3-c3noc(=O)[nH]3)cc2)c(=O)n([C@H]2CC[C@H](O[C@@H]3COC[C@@H]3O)CC2)c2ncnn12]

A mixture of 4'-({5-oxo-7-propyl-4-[(3a'R,6a'S)-tetrahydrospiro[cyclohexane-1,2'-furo[3,4-d][1,3]dioxol]-4-yl]-4,5-dihydro[1,2,4]triazolo[1,5-a]pyrimidin-6-yl}methyl)biphenyl-2-carbonitrile (0.14 g), tert-butyl(dimethyl)silyl trifluoromethanesulfonate (0.087 mL), 2,6-lutidine (0.044 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.26 g), sodium hydrogen carbonate (0.42 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.049 g) and then 1,8-diazabicyclo[5.4.0]undec-7-ene (0.041 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (10 mL). Tetrabutylammonium bromide (1.0 M tetrahydrofuran solution, 1.7 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.04 g, 26%).

¹H NMR (300 MHz, DMSO-d₆) δ0.93 (t, J=7.2 Hz, 3H), 1.22-1.41 (m, 2H), 1.47-1.60 (m, 2H), 1.64-1.74 (m, 2H), 2.09-2.21 (m, 2H), 2.51-2.67 (m, 2H), 2.89-2.97 (m, 2H), 3.44-3.56 (m, 3H), 3.74-3.84 (m, 2H), 3.96 (s, 2H), 4.01-4.15 (m, 2H), 4.53 (d, J=5.3 Hz, 1H), 4.84-4.97 (m, 1H), 7.19-7.25 (m, 2H), 7.27-7.34 (m, 2H), 7.53 (dd, J=16.7, 7.6 Hz, 2H), 7.63-7.74 (m, 2H), 8.18 (s, 1H), 12.38 (s, 1H).

EXAMPLE 208

7-butyl-4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

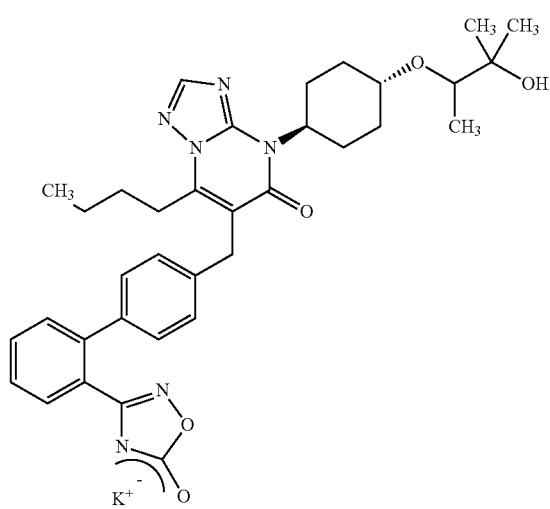 [SMILES: CCCCc1c(Cc2ccc(-c3ccccc3C3=NOC(O)N3)cc2)c(=O)n([C@H]2CC[C@H](OC(C)C(C)(C)O)CC2)c2ncnn12 ; [K+]]

7-Butyl-4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.17 g) was suspended in isopropyl alcohol (3 mL), 2N potassium hydroxide solution (0.14 mL) was added, and the solvent was evaporated under reduced pressure. The residue was solidified with diisopropyl ether to give the title compound as a colorless solid (0.15 g, 85%).

¹H NMR (300 MHz, DMSO-d₆) δ0.85 (t, J=7.3 Hz, 3H), 1.00 (s, 3H), 1.04 (d, J=6.0 Hz, 3H), 1.08 (s, 3H), 1.20-1.56 (m, 6H), 1.71 (s, 2H), 1.95-2.13 (m, 2H), 2.52-2.66 (m, 2H), 2.91-3.01 (m, 2H), 3.21-3.28 (m, 1H), 3.35-3.43 (m, 1H), 3.90 (s, 2H), 4.06 (s, 1H), 4.90 (t, J=12.0 Hz, 1H), 7.13-7.49 (m, 8H), 8.16 (s, 1H)

EXAMPLE 209

2-({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)acetamide

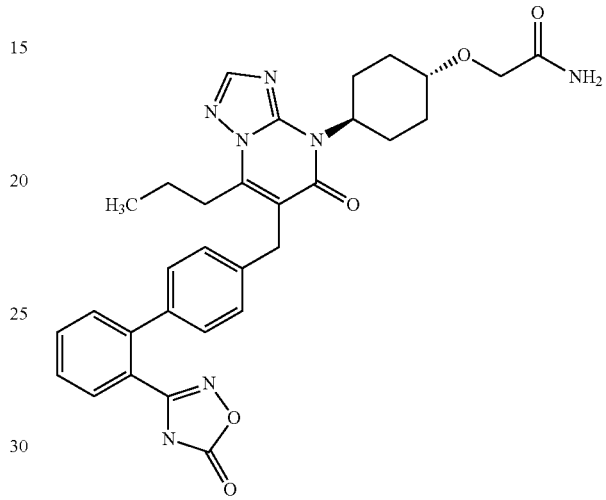

A mixture of ethyl [(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetate (0.68 g), 1N aqueous sodium hydroxide solution (10 mL), tetrahydrofuran (10 mL) and methanol (10 mL) was stirred at room temperature for 1 hr. 1 N Hydrochloric acid was added to the reaction mixture, and the mixture was extracted with ethyl acetate. The obtained ethyl acetate layer was washed with saturated brine, and dried over anhydrous magnesium sulfate. The solvent was evaporated under reduced pressure. The obtained residue was dissolved in N,N-dimethylformamide (5 mL), 1-hydroxybenzotriazole ammonium salt (0.25 g) and 1-ethyl-3-(3-dimethylaminopropyl)carbodiimide hydrochloride (0.28 g) were added, and the mixture was stirred at room temperature for 3 hr. The reaction mixture was diluted with ethyl acetate, washed with water and then with saturated brine, and dried over anhydrous magnesium sulfate. The solvent was evaporated under reduced pressure. The residue obtained by purification by silica gel column chromatography was dissolved in dimethyl sulfoxide (5 mL), and the mixture was added to a mixture of hydroxylammonium chloride (0.45 g), sodium hydrogen carbonate (0.77 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.089 g) and then 1,8-diazabicyclo[5.4.0]undec-7-ene (0.075 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.16 g, 13%).

$^1$H NMR (300 MHz, DMSO-d$_6$) δ0.93 (t, J=7.3 Hz, 3H), 1.26-1.43 (m, 2H), 1.47-1.61 (m, 2H), 1.68-1.78 (m, 2H), 2.09-2.20 (m, 2H), 2.52-2.68 (m, 2H), 2.88-2.98 (m, 2H), 3.46-3.59 (m, 1H), 3.96 (s, 2H), 4.53 (s, 2H), 4.93 (t, J=8.3 Hz, 1H), 7.18-7.26 (m, 2H), 7.28-7.35 (m, 2H), 7.47-7.59 (m, 2H), 7.62-7.73 (m, 2H), 8.19 (s, 1H)

EXAMPLE 210

({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)acetonitrile

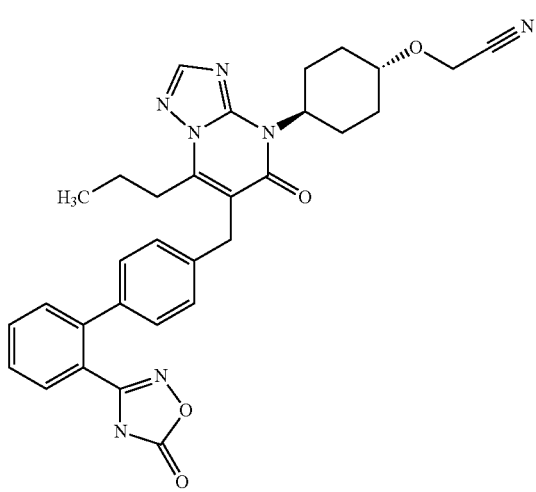 [SMILES: CCCc1c(Cc2ccc(-c3ccccc3-c3noc(=O)[nH]3)cc2)c(=O)n([C@H]2CC[C@H](OCC#N)CC2)c2ncnn12]

To a solution (10 mL) of 2-({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)acetamide (0.16 g) and pyridine (0.089 mL) in tetrahydrofuran was added trifluoroacetic acid anhydride (0.12 mL) at 0° C., and the mixture was stirred for 2 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.059 g, 38%).

$^1$H NMR (300 MHz, DMSO-d$_6$) δ0.93 (t, J=7.3 Hz, 3H), 1.26-1.43 (m, 2H), 1.47-1.61 (m, 2H), 1.68-1.78 (m, 2H), 2.09-2.20 (m, 2H), 2.52-2.68 (m, 2H), 2.88-2.98 (m, 2H), 3.46-3.59 (m, 1H), 3.96 (s, 2H), 4.53 (s, 2H), 4.93 (t, J=8.3 Hz, 1H), 7.18-7.26 (m, 2H), 7.28-7.35 (m, 2H), 7.47-7.59 (m, 2H), 7.62-7.73 (m, 2H), 8.19 (s, 1H)

EXAMPLE 211

4-[(5R,8R)-3-(1-hydroxy-1-methylethyl)-1-oxa-2-azaspiro[4.5]dec-2-en-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

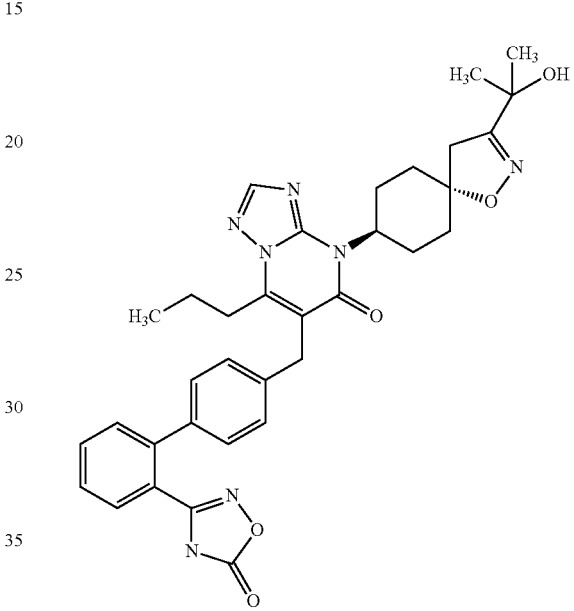

A mixture of hydroxylammonium chloride (0.23 g), sodium hydrogen carbonate (0.37 g) and dimethyl sulfoxide (10 mL) was stirred at 40° C. for 30 min, 4'-({4-[(5R,8R)-3-(1-hydroxy-1-methylethyl)-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile (0.12 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.042 g) and then 1,8-diazabicyclo[5.4.0]undec-7-ene (0.036 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.046 g, 34%).

$^1$H NMR (300 MHz, CHLOROFORM-d) δ1.06 (t, J=7.35 Hz, 3H) 1.51 (s, 6H) 1.65-1.99 (m, 8H) 2.66-2.84 (m, 2H)

2.97-3.08 (m, 4H) 4.02 (s, 2H) 5.04-5.18 (m, 1H) 7.33-7.52 (m, 6H) 7.59-7.67 (m, 1H) 7.75 (dd, J=7.72, 0.94 Hz, 1H) 7.93 (s, 1H)

EXAMPLE 212

4-[(5S,8S)-3-(1-hydroxy-1-methylethyl)-1-oxa-2-azaspiro[4.5]dec-2-en-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

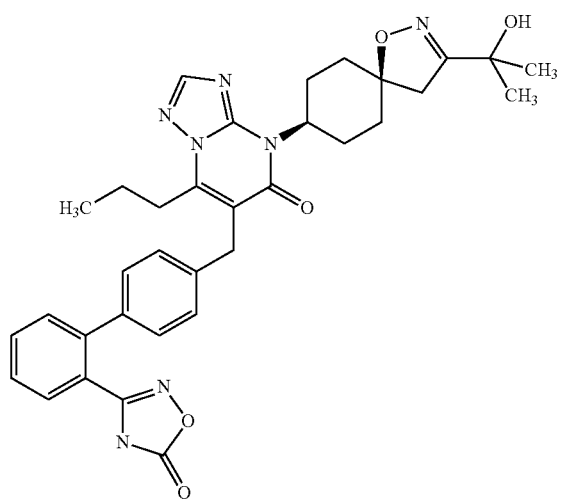 [SMILES: CCCc1c(Cc2ccc(-c3ccccc3-c3noc(=O)[nH]3)cc2)c(=O)n([C@H]2CC[C@@]3(CC2)CC(C(C)(C)O)=NO3)c2ncnn12]

A mixture of hydroxylammonium chloride (0.18 g), sodium hydrogen carbonate (0.3 g) and dimethyl sulfoxide (10 mL) was stirred at 40° C. for 30 min, 4'-({4-[(5S,8S)-3-(1-hydroxy-1-methylethyl)-1-oxa-2-azaspiro[4.5]dec-2-en-8-yl]-5-oxo-7-propyl-4,5-dihydro[1,2,4]triazolo[1,5-a]pyrimidin-6-yl}methyl)biphenyl-2-carbonitrile (0.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.034 g) and then 1,8-diazabicyclo[5.4.0]undec-7-ene (0.029 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.038 g, 34%).

$^1$H NMR (300 MHz, DMSO-$d_6$) δ0.93 (t, J=7.3 Hz, 3H) 1.32 (s, 6H) 1.47-1.75 (m, 6H) 1.83-1.96 (m, 2H) 2.77-2.98 (m, 6H) 3.98 (s, 2H) 4.90-5.04 (m, 1H) 5.13 (s, 1H) 7.18-7.25 (m, 2H) 7.29-7.35 (m, 2H) 7.46-7.59 (m, 2H) 7.61-7.73 (m, 2H) 8.20 (s, 1H) 12.38 (br. s., 1H)

EXAMPLE 213

4-{trans-4-[(3-methyl-4,5-dihydroisoxazol-5-yl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

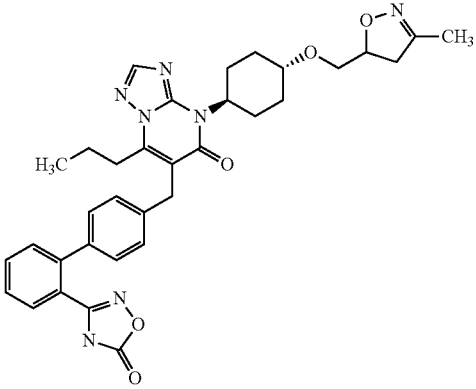 [SMILES: CCCc1c(Cc2ccc(-c3ccccc3-c3noc(=O)[nH]3)cc2)c(=O)n([C@H]2CC[C@H](OCC3CC(C)=NO3)CC2)c2ncnn12]

A mixture of hydroxylammonium chloride (0.85 g), sodium hydrogen carbonate (1.4 g) and dimethyl sulfoxide (15 mL) was stirred at 40° C. for 30 min, 4'-[(4-{trans-4-[(3-methyl-4,5-dihydroisoxazol-5-yl)methoxy]cyclohexyl}-5-oxo-7-propyl-4,5-dihydro[1,2,4]triazolo[1,5-a]pyrimidin-6-yl)methyl]biphenyl-2-carbonitrile (0.46 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.13 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.22 g, 43%).

$^1$H NMR (300 MHz, DMSO-$d_6$) δ0.92 (t, J=7.2 Hz, 3H) 1.20-1.36 (m, 2H) 1.46-1.75 (m, 4H) 1.89 (s, 3H) 2.04-2.16 (m, 2H) 2.53-2.76 (m, 3H) 2.88-3.05 (m, 3H) 3.33-3.42 (m, 1H) 3.44-3.50 (m, 2H) 3.95 (s, 2H) 4.49-4.64 (m, 1H) 4.83-4.97 (m, 1H) 7.18-7.24 (m, 2H) 7.27-7.34 (m, 2H) 7.45-7.58 (m, 2H) 7.63-7.72 (m, 2H) 8.18 (s, 1H) 12.38 (s, 1H)

EXAMPLE 214

4-{trans-4-[(3-methyl-4,5-dihydroisoxazol-5-yl)methoxy]cyclohexyl}-7-propyl-6-{[2'-(1H-tetrazol-5-yl)biphenyl-4-yl]methyl}[1,2,4]triazolo[1,5-a]pyrimidin-5(4H)-one

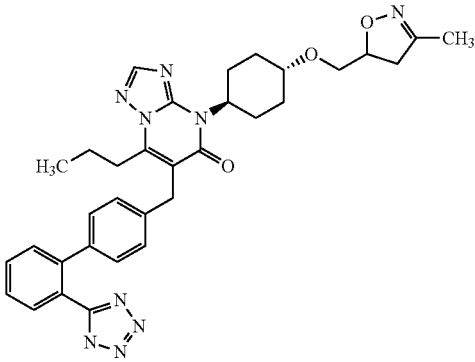 [SMILES: CCCc1c(Cc2ccc(-c3ccccc3-c3nnn[nH]3)cc2)c(=O)n([C@H]2CC[C@H](OCC3CC(C)=NO3)CC2)c2ncnn12]

A mixture of 4'-[(4-{trans-4-[(3-methyl-4,5-dihydroisoxazol-5-yl)methoxy]cyclohexyl}-5-oxo-7-propyl-4,5-dihydro[1,2,4]triazolo[1,5-a]pyrimidin-6-yl)methyl]biphenyl-2-carbonitrile (0.4 g), dibutyltin oxide (0.088 g), azidotrimethylsilane (2.4 g) and toluene (25 mL) was stirred at 110° C. for 48 hr. The reaction mixture was diluted with ethyl acetate, washed with saturated aqueous potassium fluoride solution and then with saturated brine, and dried over anhydrous magnesium sulfate. The solvent was evaporated under reduced pressure, and the residue was purified by silica gel column chromatography to give the title compound as a colorless amorphous solid (0.15 g, 35%).

$^1$H NMR (300 MHz, DMSO-d$_6$) δ0.91 (t, J=7.4 Hz, 3H) 1.20-1.36 (m, 2H) 1.44-1.58 (m, 2H) 1.63-1.72 (m, 2H) 1.89 (s, 3H) 2.03-2.15 (m, 2H) 2.53-2.75 (m, 3H) 2.85-3.04 (m, 3H) 3.33-3.41 (m, 1H) 3.47 (d, J=5.7 Hz, 2H) 3.90 (s, 2H) 4.50-4.61 (m, 1H) 4.81-4.97 (m, 1H) 6.98 (d, J=8.3 Hz, 2H) 7.18 (d, J=8.3 Hz, 2H) 7.48-7.59 (m, 2H) 7.60-7.71 (m, 2H) 8.17 (s, 1H)

EXAMPLE 215

6-{[2'-(5-oxo-4,5-dihydro-1,2,4-oxadiazol-3-yl)biphenyl-4-yl]methyl}-4-[trans-4-(2-oxopropoxy)cyclohexyl]-7-propyl[1,2,4]triazolo[1,5-a]pyrimidin-5(4H)-one

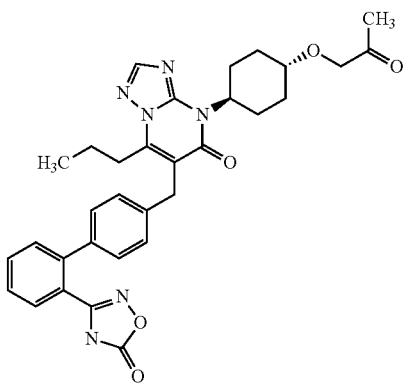 [SMILES: CCCc1c(Cc2ccc(-c3ccccc3-c3noc(=O)[nH]3)cc2)c(=O)n([C@H]2CC[C@H](OCC(C)=O)CC2)c2ncnn12]

A mixture of hydroxylammonium chloride (0.73 g), sodium hydrogen carbonate (1.2 g) and dimethyl sulfoxide (10 mL) was stirred at 50° C. for 30 min, 4'-({4-[trans-4-(2-{[tert-butyl(dimethyl)silyl]oxy}propoxy)cyclohexyl]-5-oxo-7-propyl-4,5-dihydro[1,2,4]triazolo[1,5-a]pyrimidin-6-yl}methyl)biphenyl-2-carbonitrile (0.35 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.14 g) and then 1,8-diazabicyclo[5.4.0]undec-7-ene (0.12 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetabutylammonium fluoride (1 M tetrahydrofuran solution, 1.8 mL) was added, and the mixture was stirred at room temperature for 3 hr. The reaction mixture was extracted with ethyl acetate and water, and the organic layer was washed with water and then with saturated brine, and dried over anhydrous magnesium sulfate. The solvent was evaporated under reduced pressure. The residue obtained by purification by silica gel column chromatography was dissolved in acetonitrile (15 mL), Dess-Martin reagent (0.42 g) was added, and the mixture was stirred at room temperature for 2 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as colorless crystals (0.13 g, 31%).

$^1$H NMR (300 MHz, DMSO-d$_6$) δ0.93 (t, J=7.3 Hz, 3H) 1.22-1.40 (m, 2H) 1.46-1.76 (m, 4H) 2.05 (s, 3H) 2.08-2.18 (m, 2H) 2.52-2.66 (m, 2H) 2.88-2.97 (m, 2H) 3.33-3.41 (m, 1H) 3.96 (s, 2H) 4.16 (s, 2H) 4.85-4.99 (m, 1H) 7.19-7.25 (m, 2H) 7.28-7.34 (m, 2H) 7.47-7.58 (m, 2H) 7.61-7.74 (m, 2H) 8.18 (s, 1H) 12.38 (br. s., 1H)

EXAMPLE 216

4-(trans-4-{[(2E)-2-(methoxyimino)propyl]oxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

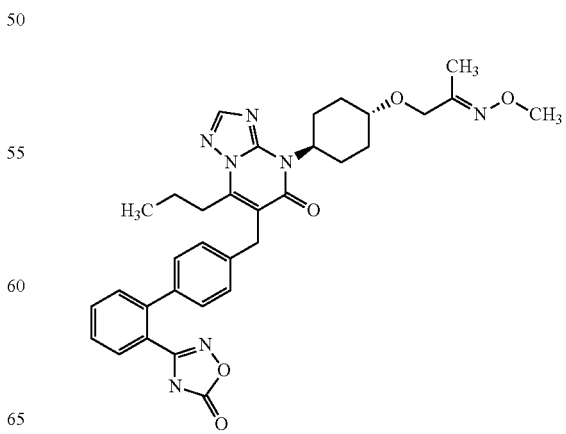

A mixture of 6-{[2'-(5-oxo-4,5-dihydro-1,2,4-oxadiazol-3-yl)biphenyl-4-yl]methyl}-4-[trans-4-(2-oxopropoxy)cyclohexyl]-7-propyl[1,2,4]triazolo[1,5-a]pyrimidin-5(4H)-one (0.095 g), (aminooxy)methane hydrochloride (0.041 g) and pyridine (5 mL) was stirred at 80° C. for 16 hr. Ethyl acetate and water were added to the reaction mixture, and the mixture was adjusted to pH 4 with 1 N hydrochloric acid. The ethyl acetate layer was washed with saturated brine, and dried over anhydrous magnesium sulfate. The solvent was evaporated under reduced pressure. The obtained residue was purified by silica gel column chromatography to give the title compound as colorless crystals (0.07 g, 70%).

$^1$H NMR (300 MHz, DMSO-$d_6$) δ0.93 (t, J=7.3 Hz, 3H) 1.22-1.76 (m, 6H) 1.80 (s, 3H) 2.05-2.15 (m, 2H) 2.52-2.64 (m, 2H) 2.89-2.97 (m, 2H) 3.27-3.35 (m, 1H) 3.78 (s, 3H) 3.93-3.99 (m, 4H) 4.85-4.98 (m, 1H) 7.19-7.24 (m, 2H) 7.28-7.34 (m, 2H) 7.46-7.58 (m, 2H) 7.62-7.72 (m, 2H) 8.18 (s, 1H) 12.38 (s, 1H)

EXAMPLE 217

4-(trans-4-{[(1R,2S)-2-hydroxycyclopentyl]oxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

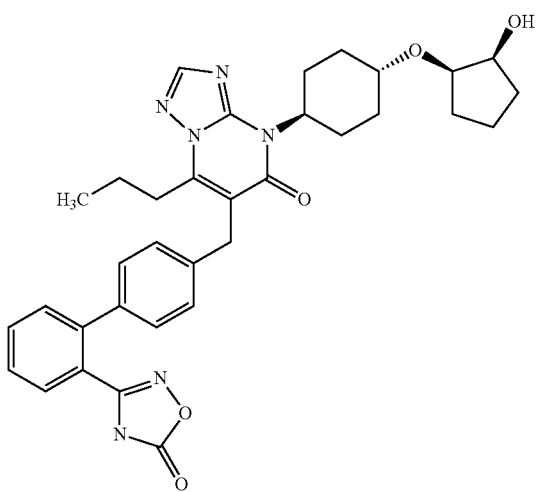 [SMILES: CCCc1c(Cc2ccc(-c3ccccc3-c3noc(=O)[nH]3)cc2)c(=O)n([C@H]2CC[C@H](O[C@@H]3CCC[C@@H]3O)CC2)c2ncnn12]

A mixture of hydroxylammonium chloride (1.6 g), sodium hydrogen carbonate (2.5 g) and dimethyl sulfoxide (15 mL) was stirred at 40° C. for 30 min, 4'-{[4-(trans-4-{[(1R,2S)-2-hydroxycyclopentyl]oxy}cyclohexyl)-5-oxo-7-propyl-4,5-dihydro[1,2,4]triazolo[1,5-a]pyrimidin-6-yl]methyl}biphenyl-2-carbonitrile (0.82 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.16 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.22 g, 24%).

$^1$H NMR (300 MHz, DMSO-$d_6$) δ0.93 (t, J=7.3 Hz, 3H) 1.22-1.77 (m, 12H) 2.04-2.21 (m, 2H) 2.52-2.65 (m, 2H) 2.87-2.98 (m, 2H) 3.38-3.51 (m, 1H) 3.70-3.78 (m, 1H) 3.87-3.99 (m, 4H) 4.84-4.97 (m, 1H) 7.18-7.24 (m, 2H) 7.28-7.34 (m, 2H) 7.47-7.59 (m, 2H) 7.62-7.74 (m, 2H) 8.18 (s, 1H) 12.38 (s, 1H)

EXAMPLE 218

4-{trans-4-[(2-oxocyclopentyl)oxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

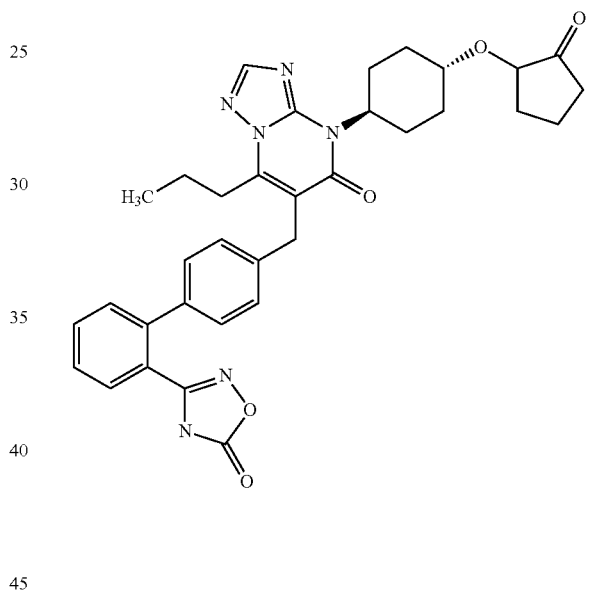

A mixture of 4-(trans-4-{[(1R,2S)-2-hydroxycyclopentyl]oxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.15 g), Dess-Martin reagent (0.2 g) and acetonitrile (10 mL) was stirred at room temperature for 2 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as colorless crystals (0.09 g, 62%).

$^1$H NMR (300 MHz, DMSO-$d_6$) δ0.93 (t, J=7.3 Hz, 3H) 1.20-1.40 (m, 2H) 1.46-1.76 (m, 6H) 1.80-1.95 (m, 1H) 2.03-2.30 (m, 5H) 2.52-2.66 (m, 2H) 2.88-2.98 (m, 2H) 3.51-3.64 (m, 1H) 3.92-4.08 (m, 3H) 4.91 (t, J=11.9 Hz, 1H) 7.19-7.25 (m, 2H) 7.27-7.34 (m, 2H) 7.47-7.58 (m, 2H) 7.63-7.72 (m, 2H) 8.18 (s, 1H) 12.38 (s, 1H)

EXAMPLE 219

({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)acetonitrile potassium salt

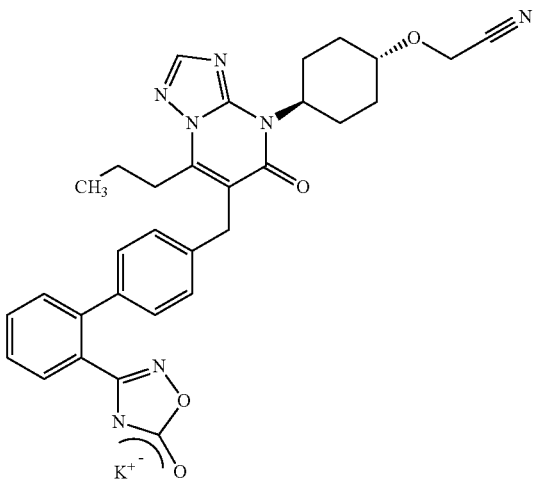 [SMILES: CCCc1c(Cc2ccc(-c3ccccc3C3=NOC(O)N3)cc2)c(=O)n([C@H]2CC[C@H](OCC#N)CC2)c2ncnn12 ; [K+]]

({trans-4-[5-Oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)acetonitrile (0.023 g) was suspended in isopropyl alcohol (5 mL), 0.5N potassium hydroxide solution (0.082 mL) was added, and the solvent was evaporated under reduced pressure. The residue was solidified with diisopropyl ether to give the title compound as a colorless solid (0.014 g, 57%).

$^1$H NMR (300 MHz, DMSO-$d_6$) δ0.96 (t, J=7.3 Hz, 3H) 1.27-1.43 (m, 2H) 1.52-1.80 (m, 4H) 2.09-2.20 (m, 2H) 2.52-2.67 (m, 2H) 2.90-3.00 (m, 2H) 3.45-3.58 (m, 1H) 3.91 (s, 2H) 4.51 (s, 2H) 4.86-4.99 (m, 1H) 7.14-7.49 (m, 8H) 8.17 (s, 1H)

EXAMPLE 220

4-{trans-4-[(1-hydroxycyclopropyl)methoxy]cyclohexyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

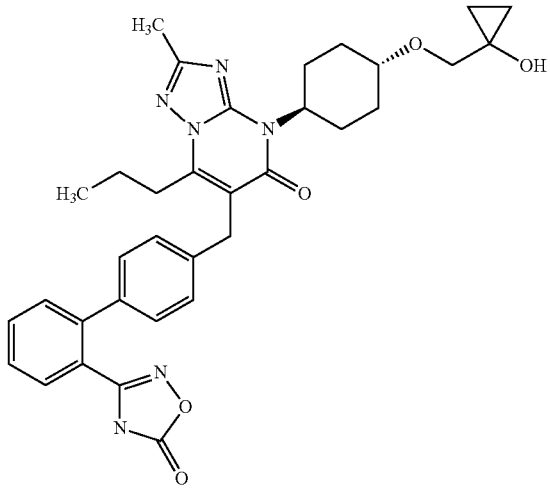 [SMILES: CCCc1c(Cc2ccc(-c3ccccc3-c3noc(=O)[nH]3)cc2)c(=O)n([C@H]2CC[C@H](OCC3(O)CC3)CC2)c2nc(C)nn12]

A mixture of hydroxylammonium chloride (0.41 g), sodium hydrogen carbonate (0.66 g) and dimethyl sulfoxide (10 mL) was stirred at 50° C. for 30 min, 4'-[(4-{trans-4-[(1-{[tert-butyl(dimethyl)silyl]oxy}cyclopropyl)methoxy]cyclohexyl}-2-methyl-5-oxo-7-propyl-4,5-dihydro[1,2,4]triazolo[1,5-a]pyrimidin-6-yl)methyl]biphenyl-2-carbonitrile (0.26 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (5 mL). N,N'-Carbonyldiimidazole (0.076 g) and then 1,8-diazabicyclo[5.4.0]undec-7-ene (0.064 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 0.98 mL) was added, and the mixture was stirred at room temperature for 3 hr. The reaction mixture was extracted with ethyl acetate and water, and the organic layer was washed with water and then with saturated brine, and dried over anhydrous magnesium sulfate. The solvent was evaporated under reduced pressure, and the residue was solidified with diisopropyl ether to give the title compound as a colorless solid (0.084 g, 35%).

$^1$H NMR (300 MHz, DMSO-$d_6$) δ0.42-0.49 (m, 2H) 0.51-0.57 (m, 2H) 0.92 (t, J=7.3 Hz, 3H) 1.19-1.74 (m, 6H) 2.06-2.17 (m, 2H) 2.35 (s, 3H) 2.52-2.65 (m, 2H) 2.84-2.92 (m, 2H) 3.35-3.42 (m, 1H) 3.44 (s, 2H) 3.93 (s, 2H) 4.79-4.93 (m, 1H) 5.28 (s, 1H) 7.19-7.24 (m, 2H) 7.26-7.31 (m, 2H) 7.52 (dd, J=16.6, 7.5 Hz, 2H) 7.61-7.71 (m, 2H) 12.39 (br. s., 1H)

EXAMPLE 221

4-[trans-4-(2-hydroxypropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

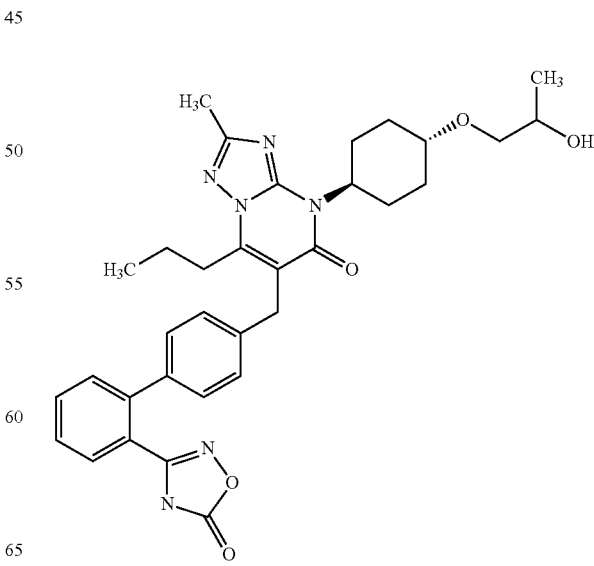

A mixture of hydroxylammonium chloride (0.42 g), sodium hydrogen carbonate (0.68 g) and dimethyl sulfoxide (10 mL) was stirred at 50° C. for 30 min, 4'-({4-[trans-4-(2-{[tert-butyl(dimethyl)silyl]oxy}propoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.27 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.079 g) and then 1,8-diazabicyclo[5.4.0]undec-7-ene (0.067 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 1 mL) was added, and the mixture was stirred at room temperature for 3 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was solidified with diisopropyl ether to give the title compound as a colorless solid (0.13 g, 54%).

$^1$H NMR (300 MHz, DMSO-$d_6$) δ0.92 (t, J=7.3 Hz, 3H) 1.03 (d, J=6.4 Hz, 3H) 1.18-1.34 (m, 2H), 1.46-1.73 (m, 4H) 2.04-2.15 (m, 2H) 2.35 (s, 3H) 2.51-2.64 (m, 2H) 2.83-2.92 (m, 2H) 3.19-3.37 (m, 3H) 3.62-3.75 (m, 1H) 3.93 (s, 2H) 4.50 (d, J=4.7 Hz, 1H) 4.79-4.93 (m, 1H) 7.18-7.24 (m, 2H) 7.26-7.32 (m, 2H) 7.47-7.58 (m, 2H) 7.62-7.72 (m, 2H) 12.36 (s, 1H)

EXAMPLE 222

4-[trans-4-(2-hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

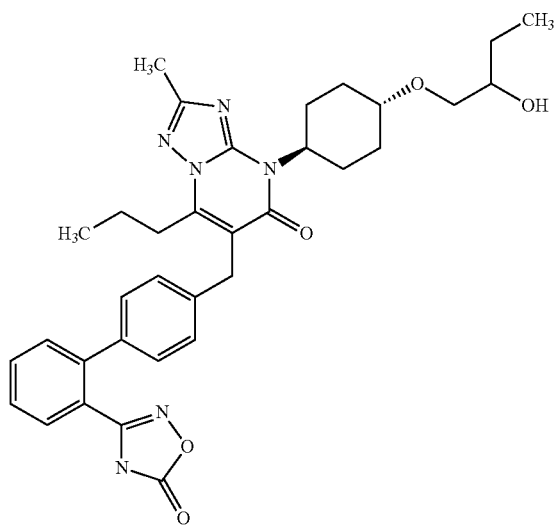 [SMILES: CCCc1c(Cc2ccc(-c3ccccc3-c3noc(=O)[nH]3)cc2)c(=O)n([C@H]2CC[C@H](OCC(O)CC)CC2)c2nc(C)nn12]

A mixture of hydroxylammonium chloride (0.46 g), sodium hydrogen carbonate (0.74 g) and dimethyl sulfoxide (10 mL) was stirred at 50° C. for 30 min, 4'-({4-[trans-4-(2-{[tert-butyl(dimethyl)silyl]oxy}butoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.29 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (10 mL). N,N'-Carbonyldiimidazole (0.086) and then 1,8-diazabicyclo[5.4.0]undec-7-ene (0.073 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (10 mL). Tetrabutylammonium fluoride (1 M tetrahydrofuran solution, 1.1 mL) was added, and the mixture was stirred at room temperature for 3 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was solidified with diisopropyl ether to give the title compound as a colorless solid (0.12 g, 45%).

$^1$H NMR (300 MHz, DMSO-$d_6$) δ0.81-0.97 (m, 8H) 1.17-1.58 (m, 6H) 1.63-1.73 (m, 2H) 2.05-2.15 (m, 2H) 2.35 (s, 3H) 2.51-2.66 (m, 2H) 2.83-2.93 (m, 2H) 3.25-3.48 (m, 2H) 3.93 (s, 2H) 4.44 (d, J=5.1 Hz, 1H) 4.86 (t, J=12.3 Hz, 1H) 7.18-7.24 (m, 2H) 7.26-7.31 (m, 2H) 7.46-7.58 (m, 2H) 7.61-7.71 (m, 2H) 12.36 (s, 1H)

EXAMPLE 223

4-[trans-4-(2-hydroxypropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

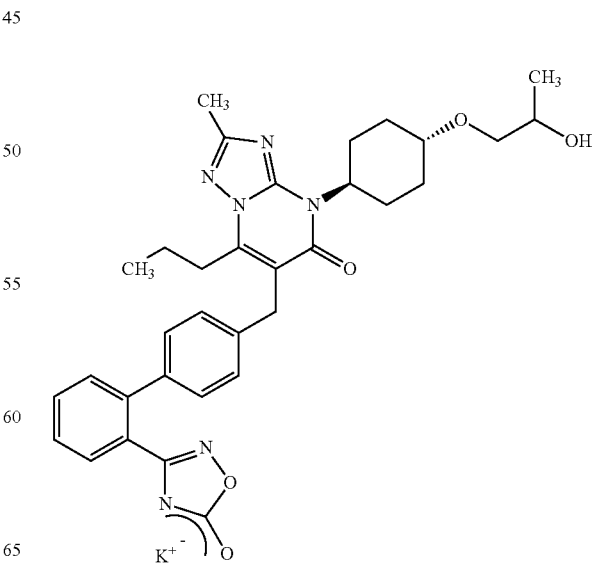

4-[trans-4-(2-Hydroxypropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.11 g) was suspended in isopropyl alcohol (5 mL), 1N potassium hydroxide solution (0.18 mL) was added, and the solvent was evaporated under reduced pressure. The residue was solidified with diisopropyl ether to give the title compound as a colorless solid (0.097 g, 87%).

$^1$H NMR (300 MHz, DMSO-$d_6$) δ0.95 (t, J=7.3 Hz, 3H) 1.03-1.05 (m, 3H) 1.18-1.37 (m, 2H) 1.50-1.75 (m, 4H) 2.04-2.17 (m, 2H) 2.35 (s, 3H) 2.52-2.63 (m, 2H) 2.84-2.95 (m, 2H), 3.19-3.36 (m, 3H) 3.63-3.82 (m, 1H) 3.88 (s, 2H) 4.28-4.56 (m, 1H) 4.80-4.92 (m, 1H) 7.11-7.50 (m, 7H)

EXAMPLE 224

4-[trans-4-(2-hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

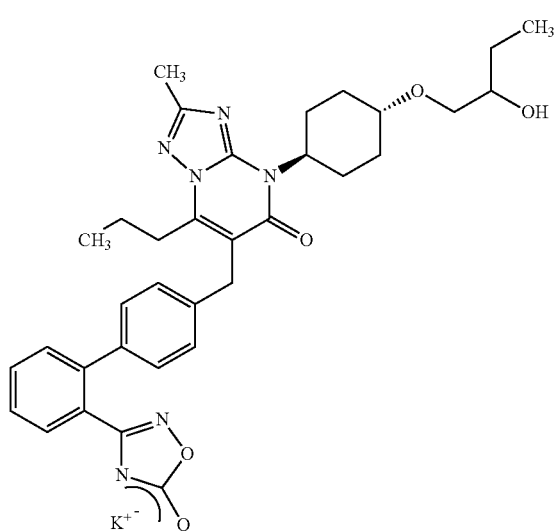 [SMILES: CCCc1c(Cc2ccc(-c3ccccc3C3=NOC(O)N3)cc2)c(=O)n([C@H]2CC[C@H](OCC(O)CC)CC2)c2nc(C)nn12 ; [K+]]

4-[trans-4-(2-Hydroxybutoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.094 g) was suspended in isopropyl alcohol (5 mL), 1N potassium hydroxide solution (0.15 mL) was added, and the solvent was evaporated under reduced pressure. The residue was solidified with diisopropyl ether to give the title compound as a colorless solid (0.089 g, 89%).

$^1$H NMR (300 MHz, DMSO-$d_6$) δ0.87 (t, J=7.3 Hz, 3H) 0.95 (t, J=7.3 Hz, 3H) 1.16-1.74 (m, 8H) 2.04-2.16 (m, 2H) 2.35 (s, 3H) 2.51-2.64 (m, 2H) 2.85-2.94 (m, 2H) 3.24-3.37 (m, 1H) 3.38-3.48 (m, 1H) 3.88 (s, 2H) 4.31-4.49 (m, 1H) 4.78-4.94 (m, 1H) 7.12-7.49 (m, 8H)

EXAMPLE 225

4-[trans-4-(2-ethyl-2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

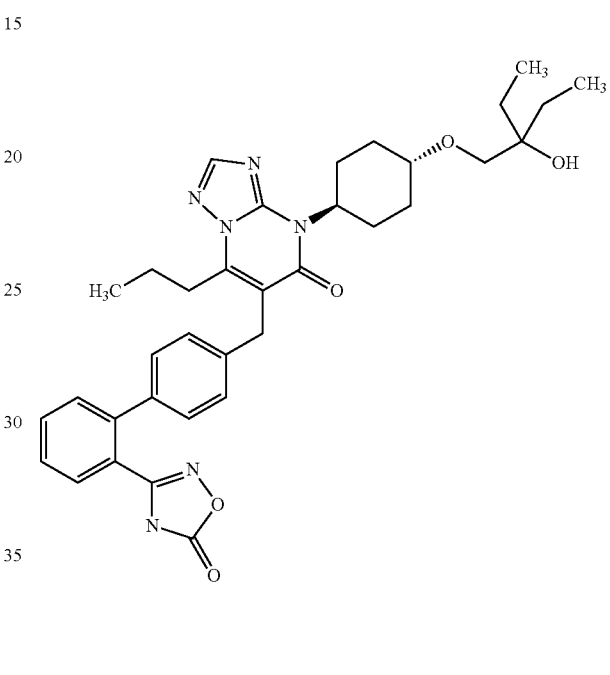

A mixture of hydroxylammonium chloride (0.46 g), sodium hydrogen carbonate (0.74 g) and dimethyl sulfoxide (15 mL) was stirred at 40° C. for 30 min, 4'-({4-[trans-4-(2-ethyl-2-hydroxybutoxy)cyclohexyl]-5-oxo-7-propyl-4,5-dihydro[1,2,4]triazolo[1,5-a]pyrimidin-6-yl}methyl)biphenyl-2-carbonitrile (0.25 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.086 g) and then 1,8-diazabicyclo[5.4.0]undec-7-ene (0.073 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.18 g, 65%).

$^1$H NMR (300 MHz, DMSO-$d_6$) δ0.80 (t, J=7.5 Hz, 6H) 0.92 (t, J=7.5 Hz, 3H) 1.17-1.31 (m, 2H) 1.38 (q, J=7.5 Hz, 4H) 1.46-1.74 (m, 4H) 2.05-2.15 (m, 2H) 2.52-2.65 (m, 2H) 2.89-2.98 (m, 2H) 3.20-3.31 (m, 3H) 3.90 (s, 1H) 3.96 (s, 2H)

4.91 (t, J=11.3 Hz, 1H) 7.19-7.25 (m, 2H) 7.27-7.35 (m, 2H) 7.47-7.58 (m, 2H) 7.62-7.72 (m, 2H) 8.18 (s, 1H) 12.38 (s, 1H)

EXAMPLE 226

1-[({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)methyl]cyclobutanecarboxamide

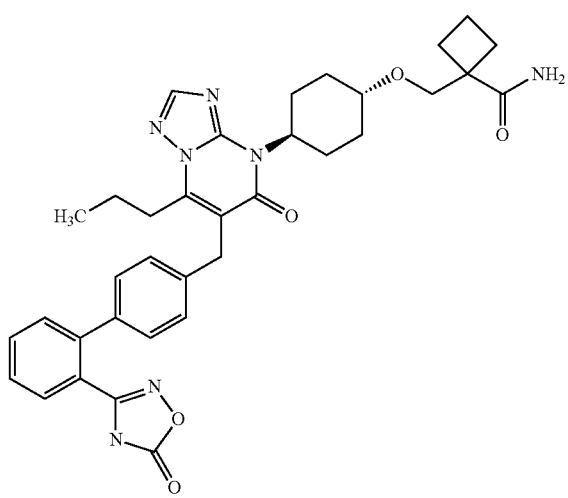 [SMILES: CCCc1c(Cc2ccc(-c3ccccc3-c3noc(=O)[nH]3)cc2)c(=O)n([C@H]2CC[C@H](OCC3(C(N)=O)CCC3)CC2)c2ncnn12]

A mixture of hydroxylammonium chloride (0.66 g), sodium hydrogen carbonate (1.1 g) and dimethyl sulfoxide (15 mL) was stirred at 40° C. for 30 min, 1-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]methyl}cyclobutanecarboxamide (0.37 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.26 g, 64%).

$^1$H NMR (300 MHz, DMSO-$d_6$) δ0.92 (t, J=7.3 Hz, 3H) 1.21-1.90 (m, 10H) 2.06-2.27 (m, 4H) 2.51-2.67 (m, 2H) 2.88-2.97 (m, 2H) 3.27-3.38 (m, 1H) 3.64 (s, 2H) 3.96 (s, 2H) 4.91 (t, J=12.1 Hz, 1H) 6.80 (s, 1H) 6.93 (s, 1H) 7.19-7.24 (m, 2H) 7.28-7.33 (m, 2H) 7.47-7.58 (m, 2H) 7.62-7.72 (m, 2H) 8.18 (s, 1H) 12.38 (s, 1H)

EXAMPLE 227

1-[({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)methyl]cyclobutanecarbonitrile

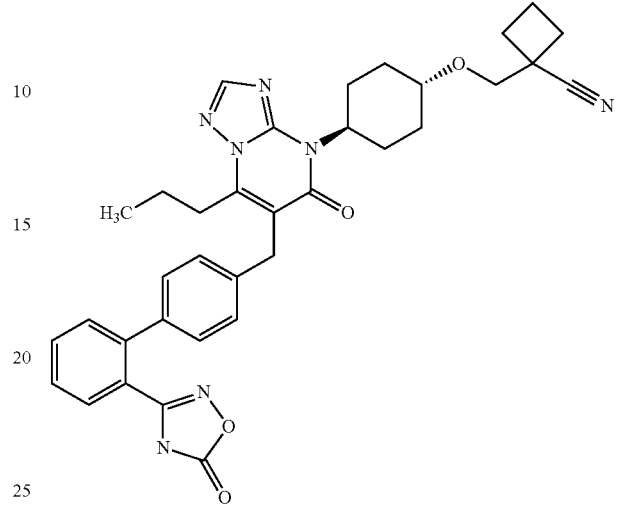

To a solution (10 mL) of 1-[({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)methyl]cyclobutanecarboxamide (0.22 g) and pyridine (0.11 mL) in tetrahydrofuran was added trifluoroacetic acid anhydride (0.093 mL) at 0° C., and the mixture was stirred for 30 min. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.15 g, 69%).

$^1$H NMR (300 MHz, DMSO-$d_6$) δ0.93 (t, J=7.3 Hz, 3H) 1.26-1.42 (m, 2H) 1.46-1.77 (m, 4H) 1.97-2.19 (m, 6H) 2.30-2.44 (m, 2H) 2.52-2.68 (m, 2H) 2.89-2.97 (m, 2H) 3.37-3.50 (m, 1H) 3.69 (s, 2H) 3.96 (s, 2H) 4.93 (t, J=12.2 Hz, 1H) 7.20-7.24 (m, 2H) 7.28-7.34 (m, 2H) 7.47-7.58 (m, 2H) 7.62-7.71 (m, 2H) 8.18 (s, 1H) 12.38 (br. s., 1H)

EXAMPLE 228

4-(trans-4-{[1-(hydroxymethyl)cyclobutyl]methoxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

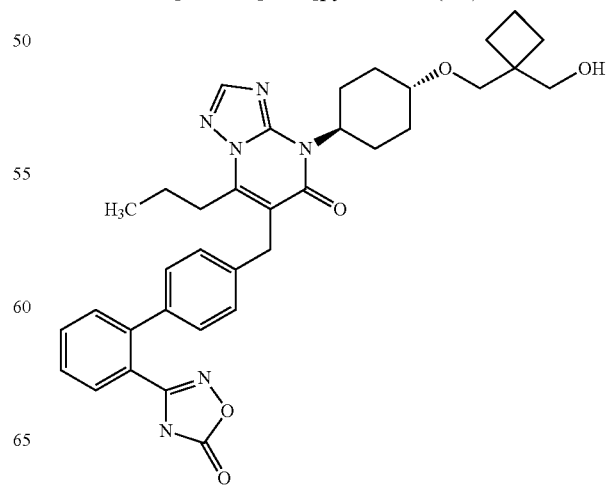

A mixture of hydroxylammonium chloride (0.48 g), sodium hydrogen carbonate (0.77 g) and dimethyl sulfoxide (10 mL) was stirred at 50° C. for 30 min, 4'-{[4-(trans-4-{[1-({[tert-butyl(dimethyl)silyl]oxy}methyl)cyclobutyl]methoxy}cyclohexyl)-5-oxo-7-propyl-4,5-dihydro[1,2,4]triazolo[1,5-a]pyrimidin-6-yl]methyl}biphenyl-2-carbonitrile (0.31 g) was added, and the mixture was stirred at 90° C. for 20 hr. After allowing to cool to room temperature, ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography, and dissolved in tetrahydrofuran (5 mL). N,N'-Carbonyldiimidazole (0.089 g) and then 1,8-diazabicyclo[5.4.0]undec-7-ene (0.075 mL) were added, and the mixture was stirred at room temperature for 2 hr. The reaction mixture was diluted with ethyl acetate, washed with 1 N hydrochloric acid and then with saturated brine, and dried over anhydrous magnesium sulfate. The solvent was evaporated under reduced pressure, and the residue was dissolved in tetrahydrofuran (5 mL). Tetrabutylammonium fluoride (1 M tetrahydrofuran solution, 1.1 mL) was added and the mixture was stirred at 70° C. for 3 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was purified by silica gel column chromatography to give the title compound as a colorless amorphous solid (0.22 g, 76%).

$^1$H NMR (300 MHz, DMSO-$d_6$) δ0.93 (t, J=7.3 Hz, 3H) 1.21-1.37 (m, 2H) 1.46-1.84 (m, 10H) 2.05-2.17 (m, 2H) 2.52-2.66 (m, 2H) 2.88-2.97 (m, 2H) 3.24-3.36 (m, 3H) 3.39 (s, 2H) 3.96 (s, 2H) 4.45 (t, J=5.3 Hz, 1H) 4.84-4.97 (m, 1H) 7.18-7.25 (m, 2H) 7.28-7.34 (m, 2H) 7.46-7.58 (m, 2H) 7.62-7.73 (m, 2H) 8.18 (s, 1H) 12.38 (br. s., 1H)

EXAMPLE 229

4-[trans-4-(2-ethyl-2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

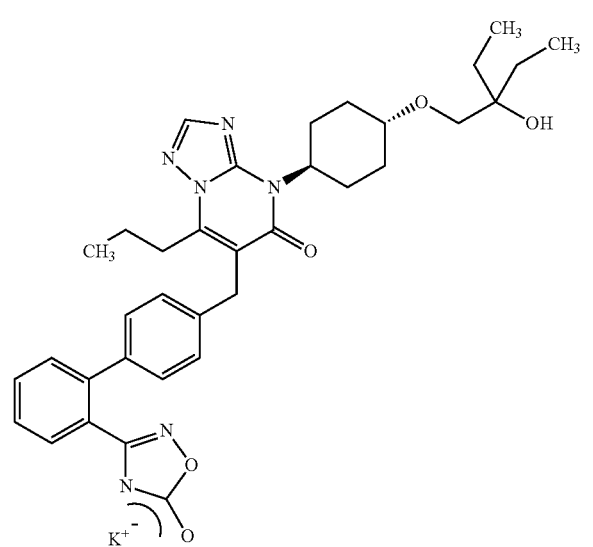

4-[trans-4-(2-Ethyl-2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.15 g) was suspended in isopropyl alcohol (5 mL), 1N potassium hydroxide solution (0.24 mL) was added, and the solvent was evaporated under reduced pressure. The residue was solidified with diisopropyl ether to give the title compound as a colorless solid (0.12 g, 74%).

$^1$H NMR (300 MHz, DMSO-$d_6$) δ0.80 (t, J=7.5 Hz, 6H) 0.96 (t, J=7.6 Hz, 3H) 1.18-1.44 (m, 6H) 1.52-1.76 (m 4H) 2.03-2.16 (m, 2H) 2.52-2.65 (m, 2H) 2.89-3.00 (m, 2H) 3.19-3.31 (m, 3H) 3.91 (s, 3H) 4.91 (t, J=12.3 Hz, 1H) 7.13-7.49 (m, 8H) 8.17 (s, 1H)

EXAMPLE 230

1-[({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)methyl]cyclobutanecarbonitrile potassium salt

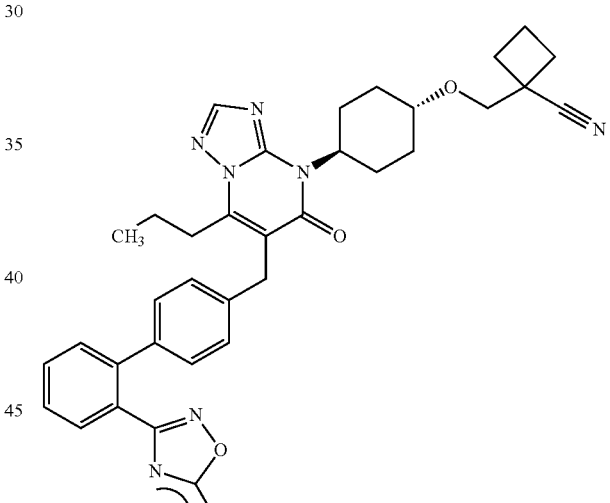

1-[({trans-4-[5-Oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)methyl]cyclobutanecarbonitrile (0.12 g) was suspended in isopropyl alcohol (5 mL), 1N potassium hydroxide solution (0.19 mL) was added, and the solvent was evaporated under reduced pressure. The residue was solidified with diisopropyl ether to give the title compound as a colorless solid (0.12 g, 74%).

$^1$H NMR (300 MHz, DMSO-$d_6$) δ0.96 (t, J=7.4 Hz, 3H) 1.26-1.42 (m, 2H) 1.52-1.78 (m, 4H) 1.96-2.19 (m, 6H) 2.31-2.44 (m, 2H) 2.52-2.68 (m, 2H) 2.91-3.00 (m, 2H) 3.37-3.49

(m, 1H) 3.69 (s, 2H) 3.91 (s, 2H) 4.92 (t, J=12.3 Hz, 1H) 7.14-7.50 (m, 8H) 8.16 (s, 1H)

EXAMPLE 231

6-{[2-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one

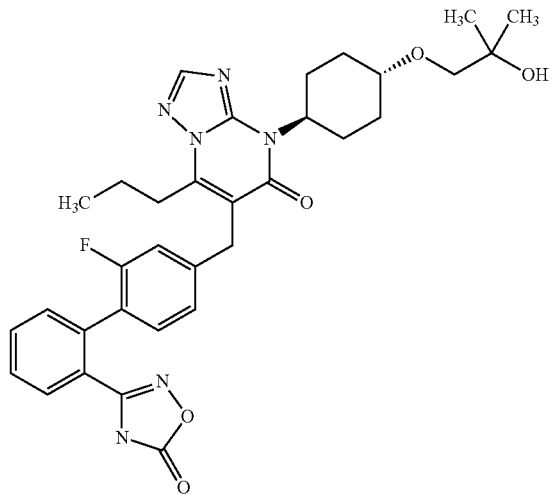 [SMILES: CCCc1c(Cc2ccc(-c3ccccc3-c3noc(=O)[nH]3)c(F)c2)c(=O)n([C@H]2CC[C@H](OCC(C)(C)O)CC2)c2ncnn12]

A mixture of hydroxylammonium chloride (0.47 g), sodium hydrogen carbonate (0.75 g) and dimethyl sulfoxide (15 mL) was stirred at 40° C. for 30 min, 2'-fluoro-4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (0.25 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.087 g) and then 1,8-diazabicyclo[5.4.0]undec-7-ene (0.074 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.14 g, 49%).

$^1$H NMR (300 MHz, DMSO-$d_6$) δ0.93 (t, J=7.3 Hz, 3H) 1.07 (s, 6H) 1.20-1.37 (m, 2H) 1.48-1.76 (m, 4H) 2.05-2.16 (m, 2H) 2.52-2.66 (m, 2H) 2.89-2.98 (m, 2H) 3.20 (s, 2H) 3.26-3.37 (m, 1H) 3.97 (s, 2H) 4.23 (s, 1H) 4.91 (t, J=12.2 Hz, 1H) 7.11-7.18 (m, 2H) 7.25 (t, J=8.0 Hz, 1H) 7.45-7.51 (m, 1H) 7.57-7.65 (m, 1H) 7.67-7.74 (m, 2H) 8.18 (s, 1H) 12.59 (br. s., 1H)

EXAMPLE 232

7-butyl-4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

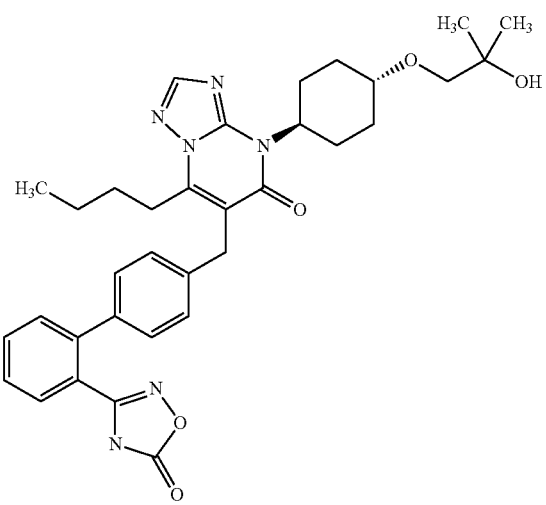 [SMILES: CCCCc1c(Cc2ccc(-c3ccccc3-c3noc(=O)[nH]3)cc2)c(=O)n([C@H]2CC[C@H](OCC(C)(C)O)CC2)c2ncnn12]

A mixture of hydroxylammonium chloride (0.41 g), sodium hydrogen carbonate (0.67 g) and dimethyl sulfoxide (15 mL) was stirred at 40° C. for 30 min, 4'-({7-butyl-4-[trans-4-(2-hydroxy-2-methylpropoxy)cyclohexyl]-5-oxo-4,5-dihydro[1,2,4]triazolo[1,5-a]pyrimidin-6-yl}methyl)biphenyl-2-carbonitrile (0.22 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.077 g) and then 1,8-diazabicyclo[5.4.0] undec-7-ene (0.065 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.15 g, 55%).

$^1$H NMR (300 MHz, DMSO-$d_6$) δ0.84 (t, J=7.2 Hz, 3H) 1.07 (s, 6H) 1.21-1.56 (m, 6H) 1.64-1.76 (m, 2H) 2.06-2.16 (m, 2H), 2.52-2.65 (m, 2H) 2.89-3.00 (m, 2H) 3.20 (s, 2H) 3.26-3.36 (m, 1H) 3.95 (s, 2H) 4.23 (s, 1H) 4.85-4.98 (m, 1H)

7.19-7.25 (m, 2H) 7.26-7.32 (m, 2H) 7.46-7.58 (m, 2H) 7.62-7.71 (m, 2H) 8.18 (s, 1H) 12.39 (br. s., 1H)

EXAMPLE 233

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one

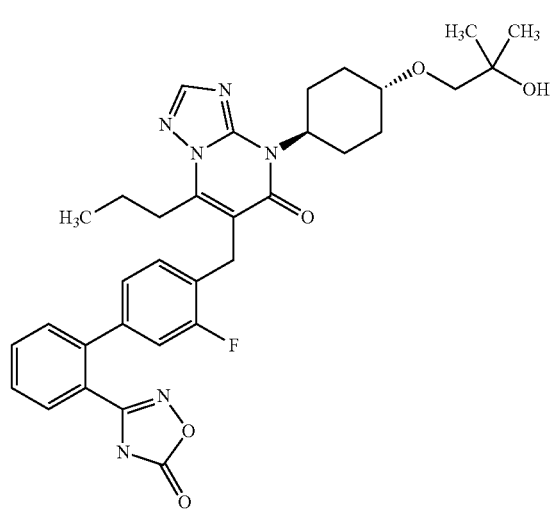 [SMILES: CCCc1c(Cc2ccc(-c3ccccc3-c3noc(=O)[nH]3)cc2F)c(=O)n([C@H]2CC[C@H](OCC(C)(C)O)CC2)c2ncnn12]

A mixture of hydroxylammonium chloride (0.34 g), sodium hydrogen carbonate (0.54 g) and dimethyl sulfoxide (10 mL) was stirred at 40° C. for 30 min, 3'-fluoro-4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (0.18 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.063 g) and then 1,8-diazabicyclo[5.4.0]undec-7-ene (0.053 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.13 g, 64%).

$^1$H NMR (300 MHz, DMSO-$d_6$) δ0.93 (t, J=7.3 Hz, 3H) 1.07 (s, 6H) 1.19-1.35 (m, 2H) 1.49-1.73 (m, 4H) 2.05-2.16 (m, 2H) 2.52-2.66 (m, 2H) 2.88-2.99 (m, 2H) 3.20 (s, 2H) 3.25-3.36 (m, 1H) 3.94 (s, 2H) 4.22 (s, 1H) 4.89 (t, J=12.2 Hz, 1H) 6.99 (dd, J=7.9, 1.7 Hz, 1H) 7.12-7.29 (m, 2H) 7.51-7.62 (m, 2H) 7.64-7.75 (m, 2H) 8.19 (s, 1H) 12.45 (br. s., 1H)

EXAMPLE 234

4-{trans-4-[2-(methylsulfanyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

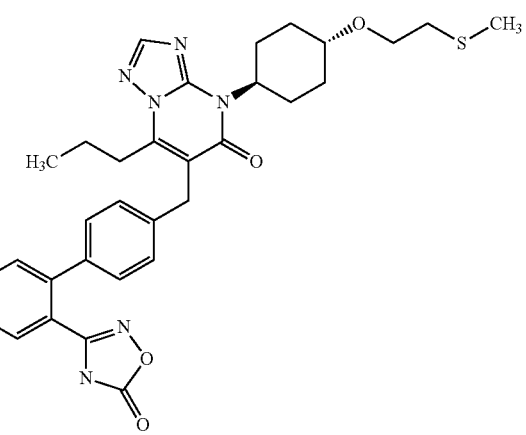

A mixture of hydroxylammonium chloride (0.39 g), sodium hydrogen carbonate (0.62 g) and dimethyl sulfoxide (10 mL) was stirred at 40° C. for 30 min, 4'-[(4-{trans-4-[2-(methylsulfanyl)ethoxy]cyclohexyl}-5-oxo-7-propyl-4,5-dihydro[1,2,4]triazolo[1,5-a]pyrimidin-6-yl)methyl]biphenyl-2-carbonitrile (0.2 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.072 g) and then 1,8-diazabicyclo[5.4.0]undec-7-ene (0.061 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.13 g, 59%).

$^1$H NMR (300 MHz, DMSO-$d_6$) δ0.93 (t, J=7.3 Hz, 3H) 1.20-1.37 (m, 2H) 1.45-1.76 (m, 4H) 2.05-2.16 (m, 5H) 2.52-2.65 (m, 4H) 2.88-2.99 (m, 2H) 3.32-3.41 (m, 1H) 3.61 (t, J=6.8 Hz, 2H) 3.95 (s, 2H) 4.91 (t, J=12.4 Hz, 1H) 7.18-7.25 (m, 2H) 7.26-7.34 (m, 2H) 7.47-7.58 (m, 2H) 7.61-7.72 (m, 2H) 8.18 (s, 1H) 12.38 (s, 1H)

EXAMPLE 235

4-{trans-4-[2-(methylsulfonyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

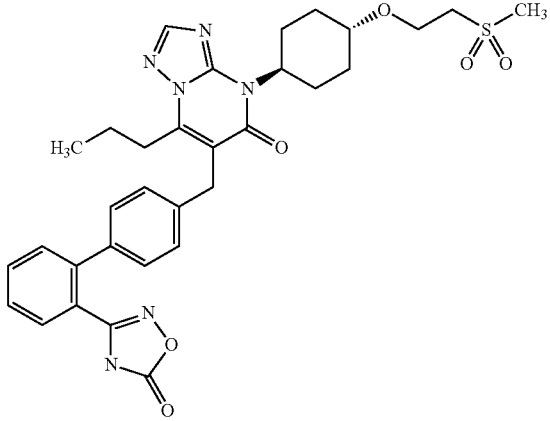 [SMILES: CCCc1c(Cc2ccc(-c3ccccc3-c3noc(=O)[nH]3)cc2)c(=O)n([C@H]2CC[C@H](OCCS(C)(=O)=O)CC2)c2ncnn12]

A mixture of 4-{trans-4-[2-(methylsulfanyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.08 g), m-chloroperbenzoic acid (0.082 g) and acetonitrile (5 mL) was stirred at room temperature for 1 hr. The reaction mixture was diluted with ethyl acetate, washed with saturated aqueous sodium hydrogen carbonate and then with saturated brine, and dried over anhydrous magnesium sulfate. The solvent was evaporated under reduced pressure, and the residue was purified by silica gel column chromatography to give the title compound as a colorless amorphous solid (0.047 g, 56%).

$^1$H NMR (300 MHz, DMSO-$d_6$) δ0.92 (t, J=7.3 Hz, 3H) 1.22-1.40 (m, 2H) 1.46-1.61 (m, 2H) 1.66-1.76 (m, 2H) 2.07-2.18 (m, 2H) 2.52-2.68 (m, 2H) 2.88-2.97 (m, 2H) 2.99 (s, 3H) 3.32-3.45 (m, 3H) 3.82 (t, J=5.7 Hz, 2H) 3.96 (s, 2H) 4.92 (t, J=12.4 Hz, 1H) 7.18-7.73 (m, 2H) 7.28-7.34 (m, 2H) 7.46-7.58 (m, 2H) 7.62-7.73 (m, 2H) 8.18 (s, 1H) 12.38 (s, 1H)

EXAMPLE 236

7-butyl-4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

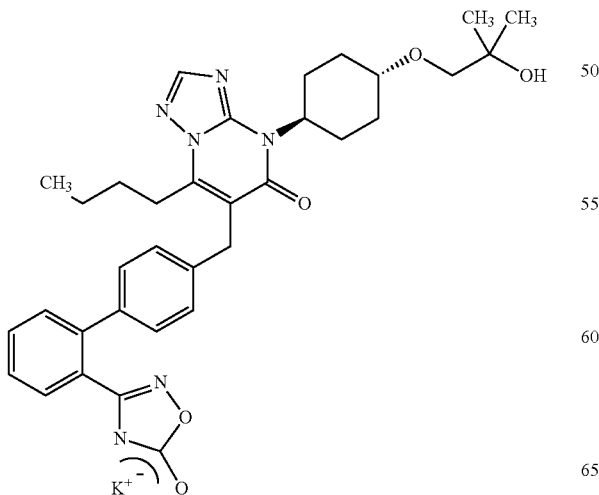

7-Butyl-4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.096 g) was suspended in isopropyl alcohol (3 mL), 1N potassium hydroxide solution (0.16 mL) was added, and the solvent was evaporated under reduced pressure. The residue was solidified with diisopropyl ether to give the title compound as a colorless solid (0.071 g, 70%).

$^1$H NMR (300 MHz, DMSO-$d_6$) δ0.86 (t, J=7.3 Hz, 3H) 1.07 (s, 6H) 1.20-1.58 (m, 6H) 1.65-1.79 (m, 2H) 2.05-2.16 (m, 2H) 2.51-2.66 (m, 2H) 2.91-3.01 (m, 2H) 3.20 (s, 2H) 3.25-3.32 (m, 1H) 3.91 (s, 2H) 4.25 (br. s., 1H) 4.92 (t, J=12.3 Hz, 1H) 7.13-7.50 (m, 8H) 8.17 (s, 1H)

EXAMPLE 237

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one potassium salt

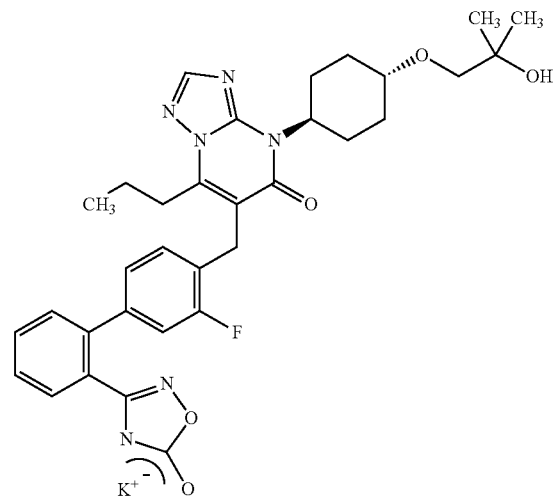

6-{[3-Fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one (0.091 g) was suspended in isopropyl alcohol (3 mL), 1N potassium hydroxide solution (0.15 mL) was added, and the solvent was evaporated under reduced pressure. The residue was solidified with diisopropyl ether to give the title compound as a colorless solid (0.075 g, 78%).

$^1$H NMR (300 MHz, DMSO-$d_6$) δ0.95 (t, J=7.3 Hz, 3H) 1.07 (s, 6H) 1.20-1.37 (m, 2H) 1.52-1.79 (m, 4H) 2.03-2.16 (m, 2H) 2.52-2.65 (m, 2H) 2.89-2.99 (m, 2H) 3.20 (s, 2H) 3.25-3.31 (m, 1H) 3.90 (s, 2H) 4.24 (s, 1H) 4.83-4.97 (m, 1H) 6.79-7.17 (m, 3H) 7.28-7.53 (m, 4H) 8.18 (s, 1H)

EXAMPLE 238

6-{[2-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one potassium salt

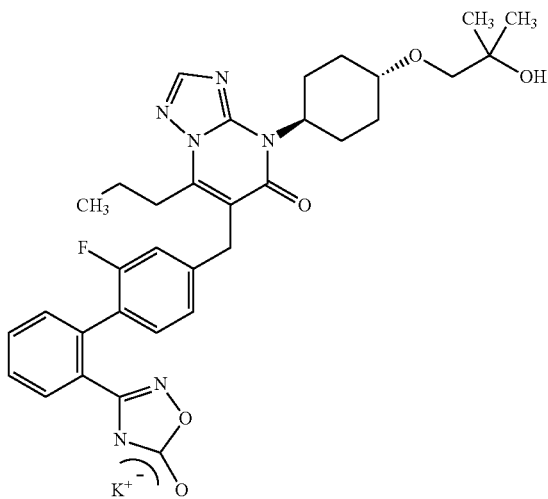

6-{[2-Fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propyl[1,2,4]triazolo[1,5-a]pyrimidin-5(4H)-one (0.091 g) was suspended in isopropyl alcohol (3 mL), 1N potassium hydroxide solution (0.15 mL) was added, and the solvent was evaporated under reduced pressure. The residue was solidified with diisopropyl ether to give the title compound as a colorless solid (0.075 g, 78%).

$^1$H NMR (300 MHz, DMSO-d$_6$) δ0.96 (t, J=7.3 Hz, 3H) 1.07 (s, 6H) 1.22-1.35 (m, 2H) 1.53-1.77 (m, 4H) 2.03-2.15 (m, 2H) 2.52-2.67 (m, 2H) 2.89-3.01 (m, 2H) 3.20 (s, 2H) 3.25-3.32 (m, 1H) 3.94 (s, 2H) 4.24 (s, 1H) 4.92 (t, J=12.2 Hz, 1H) 6.79-7.22 (m, 4H) 7.36-7.43 (m, 2H) 7.67-7.74 (m, 1H) 8.18 (s, 1H)

EXAMPLE 239

1,1-dimethyl-2-({trans-4-[2-methyl-5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)ethyl acetate

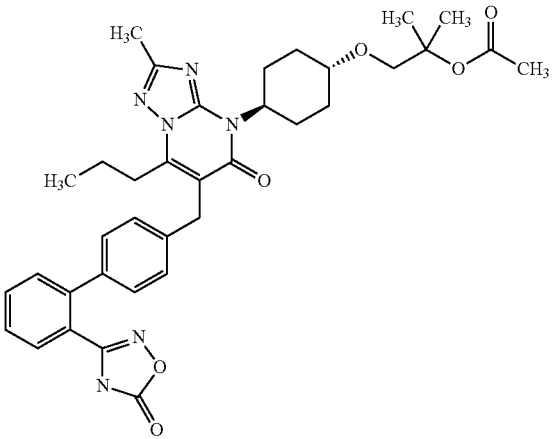 [SMILES: CCCc1c(Cc2ccc(-c3ccccc3-c3noc(=O)[nH]3)cc2)c(=O)n([C@H]2CC[C@H](OCC(C)(C)OC(C)=O)CC2)c2nc(C)nn12]

A mixture of hydroxylammonium chloride (0.18 g), sodium hydrogen carbonate (0.28 g) and dimethyl sulfoxide (10 mL) was stirred at 40° C. for 30 min, 2-[(trans-4-{6-[(2'-cyanobiphenyl-4-yl)methyl]-2-methyl-5-oxo-7-propyl[1,2,4]triazolo[1,5-a]pyrimidin-4(5H)-yl}cyclohexyl)oxy]-1,1-dimethylethyl acetate (0.1 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.033 g) and then 1,8-diazabicyclo[5.4.0]undec-7-ene (0.028 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.064 g, 58%).

$^1$H NMR (300 MHz, DMSO-d$_6$) δ0.92 (t, J=7.4 Hz, 3H) 1.20-1.39 (m, 8H) 1.44-1.73 (m, 4H) 1.93 (s, 3H) 2.03-2.14 (m, 2H) 2.35 (s, 3H) 2.52-2.65 (m, 2H) 2.83-2.93 (m, 2H) 3.24-3.31 (m, 1H) 3.57 (s, 2H) 3.93 (s, 2H) 4.87 (t, J=12.1 Hz, 1H) 7.18-7.32 (m, 4H) 7.46-7.59 (m, 2H) 7.60-7.72 (m, 2H) 12.37 (br. s., 1H)

EXAMPLE 240

7-butyl-4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}[1,2,4]triazolo[1,5-a]pyrimidin-5(4H)-one

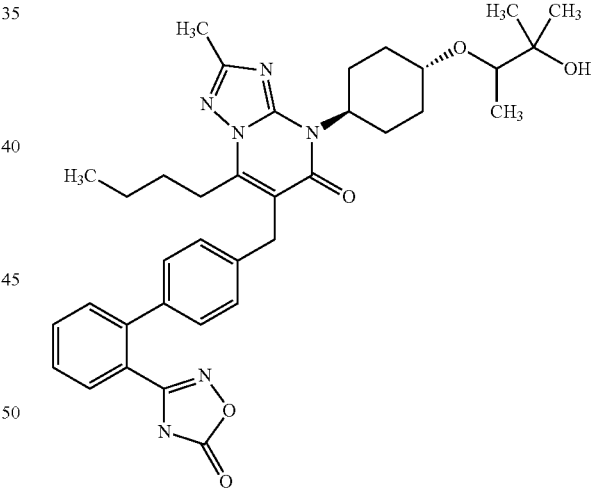

A mixture of hydroxylammonium chloride (0.59 g), sodium hydrogen carbonate (0.95 g) and dimethyl sulfoxide (10 mL) was stirred at 40° C. for 30 min, 4'-({7-butyl-4-[trans-4-(2-hydroxy-1,2-dimethylpropoxy)cyclohexyl]-2-methyl-5-oxo-4,5-dihydro[1,2,4]triazolo[1,5-a]pyrimidin-6-yl}methyl)biphenyl-2-carbonitrile (0.33 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.11 g) and then 1,8-diazabicyclo[5.4.0]undec-7-ene (0.093 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.16 g, 43%).

$^1$H NMR (300 MHz, DMSO-$d_6$) δ0.79-0.87 (m, 3H) 0.97-1.10 (m, 9H) 1.21-1.52 (m, 6H) 1.61-1.72 (m, 2H) 1.99-2.14 (m, 2H) 2.35 (s, 3H) 2.52-2.65 (m, 2H) 2.85-2.94 (m, 2H) 3.21-3.42 (m, 6H) 3.92 (s, 2H) 4.06 (s, 1H) 4.80-4.92 (m, 1H) 7.18-7.31 (m, 4H) 7.46-7.58 (m, 2H) 7.62-7.72 (m, 2H) 12.39 (br. s., 1H)

EXAMPLE 241

6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-2-methyl-7-propyl[1,2,4]triazolo[1,5-a]pyrimidin-5(4H)-one

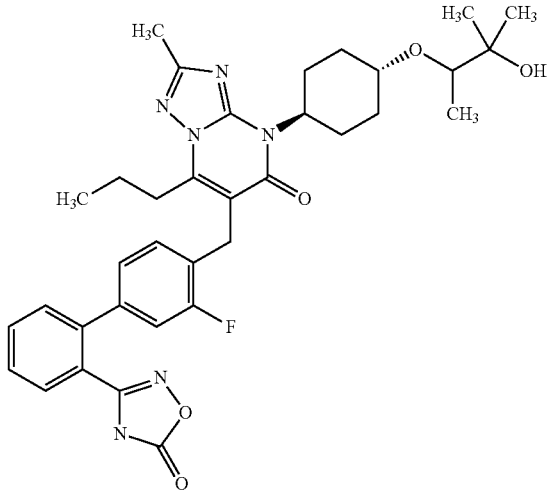 [SMILES: CCCc1c(Cc2ccc(-c3ccccc3-c3noc(=O)[nH]3)cc2F)c(=O)n([C@H]2CC[C@H](OC(C)C(C)(C)O)CC2)c2nc(C)nn12]

A mixture of hydroxylammonium chloride (0.48 g), sodium hydrogen carbonate (0.77 g) and dimethyl sulfoxide (10 mL) was stirred at 40° C. for 30 min, 3'-fluoro-4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.27 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.09 g) and then 1,8-diazabicyclo[5.4.0]undec-7-ene (0.076 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.19 g, 64%).

$^1$H NMR (300 MHz, DMSO-$d_6$) δ0.92 (t, J=7.3 Hz, 3H) 0.98-1.09 (m, 9H) 1.20-1.36 (m, 2H) 1.48-1.72 (m, 4H) 2.00-2.15 (m, 2H) 2.36 (s, 3H) 2.52-2.64 (m, 2H) 2.82-2.93 (m, 2H) 3.25 (q, J=6.2 Hz, 1H) 3.32-3.42 (m, 1H) 3.91 (s, 2H) 4.05 (s, 1H) 4.76-4.89 (m, 1H) 6.98 (dd, J=7.9, 1.7 Hz, 1H) 7.12-7.25 (m, 2H) 7.51-7.62 (m, 2H) 7.64-7.74 (m, 2H) 12.45 (br. s., 1H)

EXAMPLE 242

7-butyl-4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}[1,2,4]triazolo[1,5-a]pyrimidin-5(4H)-one potassium salt

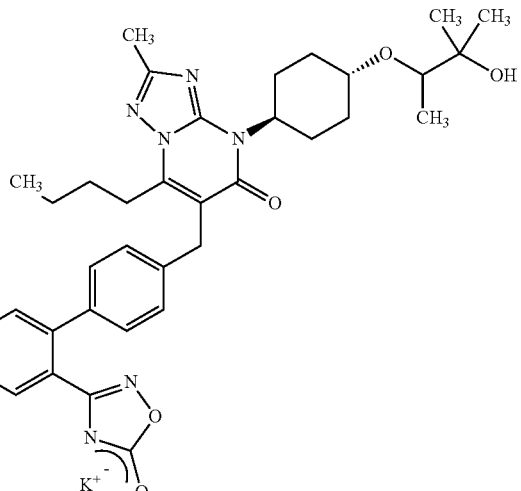

7-Butyl-4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}[1,2,4]triazolo[1,5-a]pyrimidin-5(4H)-one (0.1 g) was suspended in isopropyl alcohol (5 mL), 1N potassium hydroxide solution (0.16 mL) was added, and the solvent was evaporated under reduced pressure. The residue was solidified with diisopropyl ether to give the title compound as a colorless solid (0.075 g, 70%).

$^1$H NMR (300 MHz, DMSO-$d_6$) δ0.85 (t, J=7.3 Hz, 3H) 0.96-1.10 (m, 9H) 1.16-1.73 (m, 8H) 1.96-2.15 (m, 2H) 2.35 (s, 3H) 2.52-2.65 (m, 2H) 2.85-2.96 (m, 2H) 3.25 (q, J=6.2 Hz, 1H) 3.34-3.44 (m, 1H) 3.87 (s, 2H) 4.06 (s, 1H) 4.79-4.92 (m, 1H) 7.11-7.50 (m, 8H)

EXAMPLE 243

6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-2-methyl-7-propyl[1,2,4]triazolo[1,5-a]pyrimidin-5(4H)-one potassium salt

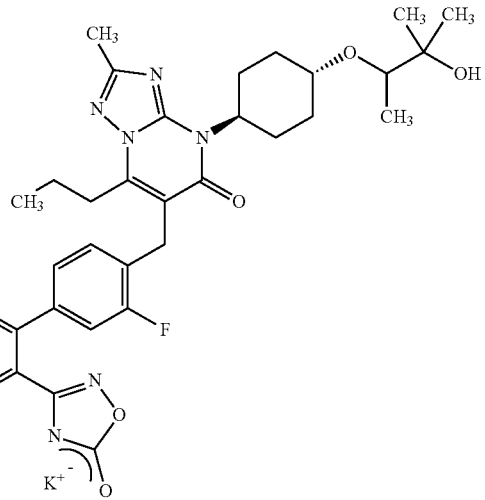

6-{[3-Fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-2-methyl-7-propyl[1,2,4]triazolo[1,5-a]pyrimidin-5(4H)-one (0.16 g) was suspended in isopropyl alcohol (5 mL), 1N potassium hydroxide solution (0.25 mL) was added, and the solvent was evaporated under reduced pressure. The residue was solidified with diisopropyl ether to give the title compound as a colorless solid (0.12 g, 69%).

$^1$H NMR (300 MHz, DMSO-$d_6$) δ0.89-1.10 (m, 12H) 1.15-1.37 (m, 2H) 1.50-1.72 (m, 4H) 1.95-2.13 (m, 2H) 2.36 (s, 3H) 2.52-2.65 (m, 2H) 2.83-2.93 (m, 2H) 3.25 (q, J=6.2 Hz, 1H) 3.34-3.43 (m, 1H) 3.87 (s, 2H) 4.06 (s, 1H) 4.84 (t, J=10.3 Hz, 1H) 6.97-7.14 (m, 3H) 7.28-7.54 (m, 4H)

EXAMPLE 244

2-({trans-4-[5-oxo-6-{[2'-(5-oxo-4,5-dihydro-1,2,4-oxadiazol-3-yl)biphenyl-4-yl]methyl}-7-propyl[1,2,4]triazolo[1,5-a]pyrimidin-4(5H)-yl]cyclohexyl}oxy)propanenitrile

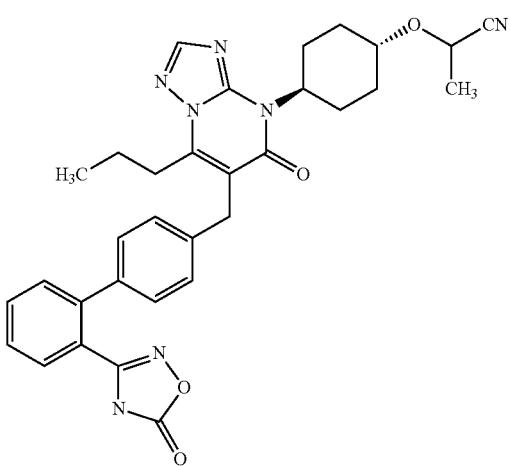 [SMILES: CCCc1c(Cc2ccc(-c3ccccc3-c3noc(=O)[nH]3)cc2)c(=O)n([C@H]2CC[C@H](OC(C)C#N)CC2)c2ncnn12]

A mixture of hydroxylammonium chloride (0.58 g), sodium hydrogen carbonate (0.93 g) and dimethyl sulfoxide (10 mL) was stirred at 40° C. for 30 min, 2-[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]propanamide (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.11 g) and then 1,8-diazabicyclo[5.4.0]undec-7-ene (0.092 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. The obtained residue was dissolved in tetrahydrofuran (10 mL), pyridine (0.18 mL) and trifluoroacetic acid anhydride (0.15 mL) were added at 0° C., and the mixture was stirred for 30 min. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.15 g, 47%).

$^1$H NMR (300 MHz, DMSO-$d_6$) δ0.93 (t, J=7.3 Hz, 3H) 1.22-1.60 (m, 7H) 1.67-1.79 (m, 2H) 2.07-2.22 (m, 2H) 2.55-2.69 (m, 2H) 2.88-2.99 (m, 2H) 3.52-3.66 (m, 1H) 3.96 (s, 2H) 4.71 (q, J=6.8 Hz, 1H) 4.85-4.99 (m, 1H) 7.19-7.25 (m, 2H) 7.28-7.34 (m, 2H) 7.47-7.58 (m, 2H) 7.61-7.72 (m, 2H) 8.19 (s, 1H) 12.38 (s, 1H)

EXAMPLE 245

6-{[3-fluoro-2'-(5-oxo-4,5-dihydro-1,2,4-oxadiazol-3-yl)biphenyl-4-yl]methyl}-4-{trans-4-[(4-hydroxy-4-methyltetrahydrofuran-3-yl)oxy]cyclohexyl}-7-propyl[1,2,4]triazolo[1,5-a]pyrimidin-5(4H)-one

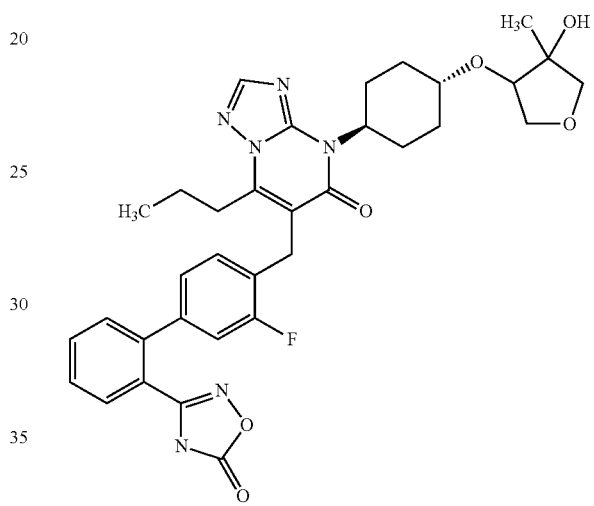

A mixture of hydroxylammonium chloride (0.13 g), sodium hydrogen carbonate (0.22 g) and dimethyl sulfoxide (10 mL) was stirred at 40° C. for 30 min, 3'-fluoro-4'-[(4-{trans-4-[(4-hydroxy-4-methyltetrahydrofuran-3-yl)oxy]cyclohexyl}-5-oxo-7-propyl-4,5-dihydro[1,2,4]triazolo[1,5-a]pyrimidin-6-yl)methyl]biphenyl-2-carbonitrile (0.077 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.025 g) and then 1,8-diazabicyclo[5.4.0]undec-7-ene (0.022 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.029 g, 34%).

$^1$H NMR (300 MHz, DMSO-$d_6$) δ0.93 (t, J=7.4 Hz, 3H) 1.10-1.75 (m, 9H) 2.01-2.25 (m, 2H) 2.52-2.67 (m, 2H) 2.87-3.00 (m, 2H) 3.41-3.56 (m, 4H) 3.71 (t, J=5.5 Hz, 1H) 3.89-

3.98 (m, 3H) 4.25 (s, 1H) 4.89 (t, J=12.1 Hz, 1H) 6.99 (dd, J=8.0, 1.9 Hz, 1H) 7.12-7.28 (m, 2H) 7.51-7.74 (m, 4H) 8.19 (s, 1H) 12.46 (br. s., 1H)

EXAMPLE 246

6-{[4'-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-2-methyl-7-propyl[1,2,4]triazolo[1,5-a]pyrimidin-5(4H)-one

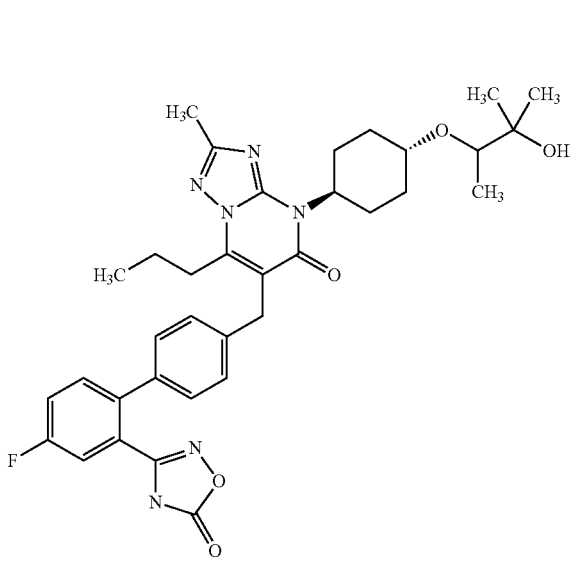 [SMILES: CCCc1c(Cc2ccc(-c3ccc(F)cc3-c3noc(=O)[nH]3)cc2)c(=O)n([C@H]2CC[C@H](OC(C)C(C)(C)O)CC2)c2nc(C)nn12]

A mixture of hydroxylammonium chloride (0.43 g), sodium hydrogen carbonate (0.69 g) and dimethyl sulfoxide (10 mL) was stirred at 40° C. for 30 min, 4-fluoro-4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.24 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.079 g) and then 1,8-diazabicyclo[5.4.0]undec-7-ene (0.067 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.15 g, 56%).

$^1$H NMR (300 MHz, DMSO-$d_6$) δ0.91 (t, J=7.2 Hz, 3H) 0.97-1.10 (m, 9H) 1.20-1.73 (m, 6H) 1.97-2.17 (m, 2H) 2.35 (s, 3H) 2.53-2.66 (m, 2H) 2.83-2.93 (m, 2H) 3.20-3.44 (m, 2H) 3.92 (s, 2H) 4.05 (s, 1H) 4.85 (t, J=11.9 Hz, 1H) 7.16-7.22 (m, 2H) 7.25-7.31 (m, 2H) 7.51-7.62 (m, 3H) 12.50 (s, 1H)

EXAMPLE 247

(+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: short)

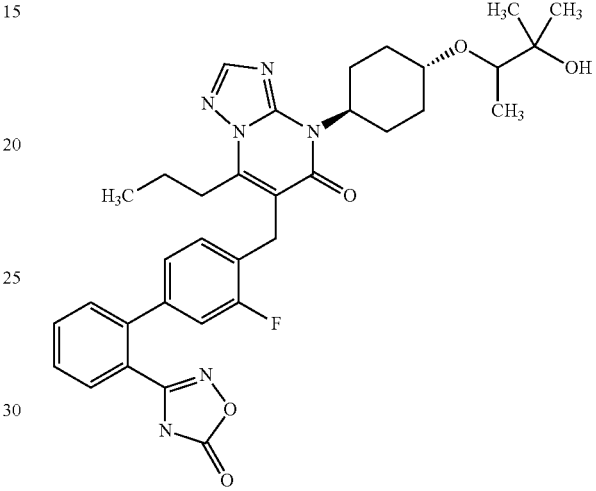

A mixture of hydroxylammonium chloride (7.5 g), sodium hydrogen carbonate (12 g) and dimethyl sulfoxide (50 mL) was stirred at 40° C. for 30 min. 3'-Fluoro-4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: short, 4 g) was added, and the mixture was stirred at 90° C. for 16 hr. The reaction mixture was diluted with ethyl acetate, washed with water and then with brine, dried over anhydrous magnesium sulfate, and concentrated under reduced pressure. The resulting residue was dissolved in tetrahydrofuran (100 mL). N,N'-Carbonyldiimidazole (1.4 g) and 1,8-diazabicyclo[5.4.0]undec-7-ene (1.2 mL) were successively added, and the mixture was stirred at room temperature for 2 hr. The reaction mixture was diluted with ethyl acetate, washed with saturated aqueous potassium hydrogensulfate solution and then with brine, and dried over anhydrous magnesium sulfate. The solvent was evaporated under reduced pressure, and the residue was purified by silica gel column chromatography to give the title compound as a colorless amorphous solid (4 g, 91%, >99% ee).

$^1$H NMR (300 MHz, DMSO-$d_6$) δ0.93 (t, J=7.3 Hz, 3H), 0.98-1.10 (m, 9H), 1.22-1.38 (m, 2H), 1.51-1.72 (m, 4H), 2.00-2.13 (m, 2H), 2.52-2.65 (m, 2H), 2.88-2.98 (m, 2H), 3.24 (q, J=6.2 Hz, 1H), 3.33-3.43 (m, 1H), 3.94 (s, 2H), 4.06 (s, 1H), 4.80-4.94 (m, 1H), 6.99 (dd, J=7.9, 1.7 Hz, 1H), 7.12-7.28 (m, 2H), 7.51-7.61 (m, 2H), 7.64-7.73 (m, 2H), 8.19 (s, 1H), 12.46 (br. s., 1H)
analysis of enantiomeric excess
column: CHIRALPAK AD-H (CG075) 4.6 mm ID×250 mL
mobile phase: CO$_2$/MeOH=600/400 (v/v)
flow rate: 2.35 ml/min
temperature: 35° C.

EXAMPLE 248

6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: long)

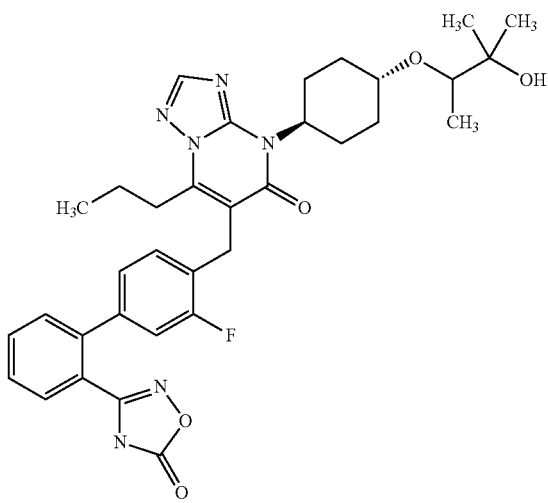 [SMILES: CCCc1c(Cc2ccc(-c3ccccc3-c3noc(=O)[nH]3)cc2F)c(=O)n([C@H]2CC[C@H](OC(C)C(C)(C)O)CC2)c2ncnn12]

A mixture of hydroxylammonium chloride (0.37 g), sodium hydrogen carbonate (0.6 g) and dimethyl sulfoxide (10 mL) was stirred at 40° C. for 30 min, 3'-fluoro-4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: long, 0.2 g) obtained in Reference Example 202 was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.069 g) and then 1,8-diazabicyclo[5.4.0]undec-7-ene (0.058 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.19 g, >99% ee).

$^1$H NMR (300 MHz, DMSO-$d_6$) δ0.89-1.10 (m, 12H) 1.20-1.73 (m, 6H) 1.94-2.14 (m, 2H) 2.52-2.67 (m, 2H) 2.88-2.98 (m, 2H) 3.24 (q, J=6.2 Hz, 1H) 3.33-3.43 (m, 1H) 3.94 (s, 2H) 4.05 (s, 1H) 4.80-4.95 (m, 1H) 6.99 (dd, J=7.9, 1.7 Hz, 1H) 7.13-7.28 (m, 2H) 7.51-7.73 (m, 4H) 8.19 (s, 1H) 12.45 (br. s., 1H)

detection: UV220 nm
concentration: 0.5 mg/ml
injection volume: 5 μl
retention time: 6.59 min
specific optical rotation $[\alpha]^{25}_D$ +24.0° (c=0.2045, in methanol)

analysis of enantiomeric excess
column: CHIRALPAK AD-H (CG075) 4.6 mm ID×250 mL
mobile phase: $CO_2$/MeOH=600/400 (v/v)
flow rate: 2.35 ml/min
temperature: 35° C.
detection: UV220 nm
concentration: 0.5 mg/ml
injection volume: 5 μl
retention time: 10.01 min

EXAMPLE 249

2-({trans-4-[6-{[3-fluoro-2'-(5-oxo-4,5-dihydro-1,2,4-oxadiazol-3-yl)biphenyl-4-yl]methyl}-2-methyl-5-oxo-7-propyl[1,2,4]triazolo[1,5-a]pyrimidin-4(5H)-yl]cyclohexyl}oxy)propanenitrile

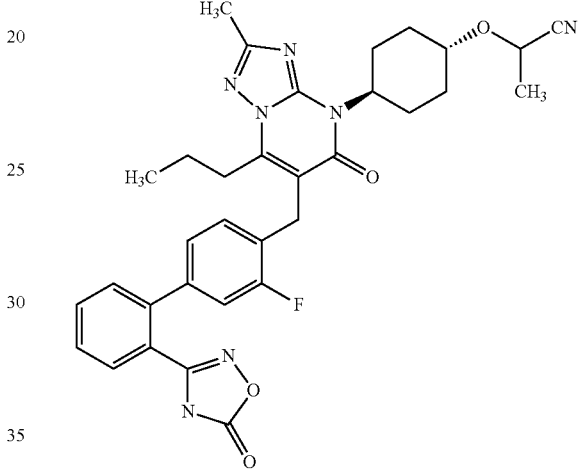

A mixture of hydroxylammonium chloride (0.68 g), sodium hydrogen carbonate (1.1 g) and dimethyl sulfoxide (10 mL) was stirred at 40° C. for 30 min, 2-[(trans-4-{6-[(2'-cyano-3-fluorobiphenyl-4-yl)methyl]-2-methyl-5-oxo-7-propyl[1,2,4]triazolo[1,5-a]pyrimidin-4(5H)-yl}cyclohexyl)oxy]propanamide (0.37 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure. The obtained residue was dissolved in tetrahydrofuran (10 mL), pyridine (0.21 mL) and trifluoroacetic acid anhydride (0.18 mL) were added at 0° C., and the mixture was stirred for 30 min. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.11 g, 28%).

$^1$H NMR (300 MHz, DMSO-$d_6$) δ0.92 (t, J=7.4 Hz, 3H) 1.20-1.77 (m, 9H) 2.05-2.20 (m, 2H) 2.37 (s, 3H) 2.42-2.58 (m, 2H) 2.83-2.93 (m, 2H) 3.50-3.63 (m, 1H) 3.92 (s, 2H)

4.71 (q, J=6.6 Hz, 1H) 4.80-4.94 (m, 1H) 6.98 (dd, J=8.0, 1.5 Hz, 1H) 7.11-7.27 (m, 2H) 7.51-7.62 (m, 2H) 7.64-7.74 (m, 2H) 12.45 (s, 1H)

EXAMPLE 250

(+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one potassium salt (retention time: short)

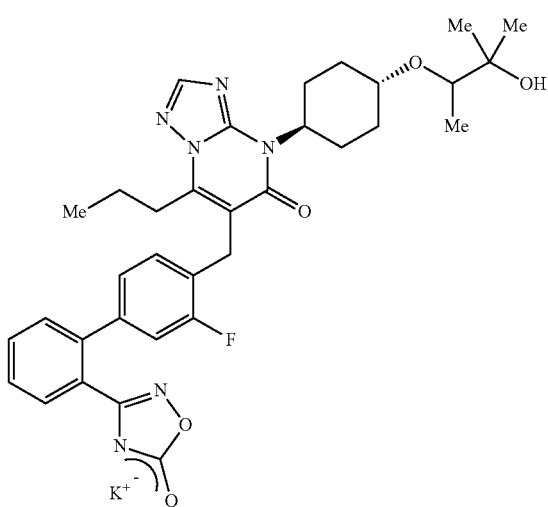 [SMILES: CCCc1c(Cc2ccc(-c3ccccc3C3=NOC(O)N3)cc2F)c(=O)n([C@H]2CC[C@H](OC(C)C(C)(C)O)CC2)c2ncnn12 ; [K+]]

To a solution of (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: short, 4.3 g) in diethyl ether (200 mL) was added a solution of potassium 2-ethylhexanate (1.5 g) in ethyl acetate (15 mL) at 40° C. The reaction mixture was cooled to room temperature, and stirred for 4 hr. The precipitated crystals were collected by filtration, washed with diisopropyl ether, and dried under reduced pressure at 140° C. to give the title compound (3.1 g, 68%, >99% ee).

$^1$H NMR (300 MHz, DMSO-$d_6$) δ0.91-1.10 (m, 12H), 1.17-1.40 (m, 2H), 1.54-1.73 (m, 4H), 1.92-2.12 (m, 2H), 2.47-2.64 (m, 2H), 2.88-2.99 (m, 2H), 3.24 (q, J=6.4 Hz, 1H), 3.29-3.41 (m, 1H), 3.90 (s, 2H), 4.05 (s, 1H), 4.80-4.95 (m, 1H), 6.98-7.17 (m, 3H), 7.29-7.53 (m, 4H), 8.18 (s, 1H)

analysis of enantiomeric excess
column: CHIRALPAK AD-H (LA145) 4.6 mm ID×250 mL
mobile phase: $CO_2$/MeOH=650/350 (v/v)
flow rate: 2.35 ml/min
pressure: 100 bar
temperature: 35° C.
detection: UV220 nm
concentration: 0.5 mg/ml
injection volume: 5 μl
retention time: 7.3 min
specific optical rotation $[\alpha]^{25}_D$ +14.2° (c=1.0055, in methanol)
melting point 154° C.

Crystal form was characterized by powder X ray diffraction pattern using CuKα X-ray radiation, having peaks selected from a list consisting of:

| diffraction angle: 2θ(°) | interplanar distance: d value (Å) |
|---|---|
| 4.4 | 20.0658 |
| 5.82 | 15.1728 |
| 6.42 | 13.7561 |
| 8.1 | 10.9063 |
| 13.38 | 6.612 |
| 14.38 | 6.1544 |
| 15.34 | 5.7713 |
| 18.78 | 4.7212 |
| 20.2 | 4.3924 |

EXAMPLE 251

6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one potassium salt (retention time: long)

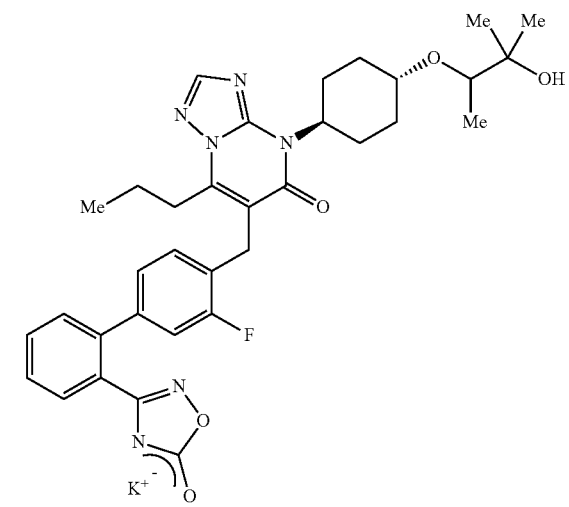 [SMILES: CCCc1c(Cc2ccc(-c3ccccc3C3=NOC(O)N3)cc2F)c(=O)n([C@H]2CC[C@H](OC(C)C(C)(C)O)CC2)c2ncnn12 ; [K+]]

6-{[3-Fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: long, 0.064 g) was suspended in isopropyl alcohol (3 mL), 1N potassium hydroxide solution (0.1 mL) was added, and the solvent was evaporated under reduced pressure. The residue was solidified with diisopropyl ether to give the title compound as a colorless solid (0.052 g, 76%>99% ee).

$^1$H NMR (300 MHz, DMSO-$d_6$) δ0.90-1.11 (m, 15H) 1.16-1.40 (m, 2H) 1.53-1.74 (m, 4H) 1.94-2.14 (m, 2H) 2.53-2.66 (m, 2H) 2.88-2.99 (m, 2H) 3.19-3.43 (m, 2H) 3.90 (s, 2H) 4.05 (s, 1H) 4.80-4.96 (m, 1H) 6.97-7.17 (m, 3H) 7.28-7.53 (m, 4H) 8.18 (s, 1H)

analysis of enantiomeric excess
column: CHIRALPAK AD-H (CG075) 4.6 mm ID×250 mL
mobile phase: CO$_2$/MeOH=650/350 (v/v)
flow rate: 2.35 ml/min
temperature: 35° C.
detection: UV220 nm
concentration: 0.5 mg/ml
injection volume: 5 μl
retention time: 9.7 min

EXAMPLE 252

6-{[3-fluoro-2'-(5-oxo-4,5-dihydro-1,2,4-oxadiazol-3-yl)biphenyl-4-yl]methyl}-4-{trans-4-[(1-hydroxy-cyclobutyl)methoxy]cyclohexyl}-7-propyl[1,2,4]triazolo[1,5-a]pyrimidin-5(4H)-one

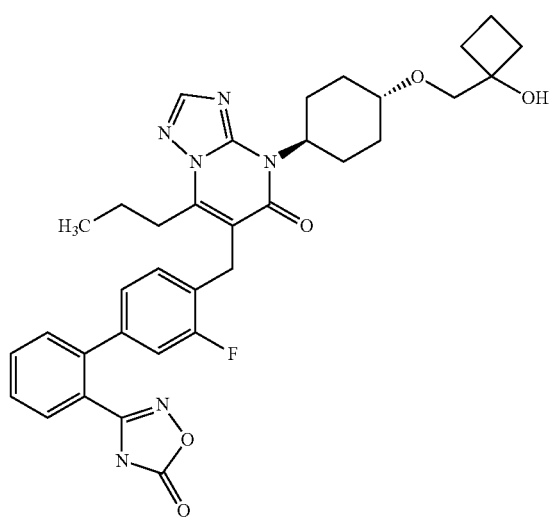 [SMILES: CCCc1c(Cc2ccc(-c3ccccc3-c3noc(=O)[nH]3)cc2F)c(=O)n([C@H]2CC[C@H](OCC3(O)CCC3)CC2)c2ncnn12]

A mixture of hydroxylammonium chloride (0.34 g), sodium hydrogen carbonate (0.55 g) and dimethyl sulfoxide (10 mL) was stirred at 40° C. for 30 min, 3'-fluoro-4'-[(4-{trans-4-[(1-hydroxycyclobutyl)methoxy]cyclohexyl}-5-oxo-7-propyl-4,5-dihydro[1,2,4]triazolo[1,5-a]pyrimidin-6-yl)methyl]biphenyl-2-carbonitrile (0.19 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.064 g) and then 1,8-diazabicyclo[5.4.0]undec-7-ene (0.054 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.13 g, 60%).

$^1$H NMR (300 MHz, DMSO-d$_6$) δ0.93 (t, J=7.4 Hz, 3H) 1.21-1.75 (m, 8H) 1.79-2.04 (m, 4H) 2.09-2.20 (m, 2H) 2.59 (br. s., 2H) 2.89-2.97 (m, 2H) 3.28-3.41 (m, 3H) 3.94 (s, 2H) 4.80-4.95 (m, 2H) 6.95-7.02 (m, 1H) 7.12-7.28 (m, 2H) 7.51-7.62 (m, 2H) 7.63-7.73 (m, 2H) 8.19 (s, 1H) 12.45 (br. s., 1H)

EXAMPLE 253

4-(cis-3-hydroxycyclobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

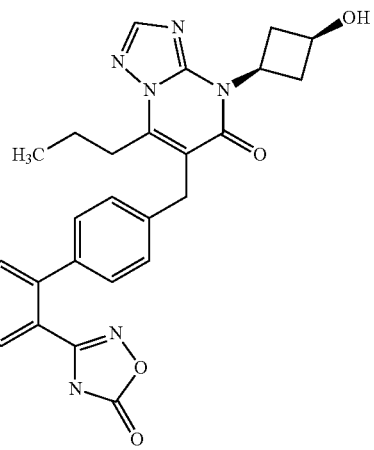

A mixture of 4'-{[4-(cis-3-hydroxycyclobutyl)-5-oxo-7-propyl-4,5-dihydro[1,2,4]triazolo[1,5-a]pyrimidin-6-yl]methyl}biphenyl-2-carbonitrile (0.28 g), tert-butyl(dimethyl)silyl trifluoromethanesulfonate (0.22 mL), 2,6-lutidine (0.11 mL) and tetrahydrofuran (10 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.66 g), sodium hydrogen carbonate (1.1 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.13 g) and then 1,8-diazabicyclo[5.4.0]undec-7-ene (0.1 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (15 mL). Tetrabutylammonium bromide (1.0 M tetrahydrofuran solution, 1.6 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.18 g, 58%).

$^1$H NMR (300 MHz, DMSO-d$_6$) δ0.92 (t, J=7.3 Hz, 3H) 1.45-1.66 (m, 2H) 2.52-2.63 (m, 2H) 2.88-3.03 (m, 4H) 3.86-

4.02 (m, 3H) 4.76-4.91 (m, 1H) 5.23 (q, J=5.8 Hz, 1H) 7.20-7.34 (m, 4H) 7.47-7.59 (m, 2H) 7.62-7.73 (m, 2H) 8.21 (s, 1H) 12.39 (s, 1H)

EXAMPLE 254

4-[cis-3-(2-hydroxy-2-methylpropoxy)cyclobutyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

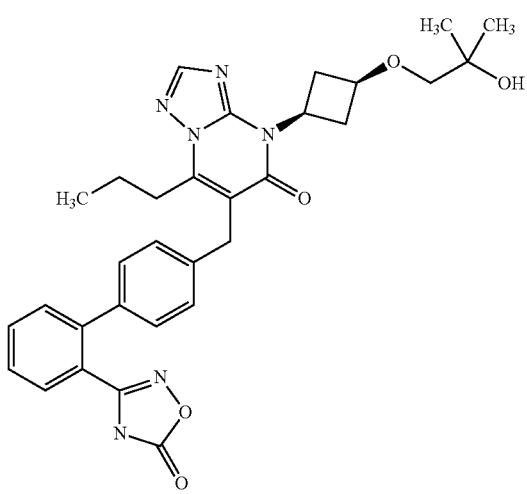 [SMILES: CCCc1c(Cc2ccc(-c3ccccc3-c3noc(=O)[nH]3)cc2)c(=O)n([C@H]2C[C@@H](OCC(C)(C)O)C2)c2ncnn12]

A mixture of hydroxylammonium chloride (0.31 g), sodium hydrogen carbonate (0.51 g) and dimethyl sulfoxide (10 mL) was stirred at 40° C. for 30 min, 4'-({4-[cis-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile (0.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.059 g) and then 1,8-diazabicyclo[5.4.0]undec-7-ene (0.05 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.069 g, 40%).

$^1$H NMR (300 MHz, DMSO-$d_6$) δ0.92 (t, J=7.3 Hz, 3H) 1.09 (s, 6H) 1.47-1.63 (m, 2H) 2.54-2.66 (m, 2H) 2.89-3.08 (m, 4H) 3.11 (s, 2H) 3.76-3.88 (m, 1H) 3.95 (s, 2H) 4.31 (s, 1H) 4.84-5.00 (m, 1H) 7.19-7.34 (m, 4H) 7.47-7.58 (m, 2H) 7.62-7.72 (m, 2H) 8.20 (s, 1H) 12.38 (br. s., 1H)

EXAMPLE 255

4-(3-oxocyclobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

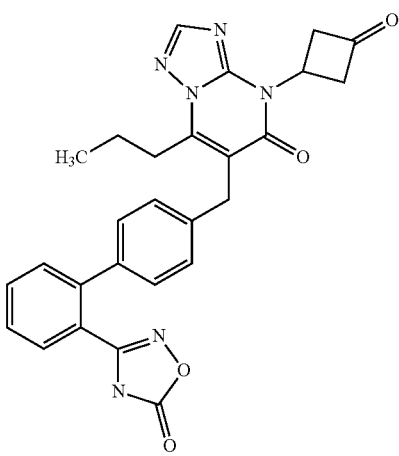 [SMILES: CCCc1c(Cc2ccc(-c3ccccc3-c3noc(=O)[nH]3)cc2)c(=O)n(C2CC(=O)C2)c2ncnn12]

A mixture of 4-(cis-3-hydroxycyclobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.1 g), Dess-Martin reagent (0.13 g) and acetonitrile (5 mL) was stirred at room temperature for 2 hr. Saturated aqueous sodium hydrogen carbonate solution and sodium thiosulfate were added to the reaction mixture, and the mixture was stirred at room temperature for 2 hr, and extracted with ethyl acetate. The organic layer was washed with saturated brine, and dried over anhydrous magnesium sulfate. The solvent was evaporated under reduced pressure. The obtained residue was purified by silica gel column chromatography to give the title compound as a colorless amorphous solid (0.077 g, 78%).

$^1$H NMR (300 MHz, DMSO-$d_6$) δ0.93 (t, J=7.3 Hz, 3H) 1.47-1.64 (m, 2H) 2.89-3.00 (m, 2H) 3.42-3.55 (m, 2H) 3.76-3.89 (m, 2H) 3.98 (s, 2H) 5.74-5.88 (m, 1H) 7.19-7.26 (m, 2H) 7.30-7.36 (m, 2H) 7.47-7.58 (m, 2H) 7.62-7.72 (m, 2H) 8.22 (s, 1H) 12.38 (br. s., 1H)

EXAMPLE 256

4-[trans-3-(2-hydroxy-2-methylpropoxy)cyclobutyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

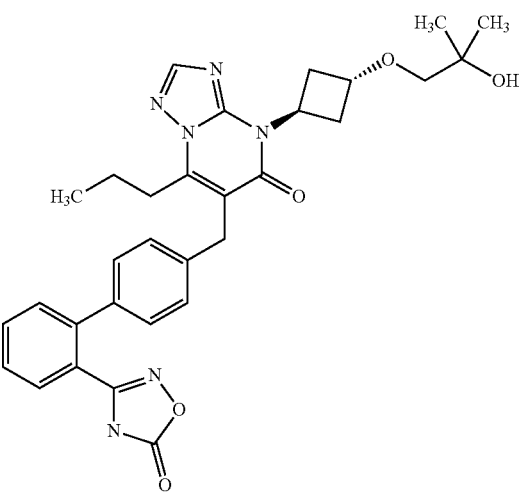 [SMILES: CCCc1c(Cc2ccc(-c3ccccc3-c3noc(=O)[nH]3)cc2)c(=O)n([C@H]2C[C@H](OCC(C)(C)O)C2)c2ncnn12]

A mixture of hydroxylammonium chloride (0.11 g), sodium hydrogen carbonate (0.18 g) and dimethyl sulfoxide (5 mL) was stirred at 40° C. for 30 min, 4'-({4-[trans-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile (0.056 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.021 g) and then 1,8-diazabicyclo[5.4.0]undec-7-ene (0.018 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.03 g, 48%).

$^1$H NMR (300 MHz, DMSO-$d_6$) δ0.92 (t, J=7.3 Hz, 3H) 1.11 (s, 6H) 1.47-1.61 (m, 2H) 2.23-2.36 (m, 2H) 2.90-3.00 (m, 2H) 3.09 (s, 2H) 3.12-3.25 (m, 2H) 3.95 (s, 2H) 4.23-4.36 (m, 2H) 5.62-5.75 (m, 1H) 7.18-7.26 (m, 2H) 7.27-7.35 (m, 2H) 7.47-7.59 (m, 2H) 7.62-7.72 (m, 2H) 8.21 (s, 1H) 12.38 (s, 1H)

EXAMPLE 257

4-(trans-3-hydroxycyclobutyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

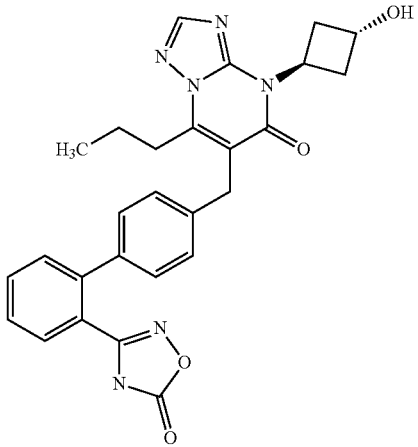 [SMILES: CCCc1c(Cc2ccc(-c3ccccc3-c3noc(=O)[nH]3)cc2)c(=O)n([C@H]2C[C@H](O)C2)c2ncnn12]

A mixture of 4'-{[4-(trans-3-hydroxycyclobutyl)-5-oxo-7-propyl-4,5-dihydro[1,2,4]triazolo[1,5-a]pyrimidin-6-yl]methyl}biphenyl-2-carbonitrile (0.13 g), tert-butyl(dimethyl)silyl trifluoromethanesulfonate (0.14 mL), 2,6-lutidine (0.069 mL) and tetrahydrofuran (5 mL) was stirred at 0° C. for 3 hr. The reaction mixture was diluted with ethyl acetate, washed with water and then with saturated brine, and dried over anhydrous magnesium sulfate. The solvent was evaporated under reduced pressure. The residue obtained by silica gel column chromatography was dissolved in dimethyl sulfoxide (5 mL), and added to a mixture of hydroxylammonium chloride (0.31 g), sodium hydrogen carbonate (0.5 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.058 g) and then 1,8-diazabicyclo[5.4.0]undec-7-ene (0.049 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was dissolved in tetrahydrofuran (5 mL). Tetrabutylammonium bromide (1.0 M tetrahydrofuran solution, 0.74 mL) was added, and the mixture was stirred at room temperature for 3 hr. The reaction mixture was extracted with 1 N hydrochloric acid and ethyl acetate, and the ethyl acetate layer was washed with saturated brine and concentrated. The residue was purified by silica gel column chromatography to give the title compound as a colorless amorphous solid (0.06 g, 41%).

$^1$H NMR (300 MHz, DMSO-$d_6$) δ0.92 (t, J=7.2 Hz, 3H) 1.46-1.62 (m, 2H) 2.11-2.23 (m, 2H) 2.88-2.98 (m, 2H) 3.15-3.29 (m, 2H) 3.95 (s, 2H) 4.44-4.54 (m, 1H) 5.11 (d, J=4.5 Hz, 1H) 5.69-5.84 (m, 1H) 7.19-7.34 (m, 4H) 7.47-7.58 (m, 2H) 7.61-7.72 (m, 2H) 8.20 (s, 1H) 12.37 (s, 1H)

EXAMPLE 258

6-{[3-fluoro-2'-(5-oxo-4,5-dihydro-1,2,4-oxadiazol-3-yl)biphenyl-4-yl]methyl}-4-{trans-4-[(1-hydroxycyclobutyl)methoxy]cyclohexyl}-7-propyl[1,2,4]triazolo[1,5-a]pyrimidin-5(4H)-one potassium salt

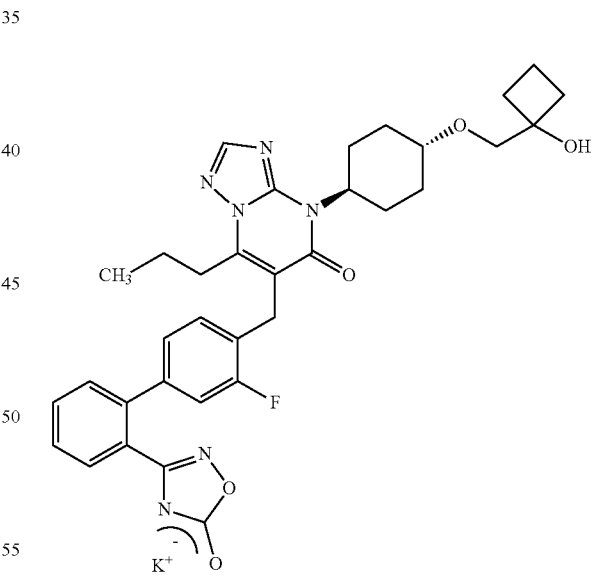

6-{[3-Fluoro-2'-(5-oxo-4,5-dihydro-1,2,4-oxadiazol-3-yl)biphenyl-4-yl]methyl}-4-{trans-4-[(1-hydroxycyclobutyl)methoxy]cyclohexyl}-7-propyl[1,2,4]triazolo[1,5-a]pyrimidin-5(4H)-one (2 g) was suspended in isopropyl alcohol (30 mL), 4N potassium hydroxide solution (0.78 mL) was added, and the solvent was evaporated under reduced pressure. The residue was solidified with diisopropyl ether to give the title compound as a colorless solid (2 g, 95%).

$^1$H NMR (300 MHz, DMSO-$d_6$) δ0.95 (t, J=7.35 Hz, 3H) 1.20-1.76 (m, 8H) 1.80-2.18 (m, 6H) 2.52-2.67 (m, 2H) 2.89-

2.99 (m, 2H) 3.29-3.42 (m, 3H) 3.90 (s, 2H) 4.80-4.98 (m, 2H) 6.98-7.17 (m, 3H) 7.28-7.54 (m, 4H) 8.18 (s, 1H)

EXAMPLE 259

4-[trans-3-(2-ethyl-2-hydroxybutoxy)cyclobutyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

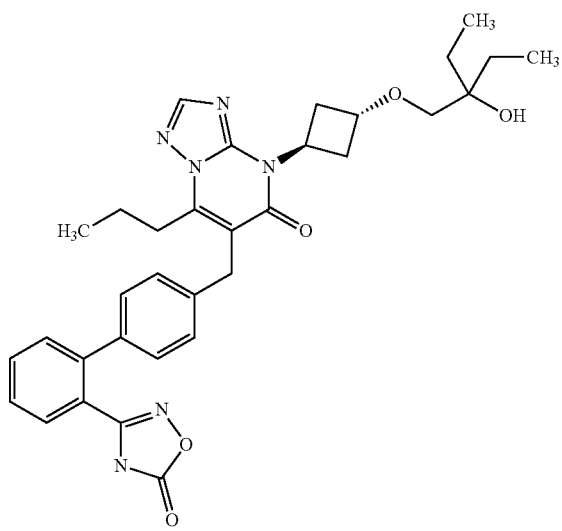 [SMILES: CCCc1c(Cc2ccc(-c3ccccc3-c3noc(=O)[nH]3)cc2)c(=O)n([C@H]2C[C@H](OCC(O)(CC)CC)C2)c2ncnn12]

A mixture of hydroxylammonium chloride (0.12 g), sodium hydrogen carbonate (0.19 g) and dimethyl sulfoxide (5 mL) was stirred at 40° C. for 30 min, 4'-({4-[trans-3-(2-ethyl-2-hydroxybutoxy)cyclobutyl]-5-oxo-7-propyl-4,5-dihydro[1,2,4]triazolo[1,5-a]pyrimidin-6-yl}methyl)biphenyl-2-carbonitrile (0.06 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.022 g) and then 1,8-diazabicyclo[5.4.0]undec-7-ene (0.018 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.052 g, 79%).

$^1$H NMR (300 MHz, DMSO-$d_6$) δ0.82 (t, J=7.19 Hz, 6H) 0.92 (t, J=7.38 Hz, 3H) 1.42 (q, J=7.57 Hz, 4H) 1.47-1.63 (m, 2H) 2.23-2.36 (m, 2H) 2.89-2.98 (m, 2H) 3.09-3.25 (m, 4H) 3.95 (s, 2H) 4.01 (s, 1H) 4.26 (t, J=6.82 Hz, 1H) 5.60-5.74 (m, 1H) 7.19-7.25 (m, 2H) 7.28-7.34 (m, 2H) 7.47-7.58 (m, 2H) 7.62-7.72 (m, 2H) 8.21 (s, 1H) 12.37 (br. s., 1H)

EXAMPLE 260

4-[trans-4-(2-hydroxy-2-methylpropoxy)cyclohexyl]-6-({5-[2-(5-oxo-4,5-dihydro-1,2,4-oxadiazol-3-yl)phenyl]thiophen-2-yl}methyl)-7-propyl[1,2,4]triazolo[1,5-a]pyrimidin-5(4H)-one

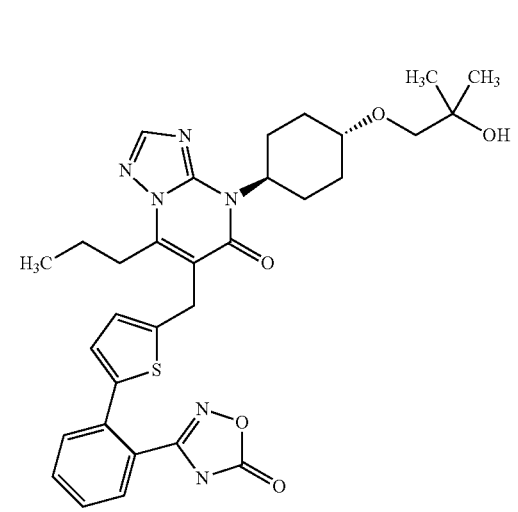 [SMILES: CCCc1c(Cc2ccc(-c3ccccc3-c3noc(=O)[nH]3)s2)c(=O)n([C@H]2CC[C@H](OCC(C)(C)O)CC2)c2ncnn12]

A mixture of hydroxylammonium chloride (0.23 g), sodium hydrogen carbonate (0.37) and dimethyl sulfoxide (5 mL) was stirred at 40° C. for 30 min, 2-[5-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)thiophen-2-yl]benzonitrile (0.12 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.043 g) and then 1,8-diazabicyclo[5.4.0]undec-7-ene (0.036 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.05 g, 38%).

$^1$H NMR (300 MHz, DMSO-$d_6$) δ0.98 (t, J=7.3 Hz, 3H) 1.07 (6H, s) 1.21-1.38 (m, 2H) 1.57-1.74 (m, 4H) 2.05-2.16 (m, 2H) 2.51-2.63 (m, 2H) 2.93-3.03 (m, 2H) 3.20 (s, 2H) 3.26-3.32 (m, 1H) 4.08 (s, 2H) 4.26 (s, 1H) 4.83-4.99 (m, 1H) 6.93-6.99 (m, 2H) 7.45-7.54 (m, 1H) 7.57-7.67 (m, 3H) 8.20 (s, 1H) 12.52 (s, 1H)

EXAMPLE 261

4-[trans-4-(2-hydroxy-2-methylpropoxy)cyclohexyl]-6-({5-[2-(5-oxo-4,5-dihydro-1,2,4-oxadiazol-3-yl)phenyl]thiophen-2-yl}methyl)-7-propyl[1,2,4]triazolo[1,5-a]pyrimidin-5(4H)-one potassium salt

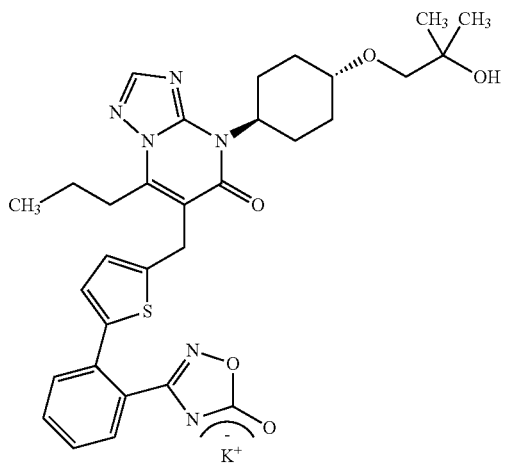 [SMILES: CCCc1c(Cc2ccc(-c3ccccc3C3=NOC(O)N3)s2)c(=O)n([C@H]2CC[C@H](OCC(C)(C)O)CC2)c2ncnn12 ; [K+]]

4-[trans-4-(2-Hydroxy-2-methylpropoxy)cyclohexyl]-6-({5-[2-(5-oxo-4,5-dihydro-1,2,4-oxadiazol-3-yl)phenyl]thiophen-2-yl}methyl)-7-propyl[1,2,4]triazolo[1,5-a]pyrimidin-5(4H)-one (0.075 g) was suspended in isopropyl alcohol (3 mL), 1N potassium hydroxide solution (0.12 mL) was added, and the solvent was evaporated under reduced pressure. The residue was solidified with diisopropyl ether to give the title compound as a colorless solid (0.06 g, 75%).

$^1$H NMR (300 MHz, DMSO-$d_6$) δ0.99 (t, J=7.3 Hz, 3H) 1.07 (s, 6H) 1.20-1.38 (m, 2H) 1.59-1.74 (m, 4H) 2.05-2.16 (m, 2H) 2.52-2.66 (m, 2H) 2.94-3.02 (m, 2H) 3.20 (s, 2H) 3.25-3.31 (m, 1H) 4.02 (s, 2H) 4.24 (br.s., 1H) 4.90 (t, J=12.2 Hz, 1H) 6.79-6.83 (m, 1H) 6.91-6.95 (m, 1H) 7.25-7.44 (m, 4H) 8.17 (s, 1H)

EXAMPLE 262

4-[trans-4-(2-hydroxy-2-methylpropoxy)cyclohexyl]-6-({6-[2-(5-oxo-4,5-dihydro-1,2,4-oxadiazol-3-yl)phenyl]pyridin-3-yl}methyl)-7-propyl[1,2,4]triazolo[1,5-a]pyrimidin-5(4H)-one

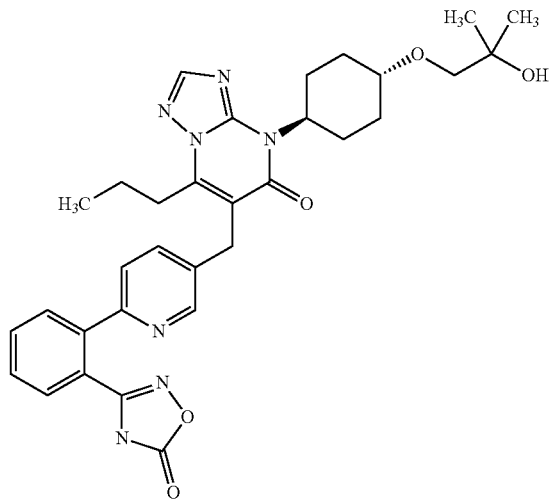 [SMILES: CCCc1c(Cc2ccc(-c3ccccc3-c3noc(=O)[nH]3)nc2)c(=O)n([C@H]2CC[C@H](OCC(C)(C)O)CC2)c2ncnn12]

Ethyl({trans-4-[6-{[6-(2-cyanophenyl)pyridin-3-yl]methyl}-5-oxo-7-propyl[1,2,4]triazolo[1,5-a]pyrimidin-4(5H)-yl]cyclohexyl}oxy)acetate (0.06 g) was dissolved in tetrahydrofuran (5 mL), and methylmagnesium bromide (1.0 M tetrahydrofuran solution, 0.32 mL) was added at room temperature. The reaction mixture was stirred for 2 hr, saturated aqueous ammonium chloride solution was added, and the mixture was extracted with ethyl acetate. The obtained ethyl acetate layer was washed with saturated brine, and dried over anhydrous magnesium sulfate. The solvent was evaporated under reduced pressure. The obtained residue was dissolved in dimethyl sulfoxide (5 mL), and the mixture was added to a mixture of hydroxylammonium chloride (0.11 g), sodium hydrogen carbonate (0.18 g) and dimethyl sulfoxide (5 mL), which had been stirred in advance at 40° C. for 30 min. The reaction mixture was stirred at 90° C. for 16 hr, diluted with ethyl acetate, washed with water and then with saturated brine, and dried over anhydrous magnesium sulfate. The solvent was evaporated under reduced pressure, and the residue was purified by silica gel column chromatography and dissolved in tetrahydrofuran (5 mL). N,N'-Carbonyldiimidazole (0.021 g) and then 1,8-diazabicyclo[5.4.0]undec-7-ene (0.018 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.011 g, 17%).

$^1$H NMR (300 MHz, CHLOROFORM-d) δ1.09 (t, J=7.3 Hz, 3H) 1.20 (s, 6H) 1.37-1.53 (m, 2H) 1.70-1.84 (m, 4H) 2.14-2.25 (m, 2H) 2.61-2.77 (m, 2H) 3.02-3.11 (m, 2H) 3.30 (s, 2H) 3.38-3.51 (m, 1H) 4.03 (s, 2H) 4.98-5.13 (m, 1H) 7.37-7.61 (m, 4H) 7.71-7.81 (m, 2H) 7.93 (s, 1H) 8.49 (d, 1H)

EXAMPLE 263

5-butyl-8-[4-(1-methylethoxy)phenyl]-6-{[2'-(5-oxo-4,5-dihydro-1,2,4-oxadiazol-3-yl)biphenyl-4-yl]methyl}[1,2,4]triazolo[4,3-a]pyrimidin-7(8H)-one

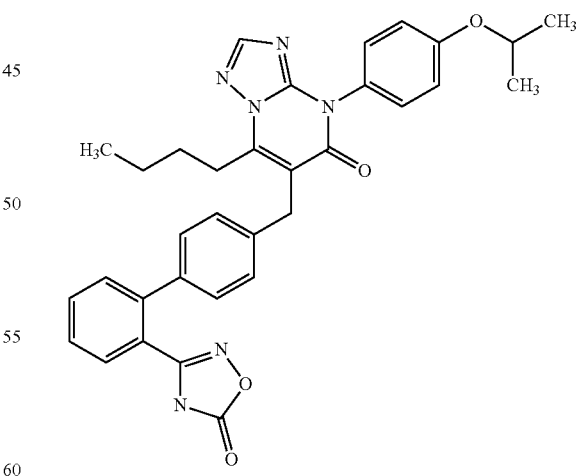

A mixture of hydroxylammonium chloride (0.66 g), sodium hydrogen carbonate (1.1 g) and dimethyl sulfoxide (15 mL) was stirred at 40° C. for 30 min, 4'-{[5-butyl-8-[4-(1-methylethoxyphenyl)-7-oxo-7,8-dihydro[1,2,4]triazolo[4,3-a]pyrimidin-6-yl]methyl}biphenyl-2-carbonitrile (0.33 g) was added, and the mixture was stirred at 90° C. for 16 hr.

The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.12 g) and then 1,8-diazabicyclo[5.4.0]undec-7-ene (0.1 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.16 g, 43%).

$^1$H NMR (300 MHz, DMSO-$d_6$) δ0.81-0.91 (m, 3H) 1.31 (d, J=6.0 Hz, 6H) 1.36-1.52 (m, 4H) 2.95 (t, J=6.2 Hz, 2H) 3.95 (s, 2H) 4.60-4.74 (m, 1H) 6.98-7.08 (m, 2H) 7.19-7.26 (m, 2H) 7.30-7.39 (m, 4H) 7.45-7.59 (m, 2H) 7.63-7.72 (m, 2H) 9.05 (s, 1H) 12.41 (s, 1H)

EXAMPLE 264

5-butyl-8-[4-(1-methylethoxy)phenyl]-6-{[2'-(5-oxo-4,5-dihydro-1,2,4-oxadiazol-3-yl)biphenyl-4-yl]methyl}[1,2,4]triazolo[4,3-a]pyrimidin-7(8H)-one potassium salt

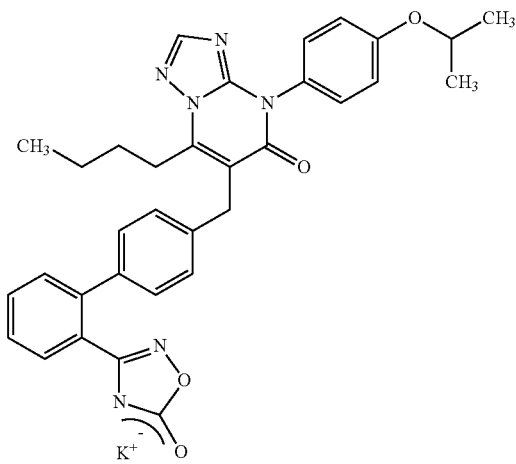 [SMILES: CCCCc1c(Cc2ccc(-c3ccccc3C3=NOC(O)N3)cc2)c(=O)n(-c2ccc(OC(C)C)cc2)c2ncnn12 ; [K+]]

5-Butyl-8-[4-(1-methylethoxy)phenyl]-6-{[2'-(5-oxo-4,5-dihydro-1,2,4-oxadiazol-3-yl)biphenyl-4-yl]methyl}[1,2,4]triazolo[4,3-a]pyrimidin-7(8H)-one (0.14 g) was suspended in isopropyl alcohol (10 mL), 2N potassium hydroxide solution (0.13 mL) was added, and the solvent was evaporated under reduced pressure. The residue was solidified with diisopropyl ether to give the title compound as a colorless solid (0.12 g, 75%).

$^1$H NMR (300 MHz, DMSO-$d_6$) δ0.87 (t, J=6.8 Hz, 3H) 1.31 (d, J=5.7 Hz, 6H) 1.37-1.55 (m, 4H) 2.91-3.02 (m, 2H) 3.90 (s, 2H) 4.59-4.75 (m, 1H) 7.03 (d, J=8.7 Hz, 2H) 7.16-7.50 (m, 10H) 9.02 (s, 1H)

EXAMPLE 265

2-methyl-6-{[2'-(5-oxo-4,5-dihydro-1,2,4-oxadiazol-3-yl)biphenyl-4-yl]methyl}-7-propyl-4-(tetrahydro-2H-pyran-4-yl)pyrazolo[1,5-a]pyrimidin-5(4H)-one

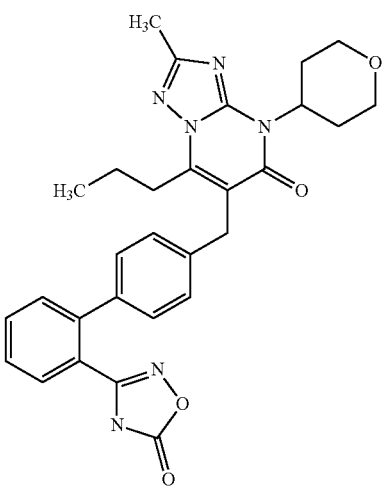 [SMILES: CCCc1c(Cc2ccc(-c3ccccc3-c3noc(=O)[nH]3)cc2)c(=O)n(C2CCOCC2)c2nc(C)nn12]

A mixture of hydroxylammonium chloride (0.33 g), sodium hydrogen carbonate (0.54 g) and dimethyl sulfoxide (10 mL) was stirred at 40° C. for 30 min, 4'-{[2-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile (0.15 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.062 g) and then 1,8-diazabicyclo[5.4.0]undec-7-ene (0.053 mL) were added, and the mixture was stirred at room temperature for 2 hr. The reaction mixture was diluted with ethyl acetate, washed with saturated potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.079 g, 47%).

$^1$H NMR (300 MHz, DMSO-$d_6$) δ0.92 (t, J=7.3 Hz, 3H) 1.42-1.65 (m, 4H) 2.27 (s, 3H) 2.51-2.62 (m, 2H) 2.83-2.95 (m, 2H) 3.39-3.54 (m, 2H) 3.86-4.04 (m, 4H) 4.76-4.94 (m, 1H) 6.20 (s, 1H) 7.17-7.32 (m, 4H) 7.53 (dd, J=16.0, 7.7 Hz, 2H) 7.60-7.72 (m, 2H) 12.36 (s, 1H)

EXAMPLE 266

2-methyl-7-propyl-4-(tetrahydro-2H-pyran-4-yl)-6-{[2'-(1H-tetrazol-5-yl)biphenyl-4-yl]methyl}pyrazolo[1,5-a]pyrimidin-5(4H)-one

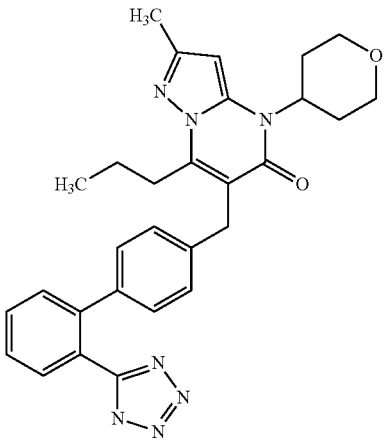 [SMILES: CCCc1c(Cc2ccc(-c3ccccc3-c3nnn[nH]3)cc2)c(=O)n(C2CCOCC2)c2cc(C)nn12]

A mixture of 4'-{[2-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile (0.1 g), dibutyltin oxide (0.011 g), azidotrimethylsilane (0.74 g) and toluene (10 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.035 g, 31%).

$^1$H NMR (300 MHz, DMSO-$d_6$) δ0.89 (t, J=7.2 Hz, 3H) 1.41-1.63 (m, 4H) 2.27 (s, 3H) 2.50-2.63 (m, 2H) 2.80-2.90 (m, 2H) 3.46 (t, J=11.0 Hz, 2H) 3.86 (s, 2H) 3.97 (dd, J=10.6, 3.0 Hz, 2H) 4.75-4.92 (m, 1H) 6.20 (s, 1H) 6.98 (d, J=8.0 Hz, 2H) 7.15 (d, J=8.3 Hz, 2H) 7.48-7.70 (m, 4H) 16.20 (br. s., 1H)

EXAMPLE 267

3-methyl-6-{[2'-(5-oxo-4,5-dihydro-1,2,4-oxadiazol-3-yl)biphenyl-4-yl]methyl}-7-propyl-4-(tetrahydro-2H-pyran-4-yl)pyrazolo[1,5-a]pyrimidin-5(4H)-one

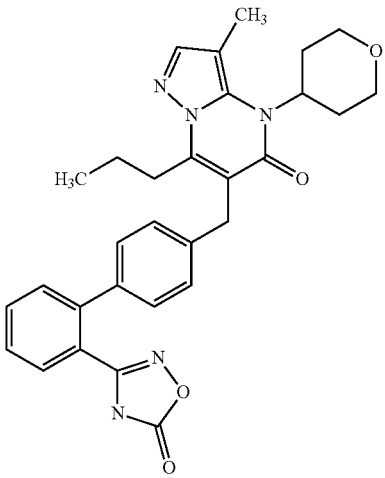 [SMILES: CCCc1c(Cc2ccc(-c3ccccc3-c3noc(=O)[nH]3)cc2)c(=O)n(C2CCOCC2)c2c(C)cnn12]

A mixture of hydroxylammonium chloride (0.67 g), sodium hydrogen carbonate (1.1 g) and dimethyl sulfoxide (10 mL) was stirred at 40° C. for 30 min, 4'-{[3-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless amorphous solid (0.2 g, 58%).

$^1$H NMR (300 MHz, DMSO-$d_6$) δ0.90 (t, J=7.3 Hz, 3H) 1.39-1.54 (m, 2H) 1.66-1.75 (m, 2H) 2.32 (s, 3H) 2.71-2.96 (m, 4H) 3.29-3.45 (m, 2H) 3.87-4.01 (m, 4H) 4.39-4.54 (m, 1H) 7.19-7.31 (m, 4H) 7.47-7.58 (m, 2H) 7.61-7.73 (m, 3H) 12.35 (br. s., 1H)

EXAMPLE 268

3-methyl-7-propyl-4-(tetrahydro-2H-pyran-4-yl)-6-{[2'-(1H-tetrazol-5-yl)biphenyl-4-yl]methyl}pyrazolo[1,5-a]pyrimidin-5(4H)-one

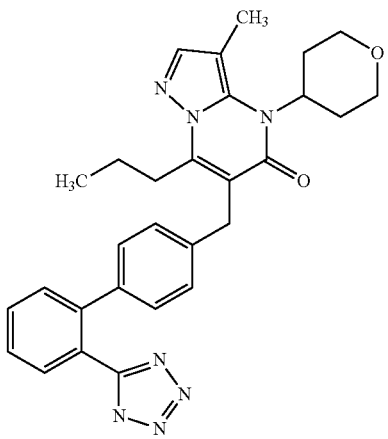 [SMILES: CCCc1c(Cc2ccc(-c3ccccc3-c3nnn[nH]3)cc2)c(=O)n(C2CCOCC2)c2c(C)cnn12]

A mixture of 4'-{[3-methyl-5-oxo-7-propyl-4-(tetrahydro-2H-pyran-4-yl)-4,5-dihydropyrazolo[1,5-a]pyrimidin-6-yl]methyl}biphenyl-2-carbonitrile (0.33 g), dibutyltin oxide (0.088 g), azidotrimethylsilane (3.5 g) and toluene (30 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as colorless crystals (0.15 g, 41%).

$^1$H NMR (300 MHz, DMSO-$d_6$) δ0.89 (t, J=7.3 Hz, 3H) 1.35-1.53 (m, 2H) 1.64-1.76 (m, 2H) 2.31 (s, 3H) 2.69-2.91 (m, 4H) 3.39 (t, J=11.4 Hz, 2H) 3.85 (s, 2H) 3.97 (dd, J=11.1, 4.0 Hz, 2H) 4.45 (t, J=11.7 Hz, 1H) 6.99 (d, J=8.3 Hz, 2H) 7.15 (d, J=8.1 Hz, 2H) 7.48-7.58 (m, 2H) 7.60-7.70 (m, 3H)

EXAMPLE 269

6-{[2'-(5-oxo-4,5-dihydro-1,2,4-oxadiazol-3-yl)biphenyl-4-yl]methyl}-7-propyl-4-(tetrahydro-2H-pyran-4-yl)pyrazolo[1,5-a]pyrimidin-5(4H)-one

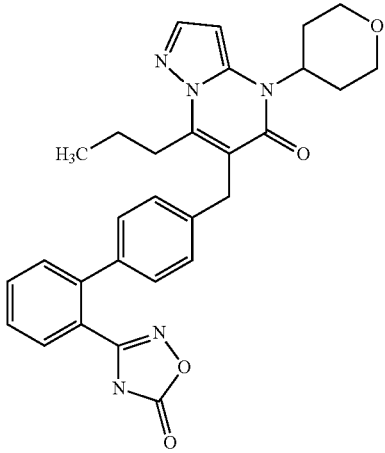 [SMILES: CCCc1c(Cc2ccc(-c3ccccc3-c3noc(=O)[nH]3)cc2)c(=O)n(C2CCOCC2)c2ccnn12]

A mixture of hydroxylammonium chloride (0.69 g), sodium hydrogen carbonate (1.1 g) and dimethyl sulfoxide (10 mL) was stirred at 40° C. for 30 min, 4'-{[5-oxo-7-propyl-4-(tetrahydro-2H-pyran-4-yl)-4,5-dihydropyrazolo[1,5-a]pyrimidin-6-yl]methyl}biphenyl-2-carbonitrile (0.3 g) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (0.13 g) and then 1,8-diazabicyclo[5.4.0]undec-7-ene (0.11 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as colorless crystals (0.18 g, 52%).

$^1$H NMR (300 MHz, DMSO-$d_6$) δ0.92 (t, J=7.2 Hz, 3H) 1.43-1.67 (m, 4H) 2.52-2.66 (m, 2H) 2.89-3.02 (m, 2H) 3.48 (t, J=11.2 Hz, 2H) 3.92-4.03 (m, 4H) 4.88 (t, J=11.4 Hz, 1H) 6.38 (d, J=1.9 Hz, 1H) 7.19-7.25 (m, 2H) 7.27-7.33 (m, 2H) 7.53 (dd, J=16.1, 7.8 Hz, 2H) 7.63-7.72 (m, 2H) 7.84 (d, J=2.3 Hz, 1H) 12.36 (s, 1H)

EXAMPLE 270

7-propyl-4-(tetrahydro-2H-pyran-4-yl)-6-{[2'-(1H-tetrazol-5-yl)biphenyl-4-yl]methyl}pyrazolo[1,5-a]pyrimidin-5(4H)-one

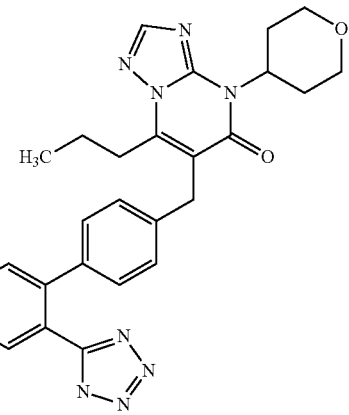

A mixture of 4'-{[5-oxo-7-propyl-4-(tetrahydro-2H-pyran-4-yl)-4,5-dihydropyrazolo[1,5-a]pyrimidin-6-yl]methyl}biphenyl-2-carbonitrile (0.33 g), dibutyltin oxide (0.083 g), azidotrimethylsilane (2.3 g) and toluene (20 mL) was stirred at 110° C. for 48 hr. The reaction mixture was diluted with ethyl acetate, washed with water and then with saturated brine, and dried over anhydrous magnesium sulfate. The solvent was evaporated under reduced pressure, and the residue was purified by silica gel column chromatography to give the title compound as a colorless amorphous solid (0.15 g, 46%).

$^1$H NMR (300 MHz, DMSO-$d_6$) δ0.91 (t, J=7.4 Hz, 3H) 1.41-1.65 (m, 4H) 2.52-2.63 (m, 2H) 2.87-2.97 (m, 2H) 3.47 (t, J=11.2 Hz, 2H) 3.89 (s, 2H) 3.94-4.02 (m, 2H) 4.86 (t, J=12.1 Hz, 1H) 6.37 (d, J=2.3 Hz, 1H) 6.99 (d, J=8.3 Hz, 2H) 7.17 (d, J=8.0 Hz, 2H) 7.53 (dd, J=13.1, 7.0 Hz, 2H) 7.59-7.70 (m, 2H) 7.83 (d, J=1.9 Hz, 1H)

EXAMPLE 271

4-[trans-4-(4-methoxyphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

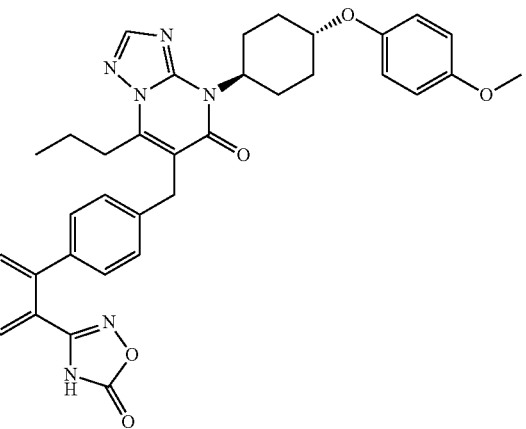

To a solution of 4'-{[4-(cis-4-hydroxycyclohexyl)-5-oxo-7-propyl-4,5-dihydro[1,2,4]triazolo[1,5-a]pyrimidin-6-yl]methyl}biphenyl-2-carbonitrile (0.46 g), 4-methoxyphenol (0.27 g) and triphenylphosphine (0.28 g) in tetrahydrofuran (1.0 mL) was added dropwise a solution of diisopropyl azodicarboxylate (0.58 mL, 1.9 M toluene solution) in tetrahydrofuran (1.5 mL) at 0° C., and the mixture was stirred at room temperature for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. A solution of the residue obtained by purification by silica gel column chromatography in dimethyl sulfoxide (2 mL) was added to a mixture of hydroxylammonium chloride (1.0 g), sodium hydrogen carbonate (1.7 g), and dimethyl sulfoxide (3 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.19 g) and then 1,8-diazabicyclo[5.4.0]undec-7-ene (0.18 mL) were added, and the mixture was stirred at room temperature for 40 min. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.24 g, 39%).

$^1$H NMR (300 MHz, CHLOROFORM-d) δ1.10 (t, J=7.35 Hz, 3H) 1.51-1.90 (m, 6H) 2.19-2.35 (m, 2H) 2.66-2.85 (m, 2H) 2.98-3.14 (m, 2H) 3.77 (s, 3H) 3.99 (s, 2H) 4.16-4.31 (m, 1H) 4.98-5.18 (m, 1H) 6.73-6.94 (m, 4H) 7.23-7.31 (m, 2H) 7.32-7.44 (m, 3H) 7.45-7.54 (m, 1H) 7.56-7.66 (m, 1H) 7.80-7.90 (m, 1H) 7.93 (s, 1H)

EXAMPLE 272

4-[cis-4-(4-methoxyphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one To a solution of 4'-{[4-(trans-4-hydroxycyclohexyl)-5-oxo-7-propyl-4,5-dihydro[1,2,4]triazolo[1,5-a]pyrimidin-6-yl]methyl}biphenyl-2-carbonitrile (0.46 g), 4-methoxyphenol (0.27 g) and triphenylphosphine (0.28 g) in tetrahydrofuran (1.0 mL) was added dropwise a solution of diisopropyl azodicarboxylate (0.58 mL, 1.9 M toluene solution) in tetrahydrofuran (1.5 mL) at 0° C., and the mixture was stirred at room temperature for 5.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. A solution of the residue obtained by purification by silica gel column chromatography in dimethyl sulfoxide (2 mL) was added to a mixture of hydroxylammonium chloride (1.0 g), sodium hydrogen carbonate (1.7 g), and dimethyl sulfoxide (3 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.19 g) and then 1,8-diazabicyclo[5.4.0]undec-7-ene (0.18 mL) were added, and the mixture was stirred at room temperature for 40 min. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.25 g, 39%).

$^1$H NMR (300 MHz, CHLOROFORM-d) δ1.10 (t, J=7.35 Hz, 3H) 1.51-1.87 (m, 6H) 2.12-2.28 (m, 2H) 2.99-3.19 (m, 4H) 3.77 (s, 3H) 4.01 (s, 2H) 4.41-4.52 (m, 1H) 4.99-5.17 (m, 1H) 6.77-6.88 (m, 2H) 6.93-7.04 (m, 2H) 7.23-7.31 (m, 2H) 7.32-7.44 (m, 3H) 7.45-7.54 (m, 1H) 7.56-7.65 (m, 1H) 7.87 (dd, J=7.72, 1.13 Hz, 1H) 7.97 (s, 1H)

EXAMPLE 273

4-[trans-4-(4-hydroxyphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

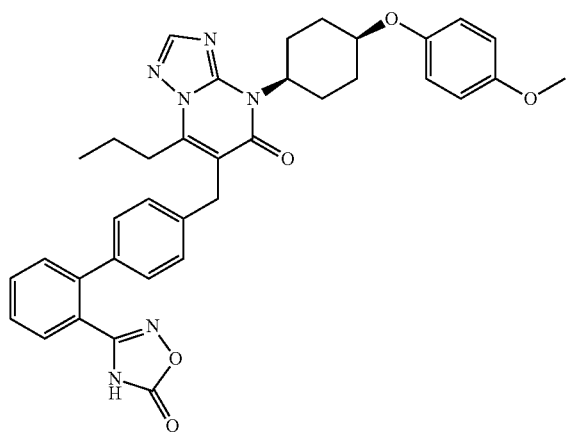 [SMILES: CCCc1c(Cc2ccc(-c3ccccc3-c3noc(=O)[nH]3)cc2)c(=O)n([C@H]2CC[C@@H](Oc3ccc(OC)cc3)CC2)c2ncnn12]

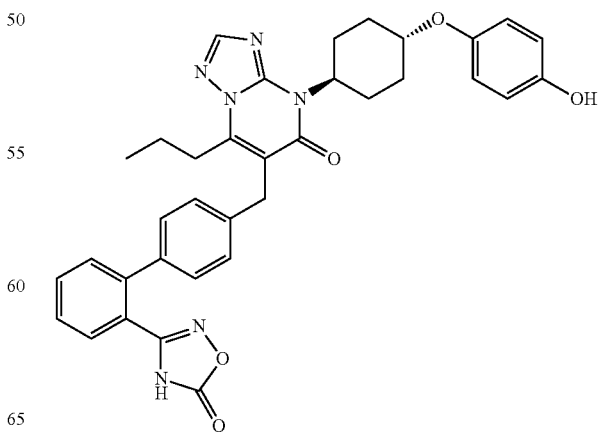

A mixture of hydroxylammonium chloride (0.34 g), sodium hydrogen carbonate (0.55 g) and dimethyl sulfoxide (3 mL) was stirred at 40° C. for 30 min, 4'-({4-[trans-4-(4-{[tert-butyl(dimethyl)silyl]oxy}phenoxy)cyclohexyl]-5-oxo-7-propyl-4,5-dihydro[1,2,4]triazolo[1,5-a]pyrimidin-6-yl}methyl)biphenyl-2-carbonitrile (0.22 g) was added, and the mixture was stirred at 90° C. for 23 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.11 g) and then 1,8-diazabicyclo[5.4.0]undec-7-ene (0.10 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.028 g, 14%).

$^1$H NMR (300 MHz, DMSO-$d_6$) δ0.93 (t, J=7.19 Hz, 3H) 1.38-1.85 (m, 6H) 2.12-2.26 (m, 2H) 2.58-2.81 (m, 2H) 2.85-3.03 (m, 2H) 3.97 (s, 2H) 4.07-4.22 (m, 1H) 4.87-5.10 (m, 1H) 6.67 (d, J=8.71 Hz, 2H) 6.80 (d, J=9.09 Hz, 2H) 7.19-7.26 (m, 2H) 7.28-7.36 (m, 2H) 7.46-7.59 (m, 2H) 7.61-7.77 (m, 2H) 8.20 (s, 1H) 8.92 (s, 1H) 12.38 (br. s., 1H)

EXAMPLE 274

4-[cis-4-(4-hydroxyphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

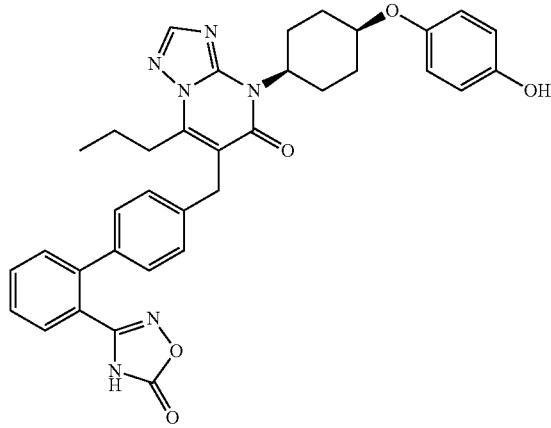 [SMILES: CCCc1c(Cc2ccc(-c3ccccc3-c3noc(=O)[nH]3)cc2)c(=O)n([C@H]2CC[C@@H](Oc3ccc(O)cc3)CC2)c2ncnn12]

A mixture of hydroxylammonium chloride (0.49 g), sodium hydrogen carbonate (0.79 g) and dimethyl sulfoxide (3 mL) was stirred at 40° C. for 30 min, 4'-({4-[cis-4-(4-{[tert-butyl(dimethyl)silyl]oxy}phenoxy)cyclohexyl]-5-oxo-7-propyl-4,5-dihydro[1,2,4]triazolo[1,5-a]pyrimidin-6-yl}methyl)biphenyl-2-carbonitrile (0.31 g) was added, and the mixture was stirred at 90° C. for 23 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (3 mL). N,N'-Carbonyldiimidazole (0.16 g) and then 1,8-diazabicyclo[5.4.0]undec-7-ene (0.15 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.028 g, 9.8%).

$^1$H NMR (300 MHz, DMSO-$d_6$) δ0.94 (t, J=7.19 Hz, 3H) 1.38-1.72 (m, 6H) 2.00-2.08 (m, 2H) 2.83-3.05 (m, 4H) 3.99 (s, 2H) 4.37-4.48 (m, 1H) 4.92-5.12 (m, 1H) 6.71 (d, J=8.71 Hz, 2H) 6.87 (d, J=8.71 Hz, 2H) 7.21-7.28 (m, 2H) 7.28-7.39 (m, 2H) 7.46-7.60 (m, 2H) 7.61-7.74 (m, 2H) 8.24 (s, 1H) 8.96 (br. s., 1H) 12.39 (br. s., 1H)

EXAMPLE 275

4-(cis-4-hydroxy-4-methylcyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

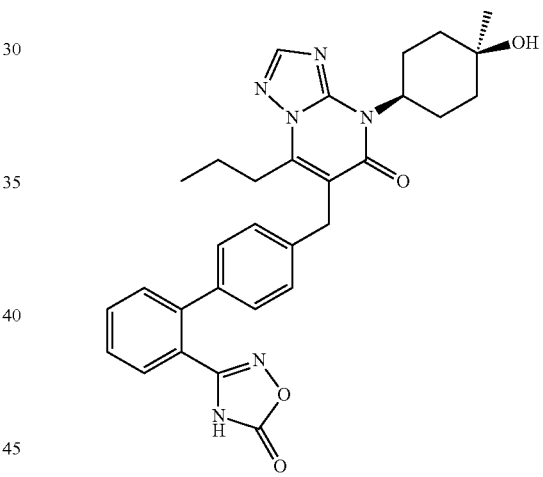

A mixture of hydroxylammonium chloride (0.89 g), sodium hydrogen carbonate (1.4 g) and dimethyl sulfoxide (3.5 mL) was stirred at 40° C. for 30 min, 4'-{[4-(cis-4-hydroxy-4-methylcyclohexyl)-5-oxo-7-propyl-4,5-dihydro[1,2,4]triazolo[1,5-a]pyrimidin-6-yl]methyl}biphenyl-2-carbonitrile (0.41 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.13 g) and then 1,8-diazabicyclo[5.4.0]undec-7-ene (0.12 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.14 g, 32%).

$^1$H NMR (300 MHz, DMSO-d$_6$) δ0.93 (t, J=7.19 Hz, 3H) 1.15 (s, 3H) 1.31-1.76 (m, 8H) 2.80-3.07 (m, 4H) 3.96 (s, 2H) 4.09 (s, 1H) 4.78-4.96 (m, 1H) 7.19-7.26 (m, 2H) 7.28-7.36 (m, 2H) 7.46-7.60 (m, 2H) 7.62-7.74 (m, 2H) 8.18 (s, 1H) 12.39 (br. s., 1H)

EXAMPLE 276

4-(trans-4-hydroxy-4-methylcyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

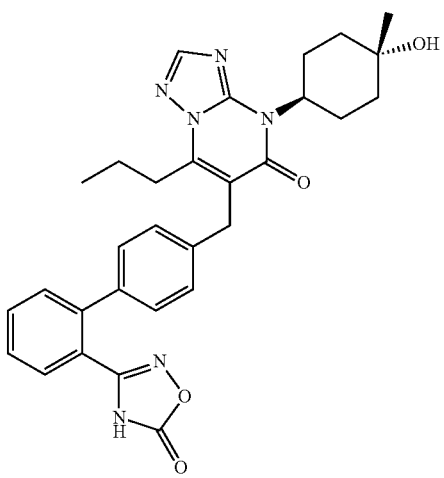 [SMILES: CCCc1c(Cc2ccc(-c3ccccc3-c3noc(=O)[nH]3)cc2)c(=O)n([C@H]2CC[C@](C)(O)CC2)c2ncnn12]

A mixture of hydroxylammonium chloride (0.76 g), sodium hydrogen carbonate (1.2 g) and dimethyl sulfoxide (3.5 mL) was stirred at 40° C. for 30 min, 4'-{[4-(trans-4-hydroxy-4-methylcyclohexyl)-5-oxo-7-propyl-4,5-dihydro[1,2,4]triazolo[1,5-a]pyrimidin-6-yl]methyl}biphenyl-2-carbonitrile (0.35 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.11 g) and then 1,8-diazabicyclo[5.4.0]undec-7-ene (0.10 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.14 g, 37%).

$^1$H NMR (300 MHz, DMSO-d$_6$) δ0.92 (t, J=7.25 Hz, 3H) 1.28 (s, 3H) 1.41-1.74 (m, 8H) 2.53-2.76 (m, 2H) 2.82-3.02 (m, 2H) 3.96 (s, 2H) 4.44 (s, 1H) 4.79-5.01 (m, 1H) 7.18-7.25 (m, 2H) 7.27-7.35 (m, 2H) 7.45-7.59 (m, 2H) 7.61-7.73 (m, 2H) 8.20 (s, 1H) 12.37 (s, 1H)

EXAMPLE 277

4-[cis-4-(4-acetylphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

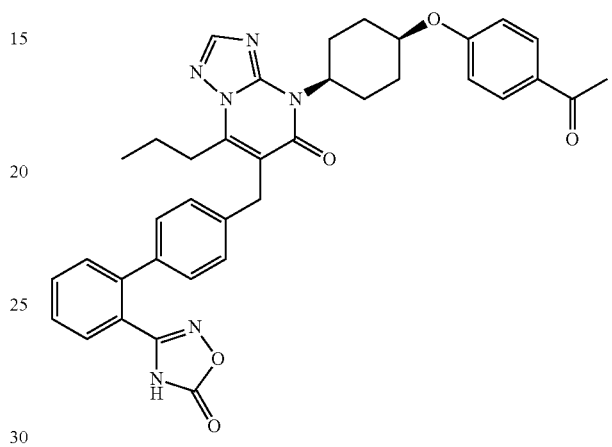

A mixture of hydroxylammonium chloride (0.88 g), sodium hydrogen carbonate (1.4 g) and dimethyl sulfoxide (3 mL) was stirred at 40° C. for 30 min, 4'-({4-[cis-4-(4-acetylphenoxy)cyclohexyl]-5-oxo-7-propyl-4,5-dihydro[1,2,4]triazolo[1,5-a]pyrimidin-6-yl}methyl)biphenyl-2-carbonitrile (0.50 g) was added, and the mixture was stirred at 90° C. for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (4 mL). N,N'-Carbonyldiimidazole (0.16 g) and then 1,8-diazabicyclo[5.4.0]undec-7-ene (0.15 mL) were added, and the mixture was stirred at room temperature for 50 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was heated under reflux in ethanol (10 mL)-20% sulfuric acid (5 mL) for 16 hr. The solvent was evaporated under reduced pressure, and the mixture was extracted with ethyl acetate. The organic layer was washed with saturated brine, and dried over anhydrous magnesium sulfate. The solvent was evaporated under reduced pressure and the residue was purified by silica gel column chromatography to give the title compound as a colorless solid (0.097 g, 17%).

$^1$H NMR (300 MHz, DMSO-d$_6$) δ0.93 (t, J=7.38 Hz, 3H) 1.46-1.62 (m, 4H) 1.66-1.85 (m, 2H) 2.01-2.18 (m, 2H) 2.46-2.56 (m, 3H) 2.78-3.01 (m, 4H) 3.97 (s, 2H) 4.72-4.88 (m, 1H) 4.93-5.12 (m, 1H) 7.12 (d, J=8.71 Hz, 2H) 7.19-7.25 (m, 2H) 7.27-7.36 (m, 2H) 7.46-7.58 (m, 2H) 7.60-7.73 (m, 2H) 7.94 (d, J=8.71 Hz, 2H) 8.23 (s, 1H) 12.37 (s, 1H)

EXAMPLE 278

4-[trans-4-(4-acetylphenoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

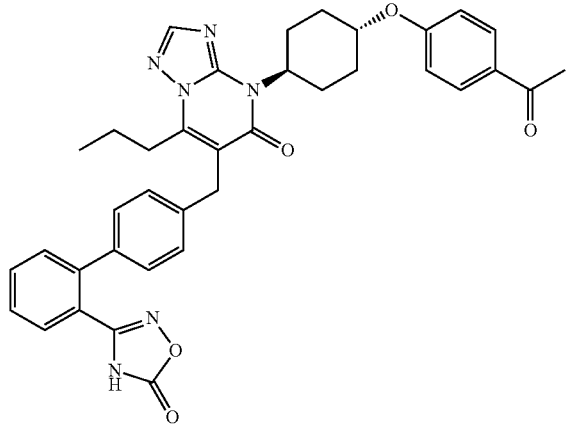 [SMILES: CCCc1c(Cc2ccc(-c3ccccc3-c3noc(=O)[nH]3)cc2)c(=O)n([C@H]2CC[C@H](Oc3ccc(C(C)=O)cc3)CC2)c2ncnn12]

A mixture of hydroxylammonium chloride (0.17 g), sodium hydrogen carbonate (0.28 g) and dimethyl sulfoxide (2 mL) was stirred at 40° C. for 30 min, 4'-({4-[trans-4-(4-acetylphenoxy)cyclohexyl]-5-oxo-7-propyl-4,5-dihydro[1,2,4]triazolo[1,5-a]pyrimidin-6-yl}methyl)biphenyl-2-carbonitrile (0.10 g) was added, and the mixture was stirred at 90° C. for 18 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.034 g) and then 1,8-diazabicyclo[5.4.0]undec-7-ene (0.032 mL) were added, and the mixture was stirred at room temperature for 1 hr. N,N'-Carbonyldiimidazole (0.034 g) and then 1,8-diazabicyclo[5.4.0]undec-7-ene (0.032 mL) were added, and the mixture was stirred at room temperature for 18 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was heated under reflux in ethanol (4 mL)-20% sulfuric acid (2 mL) for 5 hr. The solvent was evaporated under reduced pressure, and the mixture was extracted with ethyl acetate. The organic layer was washed with saturated brine, and dried over anhydrous magnesium sulfate. The solvent was evaporated under reduced pressure and the residue was purified by silica gel column chromatography and recrystallized (ethyl acetate-hexane) to give the title compound as a colorless solid (0.027 g, 24%).

$^1$H NMR (300 MHz, DMSO-d$_6$) δ0.94 (t, J=7.38 Hz, 3H) 1.47-1.66 (m, 4H) 1.70-1.85 (m, 2H) 2.15-2.32 (m, 2H) 2.44-2.54 (m, 3H) 2.67-2.85 (m, 2H) 2.89-3.01 (m, 2H) 3.97 (s, 2H) 4.45-4.62 (m, 1H) 4.90-5.08 (m, 1H) 7.10 (d, J=8.71 Hz, 2H) 7.19-7.26 (m, 2H) 7.28-7.35 (m, 2H) 7.46-7.58 (m, 2H) 7.62-7.72 (m, 2H) 7.90 (d, J=8.71 Hz, 2H) 8.21 (s, 1H) 12.39 (s, 1H)

EXAMPLE 279

4-{cis-4-[4-(1-hydroxy-1-methylethyl)phenoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

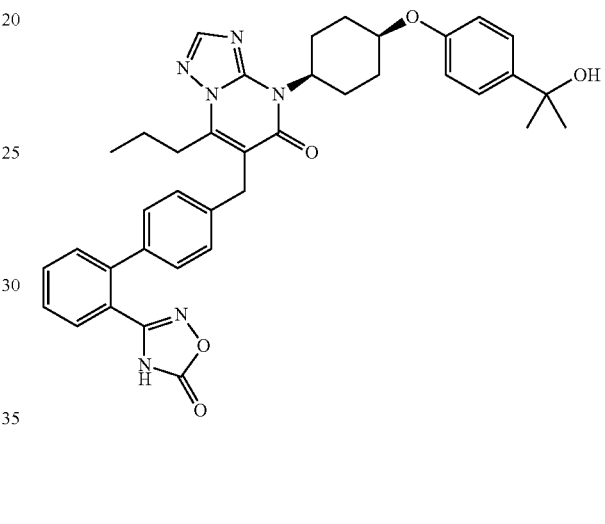

A mixture of hydroxylammonium chloride (0.36 g), sodium hydrogen carbonate (0.58 g) and dimethyl sulfoxide (3 mL) was stirred at 40° C. for 30 min, 4'-[(4-{cis-4-[4-(1-hydroxy-1-methylethyl)phenoxy]cyclohexyl}-5-oxo-7-propyl-4,5-dihydro[1,2,4]triazolo[1,5-a]pyrimidin-6-yl)methyl]biphenyl-2-carbonitrile (0.21 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.060 g) and then 1,8-diazabicyclo[5.4.0]undec-7-ene (0.055 mL) were added, and the mixture was stirred at room temperature for 1.5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.10 g, 46%).

$^1$H NMR (300 MHz, DMSO-d$_6$) δ0.93 (t, J=7.19 Hz, 3H) 1.40 (s, 6H) 1.45-1.82 (m, 6H) 1.99-2.15 (m, 2H) 2.80-3.05 (m, 4H) 3.97 (s, 2H) 4.54-4.65 (m, 1H) 4.88 (s, 1H) 4.93-5.09

(m, 1H) 6.94 (d, J=8.71 Hz, 2H) 7.19-7.26 (m, 2H) 7.28-7.42 (m, 4H) 7.47-7.58 (m, 2H) 7.62-7.73 (m, 2H) 8.23 (s, 1H) 12.38 (br. s., 1H)

EXAMPLE 280

4-{trans-4-[4-(1-hydroxy-1-methylethyl)phenoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

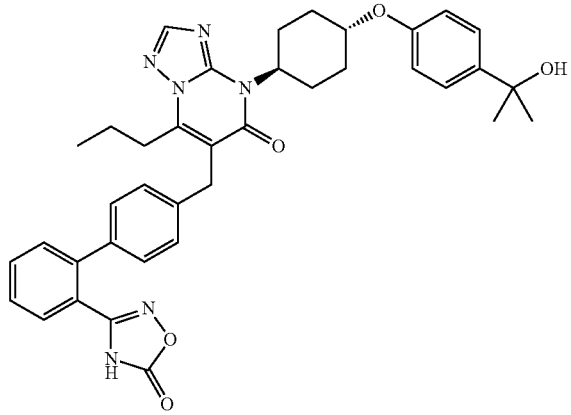 [SMILES: CCCc1c(Cc2ccc(-c3ccccc3-c3noc(=O)[nH]3)cc2)c(=O)n([C@H]2CC[C@H](Oc3ccc(C(C)(C)O)cc3)CC2)c2ncnn12]

A mixture of hydroxylammonium chloride (0.29 g), sodium hydrogen carbonate (0.47 g) and dimethyl sulfoxide (3 mL) was stirred at 40° C. for 30 min, 4'-[(4-{trans-4-[4-(1-hydroxy-1-methylethyl)phenoxy]cyclohexyl}-5-oxo-7-propyl-4,5-dihydro[1,2,4]triazolo[1,5-a]pyrimidin-6-yl)methyl]biphenyl-2-carbonitrile (0.17 g) was added, and the mixture was stirred at 90° C. for 16 hr. Hydroxylammonium chloride (0.097 g) and sodium hydrogen carbonate (0.15 g) were further added, and the mixture was stirred at 90° C. for 4 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.050 g) and then 1,8-diazabicyclo[5.4.0]undec-7-ene (0.046 mL) were added, and the mixture was stirred at room temperature for 2 hr. N,N'-Carbonyldiimidazole (0.050 g) and 1,8-diazabicyclo[5.4.0]undec-7-ene (0.046 mL) were further added, and the mixture was stirred at room temperature for 16 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.087 g, 47%).

$^1$H NMR (300 MHz, DMSO-$d_6$) δ0.93 (t, J=7.35 Hz, 3H) 1.39 (s, 6H) 1.44-1.61 (m, 4H) 1.68-1.82 (m, 2H) 2.13-2.29 (m, 2H) 2.61-2.81 (m, 2H) 2.86-3.01 (m, 2H) 3.97 (s, 2H) 4.16-4.41 (m, 1H) 4.87 (s, 1H) 4.90-5.09 (m, 1H) 6.72-6.97 (m, 2H) 7.11-7.27 (m, 2H) 7.27-7.40 (m, 4H) 7.45-7.60 (m, 2H) 7.60-7.74 (m, 2H) 8.21 (s, 1H) 12.38 (s, 1H)

EXAMPLE 281

4-[cis-4-(isoxazol-3-yloxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

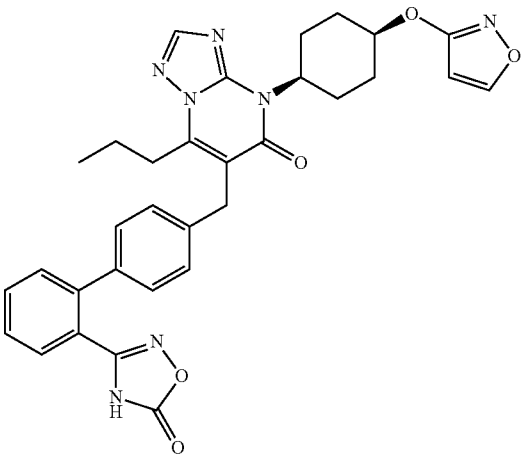 [SMILES: CCCc1c(Cc2ccc(-c3ccccc3-c3noc(=O)[nH]3)cc2)c(=O)n([C@H]2CC[C@@H](Oc3ccon3)CC2)c2ncnn12]

4'-{[4-(trans-4-Hydroxycyclohexyl)-5-oxo-7-propyl-4,5-dihydro[1,2,4]triazolo[1,5-a]pyrimidin-6-yl]methyl}biphenyl-2-carbonitrile (0.20 g), isoxazol-3-ol (0.071 g) and triphenylphosphine (0.22 g) were dissolved in tetrahydrofuran (2 mL), a solution of diisopropyl azodicarboxylate (0.44 mL, 1.9 M toluene solution) in tetrahydrofuran (1 mL) was added dropwise, and the mixture was stirred at room temperature for 18 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was added to a mixture of hydroxylammonium chloride (0.43 g), sodium hydrogen carbonate (0.7 g), and dimethyl sulfoxide (3 mL), which had been stirred at 40° C. for 30 min in advance, and the mixture was stirred at 90° C. for 18 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.081 g) and then 1,8-diazabicyclo[5.4.0]undec-7-ene (0.074 mL) were added, and the mixture was stirred at room temperature for 66 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate) to give the title compound as a colorless solid (0.055 g, 22%).

$^1$H NMR (300 MHz, DMSO-$d_6$) δ0.93 (t, J=7.35 Hz, 3H) 1.44-1.86 (m, 6H) 2.10-2.29 (m, 2H) 2.70-3.01 (m, 4H) 3.97 (s, 2H) 4.76-4.84 (m, 1H) 4.93-5.09 (m, 1H) 6.41 (d, J=1.70

Hz, 1H) 7.19-7.26 (m, 2H) 7.28-7.35 (m, 2H) 7.46-7.59 (m, 2H) 7.61-7.73 (m, 2H) 8.20 (s, 1H) 8.67 (d, J=1.88 Hz, 1H) 12.38 (s, 1H)

EXAMPLE 282

4-[trans-4-(isoxazol-3-yloxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

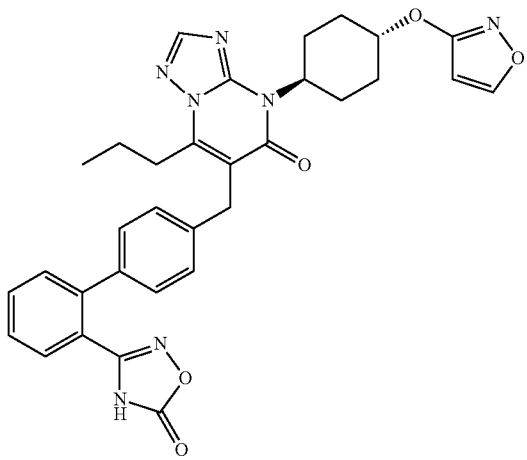 [SMILES: CCCc1c(Cc2ccc(-c3ccccc3-c3noc(=O)[nH]3)cc2)c(=O)n([C@H]2CC[C@H](Oc3ccon3)CC2)c2ncnn12]

4'-{[4-(cis-4-Hydroxycyclohexyl)-5-oxo-7-propyl-4,5-dihydro[1,2,4]triazolo[1,5-a]pyrimidin-6-yl]methyl}biphenyl-2-carbonitrile (0.50 g), isoxazol-3-ol (0.18 g) and triphenylphosphine (0.55 g) were dissolved in tetrahydrofuran (2 mL), a solution of diisopropyl azodicarboxylate (1.1 mL, 1.9 M toluene solution) in tetrahydrofuran (1 mL) was added dropwise, and the mixture was stirred at room temperature for 96 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure. The residue obtained by purification by silica gel column chromatography was added to a mixture of hydroxylammonium chloride (1.1 g), sodium hydrogen carbonate (1.7 g), and dimethyl sulfoxide (3.5 mL), which had been stirred at 40° C. for 30 min in advance, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.20 g) and then 1,8-diazabicyclo[5.4.0]undec-7-ene (0.19 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (acetone-hexane) to give the title compound as a colorless solid (0.11 g, 18%).

$^1$H NMR (300 MHz, DMSO-d$_6$) δ0.93 (t, J=7.35 Hz, 3H) 1.47-1.70 (m, 4H) 1.72-1.86 (m, 2H) 2.23-2.36 (m, 2H) 2.58-2.79 (m, 2H) 2.87-3.01 (m, 2H) 3.97 (s, 2H) 4.47-4.64 (m, 1H) 4.90-5.09 (m, 1H) 6.36 (d, J=1.70 Hz, 1H) 7.18-7.25 (m, 2H) 7.28-7.35 (m, 2H) 7.46-7.59 (m, 2H) 7.62-7.73 (m, 2H) 8.20 (s, 1H) 8.66 (d, J=1.70 Hz, 1H) 12.38 (s, 1H)

EXAMPLE 283

6-{[2'-(5-oxo-4,5-dihydro-1,2,4-oxadiazol-3-yl)biphenyl-4-yl]methyl}-7-propyl-4-[trans-4-(tetrahydro-2H-pyran-4-ylamino)cyclohexyl][1,2,4]triazolo[1,5-a]pyrimidin-5(4H)-one

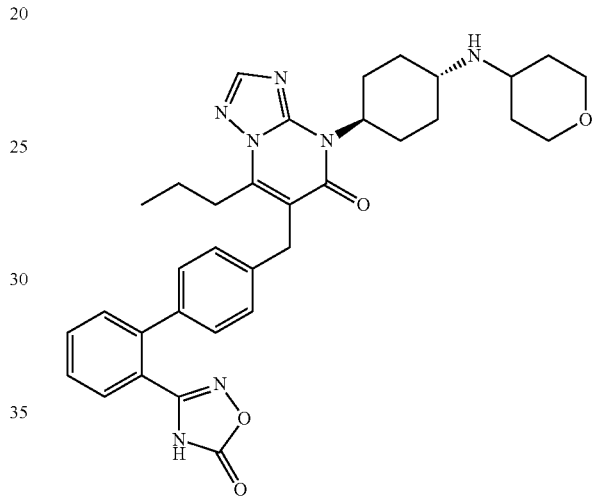

A mixture of hydroxylammonium chloride (0.47 g), sodium hydrogen carbonate (0.76 g) and dimethyl sulfoxide (2 mL) was stirred at 40° C. for 30 min, 4'-({5-oxo-7-propyl-4-[trans-4-(tetrahydro-2H-pyran-4-ylamino)cyclohexyl]-4,5-dihydro[1,2,4]triazolo[1,5-a]pyrimidin-6-yl}methyl)biphenyl-2-carbonitrile (0.25 g) was added, and the mixture was stirred at 90° C. for 16 hr. Ethyl acetate and water were added to the reaction mixture, and the mixture was extracted with ethyl acetate/2-propanol (3/1). The organic layer was dried over anhydrous sodium sulfate, and the solvent was evaporated under reduced pressure. The residue was dissolved in tetrahydrofuran (1.5 mL). N,N'-Carbonyldiimidazole (0.081 g) and then 1,8-diazabicyclo[5.4.0]undec-7-ene (0.075 mL) were added, and the mixture was stirred at room temperature for 20 hr. N,N'-Carbonyldiimidazole (0.081 g) and 1,8-diazabicyclo[5.4.0]undec-7-ene (0.075 mL) were further added, and the mixture was stirred at room temperature for 5 hr. N,N'-Carbonyldiimidazole (0.081 g) and 1,8-diazabicyclo[5.4.0]undec-7-ene (0.075 mL) were further added, and the mixture was stirred at room temperature for 20 hr. Ethyl acetate and water were added to the reaction mixture, and the mixture was adjusted to pH 6 with 1 M hydrochloric acid. The precipitate was collected by filtration and washed with methanol to give the title compound as a colorless solid (0.11 g, 41%).

$^1$H NMR (300 MHz, DMSO-d$_6$) δ0.95 (t, J=7.25 Hz, 3H) 1.31-1.78 (m, 8H) 1.78-1.97 (m, 4H) 2.59-3.12 (m, 5H) 3.19-

3.52 (m, 5H) 3.67-4.00 (m, 4H) 4.71-5.01 (m, 1H) 7.14-7.28 (m, 4H) 7.35-7.50 (m, 2H) 7.50-7.62 (m, 2H) 8.20 (s, 1H)

EXAMPLE 284

4-{trans-4-[methyl(tetrahydro-2H-pyran-4-yl)amino]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

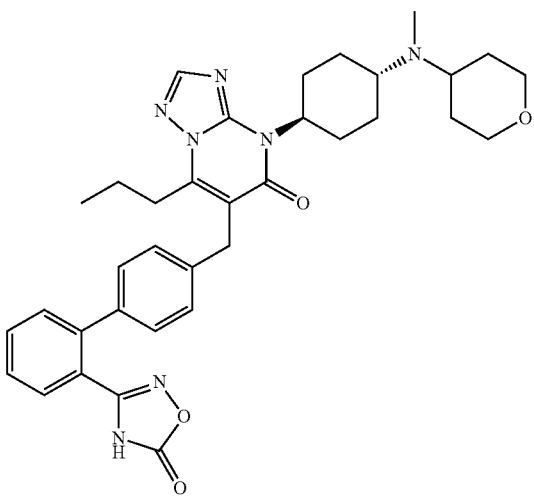 [SMILES: CCCc1c(Cc2ccc(-c3ccccc3-c3noc(=O)[nH]3)cc2)c(=O)n([C@H]2CC[C@H](N(C)C3CCOCC3)CC2)c2ncnn12]

A mixture of hydroxylammonium chloride (0.24 g), sodium hydrogen carbonate (0.40 g) and dimethyl sulfoxide (3 mL) was stirred at 40° C. for 30 min, 4'-[(4-{trans-4-[methyl(tetrahydro-2H-pyran-4-yl)amino]cyclohexyl}-5-oxo-7-propyl-4,5-dihydro[1,2,4]triazolo[1,5-a]pyrimidin-6-yl)methyl]biphenyl-2-carbonitrile (0.13 g) was added, and the mixture was stirred at 90° C. for 16 hr. Hydroxylammonium chloride (0.24 g) and sodium hydrogen carbonate (0.40 g) were added, and the mixture was further stirred at 90° C. for 6 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.046 g) and then 1,8-diazabicyclo[5.4.0]undec-7-ene (0.043 mL) were added, and the mixture was stirred at room temperature for 20 hr. Ethyl acetate and water were added to the reaction mixture, and the mixture was adjusted to pH 7 with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.044 g, 29%).

$^1$H NMR (300 MHz, DMSO-$d_6$) δ0.92 (t, J=7.38 Hz, 3H) 1.16-1.73 (m, 12H) 2.04-2.34 (m, 5H) 2.57-3.14 (m, 6H) 3.81-4.02 (m, 4H) 4.78-5.08 (m, 1H) 7.15-7.37 (m, 4H) 7.41-7.58 (m, 2H) 7.58-7.71 (m, 2H) 8.17 (s, 1H) 12.32 (br. s., 1H)

EXAMPLE 285

4-(3-methylidene-1,5-dioxaspiro[5.5]undec-9-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

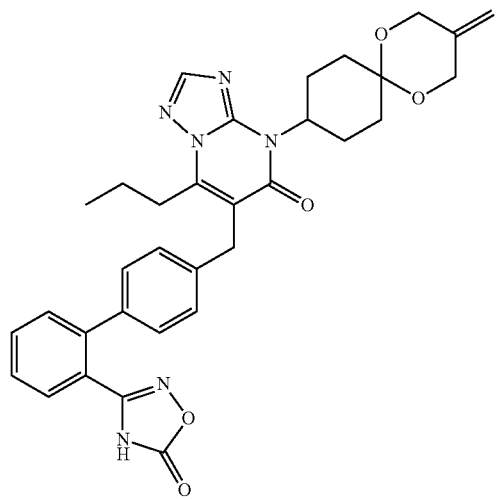 [SMILES: C=C1COC2(CCC(n3c(=O)c(Cc4ccc(-c5ccccc5-c5noc(=O)[nH]5)cc4)c(CCC)n4ncnc34)CC2)OC1]

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.20 g), 2-methylidenepropane-1,3-diol (0.067 g), 4-methylbenzenesulfonic acid (0.0072 g) and toluene (20 mL) was heated under reflux for 1.5 hr using a Dean-Stark trap. After evaporation of the solvent under reduced pressure, the residue was purified by silica gel column chromatography to give the title compound as a colorless solid (0.043 g, 19%).

$^1$H NMR (300 MHz, DMSO-$d_6$) δ0.93 (t, J=7.38 Hz, 3H) 1.31-1.67 (m, 6H) 2.23-2.40 (m, 2H) 2.61-2.85 (m, 2H) 2.86-3.00 (m, 2H) 3.96 (s, 2H) 4.29 (s, 2H) 4.32 (s, 2H) 4.87 (s, 2H) 4.90-5.08 (m, 1H) 7.16-7.25 (m, 2H) 7.26-7.36 (m, 2H) 7.44-7.59 (m, 2H) 7.61-7.75 (m, 2H) 8.20 (s, 1H) 12.37 (br. s., 1H)

EXAMPLE 286

4-(1,5-dioxaspiro[5.5]undec-9-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

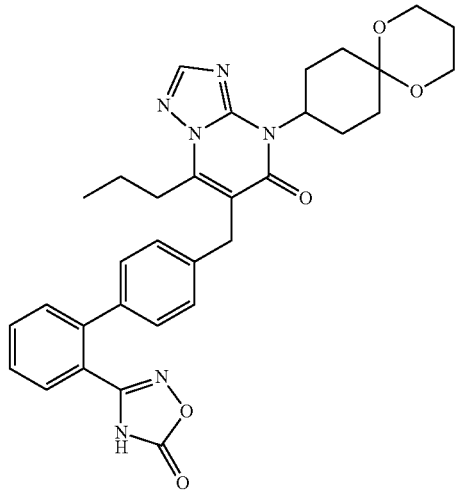 [SMILES: CCCc1c(Cc2ccc(-c3ccccc3-c3noc(=O)[nH]3)cc2)c(=O)n(C2CCC3(CC2)OCCCO3)c2ncnn12]

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.20 g), propane-1,3-diol (0.058 g), 4-methylbenzenesulfonic acid (0.0072 g) and toluene (20 mL) was heated under reflux for 3 hr using a Dean-Stark trap. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.087 g, 39%).

$^1$H NMR (300 MHz, DMSO-$d_6$) δ0.93 (t, J=7.38 Hz, 3H) 1.11-1.70 (m, 8H) 2.23-2.44 (m, 2H) 2.59-2.80 (m, 2H) 2.85-3.01 (m, 2H) 3.76-3.90 (m, 4H) 3.95 (s, 2H) 4.80-5.05 (m, 1H) 7.17-7.26 (m, 2H) 7.27-7.37 (m, 2H) 7.45-7.59 (m, 2H) 7.61-7.74 (m, 2H) 8.19 (s, 1H) 12.37 (s, 1H)

EXAMPLE 287

4-(3-hydroxy-1,5-dioxaspiro[5.5]undec-9-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

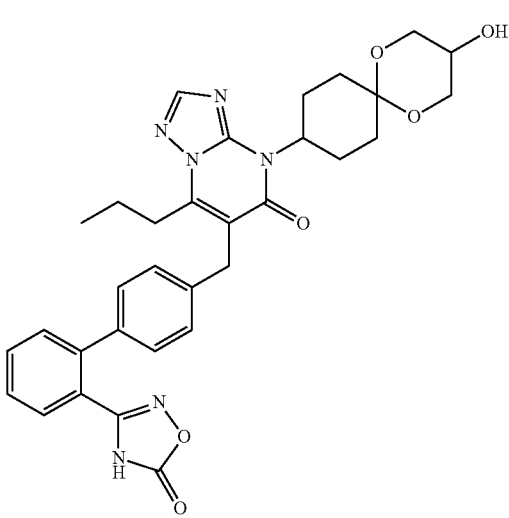 [SMILES: CCCc1c(Cc2ccc(-c3ccccc3-c3noc(=O)[nH]3)cc2)c(=O)n(C2CCC3(CC2)OCC(O)CO3)c2ncnn12]

A mixture of hydroxylammonium chloride (1.4 g), sodium hydrogen carbonate (2.3 g) and dimethyl sulfoxide (3 mL) was stirred at 40° C. for 30 min, 4'-{[4-(3-{[tert-butyl(dimethyl)silyl]oxy}-1,5-dioxaspiro[5.5]undec-9-yl)-5-oxo-7-propyl-4,5-dihydro[1,2,4]triazolo[1,5-a]pyrimidin-6-yl]methyl}biphenyl-2-carbonitrile (0.91 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.27 g) and then 1,8-diazabicyclo[5.4.0]undec-7-ene (0.24 mL) were added, and the mixture was stirred at room temperature for 1.5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (3.4 mL, 1.0 M tetrahydrofuran solution) was added and the mixture was stirred at 70° C. for 3.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.426 g, 51%).

$^1$H NMR (300 MHz, DMSO-$d_6$) δ0.92 (t, J=7.19 Hz, 3H) 1.21-1.69 (m, 6H) 2.02-2.15 (m, 2H) 2.54-2.79 (m, 2H) 2.86-3.00 (m, 2H) 3.44-3.63 (m, 3H) 3.74-3.91 (m, 2H) 3.95 (s, 2H) 4.62-5.03 (m, 2H) 7.19-7.25 (m, 2H) 7.27-7.34 (m, 2H) 7.45-7.59 (m, 2H) 7.61-7.72 (m, 2H) 8.15-8.22 (m, 1H) 12.37 (br. s., 1H)

EXAMPLE 288

4-[cis-4-(2-hydroxyethoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

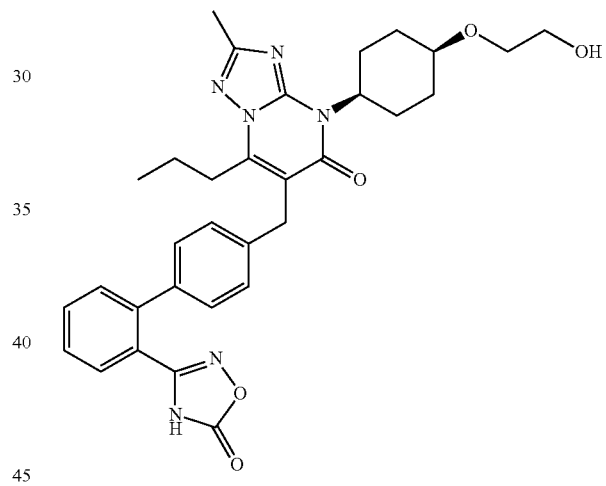

A mixture of 4'-({4-[cis-4-(2-hydroxyethoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.44 g), 2,6-lutidine (0.15 mL), tert-butyl(dimethyl)silyl trifluoromethanesulfonate (0.29 mL) and tetrahydrofuran (5 mL) was stirred at room temperature for 1.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the obtained residue was added to a mixture of hydroxylammonium chloride (0.87 g), sodium hydrogen carbonate (1.4 g), and dimethyl sulfoxide (8 mL), which had been stirred at 40° C. for 30 min in advance, and the mixture was stirred at 90° C. for 24 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (2 mL). N,N'-Carbonyldiimidazole (0.059 g) and then 1,8-diazabicyclo[5.4.0]undec-7-ene (0.055 mL) were added, and the mixture was stirred at room temperature for 5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (0.77 mL, 1.0 M tetrahydrofuran solution) was added, and the mixture was stirred at 70° C. for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.051 g, 10%).

$^1$H NMR (300 MHz, DMSO-$d_6$) δ0.92 (t, J=7.19 Hz, 3H) 1.33-1.63 (m, 6H) 1.91-2.05 (m, 2H) 2.35 (s, 3H) 2.68-2.96 (m, 4H) 3.42 (t, J=5.30 Hz, 2H) 3.50-3.62 (m, 3H) 3.93 (s, 2H) 4.43-4.51 (m, 1H) 4.77-4.97 (m, 1H) 7.18-7.25 (m, 2H) 7.26-7.32 (m, 2H) 7.45-7.59 (m, 2H) 7.61-7.74 (m, 2H) 12.36 (br. s., 1H)

EXAMPLE 289

4-[trans-4-(2-hydroxyethoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

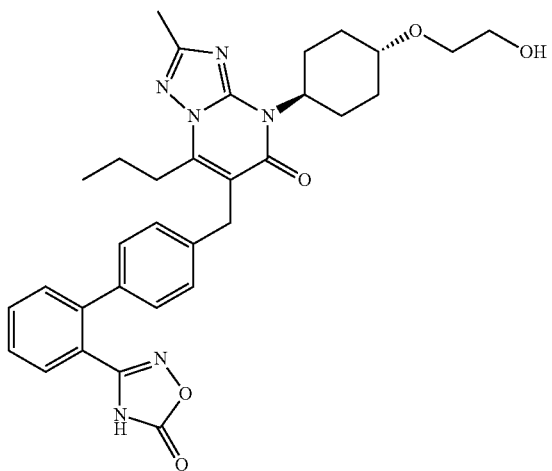 [SMILES: CCCc1c(Cc2ccc(-c3ccccc3-c3noc(=O)[nH]3)cc2)c(=O)n([C@H]2CC[C@H](OCCO)CC2)c2nc(C)nn12]

A mixture of 4'-({4-[trans-4-(2-hydroxyethoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.60 g), 2,6-lutidine (0.20 mL), tert-butyl(dimethyl)silyl trifluoromethanesulfonate (0.39 mL) and tetrahydrofuran (5 mL) was stirred at room temperature for 1.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the obtained residue was added to a mixture of hydroxylammonium chloride (1.1 g), sodium hydrogen carbonate (1.9 g), and dimethyl sulfoxide (8 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (3 mL). N,N'-Carbonyldiimidazole (0.091 g) and then 1,8-diazabicyclo[5.4.0]undec-7-ene (0.083 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (1.1 mL, 1.0 M tetrahydrofuran solution) was added, and the mixture was stirred at 70° C. for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.11 g, 17%).

$^1$H NMR (300 MHz, DMSO-$d_6$) δ0.92 (t, J=7.19 Hz, 3H) 1.21-1.38 (m, 2H) 1.43-1.60 (m, 2H) 1.62-1.77 (m, 2H) 2.04-2.19 (m, 2H) 2.35 (s, 3H) 2.52-2.67 (m, 2H) 2.80-2.95 (m, 2H) 3.24-3.39 (m, 1H) 3.47 (s, 4H) 3.93 (s, 2H) 4.55 (br. s., 1H) 4.76-4.97 (m, 1H) 7.17-7.25 (m, 2H) 7.25-7.32 (m, 2H) 7.45-7.59 (m, 2H) 7.60-7.74 (m, 2H) 12.40 (br. s., 1H)

EXAMPLE 290

4-(2,2-dimethyl-3-oxo-1,4-dioxaspiro[4.5]dec-8-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

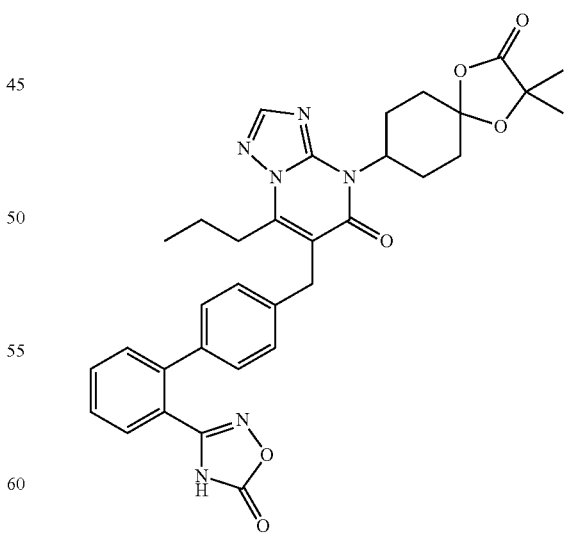

To a solution of 2-hydroxy-2-methylpropanoic acid (0.17 g) and pyridine (0.42 mL) in tetrahydrofuran (5 mL) were added trimethylsilylbromide (0.68 mL) and then N,N-dimethylaminopyridine (0.040 g), and the mixture was stirred at room temperature for 5 hr. Hexane was added to the reaction mixture, and the precipitate was filtered. The filtrate was concentrated under reduced pressure and the obtained residue (0.25 g), trimethylsilyltrifluoromethanesulfonate (0.21 mL), 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.21 g) and dichloromethane (5 mL) were mixed under an argon atmosphere at −78° C., and the mixture was stirred at room temperature for 15 hr. Trimethylsilyltrifluoromethanesulfonate (0.21 mL) was added, and the mixture was further stirred at room temperature for 3 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.037 g, 15%).

$^1$H NMR (300 MHz, DMSO-$d_6$) δ0.93 (t, J=7.19 Hz, 3H) 1.43 (s, 3H) 1.47 (s, 3H) 1.50-1.62 (m, 2H) 1.65-1.80 (m, 2H) 1.85-2.10 (m, 4H) 2.70-3.02 (m, 4H) 3.96 (s, 2H) 4.89-5.16 (m, 1H) 7.17-7.25 (m, 2H) 7.28-7.36 (m, 2H) 7.46-7.59 (m, 2H) 7.61-7.72 (m, 2H) 8.21 (s, 0.5H) 8.22 (s, 0.5H) 12.36 (br. s., 1H)

EXAMPLE 291

4-[trans-4-(2-hydroxyethoxy)-4-methylcyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

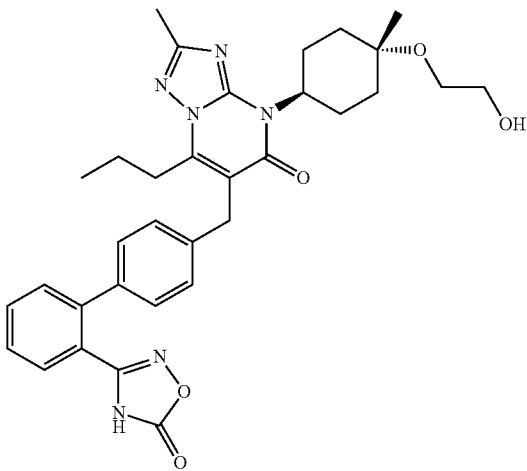 [SMILES: CCCc1c(Cc2ccc(-c3ccccc3-c3noc(=O)[nH]3)cc2)c(=O)n([C@H]2CC[C@](C)(OCCO)CC2)c2nc(C)nn12]

A mixture of 4'-({4-[trans-4-(2-hydroxyethoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.28 g), 2,6-lutidine (0.12 mL), tert-butyl(dimethyl)silyl trifluoromethanesulfonate (0.24 mL) and tetrahydrofuran (3 mL) was stirred at room temperature for 1.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the obtained residue was added to a mixture of hydroxylammonium chloride (0.55 g), sodium hydrogen carbonate (0.89 g), and dimethyl sulfoxide (10 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (1 mL). N,N'-Carbonyldiimidazole (0.024 g) and then 1,8-diazabicyclo[5.4.0]undec-7-ene (0.022 mL) were added, and the mixture was stirred at room temperature for 5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (8 mL), tetrabutylammonium fluoride (0.32 mL, 1.0 M tetrahydrofuran solution) was added, and the mixture was stirred at 70° C. for 16 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.024 g, 13%).

$^1$H NMR (300 MHz, DMSO-$d_6$) δ0.92 (t, J=7.38 Hz, 3H) 1.32 (s, 3H) 1.42-1.67 (m, 6H) 1.69-1.85 (m, 2H) 2.36 (s, 3H) 2.55-2.78 (m, 2H) 2.81-2.95 (m, 2H) 3.36-3.52 (m, 4H) 3.93 (s, 2H) 4.41-4.53 (m, 1H) 4.76-4.98 (m, 1H) 7.18-7.25 (m, 2H) 7.26-7.33 (m, 2H) 7.45-7.59 (m, 2H) 7.61-7.74 (m, 2H) 12.36 (br. s., 1H)

EXAMPLE 292

4-(1,4-dioxaspiro[4.5]dec-8-yl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

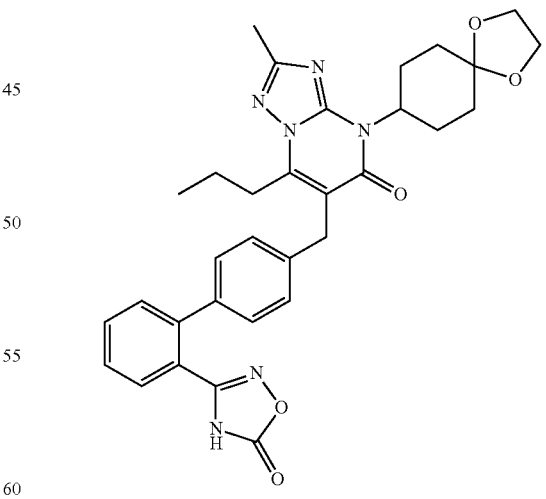

A mixture of hydroxylammonium chloride (1.9 g), sodium hydrogen carbonate (3.2 g) and dimethyl sulfoxide (15 mL) was stirred at 40° C. for 30 min, 4'-{[4-(1,4-dioxaspiro[4.5]dec-8-yl)-2-methyl-5-oxo-7-propyl-4,5-dihydro[1,2,4]triazolo[1,5-a]pyrimidin-6-yl]methyl}biphenyl-2-carbonitrile (1.0 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.37 g) and then 1,8-diazabicyclo[5.4.0]undec-7-ene (0.34 mL) were added, and the mixture was stirred at room temperature 19 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.83 g, 74%).

$^1$H NMR (300 MHz, DMSO-$d_6$) δ0.92 (t, J=7.38 Hz, 3H) 1.44-1.86 (m, 8H) 2.36 (s, 3H) 2.66-2.97 (m, 4H) 3.82-3.98 (m, 6H) 4.78-5.05 (m, 1H) 7.18-7.25 (m, 2H) 7.26-7.33 (m, 2H) 7.44-7.59 (m, 2H) 7.61-7.74 (m, 2H) 12.36 (s, 1H)

EXAMPLE 293

6-{[2'-(5-oxo-4,5-dihydro-1,2,4-oxadiazol-3-yl)biphenyl-4-yl]methyl}-7-propyl-4-(tetrahydrospiro[cyclohexane-1,2'-furo[3,4-d][1,3]dioxol]-4-yl)[1,2,4]triazolo[1,5-a]pyrimidin-5(4H)-one

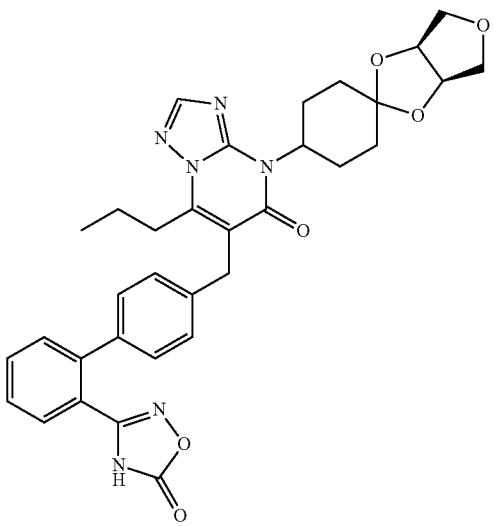 [SMILES: CCCc1c(Cc2ccc(-c3ccccc3-c3noc(=O)[nH]3)cc2)c(=O)n(C2CCC3(CC2)O[C@H]2COC[C@H]2O3)c2ncnn12]

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.30 g), tetrahydrofuran-3,4-diol (0.11 g), 4-methylbenzenesulfonic acid (0.011 g) and toluene (20 mL) was heated under reflux for 6 hr using a Dean-Stark trap. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.23 g, 68%).

$^1$H NMR (300 MHz, DMSO-$d_6$) δ0.93 (t, J=7.19 Hz, 3H) 1.40-1.98 (m, 8H) 2.67-3.00 (m, 4H) 3.32-3.41 (m, 2H) 3.87 (dd, J=25.75, 10.60 Hz, 2H) 3.95 (s, 2H) 4.69-4.85 (m, 2H) 4.86-5.06 (m, 1H) 7.18-7.25 (m, 2H) 7.27-7.33 (m, 2H) 7.44-7.58 (m, 2H) 7.61-7.74 (m, 2H) 8.20 (s, 1H) 12.37 (s, 1H)

EXAMPLE 294

4-[2-(hydroxymethyl)-1,4-dioxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

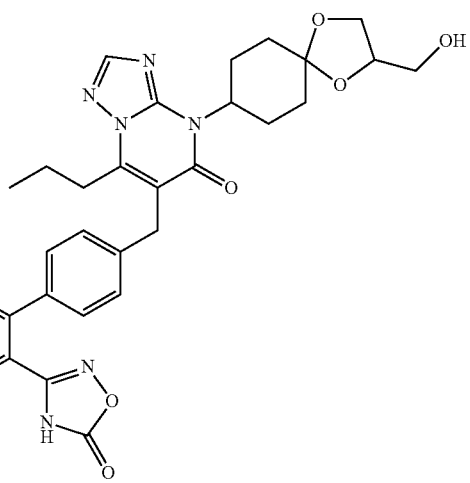

A mixture of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.30 g), 1,2-dihydroxyethyl acetate (0.15 g), 4-methylbenzenesulfonic acid (0.011 g) and toluene (20 mL) was heated under reflux for 24 hr using a Dean-Stark trap. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was dissolved in 1 M aqueous sodium hydroxide solution (3 mL), tetrahydrofuran (3 mL) and methanol (3 mL), and the mixture was stirred at 50° C. for 15 hr. The solvent was evaporated under reduced pressure, the residue was adjusted to pH 7 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and HPLC to give the title compound as a colorless solid (0.081 g, 23%).

$^1$H NMR (300 MHz, DMSO-$d_6$) δ0.93 (t, J=7.19 Hz, 3H) 1.44-1.96 (m, 8H) 2.62-3.03 (m, 4H) 3.38-3.77 (m, 3H) 3.95 (s, 2H) 3.97-4.18 (m, 2H) 4.71-4.88 (m, 1H) 4.89-5.07 (m, 1H) 7.18-7.25 (m, 2H) 7.26-7.35 (m, 2H) 7.44-7.59 (m, 2H) 7.59-7.78 (m, 2H) 8.18 (s, 0.5H) 8.19 (s, 0.5H) 12.37 (br. s., 1H)

EXAMPLE 295

2-methyl-4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

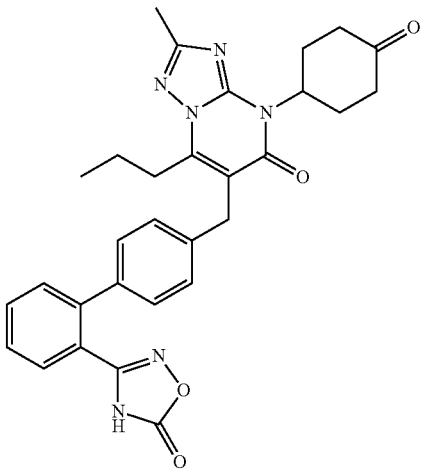 [SMILES: CCCc1c(Cc2ccc(-c3ccccc3-c3noc(=O)[nH]3)cc2)c(=O)n(C2CCC(=O)CC2)c2nc(C)nn12]

A mixture of 4-(1,4-dioxaspiro[4.5]dec-8-yl)-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.76 g), 6M hydrochloric acid (3 mL) and tetrahydrofuran (4 mL) was stirred at 70° C. for 22 hr. The reaction mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate) to give the title compound as a colorless solid (0.31 g, 44%).

$^1$H NMR (300 MHz, DMSO-$d_6$) δ0.92 (t, J=7.35 Hz, 3H) 1.43-1.62 (m, 2H) 1.92-2.08 (m, 2H) 2.24-2.34 (m, 2H) 2.36 (s, 3H) 2.55-2.74 (m, 2H) 2.76-2.98 (m, 4H) 3.95 (s, 2H) 5.30-5.54 (m, 1H) 7.18-7.25 (m, 2H) 7.27-7.34 (m, 2H) 7.46-7.59 (m, 2H) 7.62-7.72 (m, 2H) 12.38 (s, 1H)

EXAMPLE 296

4-[trans-4-(2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

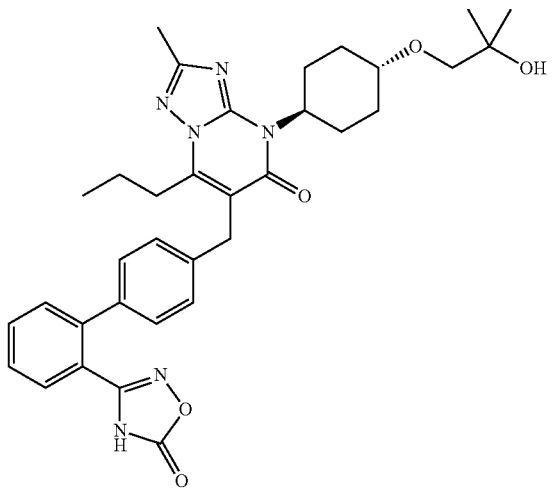 [SMILES: CCCc1c(Cc2ccc(-c3ccccc3-c3noc(=O)[nH]3)cc2)c(=O)n([C@H]2CC[C@H](OCC(C)(C)O)CC2)c2nc(C)nn12]

A mixture of hydroxylammonium chloride (0.44 g), sodium hydrogen carbonate (0.72 g) and dimethyl sulfoxide (5 mL) was stirred at 40° C. for 30 min, 4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.23 g) was added, and the mixture was stirred at 90° C. for 21 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.084 g) and then 1,8-diazabicyclo[5.4.0]undec-7-ene (0.078 mL) were added, and the mixture was stirred at room temperature for 18 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.10 g, 39%).

$^1$H NMR (300 MHz, DMSO-$d_6$) δ0.92 (t, J=7.25 Hz, 3H) 1.07 (s, 6H) 1.19-1.38 (m, 2H) 1.43-1.59 (m, 2H) 1.60-1.75 (m, 2H) 1.99-2.18 (m, 2H) 2.35 (s, 3H) 2.42-2.66 (m, 2H) 2.81-2.93 (m, 2H) 3.20 (s, 2H) 3.25-3.37 (m, 1H) 3.93 (s, 2H) 4.23 (s, 1H) 4.77-4.96 (m, 1H) 7.17-7.24 (m, 2H) 7.26-7.34 (m, 2H) 7.45-7.59 (m, 2H) 7.61-7.72 (m, 2H) 12.37 (br. s., 1H)

EXAMPLE 297

4-[cis-4-hydroxy-4-(methoxymethyl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

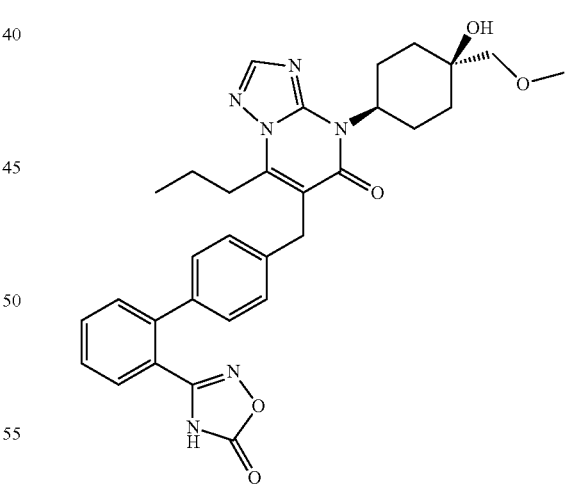

A mixture of hydroxylammonium chloride (0.73 g), sodium hydrogen carbonate (1.1 g) and dimethyl sulfoxide (5 mL) was stirred at 40° C. for 30 min, 4'-({4-[cis-4-hydroxy-4-(methoxymethyl)cyclohexyl]-5-oxo-7-propyl-4,5-dihydro[1,2,4]triazolo[1,5-a]pyrimidin-6-yl}methyl)biphenyl-2-carbonitrile (0.35 g) was added, and the mixture was stirred at 90° C. for 22 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (3 mL). N,N'-Carbonyldiimidazole (0.13 g) and then 1,8-diazabicyclo[5.4.0]undec-7-ene (0.12 mL) were added, and the mixture was stirred at room temperature for 20 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.15 g, 39%).

$^1$H NMR (300 MHz, DMSO-$d_6$) δ0.93 (t, J=7.25 Hz, 3H) 1.34-1.67 (m, 8H) 2.83-3.01 (m, 4H) 3.13 (s, 2H) 3.28 (s, 3H) 3.96 (s, 2H) 4.23 (s, 1H) 4.75-4.92 (m, 1H) 7.17-7.26 (m, 2H) 7.28-7.34 (m, 2H) 7.47-7.59 (m, 2H) 7.61-7.73 (m, 2H) 8.18 (s, 1H) 12.38 (s, 1H)

EXAMPLE 298

4-[4-(2-hydroxy-2-methylpropoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

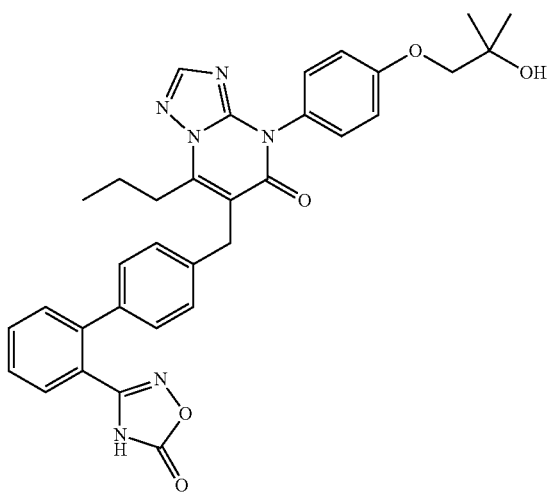 [SMILES: CCCc1c(Cc2ccc(-c3ccccc3-c3noc(=O)[nH]3)cc2)c(=O)n(-c2ccc(OCC(C)(C)O)cc2)c2ncnn12]

A mixture of hydroxylammonium chloride (0.28 g), sodium hydrogen carbonate (0.45 g) and dimethyl sulfoxide (2 mL) was stirred at 40° C. for 30 min, 4'-({4-[4-(2-hydroxy-2-methylpropoxy)phenyl]-5-oxo-7-propyl-4,5-dihydro[1,2,4]triazolo[1,5-a]pyrimidin-6-yl}methyl)biphenyl-2-carbonitrile (0.14 g) was added, and the mixture was stirred at 90° C. for 22 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.054 g) and then 1,8-diazabicyclo[5.4.0]undec-7-ene (0.049 mL) were added, and the mixture was stirred at room temperature for 60 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.052 g, 32%).

$^1$H NMR (300 MHz, DMSO-$d_6$) δ0.96 (t, J=7.25 Hz, 3H) 1.23 (s, 6H) 1.49-1.70 (m, 2H) 2.89-3.07 (m, 2H) 3.78 (s, 2H) 4.00 (s, 2H) 4.68 (s, 1H) 7.07 (d, J=8.85 Hz, 2H) 7.23 (d, J=8.10 Hz, 2H) 7.31-7.41 (m, 4H) 7.46-7.60 (m, 2H) 7.62-7.73 (m, 2H) 8.06 (s, 1H) 12.39 (br. s., 1H)

EXAMPLE 299

4-[trans-4-(2-hydroxy-1-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

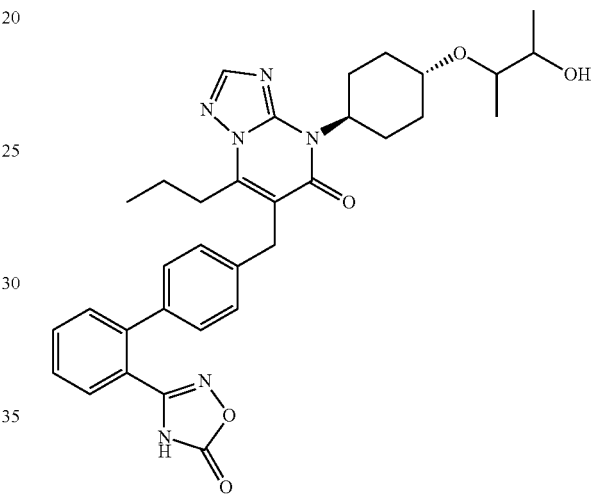

A mixture of 4'-{[5-oxo-4-(4-oxocyclohexyl)-7-propyl-4,5-dihydro[1,2,4]triazolo[1,5-a]pyrimidin-6-yl]methyl}biphenyl-2-carbonitrile (1.0 g), butane-2,3-diol (0.38 g), 4-methylbenzenesulfonic acid (0.042 g) and toluene (20 mL) was heated under reflux for 9 hr using a Dean-Stark trap. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure, and the residue was dissolved in tetrahydrofuran (20 mL), sodium cyanoborohydride (0.67 g) and boron trifluoride etherate (1.3 mL) were added, and the mixture was heated under reflux for 7 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. 40% of the residue obtained by purification by silica gel column chromatography was mixed with 2,6-lutidine (0.20 mL), tert-butyl(dimethyl)silyl trifluoromethanesulfonate (0.40 mL) and tetrahydrofuran (2 mL), and the mixture was stirred at room temperature 7 hr. The reaction mixture was added to 1 M hydrochloric acid, and the mixture was extracted with ethyl acetate. The organic layer was washed with saturated aqueous sodium hydrogen carbonate solution and then with saturated brine, and dried over anhydrous magnesium sulfate. The solvent was evaporated under reduced pressure, the obtained residue was added to a mixture of hydroxylammonium chloride (0.45 g), sodium hydrogen carbonate (0.73 g), and dimethyl sulfoxide (3 mL), which had been stirred at 40° C. for 30 min in advance, and the mixture was stirred at 90° C. for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure. The residue obtained by purification by silica gel column chromatography was dissolved in tetrahydrofuran (2 mL). N,N'-Carbonyldiimidazole (0.060 g) and then 1,8-diazabicyclo[5.4.0]undec-7-ene (0.055 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (2 mL), tetrabutylammonium fluoride (0.75 mL, 1.0 M tetrahydrofuran solution) was added, and the mixture was heated under reflux for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.067 g, 13%).

$^1$H NMR (300 MHz, DMSO-$d_6$) δ0.93 (t, J=7.35 Hz, 3H) 0.96-1.02 (m, 2.4H) 1.05 (d, J=6.22 Hz, 3.6H) 1.21-1.39 (m, 2H) 1.43-1.62 (m, 2H) 1.62-1.77 (m, 2H) 2.00-2.14 (m, 2H) 2.41-2.69 (m, 2H) 2.86-2.99 (m, 2H) 3.22-3.62 (m, 3H) 3.95 (s, 2H) 4.33 (d, J=4.52 Hz, 0.4H) 4.41 (d, J=5.09 Hz, 0.6H) 4.78-5.03 (m, 1H) 7.17-7.25 (m, 2H) 7.27-7.34 (m, 2H) 7.45-7.59 (m, 2H) 7.61-7.74 (m, 2H) 8.18 (s, 1H) 12.38 (s, 1H)

EXAMPLE 300

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

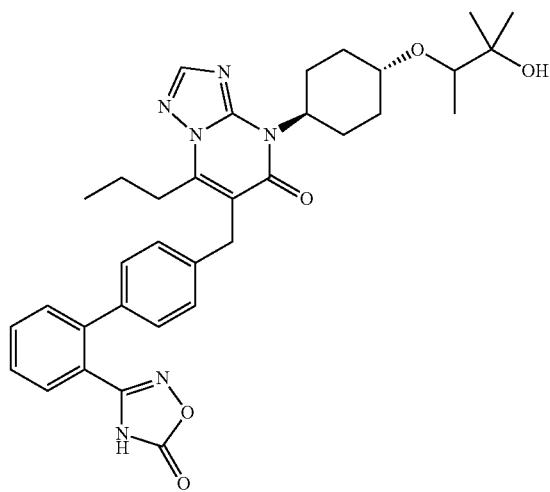 [SMILES: CCCc1c(Cc2ccc(-c3ccccc3-c3noc(=O)[nH]3)cc2)c(=O)n([C@H]2CC[C@H](OC(C)C(C)(C)O)CC2)c2ncnn12]

A mixture of hydroxylammonium chloride (0.36 g), sodium hydrogen carbonate (0.58 g) and dimethyl sulfoxide (3 mL) was stirred at 40° C. for 30 min, 4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (0.19 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.070 g) and then 1,8-diazabicyclo[5.4.0]undec-7-ene (0.065 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.12 g, 58%).

$^1$H NMR (300 MHz, DMSO-$d_6$) δ0.93 (t, J=7.35 Hz, 3H) 1.00 (s, 3H) 1.04 (d, J=6.22 Hz, 3H) 1.08 (s, 3H) 1.22-1.41 (m, 2H) 1.44-1.61 (m, 2H) 1.62-1.76 (m, 2H) 1.94-2.19 (m, 2H) 2.52-2.69 (m, 2H) 2.85-3.00 (m, 2H) 3.25 (q, J=6.22 Hz, 1H) 3.34-3.47 (m, 1H) 3.96 (s, 2H) 4.06 (s, 1H) 4.78-5.02 (m, 1H) 7.18-7.26 (m, 2H) 7.27-7.36 (m, 2H) 7.46-7.59 (m, 2H) 7.61-7.75 (m, 2H) 8.18 (s, 1H) 12.38 (br. s., 1H)

EXAMPLE 301

4-[trans-4-(2-hydroxy-1,2-dimethylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one

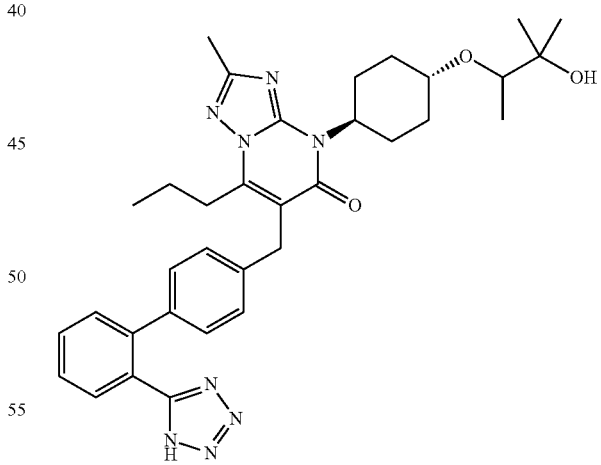

A mixture of 4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.24 g), trimethylsilylazide (1.4 g), dibutyltinoxide (0.052 g) and toluene (15 mL) was heated under reflux for 134 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (1.0 mL, 1.0 M tetrahydrofuran solution) was added, and the mixture was stirred at 70° C. for 4 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate) to give the title compound as a colorless solid (0.070 g, 26%).

$^1$H NMR (300 MHz, DMSO-$d_6$) δ0.90 (t, J=7.25 Hz, 3H) 1.00 (s, 3H) 1.03 (d, J=6.22 Hz, 3H) 1.08 (s, 3H) 1.20-1.77 (m, 6H) 2.00-2.18 (m, 2H) 2.35 (s, 3H) 2.53-2.66 (m, 2H) 2.76-2.91 (m, 2H) 3.19-3.29 (m, 1H) 3.35-3.45 (m, 1H) 3.87 (s, 2H) 4.06 (s, 1H) 4.65-4.96 (m, 1H) 6.78-8.04 (m, 9H)

EXAMPLE 302

4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

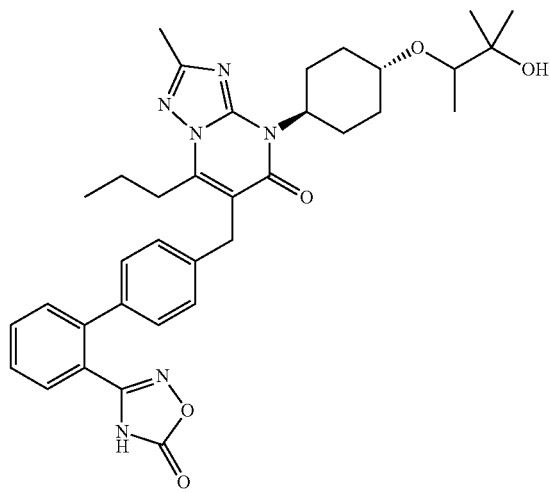 [SMILES: CCCc1c(Cc2ccc(-c3ccccc3-c3noc(=O)[nH]3)cc2)c(=O)n([C@H]2CC[C@H](OC(C)C(C)(C)O)CC2)c2nc(C)nn12]

A mixture of hydroxylammonium chloride (0.26 g), sodium hydrogen carbonate (0.42 g) and dimethyl sulfoxide (2 mL) was stirred at 40° C. for 1.5 hr, 4'-({4-[trans-4-(2-hydroxy-1,2-dimethylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.14 g) was added, and the mixture was stirred at 90° C. for 14 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.044 g) and then 1,8-diazabicyclo[5.4.0]undec-7-ene (0.041 mL) were added, and the mixture was stirred at room temperature for 4 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.078 g, 50%).

$^1$H NMR (300 MHz, DMSO-$d_6$) δ0.92 (t, J=7.25 Hz, 3H) 1.00 (s, 3H) 1.03 (d, J=6.22 Hz, 3H) 1.08 (s, 3H) 1.21-1.42 (m, 2H) 1.45-1.59 (m, 2H) 1.61-1.75 (m, 2H) 1.95-2.17 (m, 2H) 2.35 (s, 3H) 2.43-2.69 (m, 2H) 2.81-2.96 (m, 2H) 3.26 (q, J=6.22 Hz, 1H) 3.33-3.47 (m, 1H) 3.93 (s, 2H) 4.06 (s, 1H) 4.73-4.96 (m, 1H) 7.16-7.25 (m, 2H) 7.26-7.33 (m, 2H) 7.44-7.59 (m, 2H) 7.61-7.73 (m, 2H) 12.37 (s, 1H)

EXAMPLE 303

4-[trans-4-(2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

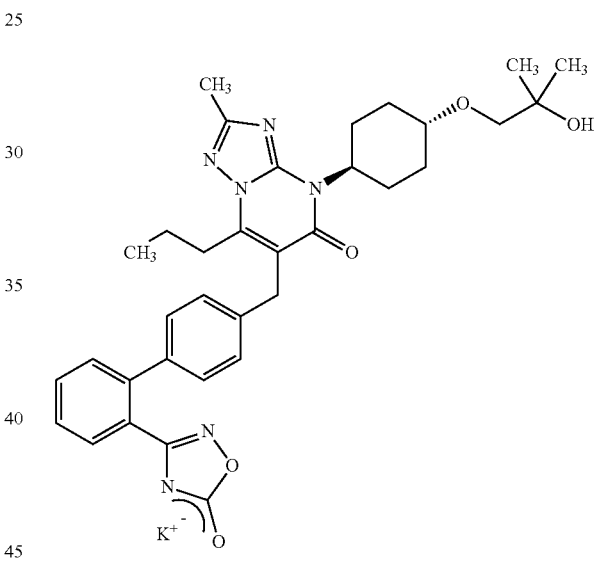

To a solution of 4-[trans-4-(2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.047 g) in tetrahydrofuran (2 mL) was added 0.1 M aqueous potassium hydroxide solution (0.77 mL), and the solvent was evaporated under reduced pressure. The residue was washed with diisopropyl ether to give the title compound as a colorless solid (0.036 g, 71%).

$^1$H NMR (300 MHz, DMSO-$d_6$) δ0.95 (t, J=7.25 Hz, 3H) 1.07 (s, 6H) 1.18-1.38 (m, 2H) 1.49-1.75 (m, 4H) 2.01-2.17 (m, 2H) 2.35 (s, 3H) 2.42-2.67 (m, 2H) 2.81-2.97 (m, 2H) 3.20 (s, 2H) 3.24-3.37 (m, 1H) 3.88 (s, 2H) 4.23 (s, 1H) 4.77-4.96 (m, 1H) 7.11-7.18 (m, 2H) 7.18-7.23 (m, 2H) 7.24-7.50 (m, 4H)

EXAMPLE 304

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

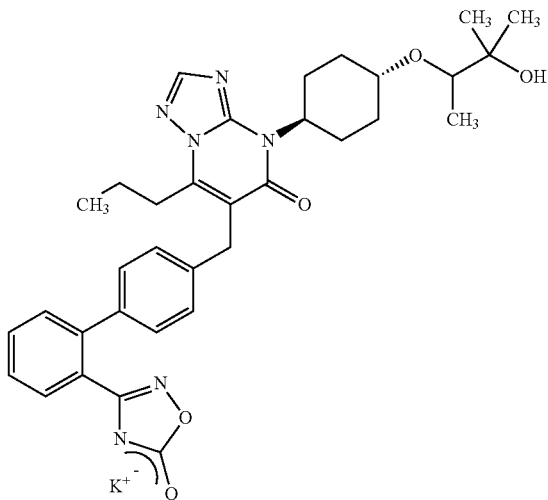 [SMILES: CCCc1c(Cc2ccc(-c3ccccc3C3=NOC(O)N3)cc2)c(=O)n([C@H]2CC[C@H](OC(C)C(C)(C)O)CC2)c2ncnn12 ; [K+]]

To a solution of 4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.095 g) in tetrahydrofuran (2 mL) was added 0.1 M aqueous potassium hydroxide solution (1.5 mL), and the solvent was evaporated under reduced pressure. The residue was washed with diisopropyl ether to give the title compound as a colorless solid (0.086 g, 85%).

$^1$H NMR (300 MHz, DMSO-$d_6$) δ 0.96 (t, J=7.35 Hz, 3H) 0.99 (s, 3H) 1.04 (d, J=6.03 Hz, 3H) 1.08 (s, 3H) 1.19-1.42 (m, 2H) 1.49-1.77 (m, 4H) 1.92-2.17 (m, 2H) 2.52-2.68 (m, 2H) 2.85-3.02 (m, 2H) 3.24 (q, J=6.22 Hz, 1H) 3.33-3.46 (m, 1H) 3.90 (s, 2H) 4.06 (s, 1H) 4.75-5.01 (m, 1H) 7.13-7.51 (m, 8H) 8.16 (s, 1H)

EXAMPLE 305

4-[trans-4-(2-hydroxy-1-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

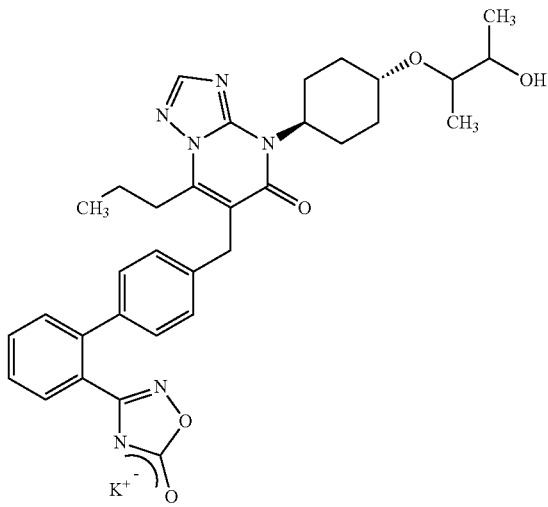 [SMILES: CCCc1c(Cc2ccc(-c3ccccc3C3=NOC(O)N3)cc2)c(=O)n([C@H]2CC[C@H](OC(C)C(C)O)CC2)c2ncnn12 ; [K+]]

To a solution of 4-[trans-4-(2-hydroxy-1-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.039 g) in tetrahydrofuran (2 mL) was added 0.1 M aqueous potassium hydroxide solution (0.65 mL), and the solvent was evaporated under reduced pressure. The residue was washed with diisopropyl ether to give the title compound as a colorless solid (0.025 g, 61%).

$^1$H NMR (300 MHz, DMSO-$d_6$) δ 0.89-1.09 (m, 9H) 1.20-1.38 (m, 2H) 1.50-1.76 (m, 4H) 1.94-2.14 (m, 2H) 2.41-2.69 (m, 2H) 2.88-3.02 (m, 2H) 3.21-3.58 (m, 3H) 3.90 (s, 2H) 4.33 (d, J=4.52 Hz, 0.5H) 4.41 (d, J=5.09 Hz, 0.5H) 4.80-5.00 (m, 1H) 7.12-7.51 (m, 8H) 8.16 (s, 1H)

EXAMPLE 306

4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

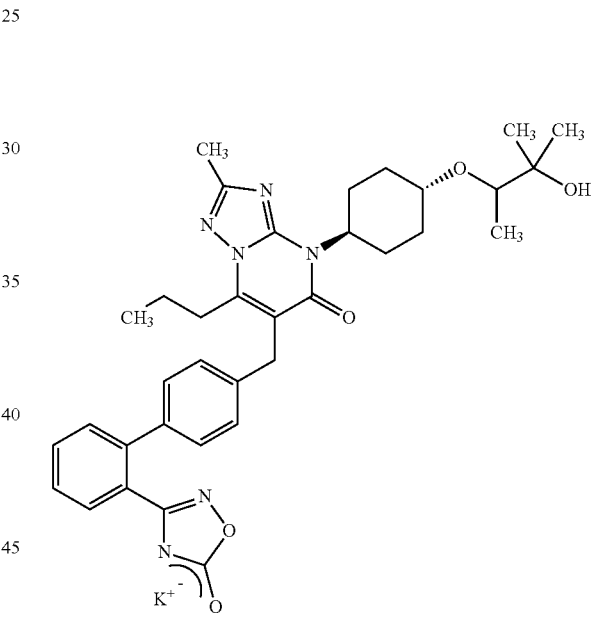

To a solution of 4-[trans-4-(2-hydroxy-1,2-dimethylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.057 g) in tetrahydrofuran (2 mL) was added 0.1 M aqueous potassium hydroxide solution (0.91 mL), and the solvent was evaporated under reduced pressure. The residue was washed with diisopropyl ether to give the title compound as a colorless solid (0.031 g, 52%).

$^1$H NMR (300 MHz, DMSO-$d_6$) δ 0.93 (t, J=7.38 Hz, 3H) 0.99 (s, 3H) 1.03 (d, J=6.06 Hz, 3H) 1.08 (s, 3H) 1.17-1.37 (m, 2H) 1.46-1.60 (m, 2H) 1.61-1.74 (m, 2H) 1.93-2.15 (m, 2H) 2.35 (s, 3H) 2.46-2.67 (m, 2H) 2.82-2.96 (m, 2H) 3.26 (q,

J=6.06 Hz, 1H) 3.34-3.43 (m, 1H) 3.91 (s, 2H) 4.06 (s, 1H) 4.75-4.96 (m, 1H) 7.15-7.28 (m, 4H) 7.37-7.52 (m, 2H) 7.52-7.64 (m, 2H)

EXAMPLE 307

4-[trans-4-(2-hydroxy-1,2-dimethylpropoxy)cyclohexyl]-7-propyl-6-{[2'-(1H-tetrazol-5-yl)biphenyl-4-yl]methyl}[1,2,4]triazolo[1,5-a]pyrimidin-5(4H)-one

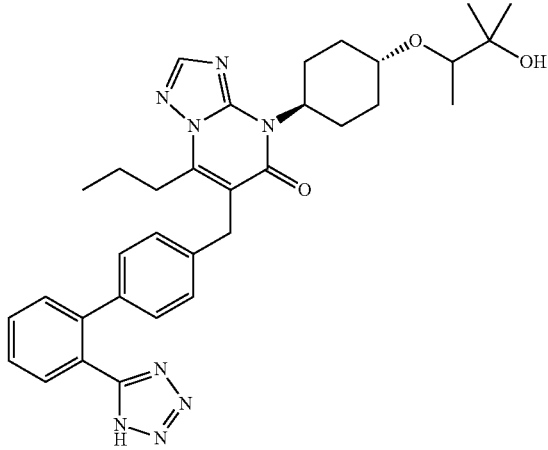 [SMILES: CCCc1c(Cc2ccc(-c3ccccc3-c3nnn[nH]3)cc2)c(=O)n([C@H]2CC[C@H](OC(C)C(C)(C)O)CC2)c2ncnn12]

A mixture of 4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (0.33 g), trimethylsilylazide (1.9 g), dibutyltinoxide (0.14 g) and toluene (15 mL) was stirred at 110° C. for 88 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (2.3 mL, 1.0 M tetrahydrofuran solution) was added, and the mixture was stirred at 70° C. for 1 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-diisopropyl ether) to give the title compound as a colorless solid (0.10 g, 30%).

$^1$H NMR (300 MHz, DMSO-d$_6$) δ 0.91 (t, J=7.25 Hz, 3H) 0.99 (s, 3H) 1.03 (d, J=6.03 Hz, 3H) 1.08 (s, 3H) 1.21-1.77 (m, 6H) 1.94-2.17 (m, 2H) 2.53-2.68 (m, 2H) 2.83-2.98 (m, 2H) 3.18-3.29 (m, 1H) 3.35-3.45 (m, 1H) 3.90 (s, 2H) 4.06 (s, 1H) 4.78-4.98 (m, 1H) 6.77-7.78 (m, 9H) 8.17 (s, 1H)

EXAMPLE 308

4-[trans-4-(2-hydroxy-1,2-dimethylpropoxy)-4-methylcyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

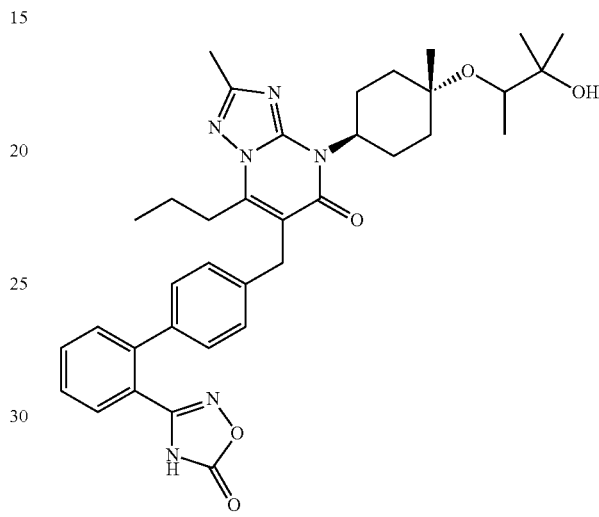

A mixture of hydroxylammonium chloride (0.30 g), sodium hydrogen carbonate (0.48 g) and dimethyl sulfoxide (2 mL) was stirred at 40° C. for 30 min, 4'-({4-[trans-4-(2-hydroxy-1,2-dimethylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.17 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.057 g) and then 1,8-diazabicyclo[5.4.0]undec-7-ene (0.052 mL) were added, and the mixture was stirred at room temperature for 1.5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and HPLC to give the title compound as a colorless solid (0.11 g, 68%).

$^1$H NMR (300 MHz, DMSO-d$_6$) δ 0.91 (t, J=7.19 Hz, 3H) 0.99 (s, 3H) 1.06 (d, J=6.06 Hz, 3H) 1.08 (s, 3H) 1.33 (s, 3H) 1.38-1.83 (m, 8H) 2.35 (s, 3H) 2.55-2.98 (m, 4H) 3.48 (q, J=5.68 Hz, 1H) 3.93 (s, 2H) 4.11-6.19 (m, 2H) 7.16-7.36 (m, 4H) 7.46-7.60 (m, 2H) 7.62-7.74 (m, 2H) 12.37 (s, 1H)

EXAMPLE 309

4-[trans-4-(2-hydroxy-1,2-dimethylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one potassium salt

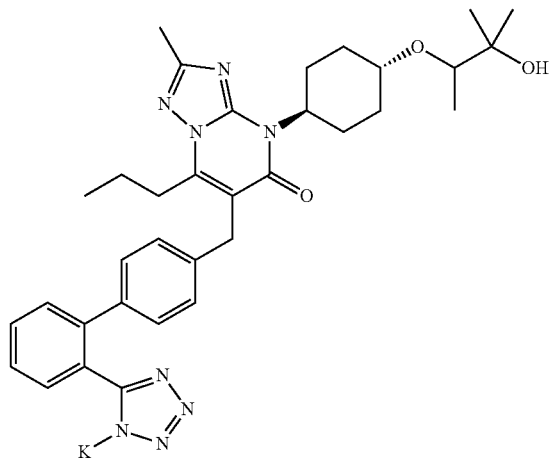

To a solution of 4-[trans-4-(2-hydroxy-1,2-dimethylpropoxy)cyclohexyl]-2-methyl-7-propyl-6-{[2'-(1H-tetrazol-5-yl)biphenyl-4-yl]methyl}[1,2,4]triazolo[1,5-a]pyrimidin-5(4H)-one (0.041 g) in tetrahydrofuran (2 mL) was added 0.1 M aqueous potassium hydroxide solution (0.67 mL), and the solvent was evaporated under reduced pressure. The residue was washed with diisopropyl ether to give the title compound as a colorless solid (0.035 g, 80%).

$^1$H NMR (300 MHz, DMSO-$d_6$) δ0.94 (t, J=7.25 Hz, 3H) 0.99 (s, 3H) 1.03 (d, J=6.22 Hz, 3H) 1.08 (s, 3H) 1.15-1.37 (m, 2H) 1.47-1.74 (m, 4H) 1.92-2.17 (m, 2H) 2.35 (s, 3H) 2.45-2.66 (m, 2H) 2.80-2.93 (m, 2H) 3.20-3.29 (m, 1H) 3.35-3.43 (m, 1H) 3.83 (s, 2H) 4.06 (s, 1H) 4.72-4.96 (m, 1H) 6.95-7.10 (m, 4H) 7.23-7.42 (m, 3H) 7.45-7.55 (m, 1H)

EXAMPLE 310

4-[trans-4-(2-hydroxy-1,2-dimethylpropoxy)-4-methylcyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

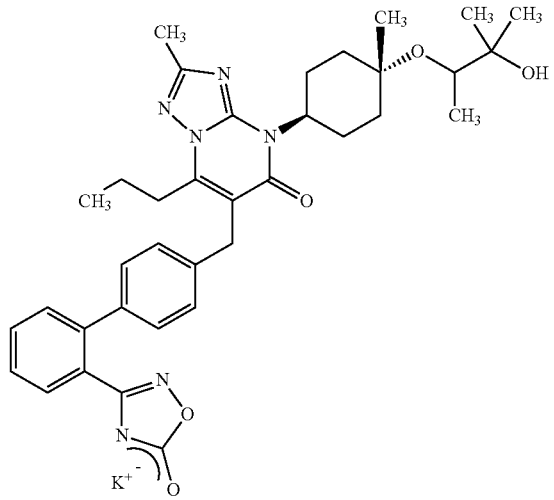 [SMILES: CCCc1c(Cc2ccc(-c3ccccc3C3=NOC(O)N3)cc2)c(=O)n([C@H]2CC[C@](C)(OC(C)C(C)(C)O)CC2)c2nc(C)nn12 ; [K+]]

To a solution of 4-[trans-4-(2-hydroxy-1,2-dimethylpropoxy)-4-methylcyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.044 g) in tetrahydrofuran (2 mL) was added 0.1 M aqueous potassium hydroxide solution (0.69 mL), and the solvent was evaporated under reduced pressure. The residue was washed with diisopropyl ether to give the title compound as a colorless solid (0.034 g, 71%).

$^1$H NMR (300 MHz, DMSO-$d_6$) δ0.95 (t, J=7.35 Hz, 3H) 0.99 (s, 3H) 1.06 (d, J=6.22 Hz, 3H) 1.08 (s, 3H) 1.33 (s, 3H) 1.42-1.85 (m, 8H) 2.35 (s, 3H) 2.54-2.81 (m, 2H) 2.82-2.99 (m, 2H) 3.48 (q, J=6.03 Hz, 1H) 3.88 (s, 2H) 3.94 (s, 1H) 4.76-5.00 (m, 1H) 7.09-7.53 (m, 8H)

EXAMPLE 311

4-[trans-4-(2-hydroxy-1,2-dimethylpropoxy)cyclohexyl]-7-propyl-6-{[2'-(1H-tetrazol-5-yl)biphenyl-4-yl]methyl}[1,2,4]triazolo[1,5-a]pyrimidin-5(4H)-one potassium salt

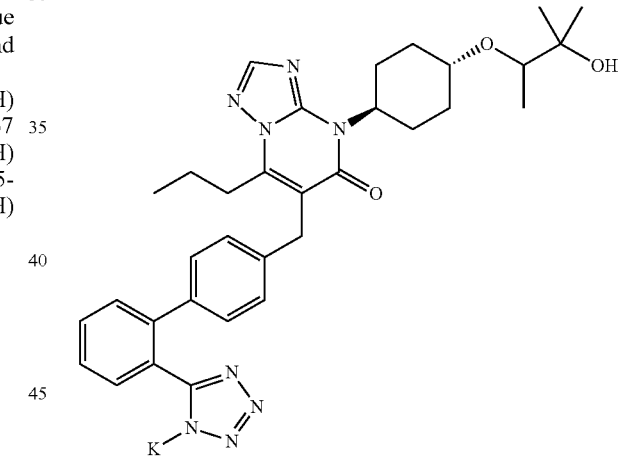

To a solution of 4-[trans-4-(2-hydroxy-1,2-dimethylpropoxy)cyclohexyl]-7-propyl-6-{[2'-(1H-tetrazol-5-yl)biphenyl-4-yl]methyl}[1,2,4]triazolo[1,5-a]pyrimidin-5(4H)-one (0.068 g) in tetrahydrofuran (2 mL) was added 0.1 M aqueous potassium hydroxide solution (1.1 mL), and the solvent was evaporated under reduced pressure. The residue was washed with diisopropyl ether to give the title compound as a colorless solid (0.062 g, 85%).

$^1$H NMR (300 MHz, DMSO-$d_6$) δ0.95 (t, J=7.19 Hz, 3H) 0.99 (s, 3H) 1.03 (d, J=6.06 Hz, 3H) 1.08 (s, 3H) 1.13-1.40 (m, 2H) 1.49-1.80 (m, 4H) 1.92-2.17 (m, 2H) 2.40-2.69 (m, 2H) 2.85-2.98 (m, 2H) 3.24 (q, J=6.06 Hz, 1H) 3.29-3.43 (m, 1H) 3.86 (s, 2H) 4.06 (s, 1H) 4.76-4.98 (m, 1H) 6.98-7.03 (m, 2H) 7.04-7.10 (m, 2H) 7.24-7.41 (m, 3H) 7.44-7.54 (m, 1H) 8.16 (s, 1H)

EXAMPLE 312

4-[trans-4-(2-hydroxy-1,2-dimethylpropoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

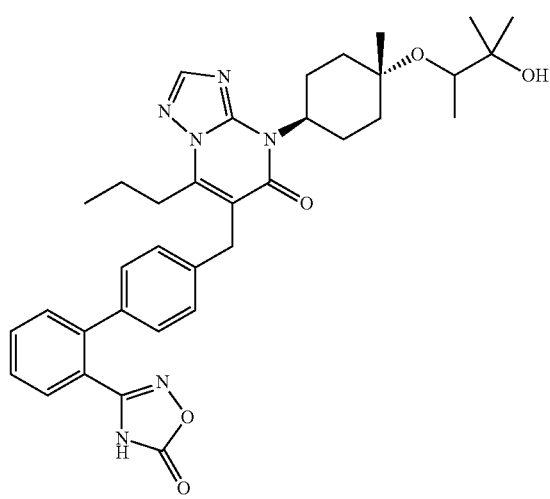 [SMILES: CCCc1c(Cc2ccc(-c3ccccc3-c3noc(=O)[nH]3)cc2)c(=O)n([C@H]2CC[C@](C)(OC(C)C(C)(C)O)CC2)c2ncnn12]

A mixture of hydroxylammonium chloride (0.91 g), sodium hydrogen carbonate (1.4 g) and dimethyl sulfoxide (5 mL) was stirred at 40° C. for 30 min, 4'-({4-[trans-4-(2-hydroxy-1,2-dimethylpropoxy)-4-methylcyclohexyl]-5-oxo-7-propyl-4,5-dihydro[1,2,4]triazolo[1,5-a]pyrimidin-6-yl}methyl)biphenyl-2-carbonitrile (0.50 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.17 g) and then 1,8-diazabicyclo[5.4.0]undec-7-ene (0.15 mL) were added, and the mixture was stirred at room temperature for 1.5 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate) to give the title compound as a colorless solid (0.26 g, 47%).

$^1$H NMR (300 MHz, DMSO-$d_6$) δ 0.93 (t, J=7.35 Hz, 3H) 0.99 (s, 3H) 1.03-1.10 (m, 6H) 1.34 (s, 3H) 1.45-1.85 (m, 8H) 2.56-2.77 (m, 2H) 2.87-3.00 (m, 2H) 3.48 (q, J=6.03 Hz, 1H) 3.94 (s, 1H) 3.96 (s, 2H) 4.80-5.07 (m, 1H) 7.17-7.26 (m, 2H) 7.27-7.36 (m, 2H) 7.47-7.59 (m, 2H) 7.61-7.75 (m, 2H) 8.21 (s, 1H) 12.38 (br. s., 1H)

EXAMPLE 313

4-[trans-4-(2-hydroxy-1,2-dimethylpropoxy)-4-methylcyclohexyl]-7-propyl-6-{[2'-(1H-tetrazol-5-yl)biphenyl-4-yl]methyl}[1,2,4]triazolo[1,5-a]pyrimidin-5(4H)-one

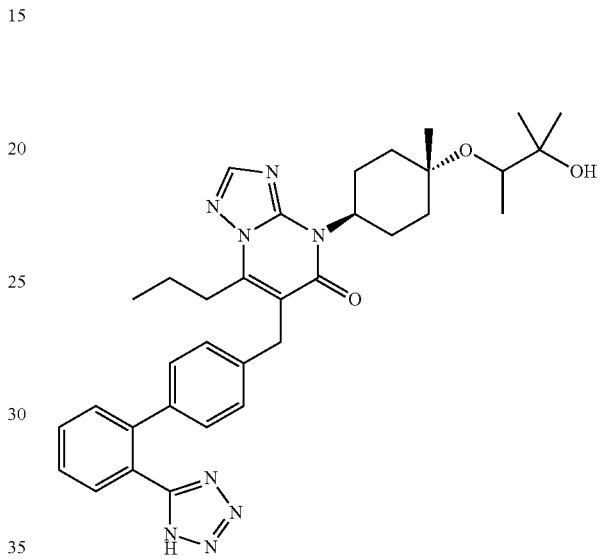

A mixture of 4'-({4-[trans-4-(2-hydroxy-1,2-dimethylpropoxy)-4-methylcyclohexyl]-5-oxo-7-propyl-4,5-dihydro[1,2,4]triazolo[1,5-a]pyrimidin-6-yl}methyl)biphenyl-2-carbonitrile (0.50 g), trimethylsilylazide (3.0 g), dibutyltinoxide (0.10 g) and toluene (10 mL) was stirred at 110° C. for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (10 mL). Tetrabutylammonium fluoride (3.5 mL, 1.0 M tetrahydrofuran solution) was added, and the mixture was heated under reflux for 1.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-diisopropyl ether) to give the title compound as a colorless solid (0.30 g, 56%).

$^1$H NMR (300 MHz, DMSO-$d_6$) δ 0.91 (t, J=7.25 Hz, 3H) 0.99 (s, 3H) 1.03-1.10 (m, 6H) 1.34 (s, 3H) 1.43-1.84 (m, 8H) 2.54-2.76 (m, 2H) 2.82-2.95 (m, 2H) 3.48 (q, J=6.15 Hz, 1H) 3.90 (s, 2H) 3.94 (s, 1H) 4.82-5.01 (m, 1H) 6.59-7.83 (m, 9H) 8.20 (s, 1H)

EXAMPLE 314

4-[trans-4-(2-hydroxy-1,2-dimethylpropoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

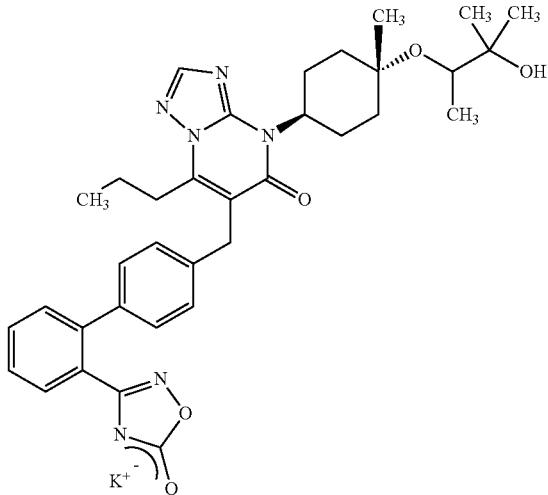 [SMILES: CCCc1c(Cc2ccc(-c3ccccc3C3=NOC(O)N3)cc2)c(=O)n([C@H]2CC[C@](C)(OC(C)C(C)(C)O)CC2)c2ncnn12 ; [K+]]

To a solution of 4-[trans-4-(2-hydroxy-1,2-dimethylpropoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.12 g) in tetrahydrofuran (5 mL) was added 0.1 M aqueous potassium hydroxide solution (2.0 mL), and the solvent was evaporated under reduced pressure. The residue was washed with diisopropyl ether to give the title compound as a colorless solid (0.11 g, 80%).

$^1$H NMR (300 MHz, DMSO-$d_6$) δ0.95 (t, J=7.35 Hz, 3H) 0.99 (s, 3H) 1.06 (d, J=6.22 Hz, 3H) 1.08 (s, 3H) 1.34 (s, 3H) 1.48-1.85 (m, 8H) 2.56-2.76 (m, 2H) 2.89-3.01 (m, 2H) 3.48 (q, J=6.03 Hz, 1H) 3.92 (s, 2H) 3.94 (s, 1H) 4.82-5.02 (m, 1H) 7.15-7.26 (m, 4H) 7.28-7.41 (m, 2H) 7.42-7.53 (m, 2H) 8.19 (s, 1H)

EXAMPLE 315

4-[4-hydroxy-4-(tetrahydro-2H-pyran-4-yl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

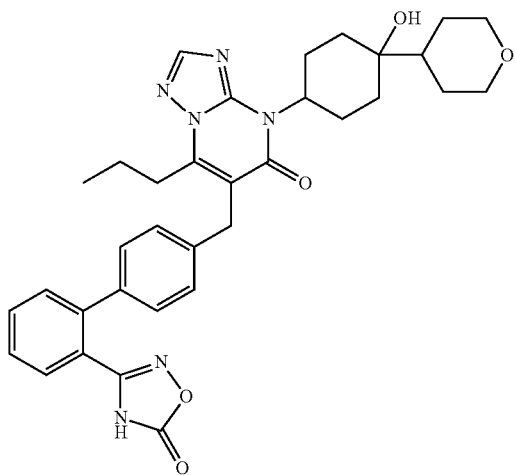 [SMILES: CCCc1c(Cc2ccc(-c3ccccc3-c3noc(=O)[nH]3)cc2)c(=O)n(C2CCC(O)(C3CCOCC3)CC2)c2ncnn12]

A mixture of hydroxylammonium chloride (0.24 g), sodium hydrogen carbonate (0.38 g) and dimethyl sulfoxide (3 mL) was stirred at 40° C. for 30 min, 4'-({4-[4-hydroxy-4-(tetrahydro-2H-pyran-4-yl)cyclohexyl]-5-oxo-7-propyl-4,5-dihydro[1,2,4]triazolo[1,5-a]pyrimidin-6-yl}methyl)biphenyl-2-carbonitrile (0.12 g) was added, and the mixture was stirred at 90° C. for 24 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.045 g) and then 1,8-diazabicyclo[5.4.0]undec-7-ene (0.042 mL) were added, and the mixture was stirred at room temperature for 3 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.020 g, 14%).

$^1$H NMR (300 MHz, DMSO-$d_6$) δ0.93 (t, J=7.25 Hz, 3H) 1.26-1.47 (m, 7H) 1.48-1.72 (m, 6H) 2.83-3.04 (m, 4H) 3.16-3.40 (m, 2H) 3.83-3.99 (m, 5H) 4.74-4.95 (m, 1H) 7.18-7.26 (m, 2H) 7.27-7.34 (m, 2H) 7.46-7.59 (m, 2H) 7.61-7.73 (m, 2H) 8.18 (s, 1H) 12.38 (br. s., 1H)

EXAMPLE 316

6-{[2'-(5-oxo-4,5-dihydro-1,2,4-oxadiazol-3-yl)biphenyl-4-yl]methyl}-7-propyl-4-[trans-4-(4H-1,2,4-triazol-3-ylmethoxy)cyclohexyl][1,2,4]triazolo[1,5-a]pyrimidin-5(4H)-one

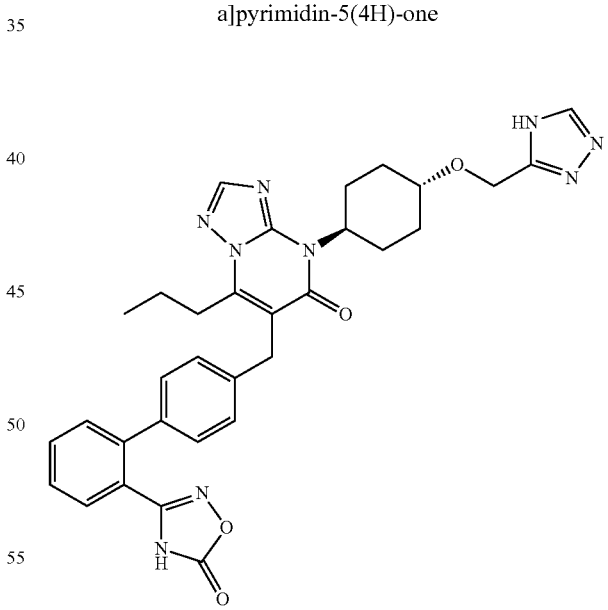

A mixture of tert-butyl 2-{[(trans-4-{6-[(2'-cyanobiphenyl-4-yl)methyl]-5-oxo-7-propyl[1,2,4]triazolo[1,5-a]pyrimidin-4(5H)-yl}cyclohexyl)oxy]acetyl}hydrazinecarboxylate (0.69 g), trifluoroacetic acid (1 mL) and toluene (7 mL) was stirred at room temperature for 1 hr. Trifluoroacetic acid (5 mL) was further added, and the mixture was stirred at 50° C. for 2 hr. 1 M Aqueous sodium hydroxide solution was added to the reaction mixture, and the mixture was extracted with ethyl acetate. The organic layer was washed with saturated brine, and dried over anhydrous magnesium sulfate. The solvent was evaporated under reduced pressure, and the residue was mixed with ethyl imidoformate hydrochloride (0.18 g), triethylamine (5 mL) and ethanol (20 mL), and the mixture was heated under reflux for 118 hr. The solvent was evaporated under reduced pressure, the residue obtained by silica gel column chromatography was added to a mixture of hydroxylammonium chloride (0.18 g), sodium hydrogen carbonate (0.30 g), and dimethyl sulfoxide (1 mL), which had been stirred at 40° C. for 30 min in advance, and the mixture was stirred at 90° C. for 24 hr. Ethyl acetate and water were added to the reaction mixture, and the mixture was extracted with ethyl acetate/2-propanol (3/1). The organic layer was dried over anhydrous sodium sulfate, and the solvent was evaporated under reduced pressure. The residue was dissolved in tetrahydrofuran (1 mL). N,N'-Carbonyldiimidazole (0.029 g) and then 1,8-diazabicyclo[5.4.0]undec-7-ene (0.027 mL) were added, and the mixture was stirred at room temperature for 1 hr. N,N'-Carbonyldiimidazole (0.058 g) and 1,8-diazabicyclo[5.4.0]undec-7-ene (0.054 mL) were added, and the mixture was stirred at room temperature for 15 hr. Ethyl acetate and water were added to the reaction mixture, and the mixture was adjusted to pH 3 with 1 M hydrochloric acid. The mixture was extracted with ethyl acetate, and the organic layer was washed with saturated brine, and dried over anhydrous magnesium sulfate. The solvent was evaporated under reduced pressure, and the residue was purified by silica gel column chromatography and HPLC to give the title compound as a colorless solid (0.020 g, 6%).

$^1$H NMR (300 MHz, DMSO-$d_6$) δ0.93 (t, J=7.35 Hz, 3H) 1.19-1.42 (m, 2H) 1.46-1.62 (m, 2H) 1.64-1.83 (m, 2H) 2.09-2.21 (m, 2H) 2.53-2.69 (m, 2H) 2.83-3.04 (m, 2H) 3.34-3.59 (m, 1H) 3.96 (s, 2H) 4.61 (s, 2H) 4.76-5.05 (m, 1H) 5.10-6.87 (m, 1H) 7.17-7.27 (m, 2H) 7.27-7.37 (m, 2H) 7.45-7.61 (m, 2H) 7.61-7.75 (m, 2H) 8.17 (s, 1H) 8.33 (s, 1H) 12.38 (s, 1H)

EXAMPLE 317

6-{[2'-(5-oxo-4,5-dihydro-1,2,4-oxadiazol-3-yl)biphenyl-4-yl]methyl}-4-{trans-4-[(5-oxo-4,5-dihydro-1,3,4-oxadiazol-2-yl)methoxy]cyclohexyl}-7-propyl[1,2,4]triazolo[1,5-a]pyrimidin-5(4H)-one

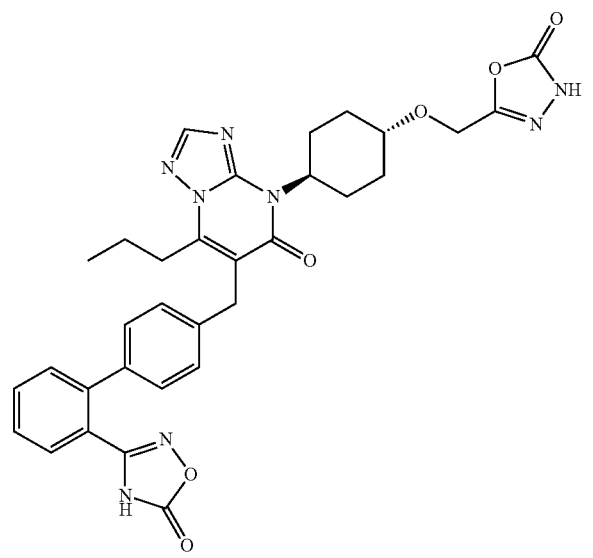 [SMILES: CCCc1c(Cc2ccc(-c3ccccc3-c3noc(=O)[nH]3)cc2)c(=O)n([C@H]2CC[C@H](OCc3n[nH]c(=O)o3)CC2)c2ncnn12]

A mixture of hydroxylammonium chloride (0.33 g), sodium hydrogen carbonate (0.53 g) and dimethyl sulfoxide (2 mL) was stirred at 40° C. for 30 min, 4'-({4-[trans-4-(1,3,4-oxadiazol-2-ylmethoxy)cyclohexyl]-5-oxo-7-propyl-4,5-dihydro[1,2,4]triazolo[1,5-a]pyrimidin-6-yl}methyl)biphenyl-2-carbonitrile (0.17 g) was added, and the mixture was stirred at 90° C. for 11 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.064 g) and then 1,8-diazabicyclo[5.4.0]undec-7-ene (0.059 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.025 g, 12%).

$^1$H NMR (300 MHz, DMSO-$d_6$) δ0.93 (t, J=7.25 Hz, 3H) 1.22-1.43 (m, 2H) 1.45-1.62 (m, 2H) 1.65-1.79 (m, 2H) 2.06-2.19 (m, 2H) 2.47-2.68 (m, 2H) 2.86-3.01 (m, 2H) 3.38-3.59 (m, 1H) 3.95 (s, 2H) 4.42 (s, 2H) 4.81-5.01 (m, 1H) 7.18-7.25 (m, 2H) 7.28-7.34 (m, 2H) 7.46-7.59 (m, 2H) 7.61-7.73 (m, 2H) 8.18 (s, 1H) 12.37 (br. s., 2H)

EXAMPLE 318

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (retention time: short)

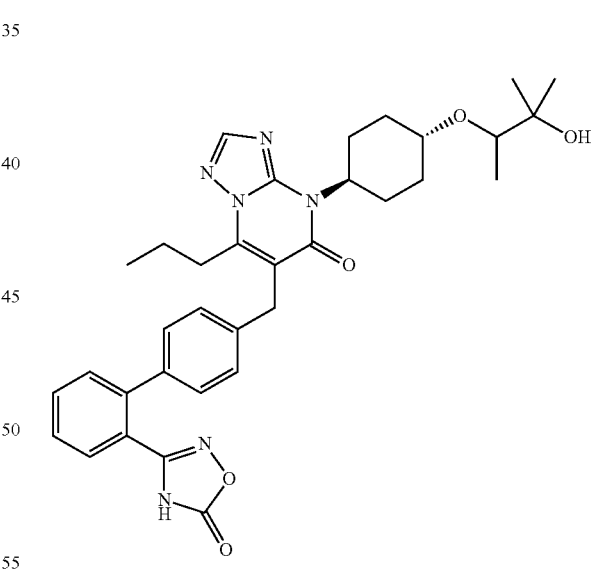

A mixture of hydroxylammonium chloride (0.16 g), sodium hydrogen carbonate (0.26 g) and dimethyl sulfoxide (1.5 mL) was stirred at 40° C. for 30 min, 4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: short, 0.088 g) obtained in Reference Example 308 was added, and the mixture was stirred at 90° C. for 10 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.031 g) and then 1,8-diazabicyclo[5.4.0]undec-7-ene (0.028 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.046 g, >99% ee, 47%).

$^1$H NMR (300 MHz, DMSO-$d_6$) δ0.93 (t, J=7.35 Hz, 3H) 0.99 (s, 3H) 1.03 (d, J=6.22 Hz, 3H) 1.08 (s, 3H) 1.21-1.39 (m, 2H) 1.44-1.61 (m, 2H) 1.62-1.77 (m, 2H) 1.96-2.17 (m, 2H) 2.46-2.69 (m, 2H) 2.85-3.02 (m, 2H) 3.25 (q, J=6.40 Hz, 1H) 3.34-3.46 (m, 1H) 3.95 (s, 2H) 4.06 (s, 1H) 4.75-5.01 (m, 1H) 7.17-7.26 (m, 2H) 7.27-7.34 (m, 2H) 7.45-7.59 (m, 2H) 7.61-7.72 (m, 2H) 8.18 (s, 1H) 12.38 (s, 1H)
enantiomeric excess measurement condition
CHIRALPACK AD-H 4.6 mm ID×150 mL LI-015
CO$_2$/2-Propanol=700/300
5.00 ml/min
retention time 1.82 min

EXAMPLE 319

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (retention time: long)

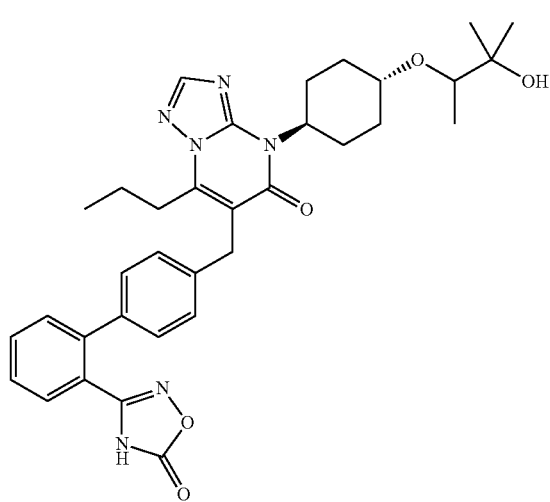 [SMILES: CCCc1c(Cc2ccc(-c3ccccc3-c3noc(=O)[nH]3)cc2)c(=O)n([C@H]2CC[C@H](OC(C)C(C)(C)O)CC2)c2ncnn12]

A mixture of hydroxylammonium chloride (0.13 g), sodium hydrogen carbonate (0.21 g) and dimethyl sulfoxide (1.5 mL) was stirred at 40° C. for 30 min, 4'-({4-[trans-4-(2-hydroxy-1,2-dimethylpropoxy)cyclohexyl]-5-oxo-7-propyl-4,5-dihydro[1,2,4]triazolo[1,5-a]pyrimidin-6-yl}methyl)biphenyl-2-carbonitrile (retention time: long, 0.071 g) obtained in Reference Example 309 was added, and the mixture was stirred at 90° C. for 10 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldi-imidazole (0.025 g) and then 1,8-diazabicyclo[5.4.0]undec-7-ene (0.023 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.046 g, >99% ee, 59%).

$^1$H NMR (300 MHz, DMSO-$d_6$) δ0.93 (t, J=7.35 Hz, 3H) 0.99 (s, 3H) 1.03 (d, J=6.40 Hz, 3H) 1.08 (s, 3H) 1.20-1.41 (m, 2H) 1.48-1.62 (m, 2H) 1.63-1.75 (m, 2H) 1.93-2.15 (m, 2H) 2.44-2.69 (m, 2H) 2.88-3.00 (m, 2H) 3.25 (q, J=6.15 Hz, 1H) 3.33-3.46 (m, 1H) 3.95 (s, 2H) 4.06 (s, 1H) 4.81-4.99 (m, 1H) 7.18-7.26 (m, 2H) 7.27-7.35 (m, 2H) 7.45-7.59 (m, 2H) 7.62-7.73 (m, 2H) 8.18 (s, 1H) 12.38 (s, 1H)
enantiomeric excess measurement condition
CHIRALPACK AD-H 4.6 mm ID×150 mL LI-015
CO$_2$/2-Propanol=700/300
5.00 ml/min
retention time 2.55 min

EXAMPLE 320

4-[1-(2-hydroxy-2-methylpropyl)-4,5,6,7-tetrahydro-1H-indazol-5-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

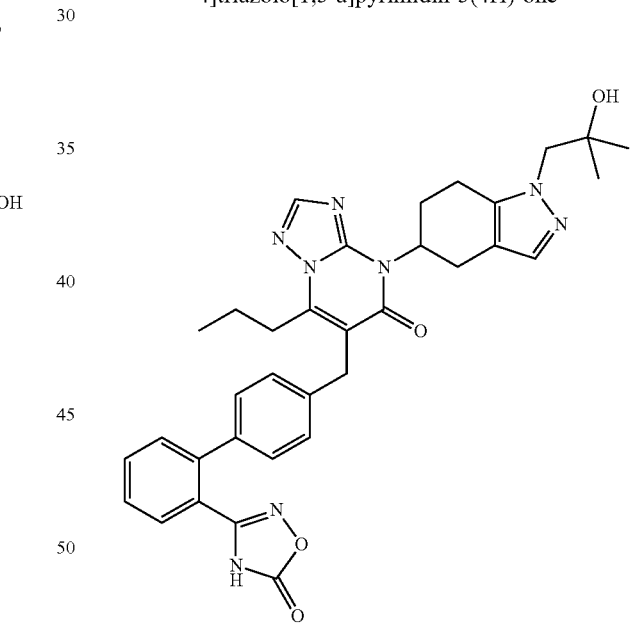

A mixture of hydroxylammonium chloride (0.12 g), sodium hydrogen carbonate (0.20 g) and dimethyl sulfoxide (2 mL) was stirred at 40° C. for 30 min, 4'-({4-[1-(2-hydroxy-2-methylpropyl)-4,5,6,7-tetrahydro-1H-indazol-5-yl]-5-oxo-7-propyl-4,5-dihydro[1,2,4]triazolo[1,5-a]pyrimidin-6-yl}methyl)biphenyl-2-carbonitrile (0.069 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.024 g) and then 1,8-diazabicyclo[5.4.0]undec-7-ene (0.022 mL) were added, and the mixture was stirred at room temperature for 1 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.022 g, 29%).

$^1$H NMR (300 MHz, DMSO-$d_6$) δ0.94 (t, J=7.19 Hz, 3H) 1.08 (s, 3H) 1.10 (s, 3H) 1.48-1.64 (m, 2H) 1.91-2.06 (m, 1H) 2.57-3.08 (m, 6H) 3.36-3.53 (m, 1H) 3.87 (s, 2H) 3.98 (s, 2H) 4.65 (s, 1H) 5.13-5.31 (m, 1H) 7.18-7.26 (m, 3H) 7.28-7.39 (m, 2H) 7.46-7.59 (m, 2H) 7.61-7.74 (m, 2H) 8.19 (s, 1H) 12.39 (br. s., 1H)

EXAMPLE 321

4-[2-(2-hydroxy-2-methylpropyl)-4,5,6,7-tetrahydro-2H-indazol-5-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

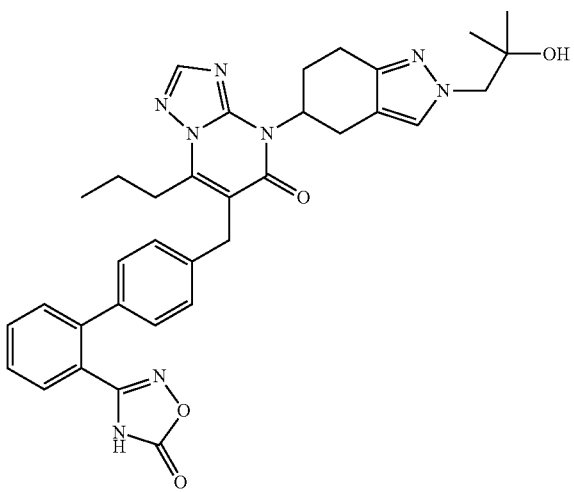 [SMILES: CCCc1c(Cc2ccc(-c3ccccc3-c3noc(=O)[nH]3)cc2)c(=O)n(C2CCc3nn(CC(C)(C)O)cc3C2)c2ncnn12]

A mixture of hydroxylammonium chloride (0.15 g), sodium hydrogen carbonate (0.25 g) and dimethyl sulfoxide (2 mL) was stirred at 40° C. for 30 min, 4'-({4-[2-(2-hydroxy-2-methylpropyl)-4,5,6,7-tetrahydro-2H-indazol-5-yl]-5-oxo-7-propyl-4,5-dihydro[1,2,4]triazolo[1,5-a]pyrimidin-6-yl}methyl)biphenyl-2-carbonitrile (0.085 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.030 g) and then 1,8-diazabicyclo[5.4.0]undec-7-ene (0.027 mL) were added, and the mixture was stirred at room temperature for 1 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.032 g, 34%).

$^1$H NMR (300 MHz, DMSO-$d_6$) δ0.94 (t, J=7.38 Hz, 3H) 1.05 (s, 6H) 1.42-1.67 (m, 2H) 1.91-2.04 (m, 1H) 2.58-3.06 (m, 6H) 3.39-3.56 (m, 1H) 3.91 (s, 2H) 3.98 (s, 2H) 4.65 (s, 1H) 5.09-5.33 (m, 1H) 7.17-7.26 (m, 2H) 7.27-7.35 (m, 2H) 7.38 (s, 1H) 7.46-7.58 (m, 2H) 7.60-7.73 (m, 2H) 8.19 (s, 1H) 12.39 (br. s., 1H)

EXAMPLE 322

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt (retention time: short)

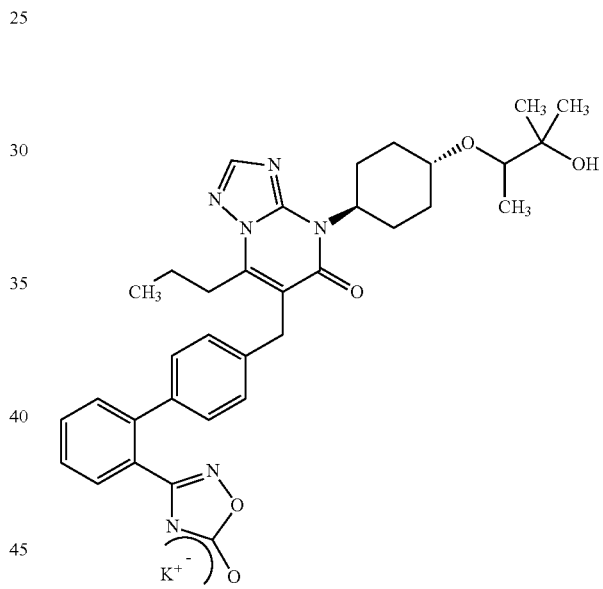

To a solution of 4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (retention time: short, 0.028 g) in tetrahydrofuran (2 mL) was added 0.1 M aqueous potassium hydroxide solution (0.47 mL), and the solvent was evaporated under reduced pressure. The residue was washed with diisopropyl ether to give the title compound as a colorless solid (0.020 g, 66%).

$^1$H NMR (300 MHz, DMSO-$d_6$) δ0.95 (t, J=7.25 Hz, 3H) 0.99 (s, 3H) 1.03 (d, J=6.22 Hz, 3H) 1.08 (s, 3H) 1.19-1.34 (m, 2H) 1.49-1.77 (m, 4H) 1.92-2.15 (m, 2H) 2.41-2.74 (m, 2H) 2.87-3.02 (m, 2H) 3.26 (q, J=6.22 Hz, 1H) 3.34-3.45 (m, 1H) 3.91 (s, 2H) 4.06 (s, 1H) 4.80-4.99 (m, 1H) 7.13-7.26 (m, 4H) 7.30-7.42 (m, 2H) 7.43-7.53 (m, 2H) 8.17 (s, 1H)

591

EXAMPLE 323

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt (retention time: long)

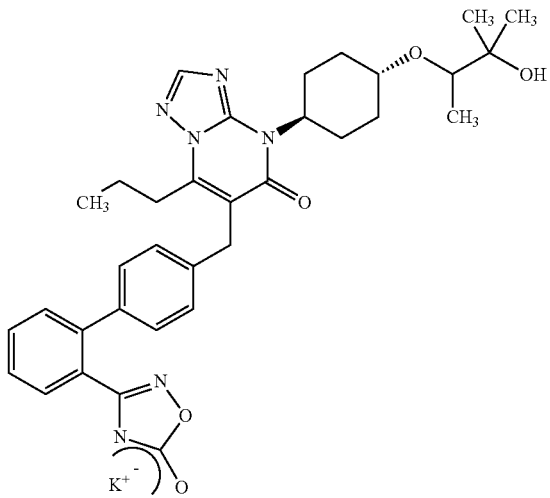 [SMILES: CCCc1c(Cc2ccc(-c3ccccc3C3=NOC(O)N3)cc2)c(=O)n([C@H]2CC[C@H](OC(C)C(C)(C)O)CC2)c2ncnn12 ; [K+]]

To a solution of 4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (retention time: long) (0.032 g) in tetrahydrofuran (2 mL) was added 0.1 M aqueous potassium hydroxide solution (0.53 mL), and the solvent was evaporated under reduced pressure. The residue was washed with diisopropyl ether to give the title compound as a colorless solid (0.026 g, 74%).

$^1$H NMR (300 MHz, DMSO-$d_6$) δ0.95 (t, J=7.38 Hz, 3H) 0.99 (s, 3H) 1.03 (d, J=6.06 Hz, 3H) 1.08 (s, 3H) 1.17-1.42 (m, 2H) 1.49-1.77 (m, 4H) 1.93-2.19 (m, 2H) 2.45-2.73 (m, 2H) 2.88-3.00 (m, 2H) 3.24 (q, J=6.44 Hz, 1H) 3.34-3.44 (m, 1H) 3.91 (s, 2H) 4.06 (s, 1H) 4.80-5.05 (m, 1H) 7.14-7.25 (m, 4H) 7.27-7.39 (m, 2H) 7.41-7.52 (m, 2H) 8.16 (s, 1H)

EXAMPLE 324

4-{trans-4-[(5-methyl-1,3,4-oxadiazol-2-yl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

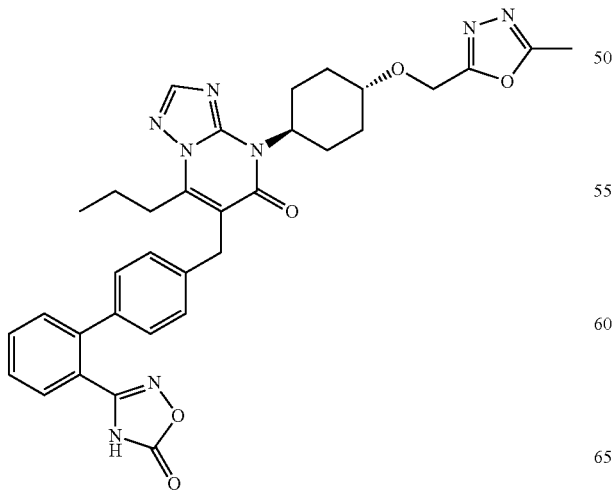

592

A mixture of hydroxylammonium chloride (0.45 g), sodium hydrogen carbonate (0.72 g) and dimethyl sulfoxide (5 mL) was stirred at 40° C. for 30 min, 4'-[(4-{trans-4-[(5-methyl-1,3,4-oxadiazol-2-yl)methoxy]cyclohexyl}-5-oxo-7-propyl-4,5-dihydro[1,2,4]triazolo[1,5-a]pyrimidin-6-yl)methyl]biphenyl-2-carbonitrile (0.24 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure. The residue obtained by silica gel column chromatography was dissolved in tetrahydrofuran (3 mL). N,N'-Carbonyldiimidazole (0.084 g) and then 1,8-diazabicyclo[5.4.0]undec-7-ene (0.078 mL) were added, and the mixture was stirred at room temperature for 120 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.041 g, 15%).

$^1$H NMR (300 MHz, DMSO-$d_6$) δ0.93 (t, J=7.38 Hz, 3H) 1.21-1.44 (m, 2H) 1.45-1.60 (m, 2H) 1.62-1.81 (m, 2H) 2.03-2.22 (m, 2H) 2.43-2.70 (m, 5H) 2.83-3.00 (m, 2H) 3.44-3.57 (m, 1H) 3.95 (s, 2H) 4.72 (s, 2H) 4.84-5.02 (m, 1H) 7.17-7.25 (m, 2H) 7.28-7.37 (m, 2H) 7.46-7.59 (m, 2H) 7.61-7.76 (m, 2H) 8.18 (s, 1H) 12.38 (br. s., 1H)

EXAMPLE 325

6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxypropoxy)cyclohexyl][1,2,4]triazolo[1,5-a]pyrimidin-5(4H)-one

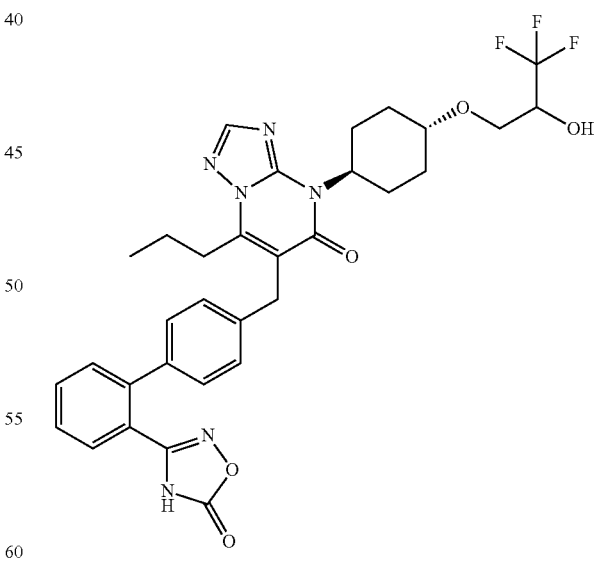

A mixture of hydroxylammonium chloride (0.098 g), sodium hydrogen carbonate (0.15 g) and dimethyl sulfoxide (2 mL) was stirred at 40° C. for 30 min, 4'-({5-oxo-7-propyl-4-[trans-4-(3,3,3-trifluoro-2-hydroxypropoxy)cyclohexyl]-4,5-dihydro[1,2,4]triazolo[1,5-a]pyrimidin-6-yl}methyl)biphenyl-2-carbonitrile (0.054 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.016 g) and then 1,8-diazabicyclo[5.4.0]undec-7-ene (0.015 mL) were added, and the mixture was stirred at room temperature for 2.5 hr. N,N'-Carbonyldiimidazole (0.016 g) and 1,8-diazabicyclo[5.4.0]undec-7-ene (0.015 mL) were added, and the mixture was stirred at room temperature for 2 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.035 g, 58%).

$^1$H NMR (300 MHz, DMSO-$d_6$) δ0.93 (t, J=7.38 Hz, 3H) 1.23-1.42 (m, 2H) 1.46-1.60 (m, 2H) 1.62-1.78 (m, 2H) 2.03-2.21 (m, 2H) 2.52-2.69 (m, 2H) 2.84-3.02 (m, 2H) 3.35-3.48 (m, 1H) 3.49-3.58 (m, 1H) 3.60-3.71 (m, 1H) 3.95 (s, 2H) 3.99-4.18 (m, 1H) 4.79-5.01 (m, 1H) 6.33 (d, J=6.82 Hz, 1H) 7.17-7.25 (m, 2H) 7.26-7.37 (m, 2H) 7.41-7.57 (m, 2H) 7.59-7.72 (m, 2H) 8.18 (s, 1H) 12.38 (br. s., 1H)

EXAMPLE 326

4-[trans-4-(2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

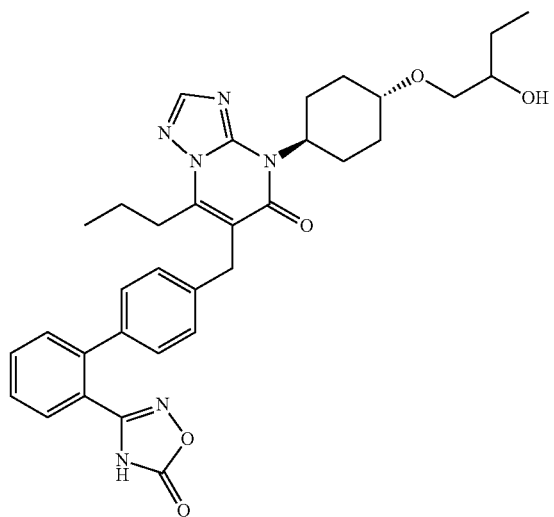

A mixture of 4'-({4-[trans-4-(2-hydroxybutoxy)cyclohexyl]-5-oxo-7-propyl-4,5-dihydro[1,2,4]triazolo[1,5-a]pyrimidin-6-yl}methyl)biphenyl-2-carbonitrile (0.48 g), 2,6-lutidine (0.21 mL), tert-butyl(dimethyl)silyl trifluoromethanesulfonate (0.41 mL) and tetrahydrofuran (5 mL) was stirred at room temperature for 3 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, the obtained residue was added to a mixture of hydroxylammonium chloride (0.93 g), sodium hydrogen carbonate (1.5 g), and dimethyl sulfoxide (5 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). N,N'-Carbonyldiimidazole (0.17 g) and then 1,8-diazabicyclo[5.4.0]undec-7-ene (0.16 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (5 mL). Tetrabutylammonium fluoride (2.2 mL, 1.0 M tetrahydrofuran solution) was added, and the mixture was stirred at 70° C. for 44 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.22 g, 42%).

$^1$H NMR (300 MHz, DMSO-$d_6$) δ0.87 (t, J=7.35 Hz, 3H) 0.93 (t, J=7.35 Hz, 3H) 1.14-1.62 (m, 6H) 1.64-1.77 (m, 2H) 2.02-2.16 (m, 2H) 2.51-2.68 (m, 2H) 2.84-3.00 (m, 2H) 3.25-3.37 (m, 3H) 3.38-3.52 (m, 1H) 3.95 (s, 2H) 4.47 (d, J=4.90 Hz, 1H) 4.77-5.03 (m, 1H) 7.18-7.26 (m, 2H) 7.27-7.38 (m, 2H) 7.47-7.59 (m, 2H) 7.62-7.74 (m, 2H) 8.18 (s, 1H) 12.38 (s, 1H)

EXAMPLE 327

4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

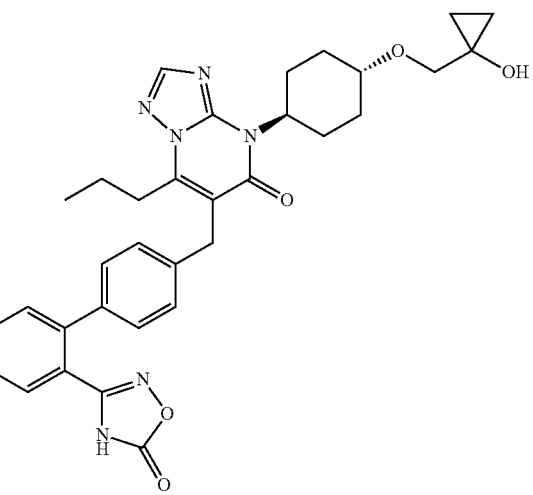

A mixture of hydroxylammonium chloride (0.39 g), sodium hydrogen carbonate (0.63 g) and dimethyl sulfoxide (4 mL) was stirred at 40° C. for 30 min, 4'-[(4-{trans-4-[(1-{[tert-butyl(dimethyl)silyl]oxy}cyclopropyl)methoxy]cyclohexyl}-5-oxo-7-propyl-4,5-dihydro[1,2,4]triazolo[1,5-a]pyrimidin-6-yl)methyl]biphenyl-2-carbonitrile (0.24 g) was added, and the mixture was stirred at 90° C. for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (3 mL). N,N'-Carbonyldiimidazole (0.073 g) and then 1,8-diazabicyclo[5.4.0]undec-7-ene (0.067 mL) were added, and the mixture was stirred at room temperature for 1 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was dissolved in tetrahydrofuran (5 mL). Tetrabutylammonium fluoride (0.94 mL, 1.0 M tetrahydrofuran solution) was added and the mixture was stirred at 70° C. for 3.5 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.076 g, 34%).

$^1$H NMR (300 MHz, DMSO-$d_6$) δ0.41-0.49 (m, 2H) 0.50-0.61 (m, 2H) 0.93 (t, J=7.38 Hz, 3H) 1.20-1.40 (m, 2H) 1.46-1.62 (m, 2H) 1.63-1.80 (m, 2H) 2.06-2.22 (m, 2H) 2.52-2.67 (m, 2H) 2.87-3.01 (m, 2H) 3.34-3.42 (m, 1H) 3.44 (s, 2H) 3.96 (s, 2H) 4.74-5.04 (m, 1H) 5.27 (s, 1H) 7.18-7.26 (m, 2H) 7.28-7.36 (m, 2H) 7.45-7.60 (m, 2H) 7.62-7.73 (m, 2H) 8.18 (s, 1H) 12.39 (s, 1H)

EXAMPLE 328

4-[trans-4-(2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

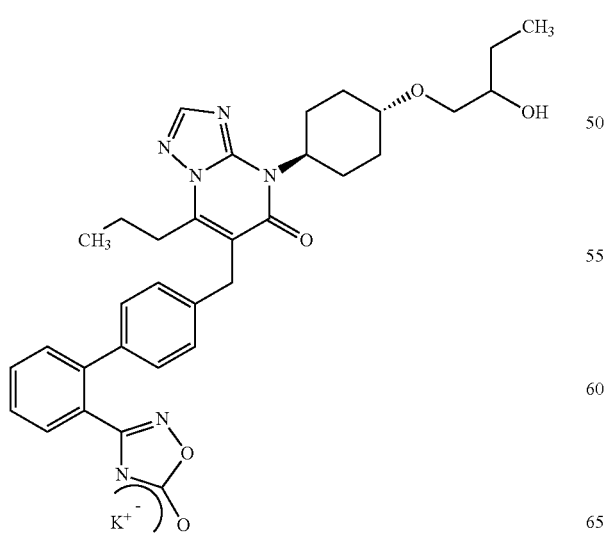

To a solution of 4-[trans-4-(2-hydroxybutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.050 g) in tetrahydrofuran (2 mL) was added 0.1 M aqueous potassium hydroxide solution (0.83 mL), and the solvent was evaporated under reduced pressure. The residue was washed with diisopropyl ether to give the title compound as a colorless solid (0.049 g, 92%).

$^1$H NMR (300 MHz, DMSO-$d_6$) δ0.87 (t, J=7.54 Hz, 3H) 0.94 (t, J=7.35 Hz, 3H) 1.16-1.80 (m, 8H) 2.02-2.17 (m, 2H) 2.53-2.68 (m, 2H) 2.88-3.02 (m, 2H) 3.22-3.37 (m, 3H) 3.37-3.49 (m, 1H) 3.92 (s, 2H) 4.46 (d, J=4.90 Hz, 1H) 4.80-5.03 (m, 1H) 7.22 (s, 4H) 7.32-7.45 (m, 2H) 7.46-7.58 (m, 2H) 8.17 (s, 1H)

EXAMPLE 329

4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

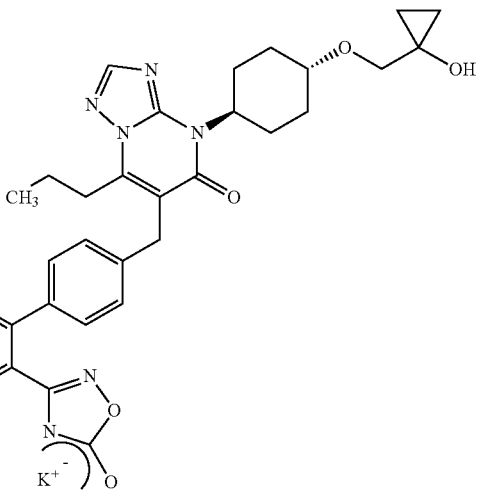

To a solution of 4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.048 g) in tetrahydrofuran (2 mL) was added 0.1 M aqueous potassium hydroxide solution (0.80 mL), and the solvent was evaporated under reduced pressure. The residue was washed with diisopropyl ether to give the title compound as a colorless solid (0.043 g, 84%).

$^1$H NMR (300 MHz, DMSO-$d_6$) δ0.42-0.50 (m, 2H) 0.51-0.60 (m, 2H) 0.95 (t, J=7.25 Hz, 3H) 1.18-1.40 (m, 2H) 1.49-1.78 (m, 4H) 2.02-2.20 (m, 2H) 2.52-2.69 (m, 2H) 2.86-3.04 (m, 2H) 3.37-3.41 (m, 1H) 3.44 (s, 2H) 3.91 (s, 2H) 4.82-5.03 (m, 1H) 5.27 (s, 1H) 7.13-7.26 (m, 4H) 7.30-7.40 (m, 2H) 7.41-7.54 (m, 2H) 8.17 (s, 1H)

EXAMPLE 330

6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxypropoxy)cyclohexyl][1,2,4]triazolo[1,5-a]pyrimidin-5(4H)-one potassium salt

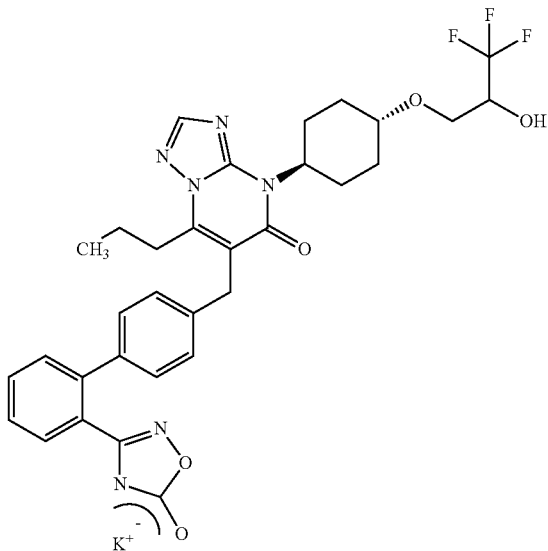 [SMILES: CCCc1c(Cc2ccc(-c3ccccc3C3=NOC(O)N3)cc2)c(=O)n([C@H]2CC[C@H](OCC(O)C(F)(F)F)CC2)c2ncnn12 ; [K+]]

To a solution of 6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxypropoxy)cyclohexyl][1,2,4]triazolo[1,5-a]pyrimidin-5(4H)-one (0.021 g) in tetrahydrofuran (2 mL) was added 0.1 M aqueous potassium hydroxide solution (0.33 mL), and the solvent was evaporated under reduced pressure. The residue was washed with diisopropyl ether to give the title compound as a colorless solid (0.015 g, 67%).

$^1$H NMR (300 MHz, DMSO-$d_6$) δ0.95 (t, J=7.35 Hz, 3H) 1.20-1.34 (m, 2H) 1.51-1.80 (m, 4H) 2.02-2.18 (m, 2H) 2.53-2.70 (m, 2H) 2.88-3.02 (m, 2H) 3.35-3.46 (m, 1H) 3.47-3.58 (m, 1H) 3.60-3.71 (m, 1H) 3.91 (s, 2H) 4.02-4.18 (m, 1H) 4.79-5.04 (m, 1H) 6.32 (d, J=6.59 Hz, 1H) 7.14-7.26 (m, 4H) 7.28-7.41 (m, 2H) 7.42-7.57 (m, 2H) 8.16 (s, 1H)

EXAMPLE 331

4-{trans-4-[(2-hydroxybut-3-en-1-yl)oxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

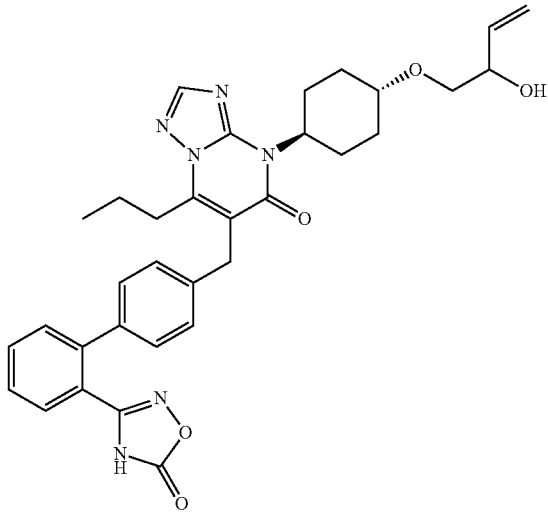 [SMILES: C=CC(O)CO[C@H]1CC[C@H](n2c(=O)c(Cc3ccc(-c4ccccc4-c4noc(=O)[nH]4)cc3)c(CCC)n3ncnc32)CC1]

A mixture of 4'-[(4-{trans-4-[(2-hydroxybut-3-en-1-yl)oxy]cyclohexyl}-5-oxo-7-propyl-4,5-dihydro[1,2,4]triazolo[1,5-a]pyrimidin-6-yl)methyl]biphenyl-2-carbonitrile (0.33 g), 2,6-lutidine (0.18 mL), tert-butyl(dimethyl)silyl trifluoromethanesulfonate (0.35 mL) and tetrahydrofuran (4 mL) was stirred at room temperature for 1 hr. The reaction mixture was added to 1 M hydrochloric acid, and the mixture was extracted with ethyl acetate. The organic layer was washed with saturated sodium hydrogen carbonate and then with saturated brine, and dried over anhydrous magnesium sulfate. The solvent was evaporated under reduced pressure, the obtained residue was added to a mixture of hydroxylammonium chloride (0.63 g), sodium hydrogen carbonate (1.0 g), and dimethyl sulfoxide (5 mL), which had been stirred at 40° C. for 30 min in advance, and the mixture was stirred at 90° C. for 20 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (4 mL). N,N'-Carbonyldiimidazole (0.11 g) and then 1,8-diazabicyclo[5.4.0]undec-7-ene (0.10 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (5 mL). Tetrabutylammonium fluoride (1.5 mL, 1.0 M tetrahydrofuran solution) was added, and the mixture was stirred at 70° C. for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and HPLC and recrystallized (ethyl acetate-diisopropyl ether) to give the title compound as a colorless solid (0.040 g, 9%).

$^1$H NMR (300 MHz, DMSO-$d_6$) δ0.93 (t, J=7.35 Hz, 3H) 1.20-1.42 (m, 2H) 1.48-1.63 (m, 2H) 1.64-1.79 (m, 2H) 2.03-2.20 (m, 2H) 2.53-2.67 (m, 2H) 2.85-2.99 (m, 2H) 3.32-3.40 (m, 3H) 3.95 (s, 2H) 4.00-4.13 (m, 1H) 4.87 (d, J=4.90 Hz, 1H) 4.89-4.99 (m, 1H) 5.01-5.12 (m, 1H) 5.19-5.31 (m, 1H) 5.78-5.94 (m, 1H) 7.18-7.25 (m, 2H) 7.26-7.33 (m, 2H) 7.44-7.58 (m, 2H) 7.60-7.72 (m, 2H) 8.18 (s, 1H) 12.36 (br. s., 1H)

EXAMPLE 332

4-[trans-4-(2-cyclopropyl-2-hydroxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

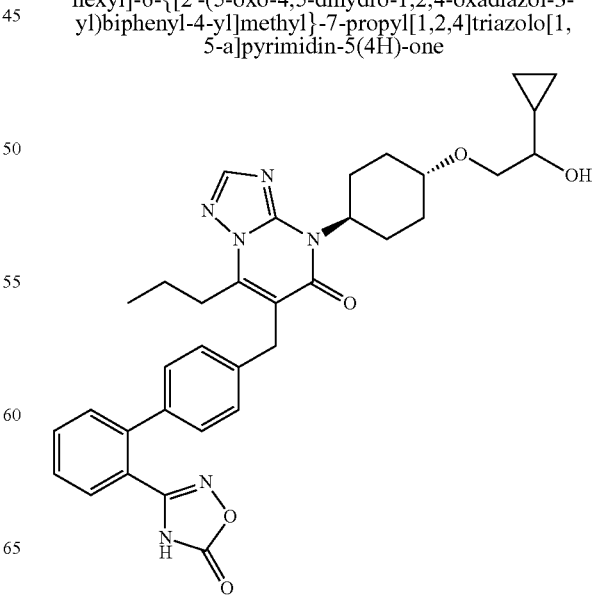

A mixture of 4'-({4-[trans-4-(2-cyclopropyl-2-hydroxyethoxy)cyclohexyl]-5-oxo-7-propyl-4,5-dihydro[1,2,4]triazolo[1,5-a]pyrimidin-6-yl}methyl)biphenyl-2-carbonitrile (0.17 g), 2,6-lutidine (0.072 mL), tert-butyl(dimethyl)silyl trifluoromethanesulfonate (0.14 mL) and tetrahydrofuran (4 mL) was stirred at room temperature for 3 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure and the obtained residue was added to a mixture of hydroxylammonium chloride (0.32 g), sodium hydrogen carbonate (0.52 g), and dimethyl sulfoxide (5 mL), which had been stirred at 40° C. for 30 min in advance, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (4 mL). N,N'-Carbonyldiimidazole (0.060 g) and then 1,8-diazabicyclo[5.4.0]undec-7-ene (0.055 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was dissolved in tetrahydrofuran (5 mL). Tetrabutylammonium fluoride (0.78 mL, 1.0 M tetrahydrofuran solution) was added, and the mixture was stirred at 70° C. for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.11 g, 62%).

$^1$H NMR (300 MHz, DMSO-$d_6$) δ0.17-0.27 (m, 2H) 0.29-0.39 (m, 2H) 0.73-0.87 (m, 1H) 0.92 (t, J=7.19 Hz, 3H) 1.18-1.40 (m, 2H) 1.45-1.61 (m, 2H) 1.62-1.77 (m, 2H) 2.03-2.21 (m, 2H) 2.53-2.69 (m, 2H) 2.87-2.99 (m, 2H) 3.01-3.13 (m, 1H) 3.33-3.51 (m, 3H) 3.96 (s, 2H) 4.47 (d, J=4.92 Hz, 1H) 4.77-5.03 (m, 1H) 7.16-7.24 (m, 2H) 7.27-7.35 (m, 2H) 7.46-7.59 (m, 2H) 7.62-7.74 (m, 2H) 8.18 (s, 1H) 12.37 (s, 1H)

EXAMPLE 333

4-{trans-4-[(2-hydroxybut-3-en-1-yl)oxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

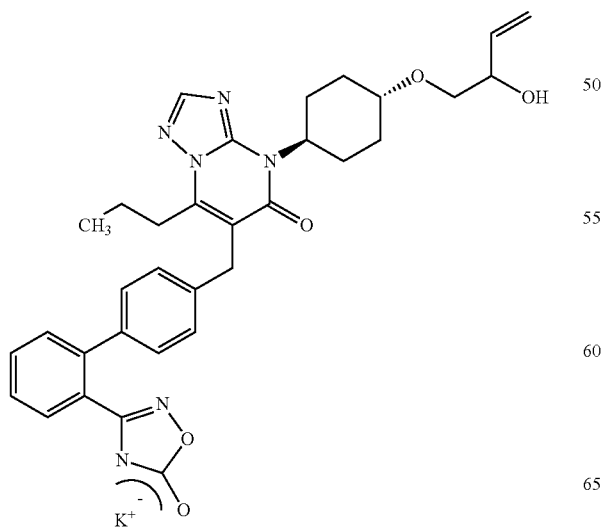

To a solution of 4-{trans-4-[(2-hydroxybut-3-en-1-yl)oxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.023 g) in tetrahydrofuran (2 mL) was added 0.1 M aqueous potassium hydroxide solution (0.38 mL), and the solvent was evaporated under reduced pressure. The residue was washed with diisopropyl ether to give the title compound as a colorless solid (0.018 g, 75%).

$^1$H NMR (300 MHz, DMSO-$d_6$) δ0.95 (t, J=7.19 Hz, 3H) 1.18-1.37 (m, 2H) 1.48-1.80 (m, 4H) 1.99-2.21 (m, 2H) 2.53-2.66 (m, 2H) 2.87-3.01 (m, 1H) 3.23-3.42 (m, 4H) 3.92 (s, 2H) 4.01-4.15 (m, 1H) 4.80-4.99 (m, 2H) 5.01-5.12 (m, 1H) 5.19-5.32 (m, 1H) 5.86 (ddd, J=17.42, 10.60, 4.92 Hz, 1H) 7.21 (s, 4H) 7.29-7.42 (m, 2H) 7.43-7.54 (m, 2H) 8.17 (s, 1H)

EXAMPLE 334

4-[trans-4-(2-cyclopropyl-2-hydroxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

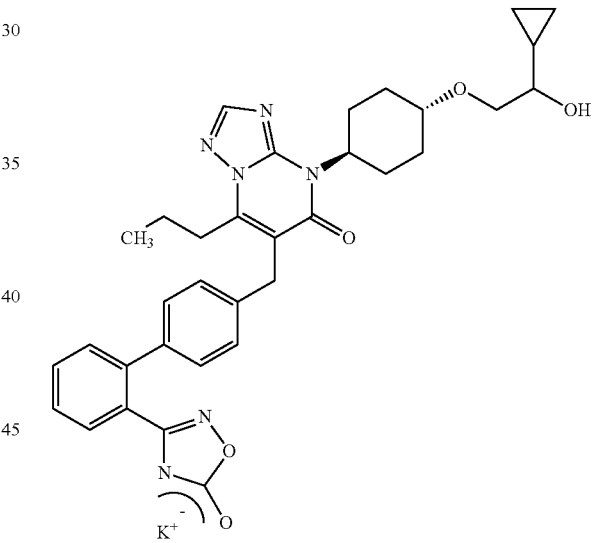

To a solution of 4-[trans-4-(2-cyclopropyl-2-hydroxyethoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.093 g) in tetrahydrofuran (2 mL) was added 0.1 M aqueous potassium hydroxide solution (1.5 mL), and the solvent was evaporated under reduced pressure. The residue was washed with diisopropyl ether to give the title compound as a colorless solid (0.093 g, 93%).

$^1$H NMR (300 MHz, DMSO-$d_6$) δ0.12-0.42 (m, 4H) 0.70-0.88 (m, 1H) 0.95 (t, J=7.19 Hz, 3H) 1.18-1.38 (m, 2H) 1.48-1.83 (m, 4H) 1.97-2.19 (m, 2H) 2.53-2.70 (m, 2H) 2.86-3.00 (m, 2H) 3.02-3.14 (m, 1H) 3.21-3.51 (m, 3H) 3.91 (s, 2H) 4.37-4.59 (m, 1H) 4.83-5.04 (m, 1H) 7.13-7.26 (m, 4H) 7.28-7.41 (m, 2H) 7.42-7.56 (m, 2H) 8.17 (s, 1H)

EXAMPLE 335

6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxy-2-methylpropoxy)cyclohexyl][1,2,4]triazolo[1,5-a]pyrimidin-5(4H)-one

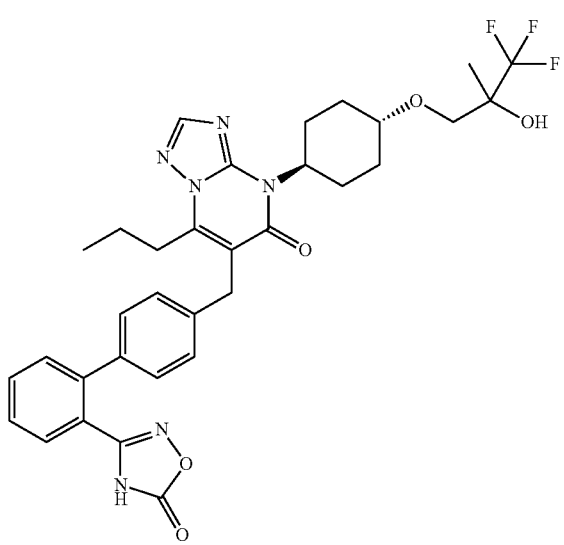 [SMILES: CCCc1c(Cc2ccc(-c3ccccc3-c3noc(=O)[nH]3)cc2)c(=O)n([C@H]2CC[C@H](OCC(C)(O)C(F)(F)F)CC2)c2ncnn12]

A mixture of hydroxylammonium chloride (0.16 g), sodium hydrogen carbonate (0.26 g) and dimethyl sulfoxide (3 mL) was stirred at 40° C. for 30 min, 4'-({5-oxo-7-propyl-4-[trans-4-(3,3,3-trifluoro-2-hydroxy-2-methylpropoxy)cyclohexyl]-4,5-dihydro[1,2,4]triazolo[1,5-a]pyrimidin-6-yl}methyl)biphenyl-2-carbonitrile (0.092 g) was added, and the mixture was stirred at 90° C. for 19 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (3 mL). N,N'-Carbonyldiimidazole (0.031 g) and then 1,8-diazabicyclo[5.4.0]undec-7-ene (0.028 mL) were added, and the mixture was stirred at room temperature for 1.5 hr. The reaction mixture was diluted with ethyl acetate, 1 M hydrochloric acid was added, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.063 g, 62%).

$^1$H NMR (300 MHz, DMSO-d$_6$) δ 0.92 (t, J=7.38 Hz, 3H) 1.18-1.41 (m, 5H) 1.46-1.81 (m, 4H) 2.02-2.21 (m, 2H) 2.52-2.69 (m, 2H) 2.82-3.02 (m, 2H) 3.28-3.42 (m, 1H) 3.43-3.49 (m, 1H) 3.51-3.60 (m, 1H) 3.95 (s, 2H) 4.80-5.00 (m, 1H) 5.93 (s, 1H) 7.17-7.24 (m, 2H) 7.27-7.36 (m, 2H) 7.45-7.59 (m, 2H) 7.61-7.73 (m, 2H) 8.18 (s, 1H) 12.37 (s, 1H)

EXAMPLE 336

4-[trans-4-(3-fluoro-2-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

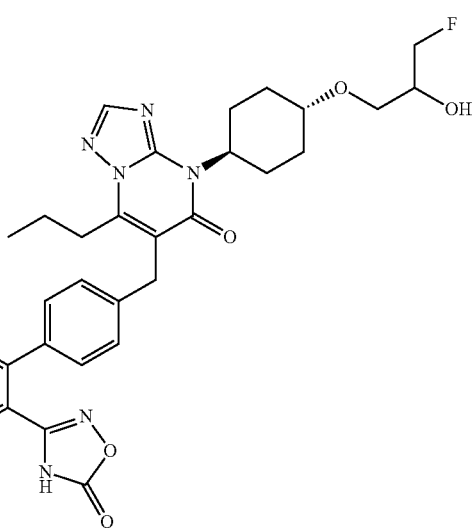

A mixture of 4'-({4-[trans-4-(3-fluoro-2-hydroxypropoxy)cyclohexyl]-5-oxo-7-propyl-4,5-dihydro[1,2,4]triazolo[1,5-a]pyrimidin-6-yl}methyl)biphenyl-2-carbonitrile (0.088 g), 2,6-lutidine (0.038 mL), tert-butyl(dimethyl)silyl trifluoromethanesulfonate (0.075 mL) and tetrahydrofuran (1 mL) was stirred at room temperature for 2 hr. The reaction mixture was added to 1 M hydrochloric acid, and the mixture was extracted with ethyl acetate. The organic layer was washed with saturated aqueous sodium hydrogen carbonate solution and then with saturated brine, and dried over anhydrous magnesium sulfate. The solvent was evaporated under reduced pressure, the obtained residue was added to a mixture of hydroxylammonium chloride (0.17 g), sodium hydrogen carbonate (0.27 g), and dimethyl sulfoxide (3 mL), which had been stirred at 40° C. for 30 min in advance, and the mixture was stirred at 90° C. for 12 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.032 g) and then 1,8-diazabicyclo[5.4.0]undec-7-ene (0.029 mL) were added, and the mixture was stirred at room temperature for 2 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was dissolved in tetrahydrofuran (3 mL). Tetrabutylammonium fluoride (0.40 mL, 1.0 M tetrahydrofuran solution) was added, and the mixture was stirred at 70° C. for 2 hr. The reaction mixture was added to 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.061 g, 62%).

$^1$H NMR (300 MHz, DMSO-$d_6$) δ 0.92 (t, J=7.38 Hz, 3H) 1.17-1.40 (m, 2H) 1.45-1.63 (m, 2H) 1.63-1.81 (m, 2H) 2.01-2.17 (m, 2H) 2.52-2.67 (m, 2H) 2.85-3.03 (m, 2H) 3.33-3.39 (m, 1H) 3.42 (d, J=5.68 Hz, 2H) 3.65-3.87 (m, 1H) 3.95 (s, 2H) 4.28 (ddd, J=23.10, 9.47, 3.41 Hz, 1H) 4.44 (ddd, J=23.10, 9.47, 3.41 Hz, 1H) 4.77-5.00 (m, 1H) 5.12 (d, J=5.30 Hz, 1H) 7.18-7.25 (m, 2H) 7.26-7.36 (m, 2H) 7.46-7.59 (m, 2H) 7.61-7.76 (m, 2H) 8.18 (s, 1H) 12.37 (s, 1H)

EXAMPLE 337

4-[trans-4-(3-fluoro-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

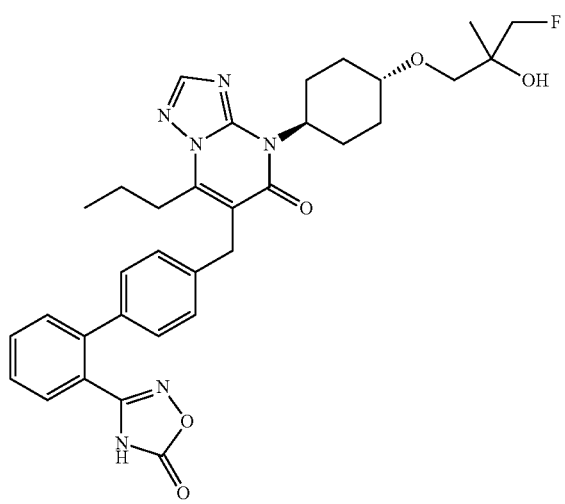 [SMILES: CCCc1c(Cc2ccc(-c3ccccc3-c3noc(=O)[nH]3)cc2)c(=O)n([C@H]2CC[C@H](OCC(C)(O)CF)CC2)c2ncnn12]

A mixture of hydroxylammonium chloride (0.18 g), sodium hydrogen carbonate (0.30 g) and dimethyl sulfoxide (3 mL) was stirred at 40° C. for 30 min, 4'-({4-[trans-4-(3-fluoro-2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (0.10 g) was added, and the mixture was stirred at 90° C. for 24 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.036 g) and then 1,8-diazabicyclo[5.4.0]undec-7-ene (0.033 mL) were added, and the mixture was stirred at room temperature for 2 hr. Ethyl acetate and water were added to the reaction mixture, and the mixture was neutralized with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.078 g, 70%).

$^1$H NMR (300 MHz, DMSO-$d_6$) δ 0.92 (t, J=7.19 Hz, 3H) 1.06 (d, J=2.27 Hz, 3H) 1.20-1.37 (m, 2H) 1.44-1.79 (m, 4H) 2.01-2.19 (m, 2H) 2.52-2.67 (m, 2H) 2.84-3.00 (m, 2H) 3.22-3.43 (m, 3H) 3.95 (s, 2H) 4.19 (d, J=47.71 Hz, 2H) 4.77 (s, 1H) 4.82-5.06 (m, 1H) 7.16-7.25 (m, 2H) 7.27-7.36 (m, 2H) 7.45-7.59 (m, 2H) 7.62-7.74 (m, 2H) 8.18 (s, 1H) 12.37 (s, 1H)

EXAMPLE 338

4-{trans-4-[(1-hydroxycyclobutyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

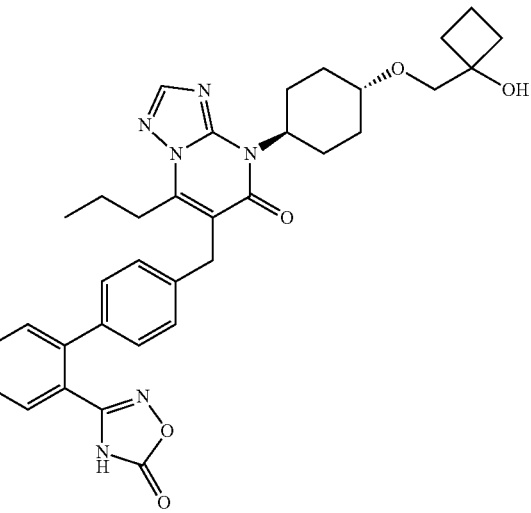

A mixture of hydroxylammonium chloride (0.18 g), sodium hydrogen carbonate (0.29 g) and dimethyl sulfoxide (4 mL) was stirred at 40° C. for 30 min, 4'-[(4-{trans-4-[(1-hydroxycyclobutyl)methoxy]cyclohexyl}-5-oxo-7-propyl-4,5-dihydro[1,2,4]triazolo[1,5-a]pyrimidin-6-yl)methyl]biphenyl-2-carbonitrile (0.095 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.034 g) and then 1,8-diazabicyclo[5.4.0]undec-7-ene (0.031 mL) were added, and the mixture was stirred at room temperature for 4 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.048 g, 46%).

$^1$H NMR (300 MHz, DMSO-$d_6$) δ 0.93 (t, J=7.16 Hz, 3H) 1.21-2.04 (m, 12H) 2.07-2.20 (m, 2H) 2.52-2.71 (m, 2H) 2.87-3.01 (m, 2H) 3.34-3.45 (m, 3H) 3.96 (s, 2H) 4.84 (s, 1H)

4.86-5.01 (m, 1H) 7.18-7.25 (m, 2H) 7.27-7.36 (m, 2H) 7.45-7.59 (m, 2H) 7.61-7.73 (m, 2H) 8.18 (s, 1H) 12.30 (br. s., 1H)

EXAMPLE 339

4-{trans-4-[3-fluoro-2-(fluoromethyl)-2-hydroxypropoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

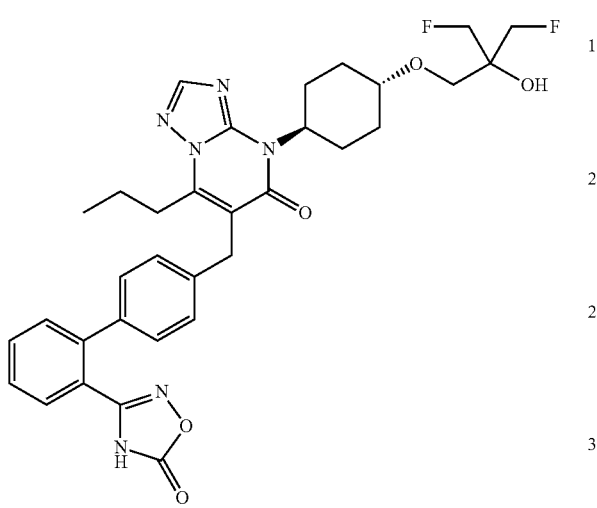

A mixture of hydroxylammonium chloride (0.29 g), sodium hydrogen carbonate (0.47 g) and dimethyl sulfoxide (4 mL) was stirred at 40° C. for 30 min, 4'-[(4-{trans-4-[3-fluoro-2-(fluoromethyl)-2-hydroxypropoxy]cyclohexyl}-5-oxo-7-propyl-4,5-dihydro[1,2,4]triazolo[1,5-a]pyrimidin-6-yl)methyl]biphenyl-2-carbonitrile (0.16 g) was added, and the mixture was stirred at 90° C. for 24 hr and then at room temperature for 34 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.055 g) and then 1,8-diazabicyclo[5.4.0]undec-7-ene (0.051 mL) were added, and the mixture was stirred at room temperature for 2 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.10 g, 61%).

$^1$H NMR (300 MHz, DMSO-$d_6$) δ0.92 (t, J=7.35 Hz, 3H) 1.21-1.39 (m, 2H) 1.44-1.77 (m, 4H) 2.04-2.18 (m, 2H) 2.52-2.68 (m, 2H) 2.86-3.00 (m, 2H) 3.26-3.40 (m, 1H) 3.45 (s, 2H) 3.95 (s, 2H) 4.36 (d, J=47.47 Hz, 4H) 4.82-5.00 (m, 1H) 5.35 (s, 1H) 7.16-7.26 (m, 2H) 7.27-7.34 (m, 2H) 7.46-7.60 (m, 2H) 7.62-7.74 (m, 2H) 8.18 (s, 1H) 12.37 (s, 1H)

EXAMPLE 340

4-[trans-4-(3-fluoro-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

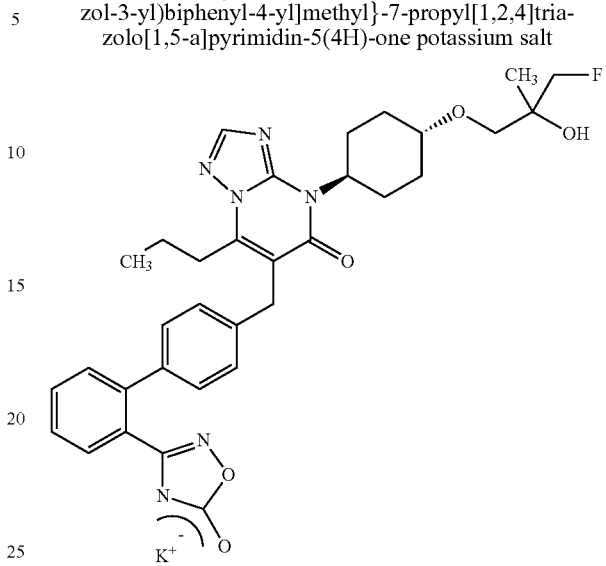

To a solution of 4-[trans-4-(3-fluoro-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.052 g) in tetrahydrofuran (2 mL) was added 0.1 M aqueous potassium hydroxide solution (0.85 mL), and the solvent was evaporated under reduced pressure. The residue was washed with diisopropyl ether to give the title compound as a colorless solid (0.038 g, 68%).

$^1$H NMR (300 MHz, DMSO-$d_6$) δ0.94 (t, J=7.25 Hz, 3H) 1.06 (d, J=2.07 Hz, 3H) 1.19-1.38 (m, 2H) 1.47-1.84 (m, 4H) 1.98-2.17 (m, 2H) 2.52-2.67 (m, 2H) 2.87-3.01 (m, 2H) 3.20-3.42 (m, 3H) 3.93 (s, 2H) 4.19 (d, J=47.85 Hz, 2H) 4.77 (s, 1H) 4.81-5.01 (m, 1H) 7.16-7.27 (m, 4H) 7.34-7.47 (m, 2H) 7.49-7.58 (m, 2H) 8.17 (s, 1H)

EXAMPLE 341

4-{trans-4-[(1-hydroxycyclobutyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

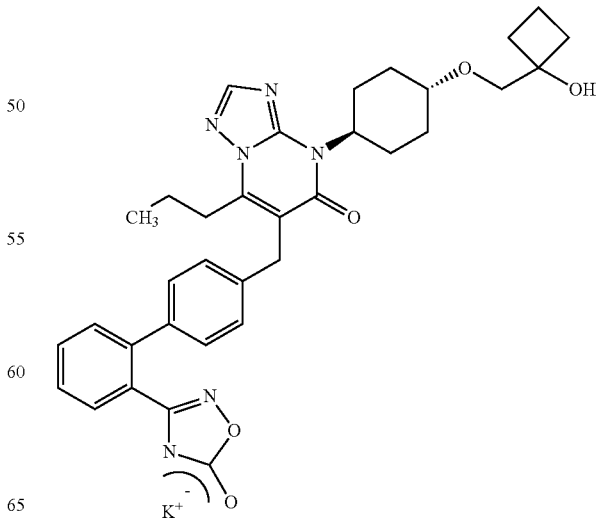

To a solution of 4-{trans-4-[(1-hydroxycyclobutyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.030 g) in tetrahydrofuran (2 mL) was added 0.1 M aqueous potassium hydroxide solution (0.49 mL), and the solvent was evaporated under reduced pressure. The residue was washed with diisopropyl ether to give the title compound as a colorless solid (0.020 g, 63%).

$^1$H NMR (300 MHz, DMSO-$d_6$) δ0.94 (t, J=7.35 Hz, 3H) 1.18-2.23 (m, 14H) 2.53-2.67 (m, 2H) 2.89-3.01 (m, 2H) 3.33-3.43 (m, 3H) 3.93 (s, 2H) 4.83 (s, 1H) 4.85-4.99 (m, 1H) 7.22 (s, 4H) 7.33-7.46 (m, 2H) 7.47-7.57 (m, 2H) 8.17 (s, 1H)

EXAMPLE 342

4-{trans-4-[3-fluoro-2-(fluoromethyl)-2-hydroxypropoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

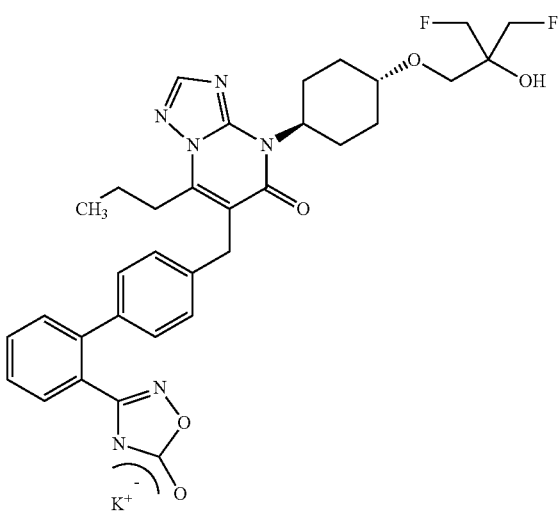 [SMILES: CCCc1c(Cc2ccc(-c3ccccc3C3=NOC(O)N3)cc2)c(=O)n([C@H]2CC[C@H](OCC(O)(CF)CF)CC2)c2ncnn12 ; [K+]]

To a solution of 4-{trans-4-[3-fluoro-2-(fluoromethyl)-2-hydroxypropoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.081 g) in tetrahydrofuran (2 mL) was added 0.1 M aqueous potassium hydroxide solution (1.2 mL), and the solvent was evaporated under reduced pressure. The residue was washed with diisopropyl ether to give the title compound as a colorless solid (0.063 g, 73%).

$^1$H NMR (300 MHz, DMSO-$d_6$) δ0.94 (t, J=7.35 Hz, 3H) 1.20-1.39 (m, 2H) 1.46-1.82 (m, 4H) 2.00-2.20 (m, 2H) 2.52-2.67 (m, 2H) 2.87-3.02 (m, 2H) 3.33-3.40 (m, 1H) 3.45 (s, 2H) 3.93 (s, 2H) 4.36 (d, J=47.47 Hz, 4H) 4.81-5.00 (m, 1H) 5.35 (s, 1H) 7.22 (s, 4H) 7.32-7.46 (m, 2H) 7.47-7.57 (m, 2H) 8.17 (s, 1H)

EXAMPLE 343

6-{[2'-(5-oxo-4,5-dihydro-1,2,4-oxadiazol-3-yl)biphenyl-4-yl]methyl}-7-propyl-4-[trans-4-(tetrahydrofuran-2-ylmethoxy)cyclohexyl][1,2,4]triazolo[1,5-a]pyrimidin-5(4H)-one

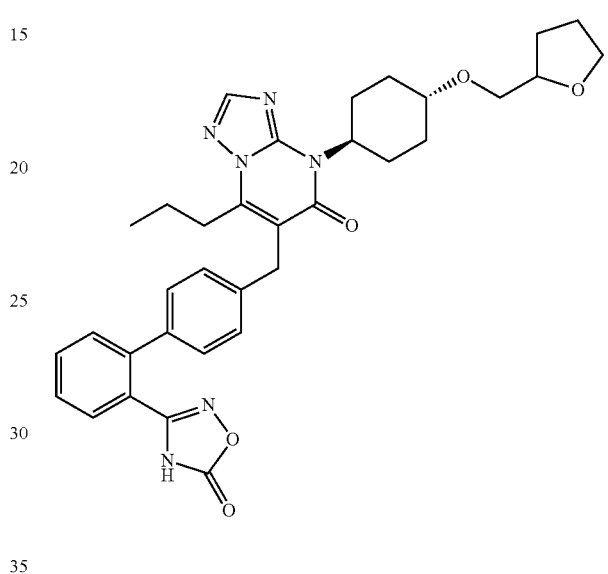

A mixture of hydroxylammonium chloride (0.24 g), sodium hydrogen carbonate (0.39 g) and dimethyl sulfoxide (5 mL) was stirred at 40° C. for 30 min, 4'-({5-oxo-7-propyl-4-[trans-4-(tetrahydrofuran-2-ylmethoxy)cyclohexyl]-4,5-dihydro[1,2,4]triazolo[1,5-a]pyrimidin-6-yl}methyl)biphenyl-2-carbonitrile (0.12 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.045 g) and then 1,8-diazabicyclo[5.4.0]undec-7-ene (0.042 mL) were added, and the mixture was stirred at room temperature for 5 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography and HPLC to give the title compound as a colorless solid (0.062 g, 43%).

$^1$H NMR (300 MHz, DMSO-$d_6$) δ0.92 (t, J=7.25 Hz, 3H) 1.18-1.98 (m, 10H) 2.02-2.18 (m, 2H) 2.52-2.68 (m, 2H) 2.87-3.01 (m, 2H) 3.25-3.48 (m, 3H) 3.56-3.66 (m, 1H) 3.68-3.80 (m, 1H) 3.83-3.93 (m, 1H) 3.95 (s, 2H) 4.79-5.02 (m, 1H) 7.18-7.26 (m, 2H) 7.28-7.35 (m, 2H) 7.47-7.59 (m, 2H) 7.61-7.75 (m, 2H) 8.18 (s, 1H) 12.37 (s, 1H)

EXAMPLE 344

4-{trans-4-[(1-hydroxycyclopentyl)methoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

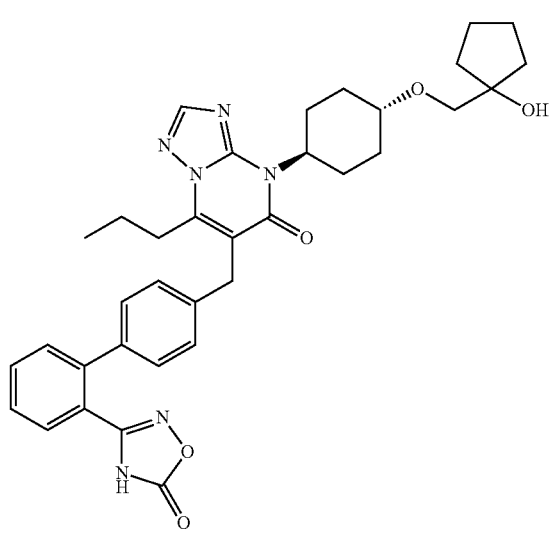 [SMILES: CCCc1c(Cc2ccc(-c3ccccc3-c3noc(=O)[nH]3)cc2)c(=O)n([C@H]2CC[C@H](OCC3(O)CCCC3)CC2)c2ncnn12]

A mixture of hydroxylammonium chloride (0.050 g), sodium hydrogen carbonate (0.081 g) and dimethyl sulfoxide (2 mL) was stirred at 40° C. for 30 min, 4'-[(4-{trans-4-[(1-hydroxycyclopentyl)methoxy]cyclohexyl}-5-oxo-7-propyl-4,5-dihydro[1,2,4]triazolo[1,5-a]pyrimidin-6-yl)methyl]biphenyl-2-carbonitrile (0.026 g) was added, and the mixture was stirred at 90° C. for 24 hr and then at room temperature for 58 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.010 g) and then 1,8-diazabicyclo[5.4.0]undec-7-ene (0.0090 mL) were added, and the mixture was stirred at room temperature for 5 hr. The reaction mixture was diluted with ethyl acetate, adjusted to pH 4 with 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.0070 g, 23%).

$^1$H NMR (300 MHz, CHLOROFORM-d) δ1.08 (t, J=7.35 Hz, 3H) 1.34-1.89 (m, 14H) 2.09-2.26 (m, 2H) 2.55-2.78 (m, 2H) 2.99-3.14 (m, 2H) 3.33-3.54 (m, 3H) 3.98 (s, 2H) 4.90-5.14 (m, 1H) 7.21-7.29 (m, 2H) 7.30-7.37 (m, 2H) 7.40 (dd, J=7.63, 1.04 Hz, 1H) 7.45-7.53 (m, 1H) 7.57-7.65 (m, 1H) 7.85 (dd, J=7.72, 1.13 Hz, 1H) 7.91 (s, 1H)

EXAMPLE 345

4-[trans-4-(2-hydroxy-2-methylbutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

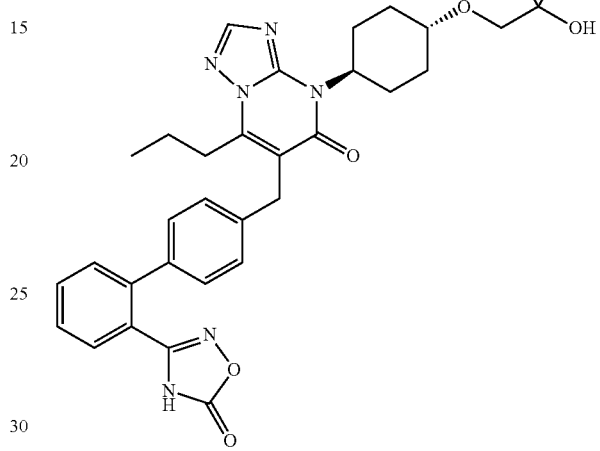

A mixture of hydroxylammonium chloride (0.11 g), sodium hydrogen carbonate (0.18 g) and dimethyl sulfoxide (3 mL) was stirred at 40° C. for 30 min, 4'-({4-[trans-4-(2-hydroxy-2-methylbutoxy)cyclohexyl]-5-oxo-7-propyl-4,5-dihydro[1,2,4]triazolo[1,5-a]pyrimidin-6-yl}methyl)biphenyl-2-carbonitrile (0.060 g) was added, and the mixture was stirred at 90° C. for 24 hr and then at room temperature for 35 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.021 g) and then 1,8-diazabicyclo[5.4.0]undec-7-ene (0.019 mL) were added, and the mixture was stirred at room temperature for 1 hr. Ethyl acetate and water were added to the reaction mixture, and the mixture was adjusted to pH 4 with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.049 g, 73%).

$^1$H NMR (300 MHz, DMSO-d$_6$) δ0.81 (t, J=7.54 Hz, 3H) 0.92 (t, J=7.35 Hz, 3H) 1.02 (s, 3H) 1.21-1.32 (m, 2H) 1.37 (q, J=7.35 Hz, 2H) 1.47-1.61 (m, 2H) 1.63-1.77 (m, 2H) 2.03-2.18 (m, 2H) 2.52-2.67 (m, 2H) 2.87-2.99 (m, 2H) 3.15-3.26 (m, 2H) 3.27-3.37 (m, 1H) 3.95 (s, 2H) 4.06 (s, 1H) 4.75-5.04 (m, 1H) 7.14-7.25 (m, 2H) 7.26-7.36 (m, 2H) 7.47-7.60 (m, 2H) 7.61-7.77 (m, 2H) 8.18 (s, 1H) 12.37 (s, 1H)

EXAMPLE 346

6-{[2'-(5-oxo-4,5-dihydro-1,2,4-oxadiazol-3-yl)biphenyl-4-yl]methyl}-7-propyl-4-[trans-4-(tetrahydrofuran-2-ylmethoxy)cyclohexyl][1,2,4]triazolo[1,5-a]pyrimidin-5(4H)-one potassium salt

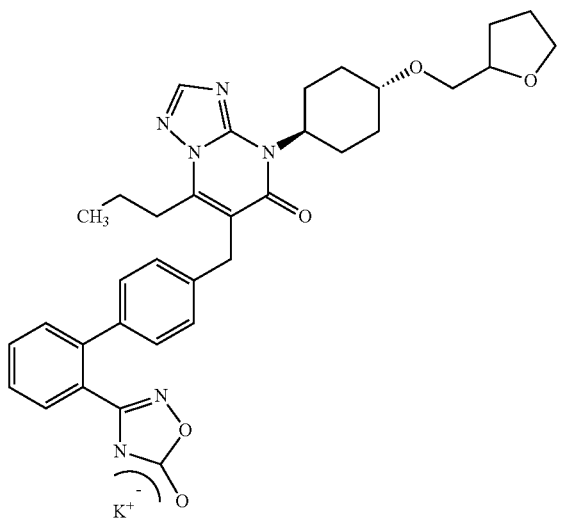 [SMILES: CCCc1c(Cc2ccc(-c3ccccc3C3=NOC(O)N3)cc2)c(=O)n([C@H]2CC[C@H](OCC3CCCO3)CC2)c2ncnn12 ; [K+]]

To a solution of 6-{[2'-(5-oxo-4,5-dihydro-1,2,4-oxadiazol-3-yl)biphenyl-4-yl]methyl}-7-propyl-4-[trans-4-(tetrahydrofuran-2-ylmethoxy)cyclohexyl][1,2,4]triazolo[1,5-a]pyrimidin-5(4H)-one (0.042 g) in tetrahydrofuran (2 mL) was added 0.1 M aqueous potassium hydroxide solution (0.68 mL), and the solvent was evaporated under reduced pressure. The residue was washed with diisopropyl ether to give the title compound as a colorless solid (0.027 g, 62%).

$^1$H NMR (300 MHz, DMSO-$d_6$) δ0.95 (t, J=7.19 Hz, 3H) 1.17-1.35 (m, 2H) 1.45-1.96 (m, 8H) 2.00-2.17 (m, 2H) 2.52-2.68 (m, 2H) 2.87-3.02 (m, 2H) 3.34-3.48 (m, 3H) 3.54-3.66 (m, 1H) 3.67-3.79 (m, 1H) 3.82-3.99 (m, 3H) 4.78-5.04 (m, 1H) 7.10-7.27 (m, 4H) 7.29-7.55 (m, 4H) 8.16 (s, 1H)

EXAMPLE 347

4-[trans-4-(2-hydroxy-2-methylbutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

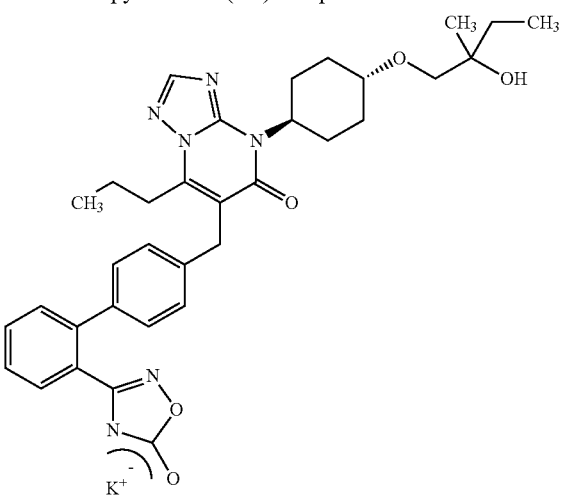

To a solution of 4-[trans-4-(2-hydroxy-2-methylbutoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.026 g) in tetrahydrofuran (2 mL) was added 0.1 M aqueous potassium hydroxide solution (0.43 mL), and the solvent was evaporated under reduced pressure. The residue was washed with diisopropyl ether to give the title compound as a colorless solid (0.022 g, 77%).

$^1$H NMR (300 MHz, DMSO-$d_6$) δ0.81 (t, J=7.57 Hz, 3H) 0.95 (t, J=7.19 Hz, 3H) 1.01 (s, 3H) 1.18-1.47 (m, 4H) 1.51-1.83 (m, 4H) 1.99-2.19 (m, 2H) 2.52-2.69 (m, 2H) 2.86-3.04 (m, 2H) 3.18 (d, J=9.09 Hz, 1H) 3.24 (d, J=9.09 Hz, 1H) 3.27-3.31 (m, 1H) 3.91 (s, 2H) 4.06 (s, 1H) 4.82-5.03 (m, 1H) 7.14-7.27 (m, 4H) 7.29-7.54 (m, 4H) 8.16 (s, 1H)

EXAMPLE 348

4-[trans-4-(1-ethyl-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

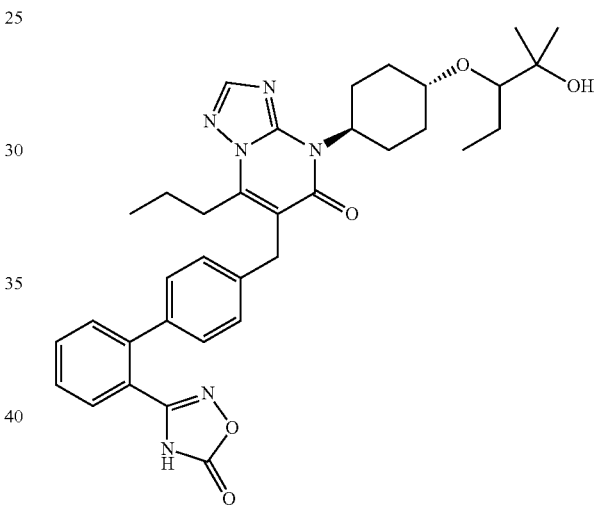

A mixture of hydroxylammonium chloride (0.23 g), sodium hydrogen carbonate (0.37 g) and dimethyl sulfoxide (5 mL) was stirred at 40° C. for 30 min, 4'-({4-[trans-4-(1-ethyl-2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (0.12 g) was added, and the mixture was stirred at 90° C. for 11 hr. Water was added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.044 g) and then 1,8-diazabicyclo[5.4.0]undec-7-ene (0.040 mL) were added, and the mixture was stirred at room temperature for 4 hr. Ethyl acetate and water were added to the reaction mixture, and the mixture was adjusted to pH 4 with 1 M hydrochloric acid, and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.080 g, 56%).

¹H NMR (300 MHz, DMSO-d₆) δ0.85-0.98 (m, 6H) 1.02 (s, 3H) 1.08 (s, 3H) 1.13-1.79 (m, 8H) 2.01-2.23 (m, 2H) 2.52-2.65 (m, 2H) 2.86-2.98 (m, 2H) 3.03 (dd, J=8.95, 2.73 Hz, 1H) 3.44-3.63 (m, 1H) 3.95 (s, 2H) 4.11 (s, 1H) 4.76-5.03 (m, 1H) 7.18-7.26 (m, 2H) 7.27-7.35 (m, 2H) 7.46-7.59 (m, 2H) 7.62-7.79 (m, 2H) 8.18 (s, 1H) 12.38 (s, 1H)

EXAMPLE 349

4-[trans-4-(1-ethyl-2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

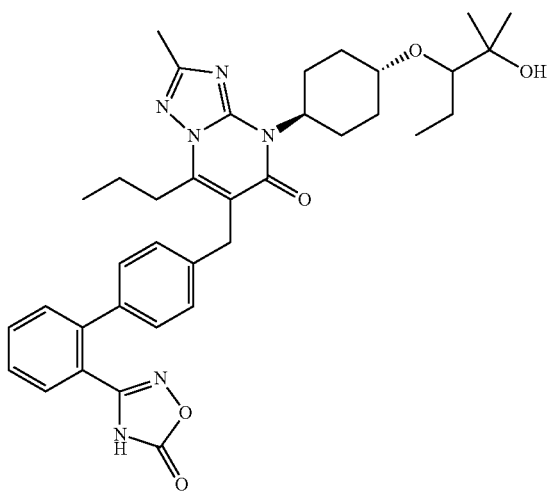 [SMILES: CCCc1c(Cc2ccc(-c3ccccc3-c3noc(=O)[nH]3)cc2)c(=O)n([C@H]2CC[C@H](OC(CC)C(C)(C)O)CC2)c2nc(C)nn12]

A mixture of hydroxylammonium chloride (0.21 g), sodium hydrogen carbonate (0.34 g) and dimethyl sulfoxide (5 mL) was stirred at 40° C. for 30 min, 4'-({4-[trans-4-(1-ethyl-2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.11 g) was added, and the mixture was stirred at 90° C. for 11 hr. Water was added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.040 g) and then 1,8-diazabicyclo[5.4.0]undec-7-ene (0.037 mL) were added, and the mixture was stirred at room temperature for 4 hr. Ethyl acetate and water were added to the reaction mixture, and the mixture was adjusted to pH 4 with 1 M hydrochloric acid, and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.079 g, 60%).

¹H NMR (300 MHz, DMSO-d₆) δ0.87-0.98 (m, 6H) 1.02 (s, 3H) 1.08 (s, 3H) 1.13-1.77 (m, 8H) 2.04-2.19 (m, 2H) 2.35 (s, 3H) 2.52-2.64 (m, 2H) 2.82-2.95 (m, 2H) 3.04 (dd, J=9.14, 2.73 Hz, 1H) 3.42-3.63 (m, 1H) 3.93 (s, 2H) 4.12 (s, 1H) 4.71-4.99 (m, 1H) 7.17-7.24 (m, 2H) 7.26-7.34 (m, 2H) 7.46-7.60 (m, 2H) 7.62-7.75 (m, 2H) 12.38 (s, 1H)

EXAMPLE 350

4-[trans-4-(1-ethyl-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

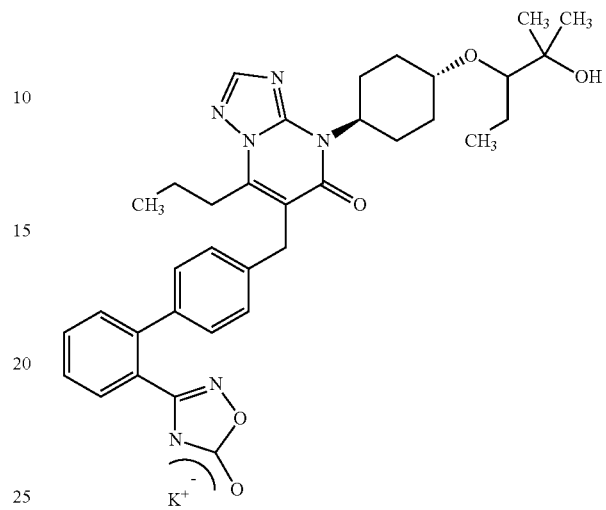

To a solution of 4-[trans-4-(1-ethyl-2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.058 g) in tetrahydrofuran (2 mL) was added 0.1 M aqueous potassium hydroxide solution (0.93 mL), and the solvent was evaporated under reduced pressure. The residue was washed with diisopropyl ether to give the title compound as a colorless solid (0.054 g, 87%).

¹H NMR (300 MHz, DMSO-d₆) δ0.87-0.99 (m, 6H) 1.02 (s, 3H) 1.08 (s, 3H) 1.13-1.78 (m, 8H) 2.03-2.21 (m, 2H) 2.52-2.68 (m, 2H) 2.90-2.99 (m, 2H) 3.03 (dd, J=9.04, 2.64 Hz, 1H) 3.41-3.61 (m, 1H) 3.91 (s, 2H) 4.11 (s, 1H) 4.74-5.03 (m, 1H) 7.13-7.24 (m, 4H) 7.26-7.54 (m, 4H) 8.16 (s, 1H)

EXAMPLE 351

4-[trans-4-(1-ethyl-2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

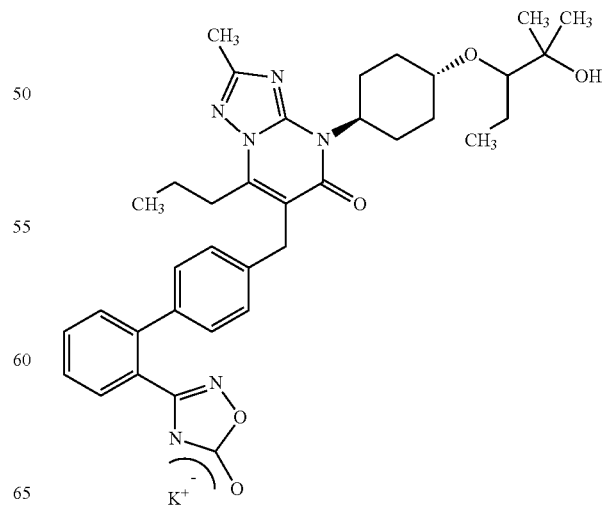

To a solution of 4-[trans-4-(1-ethyl-2-hydroxy-2-methyl-propoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.057 g) in tetrahydrofuran (2 mL) was added 0.1 M aqueous potassium hydroxide solution (0.90 mL), and the solvent was evaporated under reduced pressure. The residue was washed with diisopropyl ether to give the title compound as a colorless solid (0.053 g, 87%).

$^1$H NMR (300 MHz, DMSO-$d_6$) δ0.85-0.99 (m, 6H) 1.02 (s, 3H) 1.08 (s, 3H) 1.12-1.79 (m, 8H) 2.05-2.21 (m, 2H) 2.35 (s, 3H) 2.52-2.66 (m, 2H) 2.81-2.97 (m, 2H) 3.04 (dd, J=9.04, 2.64 Hz, 1H) 3.44-3.61 (m, 1H) 3.88 (s, 2H) 4.12 (s, 1H) 4.70-4.99 (m, 1H) 7.11-7.25 (m, 4H) 7.26-7.56 (m, 4H)

EXAMPLE 352

4-[trans-4-(3,3-difluoro-2-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

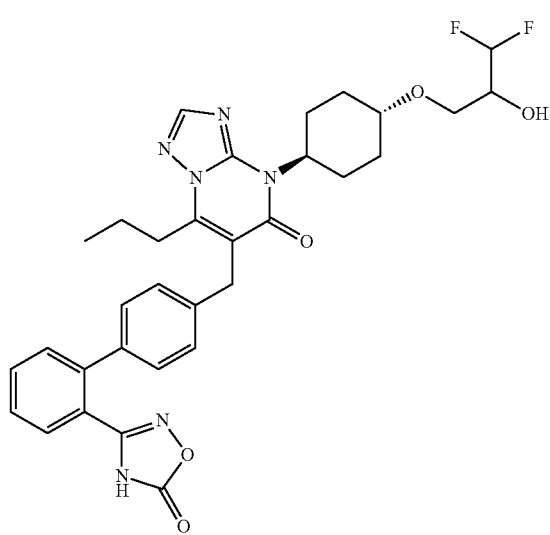 [SMILES: CCCc1c(Cc2ccc(-c3ccccc3-c3noc(=O)[nH]3)cc2)c(=O)n([C@H]2CC[C@H](OCC(O)C(F)F)CC2)c2ncnn12]

A mixture of hydroxylammonium chloride (0.18 g), sodium hydrogen carbonate (0.24 g) and dimethyl sulfoxide (3 mL) was stirred at 40° C. for 30 min, 4'-({4-[trans-4-(2-{[tert-butyl(dimethyl)silyl]oxy}-3,3-difluoropropoxy)cyclohexyl]-5-oxo-7-propyl-4,5-dihydro[1,2,4]triazolo[1,5-a]pyrimidin-6-yl}methyl)biphenyl-2-carbonitrile (0.12 g) was added, and the mixture was stirred at 90° C. for 21 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.035 g) and then 1,8-diazabicyclo[5.4.0]undec-7-ene (0.032 mL) were added, and the mixture was stirred at room temperature for 2 hr. Thereafter, tetrabutylammonium fluoride (0.44 mL, 1.0 M tetrahydrofuran solution) was added, and the mixture was stirred at 70° C. for 2 hr. To the reaction mixture was added 1 M hydrochloric acid, and the mixture was extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.080 g, 73%).

$^1$H NMR (300 MHz, DMSO-$d_6$) δ0.93 (t, J=7.35 Hz, 3H) 1.21-1.39 (m, 2H) 1.45-1.81 (m, 4H) 2.03-2.20 (m, 2H) 2.51-2.68 (m, 2H) 2.86-3.00 (m, 2H) 3.33-3.44 (m, 1H) 3.45-3.60 (m, 2H) 3.65-3.85 (m, 1H) 3.96 (s, 2H) 4.74-5.09 (m, 1H) 5.63 (d, J=6.22 Hz, 1H) 5.89 (dt, J=55.53, 3.67 Hz, 1H) 7.18-7.25 (m, 2H) 7.27-7.36 (m, 2H) 7.47-7.60 (m, 2H) 7.61-7.77 (m, 2H) 8.18 (s, 1H) 12.38 (s, 1H)

EXAMPLE 353

4-[trans-4-(3,3-difluoro-2-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

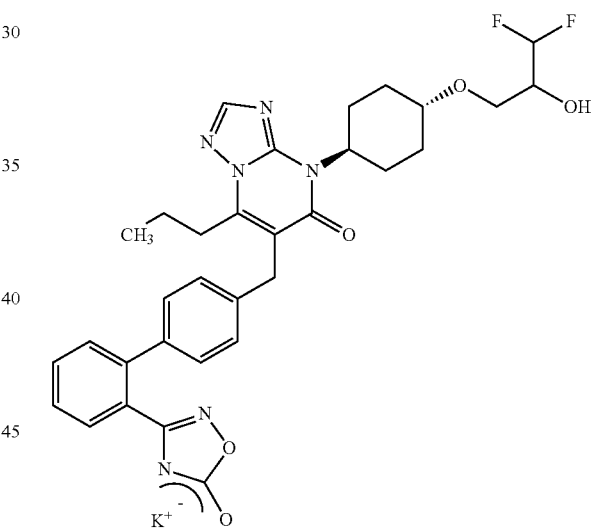

To a solution of 4-[trans-4-(3,3-difluoro-2-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.055 g) in tetrahydrofuran (2 mL) was added 0.1 M aqueous potassium hydroxide solution (0.89 mL), and the solvent was evaporated under reduced pressure. The residue was washed with diisopropyl ether to give the title compound as a colorless solid (0.055 g, 94%).

$^1$H NMR (300 MHz, DMSO-$d_6$) δ0.96 (t, J=7.35 Hz, 3H) 1.17-1.41 (m, 2H) 1.52-1.82 (m, 4H) 2.03-2.18 (m, 2H) 2.52-2.68 (m, 2H) 2.89-3.03 (m, 2H) 3.34-3.42 (m, 1H) 3.44-3.63 (m, 2H) 3.66-3.84 (m, 1H) 3.91 (s, 2H) 4.78-5.01 (m, 1H)

5.63 (d, J=6.03 Hz, 1H) 5.89 (dt, J=55.53, 3.67 Hz, 1H) 7.13-7.51 (m, 8H) 8.16 (s, 1H)

EXAMPLE 354

4-[trans-4-(3-fluoro-2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

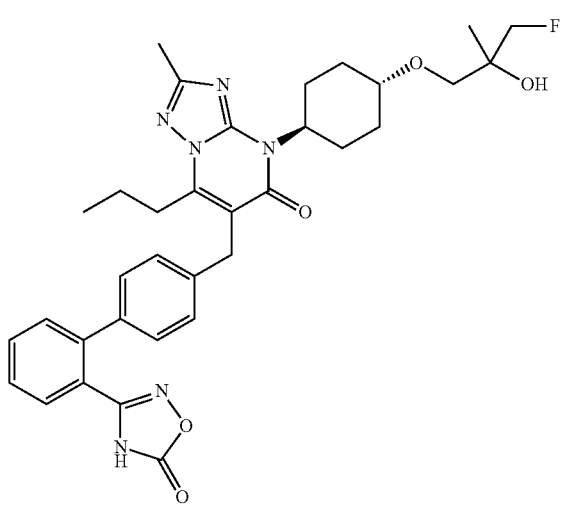 [SMILES: CCCc1c(Cc2ccc(-c3ccccc3-c3noc(=O)[nH]3)cc2)c(=O)n([C@H]2CC[C@H](OCC(C)(O)CF)CC2)c2nc(C)nn12]

A mixture of hydroxylammonium chloride (0.17 g), sodium hydrogen carbonate (0.27 g) and dimethyl sulfoxide (3 mL) was stirred at 40° C. for 30 min, 4'-({4-[trans-4-(3-fluoro-2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.094 g) was added, and the mixture was stirred at 90° C. for 14 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.033 g) and then 1,8-diazabicyclo[5.4.0]undec-7-ene (0.030 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.066 g, 63%).

$^1$H NMR (300 MHz, DMSO-d$_6$) δ0.92 (t, J=7.38 Hz, 3H) 1.06 (d, J=2.27 Hz, 3H) 1.18-1.39 (m, 2H) 1.44-1.77 (m, 4H) 2.02-2.18 (m, 2H) 2.35 (s, 3H) 2.52-2.67 (m, 2H) 2.81-2.97 (m, 2H) 3.19-3.43 (m, 3H) 3.93 (s, 2H) 4.19 (d, J=47.71 Hz, 2H) 4.78 (s, 1H) 4.80-4.97 (m, 1H) 7.18-7.25 (m, 2H) 7.26-7.35 (m, 2H) 7.44-7.59 (m, 2H) 7.61-7.76 (m, 2H) 12.37 (s, 1H)

EXAMPLE 355

4-[trans-4-(1-ethyl-2-hydroxy-2-methylpropoxy)cyclohexyl]-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

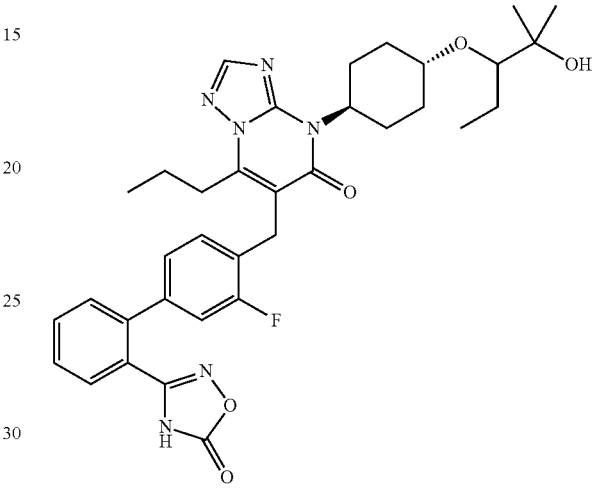

A mixture of hydroxylammonium chloride (0.37 g), sodium hydrogen carbonate (0.59 g, and dimethyl sulfoxide (5 mL) was stirred at 40° C. for 30 min, 4'-({4-[trans-4-(1-ethyl-2-hydroxy-2-methylpropoxy)cyclohexyl]-5-oxo-7-propyl-4,5-dihydro[1,2,4]triazolo[1,5-a]pyrimidin-6-yl}methyl)-3'-fluorobiphenyl-2-carbonitrile (0.20 g) was added, and the mixture was stirred at 90° C. for 24 hr and then at room temperature for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.069 g) and then 1,8-diazabicyclo[5.4.0]undec-7-ene (0.064 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.16 g, 73%).

$^1$H NMR (300 MHz, DMSO-d$_6$) δ0.93 (t, J=7.38 Hz, 6H) 1.01 (s, 3H) 1.08 (s, 3H) 1.12-1.76 (m, 8H) 2.02-2.21 (m, 2H) 2.52-2.68 (m, 2H) 2.83-2.98 (m, 2H) 3.03 (dd, J=9.09, 2.65 Hz, 1H) 3.42-3.64 (m, 1H) 3.94 (s, 2H) 4.10 (s, 1H) 4.74-4.98 (m, 1H) 6.99 (dd, J=8.14, 1.70 Hz, 1H) 7.16 (dd, J=11.17, 1.70 Hz, 1H) 7.20-7.32 (m, 1H) 7.49-7.63 (m, 2H) 7.64-7.74 (m, 2H) 8.19 (s, 1H) 12.45 (s, 1H)

EXAMPLE 356

4-{trans-4-[(1-hydroxycyclobutyl)methoxy]cyclohexyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

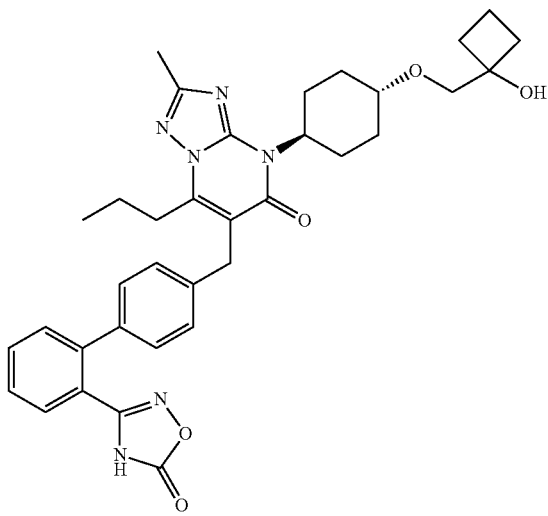 [SMILES: CCCc1c(Cc2ccc(-c3ccccc3-c3noc(=O)[nH]3)cc2)c(=O)n([C@H]2CC[C@H](OCC3(O)CCC3)CC2)c2nc(C)nn12]

A mixture of hydroxylammonium chloride (0.18 g), sodium hydrogen carbonate (0.29 g) and dimethyl sulfoxide (5 mL) was stirred at 40° C. for 30 min, 4'-[(4-{trans-4-[(1-hydroxycyclobutyl)methoxy]cyclohexyl}-2-methyl-5-oxo-7-propyl-4,5-dihydro[1,2,4]triazolo[1,5-a]pyrimidin-6-yl)methyl]biphenyl-2-carbonitrile (0.098 g) was added, and the mixture was stirred at 90° C. for 24 hr and then at room temperature for 38 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.028 g) and then 1,8-diazabicyclo[5.4.0]undec-7-ene (0.031 mL) were added, and the mixture was stirred at room temperature for 30 min. Ethyl acetate and water were added to the reaction mixture, and the mixture was adjusted to pH 4 with 1 M hydrochloric acid, and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.034 g, 32%).

$^1$H NMR (300 MHz, DMSO-$d_6$) δ0.92 (t, J=7.35 Hz, 3H) 1.20-2.05 (m, 12H) 2.09-2.21 (m, 2H) 2.35 (s, 3H) 2.52-2.68 (m, 2H) 2.81-2.97 (m, 2H) 3.33-3.44 (m, 3H) 3.93 (s, 2H) 4.77-4.97 (m, 2H) 7.18-7.25 (m, 2H) 7.26-7.34 (m, 2H) 7.47-7.59 (m, 2H) 7.61-7.75 (m, 2H) 12.37 (s, 1H)

EXAMPLE 357

4-[trans-4-(3-fluoro-2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

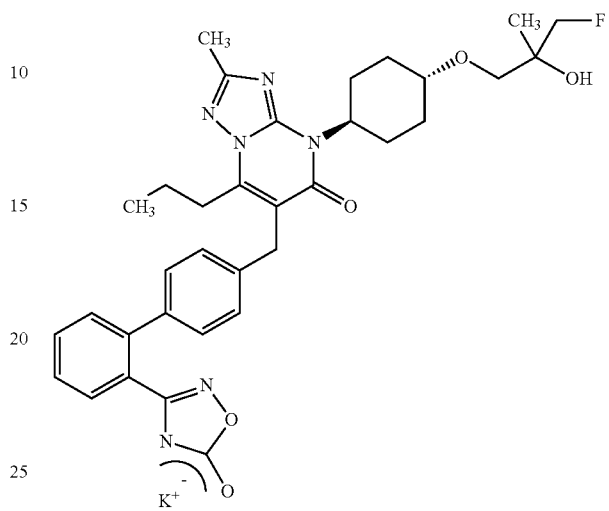

To a solution of 4-[trans-4-(3-fluoro-2-hydroxy-2-methylpropoxy)cyclohexyl]-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.041 g) in tetrahydrofuran (2 mL) was added 0.1 M aqueous potassium hydroxide solution (0.65 mL), and the solvent was evaporated under reduced pressure. The residue was washed with diisopropyl ether to give the title compound as a colorless solid (0.037 g, 85%).

$^1$H NMR (300 MHz, DMSO-$d_6$) δ0.94 (t, J=7.38 Hz, 3H) 1.06 (d, J=2.27 Hz, 3H) 1.18-1.42 (m, 2H) 1.48-1.79 (m, 4H) 2.02-2.16 (m, 2H) 2.35 (s, 3H) 2.52-2.66 (m, 2H) 2.82-2.98 (m, 2H) 3.21-3.42 (m, 3H) 3.88 (s, 2H) 4.23 (d, J=48.09 Hz, 2H) 4.77 (s, 1H) 4.80-4.97 (m, 1H) 7.11-7.25 (m, 4H) 7.26-7.53 (m, 4H)

EXAMPLE 358

4-[trans-4-(1-ethyl-2-hydroxy-2-methylpropoxy)cyclohexyl]-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

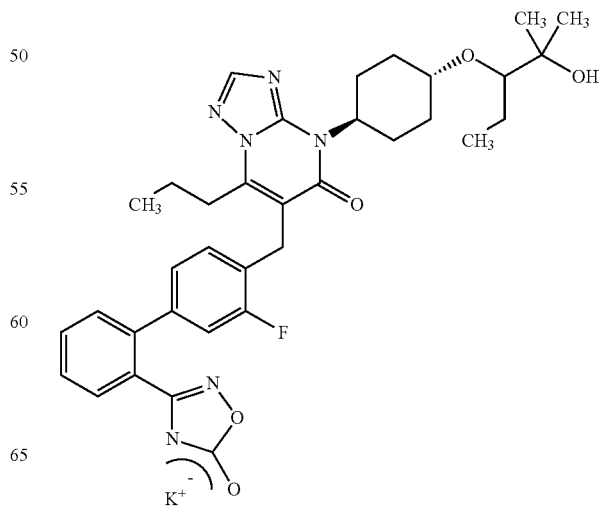

To a solution of 4-[trans-4-(1-ethyl-2-hydroxy-2-methylpropoxy)cyclohexyl]-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.11 g) in tetrahydrofuran (2 mL) was added 0.1 M aqueous potassium hydroxide solution (1.8 mL), and the solvent was evaporated under reduced pressure. The residue was washed with diisopropyl ether to give the title compound as a colorless solid (0.11 g, 89%).

$^1$H NMR (300 MHz, DMSO-$d_6$) δ0.87-0.98 (m, 6H) 1.01 (s, 3H) 1.08 (s, 3H) 1.13-1.80 (m, 8H) 1.98-2.21 (m, 2H) 2.52-2.66 (m, 2H) 2.86-2.98 (m, 2H) 3.03 (dd, J=8.90, 2.08 Hz, 1H) 3.42-3.61 (m, 1H) 3.90 (s, 2H) 4.10 (s, 1H) 4.77-5.02 (m, 1H) 6.96-7.20 (m, 3H) 7.29-7.57 (m, 4H) 8.17 (s, 1H)

EXAMPLE 359

4-{trans-4-[(1-hydroxycyclobutyl)methoxy]cyclohexyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

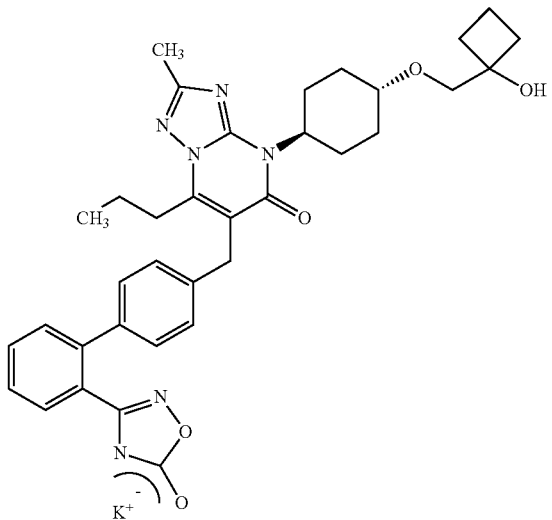 [SMILES: CCCc1c(Cc2ccc(-c3ccccc3C3=NOC(O)N3)cc2)c(=O)n([C@H]2CC[C@H](OCC3(O)CCC3)CC2)c2nc(C)nn12 ; [K+]]

To a solution of 4-{trans-4-[(1-hydroxycyclobutyl)methoxy]cyclohexyl}-2-methyl-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.019 g) in tetrahydrofuran (2 mL) was added 0.1 M aqueous potassium hydroxide solution (0.30 mL), and the solvent was evaporated under reduced pressure. The residue was washed with diisopropyl ether to give the title compound as a colorless solid (0.016 g, 80%).

$^1$H NMR (300 MHz, DMSO-$d_6$) δ0.95 (t, J=7.19 Hz, 3H) 1.20-2.24 (m, 14H) 2.35 (s, 3H) 2.51-2.68 (m, 2H) 2.83-2.97 (m, 2H) 3.32-3.43 (m, 3H) 3.88 (s, 2H) 4.78-4.97 (m, 2H) 7.11-7.24 (m, 4H) 7.25-7.50 (m, 4H)

EXAMPLE 360

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-2-methyl-7-propyl[1,2,4]triazolo[1,5-a]pyrimidin-5(4H)-one

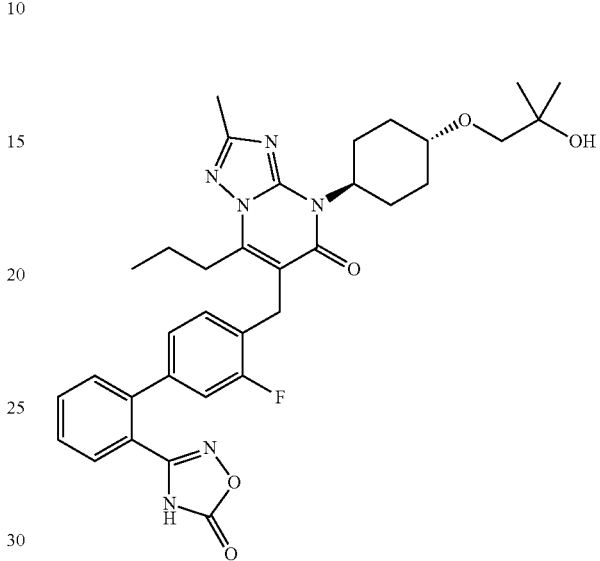

A mixture of hydroxylammonium chloride (0.70 g), sodium hydrogen carbonate (1.1 g) and dimethyl sulfoxide (6 mL) was stirred at 40° C. for 30 min, 3'-fluoro-4'-({4-[trans-4-(2-hydroxy-2-methylpropoxy)cyclohexyl]-2-methyl-5-oxo-7-propyl-4,5-dihydro[1,2,4]triazolo[1,5-a]pyrimidin-6-yl}methyl)biphenyl-2-carbonitrile (0.39 g) was added and the mixture was stirred at 90° C. for 24 hr and then at room temperature for 38 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (4 mL). N,N'-Carbonyldiimidazole (0.13 g) and then 1,8-diazabicyclo[5.4.0]undec-7-ene (0.12 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.30 g, 69%).

$^1$H NMR (300 MHz, DMSO-$d_6$) δ0.92 (t, J=7.35 Hz, 3H) 1.07 (s, 6H) 1.20-1.41 (m, 2H) 1.45-1.77 (m, 4H) 2.01-2.22 (m, 2H) 2.36 (s, 3H) 2.52-2.66 (m, 2H) 2.78-2.99 (m, 2H) 3.20 (s, 2H) 3.23-3.31 (m, 1H) 3.91 (s, 2H) 4.23 (s, 1H) 4.72-5.00 (m, 1H) 6.99 (dd, J=7.91, 1.70 Hz, 1H) 7.10-7.31 (m, 2H) 7.48-7.63 (m, 2H) 7.65-7.76 (m, 2H) 12.45 (s, 1H)

EXAMPLE 361

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-2-methyl-7-propyl[1,2,4]triazolo[1,5-a]pyrimidin-5(4H)-one potassium salt

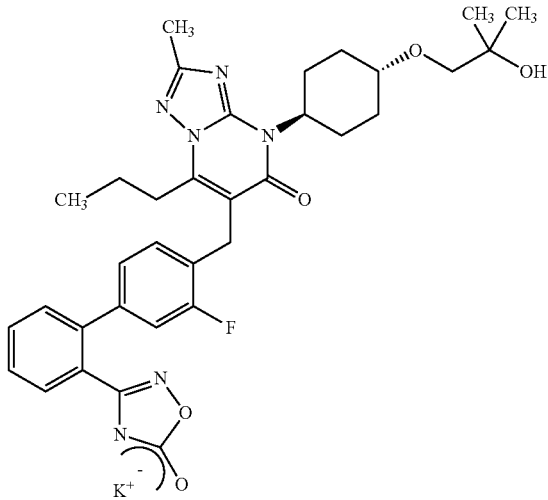 [SMILES: CCCc1c(Cc2ccc(-c3ccccc3C3=NOC(O)N3)cc2F)c(=O)n([C@H]2CC[C@H](OCC(C)(C)O)CC2)c2nc(C)nn12 ; [K+]]

To a solution of 6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-2-methyl-7-propyl[1,2,4]triazolo[1,5-a]pyrimidin-5(4H)-one (0.093 g) in tetrahydrofuran (2 mL) was added 0.1 M aqueous potassium hydroxide solution (1.4 mL), and the solvent was evaporated under reduced pressure. The residue was washed with diisopropyl ether to give the title compound as a colorless solid (0.083 g, 83%).

$^1$H NMR (300 MHz, DMSO-$d_6$) δ0.94 (t, J=7.25 Hz, 3H) 1.06 (s, 6H) 1.18-1.38 (m, 2H) 1.49-1.78 (m, 4H) 1.98-2.22 (m, 2H) 2.36 (s, 3H) 2.52-2.68 (m, 2H) 2.81-3.00 (m, 2H) 3.20 (s, 2H) 3.24-3.31 (m, 1H) 3.87 (s, 2H) 4.23 (s, 1H) 4.69-4.99 (m, 1H) 6.88-7.17 (m, 3H) 7.24-7.57 (m, 4H)

EXAMPLE 362

6-{[3-fluoro-2'-(5-oxo-4,5-dihydro-1,2,4-oxadiazol-3-yl)biphenyl-4-yl]methyl}-4-(trans-4-{[1-(1-hydroxy-1-methylethyl)cyclopropyl]oxy}cyclohexyl)-7-propyl[1,2,4]triazolo[1,5-a]pyrimidin-5(4H)-one

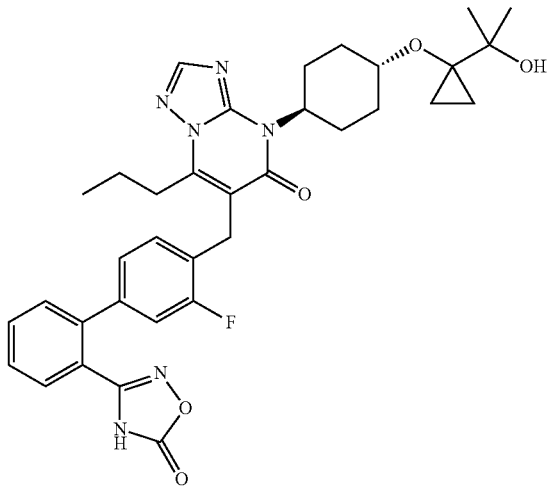 [SMILES: CCCc1c(Cc2ccc(-c3ccccc3-c3noc(=O)[nH]3)cc2F)c(=O)n([C@H]2CC[C@H](OC3(C(C)(C)O)CC3)CC2)c2ncnn12]

A mixture of hydroxylammonium chloride (0.059 g), sodium hydrogen carbonate (0.094 g) and dimethyl sulfoxide (2 mL) was stirred at 40° C. for 30 min, 3'-fluoro-4'-{[4-(trans-4-{[1-(1-hydroxy-1-methylethyl)cyclopropyl]oxy}cyclohexyl)-5-oxo-7-propyl-4,5-dihydro[1,2,4]triazolo[1,5-a]pyrimidin-6-yl]methyl}biphenyl-2-carbonitrile (0.032 g) was added and the mixture was stirred at 90° C. for 24 hr and then at room temperature for 40 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.011 g) and then 1,8-diazabicyclo[5.4.0]undec-7-ene (0.010 mL) were added, and the mixture was stirred at room temperature for 30 min. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.017 g, 47%).

$^1$H NMR (300 MHz, DMSO-$d_6$) δ0.55-0.66 (m, 2H) 0.67-0.78 (m, 2H) 0.93 (t, J=7.19 Hz, 3H) 1.14 (s, 6H) 1.21-1.39 (m, 2H) 1.46-1.74 (m, 4H) 1.88-2.06 (m, 2H) 2.53-2.69 (m, 2H) 2.83-2.98 (m, 2H) 3.41-3.63 (m, 1H) 3.93 (s, 2H) 4.20 (s, 1H) 4.72-4.96 (m, 1H) 6.99 (d, J=7.95 Hz, 1H) 7.09-7.33 (m, 2H) 7.50-7.63 (m, 2H) 7.65-7.79 (m, 2H) 8.19 (s, 1H) 12.45 (br. s., 1H)

EXAMPLE 363

4-(trans-4-{[1-(1-hydroxy-1-methylethyl)cyclopropyl]oxy}cyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

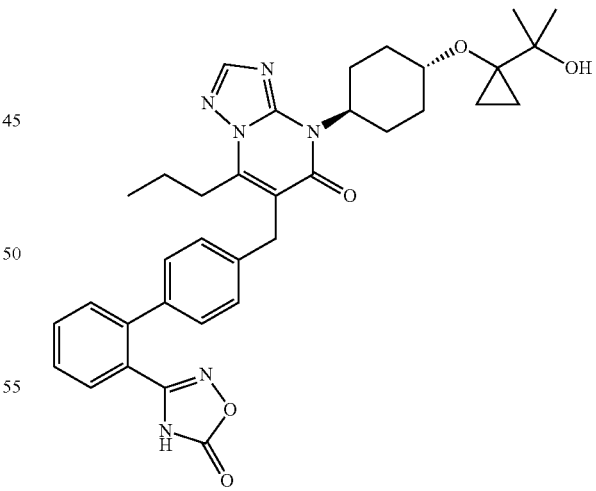

A mixture of hydroxylammonium chloride (0.092 g), sodium hydrogen carbonate (0.14 g) and dimethyl sulfoxide (3 mL) was stirred at 40° C. for 30 min, 4'-{[4-(trans-4-{[1-(1-hydroxy-1-methylethyl)cyclopropyl]oxy}cyclohexyl)-5-oxo-7-propyl-4,5-dihydro[1,2,4]triazolo[1,5-a]pyrimidin-6-yl]methyl}biphenyl-2-carbonitrile (0.049 g) was added and the mixture was stirred at 90° C. for 24 hr and then at room temperature for 38 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.018 g) and then 1,8-diazabicyclo[5.4.0]undec-7-ene (0.017 mL) were added, and the mixture was stirred at room temperature for 45 min. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.025 g, 45%).

$^1$H NMR (300 MHz, DMSO-d$_6$) δ0.59-0.67 (m, 2H) 0.68-0.77 (m, 2H) 0.92 (t, J=7.35 Hz, 3H) 1.14 (s, 6H) 1.20-1.71 (m, 6H) 1.93-2.07 (m, 2H) 2.52-2.68 (m, 2H) 2.85-2.99 (m, 2H) 3.41-3.64 (m, 1H) 3.95 (s, 2H) 4.21 (s, 1H) 4.73-4.98 (m, 1H) 7.15-7.26 (m, 2H) 7.27-7.37 (m, 2H) 7.46-7.60 (m, 2H) 7.62-7.78 (m, 2H) 8.17 (s, 1H) 12.37 (br. s., 1H)

EXAMPLE 364

4-{trans-4-[3-fluoro-2-(fluoromethyl)-2-hydroxy-1-methylpropoxy]cyclohexyl}-6-{[3-fluoro-2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

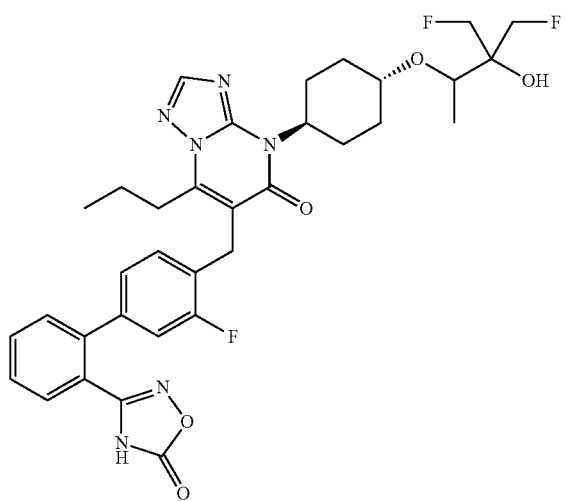 [SMILES: CCCc1c(Cc2ccc(-c3ccccc3-c3noc(=O)[nH]3)cc2F)c(=O)n([C@H]2CC[C@H](OC(C)C(O)(CF)CF)CC2)c2ncnn12]

A mixture of 3'-fluoro-4'-{[4-(trans-4-{1-[2-(fluoromethyl)oxiran-2-yl]ethoxy}cyclohexyl)-5-oxo-7-propyl-4,5-dihydro[1,2,4]triazolo[1,5-a]pyrimidin-6-yl]methyl}biphenyl-2-carbonitrile (0.079 g), tetrabutylammonium dihydrogen trifluoride (0.12 g) and chlorobenzene (0.5 mL) was stirred at 120° C. for 24 hr. Tetrabutylammonium dihydrogen trifluoride (0.12 g) was further added, and the mixture was further stirred at 120° C. for 3 days. The reaction mixture was purified by silica gel column chromatography, the obtained residue was added to a mixture of hydroxylammonium chloride (0.066 g), sodium hydrogen carbonate (0.10 g), and dimethyl sulfoxide (3 mL), which had been stirred at 40° C. for 30 min in advance, and the mixture was stirred at 90° C. for 48 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.012 g) and then 1,8-diazabicyclo[5.4.0]undec-7-ene (0.011 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and HPLC to give the title compound as a colorless solid (0.016 g, 17%).

$^1$H NMR (300 MHz, DMSO-d$_6$) δ0.93 (t, J=7.35 Hz, 3H) 1.04-1.78 (m, 9H) 1.91-2.18 (m, 2H) 2.52-2.70 (m, 2H) 2.87-3.01 (m, 2H) 3.35-3.47 (m, 1H) 3.54-3.71 (m, 1H) 3.93 (s, 2H) 4.21-4.54 (m, 4H) 4.75-4.99 (m, 1H) 5.21 (s, 1H) 6.90-7.34 (m, 3H) 7.40-7.74 (m, 4H) 8.19 (s, 1H) 12.47 (br. s., 1H)

EXAMPLE 365

6-{[3-fluoro-2'-(5-oxo-4,5-dihydro-1,2,4-oxadiazol-3-yl)biphenyl-4-yl]methyl}-4-[cis-3-(2-hydroxy-2-methylpropoxy)cyclobutyl]-7-propyl[1,2,4]triazolo[1,5-a]pyrimidin-5(4H)-one

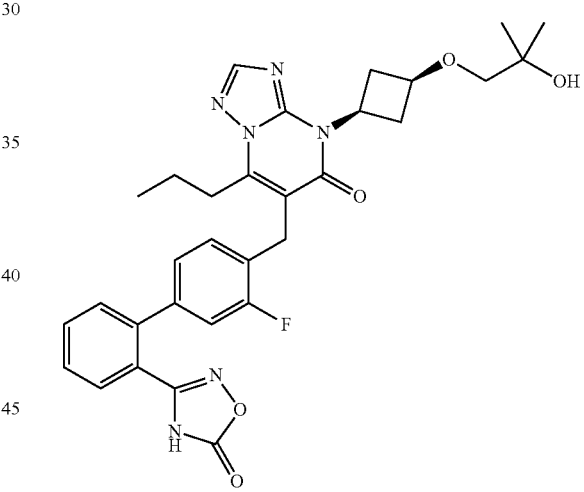

A mixture of hydroxylammonium chloride (0.34 g), sodium hydrogen carbonate (0.55 g) and dimethyl sulfoxide (4 mL) was stirred at 40° C. for 30 min, 3'-fluoro-4'-({4-[cis-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile (0.17 g) was added, and the mixture was stirred at 90° C. for 15 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.064 g) and then 1,8-diazabicyclo[5.4.0]undec-7-ene (0.059 mL) were added, and the mixture was stirred at room temperature for 1 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.13 g, 70%).

$^1$H NMR (300 MHz, DMSO-d$_6$) δ0.93 (t, J=7.38 Hz, 3H) 1.09 (s, 6H) 1.42-1.76 (m, 2H) 2.53-2.70 (m, 2H) 2.84-3.07 (m, 4H) 3.11 (s, 2H) 3.75-3.86 (m, 1H) 3.93 (s, 2H) 4.29 (s, 1H) 4.79-5.05 (m, 1H) 6.89-7.04 (m, 1H) 7.09-7.35 (m, 2H) 7.46-7.78 (m, 4H) 8.21 (s, 1H) 12.46 (br. s., 1H)

EXAMPLE 366

6-{[3-fluoro-2'-(5-oxo-4,5-dihydro-1,2,4-oxadiazol-3-yl)biphenyl-4-yl]methyl}-4-[cis-3-(2-hydroxy-2-methylpropoxy)cyclobutyl]-7-propyl[1,2,4]triazolo[1,5-a]pyrimidin-5(4H)-one potassium salt

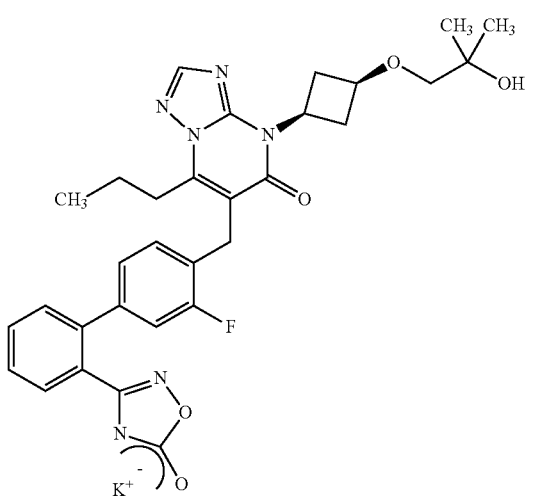 [SMILES: CCCc1c(Cc2ccc(-c3ccccc3C3=NOC(O)N3)cc2F)c(=O)n([C@H]2C[C@@H](OCC(C)(C)O)C2)c2ncnn12 ; [K+]]

To a solution of 6-{[3-fluoro-2'-(5-oxo-4,5-dihydro-1,2,4-oxadiazol-3-yl)biphenyl-4-yl]methyl}-4-[cis-3-(2-hydroxy-2-methylpropoxy)cyclobutyl]-7-propyl[1,2,4]triazolo[1,5-a]pyrimidin-5(4H)-one (0.051 g) in tetrahydrofuran (2 mL) was added 0.1 M aqueous potassium hydroxide solution (0.86 mL), and the solvent was evaporated under reduced pressure. The residue was washed with diisopropyl ether to give the title compound as a colorless solid (0.045 g, 84%).

$^1$H NMR (300 MHz, DMSO-d$_6$) δ0.95 (t, J=7.25 Hz, 3H) 1.09 (s, 6H) 1.49-1.74 (m, 2H) 2.54-2.67 (m, 2H) 2.79-3.07 (m, 4H) 3.11 (s, 2H) 3.66-3.85 (m, 1H) 3.89 (s, 2H) 4.31 (s, 1H) 4.70-5.09 (m, 1H) 6.93-7.24 (m, 3H) 7.25-7.64 (m, 4H) 8.20 (s, 1H)

EXAMPLE 367

6-{[3-fluoro-2'-(5-oxo-4,5-dihydro-1,2,4-oxadiazol-3-yl)biphenyl-4-yl]methyl}-4-[trans-3-(2-hydroxy-2-methylpropoxy)cyclobutyl]-7-propyl[1,2,4]triazolo[1,5-a]pyrimidin-5(4H)-one

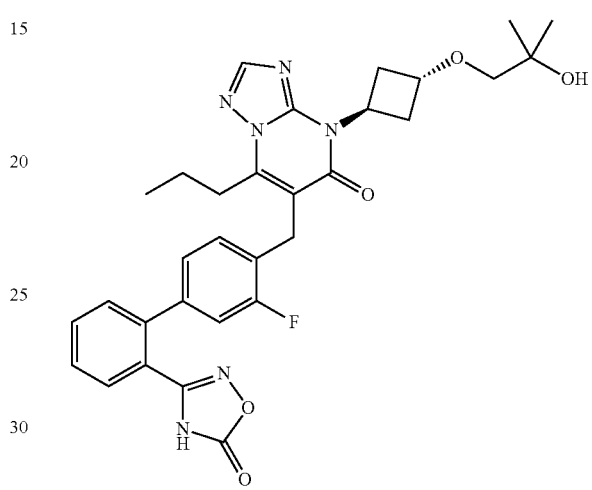

A mixture of hydroxylammonium chloride (0.13 g), sodium hydrogen carbonate (0.21 g) and dimethyl sulfoxide (4 mL) was stirred at 40° C. for 30 min, 3'-fluoro-4'-({4-[trans-3-(2-hydroxy-2-methylpropoxy)cyclobutyl]-5-oxo-7-propyl-4,5-dihydro[1,2,4]triazolo[1,5-a]pyrimidin-6-yl}methyl)biphenyl-2-carbonitrile (0.066 g) was added, and the mixture was stirred at 90° C. for 14 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (1 mL). N,N'-Carbonyldiimidazole (0.025 g) and then 1,8-diazabicyclo[5.4.0]undec-7-ene (0.023 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (0.054 g, 73%).

$^1$H NMR (300 MHz, DMSO-d$_6$) δ0.93 (t, J=7.35 Hz, 3H) 1.11 (s, 6H) 1.42-1.67 (m, 2H) 2.21-2.38 (m, 2H) 2.86-2.97 (m, 2H) 3.09 (s, 2H) 3.11-3.25 (m, 2H) 3.93 (s, 2H) 4.21-4.31 (m, 1H) 4.33 (s, 1H) 5.49-5.78 (m, 1H) 6.99 (dd, J=7.91, 1.70

Hz, 1H) 7.10-7.32 (m, 2H) 7.49-7.63 (m, 2H) 7.64-7.76 (m, 2H) 8.22 (s, 1H) 12.46 (s, 1H)

EXAMPLE 368

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)-4-methylcyclohexyl]-2-methyl-7-propyl[1,2,4]triazolo[1,5-a]pyrimidin-5(4H)-one

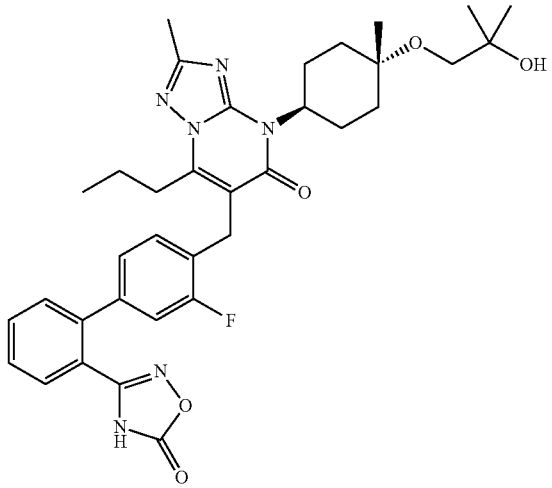 [SMILES: CCCc1c(Cc2ccc(-c3ccccc3-c3noc(=O)[nH]3)cc2F)c(=O)n([C@H]2CC[C@](C)(OCC(C)(C)O)CC2)c2nc(C)nn12]

A mixture of hydroxylammonium chloride (0.34 g), sodium hydrogen carbonate (0.56 g) and dimethyl sulfoxide (5 mL) was stirred at 40° C. for 30 min, 3'-fluoro-4'-({4-[trans-4-(2-hydroxy-2-methylpropoxy)-4-methylcyclohexyl]-2-methyl-5-oxo-7-propyl-4,5-dihydro[1,2,4]triazolo[1,5-a]pyrimidin-6-yl}methyl)biphenyl-2-carbonitrile (0.19 g) was added, and the mixture was stirred at 90° C. for 14 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (2 mL). N,N'-Carbonyldiimidazole (0.065 g) and then 1,8-diazabicyclo[5.4.0]undec-7-ene (0.060 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography and recrystallized (ethyl acetate-hexane) to give the title compound as a colorless solid (0.092 g, 43%).

$^1$H NMR (300 MHz, DMSO-$d_6$) δ0.92 (t, J=7.35 Hz, 3H) 1.06 (s, 6H) 1.30 (s, 3H) 1.40-1.87 (m, 8H) 2.37 (s, 3H) 2.54-2.76 (m, 2H) 2.79-2.96 (m, 2H) 3.12 (s, 2H) 3.92 (s, 2H) 4.14 (s, 1H) 4.73-4.98 (m, 1H) 6.99 (dd, J=7.91, 1.70 Hz, 1H) 7.10-7.27 (m, 2H) 7.50-7.62 (m, 2H) 7.63-7.78 (m, 2H) 12.45 (s, 1H)

EXAMPLE 369

6-{[3-fluoro-2'-(5-oxo-4,5-dihydro-1,2,4-oxadiazol-3-yl)biphenyl-4-yl]methyl}-4-[trans-3-(2-hydroxy-2-methylpropoxy)cyclobutyl]-7-propyl[1,2,4]triazolo[1,5-a]pyrimidin-5(4H)-one potassium salt

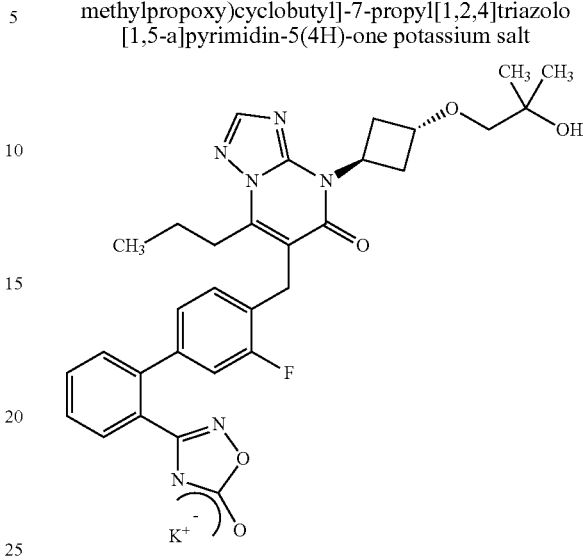

To a solution of 6-{[3-fluoro-2'-(5-oxo-4,5-dihydro-1,2,4-oxadiazol-3-yl)biphenyl-4-yl]methyl}-4-[trans-3-(2-hydroxy-2-methylpropoxy)cyclobutyl]-7-propyl[1,2,4]triazolo[1,5-a]pyrimidin-5(4H)-one (0.054 g) in tetrahydrofuran (2 mL) was added 0.1 M aqueous potassium hydroxide solution (0.91 mL), and the solvent was evaporated under reduced pressure. The residue was washed with diisopropyl ether to give the title compound as a colorless solid (0.032 g, 55%).

$^1$H NMR (300 MHz, DMSO-$d_6$) δ0.95 (t, J=7.35 Hz, 3H) 1.11 (s, 6H) 1.54-1.70 (m, 2H) 2.20-2.39 (m, 2H) 2.84-3.02 (m, 2H) 3.09 (s, 2H) 3.11-3.26 (m, 2H) 3.89 (s, 2H) 4.17-4.47 (m, 2H) 5.55-5.81 (m, 1H) 6.95-7.20 (m, 3H) 7.26-7.56 (m, 4H) 8.21 (s, 1H)

EXAMPLE 370

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)-4-methylcyclohexyl]-2-methyl-7-propyl[1,2,4]triazolo[1,5-a]pyrimidin-5(4H)-one potassium salt

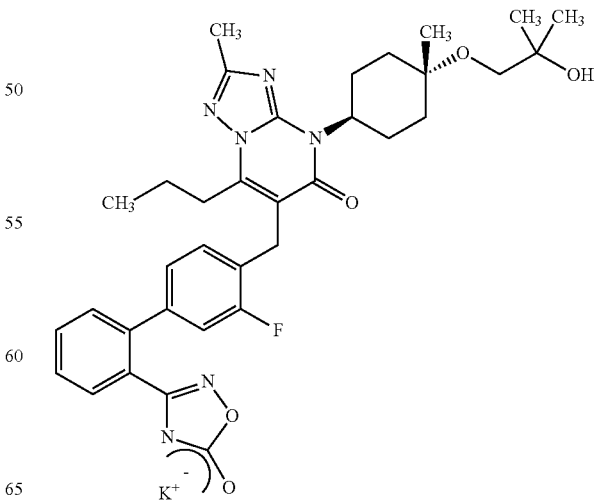

To a solution of 6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)-4-methylcyclohexyl]-2-methyl-7-propyl[1,2,4]triazolo[1,5-a]pyrimidin-5(4H)-one (0.036 g) in tetrahydrofuran (2 mL) was added 0.1 M aqueous potassium hydroxide solution (0.56 mL), and the solvent was evaporated under reduced pressure. The residue was washed with diisopropyl ether to give the title compound as a colorless solid (0.022 g, 59%).

$^1$H NMR (300 MHz, DMSO-$d_6$) δ 0.94 (t, J=7.25 Hz, 3H) 1.05 (s, 6H) 1.30 (s, 3H) 1.40-1.88 (m, 8H) 2.36 (s, 3H) 2.55-2.75 (m, 2H) 2.82-2.96 (m, 2H) 3.12 (s, 2H) 3.88 (s, 2H) 4.14 (s, 1H) 4.72-5.04 (m, 1H) 6.89-7.16 (m, 3H) 7.25-7.55 (m, 4H)

EXAMPLE 371

6-{[3-fluoro-2'-(5-oxo-4,5-dihydro-1,2,4-oxadiazol-3-yl)biphenyl-4-yl]methyl}-4-{trans-4-[1-(1-hydroxycyclobutyl)ethoxy]cyclohexyl}-7-propyl[1,2,4]triazolo[1,5-a]pyrimidin-5(4H)-one

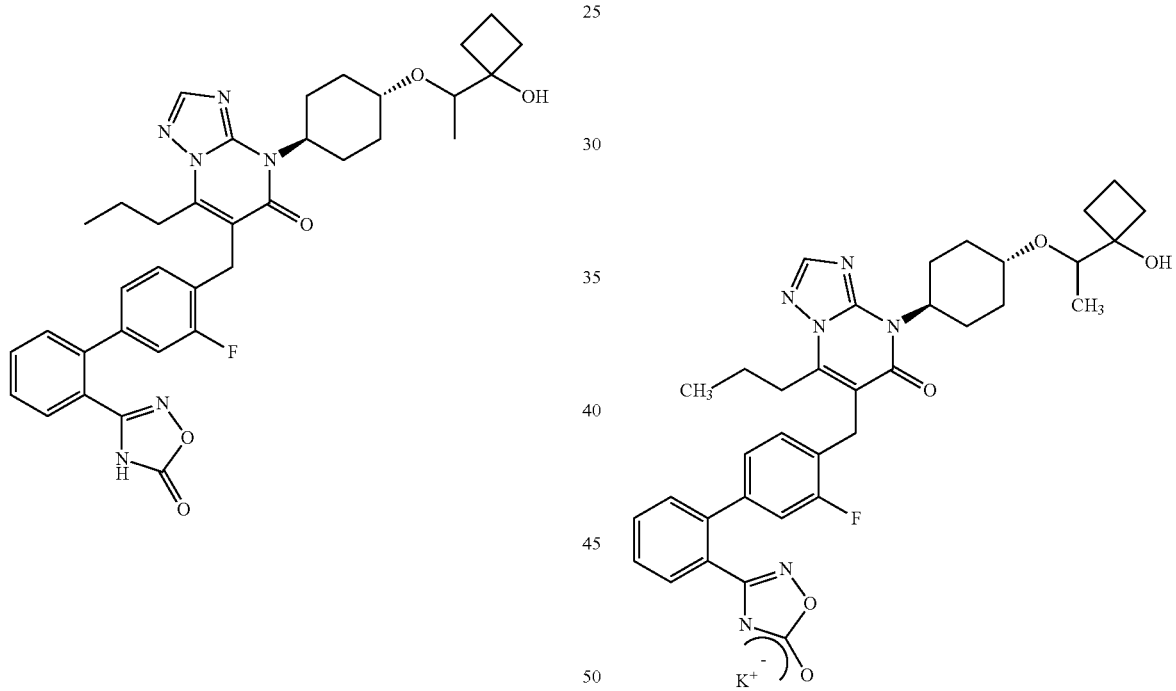

A mixture of hydroxylammonium chloride (2.7 g), sodium hydrogen carbonate (4.3 g) and dimethyl sulfoxide (15 mL) was stirred at 40° C. for 30 min, 3'-fluoro-4'-[(4-{trans-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (1.5 g) was added, and the mixture was stirred at 90° C. for 16 hr. Ethyl acetate and water were added to the reaction mixture, and the mixture was extracted with ethyl acetate. The organic layer was washed with saturated brine, and dried over anhydrous magnesium sulfate. The solvent was evaporated under reduced pressure, and the residue was dissolved in tetrahydrofuran (15 mL). N,N'-Carbonyldiimidazole (0.50 g) and then 1,8-diazabicyclo[5.4.0]undec-7-ene (0.46 mL) were added, and the mixture was stirred at room temperature for 2 hr. Ethyl acetate and water were added to the reaction mixture, and the mixture was acidified with 1 M hydrochloric acid and extracted with ethyl acetate. The organic layer was washed with saturated brine, and dried over anhydrous magnesium sulfate. The solvent was evaporated under reduced pressure, and the residue was purified by silica gel column chromatography to give the title compound as a colorless solid (1.3 g, 81%).

$^1$H NMR (300 MHz, DMSO-$d_6$) δ 0.93 (t, J=7.19 Hz, 3H) 1.01 (d, J=6.06 Hz, 3H) 1.22-1.92 (m, 10H) 1.99-2.22 (m, 4H) 2.53-2.70 (m, 2H) 2.81-3.04 (m, 2H) 3.34-3.46 (m, 2H) 3.94 (s, 2H) 4.64 (s, 1H) 4.79-5.00 (m, 1H) 6.99 (dd, J=7.95, 1.89 Hz, 1H) 7.09-7.30 (m, 2H) 7.50-7.63 (m, 2H) 7.64-7.76 (m, 2H) 8.19 (s, 1H) 12.44 (s, 1H)

EXAMPLE 372

6-{[3-fluoro-2'-(5-oxo-4,5-dihydro-1,2,4-oxadiazol-3-yl)biphenyl-4-yl]methyl}-4-{trans-4-[1-(1-hydroxycyclobutyl)ethoxy]cyclohexyl}-7-propyl[1,2,4]triazolo[1,5-a]pyrimidin-5(4H)-one potassium salt

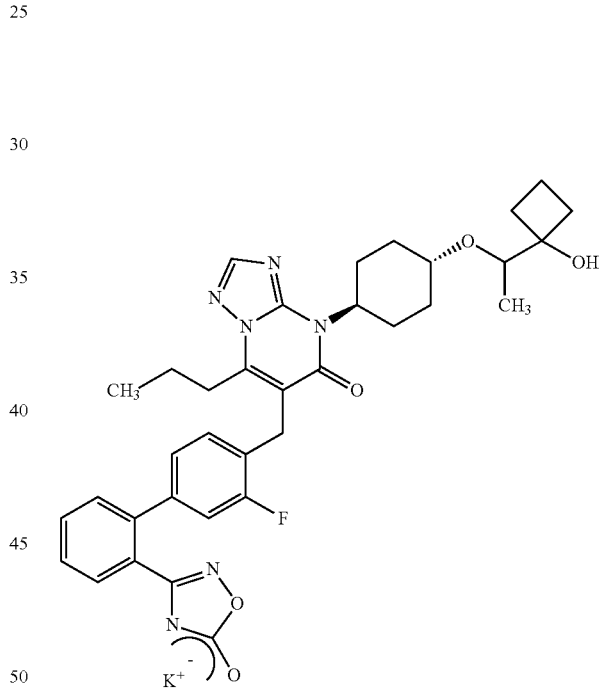

To a solution of 6-{[3-fluoro-2'-(5-oxo-4,5-dihydro-1,2,4-oxadiazol-3-yl)biphenyl-4-yl]methyl}-4-{trans-4-[1-(1-hydroxycyclobutyl)ethoxy]cyclohexyl}-7-propyl[1,2,4]triazolo[1,5-a]pyrimidin-5(4H)-one (1.3 g) in tetrahydrofuran (10 mL) was added 8M aqueous potassium hydroxide solution (0.26 mL), and the solvent was evaporated under reduced pressure. The residue was washed with diisopropyl ether to give the title compound as a colorless solid (1.3 g, 93%).

$^1$H NMR (300 MHz, DMSO-$d_6$) δ 0.88-1.07 (m, 6H) 1.15-2.22 (m, 14H) 2.53-3.06 (m, 4H) 3.34-3.48 (m, 2H) 3.90 (s, 2H) 4.64 (br. s., 1H) 4.79-5.00 (m, 1H) 6.94-7.18 (m, 3H) 7.26-7.57 (m, 4H) 8.18 (s, 1H)

EXAMPLE 373

4-(1-benzylpiperidin-4-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

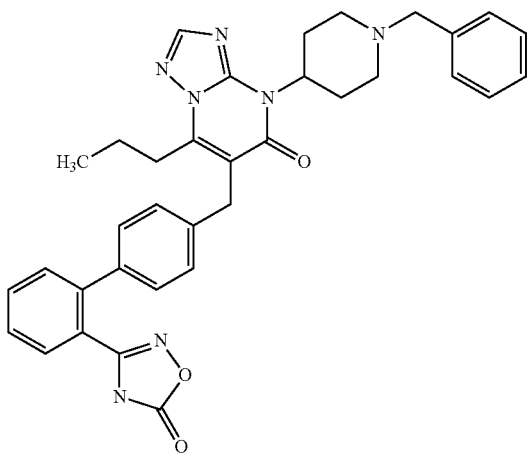 [SMILES: CCCc1c(Cc2ccc(-c3ccccc3-c3noc(=O)[nH]3)cc2)c(=O)n(C2CCN(Cc3ccccc3)CC2)c2ncnn12]

A mixture of hydroxylammonium chloride (1.44 g), sodium hydrogen carbonate (2.32 g) and dimethyl sulfoxide (15 mL) was stirred at 50° C. for 30 min, a solution of 4'-{[4-(1-benzylpiperidin-4-yl)-5-oxo-7-propyl-4,5-dihydro[1,2,4]triazolo[1,5-a]pyrimidin-6-yl]methyl}biphenyl-2-carbonitrile (749 mg) in dimethyl sulfoxide (3 mL) was added, and the mixture was stirred at 90° C. for 17 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (269 mg) and then 1,8-diazabicyclo[5.4.0]undec-7-ene (0.25 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→10/90 (volume ratio)], and crystallized from a mixture of ethyl acetate and diisopropyl ether to give the title compound as colorless crystals (133 mg, 16%).

$^1$H NMR (300 MHz, DMSO-$d_6$) δ0.92 (t, J=7.2 Hz, 3H), 1.50-1.65 (m, 4H), 2.08-2.20 (m, 2H), 2.70-3.00 (m, 6H), 3.56 (s, 2H), 3.95 (s, 2H), 4.88-5.00 (m, 1H), 7.20 (d, J=8.1 Hz, 2H), 7.29 (d, J=8.1 Hz, 2H), 7.33-7.34 (m, 5H), 7.45-7.54 (m, 2H), 7.61-7.68 (m, 2H), 8.18 (s, 1H), 12.20 (br s, 1H).

EXAMPLE 374

4-(1-ethylpiperidin-4-yl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

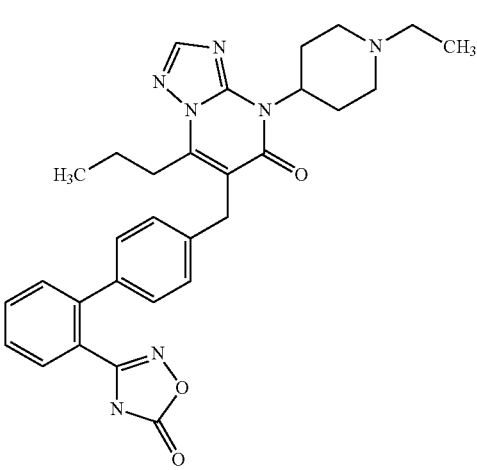 [SMILES: CCCc1c(Cc2ccc(-c3ccccc3-c3noc(=O)[nH]3)cc2)c(=O)n(C2CCN(CC)CC2)c2ncnn12]

A mixture of hydroxylammonium chloride (313 mg), sodium hydrogen carbonate (504 mg) and dimethyl sulfoxide (3 mL) was stirred at 60° C. for 30 min, a solution of 4'-{[4-(1-ethylpiperidin-4-yl)-5-oxo-7-propyl-4,5-dihydro[1,2,4]triazolo[1,5-a]pyrimidin-6-yl]methyl}biphenyl-2-carbonitrile (145 mg) in dimethyl sulfoxide (2 mL) was added, and the mixture was stirred at 90° C. for 17 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (58 mg) and then 1,8-diazabicyclo[5.4.0]undec-7-ene (55 mg) were added, and the mixture was stirred at room temperature for 15 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: methanol/ethyl acetate=10/90→30/70 (volume ratio)] and crystallized from acetonitrile to give the title compound as colorless crystals (57 mg, 35%).

$^1$H NMR (300 MHz, DMSO-$d_6$) δ0.93 (t, J=7.2 Hz, 3H), 1.24 (t, J=7.2 Hz, 3H), 1.51-1.59 (m, 2H), 1.95-1.99 (m, 2H), 2.91-3.20 (m, 8H), 3.48-3.62 (m, 2H), 3.97 (s, 2H), 5.15-5.25

(m, 1H), 7.21 (d, J=8.1 Hz, 2H), 7.32 (d, J=8.1 Hz, 2H), 7.47-7.57 (m, 2H), 7.64-7.71 (m, 2H), 8.23 (s, 1H), 12.39 (br s, 1H).

EXAMPLE 375

6-{[2'-(5-oxo-4,5-dihydro-1,2,4-oxadiazol-3-yl)biphenyl-4-yl]methyl}-7-propyl-4-[1-(tetrahydro-2H-pyran-4-yl)piperidin-4-yl][1,2,4]triazolo[1,5-a]pyrimidin-5(4H)-one

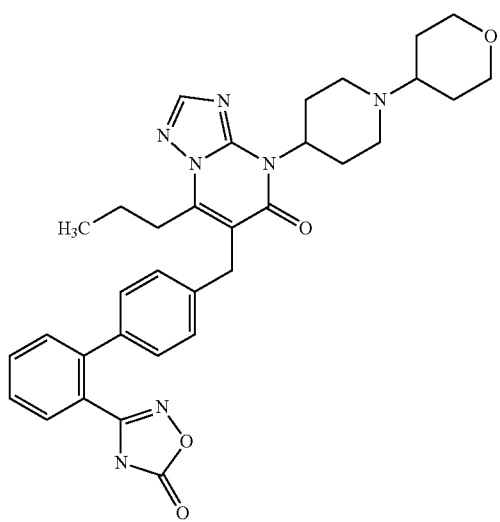 [SMILES: CCCc1c(Cc2ccc(-c3ccccc3-c3noc(=O)[nH]3)cc2)c(=O)n(C2CCN(C3CCOCC3)CC2)c2ncnn12]

A mixture of hydroxylammonium chloride (615 mg), sodium hydrogen carbonate (911 mg) and dimethyl sulfoxide (6 mL) was stirred at 60° C. for 30 min, a solution of 4'-({5-oxo-7-propyl-4-[1-(tetrahydro-2H-pyran-4-yl)piperidin-4-yl]-4,5-dihydro[1,2,4]triazolo[1,5-a]pyrimidin-6-yl}methyl)biphenyl-2-carbonitrile (317 mg) in dimethyl sulfoxide (3 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (115 mg) and then 1,8-diazabicyclo[5.4.0]undec-7-ene (108 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: methanol/ethyl acetate=5/95→30/70 (volume ratio)] and crystallized from acetonitrile to give the title compound as colorless crystals (108 mg, 31%).

$^1$H NMR (300 MHz, DMSO-d$_6$) δ0.93 (t, J=6.9 Hz, 3H), 1.52-2.12 (m, 8H), 2.94-3.98 (m, 15H), 5.22 (br s, 1H), 7.21 (d, J=7.8 Hz, 2H), 7.32 (d, J=7.8 Hz, 2H), 7.47-7.57 (m, 2H), 7.64-7.68 (m, 2H), 9.85 (br s, 1H), 12.47 (br s, 1H).

EXAMPLE 376

4-[4-(1-hydroxy-1-methylethyl)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

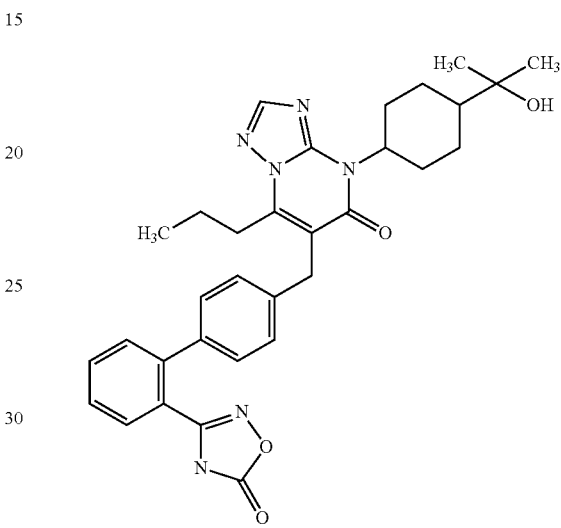

A mixture of hydroxylammonium chloride (208 mg), sodium hydrogen carbonate (336 mg) and dimethyl sulfoxide (3 mL) was stirred at 60° C. for 30 min, a solution of 4'-({4-[4-(1-hydroxy-1-methylethyl)cyclohexyl]-5-oxo-7-propyl-4,5-dihydro[1,2,4]triazolo[1,5-a]pyrimidin-6-yl}methyl)biphenyl-2-carbonitrile (100 mg) in dimethyl sulfoxide (1 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (8 mL). N,N'-Carbonyldiimidazole (39 mg) and then 1,8-diazabicyclo[5.4.0]undec-7-ene (37 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] to give the title compound as a colorless amorphous compound (37 mg, 33%).

$^1$H NMR (300 MHz, CDCl$_3$) δ1.07 (t, J=7.5 Hz, 3H), 1.17 (s, 6H), 1.23-1.32 (m, 1H), 1.40-1.52 (m, 1H), 1.62-1.82 (m, 6H), 1.97-2.01 (m, 2H), 2.55-2.69 (m, 2H), 3.02-3.08 (m, 2H), 3.97 (s, 2H), 4.91-5.02 (m, 1H), 7.25 (d, J=8.1 Hz, 2H), 7.32 (d, J=8.1 Hz, 2H), 7.39-7.42 (m, 1H), 7.45-7.50 (m, 1H), 7.56-7.62 (m, 1H), 7.80-7.83 (m, 1H), 7.90 (s, 1H), 8.19 (br s, 1H).

EXAMPLE 377

6-{[2'-(5-oxo-4,5-dihydro-1,2,4-oxadiazol-3-yl)biphenyl-4-yl]methyl}-7-propyl-4-[1-(tetrahydro-2H-pyran-4-ylcarbonyl)piperidin-4-yl][1,2,4]triazolo[1,5-a]pyrimidin-5(4H)-one

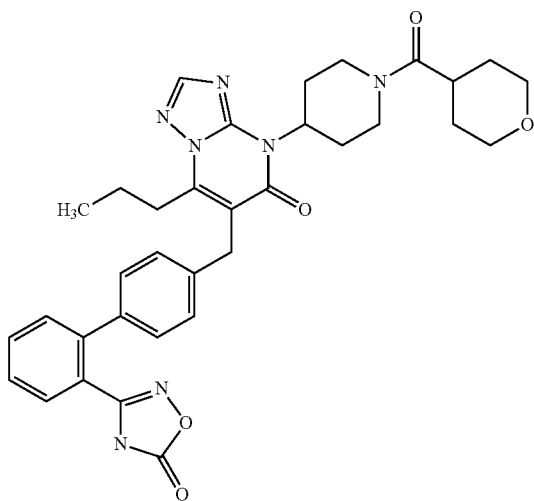 [SMILES: CCCc1c(Cc2ccc(-c3ccccc3-c3noc(=O)[nH]3)cc2)c(=O)n(C2CCN(C(=O)C3CCOCC3)CC2)c2ncnn12]

A mixture of hydroxylammonium chloride (967 mg), sodium hydrogen carbonate (1.68 g) and dimethyl sulfoxide (9 mL) was stirred at 60° C. for 30 min, 4'-({5-oxo-7-propyl-4-[1-(tetrahydro-2H-pyran-4-ylcarbonyl)piperidin-4-yl]-4,5-dihydro[1,2,4]triazolo[1,5-a]pyrimidin-6-yl}methyl)biphenyl-2-carbonitrile (518 mg, dimethyl sulfoxide (3 mL) solution) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (6 mL). N,N'-Carbonyldiimidazole (178 mg) and then 1,8-diazabicyclo[5.4.0]undec-7-ene (167 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: methanol/ethyl acetate=5/95→30/70 (volume ratio)] and crystallized from acetonitrile to give the title compound as colorless crystals (253 mg, 44%).

$^1$H NMR (300 MHz, DMSO-d$_6$) δ0.93 (t, J=7.5 Hz, 3H), 1.53-1.79 (m, 8H), 2.45-2.70 (m, 3H), 2.90-2.96 (m, 3H), 3.12-3.19 (m, 1H), 3.39 (br s, 2H), 3.85 (br s, 2H), 3.96 (s, 2H), 4.14 (br d, J=12.3 Hz, 1H), 4.57 (br d, J=12.3 Hz, 1H), 5.11-5.21 (m, 1H), 7.21 (d, J=8.4, 2H), 7.31 (d, J=8.4 Hz, 2H), 7.48-7.56 (m, 2H), 7.63-7.70 (m, 2H), 8.17 (s, 1H), 12.37 (s, 1H).

EXAMPLE 378

4-[1-(2-hydroxyethyl)piperidin-4-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

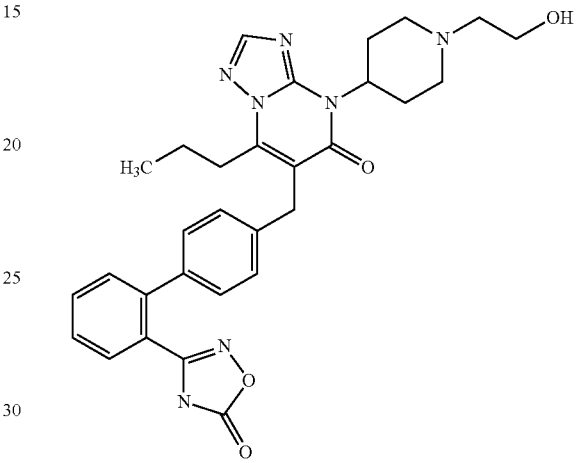

A mixture of hydroxylammonium chloride (417 mg), sodium hydrogen carbonate (672 mg) and dimethyl sulfoxide (15 mL) was stirred at 40° C. for 30 min, 4'-({4-[1-(2-hydroxyethyl)piperidin-4-yl]-5-oxo-7-propyl-4,5-dihydro[1,2,4]triazolo[1,5-a]pyrimidin-6-yl}methyl)biphenyl-2-carbonitrile (200 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (81 mg) and then 1,8-diazabicyclo[5.4.0]undec-7-ene (76 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: methanol/ethyl acetate=5/95→30/70 (volume ratio)] and crystallized from acetonitrile to give the title compound as colorless crystals (51 mg, 23%).

$^1$H NMR (300 MHz, DMSO-d$_6$) δ0.94 (t, J=7.5 Hz, 3H), 1.50-1.68 (m, 4H), 2.30-2.40 (m, 2H), 2.58 (br s, 2H), 2.76-2.95 (m, 4H), 3.12-3.15 (m, 2H), 3.54-3.58 (m, 2H), 3.95 (s, 2H), 4.40-4.80 (br, 1H), 4.90-5.00 (m, 1H), 7.21 (d, J=8.4 Hz,

2H), 7.27 (d, J=8.4 Hz, 2H), 7.41-7.50 (m, 2H), 7.57-7.63 (m, 2H), 8.18 (s, 1H), 11.20-12.20 (br, 1H).

EXAMPLE 379

4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

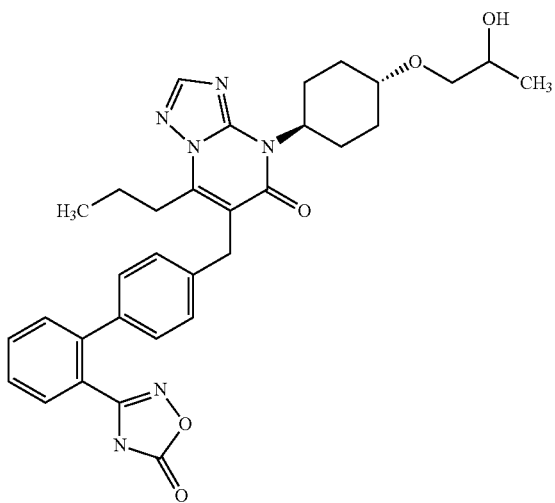 [SMILES: CCCc1c(Cc2ccc(-c3ccccc3-c3noc(=O)[nH]3)cc2)c(=O)n([C@H]2CC[C@H](OCC(C)O)CC2)c2ncnn12]

A mixture of hydroxylammonium chloride (271 mg), sodium hydrogen carbonate (437 mg) and dimethyl sulfoxide (3 mL) was stirred at 60° C. for 30 min, 4'-({4-[trans-4-(2-hydroxypropoxy)cyclohexyl]-5-oxo-7-propyl-4,5-dihydro[1,2,4]triazolo[1,5-a]pyrimidin-6-yl}methyl)biphenyl-2-carbonitrile (138 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.17 g) and then 1,8-diazabicyclo[5.4.0]undec-7-ene (0.14 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] to give the title compound as a colorless amorphous compound (57 mg, 37%).

$^1$H NMR (300 MHz, CDCl$_3$) δ1.08 (t, J=7.5 Hz, 3H), 1.13 (d, J=6.0 Hz, 3H), 1.35-1.47 (m, 2H), 1.72-1.80 (m, 4H), 2.14-2.18 (m, 2H), 2.60-2.72 (m, 3H), 3.03-3.08 (m, 2H), 3.20-3.26 (m, 1H), 3.38-3.50 (m, 2H), 3.89-3.97 (m, 3H), 4.97-5.05 (m, 1H), 7.25 (d, J=8.4 Hz, 2H), 7.31 (d, J=8.4 Hz, 2H), 7.39-7.41 (m, 1H), 7.45-7.51 (m, 1H), 7.57-7.62 (m, 1H), 7.79-7.82 (m, 1H), 7.90 (s, 1H), 8.21 (br s, 1H).

EXAMPLE 380

4-[1-(2-hydroxy-2-methylpropyl)piperidin-4-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one trifluoroacetate

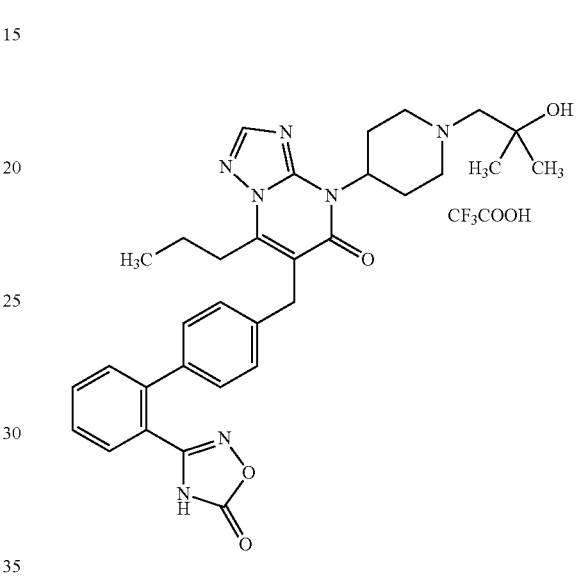

A mixture of hydroxylammonium chloride (646 mg), sodium hydrogen carbonate (1.04 g) and dimethyl sulfoxide (3 mL) was stirred at 60° C. for 30 min, 4'-({4-[1-(2-hydroxy-2-methylpropyl)piperidin-4-yl]-5-oxo-7-propyl-4,5-dihydro[1,2,4]triazolo[1,5-a]pyrimidin-6-yl}methyl)biphenyl-2-carbonitrile (325 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (122 mg) and then 1,8-diazabicyclo[5.4.0]undec-7-ene (114 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by preparative HPLC [eluent: 0.1% trifluoroacetic acid-containing acetonitrile/0.1% trifluoroacetic acid containing-water=5/95→100/0 (volume ratio)] to give the title compound as a colorless amorphous compound (165 mg, 38%).

$^1$H NMR (300 MHz, DMSO-d$_6$) δ0.93 (t, J=7.5 Hz, 3H), 1.27 (s, 6H), 1.54-1.57 (m, 2H), 1.88-1.91 (m, 2H), 2.94 (br s, 2H), 3.09-3.77 (m, 8H), 3.97 (s, 2H), 5.10-5.25 (m, 2H), 7.21

(d, J=7.5 Hz, 2H), 7.32 (d, J=7.5 Hz, 2H), 7.47-7.57 (m, 2H), 7.63-7.70 (m, 2H), 8.23 (s, 1H), 9.16-9.34 (br, 1H), 12.43 (br s, 1H).

EXAMPLE 381

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

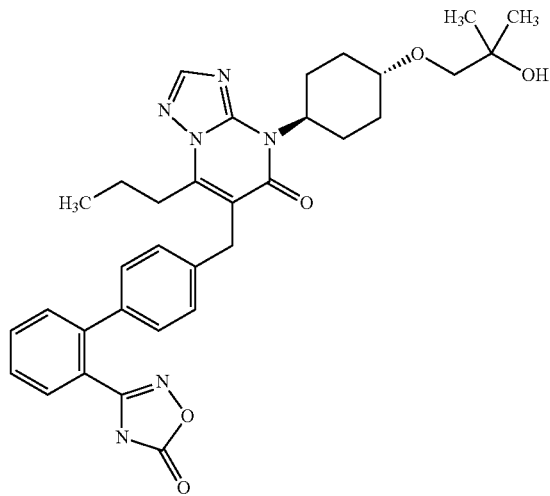 [SMILES: CCCc1c(Cc2ccc(-c3ccccc3-c3noc(=O)[nH]3)cc2)c(=O)n([C@H]2CC[C@H](OCC(C)(C)O)CC2)c2ncnn12]

A mixture of hydroxylammonium chloride (459 mg), sodium hydrogen carbonate (739 mg) and dimethyl sulfoxide (3 mL) was stirred at 60° C. for 30 min, 4'-({4-[trans-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (237 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (86 mg) and then 1,8-diazabicyclo[5.4.0]undec-7-ene (81 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] to give the title compound as a colorless amorphous compound (102 mg, 39%).

$^1$H NMR (300 MHz, DMSO-$d_6$) δ0.91 (t, J=7.5 Hz, 3H), 1.05 (s, 6H), 1.22-1.34 (m, 2H), 1.49-1.56 (m, 2H), 1.66-1.70 (m, 2H), 2.07-2.11 (m, 2H), 2.50-2.62 (m, 2H), 2.89-2.94 (m, 2H), 3.18 (s, 2H), 3.28-3.36 (m, 1H), 3.94 (s, 2H), 4.22 (s, 1H), 4.85-4.93 (m, 1H), 7.19 (d, J=8.1 Hz, 2H), 7.28 (d, J=8.1 Hz, 2H), 7.46-7.54 (m, 2H), 7.61-7.68 (m, 2H), 8.15 (s, 1H), 12.00-12.70 (br, 1H).

EXAMPLE 382

4-[1-(4-hydroxyphenyl)piperidin-4-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

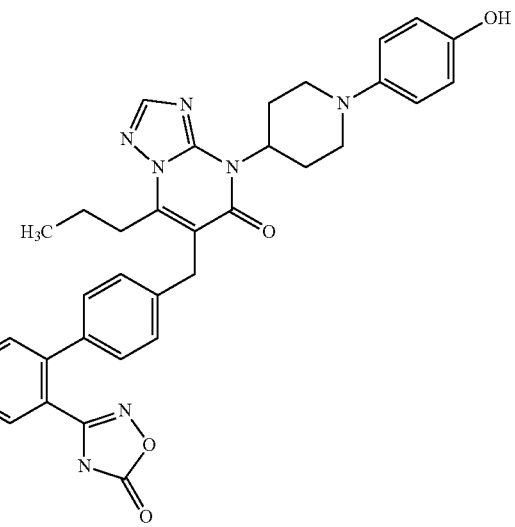

A mixture of hydroxylammonium chloride (344 mg), sodium hydrogen carbonate (554 mg) and dimethyl sulfoxide (3 mL) was stirred at 60° C. for 30 min, 4'-({4-[1-(4-hydroxyphenyl)piperidin-4-yl]-5-oxo-7-propyl-4,5-dihydro[1,2,4]triazolo[1,5-a]pyrimidin-6-yl}methyl)biphenyl-2-carbonitrile (180 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (65 mg) and then 1,8-diazabicyclo[5.4.0]undec-7-ene (61 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=70/30→45/55 (volume ratio)] and crystallized from a mixture of ethyl acetate and diisopropyl ether to give the title compound as colorless crystals (72 mg, 36%).

$^1$H NMR (300 MHz, DMSO-$d_6$) δ0.93 (t, J=7.2 Hz, 3H), 1.52-1.59 (m, 2H), 1.70-1.73 (m, 2H), 2.63-2.70 (m, 2H), 2.80-2.97 (m, 4H), 3.56 (br d, J=12.6 Hz, 2H), 3.97 (s, 2H), 4.97-5.05 (m, 1H), 6.64 (d, J=9.0 Hz, 2H), 6.83 (d, J=9.0 Hz,

2H), 7.21 (d, J=8.4 Hz, 2H), 7.31 (d, J=8.4 Hz, 2H), 7.48-7.56 (m, 2H), 7.63-7.70 (m, 2H), 8.18 (s, 1H), 8.82 (s, 1H), 12.36 (br s, 1H).

EXAMPLE 383

4-[cis-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

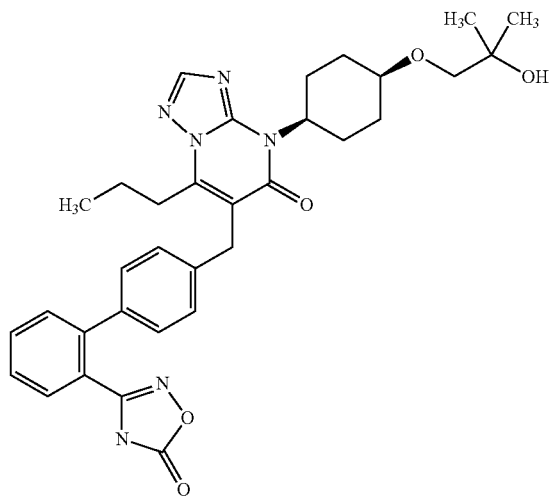 [SMILES: CCCc1c(Cc2ccc(-c3ccccc3-c3noc(=O)[nH]3)cc2)c(=O)n([C@H]2CC[C@@H](OCC(C)(C)O)CC2)c2ncnn12]

(m, 1H), 7.21 (d, J=8.4 Hz, 2H), 7.30 (d, J=8.4 Hz, 2H), 7.48-7.56 (m, 2H), 7.63-7.70 (m, 2H), 8.13 (s, 1H), 12.35 (br s, 1H).

EXAMPLE 384

4-[cis-4-(2-hydroxy-2-methylpropoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

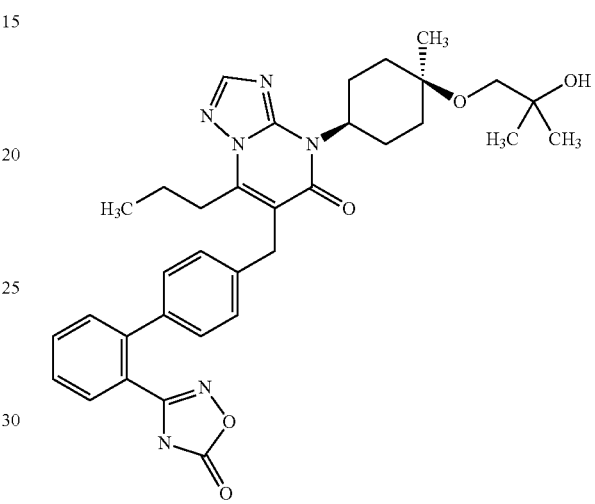

A mixture of hydroxylammonium chloride (1.20 g), sodium hydrogen carbonate (1.93 g) and dimethyl sulfoxide (5 mL) was stirred at 60° C. for 30 min, 4'-({4-[cis-4-(2-hydroxy-2-methylpropoxy)cyclohexyl]-5-oxo-7-propyl-4,5-dihydro[1,2,4]triazolo[1,5-a]pyrimidin-6-yl}methyl)biphenyl-2-carbonitrile (620 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (224 mg) and then 1,8-diazabicyclo[5.4.0]undec-7-ene (210 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] to give the title compound as a colorless amorphous compound (479 mg, 70%).

$^1$H NMR (300 MHz, DMSO-$d_6$) δ0.92 (t, J=7.5 Hz, 3H), 1.18 (s, 6H), 1.40-1.57 (m, 6H), 1.97-2.02 (m, 2H), 2.78-3.14 (m, 4H), 3.55 (br s, 1H), 3.96 (s, 2H), 4.20 (s, 1H), 4.89-4.97

A mixture of hydroxylammonium chloride (532 mg), sodium hydrogen carbonate (857 mg) and dimethyl sulfoxide (3 mL) was stirred at 60° C. for 30 min, 4'-({4-[cis-4-(2-hydroxy-2-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile (282 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (101 mg) and then 1,8-diazabicyclo[5.4.0]undec-7-ene (94 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] and crystallized from diisopropyl ether to give the title compound as colorless crystals (166 mg, 53%).

$^1$H NMR (300 MHz, DMSO-$d_6$) δ0.92 (t, J=7.5 Hz, 3H), 1.11 (s, 3H), 1.20 (s, 6H), 1.37-1.57 (m, 6H), 1.88 (br d, J=14.4 Hz, 2H), 2.81-2.94 (m, 4H), 3.06 (s, 2H), 3.95 (s, 2H), 4.20 (s, 1H), 4.89-4.97 (m, 1H), 7.21 (d, J=8.4 Hz, 2H), 7.30 (d, J=8.4 Hz, 2H), 7.47-7.56 (m, 2H), 7.62-7.70 (m, 2H), 8.09 (s, 1H), 12.33 (br s, 1H).

EXAMPLE 385

4-[trans-4-(2-hydroxy-2-methylpropoxy)-4-methylcyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

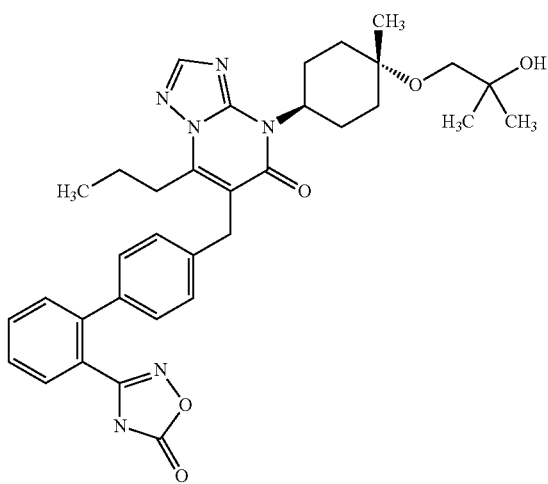 [SMILES: CCCc1c(Cc2ccc(-c3ccccc3-c3noc(=O)[nH]3)cc2)c(=O)n([C@H]2CC[C@](C)(OCC(C)(C)O)CC2)c2ncnn12]

A mixture of hydroxylammonium chloride (240 mg), sodium hydrogen carbonate (386 mg) and dimethyl sulfoxide (3 mL) was stirred at 60° C. for 30 min, 4'-({4-[trans-4-(2-hydroxy-2-methylpropoxy)-4-methylcyclohexyl]-5-oxo-7-propyl-4,5-dihydro[1,2,4]triazolo[1,5-a]pyrimidin-6-yl}methyl)biphenyl-2-carbonitrile (125 mg) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (45 mg) and then 1,8-diazabicyclo[5.4.0]undec-7-ene (43 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=65/35→35/65 (volume ratio)] and crystallized from diisopropyl ether to give the title compound as colorless crystals (42 mg, 30%).

$^1$H NMR (300 MHz, DMSO-$d_6$) δ0.93 (t, J=7.2 Hz, 3H), 1.07 (s, 6H), 1.31 (s, 3H), 1.50-1.63 (m, 6H), 1.78 (br d, J=12.0 Hz, 2H), 2.54-2.72 (m, 2H), 2.90-2.95 (m, 2H), 3.12 (s, 2H), 3.96 (s, 2H), 4.14 (s, 1H), 4.89-4.97 (m, 1H), 7.21 (d, J=8.1 Hz, 2H), 7.30 (d, J=8.1 Hz, 2H), 7.47-7.56 (m, 2H), 7.62-7.69 (m, 2H), 8.19 (s, 1H), 12.35 (br s, 1H).

EXAMPLE 386

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

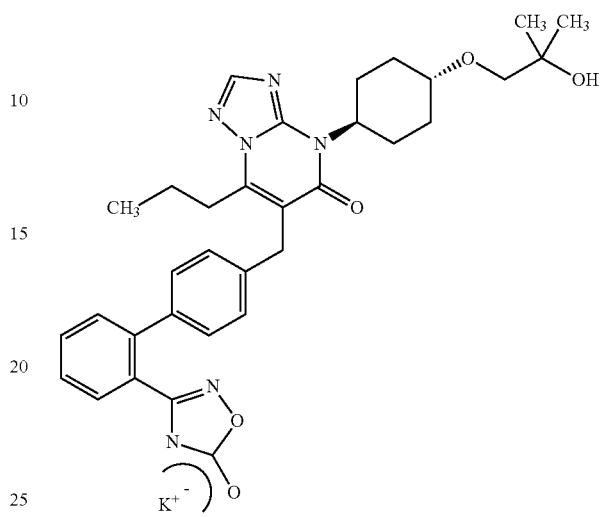

To a solution of 4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (350 mg) in ethanol (2 mL) was added 8M aqueous potassium hydroxide solution (73 μL), and the mixture was stirred at room temperature for 30 min. The solvent was evaporated under reduced pressure to give the colorless amorphous title compound (320 mg, 86%).

$^1$H NMR (300 MHz, DMSO-$d_6$) δ0.96 (t, J=7.5 Hz, 3H), 1.07 (s, 6H), 1.23-1.35 (m, 2H), 1.57-1.72 (m, 4H), 2.08-2.12 (m, 2H), 2.52-2.64 (m, 2H), 2.90-2.98 (m, 2H), 3.20 (s, 2H), 3.27-3.33 (m, 1H), 3.91 (s, 2H), 4.25 (s, 1H), 4.87-4.95 (m, 1H), 7.17 (d, J=8.4 Hz, 2H), 7.21 (d, J=8.4 Hz, 2H), 7.25-7.36 (m, 2H), 7.38-7.48 (m, 2H), 8.16 (s, 1H).

EXAMPLE 387

6-{[2'-(5-oxo-4,5-dihydro-1,2,4-oxadiazol-3-yl)biphenyl-4-yl]methyl}-7-propyl-4-(tetrahydro-2H-pyran-4-yl)[1,2,3]triazolo[1,5-a]pyrimidin-5(4H)-one

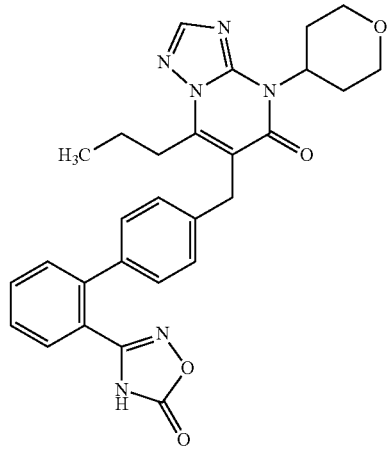 [SMILES: CCCc1c(Cc2ccc(-c3ccccc3-c3noc(=O)[nH]3)cc2)c(=O)n(C2CCOCC2)c2ncnn12]

A mixture of hydroxylammonium chloride (438 mg), sodium hydrogen carbonate (706 mg) and dimethyl sulfoxide (3 mL) was stirred at 60° C. for 30 min, 4'-{[5-oxo-7-propyl-4-(tetrahydro-2H-pyran-4-yl)-4,5-dihydro[1,2,3]triazolo[1,5-a]pyrimidin-6-yl]methyl}biphenyl-2-carbonitrile (192 mg) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (83 mg) and then 1,8-diazabicyclo[5.4.0]undec-7-ene (78 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=70/30→30/70 (volume ratio)] and crystallized from diisopropyl ether to give the title compound as colorless crystals (137 mg, 64%).

$^1$H NMR (300 MHz, DMSO-$d_6$) δ0.95 (t, J=7.5 Hz, 3H), 1.55-1.66 (m, 4H), 2.40-2.51 (m, 2H), 3.09 (t, J=7.5 Hz, 2H), 3.44-3.51 (m, 2H), 3.99 (br s, 4H), 4.82-4.94 (m, 1H), 7.22 (d, J=8.1 Hz, 2H), 7.32 (d, J=8.1 Hz, 2H), 7.48-7.56 (m, 2H), 7.63-7.70 (m, 2H), 7.96 (s, 1H), 12.37 (br s, 1H).

EXAMPLE 388

4-[5-hydroxytricyclo[3.3.1.1$^{3,7}$]dec-2-yl]-6-{[2'-(5-oxo-4,5-dihydro-1,2,4-oxadiazol-3-yl)biphenyl-4-yl]methyl}-7-propyl[1,2,4] triazolo[1,5-a]pyrimidin-5(4H)-one (less polar isomer)

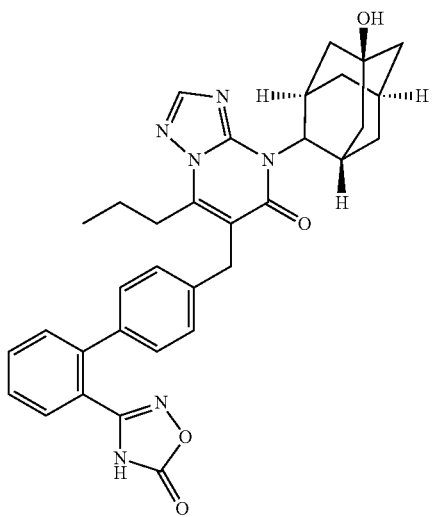 [SMILES: CCCc1c(Cc2ccc(-c3ccccc3-c3noc(=O)[nH]3)cc2)c(=O)n(C2[C@@H]3C[C@@H]4C[C@H]2C[C@@](O)(C4)C3)c2ncnn12]

A mixture of hydroxylammonium chloride (177 mg), sodium hydrogen carbonate (286 mg) and dimethyl sulfoxide (2 mL) was stirred at 60° C. for 30 min, a solution of 4'-({4-[(1R,3S,5S,7S)-5-hydroxytricyclo[3.3.1.1$^{3,7}$]dec-2-yl]-5-oxo-7-propyl-4,5-dihydro[1,2,4]triazolo[1,5-a]pyrimidin-6-yl}methyl)biphenyl-2-carbonitrile (less polar isomer) (90 mg) in dimethyl sulfoxide (1 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (8 mL). N,N'-Carbonyldiimidazole (34 mg) and then 1,8-diazabicyclo[5.4.0]undec-7-ene (32 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→0/100 (volume ratio)] to give the title compound as a colorless amorphous compound (27 mg, 27%).

$^1$H NMR (300 MHz, CDCl$_3$) δ1.10 (t, J=7.5 Hz, 3H), 1.56-1.88 (m, 12H), 2.16-2.35 (m, 2H), 2.99-3.10 (m, 4H), 3.93 (s, 2H), 4.61 (br s, 1H), 7.27 (d, J=9.0 Hz, 2H), 7.30 (d, J=9.0 Hz, 2H), 7.40-7.48 (m, 2H), 7.56-7.62 (m, 1H), 7.71-7.74 (m, 1H), 7.87 (1, 1H), 8.00-9.00 (br, 1H).

EXAMPLE 389

4-[5-hydroxytricyclo[3.3.1.1$^{3,7}$]dec-2-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (highly-polar isomer)

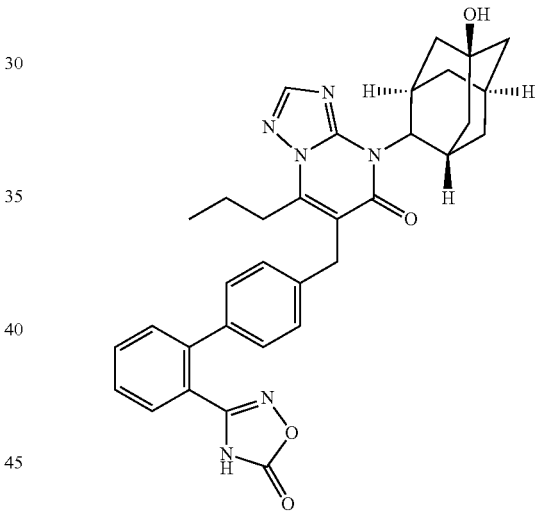

A mixture of hydroxylammonium chloride (198 mg), sodium hydrogen carbonate (319 mg) and dimethyl sulfoxide (2 mL) was stirred at 60° C. for 30 min, a solution of 4'-({4-[(1R,3S,5S,7S)-5-hydroxytricyclo[3.3.1.1$^{3,7}$]dec-2-yl]-5-oxo-7-propyl-4,5-dihydro[1,2,4]triazolo[1,5-a]pyrimidin-6-yl}methyl)biphenyl-2-carbonitrile (highly-polar isomer) (99 mg) in dimethyl sulfoxide (1 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (8 mL). N,N'-Carbonyldiimidazole (37 mg) and then 1,8-diazabicyclo[5.4.0]undec-7-ene (35 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=60/40→35/65 (volume ratio)] to give the title compound as a colorless amorphous compound (56 mg, 51%).

$^1$H NMR (300 MHz, CDCl$_3$) δ1.06 (t, J=7.2 Hz, 3H), 1.52 (br d, J=12.9 Hz, 2H), 1.68-1.84 (m, 7H), 1.94-1.98 (m, 2H), 2.16-2.25 (m, 3H), 2.92 (br s, 2H), 3.00-3.06 (m, 2H), 3.96 (s, 2H), 4.76 (br s, 1H), 7.24 (d, J=9.0 Hz, 2H), 7.28 (d, J=9.0 Hz, 2H), 7.38-7.41 (m, 1H), 7.44-7.50 (m, 1H), 7.56-7.62 (m, 1H), 7.77-7.80 (m, 1H), 7.88 (s, 1H), 8.00-9.00 (br, 1H).

EXAMPLE 390

6-{[2'-(5-oxo-4,5-dihydro-1,2,4-oxadiazol-3-yl)biphenyl-4-yl]methyl}-4-(7-oxooxepan-4-yl)-7-propyl[1,2,4]triazolo[1,5-a]pyrimidin-5(4H)-one

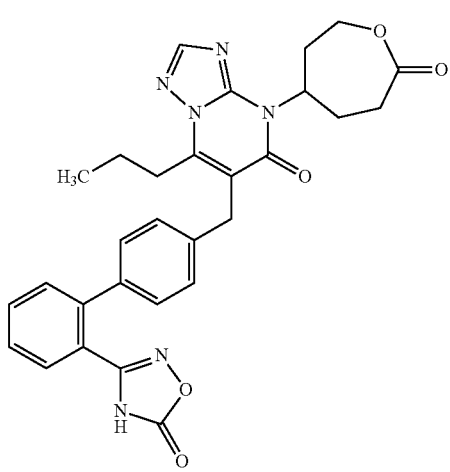 [SMILES: CCCc1c(Cc2ccc(-c3ccccc3-c3noc(=O)[nH]3)cc2)c(=O)n(C2CCOC(=O)CC2)c2ncnn12]

To a solution of 4-(4-oxocyclohexyl)-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (262 mg) in acetonitrile (10 mL) was added m-chloroperbenzoic acid (129 mg), and the mixture was stirred at room temperature for 15 hr. The reaction mixture was diluted with ethyl acetate, washed with 5% aqueous sodium thiosulfate solution and then with saturated brine, and dried over anhydrous magnesium sulfate. The solvent was evaporated under reduced pressure, and the residue was purified by silica gel chromatography [eluent: hexane/ethyl acetate=40/60→0/100 (volume ratio)] and crystallized from a mixture of ethyl acetate and diisopropyl ether to give the title compound as colorless crystals (204 mg, 75%).

$^1$H NMR (300 MHz, CDCl$_3$) δ1.07 (t, J=7.5 Hz, 3H), 1.69-1.81 (m, 2H), 1.88-2.02 (m, 2H), 2.67-2.71 (m, 2H), 2.85-3.19 (m, 4H), 3.95 (s, 2H), 4.22-4.37 (m, 2H), 5.22-5.30 (m, 1H), 7.22-7.28 (m, 4H), 7.40-7.43 (m, 1H), 7.44-7.50 (m, 1H), 7.57-7.62 (m, 1H), 7.71-7.74 (m, 1H), 7.87 (s, 1H), 9.00-9.35 (br, 1H).

EXAMPLE 391

4-[(5S,8S)-2-(hydroxymethyl)-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

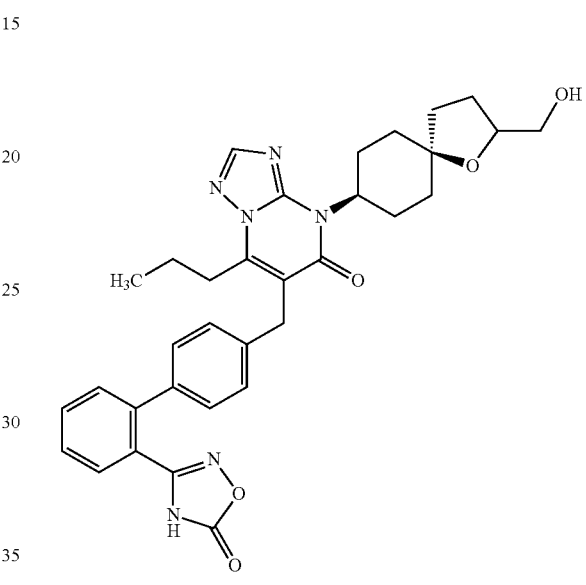

A mixture of hydroxylammonium chloride (605 mg), sodium hydrogen carbonate (975 mg) and dimethyl sulfoxide (3 mL) was stirred at 60° C. for 30 min, a solution of 4'-({4-[(5S,8S)-2-(hydroxymethyl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (314 mg) in dimethyl sulfoxide (2 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (114 mg) and then 1,8-diazabicyclo[5.4.0]undec-7-ene (107 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=40/60→0/100 (volume ratio)] to give the title compound as a colorless amorphous compound (27 mg, 8%).

$^1$H NMR (300 MHz, CDCl$_3$) δ1.09 (t, J=7.5 Hz, 3H), 1.43-1.94 (m, 12H), 2.77-3.10 (m, 5H), 3.43 (dd, J=11.7, 6.6 Hz, 1H), 3.64 (dd, J=11.4, 3.0 Hz, 1H), 3.95 (s, 2H), 4.00-4.10

(m, 1H), 4.87-4.97 (m, 1H), 7.24-7.30 (m, 4H), 7.40-7.48 (m, 2H), 7.56-7.61 (m, 1H), 7.76-7.79 (m, 1H), 7.91 (s, 1H), 8.00-9.50 (br, 1H).

EXAMPLE 392

4-[(5R,8R)-2-(hydroxymethyl)-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

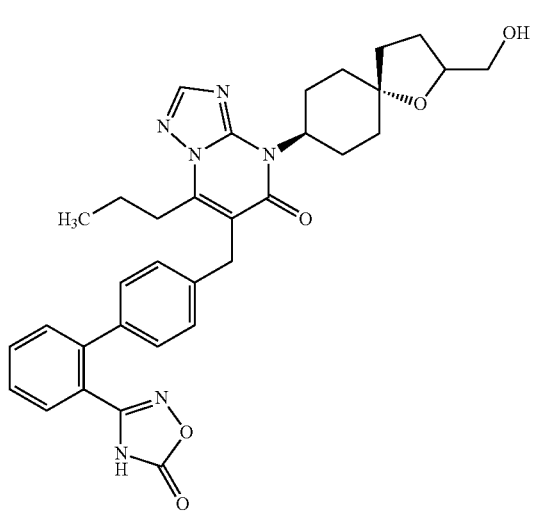

A mixture of hydroxylammonium chloride (271 mg), sodium hydrogen carbonate (437 mg) and dimethyl sulfoxide (1.5 mL) was stirred at 60° C. for 30 min, a solution of 4'-({4-[(5R,8R)-2-(hydroxymethyl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (138 mg) in dimethyl sulfoxide (1.5 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (52 mg) and then 1,8-diazabicyclo[5.4.0]undec-7-ene (49 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=40/60→0/100 (volume ratio)] to give the title compound as a colorless amorphous compound (29 mg, 19%).

$^1$H NMR (300 MHz, CDCl$_3$) δ1.07 (t, J=7.5 Hz, 3H), 1.58-1.87 (m, 9H), 1.92-2.06 (m, 4H), 2.63-2.74 (m, 2H), 3.01-3.07 (m, 2H), 3.44 (dd, J=11.7, 5.7 Hz, 1H), 3.64 (dd, J=11.7, 3.3 Hz, 1H), 3.96 (s, 2H), 4.05-4.12 (m, 1H), 4.97-5.05 (m, 1H), 7.25 (d, J=8.4 Hz, 2H), 7.30 (d, J=8.4 Hz, 2H), 7.40-7.43 (m, 1H), 7.45-7.51 (m, 1H), 7.57-7.63 (m, 1H), 7.76-7.79 (m, 1H), 7.90 (s, 1H), 8.20-9.50 (br, 1H).

EXAMPLE 393

4-[(5S,8S)-2-(2-hydroxypropan-2-yl)-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

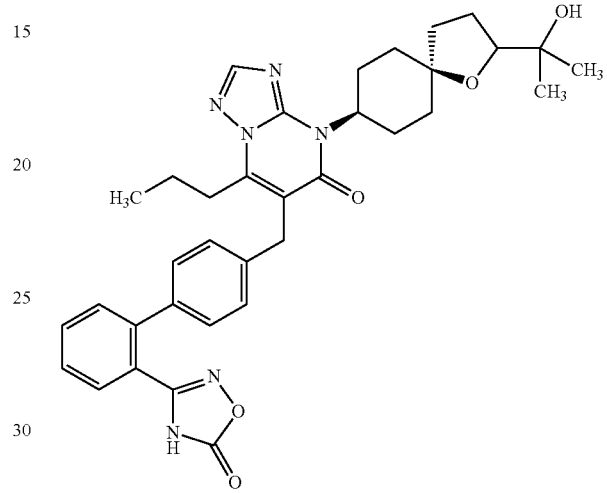

A mixture of hydroxylammonium chloride (292 mg), sodium hydrogen carbonate (470 mg) and dimethyl sulfoxide (1.5 mL) was stirred at 60° C. for 30 min, a solution of 4'-({4-[(5S,8S)-2-(2-hydroxypropan-2-yl)-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (158 mg) in dimethyl sulfoxide (1.5 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (55 mg) and then 1,8-diazabicyclo[5.4.0]undec-7-ene (52 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (39 mg, 22%).

$^1$H NMR (300 MHz, CDCl$_3$) δ1.08 (t, J=7.5 Hz, 3H), 1.13 (s, 3H), 1.23 (s, 3H), 1.44-1.58 (m, 4H), 1.71-1.86 (m, 8H), 2.20-2.80 (br, 1H), 2.84-3.00 (m, 2H), 3.04-3.09 (m, 2H), 3.77-3.82 (m, 1H), 3.97 (s, 2H), 4.91-4.99 (m, 1H), 7.26 (d, J=9.0 Hz, 2H), 7.29 (d, J=9.0 Hz, 2H), 7.39-7.43 (m, 1H), 7.43-7.49 (m, 1H), 7.56-7.61 (m, 1H), 7.78-7.81 (m, 1H), 7.90 (s, 1H), 8.50-9.50 (br, 1H).

EXAMPLE 394

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl[1,2,3]triazolo[1,5-a]pyrimidin-5(4H)-one

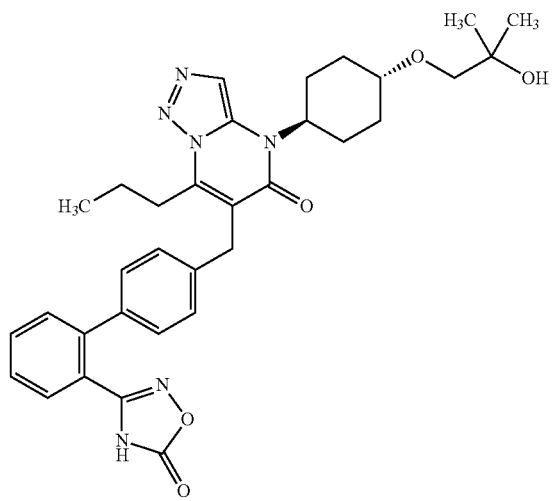 [SMILES: CCCc1c(Cc2ccc(-c3ccccc3-c3noc(=O)[nH]3)cc2)c(=O)n([C@H]2CC[C@H](OCC(C)(C)O)CC2)c2cnnn12]

A mixture of hydroxylammonium chloride (292 mg), sodium hydrogen carbonate (470 mg) and dimethyl sulfoxide (2 mL) was stirred at 60° C. for 30 min, a solution of 4'-({4-[trans-4-(2-hydroxy-2-methylpropoxy)cyclohexyl]-5-oxo-7-propyl-4,5-dihydro[1,2,3]triazolo[1,5-a]pyrimidin-6-yl}methyl)biphenyl-2-carbonitrile (153 mg) in dimethyl sulfoxide (2 mL) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (55 mg) and then 1,8-diazabicyclo[5.4.0]undec-7-ene (52 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→30/70 (volume ratio)] to give the title compound as a colorless amorphous compound (68 mg, 41%).

$^1$H NMR (300 MHz, DMSO-$d_6$) δ0.95 (t, J=7.2 Hz, 3H), 1.08 (s, 6H), 1.28-1.40 (m, 2H), 1.55-1.62 (m, 2H), 1.68-1.71 (m, 2H), 2.08-2.12 (m, 2H), 2.20-2.32 (m, 2H), 3.06-3.11 (m, 2H), 3.19 (s, 2H), 3.34-3.50 (m, 1H), 3.97 (s, 2H), 4.26 (s, 1H), 4.70 (br s, 1H), 7.22 (d, J=8.1 Hz, 2H), 7.31 (d, J=8.1 Hz, 2H), 7.48-7.56 (m, 2H), 7.63-7.70 (m, 2H), 8.02 (s, 1H), 12.20-12.60 (br, 1H).

EXAMPLE 395

4-[(5S,8S)-3-hydroxy-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

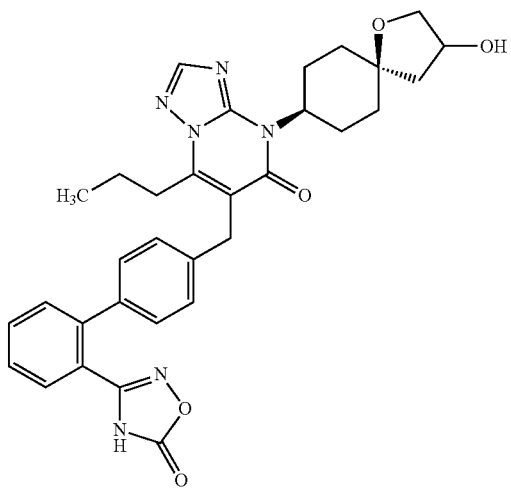

A mixture of hydroxylammonium chloride (469 mg), sodium hydrogen carbonate (756 mg) and dimethyl sulfoxide (1.5 mL) was stirred at 60° C. for 30 min, a solution of 4'-({4-[(5S,8S)-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (238 mg) in dimethyl sulfoxide (1.5 mL) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (97 mg) and then 1,8-diazabicyclo[5.4.0]undec-7-ene (91 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=35/65→0/100 (volume ratio)] to give the title compound as a colorless amorphous compound (170 mg, 65%).

$^1$H NMR (300 MHz, CDCl$_3$) δ1.07 (t, J=7.5 Hz, 3H), 1.45-1.64 (m, 4H), 1.70-1.82 (m, 4H), 1.91-1.98 (m, 1H), 2.07-2.12 (m, 1H), 2.20-2.50 (br, 1H), 2.83-2.97 (m, 2H), 3.02-3.07 (m, 2H), 3.78 (d, J=9.9 Hz, 1H), 3.87 (dd, J=9.9, 4.2 Hz, 1H), 3.94 (s, 2H), 4.41-4.44 (m, 1H), 4.90-4.98 (m, 1H), 7.24 (d, J=8.4 Hz, 2H), 7.27 (d, J=8.4 Hz, 2H), 7.39-7.47 (m, 2H), 7.55-7.60 (m, 1H), 7.72-7.75 (m, 1H), 7.89 (s, 1H), 8.60-9.60 (br, 1H).

EXAMPLE 396

4-[(5R,8R)-3-hydroxy-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

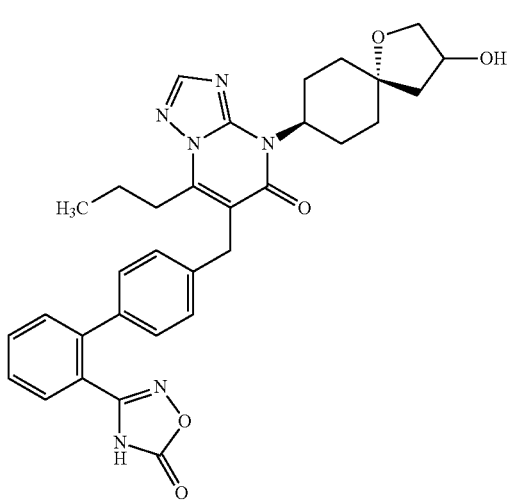

A mixture of hydroxylammonium chloride (208 mg), sodium hydrogen carbonate (336 mg) and dimethyl sulfoxide (1.5 mL) was stirred at 60° C. for 30 min, a solution of 4'-({4-[(5R,8R)-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (105 mg) in dimethyl sulfoxide (1.5 mL) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (39 mg) and then 1,8-diazabicyclo[5.4.0]undec-7-ene (37 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→0/100 (volume ratio)] to give the title compound as a colorless amorphous compound (35 mg, 30%).

$^1$H NMR (300 MHz, CDCl$_3$) δ1.11 (t, J=7.5 Hz, 3H), 1.64-1.81 (m, 8H), 2.05-2.20 (m, 3H), 2.68-2.77 (m, 2H), 3.03-3.08 (m, 2H), 3.83 (dd, J=9.9, 2.1 Hz, 1H), 3.95 (dd, J=9.9, 3.9 Hz, 1H), 3.98 (s, 2H), 4.54 (br s, 1H), 4.96-5.04 (m, 1H), 7.25 (d, J=8.1 Hz, 2H), 7.31 (d, J=8.1 Hz, 2H), 7.39-7.42 (m, 1H), 7.46-7.51 (m, 1H), 7.57-7.63 (m, 1H), 7.82-7.85 (m, 1H), 7.92 (s, 1H), 7.94-8.06 (br, 1H).

EXAMPLE 397

4-[(5R,8R)-3-hydroxy-3-methyl-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

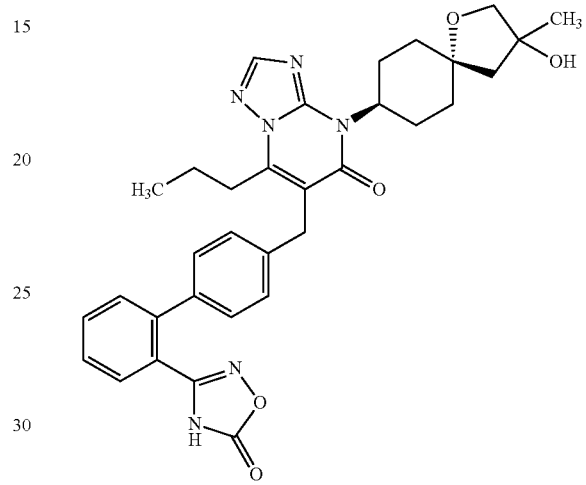

A mixture of hydroxylammonium chloride (208 mg), sodium hydrogen carbonate (336 mg) and dimethyl sulfoxide (1.5 mL) was stirred at 60° C. for 30 min, a solution of 4'-({4-[(5R,8R)-3-hydroxy-3-methyl-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (109 mg) in dimethyl sulfoxide (1.5 mL) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (39 mg) and then 1,8-diazabicyclo[5.4.0]undec-7-ene (37 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=40/60→15/85 (volume ratio)] to give the title compound as a colorless amorphous compound (30 mg, 25%).

$^1$H NMR (300 MHz, CDCl$_3$) δ1.09 (t, J=7.5 Hz, 3H), 1.42 (s, 3H), 1.60-2.08 (m, 10H), 2.27 (d, J=14.8 Hz, 1H), 2.59-2.78 (m, 2H), 3.03-3.08 (m, 2H), 3.67 (d, J=9.3 Hz, 1H), 3.77 (d, J=9.3 Hz, 1H), 3.98 (s, 2H), 4.99-5.07 (m, 1H), 7.26 (d, J=8.4 Hz, 2H), 7.34 (d, J=8.4 Hz, 2H), 7.38-7.41 (m, 1H), 7.46-7.52 (m, 1H), 7.57-7.63 (m, 1H), 7.84-7.87 (m, 1H), 7.91 (s, 1H), 8.00-9.00 (br, 1H).

EXAMPLE 398

4-[(5R,8R)-3-ethyl-3-hydroxy-1-oxaspiro[4.5]dec-8-yl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

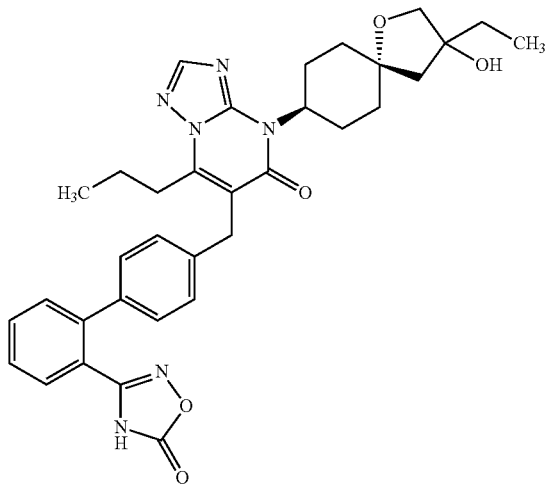

A mixture of hydroxylammonium chloride (202 mg), sodium hydrogen carbonate (319 mg) and dimethyl sulfoxide (1.5 mL) was stirred at 60° C. for 30 min, a solution of 4'-({4-[(5R,8R)-3-ethyl-3-hydroxy-1-oxaspiro[4.5]dec-8-yl]-5-oxo-7-propyl-4,5-dihydro[1,2,4]triazolo[1,5-a]pyrimidin-6-yl}methyl)biphenyl-2-carbonitrile (105 mg) in dimethyl sulfoxide (1.5 mL) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (39 mg) and then 1,8-diazabicyclo[5.4.0]undec-7-ene (37 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (27 mg, 23%).

$^1$H NMR (300 MHz, CDCl$_3$) δ1.01 (t, J=7.5 Hz, 3H), 1.07 (t, J=7.2 Hz, 3H), 1.60-1.88 (m, 11H), 2.03-2.12 (m, 1H), 2.19 (d, J=13.5 Hz, 1H), 2.57-2.75 (m, 2H), 3.02-3.07 (m, 2H), 3.68 (d, J=9.6 Hz, 1H), 3.74 (d, J=9.6 Hz, 1H), 3.96 (s, 2H), 4.96-5.04 (m, 1H), 7.25 (d, J=8.4 Hz, 2H), 7.30 (d, J=8.4 Hz, 2H), 7.39-7.42 (m, 1H), 7.45-7.51 (m, 1H), 7.57-7.62 (m, 1H), 7.78-7.81 (m, 1H), 7.90 (s, 1H), 8.05-8.80 (br, 1H).

EXAMPLE 399

4-(1,4-dioxaspiro[4.5]dec-8-yl)-6-{[2'-(5-oxo-4,5-dihydro-1,2,4-oxadiazol-3-yl)biphenyl-4-yl]methyl}-7-propyl-2-(trifluoromethyl)[1,2,4]triazolo[1,5-a]pyrimidin-5(4H)-one

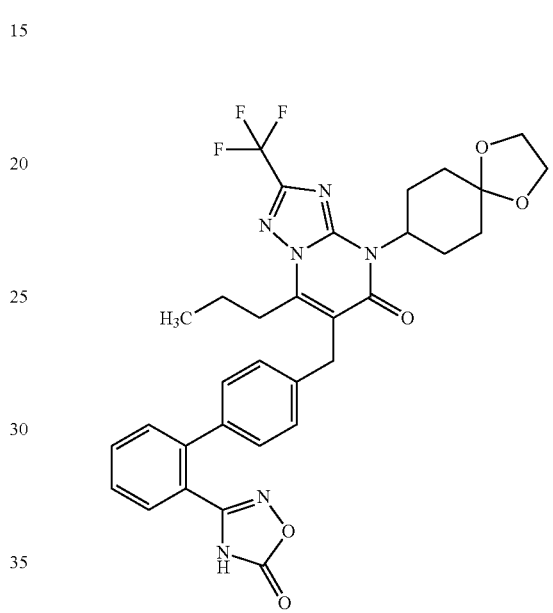

A mixture of hydroxylammonium chloride (396 mg), sodium hydrogen carbonate (638 mg) and dimethyl sulfoxide (3 mL) was stirred at 60° C. for 30 min, 4'-{[4-(1,4-dioxaspiro[4.5]dec-8-yl)-5-oxo-7-propyl-2-(trifluoromethyl)-4,5-dihydro[1,2,4]triazolo[1,5-a]pyrimidin-6-yl]methyl}biphenyl-2-carbonitrile (220 mg) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (75 mg) and then 1,8-diazabicyclo[5.4.0]undec-7-ene (70 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=70/30→30/70 (volume ratio)] to give the title compound as a colorless amorphous compound (162 mg, 67%).

$^1$H NMR (300 MHz, CDCl$_3$) δ1.07 (t, J=7.2 Hz, 3H), 1.67-1.89 (m, 8H), 2.79-2.93 (m, 2H), 3.03-3.08 (m, 2H), 3.91-4.01 (m, 6H), 4.93-5.02 (m, 1H), 7.24 (d, J=8.4 Hz, 2H), 7.28 (d, J=8.4 Hz, 2H), 7.39-7.42 (m, 1H), 7.44-7.50 (m, 1H), 7.57-7.62 (m, 1H), 7.73-7.76 (m, 1H), 8.40-9.60 (br, 1H).

EXAMPLE 400

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propyl-2-(trifluoromethyl)[1,2,4]triazolo[1,5-a]pyrimidin-5(4H)-one

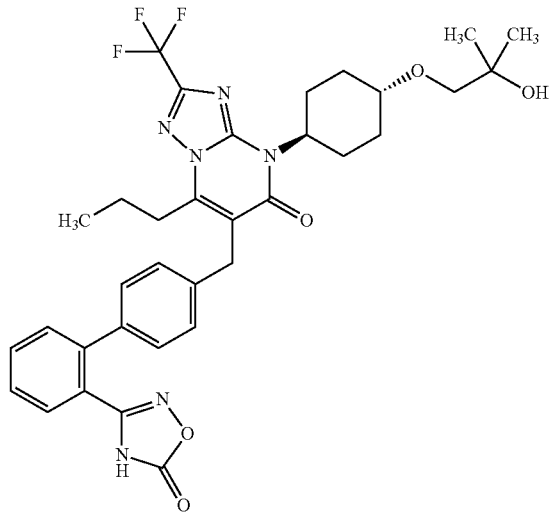 [SMILES: CCCc1c(Cc2ccc(-c3ccccc3-c3noc(=O)[nH]3)cc2)c(=O)n([C@H]2CC[C@H](OCC(C)(C)O)CC2)c2nc(C(F)(F)F)nn12]

A mixture of hydroxylammonium chloride (344 mg), sodium hydrogen carbonate (554 mg) and dimethyl sulfoxide (2 mL) was stirred at 60° C. for 30 min, 4'-({4-[trans-4-(2-hydroxy-2-methylpropoxy)cyclohexyl]-5-oxo-7-propyl-2-(trifluoromethyl)-4,5-dihydro[1,2,4]triazolo[1,5-a]pyrimidin-6-yl}methyl)biphenyl-2-carbonitrile (200 mg) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (65 mg) and then 1,8-diazabicyclo[5.4.0]undec-7-ene (61 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (149 mg, 68%).

$^1$H NMR (300 MHz, CDCl$_3$) δ1.07 (t, J=7.5 Hz, 3H), 1.17 (s, 6H), 1.34-1.48 (m, 2H), 1.68-1.81 (m, 4H), 2.15-2.18 (m, 2H), 2.30-2.55 (br, 1H), 2.57-2.71 (m, 2H), 3.02-3.07 (m, 2H), 3.29 (s, 2H), 3.36-3.46 (m, 1H), 3.97 (s, 2H), 4.95-5.04 (m, 1H), 7.24 (d, J=8.4 Hz, 2H), 7.29 (d, J=8.4 Hz, 2H), 7.40-7.42 (m, 1H), 7.45-7.50 (m, 1H), 7.57-7.63 (m, 1H), 7.73-7.76 (m, 1H), 8.00-9.50 (br, 1H).

EXAMPLE 401

4-[cis-4-(2-hydroxy-2-methylpropyl)-4-methoxycyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

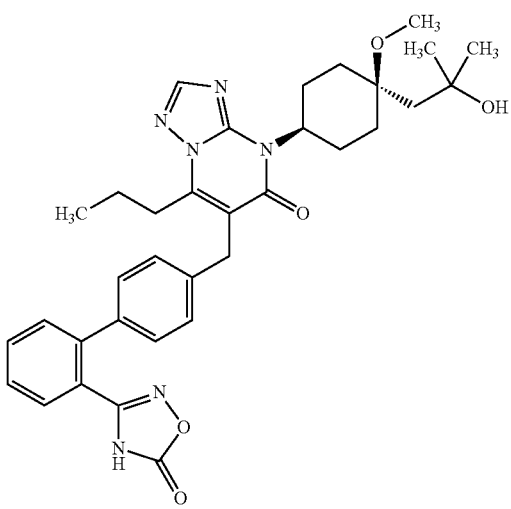 [SMILES: CCCc1c(Cc2ccc(-c3ccccc3-c3noc(=O)[nH]3)cc2)c(=O)n([C@H]2CC[C@@](CC(C)(C)O)(OC)CC2)c2ncnn12]

A mixture of hydroxylammonium chloride (146 mg), sodium hydrogen carbonate (235 mg) and dimethyl sulfoxide (1 mL) was stirred at 60° C. for 30 min, a solution of 4'-({4-[cis-4-(2-hydroxy-2-methylpropyl)-4-methoxycyclohexyl]-5-oxo-7-propyl-4,5-dihydro[1,2,4]triazolo[1,5-a]pyrimidin-6-yl}methyl)biphenyl-2-carbonitrile (79 mg) in dimethyl sulfoxide (1 mL) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (28 mg) and then 1,8-diazabicyclo[5.4.0]undec-7-ene (26 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=60/40→40/60 (volume ratio)] to give the title compound as a colorless amorphous compound (54 mg, 63%).

$^1$H NMR (300 MHz, DMSO-d$_6$) δ0.93 (t, J=7.2 Hz, 3H), 1.19 (s, 6H), 1.39-1.56 (m, 6H), 1.59 (s, 2H), 2.06-2.11 (m, 2H), 2.68-2.80 (m, 2H), 2.90-2.96 (m, 2H), 3.10 (s, 3H), 3.95 (s, 2H), 4.08 (s, 1H), 4.82-4.90 (m, 1H), 7.21 (d, J=8.4 Hz,

2H), 7.30 (d, J=8.4 Hz, 2H), 7.48-7.56 (m, 2H), 7.62-7.69 (m, 2H), 8.18 (s, 1H), 11.80-12.80 (br, 1H).

EXAMPLE 402

4-[cis-4-(3-hydroxy-3-methylbutyl)-4-methoxycyclohexyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

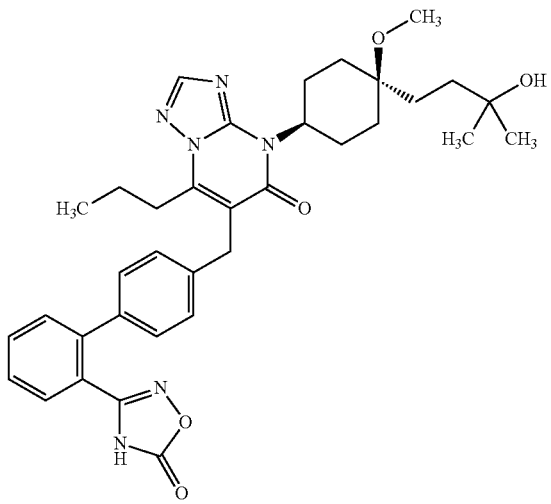 [SMILES: CCCc1c(Cc2ccc(-c3ccccc3-c3noc(=O)[nH]3)cc2)c(=O)n([C@H]2CC[C@@](CCC(C)(C)O)(OC)CC2)c2ncnn12]

A mixture of hydroxylammonium chloride (723 mg), sodium hydrogen carbonate (1.16 g) and dimethyl sulfoxide (2 mL) was stirred at 60° C. for 30 min, a solution of 4'-({4-[cis-4-(3-hydroxy-3-methylbutyl)-4-methoxycyclohexyl]-5-oxo-7-propyl-4,5-dihydro[1,2,4]triazolo[1,5-a]pyrimidin-6-yl}methyl)biphenyl-2-carbonitrile (390 mg) in dimethyl sulfoxide (2 mL) was added, and the mixture was stirred at 90° C. for 17 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (135 mg) and then 1,8-diazabicyclo[5.4.0]undec-7-ene (126 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→25/75 (volume ratio)] to give the title compound as a colorless amorphous compound (323 mg, 75%).

$^1$H NMR (300 MHz, DMSO-d$_6$) δ0.93 (t, J=7.2 Hz, 3H), 1.08 (s, 6H), 1.26-1.58 (m, 10H), 1.88-1.92 (m, 2H), 2.69-2.80 (m, 2H), 2.90-2.96 (m, 2H), 3.08 (s, 3H), 3.95 (s, 2H), 4.09 (s, 1H), 4.84-4.92 (m, 1H), 7.21 (d, J=8.1 Hz, 2H), 7.30 (d, J=8.1 Hz, 2H), 7.48-7.56 (m, 2H), 7.63-7.70 (m, 2H), 8.18 (s, 1H), 12.36 (br s, 1H).

EXAMPLE 403

6-{[3-fluoro-2'-(5-oxo-4,5-dihydro-1,2,4-oxadiazol-3-yl)biphenyl-4-yl]methyl}-4-[trans-3-(2-hydroxy-2-methylpropoxy)cyclobutyl]-2-methyl-7-propyl[1,2,4]triazolo[1,5-a]pyrimidin-5(4H)-one

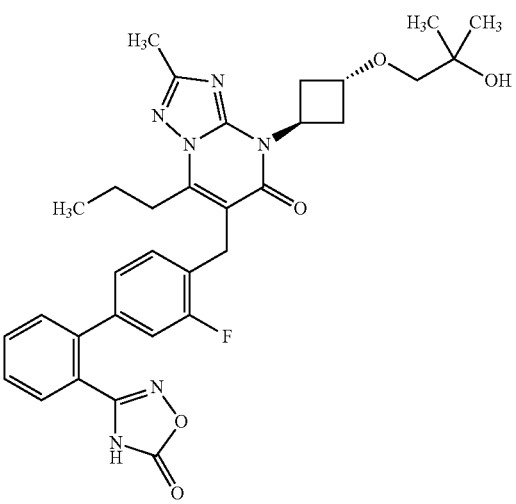 [SMILES: CCCc1c(Cc2ccc(-c3ccccc3-c3noc(=O)[nH]3)cc2F)c(=O)n([C@H]2C[C@H](OCC(C)(C)O)C2)c2nc(C)nn12]

A mixture of hydroxylammonium chloride (834 mg), sodium hydrogen carbonate (1.34 g) and dimethyl sulfoxide (2 mL) was stirred at 60° C. for 30 min, a solution of 3'-fluoro-4'-({4-[trans-3-(2-hydroxy-2-methylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile (437 mg) in dimethyl sulfoxide (3 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (156 mg) and then 1,8-diazabicyclo[5.4.0]undec-7-ene (146 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→35/65 (volume ratio)] to give the title compound as a colorless amorphous compound (328 mg, 68%).

$^1$H NMR (300 MHz, DMSO-d$_6$) δ0.93 (t, J=7.2 Hz, 3H), 1.11 (s, 6H), 1.52-1.60 (m, 2H), 2.24-2.31 (m, 2H), 2.37 (s, 3H), 2.85-2.90 (m, 2H), 3.08 (s, 2H), 3.11-3.21 (m, 2H), 3.90 (s, 2H), 4.24-4.28 (m, 1H), 4.33 (s, 1H), 5.56-5.67 (m, 1H), 6.96-6.99 (m, 1H), 7.13-7.24 (m, 2H), 7.51-7.59 (m, 2H), 7.65-7.71 (m, 2H), 12.45 (br s, 1H).

EXAMPLE 404

6-{[3-fluoro-2'-(5-oxo-4,5-dihydro-1,2,4-oxadiazol-3-yl)biphenyl-4-yl]methyl}-4-[cis-3-(2-hydroxy-2-methylpropoxy)cyclobutyl]-2-methyl-7-propyl[1,2,4]triazolo[1,5-a]pyrimidin-5(4H)-one

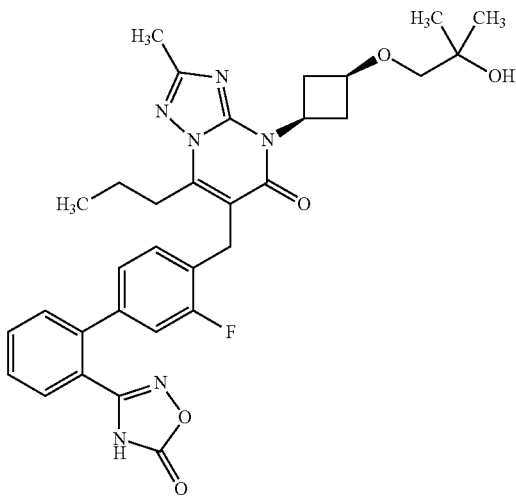 [SMILES: CCCc1c(Cc2ccc(-c3ccccc3-c3noc(=O)[nH]3)cc2F)c(=O)n([C@H]2C[C@@H](OCC(C)(C)O)C2)c2nc(C)nn12]

A mixture of hydroxylammonium chloride (1.16 g), sodium hydrogen carbonate (1.87 g) and dimethyl sulfoxide (2 mL) was stirred at 60° C. for 30 min, a solution of 3'-fluoro-4'-({4-[cis-3-(2-hydroxy-2-methylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile (606 mg) in dimethyl sulfoxide (3 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (216 mg) and then 1,8-diazabicyclo[5.4.0]undec-7-ene (202 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→35/65 (volume ratio)] to give the title compound as a colorless amorphous compound (542 mg, 81%).

$^1$H NMR (300 MHz, DMSO-$d_6$) δ0.92 (t, J=7.2 Hz, 3H), 1.09 (s, 6H), 1.52-1.60 (m, 2H), 2.36 (s, 3H), 2.51-2.61 (m, 2H), 2.85-2.90 (m, 2H), 2.96-3.05 (m, 2H), 3.10 (s, 2H), 3.76-3.85 (m, 1H), 3.99 (s, 2H), 4.30 (s, 1H), 4.81-4.91 (m, 1H), 6.96-6.99 (m, 1H), 7.12-7.24 (m, 2H), 7.50-7.58 (m, 2H), 7.64-7.70 (m, 2H), 12.47 (br s, 1H).

EXAMPLE 405

6-{[3-fluoro-2'-(5-oxo-4,5-dihydro-1,2,4-oxadiazol-3-yl)biphenyl-4-yl]methyl}-4-[cis-3-(2-hydroxy-1,2-dimethylpropoxy)cyclobutyl]-2-methyl-7-propyl[1,2,4]triazolo[1,5-a]pyrimidin-5(4H)-one

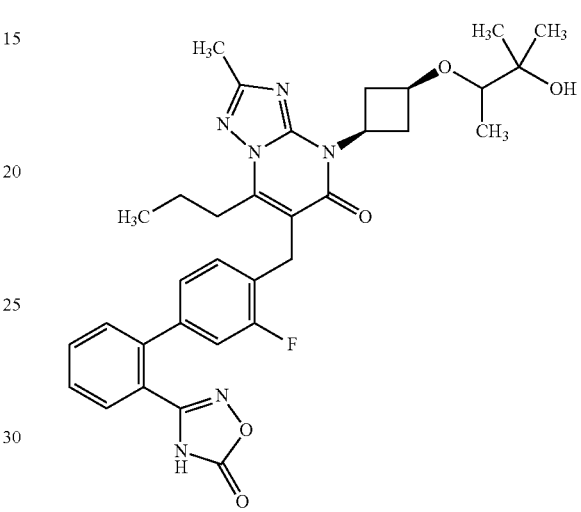

A mixture of hydroxylammonium chloride (806 mg), sodium hydrogen carbonate (1.29 g) and dimethyl sulfoxide (2 mL) was stirred at 60° C. for 30 min, a solution of 3'-fluoro-4'-({4-[cis-3-(2-hydroxy-1,2-dimethylpropoxy)cyclobutyl]-2-methyl-5-oxo-7-propyl-4,5-dihydro[1,2,4]triazolo[1,5-a]pyrimidin-6-yl}methyl)biphenyl-2-carbonitrile (430 mg) in dimethyl sulfoxide (2 mL) was added, and the mixture was stirred at 90° C. for 16 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (150 mg) and then 1,8-diazabicyclo[5.4.0]undec-7-ene (141 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→35/65 (volume ratio)] to give the title compound as a colorless amorphous compound (542 mg, 81%).

$^1$H NMR (300 MHz, DMSO-$d_6$) δ0.92 (t, J=7.2 Hz, 3H), 1.02 (s, 3H), 1.03 (d, J=6.3 Hz, 3H), 1.12 (s, 3H), 1.52-1.57 (m, 2H), 2.36 (s, 3H), 2.54-2.58 (m, 2H), 2.85-2.90 (m, 2H), 2.96-3.08 (m, 2H), 3.14 (q, J=6.3 Hz, 1H), 3.85-3.94 (m, 3H), 4.13 (s, 1H), 4.83-4.95 (m, 1H), 6.96-6.99 (m, 1H), 7.12-7.16 (m, 1H), 7.21 (t, J=7.8 Hz, 1H), 7.51-7.59 (m, 2H), 7.65-7.70 (m, 2H), 12.47 (br s, 1H).

EXAMPLE 406

4-{trans-4-[1-(1-hydroxycyclobutyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

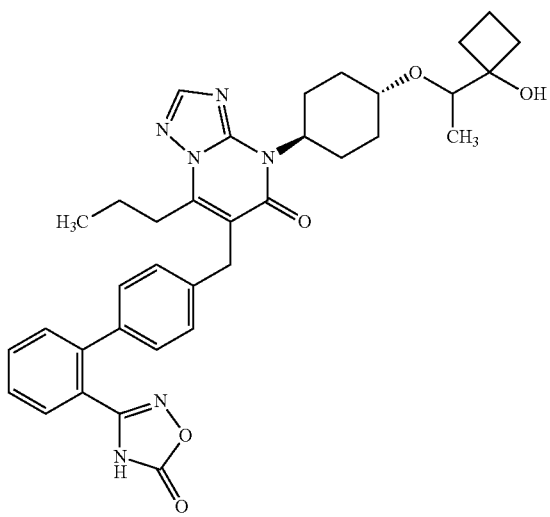 [SMILES: CCCc1c(Cc2ccc(-c3ccccc3-c3noc(=O)[nH]3)cc2)c(=O)n([C@H]2CC[C@H](OC(C)C3(O)CCC3)CC2)c2ncnn12]

A mixture of hydroxylammonium chloride (2.67 g), sodium hydrogen carbonate (4.30 g) and dimethyl sulfoxide (7 mL) was stirred at 60° C. for 30 min, a solution of 4'-[(4-{trans-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (1.45 g) in dimethyl sulfoxide (8 mL) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (10 mL). N,N'-Carbonyldiimidazole (503 mg) and then 1,8-diazabicyclo[5.4.0]undec-7-ene (472 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=50/50→35/65 (volume ratio)] to give the title compound as a colorless amorphous compound (890 mg, 56%).

$^1$H NMR (300 MHz, CDCl$_3$) δ1.08 (t, J=7.5 Hz, 3H), 1.14 (d, J=6.3 Hz, 3H), 1.32-1.59 (m, 3H), 1.70-1.90 (m, 4H), 1.98-2.17 (m, 6H), 2.41 (br s, 2H), 2.59-2.74 (m, 2H), 3.03-3.08 (m, 2H), 3.46-3.58 (m, 2H), 3.97 (s, 2H), 4.97-5.05 (m, 1H), 7.25 (d, J=7.8 Hz, 2H), 7.32 (d, J=7.8 Hz, 2H), 7.39-7.42 (m, 1H), 7.45-7.51 (m, 1H), 7.57-7.63 (m, 1H), 7.80-7.83 (m, 1H), 7.91 (s, 1H), 8.20 (br s, 1H).

EXAMPLE 407

4-{trans-4-[1-(1-hydroxycyclobutyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one potassium salt

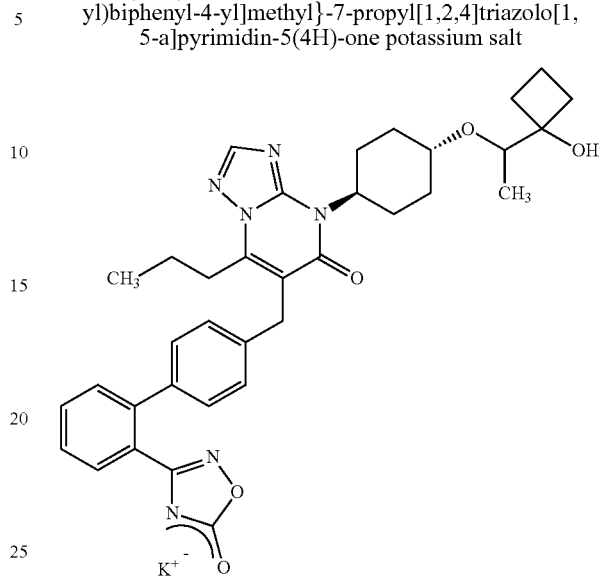

To a solution of 4-{trans-4-[1-(1-hydroxycyclobutyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (860 mg) in isopropanol (5 mL) was added 8N aqueous potassium hydroxide solution (173 µL), and the mixture was stirred at room temperature 10 min. The solvent was evaporated under reduced pressure, the obtained residue was mixed with diisopropyl ether (15 mL), and the mixture was stirred at room temperature for 3 hr. The precipitate was collected by filtration, and dried to give the title compound as a white powder (905 mg, 99%).

$^1$H NMR (300 MHz, DMSO-d$_6$) δ0.96 (t, J=7.5 Hz, 3H), 1.01 (d, J=6.9 Hz, 3H), 1.17-2.13 (m, 15H), 2.50-2.60 (m, 2H), 2.92-2.97 (m, 2H), 3.31-3.43 (m, 2H), 3.90 (s, 2H), 4.85-4.95 (m, 1H), 7.16 (d, J=8.4 Hz, 2H), 7.21 (d, J=8.4 Hz, 2H), 7.25-7.47 (m, 4H), 8.16 (s, 1H).

EXAMPLE 408

4-{cis-4-[1-(1-hydroxycyclobutyl)ethoxy]cyclohexyl}-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

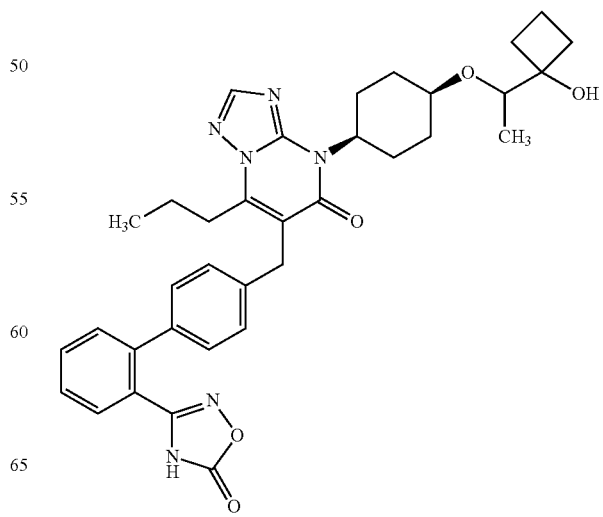

A mixture of hydroxylammonium chloride (0.92 g), sodium hydrogen carbonate (1.48 g) and dimethyl sulfoxide (3 mL) was stirred at 60° C. for 30 min, a solution of 4'-[(4-{cis-4-[1-(1-hydroxycyclobutyl)ethoxy]cyclohexyl}-5-oxo-7-propyl-4,5-dihydro[1,2,4]triazolo[1,5-a]pyrimidin-6-yl)methyl]biphenyl-2-carbonitrile (0.50 g) in dimethyl sulfoxide (4 mL) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (178 mg) and then 1,8-diazabicyclo[5.4.0]undec-7-ene (167 mg) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel chromatography [eluent: hexane/ethyl acetate=60/40→35/65 (volume ratio)] to give the title compound as a colorless amorphous compound (278 mg, 51%).

$^1$H NMR (300 MHz, CDCl$_3$) δ1.08 (t, J=7.5 Hz, 3H), 1.16 (d, J=6.3 Hz, 3H), 1.37-1.62 (m, 6H), 1.72-2.21 (m, 8H), 2.76-3.09 (m, 4H), 3.52 (q, J=6.3 Hz, 1H), 3.76 (br s, 1H), 3.76-3.96 (m, 1H), 3.96 (s, 2H), 4.98-5.06 (m, 1H), 7.26 (d, J=8.4 Hz, 2H), 7.30 (d, J=8.4 Hz, 2H), 7.41-7.49 (m, 2H), 7.56-7.62 (m, 1H), 7.79-7.81 (m, 1H), 7.91 (s, 1H), 8.20-9.60 (br, 1H).

EXAMPLE 409

4-[4-(2-hydroxy-1,1,2-trimethylpropoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

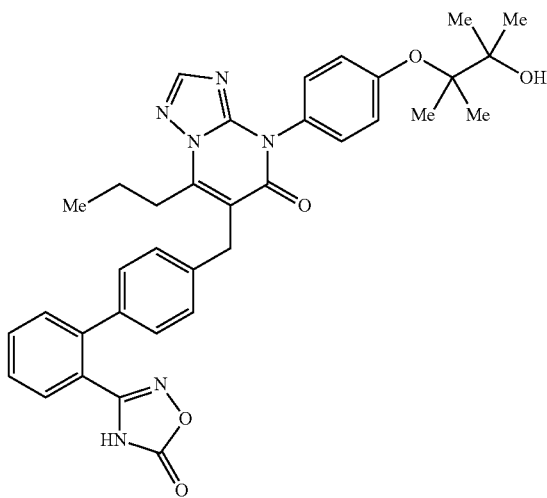 [SMILES: CCCc1c(Cc2ccc(-c3ccccc3-c3noc(=O)[nH]3)cc2)c(=O)n(-c2ccc(OC(C)(C)C(C)(C)O)cc2)c2ncnn12]

A mixture of hydroxylammonium chloride (1.5 g), sodium hydrogen carbonate (2.2 g) and dimethyl sulfoxide (9 mL) was stirred at 50° C. for 30 min, 4'-({4-[4-(2-hydroxy-1,1,2-trimethylpropoxy)phenyl]-5-oxo-7-propyl-4,5-dihydro[1,2,4]triazolo[1,5-a]pyrimidin-6-yl}methyl)biphenyl-2-carbonitrile (0.98 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (9 mL). N,N'-Carbonyldiimidazole (0.34 g) and then 1,8-diazabicyclo[5.4.0]undec-7-ene (0.31 mL) were added, and the mixture was stirred at room temperature for 1 hr. The reaction mixture was diluted with ethyl acetate, washed with 1 M hydrochloric acid, saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.52 g, 48%).

$^1$H NMR (300 MHz, DMSO-d$_6$) δ0.97 (t, J=7.4 Hz, 3H), 1.26 (s, 12H), 1.53-1.68 (m, 2H), 2.96-3.03 (m, 2H), 4.00 (s, 2H), 4.44 (s, 1H), 7.07-7.76 (m, 12H), 8.07 (s, 1H), 12.39 (s, 1H)

EXAMPLE 410

4-[4-(2-hydroxy-1,1-dimethylpropoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

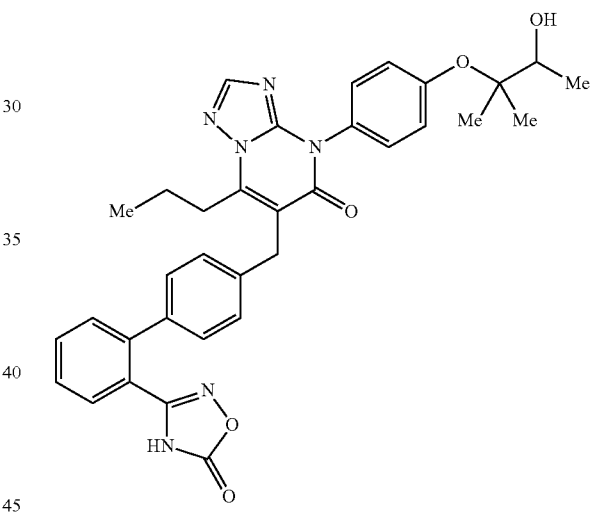

A mixture of hydroxylammonium chloride (1.1 g), sodium hydrogen carbonate (1.6 g) and dimethyl sulfoxide (6 mL) was stirred at 50° C. for 30 min, 4'-({4-[4-(2-hydroxy-1,1-dimethylpropoxy)phenyl]-5-oxo-7-propyl-4,5-dihydro[1,2,4]triazolo[1,5-a]pyrimidin-6-yl}methyl)biphenyl-2-carbonitrile (0.70 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (6 mL). N,N'-Carbonyldiimidazole (0.25 g) and then 1,8-diazabicyclo[5.4.0]undec-7-ene (0.23 mL) were added, and the mixture was stirred at room temperature for 1 hr. The reaction mixture was diluted with ethyl acetate, washed with 1 M hydrochloric acid and then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.34, 43%).

¹H NMR (300 MHz, CHLOROFORM-d) δ1.14 (t, J=7.4 Hz, 3H), 1.21 (d, J=6.4 Hz, 3H), 1.27 (s, 6H), 1.77-1.92 (m, 2H), 2.57-2.68 (m, 1H), 3.09-3.23 (m, 2H), 3.86 (q, J=6.4 Hz, 1H), 4.02 (s, 2H), 7.04-8.38 (m, 14H)

EXAMPLE 411

4-[4-(1,1-dimethyl-2-oxopropoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one

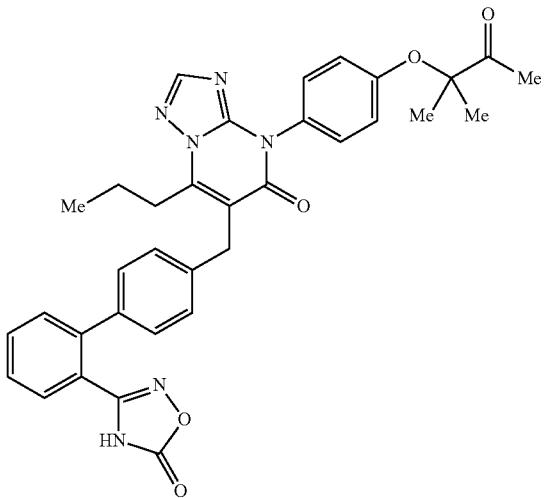 [SMILES: CCCc1c(Cc2ccc(-c3ccccc3-c3noc(=O)[nH]3)cc2)c(=O)n(-c2ccc(OC(C)(C)C(C)=O)cc2)c2ncnn12]

To a solution of 4-[4-(2-hydroxy-1,1-dimethylpropoxy)phenyl]-6-{[2'-(5-oxo-4,5-dihydro-1,2,4-oxadiazol-3-yl)biphenyl-4-yl]methyl}-7-propyl[1,2,4]triazolo[1,5-a]pyrimidin-5(4H)-one (0.24 g) in methylene chloride (4 mL) was added 1,1,1-tris(acetyloxy)-1,1-dihydro-1,2-benziodoxol-3-(1H)-one (0.25 g), and the mixture was stirred for 3 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.20 g, 85%).

¹H NMR (300 MHz, DMSO-d₆) δ0.97 (t, J=7.3 Hz, 3H), 1.49 (s, 6H), 1.53-1.68 (m, 2H), 2.28 (s, 3H), 2.94-3.03 (m, 2H), 3.99 (s, 2H), 6.83-7.74 (m, 12H), 8.06 (s, 1H), 12.39 (s, 1H)

EXAMPLE 412

4-(trans-4-hydroxycyclohexyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

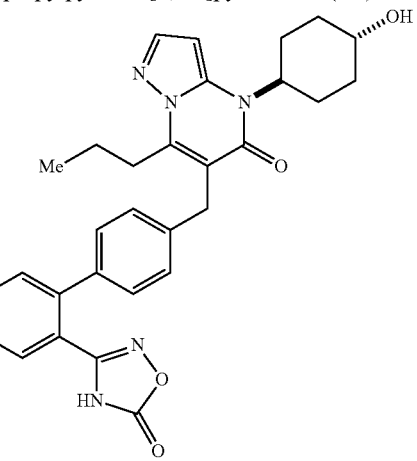

A mixture of hydroxylammonium chloride (0.70 g), sodium hydrogen carbonate (1.0 g) and dimethyl sulfoxide (5 mL) was stirred at 50° C. for 30 min, 4'-{[4-(trans-4-hydroxycyclohexyl)-5-oxo-7-propyl-4,5-dihydropyrazolo[1,5-a]pyrimidin-6-yl]methyl}biphenyl-2-carbonitrile (0.47 g) was added, and the mixture was stirred at 90° C. for 23 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.20 g) and then 1,8-diazabicyclo[5.4.0]undec-7-ene (0.18 mL) were added, and the mixture was stirred at room temperature for 1 hr. The reaction mixture was diluted with ethyl acetate, washed with 1 M hydrochloric acid, then saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless solid (0.48 g, 90%).

¹H NMR (300 MHz, DMSO-d₆) δ0.92 (t, J=7.3 Hz, 3H), 1.27-1.98 (m, 6H), 2.19-2.53 (m, 4H), 2.89-3.02 (m, 2H), 3.49-3.65 (m, 1H), 3.93 (s, 2H), 4.53-4.92 (m, 2H), 6.40 (d, J=2.1 Hz, 1H), 7.15-7.87 (m, 9H), 12.36 (s, 1H)

EXAMPLE 413

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

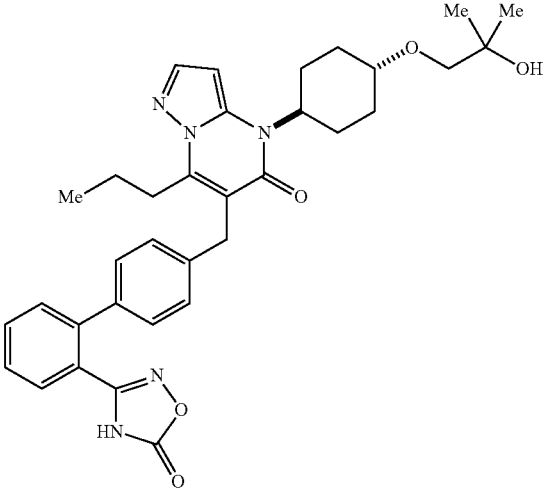

A mixture of hydroxylammonium chloride (42 g), sodium hydrogen carbonate (61 g) and dimethyl sulfoxide (240 mL) was stirred at 50° C. for 30 min. 4'-({4-[trans-4-(2-Hydroxy-2-methylpropoxy)cyclohexyl]-5-oxo-7-propyl-4,5-dihydropyrazolo[1,5-a]pyrimidin-6-yl}methyl)biphenyl-2-carbonitrile (32 g) was added, and the mixture was stirred at 90° C. for 15 hr. The mixture was allowed to cool to room temperature, and the reaction mixture was diluted with ethyl acetate and water. After extraction with ethyl acetate, the organic layer was washed with brine, and dried over anhydrous magnesium sulfate. The solvent was evaporated under reduced pressure, and the residue was dissolved in tetrahydrofuran (300 mL). N,N'-Carbonyldiimidazole (11.5 g) and 1,8-diazabicyclo[5.4.0]undec-7-ene (10.6 mL) were successively added to the tetrahydrofuran solution mentioned above, and the mixture was stirred at room temperature for 2 hr. The reaction mixture was diluted with ethyl acetate, and 1 M hydrochloric acid was added. After extraction with ethyl acetate, the organic layer was successively washed with saturated aqueous sodium hydrogen carbonate and brine, and dried over anhydrous magnesium sulfate. The solvent was evaporated under reduced pressure, and the residue was purified by silica gel column chromatography to give the title compound as an amorphous solid. The solid was dissolved in acetone, and crystallized. The resulting solid was collected by filtration, washed with acetone, and dried under reduced pressure to give the title compound as a colorless solid (25.9 g, 73%).

$^1$H NMR (300 MHz, DMSO-d$_6$) δ0.92 (t, J=7.4 Hz, 3H), 1.07 (s, 6H), 1.25-1.76 (m, 6H), 2.02-2.48 (m, 4H), 2.89-3.00 (m, 2H), 3.20 (s, 2H), 3.33-3.46 (m, 1H), 3.93 (s, 2H), 4.24 (s, 1H), 4.67 (br. s., 1H), 6.41 (d, J=2.3 Hz, 1H), 7.17-7.85 (m, 9H), 12.35 (br. s., 1H)

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 9.94 | 8.8912 |
| 15.08 | 5.8702 |
| 15.7 | 5.6398 |
| 15.82 | 5.5973 |
| 18.6 | 4.7665 |
| 18.66 | 4.7513 |
| 19.52 | 4.5439 |
| 19.96 | 4.4447 |
| 23.08 | 3.8504 |

EXAMPLE 414

4-(4-oxocyclohexyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

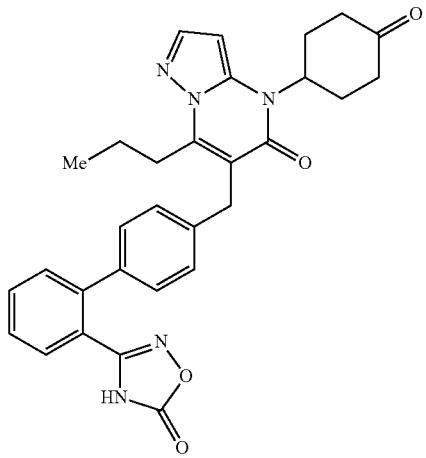 [SMILES: CCCc1c(Cc2ccc(-c3ccccc3-c3noc(=O)[nH]3)cc2)c(=O)n(C2CCC(=O)CC2)c2ccnn12]

To a solution of 4-(trans-4-hydroxycyclohexyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.20 g) in methylene chloride (4 mL) was added 1,1,1-tris(acetyloxy)-1,1-dihydro-1,2-benziodoxol-3-(1H)-one (0.24 g), and the mixture was stirred for 18 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.091 g, 45%).

$^1$H NMR (300 MHz, DMSO-d$_6$) δ0.92 (t, J=7.2 Hz, 3H), 1.44-1.59 (m, 2H), 1.88-2.05 (m, 2H), 2.23-2.39 (m, 2H), 2.57-3.04 (m, 6H), 3.95 (s, 2H), 5.18 (br. s., 1H), 6.51 (d, J=2.3 Hz, 1H), 7.15-7.88 (m, 9H), 12.35 (s, 1H)

EXAMPLE 415

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

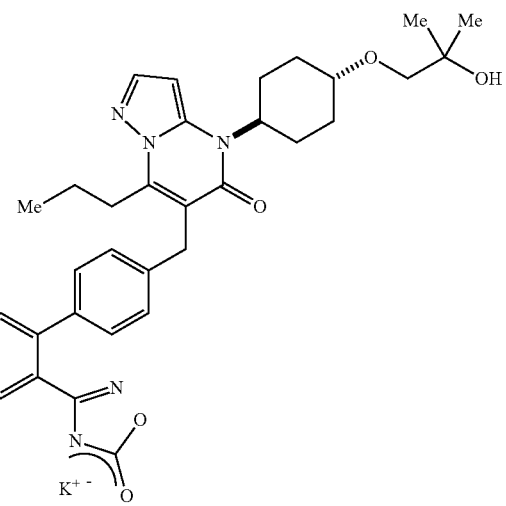

To a solution (2 mL) of 4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.16 g) in ethanol was added 8M aqueous potassium hydroxide solution (0.034 mL), and the mixture was stirred at room temperature for 1 hr. The reaction mixture was concentrated under reduced pressure, and the residue was solidified with diisopropyl ether to give the title compound as a colorless amorphous solid (0.16 g, 94%).

$^1$H NMR (300 MHz, DMSO-$d_6$) δ0.95 (t, J=7.4 Hz, 3H), 1.07 (s, 6H), 1.25-1.44 (m, 2H), 1.49-1.74 (m, 4H), 2.03-2.14 (m, 2H), 2.29-2.47 (m, 2H), 2.91-3.01 (m, 2H), 3.20 (s, 2H), 3.35-3.48 (m, 1H), 3.88 (s, 2H), 4.25 (br. s., 1H), 4.50-4.85 (m, 1H), 6.40 (d, J=2.3 Hz, 1H), 7.11-7.50 (m, 8H), 7.81 (d, J=2.3 Hz, 1H)

EXAMPLE 416

4-[trans-4-(2-hydroxy-2-methylpropoxy)cyclohexyl]-7-propyl-6-{[2'-(1H-tetrazol-5-yl)biphenyl-4-yl]methyl}pyrazolo[1,5-a]pyrimidin-5(4H)-one

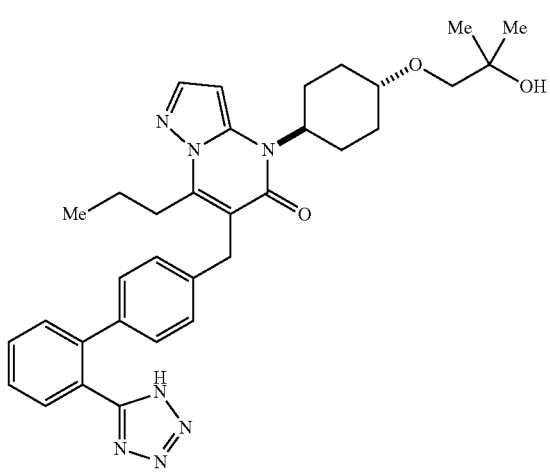

A mixture of 4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile (0.15 g), trimethylsilylazide (0.54 mL), dibutyltinoxide (0.086 g) and toluene (3 mL) was stirred at 100° C. for 5 days. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was dissolved in tetrahydrofuran (2 mL). Tetrabutylammonium fluoride (1.0 M tetrahydrofuran solution, 0.9 mL) was added, and the mixture was stirred at room temperature for 15 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.075 g, 45%).

$^1$H NMR (300 MHz, CHLOROFORM-d) δ1.08 (t, J=7.3 Hz, 3H), 1.20 (s, 6H), 1.34-1.90 (m, 6H), 2.12-2.53 (m, 4H), 3.05-3.13 (m, 2H), 3.26-3.52 (m, 4H), 3.98 (s, 2H), 4.46-4.92 (m, 1H), 6.00 (d, J=2.1 Hz, 1H), 7.13-8.29 (m, 9H), 12.06 (s, 1H)

EXAMPLE 417

4-[trans-4-(2-hydroxy-1,2-dimethylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

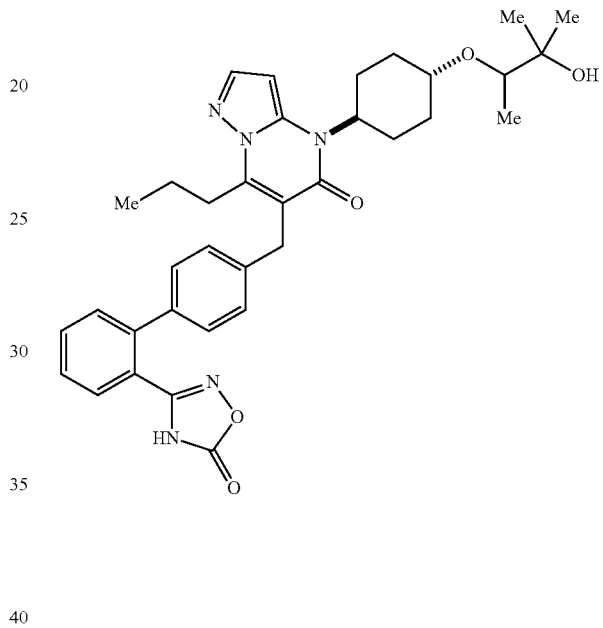

A mixture of hydroxylammonium chloride (0.68 g), sodium hydrogen carbonate (1.0 g) and dimethyl sulfoxide (5 mL) was stirred at 50° C. for 30 min, 4'-({4-[trans-4-(2-hydroxy-1,2-dimethylpropoxy)cyclohexyl]-5-oxo-7-propyl-4,5-dihydropyrazolo[1,5-a]pyrimidin-6-yl}methyl)biphenyl-2-carbonitrile (0.45 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.16 g) and then 1,8-diazabicyclo[5.4.0]undec-7-ene (0.15 mL) were added, and the mixture was stirred at room temperature for 3 hr. The reaction mixture was diluted with ethyl acetate, washed with 1 M hydrochloric acid and with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.37 g, 73%).

$^1$H NMR (300 MHz, DMSO-$d_6$) δ0.92 (t, J=7.3 Hz, 3H), 1.00 (s, 3H), 1.05 (d, J=6.2 Hz, 3H), 1.09 (s, 3H), 1.23-1.72 (m, 6H), 1.92-2.14 (m, 2H), 2.27-2.48 (m, 2H), 2.89-2.99 (m, 2H), 3.24 (q, J=6.2 Hz, 1H), 3.39-3.54 (m, 1H), 3.93 (s, 2H), 4.06 (s, 1H), 4.67 (br. s., 1H), 6.43 (d, J=2.1 Hz, 1H), 7.15-7.89 (m, 9H), 12.36 (br. s., 1H)

EXAMPLE 418

4-[trans-4-(2-hydroxybutoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

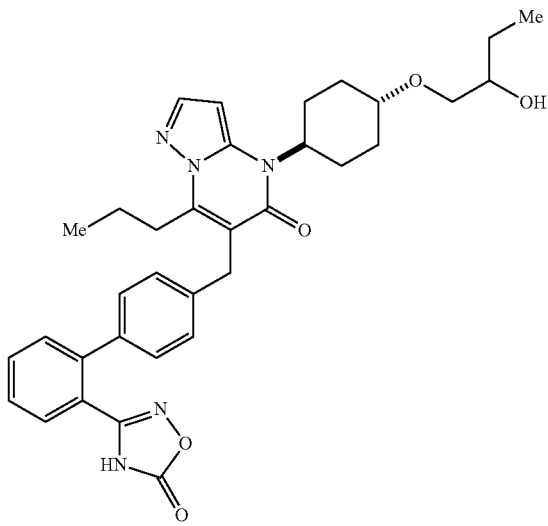

To a solution of 4'-({4-[trans-4-(2-hydroxyethoxy)cyclohexyl]-5-oxo-7-propyl-4,5-dihydropyrazolo[1,5-a]pyrimidin-6-yl}methyl)biphenyl-2-carbonitrile (0.64 g) in methylene chloride (6 mL) was added 1,1,1-tris(acetyloxy)-1,1-dihydro-1,2-benziodoxol-3-(1H)-one (1.1 g), and the mixture was stirred for 5 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. This was dissolved in tetrahydrofuran (4 mL), ethylmagnesium bromide was added dropwise (3 M tetrahydrofuran solution, 0.26 mL) at 0° C., and the mixture was stirred for 4 hr. The mixture was diluted with ethyl acetate and then saturated aqueous ammonium chloride solution were added. The mixture was extracted with ethyl acetate, and the organic layer was washed with saturated brine, dried over anhydrous magnesium sulfate, and concentrated. The residue was crudely purified by silica gel column chromatography. This was dissolved in dimethyl sulfoxide (1.1 mL), hydroxylammonium chloride (0.12 g) and sodium hydrogen carbonate (0.19 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (1.1 mL). N,N'-Carbonyldiimidazole (0.027 g) and then 1,8-diazabicyclo[5.4.0]undec-7-ene (0.025 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.046 g, 6%).

$^1$H NMR (300 MHz, DMSO-$d_6$) δ0.83-0.97 (m, 6H), 1.20-1.75 (m, 8H), 2.02-2.15 (m, 2H), 2.26-2.48 (m, 2H), 2.83-2.99 (m, 2H), 3.22-3.50 (m, 4H), 3.93 (s, 2H), 4.40-4.85 (m, 2H), 6.41 (d, J=1.9 Hz, 1H), 7.16-7.89 (m, 9H), 12.35 (br. s., 1H)

EXAMPLE 419

4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

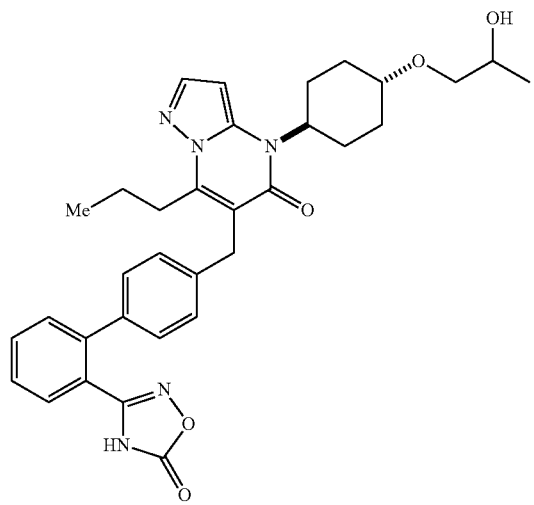

A mixture of hydroxylammonium chloride (0.91 g), sodium hydrogen carbonate (1.38 g) and dimethyl sulfoxide (5 mL) was stirred at 50° C. for 30 min, 4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (0.57 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.21 g) and then 1,8-diazabicyclo[5.4.0]undec-7-ene (0.20 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.48 g, 76%).

$^1$H NMR (300 MHz, DMSO-$d_6$) δ0.92 (t, J=7.2 Hz, 3H), 1.04 (d, J=6.1 Hz, 3H), 1.24-1.75 (m, 6H), 2.02-2.16 (m, 2H), 2.28-2.47 (m, 2H), 2.90-2.98 (m, 2H), 3.17-3.26 (m, 1H), 3.29-3.47 (m, 2H), 3.60-3.78 (m, 1H), 3.93 (s, 2H), 4.51 (d,

J=4.5 Hz, 1H), 4.66 (br. s., 1H), 6.41 (d, J=1.9 Hz, 1H), 7.17-7.88 (m, 9H), 12.36 (s, 1H)

EXAMPLE 420

6-{[2'-(5-oxo-4,5-dihydro-1,2,4-oxadiazol-3-yl)biphenyl-4-yl]methyl}-4-[trans-4-(2-oxopropoxy)cyclohexyl]-7-propylpyrazolo[1,5-a]pyrimidin-5(4H)-one

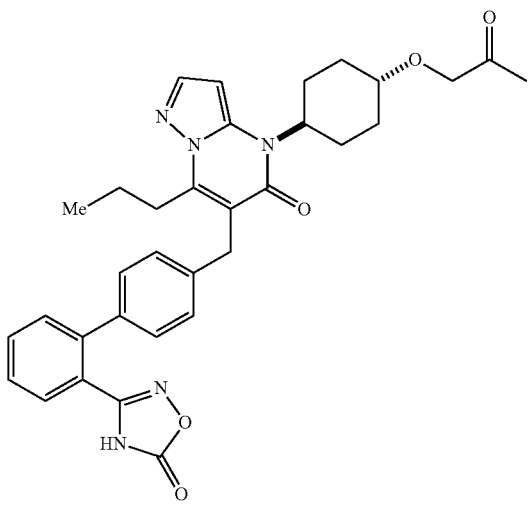

To a solution of 4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5 (4H)-one (0.38 g) in methylene chloride (3 mL) was added 1,1,1-tris(acetyloxy)-1,1-dihydro-1,2-benziodoxol-3-(1H)-one (0.55 g), and the mixture was stirred for 15 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.34 g, 90%).

$^1$H NMR (300 MHz, DMSO-d$_6$) δ0.92 (t, J=7.2 Hz, 3H), 1.28-1.76 (m, 6H), 2.02-2.17 (m, 5H), 2.29-2.48 (m, 2H), 2.88-3.01 (m, 2H), 3.44 (t, J=11.0 Hz, 1H), 3.93 (s, 2H), 4.14 (s, 2H), 4.65 (br. s., 1H), 6.41 (d, J=2.3 Hz, 1H), 7.19-7.88 (m, 9H), 12.36 (s, 1H)

EXAMPLE 421

4-[trans-4-(2-cyclopropyl-2-hydroxyethoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

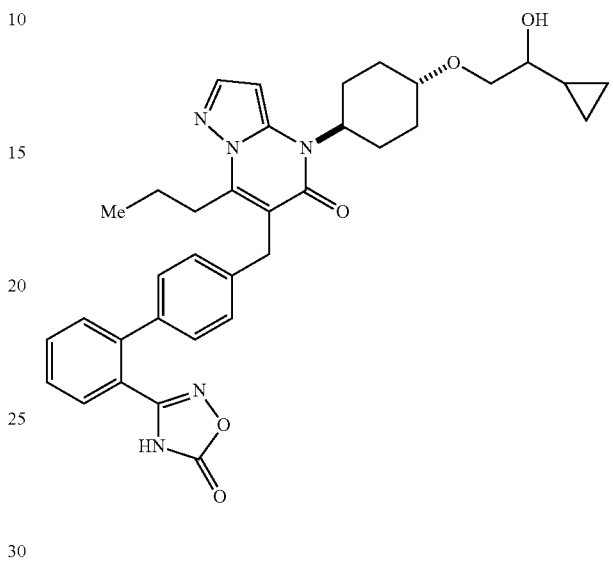

A mixture of hydroxylammonium chloride (0.68 g), sodium hydrogen carbonate (1.0 g) and dimethyl sulfoxide (4 mL) was stirred at 50° C. for 30 min, 4'-({4-[trans-4-(2-cyclopropyl-2-hydroxyethoxy)cyclohexyl]-5-oxo-7-propyl-4,5-dihydropyrazolo[1,5-a]pyrimidin-6-yl}methyl)biphenyl-2-carbonitrile (0.45 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (0.16 g) and then 1,8-diazabicyclo[5.4.0]undec-7-ene (0.15 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.40 g, 81%).

$^1$H NMR (300 MHz, DMSO-d$_6$) δ0.17-0.42 (m, 4H), 0.74-0.88 (m, 1H), 0.92 (t, J=7.3 Hz, 3H), 1.25-1.74 (m, 6H), 2.05-2.17 (m, 2H), 2.28-2.47 (m, 2H), 2.87-3.13 (m, 3H), 3.35-3.49 (m, 3H), 3.93 (s, 2H), 4.50 (d, J=4.9 Hz, 1H), 4.69 (br. s., 1H), 6.42 (d, J=2.1 Hz, 1H), 7.18-7.86 (m, 9H), 12.38 (s, 1H)

EXAMPLE 422

4-[trans-4-(2-hydroxy-3-methylbutoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

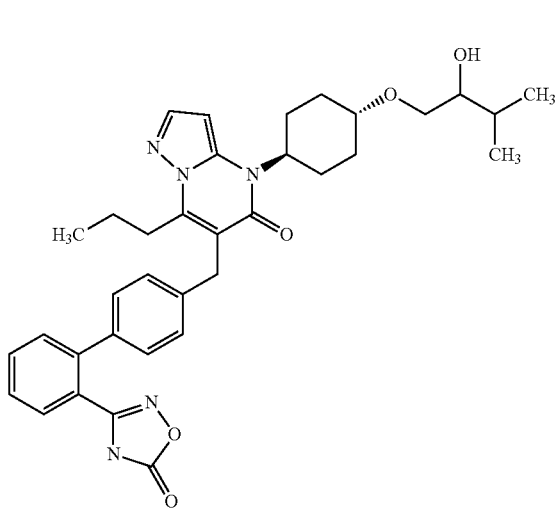 [SMILES: CCCc1c(Cc2ccc(-c3ccccc3-c3noc(=O)[nH]3)cc2)c(=O)n([C@H]2CC[C@H](OCC(O)C(C)C)CC2)c2ccnn12]

A mixture of hydroxylammonium chloride (0.47 g), sodium hydrogen carbonate (0.71 g) and dimethyl sulfoxide (3 mL) was stirred at 50° C. for 30 min, 4'-({4-[trans-4-(2-hydroxy-3-methylbutoxy)cyclohexyl]-5-oxo-7-propyl-4,5-dihydropyrazolo[1,5-a]pyrimidin-6-yl}methyl)biphenyl-2-carbonitrile (0.31 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.11 g) and then 1,8-diazabicyclo[5.4.0]undec-7-ene (0.10 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.29 g, 85%).

$^1$H NMR (300 MHz, DMSO-$d_6$) δ0.83 (d, J=6.8 Hz, 3H), 0.87 (d, J=7.0 Hz, 3H), 0.92 (t, J=7.3 Hz, 3H), 1.24-1.73 (m, 7H), 2.03-2.17 (m, 2H), 2.25-2.48 (m, 2H), 2.86-2.99 (m, 2H), 3.26-3.46 (m, 3H), 3.93 (s, 2H), 4.41 (d, J=4.5 Hz, 1H), 4.68 (br. s., 1H), 6.42 (d, J=2.1 Hz, 1H), 7.17-7.90 (m, 9H), 12.38 (br. s., 1H)

EXAMPLE 423

4-[trans-4-(2-cyclopropyl-2-oxoethoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

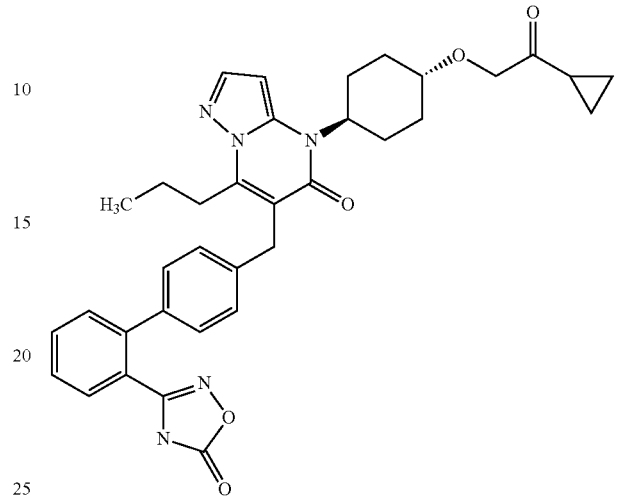

To a solution of 4-[trans-4-(2-cyclopropyl-2-hydroxyethoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.25 g) in methylene chloride (3 mL) was added 1,1,1-tris(acetyloxy)-1,1-dihydro-1,2-benziodoxol-3-(1H)-one (0.35 g), and the mixture was stirred for 2 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.21 g, 83%).

$^1$H NMR (300 MHz, DMSO-$d_6$) δ0.81-0.99 (m, 7H), 1.31-1.76 (m, 6H), 2.05-2.48 (m, 5H), 2.87-3.00 (m, 2H), 3.39-3.53 (m, 1H), 3.93 (s, 2H), 4.29 (s, 2H), 4.68 (br. s., 1H), 6.43 (d, J=2.3 Hz, 1H), 7.18-7.86 (m, 9H), 12.39 (br. s., 1H)

EXAMPLE 424

4-[trans-4-(3-methyl-2-oxobutoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

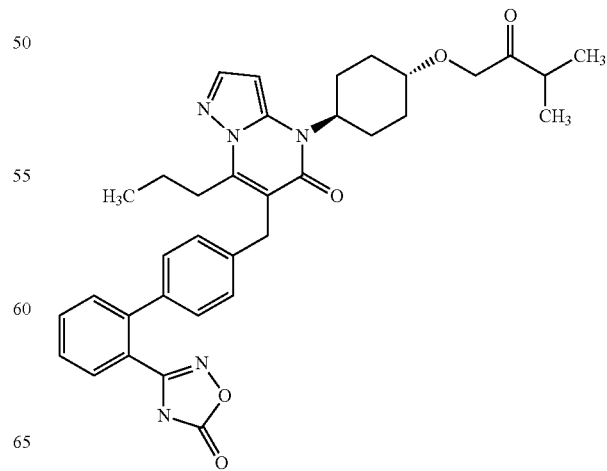

To a solution of 4-[trans-4-(2-hydroxy-3-methylbutoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.19 g) in methylene chloride (2 mL) was added 1,1,1-tris(acetyloxy)-1,1-dihydro-1,2-benziodoxol-3-(1H)-one (0.26 g), and the mixture was stirred for 2 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.047 g, 25%).

$^1$H NMR (300 MHz, DMSO-$d_6$) δ0.92 (t, J=7.3 Hz, 3H), 1.01 (d, J=6.8 Hz, 6H), 1.30-1.75 (m, 6H), 2.04-2.47 (m, 4H), 2.73 (spt, J=6.9 Hz, 1H), 2.89-2.99 (m, 2H), 3.38-3.48 (m, 1H), 3.93 (s, 2H), 4.26 (s, 2H), 4.67 (br. s., 1H), 6.42 (d, J=2.1 Hz, 1H), 7.06-7.93 (m, 9H), 12.38 (br. s., 1H)

EXAMPLE 425

4-(trans-4-{[(1R,2S)-2-hydroxy-2-methylcyclopropyl]oxy}cyclohexyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

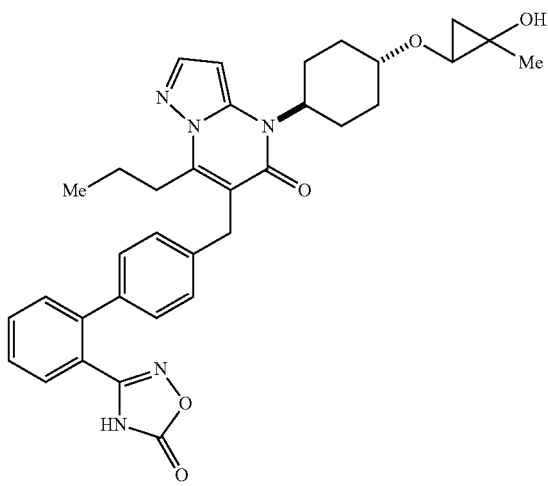

A mixture of hydroxylammonium chloride (0.56 g), sodium hydrogen carbonate (0.84 g) and dimethyl sulfoxide (3.5 mL) was stirred at 50° C. for 30 min, 4'-({4-[trans-4-({2-methyl-2-[(triethylsilyl)oxy]cyclopropyl}oxy)cyclohexyl]-5-oxo-7-propyl-4,5-dihydropyrazolo[1,5-a]pyrimidin-6-yl}methyl)biphenyl-2-carbonitrile (0.44 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.13 g) and then 1,8-diazabicyclo[5.4.0]undec-7-ene (0.12 mL) were added, and the mixture was stirred at room temperature for 1 hr. To the reaction mixture was added tetrabutylammonium fluoride (1 M tetrahydrofuran solution, 1.5 mL), and the mixture was stirred at 60° C. for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.11 g, 28%).

$^1$H NMR (300 MHz, DMSO-$d_6$) δ0.55 (d, J=5.7 Hz, 2H), 0.93 (t, J=7.3 Hz, 3H), 1.20 (s, 3H), 1.30-1.76 (m, 6H), 2.08-2.22 (m, 2H), 2.29-2.48 (m, 2H), 2.89-3.03 (m, 3H), 3.48-3.64 (m, 1H), 3.94 (s, 2H), 4.68 (br. s., 1H), 4.88 (s, 1H), 6.43 (d, J=2.1 Hz, 1H), 7.18-7.88 (m, 9H), 12.39 (br. s., 1H)

EXAMPLE 426

4-(trans-4-{[(1R,2R)-2-hydroxy-2-methylcyclopropyl]oxy}cyclohexyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

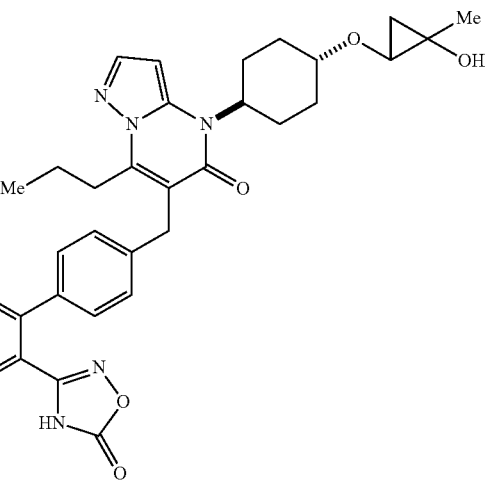

A mixture of hydroxylammonium chloride (0.56 g), sodium hydrogen carbonate (0.84 g) and dimethyl sulfoxide (3.5 mL) was stirred at 50° C. for 30 min, 4'-({4-[trans-4-({2-methyl-2-[(triethylsilyl)oxy]cyclopropyl}oxy)cyclohexyl]-5-oxo-7-propyl-4,5-dihydropyrazolo[1,5-a]pyrimidin-6-yl}methyl)biphenyl-2-carbonitrile (0.44 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.13 g) and then 1,8-diazabicyclo[5.4.0]undec-7-ene (0.12 mL) were added, and the mixture was stirred at room temperature for 1 hr. To the reaction mixture was added tetrabutylammonium fluoride (1 M tetrahydrofuran solution, 1.5 mL), and the mixture was stirred at 60° C. for 2 hr. The reaction mixture was diluted with ethyl acetate, washed with 1 M hydrochloric acid and then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.82 g, 20%).

$^1$H NMR (300 MHz, DMSO-$d_6$) δ0.92 (t, J=7.3 Hz, 3H), 1.18 (d, J=6.8 Hz, 2H), 1.28-1.73 (m, 6H), 2.01-2.19 (m, 5H), 2.26-2.48 (m, 2H), 2.91-3.01 (m, 2H), 3.37-3.55 (m, 2H), 3.93 (s, 2H), 3.98-4.07 (m, 1H), 4.72 (br. s., 1H), 6.44 (d, J=2.3 Hz, 1H), 7.17-7.87 (m, 9H), 12.40 (br. s., 1H)

EXAMPLE 427

4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

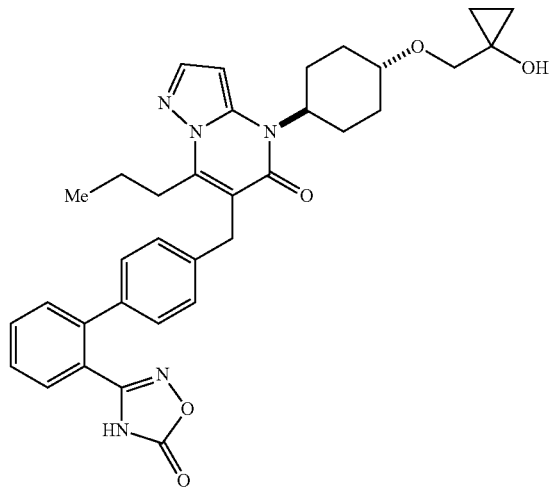

A mixture of hydroxylammonium chloride (0.83 g), sodium hydrogen carbonate (1.26 g) and dimethyl sulfoxide (5 mL) was stirred at 50° C. for 30 min, 4'-[(4-{trans-4-[(1-{[tert-butyl(dimethyl)silyl]oxy}cyclopropyl)methoxy]cyclohexyl}-5-oxo-7-propyl-4,5-dihydropyrazolo[1,5-a]pyrimidin-6-yl)methyl]biphenyl-2-carbonitrile (0.67 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.20 g) and then 1,8-diazabicyclo[5.4.0]undec-7-ene (0.18 mL) were added, and the mixture was stirred at room temperature for 1 hr. To the reaction mixture was added tetrabutylammonium fluoride (1 M tetrahydrofuran solution, 5 mL), and the mixture was stirred at 60° C. for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.27 g, 44%).

$^{1}$H NMR (300 MHz, DMSO-$d_6$) δ0.40-0.59 (m, 4H), 0.92 (t, J=7.2 Hz, 3H), 1.25-1.75 (m, 6H), 2.02-2.47 (m, 4H), 2.90-3.01 (m, 2H), 3.36-3.53 (m, 3H), 3.93 (s, 2H), 4.49-4.80 (m, 1H), 5.26 (s, 1H), 6.41 (d, J=2.3 Hz, 1H), 7.17-7.86 (m, 9H), 12.35 (s, 1H)

EXAMPLE 428

6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxypropoxy)cyclohexyl]pyrazolo[1,5-a]pyrimidin-5(4H)-one

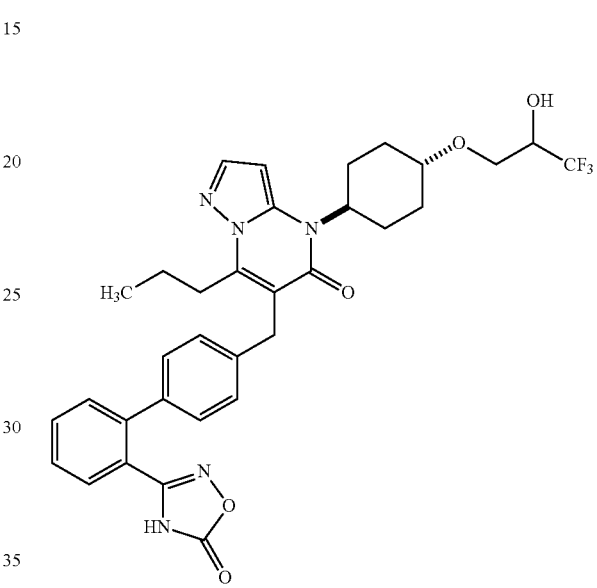

A mixture of hydroxylammonium chloride (0.97 g), sodium hydrogen carbonate (1.46 g) and dimethyl sulfoxide (6 mL) was stirred at 50° C. for 30 min, 4'-({5-oxo-7-propyl-4-[trans-4-(3,3,3-trifluoro-2-hydroxypropoxy)cyclohexyl]-4,5-dihydropyrazolo[1,5-a]pyrimidin-6-yl}methyl)biphenyl-2-carbonitrile (0.67 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (6 mL). N,N'-Carbonyldiimidazole (0.23 g) and then 1,8-diazabicyclo[5.4.0]undec-7-ene (0.21 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.53 g, 72%).

$^{1}$H NMR (300 MHz, DMSO-$d_6$) δ0.92 (t, J=7.4 Hz, 3H), 1.25-1.75 (m, 6H), 2.04-2.17 (m, 2H), 2.31-2.47 (m, 2H), 2.88-3.01 (m, 2H), 3.41-3.70 (m, 3H), 3.93 (s, 2H), 4.03-4.18

(m, 1H), 4.54-4.83 (m, 1H), 6.33 (d, J=6.4 Hz, 1H), 6.41 (d, J=2.3 Hz, 1H), 7.18-7.85 (m, 9H), 12.35 (s, 1H)

EXAMPLE 429 trans-4-[5-oxo-6-{[2'-(5-oxo-4,5-dihydro-1,2,4-oxadiazol-3-yl)biphenyl-4-yl]methyl}-7-propylpyrazolo[1,5-a]pyrimidin-4(5H)-yl]cyclohexyl 2-(acetyloxy)-2-methylpropanoate

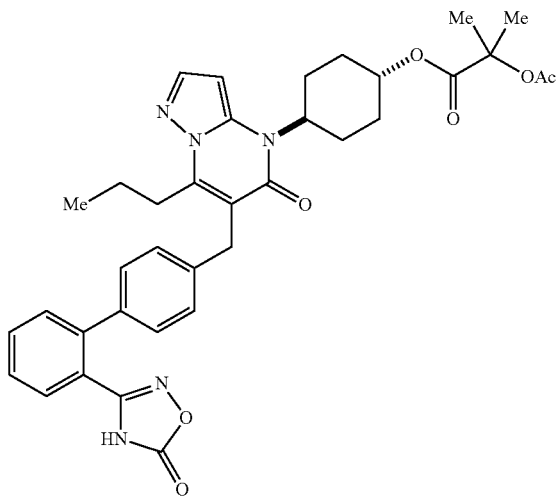

A mixture of hydroxylammonium chloride (0.66 g), sodium hydrogen carbonate (1.0 g) and dimethyl sulfoxide (4 mL) was stirred at 50° C. for 30 min, trans-4-{6-[(2'-cyanobiphenyl-4-yl)methyl]-5-oxo-7-propylpyrazolo[1,5-a]pyrimidin-4(5H)-yl}cyclohexyl 2-(acetyloxy)-2-methylpropanoate (0.67 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (0.15 g) and then 1,8-diazabicyclo[5.4.0]undec-7-ene (0.14 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.28 g, 55%).

$^1$H NMR (300 MHz, DMSO-d$_6$) δ0.92 (t, J=7.4 Hz, 3H), 1.41-1.77 (m, 12H), 1.92-2.04 (m, 5H), 2.37-2.57 (m, 2H), 2.88-3.00 (m, 2H), 3.94 (s, 2H), 4.59-4.92 (m, 2H), 6.52 (d, J=1.9 Hz, 1H), 7.17-7.88 (m, 9H), 12.40 (s, 1H)

EXAMPLE 430 trans-4-[5-oxo-6-{[2'-(5-oxo-4,5-dihydro-1,2,4-oxadiazol-3-yl)biphenyl-4-yl]methyl}-7-propylpyrazolo[1,5-a]pyrimidin-4(5H)-yl]cyclohexyl 2-hydroxy-2-methylpropanoate

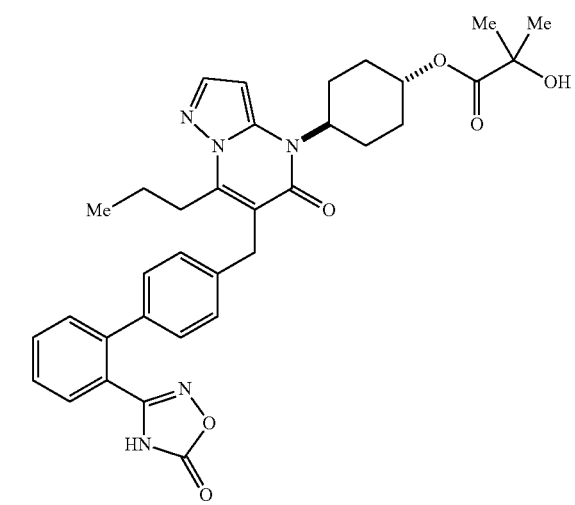

A mixture of hydroxylammonium chloride (0.66 g), sodium hydrogen carbonate (1.0 g) and dimethyl sulfoxide (4 mL) was stirred at 50° C. for 30 min, trans-4-{6-[(2'-cyanobiphenyl-4-yl)methyl]-5-oxo-7-propylpyrazolo[1,5-a]pyrimidin-4(5H)-yl}cyclohexyl 2-(acetyloxy)-2-methylpropanoate (0.67 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (0.15 g) and then 1,8-diazabicyclo[5.4.0]undec-7-ene (0.14 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.083 g, 17%).

¹H NMR (300 MHz, DMSO-d₆) δ0.92 (t, J=7.2 Hz, 3H), 1.29 (s, 6H), 1.43-1.78 (m, 6H), 1.97-2.07 (m, 2H), 2.39-2.57 (m, 2H), 2.90-3.01 (m, 2H), 3.94 (s, 2H), 4.55-4.95 (m, 2H), 5.23 (s, 1H), 6.52 (d, J=2.3 Hz, 1H), 7.16-7.88 (m, 9H), 12.36 (s, 1H)

EXAMPLE 431

6-{[2'-(5-oxo-4,5-dihydro-1,2,4-oxadiazol-3-yl)biphenyl-4-yl]methyl}-7-propyl-4-[trans-4-(3,3,3-trifluoro-2-oxopropoxy)cyclohexyl]pyrazolo[1,5-a]pyrimidin-5(4H)-one

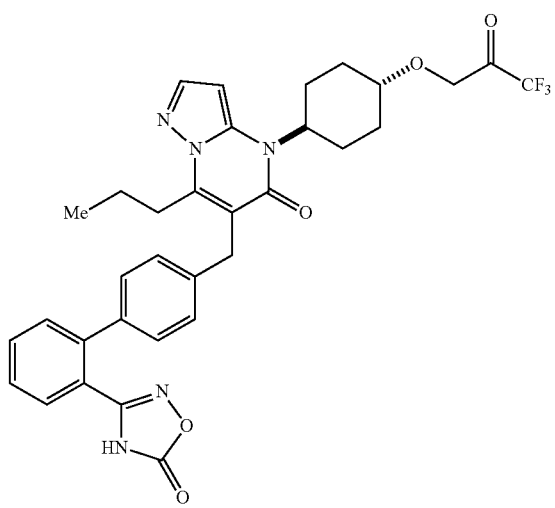

To a solution of 6-{[2'-(5-oxo-4,5-dihydro-1,2,4-oxadiazol-3-yl)biphenyl-4-yl]methyl}-7-propyl-4-[trans-4-(3,3,3-trifluoro-2-hydroxypropoxy)cyclohexyl]pyrazolo[1,5-a]pyrimidin-5(4H)-one (0.14 g) in methylene chloride (2 mL) was added 1,1,1-tris(acetyloxy)-1,1-dihydro-1,2-benziodoxol-3-(1H)-one (0.14 g), and the mixture was stirred for 3 hr. Ethyl acetate, water and sodium thiosulfate were added to the reaction mixture, and the mixture was stirred for 30 min. After stirring, the mixture was extracted with ethyl acetate. The organic layer was washed with saturated brine, dried over anhydrous magnesium sulfate, and the solvent was evaporated. The residue was purified by silica gel column chromatography to give the title compound as a colorless amorphous solid (0.098 g, 73%).

¹H NMR (300 MHz, DMSO-d₆) δ0.92 (t, J=7.4 Hz, 3H), 1.27-1.79 (m, 6H), 2.03-2.49 (m, 4H), 2.90-3.00 (m, 2H), 3.41-3.54 (m, 1H), 3.94 (s, 2H), 4.48-4.85 (m, 1H), 6.41 (d, J=2.3 Hz, 1H), 6.88 (s, 2H), 7.18-7.87 (m, 9H), 12.36 (s, 1H)

EXAMPLE 432

4-[trans-4-(2-cyclopropyl-2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

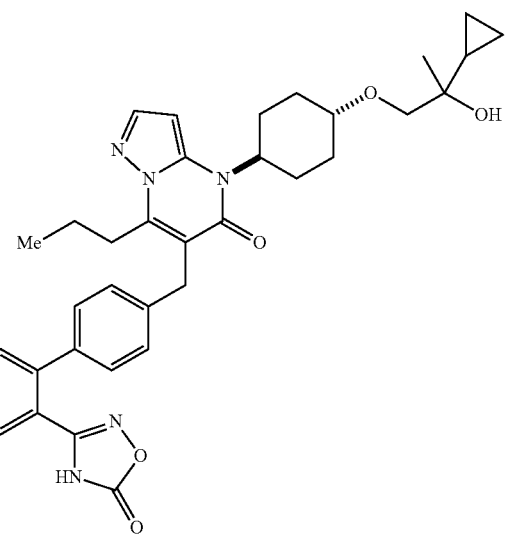

A mixture of hydroxylammonium chloride (0.33 g), sodium hydrogen carbonate (0.49 g) and dimethyl sulfoxide (2 mL) was stirred at 50° C. for 30 min, 4'-({4-[trans-4-(2-cyclopropyl-2-hydroxypropoxy)cyclohexyl]-5-oxo-7-propyl-4,5-dihydropyrazolo[1,5-a]pyrimidin-6-yl}methyl)biphenyl-2-carbonitrile (0.22 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (0.076 g) and then with 1,8-diazabicyclo[5.4.0]undec-7-ene (0.070 mL) was added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.13 g, 52%).

¹H NMR (300 MHz, DMSO-d₆) δ0.10-0.40 (m, 4H), 0.82-0.98 (m, 4H), 1.08 (s, 3H), 1.26-1.76 (m, 6H), 2.01-2.47 (m, 4H), 2.87-3.01 (m, 2H), 3.21-3.49 (m, 3H), 3.86-3.97 (m, 3H), 4.47-4.91 (m, 1H), 6.41 (s, 1H), 7.13-7.89 (m, 9H), 12.34 (br. s., 1H)

EXAMPLE 433

4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

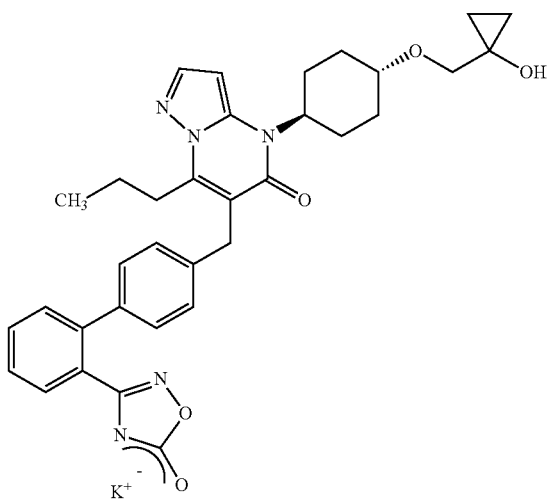 [SMILES: CCCc1c(Cc2ccc(-c3ccccc3C3=NOC(O)N3)cc2)c(=O)n([C@H]2CC[C@H](OCC3(O)CC3)CC2)c2ccnn12 ; [K+]]

To a solution (2 mL) of 4-{trans-4-[(1-hydroxycyclopropyl)methoxy]cyclohexyl}-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.21 g) in ethanol was added 8M aqueous potassium hydroxide solution (0.043 mL), and the mixture was stirred at room temperature for 1 hr. The reaction mixture was concentrated under reduced pressure, and the residue was solidified with diisopropyl ether to give the title compound as a colorless amorphous solid (0.20 g, 89%).

$^1$H NMR (300 MHz, DMSO-$d_6$) δ 0.42-0.59 (m, 4H), 0.95 (t, J=7.3 Hz, 3H), 1.23-1.73 (m, 6H), 2.04-2.47 (m, 4H), 2.90-3.00 (m, 2H), 3.36-3.53 (m, 3H), 3.88 (s, 2H), 4.54-4.84 (m, 1H), 5.26 (s, 1H), 6.38 (d, J=2.1 Hz, 1H), 7.11-7.51 (m, 8H), 7.81 (d, J=2.1 Hz, 1H)

EXAMPLE 434

7-butyl-4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}pyrazolo[1,5-a]pyrimidin-5(4H)-one

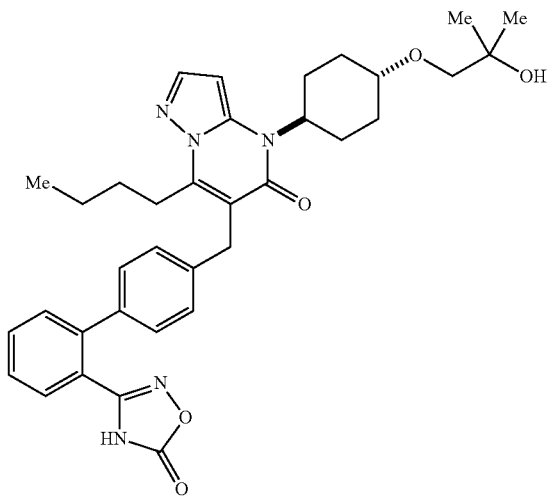

A mixture of hydroxylammonium chloride (0.49 g), sodium hydrogen carbonate (0.74 g) and dimethyl sulfoxide (3 mL) was stirred at 50° C. for 30 min, 4'-({7-butyl-4-[trans-4-(2-hydroxy-2-methylpropoxy)cyclohexyl]-5-oxo-4,5-dihydropyrazolo[1,5-a]pyrimidin-6-yl}methyl)biphenyl-2-carbonitrile (0.31 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.12 g) and then 1,8-diazabicyclo[5.4.0]undec-7-ene (0.11 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.27 g, 75%).

$^1$H NMR (300 MHz, DMSO-$d_6$) δ 0.79-0.89 (m, 3H), 1.07 (s, 6H), 1.26-1.53 (m, 6H), 1.62-1.72 (m, 2H), 2.02-2.15 (m, 2H), 2.29-2.46 (m, 2H), 2.92-3.02 (m, 2H), 3.20 (s, 2H), 3.34-3.46 (m, 1H), 3.93 (s, 2H), 4.25 (s, 1H), 4.67 (br. s., 1H), 6.42 (d, J=2.3 Hz, 1H), 7.17-7.87 (m, 9H), 12.38 (s, 1H)

EXAMPLE 435

6-{[3-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propylpyrazolo[1,5-a]pyrimidin-5(4H)-one

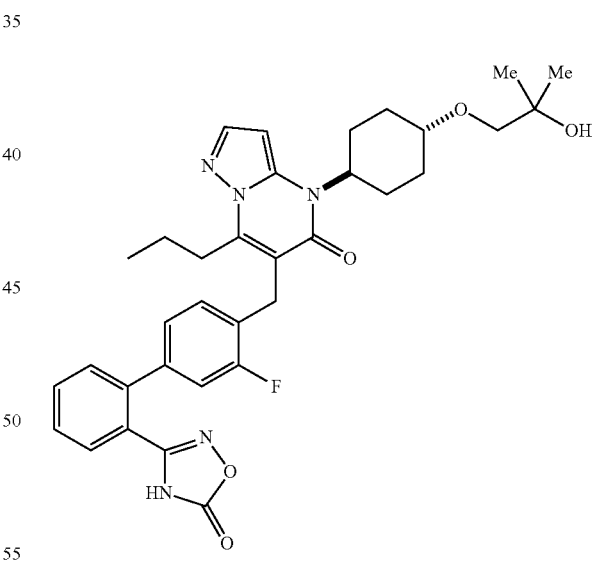

A mixture of hydroxylammonium chloride (0.39 g), sodium hydrogen carbonate (0.59 g) and dimethyl sulfoxide (2.5 mL) was stirred at 50° C. for 30 min, 3'-fluoro-4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile (0.22 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL).

N,N'-Carbonyldiimidazole (0.091 g) and then 1,8-diazabicyclo[5.4.0]undec-7-ene (0.084 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.23 g, 78%).

$^1$H NMR (300 MHz, DMSO-d$_6$) δ0.92 (t, J=7.4 Hz, 3H), 1.07 (s, 6H), 1.26-1.73 (m, 6H), 2.03-2.14 (m, 2H), 2.24-2.46 (m, 2H), 2.90-2.99 (m, 2H), 3.19 (s, 2H), 3.34-3.45 (m, 1H), 3.92 (s, 2H), 4.24 (s, 1H), 4.64 (br. s., 1H), 6.43 (d, J=2.3 Hz, 1H), 6.93-7.86 (m, 8H), 12.44 (s, 1H)

EXAMPLE 436

7-butyl-4-[trans-4-(2-hydroxypropoxy)cyclohexyl]-6-{[2'-(5-oxo-4,5-dihydro-1,2,4-oxadiazol-3-yl)biphenyl-4-yl]methyl}pyrazolo[1,5-a]pyrimidin-5(4H)-one

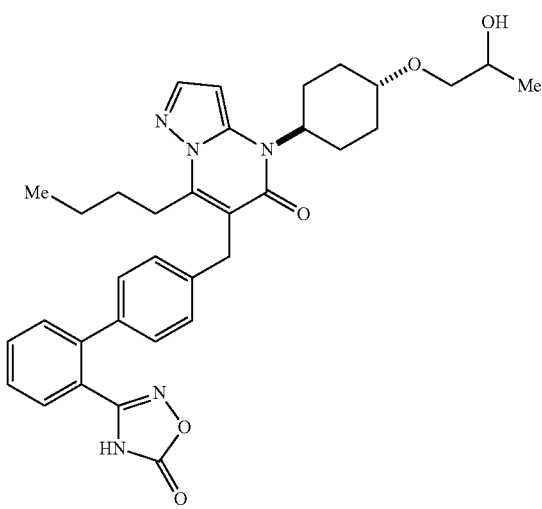

A mixture of hydroxylammonium chloride (0.43 g), sodium hydrogen carbonate (0.66 g) and dimethyl sulfoxide (3 mL) was stirred at 50° C. for 30 min, 4'-({7-butyl-4-[trans-4-(2-hydroxypropoxy)cyclohexyl]-5-oxo-4,5-dihydropyrazolo[1,5-a]pyrimidin-6-yl}methyl)biphenyl-2-carbonitrile (0.27 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.10 g) and then 1,8-diazabicyclo[5.4.0]undec-7-ene (0.090 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.22 g, 70%).

$^1$H NMR (300 MHz, DMSO-d$_6$) δ0.80-0.88 (m, 3H), 1.04 (d, J=6.4 Hz, 3H), 1.25-1.52 (m, 6H), 1.60-1.74 (m, 2H), 2.03-2.16 (m, 2H), 2.28-2.47 (m, 2H), 2.90-3.02 (m, 2H), 3.17-3.25 (m, 1H), 3.30-3.47 (m, 2H), 3.62-3.76 (m, 1H), 3.93 (s, 2H), 4.48-4.82 (m, 2H), 6.42 (d, J=1.9 Hz, 1H), 7.17-7.86 (m, 9H), 12.38 (s, 1H)

EXAMPLE 437

6-{[3-fluoro-2'-(5-oxo-4,5-dihydro-1,2,4-oxadiazol-3-yl)biphenyl-4-yl]methyl}-4-[trans-4-(2-hydroxypropoxy)cyclohexyl]-7-propylpyrazolo[1,5-a]pyrimidin-5(4H)-one

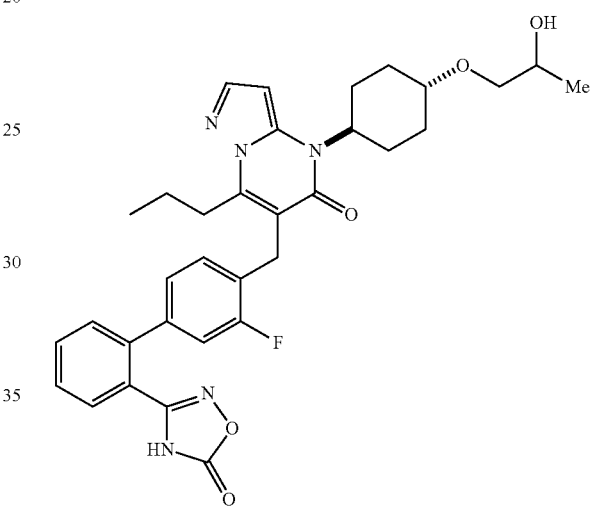

A mixture of hydroxylammonium chloride (0.43 g), sodium hydrogen carbonate (0.66 g) and dimethyl sulfoxide (3 mL) was stirred at 50° C. for 30 min, 3'-fluoro-4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (0.27 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.10 g) and then 1,8-diazabicyclo[5.4.0]undec-7-ene (0.090 mL) were added, and the mixture was stirred at room temperature for 2 hr. The reaction mixture was diluted with ethyl acetate, washed with 1 M hydrochloric acid and then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.21 g, 68%).

$^1$H NMR (300 MHz, DMSO-d$_6$) δ0.92 (t, J=7.4 Hz, 3H), 1.03 (d, J=6.1 Hz, 3H), 1.25-1.74 (m, 6H), 2.02-2.46 (m, 4H), 2.90-3.00 (m, 2H), 3.17-3.45 (m, 3H), 3.62-3.76 (m, 1H), 3.92 (s, 2H), 4.46-4.85 (m, 2H), 6.43 (d, J=2.3 Hz, 1H), 6.95-7.89 (m, 8H), 12.44 (s, 1H)

EXAMPLE 438

7-butyl-4-[trans-4-(2-hydroxy-2-methylpropoxy)cyclohexyl]-6-{[2'-(1H-tetrazol-5-yl)biphenyl-4-yl]methyl}pyrazolo[1,5-a]pyrimidin-5(4H)-one

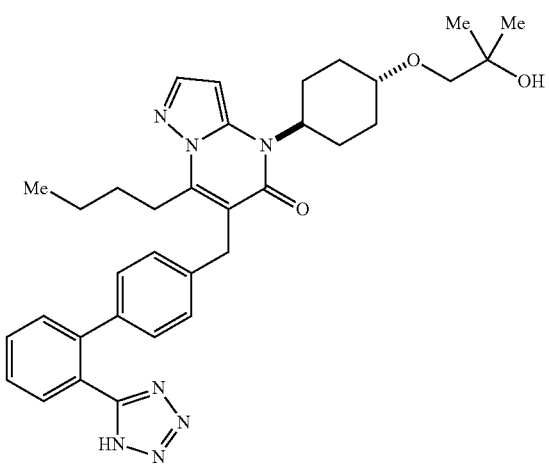

A mixture of 4'-({7-butyl-4-[trans-4-(2-hydroxy-2-methylpropoxy)cyclohexyl]-5-oxo-4,5-dihydropyrazolo[1,5-a]pyrimidin-6-yl}methyl)biphenyl-2-carbonitrile (0.27 g), trimethylsilylazide (0.66 mL), dibutyltinoxide (0.060 g) and toluene (3 mL) was stirred at 100° C. for 20 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was dissolved in tetrahydrofuran (3 mL). Tetrabutylammonium fluoride (1.0 M tetrahydrofuran solution, 0.75 mL) was added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.13 g, 46%).

$^1$H NMR (300 MHz, DMSO-$d_6$) δ0.77-0.86 (m, 3H), 1.07 (s, 6H), 1.26-1.73 (m, 8H), 2.03-2.46 (m, 4H), 2.87-2.97 (m, 2H), 3.20 (s, 2H), 3.35-3.46 (m, 1H), 3.87 (s, 2H), 4.24 (s, 1H), 4.67 (br. s., 1H), 6.40 (d, J=2.1 Hz, 1H), 6.94-7.86 (m, 10H)

EXAMPLE 439

6-{[3-fluoro-2'-(1H-tetrazol-5-yl)biphenyl-4-yl]methyl}-4-[trans-4-(2-hydroxy-2-methylpropoxy)cyclohexyl]-7-propylpyrazolo[1,5-a]pyrimidin-5(4H)-one

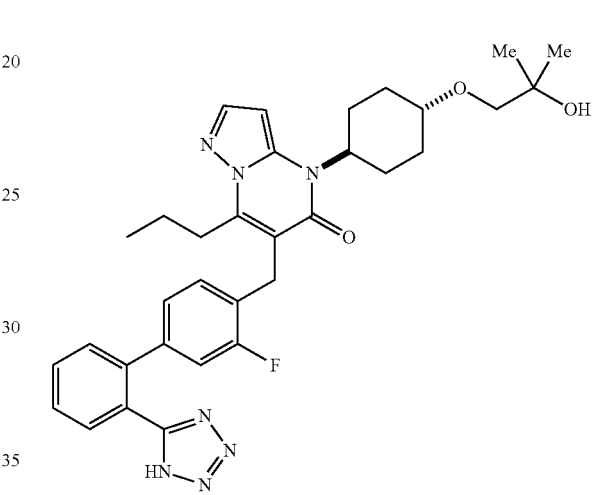

A mixture of 3'-fluoro-4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile (0.26 g), trimethylsilylazide (0.66 mL), dibutyltinoxide (0.060 g) and toluene (3 mL) was stirred at 100° C. for 20 hr. Ethyl acetate and water were added to the reaction mixture, and the mixture was extracted with ethyl acetate. The organic layer was washed with water and then with saturated brine, and dried over anhydrous magnesium sulfate. The solvent was evaporated under reduced pressure, and the residue was dissolved in tetrahydrofuran (3 mL). Tetrabutylammonium fluoride (1.0 M tetrahydrofuran solution, 0.9 mL) was added, and the mixture was stirred at room temperature for 15 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.13 g, 46%).

$^1$H NMR (300 MHz, DMSO-$d_6$) δ0.91 (t, J=7.3 Hz, 3H), 1.07 (s, 6H), 1.26-1.70 (m, 6H), 2.02-2.44 (m, 4H), 2.84-2.96

(m, 2H), 3.19 (s, 2H), 3.35-3.46 (m, 1H), 3.87 (s, 2H), 4.23 (s, 1H), 4.65 (br. s., 1H), 6.42 (d, J=2.1 Hz, 1H), 6.73-7.85 (m, 9H)

EXAMPLE 440

4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (optically active form, retention time: short)

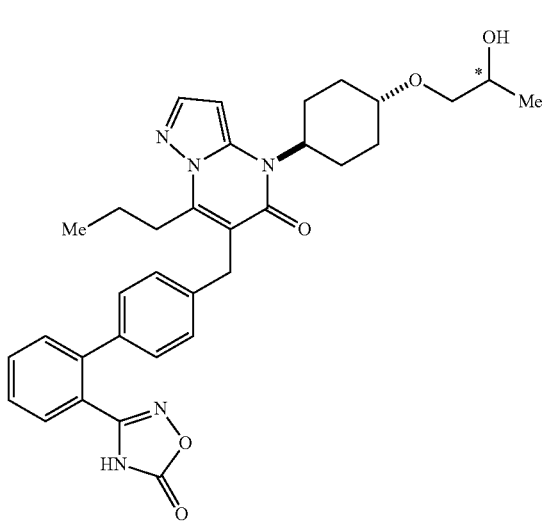

A mixture of hydroxylammonium chloride (0.69 g), sodium hydrogen carbonate (1.1 g) and dimethyl sulfoxide (4 mL) was stirred at 50° C. for 30 min, 4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (optically active form, retention time: short, 98.8% ee, 0.42 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (0.16 g) and then 1,8-diazabicyclo[5.4.0]undec-7-ene (0.15 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.24 g, 51%).

$^1$H NMR (300 MHz, DMSO-$d_6$) δ0.92 (t, J=7.3 Hz, 3H), 1.04 (d, J=6.4 Hz, 3H), 1.23-1.75 (m, 6H), 2.02-2.47 (m, 4H), 2.88-3.47 (m, 5H), 3.59-3.78 (m, 1H), 3.93 (s, 2H), 4.52 (d, J=4.7 Hz, 1H), 4.68 (br. s., 1H), 6.41 (d, J=2.1 Hz, 1H), 7.18-7.86 (m, 9H), 12.36 (s, 1H)

HPLC (CHIRALPAK AD-H, CO$_2$/MeOH=750/250, 2.35 mL/min), 2.80 min, 98.8% ee

EXAMPLE 441

4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (optically active form, retention time: long)

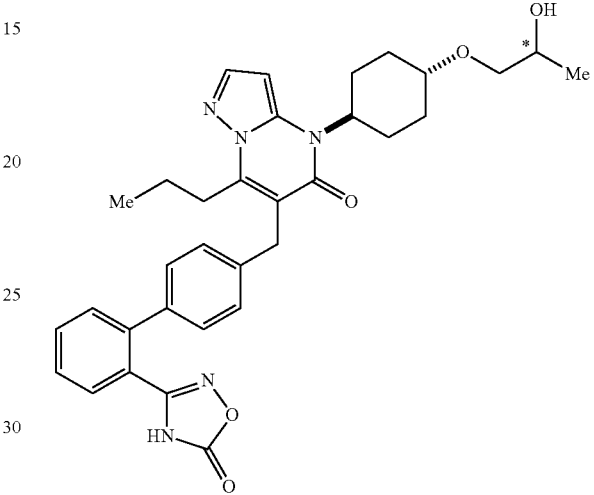

A mixture of hydroxylammonium chloride (0.69 g), sodium hydrogen carbonate (1.1 g) and dimethyl sulfoxide (4 mL) was stirred at 50° C. for 30 min, 4'-({4-[trans-4-(2-hydroxypropoxy)cyclohexyl]-5-oxo-7-propyl-4,5-dihydropyrazolo[1,5-a]pyrimidin-6-yl}methyl)biphenyl-2-carbonitrile (optically active form, retention time: long, 99.3% ee, 0.42 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (4 mL). N,N'-Carbonyldiimidazole (0.16 g) and then 1,8-diazabicyclo[5.4.0]undec-7-ene (0.15 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.32 g, 66%).

$^1$H NMR (300 MHz, DMSO-$d_6$) δ0.92 (t, J=7.3 Hz, 3H), 1.04 (d, J=6.4 Hz, 3H), 1.23-1.75 (m, 6H), 2.02-2.47 (m, 4H), 2.88-3.47 (m, 5H), 3.59-3.78 (m, 1H), 3.93 (s, 2H), 4.52 (d, J=4.7 Hz, 1H), 4.68 (br. s., 1H), 6.41 (d, J=2.1 Hz, 1H), 7.18-7.86 (m, 9H), 12.36 (s, 1H)

EXAMPLE 442

3-fluoro-4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

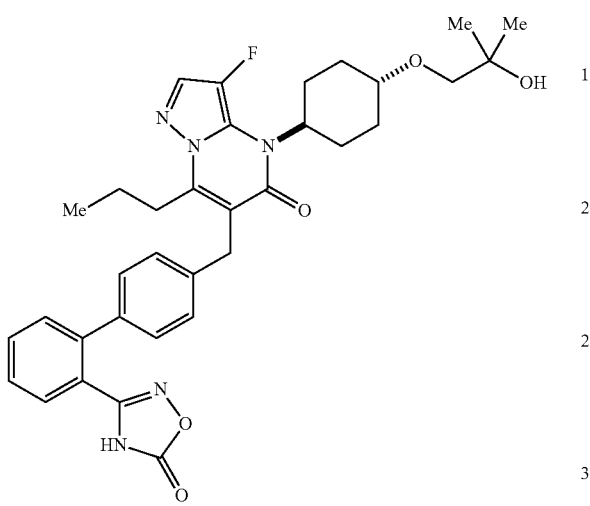

To a solution of ethyl [(trans-4-{6-[(2'-cyanobiphenyl-4-yl)methyl]-3-fluoro-5-oxo-7-propylpyrazolo[1,5-a]pyrimidin-4(5H)-yl}cyclohexyl)oxy]acetate (0.087 g) in tetrahydrofuran (1.5 mL) was added dropwise methylmagnesium bromide (1 M tetrahydrofuran solution, 0.5 mL) at 0° C., and the mixture was stirred for 3 hr. To the reaction mixture were added ethyl acetate and then saturated aqueous ammonium chloride solution. The mixture was extracted with ethyl acetate, and the organic layer was washed with saturated brine, dried over anhydrous magnesium sulfate, and concentrated. The residue was dissolved in dimethyl sulfoxide (1 mL), hydroxylammonium chloride (0.11 g) and sodium hydrogen carbonate (0.17 g) were added and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (0.042 g) and then 1,8-diazabicyclo[5.4.0]undec-7-ene (0.039 mL) were added, and the mixture was stirred at room temperature for 3 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.037 g, 47%).

HPLC (CHIRALPAK AD-H, $CO_2$/MeOH=750/250, 2.35 mL/min), 3.12 min, 93.3% ee $^1$H NMR (300 MHz, DMSO-$d_6$) δ 0.91 (t, J=7.3 Hz, 3H), 1.06 (s, 6H), 1.21-1.54 (m, 4H), 1.72-1.85 (m, 2H), 2.06-2.30 (m, 4H), 2.87-2.98 (m, 2H), 3.19 (s, 2H), 3.21-3.28 (m, 1H), 3.93 (s, 2H), 4.23 (s, 1H), 4.75 (br. s., 1H), 7.15-8.14 (m, 9H), 12.37 (br. s., 1H)

EXAMPLE 443

7-butyl-4-[trans-4-(2-hydroxy-2-methylpropoxy)cyclohexyl]-6-({6-[2-(5-oxo-4,5-dihydro-1,2,4-oxadiazol-3-yl)phenyl]pyridin-3-yl}methyl)pyrazolo[1,5-a]pyrimidin-5(4H)-one

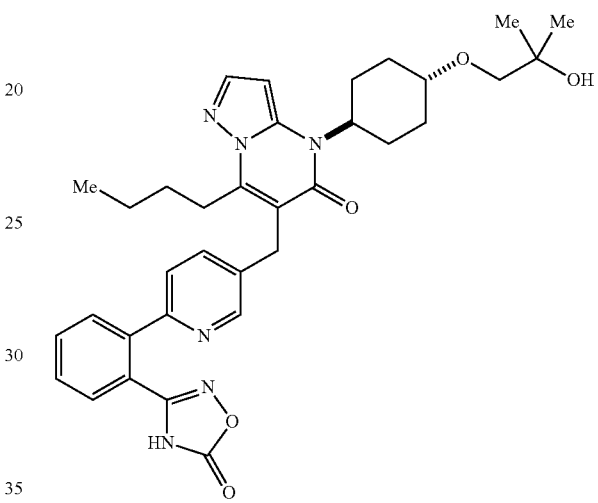

A mixture of hydroxylammonium chloride (0.35 g), sodium hydrogen carbonate (0.53 g) and dimethyl sulfoxide (2 mL) was stirred at 50° C. for 30 min, 2-[5-({7-butyl-4-[trans-4-(2-hydroxy-2-methylpropoxy)cyclohexyl]-5-oxo-4,5-dihydropyrazolo[1,5-a]pyrimidin-6-yl}methyl)pyridin-2-yl]benzonitrile (0.17 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.082 g) and then 1,8-diazabicyclo[5.4.0]undec-7-ene (0.075 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.098 g, 53%).

$^1$H NMR (300 MHz, DMSO-$d_6$) δ 0.81-0.89 (m, 3H), 1.07 (s, 6H), 1.26-1.73 (m, 8H), 2.03-2.45 (m, 4H), 2.96-3.04 (m, 2H), 3.19 (s, 2H), 3.35-3.46 (m, 1H), 3.94 (s, 2H), 4.25 (s,

1H), 4.66 (br. s., 1H), 6.42 (d, J=2.3 Hz, 1H), 7.53-7.87 (m, 7H), 8.49 (d, J=1.7 Hz, 1H), 12.35 (br. s., 1H)

EXAMPLE 444

6-{[2-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]-7-propylpyrazolo[1,5-a]pyrimidin-5(4H)-one

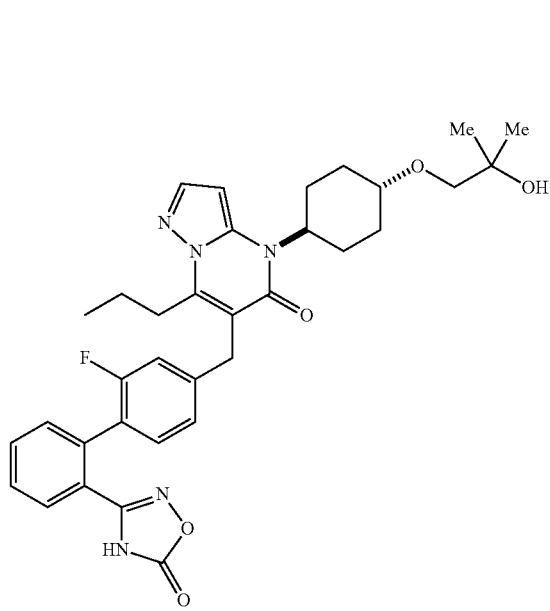

A mixture of hydroxylammonium chloride (0.35 g), sodium hydrogen carbonate (0.53 g) and dimethyl sulfoxide (2 mL) was stirred at 50° C. for 30 min, 2'-fluoro-4'-({4-[trans-4-(2-hydroxy-2-methylpropoxy)cyclohexyl]-5-oxo-7-propyl-4,5-dihydropyrazolo[1,5-a]pyrimidin-6-yl}methyl)biphenyl-2-carbonitrile (0.23 g) was added, and the mixture was stirred at 90° C. for 3 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (0.082 g) and then 1,8-diazabicyclo[5.4.0]undec-7-ene (0.075 mL) were added, and the mixture was stirred at room temperature for 2 hr. The reaction mixture was diluted with ethyl acetate, and washed with 1 M hydrochloric acid and then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.14 g, 56%).

$^1$H NMR (300 MHz, DMSO-d$_6$) δ0.93 (t, J=7.3 Hz, 3H), 1.07 (s, 6H), 1.29-1.75 (m, 6H), 2.04-2.43 (m, 4H), 2.91-3.00 (m, 2H), 3.20 (s, 2H), 3.36-3.46 (m, 1H), 3.95 (s, 2H), 4.25 (s, 1H), 4.45-4.93 (m, 1H), 6.42 (d, J=2.3 Hz, 1H), 7.07-7.87 (m, 8H), 12.59 (s, 1H)

EXAMPLE 445

4-[trans-4-(2-hydroxy-2-methylpropoxy)cyclohexyl]-6-{[2-methyl-2'-(5-oxo-4,5-dihydro-1,2,4-oxadiazol-3-yl)biphenyl-4-yl]methyl}-7-propylpyrazolo[1,5-a]pyrimidin-5(4H)-one

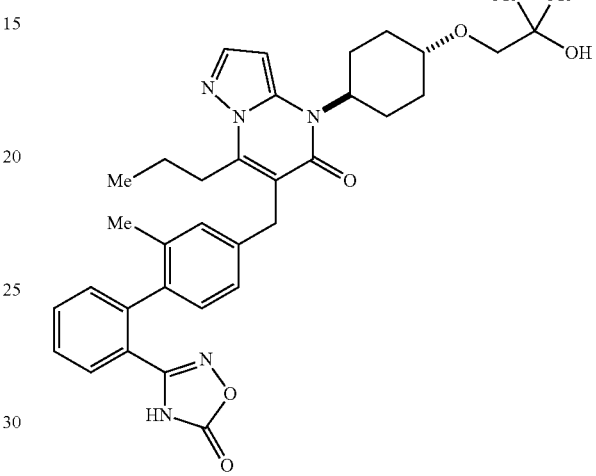

To a solution of 4'-{[4-(trans-4-hydroxycyclohexyl)-5-oxo-7-propyl-4,5-dihydropyrazolo[1,5-a]pyrimidin-6-yl]methyl}-2'-methylbiphenyl-2-carbonitrile (0.88 g) and rhodium acetate (dimer, 0.080 g) in toluene (10 mL) was added dropwise ethyl diazoacetate (0.95 mL) at 80° C., and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was crudely purified by silica gel column chromatography. This was dissolved in tetrahydrofuran (2 mL), methylmagnesium bromide (1.4 M tetrahydrofuran solution, 1.6 mL) was added dropwise thereto at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. This was dissolved in dimethyl sulfoxide (3 mL), hydroxylammonium chloride (0.41 g) and sodium hydrogen carbonate (0.62 g) were added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.096 g) and then 1,8-diazabicyclo[5.4.0]undec-7-ene (0.088 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.084 g, 28%).

$^1$H NMR (300 MHz, DMSO-d$_6$) δ0.91 (t, J=7.2 Hz, 3H), 1.08 (s, 6H), 1.26-1.75 (m, 6H), 1.98 (s, 3H), 2.03-2.47 (m, 4H), 2.93 (t, J=7.8 Hz, 2H), 3.20 (s, 2H), 3.35-3.46 (m, 1H), 3.89 (s, 2H), 4.25 (s, 1H), 4.67 (br. s., 1H), 6.41 (d, J=2.3 Hz, 1H), 6.89-7.85 (m, 8H), 12.39 (s, 1H)

EXAMPLE 446

4-[trans-4-(2-hydroxy-2-methylpropoxy)cyclohexyl]-6-{1-[2'-(5-oxo-4,5-dihydro-1,2,4-oxadiazol-3-yl)biphenyl-4-yl]ethyl}-7-propylpyrazolo[1,5-a]pyrimidin-5(4H)-one

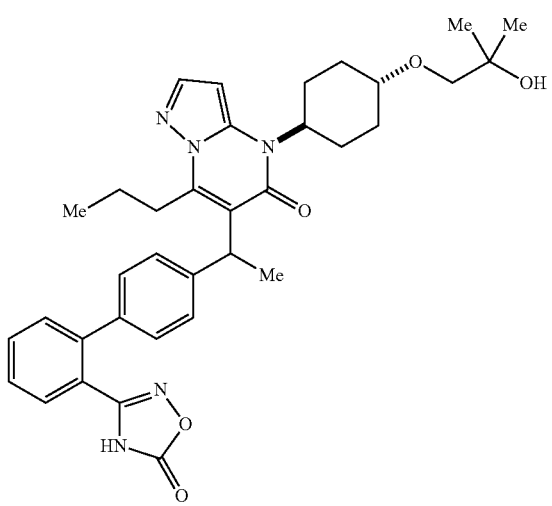

To a solution of 4'-{1-[4-(trans-4-hydroxycyclohexyl)-5-oxo-7-propyl-4,5-dihydropyrazolo[1,5-a]pyrimidin-6-yl]ethyl}biphenyl-2-carbonitrile (0.33 g) and rhodium acetate (dimer, 0.030 g) in toluene (4 mL) was added dropwise ethyldiazoacetate (0.36 mL) at 80° C., and the mixture was stirred for 3 hr. Ethyl acetate and water were added to the reaction mixture, and the mixture was extracted with ethyl acetate. The organic layer was washed with water and then with saturated brine, dried over anhydrous magnesium sulfate, and concentrated. The residue was crudely purified by silica gel column chromatography. This was dissolved in tetrahydrofuran (2 mL), methylmagnesium bromide (1.4 M tetrahydrofuran solution, 0.62 mL) was added dropwise at 0° C., and the mixture was stirred for 2 hr. To the reaction mixture were added ethyl acetate and then saturated aqueous ammonium chloride solution, and the mixture was extracted with ethyl acetate. The organic layer was washed with saturated brine, dried over anhydrous magnesium sulfate, and concentrated. This was dissolved in dimethyl sulfoxide (1 mL), hydroxylammonium chloride (0.17 g) and sodium hydrogen carbonate (0.25 g) were added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (1 mL). N,N'-Carbonyldiimidazole (0.036 g) and then 1,8-diazabicyclo[5.4.0]undec-7-ene (0.033 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.038 g, 34%).

$^1$H NMR (300 MHz, DMSO-d$_6$) δ0.91 (t, J=7.2 Hz, 3H), 1.08 (s, 6H), 1.26-1.75 (m, 6H), 1.98 (s, 3H), 2.03-2.47 (m, 4H), 2.93 (t, J=7.8 Hz, 2H), 3.20 (s, 2H), 3.35-3.46 (m, 1H), 3.89 (s, 2H), 4.25 (s, 1H), 4.67 (br. s., 1H), 6.41 (d, J=2.3 Hz, 1H), 6.89-7.85 (m, 8H), 12.39 (s, 1H)

EXAMPLE 447

4-(1,4-dioxaspiro[4.5]dec-8-yl)-6-{[2-nitro-2'-(5-oxo-4,5-dihydro-1,2,4-oxadiazol-3-yl)biphenyl-4-yl]methyl}-7-propylpyrazolo[1,5-a]pyrimidin-5(4H)-one

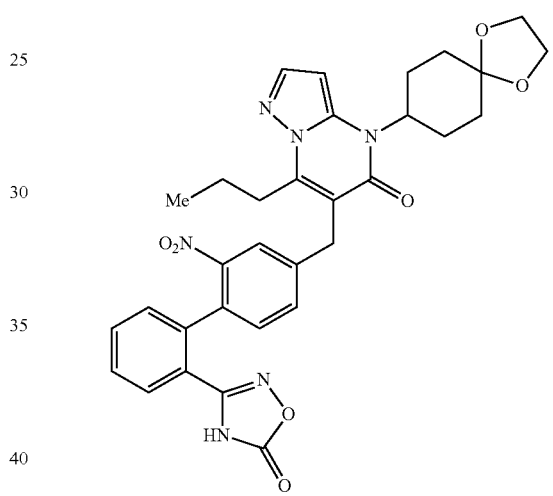

A mixture of hydroxylammonium chloride (0.45 g), sodium hydrogen carbonate (0.68 g) and dimethyl sulfoxide (3 mL) was stirred at 50° C. for 30 min, 4'-{[4-(1,4-dioxaspiro[4.5]dec-8-yl)-5-oxo-7-propyl-4,5-dihydropyrazolo[1,5-a]pyrimidin-6-yl]methyl}-2'-nitrobiphenyl-2-carbonitrile (0.30 g) was added, and the mixture was stirred at 90° C. for 3 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.105 g) and then 1,8-diazabicyclo[5.4.0]undec-7-ene (0.097 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a colorless amorphous solid (0.15 g, 44%).

$^1$H NMR (300 MHz, DMSO-d$_6$) δ0.94 (t, J=7.3 Hz, 3H), 1.43-1.85 (m, 8H), 2.54-2.66 (m, 2H), 2.95-3.07 (m, 2H), 3.85-3.97 (m, 4H), 4.06 (s, 2H), 4.80 (br. s., 1H), 6.25 (d, J=1.1 Hz, 1H), 7.26-8.05 (m, 8H), 12.71 (br. s., 1H)

EXAMPLE 448

7-butyl-6-{[2-fluoro-2'-(5-oxo-4,5-dihydro-1,2,4-oxadiazol-3-yl)biphenyl-4-yl]methyl}-4-[trans-4-(2-hydroxy-2-methylpropoxy)cyclohexyl]pyrazolo[1,5-a]pyrimidin-5(4H)-one

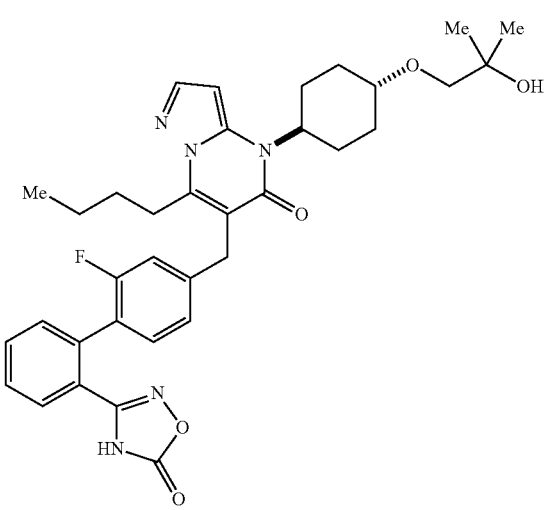

A mixture of hydroxylammonium chloride (0.46 g), sodium hydrogen carbonate (0.69 g) and dimethyl sulfoxide (3 mL) was stirred at 50° C. for 30 min, 4'-({7-butyl-4-[trans-4-(2-hydroxy-2-methylpropoxy)cyclohexyl]-5-oxo-4,5-dihydropyrazolo[1,5-a]pyrimidin-6-yl}methyl)-2'-fluorobiphenyl-2-carbonitrile (0.31 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.14 g) and then 1,8-diazabicyclo[5.4.0]undec-7-ene (0.12 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.11 g, 44%).

$^1$H NMR (300 MHz, DMSO-$d_6$) δ0.77-0.89 (m, 3H), 1.08 (s, 6H), 1.28-1.52 (m, 6H), 1.61-1.75 (m, 2H), 2.03-2.15 (m, 2H), 2.29-2.47 (m, 2H), 2.93-3.02 (m, 2H), 3.20 (s, 2H), 3.36-3.48 (m, 1H), 3.95 (s, 2H), 4.24 (s, 1H), 4.66 (br. s., 1H), 6.42 (d, J=2.3 Hz, 1H), 7.04-7.88 (m, 8H), 12.59 (br. s., 1H)

EXAMPLE 449

4-[4-(1-methylethoxy)phenyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

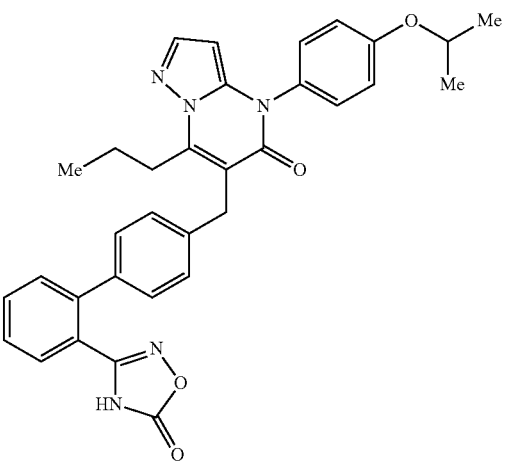 [SMILES: CCCc1c(Cc2ccc(-c3ccccc3-c3noc(=O)[nH]3)cc2)c(=O)n(-c2ccc(OC(C)C)cc2)c2ccnn12]

A mixture of hydroxylammonium chloride (0.33 g), sodium hydrogen carbonate (0.50 g) and dimethyl sulfoxide (2 mL) was stirred at 50° C. for 30 min, 4'-({4-[4-(1-methylethoxy)phenyl]-5-oxo-7-propyl-4,5-dihydropyrazolo[1,5-a]pyrimidin-6-yl}methyl)biphenyl-2-carbonitrile (0.20 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.097 g) and then 1,8-diazabicyclo[5.4.0]undec-7-ene (0.090 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.15 g, 69%).

$^1$H NMR (300 MHz, DMSO-$d_6$) δ0.96 (t, J=7.2 Hz, 3H), 1.31 (d, J=6.1 Hz, 6H), 1.49-1.66 (m, 2H), 2.96-3.06 (m, 2H), 3.98 (s, 2H), 4.60-4.76 (m, 1H), 5.44 (d, J=2.3 Hz, 1H), 7.02-7.76 (m, 13H), 12.37 (s, 1H)

EXAMPLE 450

4-[trans-4-(2-hydroxy-2-methylpropoxy)cyclohexyl]-6-{[3-methoxy-2'-(5-oxo-4,5-dihydro-1,2,4-oxadiazol-3-yl)biphenyl-4-yl]methyl}-7-propylpyrazolo[1,5-a]pyrimidin-5(4H)-one

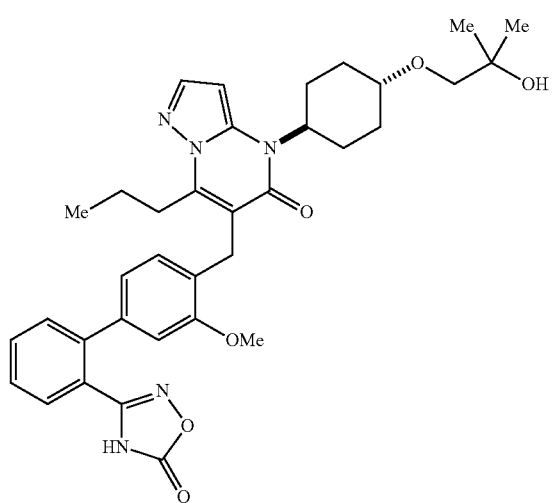

A mixture of hydroxylammonium chloride (0.64 g), sodium hydrogen carbonate (0.97 g) and dimethyl sulfoxide (5 mL) was stirred at 50° C. for 30 min, 4'-({4-[trans-4-(2-hydroxy-2-methylpropoxy)cyclohexyl]-5-oxo-7-propyl-4,5-dihydropyrazolo[1,5-a]pyrimidin-6-yl}methyl)-3'-methoxybiphenyl-2-carbonitrile (0.44 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (5 mL). N,N'-Carbonyldiimidazole (0.15 g) and then 1,8-diazabicyclo[5.4.0]undec-7-ene (0.14 mL) were added, and the mixture was stirred at room temperature for 1 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.34 g, 71%).

$^1$H NMR (300 MHz, DMSO-$d_6$) δ 0.90 (t, J=7.3 Hz, 3H), 1.07 (s, 6H), 1.25-1.75 (m, 6H), 2.02-2.15 (m, 2H), 2.26-2.47 (m, 2H), 2.82-2.94 (m, 2H), 3.19 (s, 2H), 3.36-3.46 (m, 1H), 3.76-3.87 (m, 5H), 4.24 (s, 1H), 4.65 (br. s., 1H), 6.41 (d, J=2.1 Hz, 1H), 6.75-7.87 (m, 8H), 12.36 (br. s., 1H)

EXAMPLE 451

4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

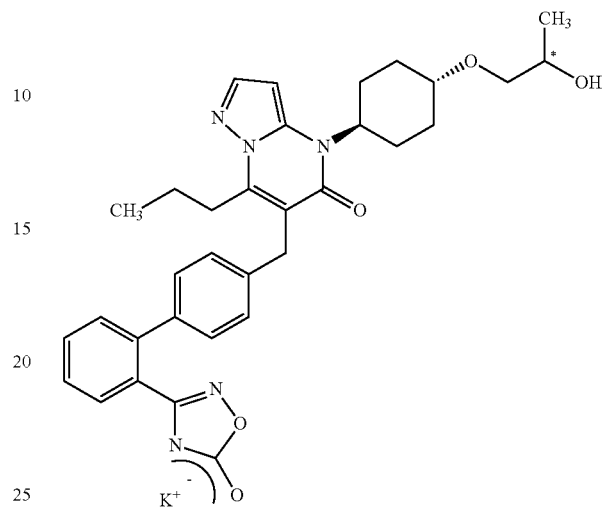

To a solution (1 mL) of 4-[trans-4-(2-hydroxypropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (0.10 g) in ethanol was added 8M aqueous potassium hydroxide solution (0.021 mL), and the mixture was stirred at room temperature for 1 hr. The reaction mixture was concentrated under reduced pressure, and the residue was solidified with diisopropyl ether to give the title compound as a colorless amorphous solid (0.11 g, 99%).

$^1$H NMR (300 MHz, DMSO-$d_6$) δ 0.95 (t, J=7.2 Hz, 3H), 1.04 (d, J=6.1 Hz, 3H), 1.23-1.75 (m, 6H), 2.01-2.47 (m, 4H), 2.91-3.01 (m, 2H), 3.17-3.25 (m, 1H), 3.33-3.47 (m, 2H), 3.63-3.75 (m, 1H), 3.88 (s, 2H), 4.50 (d, J=4.5 Hz, 1H), 4.68 (br. s., 1H), 6.39 (d, J=1.9 Hz, 1H), 7.09-7.50 (m, 8H), 7.81 (d, J=1.9 Hz, 1H).

EXAMPLE 452

4-[trans-4-(2-hydroxy-2-methylpropoxy)cyclohexyl]-6-{[2-methoxy-2'-(5-oxo-4,5-dihydro-1,2,4-oxadiazol-3-yl)biphenyl-4-yl]methyl}-7-propylpyrazolo[1,5-a]pyrimidin-5(4H)-one

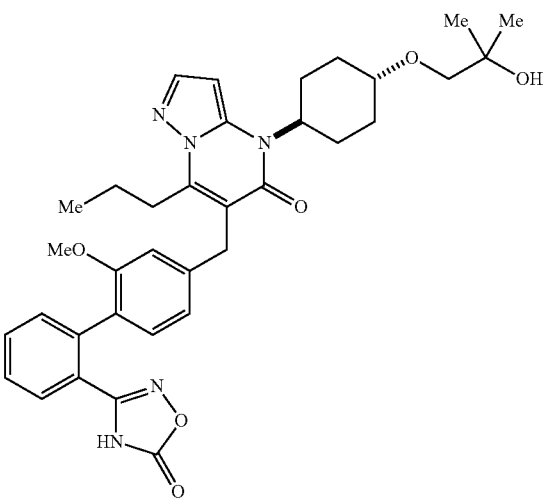

A mixture of hydroxylammonium chloride (0.16 g), sodium hydrogen carbonate (0.25 g) and dimethyl sulfoxide (1 mL) was stirred at 50° C. for 30 min, 4'-({4-[trans-4-(2-hydroxy-2-methylpropoxy)cyclohexyl]-5-oxo-7-propyl-4,5-dihydropyrazolo[1,5-a]pyrimidin-6-yl}methyl)-2'-methoxybiphenyl-2-carbonitrile (0.085 g) was added, and the mixture was stirred at 90° C. for 20 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (0.030 g) and then 1,8-diazabicyclo[5.4.0]undec-7-ene (0.027 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.058 g, 62%).

$^1$H NMR (300 MHz, DMSO-d$_6$) δ 0.94 (t, 3H), 1.08 (s, 6H), 1.27-1.75 (m, 6H), 2.03-2.47 (m, 4H), 2.92-3.02 (m, 2H), 3.34-3.46 (m, 1H), 3.57 (s, 3H), 3.94 (s, 2H), 4.24 (s, 1H), 4.66 (br. s., 1H), 6.41 (d, J=2.1 Hz, 1H), 6.79-7.87 (m, 8H), 12.36 (s, 1H)

EXAMPLE 453

4-[4-(2-hydroxy-2-methylpropoxy)phenyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

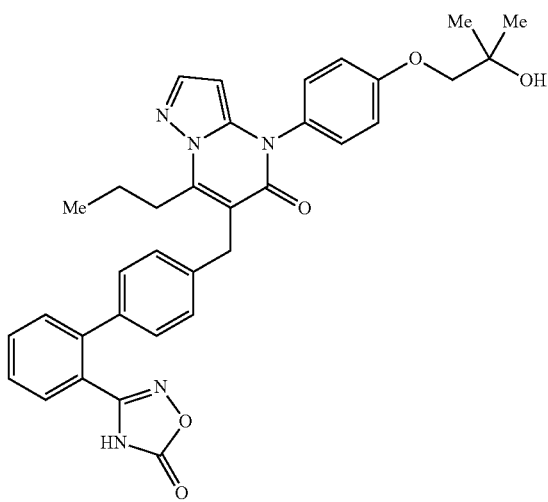 [SMILES: CCCc1c(Cc2ccc(-c3ccccc3-c3noc(=O)[nH]3)cc2)c(=O)n(-c2ccc(OCC(C)(C)O)cc2)c2ccnn12]

A mixture of hydroxylammonium chloride (0.38 g), sodium hydrogen carbonate (0.58 g) and dimethyl sulfoxide (2.5 mL) was stirred at 50° C. for 30 min, 4'-({4-[4-(2-hydroxy-2-methylpropoxy)phenyl]-5-oxo-7-propyl-4,5-dihydropyrazolo[1,5-a]pyrimidin-6-yl}methyl)biphenyl-2-carbonitrile (0.25 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.090 g) and then 1,8-diazabicyclo[5.4.0]undec-7-ene (0.082 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.19 g, 68%).

$^1$H NMR (300 MHz, DMSO-d$_6$) δ 0.96 (t, J=7.4 Hz, 3H), 1.23 (s, 6H), 1.50-1.66 (m, 2H), 2.96-3.05 (m, 2H), 3.98 (s, 2H), 4.67 (s, 1H), 5.44 (d, J=2.3 Hz, 1H), 7.05-7.76 (m, 13H), 12.37 (s, 1H)

EXAMPLE 454

4-(4-{[(1R,2S)-2-hydroxy-1-methylpropyl]oxy}phenyl)-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

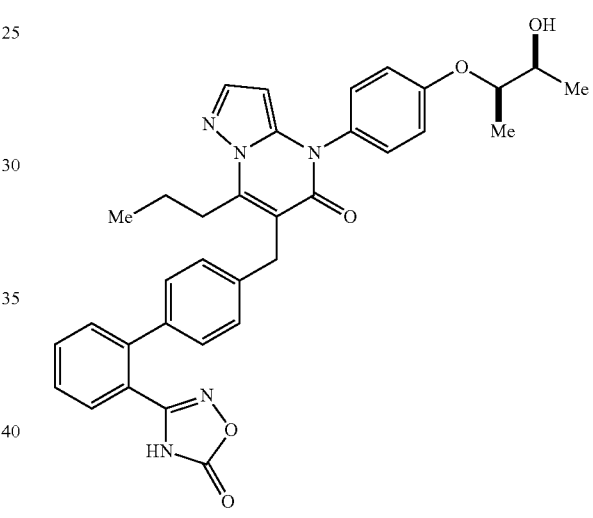

A mixture of hydroxylammonium chloride (0.32 g), sodium hydrogen carbonate (0.48 g) and dimethyl sulfoxide (2 mL) was stirred at 50° C. for 30 min, 4'-{[4-(4-{[(1R,2S)-2-hydroxy-1-methylpropyl]oxy}phenyl)-5-oxo-7-propyl-4,5-dihydropyrazolo[1,5-a]pyrimidin-6-yl]methyl}biphenyl-2-carbonitrile (0.20 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (2 mL). N,N'-Carbonyldiimidazole (0.062 g) and then 1,8-diazabicyclo[5.4.0]undec-7-ene (0.057 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.11 g, 47%).

$^1$H NMR (300 MHz, DMSO-d$_6$) δ 0.96 (t, J=7.4 Hz, 3H), 1.11 (d, J=6.1 Hz, 3H), 1.21 (d, J=6.4 Hz, 3H), 1.49-1.66 (m,

2H), 2.96-3.06 (m, 2H), 3.73-3.85 (m, 1H), 3.98 (s, 2H), 4.30-4.41 (m, 1H), 4.82 (d, J=4.9 Hz, 1H), 5.45 (d, J=1.9 Hz, 1H), 7.05-7.75 (m, 13H), 12.37 (s, 1H)

EXAMPLE 455

4-[4-(2-hydroxypropoxy)phenyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

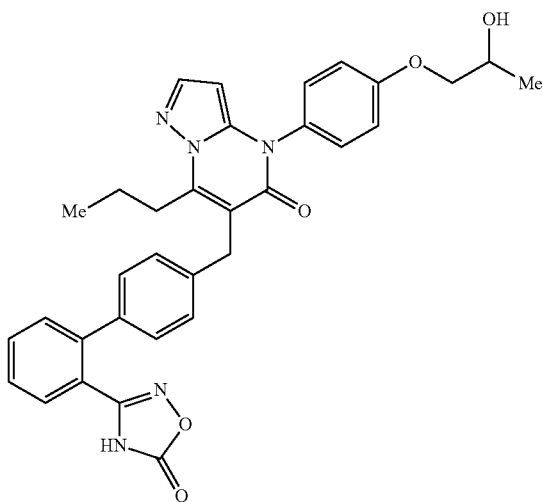 [SMILES: CCCc1c(Cc2ccc(-c3ccccc3-c3noc(=O)[nH]3)cc2)c(=O)n(-c2ccc(OCC(C)O)cc2)c2ccnn12]

A mixture of hydroxylammonium chloride (0.48 g), sodium hydrogen carbonate (0.72 g) and dimethyl sulfoxide (3 mL) was stirred at 50° C. for 30 min, 4'-({4-[4-(2-hydroxypropoxy)phenyl]-5-oxo-7-propyl-4,5-dihydropyrazolo[1,5-a]pyrimidin-6-yl}methyl)biphenyl-2-carbonitrile (0.30 g) was added, and the mixture was stirred at 90° C. for 15 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (3 mL). N,N'-Carbonyldiimidazole (0.092 g) and then 1,8-diazabicyclo[5.4.0]undec-7-ene (0.072 mL) were added, and the mixture was stirred at room temperature for 2 hr. The reaction mixture was diluted with ethyl acetate, washed with 1 M hydrochloric acid, then with saturated aqueous sodium hydrogen carbonate solution and saturated brine, and dried over anhydrous magnesium sulfate. The solvent was evaporated under reduced pressure, and the residue was purified by silica gel column chromatography to give the title compound as a pale-yellow amorphous solid (0.13 g, 38%).

$^1$H NMR (300 MHz, DMSO-d$_6$) δ0.96 (t, J=7.3 Hz, 3H), 1.18 (d, J=6.2 Hz, 3H), 1.51-1.65 (m, 2H), 2.95-3.06 (m, 2H), 3.82-4.01 (m, 5H), 4.91 (d, J=4.7 Hz, 1H), 5.43 (d, J=2.1 Hz, 1H), 7.06-7.75 (m, 13H), 12.37 (s, 1H)

EXAMPLE 456

4-[4-(2-hydroxy-1,1-dimethylethoxy)phenyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

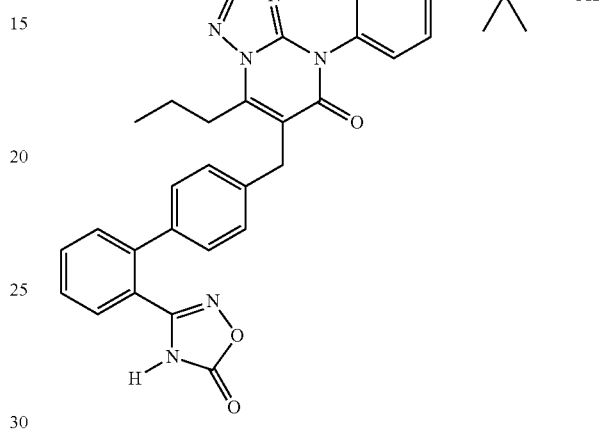

A mixture of 4'-[(5-oxo-7-propyl-4,5-dihydro[1,2,4]triazolo[1,5-a]pyrimidin-6-yl)methyl]biphenyl-2-carbonitrile (0.68 g), {4-[2-(acetyloxy)-1,1-dimethylethoxy]phenyl}boronic acid (0.94 g), copper(II) acetate (0.68 g), pyridine (2.0 mL), triethylamine (1.0 mL), molecular sieves 4A (2.00 g) and tetrahydrofuran (20 mL) was stirred at room temperature for 1 day. To the reaction mixture was added ethyl acetate (100 mL), and the mixture was stirred at room temperature for 1 hr, and the insoluble material was filtered off. The filtrate was concentrated, and the residue was purified by silica gel column chromatography to give 2-(4-{6-[(2'-cyanobiphenyl-4-yl)methyl]-5-oxo-7-propyl[1,2,4]triazolo[1,5-a]pyrimidin-4(5H)-yl}phenoxy)-2-methylpropyl acetate as a colorless oil (0.85 g, 80%). A mixture of hydroxylammonium chloride (1.55 g), sodium hydrogen carbonate (2.50 g) and dimethyl sulfoxide (15 mL) was stirred at 40° C. for 30 min, 2-(4-{6-[(2'-cyanobiphenyl-4-yl)methyl]-5-oxo-7-propyl[1,2,4]triazolo[1,5-a]pyrimidin-4(5H)-yl}phenoxy)-2-methylpropyl acetate (0.85 g) was added, and the mixture was stirred at 90° C. for 18 hr. The reaction mixture was diluted with ethyl acetate, washed with water and then with saturated brine, and dried over anhydrous magnesium sulfate. The solvent was evaporated under reduced pressure, and the residue was dissolved in tetrahydrofuran (15 mL). N,N'-Carbonyldiimidazole (0.36 g) and then 1,8-diazabicyclo[5.4.0]undec-7-ene (0.33 mL) were added, and the mixture was stirred at room temperature for 2 hr. The reaction mixture was diluted with ethyl acetate, washed with saturated aqueous potassium hydrogensulfate solution and then with saturated brine, and dried over anhydrous magnesium sulfate. The solvent was evaporated under reduced pressure, and the residue was purified by silica gel column chromatography to give the title compound as a colorless solid (0.25 g, 28%).

$^1$H NMR (300 MHz, CDCl$_3$) δ1.14 (t, J=7.5 Hz, 3H), 1.33 (s, 6H), 1.78-1.96 (m, 2H), 2.21 (br. s, 1H), 3.10-3.24 (m, 2H), 3.59 (s, 2H), 4.02 (s, 2H), 7.06-7.16 (m, 2H), 7.18-7.52 (m, 8H), 7.56-7.63 (m, 1H), 7.77-7.84 (m, 1H), 7.86 (s, 1H)

EXAMPLE 457

7-butyl-6-{[3-fluoro-2'-(1H-tetrazol-5-yl)biphenyl-4-yl]methyl}-4-[trans-4-(2-hydroxy-2-methylpropoxy)cyclohexyl][1,2,4]triazolo[1,5-a]pyrimidin-5(4H)-one

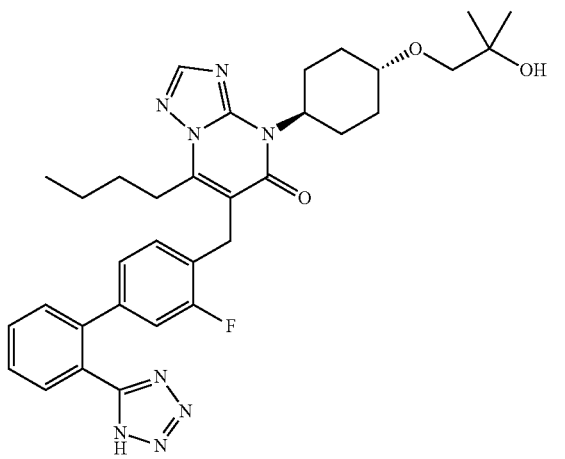 [SMILES: CCCCc1c(Cc2ccc(-c3ccccc3-c3nnn[nH]3)cc2F)c(=O)n([C@H]2CC[C@H](OCC(C)(C)O)CC2)c2ncnn12]

A mixture of 4'-({7-butyl-4-[trans-4-(2-hydroxy-2-methylpropoxy)cyclohexyl]-5-oxo-4,5-dihydro[1,2,4]triazolo[1,5-a]pyrimidin-6-yl}methyl)-3'-fluorobiphenyl-2-carbonitrile (0.76 g), dibutyltin oxide (0.17 g), azidotrimethylsilane (4.60 g) and toluene (15 mL) was refluxed overnight. The reaction mixture was diluted with ethyl acetate, washed with water and then with saturated brine, and dried over anhydrous magnesium sulfate. The solvent was evaporated under reduced pressure. To a solution of the residue in tetrahydrofuran (15 mL) was added tetrabutylammonium fluoride (1.0 M tetrahydrofuran solution, 3 mL) at room temperature, and the mixture was refluxed for 3 hr. The reaction mixture was poured into 1 M hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.58 g, 71%).

$^1$H NMR (300 MHz, CDCl$_3$) δ0.96 (t, J=7.2 Hz, 3H), 1.19 (s, 6H), 1.34-1.84 (m, 8H), 2.12-2.24 (m, 2H), 2.39 (br. s, 1H), 2.58-2.76 (m, 2H), 3.04-3.12 (m, 2H), 3.29 (s, 2H), 3.34-3.50 (m, 1H), 3.97 (s, 2H), 4.96-5.10 (m, 1H), 6.84-6.99 (m, 2H), 7.22-7.30 (m, 1H), 7.37-7.42 (m, 1H), 7.50-7.62 (m, 2H), 7.91 (s, 1H), 8.07-8.13 (m, 1H)

EXAMPLE 458

(+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one, and (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one monopotassium salt (1/1) hydrate

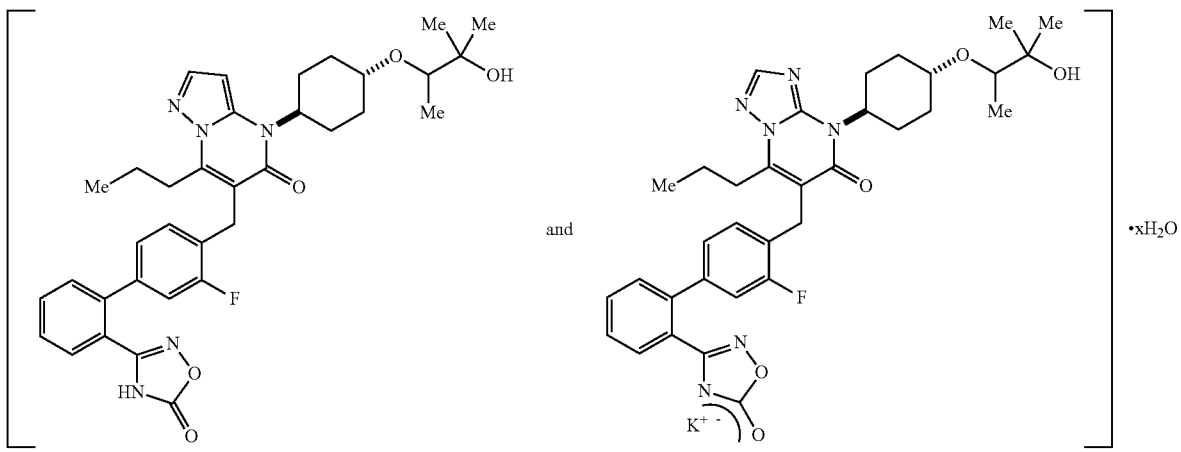

A solution of (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: short, 107 g) and potassium 2-ethylhexanoate (28.9 g) in ethanol (214 mL) was heated to 60° C., and heptane (1066 mL) was added. The reaction mixture was stirred at 60° C. for 16 hr, and the obtained crystals were collected by filtration and washed with diisopropyl ether (89.6 g, 80%).

(+)-6-{[3-Fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one and (+)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5- a]pyrimidine- 5(4H)-one monopotassium salt (1/1) hydrate (94.9 g) obtained by the above-mentioned method was suspended in ethanol (475 mL) and dissolved by heating to 65° C. Heptane (1423 mL) was added at internal temperature 60° C., a seed crystal was added, and the mixture was stirred at the same temperature for 3 hr. At the same temperature, moreover, heptane (475 mL) was added, and the mixture was stirred at the same temperature for 1 hr and then at room temperature for 30 min. The obtained crystals were collected by filtration, and washed with heptane:ethanol (4:1) (86.2 g, 91%, >99% ee).

$^1$H NMR (300 MHz, DMSO-$d_6$) δ0.90-1.10 (m, 12H), 1.16-1.40 (m, 2H), 1.49-1.74 (m, 4H), 1.93-2.15 (m, 2H), 2.47-2.68 (m, 2H), 2.87-3.01 (m, 2H), 3.25 (q, J=6.2 Hz, 1H), 3.30-3.44 (m, 1H), 3.92 (s, 2H), 4.79-4.95 (m, 1H), 7.00 (dd, J=8.0, 1.6 Hz, 1H), 7.08-7.23 (m, 2H), 7.38-7.63 (m, 4H), 8.19 (s, 1H)

analysis of enantiomeric excess column: CHIRALPAK AD-H (LA145) 4.6 mm ID×250 mL mobile phase: CO$_2$/MeOH=650/350 (v/v)

flow rate: 2.35 ml/min pressure: 100 bar temperature: 35° C.

detection: UV220 nm concentration: 0.5 mg/ml injection volume: 5 µl retention time: 7.3 min specific optical rotation $[\alpha]^{25}_D$ +14.6° (c=1.0490, in methanol)

Anal. Calcd for $C_{68}H_{77}N_{12}O_{10}F_2K:H_2O$: C, 61.99; H, 6.04; N, 12.76.

Found: C, 62.03; H, 6.07; N, 12.69.

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 4.66 | 18.9468 |
| 5.8 | 15.2251 |
| 6.52 | 13.5453 |
| 9.34 | 9.461 |
| 12.14 | 7.2844 |
| 13.08 | 6.763 |
| 13.16 | 6.722 |
| 15.8 | 5.6043 |
| 19.64 | 4.5164 |
| 19.7 | 4.5027 |

EXAMPLE 459

(−)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one potassium salt (retention time: long)

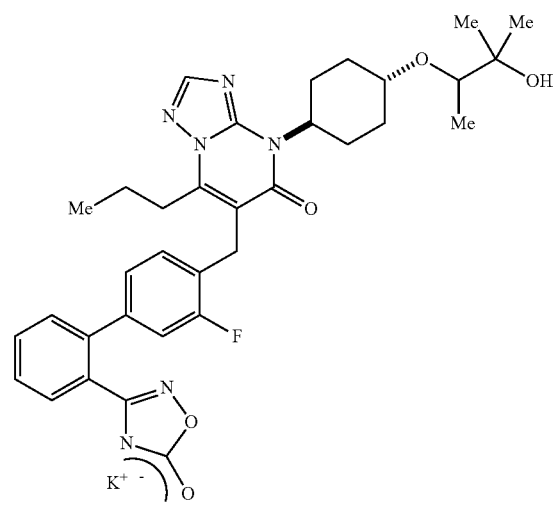

To a solution (30 mL) of 6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: long, 3 g) in isopropyl alcohol was added 4N aqueous potassium hydroxide solution (1.2 mL) at room temperature. The reaction mixture was concentrated under reduced pressure, the obtained solid was suspended in diisopropyl ether, and the mixture was stirred for 1 day. The obtained solid was collected by filtration and washed with diisopropyl ether to give the title compound (2.8 g, 88%, >99.9% ee).

$^1$H NMR (300 MHz, DMSO-$d_6$) δ 0.90-1.11 (m, 15H), 1.17-1.39 (m, 2H), 1.54-1.74 (m, 4H), 1.94-2.14 (m, 2H), 2.52-2.65 (m, 2H), 2.90-2.99 (m, 2H), 3.24 (q, J=6.4 Hz, 1H), 3.34-3.43 (m, 1H), 3.90 (s, 2H), 4.05 (s, 1H), 4.80-4.96 (m, 1H), 6.97-7.17 (m, 3H), 7.28-7.53 (m, 4H), 8.18 (s, 1H)

analysis of enantiomeric excess column: CHIRALPAK AD-H (CG075) 4.6 mm ID×250 mL mobile phase: CO$_2$/MeOH=650/350 (v/v)

flow rate: 2.35 ml/min temperature: 35° C.

detection: UV220 nm concentration: 0.5 mg/ml injection volume: 5 µl retention time: 9.7 min specific optical rotation $[\alpha]^{25}_D$ −13.6° (c=0.4205, in methanol)

EXAMPLE 460

(−)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one and (−)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one monopotassium salt (1/1) hydrate

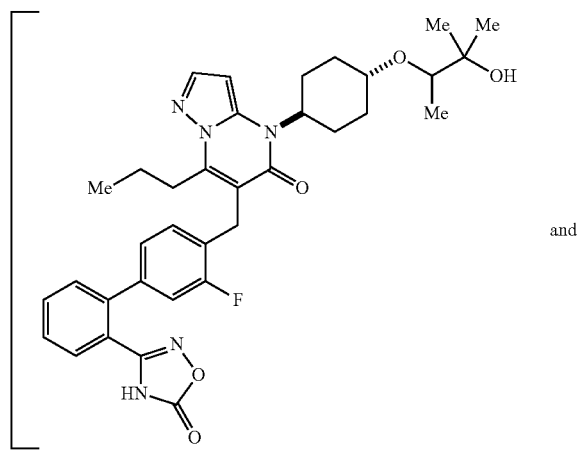 and 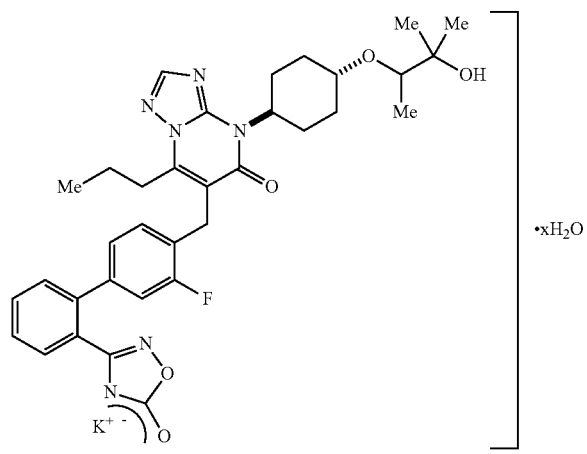

A solution (0.64 mL) of 6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one (retention time: long, 0.32 mg) and potassium 2-ethylhexanoate (86 mg) in ethanol was heated to 60° C., and heptane (1.9 mL) was added. The reaction mixture was stirred at 60° C. for 1 hr, heptane (1.3 mL) was added, and the mixture was further stirred at 60° C. for 1 hr. The reaction mixture was cooled to room temperature, and the obtained crystals were collected by filtration and washed with diisopropyl ether (249 mg, 74%).

(−)-6-{[3-Fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one and (−)-6-{[3-fluoro-2'-(5-oxo-4,5-dihydro-1,2,4-oxadiazol-3-yl)biphenyl-4-yl]methyl}-4-[trans-4-(2-hydroxy-1,2-dimethylpropoxy)cyclohexyl]-7-propyl[1,2,4]triazolo[1,5-a]pyrimidin-5(4H)-one monopotassium salt (1/1) hydrate (249 mg) obtained by the above-mentioned method was suspended in ethanol (1.75 mL), and dissolved by heating to 60° C. Heptane (5.25 mL) was added at internal temperature 60° C., a seed crystal was added, and the mixture was stirred at the same temperature for 3 hr. At the same temperature, moreover, heptane (1.75 mL) was added, and the mixture was stirred at the same temperature for 1 hr and then at room temperature for 30 min. The obtained crystals were collected by filtration, and washed with heptane:ethanol (4:1) (211 mg, 85%, >99.0% ee).

$^1$H NMR (300 MHz, DMSO-$d_6$) δ 0.89-1.11 (m, 12H), 1.18-1.38 (m, 2H), 1.51-1.73 (m, 4H), 1.94-2.14 (m, 2H), 2.51-2.66 (m, 2H), 2.88-2.98 (m, 2H), 3.24 (q, J=6.0 Hz, 1H), 3.29-3.43 (m, 1H), 3.92 (s, 2H), 4.06 (br. s., 1H), 4.79-4.95 (m, 1H), 7.00 (dd, J=7.9, 1.5 Hz, 1H), 7.08-7.23 (m, 2H), 7.39-7.63 (m, 4H), 8.18 (s, 1H)

analysis of enantiomeric excess
column: CHIRALPAK AD-H (LA145) 4.6 mm ID×250 mL
mobile phase: $CO_2$/MeOH=650/350 (v/v)
flow rate: 2.35 ml/min
pressure: 100 bar
temperature: 35° C.
detection: UV220 nm
concentration: 1.0 mg/ml
injection volume: 5 μl
retention time: 10.9 min
specific optical rotation $[\alpha]^{25}_D$ −13.0° (c=0.4985, in methanol)

Anal. Calcd for $C_{68}H_{77}N_{12}O_{10}F_2K \cdot H_2O$: C, 61.99; H, 6.04; N, 12.76.
Found: C, 62.21; H, 5.94; N, 12.83.

EXAMPLE 461

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one

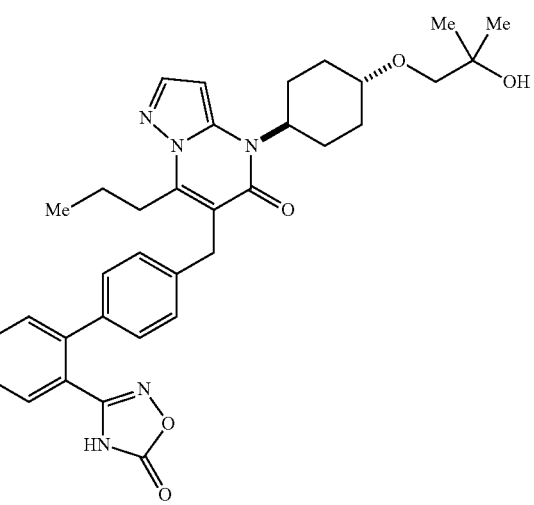

4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (5.0 g) obtained in Example 413 was dissolved in 90% acetone water (40 mL) prepared in advance at 25-30° C., water (8 mL) was added, then a seed crystal (25 mg) was added and the mixture was stirred overnight at 20-30° C. After stirring, water (24 mL) was added dropwise at 20-30° C. for 4 hr and 10 min. After the completion of the dropwise addition, the mixture was stirred at the same temperature for 2 hr and 30 min. After stirring, the crystals were collected by filtration and washed with 50% acetone/water (15 mL) prepared in advance to give wet crystals. The obtained wet crystals were dried under reduced pressure at 40° C. to give the title compound as a crystalline powder (4.72 g, 94.4%).

The title compound was also obtained by the following method.

4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (3.0 g) obtained in Example 413 was suspended in acetone (39 mL), and the suspension was dissolved by heating to 45-50° C. and n-heptane (39 mL) was further added. After the addition, the mixture was cooled to 25-35° C., a seed crystal (15 mg) was added, and the mixture was stirred at 20-30° C. overnight. After stirring, the crystals were collected by filtration and washed with acetone/n-heptane (1:1, 9 mL) prepared in advance to give wet crystals. The obtained wet crystals were dried under reduced pressure at 40° C. to give the title compound as a crystalline powder (1.83 g, yield: 61.0%).

$^1$H NMR (300 MHz, DMSO-$d_6$) δ 0.93 (t, J=7.3 Hz, 3H), 1.08 (s, 6H), 1.36 (dd, J=9.1, 12.6 Hz, 2H), 1.52 (dd, J=7.6, 7.9 Hz, 2H), 1.68 (d, J=9.3 Hz, 2H), 2.10 (d, J=7.2 Hz, 2H), 2.39 (m, 2H), 2.96 (t, J=12.8 Hz, 2H), 3.21 (s, 2H), 3.40 (m, 1H), 3.94 (s, 2H), 4.25 (s, 1H), 6.42 (s, 1H), 7.23 (d, J=8.2 Hz, 2H), 7.30 (d, J=8.2 Hz, 2H), 7.51 (d, J=7.9 Hz, 1H), 7.55 (dd, J=7.6, 7.6 Hz, 1H), 7.66 (d, J=7.5 Hz, 1H), 7.69 (dd, J=7.5, 7.5 Hz, 1H), 7.83 (d, J=2.2 Hz, 1H), 12.36 (s, 1H)

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 9.66 | 9.1483 |
| 9.92 | 8.9091 |
| 10.68 | 8.2767 |
| 15.82 | 5.5973 |
| 16.32 | 5.4269 |
| 17.22 | 5.1452 |
| 19.02 | 4.6622 |
| 19.36 | 4.581 |
| 19.78 | 4.4847 |
| 20.02 | 4.4315 |
| 20.68 | 4.2915 |
| 23.54 | 3.7762 |

EXAMPLE 462

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

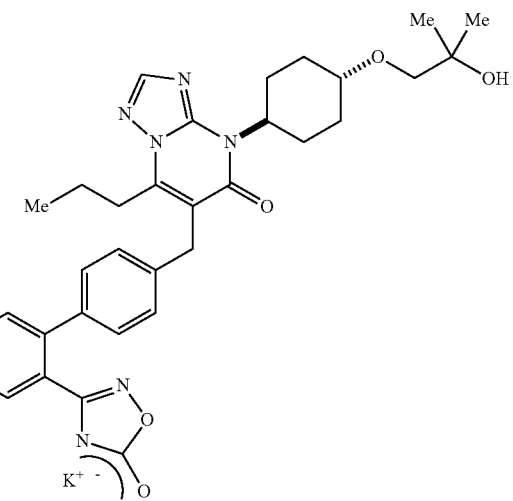

4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (1.16 g) was dissolved in acetonitrile (5 mL), and 8 M aqueous potassium hydroxide solution (242 μL) was added at 40° C. The reaction mixture was cooled to room temperature. After confirmation of crystal precipitation, the reaction mixture was further stirred at 5° C. for 1 hr. The obtained crystals were collected by filtration, and washed with acetonitrile (0.83 g, 67%).

$^1$H NMR (300 MHz, DMSO-$d_6$) δ 0.95 (t, J=7.3 Hz, 3H), 1.08 (s, 6H), 1.27-1.42 (m, 2H), 1.57 (dq, J=15.1, 7.5 Hz, 2H), 1.68 (d, J=10.7 Hz, 2H), 2.09 (d, J=10.4 Hz, 2H), 2.38 (d, J=12.0 Hz, 2H), 2.92-3.01 (m, 2H), 3.20 (s, 2H), 3.28-3.44 (m, 1H), 3.89 (s, 2H), 4.25 (br. s., 1H), 4.49-4.88 (m, 1H), 6.40 (d, J=2.2 Hz, 1H), 7.12-7.18 (m, 2H), 7.18-7.24 (m, 2H), 7.28 (d, J=7.6 Hz, 1H), 7.31-7.37 (m, 1H), 7.38-7.44 (m, 1H), 7.48 (d, J=7.3 Hz, 1H), 7.81 (d, J=1.9 Hz, 1H)

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 14.98 | 5.9092 |
| 15.02 | 5.8935 |
| 15.08 | 5.8702 |
| 16.6 | 5.336 |
| 16.68 | 5.3106 |
| 18.78 | 4.7212 |
| 18.86 | 4.7014 |
| 19.34 | 4.5857 |
| 19.42 | 4.567 |
| 21.32 | 4.1641 |

EXAMPLE 463

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

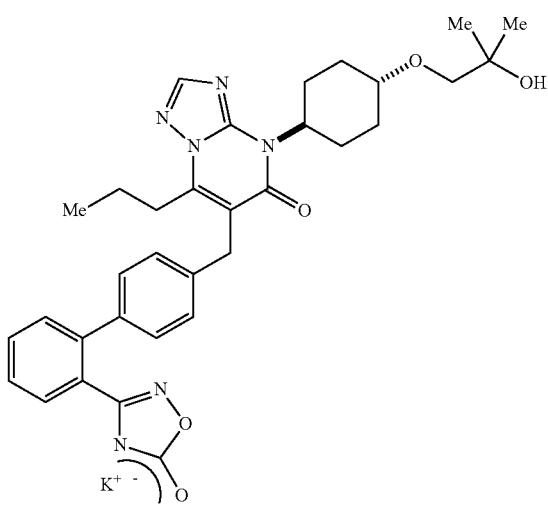

4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt (0.1 g) was dissolved in ethyl acetate (1 mL) at 50° C., and the solution was cooled to room temperature. Heptane (0.5 mL) was added, and the mixture was stirred under ice-cooling for 1 hr. The obtained crystals were collected by filtration, and washed with heptane (0.085 g, 85%).

$^1$H NMR (300 MHz, DMSO-$d_6$) δ 0.95 (t, J=7.3 Hz, 3H), 1.08 (s, 6H), 1.27-1.42 (m, 2H), 1.57 (dq, J=15.1, 7.5 Hz, 2H), 1.68 (d, J=10.7 Hz, 2H), 2.09 (d, J=10.4 Hz, 2H), 2.38 (d, J=12.0 Hz, 2H), 2.92-3.01 (m, 2H), 3.20 (s, 2H), 3.28-3.44 (m, 1H), 3.89 (s, 2H), 4.25 (br. s., 1H), 4.49-4.88 (m, 1H), 6.40 (d, J=2.2 Hz, 1H), 7.12-7.18 (m, 2H), 7.18-7.24 (m, 2H), 7.28 (d, J=7.6 Hz, 1H), 7.31-7.37 (m, 1H), 7.38-7.44 (m, 1H), 7.48 (d, J=7.3 Hz, 1H), 7.81 (d, J=1.9 Hz, 1H)

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 4.36 | 20.2498 |
| 8.8 | 10.0403 |
| 15.06 | 5.878 |
| 16.62 | 5.3296 |
| 17.68 | 5.0124 |
| 18.82 | 4.7113 |
| 19.34 | 4.5857 |
| 21.36 | 4.1564 |
| 22.02 | 4.0333 |
| 22.32 | 3.9798 |

EXAMPLE 464

4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one potassium salt

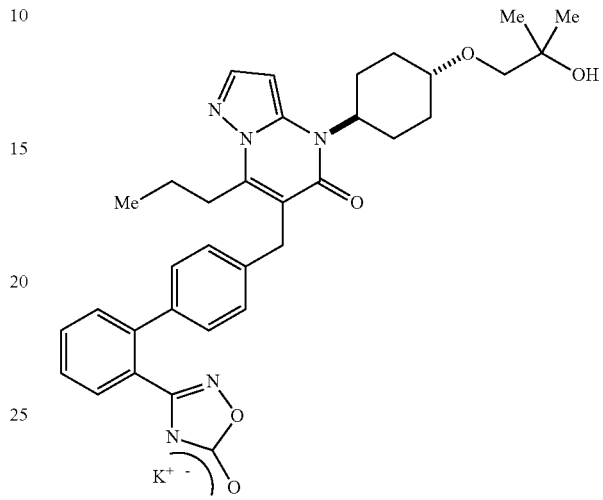

To 4-[trans-4-(2-hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one (10 g) were added ethanol (30 mL) and 8 M potassium hydroxide (2.1 ml), and the mixture was dissolved by stirring at room temperature. After the mixture was concentrated, ethyl acetate (50 mL) was added to the residue and the mixture was concentrated again. Ethyl acetate (30 mL) was added to dissolve the concentrated residue and insoluble material was removed by filtration using ethyl acetate (20 mL). After heating to 60° C., a seed crystal was added to allow crystallization. After crystallization, n-heptane (25 mL) was added dropwise at 60° C., and the mixture was stirred at the same temperature for about 1 hr, allowed to cool to room temperature, and stirred for about 15 hr. The crystals were collected by filtration and washed with ethyl acetate/n-heptane (1:4, 30 mL) and dried under reduced pressure at 40° C. to give the title compound as a colorless amorphous solid (9.5 g, 89%).

$^1$H NMR (300 MHz, DMSO-$d_6$) δ 0.95 (t, J=7.3 Hz, 3H), 1.08 (s, 6H), 1.27-1.42 (m, 2H), 1.57 (dq, J=15.1, 7.5 Hz, 2H), 1.68 (d, J=10.7 Hz, 2H), 2.09 (d, J=10.4 Hz, 2H), 2.38 (d, J=12.0 Hz, 2H), 2.92-3.01 (m, 2H), 3.20 (s, 2H), 3.28-3.44 (m, 1H), 3.89 (s, 2H), 4.25 (br. s., 1H), 4.49-4.88 (m, 1H), 6.40 (d, J=2.2 Hz, 1H), 7.12-7.18 (m, 2H), 7.18-7.24 (m, 2H), 7.28 (d, J=7.6 Hz, 1H), 7.31-7.37 (m, 1H), 7.38-7.44 (m, 1H), 7.48 (d, J=7.3 Hz, 1H), 7.81 (d, J=1.9 Hz, 1H)

Crystal form was characterized by powder X ray diffraction pattern using CuKα X-ray radiation, having peaks selected from a list consisting of:

diffraction angle: 2θ(°) interplanar distance: d value (Å)

| | |
|---|---|
| 5.34 | 16.5355 |
| 7.36 | 12.0011 |
| 7.82 | 11.2962 |
| 11.74 | 7.5317 |
| 12.34 | 7.1668 |
| 16.2 | 5.4668 |

| | |
|---|---|
| 18.98 | 4.6719 |
| 19.78 | 4.4847 |
| 24.78 | 3.59 |

EXPERIMENTAL EXAMPLE 1

Evaluation of AT1 Receptor Antagonistic Activity (1) Preparation of human AT1 Receptor-Expressing CHO-K1 Cellular Membrane Fraction CHO-K1 cell (RIKEN, Japan) capable of stable expression of human AT1 receptor was cultured, recovered, suspended in homogenize buffer (10 mM NaHCO$_3$ (pH 7.4), 5 mM EDTA, 1× Complete EDTA free) [manufactured by Roche, Switzerland], and homogenized. The homogenate was centrifuged at low-speed (900×g, 10 min, 4° C.), and the supernatant was recovered and ultracentrifuged (90,000×g, 1 hr, 4° C.). The supernatant was discarded, and the pellets were resuspended in suspension buffer (50 mM Tris (pH 7.4), 1 mM EDTA, 1× Complete EDTA free).

(2) Evaluation of AT1 Receptor Antagonistic Activity

The binding assay was performed using 22.5 pM [$^{125}$I]-angiotensin II [manufactured by PerkinElmer, USA] (9 μg) in the presence of AT1 membrane and test compound in 100 μL (total reaction volume) of reaction buffer (50 mM Tris (pH 7.4), 10 mM MgCl$_2$ supplemented or not supplemented with 0.3 mg/mL fatty acid-free bovine serum albumin [manufactured by Wako Pure Chemical Industries, Ltd., Japan]). The reaction mixture was incubated in 96 well polypropylene plate for 1 hr at room temperature, and the reaction was quenched by rapid filtration (96 well cell harvester) through a GF/C filter treated with wash buffer (50 mM Tris (pH 7.4)). Subsequently, the filter was washed 5 times with 0.3 mL of ice-cooled wash buffer. The filter was air-dried, and [$^{125}$I]-angiotensin II binding radioactivity was assayed with Top Count scintillation counter. Total binding was measured in the presence of 1% DMSO and nonspecific binding was measured in the presence of 1 μM Candesartan. The binding data B/B0(%) was analyzed by GraphPad Prism program (GraphPad Software Inc.) and the IC$_{50}$ value (compound concentration showing 50% of the maximum value of inhibition percent) of the test compound was calculated.

The AT1 receptor binding ratio of [$^{125}$I]-angiotensin II (hereinafter to be abbreviated as [$^{125}$I]-AII in the formula) (B/B0(%)) was calculated from the following formula.

$$B/B0\ (\%) = \frac{([^{125}I]\ AII\ \text{binding level in the presence of test compound} - \text{non-specific binding level})}{([^{125}I]\ AII\ \text{total binding level in the absence of test compound} - \text{non-specific binding level})} \times 100$$

The non-specific binding level is the [$^{125}$I]-angiotensin II binding level obtained in the presence of 1 μM cold angiotensin II.

The results are shown in Tables 1 to 5.

EXPERIMENTAL EXAMPLE 2

Evaluation of PPARγ Agonistic Activity (1) Cloning of Human PPARγ Gene

Human PPARγ gene was cloned by a PCR method using heart cDNA [manufactured by Toyobo Co., Ltd., QUICK-Clone cDNA] as a template, and a primer set shown below which was prepared by reference to the base sequence of PPARγ gene reported by Greene et al. [Gene Expr., 1995, vol. 4(4-5), pp. 281-299].

PAG-U:
(SEQ ID NO: 1)
5'-GTG GGT ACC GAA ATG ACC ATG GTT GAC ACA GAG-3'

PAG-L:
(SEQ ID NO: 2)
5'-GGG GTC GAC CAG GAC TCT CTG CTA GTA CAA GTC-3'

PCR reaction was performed according to Hot Start method using AmpliWax PCR Gem 100 [manufactured by Takara Shuzo Co., Ltd., Japan]. First, 10×LA PCR Buffer (2 μl), 2.5 mM dNTP solution (3 μl), 12.5 μM primer solution (each 2.5 μl) and sterile distilled water (10 μl) were mixed to give a bottom layer solution mixture. In addition, human heart cDNA (1 ng/ml, 1 μl) as a template, 10×LA PCR Buffer (3 μl), 2.5 mM dNTP solution (1 μl), TaKaRa LA Taq DNA polymerase [manufactured by Takara Shuzo Co., Ltd., Japan] (0.5 μl) and sterile distilled water (24.5 μl) were mixed to give a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube comprising the reaction mixture was set on a thermal cycler [manufactured by PerkinElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment comprising PPARγ gene was recovered from the gel, and then inserted into pT7 Blue-T vector [manufactured by Takara Shuzo Co., Ltd., Japan] to obtain plasmid pTBT-hPPARγ.

(2) Cloning of Human RXRα Gene

A human RXRα gene was cloned by a PCR method using kidney cDNA [manufactured by Toyobo Co., Ltd., QUICK-Clone cDNA] as a template, and a primer set shown below which was prepared with reference to the base sequence of RXRα gene reported by Mangelsdorf, D. J. et al. (Nature, 1990, vol. 345 (6272), pp. 224-229).

XRA-U:
(SEQ ID NO: 3)
5'-TTA GAA TTC GAC ATG GAC ACC AAA CAT TTC CTG-3'

XRA-L:
(SEQ ID NO: 4)
5'-CCC CTC GAG CTA AGT CAT TTG GTG CGG CGC CTC-3'

PCR reaction was performed according to Hot Start method using AmpliWax PCR Gem 100 [manufactured by Takara Shuzo Co., Ltd., Japan]. First, 10×LA PCR Buffer (2 μl), 2.5 mM dNTP solution (3 μl), 12.5 μM primer solution (each 2.5 μl) and sterile distilled water (10 μl) were mixed to give a bottom layer solution mixture. In addition, human kidney cDNA (1 ng/ml, 1 μl) as a template, 10×LA PCR Buffer (3 μl), 2.5 mM dNTP solution (1 μl), TaKaRa LA Taq DNA polymerase [manufactured by Takara Shuzo Co., Ltd., Japan] (0.5 μl) and sterile distilled water (24.5 μl) were mixed to give a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube comprising the reaction mixture was set on a thermal cycler [manufactured by Perki-nElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment comprising RXRα gene was recovered from the gel, and then inserted into pT7 Blue-T vector [manufactured by Takara Shuzo Co., Ltd., Japan] to obtain plasmid pTBT-hRXRα.

(3) Construction of Reporter Plasmid

A DNA fragment comprising PPAR-response element (PPRE) of an acyl CoA oxidase was prepared using the following 5'-terminal phosphorylated synthetic DNA.

```
PPRE-U:
                                          (SEQ ID NO: 5)
5'-pTCGACAGGGGACCAGGACAAAGGTCACGTTCGGGAG-3'

PPRE-L:
                                          (SEQ ID NO: 6)
5'-pTCGACTCCCGAACGTGACCTTTGTCCTGGTCCCCTG-3'
```

First, PPRE-U and PPRE-L were annealed and inserted to SalI site of plasmid pBlueScript SK+. By determining the base sequence of the inserted fragment, plasmid pBSS-PPRE4, in which 4 PPREs were ligated in tandem, was selected.

An HSV thymidine kinase minimum promoter (TK promoter) region was cloned by a PCR method using pRL-TK vector [manufactured by Promega, USA] as a template, and a primer set shown below which was prepared with reference to the base sequence of the promoter region of thymidine kinase gene reported by Luckow, B et al. (Nucleic Acids Res., 1987, vol. 15(13), p. 5490).

```
TK-U:
5'-CCCAGATCTCCCCAGCGTCTTGTCATTG-3'  (SEQ ID NO: 7)

TK-L:
5'-TCACCATGGTCAAGCTTTTAAGCGGGTC-3'  (SEQ ID NO: 8)
```

PCR reaction was performed according to Hot Start method using AmpliWax PCR Gem 100 [manufactured by Takara Shuzo Co., Ltd., Japan]. First, 10×LA PCR Buffer (2 μl), 2.5 mM dNTP solution (3 μl), 12.5 μM primer solution (each 2.5 μl) and sterile distilled water (10 μl) were mixed to give a bottom layer solution mixture. In addition, pRL-TK vector [manufactured by Promega, USA] (1 μl) as a template, 10×LA PCR Buffer (3 μl), 2.5 mM dNTP solution (1 μl), TaKaRa LA Taq DNA polymerase [manufactured by Takara Shuzo Co., Ltd., Japan] (0.5 μl) and sterile distilled water (24.5 μl) were mixed to give a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, the top layer solution mixture was added to the mixture to prepare the reaction mixture for PCR. A tube comprising the reaction mixture was set on a thermal cycler [manufactured by Perki-nElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 140 bp DNA fragment comprising TK promoter was recovered from the gel, and then inserted into pT7 Blue-T vector [manufactured by Takara Shuzo Co., Ltd., Japan]. By digesting the plasmid thus obtained with the restriction enzymes BglII and NcoI, a fragment comprising TK promoter was obtained, which was ligated to the BglII-NcoI fragment of plasmid pGL3-Basic vector [manufactured by Promega, USA] to obtain plasmid pGL3-TK.

A 4.9 kb NheI-XhoI fragment of plasmid pGL3-TK thus obtained was ligated to a 200 bp NheI-XhoI fragment of plasmid pBSS-PPRE4 to obtain plasmid pGL3-4ERPP-TK.

This plasmid pGL3-4ERPP-TK was digested with BamHI [manufactured by Takara Shuzo Co., Ltd., Japan], and then treated with T4DNA polymerase [manufactured by Takara Shuzo Co., Ltd., Japan] to form a blunt-end, whereby obtaining a DNA fragment.

On the other hand, pGFP-C1 [manufactured by Toyobo Co., Ltd., Japan] was digested with Bsu36I (manufactured by NEB, UK], and then treated with T4DNA polymerase [manufactured by Takara Shuzo Co., Ltd., Japan] to form a blunt-end, whereby obtaining a 1.6 kb DNA fragment.

The both DNA fragments were ligated to construct a reporter plasmid pGL3-4ERPP-TK neo.

(4) Construction of Expression Plasmid for Human PPARγ and RXRα

A 7.8 kb FspI-NotI fragment of plasmid pVgRXR [manufactured by Invitrogen, USA] was ligated to a 0.9 kb FspI-NotI fragment comprising RXRα gene of plasmid pTBT-hRXRα obtained in the above-mentioned (2) to prepare plasmid pVgRXR2. Then, pVgRXR2 was digested with BstXI, and then treated with T4DNA polymerase [manufactured by Takara Shuzo Co., Ltd., Japan] to give a blunt-ended product. Then digestion with KpnI gave a 6.5 kb DNA fragment.

On the other hand, plasmid pTBT-hPPARγ obtained in the above-mentioned (1) was digested with SalI, and then treated with T4DNA polymerase [manufactured by Takara Shuzo Co., Ltd., Japan] to give a blunt-ended product. Then digestion with KpnI gave a 1.4 kb DNA fragment comprising human PPARγ gene.

The both DNA fragments were ligated to construct plasmid pVgRXR2-hPPARγ.

(5) Introduction of Human PPARγ- and RXRα-Expression Plasmid and Reporter Plasmid into CHO-K1 Cell as Well as Establishment of Expressed Cell A CHO-K1 cell cultured in a 150 cm$^2$ cell culture flask [manufactured by Corning Costar Corporation, USA] comprising Ham's F12 medium [manufactured by INVITROGEN, USA] supplemented with 10% fetal bovine serum [manufactured by INVITROGEN, USA] was taken off by treating with 0.5 g/L trypsin-0.2 g/L EDTA (ethylenediamine tetraacetate) [manufactured by Life Technologies, Inc., USA], and then the cell was washed with PBS (Phosphate-buffered saline) [manufactured by INVITROGEN, USA], centrifuged (1000 rpm, 5 minutes) and suspended in PBS. Subsequently, DNA was introduced into the cell under the conditions shown below using GENE PULSER [manufactured by Bio-Rad Laboratories, USA].

Namely, to a cuvette having a 0.4 cm gap were added $8\times10^6$ cells and 10 μg of plasmid pVgRXR2-hPPARγ obtained in the above-mentioned (4) and 10 μg of reporter plasmid pGL3-4ERPP-TK neo obtained in the above-mentioned (3), which was subjected to electroporation at the voltage of 0.25 kV under the capacitance of 960 μF. Subsequently, the cell was transferred into a F12 medium comprising 10% fetal bovine serum and cultured for 24 hours, and then the cell was taken off again and centrifuged. Then, the pellet was suspended in Ham's F12 medium comprising 10% fetal bovine serum supplemented with 500 μg/ml of Geneticin [manufactured by INVITROGEN, USA] and 250 μg/ml of Zeocin [manufactured by INVITROGEN, USA]. The obtained suspension was diluted to the density of $10^4$ cells/ml and inoculated in a 96-well plate [manufactured by Corning Costar Corporation, USA], which was cultured in a $CO_2$ gas incubator at 37° C., whereby obtaining a Geneticin- and Zeocin-resistant transformant.

Subsequently, after the transformed cell line thus obtained was cultured in a 24-well plate [manufactured by Corning Costar Corporation, USA], a cell line in which expression of the luciferase was induced, i.e., PPARγ:RXRα:4ERPP/CHO-K1 cell was selected by the addition of 10 μM pioglitazone hydrochloride.

(6) Evaluation of PPARγ Agonistic Activity

PPARγ:RXRα:4ERPP/CHO-K1 cells obtained in the above-mentioned (5) were cultured in F12 medium [manufactured by INVITROGEN, USA] containing 10% fetal bovine serum [manufactured by MOREGATE, Australia], seeded in a 96 well half-area white plate [manufactured by Corning Coster Corporation, USA] at $5\times10^3$ cells/well, and cultured in a $CO_2$ incubator at 37° C. overnight.

Then, the medium was removed from the 96 well half-area white plate, hamF12 medium containing 0.1% fatty acid-free bovine serum albumin (BSA) (45 μl) and a test compound (5 μl) were added, and the mixture was cultured in the $CO_2$ incubator at 37° C. for 1 day. After removing the medium, Picagene 7.5 [manufactured by Dai Nippon Inki, Japan] (20 μl) diluted 2-fold with HBSS (HANKS' BALANCED SALT SOLUTION) [manufactured by BIO WHITTAKER, USA] was added, and the mixture was stirred. Using 1420 ARVO Multilabel Counter [manufactured by PerkinElmer, USA], luciferase activity was measured.

The percentage (%) was calculated from the luciferase activity of the test compound when the luciferase activity of the control compound (compound X: 5-[3-(4-{[2-(2-furyl)-5-methyl-1,3-oxazol-4-yl]methoxy}-3-methoxyphenyl)propyl]-1,3-oxazolidine-2,4-dione) (1 μM) was taken as 100% and the luciferase activity of the test compound non-administration group was taken as 0%. The results are shown in Table 1 to Table 5.

TABLE 1

| Example No. | AT1 receptor antagonistic activity ($IC_{50}$ (nM)) | PPARγ agonistic activity (activation % ($10^{-6}$ M)) |
|---|---|---|
| 2 | 1.3 | 18 |
| 4 | 2.6 | 39 |
| 5 | 1.7 | 18 |
| 7 | 2.4 | 26 |
| 9 | 2.1 | 17 |
| 10 | 1.8 | 18 |
| 21 | 2.0 | 31 |
| 28 | 3.0 | 49 |

TABLE 1-continued

| Example No. | AT1 receptor antagonistic activity ($IC_{50}$ (nM)) | PPARγ agonistic activity (activation % ($10^{-6}$ M)) |
|---|---|---|
| 29 | 3.0 | 16 |
| 37 | 2.5 | 33 |
| 43 | 2.1 | 34 |
| 68 | 1.7 | 17 |
| 69 | 1.4 | 27 |
| 73 | 1.5 | 20 |
| 74 | 2.1 | 25 |
| 78 | 1.8 | 21 |
| 83 | 1.5 | 16 |
| 107 | 1.9 | 16 |
| 108 | 1.5 | 16 |
| 109 | 2.2 | 16 |
| 113 | 1.5 | 20 |
| 114 | 2.0 | 16 |
| 117 | 1.3 | 18 |
| 120 | 2.0 | 18 |
| 121 | 1.9 | 31 |
| 124 | 2.4 | 21 |

TABLE 2

| Example No. | AT1 receptor antagonistic activity ($IC_{50}$ (nM)) | PPARγ agonistic activity (activation % ($10^{-6}$ M)) |
|---|---|---|
| 125 | 1.9 | 23 |
| 131 | 2.9 | 15 |
| 134 | 1.3 | 26 |
| 135 | 0.9 | 26 |
| 136 | 1.3 | 17 |
| 137 | 1.4 | 20 |
| 138 | 1.3 | 8 |
| 139 | 1.7 | 6 |
| 144 | 1.4 | 20 |
| 147 | 1.0 | 26 |
| 148 | 1.9 | 52 |
| 150 | 1.4 | 58 |
| 151 | 1.6 | 35 |
| 152 | 2.4 | 39 |
| 153 | 1.9 | 53 |
| 154 | 2.1 | 33 |
| 155 | 1.6 | 18 |
| 158 | 2.5 | 37 |
| 160 | 1.3 | 26 |
| 161 | 1.2 | 47 |
| 163 | 1.6 | 40 |
| 164 | 1.0 | 18 |
| 166 | 1.3 | 22 |
| 167 | 0.8 | 43 |
| 168 | 1.4 | 54 |
| 169 | 1.4 | 54 |
| 170 | 1.6 | 20 |
| 173 | 1.7 | 28 |
| 179 | 1.9 | 41 |
| 180 | 3.5 | 31 |
| 181 | 3.2 | 18 |
| 183 | 2.5 | 30 |
| 184 | 2.5 | 41 |

TABLE 3

| Example No. | AT1 receptor antagonistic activity ($IC_{50}$ (nM)) | PPARγ agonistic activity (activation % ($10^{-6}$ M)) |
|---|---|---|
| 185 | 2.3 | 22 |
| 186 | 2.1 | 24 |
| 188 | 1.9 | 25 |
| 189 | 3.1 | 35 |
| 191 | 1.6 | 34 |
| 193 | 2.0 | 28 |

TABLE 3-continued

| Example No. | AT1 receptor antagonistic activity (IC$_{50}$ (nM)) | PPARγ agonistic activity (activation % (10$^{-6}$ M)) |
|---|---|---|
| 195 | 2.5 | 19 |
| 197 | 2.0 | 17 |
| 204 | 2.7 | 26 |
| 205 | 2.7 | 27 |
| 206 | 2.2 | 23 |
| 210 | 1.9 | 33 |
| 215 | 1.9 | 24 |
| 216 | 1.6 | 23 |
| 225 | 2.3 | 21 |
| 227 | 2.5 | 23 |
| 228 | 1.5 | 27 |
| 232 | 2.1 | 35 |
| 233 | 1.9 | 26 |
| 244 | 2.3 | 29 |
| 247 | 2.3 | 17 |
| 248 | 2.2 | 19 |
| 249 | 2.5 | 35 |
| 252 | 2.4 | 40 |
| 259 | 2.3 | 28 |
| 269 | 2.2 | 16 |
| 271 | 2.4 | 43 |
| 272 | 2.8 | 28 |
| 273 | 1.7 | 48 |

TABLE 4

| Example No. | AT1 receptor antagonistic activity (IC$_{50}$ (nM)) | PPARγ agonistic activity (activation % (10$^{-6}$ M)) |
|---|---|---|
| 274 | 2.2 | 42 |
| 275 | 2.5 | 31 |
| 277 | 2.2 | 20 |
| 278 | 2.7 | 22 |
| 280 | 1.9 | 16 |
| 281 | 1.8 | 42 |
| 282 | 2.2 | 53 |
| 285 | 3.1 | 34 |
| 286 | 3.1 | 39 |
| 288 | 2.7 | 17 |
| 290 | 3.2 | 25 |
| 292 | 1.9 | 46 |
| 293 | 2.3 | 28 |
| 294 | 2.1 | 31 |
| 296 | 1.7 | 29 |
| 297 | 2.8 | 53 |
| 299 | 1.8 | 19 |
| 300 | 1.8 | 16 |
| 318 | 1.8 | 17 |
| 319 | 2.0 | 16 |
| 325 | 2.0 | 31 |
| 326 | 1.8 | 29 |
| 331 | 2.0 | 33 |
| 335 | 1.9 | 19 |
| 337 | 1.9 | 24 |
| 338 | 1.6 | 36 |
| 339 | 1.4 | 27 |
| 345 | 2.1 | 18 |
| 348 | 1.9 | 19 |
| 352 | 1.4 | 20 |
| 354 | 1.2 | 18 |
| 355 | 1.7 | 25 |

TABLE 5

| Example No. | AT1 receptor antagonistic activity (IC$_{50}$ (nM)) | PPARγ agonistic activity (activation % (10$^{-6}$ M)) |
|---|---|---|
| 360 | 1.7 | 19 |
| 362 | 2.5 | 26 |
| 363 | 2.3 | 22 |
| 364 | 2.8 | 29 |
| 367 | 2.2 | 25 |
| 368 | 2.2 | 19 |
| 371 | 2.1 | 33 |
| 373 | 3.2 | 16 |
| 376 | 1.2 | 19 |
| 379 | 2.2 | 34 |
| 381 | 2.3 | 32 |
| 382 | 2.9 | 35 |
| 385 | 2.0 | 23 |
| 391 | 3.1 | 28 |
| 392 | 2.2 | 20 |
| 403 | 2.1 | 17 |
| 404 | 2.7 | 28 |
| 413 | 1.6 | 25 |
| 419 | 2.0 | 21 |
| 420 | 2.2 | 21 |
| 427 | 1.9 | 18 |
| 428 | 1.9 | 27 |
| 434 | 2.1 | 25 |
| 435 | 1.7 | 30 |
| 436 | 1.8 | 32 |
| 437 | 1.6 | 30 |
| 440 | 1.8 | 16 |
| 441 | 1.6 | 19 |
| 442 | 2.0 | 22 |
| 457 | 1.8 | 19 |

The Example compounds shown in the above Tables are all free forms.

As is clear from the above-mentioned Tables, the compound of the present invention showed a superior AT1 receptor antagonistic activity and a PPARγ agonistic activity.

EXPERIMENTAL EXAMPLE 3

Male SHRs (28-40 weeks old, Japan SLC, Inc., Japan) were anesthetized with sodium pentobarbital (50 mg/kg, i.p.). The left femoral artery was cannulated with a polyethylene catheter filled with saline comprising heparin (200 U/mL). The catheter was exteriorized at the back of the neck and each SHR was individually housed in a cage and left two or four days to recover. The mean blood pressure (MBP) was obtained from the systemic blood pressure which was monitored from the femoral artery using a pressure transducer connected to a polygraph system (Nihon Kohden Corporation). The heart rate was measured from the blood pressure pulse intervals. The rats which had MBP over 150 mmHg were used for the experiment. When the blood pressure had stabilized, vehicle (0.5 w/v % methylcellulose) or compounds were orally administered. All compounds were suspended in 0.5 w/v % methylcellulose and orally administered at a volume of 2 mL/kg. The MBP was measured during 24 hours after the administration. The results are shown in Table 6.

TABLE 6

| Example | Dose (mg/kg) | Maximum MBP reduction (mmHg) |
|---|---|---|
| 413 | 10 | 79 |
| 415 | 3 | 63 |
| 458 | 30 | 70 |
| 459 | 3 | 64 |

As clear from Table 6, the compound of the present invention was shown superior antihypertensive effect.

EXPERIMENTAL EXAMPLE 4

Male 25-31 weeks-old Wistar fatty rats (Takeda Pharmaceutical Company) were divided to each group with equalization of plasma levels of triglyceride, glucose and body weight in fed condition. The groups of rats were treated with vehicle (0.5 w/v % methylcellulose) or compounds. All compounds were suspended in 0.5 w/v % methylcellulose and orally administered at a volume of 2 mL/kg, once a day for 2 weeks. The next day of the final administration, blood was collected from the tail vein to measure plasma parameters. Heparin was used as an anticoagulant. Plasma levels of triglyceride and glucose were measured enzymatically using Hitachi Autoanalyser 9000. The inhibition rates from vehicle treatment group were calculated for each compound after the treatment for 2 weeks. The results are shown in Table 7.

TABLE 7

| Example | Dose (mg/kg) | Inhibition rate of plasma triglyceride (%) | Inhibition rate of plasma glucose (%) |
|---|---|---|---|
| 413 | 3 | 12.0 | 6.5 |
|  | 10 | 21.5 | 19.1 |
|  | 30 | 46.0 | 53.3 |
| 415 | 3 | 38.1 | 25.1 |
|  | 10 | 57.7 | 54.3 |
| 458 | 3 | 33.5 | −0.2 |
|  | 10 | 39.0 | 6.9 |
|  | 30 | 59.2 | 43.3 |

As is clear from Table 7, the compound of the present invention showed a superior plasma glucose and triglyceride lowering effect.

FORMULATION EXAMPLES

Formulation Example 1

Capsule

| | |
|---|---|
| (1) compound of Example 1 | 10 mg |
| (2) lactose | 90 mg |
| (3) crystalline cellulose | 70 mg |
| (4) magnesium stearate | 10 mg |
| 1 capsule | 180 mg |

(1), (2), (3) and ½ of (4) are blended and granulated. The rest of (4) is added and the whole is filled in a gelatin capsule.

Formulation Example 2

Tablet

| | |
|---|---|
| (1) compound of Example 1 | 10 mg |
| (2) lactose | 35 mg |
| (3) cornstarch | 150 mg |
| (4) crystalline cellulose | 30 mg |
| (5) magnesium stearate | 5 mg |
| 1 tablet | 230 mg |

(1), (2), (3), ⅔ of (4) and ½ of (5) are blended and granulated. The rest of (4) and (5) is added to the granules and the mixture is compression molded to give tablet.

Formulation Example 3

Injection

| | |
|---|---|
| (1) compound of Example 1 | 10 mg |
| (2) inositol | 100 mg |
| (3) benzyl alcohol | 20 mg |
| 1 ampoule | 130 mg |

(1), (2) and (3) are dissolved in distilled water for injection to the total amount of 2 mL and filled in an ampoule. All steps are performed under aseptic conditions.

INDUSTRIAL APPLICABILITY

The compound of the present invention has an angiotensin II receptor antagonistic activity and a peroxisome proliferator-activated receptor (PPAR) γ agonistic activity, and is useful as a medicament such as an agent for the prophylaxis or treatment of circulatory diseases such as hypertension, cardiac diseases (cardiac hypertrophy, cardiac failure, myocardial infarction etc.), arteriosclerosis, renal diseases (diabetic nephropathy, chronic glomerulonephritis etc.), ophthalmic diseases, liver diseases, cerebral apoplexy and the like and/or metabolic diseases such as hyperlipidemia, obesity, diabetes etc., and the like.

This application is based on Japanese patent application No. 2009-020720, the contents of which are incorporated in full herein by this reference.

The invention claimed is:

1. 4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one or a salt thereof.

2. A medicament comprising an effective amount of the compound according to claim 1 and a pharmaceutically acceptable carrier.

3. 4-[trans-4-(2-Hydroxy-2-methylpropoxy)cyclohexyl]-6-{[2'-(5-oxo-4,5-dihydro-1,2,4-oxadiazol-3-yl)biphenyl-4-yl]methyl}-7-propylpyrazolo[1,5-a]pyrimidin-5(4H)-one.

4. A medicament comprising an effective amount of the compound according to claim 3 and a pharmaceutically acceptable carrier.

* * * * *